US012310975B2

(12) United States Patent
Berlin et al.

(10) Patent No.: US 12,310,975 B2
(45) Date of Patent: May 27, 2025

(54) MODULATORS OF BCL6 PROTEOLYSIS AND ASSOCIATED METHODS OF USE

(71) Applicant: Arvinas Operations, Inc., New Haven, CT (US)

(72) Inventors: Michael Berlin, Flemington, NJ (US); Hanqing Dong, Madison, CT (US); Dan Sherman, Madison, CT (US); Lawrence Snyder, Killingworth, CT (US); Jing Wang, Milford, CT (US); Wei Zhang, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 268 days.

(21) Appl. No.: 17/073,135

(22) Filed: Oct. 16, 2020

(65) Prior Publication Data
US 2022/0323457 A1   Oct. 13, 2022

Related U.S. Application Data

(60) Provisional application No. 62/916,588, filed on Oct. 17, 2019.

(51) Int. Cl.
| | |
|---|---|
| A61K 31/496 | (2006.01) |
| A61K 31/4985 | (2006.01) |
| A61K 31/506 | (2006.01) |
| A61K 31/5355 | (2006.01) |
| A61K 31/5377 | (2006.01) |
| A61K 31/55 | (2006.01) |
| A61K 31/551 | (2006.01) |
| C07D 401/14 | (2006.01) |
| C07D 405/14 | (2006.01) |
| C07D 413/14 | (2006.01) |
| C07D 417/14 | (2006.01) |
| C07D 471/10 | (2006.01) |
| C07D 487/04 | (2006.01) |
| C07D 487/08 | (2006.01) |
| C07D 487/10 | (2006.01) |

(52) U.S. Cl.
CPC .......... *A61K 31/551* (2013.01); *A61K 31/496* (2013.01); *A61K 31/4985* (2013.01); *A61K 31/506* (2013.01); *A61K 31/5355* (2013.01); *A61K 31/5377* (2013.01); *A61K 31/55* (2013.01); *C07D 401/14* (2013.01); *C07D 405/14* (2013.01); *C07D 413/14* (2013.01); *C07D 417/14* (2013.01); *C07D 471/10* (2013.01); *C07D 487/04* (2013.01); *C07D 487/08* (2013.01); *C07D 487/10* (2013.01)

(58) Field of Classification Search
CPC .. C07D 401/14; C07D 405/14; C07D 413/14; C07D 417/14; C07D 471/10; C07D 487/04; C07D 487/08; C07D 487/10; C07D 401/12; A61K 31/551; A61K 31/496; A61K 31/4985; A61K 31/506; A61K 31/5355; A61K 31/5377; A61K 31/55; A61K 45/06; A61K 47/64; A61K 35/00; A61K 47/55

See application file for complete search history.

(56) References Cited

U.S. PATENT DOCUMENTS

| | | | |
|---|---|---|---|
| 4,522,811 A | 6/1985 | Eppstein et al. | |
| 6,306,663 B1 | 10/2001 | Kenten et al. | |
| 6,670,348 B1 | 12/2003 | Rosen et al. | |
| 7,041,298 B2 | 5/2006 | Deshaies et al. | |
| 7,208,157 B2 | 4/2007 | Dashaies et al. | |
| 8,338,464 B2 * | 12/2012 | Melnick .................. | A61P 35/00 514/367 |
| 9,447,070 B2 | 9/2016 | Muller et al. | |
| 9,500,653 B2 | 11/2016 | Crews et al. | |
| 9,632,089 B2 | 4/2017 | Crews et al. | |
| 10,647,698 B2 | 5/2020 | Crew et al. | |

(Continued)

FOREIGN PATENT DOCUMENTS

| | | |
|---|---|---|
| CN | 1844118 A | 10/2006 |
| CN | 103688176 A | 3/2014 |

(Continued)

OTHER PUBLICATIONS

Cerchietti, L.C., et al.(2010), A Small-Molecule Inhibitor of BCL6 Kills DLBCL Cells In Vitro and In Vivo, Cancer Cell, 17, 4, pp. 400-411, Apr. 13, 2010.

(Continued)

*Primary Examiner* — Amanda L. Aguirre
(74) *Attorney, Agent, or Firm* — McCarter & English, LLP; Michael J. DeGrazia; James M. Alburger

(57) ABSTRACT

Bifunctional compounds, which find utility as modulators of B-cell lymphoma 6 protein (BCL6; target protein), are described herein. In particular, the bifunctional compounds of the present disclosure contain on one end a Von Hippel-Lindau, cereblon, Inhibitors of Apotosis Proteins or mouse double-minute homolog 2 ligand that binds to the respective E3 ubiquitin ligase and on the other end a moiety which binds the target protein, such that the target protein is placed in proximity to the ubiquitin ligase to effect degradation (and inhibition) of target protein. The bifunctional compounds of the present disclosure exhibit a broad range of pharmacological activities associated with degradation/inhibition of target protein. Diseases or disorders that result from aggregation or accumulation of the target protein are treated or prevented with compounds and compositions of the present disclosure.

5 Claims, 3 Drawing Sheets

(56) References Cited

U.S. PATENT DOCUMENTS

| | | | |
|---|---|---|---|
| 11,439,635 B2* | 9/2022 | Barish | A61K 31/427 |
| 11,505,539 B2* | 11/2022 | Isaac | A61P 35/02 |
| 11,512,095 B2* | 11/2022 | Bellenie | C07D 471/04 |
| 11,518,764 B2* | 12/2022 | Al-awar | A61P 35/00 |
| 11,827,627 B2 | 11/2023 | Beck et al. | |
| 11,883,393 B2 | 1/2024 | Snyder et al. | |
| 11,986,532 B2 | 5/2024 | Sherman | |
| 12,043,612 B2 | 7/2024 | Allan et al. | |
| 2003/0096841 A1 | 5/2003 | Robarge et al. | |
| 2008/0051432 A1 | 2/2008 | Zhang | |
| 2008/0214501 A1 | 9/2008 | Pan et al. | |
| 2012/0014979 A1* | 1/2012 | Dent | G01N 33/564 424/185.1 |
| 2012/0270800 A1 | 10/2012 | Verdine et al. | |
| 2014/0302523 A1 | 10/2014 | Crews et al. | |
| 2014/0356322 A1* | 12/2014 | Crews | A61K 31/5377 514/19.5 |
| 2015/0119435 A1 | 4/2015 | Crews et al. | |
| 2015/0291562 A1* | 10/2015 | Crew | A61P 25/28 435/375 |
| 2015/0344473 A1 | 10/2015 | Du et al. | |
| 2016/0022642 A1 | 1/2016 | Crews et al. | |
| 2016/0045607 A1 | 2/2016 | Crew et al. | |
| 2016/0058872 A1 | 3/2016 | Crew et al. | |
| 2016/0136230 A1 | 5/2016 | Campos et al. | |
| 2016/0214972 A1 | 7/2016 | Jin et al. | |
| 2016/0243247 A1 | 8/2016 | Bradner et al. | |
| 2016/0272639 A1 | 9/2016 | Crew et al. | |
| 2016/0368911 A1 | 12/2016 | Campos et al. | |
| 2017/0008904 A1 | 1/2017 | Crew et al. | |
| 2017/0037004 A1 | 2/2017 | Crew et al. | |
| 2017/0065719 A1 | 3/2017 | Qian et al. | |
| 2017/0121321 A1* | 5/2017 | Crews | A61K 47/55 |
| 2017/0281784 A1 | 10/2017 | Wang et al. | |
| 2017/0307614 A1 | 10/2017 | Crews et al. | |
| 2017/0327469 A1 | 11/2017 | Crew et al. | |
| 2018/0015087 A1 | 1/2018 | Liu et al. | |
| 2018/0072711 A1 | 3/2018 | Crew et al. | |
| 2018/0099940 A1 | 4/2018 | Crew et al. | |
| 2018/0125821 A1 | 5/2018 | Crew et al. | |
| 2018/0147202 A1 | 5/2018 | Crew et al. | |
| 2018/0155322 A1 | 6/2018 | Crew et al. | |
| 2018/0177750 A1 | 6/2018 | Crew et al. | |
| 2018/0179183 A1 | 6/2018 | Crew et al. | |
| 2018/0193470 A1 | 7/2018 | Crew et al. | |
| 2018/0215731 A1 | 8/2018 | Crew et al. | |
| 2018/0228907 A1 | 8/2018 | Crew et al. | |
| 2018/0237418 A1 | 8/2018 | Crew et al. | |
| 2018/0256586 A1 | 9/2018 | Crew et al. | |
| 2022/0081416 A1 | 3/2022 | Boulton et al. | |
| 2022/0372016 A1 | 11/2022 | Phillips et al. | |
| 2022/0395576 A1 | 12/2022 | Berlin et al. | |
| 2024/0190841 A1 | 6/2024 | Sherman | |

FOREIGN PATENT DOCUMENTS

| | | |
|---|---|---|
| EP | 2985285 | 2/2016 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2005/016326 | 2/2005 |
| WO | WO 2006/113942 | 10/2006 |
| WO | WO 2007/106670 | 9/2007 |
| WO | WO 2008/011392 | 1/2008 |
| WO | WO 2009/015254 | 1/2009 |
| WO | WO 2010/053732 A1 | 5/2010 |
| WO | WO 2010/141805 | 12/2010 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2012/142498 | 10/2012 |
| WO | WO 2017/176958 | 10/2012 |
| WO | WO 2013/106646 | 7/2013 |
| WO | WO 2013/170147 | 11/2013 |
| WO | WO 2014/108452 | 7/2014 |
| WO | WO 2014/123418 | 8/2014 |
| WO | WO 2015/000868 | 1/2015 |
| WO | WO 2015/160845 | 10/2015 |
| WO | WO 2016/105518 | 6/2016 |
| WO | WO 2016/146985 | 9/2016 |
| WO | WO-2016149668 A1 | 9/2016 |
| WO | WO 2016/169989 | 10/2016 |
| WO | WO 2016/172134 | 10/2016 |
| WO | WO 2016/197114 | 12/2016 |
| WO | WO-2016187723 A1 | 12/2016 |
| WO | WO-2017/007612 A1 | 1/2017 |
| WO | WO 2017/011590 | 1/2017 |
| WO | WO 2017/024317 | 2/2017 |
| WO | WO 2017/024318 A1 | 2/2017 |
| WO | WO 2017/024319 A1 | 2/2017 |
| WO | WO 2017/030814 | 2/2017 |
| WO | WO 2017/046036 | 3/2017 |
| WO | WO 2017/079267 | 5/2017 |
| WO | WO 2017/117473 | 7/2017 |
| WO | WO 2017/117474 | 7/2017 |
| WO | WO 2017/161119 | 9/2017 |
| WO | WO 2017/176957 | 10/2017 |
| WO | WO 2017/185023 | 10/2017 |
| WO | WO 2017/185031 | 10/2017 |
| WO | WO 2017/185034 | 10/2017 |
| WO | WO 2017/185036 | 10/2017 |
| WO | WO 2017/197051 | 11/2017 |
| WO | WO 2017/197055 | 11/2017 |
| WO | WO 2017/197056 A1 | 11/2017 |
| WO | WO 2017/223415 | 12/2017 |
| WO | WO 2017/223452 | 12/2017 |
| WO | WO 2018/052945 A1 | 3/2018 |
| WO | WO 2018/052949 | 3/2018 |
| WO | WO 2018/064589 A1 | 4/2018 |
| WO | WO 2018/089736 A1 | 5/2018 |
| WO | WO 2018/098275 | 5/2018 |
| WO | WO 2018/098280 A1 | 5/2018 |
| WO | WO 2018/098288 | 5/2018 |
| WO | WO 2018/106870 | 6/2018 |
| WO | WO 2018/108704 A1 | 6/2018 |
| WO | WO-2018102725 A1 | 6/2018 |
| WO | WO 2018/148440 | 8/2018 |
| WO | WO 2018/215801 A1 | 11/2018 |
| WO | WO-2018215798 A1 | 11/2018 |
| WO | WO 2018/237026 A1 | 12/2018 |
| WO | WO 2019/060742 A1 | 3/2019 |
| WO | WO-2019060693 A1 | 3/2019 |
| WO | WO 2019/084026 A1 | 5/2019 |
| WO | WO 2019/084030 A1 | 5/2019 |
| WO | WO 2019/099868 A3 | 5/2019 |
| WO | WO 2019/099926 A1 | 5/2019 |
| WO | WO 2019/119138 A1 | 6/2019 |
| WO | WO 2019/195201 A1 | 10/2019 |
| WO | WO-2021074620 A1 | 4/2021 |
| WO | WO-2021077010 A1 | 4/2021 |
| WO | WO-2023015164 A1 | 2/2023 |
| WO | WO-2024086759 A1 | 4/2024 |
| WO | WO-2024151557 A1 | 7/2024 |

OTHER PUBLICATIONS

Yu, et al., (2015), BCL6 induces EMT by promoting the ZEB1-mediated transcription repression of E-cadherin in breast cancer cells, Cancer Letters, 365, 2, pp. 190-200, Sep. 1, 2015.

Cardenas, MG, et al., Rationally designed BCL6 inhibitors target activated B cell diffuse large B cell lymphoma. J Clin Invest. Sep. 1, 2016;126(9):3351-62.

Hurtz, Christian, et al (2019), Rationale for targeting BCL6 in MLL-rearranged acute lymphoblastic leukemia, Genes & development, 33, 17-18, pp. 1265-1279, Aug. 8, 2019.

(56) References Cited

OTHER PUBLICATIONS

Beveridge, R., et al., Native Mass Spectrometry Can Effectively Predict PROTAC Efficacy, ACS Cent. Sci. Jul. 6, 2020, 6, 1223-1230.
Ahn, et al., "HIF-lalpha peptide derivatives with modifications at the hydroxyproline residue as activators of HIF-lalpha", Bioorg Med Chem Lett. 19(15), 2009, 4403-4405 (May 27, 2009).
Bellenie BR, et al., Achieving In Vivo Target Depletion through the Discovery and Optimization of Benzimidazolone BCL6 Degraders. J Med Chem. Apr. 23, 2020;63(8):4047-4068.
Bondeson DP, et al. (Jan. 18, 2018) "Lessons in PROTAC Design from Selective Degradation with a Promiscuous Warhead." Cell Chem Biol 25(1):78-87 e75.
Bondeson, et al., (Jan. 2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Bouzide, et al., Silver(I) oxide-mediated facile and practical sulfonylation of alcohols, Tetrahedron. Lett., 42, 8781-8783, (Oct. 9, 2001).
Buckley, et al., "HaloPROTACS: use of small molecule PROTACS to induce degradation of HaloTag fusion proteins", ACS Chem Biol. 10(8), 2015, 1831-1837 Aug. 21, 2015.
Buckley, et al., "Small-molecule inhibitors of the interaction between the E3 ligase VHL and HIF1a", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.
Burslem GM, et al. (Jan. 18, 2018) "The Advantages of Targeted Protein Degradation Over Inhibition: An RTK Case Study." Cell Chem Biol 25(1):67-77 e63.
Burslem, et al., (Sep. 13, 2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336 Jan. 1, 2004.
Cardenas MG, et al., Rationally designed BCL6 inhibitors target activated B cell diffuse large B cell lymphoma. J Clin Invest. Sep. 1, 2016;126(9):3351-62 (Have).
Carmony, KC, et al., "PROTAC-Induced Proteolytic Targeting", Methods Mol. Biol., 2012, vol. 832, pp. 627-638. Dec. 5, 2013.
CAS Registry No. 1004933-70-3, which entered STN on Feb. 21, 2008.
CAS Registry No. 871986-52-6 entered STN Jan. 16, 2006.
CAS RN 1542127-97-8 STN Entry, Feb. 11, 2014.
Chan, et al., (Jun. 8, 2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds. " *J Med Chem* 61(2):504-513.
Chen, Jin-Quan, et al., A review on the latest progress of Chan-Lam coupling reaction, Advanced Synthesis and Catalysis 62 (16), 3311-3331 (Jul. 14, 2020).
Churcher I, (Jan. 25, 2018) "Protac-Induced Protein Degradation in Drug Discovery: Breaking the Rules or Just Making New Ones?" *J Med Chem* 61(2):444-452.
Contino-Pepin, Christiane, et al., "Preliminary biological evaluations of new thalidomide analogues for multiple sclerosis application", Bioorganic & Medicinal Chemistry Letter 19 (2009), 878-881 Dec. 7, 2008.
Corson, et al., "Design and applications of bifunctional small molecules: why two heads are better than one", ACS Chemical Biology vol. 3 No. 11, pp. 677-692; Nov. 21, 2008.
Crew AP, et al. (Jan. 25, 2018) "Identification and Characterization of Von Hippel-Lindau-Recruiting Proteolysis Targeting Chimeras (PROTACs) of TANK-Binding Kinase 1." *J Med Chem* 61(2):583-598.

Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (Jun. 25, 2010).
Cromm, et al., (Sep. 21, 2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al., "Impact of Linker Length on the Activity of PROTACs," Mol. Biosyst., 2011, vol. 7, No. 2, pp. 359-364 (Feb. 2011).
Cyrus, K. et al., "Two-Headed PROTAC: An Effective New Tool for Targeted Protein Degradation," Chembiochem., 2010, vol. 11, pp. 1531-1534 Jul. 26, 2010.
Duplantier, et al., Discovery, SAR, and Pharmacokinetics of a Novel 3-Hydroxyquinolin-2(1H)-one Series of Potent d-Amino Acid Oxidase (DAAO) Inhibitors, (May 13, 2009), J. Med. Chem. 52, 3576-3585.
Fischer, et al., "Structure of the DDB1-DRBN E3 Ubiquitin ligase in complex with thalidomide", Nature, vol. 512, pp. 49-53 (Jul. 16, 2014).
Gadd, M.S., et al., "Structural basis of PROTAC cooperative recognition for selective protein degradation", Nat Chem Biol 13, 514-521 (Mar. 13, 2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (Oct. 15, 1991).
Gosink, M. et al., "Redirecting the specificity of ubiquitination by modifying ubiquitin-conjugating enzymes", Pro. Natl. Acad Sci, vol. 92, pp. 9117-9121, 1995 (Sep. 26, 1995).
Guo W, et al., Synthesis and Biological Evaluation of B-Cell Lymphoma 6 Inhibitors of N-Phenyl-4-pyrimidinamine Derivatives Bearing Potent Activities against Tumor Growth. J Med Chem. Jan. 23, 2020;63(2):676-695.
Han, Xin, et al., Discovery of ARD-69 as a Highly Potent Proteolysis Targeting Chimera (PROTAC) Degrader of Androgen Receptor (AR) for the Treatment of Prostate Cancer, Journal of Medicinal Chemistry 2019 62 (2), 941-964, DOI: 10.1021/acs.jmedchem.8b01631 Jan. 24, 2019.
Hines, J., et al., "Posttranslational protein knockdown coupled to receptor tyrosine kinase activation with phosphoPROTACs", Proc Natl Acad Sci USA 110, 8942-8947 (May 14, 2013).
Hon, et al., "Structural basis for the recognition of hydroxyproline in Hlf-1 alpha by pVHL", Nature 417, Jun. 27, 2002, 975-978.
Hu, Jiantao, et al., Discovery of ERD-308 as a Highly Potent Proteolysis Targeting Chimera (PROTAC) Degrader of Estrogen Receptor (ER), DOI: 10.1021/acs.jmedchem.8b01572, Journal of Medicinal Chemistry, vol. 62, pp. 1420-1442, Jan. 18, 2019, http://dx.doi.org/10.1021/acs.jmedchem.8b01572.
Huang HT, et al. (Jan. 18, 2018) "A Chemoproteomic Approach to Query the Degradable Kinome Using a Multi-kinase Degrader." *Cell Chem Biol* 25(1):88-99 e86.
Huang, et al., (Apr. 2016) "Drugging the undruggables: exploring the ubiquitin system for drug development." *Cell Res* 26(4):484-498.
Hughes, et al., (Nov. 8, 2017) "Molecular recognition of ternary complexes: a new dimension in the structure-guided design of chemical degraders." *Essays Biochem* 61(5):505-516.
Itoh, et al., "Development of target protein selective degradation inducer for protein knockdown," Bioorg. Med. Chem., 2011, 19, 3229-3241. Mar. 28, 2011.
Itoh, et al., "Protein knockdown using methyl bestatin-ligand hybrid molecules: design and synthesis of inducers of ubiquitination-mediated degradation of cellular retinoic acid-binding proteins," J. AM. Chem. Soc., 2010, 132, 5820-5826.Apr. 28, 2010.

(56) References Cited

OTHER PUBLICATIONS

Ivan, M., et al., "HIFa Targeted for VHL-Mediated Destruction by Proline Hydroxylation: Implications for O2 Sensing", Science, vol. 292, No. 5516, pp. 464-468, Apr. 20, 2001.

Jang, E.R. et al., "Targeted Degradation of Proteins by PROTACs," Curr. Protoc. Chem. Biol., 2010, vol. 2, No. 2, pp. 71-87 Jun. 1, 2010.

Kamada Y, et al., Discovery of a B-Cell Lymphoma 6 Protein-Protein Interaction Inhibitor by a Biophysics-Driven Fragment-Based Approach. J Med Chem. May 25, 2017;60(10):4358-4368.

Kerres N, et al., Chemically Induced Degradation of the Oncogenic Transcription Factor BCL6. Cell Rep. Sep. 19, 2017;20(12):2860-2875.

Knott, Edward (1955). "Compounds containing sulphur chromophores. Part I. The action of bases on heterocyclic sulphide quarternary salts", Journal of The Chemical Society (resumed). 10.1039/jr9550000916. 949-954.

Kronke, et al, "Lenalidomide Causes Selective Degradation of IKZF1 and IKZF3 in Multiple Myeloma Cells", Science 343, 301-305 (Jan. 17, 2014).

Lai, A.C., et al., "Modular PROTAC Design for the Degradation of Oncogenic BCR-ABL", Angew Chem Int Ed Engl 55, 807-810 (Jan. 11, 2016).

Lai, et al., (Feb. 2017) "Induced protein degradation: an emerging drug discovery paradigm." Nat Rev Drug Discov 16(2):101-114.

Lala, et al., "Role of nitric oxide in tumor progression: Lessons from experimental tumors", Cancer and Metastasis Reviews 17:91-106 (Mar. 1998).

Lebraud, H., et al., "Protein Degradation by In-Cell Self-Assembly of Proteolysis Targeting Chimeras", ACS Central Science, 2, 927-934 (Dec. 5, 2016).

Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.

Levine, et al., Targeting the androgen receptor with steroid conjugates, J. Med. Chem., vol. 57., No. 20. pp. 8224-8237, (Sep. 14, 2014).

Li, Yan, et al., "Single polymer-drug conjugate carrying two drugs for fixed-dose co-delivery", Medicinal Chemistry, 2014, vol. 4(10): 676-683 Jan. 2014.

Liu, K., et al., "Design and biological characterization of hybrid compounds of curcumin and thalidomide for multiple myeloma", Org. Biomol. Chem. 2013, 11, 4757-476 , Jun. 11, 2013.

Lopez-Girona, A. et al., Cereblon is a direct protein target for immunomodulatory and antiproliferative activities of lenalidomide and pomalidomide, Leukemia 26: 2326-2335, Nov. 2012.

Lu, et al., "Hijacking the E3 ubiquitin ligase cereblon to efficiently target BRD4", Chem Biol 22(6), 2015, 755-763, Jun. 18, 2015.

Lu, et al., "The myeloma drug lenalidomide promotes the cereblon-dependent destruction of ikaros proteins", Science 343, 305-309 (Jan. 17, 2014).

Maniaci C, et al. (Oct. 10, 2017) "Homo-PROTACs: bivalent small-molecule dimerizers of the VHL E3 ubiquitin ligase to induce self-degradation." Nat Commun 8(1):830 1-13.

McCoull W, et al. Discovery of Pyrazolo[1,5-a]pyrimidine B-Cell Lymphoma 6 (BCL6) Binders and Optimization to High Affinity Macrocyclic Inhibitors, J Med Chem. May 25, 2017;60, 4386-4402.

McCoull W, et al., Development of a Novel B-Cell Lymphoma 6 (BCL6) PROTAC To Provide Insight into Small Molecule Targeting of BCL6. ACS Chem Biol. Nov. 16, 2018;13(11):3131-3141.

Medline Plus Trusted Health Information for You, www.nlm.nih.gov/medlineplus/cancer.html pp. 1-10, (Jul. 6, 2007).

Min, Jung-hyun, et al., "Structure of an HIV-1-alpha-pVHL complex: hydroxyproline recognition in signaling", Jun. 7, 2002, 296: 1886-1889.

Muller, G., et al., "Amino-Substituted Thalodomide Analogs: Potent Inhibitors of TNF-α Production", Bioorganic & Medicinal Chemistry Letters 9 (Jun. 7, 1999) 1625-1630.

Neklesa, T.K., et al., "Chemical biology: Greasy tags for protein removal", Nature 487, 308-309 (Jul. 18, 2012).

Neklesa, Targeted protein degradation by PROTACs. Pharmacology & Therapeutics 174, 138-144 (Jun. 2017).

Noguchi-Yachide, et al., BET Bromodomain as a Target of Epigenitic Therapy, Chemical and Pharmaceutical Bulletin, Jun. 1, 2016, vol. 64, Iss 6, pp. 540-547.

Ohoka, N. et al. SNIPER(TACC3) induces cytoplasmic vacuolization and sensitizes cancer cells to Bortezomib. Cancer Sci. 108, 1032-1041 (May 2017).

Osher EL, et al., A genetically selected cyclic peptide inhibitor of BCL6 homodimerization. Bioorg Med Chem. Jul. 15, 2018;26(11):3034-3038.

Ottis P, et al. (Oct. 20, 2017) "Assessing Different E3 Ligases for Small Molecule Induced Protein Ubiquitination and Degradation." ACS Chem Biol 12(10):2570-2578.

Ottis, et al., (Apr. 21, 2017) "Proteolysis-Targeting Chimeras: Induced Protein Degradation as a Therapeutic Strategy." ACS Chem Biol 12(4):892-898.

Pfaff, P., et al., Reversible Spatiotemporal Control of Induced Protein Degradation, by Bistable Photo PROTACS, ACS Cent. Sci. 2019., 5, pp. 1682-1690 (2019).

Powell, C. E. et al. Chemically Induced Degradation of Anaplastic Lymphoma Kinase (ALK). J. Med. Chem. 61, 4249-4255 (May 10, 2018).

Puppala, D. et al., "Development of an Aryl Hydrocarbon Receptor Antagonist Using the Proteolysis-Targeting chimeric Molecules Approach: A Potential Tool for Chemoprevention," Mol. Pharmacol., (Apr. 2008), vol. 73, No. 4, pp. 1064-1071.

Raina et al., "Chemical Inducers of Targeted Protein Degradation," The Journal of Biological Chemistry, 2010, vol. 285, No. 15, pp. 11057-11060. Feb. 10, 2010.

Raina, et al., (Aug. 2017) "Targeted protein knockdown using small molecule degraders." Curr Opin Chem Biol 39:46-53.

Raina, K., et al., "PROTAC-induced BET protein degradation as a therapy for castration-resistant prostate cancer", Proc Natl Acad Sci USA 113, 7124-7129 (Jun. 28, 2016).

Remillard D, et al. (May 15, 2017) "Degradation of the BAF Complex Factor BRD9 by Heterobifunctional Ligands." Angew Chem Int Ed Engl 56(21):5738-5743.

Rodriguez-Gonzalez, et al., "Targeting steroid hormone receptors for ubiquitination and degradation in breast and prostate cancer", Oncogene. 27(57), Dec. 4, 2008, 7201-7211.

Rosania et al., "Targeting hyperproliferative disorders with cyclin dependent kinase inhibitors", Exp. Opin. Ther. Patents (2000) 10(2):215-230 (Feb. 25, 2005).

Rotili, D., et al., "Photoactivable peptides for identifying enzyme-substrate and protein-protein interactions", Chem Commun (Carob) 47(5), Feb. 2011, 1488-1490.

Ruchelman, A., et al., "Isosteric analogs of lenalidominde and pomalidomide: Synthesis and biological activity", Bioorganic & Medicinal Chemistry Letters 23 (Jan. 1, 2013) 360-365.

Sakamoto, et al., "Development of Protacs to target cancer-promoting proteins for ubiquitination and degradation", Mol Cell Proteomics. 2(12), Dec. 2003, 1350-1358.

Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.

Salami, J. & Crews, C. M. Waste disposal—An attractive strategy for cancer therapy. Science 355, 1163-1167 (Mar. 17, 2017).

Sameshima T, et al., Discovery of an Irreversible and Cell-Active BCL6 Inhibitor Selectively Targeting Cys53 Located at the Protein-Protein Interaction Interface. Biochemistry. Feb. 27, 2018;57(8):1369-1379.

Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491 (Jan. 25, 2018).

Schlager S, et al., Inducible knock-out of BCL6 in lymphoma cells results in tumor stasis. Oncotarget. Mar. 3, 2020;11(9):875-890.

Schneekloth, et al., "Chemical Genetic Control of Protein Levels: Selective in Vivo Targeted Degradation", J Am Chem Soc. 126(12), Mar. 31, 2004, 3748-3754.

(56) References Cited

OTHER PUBLICATIONS

Schneekloth, et al., Targeted intracellular protein degradation induced by a small molecule: En route to chemical proteomics, Bioorg. Med. Chem. Lett. 18 (Nov. 15, 2008) 5904-590.
Stanton, et al., (Mar. 9, 2018) "Chemically induced proximity in biology and medicine." *Science* 359(6380).
Stewart, Scott G., et al., "Efforts toward elucidating Thalidomide's molecular target: An Expedient Synthesis of the first Thalidomide Biotin Analogue" Org. Biomol., Chem., Jul. 13, 2010; 8, 4059-4062.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, B. et al. BET protein proteolysis targeting chimera (PROTAC) exerts potent lethal activity against mantle cell lymphoma cells. Leukemia 32, 343-352 (Feb. 2018).
Teng M, et al., Rationally Designed Covalent BCL6 Inhibitor That Targets a Tyrosine Residue in the Homodimer Interface. ACS Med Chem Lett. Apr. 3, 2020;11(6):1269-1273.
Toure, et al., (Feb. 5, 2016) "Small-Molecule PROTACS: New Approaches to Protein Degradation." *Angew Chem Int Ed Engl* 55(6):1966-1973.
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556 (Jul. 23, 1996).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Watson, Iain D.G., et al., Abstract 7: Discovery of OICR-10268: A potent and selective BCL6 inhibitor, Conference: Proceedings: AACR Annual Meeting 2019; Mar. 29-Apr. 3, 2019; Atlanta, GA, DOI: 10.1158/1538-7445.AM2019-7.
Winter, et al., "Phthalimide Conjugation as a strategy for in vivo target protein degradation", Science, 2015 vol. 348 (6241), pp. 1376-1381 [Pub online: May 21, 2015].
Yasui T, et al.. Discovery of a novel B-cell lymphoma 6 (BCL6)-corepressor interaction inhibitor by utilizing structure-based drug design. Bioorg Med Chem. Sep. 1, 2017;25(17):4876-4886.
Zengerle, et al., "Selective Small Molecule Induced Degradation of the BET Bromodomain Protein BRD4" ACS Chemical Biology, Jun. 2, 2015, vol. 10, pp. 1770-1777.
Zhang, D. et al., "Targeted Degradation of Proteins by Small Molecules: A Novel Tool for Functional Proteomics," comb Chem. High Throughput Screen., Nov. 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (Mar. 24, 2017).
International Search Report and Written Opinion for PCT/US2020/056145, Dated Dec. 1, 2020.
Mullard, A., "First targeted protein degrader hits the clinic", Nature Reviews, Drug Discovery (Apr. 2019); 18: 237-239.
Scudellari, M., "The protein slayers", Nature (Mar. 21, 2019); 567: 298-300.
Cerchietti, L. C., et al., "A peptomimetic inhibitor of BCL6 with potent antilymphoma effects in vitro and in vivo", Blood. Apr. 9, 2009; 113(15): 3397-405. Epub Oct. 16, 2008.
Co-pending U.S. Appl. No. 18/610,001, inventor Berlin; Michael, filed Mar. 19, 2024.
Houston, J. G., "The Promise of PROTAC® Protein Degraders: What's Next for Arvinas' Pipeline & Platform", Arvinas Presentation (Oct. 14, 2020); 23 pages.
Co-pending U.S. Appl. No. 18/407,150, inventors Sherman; Dan et al., filed Jan. 8, 2024.
Co-pending U.S. Appl. No. 18/490,704, inventor Sherman; Dan , filed Oct. 19, 2023.
Khadra, A., et al., "Pd-PEPPSI-IPent$^{Cl}$ : A Useful Catalyst for the Coupling of 2-Aminopyridine Derivatives", Chemistry—A European Journal (2017); 23(13): 3206-3212.
Thirumurugan, P., et al., "Click chemistry for drug development and diverse chemical-biology applications", Chemical Reviews (2013); 113(7): 4905-4979.
Garrido, J., "Influencia de los agentes exteriores sobre la forma de los cristales", Forma y estructura de los cristales, Exedra (1973); Chapter V: 204-225; 34 pages with English Translation.
Giron, D., "Thermal analysis and calorimetric methods in the characterisation of polymorphs and solvates", Thermochimica Acta (1995); 248: 1-59.
Lien, E. J., "Atomic and Molecular Structure and the States of Matter", Remington's Pharmaceutical Sciences, 16$^{th}$ Edition (1980); pp. 160-181.
Nies, A. S., et al., "Principles of Therapeutics", Goodman & Gilman's the Pharmacological Basis of Therapeutics (copyright 1996); 9th Edition, Chapter 3; pp. 43-62.

\* cited by examiner

MODULATORS OF BCL6 PROTEOLYSIS AND ASSOCIATED METHODS OF USE

CROSS-REFERENCE TO RELATED APPLICATION

This application claims priority to U.S. Provisional Patent Application No. 62/916,588, filed 17 Oct. 2019 and titled MODULATORS OF BCL6 PROTEOLYSIS AND ASSOCIATED METHODS OF USE, which is incorporated herein by reference in its entirety for all purposes.

INCORPORATION BY REFERENCE

U.S. patent application Ser. No. 15/230,354, filed on Aug. 5, 2016, published as U.S. Patent Application Publication No. 2017/0065719; and U.S. patent application Ser. No. 15/206,497 filed 11 Jul. 2016, published as U.S. Patent Application Publication No. 2017/0008904; and U.S. patent application Ser. No. 15/209,648 filed 13 Jul. 2016, published as U.S. Patent Application Publication No. 2017/0037004; and U.S. patent application Ser. No. 15/730,728, filed on Oct. 11, 2017, published as U.S. Patent Application Publication No. 2018/0099940; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. patent application Ser. No. 15/885,671, filed Jan. 31, 2018, published as U.S. Patent Application Publication No. 2018/0215731 A1; and International Patent Application No. PCT/US2016/023258, filed Mar. 18, 2016, published as International Patent Application Publication No. WO2016/149668, are incorporated herein by reference in their entirety. Furthermore, all references cited herein are incorporated by reference herein in their entirety.

FIELD OF THE INVENTION

The description provides bifunctional compounds comprising a target protein binding moiety and a E3 ubiquitin ligase binding moiety, and associated methods of use. The bifunctional compounds are useful as modulators of targeted ubiquitination, such as B-cell lymphoma 6 protein (BCL6), which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those that are described in U.S. Patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease associated with overexpression or aggregation of B-cell lymphoma 6 protein (BCL6). However, non-specific effects, and the inability to target and modulate BCL6, remain as obstacles to the development of effective treatments. As such, small-molecule therapeutic agents that target BCL6 and that leverage or potentiate E3 ubiquitin ligase (e.g., VHL's and cereblon's) substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/ inhibition of targeted polypeptides from virtually any protein class or family. In addition, the description provides methods of using an effective amount of the compounds as described herein for the treatment or amelioration of a disease condition, such as cancer, e.g., lymphoma, B-cell non-Hodgkin lymphomas, large B-cell lymphoma, Burkitt's lymphoma, follicular lymphoma, intravascular large B-cell lymphoma, B-cell leukemia, B-cell acute lymphoblastic leukemia, chronic myeloid leukemia, non-small cell lung cancer.

As such, in one aspect the disclosure provides bifunctional compounds, which comprise an E3 ubiquitin ligase binding moiety (i.e., a ligand for an E3 ubquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM) or a cereblon E3 ubiquitin ligase binding moiety (CLM). For example, the structure of the bifunctional compound can be depicted as:

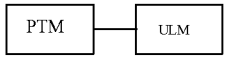

The respective positions of the PTM and ULM moieties (e.g., VLM or CLM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

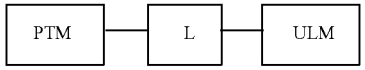

where PTM is a protein/polypeptide targeting moiety, L is a linker, e.g., a bond or a chemical group coupling PTM to ULM, and ULM is a Von Hippel-Lindau E3 ubiquitin ligase (VHL) binding moiety (VLM) or a cereblon E3 ubiquitin ligase binding moiety (CLM).

For example, the structure of the bifunctional compound can be depicted as:

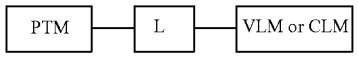

wherein: PTM is a protein/polypeptide targeting moiety; "L" is a linker (e.g. a bond or a chemical linker group) coupling the PTM and at least one of VLM, CLM, or a combination thereof; VLM is Von Hippel-Lindau E3 ubiquitin ligase binding moiety that binds to VHL E3 ligase; and CLM is cereblon E3 ubiquitin ligase binding moiety that binds to cereblon.

In certain embodiments, the compounds as described herein comprise multiple independently selected ULMs, multiple PTMs, multiple chemical linkers or a combination thereof.

In additional embodiments, VLM can be hydroxyproline or a derivative thereof. Furthermore, other contemplated VLMs are included in U.S. Patent Application Publication No. 2014/0302523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising a PTM and a VLM, or a PTM and a CLM, preferably linked through a linker moiety, as otherwise described herein, wherein the VLM/CLM is coupled to the PTM through a linker to target protein that binds to PTM for degradation. Similarly, the PTM can be coupled to VLM or CLM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
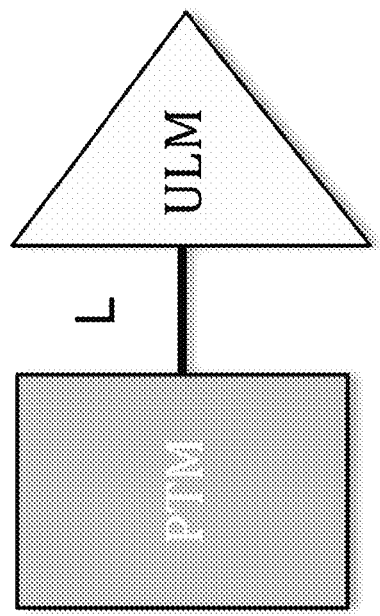
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
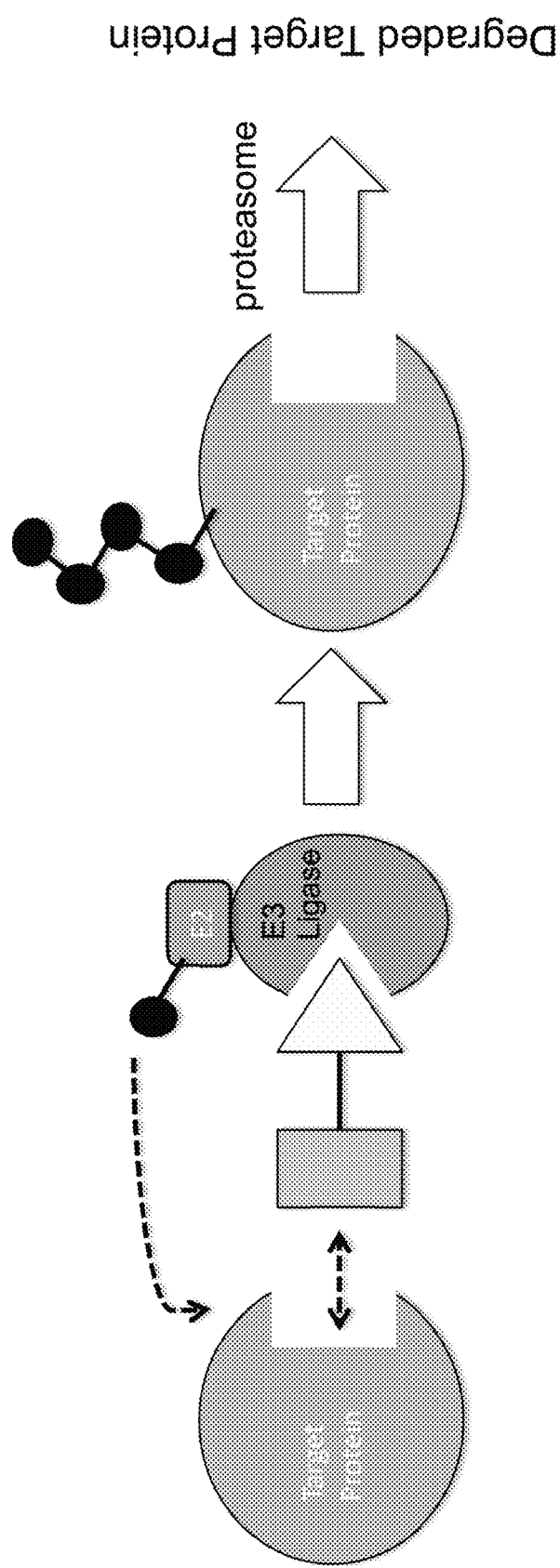

Presently described are compositions and methods that relate to the surprising and unexpected discovery that an E3 ubiquitin ligase protein (e.g., a Von Hippel-Lindau E3 ubiquitin ligase (VHL) or a cereblon E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquitin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as cereblon or VHL. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or bifunctional degradation molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, cereblon an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is a cereblon E3 ubiquitin ligase binding moiety (a "CLM") and/or a Von Hippel-Lindae E3 ubiquitin ligase (VHL) binding moiety (VLM). In an exemplary embodiment, the ULM is coupled to a target protein binding moiety (PTM) via a chemical linker (L) according to the structure:

(A) PTM-L-ULM wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, VLM, and CLM are used in their inclusive sense unless the context indicates otherwise. For example, the term ULM is inclusive of all ULMs, including those that bind cereblon (i.e., CLM) and VHL (i.e., VLM). Further, the term VLM is inclusive of all possible VHL binding moieties and the term CLM is inclusive of all cereblon binding moieties.

In another aspect, the present disclosure provides bifunctional or multifunctional compounds useful for regulating protein activity by inducing the degradation of a target protein. In certain embodiments, the compound comprises a VLM or a CLM coupled, e.g., linked covalently, directly or indirectly, to a moiety that binds a target protein (i.e., a protein targeting moiety or a "PTM"). In certain embodiments, the VLM/CLM and PTM are joined or coupled via a chemical linker (L). The VLM binds VHL, and CLM binds the cereblon E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

(B) PTM-CLM (C) PTM-VLM.

In certain embodiments, the bifunctional compound further comprises a chemical linker ("L"). For example, the bifunctional compound can be depicted as:

(D) PTM-L-CLM (E) PTM-L-VLM, wherein the PTM is a protein/polypeptide targeting moiety, the L is a chemical linker, the CLM is a cereblon E3 ubiquitin ligase binding moiety, and the VLM is a VHL binding moiety.

In certain embodiments, the ULM (e.g., a CLM or a VLM) shows activity or binds to the E3 ubiquitin ligase (e.g., cereblon E3 ubiquitin ligase or VHL) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL and/or cereblon) or a combination thereof. In any of the aspects or embodiments described herein, the PTMs and ULMs (e.g., VLM and/or CLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as a VLM, a CLM, a VLM', and/or a CLM'.

In additional embodiments, the description provides the compounds as described herein including their enantiomers, diastereomers, solvates and polymorphs, including pharmaceutically acceptable salt forms thereof, e.g., acid and base salt forms.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azain- dolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

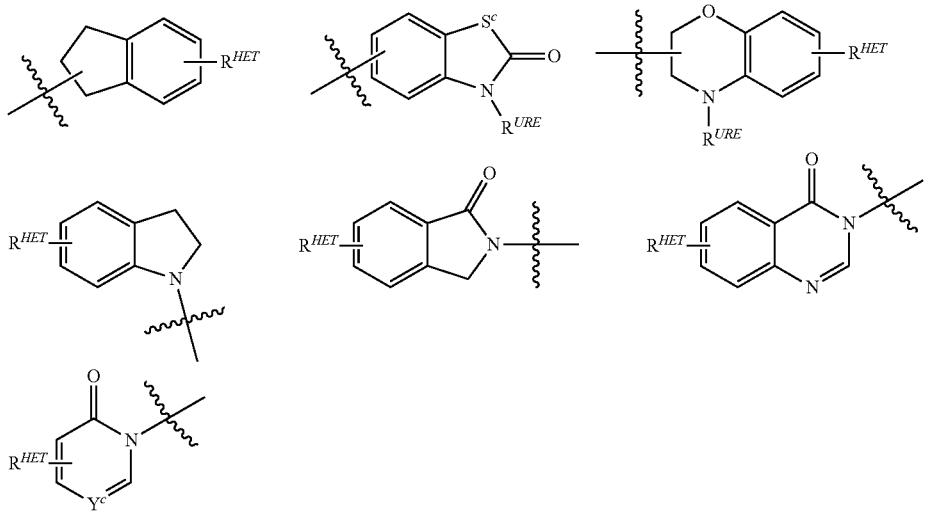

wherein:
S$^c$ is CHR$^{SS}$, NR$^{URE}$, or O;
R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O) (C$_1$-C$_6$ alkyl) (preferably substituted with one or two hydroxyl groups or up to three halo groups);
R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
Y$^c$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocylooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defnied herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

Exemplary CLMs

Neo-Imide Compounds

In one aspect the description provides compounds useful for binding and/or inhibiting cereblon. In certain embodiments, the compound is selected from the group consisting of chemical structures:

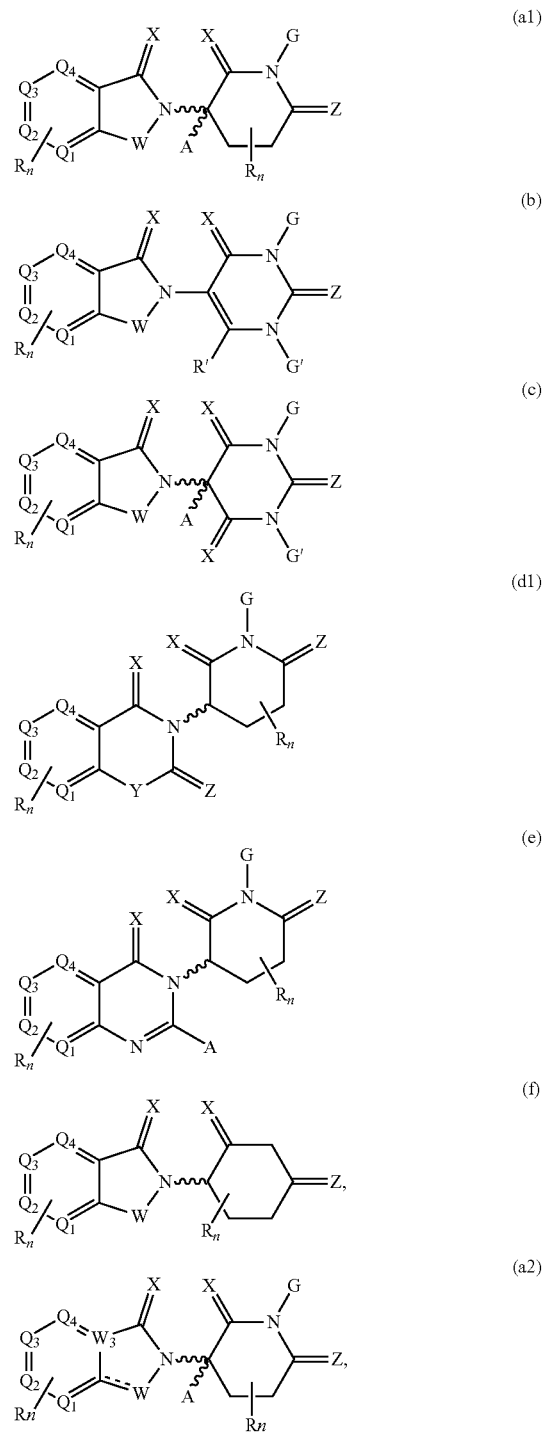

-continued

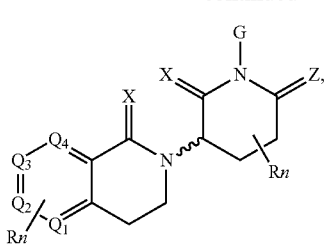
(d2)

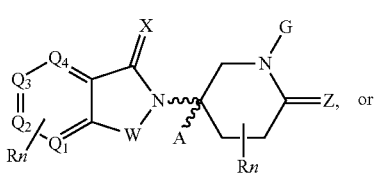
(a3)

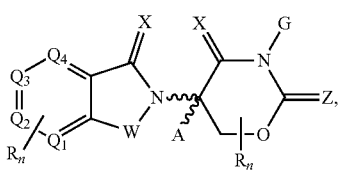
(a4)

wherein:
W of Formulas (a) through (f) is independently selected from the group $CH_2$, O, CHR, C=O, $SO_2$, NH, N, optionally substituted cyclopropyl group, optionally substituted cyclobutyl group, and N-alkyl;
$W_3$ is selected from C or N;
X of Formulas (a) through (f) is independently selected from the group absent, O, S and $CH_2$;
Y of Formulas (a) through (f) is independently selected from the group $CH_2$, —C=CR', NH, N-alkyl, N-aryl, N-heteroaryl, N-cycloalkyl, N-heterocyclyl, O, and S;
Z of Formulas (a) through (f) is independently selected from the group absent, O, and S or $CH_2$ except that both X and Z cannot be $CH_2$ or absent;
G and G' of Formulas (a) through (f) are independently selected from the group H, optionally substituted linear or branched alkyl, OH, R'OCOOR, R'OCONRR", $CH_2$-heterocyclyl optionally substituted with R', and benzyl optionally substituted with R';
Q1-Q4 of Formulas (a) through (f) represent a carbon C or N substituted with a group independently selected from H, R, N or N-oxide;
A of Formulas (a) through (f) is independently selected from the group H, optionally substituted linear or branched alkyl, cycloalkyl, Cl and F;
n of Formulas (a) through (f) represent an integer from 1 to 10 (e.g., 1-4, 1, 2, 3, 4, 5, 6, 7, 8, 9, or 10);
R of Formulas (a) through (f) comprises, but is not limited to: H, —C(=O)R' (e.g., a carboxy group), —CONR'R" (e.g., an amide group), —OR' (e.g., OH or $OCH_3$), —NR'R" (e.g., an amine group), —SR', —$SO_2$R', —$SO_2$NR'R", —CR'R"—, —CR'NR'R"—, (—CR'O)$_n$R", optionally substituted heterocyclyl, optionally substituted aryl, (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl, optionally substituted alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

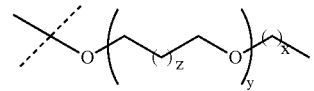

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

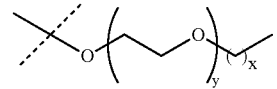

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substitutued heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O) (C=N—R')R", —$SF_5$ and —$OCF_3$;
each of x, y, and z are independently 0, 1, 2, 3, 4, 5, or 6;
R' and R" of Formulas (a) through (f) are independently selected from H, optionally substituted linear or branched alkyl (e.g, methyl or ethyl), optionally substituted cycloalkyl, optionally substituted aryl, optionally substituted heteroaryl, optionally substituted heterocyclic, —C(=O)R, optionally substituted heterocyclyl;
n' of Formulas (a) through (f) is an integer from 1-10 (e.g. 1-4, 1, 2, 3, 4, 5, 6, 7, 8, 9, or 10);
represents a single bond or a double bond; and
of Formulas (a) through (f) represents a bond that may be stereospecific ((R) or (S)) or non-stereospecific.

Exemplary CLMs

In any of the compounds described herein, the CLM comprises a chemical structure selected from the group:

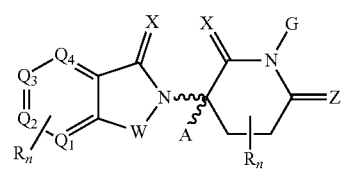
(a1)

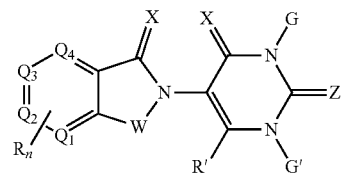
(b)

-continued

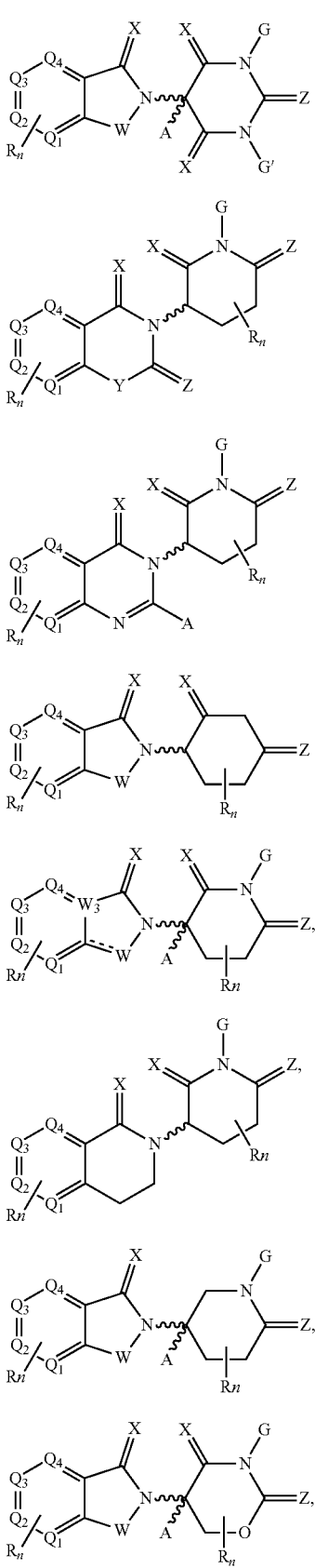

wherein:
W of Formulas (a) through (f) is independently selected from the group $CH_2$, O, CHR, C=O, $SO_2$, NH, N, optionally substituted cyclopropyl group, optionally substituted cyclobutyl group, and N-alkyl;

$W_3$ is selected from C or N;

X of Formulas (a) through (f) is independently selected from the group O, S and $CH_2$;

Y of Formulas (a) through (f) is independently selected from the group $CH_2$, —C=CR', NH, N-alkyl, N-aryl, N-hetaryl, N-cycloalkyl, N-heterocyclyl, O, and S;

Z of Formulas (a) through (f) is independently selected from the group O, and S or CH2 except that both X and Z cannot be $CH_2$ or absent;

G and G' of Formulas (a) through (f) are independently selected from the group H, optionally substituted linear or branched alkyl, OH, R'OCOOR, R'OCONRR", $CH_2$-heterocyclyl optionally substituted with R', and benzyl optionally substituted with R';

Q1-Q4 of Formulas (a) through (f) represent a carbon C or N substituted with a group independently selected from H, R, N or N-oxide;

A of Formulas (a) through (f) is independently selected from the group H, optionally substituted linear or branched alkyl, cycloalkyl, Cl and F;

n of Formulas (a) through (f) represent an integer from 1 to 10 (e.g., 1-4, 1, 2, 3, 4, 5, 6, 7, 8, 9, or 10);

R of Formulas (a) through (f) comprises, but is not limited to: H, —C(=O)R' (e.g., a carboxy group), —CONR'R" (e.g., an amide group), —OR' (e.g., OH), —NR'R" (e.g. an amine group), —SR', —SO2R', —SO2NR'R", —CR'R"—, —CR'NR'R"—, (—CR'O)$_n$R", optionally substituted aryl (e.g., an optionally substituted C5-C7 aryl), optionally substituted alkyl-aryl (e.g., an alkyl-aryl comprising at least one of an optionally substituted $C_1$-$C_6$ alkyl, an optionally substituted C5-C7 aryl, or combinations thereof), optionally substituted hetaryl, -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

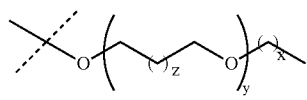

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

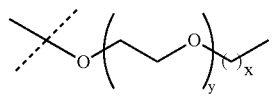

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R') R", —SF5 and —OCF3;

each of x, y, and z are independently 0, 1, 2, 3, 4, 5, or 6;

R' and R" of Formulas (a) through (f) are independently selected from a bond, H, optionally substituted linear or branched alkyl, optionally substituted cycloalkyl, optionally substituted aryl, optionally substituted heteroaryl, optionally substituted heterocyclic, —C(=O)R, optionally substituted heterocyclyl;

n' of Formulas (a) through (f) is an integer from 1-10 (e.g., 1-4, 1, 2, 3, 4, 5, 6, 7, 8, 9, or 10); and ∿ of Formulas (a) through (f) represents a bond that may be stereospecific ((R) or (S)) or non-stereospecific.

In certain embodiments described herein, the CLM or ULM comprises a chemical structure selected from the group:

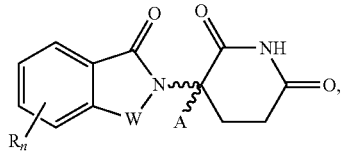

Formula (g)

wherein:
W of Formula (g) is independently selected from the group $CH_2$, O, C=O, NH, and N-alkyl;

A of Formula (g) is selected from a H, methyl, or optionally substituted linear or branched alkyl;

n is an integer from 1 to 4;

R of Formula (g) is independently selected from a H, O, OH, N, NH, $NH_2$, methyl, optionally substituted linear or branched alkyl (e.g., optionally substituted linear or branched C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy), wherein one R or W is optionally modified to be covalently joined to a PTM, a chemical linker group (L), a ULM, CLM (or CLM'), or combination thereof; and ∿ of Formula (g) represents a bond that may be stereospecific ((R) or (S)) or non-stereo specific.

In any aspect or embodiment described herein, R is selected from: O, OH, N, NH, $NH_2$, $C_1$-$C_6$ alkyl, $C_1$-$C_6$ alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy).

In any aspect or embodiment described herein, at least one R (e.g. an R group selected from the following O, OH, N, NH, $NH_2$, $C_1$-$C_6$ alkyl, $C_1$-$C_6$ alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) or W is modified to be covalently joined to a PTM, a chemical linker group (L), a ULM, a CLM' (e.g., CLM' is an additional CLM that has the same or different structure as a first CLM), or a combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

In any of the aspects or embodiments described herein, $R_n$ comprises from 1 to 4 independently selected functional groups or atoms, for example, O, OH, N, $C_1$-$C_6$ alkyl, $C_1$-$C_6$ alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, on the aryl or heteroaryl of the CLM, and optionally, one of which is modified to be covalently joined to a PTM, a chemical linker group (L), a ULM, CLM (or CLM') or combination thereof.

More specifically, non-limiting examples of CLMs include those shown below as well as those "hybrid" molecules that arise from the combination of 1 or more of the different features shown in the molecules below.

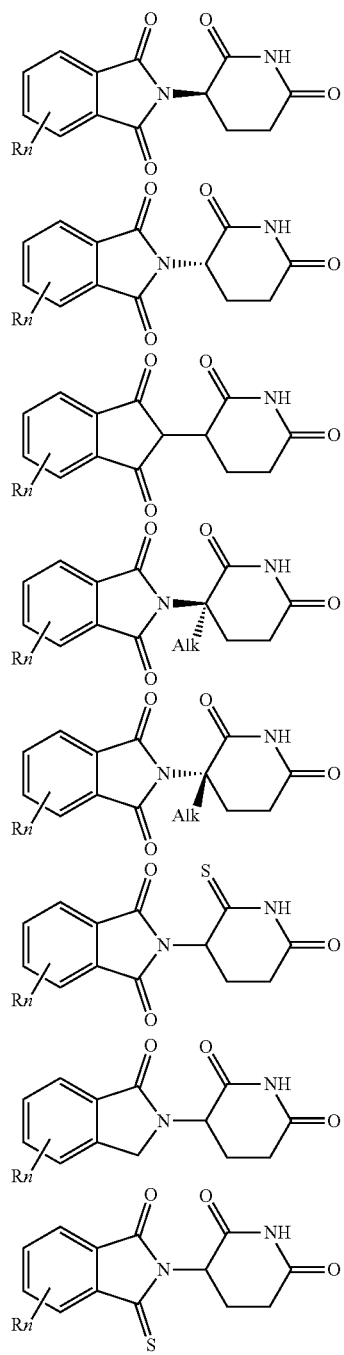

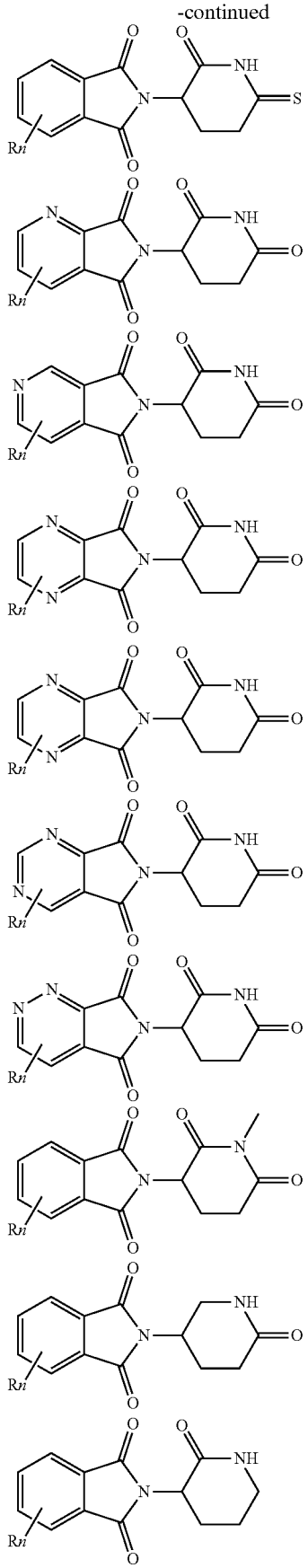
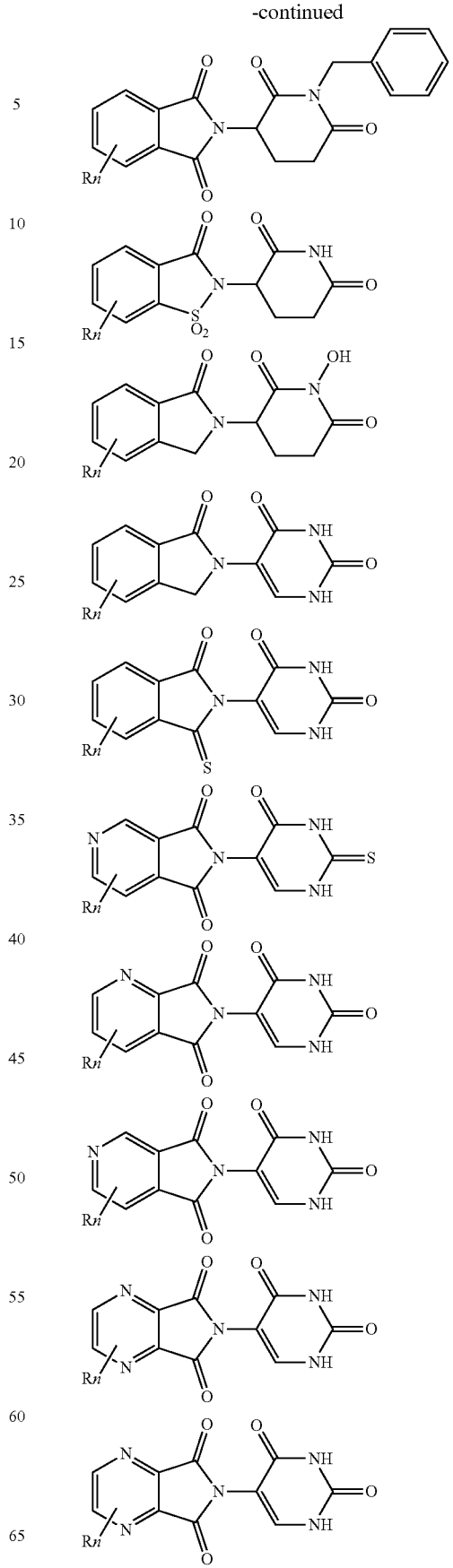

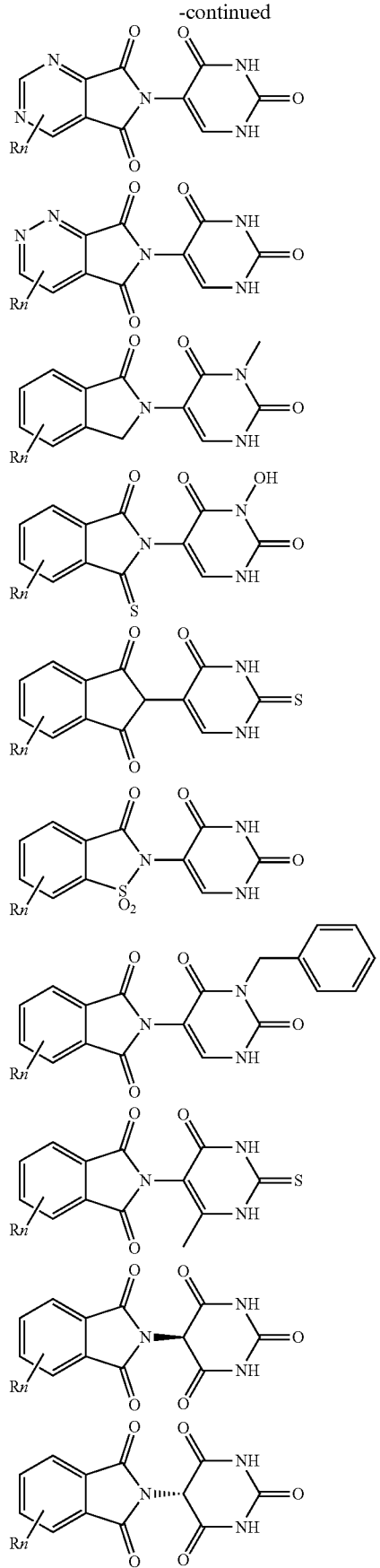
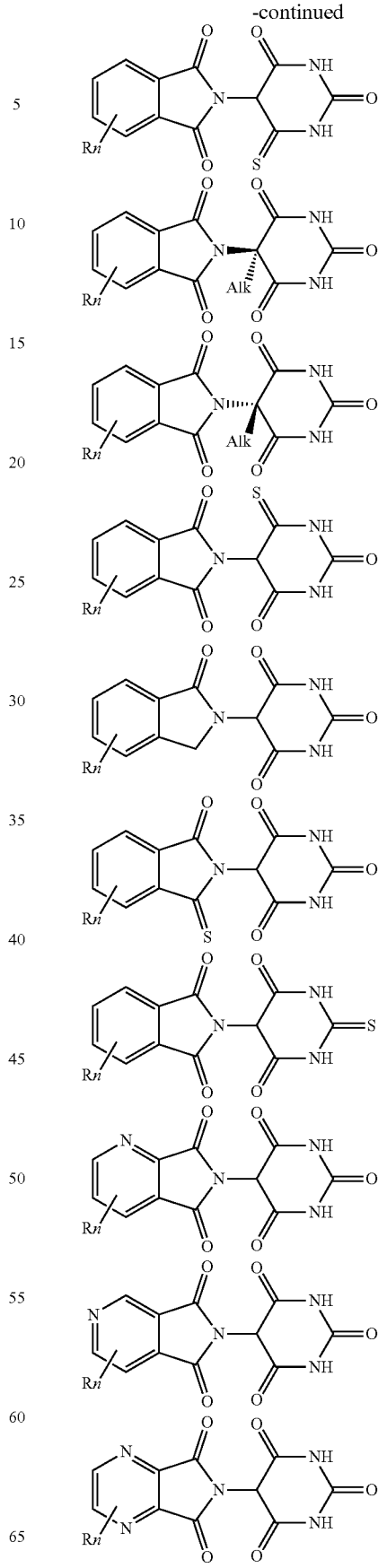

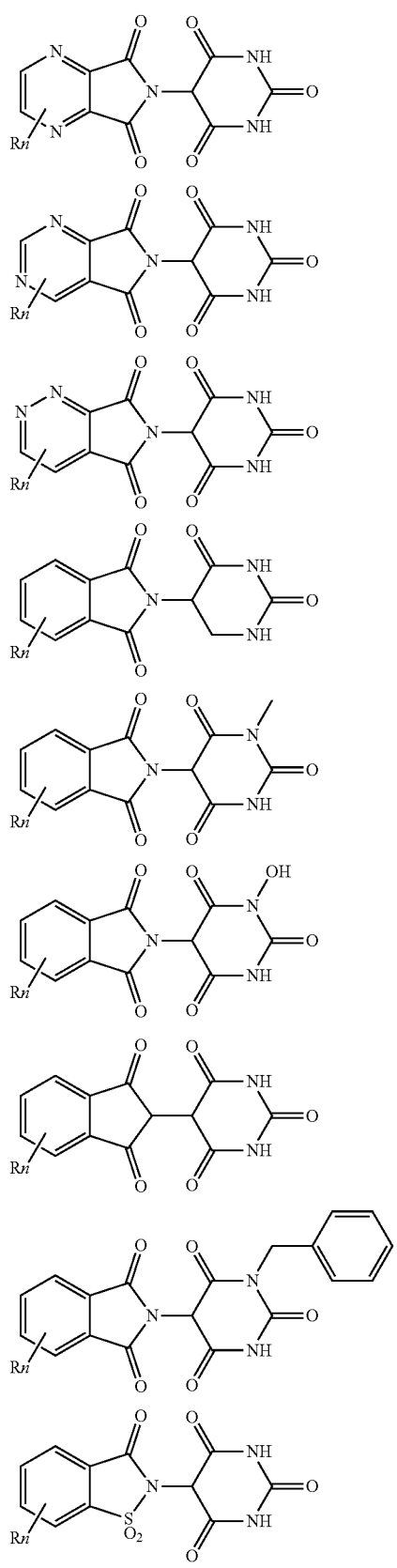
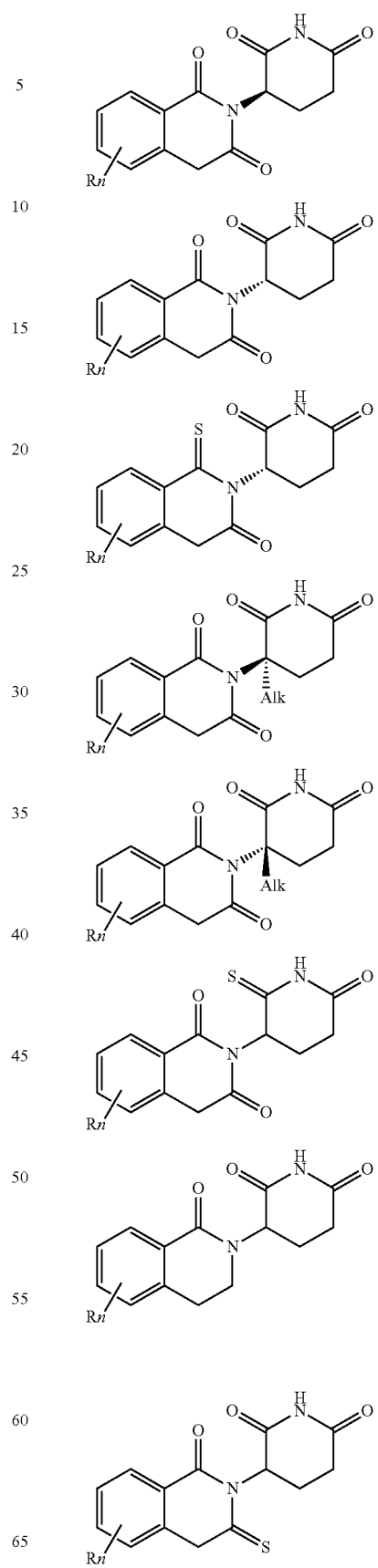

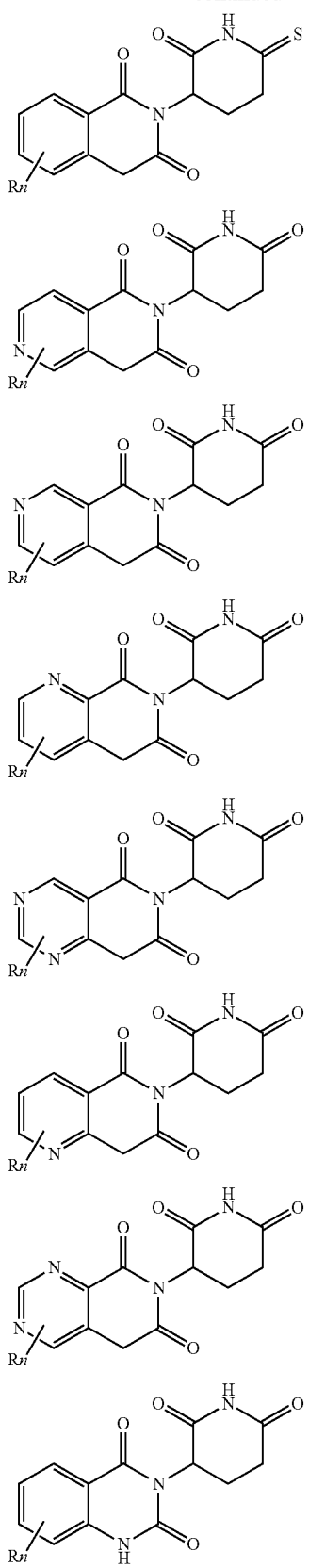
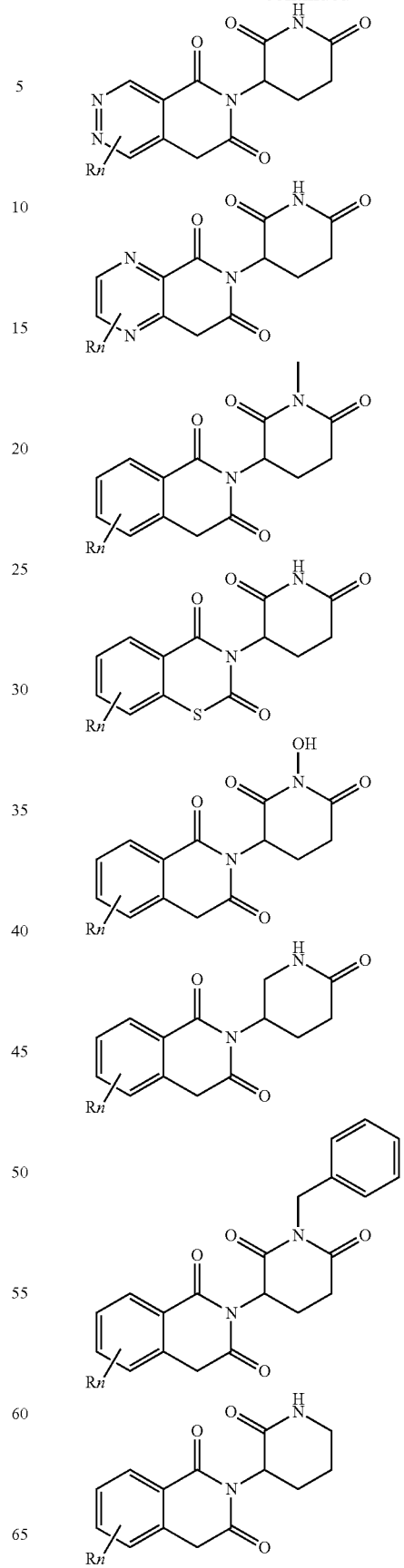

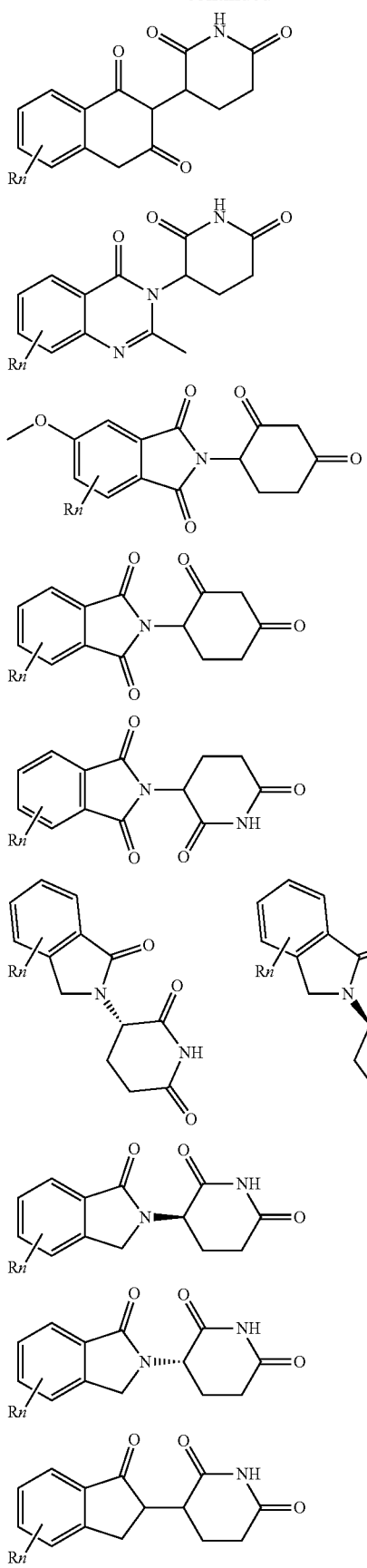
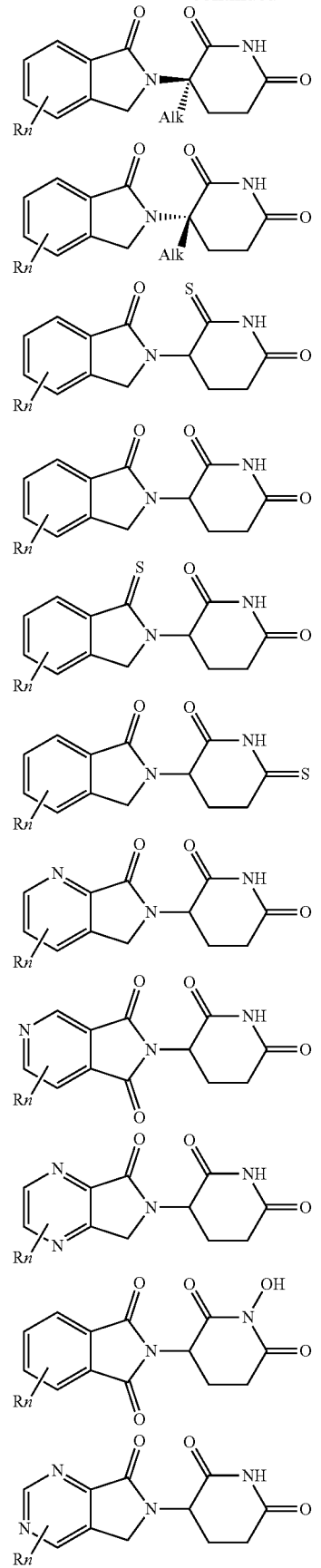

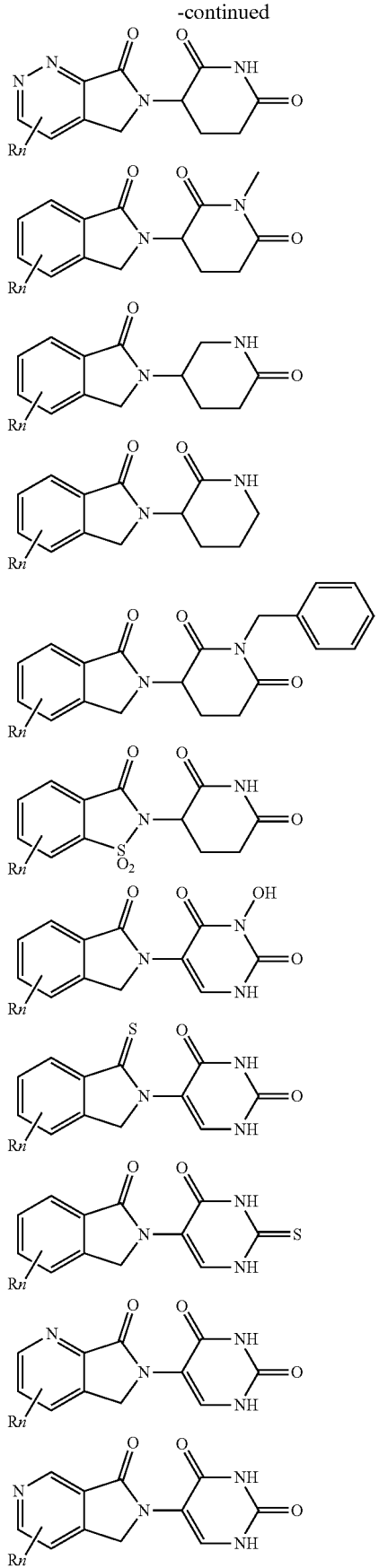
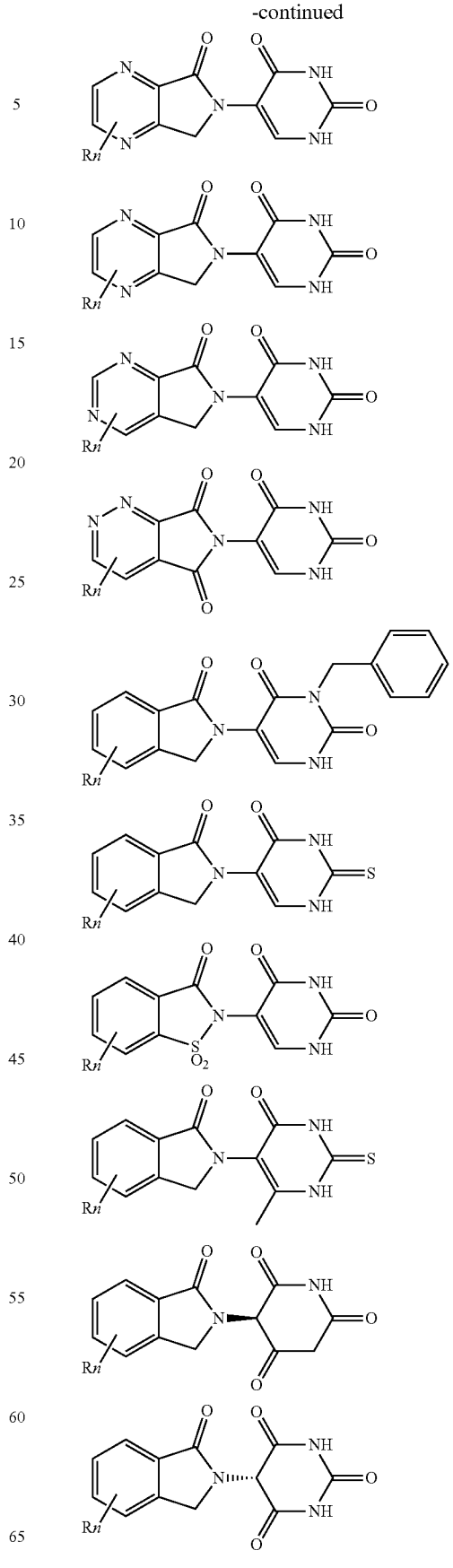

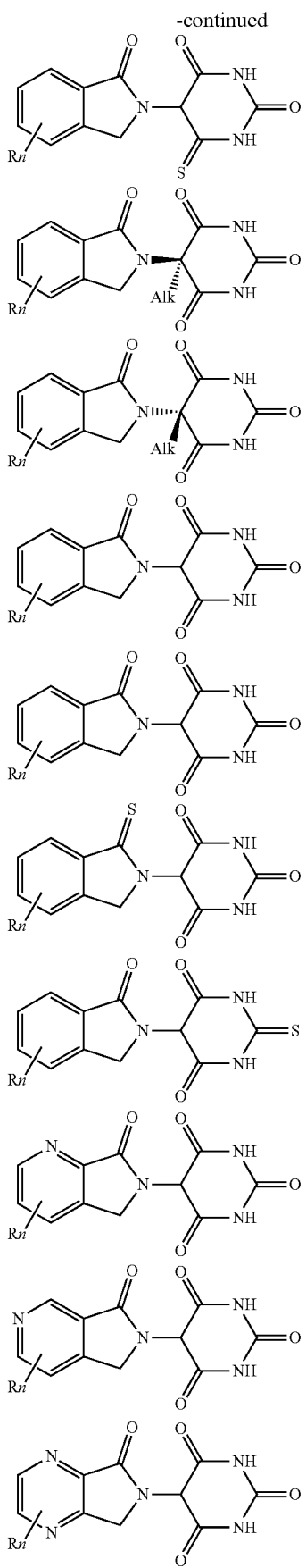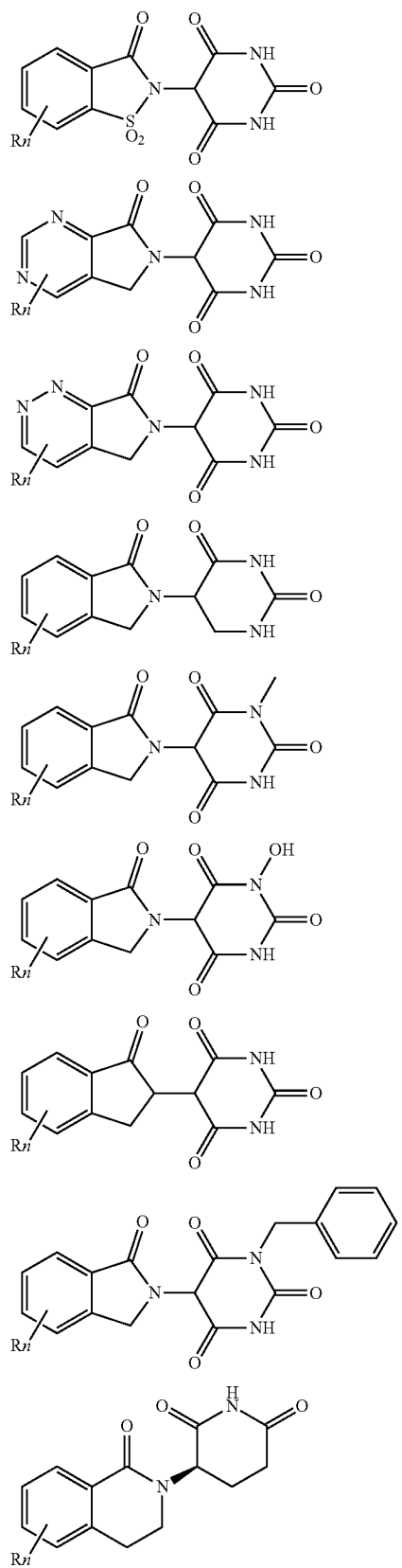

-continued
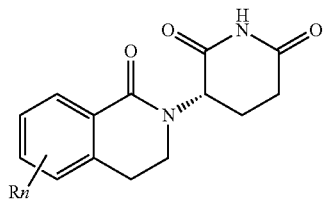
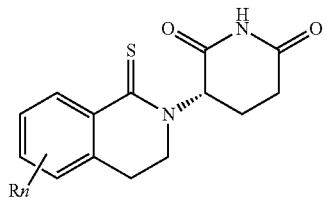
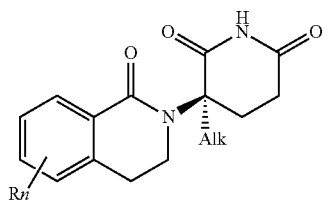
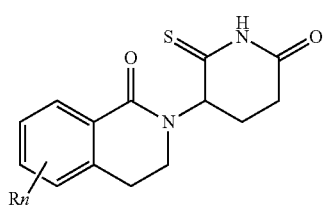
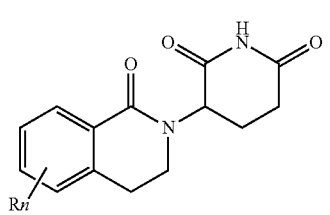
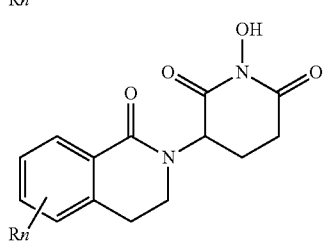
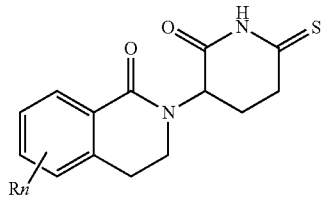
-continued
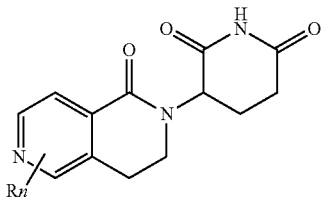
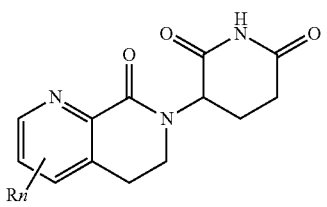
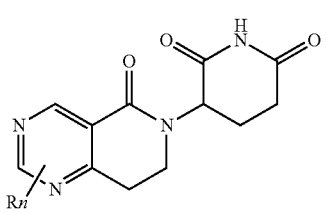
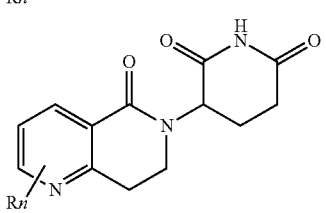
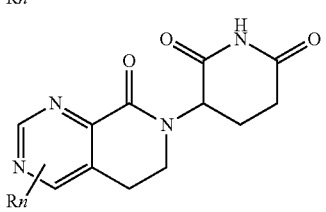
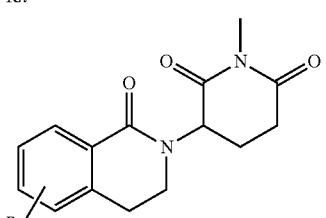
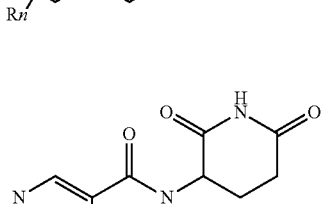

-continued
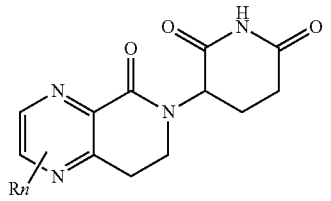
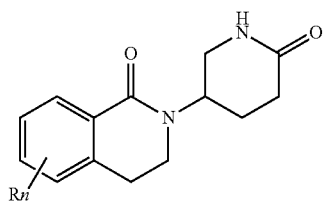
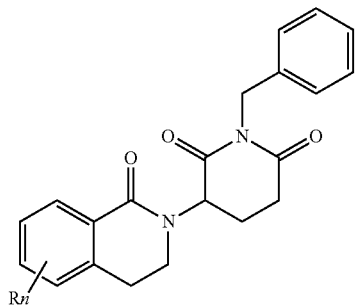
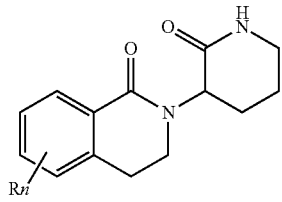
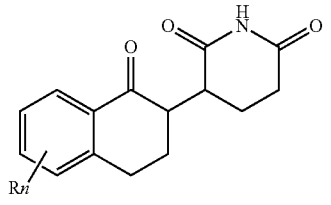
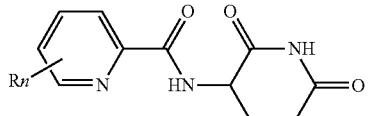
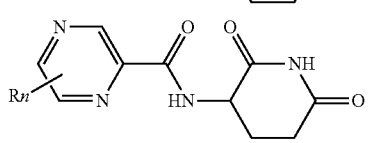
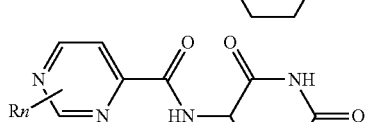
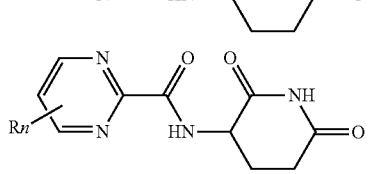
-continued
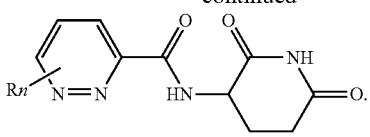
In any of the compounds described herein, the CLM comprises a chemical structure selected from the group:
(h)
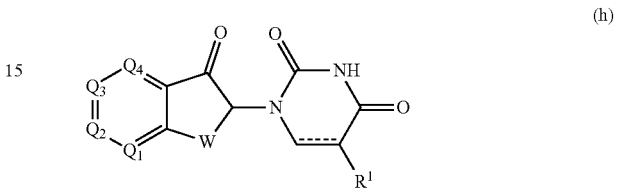
(i)
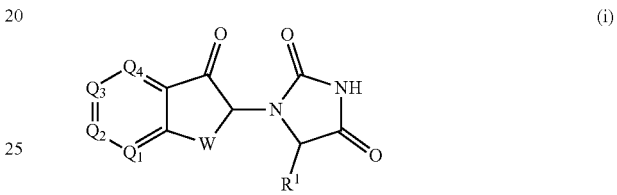
(j)
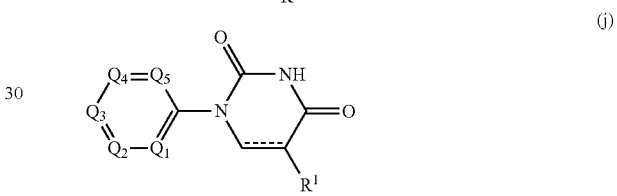
(k)
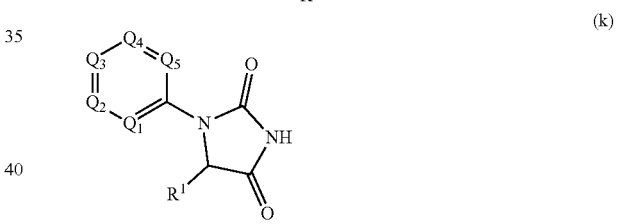
(l)
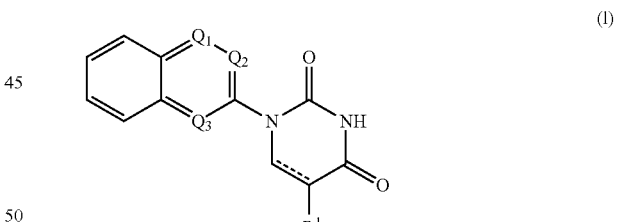
(m)
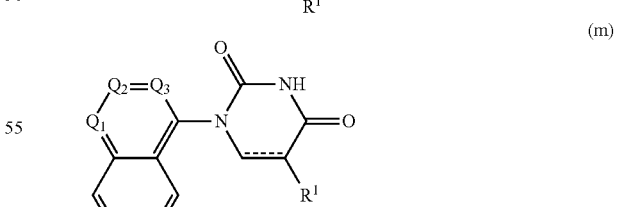
(n)
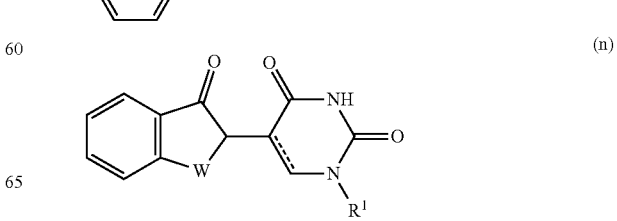

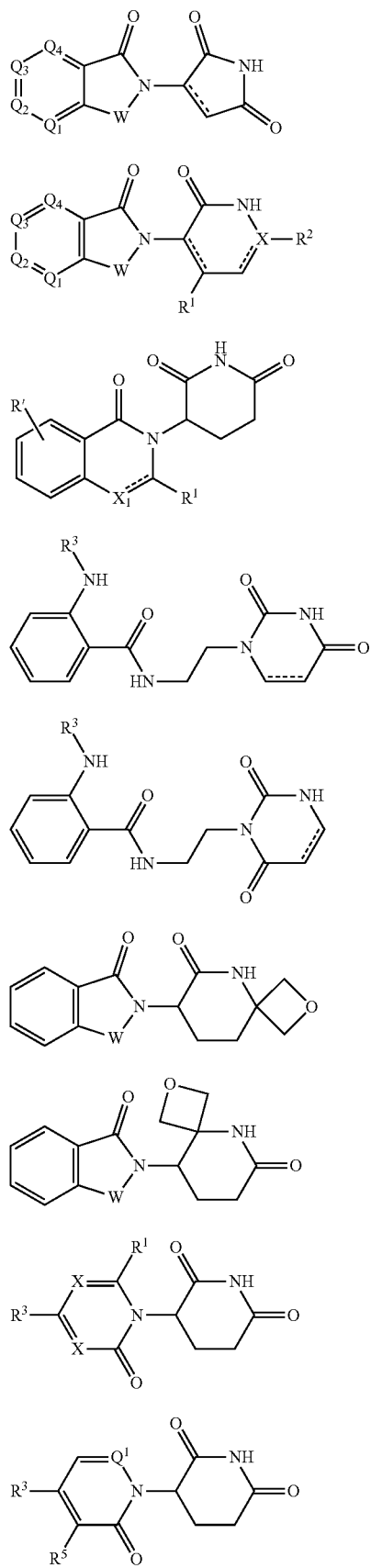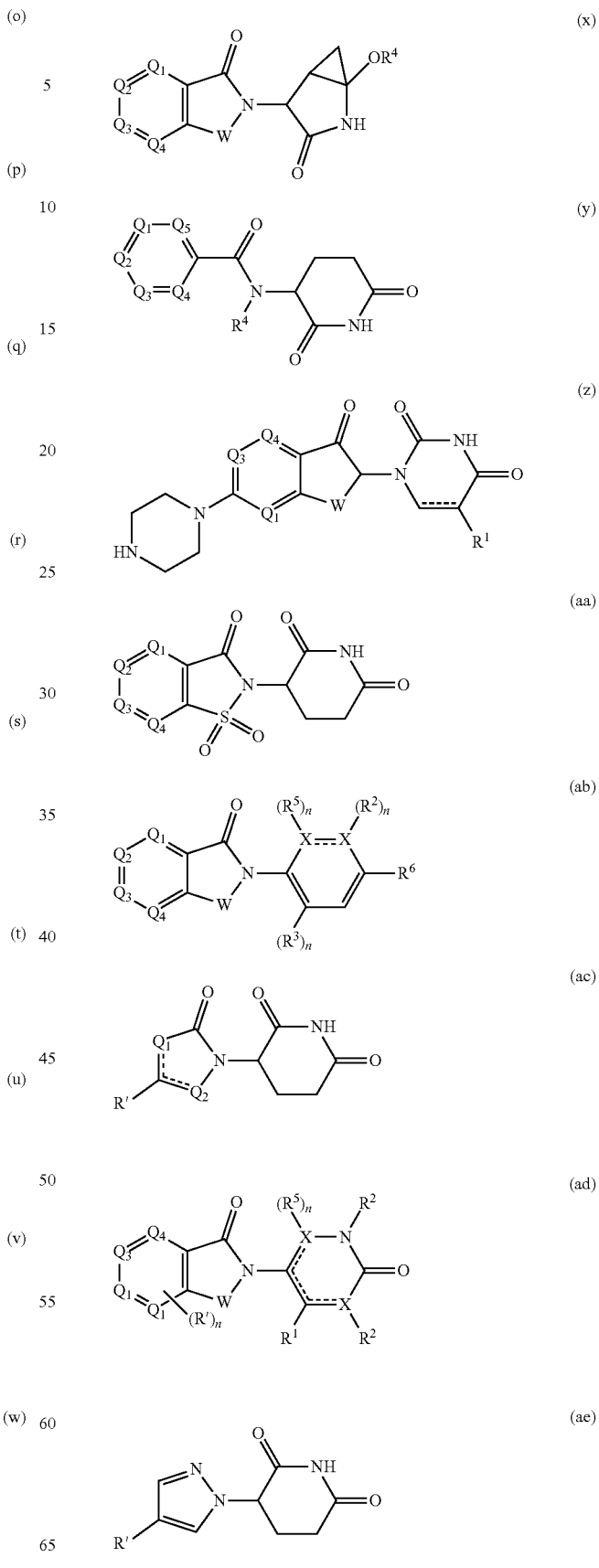

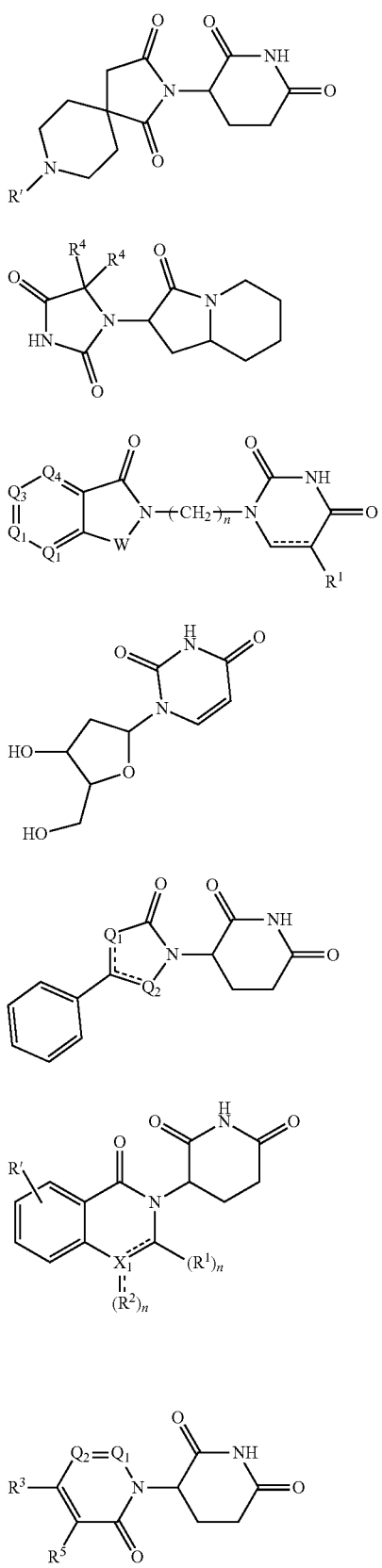

wherein:
- W is independently selected from $CH_2$, O, CHR, C=O, $SO_2$, NH, N, optionally substituted cyclopropyl group, optionally substituted cyclobutyl group, and N-alkyl (e.g., $CH_2$, CHR, C=O, $SO_2$, NH, and N-alkyl);
- $Q_1$, $Q_2$, $Q_3$, $Q_4$, $Q_5$ are each independently represent a carbon C or N substituted with a group independently selected from R', N or N-oxide;
- $R^1$ is selected from absent, H, OH, CN, C1-C3 alkyl, C=O;
- $R^2$ is selected from the group absent, H, OH, CN, C1-C3 alkyl, $CHF_2$, $CF_3$, CHO, C(=O)$NH_2$;
- $R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl), 3-5 membered cycloalkyl or cycloheteroalkyl;
- $R^4$ is selected from H, alkyl, substituted alkyl;
- $R^5$ and $R^6$ are each independently H, halogen, C(=O)R', CN, OH, $CF_3$;
- X is C, CH, C=O, or N;
- $X_1$ is C=O, N, CH, or $CH_2$;
- R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(=O)$OR^2$, C(=O)$R^2$, optionally substituted phenyl;
- n is 0-4;
- ⇌ is a single or double bond; and
- the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$.

In any of the embodiments described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

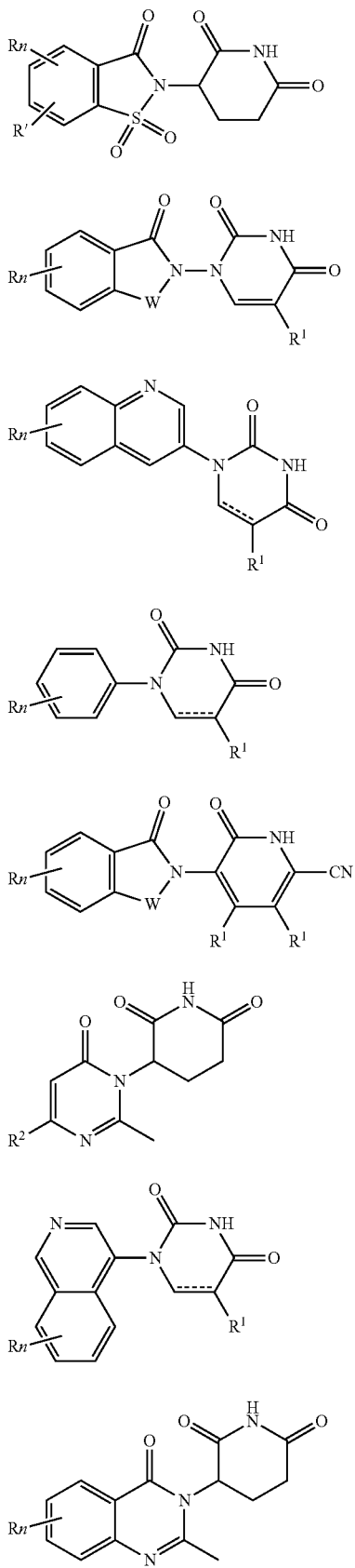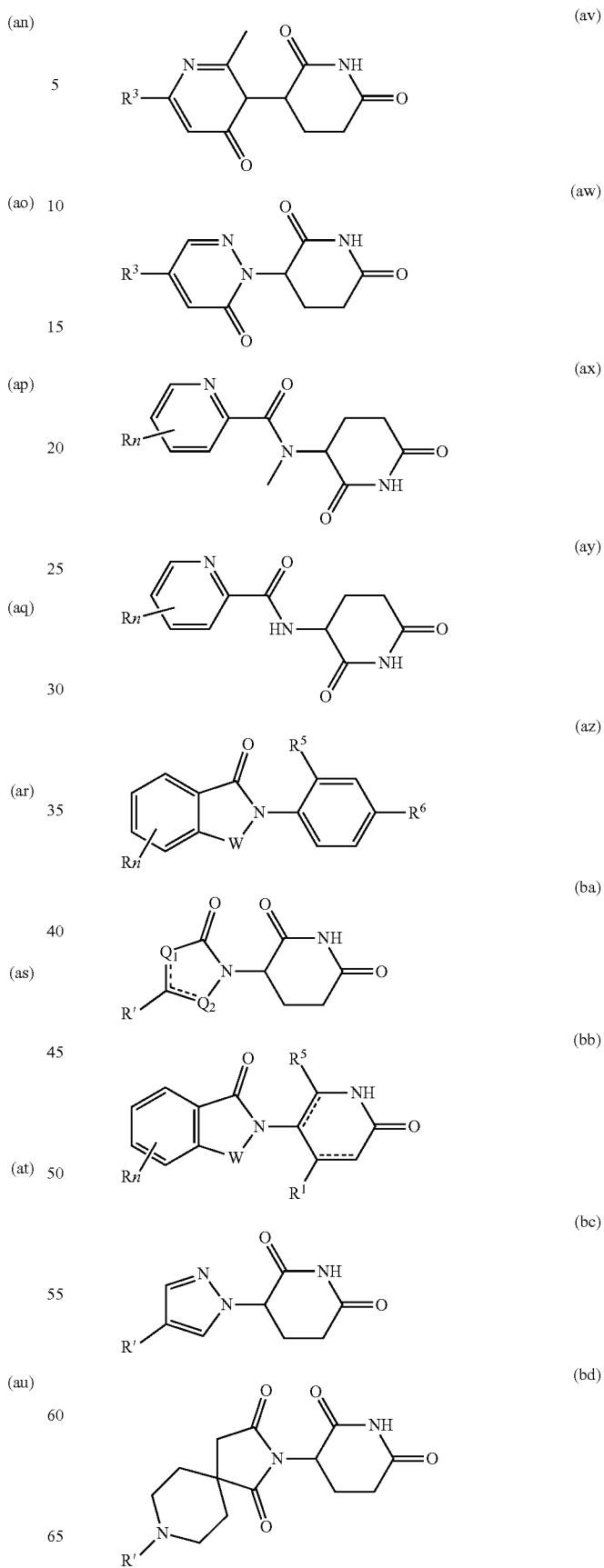

-continued (be) 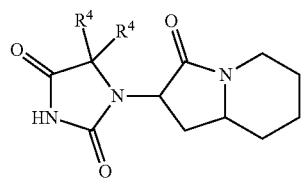

(bf) 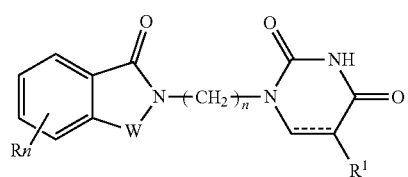

(bg) 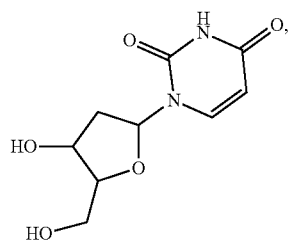

wherein:
W is independently selected from the group CH$_2$, CHR, C=O, SO$_2$, NH, and N-alkyl;
R$^1$ is selected from the group absent, H, CH, CN, C1-C3 alkyl;
R$^2$ is H or a C1-C3 alkyl;
R$^3$ is selected from H, alkyl, substituted alkyl, alkoxy, substituted alkoxy;
R$^4$ is methyl or ethyl;
R$^5$ is H or halo;
R$^6$ is H or halo;
R of the CLM is H;
R' is H or an attachment point for a PTM, a PTM', a chemical linker group (L), a ULM, a CLM, a CLM',
Q$_1$ and Q$_2$ are each independently C or N substituted with a group independently selected from H or C1-C3 alkyl;
══ is a single or double bond; and
Rn comprises a functional group or an atom.

In any of the embodiments described herein, the W, R$^1$, R$^2$, Q$_1$, Q$_2$, Q$_3$, Q$_4$, and Rn can independently be covalently coupled to a linker and/or a linker to which is attached one or more PTM, ULM, ULM', CLM or CLM' groups.

In any of the embodiments described herein, the R$^1$, R$^2$, Q$_1$, Q$_2$, Q$_3$, Q$_4$, and Rn can independently be covalently coupled to a linker and/or a linker to which is attached one or more PTM, ULM, ULM', CLM or CLM' groups.

In any of the embodiments described herein, the Q$_1$, Q$_2$, Q$_3$, Q$_4$, and Rn can independently be covalently coupled to a linker and/or a linker to which is attached one or more PTM, ULM, ULM', CLM or CLM' groups.

In any aspect or embodiment described herein, R$_n$ is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

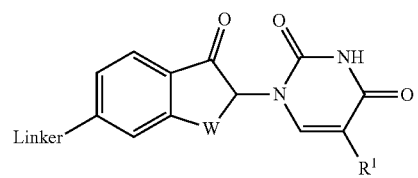
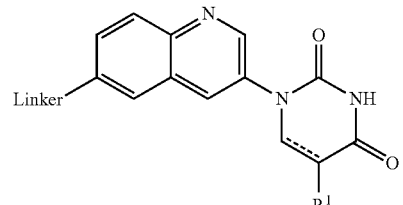
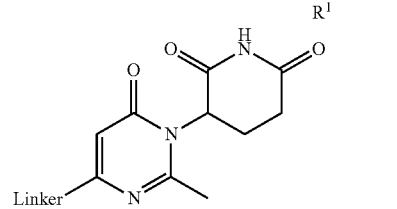
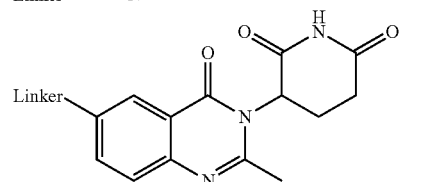
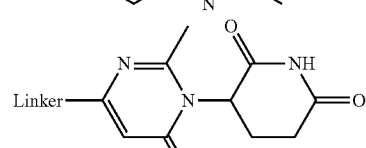
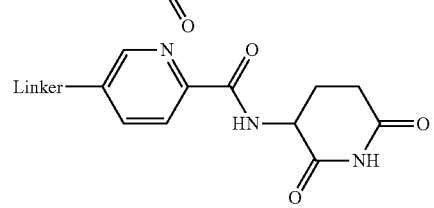
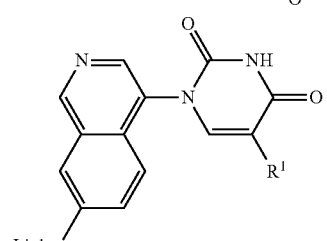
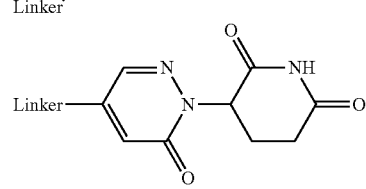
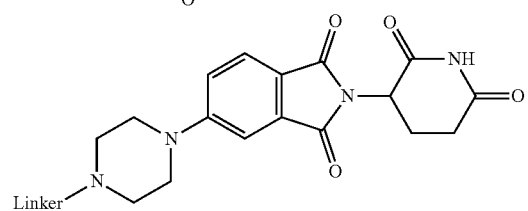

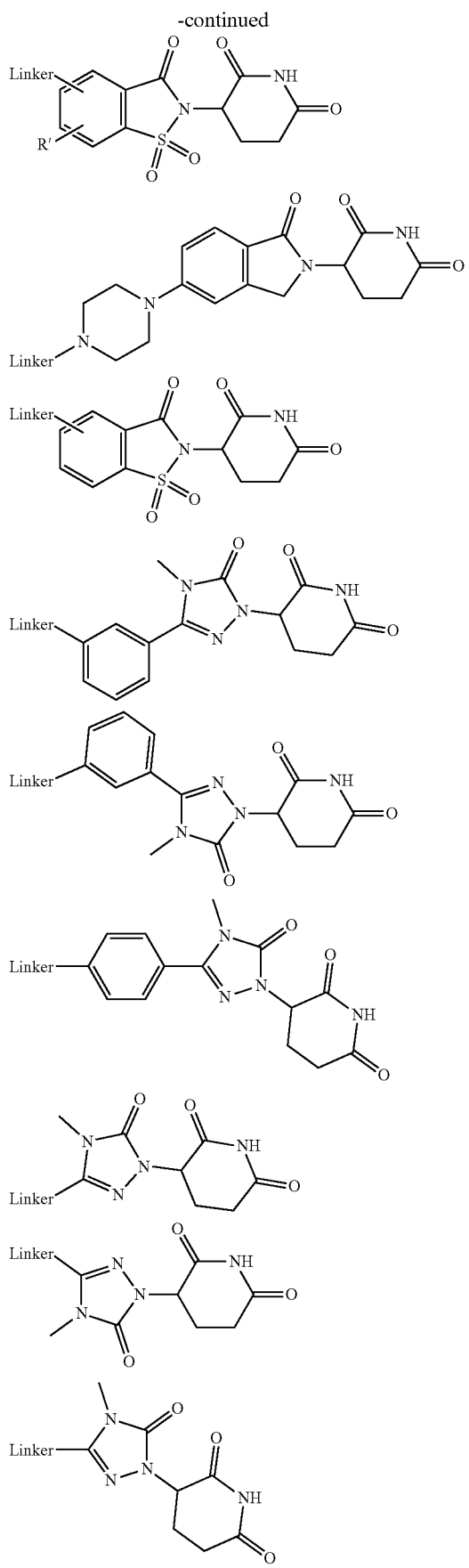
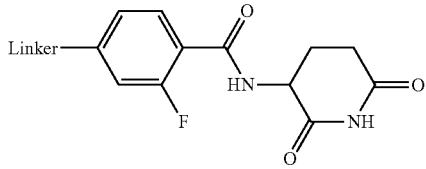
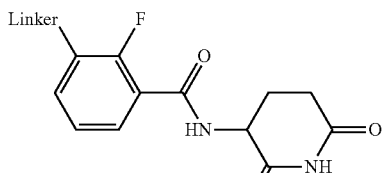
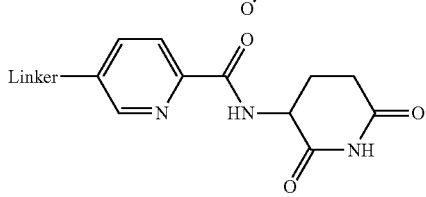
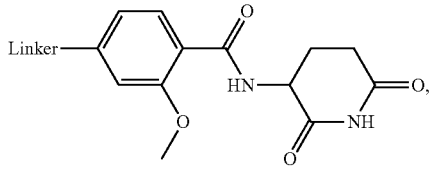
wherein R' is a halogen and $R^1$ is as described in any aspect or embodiment described herein.
In certain cases, "CLM" can be imides that bind to cereblon E3 ligase. These imides and linker attachment point can be but not limited to the following structures:
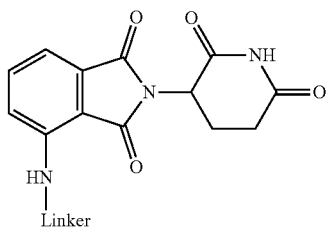
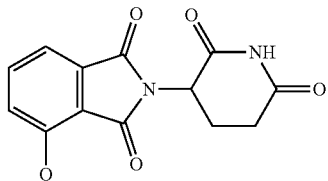
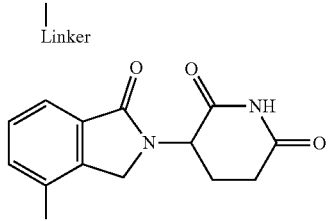

53
-continued

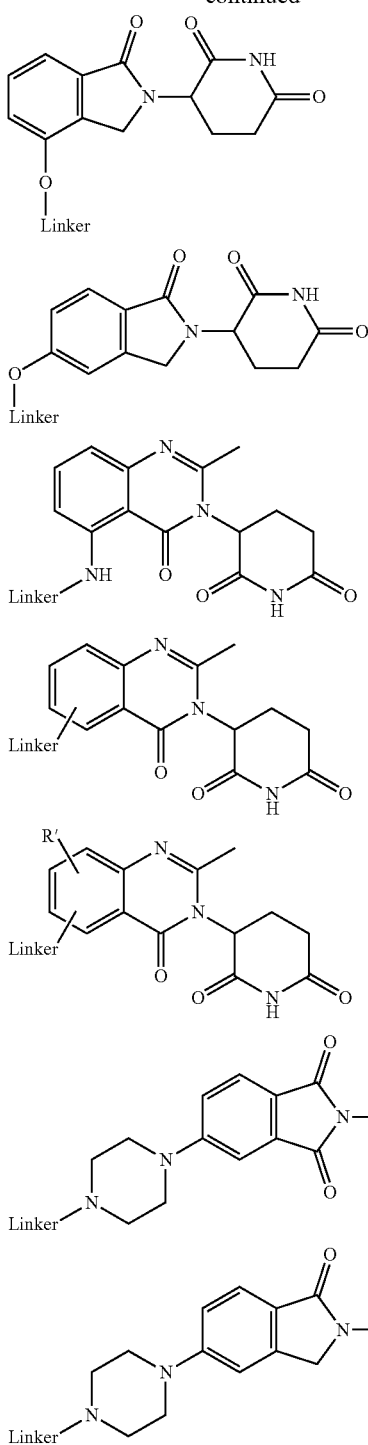

Exemplary VLMs

In certain embodiments of the compounds as described herein, ULM is VLM and comprises a chemical structure selected from the group ULM-a:

ULM-a $$\left[ \begin{array}{c} W^3 - X^1 - N \diagup R^P \\ \phantom{W^3 - X^1 - } X^2 \\ \phantom{W^3 - X^1 - X^2 - } W^4 \end{array} \right] \text{----},$$

wherein:
a dashed line indicates the attachment of at least one PTM, another ULM or VLM or CLM (i.e., ULM' or VLM' or CLM'), or a chemical linker moiety coupling at least one PTM, a ULM' or a VLM' or a CLM' to the other end of the linker;

$X^1$, $X^2$ of Formula ULM-a are each independently selected from the group of a bond, O, $NR^{Y3}$, $CR^{Y3}R^{Y4}$, C=O, C=S, SO, and $SO_2$;

$R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);

$R^P$ of Formula ULM-a is 0, 1, 2, or 3 groups, each independently selected from the group H, halo, —OH, $C_{1-3}$ alkyl, C=O;

$W^3$ of Formula ULM-a is selected from the group of an optionally substituted T, an optionally substituted -T-N$(R^{1a}R^{1b})X^3$, optionally substituted -T-N$(R^{1a}R^{1b})$ optionally substituted -T-Aryl, an optionally substituted -T-Heteroaryl, an optionally substituted T-biheteroaryl, an optionally substituted -T-heterocyclyl, an optionally substituted -T-bieterocyclyl, an optionally substituted —NR$^1$-T-Aryl, an optionally substituted —NR$^1$-T-Heteroaryl or an optionally substituted —NR$^1$-T-heterocyclyl;

$X^3$ of Formula ULM-a is C=O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, $N(R^{Y3}R^{Y4})$C=O, $N(R^{Y3}R^{Y4})$C=S, $N(R^{Y3}R^{Y4})$SO, and $N(R^{Y3}R^{Y4})SO_2$;

T of Formula ULM-a is selected from the group of an optionally substituted alkyl, —$(CH_2)_n$— group, —$(CH_2)_n$—O—$C_1$-$C_6$ alkyl which is optionally substituted, linear, branched, or —$(CH_2)_n$—O-heterocyclyl which is optionally substituted, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) NR$^1$R$^{1a}$, or NR$^1$R$^{1a}$ or R$^1$ and R$^{1a}$ are joined to form an optionally substituted heterocyclyl, or —OH groups or an amino acid side chain optionally substituted;

$W^4$ of Formula ULM-a is an optionally substituted —NR1-T-Aryl wherein the aryl group may be optionally substituted with an optionally substituted 5-6 membered heteroaryl or an optionally substituted aryl, an optionally substituted —NR1-T-Heteroaryl group with an optionally substituted aryl or an optionally substituted heteroaryl, or an optionally substituted —NR1-T-heterocyclyl, where —NR1 is covalently bonded to $X^2$ and R1 is H or $CH_3$, preferably H; and n is 0 to 6, often 0, 1, 2, or 3, preferably 0 or 1.

In any of the embodiments described herein, T is selected from the group of an optionally substituted alkyl, $-(CH_2)_n-$ group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, $C(O)NR^1R^{1a}$, or $NR^1R^{1a}$ or $R^1$ and $R^{1a}$ are joined to form an optionally substituted heterocycle, or —OH groups or an amino acid side chain optionally substituted; and n is 0 to 6, often 0, 1, 2, or 3, preferably 0 or 1.

In certain embodiments, $W^4$ of Formula ULM-a is

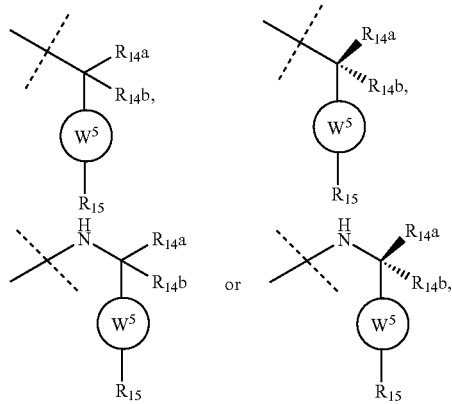

wherein: $W^5$ is optionally substituted (e.g., $W^5$ is an optionally substituted phenyl, an optionally substituted napthyl, or an optionally substituted 5-10 membered heteroaryl)(e.g., $W^5$ is optionally substituted with one or more [such as 1, 2, 3, 4, or 5] halo, CN, optionally substituted alkyl, optionally substituted haloalkyl, optionally substituted alkoxy, hydroxy, or optionally substituted haloalkoxy), and $R_{14a}$, $R_{14b}$, are each independently selected from the group of H, haloalkyl (e.g., fluoalkyl), optionally substituted alkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine.

In any of the embodiments, $W^5$ of Formula ULM-a is selected from the group of an optionally substituted phenyl, an optionally substituted napthyl, or an optionally substituted 5-10 membered heteroaryl (e.g., $W^5$ is optionally substituted with one or more [such as 1, 2, 3, 4, or 5] halo, CN, optionally substituted alkyl, optionally substituted haloalkyl, optionally substituted alkoxy, hydroxy, or optionally substituted haloalkoxy), $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; optionally substituted aryl, optionally substituted heteroaryl, optionally substituted cycloalkyl, or optionally substituted cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C=O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

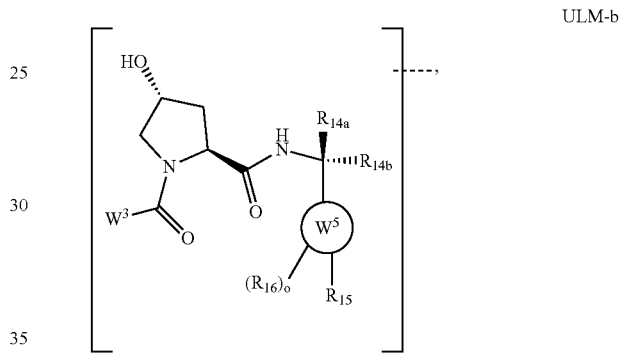

ULM-b wherein:
$W^3$ of Formula ULM-b is selected from the group of an optionally substituted aryl, optionally substituted heteroaryl, or

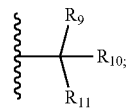

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclyl, optionally substituted alkoxy, optionally substituted heteroaryl, optionally substituted aryl,

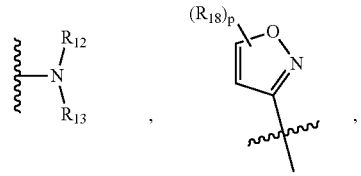

-continued

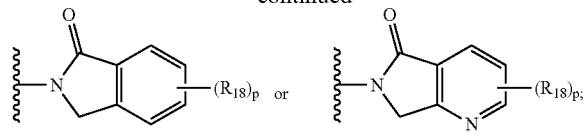

- $R_{12}$ of Formula ULM-b is selected from the group of H or optionally substituted alkyl;
- $R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
- $R_{14a}$, $R_{14b}$ of Formula ULM-b, are each independently selected from the group of H, haloalkyl (e.g. fluoroalkyl), optionally substituted alkyl, optionally substitute alkoxy, aminomethyl, alkylaminomethyl, alkoxymethyl, optionally substituted hydroxyl alkyl, optionally substituted alkylamine, optionally substituted heterolkyl, optionally substituted alkyl-heterocycloalkyl, optionally substituted alkoxy-heterocycloalkyl, $CONR_{27a}R_{27b}$, $CH_2NHCOR_{26}$, or $(CH_2)N(CH3)COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalky, spirocycloalkyl or spiroheterocyclyl, wherein the spiroheterocyclyl is not epoxide or aziridine;
- $W^5$ of Formula ULM-b is selected from the group of an optionally substituted phenyl or an optionally substituted 5-10 membered heteroaryl (e.g., $W^5$ is optionally substituted with one or more [such as 1, 2, 3, 4, or 5] halo, CN, optionally substituted alkyl, optionally substituted haloalkyl, optionally substituted alkoxy, hydroxy, or optionally substituted haloalkoxy),
- $R_{15}$ of Formula ULM-b is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;
- each $R_{16}$ of Formula ULM-b is independently selected from the group of CN, halo, optionally substituted alkyl, optionally substituted haloalkyl, hydroxy, or optionally substituted haloalkoxy;
- o of Formula ULM-b is 0, 1, 2, 3, or 4;
- $R_{18}$ of Formula ULM-b is independently selected from the group of H, halo, optionally substituted alkoxy, cyano, optionally substituted alkyl, haloalkyl, haloalkoxy or a linker; and
- p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In any aspect or embodiment described herein, $R_{15}$ of Formula ULM-b is selected from the group of H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl, wherein each $R_{26}$ is independently selected from H, optionally substituted alkyl or $NR_{27a}R_{27b}$; and each $R_{27a}$ and $R_{27b}$ is independently H, optionally substituted alkyl, or $R_{27a}$ and $R_{27b}$ together with the nitrogen atom to which they are attached form a 4-6 membered heterocyclyl.

In certain embodiments, $R_{15}$ of Formula ULM-b is

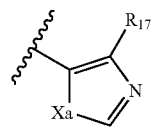

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

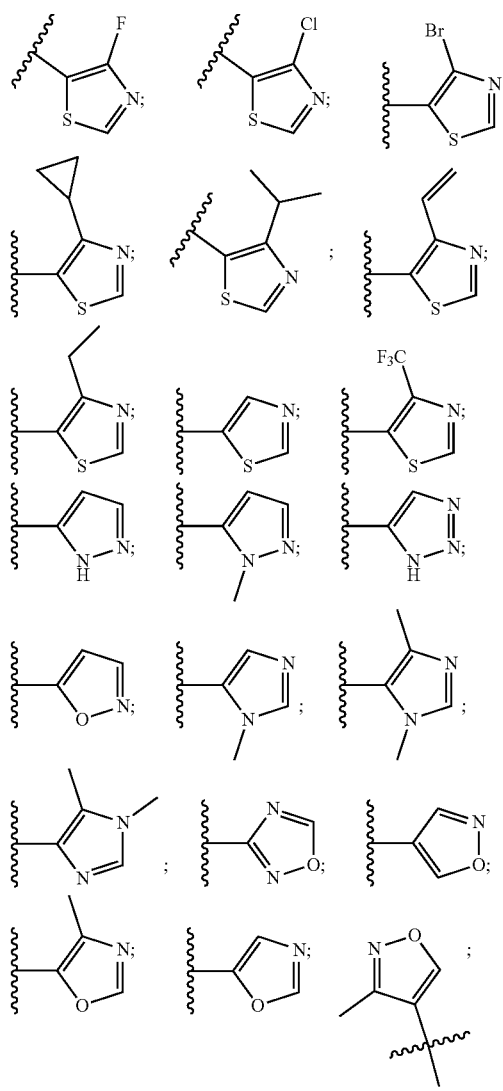

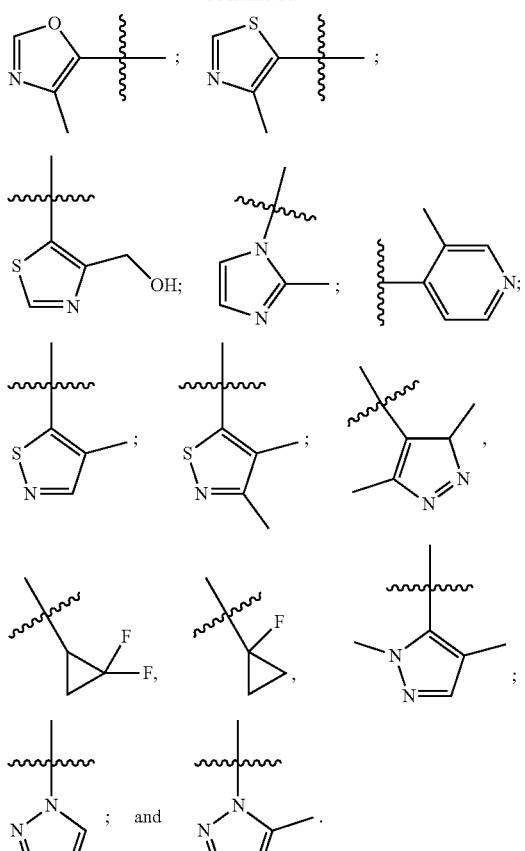

In certain embodiments, $R_{11}$ of Formula ULM-b is selected from the group consisting of:

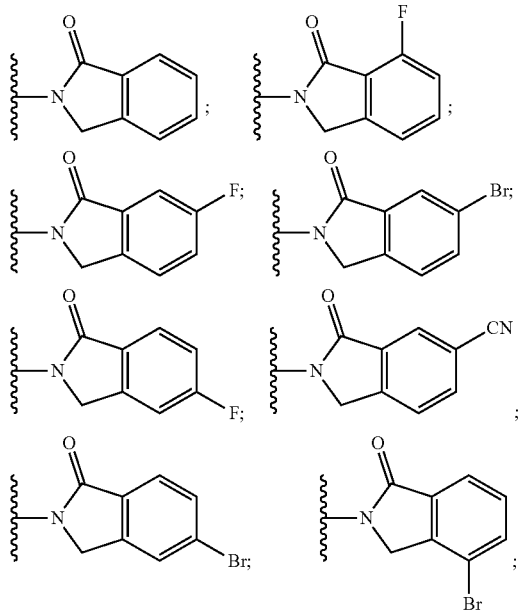

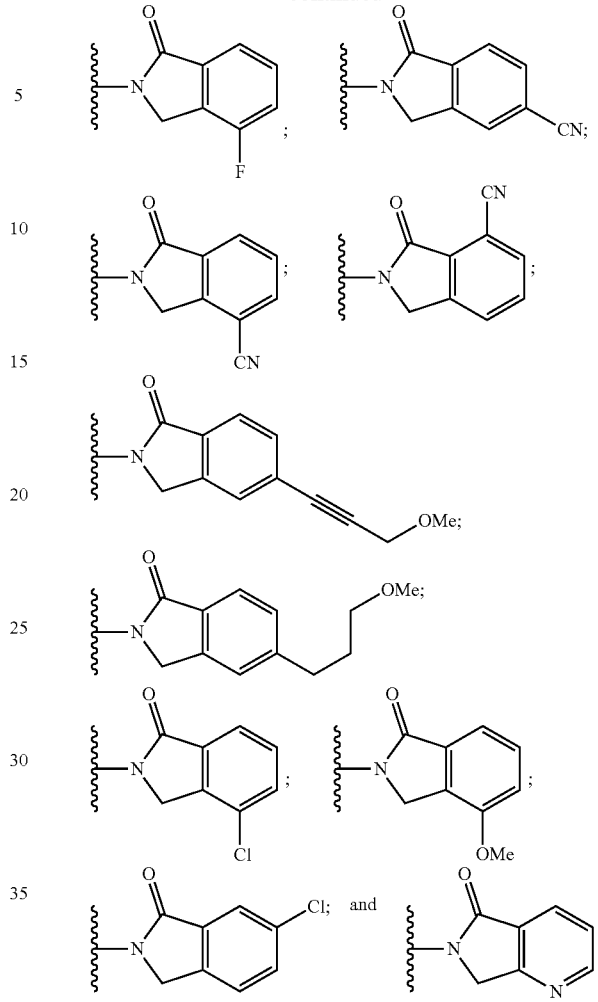

In certain embodiments, $R_{14a}$, $R_{14b}$ of Formula ULM-b, are each independently selected from the group of H, optionally substituted haloalkyl, optionally substituted alkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered cycloalkyl, heterocycloalkyl, spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted; $R_{26}$ and $R_{27}$ are as described above.

In certain embodiments, $R_{15}$ of Formula ULM-b is selected from H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl (e.g. optionally substituted fluoroalkyl), optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

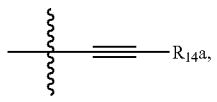

wherein $R_{26}$, $R_{27}$, $R_{30}$ and $R_{14}a$ are as described above.

In certain embodiments, $R_{14a}$, $R_{14b}$ of Formula ULM-b, are each independently selected from the group of H, optionally substituted haloalkyl, optionally substituted alkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted;

$R_{15}$ of Formula ULM-b is selected from H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

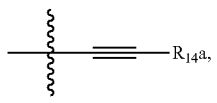

wherein $R_{26}$, $R_{27}$, $R_{30}$ and $R_{14a}$ are as described above.

In certain embodiments, ULM has a chemical structure selected from the group of:

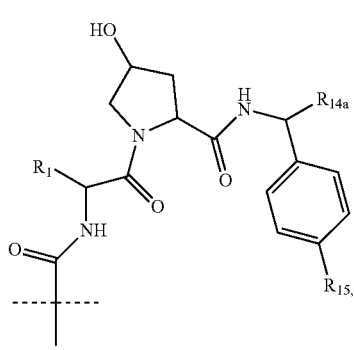

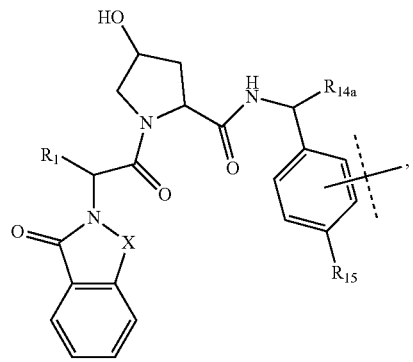

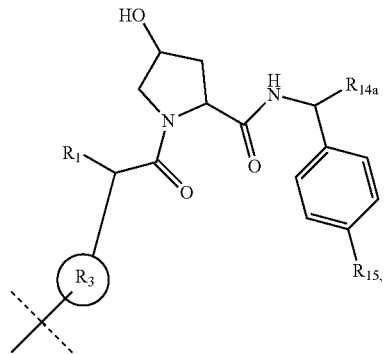

wherein:
$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted cycloalkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, optionally substituted cycloalkyl, or optionally substituted cycloheteroalkyl;

X of Formulas ULM-c, ULM-d, and ULM-e is C, $CH_2$, or C=O $R_3$ of Formulas ULM-c, ULM-d, and ULM-e is absent or an optionally substituted 5 or 6 membered heteroaryl; and the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

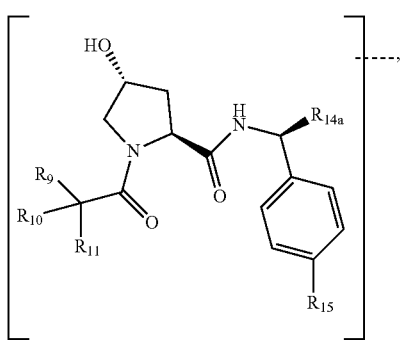

ULM-f

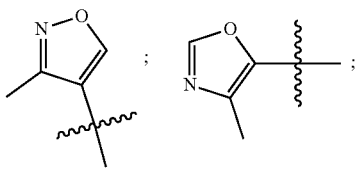

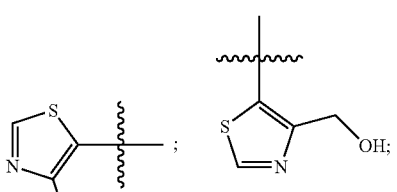

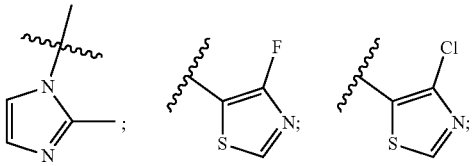

wherein:
- $R_{14a}$ of Formula ULM-f is H, haloalkyl, optionally substituted alkyl, methyl, fluoromethyl, hydroxymethyl, ethyl, isopropyl, or cyclopropyl;
- $R_9$ of Formula ULM-f is H;
- $R_{10}$ of Formula ULM-f is H, ethyl, isopropyl, tert-butyl, sec-butyl, cyclopropyl, cyclobutyl, cyclopentyl, or cyclohexyl;
- $R_{11}$ of Formula ULM-f is

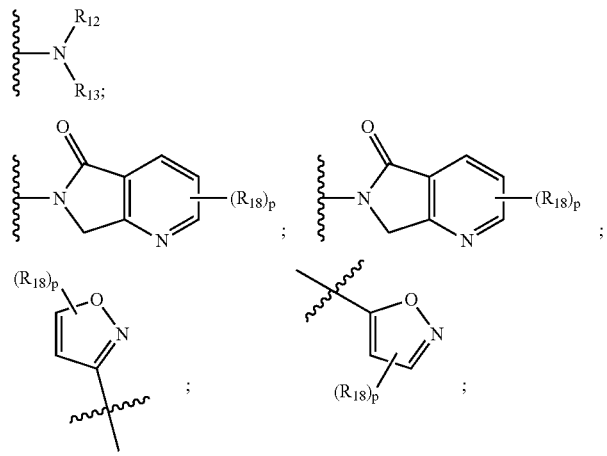

or optionally substituted heteroaryl;
- p of Formula ULM-f is 0, 1, 2, 3, or 4;
- each $R_{18}$ of Formula ULM-f is independently halo, optionally substituted alkoxy, cyano, optionally substituted alkyl, haloalkyl, haloalkoxy or a linker;
- $R_{12}$ of Formula ULM-f is H, C=O;
- $R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
- $R_{15}$ of Formula ULM-f is selected from the group consisting of H, halogen, Cl, CN, OH, $NO_2$, optionally substituted haloalkyl, optionally substituted heteroaryl, optionally substituted aryl;

-continued

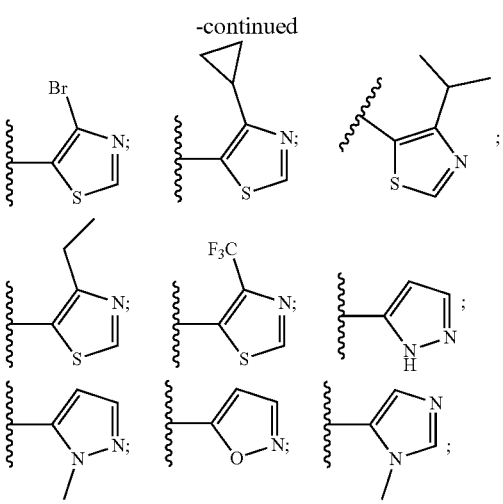

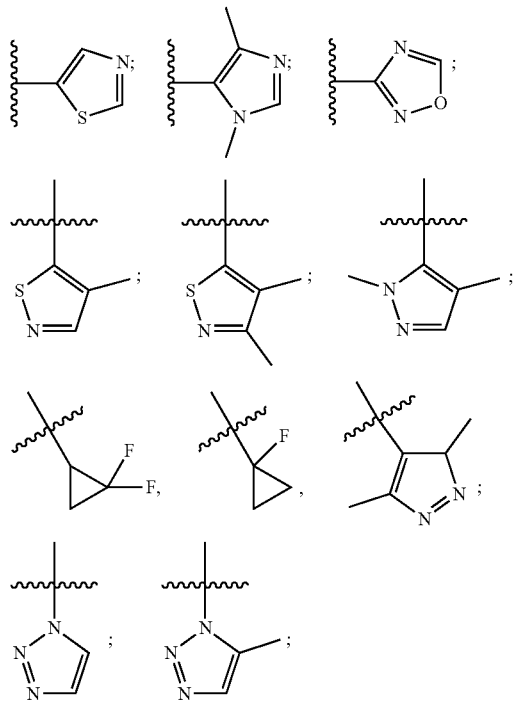
and
wherein the dashed line of Formula ULM-f indicates the site of attachment of at least one
PTM, another ULM (ULM') or a chemical linker moiety coupling at least one PTM or a ULM' or both to ULM.
In certain embodiments, the ULM is selected from the following structures:
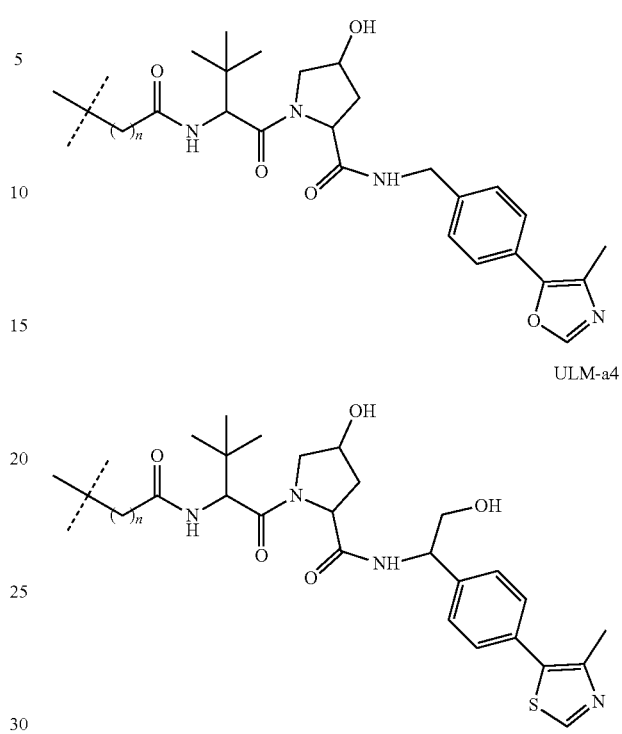
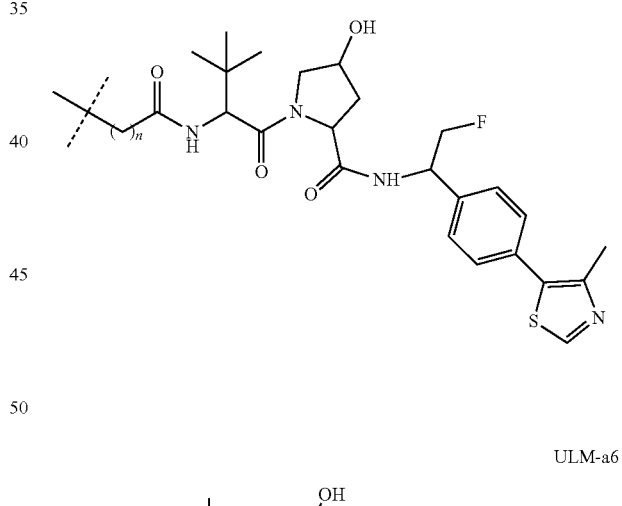
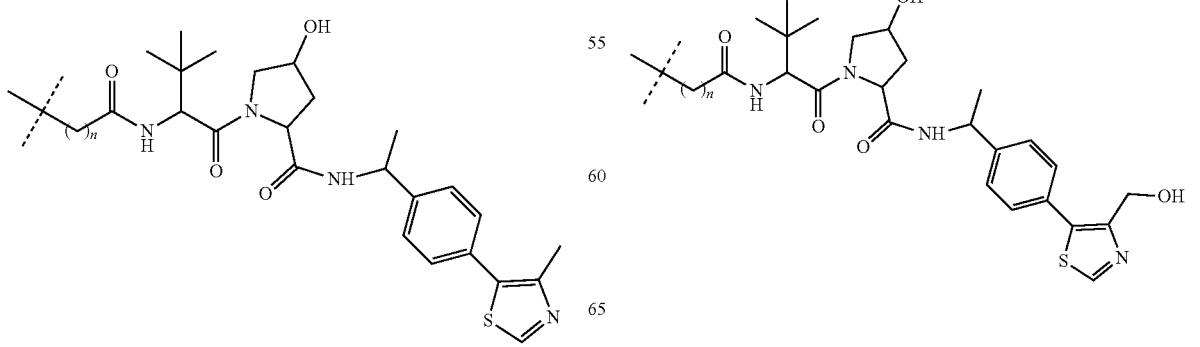

ULM-a7
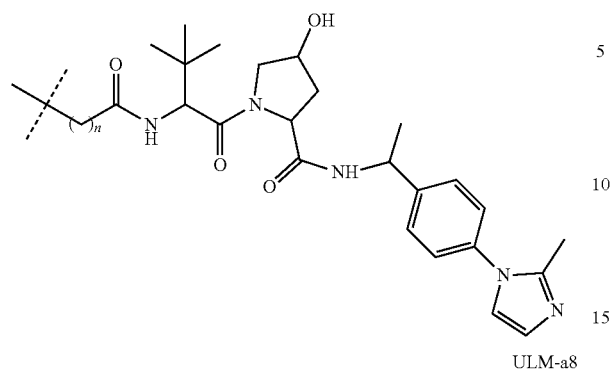
ULM-a8
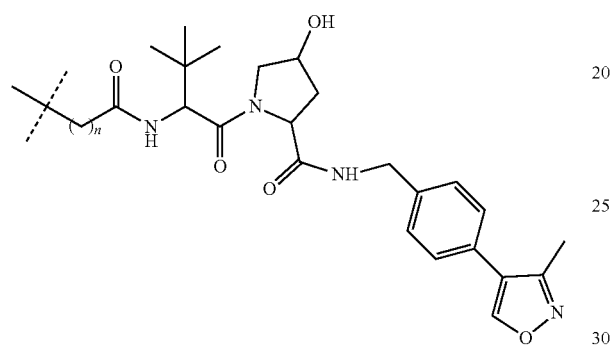
ULM-a9
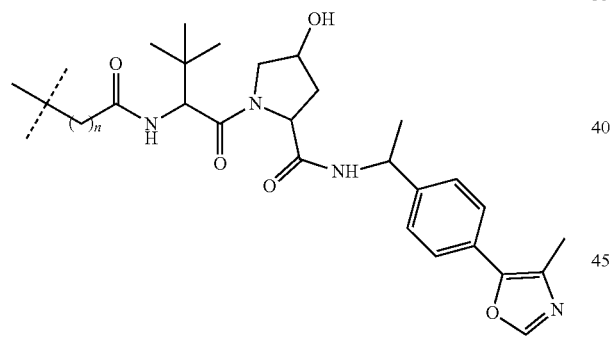
ULM-a10
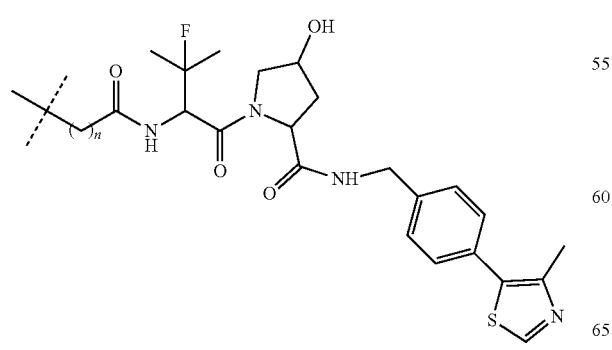
ULM-a11
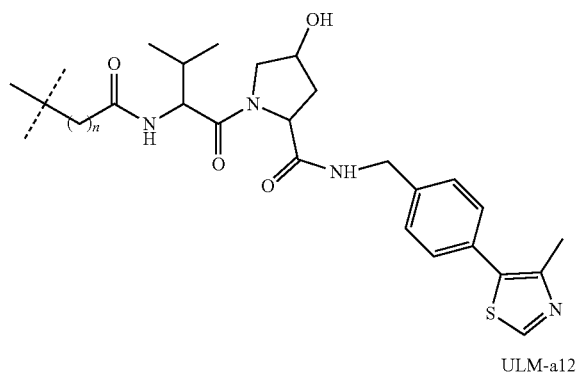
ULM-a12
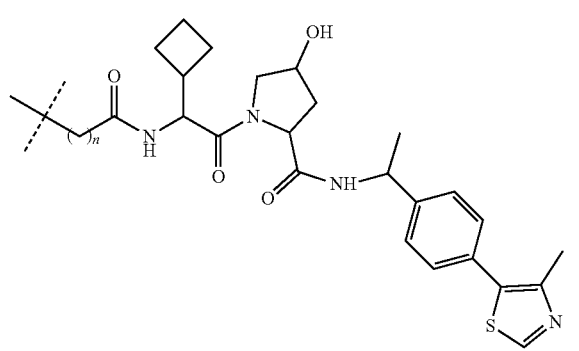
ULM-a13
ULM-a14
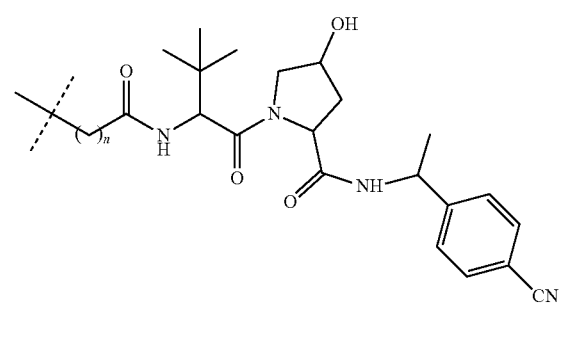

ULM-a15
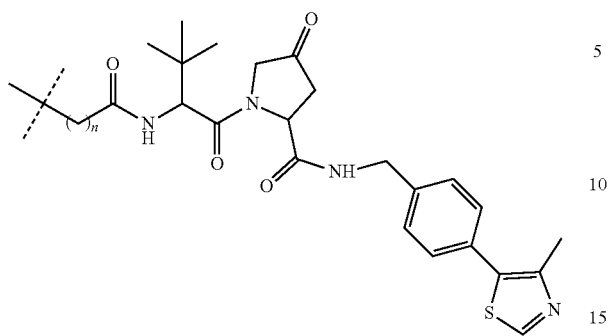
wherein n is 0 or 1.
In certain embodiments, the ULM is selected from the following structures:
ULM-b1
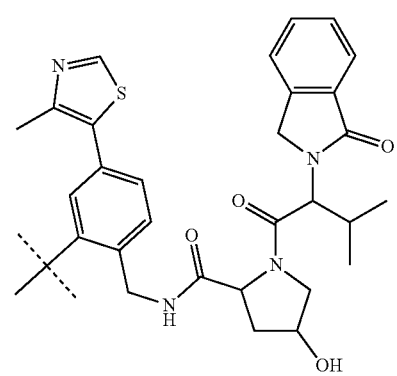
ULM-b2
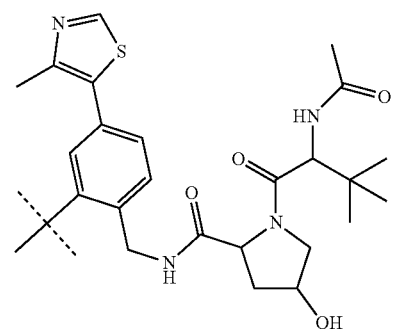
ULM-b3
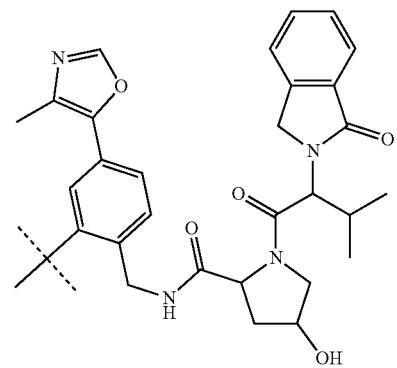
ULM-b4
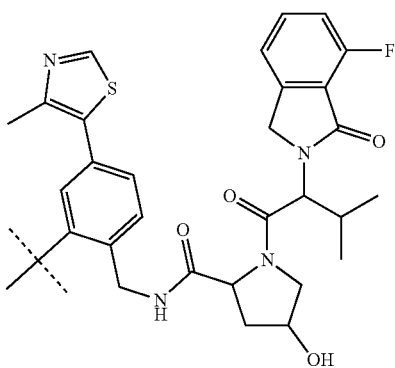
ULM-b5
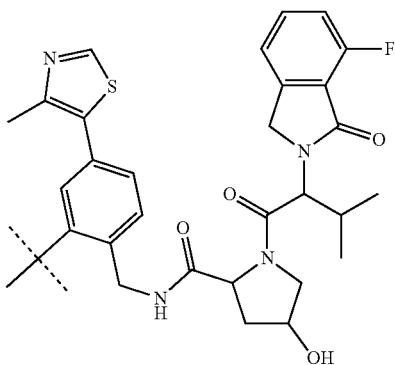
ULM-b6
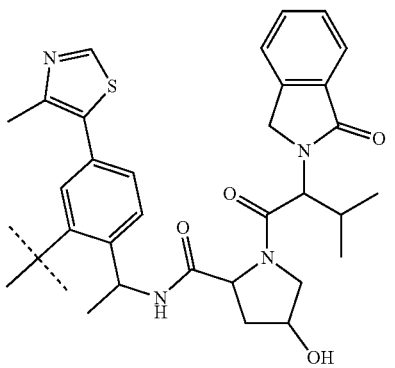
ULM-b7
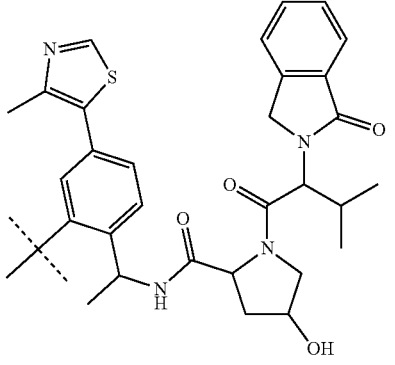

ULM-b8
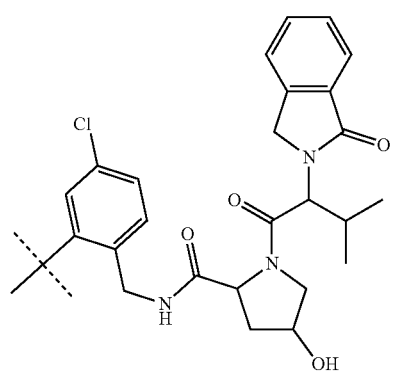
ULM-b9
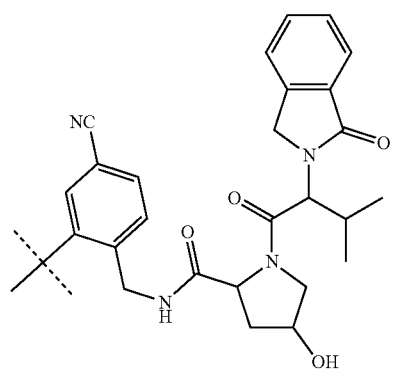
ULM-b10
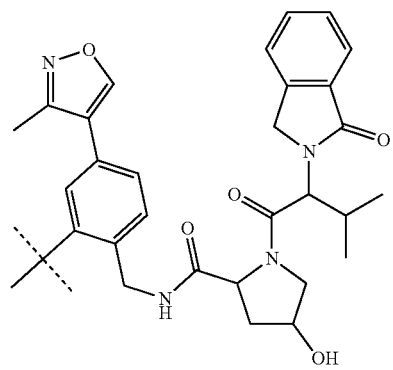
ULM-b11
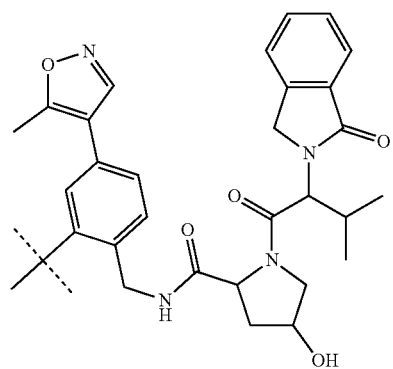
ULM-b12
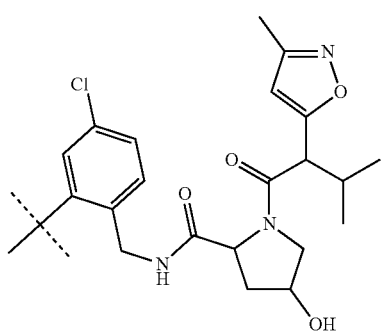
ULM-c1
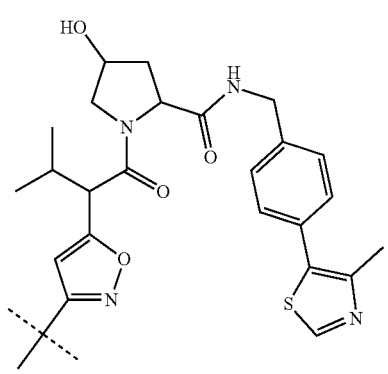
ULM-c2
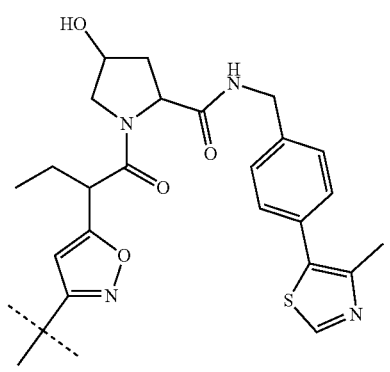
ULM-c3
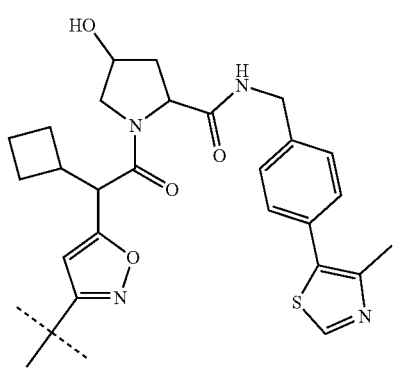

ULM-c4
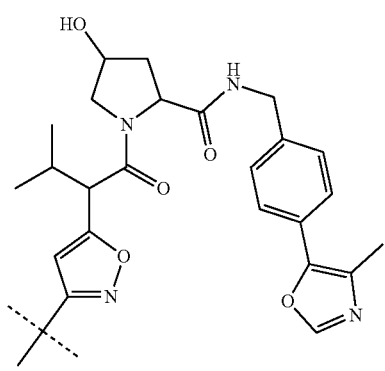
ULM-c5
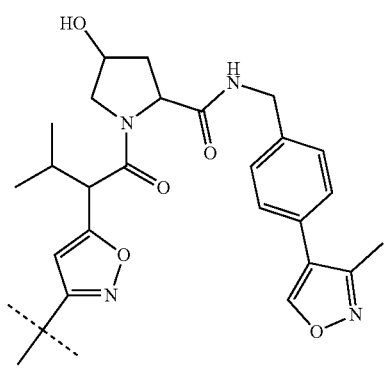
ULM-c6
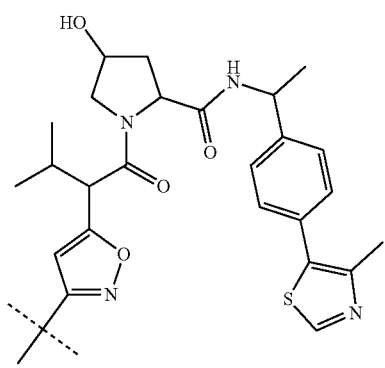
ULM-c7
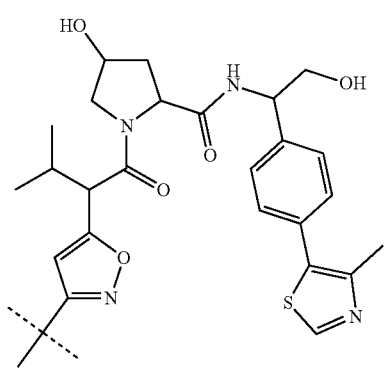
ULM-c8
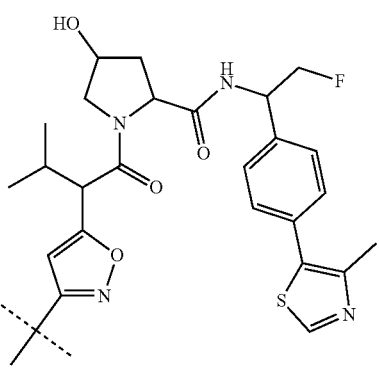
ULM-c9
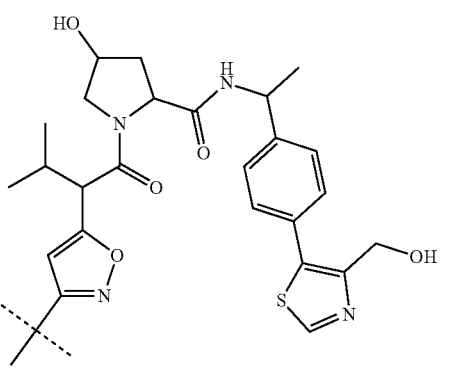
ULM-c10
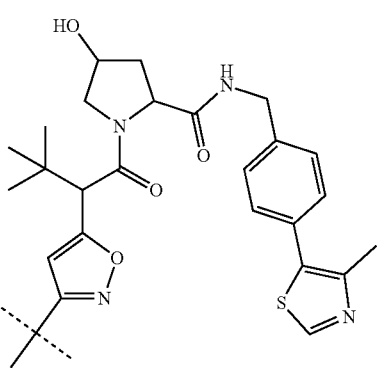
ULM-c11
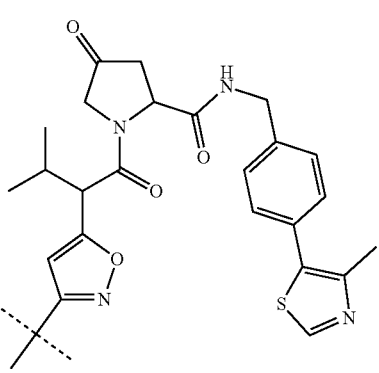

-continued
ULM-c12
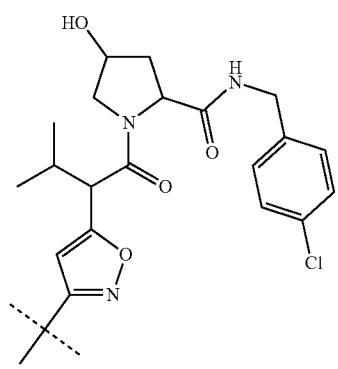
ULM-c13
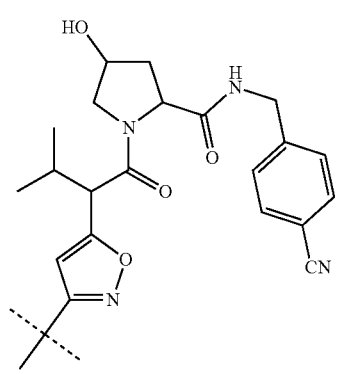
ULM-c14
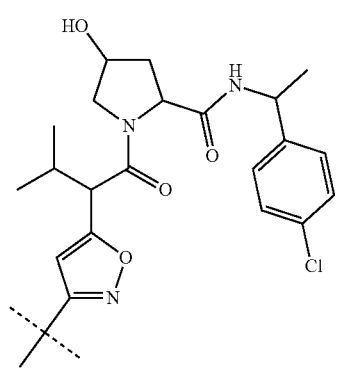
ULM-c15
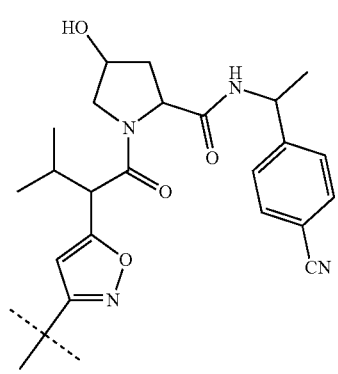
-continued
ULM-d1
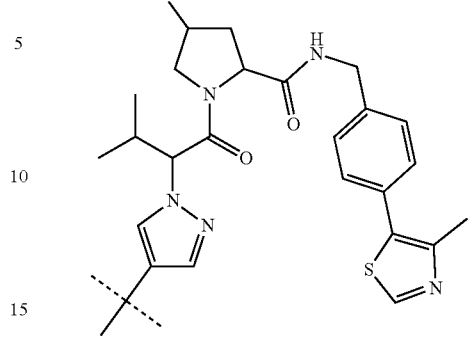
ULM-d2
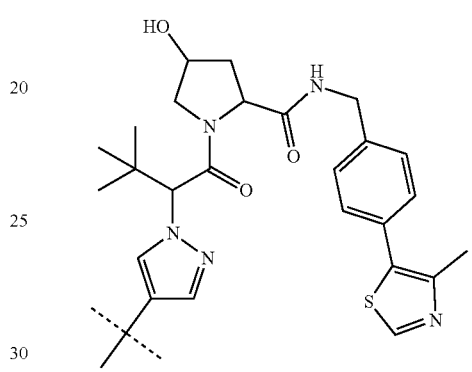
ULM-d3
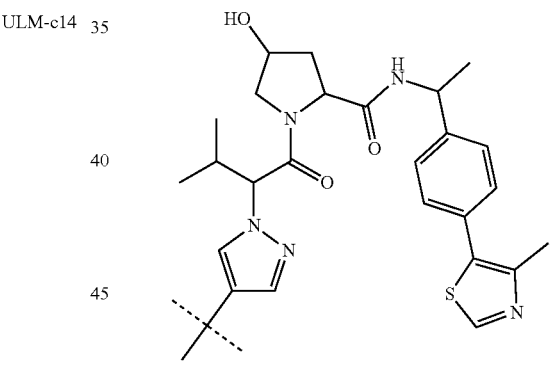
ULM-d4
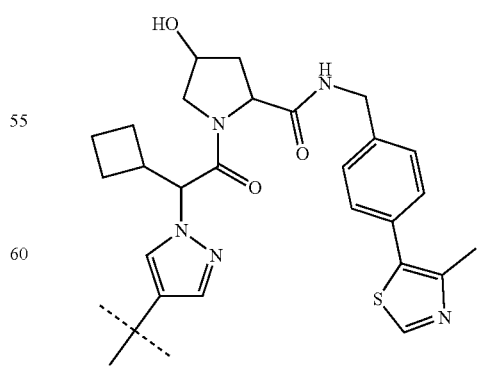

-continued

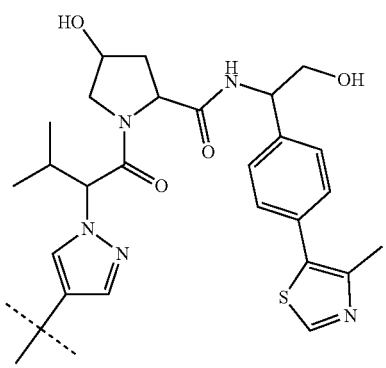
ULM-d5

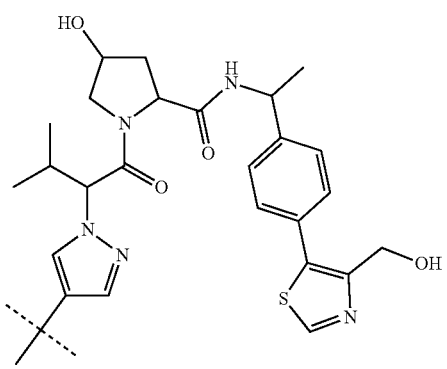
ULM-d6

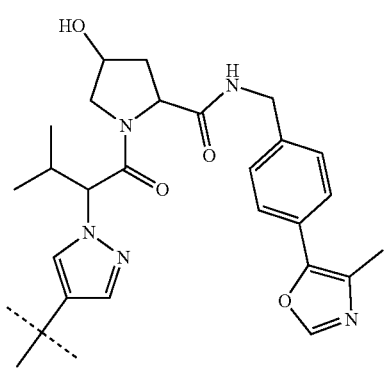
ULM-d7

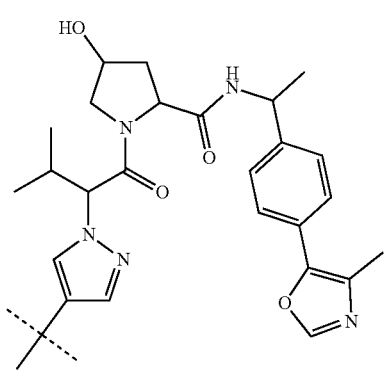
ULM-d8

-continued

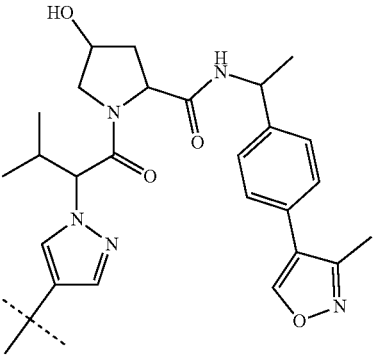
ULM-d9 wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

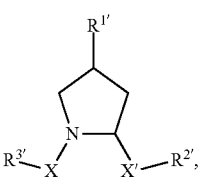
ULM-g or a pharmaceutically acceptable salt thereof, wherein:
R$^{1'}$ of ULM-g is an optionally substituted C$_1$-C$_6$ alkyl group, an optionally substituted —(CH$_2$)$_n$OH, an optionally substituted —(CH$_2$)$_n$SH, an optionally substituted (CH$_2$)$_n$—O—(C$_1$-C$_6$)alkyl group, an optionally substituted (CH$_2$)$_n$—WCOCW—(C$_0$-C$_6$)alkyl group containing an epoxide moiety WCOCW where each W is independently H or a C$_1$-C$_3$ alkyl group, an optionally substituted —(CH$_2$)$_n$COOH, an optionally substituted —(CH$_2$)$_n$C(O)—(C$_1$-C$_6$ alkyl), an optionally substituted —(CH$_2$)$_n$NHC(O)—R″, an optionally substituted —(CH$_2$)$_n$C(O)—NR″, an optionally substituted —(CH$_2$)$_n$OC(O)—N(R″)$_2$, —(CH$_2$O)$_n$H, an optionally substituted —(CH$_2$)$_n$OC(O)—(C$_1$-C$_6$ alkyl), an optionally substituted —(CH$_2$)$_n$C(O)—O—(C$_1$-C$_6$ alkyl), an optionally substituted —(CH$_2$O)$_n$COOH, an optionally substituted —(OCH$_2$)$_n$O—(C$_1$-C$_6$ alkyl), an optionally substituted —(CH$_2$O)$_n$C(O)—(C$_1$-C$_6$ alkyl), an optionally substituted —(OCH$_2$)$_n$NHC(O)—R$_1$, an optionally substituted —(CH$_2$O)$_n$C(O)—N(R")$_2$, —(CH$_2$CH$_2$O)$_n$H, an optionally substituted —(CH$_2$CH$_2$O)$_n$COOH, an optionally substituted —(OCH$_2$CH$_2$)$_n$O—(C$_1$-C$_6$ alkyl), an optionally substituted —(CH$_2$CH$_2$O)$_n$C(O)—(C$_1$-C$_6$ alkyl), an optionally substituted —(OCH$_2$CH$_2$)$_n$NHC(O)—R', an optionally substituted —(CH$_2$CH$_2$O)$_n$C(O)—N(R")$_2$, an optionally substituted —SO$_2$R$_S$, an optionally substituted S(O)R$_S$, NO$_2$, CN or halogen (F, Cl, Br, I, preferably F or Cl);

each R" of ULM-g is independently H or a C$_1$-C$_6$ alkyl group which may be optionally substituted with one or two hydroxyl groups or up to three halogen groups (preferably fluorine);

R$_S$ of ULM-g is a C$_1$-C$_6$ alkyl group, an optionally substituted aryl, heteroaryl or heterocyclyl group or a —(CH$_2$)$_m$N(R")$_2$ group;

X and X' of ULM-g are each independently C=O, C=S, —S(O), S(O)$_2$, (preferably X and X' are both C=O);

R$^{2'}$ of ULM-g is an optionally substituted —(CH$_2$)$_n$—(C=O)$_u$(NR")$_v$(SO$_2$)$_w$alkyl group, an optionally substituted —(CH$_2$)$_n$—(C=O)$_u$(NR")$_v$(SO$_2$)$_w$NR$_{1N}$R$_{2N}$ group, an optionally substituted —(CH$_2$)$_n$—(C=O)$_u$(NR")$_v$(SO$_2$)$_w$-Aryl, an optionally substituted —(CH$_2$)$_n$—(C=O)$_u$(NR")$_v$(SO$_2$)$_w$-Heteroaryl, an optionally substituted —(CH$_2$)$_n$—(C=O)$_v$NR"(SO$_2$)$_w$-Heterocycle, an optionally substituted —NR"—(CH$_2$)$_n$—C(O)$_u$(NR")$_v$(SO$_2$)$_w$-alkyl, an optionally substituted —NR"—(CH$_2$)$_n$—C(O)$_u$(NR")$_v$(SO$_2$)$_w$—NR$_{1N}$R$_{2N}$, an optionally substituted —NR"—(CH$_2$)$_n$—C(O)$_u$(NR")$_v$(SO$_2$)$_w$—NR"C(O)R$_{1N}$, an optionally substituted —NR"—(CH$_2$)$_n$—(C=O)$_u$(NR")$_v$(SO$_2$)$_w$-Aryl, an optionally substituted —NR"—(CH$_2$)$_n$—(C=O)$_u$(NR")$_v$(SO$_2$)$_w$-Heteroaryl or an optionally substituted —NR"—(CH$_2$)$_n$—(C=O)$_v$NR"(SO$_2$)$_w$-Heterocycle, an optionally substituted —X$^{R2'}$-alkyl group; an optionally substituted —X$^{R2'}$-Aryl group; an optionally substituted —X$^{R2'}$-Heteroaryl group; an optionally substituted —X$^{R2'}$-Heterocycle group; an optionally substituted;

R$^{3'}$ of ULM-g is an optionally substituted alkyl, an optionally substituted —(CH$_2$)$_n$—(O)$_u$(NR$_1$)$_v$(SO$_2$)$_w$-alkyl, an optionally substituted —(CH$_2$)$_n$—C(O)$_u$(NR")$_v$(SO$_2$)$_w$—NR$_{1N}$R$_{2N}$, an optionally substituted —(CH$_2$)$_n$—C(O)$_u$(NR")$_v$(SO$_2$)$_w$—NR"C(O)R$_{1N}$, an optionally substituted —(CH$_2$)$_n$—C(O)$_u$(NR")$_v$(SO$_2$)$_w$—C(O)N(R")$_2$, an optionally substituted —(CH$_2$)$_n$—C(O)$_u$(NR")$_v$(SO$_2$)$_w$-Aryl, an optionally substituted —(CH$_2$)$_n$—C(O)$_u$(NR")$_v$(SO$_2$)$_w$-Heteroaryl, an optionally substituted —(CH$_2$)$_n$—C(O)$_u$(NR")$_v$(SO$_2$)$_w$-Heterocycle, an optionally substituted —NR"—(CH$_2$)$_n$—C(O)$_u$(NR")$_v$(SO$_2$)$_w$-alkyl, an optionally substituted —NR"—(CH$_2$)$_n$—C(O)$_u$(NR")$_v$(SO$_2$)$_w$—NR$_{1N}$R$_{2N}$, an optionally substituted —NR"—(CH$_2$)$_n$—C(O)$_u$(NR")$_v$(SO$_2$)$_w$—NR"C(O)R$_{1N}$, an optionally substituted —NR"—(CH$_2$)$_n$—C(O)$_u$(NR")$_v$(SO$_2$)$_w$-Aryl, an optionally substituted —NR"—(CH$_2$)$_n$—C(O)$_u$(NR")$_v$(SO$_2$)$_w$-Heteroaryl, an optionally substituted —NR"—(CH$_2$)$_n$—C(O)$_u$(NR")$_v$(SO$_2$)$_w$-Heterocycle, an optionally substituted —O—(CH$_2$)n-(C=O)$_u$(NR")$_v$(SO$_2$)$_w$-alkyl, an optionally substituted —O—(CH$_2$)n-(C=O)$_u$(NR")$_v$(SO$_2$)$_w$—NR$_{1N}$R$_{2N}$, an optionally substituted —O—(CH$_2$)n-(C=O)$_u$(NR")$_v$(SO$_2$)$_w$—NR$_1$C(O)R$_{1N}$, an optionally substituted —O—(CH$_2$)n-(C=O)$_u$(NR")$_v$(SO$_2$)$_w$-Aryl, an optionally substituted —O—(CH$_2$)$_n$—(C=O)$_u$(NR")$_v$(SO$_2$)$_w$-Heteroaryl or an optionally substituted —O—(CH$_2$)$_n$—(C=O)$_u$(NR")$_v$(SO$_2$)$_w$-heterocyclyl; —(CH$_2$)$_n$—(V)$_{n'}$—(CH$_2$)$_n$—(V)$_{n'}$-alkyl group, an optionally substituted —(CH$_2$)$_n$—(V)$_{n'}$—(CH$_2$)$_n$—(V)$_{n'}$-Aryl group, an optionally substituted —(CH$_2$)$_n$—(V)$_{n'}$—(CH$_2$)$_n$—(V)$_{n'}$-Heteroaryl group, an optionally substituted —(CH$_2$)$_n$—(V)$_{n'}$—(CH$_2$)$_n$—(V)$_{n'}$-heterocyclyl group, an optionally substituted —(CH$_2$)$_n$—N(R$_1$)(C=O)$_{m'}$—(V)$_{n'}$-alkyl group, an optionally substituted —(CH$_2$)$_n$—N(R$_1$)(C=O)$_{m'}$—(V)$_{n'}$-Aryl group, an optionally substituted —(CH$_2$)$_n$—N(R$_1$)(C=O)$_{m'}$—(V)$_{n'}$-Heteroaryl group, an optionally substituted —(CH$_2$)$_n$—N(R$_1$)(C=O)$_{m'}$—(V)$_{n'}$-heterocycyl group, an optionally substituted —X$^{R3'}$-alkyl group; an optionally substituted —X$^{R3'}$-Aryl group; an optionally substituted —X$^{R3'}$-Heteroaryl group; an optionally substituted —X$^{R3'}$-heterocylyl group; an optionally substituted;

R$_{1N}$ and R$_{2N}$ of ULM-g are each independently H, C$_1$-C$_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-heterocylyl group;

V of ULM-g is O, S or NR";

R$_{1'}$ of ULM-g are each independently H or a C$_1$-C$_3$ alkyl group;

X$^{R2'}$ and X$^{R3'}$ of ULM-g are each independently an optionally substituted —CH$_2$)$_n$—, —CH$_2$)$_n$—CH(X$_v$)=CH(X$_v$)— (cis or trans), —CH$_2$)$_n$—CH=CH—, —(CH$_2$CH$_2$O)$_n$— or a C$_3$-C$_6$ cycloalkyl group, where X$_v$ is H, a halo or a C$_1$-C$_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of R$^{1'}$, R$^{2'}$, R$^{3'}$, X and X' of ULM-g is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

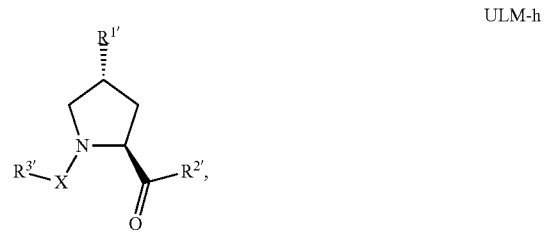

ULM-h wherein:

each of R$^{1'}$, R$^{2'}$ and R$^{3'}$ of ULM-h are the same as above and X is C=O, C=S, —S(O) group or a S(O)$_2$ group, more preferably a C=O group, and any one or more of R¹', R²' and R³' of ULM-h are optionally modified to bind a linker group to which is further covalently bonded to the PTM group when PTM is not ULM', or when PTM is ULM', any one or more of R¹', R²', R³' of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

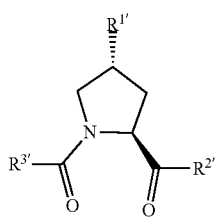

ULM-i wherein:
any one or more of R¹', R²' and R³' of ULM-I are optionally modified to bind a linker group to which is further covalently bonded to the PTM group when PTM is not ULM', or when PTM is ULM', any one or more of R¹', R²', R³' of each of ULM and ULM' are optionally modified to be covalently bonded to each other directly or through a linker group, or a pharmaceutically acceptable salt, enantiomer, diastereomer, solvate or polymorph thereof.

In further preferred aspects of the disclosure, R¹' of ULM-g through ULM-i is preferably a hydroxyl group or a group which may be metabolized to a hydroxyl or carboxylic group, such that the compound represents a prodrug form of an active compound. Exemplary preferred R¹' groups include, for example, —(CH₂)ₙOH, (CH₂)ₙ—O—(C₁-C₆)alkyl group, —(CH₂)ₙCOOH, —(CH₂O)ₙH, an optionally substituted —(CH₂)ₙOC(O)—(C₁-C₆ alkyl), or an optionally substituted —(CH₂)ₙC(O)—O—(C₁-C₆ alkyl), wherein n is 0 or 1. Where R¹' is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a S(O)₂ group, more preferably a C=O group;

R²' of ULM-g through ULM-i is preferably an optionally substituted —NR"-T-Aryl (e.g., an optionally substituted NH-T-aryl or an optionally substituted N(CH₃)-T-aryl), an optionally substituted —NR"-T-Heteroaryl group (e.g., an optionally substituted NH-T-heteroaryl or an optionally substituted N(CH₃)-T-heteroaryl), or an optionally substituted —NR"-T-heterocylcl (e.g., an optionally substituted NH-T-heterocylcl or an optionally substituted N(CH₃)-T-heterocylcl), where R" is H or CH₃, preferably H and T is an optionally substituted —(CH₂)ₙ— group, wherein each one of the methylene groups may be optionally substituted with one or two substituents, preferably selected from halogen, an amino acid sidechain as otherwise described herein or a C₁-C₃ alkyl group, preferably one or two methyl groups, which may be optionally substituted; and n is 0 to 6, often 0, 1, 2 or 3, preferably 0 or 1. Alternatively, T may also be a —(CH₂O)ₙ— group, a —(OCH₂)ₙ— group, a —(CH₂CH₂O)ₙ— group, a —(OCH₂CH₂)ₙ— group, all of which groups are optionally substituted.

Preferred Aryl groups for R²' of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, C₁-C₆ alkyl, preferably CH₃, CF₃, OMe, OCF₃, NO₂, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, CH₃, CF₃, OMe, OCF₃, NO₂, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

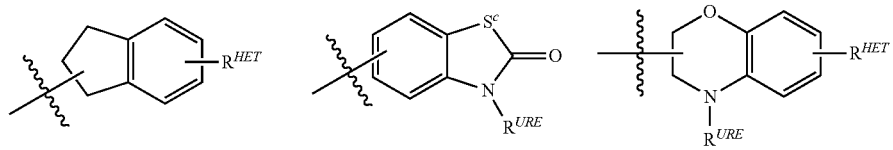

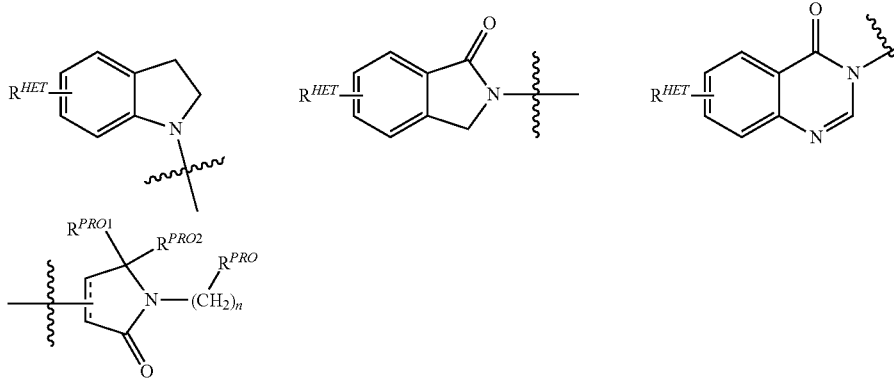

wherein:
- $S^c$ of ULM-g through ULM-i is $CHR^{SS}$, $NR^{URE}$, or $O$;
- $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
- $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
- $R^{UBE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocyclyl, preferably for example piperidine, morpholine, pyrrolidine, tetrahydrofuran);
- $R^{PRO}$ of ULM-g through ULM-i is H, optionally substituted $C_1$-$C_6$ alkyl or an optionally substituted aryl (phenyl or napthyl), heteroaryl or heterocyclylgroup selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
- $R^{PRO1}$ and $R^{PRO2}$ of ULM-g through ULM-i are each independently H, an optionally subsituted $C_1$-$C_3$ alkyl group or together form a keto group; and
- each n of ULM-g through ULM-i is independently 0, 1, 2, 3, 4, 5, or 6 (preferably 0 or 1), or an optionally substituted heterocyclyl, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects,

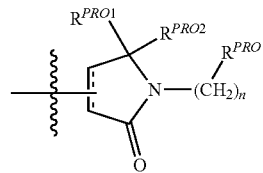

of ULM-g through ULM-i is a

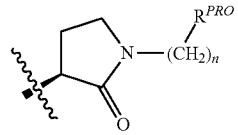

or

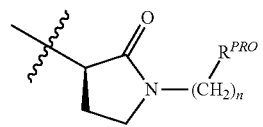

group, where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

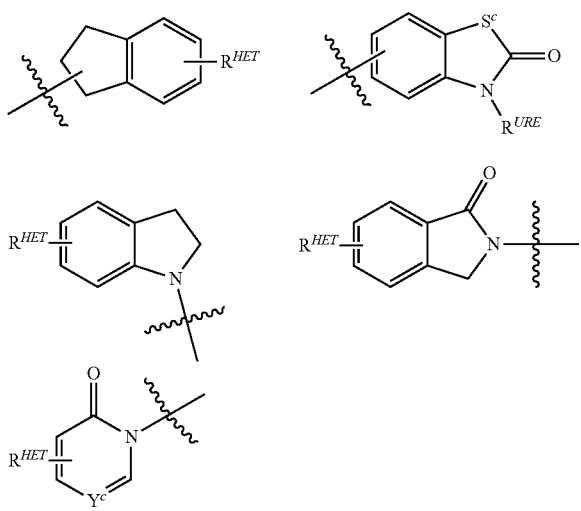

wherein:
- $S^c$ of ULM-g through ULM-i is $CHR^{SS}$, $NR^{URE}$, or O;
- $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);
- $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
- $R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
- $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocyclylgroups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

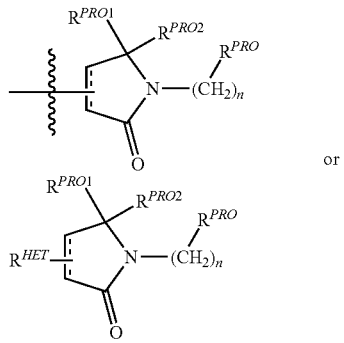

preferably, a

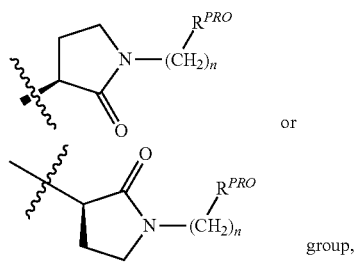

group, wherein:
- $R^{PRO}$ of ULM-g through ULM-i is H, optionally substituted $C_1$-$C_6$ alkyl or an optionally substituted aryl, heteroaryl or heterocyclylgroup;
- $R^{PRO1}$ and $R^{PRO2}$ of ULM-g through ULM-i are each independently H, an optionally substituted $C_1$-$C_3$ alkyl group or together form a keto group and
- each n of ULM-g through ULM-i is independently 0, 1, 2, 3, 4, 5, or 6 (often 0 or 1), each of which groups may be optionally connected to a PTM group (including a ULM' group) via a linker group.

Preferred R$^{2'}$ substituents of ULM-g through ULM-i also include specifically (and without limitation to the specific compound disclosed) the R$^{2'}$ substituents which are found in the identified compounds disclosed herein (which includes the specific compounds which are disclosed in the present specification, and the figures which are attached hereto). Each of these R$^{2'}$ substituents may be used in conjunction with any number of R$^{3'}$ substituents which are also disclosed herein.

R$^{3'}$ of ULM-g through ULM-i is preferably an optionally substituted -T-Aryl, an optionally substituted-T-Heteroaryl, an optionally substituted -T-Heterocycle, an optionally substituted-NR"-T-Aryl (e.g., an optionally substituted NH-T-aryl, an optionally substituted N(CH$_3$)-T-aryl, or or an optionally substituted N(C$_1$-C$_3$ alkyl)-T-aryl), an optionally substituted —NR"-T-Heteroaryl (e.g., an optionally substituted NH-T-heteroaryl, an optionally substituted N(CH$_3$)-T-heteroaryl, or an optionally substituted N(C$_1$-C$_3$ alkyl)-T-heteroaryl), or an optionally substituted-NR$^1$-T-heterocyclyl (e.g., an optionally substituted NH-T-heterocyclyl, an optionally substituted N(CH$_3$)-T-heterocyclyl, or or an optionally substituted N(C$_1$-C$_3$ alkyl)-T-heterocyclyl), where R" is H or a C$_1$-C$_3$ alkyl group, preferably H or CH$_3$, T is an optionally substituted —(CH$_2$)$_n$— group, wherein each one of the methylene groups may be optionally substituted with one or two substituents, preferably selected from halogen, a C$_1$-C$_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, each of which groups is optionally substituted.

Preferred aryl groups for R$^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —(CH$_2$)$_m$—NR"C(O)R" group where m is the same as above), a halo (often F or Cl), OH, CH$_3$, CF$_3$, OMe, OCF$_3$, NO$_2$, CN or a S(O)$_2$R$_S$ group (R$_S$ is a a C$_1$-C$_6$ alkyl group, an optionally substituted aryl, heteroaryl or heterocylcl group or a —(CH$_2$)$_m$N(R")$_2$ group), each of which may be substituted in ortho-, meta- and/or para-positions of the phenyl ring, preferably para-), or an Aryl (preferably phenyl), Heteroaryl or heterocyclyl. Preferably said substituent phenyl group is an optionally substituted phenyl group (i.e., the substituent phenyl group itself is preferably substituted with at least one of F, Cl, OH, SH, COOH, CH$_3$, CF$_3$, OMe, OCF$_3$, NO$_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methyl-substituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo- (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for R$^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

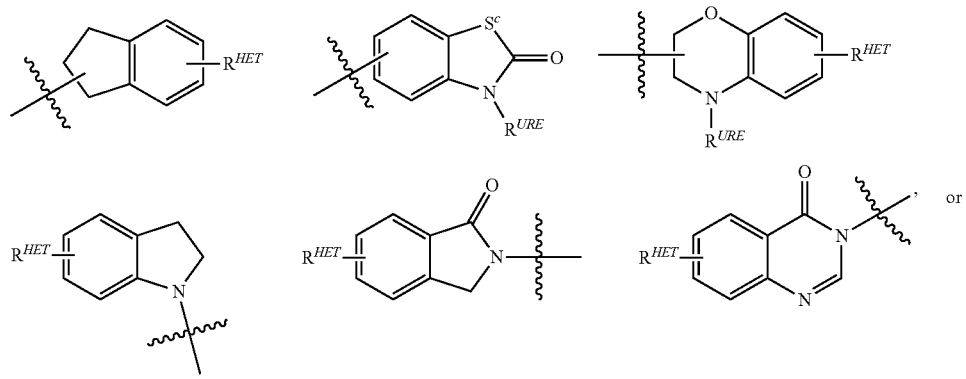

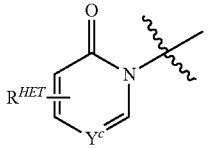

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted, and
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

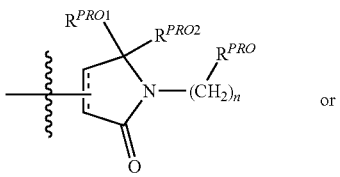

-continued

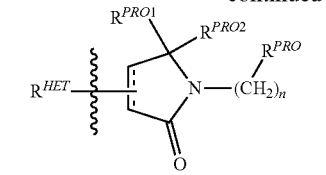

preferably, a

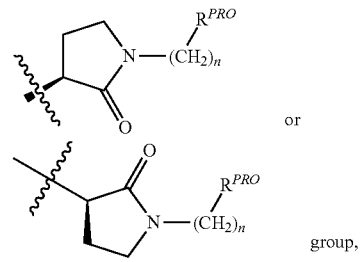

group, wherein:
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group, and
each n of ULM-g through ULM-i is 0, 1, 2, 3, 4, 5, or 6 (preferably 0 or 1), wherein each of said Heteocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:
R$_1$ of ULM-g through ULM-i is H or a C$_1$-C$_3$ alkyl group (preferably H);

X$^{R2'}$ of ULM-g through ULM-i is an optionally substituted —CH$_2$)$_n$—, —(CH$_2$)$_n$—CH(X$_v$)=CH(X$_v$)— (cis or trans), —(CH$_2$)$_n$—CH≡CH—, —(CH$_2$CH$_2$O)$_n$— or a C$_3$-C$_6$ cycloalkyl group; and X$_v$ of ULM-g through ULM-i is H, a halo or a C$_1$-C$_3$ alkyl group which is optionally substituted with one or two hydroxyl groups or up to three halogen groups;

Alkyl of ULM-g through ULM-i is an optionally substituted C1-C$_{10}$ alkyl (preferably a C$_1$-C$_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a C$_1$-C$_3$ alkyl group, preferably methyl or a halo group, preferably F or Cl) or a group according to the chemical structure:

an optionally substituted —C(O)(C$_1$-C$_6$ alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximi-

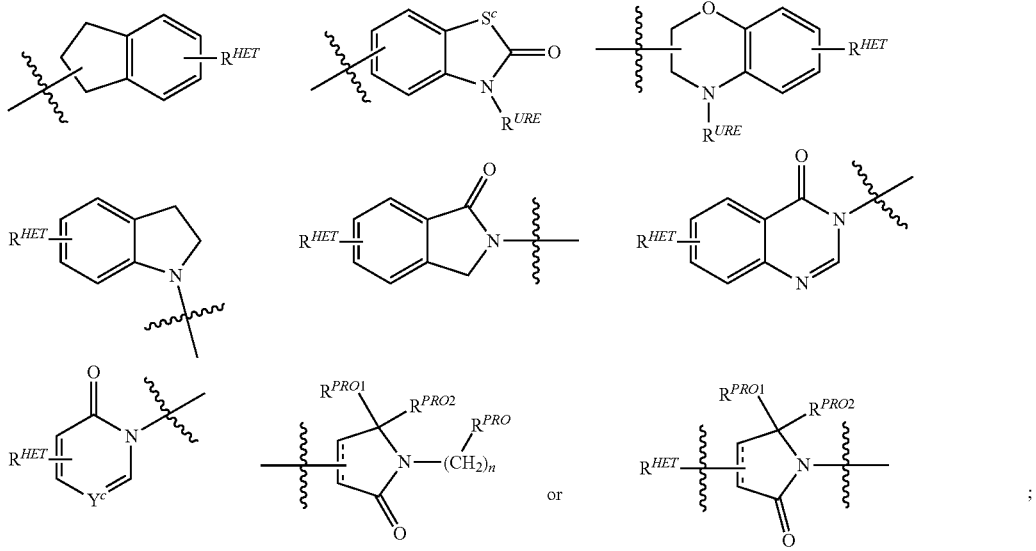

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or dazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ of ULM-g through ULM-i are each independently H, an optionally subsituted C$_1$-C$_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present disclosure, R$^{3'}$ of ULM-g through ULM-i is an optionally substituted —(CH$_2$)$_n$—(V)$_{n'}$—(CH$_2$)$_n$—(V)$_{n'}$—R$^{S3'}$ group, an optionally substituted -(CH$_2$)$_n$-N(R$_{1'}$)(C=O)$_{m'}$-(V)$_{n'}$-R$^{S3'}$ group, an optionally substituted -X$^{R3'}$-alkyl group, an optionally substituted -X$^{R3'}$-Aryl group; an optionally substituted -X$^{R3'}$-HET group, an optionally substituted -X$^{R3'}$-Aryl-HET group or an optionally substituted -X$^{R3'}$-HET-Aryl group, wherein:

R$^{S3'}$ is an optionally substituted alkyl group (C$_1$-C$_{10}$, preferably C$_1$-C$_6$ alkyl), an optionally substituted Aryl group or a HET group;

R$_{1'}$ is H or a C$_1$-C$_3$ alkyl group (preferably H);

V is O, S or NR$_{1'}$;

X$^{R3'}$ is -(CH$_2$)$_n$-, -(CH$_2$CH$_2$O)$_n$-, -CH$_2$)$_n$-CH(X$_v$)=CH(X$_v$)- (cis or trans), -CH$_2$)$_n$-CH≡CH-, or a C$_3$-C$_6$ cycloalkyl group, all optionally substituted;

X$_v$ is H, a halo or a C$_1$-C$_3$ alkyl group which is optionally substituted with one or two hydroxyl groups or up to three halogen groups;

Alkyl is an optionally substituted C$_1$-C$_{10}$ alkyl (preferably a C$_1$-C$_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a C$_1$-C$_3$ alkyl group, preferably methyl or a halo group, preferably F or Cl), or a group according to the chemical structure:

or an optionally substituted acetylenic group -C≡C-R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O-(C$_1$-C$_6$ alkyl) (preferably substituted with one or two hydroxyl groups or up to three halo groups) or an optionally substituted -C(O)(C$_1$-C$_6$ alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a -C(O)(C$_0$-C$_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

Y$^C$ of ULM-g through ULM-i is N or C-R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group -C≡C-R$_a$ where R$_a$ is H or a C$_1$-C$_6$ alkyl group (preferably C$_1$-C$_3$ alkyl);

R$^{PRO}$ of ULM-g through ULM-i is H, optionally substituted C$_1$-C$_6$ alkyl or an optionally substituted aryl (phenyl or napthyl), heteroaryl or heterocyclyl group selected from the group consisting of oxazole, isoxa

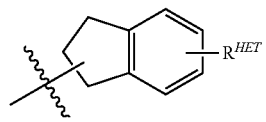 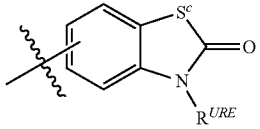 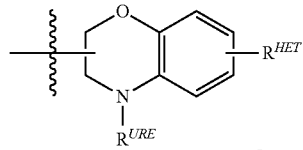

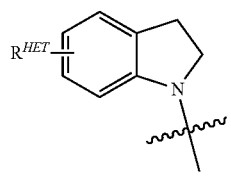 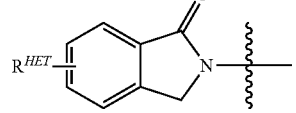 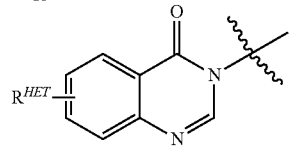

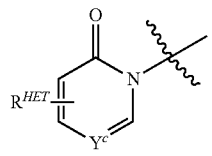 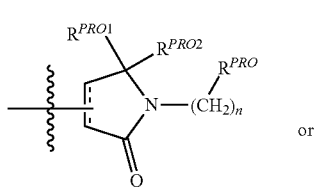 or 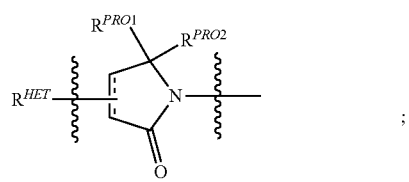 ;

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups)

zole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

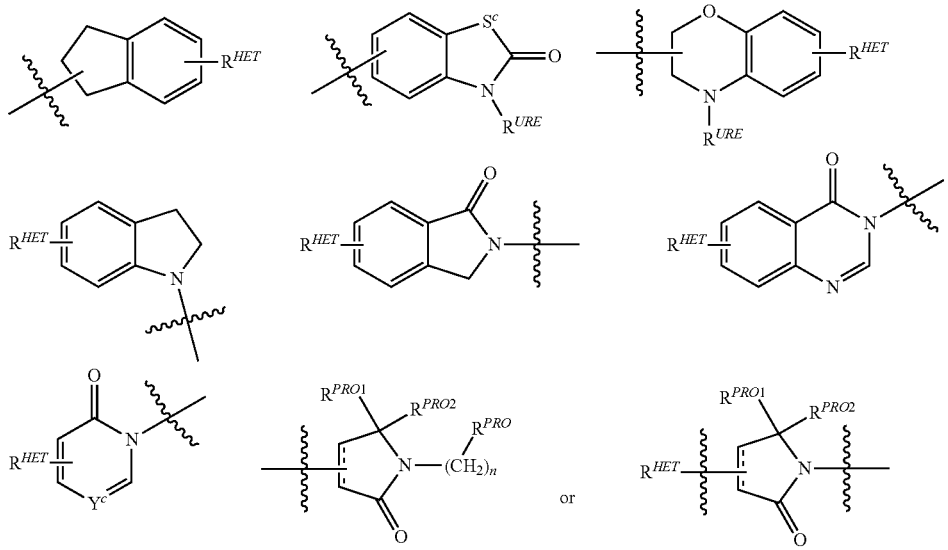

wherein:
said Aryl of ULM-g through ULM-i is phenyl which is optionally substituted with one or two substitutents, wherein said substituent(s) is preferably selected from —$(CH_2)_nOH$, $C_1$-$C_6$ alkyl which itself is further optionally substituted with CN, halo (up to three halo groups), OH, —$(CH_2)_nO(C_1$-$C_6)$alkyl, amine, mono- or di-$(C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_nOH$, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)$(C_0$-$C_6)$ alkyl, —$(CH_2)_n$—C(O)O$(C_0$-$C_6)$alkyl, —$(CH_2)_n$—OC(O)$(C_0$-$C_6)$alkyl, amine, mono- or di-$(C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—$(C_1$-$C_6)$alkyl group, a —$(V)_{m'}$—$(CH_2CH_2O)_n$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or $S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—$(C_1$-$C_6$ alkyl) (preferably substituted with one or two hydroxyl groups or up to three halo groups) or an optionally substituted —C(O)$(C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)$(C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^c$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally subsituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

(preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{UBE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclylgroup;

$R^{PRO1}$ and $R^{PRO2}$ of ULM-g through ULM-i are each independently H, an optionally subsituted $C_1$-$C_3$ alkyl group or together form a keto group;

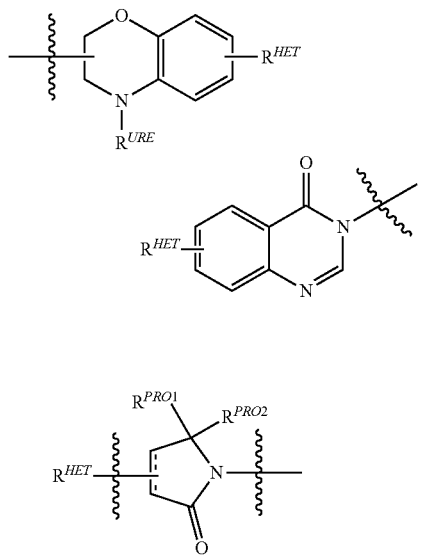

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM'group) via a linker group.

In still additional embodiments, preferred compounds include those according to the chemical structure:

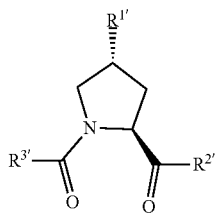

ULM-i

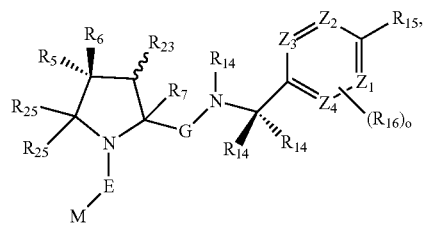

ULM-j wherein:

$R^{1'}$ of ULM-i is OH or a group which is metabolized in a patient or subject to OH;

$R^{2'}$ of ULM-i is a —NH—CH$_2$-Aryl-HET (preferably, a phenyl linked directly to a methyl substituted thiazole);

$R^{3'}$ of ULM-i is a —CHR$^{CR3'}$—NH—C(O)—R$^{3P1}$ group or a —CHR$^{CR3'}$—R$^{3P2}$ group;

R$^{CR3'}$ of ULM-i is a C$_1$-C$_4$ alkyl group, preferably methyl, isopropyl or tert-butyl;

R$^{3P1}$ of ULM-i is C$_1$-C$_3$ alkyl (preferably methyl), an optionally substituted oxetane group (preferably methyl substituted, a —(CH$_2$)$_n$OCH$_3$ group where n is 1 or 2 (preferably 2), or a

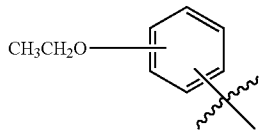

group (the ethyl ether group is preferably meta-substituted on the phenyl moiety), a morpholino grop (linked to the carbonyl at the 2- or 3-position;

R$^{3P2}$ of ULM-i is a

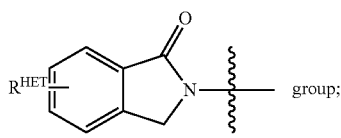

Aryl of ULM-i is phenyl;

HET of ULM-i is an optionally substituted thiazole or isothiazole; and

R$^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

wherein:

each R$_5$ and R$_6$ of ULM-j is independently OH, SH, or optionally substituted alkyl or R$_5$, R$_6$, and the carbon atom to which they are attached form a carbonyl;

R$_7$ of ULM-j is H or optionally substituted alkyl;

E of ULM-j is a bond, C=O, or C=S;

G of ULM-j is a bond, optionally substituted alkyl, —COOH or C=J;

J of ULM-j is O or N—R$_8$;

R$_8$ of ULM-j is H, CN, optionally substituted alkyl or optionally substituted alkoxy;

M of ULM-j is optionally substituted aryl, optionally substituted heteroaryl, optionally substituted heterocyclylor

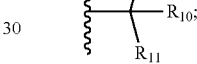

each R$_9$ and R$_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or R$_9$, R$_{10}$, and the carbon atom to which they are attached form an optionally substituted cycloalkyl;

R$_{11}$ of ULM-j is optionally substituted heterocyclyl, optionally substituted alkoxy, optionally substituted heteroaryl, optionally substituted aryl, or

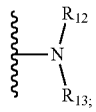

R$_{12}$ of ULM-j is H or optionally substituted alkyl;

R$_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate, each R$_{14}$ of ULM-j is independently H, haloalkyl, optionally substituted cycloalkyl, optionally substituted alkyl or optionally substituted heterocyclyl;

R$_{15}$ of ULM-j is H, CN, optionally substituted heteroaryl, haloalkyl, optionally substituted aryl, optionally substituted alkoxy, or optionally substituted heterocyclyl;

each R$_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

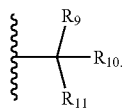

In certain embodiments, wherein E of ULM-j is C=O, $R_{11}$ is optionally substituted heterocyclylor

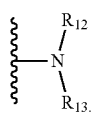

and M is

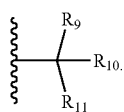

In certain embodiments, wherein E of ULM-j is C=O, M is

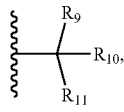

and $R_{11}$ is

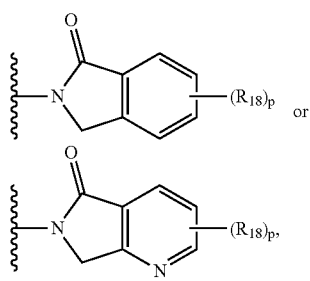

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

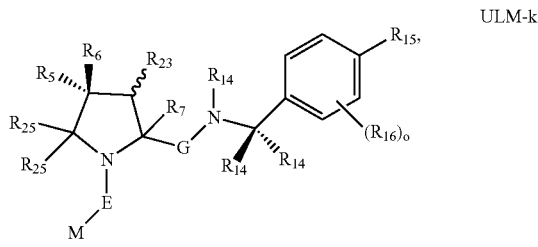

wherein:
G of ULM-k is C=J, J is O;
$R_7$ of ULM-k is H;
each $R_{14}$ of ULM-k is H;
o of ULM-k is 0;
$R_{15}$ of ULM-k is

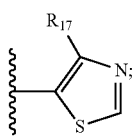

and
$R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

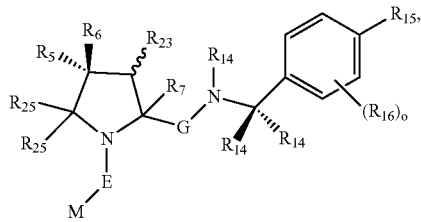

wherein:
G of ULM-k is C=J, J is O;
$R_7$ of ULM-k is H;
each $R_{14}$ of ULM-k is H;
o of ULM-k is 0; and
$R_{15}$ of ULM-k is selected from the group consisting of:

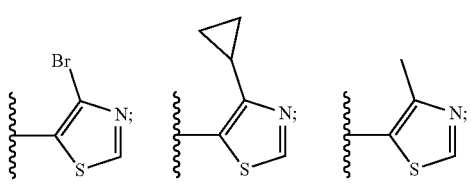

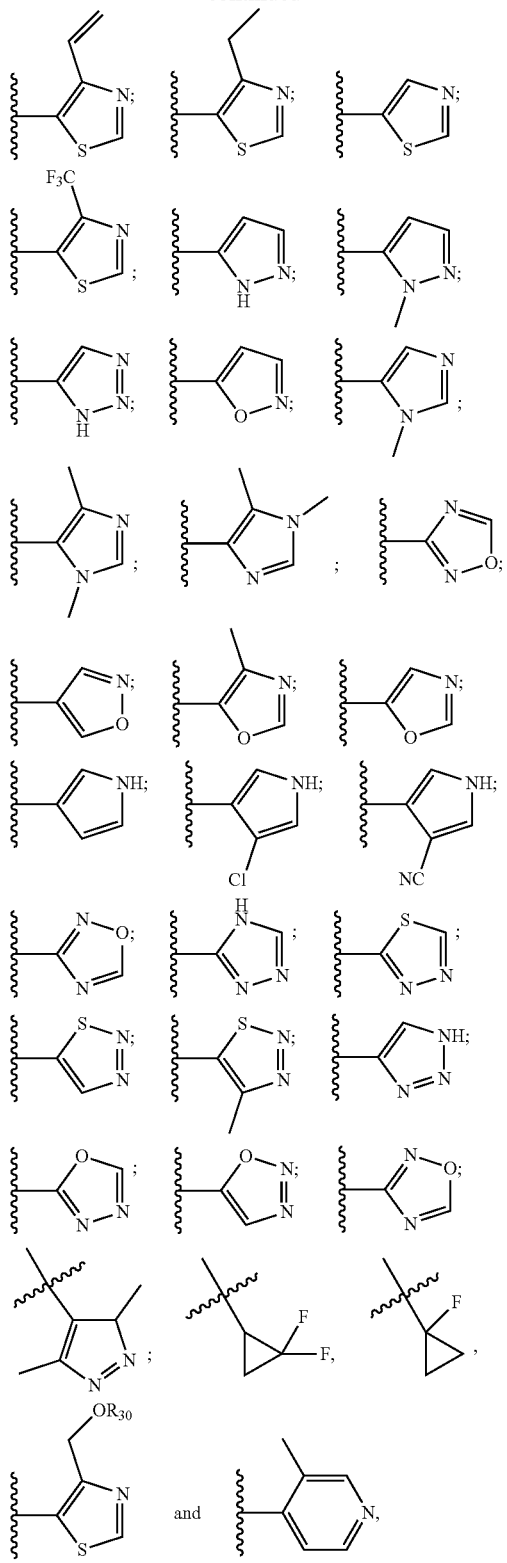
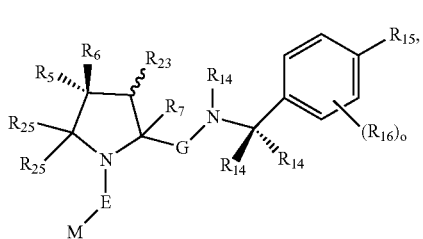
wherein:
E of ULM-k is C=O;
M of ULM-k is
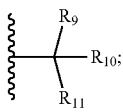
and
$R_{11}$ of ULM-k is selected from the group consisting of:
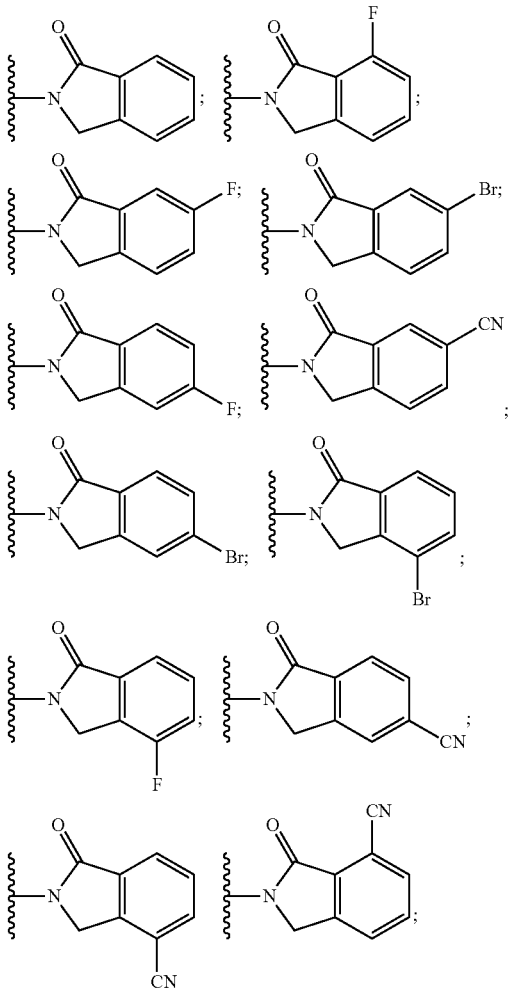
wherein $R_{30}$ of ULM-k is H or an optionally substituted alkyl.
In other embodiments, ULM and where present, ULM', are each independently a group according to the chemical structure:

-continued

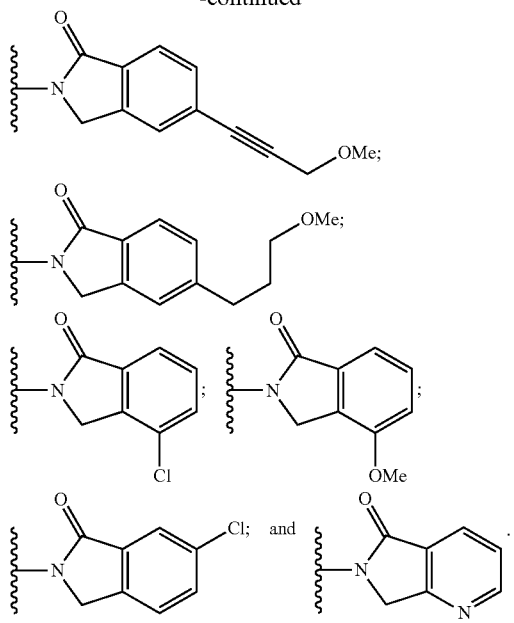

In still other embodiments, a compound of the chemical structure,

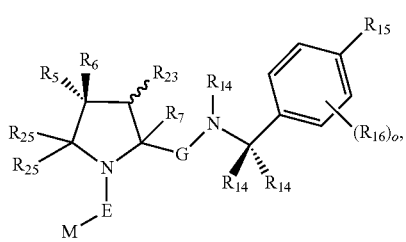

ULM-k
wherein E of ULM-k is C=O;
R$_{11}$ of ULM-k is

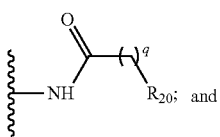

and
M of ULM-k is

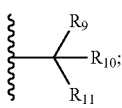

q of ULM-k is 1 or 2;
R$_{20}$ of ULM-k is H, optionally substituted alkyl, optionally substituted cycloalkyl, optionally substituted aryl, or

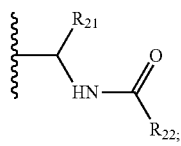

R$_{21}$ of ULM-k is H or optionally substituted alkyl; and
R$_{22}$ of ULM-k is H, optionally substituted alkyl, optionally substituted alkoxy, or haloalkyl.

In any embodiment described herein, R$_{11}$ of ULM-j or ULM-k is selected from the group consisting of:

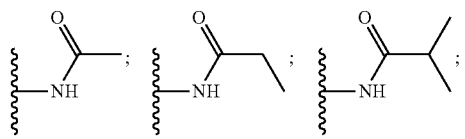

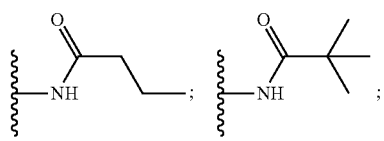

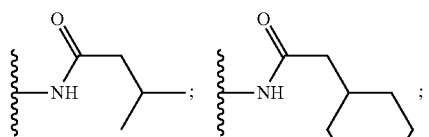

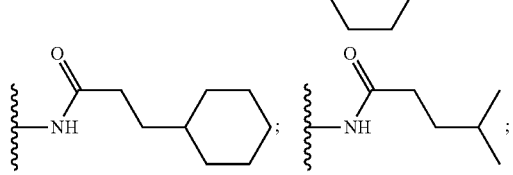

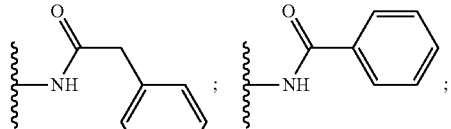

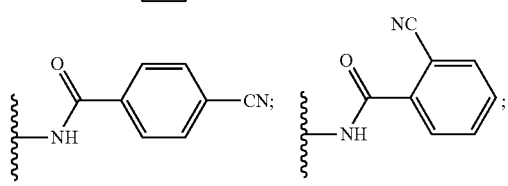

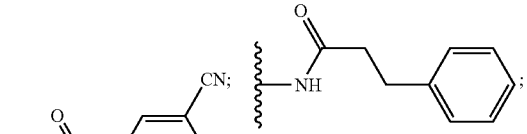

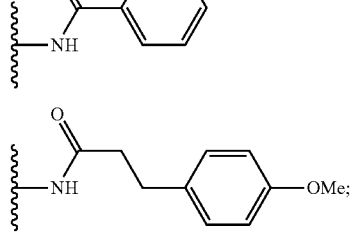

107
-continued
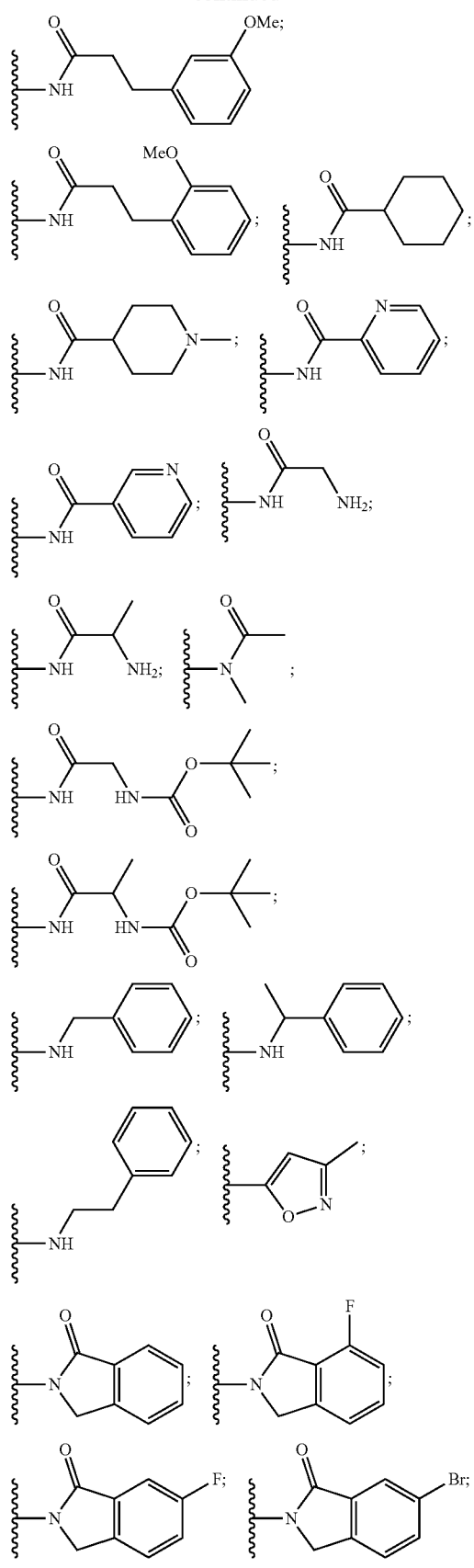
108
-continued
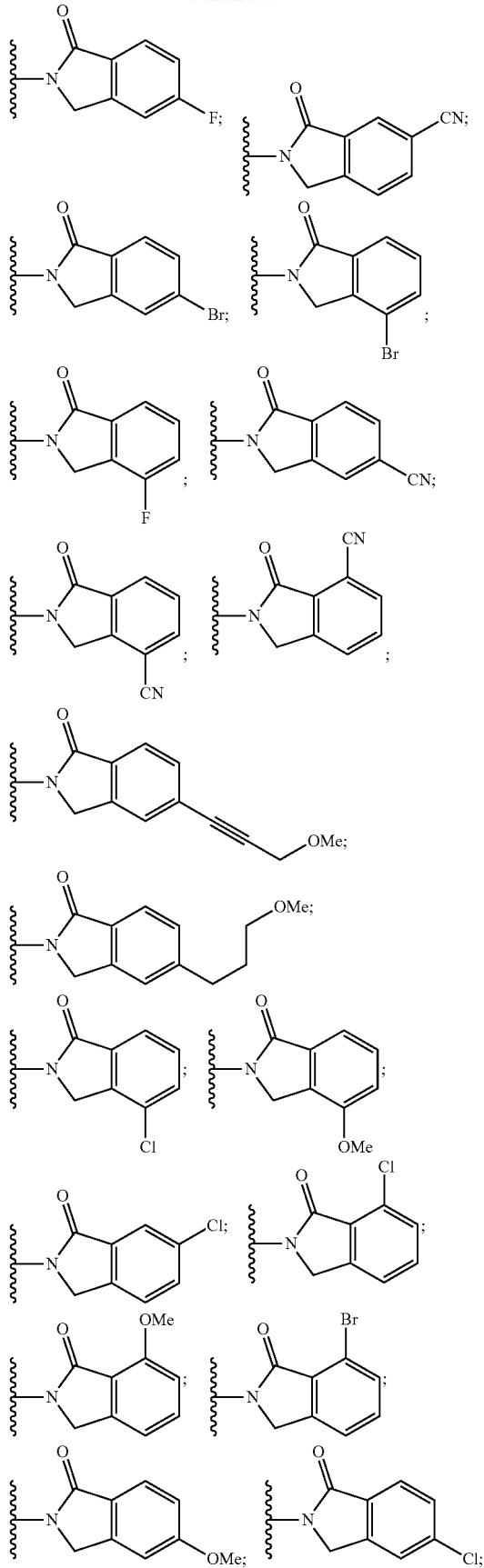

-continued
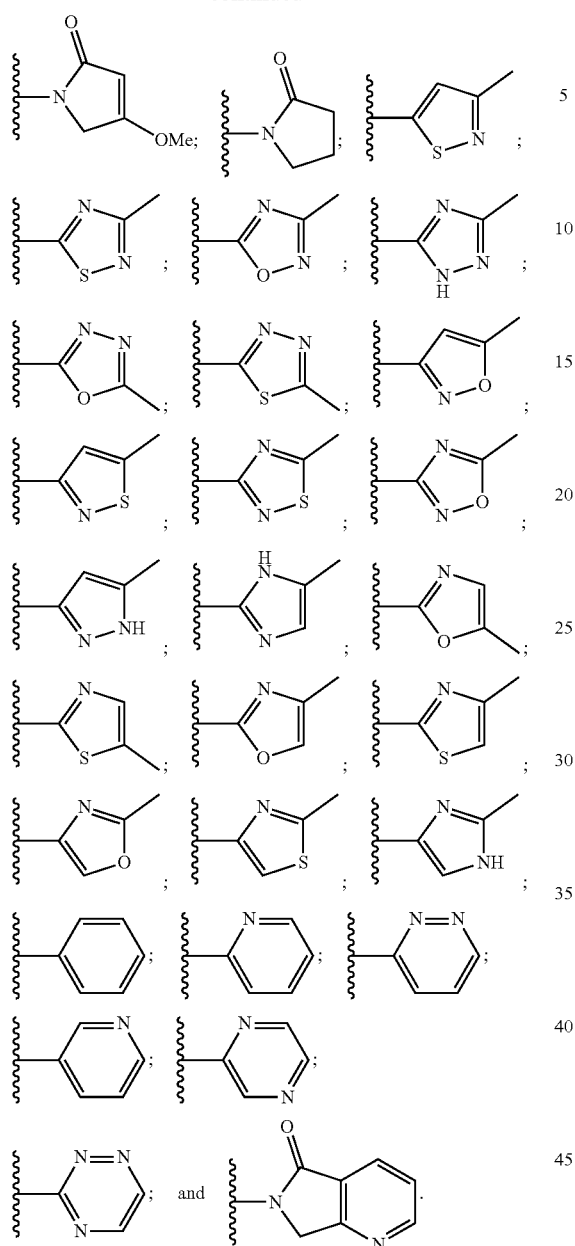
In certain embodiments, $R_{11}$ of ULM-j or ULM-k is selected from the group consisting of:
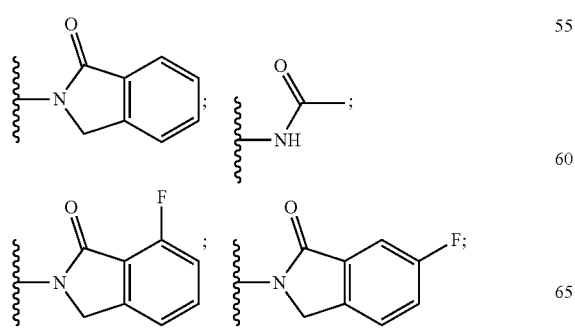
-continued
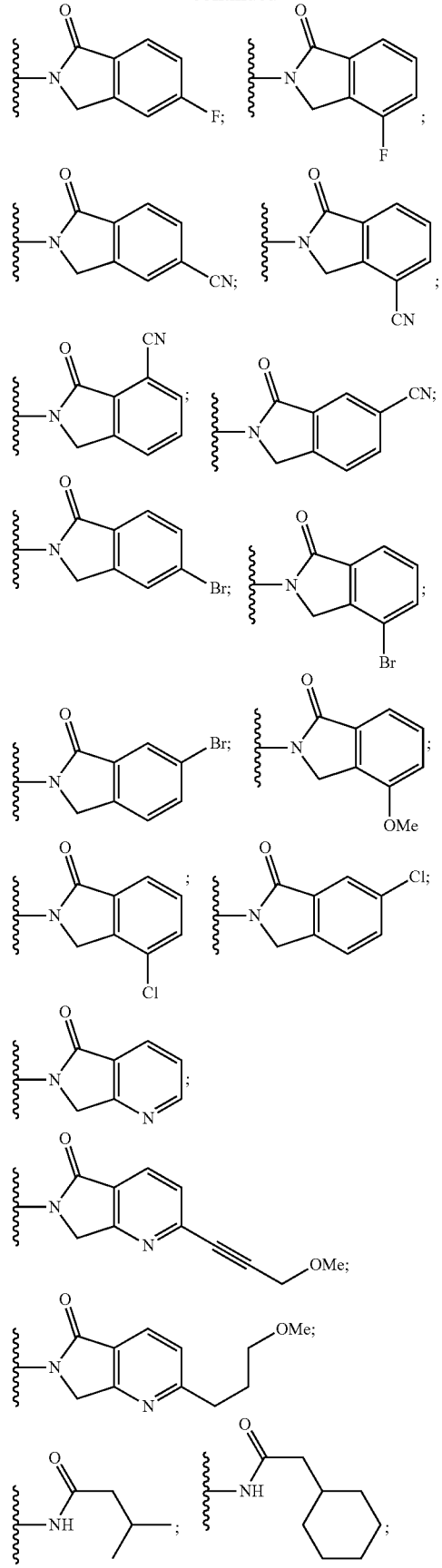

111
-continued

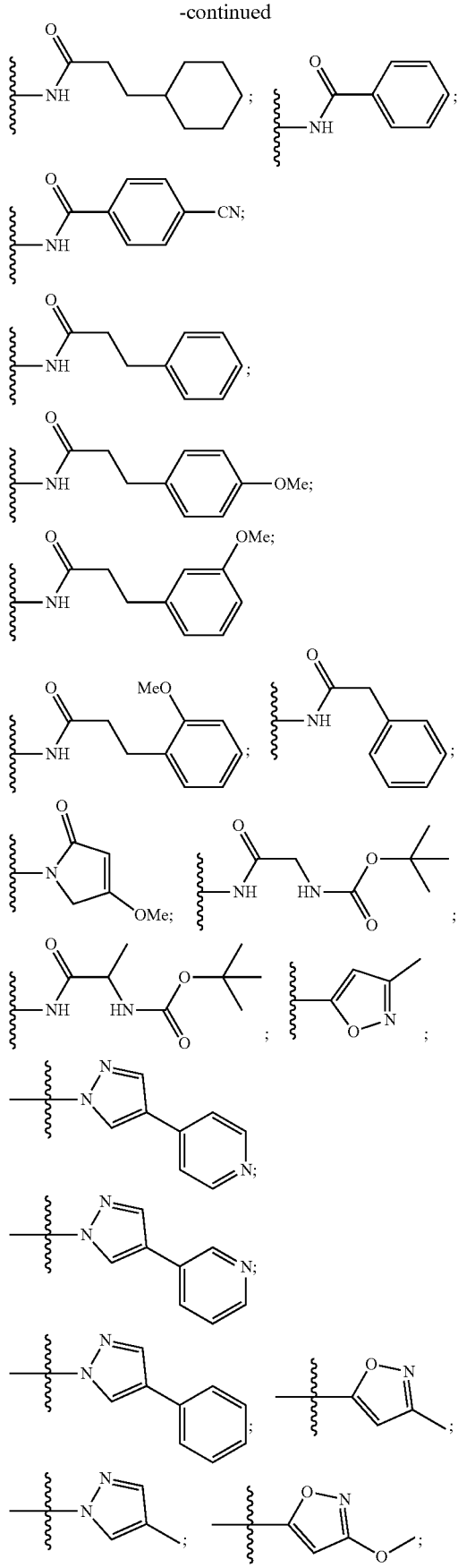

112
-continued

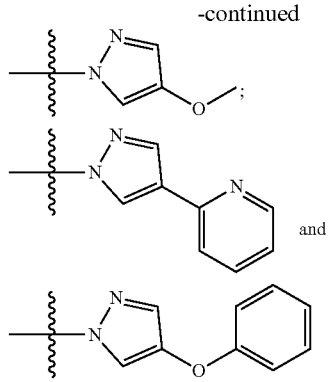

In certain embodiments, ULM (or when present ULM') is a group according to the chemical structure:

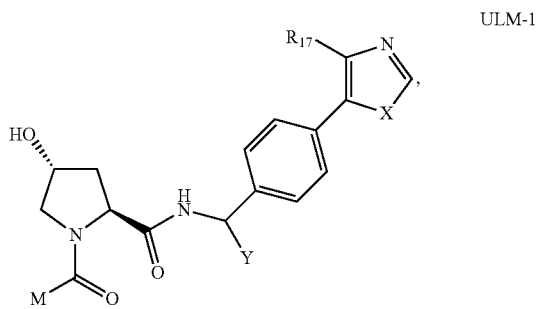

ULM-1 wherein:
X of ULM-1 is O or S;
Y of ULM-1 is H, methyl or ethyl;
$R_{17}$ of ULM-1 is H, methyl, ethyl, hydoxymethyl or cyclopropyl;
M of ULM-1 is optionally substituted aryl, optionally substituted heteroaryl,

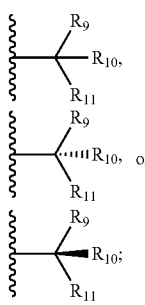

$R_9$ of ULM-1 is H;
$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;
$R_{11}$ of ULM-1 is optionally substituted heteroaromatic, optionally substituted heterocyclyl, optionally substituted aryl or

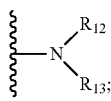

$R_{12}$ of ULM-1 is H or optionally substituted alkyl; and
$R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

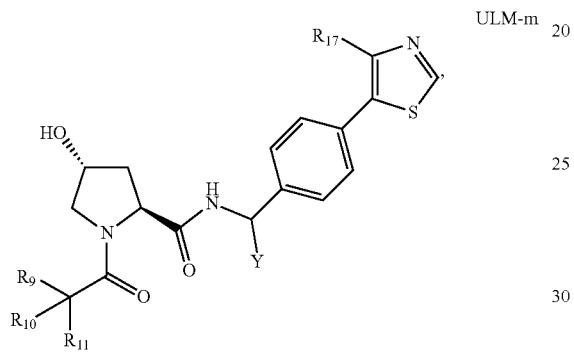

ULM-m wherein:
Y of ULM-m is H, methyol or ethyl
$R_9$ of ULM-m is H;
$R_{10}$ is isopropyl, tert-butyl, sec-butyl, cyclopentyl, or cyclohexyl;
$R_{11}$ of ULM-m is optionally substituted amide, optionally substituted isoindolinone, optionally substituted isooxazole, optionally substituted heterocyclyls.

In other preferred embodiments of the disclosure, ULM and where present, ULM', are each independently a group according to the chemical structure:

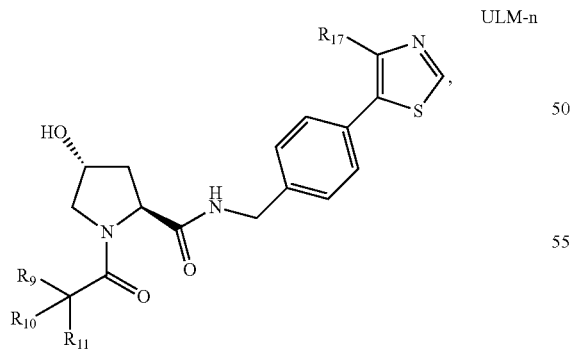

ULM-n wherein:
$R_{17}$ of ULM-n is methyl, ethyl, or cyclopropyl; and
$R_9$, $R_{10}$, and $R_{11}$ of ULM-n are as defined above. In other instances, $R_9$ is H; and
$R_{10}$ of ULM-n is H, alkyl, or or cycloalkyl (preferably, isopropyl, tert-butyl, sec-butyl, cyclopentyl, or cyclohexyl).

In other preferred embodiments of the disclosure, ULM and where present, ULM', are each independently a group according to the chemical structure:

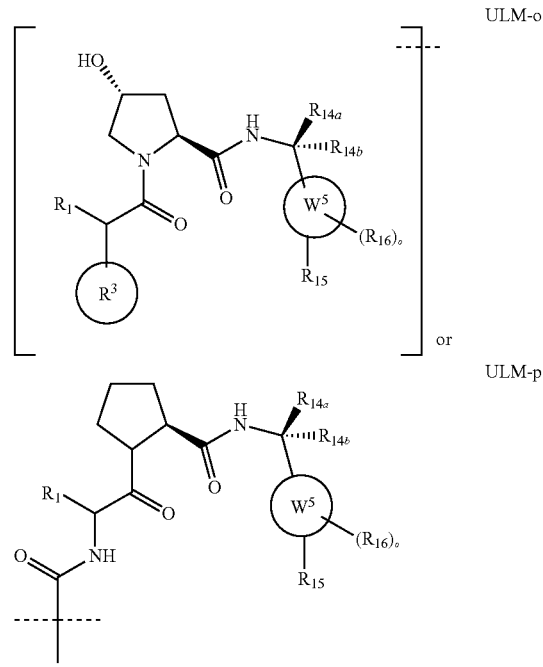

or a pharmaceutically acceptable salt thereof, wherein:
$R_1$ is H, optionally substituted alkyl or optionally substituted cycloalkyl;
$R_3$ is an optionally substituted 5-6 membered heteroaryl;
$W^5$ is optionally substituted phenyl, optionally substituted napthyl or optionally substituted pyridinyl;
one of $R_{14a}$ and $R_{14b}$ is H, optionally substituted alkyl, optionally substituted haloalkyl (e.g., fluoroalkyl), optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;
$R_{15}$ is CN, optionally substituted fluoroalkyl,

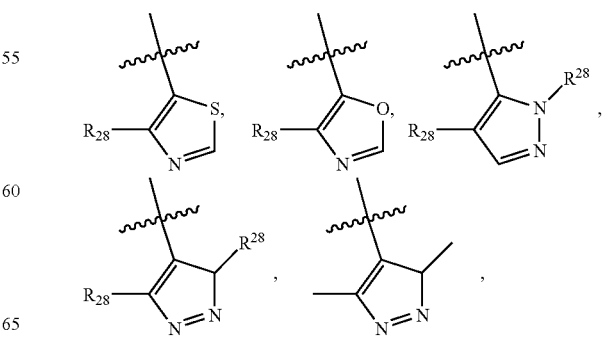

optionally substituted

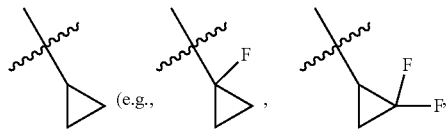
(e.g., ),

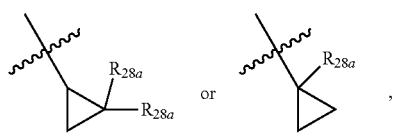

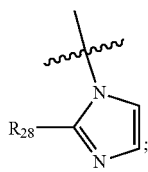

wherein R$_{28a}$ is halo, optionally substituted alkyl or fluoroalkyl), or

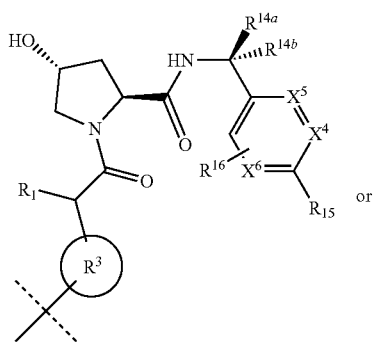

each R$_{16}$ is independently selected from halo, CN, optionally substituted alkyl, optionally substituted haloalkyl, hydroxy, or haloalkoxy;

each R$_{26}$ is independently H, optionally substituted alkyl or NR$_{27a}$R$_{27b}$;

each R$_{27a}$ and R$_{27b}$ is independently H, optionally substituted alkyl, or R$_{27a}$ and R$_{27b}$ together with the nitrogen atom to which they are attached form a 4-6 membered heterocyclyl;

R$_{28}$ is H, optionally substituted alkyl, optionally substituted alkoxy, optionally substituted heteroalkyl, optionally substituted alkylamine, optionally substituted hydroxyalkyl, amine, optionally substituted alkynyl, or optionally substituted cycloalkyl; and o is 0, 1 or 2.

In any of the aspects or embodiments described herein, the ULM is of the formula:

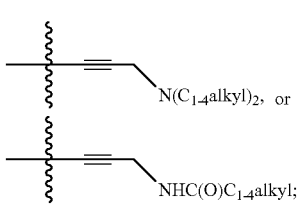

-continued

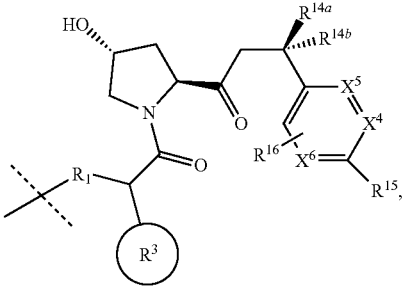

wherein:
each of X$^4$, X$^5$, and X$^6$ is selected from CH and N, wherein no more than 2 are N;
R$^1$ is C1-6 alkyl;
one of R$^{14a}$ and R$^{14b}$ is H, optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, COR$^{26}$, CONR$^{27a}$R$^{27b}$, NHCOR$^{26}$, or NHCH$_3$COR$^{26}$; and the other of R$^{14a}$ and R$^{14b}$ is H; or R$^{14a}$ and R$^{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;
each R$_{27a}$ and R$_{27b}$ is independently H or C$_{1-6}$ alkyl;
q is 1, 2, 3 or 4;
R$^{15}$ is,

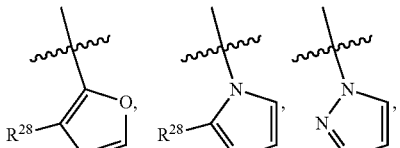

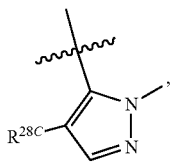

or CN;
R$^{28}$ is H, methyl, CH$_2$N(Me)$_2$, CH$_2$OH, CH$_2$O(C$_{1-4}$alkyl), CH$_2$NHC(O)C$_{1-4}$alkyl, NH$_2$,

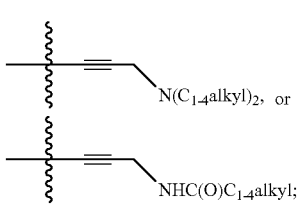

R$^{28C}$ is H, methyl, fluoro, or chloro; and
R$^{16}$ is H, C$_{1-4}$alkyl, fluoro, chloro, CN, or C$_{1-4}$alkoxy.

In any aspect or embodiment described herein, R$^{14a}$ and R$^{14b}$ are selected from: H, C$_{1-4}$ alkyl, C$_{1-4}$ cycloalkyl, C$_{1-4}$ haloalkyl, $C_{1-4}$ hydroxyalkyl, $C_{1-4}$ alkyloxyalkyl, $C_{1-4}$ alkyl-$NR_{27a}R_{27b}$ and $CONR_{27a}R_{27b}$.

In any aspect or embodiment described herein, at least one of $R^{14a}$ and $R^{14b}$ is H (e.g., both $R^{14a}$ and $R^{14b}$ are H).

In any aspect or embodiment described herein, at least one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$. Alternatively, in any aspect or embodiment described herein, one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H.

In any aspect or embodiment described herein, $R^{14a}$ and $R^{14b}$ together with the carbon atom to which they are attached form

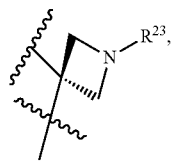

wherein $R^{23}$ is selected from H, $C_{1-4}$alkyl, —$C(O)C_{1-4}$alkyl.

In other preferred embodiments of the disclosure, ULM and where present, ULM', are each independently a group according to the chemical structure:

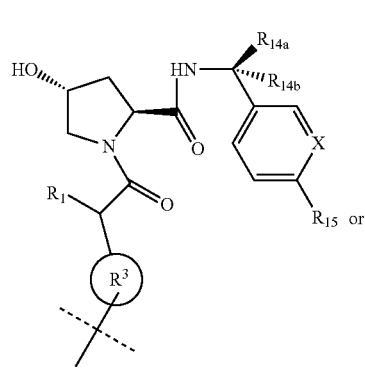
ULM-q

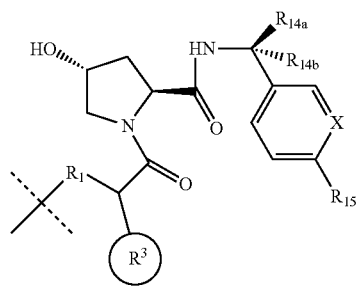
ULM-r or a pharmaceutically acceptable salt thereof, wherein:

X is CH or N; and $R_1$, $R_3$, $R_{14a}$, $R_{14b}$, and $R_{15}$ of ULM-q and ULM-r are the same as defined for ULM-o and ULM-p.

In any of the aspects or embodiments described herein, $R_1$ is $C_{1-6}$ alkyl.

In any of the aspects or embodiments described herein, one of $R_{14a}$ and $R_{14b}$ is H, $C_{1-6}$ alkyl, $C_{1-6}$ haloalkyl, optionally substitute $C_{1-4}$ alkylamine, $C_{1-6}$ alkoxy, $(CH_2)_qC_{1-6}$ alkoxy, $(CH_2)_qC_{1-6}$ alkoxy-$C_3$-$C_7$ heterocycloalkyl, $(CH_2)_qOH$, $(CH_2)_qNR_{27a}R_{27b}$, $(CH_2)_qNHCOC_{1-6}$ alkyl, $C_{3-6}$ cycloalkyl, or $NR_{27a}R_{27b}$; each $R_{26}$ is independently H, $C_{1-6}$ alkyl or $NR_{27a}R_{27b}$; each $R_{27a}$ and $R_{27b}$ is independently H or $C_{1-6}$ alkyl; and q is 1, 2, 3 or 4.

In any of the aspects or embodiments described herein, one of $R_{14a}$ and $R_{14b}$ is H, $C_{1-4}$ alkyl, $C_{1-4}$ haloalkyl, $C_{1-4}$ alkoxy, optionally substituted $C_{1-4}$ alkylamine, $(CH_2)_qC_{1-6}$ alkoxy, $(CH_2)_qC_{1-6}$ alkoxy-$C_3$-$C_7$ heterocycloalkyl, $(CH_2)_qOH$, $(CH_2)_qNR_{27a}R_{27b}$, $(CH_2)_qNHCOC_{1-6}$ alkyl, $C_{3-6}$ cycloalkyl, or $NR_{27a}R_{27b}$; each $R_{26}$ is independently H, $C_{1-4}$ alkyl or $NR_{27a}R_{27b}$; each $R_{27a}$ and $R_{27b}$ is independently H or $C_{1-4}$ alkyl; and q is 1 or 2.

In any of the aspects or embodiments described herein, $R_{28}$ is $C_{1-6}$ alkyl, $C_{3-6}$ cycloalkyl, $C_{1-6}$ haloalkyl, $(CH_2)_qOC_{1-6}$alkyl, $(CH_2)_qOH$, $(CH_2)_qNR_{27a}R_{27b}$, $(CH_2)_qNHCOC_{1-6}$ alkyl, or

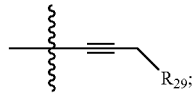

$R_{29}$ is H, $C_{1-6}$ alkyl, $NR_{27a}R_{27b}$ or $_qNHCOC_{1-6}$ alkyl; and wherein q is 1 or 2.

In any of the aspects or embodiments described herein, $R^3$ is isoxazolyl, 4-chloroisoxazolyl, 4-fluoroisoxazolyl, or pyrazolyl. In any of the aspects or embodiments described herein, X is CH.

In any aspect or embodiment described herein, the ULM is according to the formula:

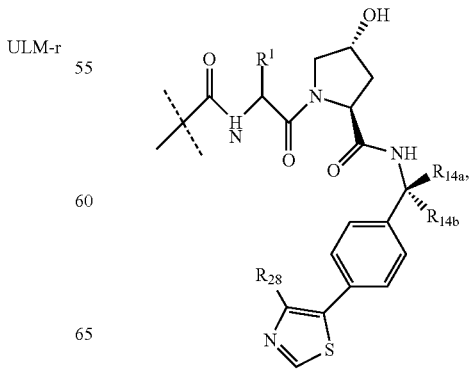

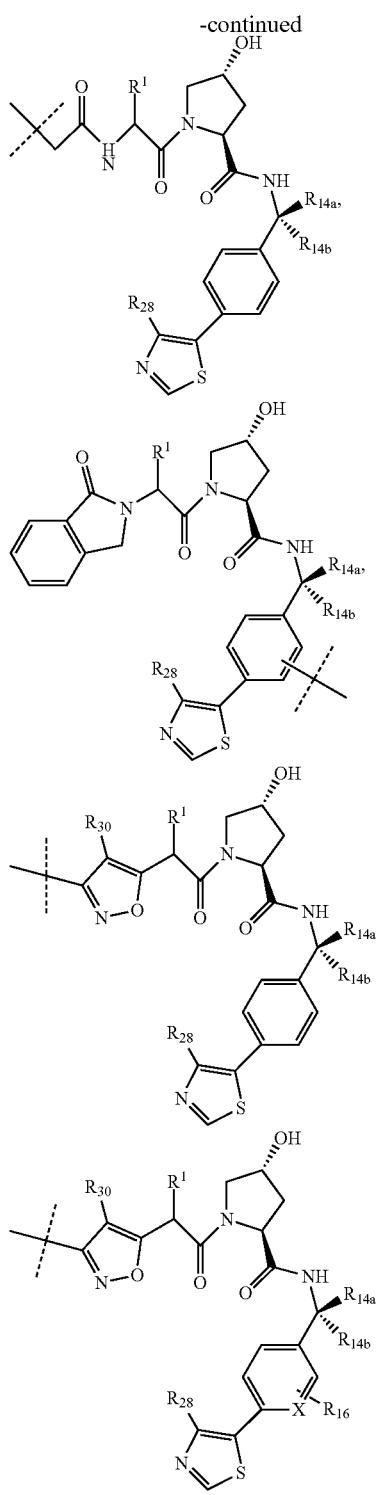

In any of the aspects or embodiments described herein, the ULM is according to the formula:
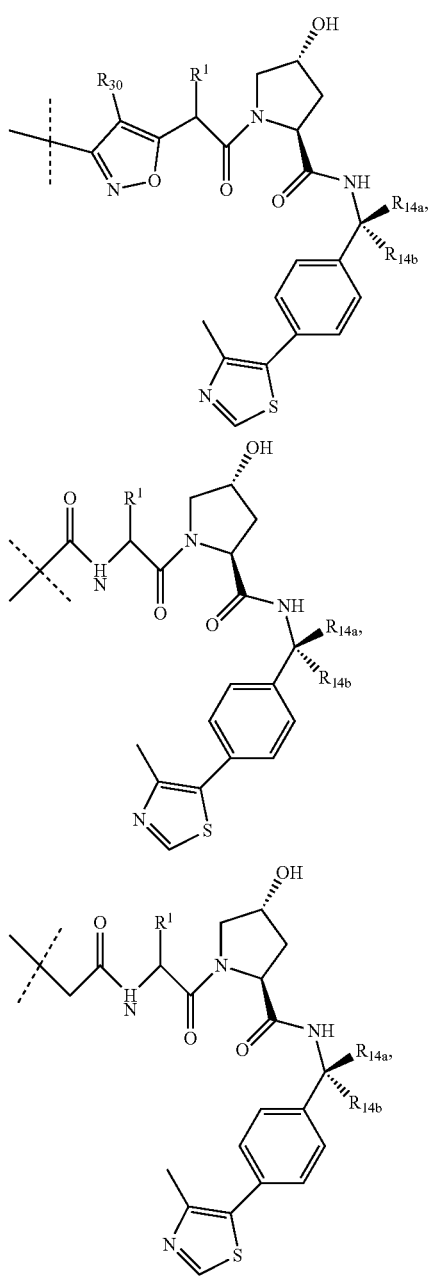
or a pharmaceutically acceptable salt thereof, wherein:
R$_1$, R$_{14a}$ and R$_{14b}$ are as described herein;
X is CH or N;
R$_{30}$ is H, F or Cl;
R$^{16}$ is H, C$_{1-4}$ alkyl, fluoro, chloro, CN, or C$_{1-4}$alkoxy; and
R$_{28}$ is H, methyl, CH$_2$N(Me)$_2$, CH$_2$OH, CH$_2$O(C$_{1-4}$alkyl), CH$_2$NHC(O)C$_{1-4}$alkyl, NH$_2$,

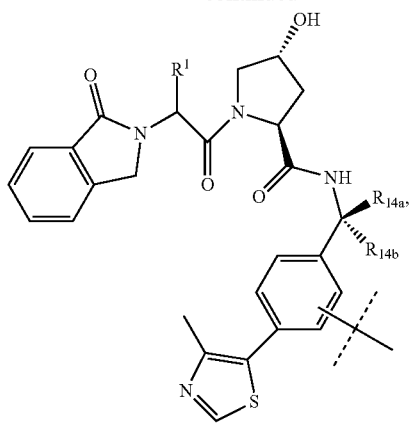

or a pharmaceutically acceptable salt thereof, wherein:

each of $R_1$, $R_{14a}$, $R_{14b}$ are as described herein; and $R_{30}$ is H, F or Cl.

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

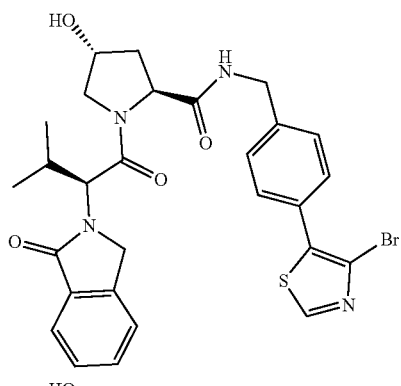

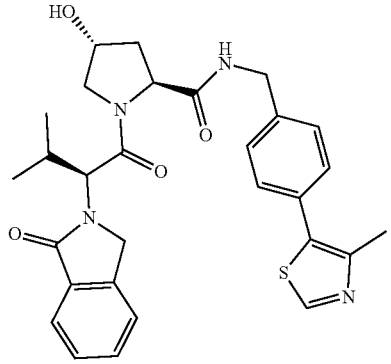

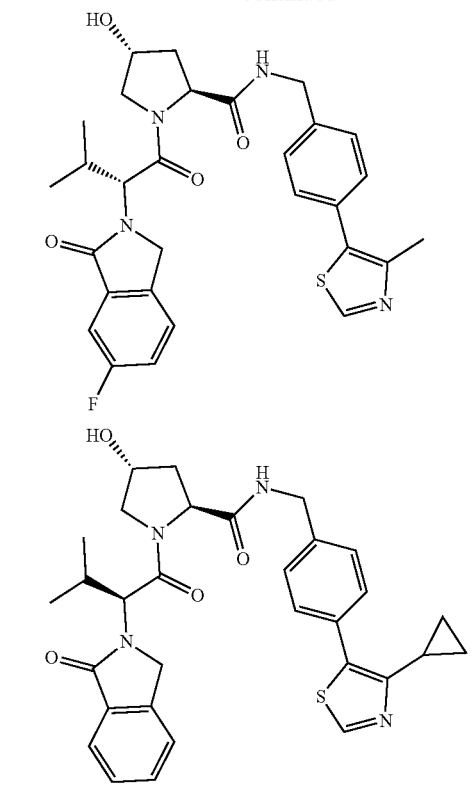

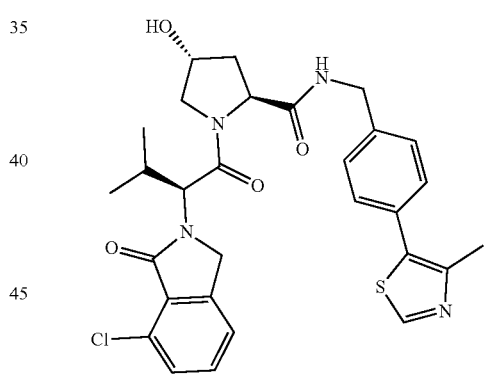

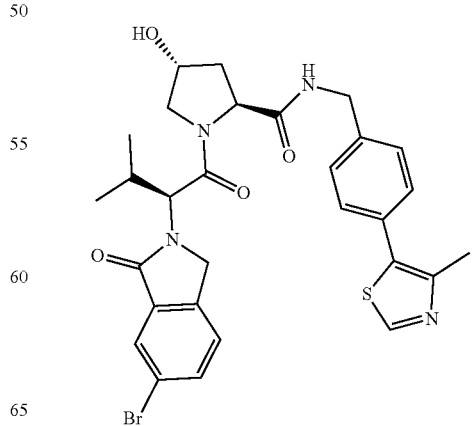

123
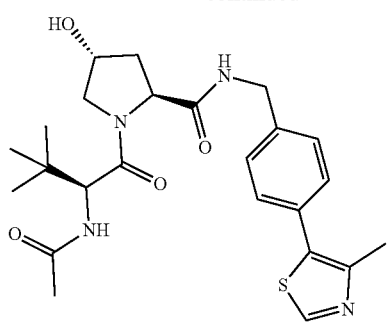
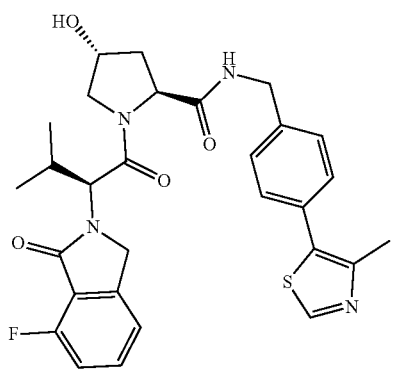
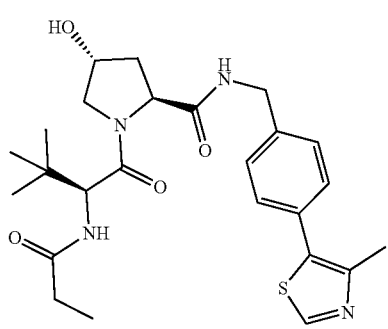
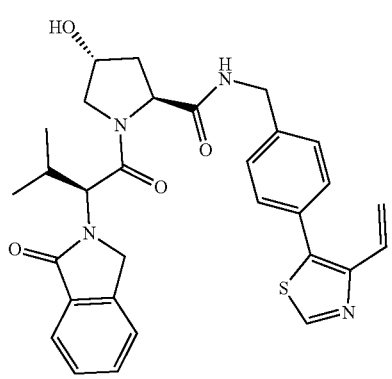
124
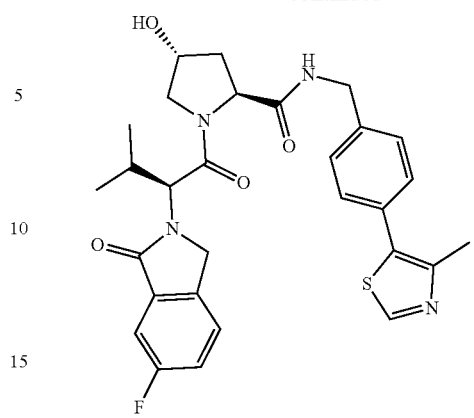
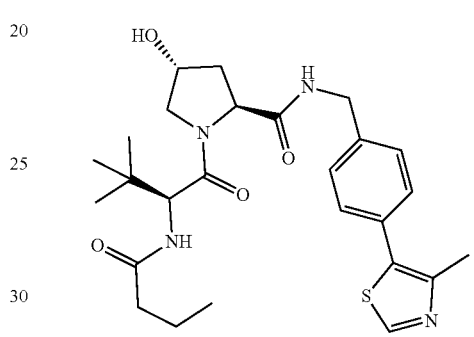
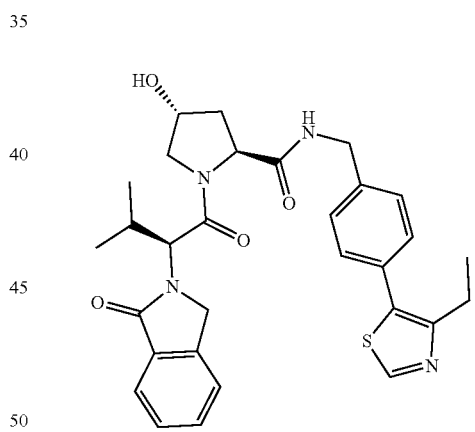
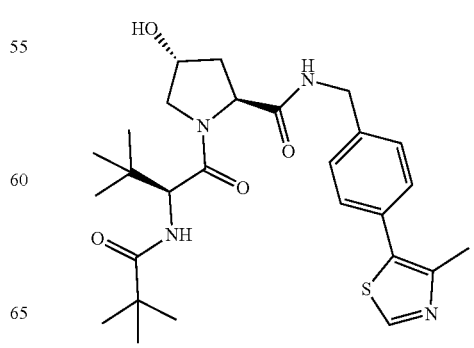

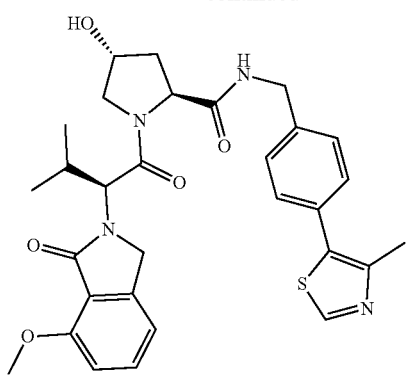
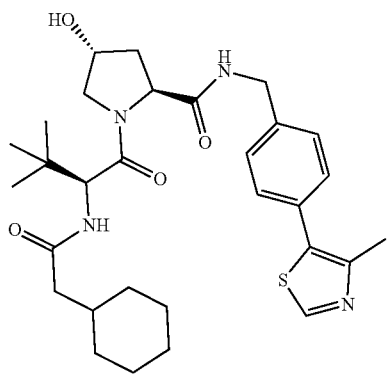
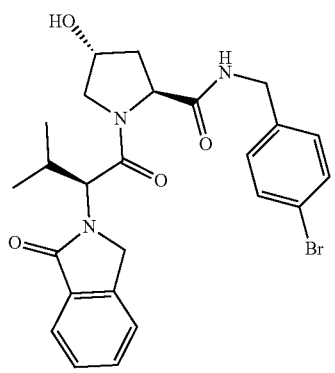
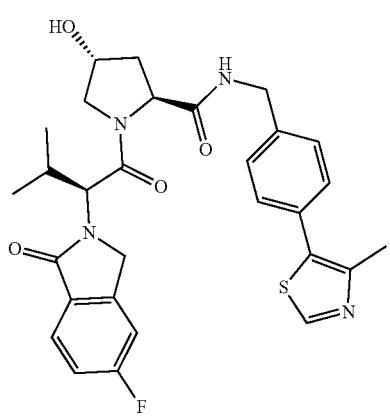
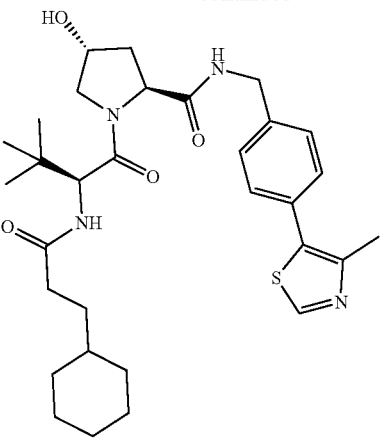
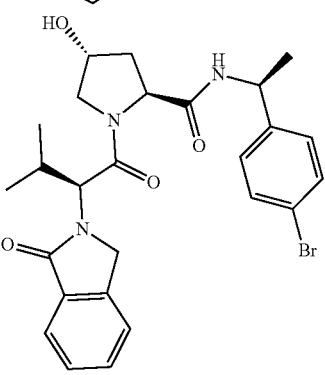
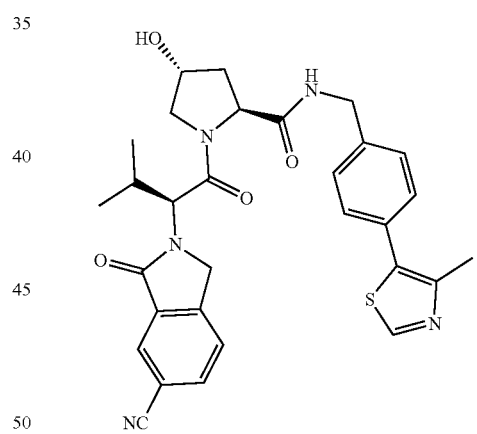
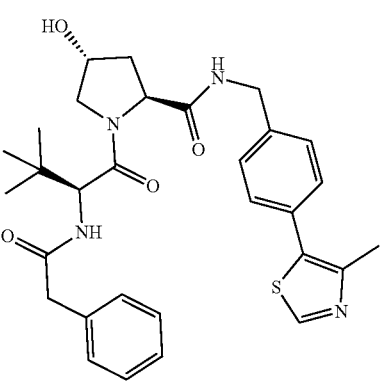

127
-continued
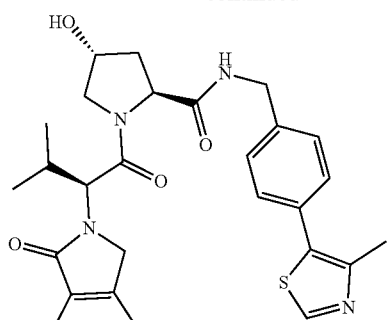
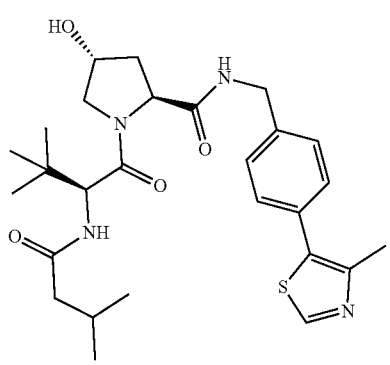
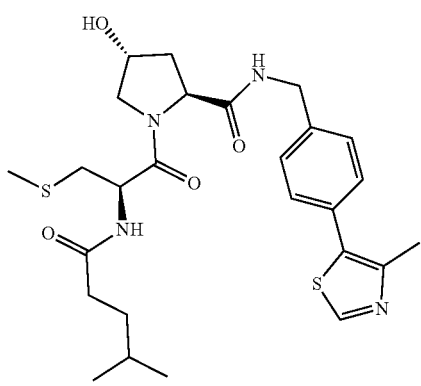
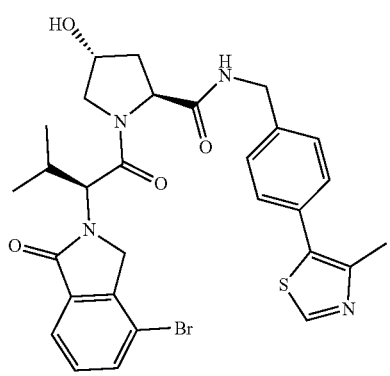
128
-continued
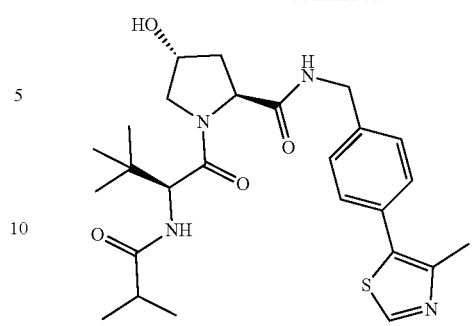
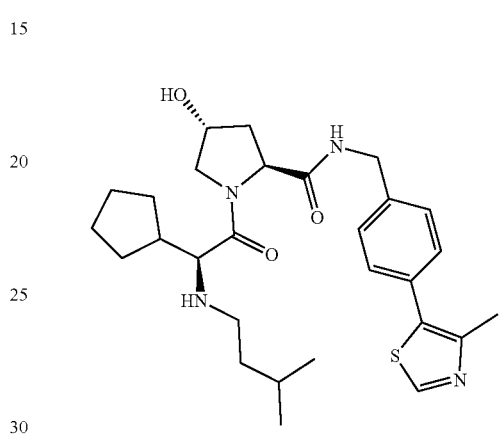
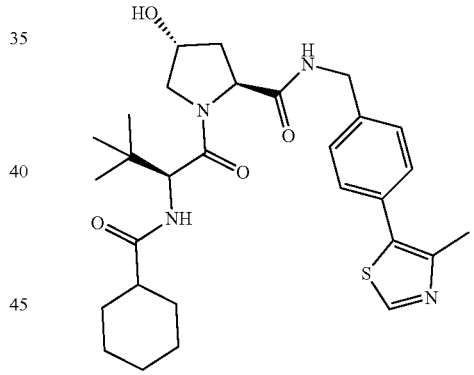
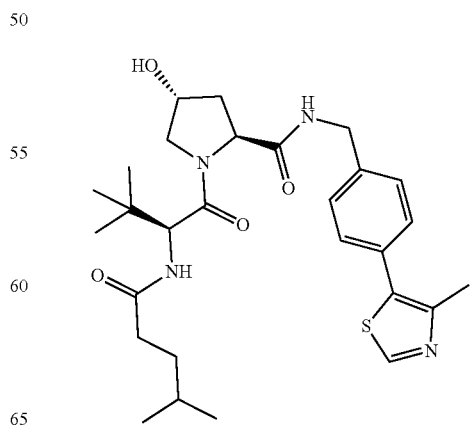

129
-continued
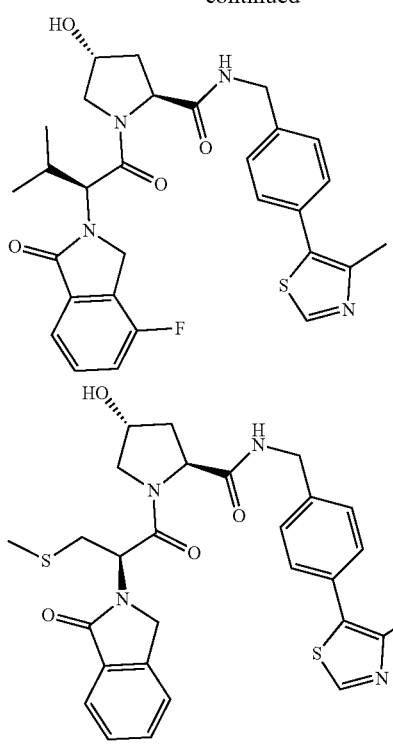
130
-continued
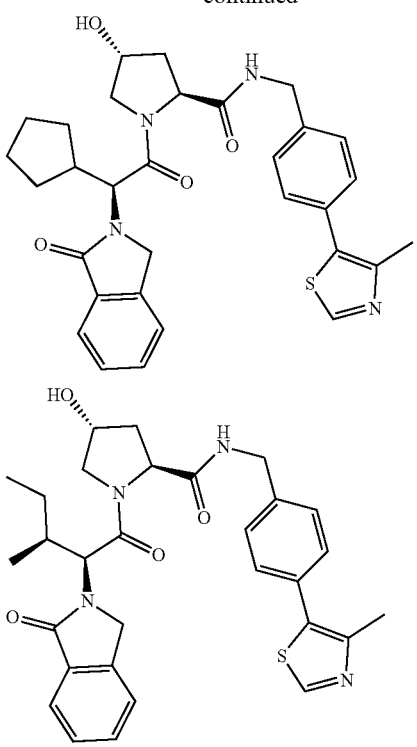
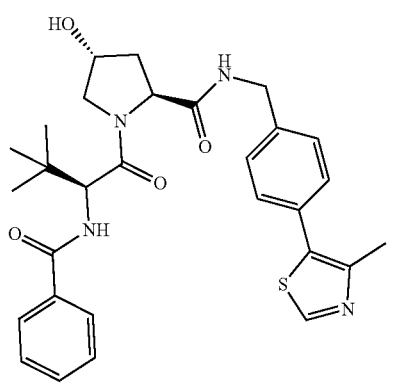
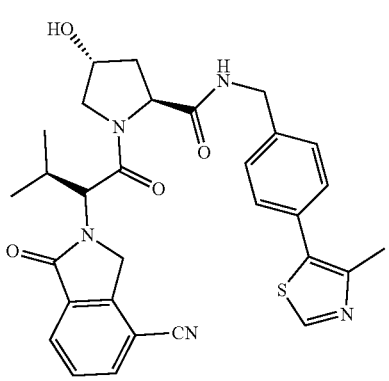
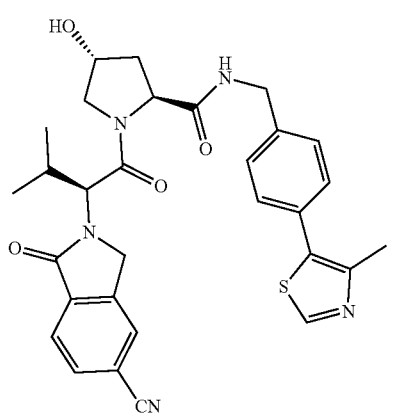
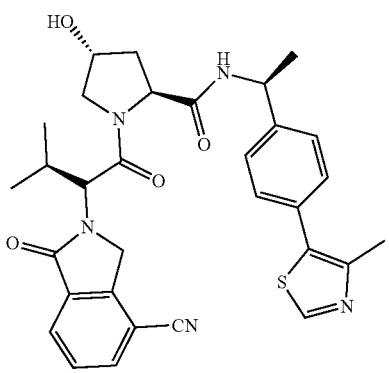

131
-continued
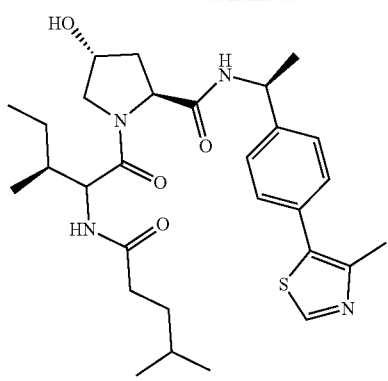 [SMILES: CC[C@H](C)C(NC(=O)CCC(C)C)C(=O)N1C[C@H](O)C[C@H]1C(=O)N[C@@H](C)c1ccc(-c2scnc2C)cc1]
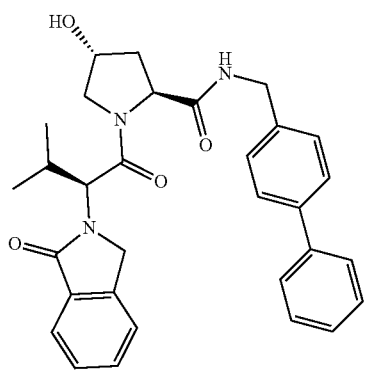
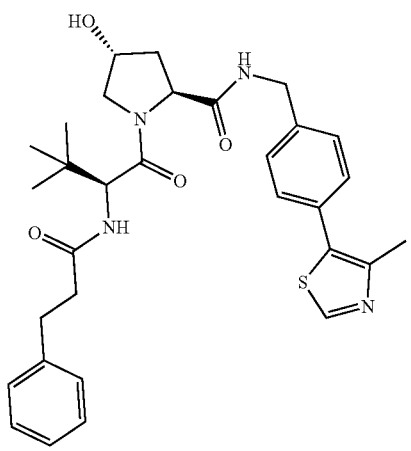
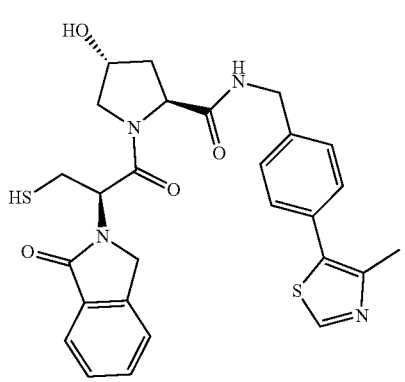
132
-continued
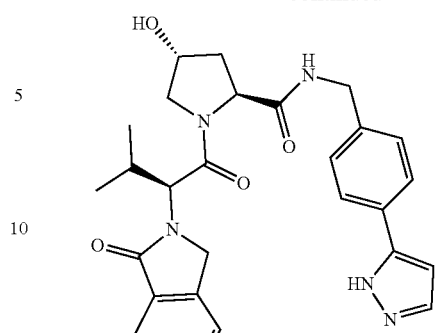
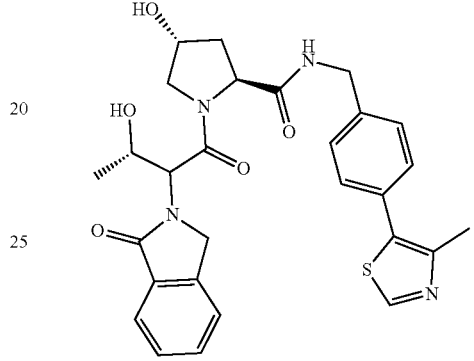
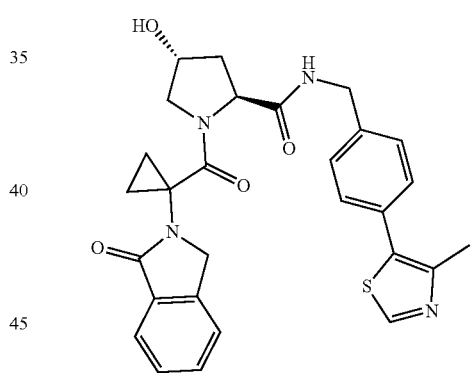
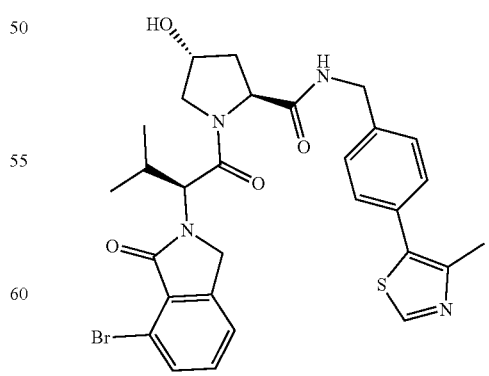

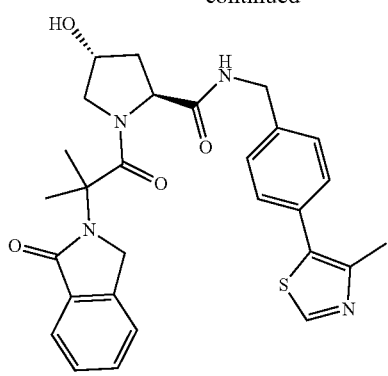
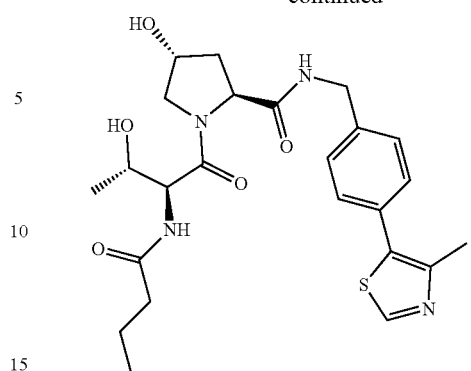
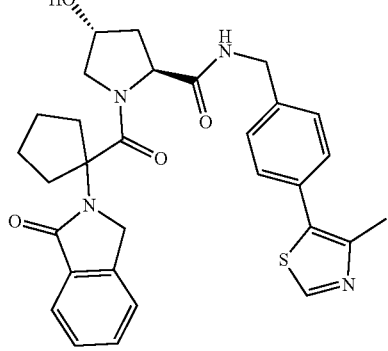
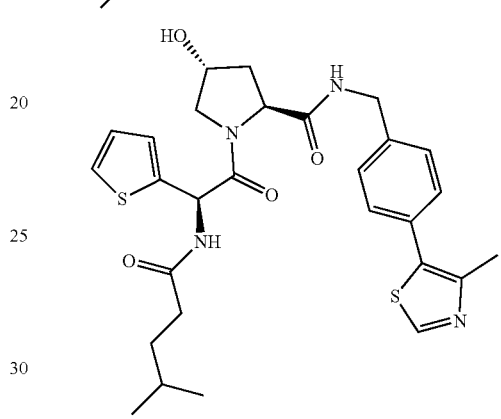
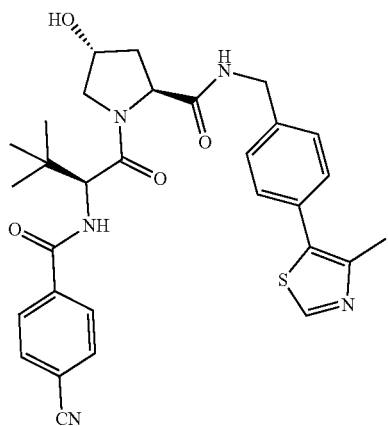
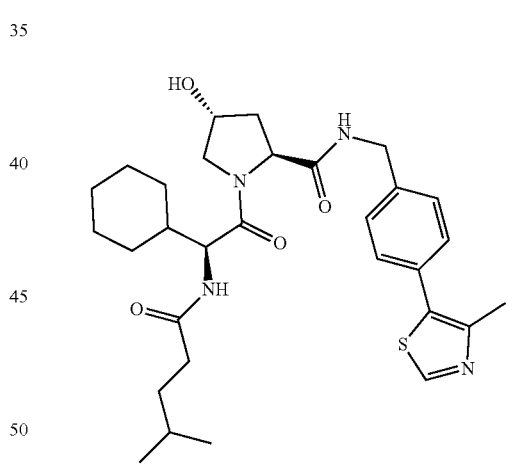
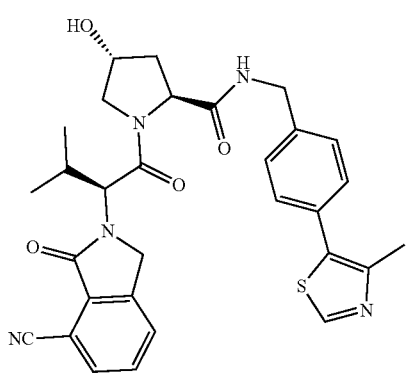
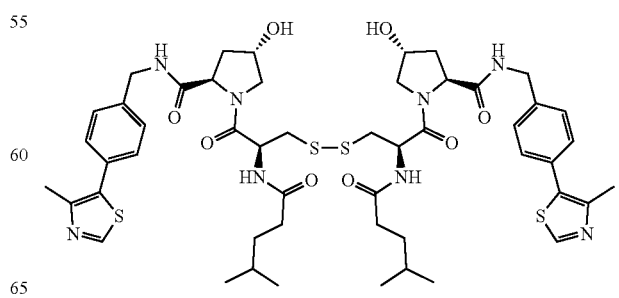

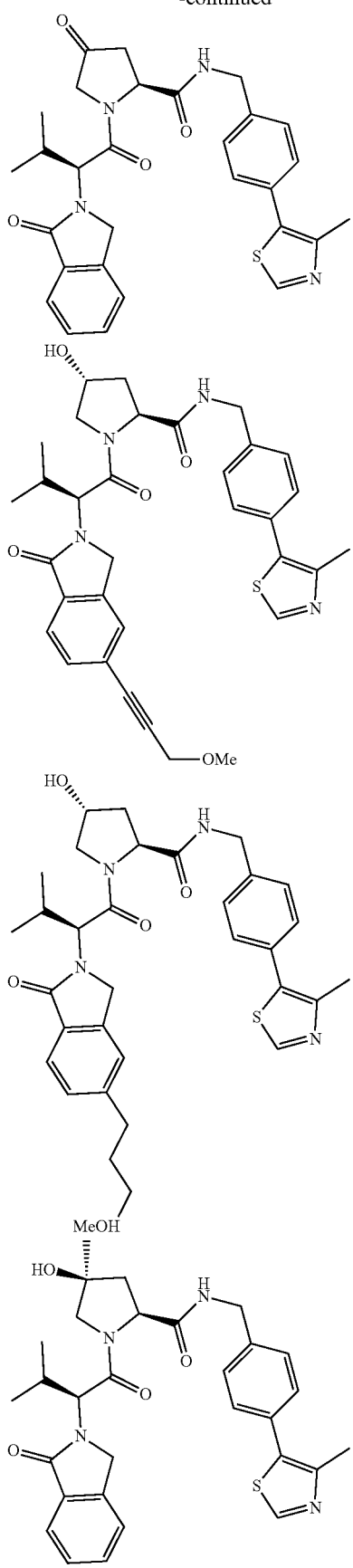
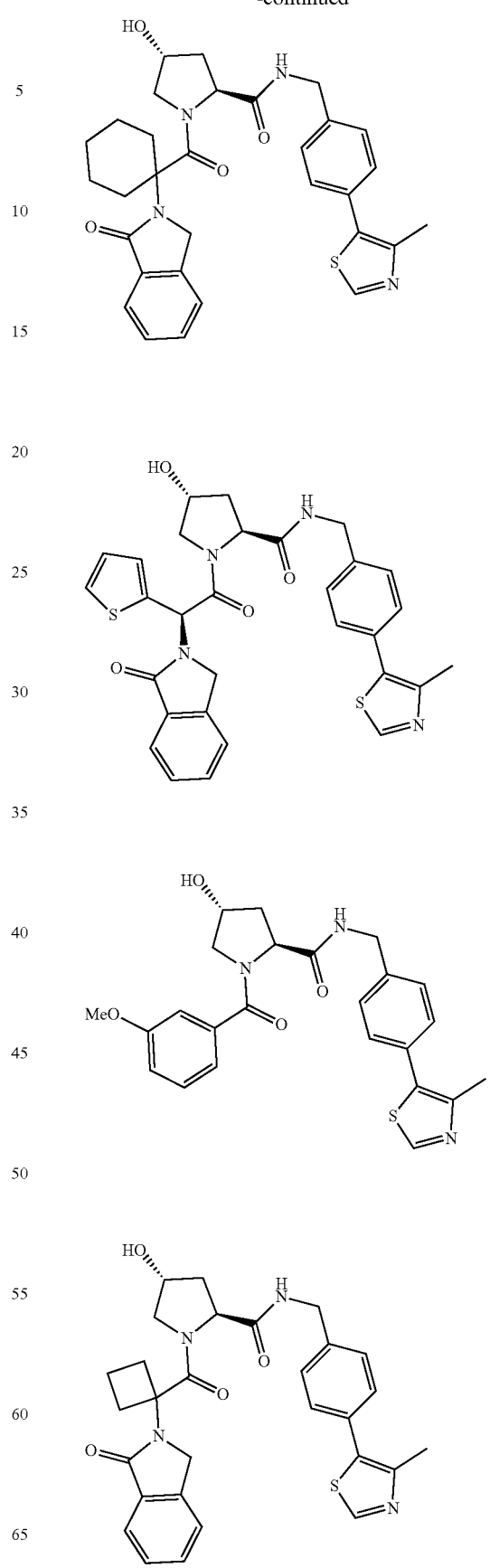

137
-continued
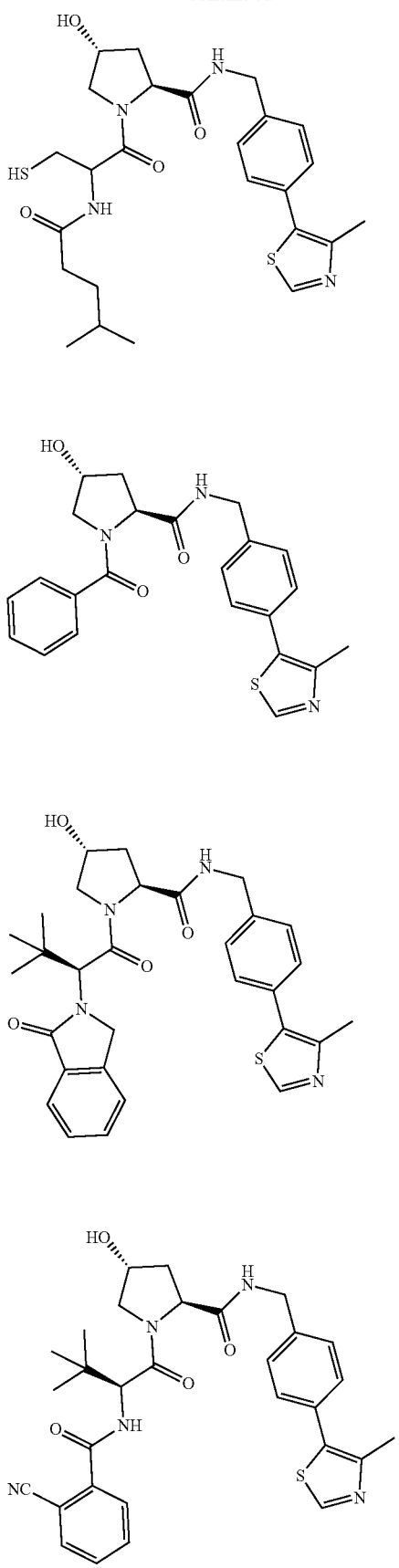
138
-continued
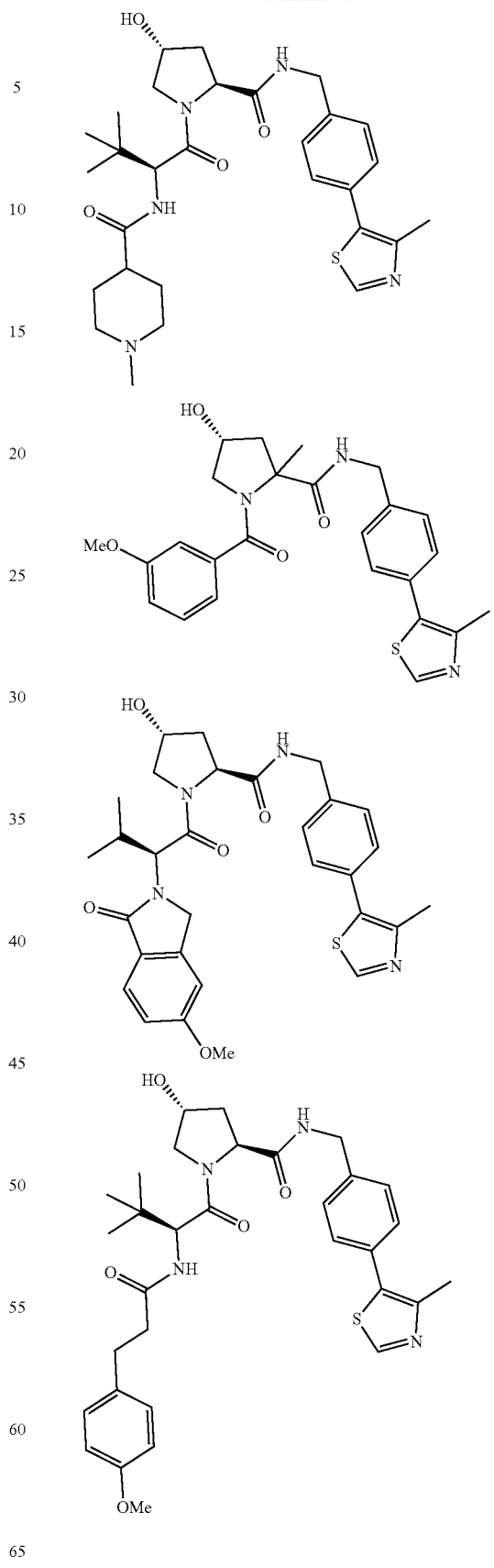

139
-continued
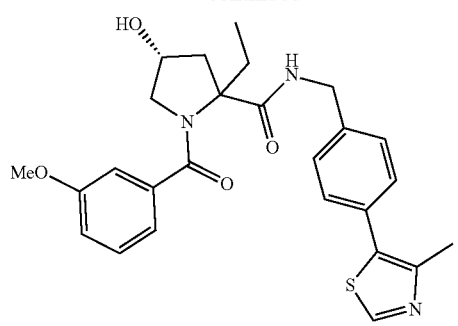
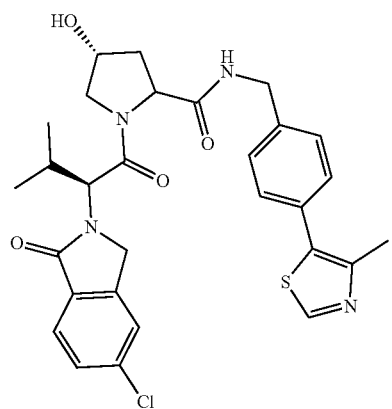
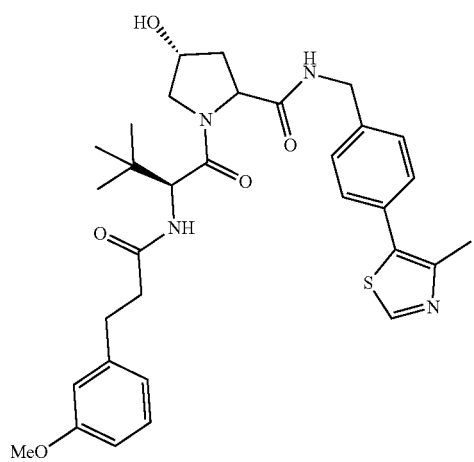
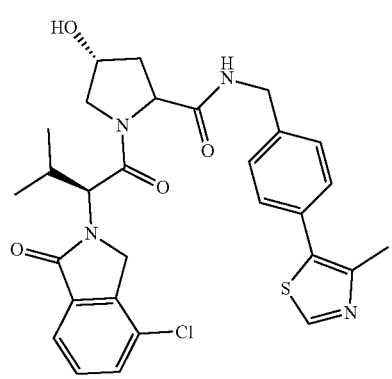
140
-continued
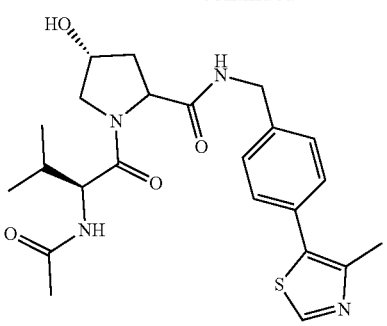
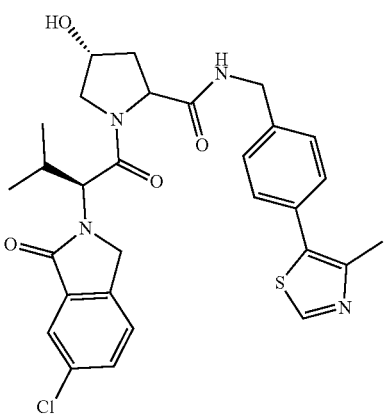
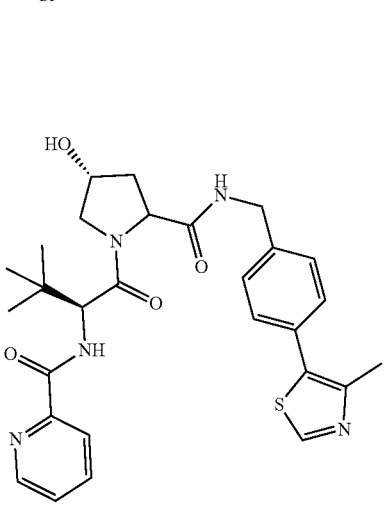

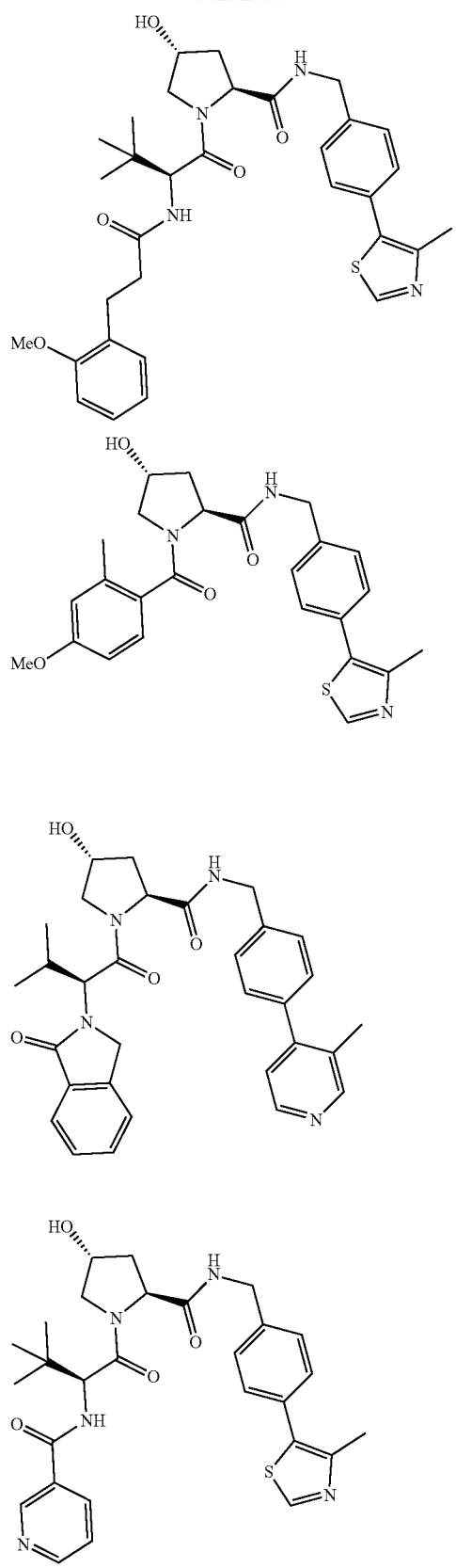
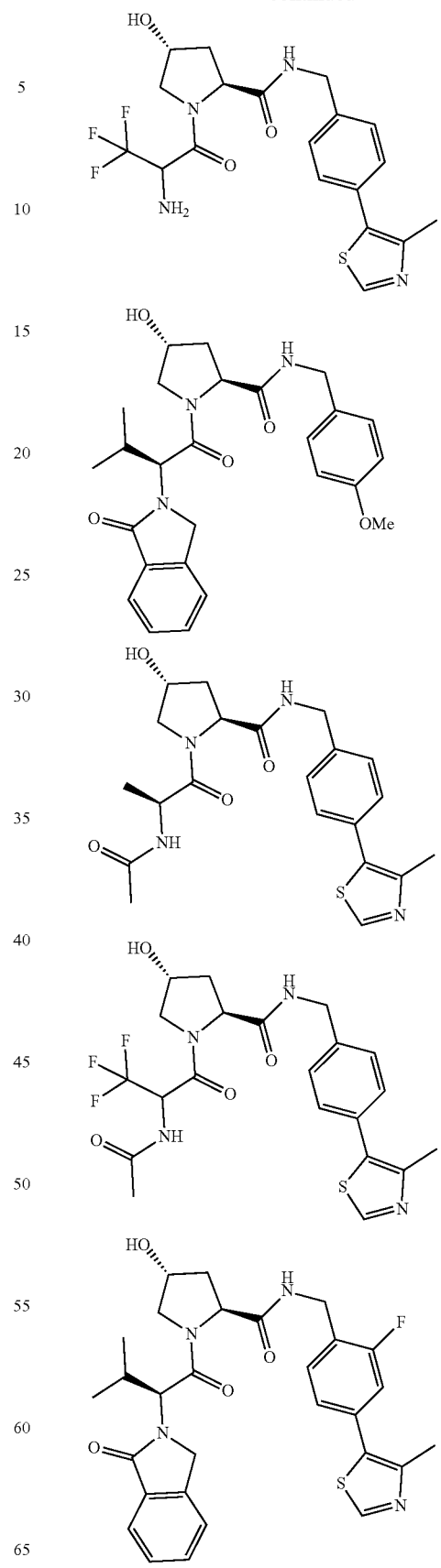

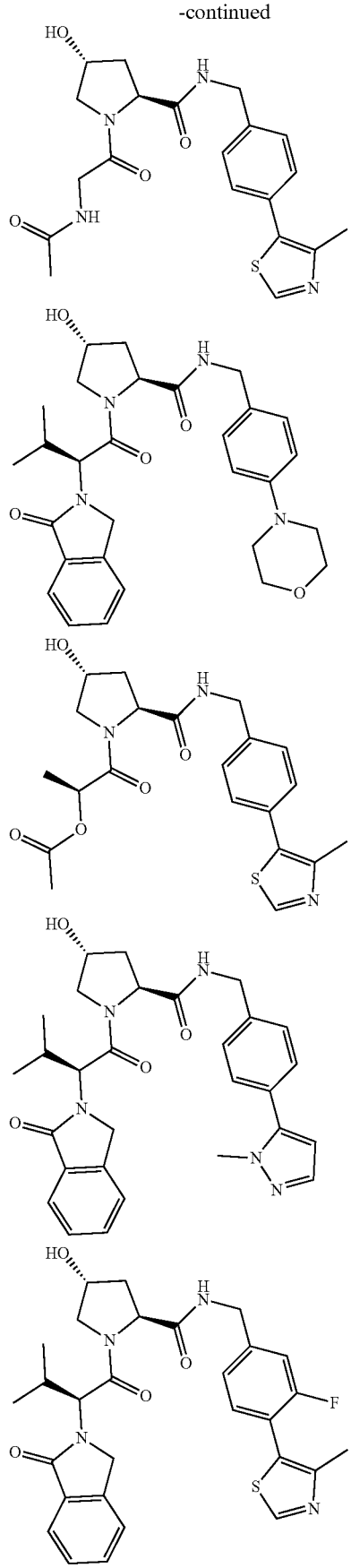
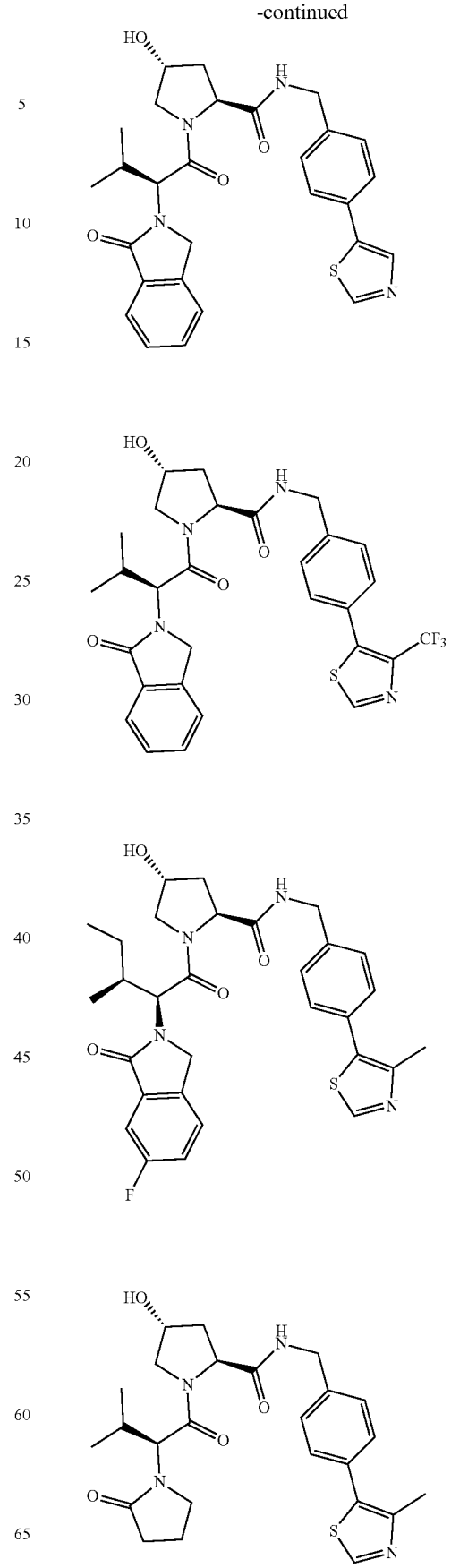

145
-continued
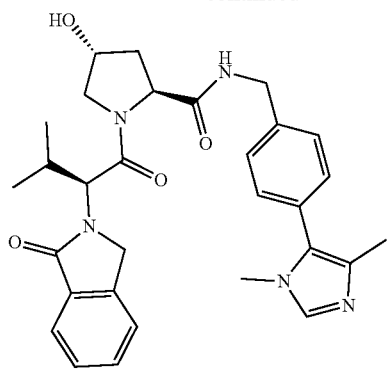
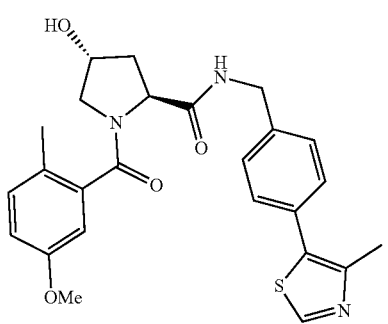
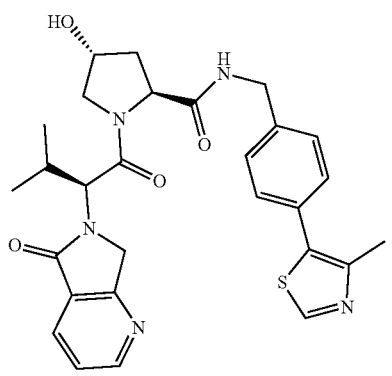
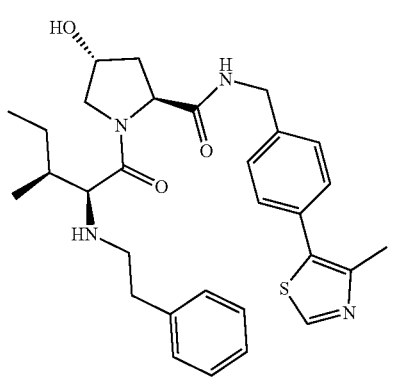
146
-continued
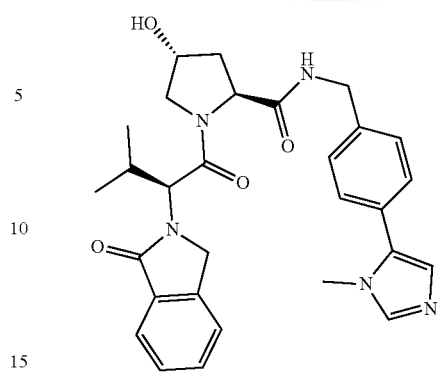
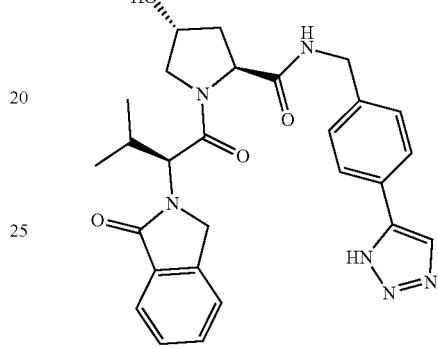
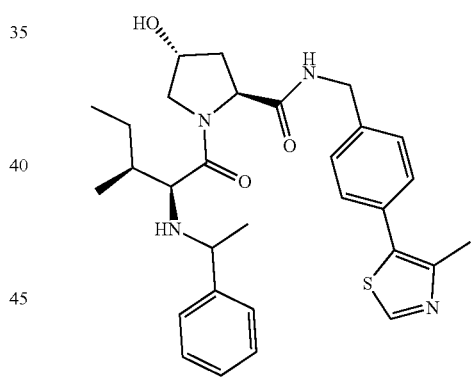
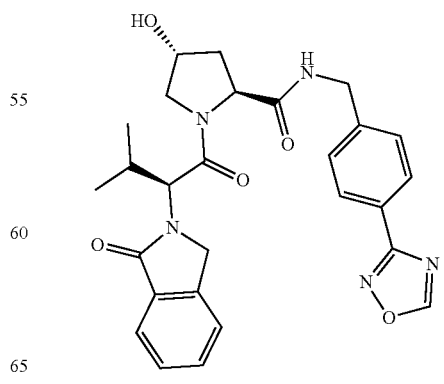

147
-continued
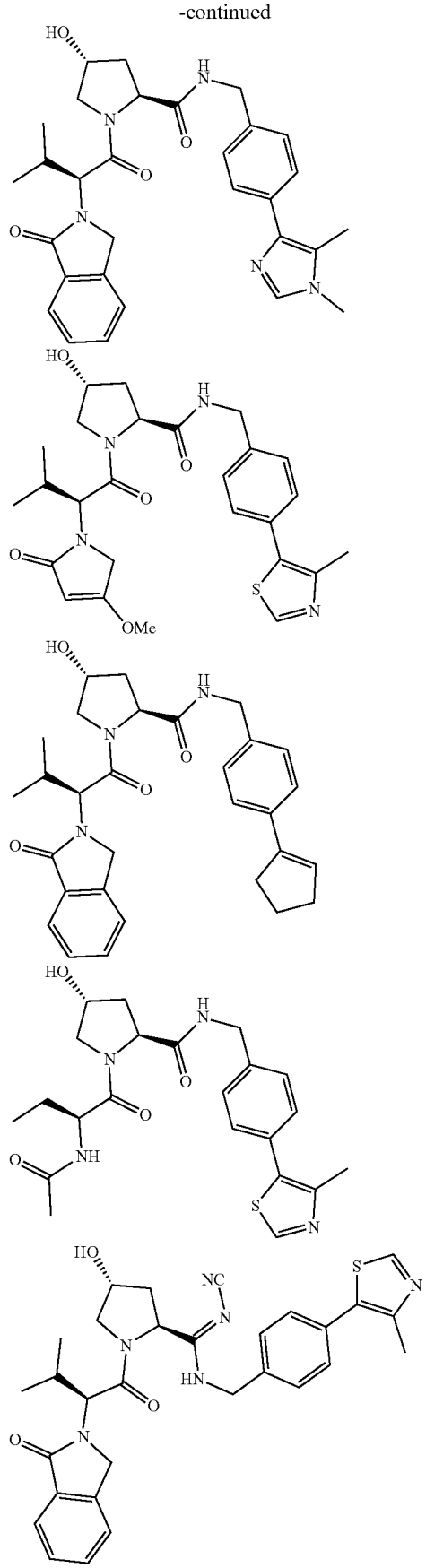
148
-continued
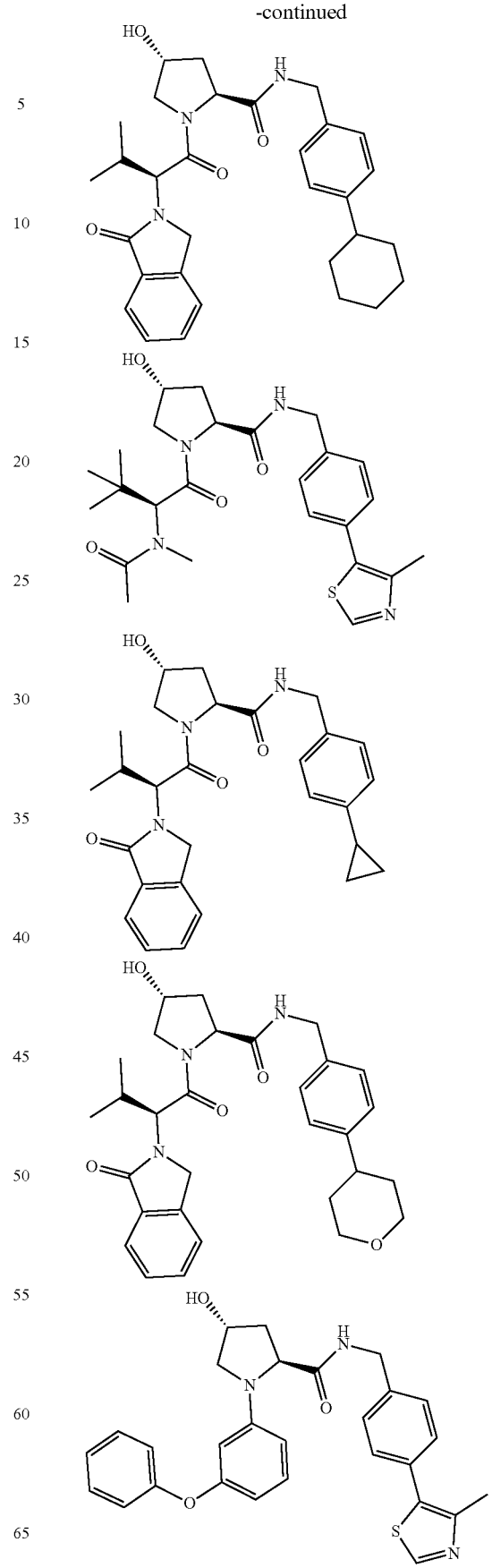

149
-continued
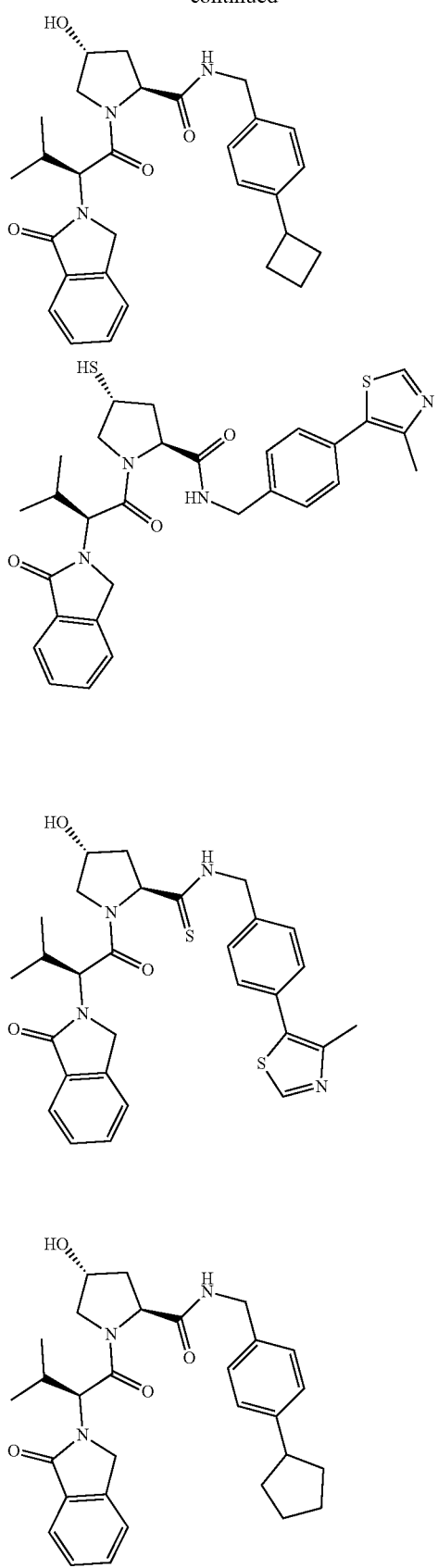
150
-continued
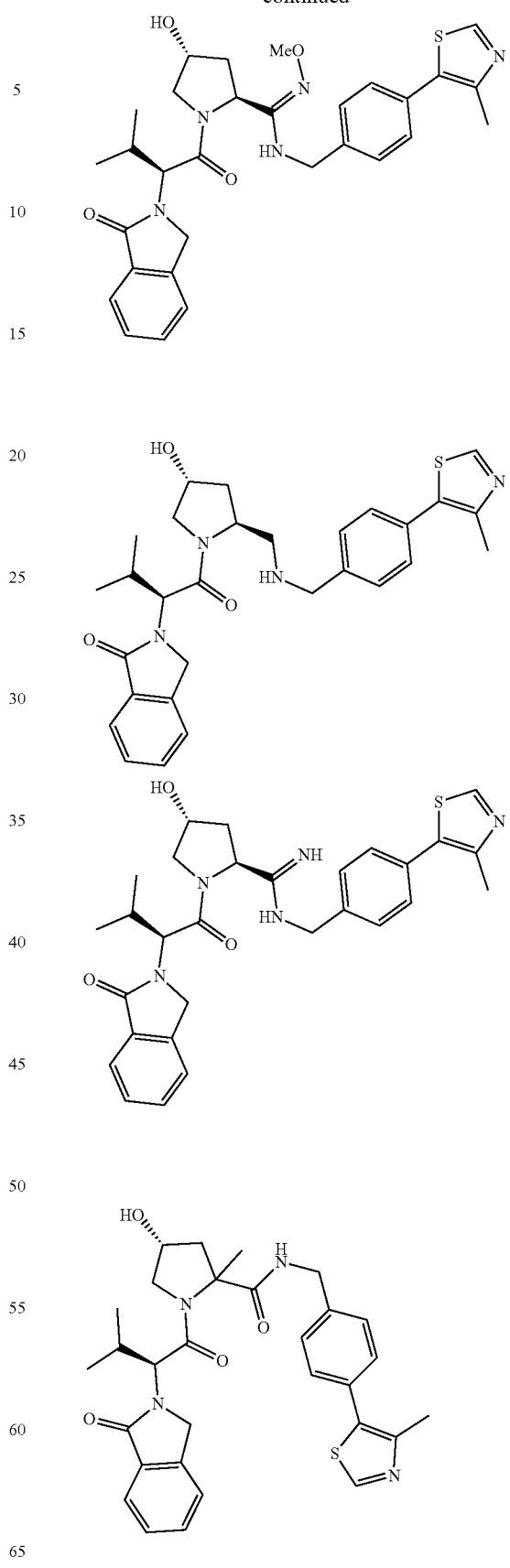

151
-continued
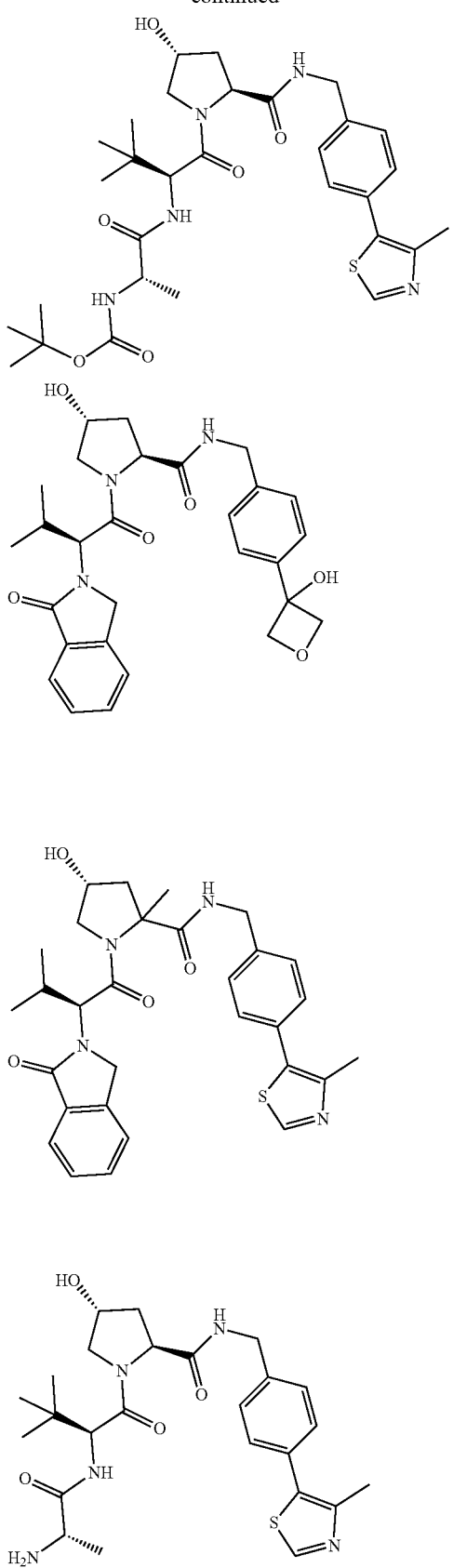
152
-continued
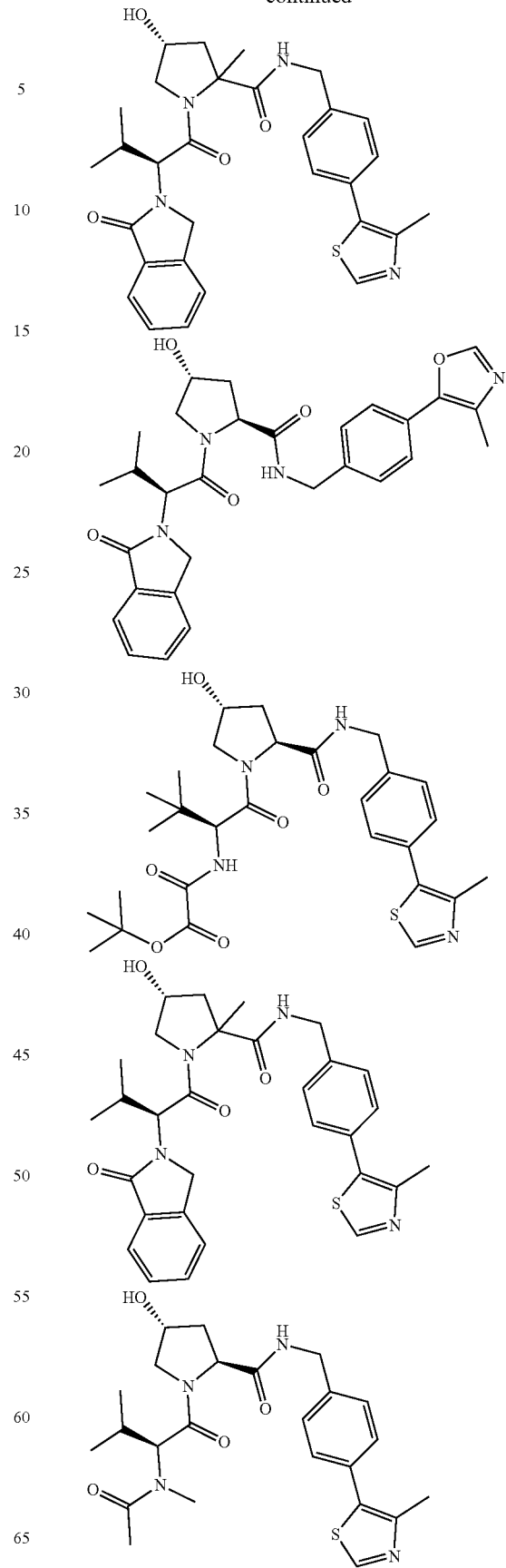

153
-continued
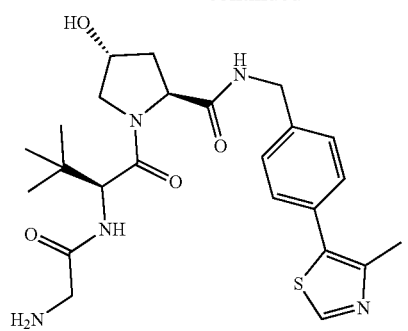
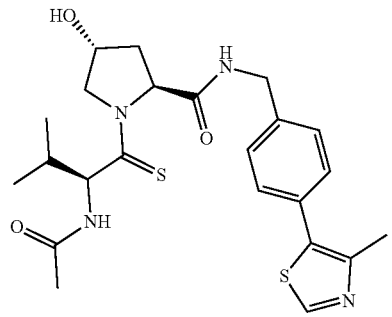
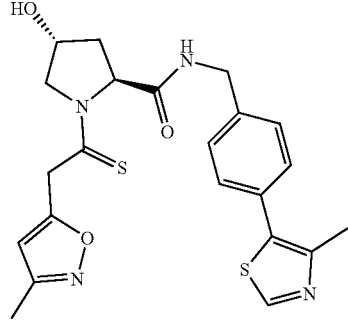
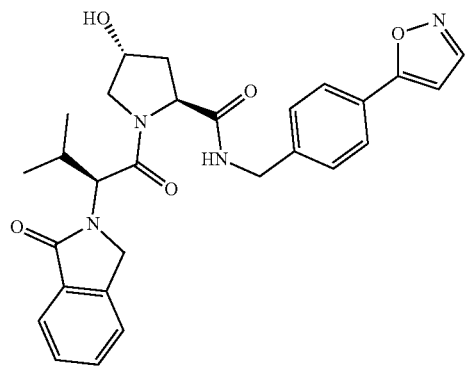
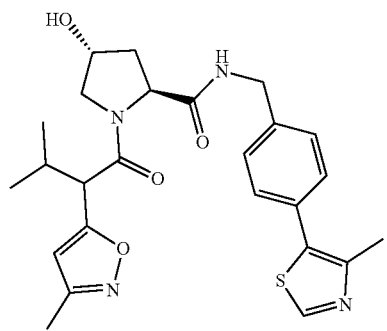
154
-continued
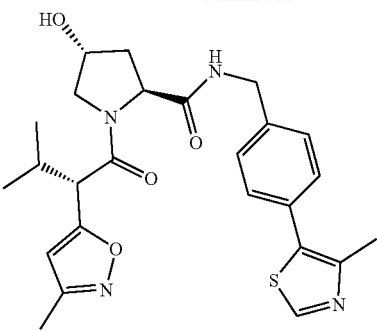
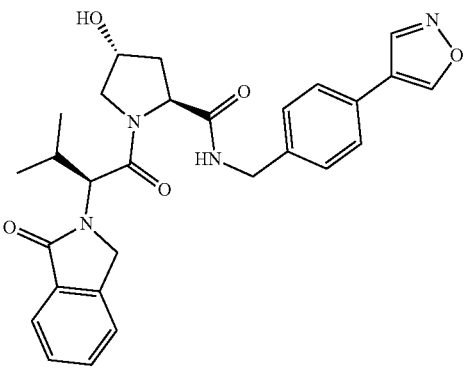
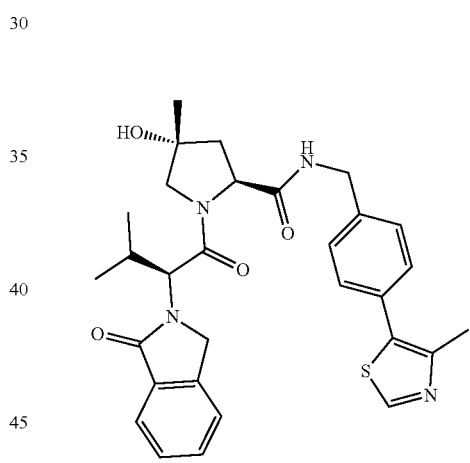
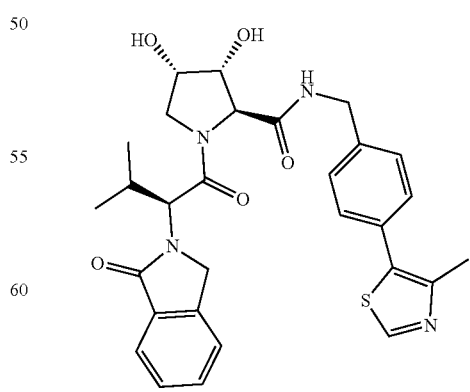

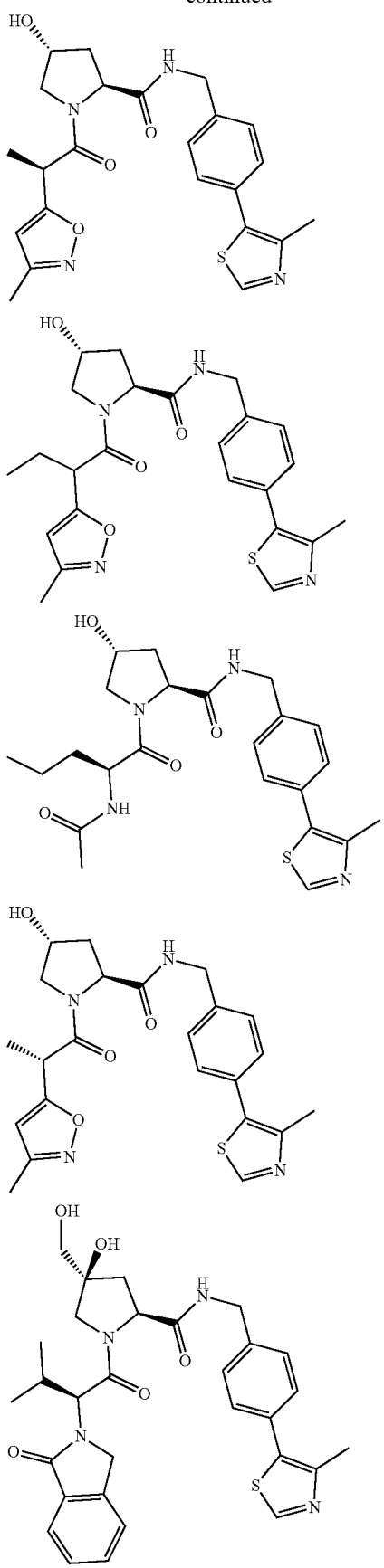
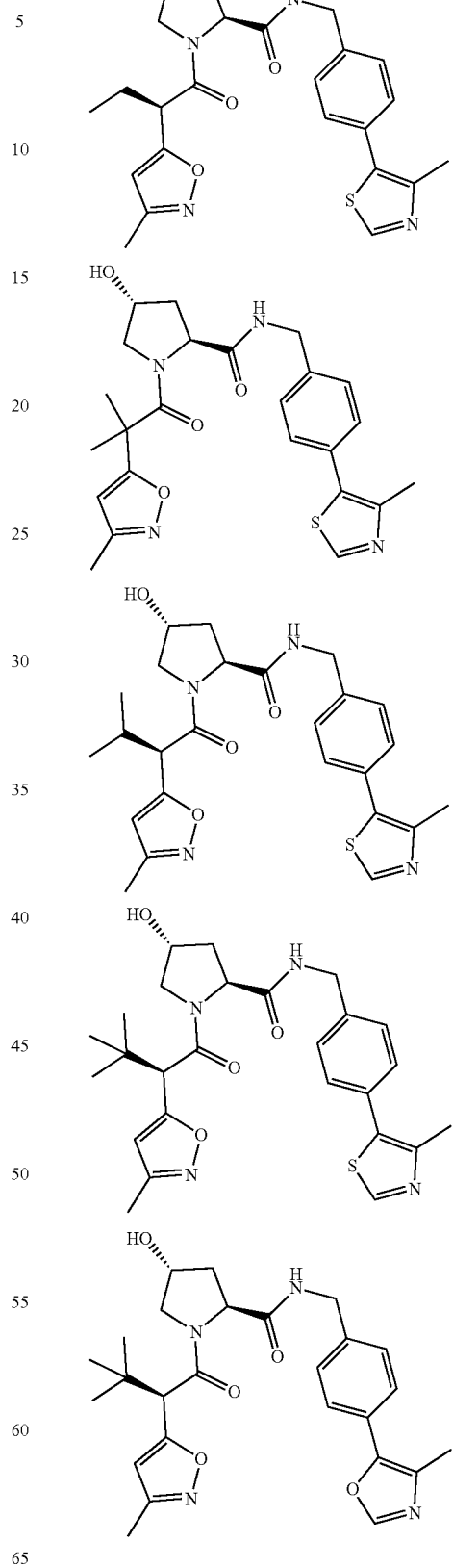

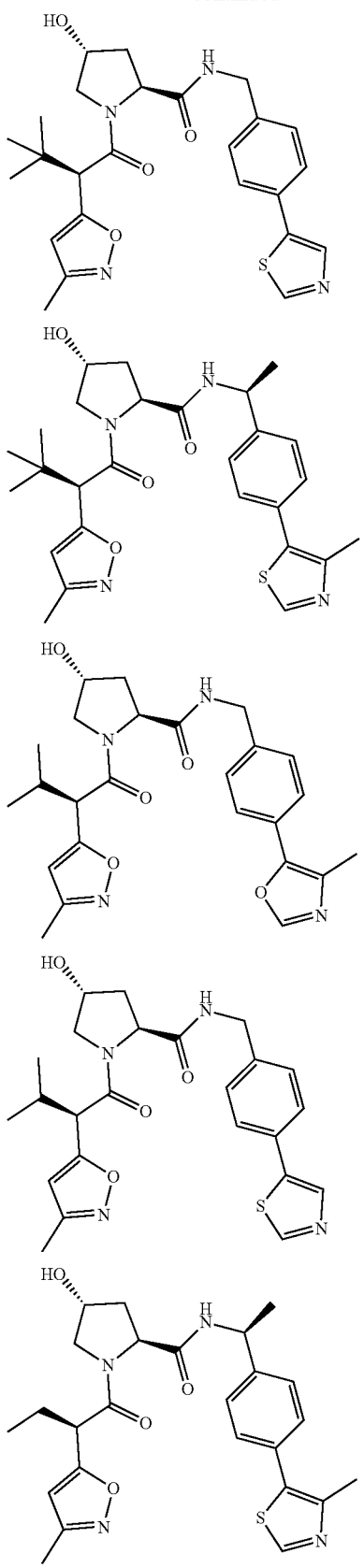
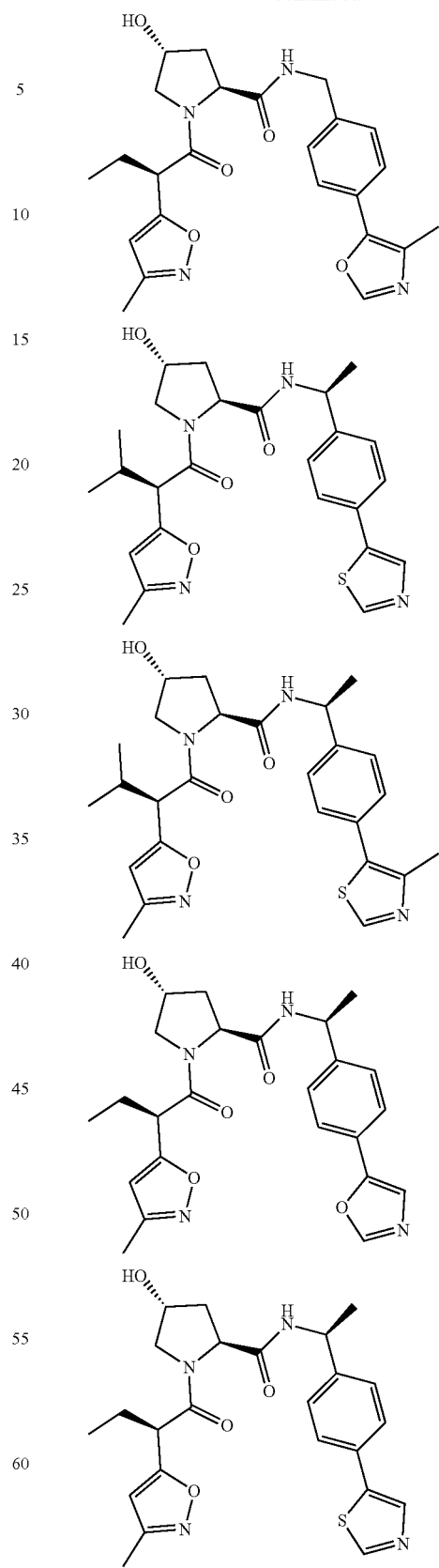

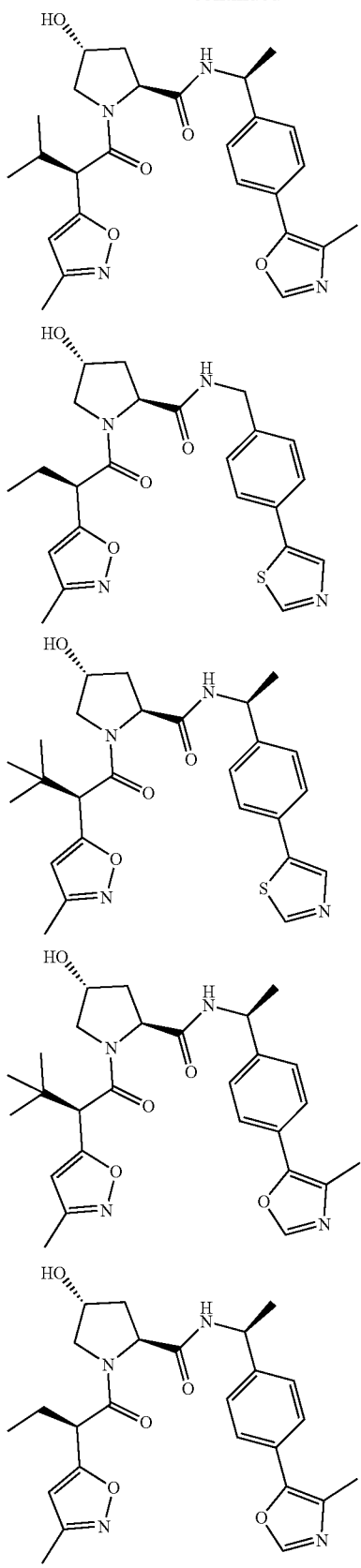
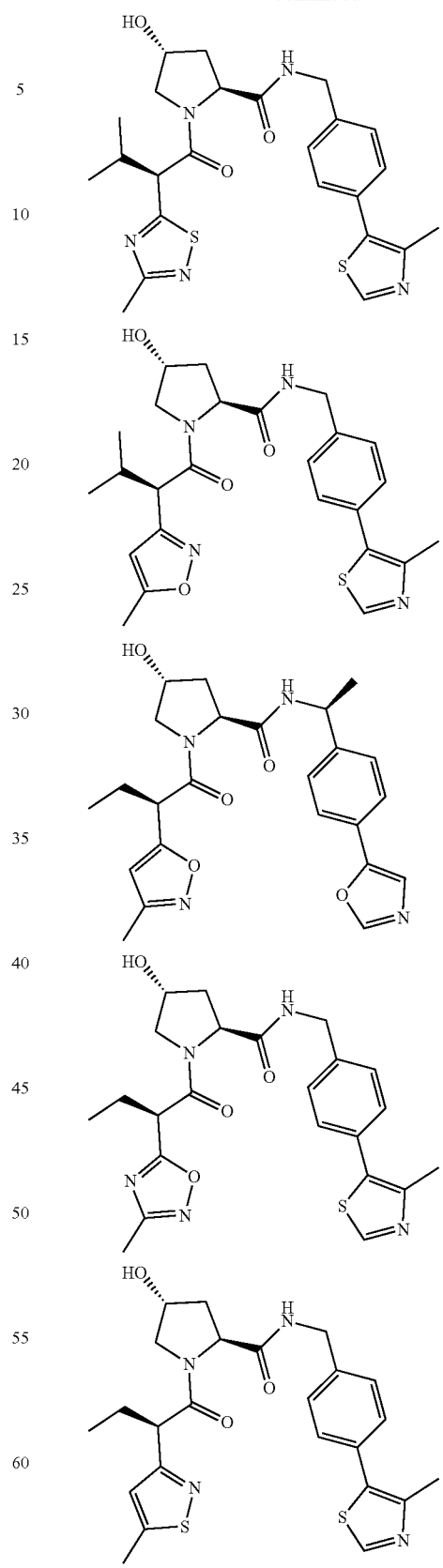

161
-continued
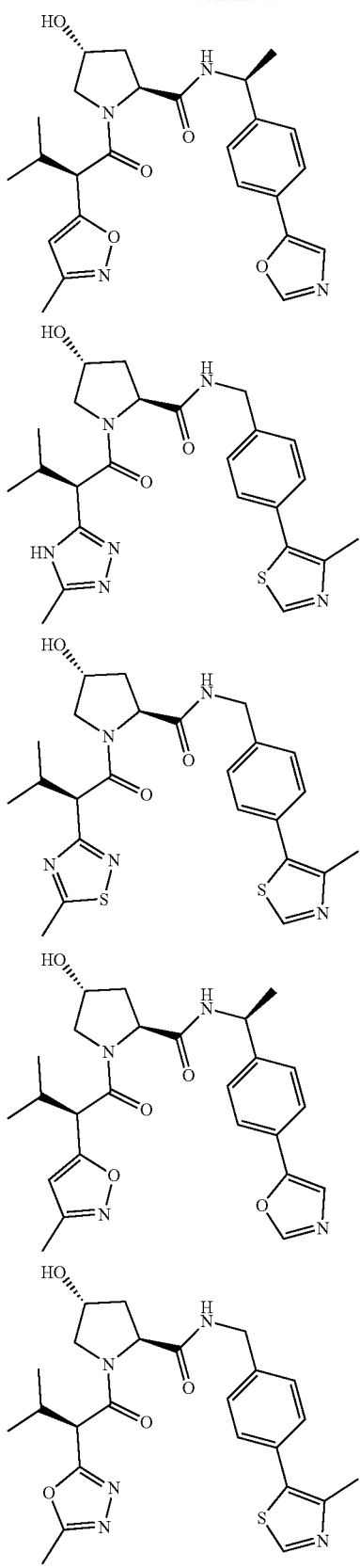
162
-continued
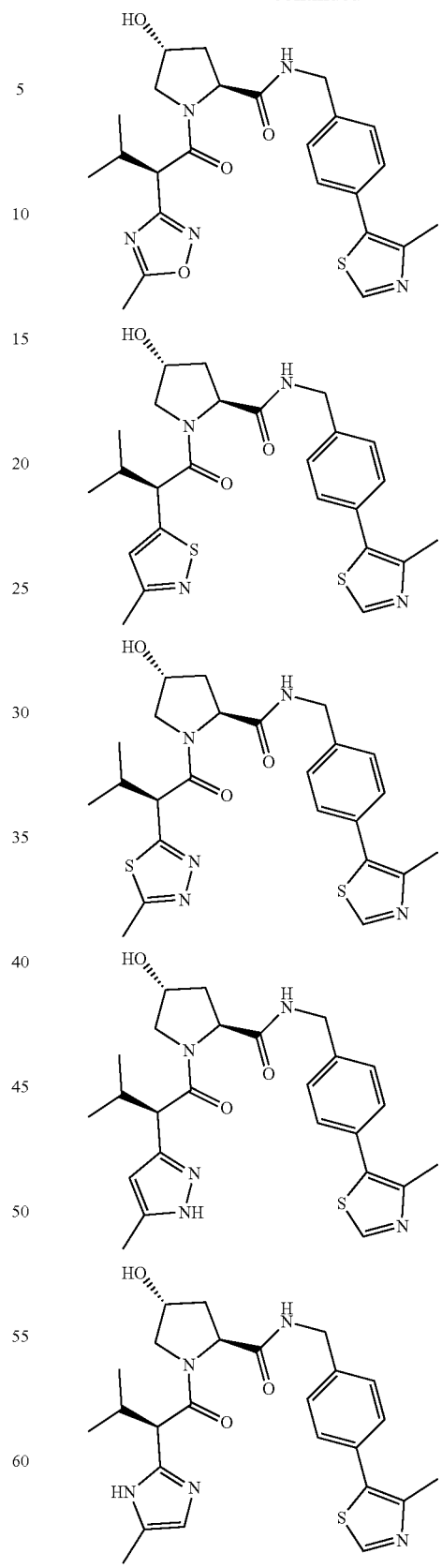

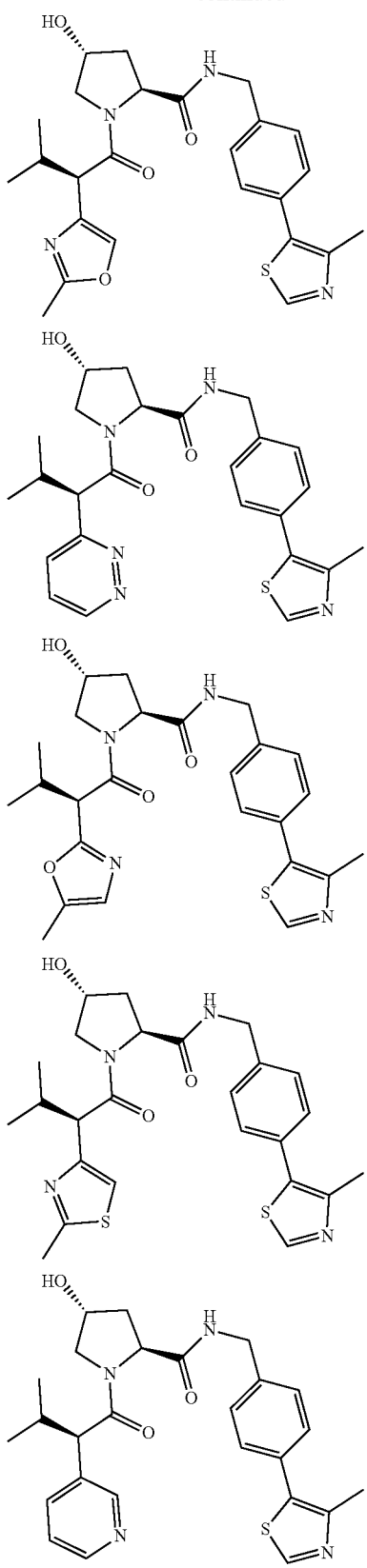
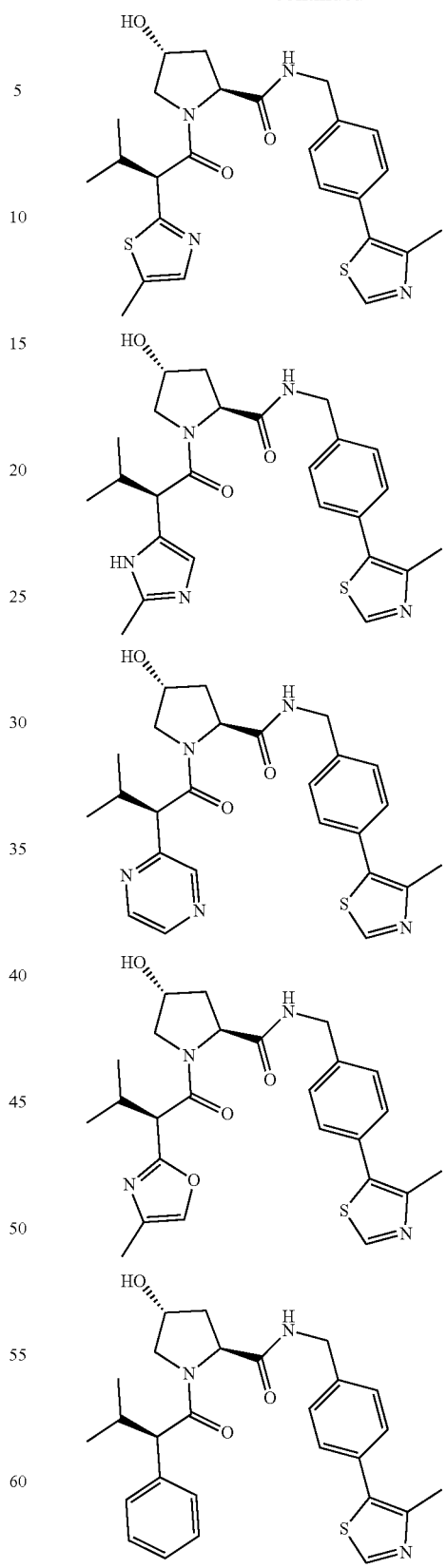

165
-continued
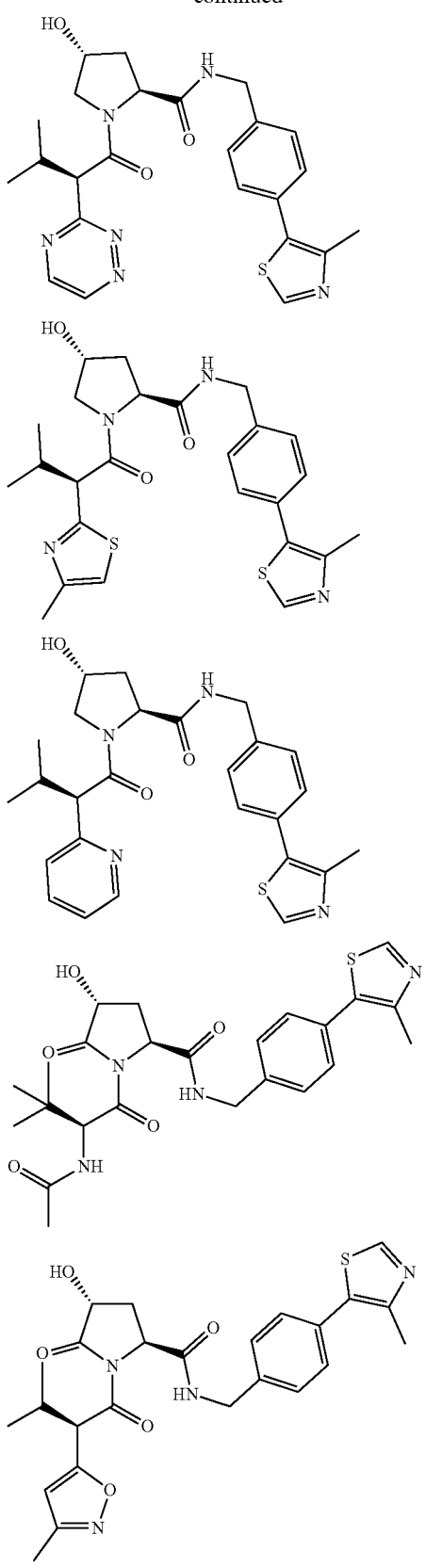
166
-continued
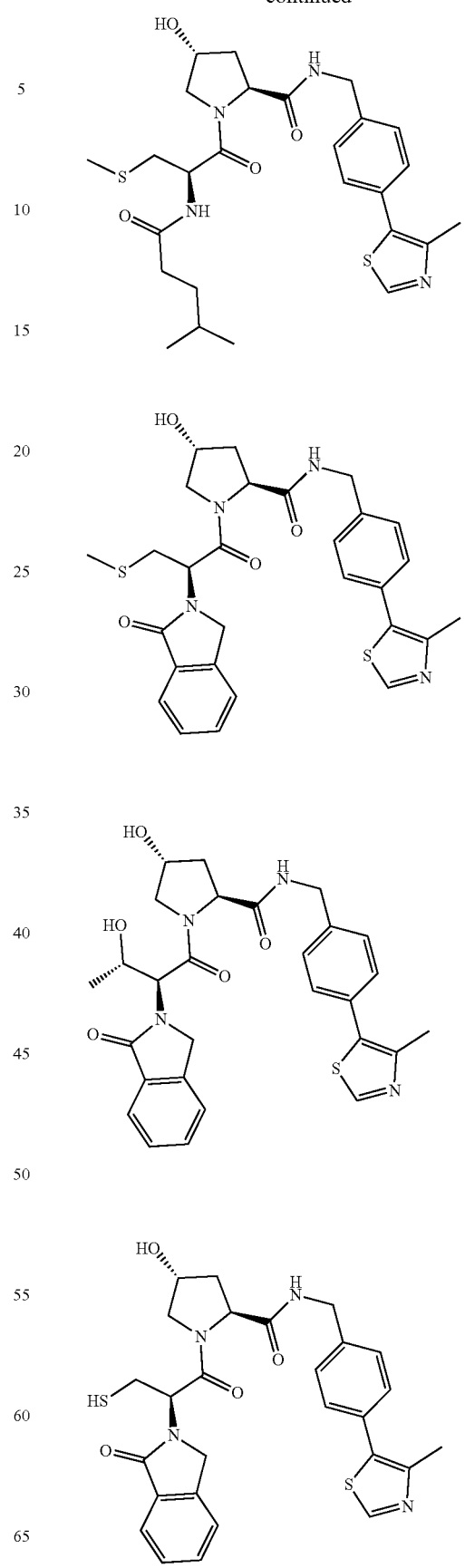

167
-continued
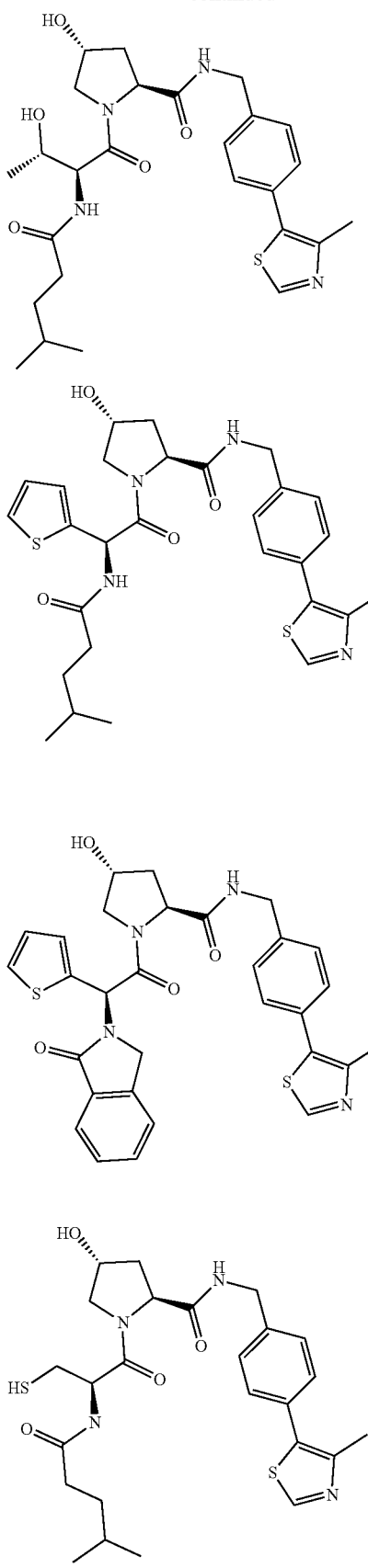
168
-continued
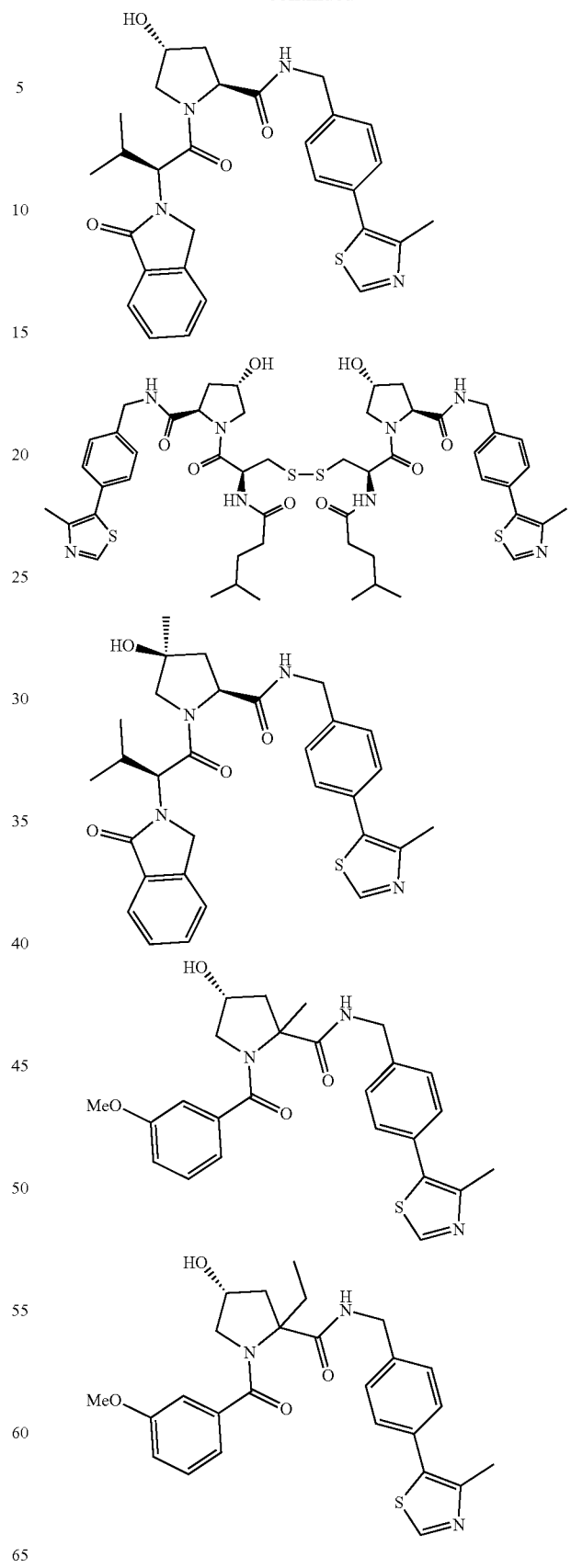

169
-continued
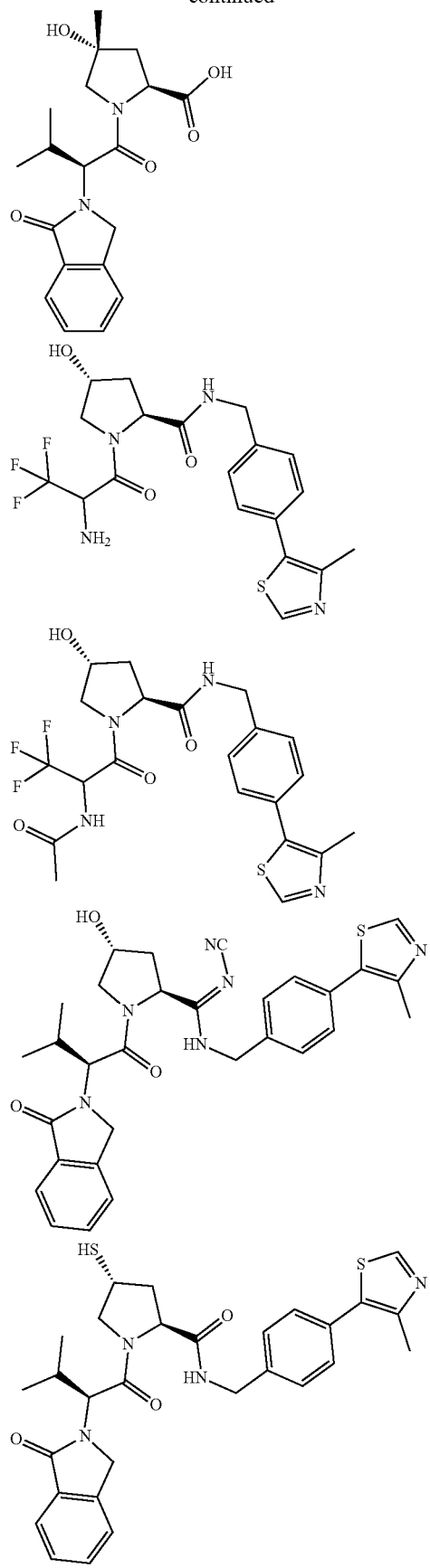
170
-continued
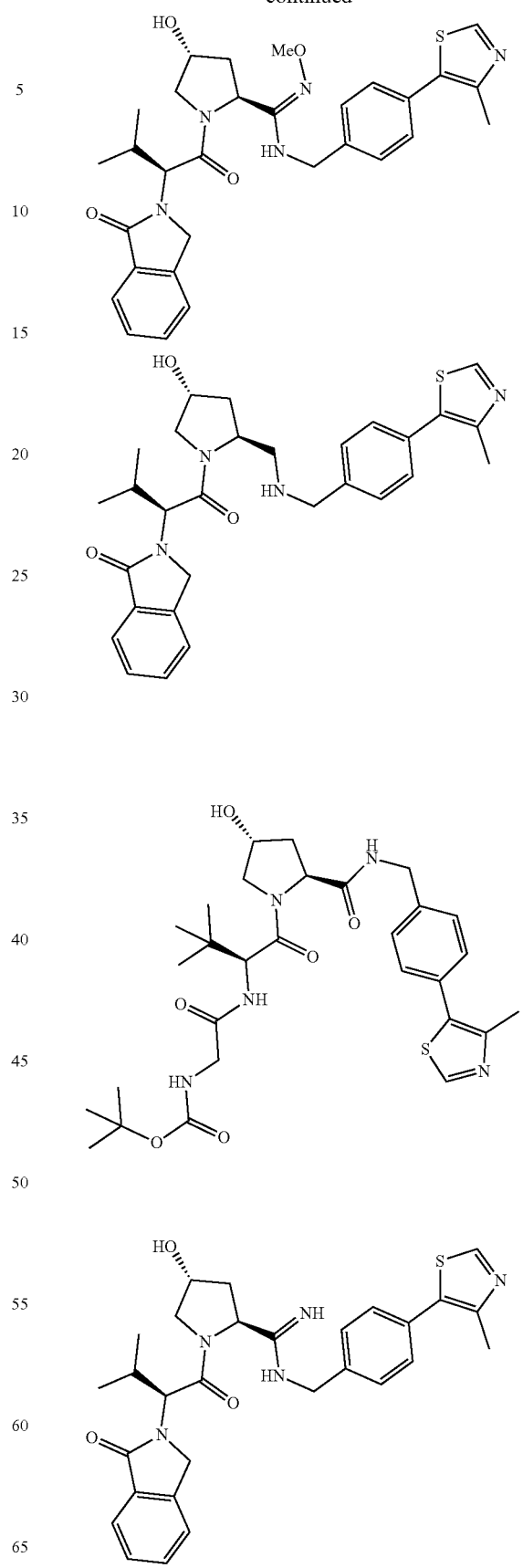

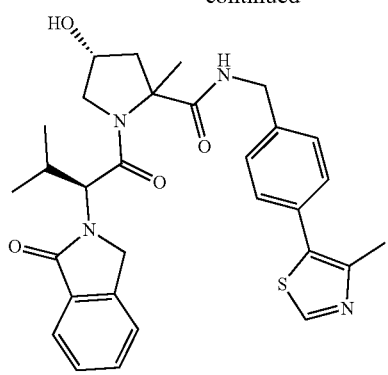
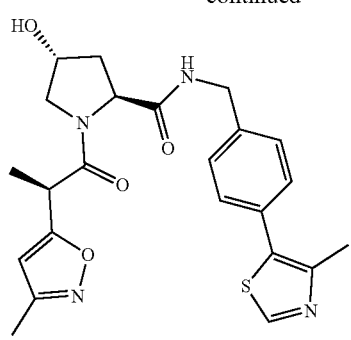
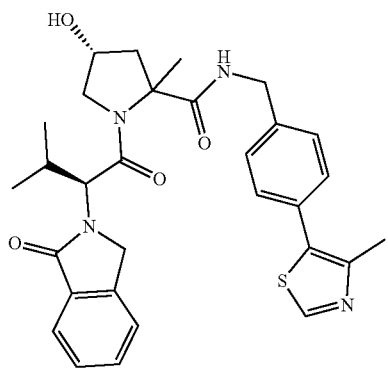
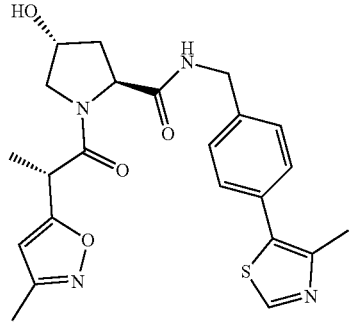
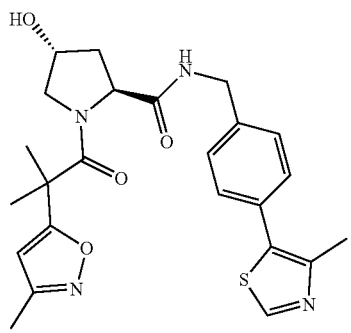
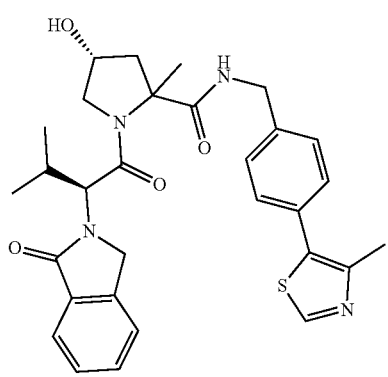
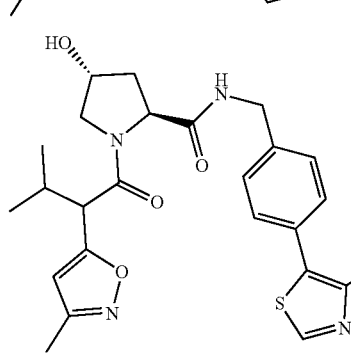
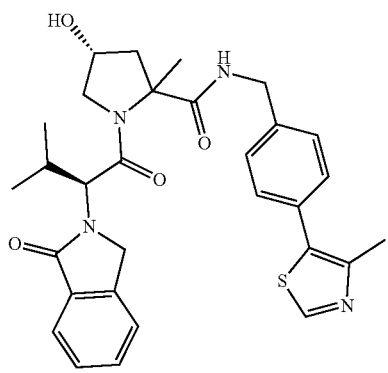

173
-continued
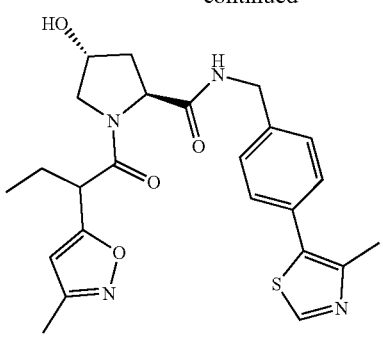
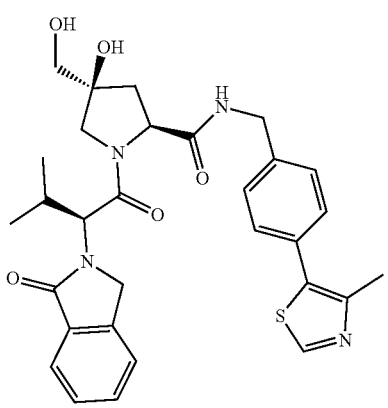
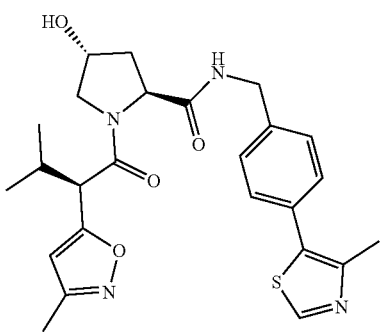
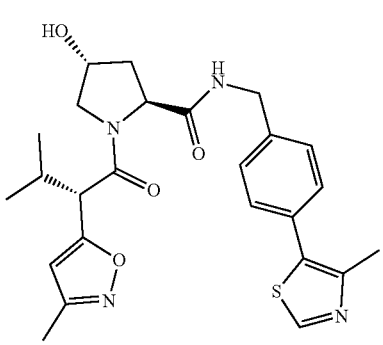
174
-continued
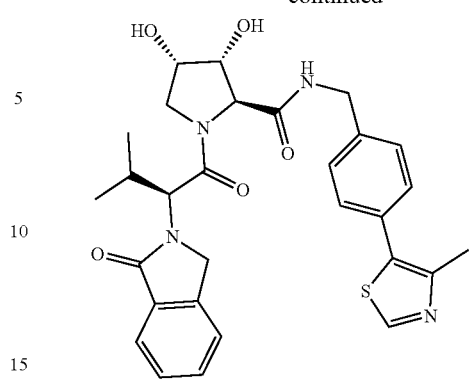
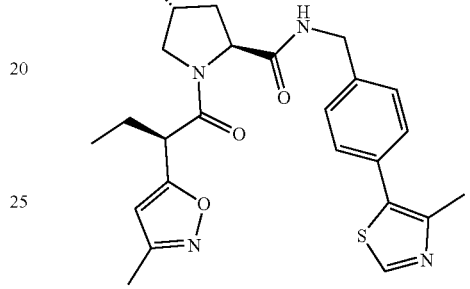
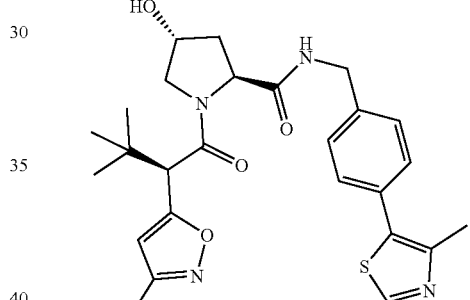
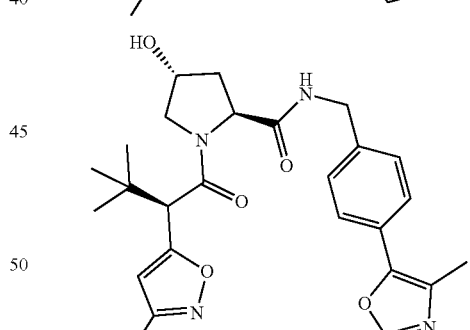
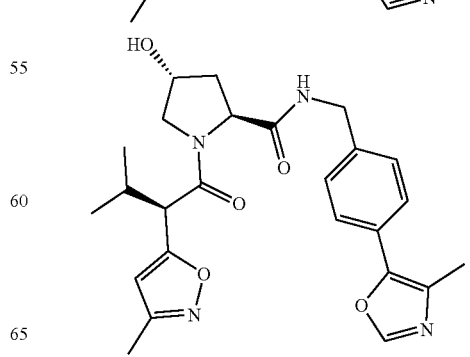

175
-continued
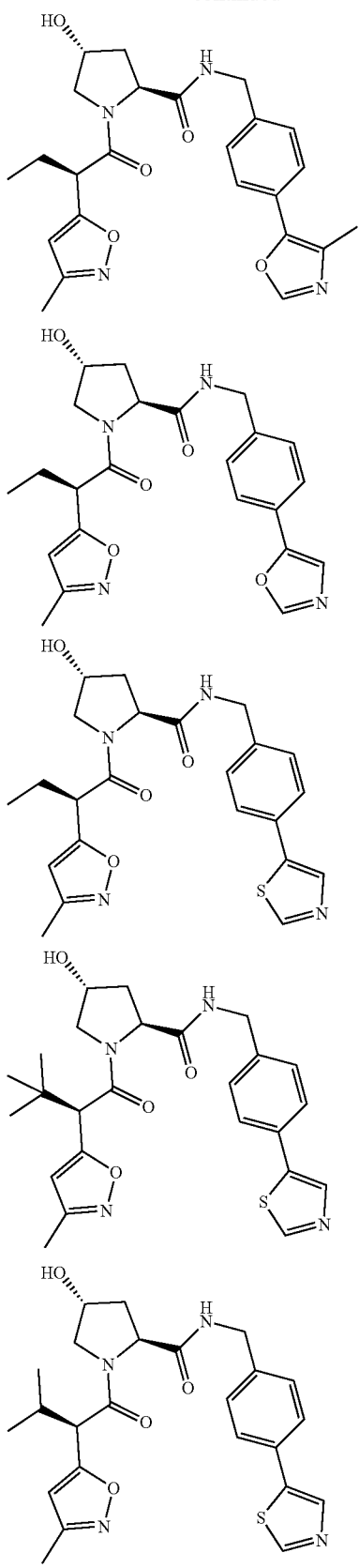
176
-continued
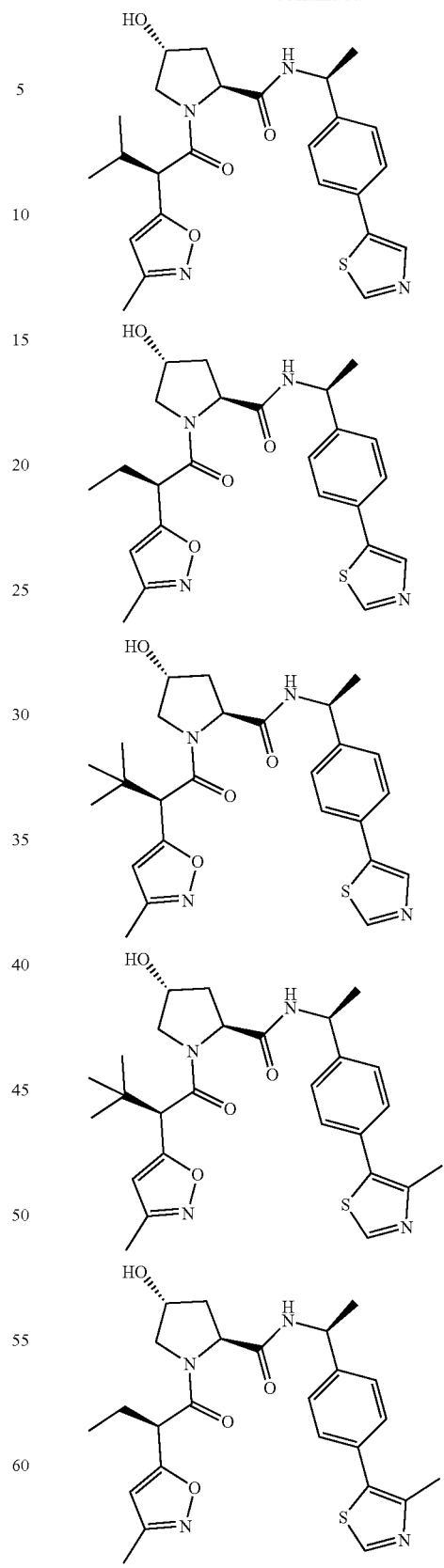

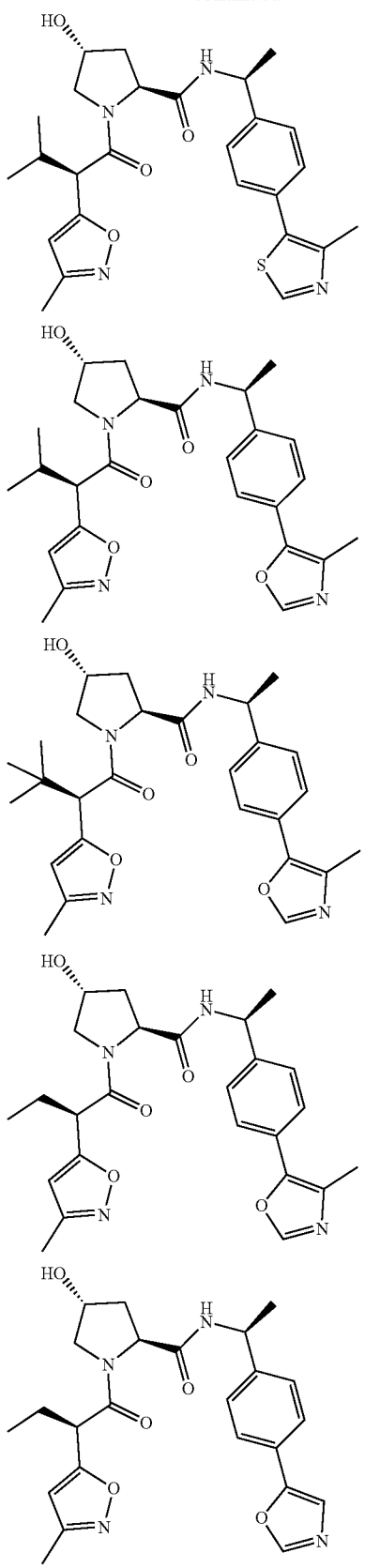
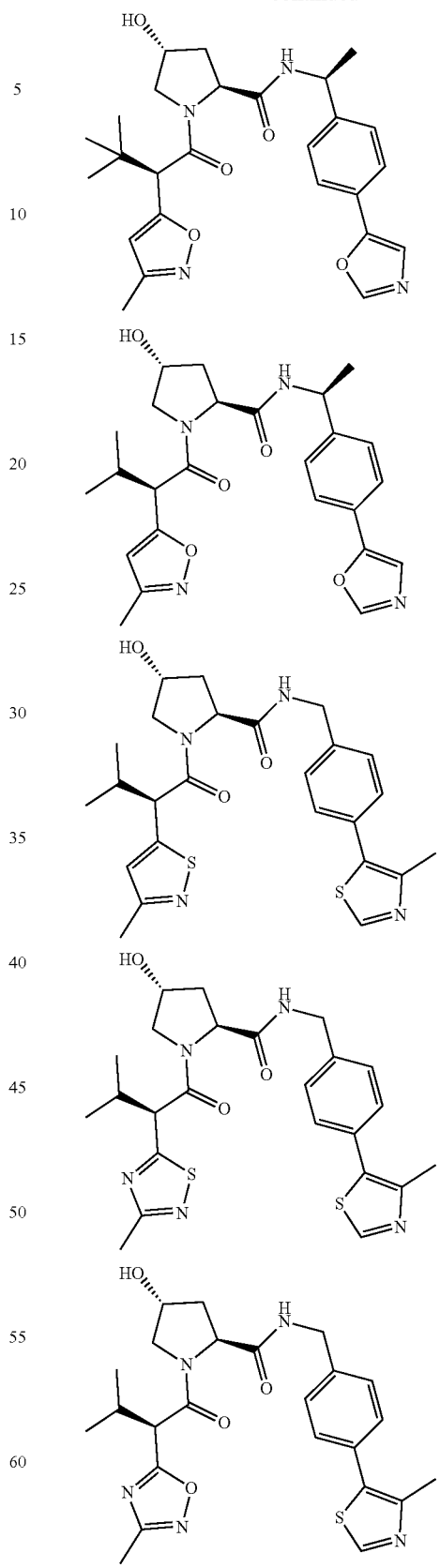

179 -continued
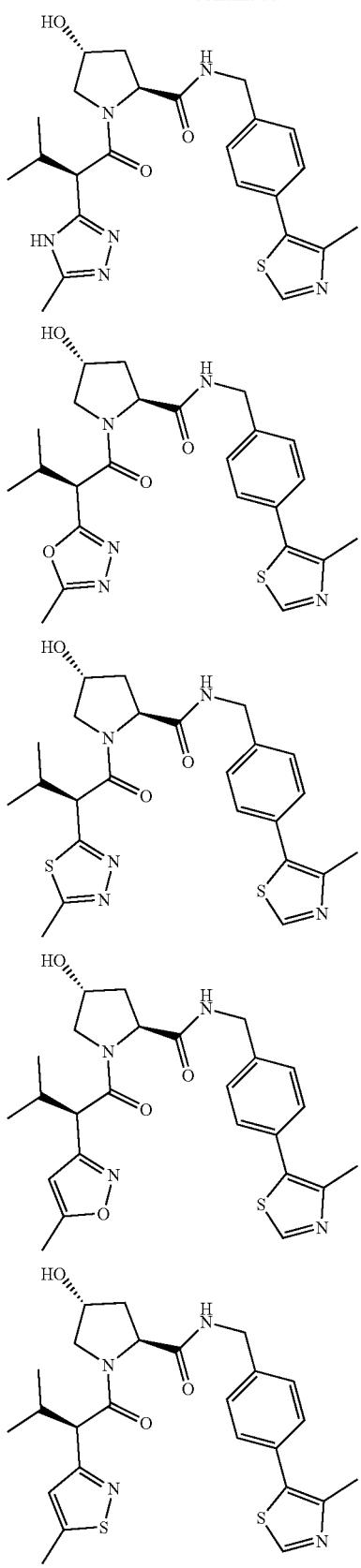
180 -continued
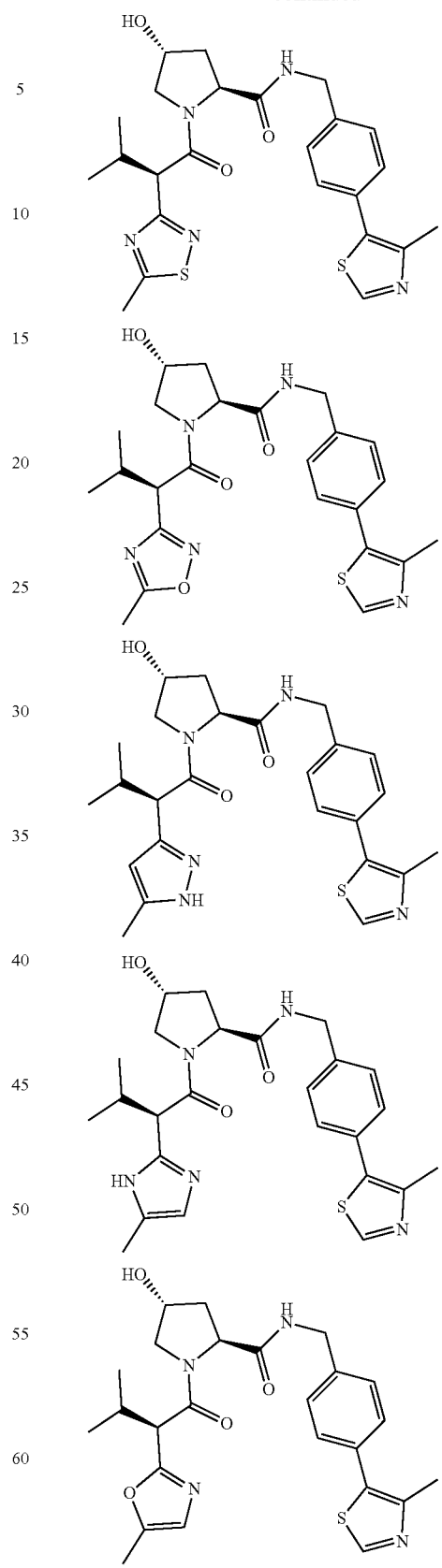

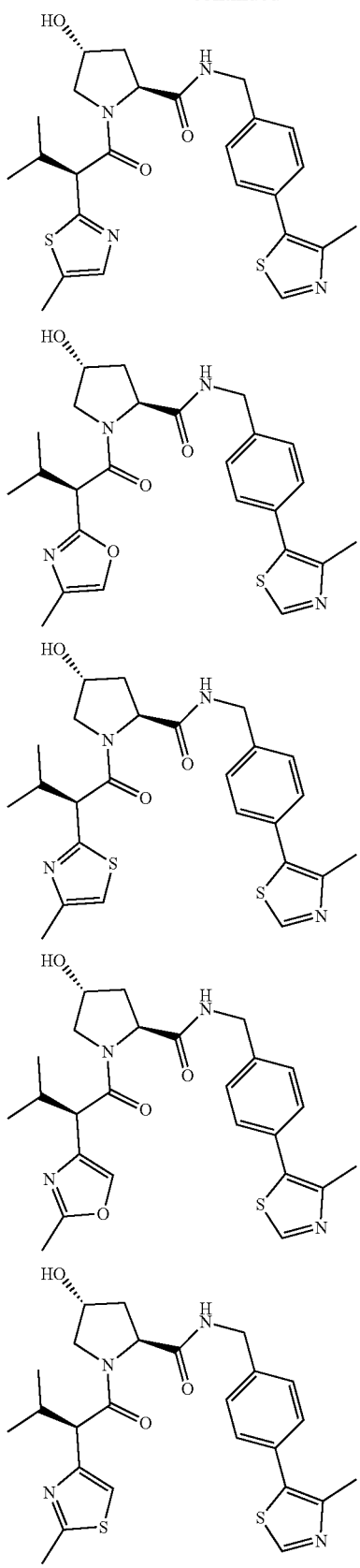
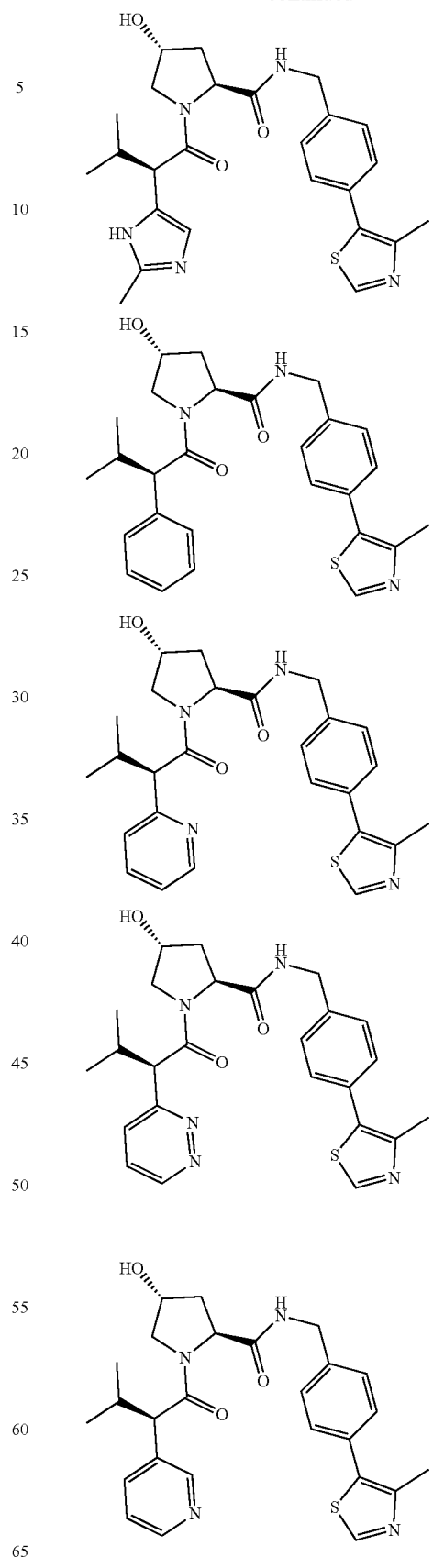

183
-continued
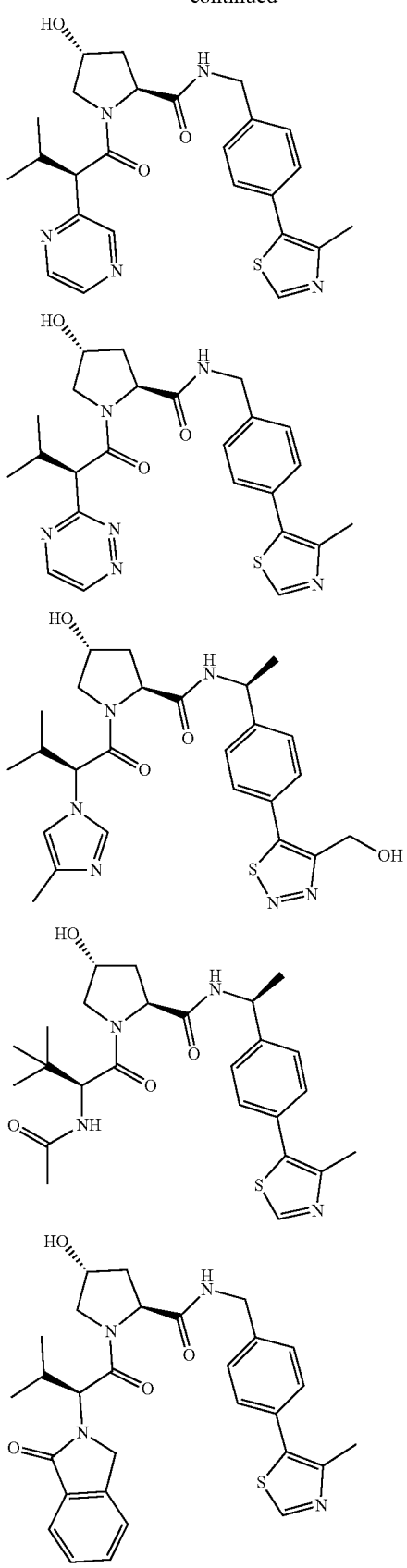
184
-continued
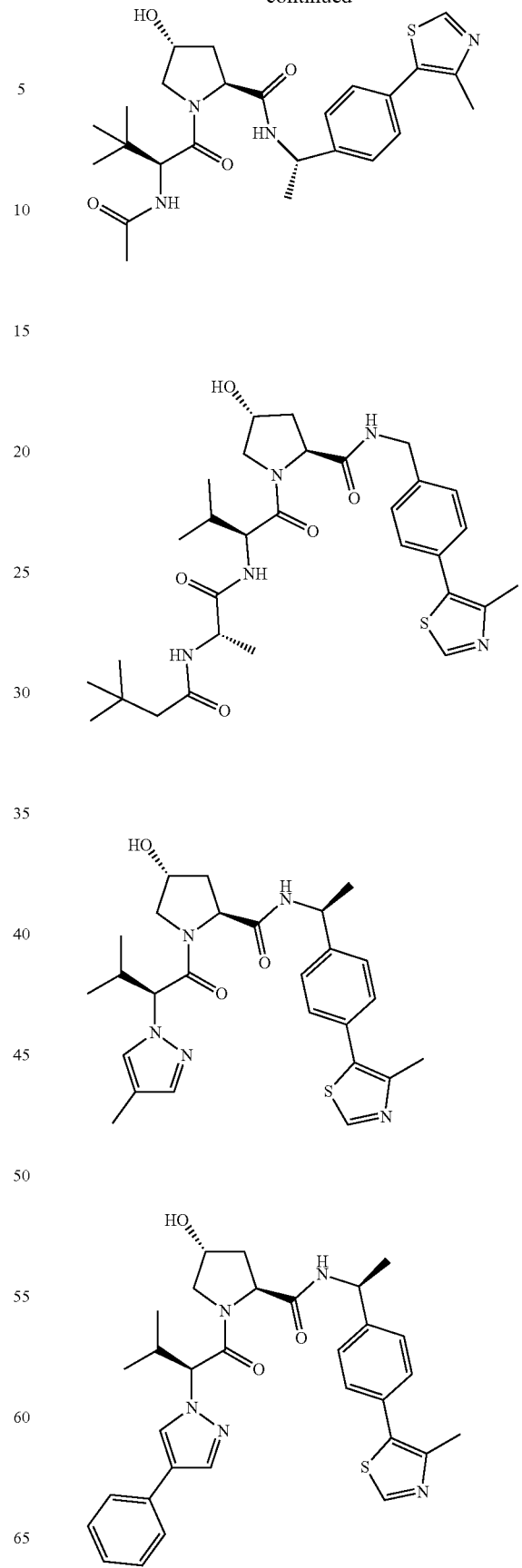

185
-continued
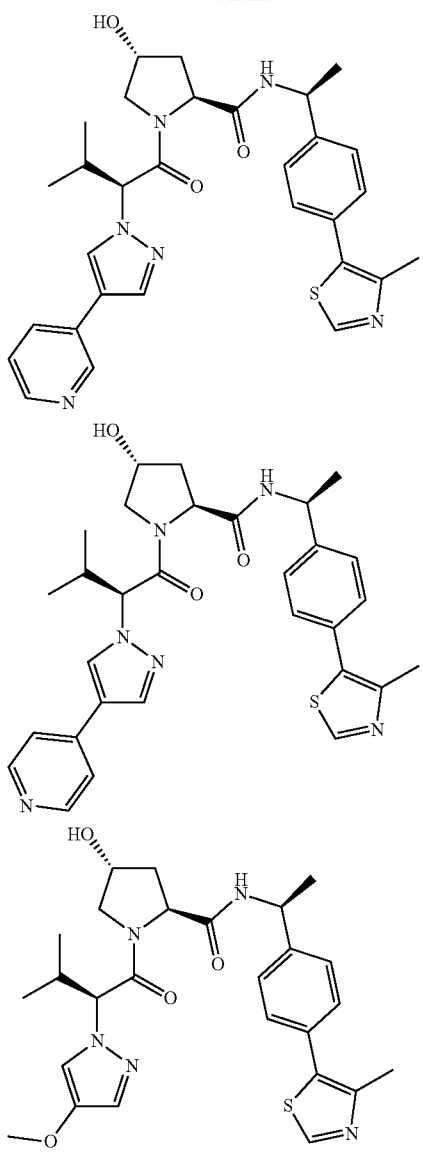
186
-continued
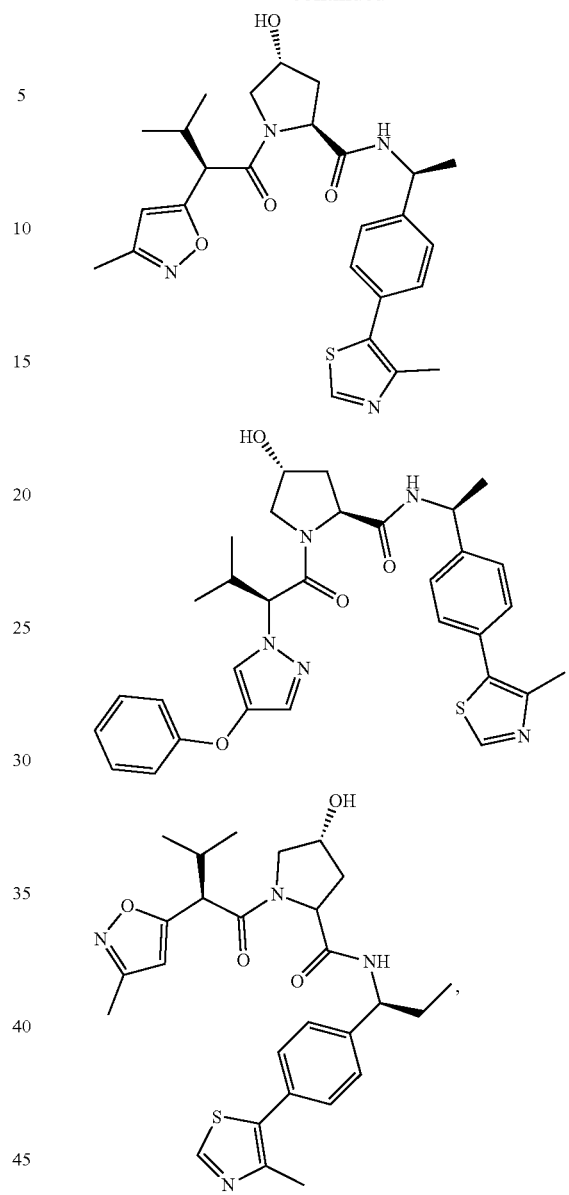
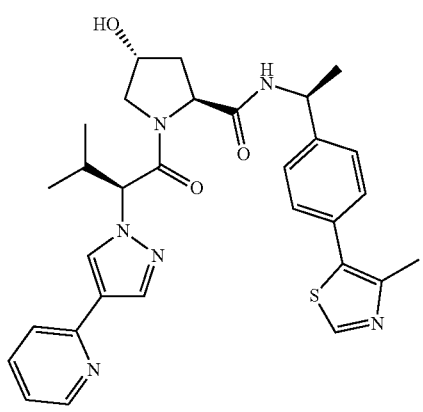
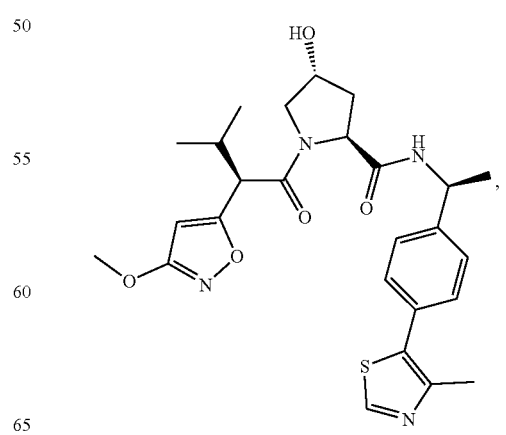

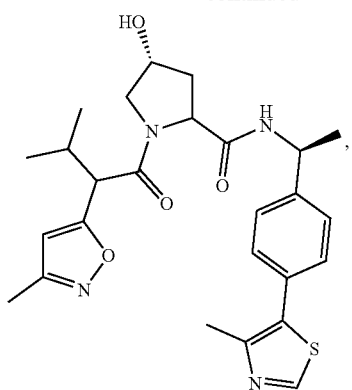
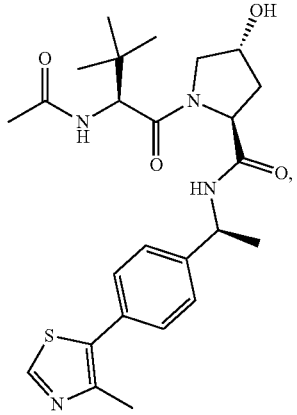
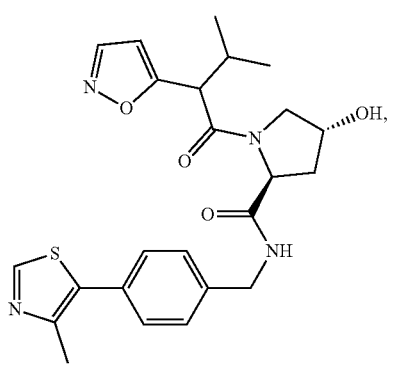
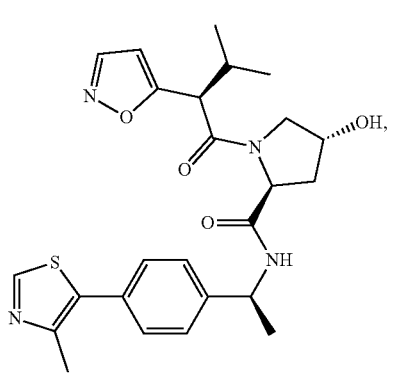
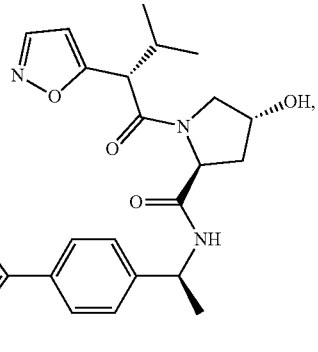
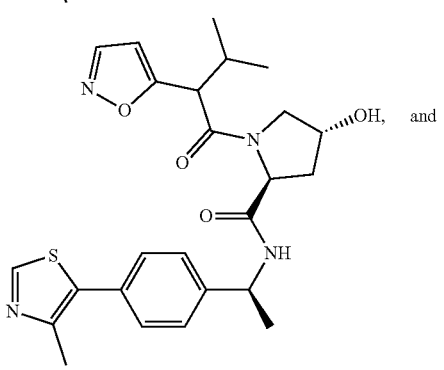
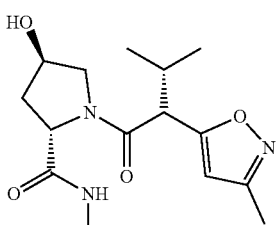
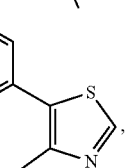
wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.
In any aspect or embodiment described herein, the ULM is selected from the group consisting of:
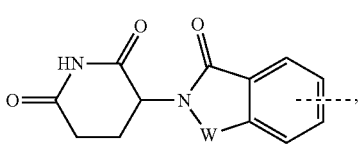
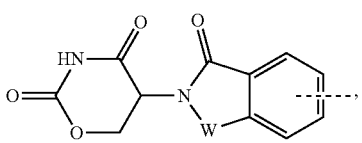

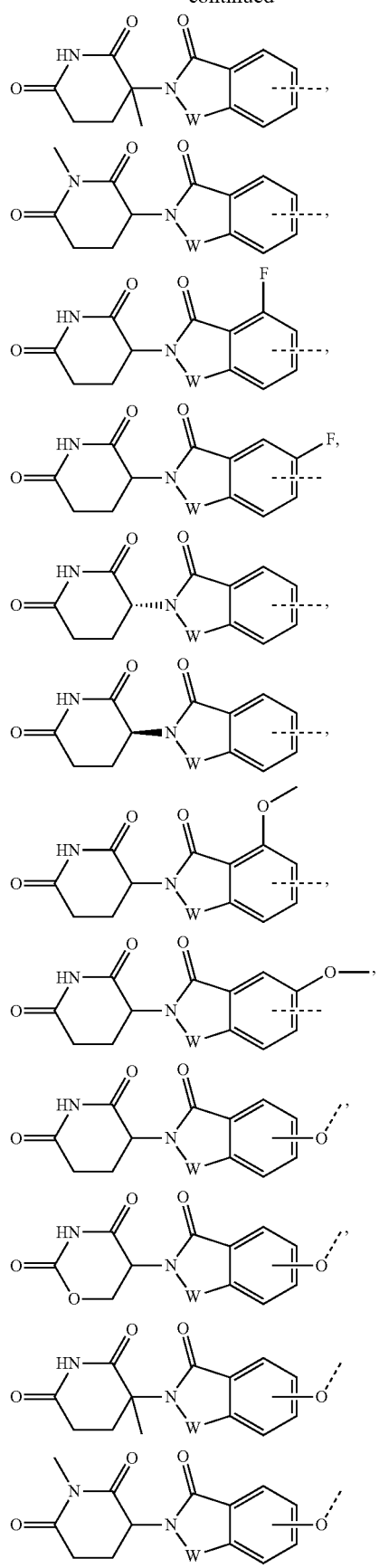
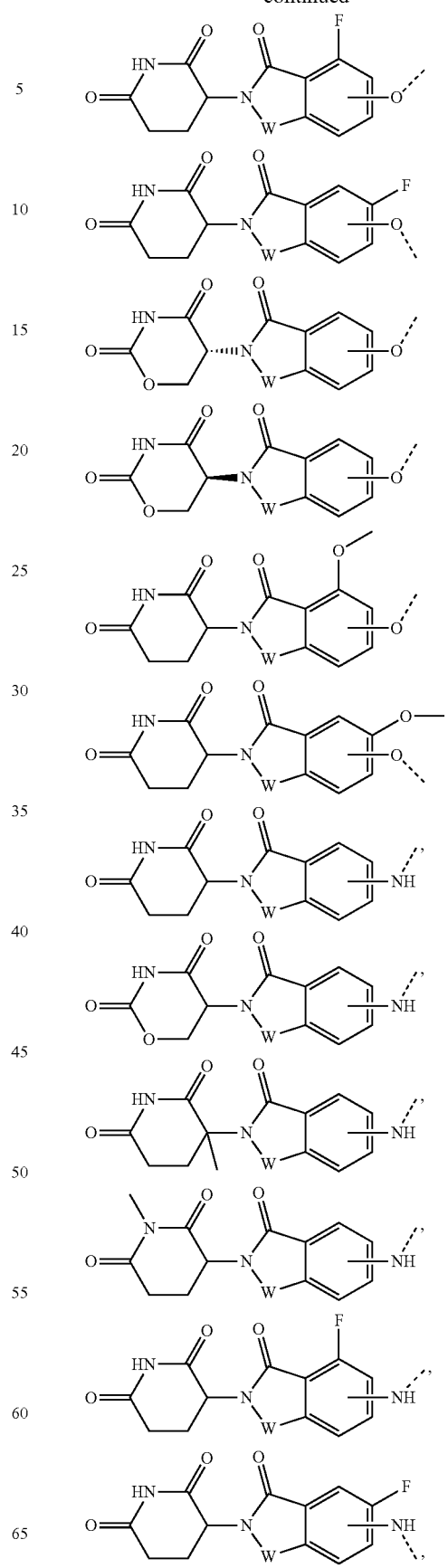

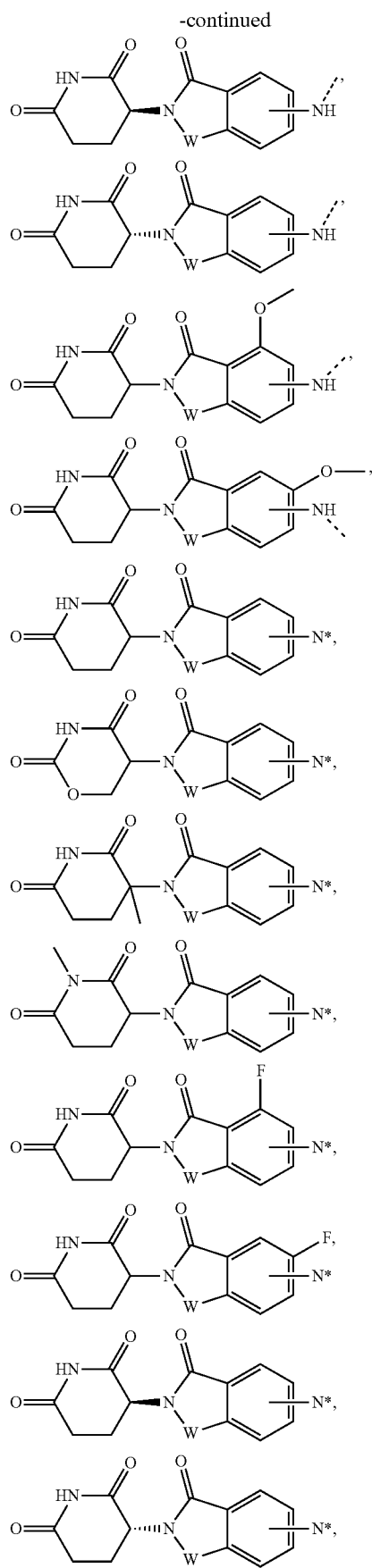
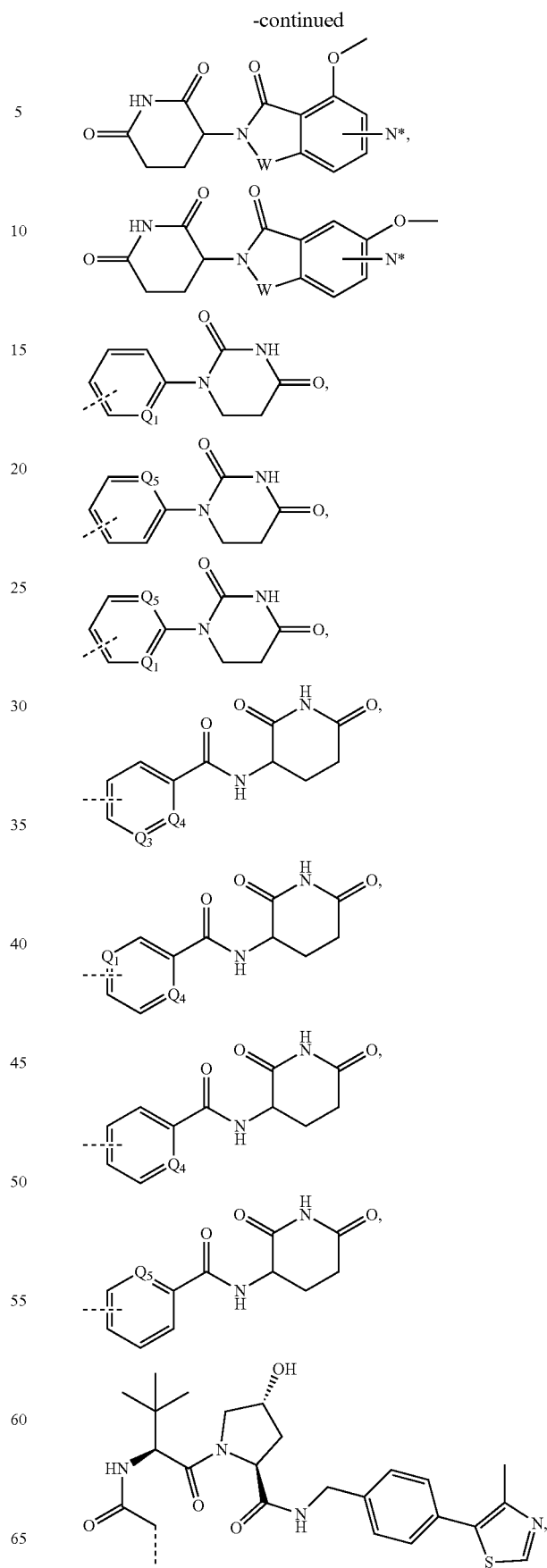

193
-continued
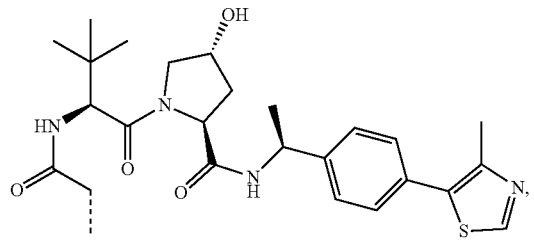
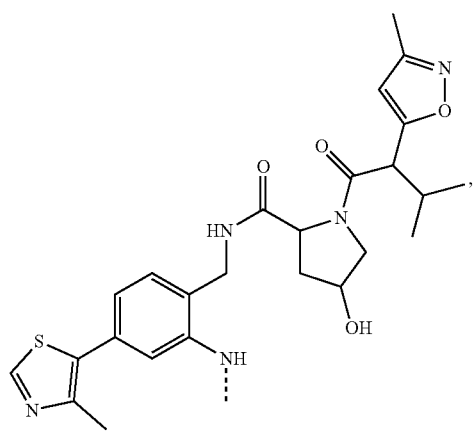
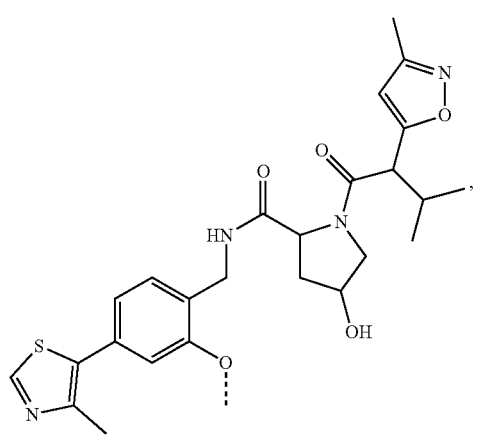
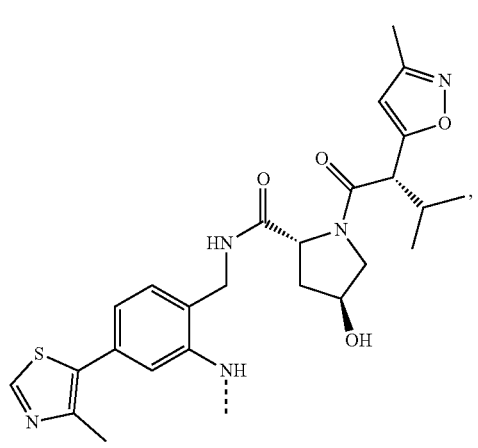
194
-continued
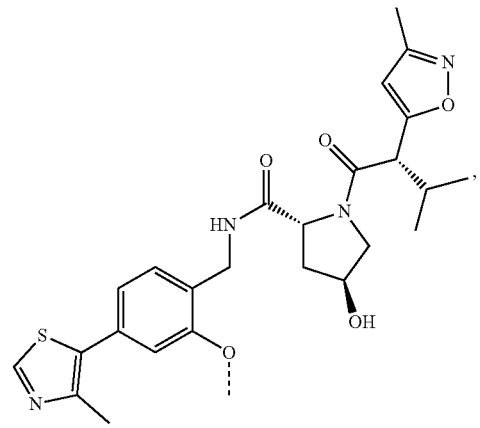
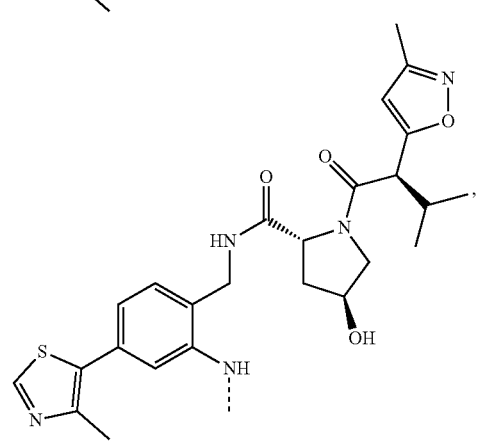
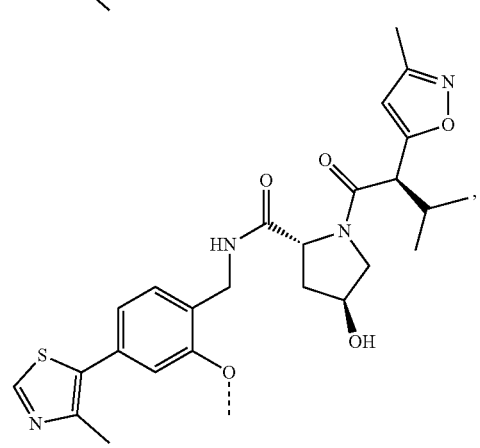
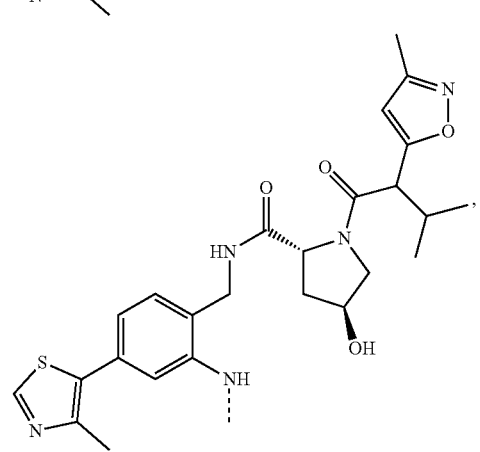

-continued

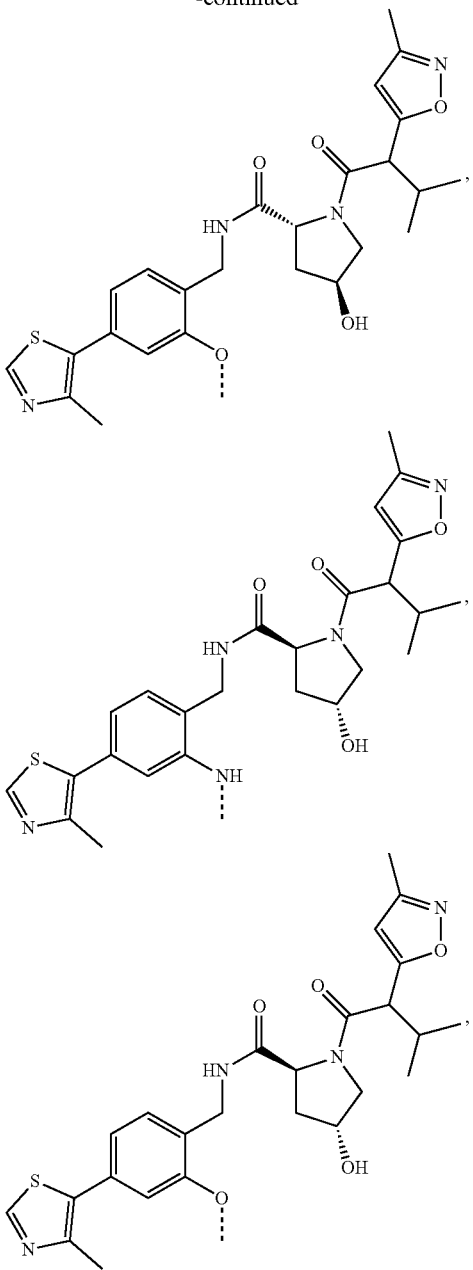

wherein:

$Q_1$, $Q_3$, $Q_4$, and $Q_5$ are independently a nitrogen atom or a carbon atom with a hydrogen, halogen, OH, or $C_{1-3}$ alkoxyl group;

⟋⟋ of the ULM indicates the point of attachment with a chemical linker group or a PTM; and N* is a nitrogen atom that is shared with a chemical linker group or PTM.

Exemplary Linkers

In certain embodiments, the compounds as described herein include one or more PTMs chemically linked or coupled to one or more ULMs (e.g., at least one of CLM, VLM, or a combination thereof) via a chemical linker (L). In certain embodiments, the linker group L is a group comprising one or more covalently connected structural units (e.g., $-A^L_1 \ldots (A^L)_q$- or $-(A^L)_q$-), wherein $A^L_1$ is a group coupled to PTM, and $(A^L)_q$ is a group coupled to ULM.

In any aspect or embodiment described herein, the linker (L) to ULM (e.g., VLM or CLM) connection or coupling is a stable L-ULM connection. For example, in any aspect or embodiment described herein, when a linker (L) and a ULM is connected via a heteroatom, any subsequent heteroatom, if present, is separated by at least one single carbon atom (e.g., —$CH_2$—), such as with an acetal or aminal group. By way of further example, in any aspect or embodiment described herein, when a linker (L) and a ULM is connected via a heteroatom, the heteroatom is not part of an ester.

In any aspect or embodiment described herein, the linker group L is a bond or a chemical linker group represented by the formula -$(A^L)_q$-, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to the PTM and the ULM, and provides for sufficient binding of the PTM to the protein target and the ULM to an E3 ubiquitin ligase to result in target protein ubiquitination.

In any aspect or embodiment described herein, the linker group L is -$(A^L)_q$-, wherein:

$(A^L)_q$ is a group which is connected to at least one of a ULM (such as a CLM or a VLM), PTM moiety, or a combination thereof;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocyclyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl)$_2$, Si(OH)$_3$, Si($C_{1-8}$alkyl)$_3$, Si(OH)($C_{1-8}$alkyl)$_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, NH $SO_2NH(C_{1-8}alkyl)$, NH $SO_2N(C_{1-8}alkyl)_2$, NH $SO_2NH_2$.

In any aspect or embodiment described herein, q of the linker is an integer greater than or equal to 0. In certain embodiments, q is an integer greater than or equal to 1.

In any aspect or embodiment described herein, e.g., where q of the linker is greater than 2, $(A^L)_q$ is a group which is $A^L_1$ and $(A^L)_q$ wherein the units $A^L$ are couple a PTM to a ULM.

In any aspect or embodiment described herein, e.g., where q of the linker is 2, $(A^L)_q$ is a group which is connected to $A^L_1$ and to a ULM.

In any aspect or embodiment described herein, e.g., where q of the linker is 1, the structure of the linker group L is -$A^L_1$-, and $A^L_1$ is a group which is connected to a ULM moiety and a PTM moiety.

In any aspect or embodiment described herein, the unit $A^L$ of linker (L) comprises a group represented by a general structure selected from the group consisting of:
—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocyclyl)-CH$_2$, —NR(CH$_2$CH$_2$)$_n$-(heterocyclyl)-(heterocyclyl)-CH$_2$, —N(R1R2)-(heterocyclyl)-CH$_2$; where n of the linker can be 0 to 10;

R of the linker can be H, lower alkyl;

R1 and R2 of the linker can form a ring with the connecting N.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linker or adjacently located).

In any aspect or embodiment describe herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally substituted with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{5-13}$ heteocyclyl optionally substituted with 0-6 $R^{L1}$ and/or $R^{L2}$ groups, $C_{5-13}$ spiroheterocyclyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, NH $SO_2NH(C_{1-8}$alkyl), NH $SO_2N(C_{1-8}$alkyl$)_2$, NH $SO_2NH_2$. In any aspect or embodiment described herein, the linker (L) does not have heteroatom-heteroatom bonding (e.g., no heteroatoms are covalently linker or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

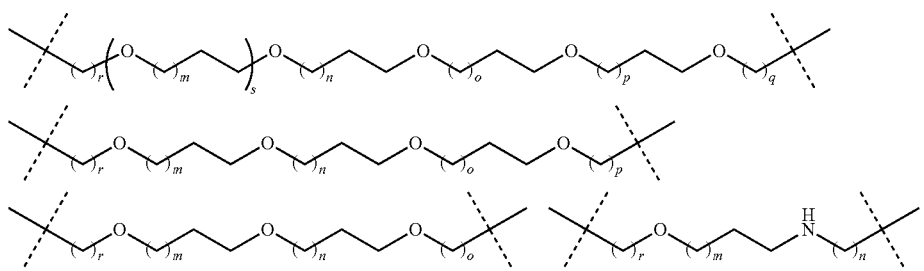

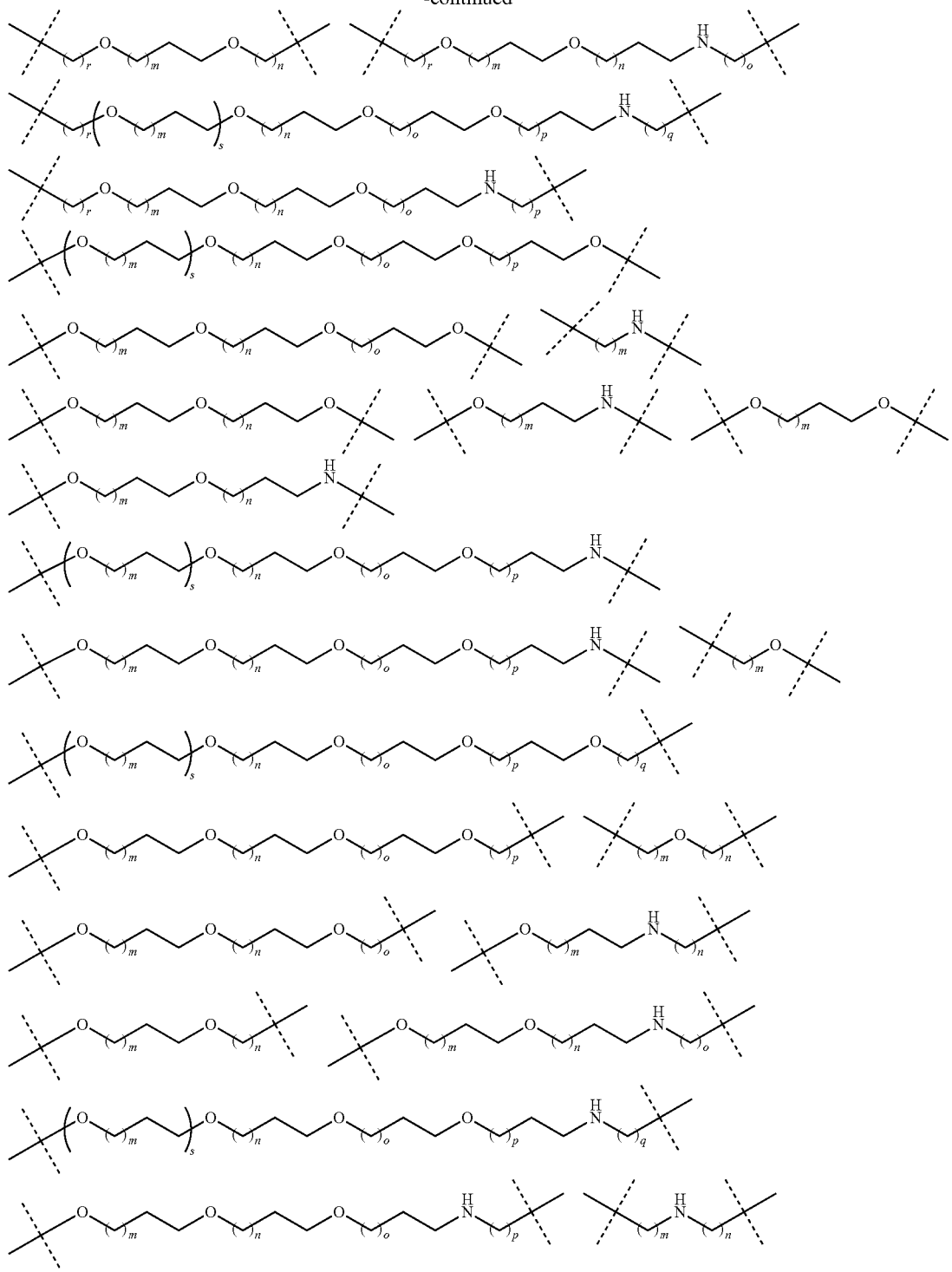

wherein carbon or oxygen may be substituted with a heteroatom selected from N, S, P, or Si atoms with an appropriate number of hydrogens to complete valency, and m, n, o, p, q, r, and s are independently selected from 0, 1, 2, 3, 4, 5, 6, 7, 8, 9, 10, 11, 12, 13, 14, 15, 16, 17, 18, 19, and 20.

In any aspect or embodiment described herein, the unit $A^L$ of the linker (L) comprises a group represented by a general structure selected from the group consisting of:

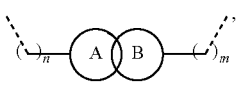

-continued

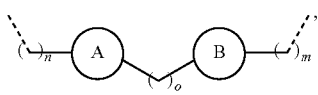

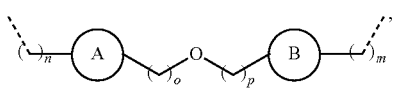

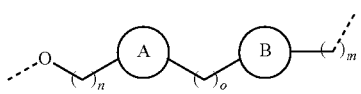

wherein:

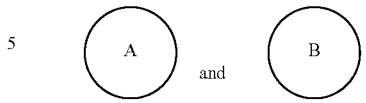

are each independently a 3-7 membered cycloalkyl or heterocycloalkyl (e.g., 4-6 membered cycloalkyl or heterocycloalkyl), wherein overlapping circles indicates spirocyclic rings;

each m, n, o, and p is independently 0, 1, 2, 3, 4, 5, or 6; and

⸺ indicates the attachment point to the PTM or the ULM.

In any aspect or embodiment described herein, the unit $A^L$ of the linker (L) comprises a group represented by a general structure selected from the group consisting of:

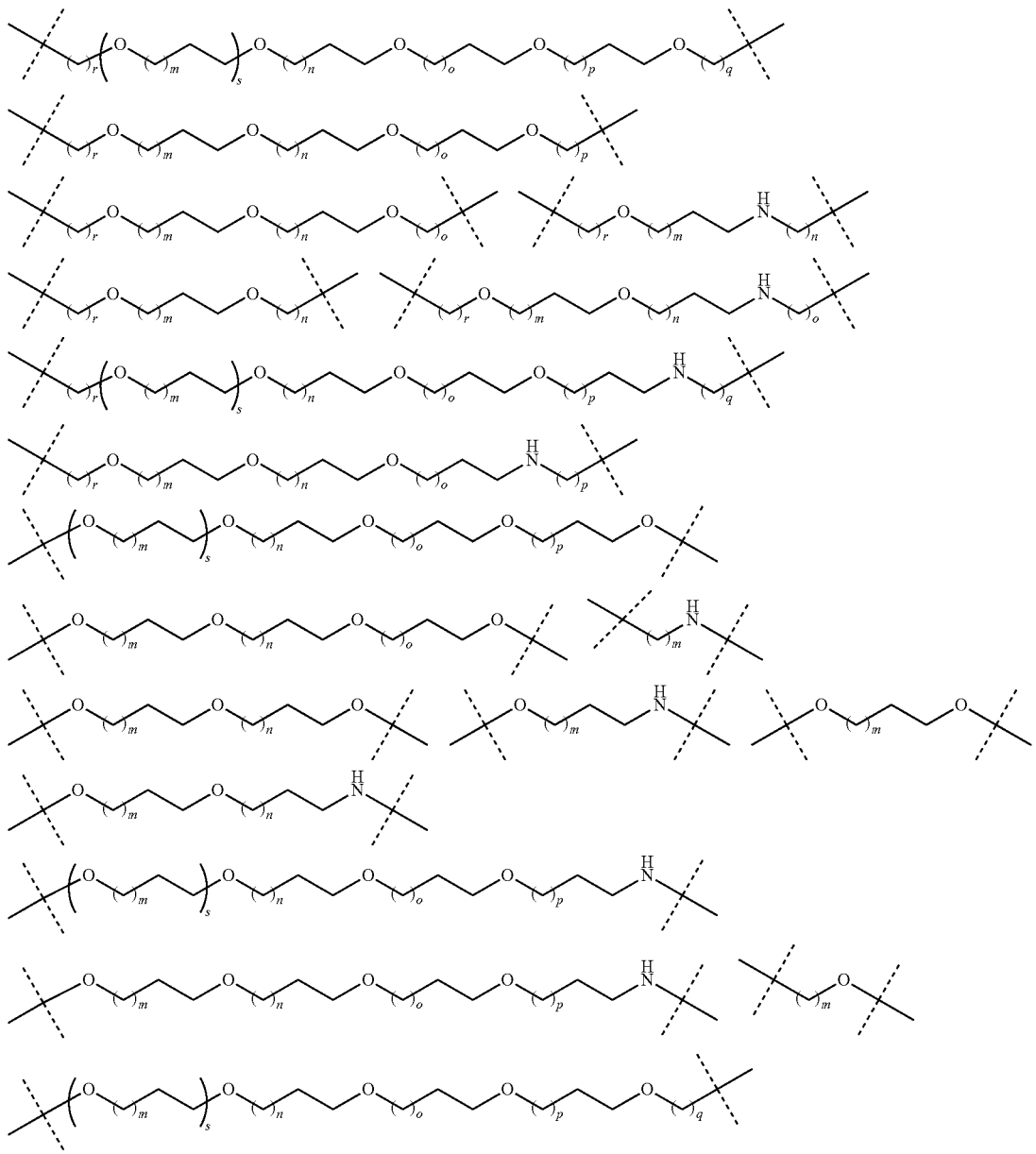

-continued
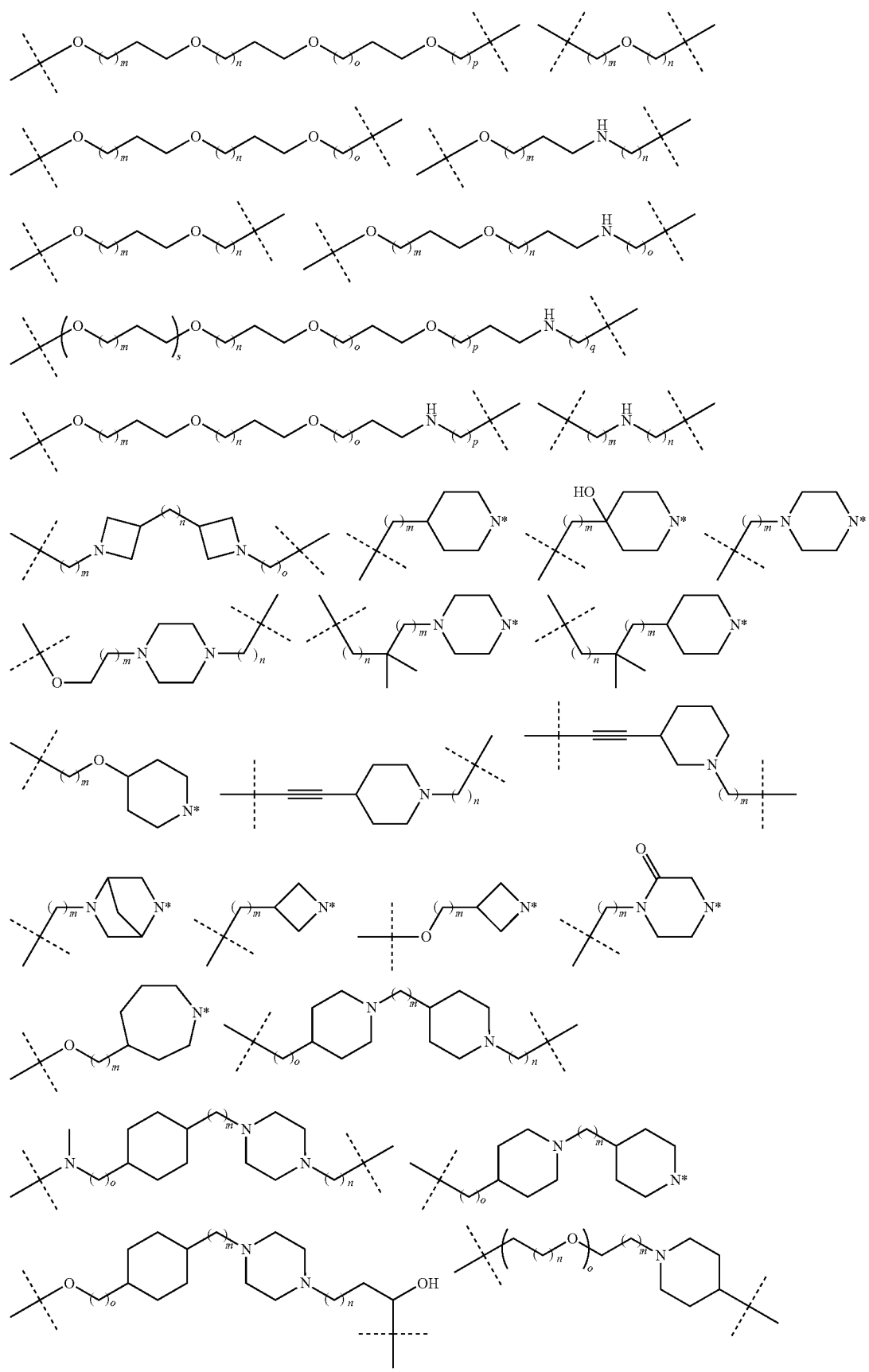

-continued
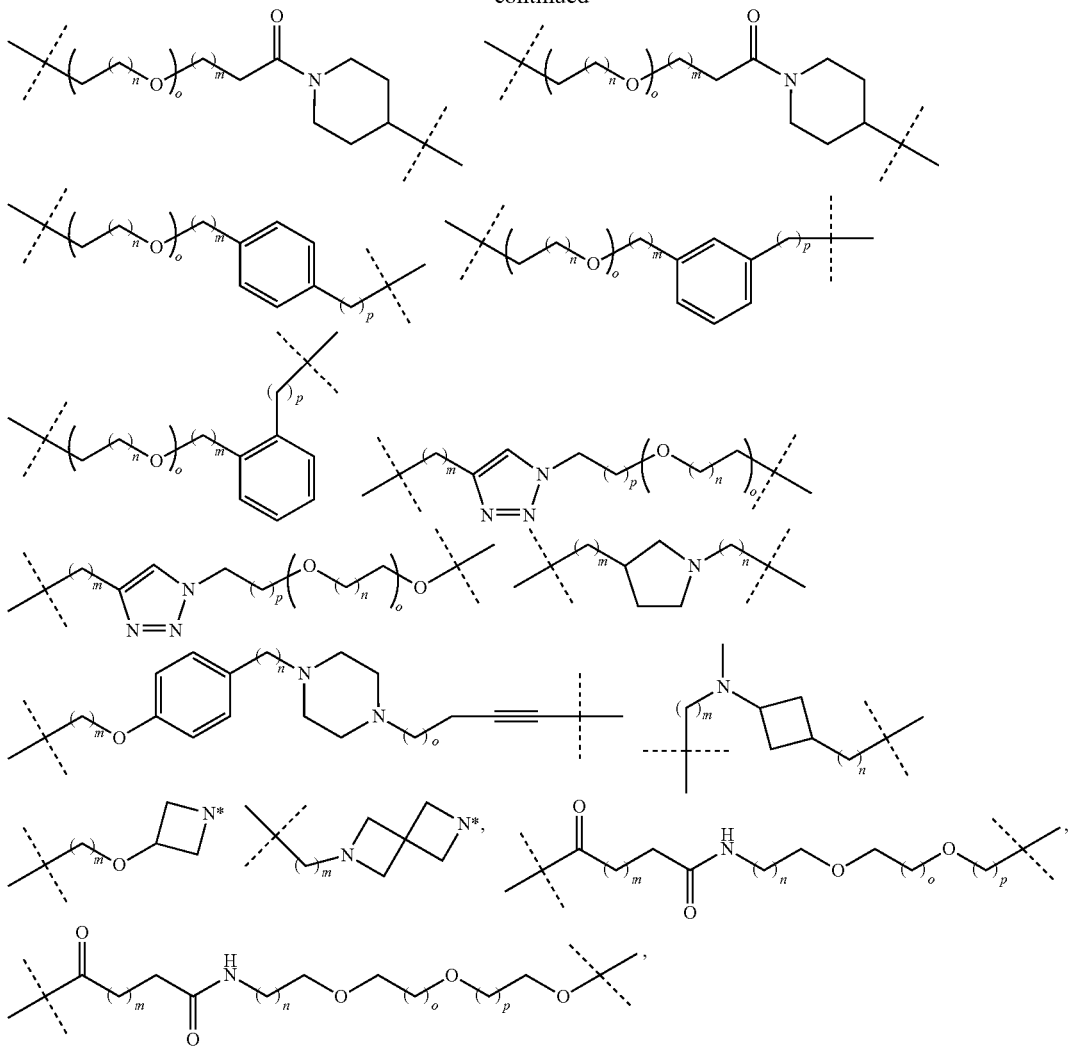
wherein:
N* is a nitrogen atom that is covalently linked to the ULM or PTM, or that is shared with the ULM or PTM;
⌿ indicates the attachment point to the PTM or the ULM; and
each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of the linker (L) is selected from:
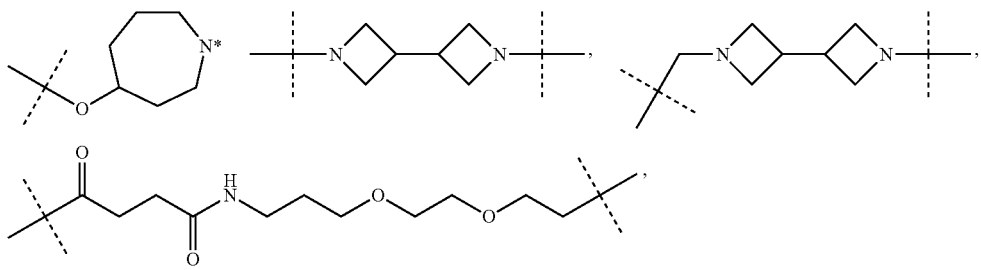

-continued
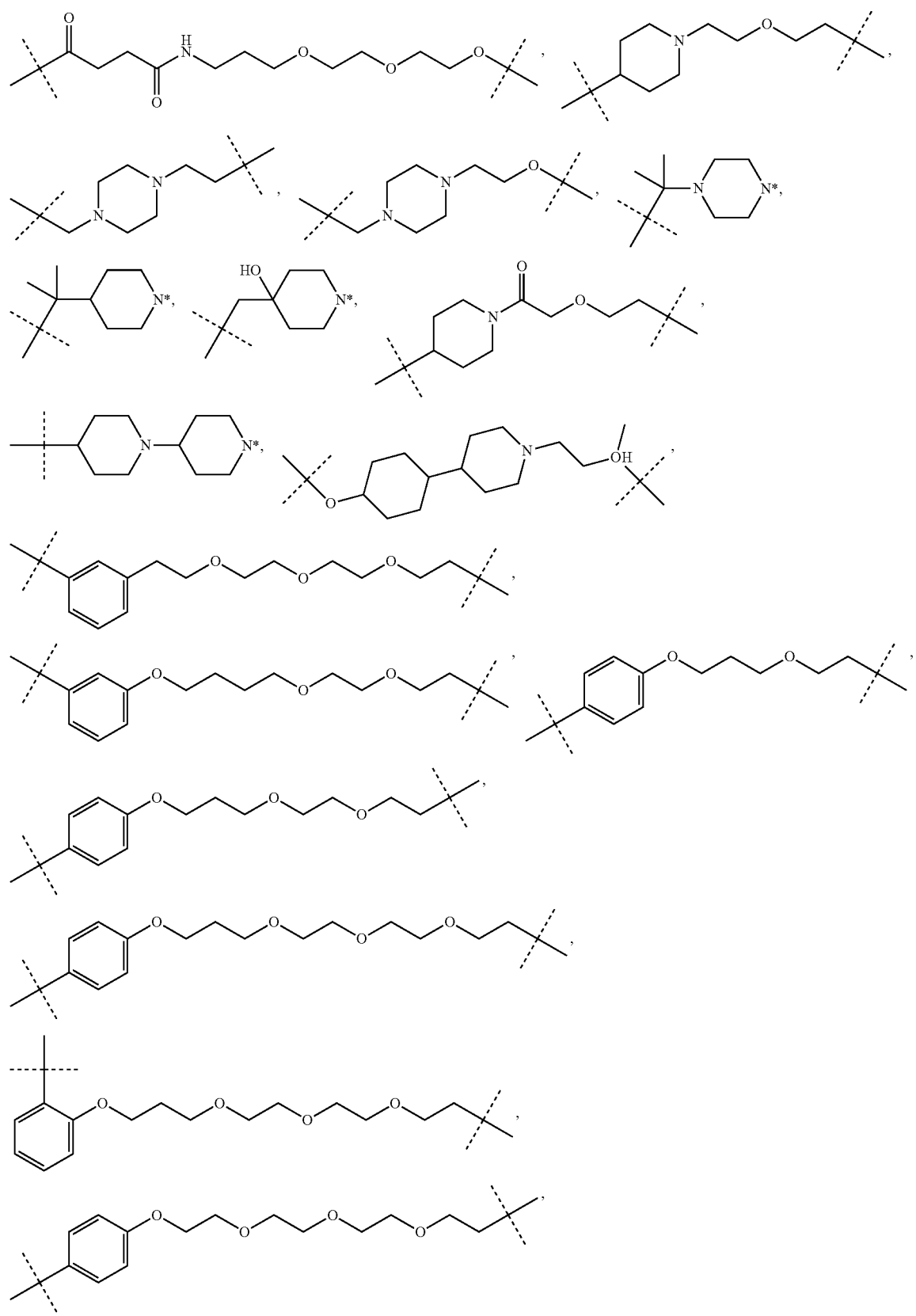

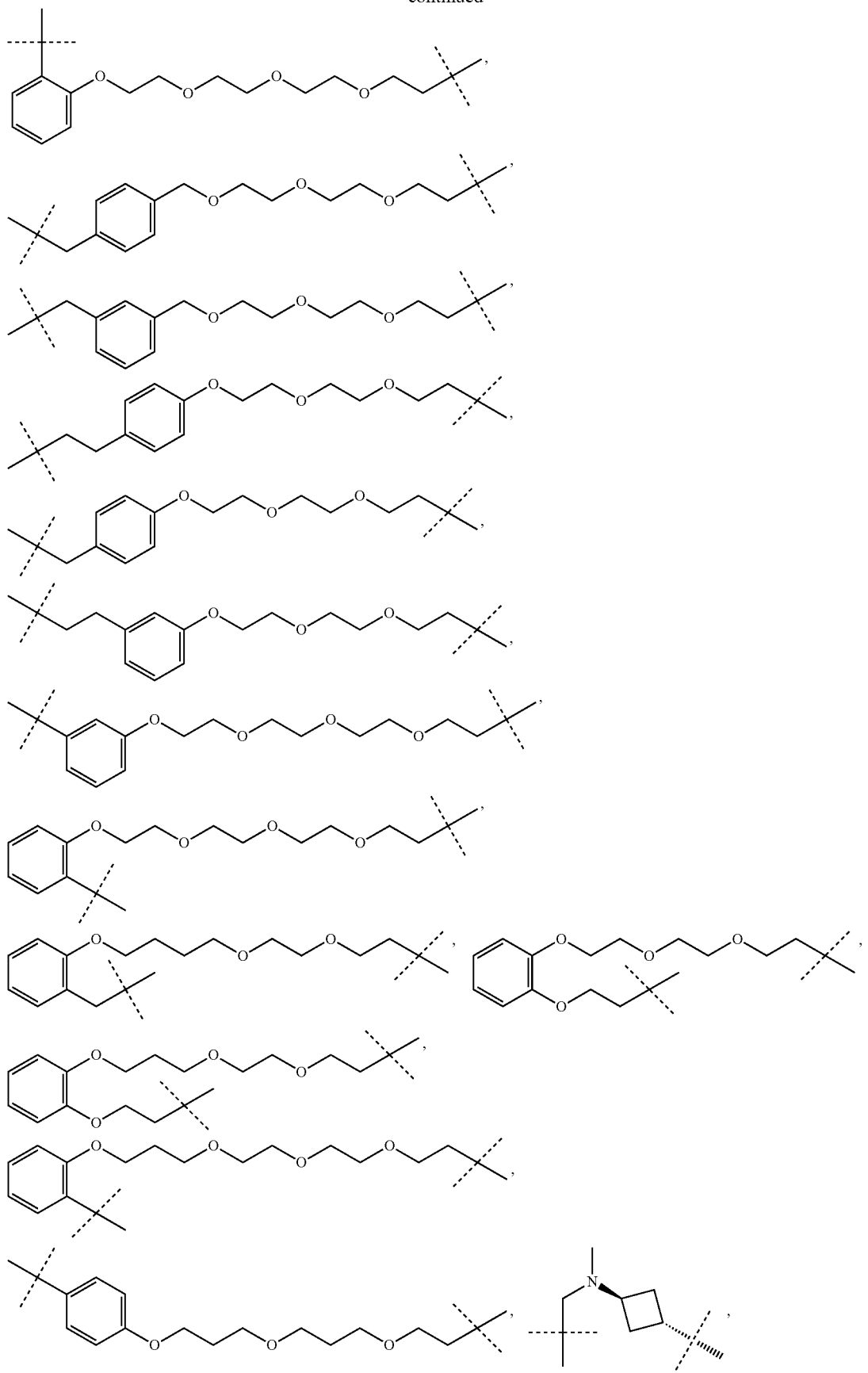

-continued
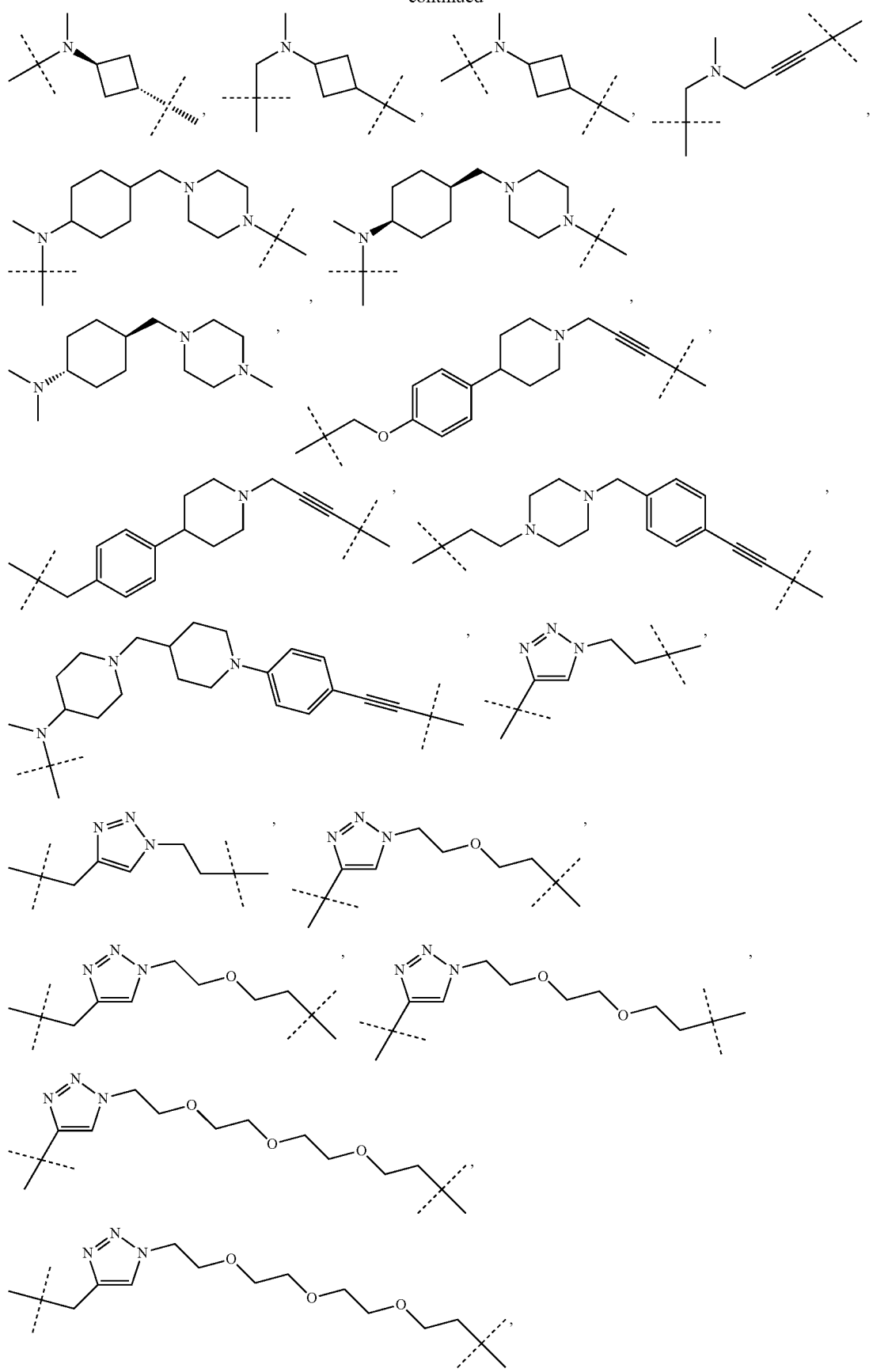

213 214
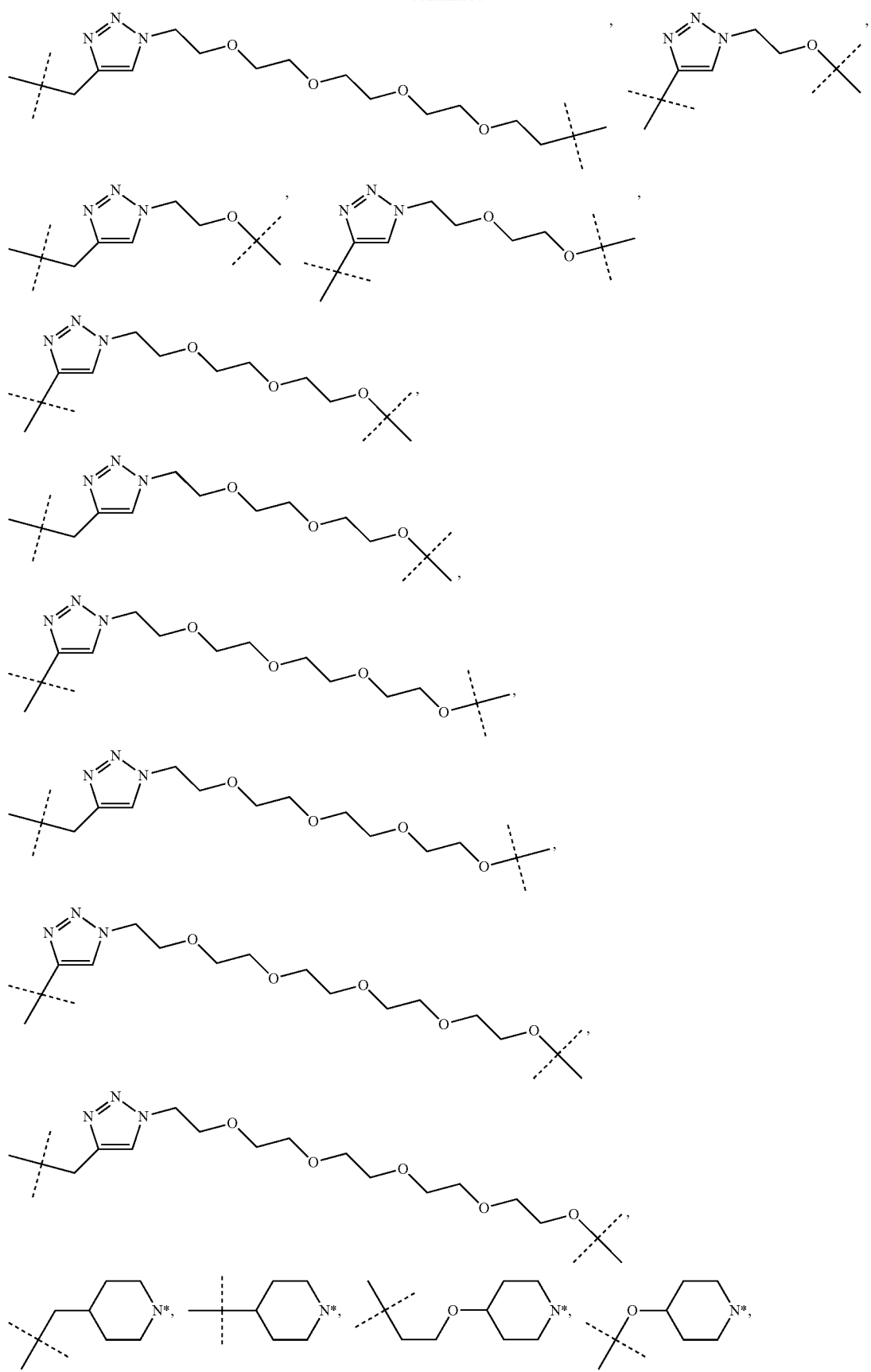

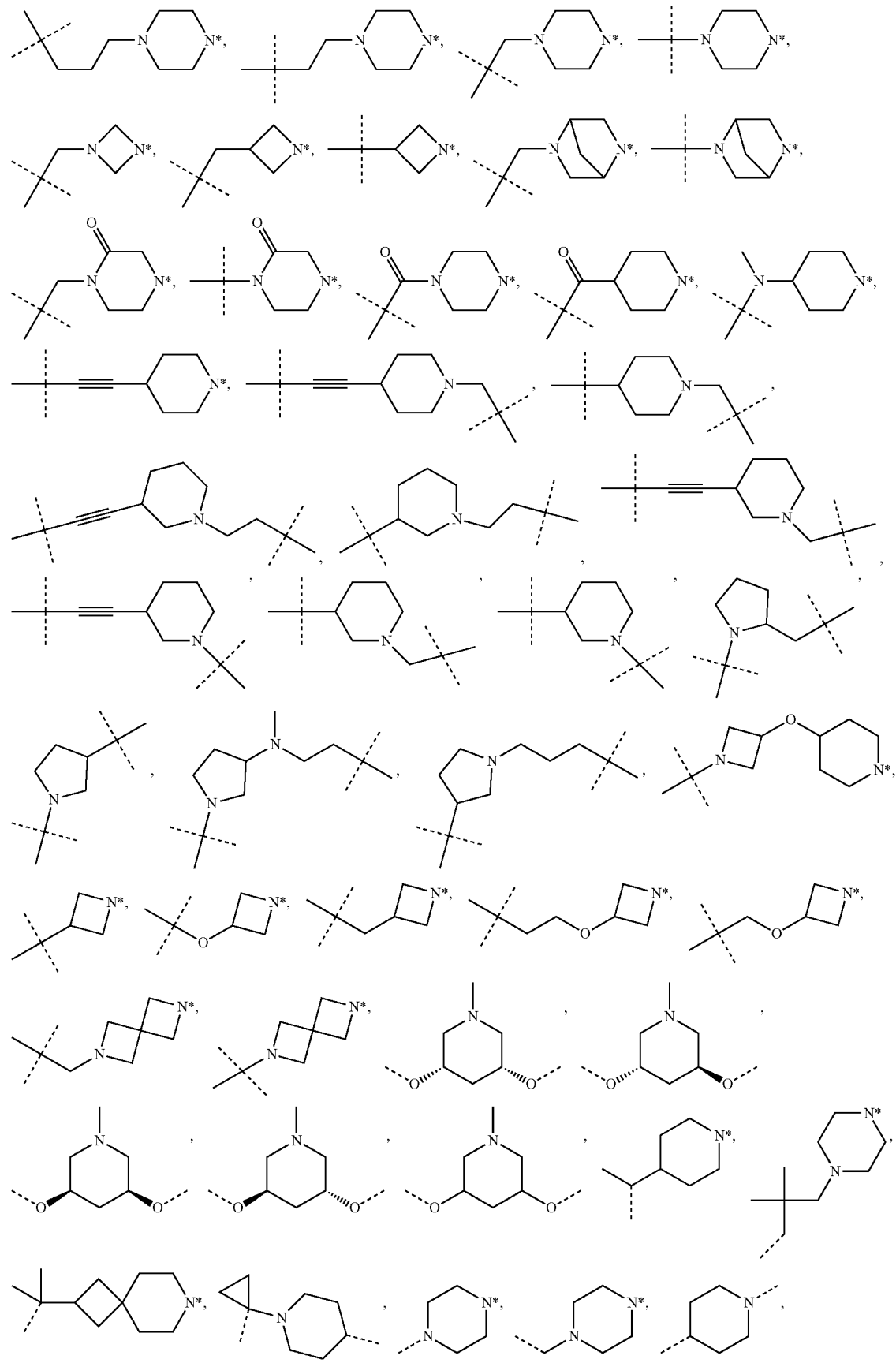

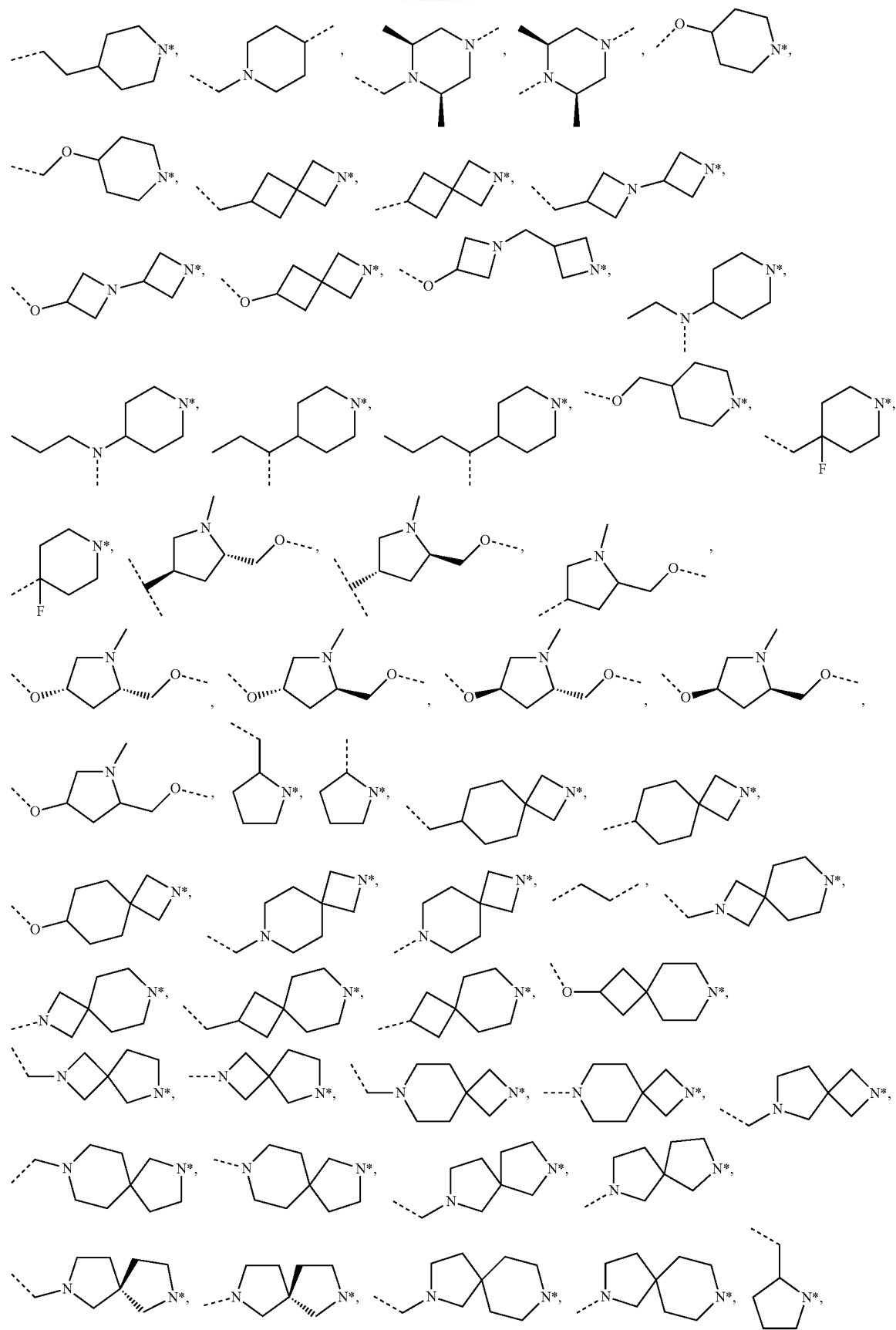

-continued
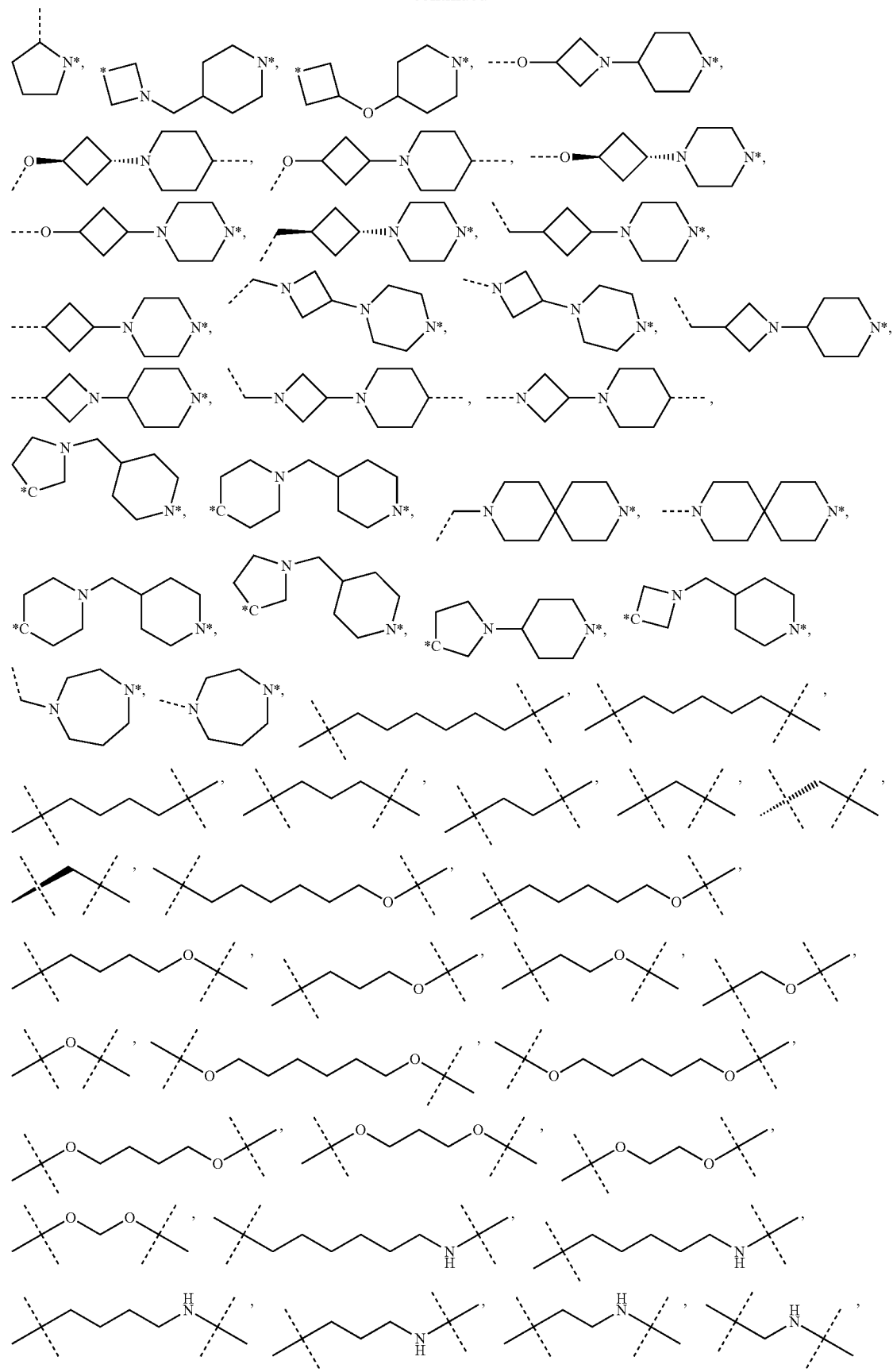

-continued
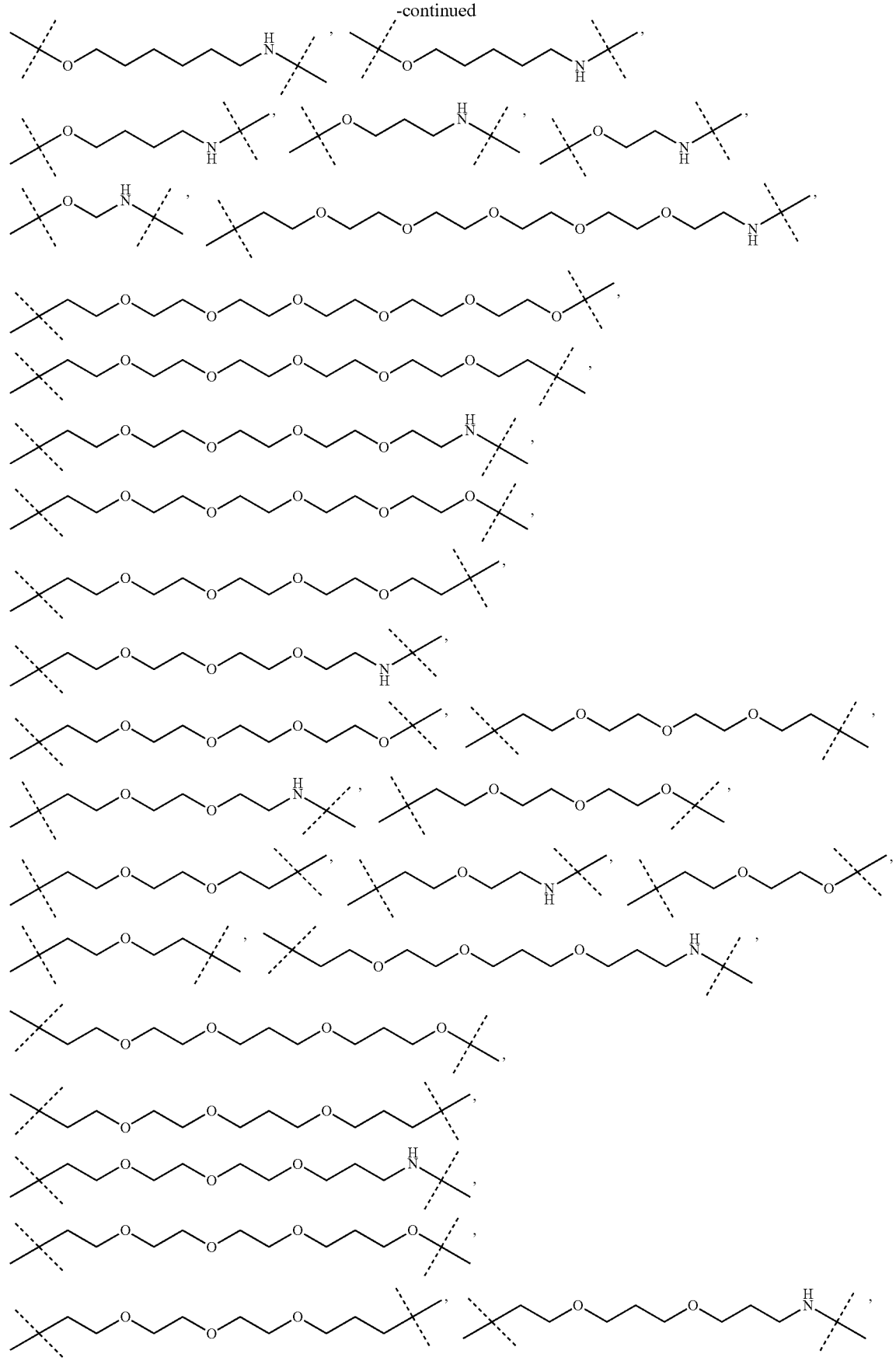

-continued

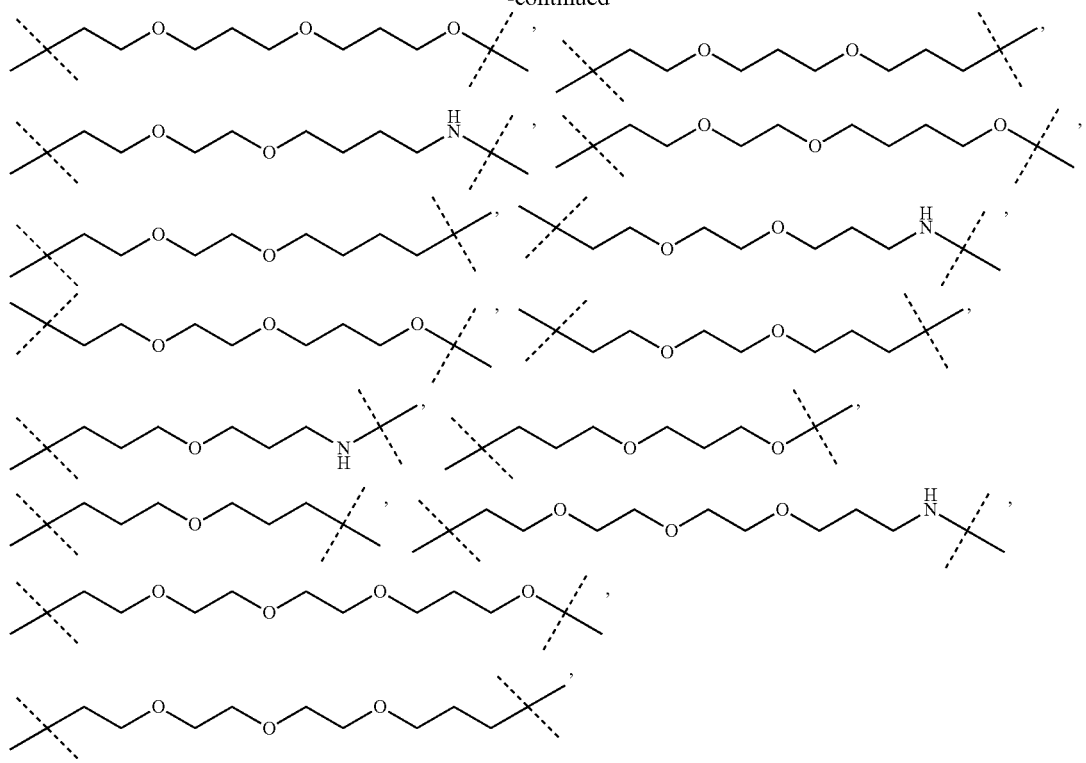

wherein N* is a nitrogen atom that is covalently linked to the ULM or PTM, or that is shared with the ULM or PTM, and ⸺ indicates the point of attachment with the ULM or the PTM.

In any aspect or embodiment described herein, the unit $A^L$ of linker (L) comprises a group represented by a general structure selected from the group consisting of:

—N(R)—(CH2)$_m$O(CH2)$_n$-O(CH2)$_o$-O(CH2)$_p$-O(CH2)$_q$-O(CH2)$_r$-OCH2-,

—O—(CH2)$_m$-O(CH2)$_n$-O(CH2)$_o$-O(CH2)$_p$-O(CH2)$_q$-O(CH2)$_r$-OCH2-,

—O—(CH2)$_m$-O(CH2)$_n$-O(CH2)$_o$-O(CH2)$_p$-O(CH2)$_q$-O(CH2)$_r$-O—;

—N(R)—(CH2)$_m$-O(CH2)$_n$-O(CH2)$_o$-O(CH2)$_p$-O(CH2)$_q$-O(CH2)$_r$-O—;

—(CH2)$_m$-O(CH2)$_n$-O(CH2)$_o$-O(CH2)$_p$-O(CH2)$_q$-O(CH2)$_r$-O—;

—(CH2)$_m$-O(CH2)$_n$-O(CH2)$_o$-O(CH2)$_p$-O(CH2)$_q$-O(CH2)$_r$-OCH2-;

-continued

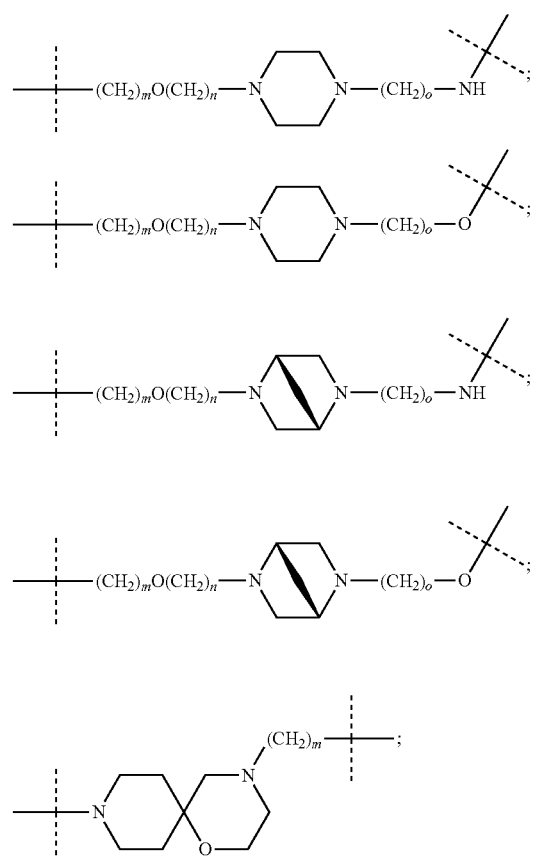

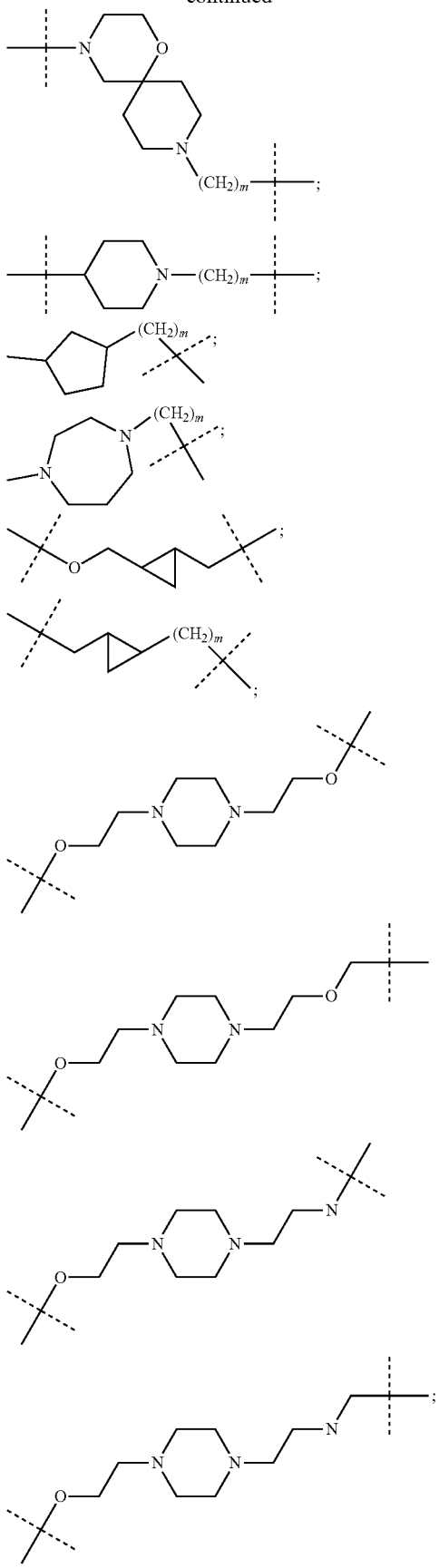
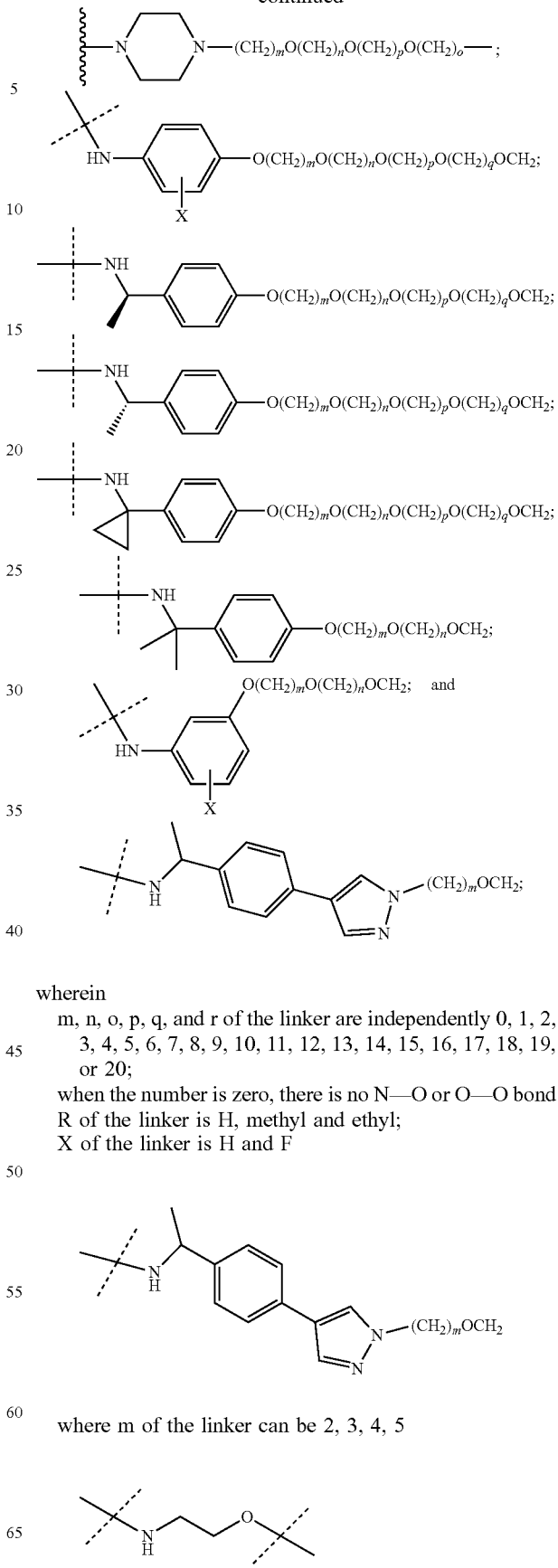
wherein
m, n, o, p, q, and r of the linker are independently 0, 1, 2, 3, 4, 5, 6, 7, 8, 9, 10, 11, 12, 13, 14, 15, 16, 17, 18, 19, or 20;
when the number is zero, there is no N—O or O—O bond
R of the linker is H, methyl and ethyl;
X of the linker is H and F
where m of the linker can be 2, 3, 4, 5

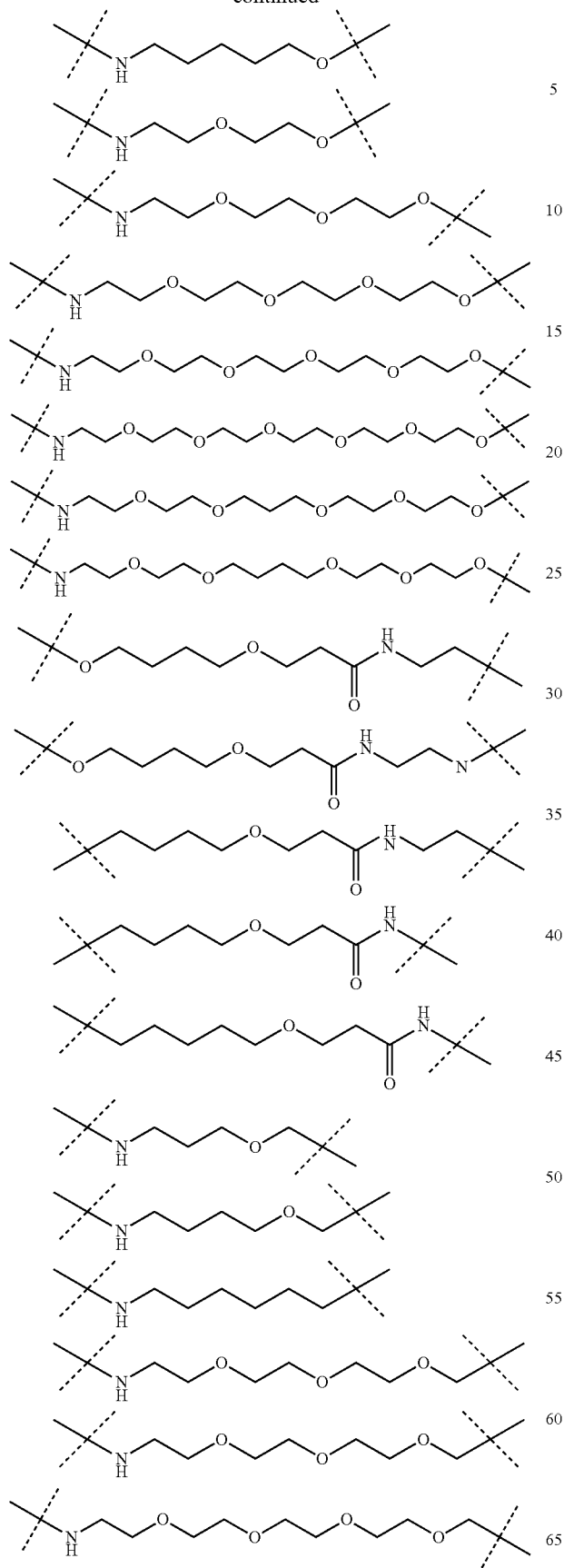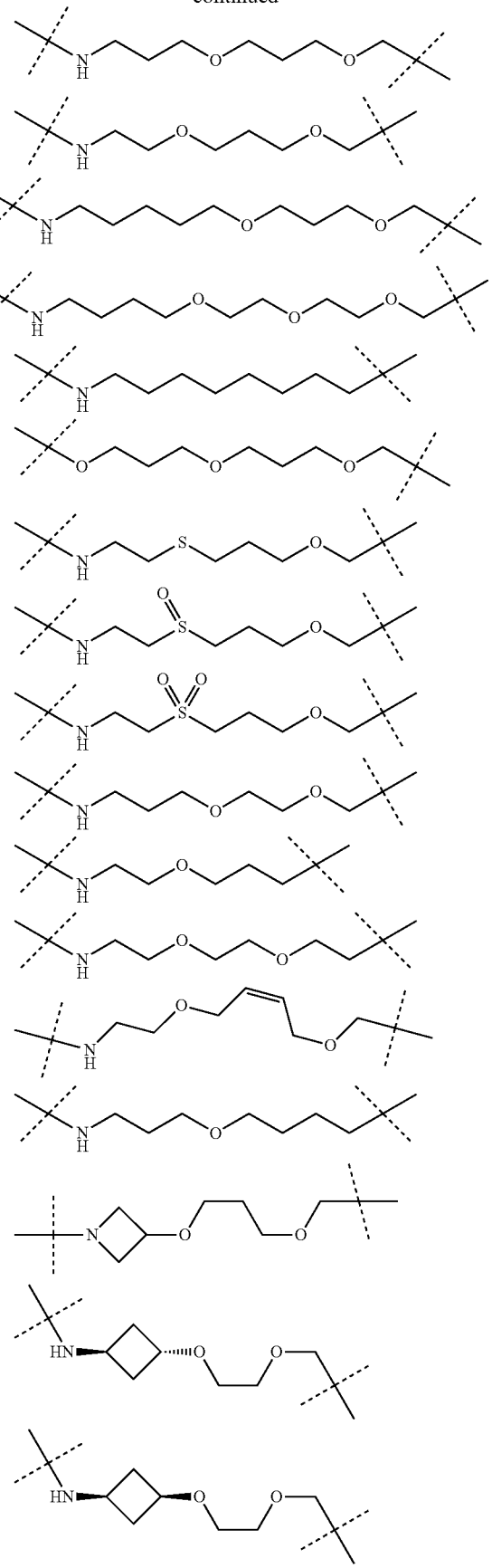

229
-continued
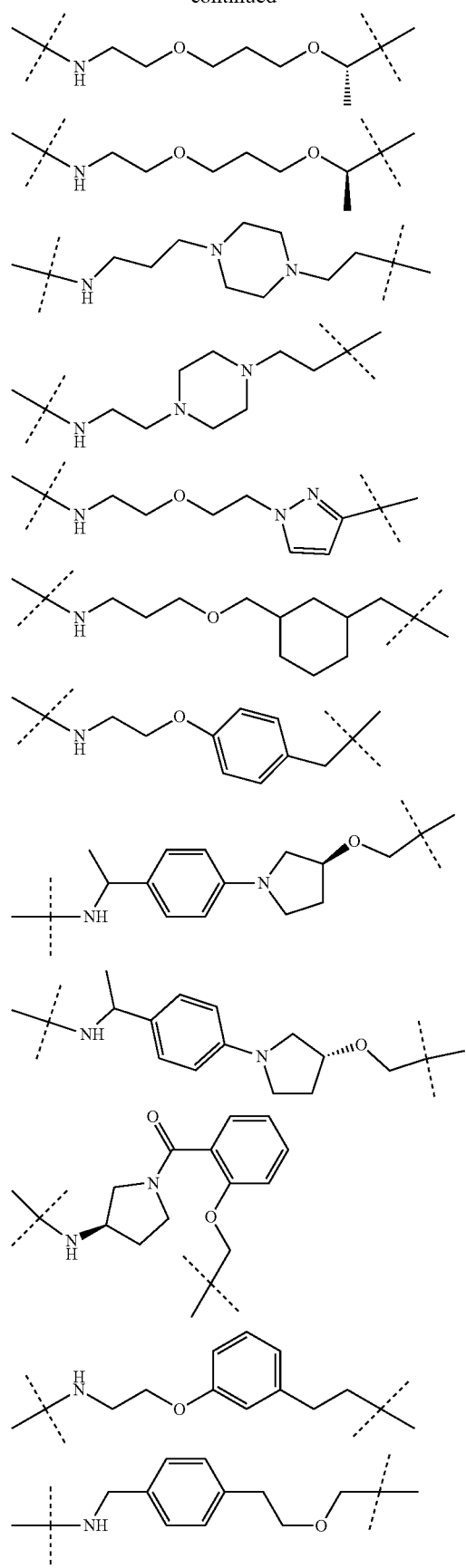
230
-continued
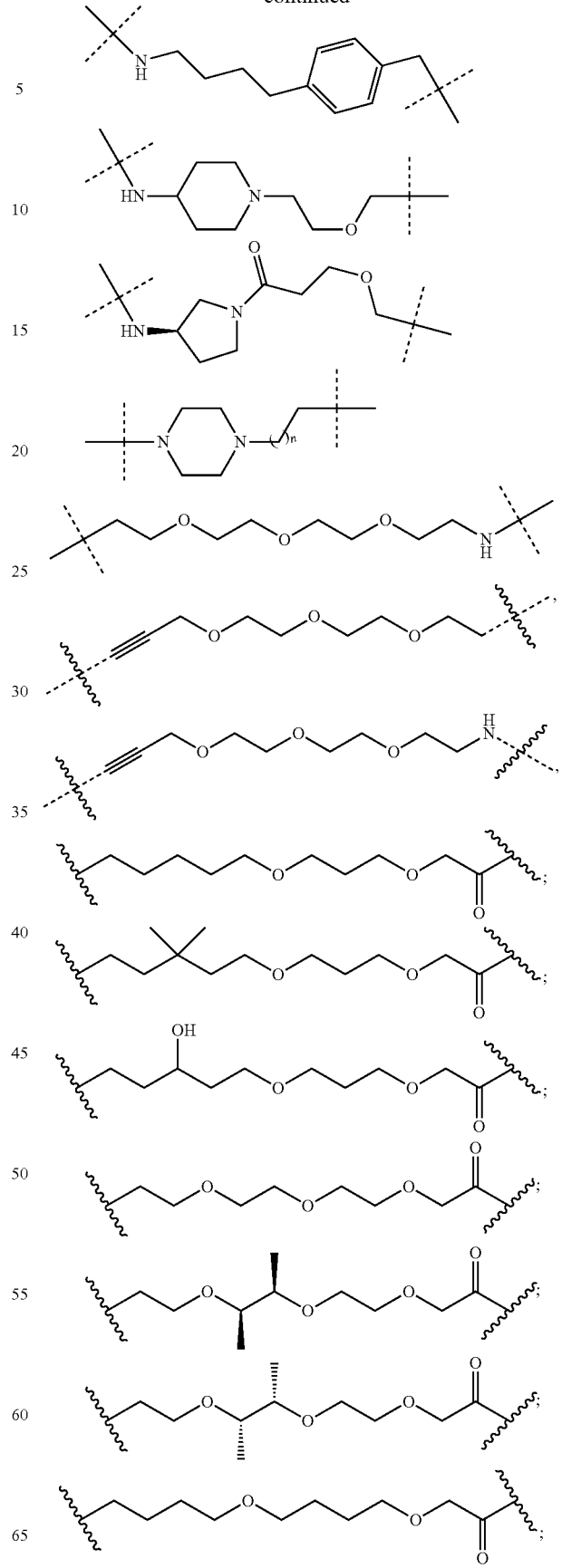

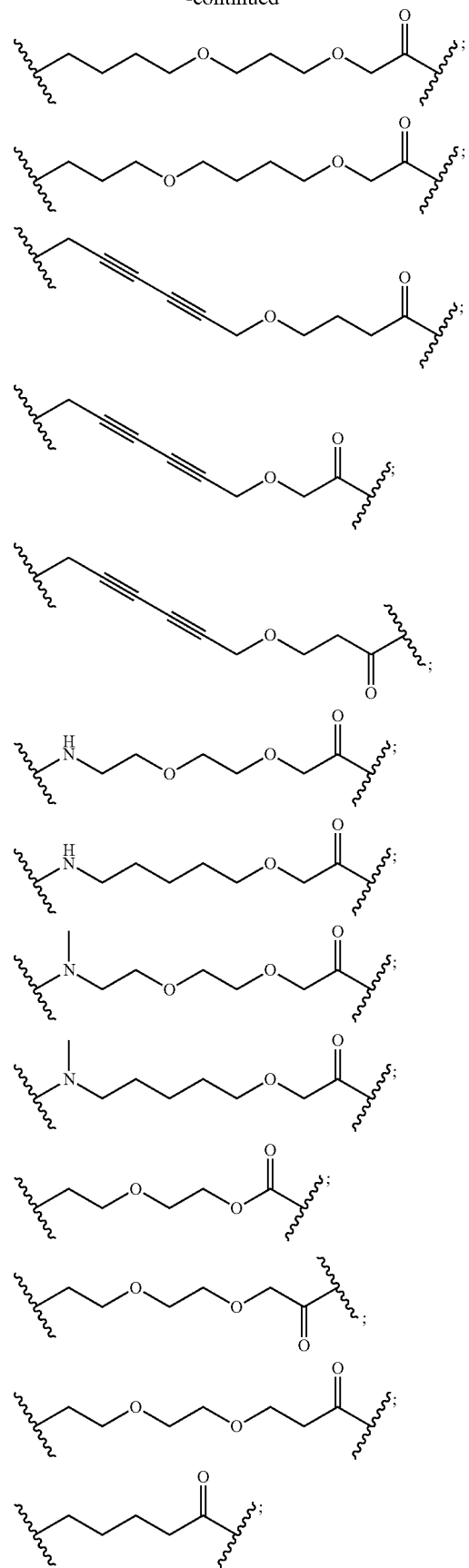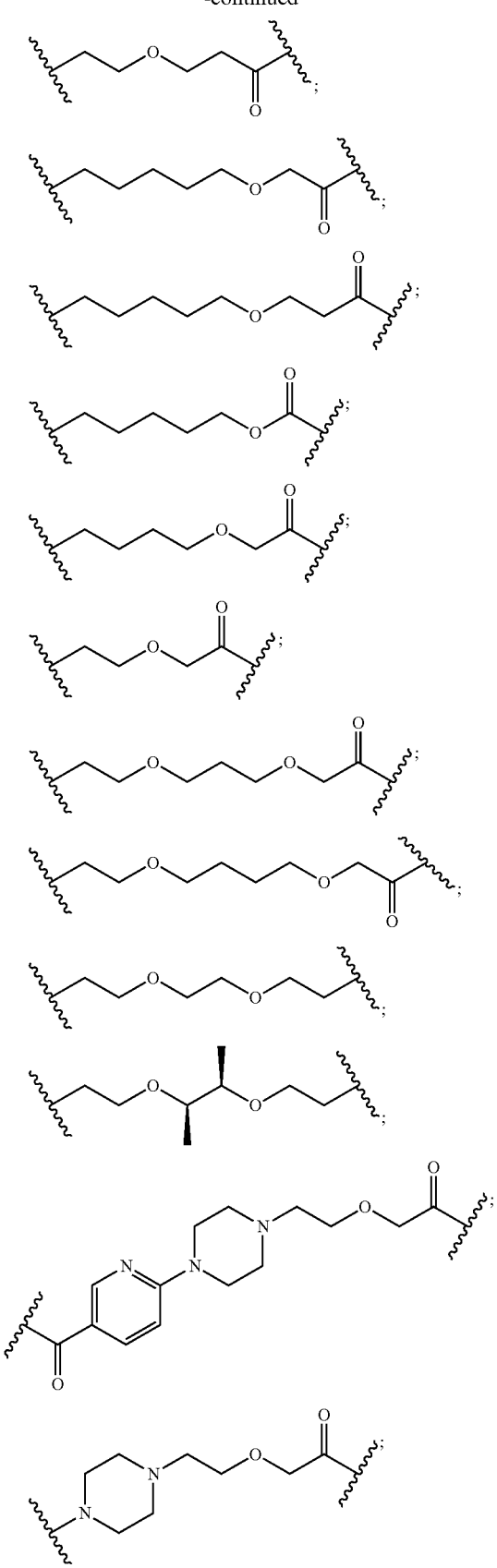

233
-continued
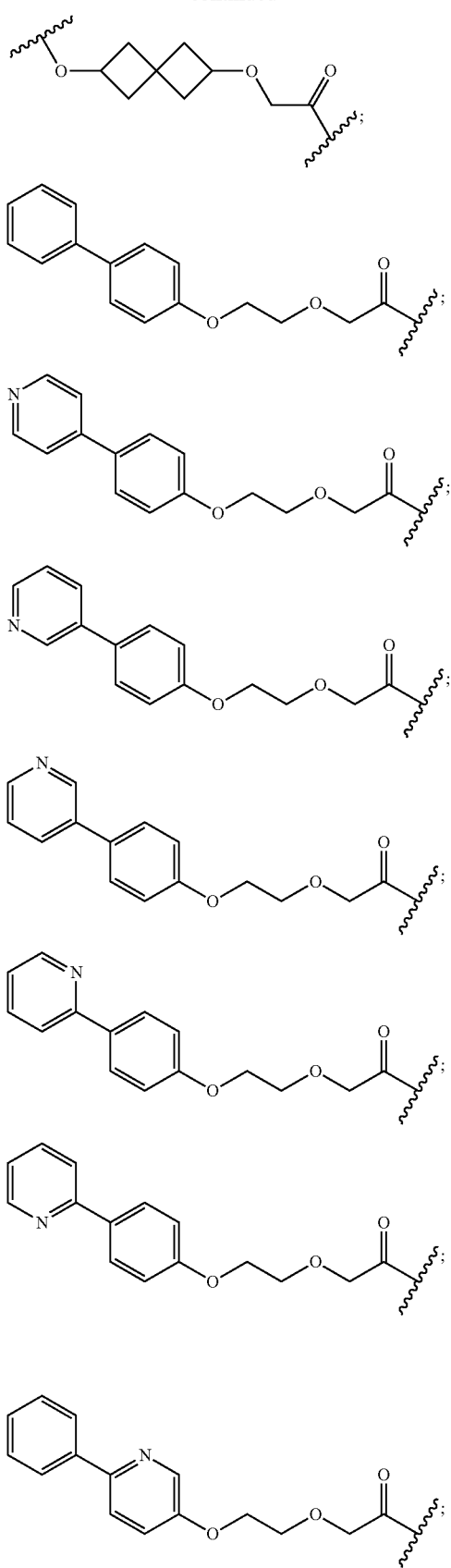
234
-continued
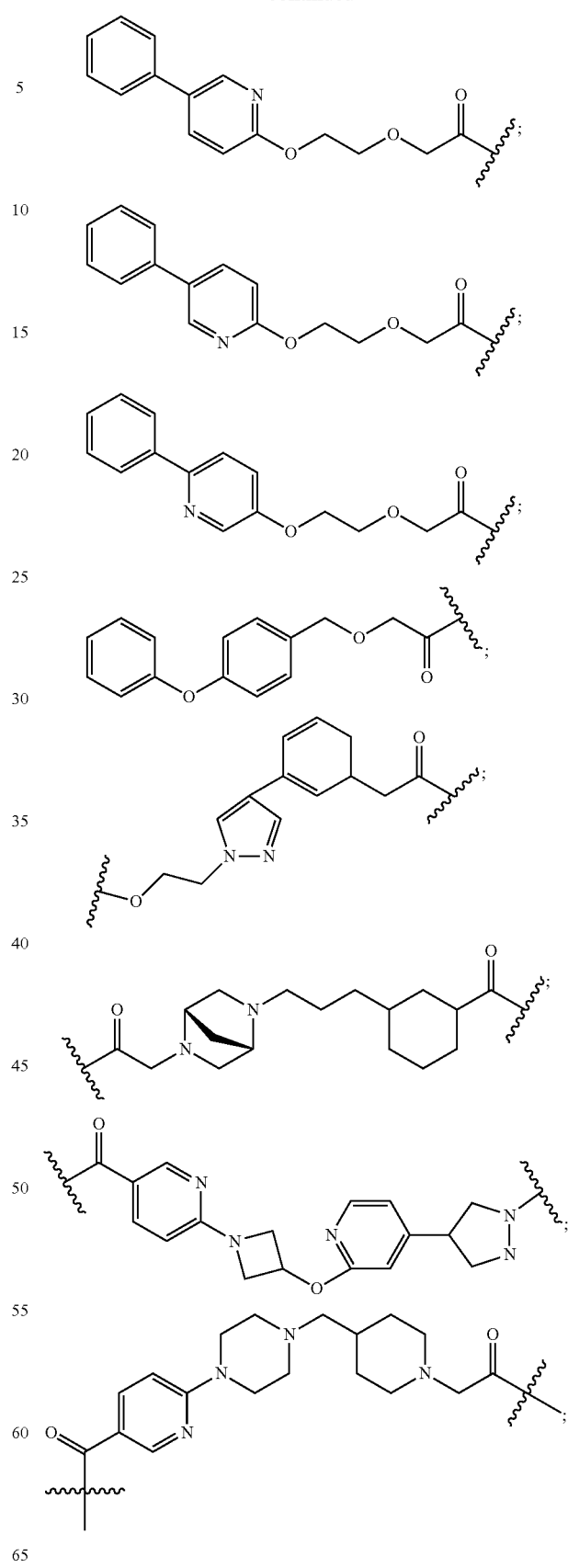

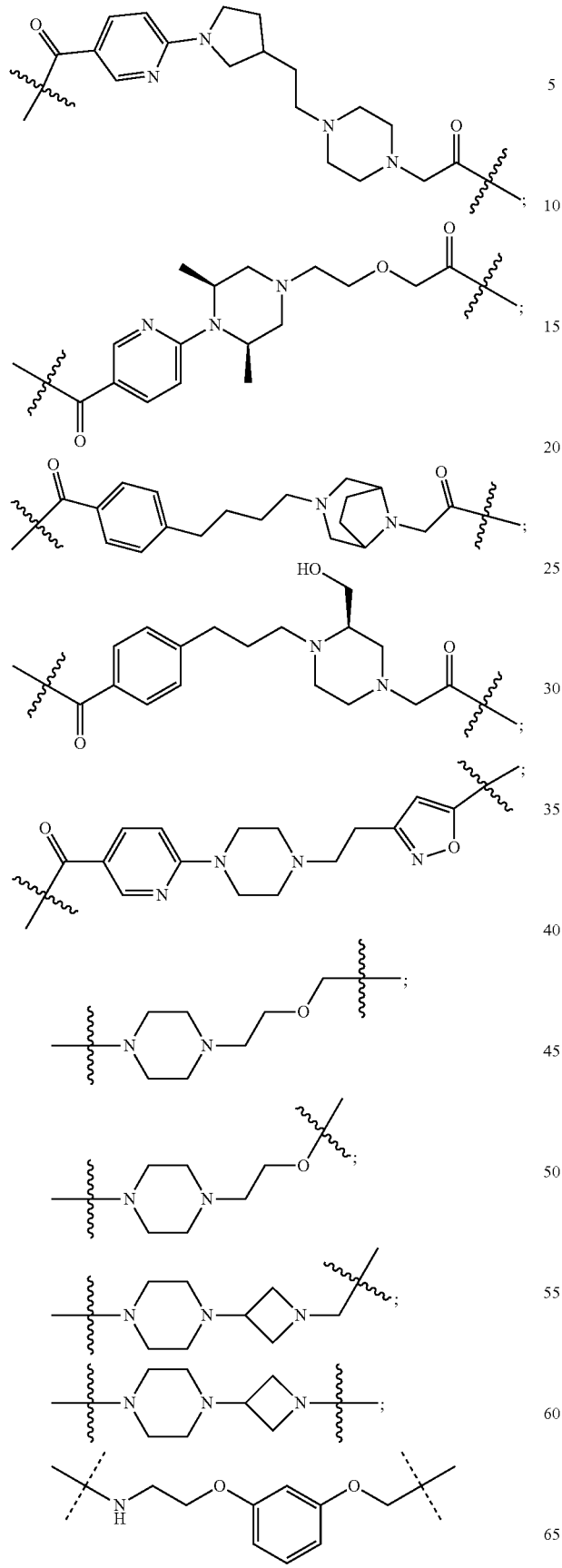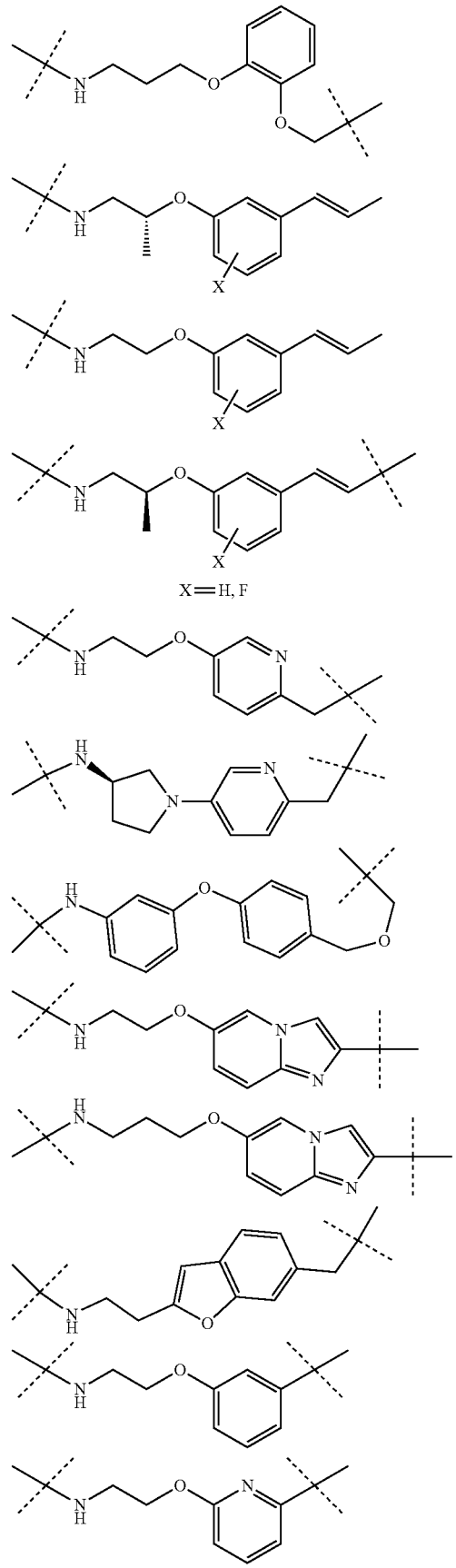

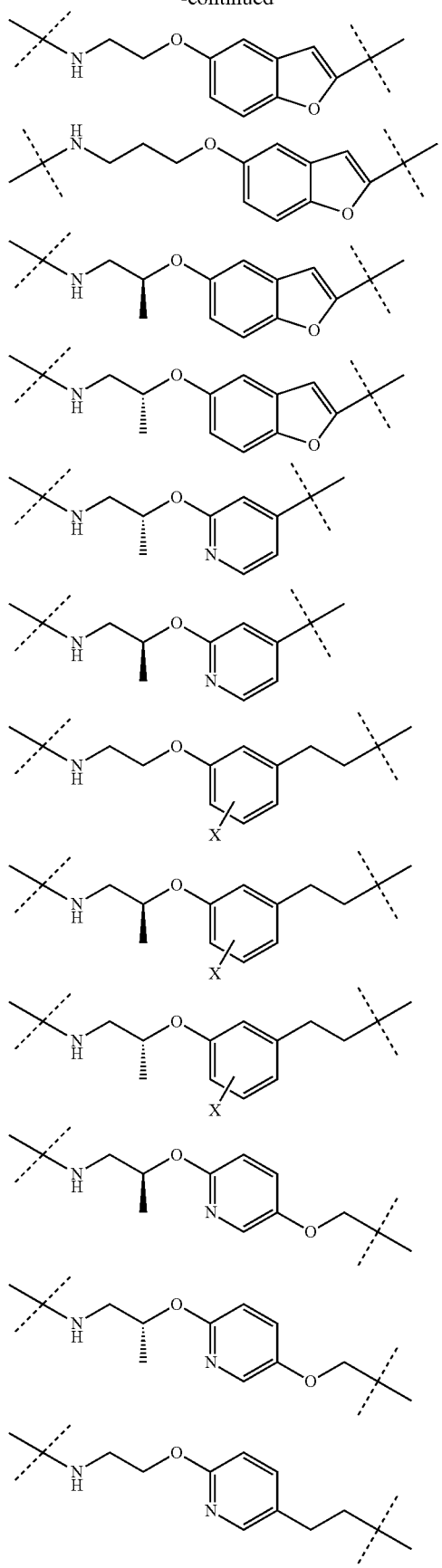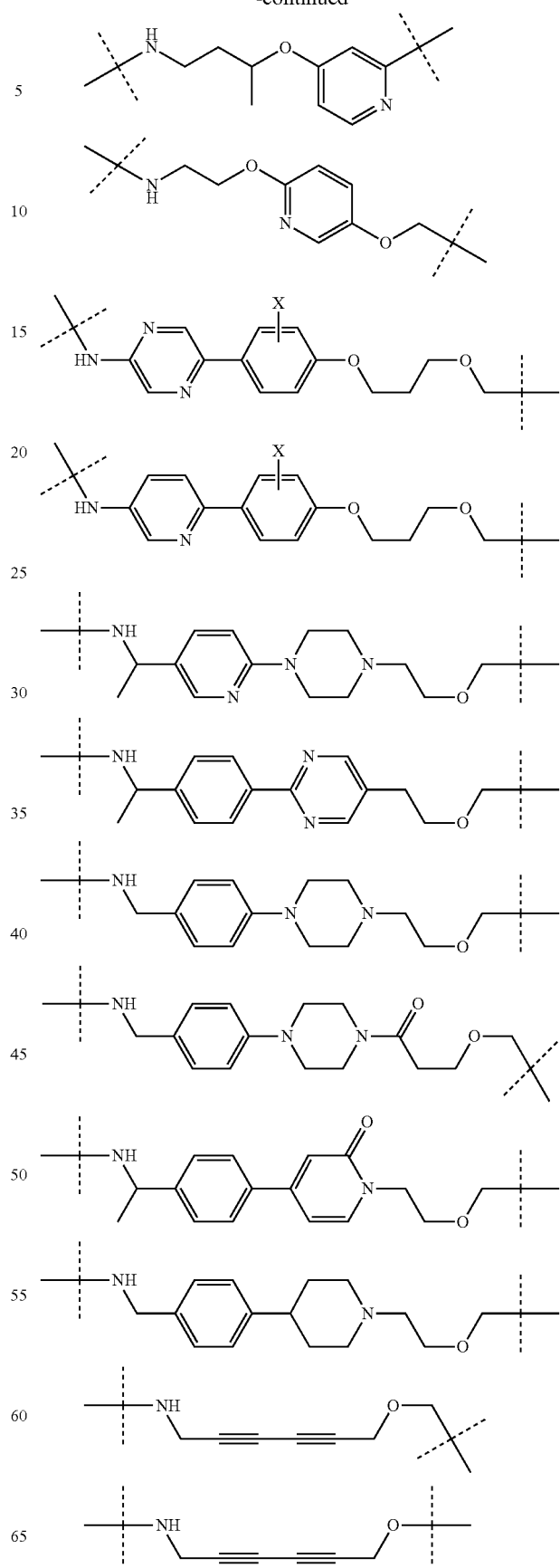

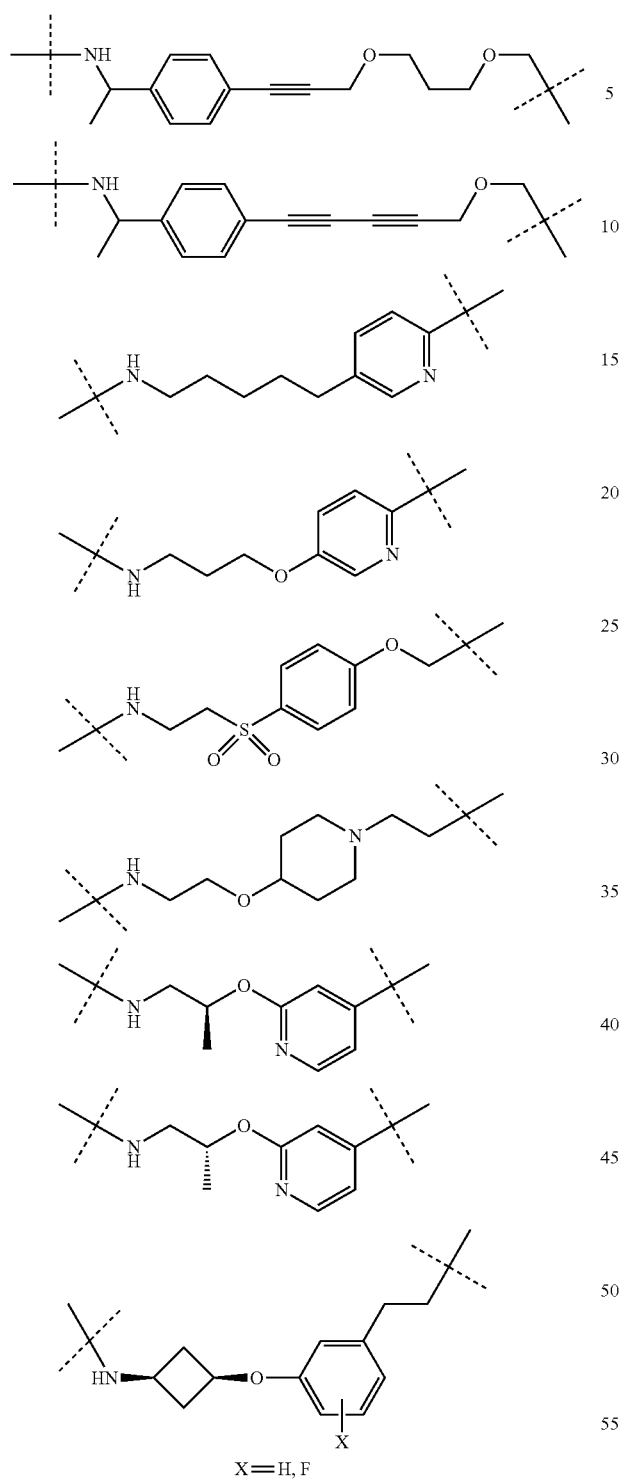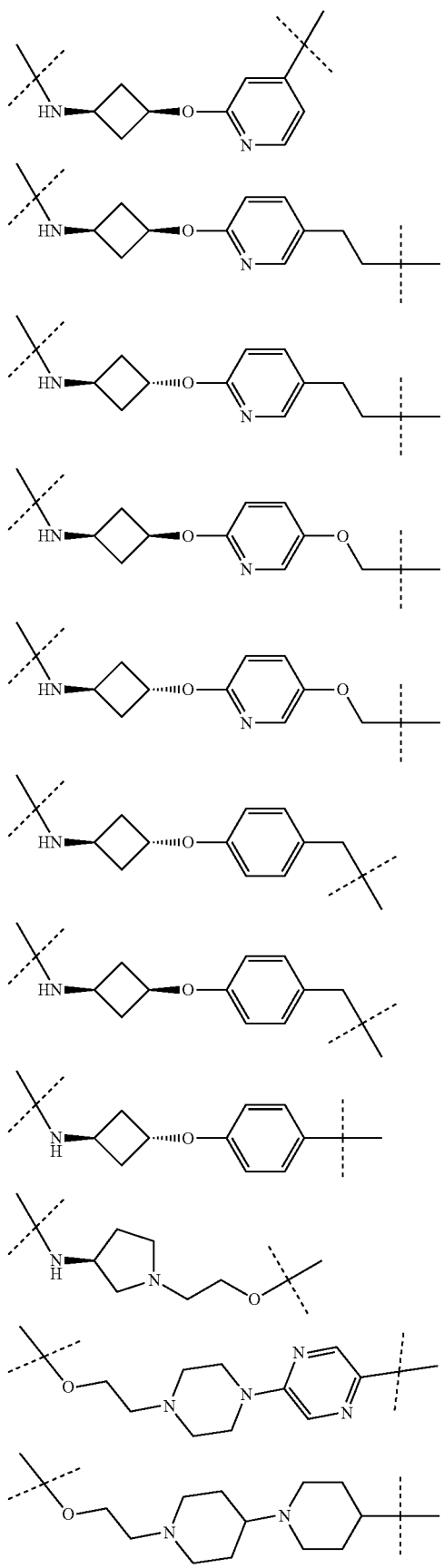

241
-continued
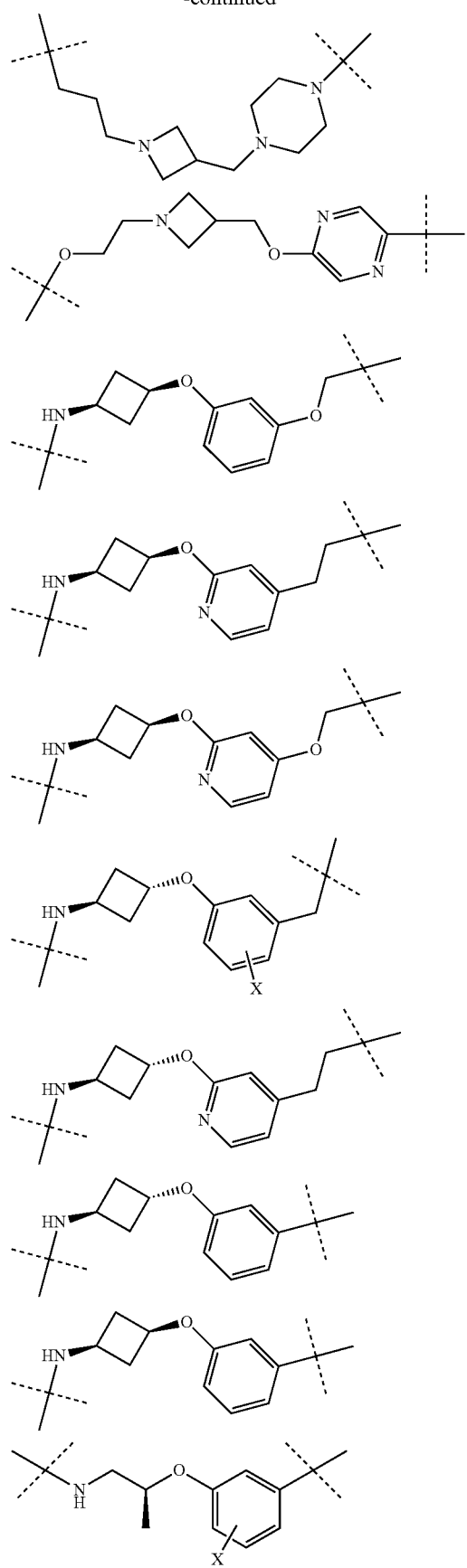
242
-continued
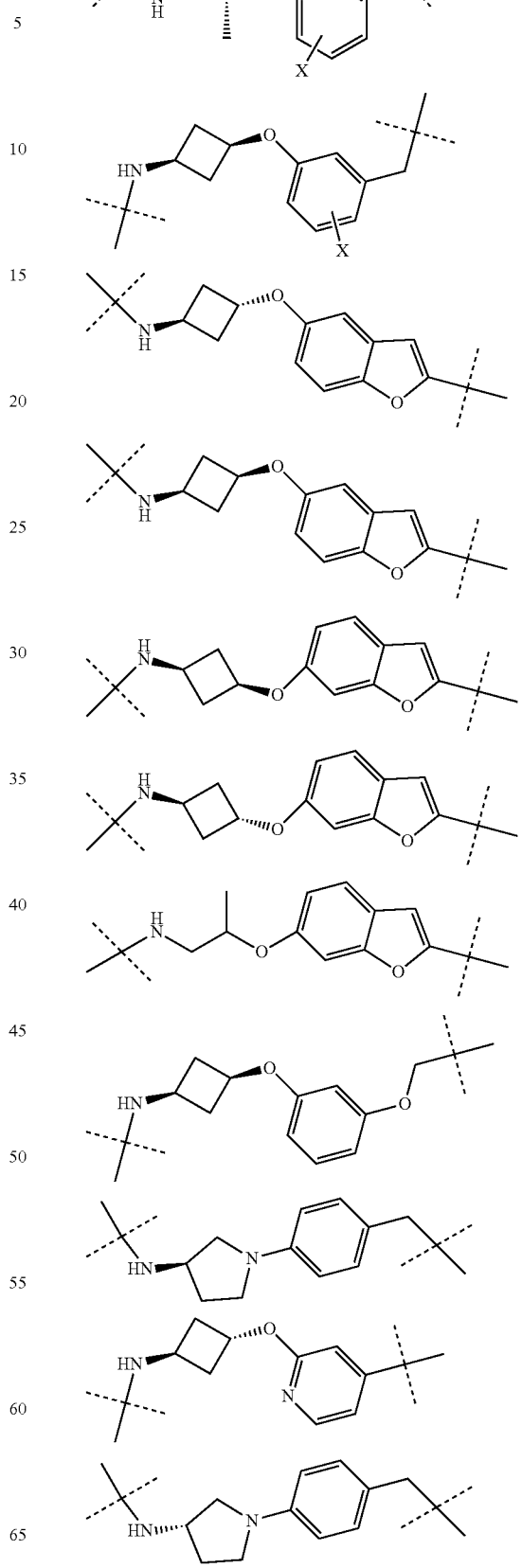

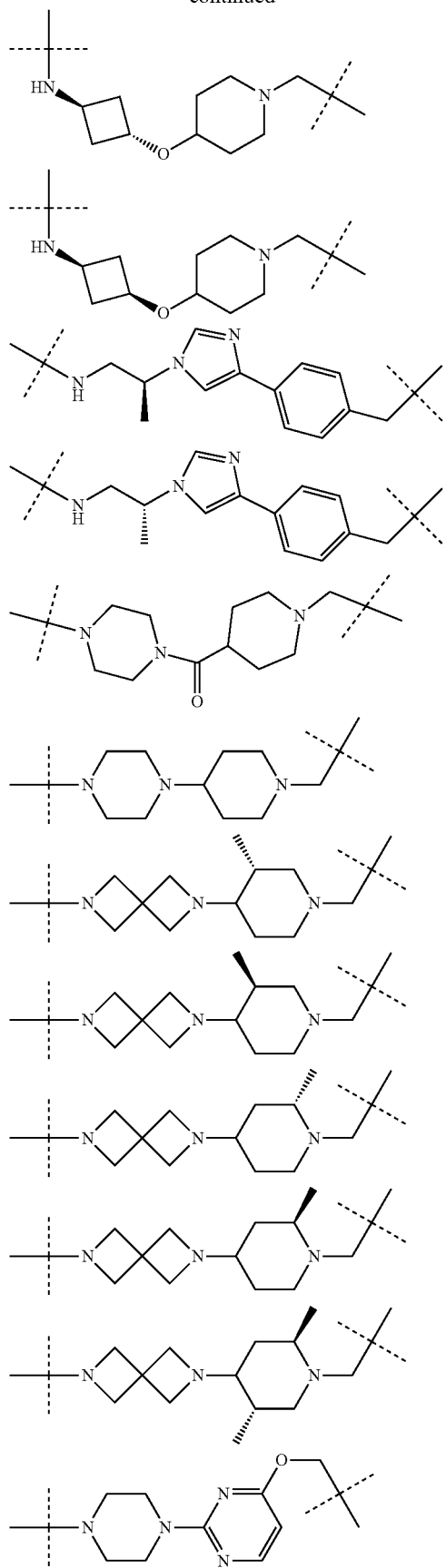
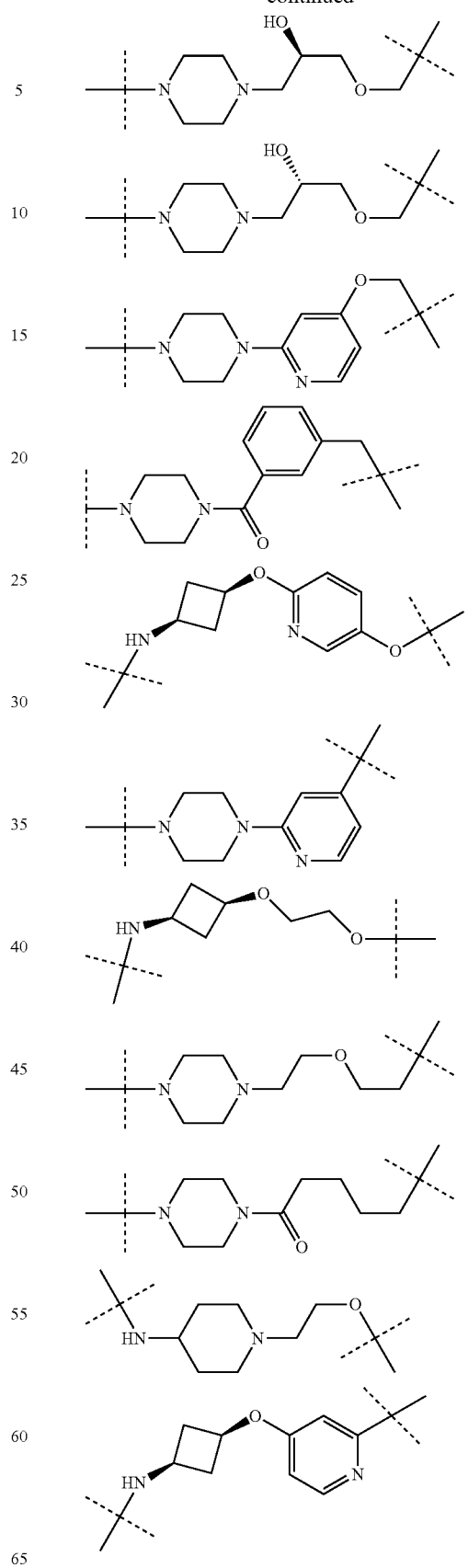

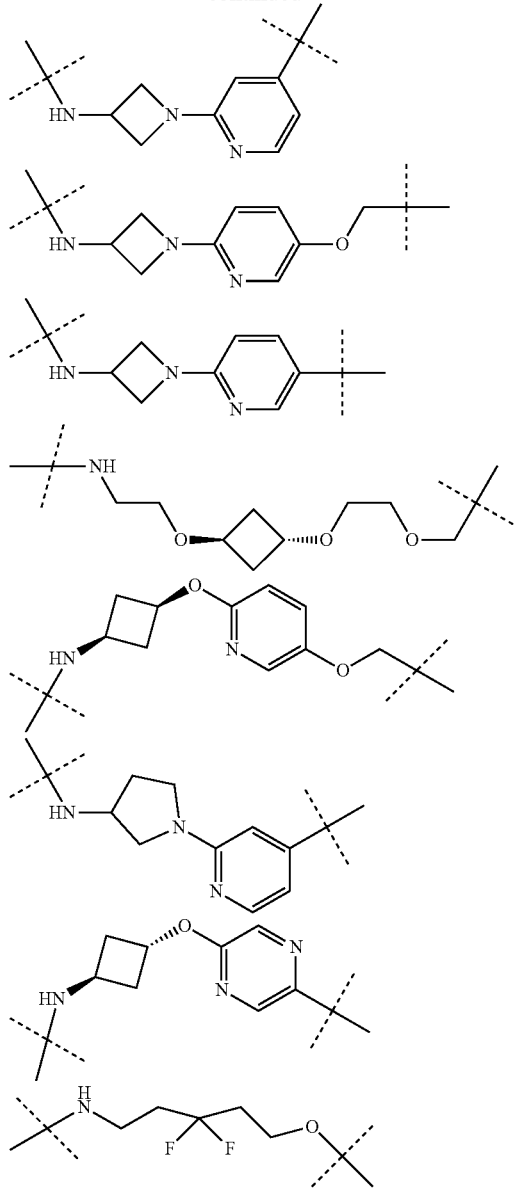
where each n and m of the linker can independently be 0, 1, 2, 3, 4, 5, 6.
In any aspect or embodiment described herein, the unit $A^L$ of linker (L) is selected from the group consisting of:
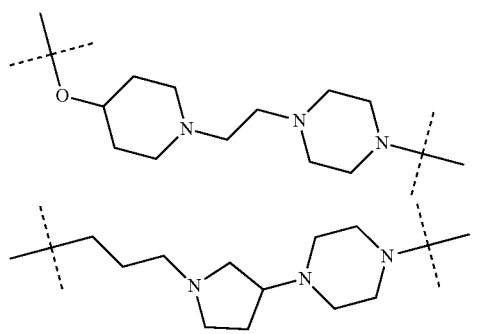
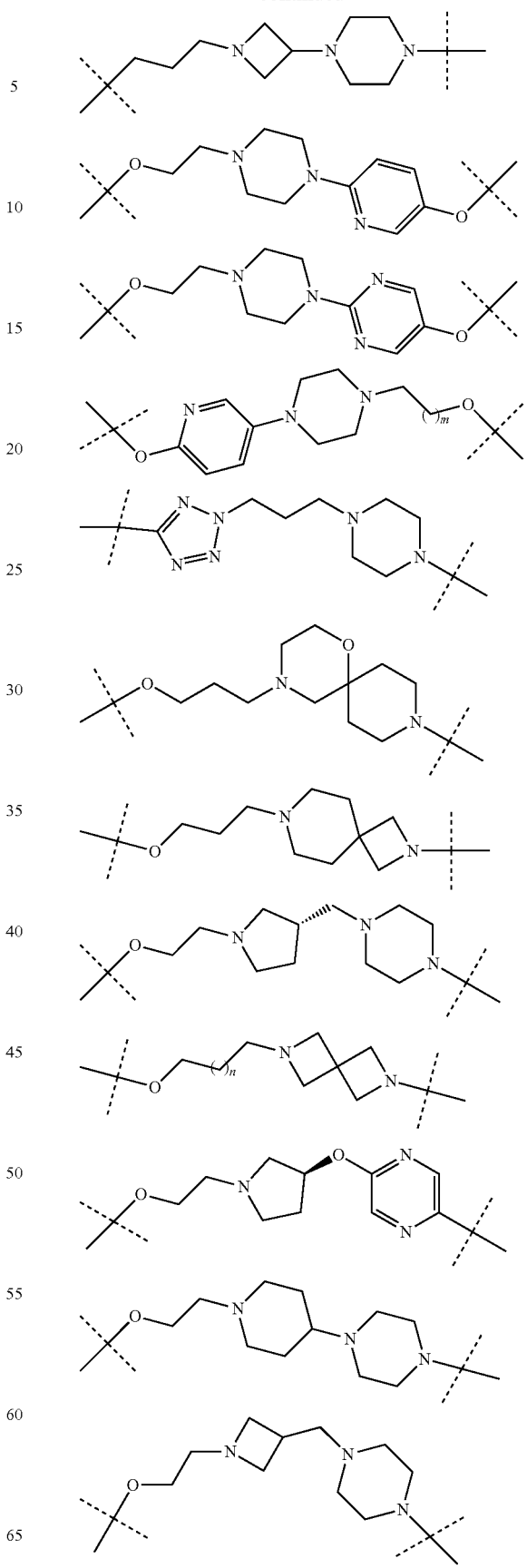

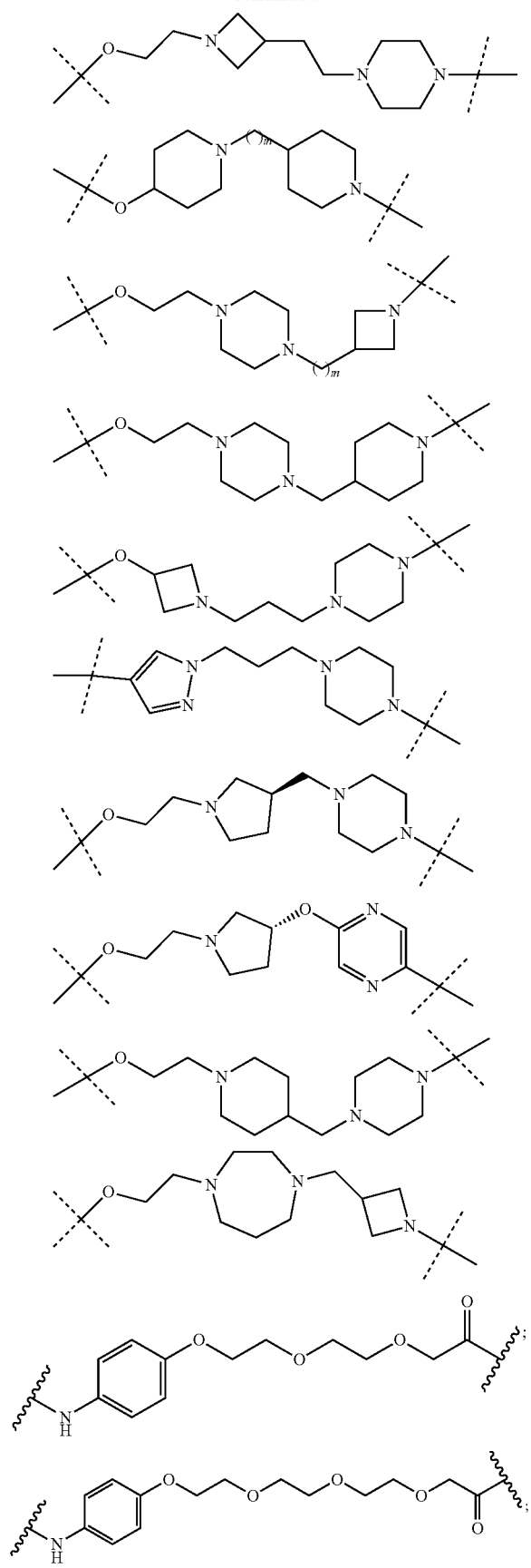
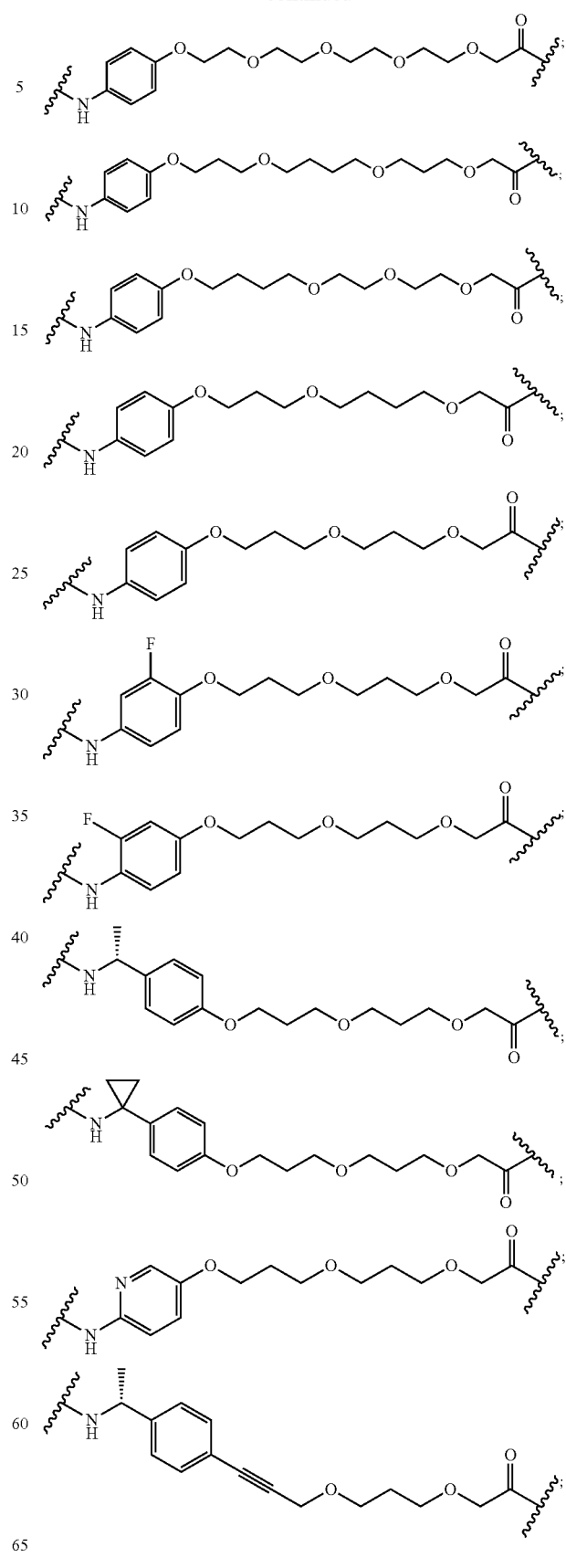

249
-continued
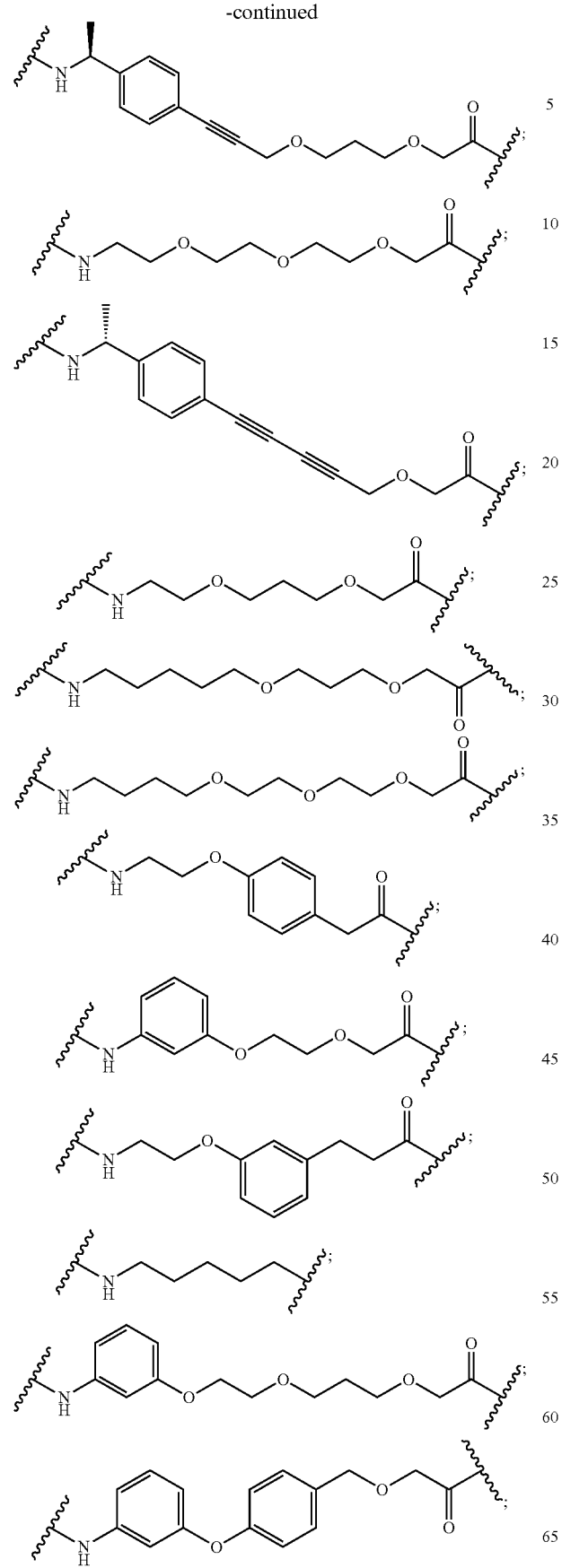
250
-continued
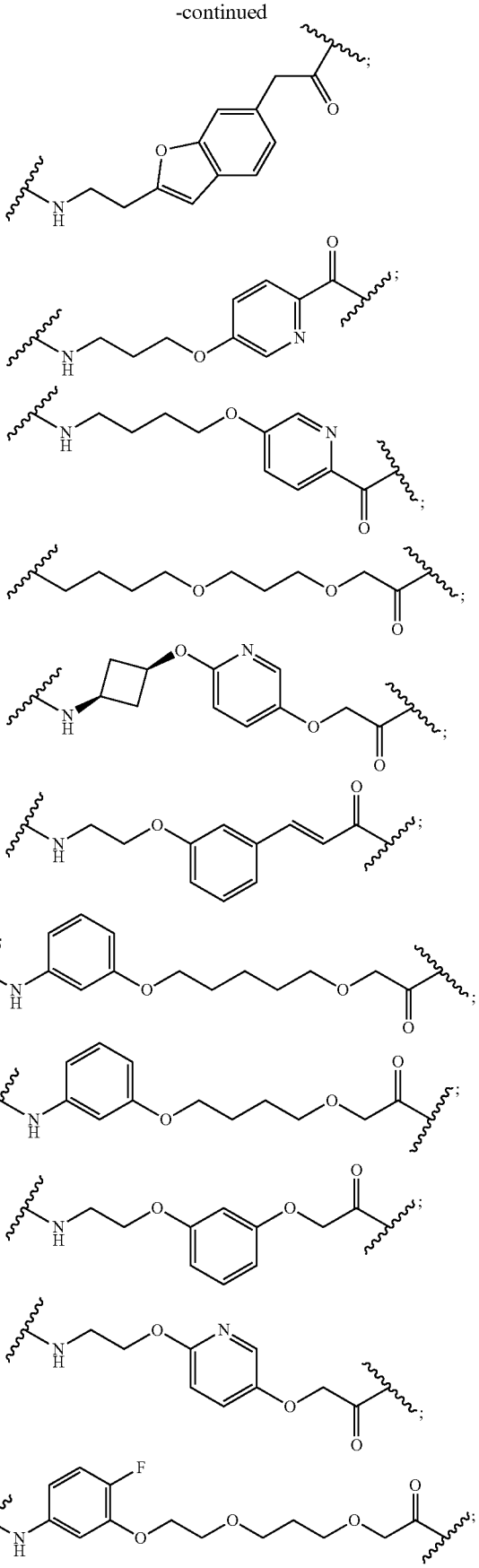

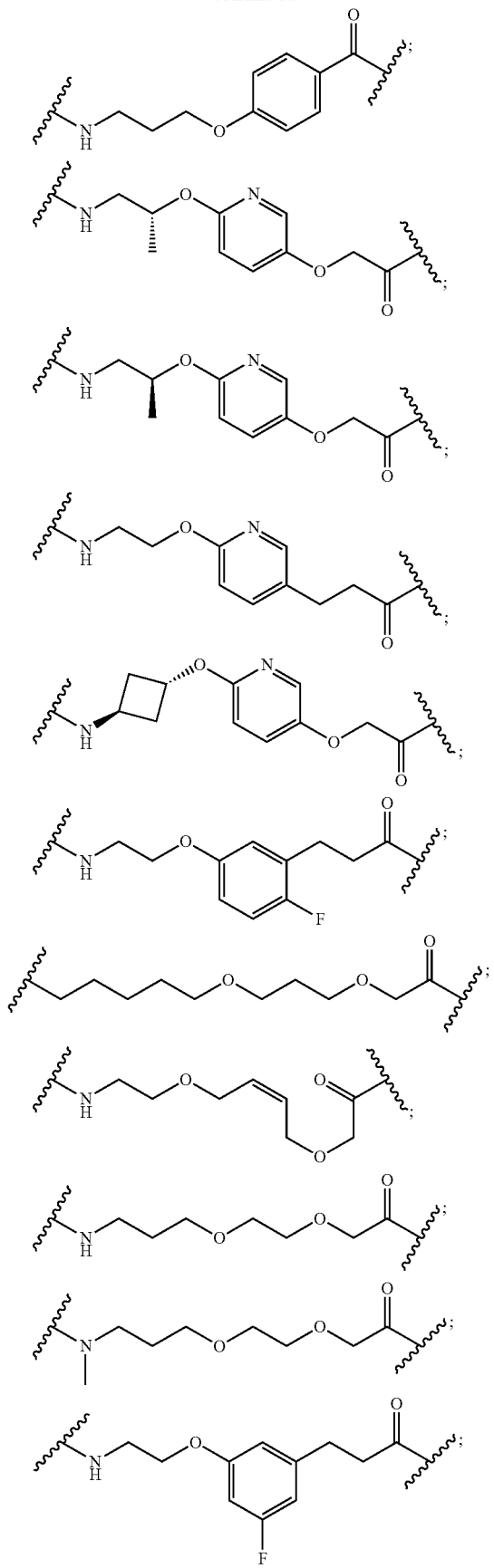
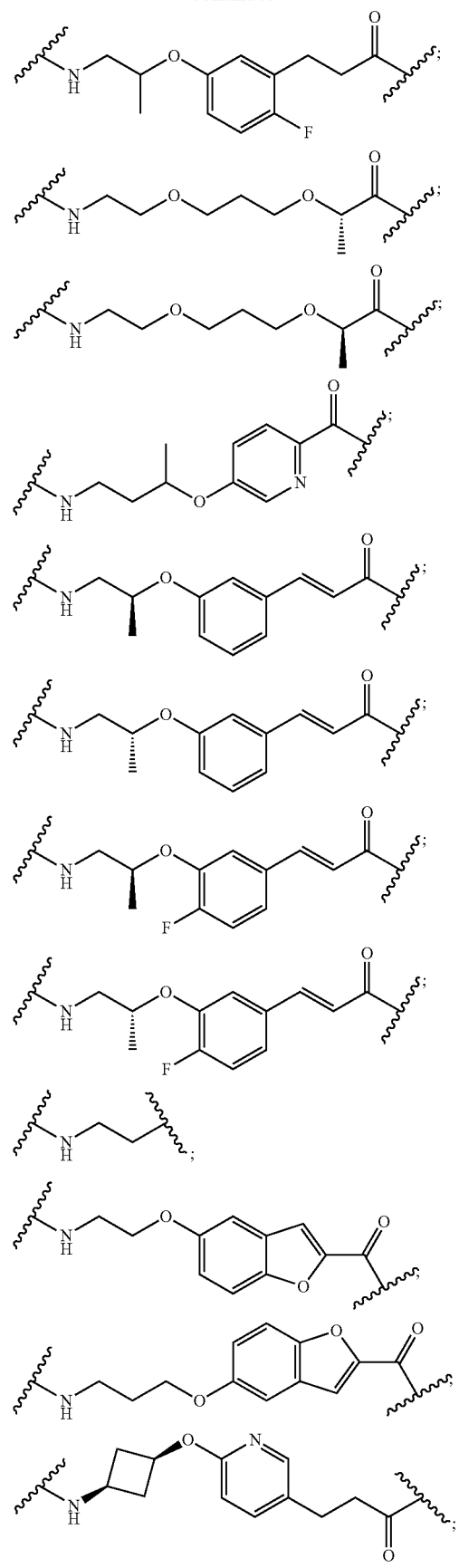

253
-continued
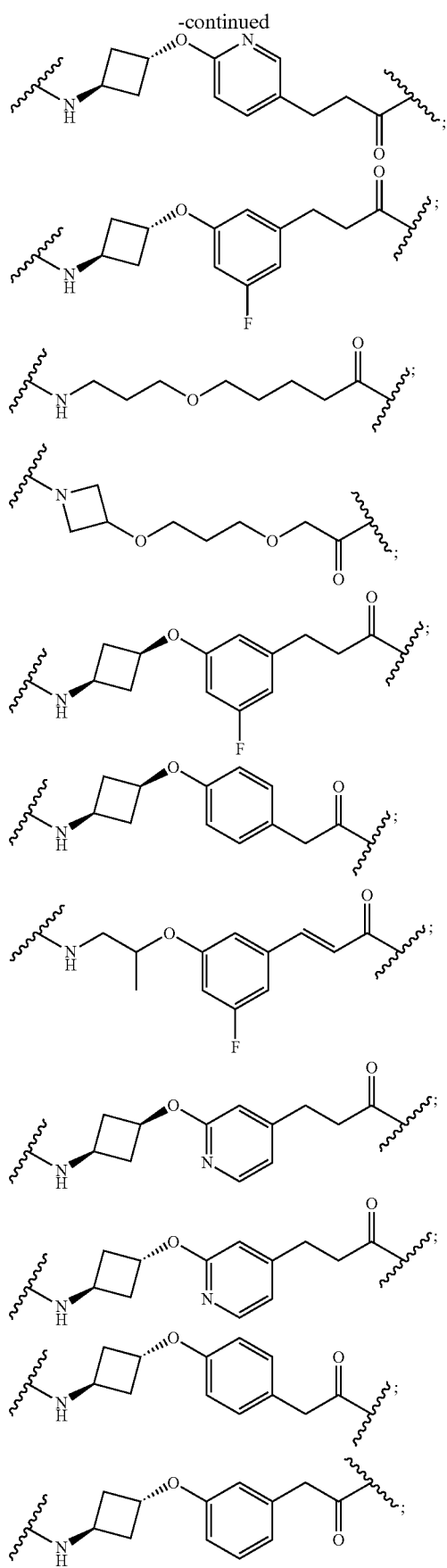
254
-continued
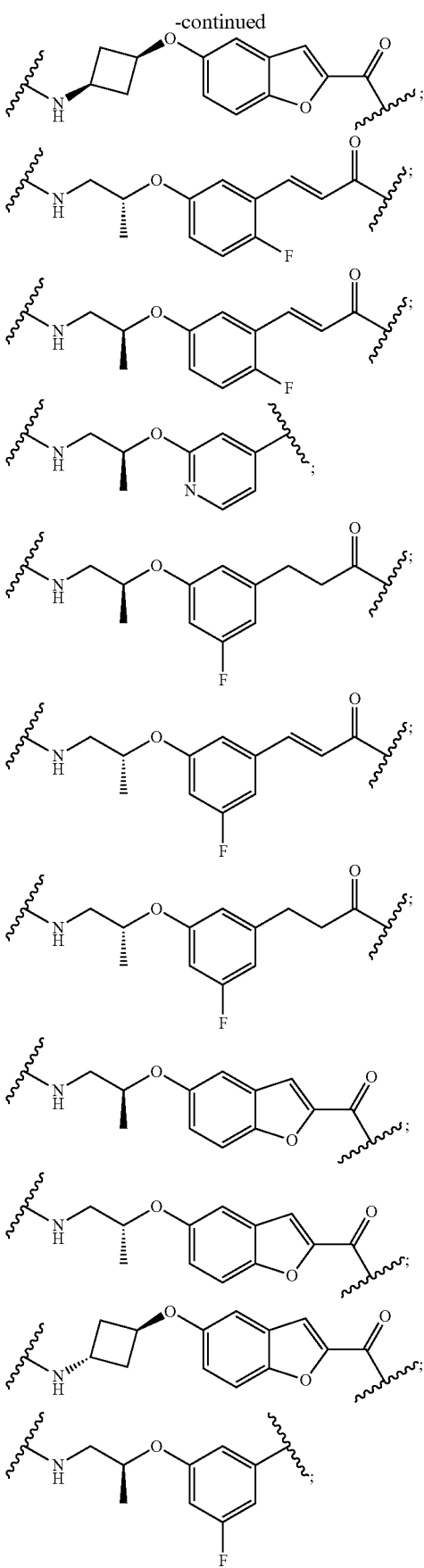

-continued
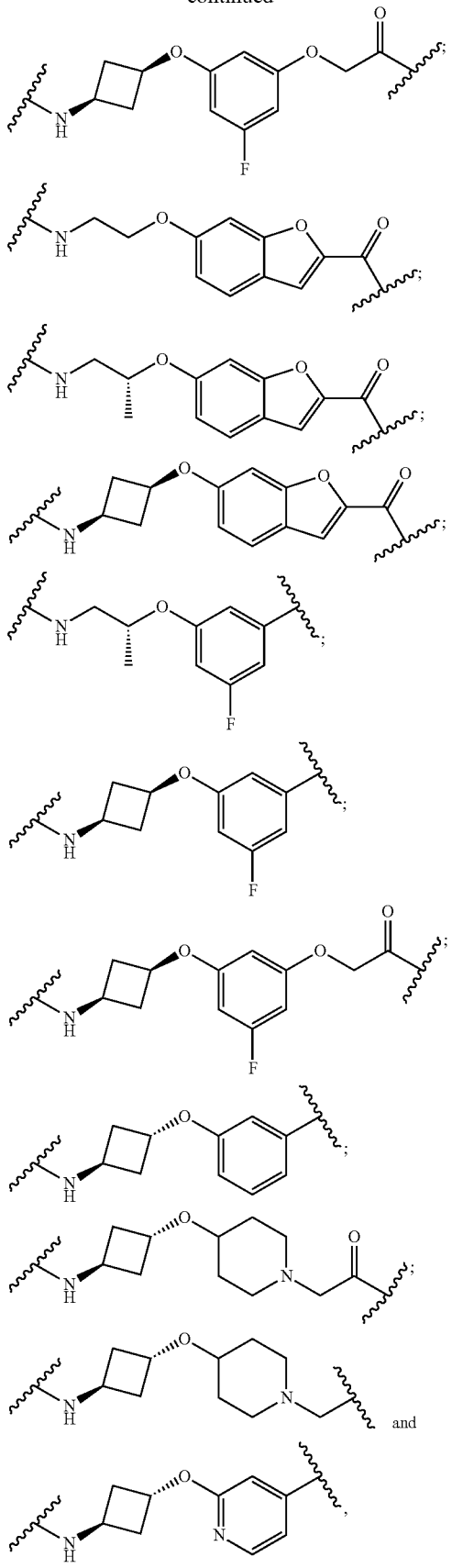
wherein each m and n is independently selected from 0, 1, 2, 3, 4, 5, or 6.
In any aspect or embodiment described herein, the unit $A^L$ of linker (L) is selected from the group consisting of:

-continued

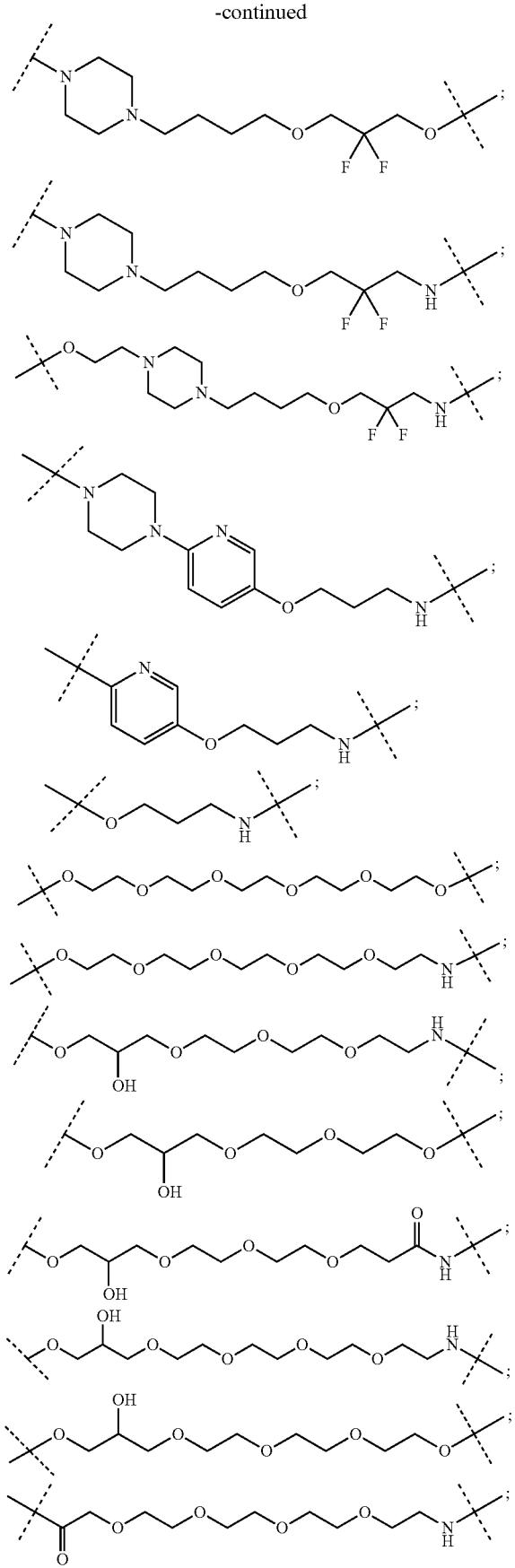
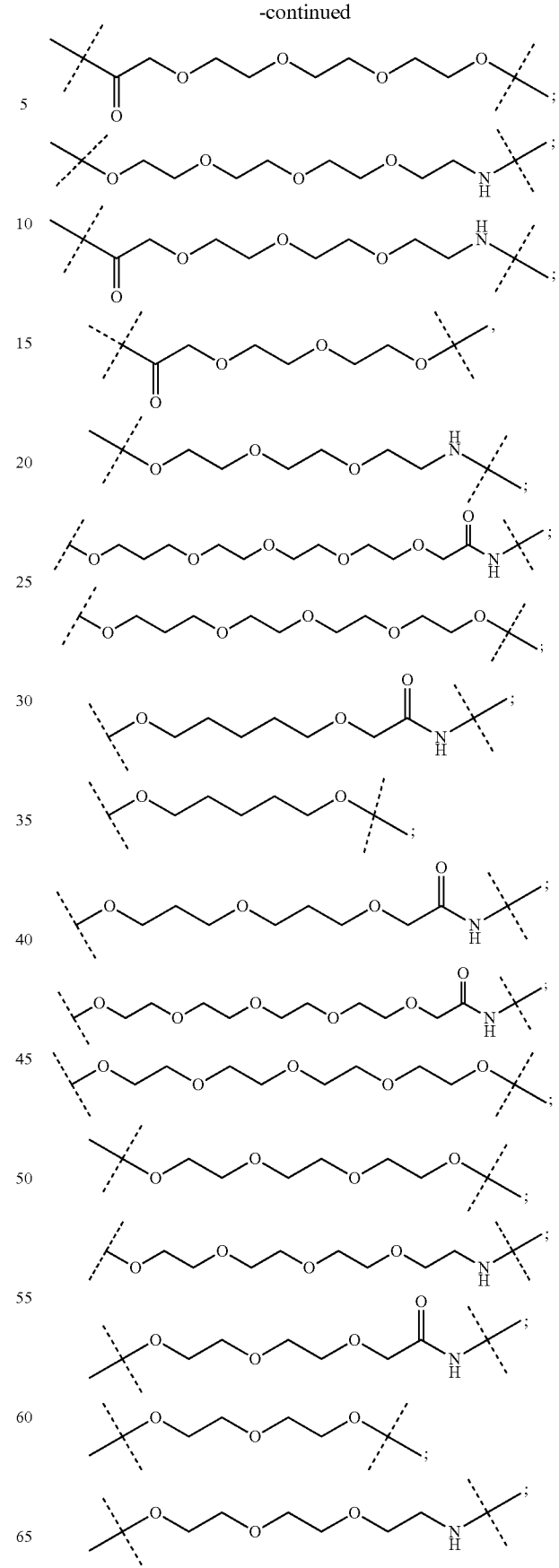

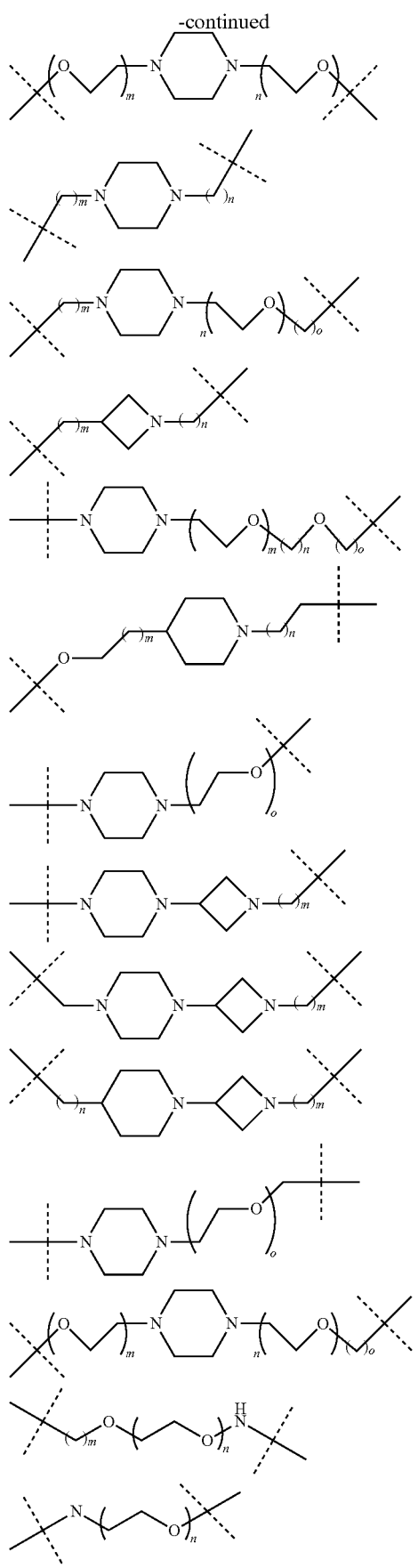
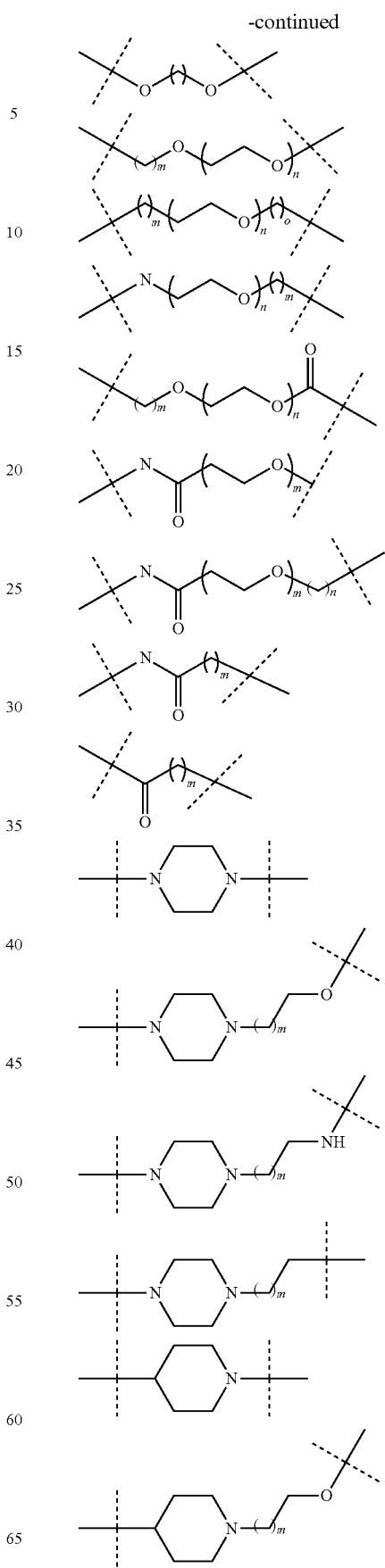

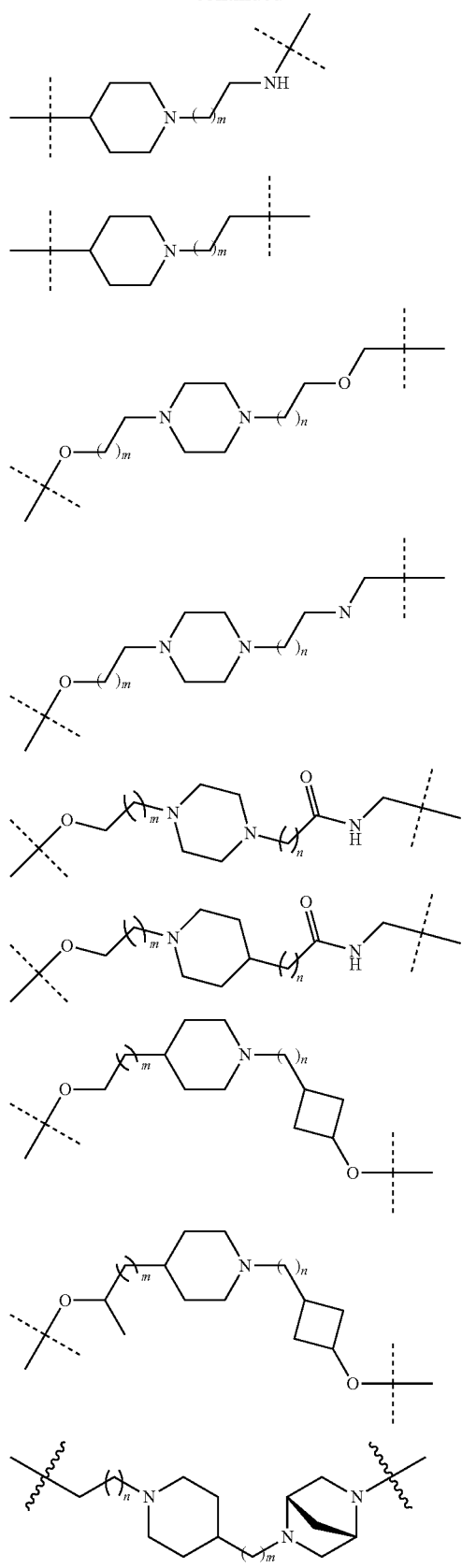
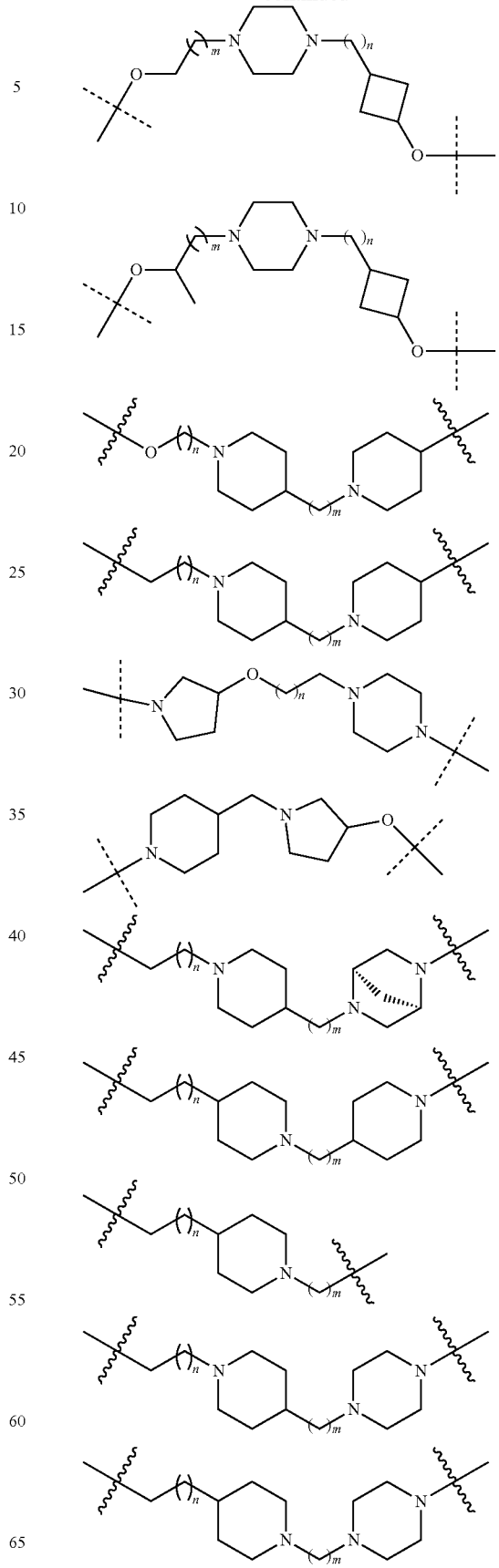

265
-continued
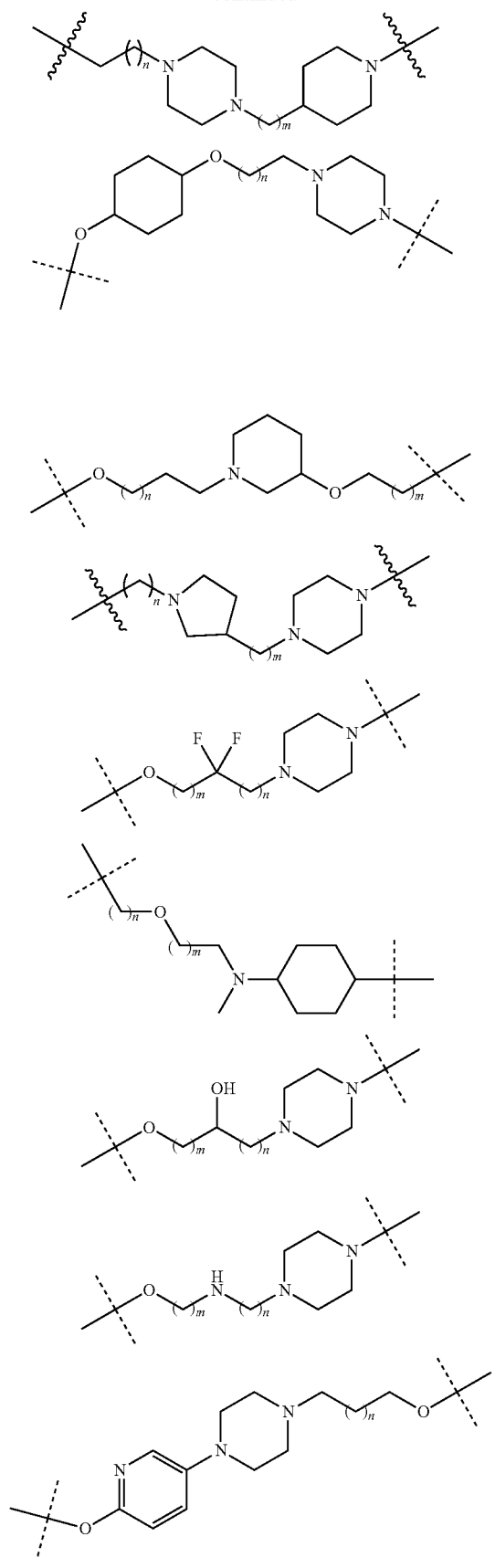
266
-continued
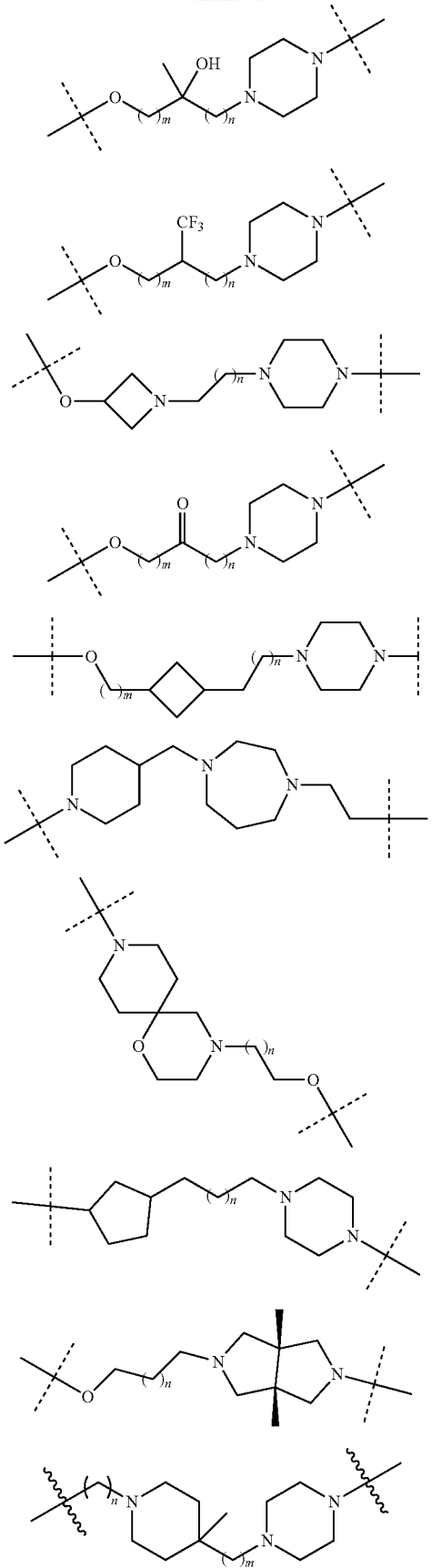

267
-continued
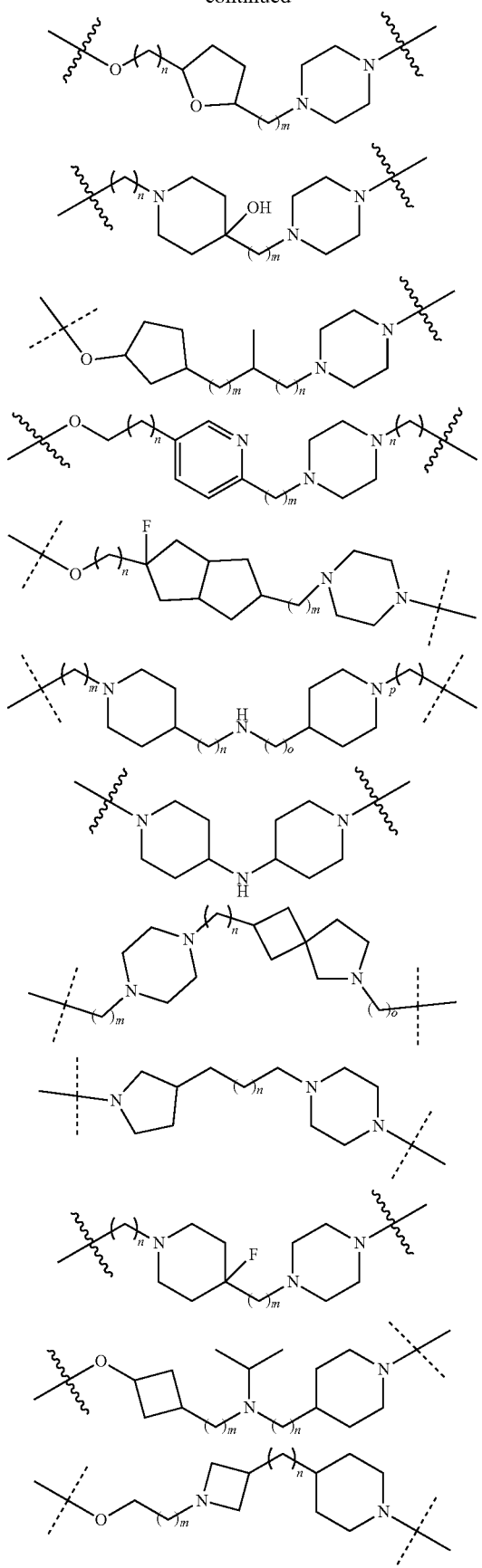
268
-continued
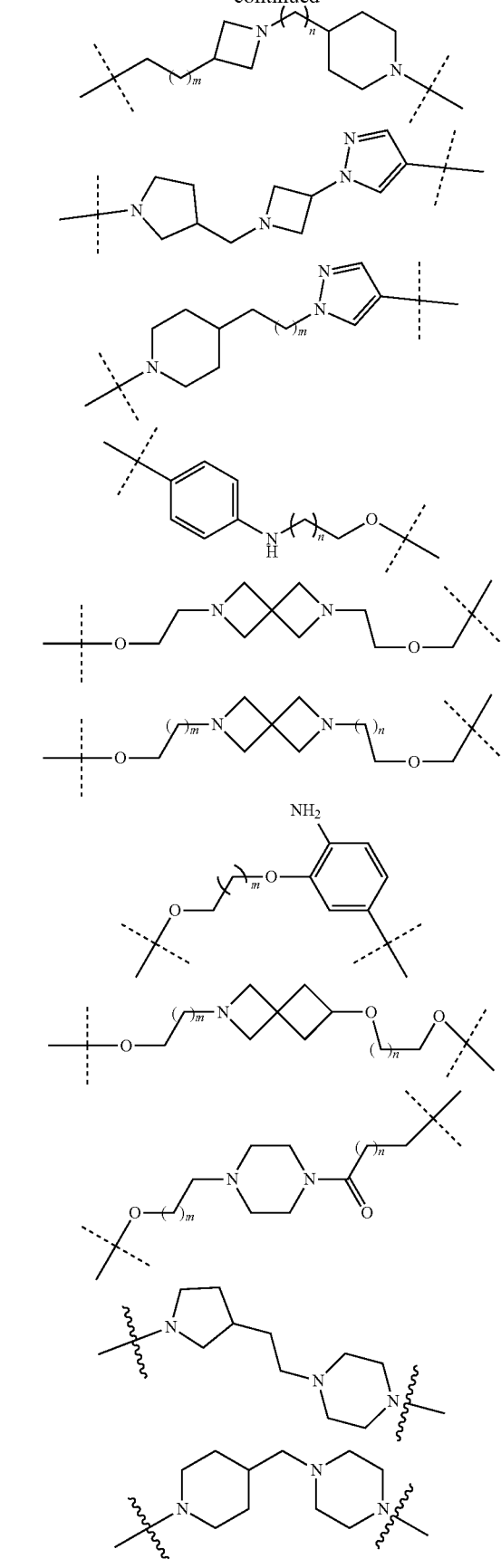

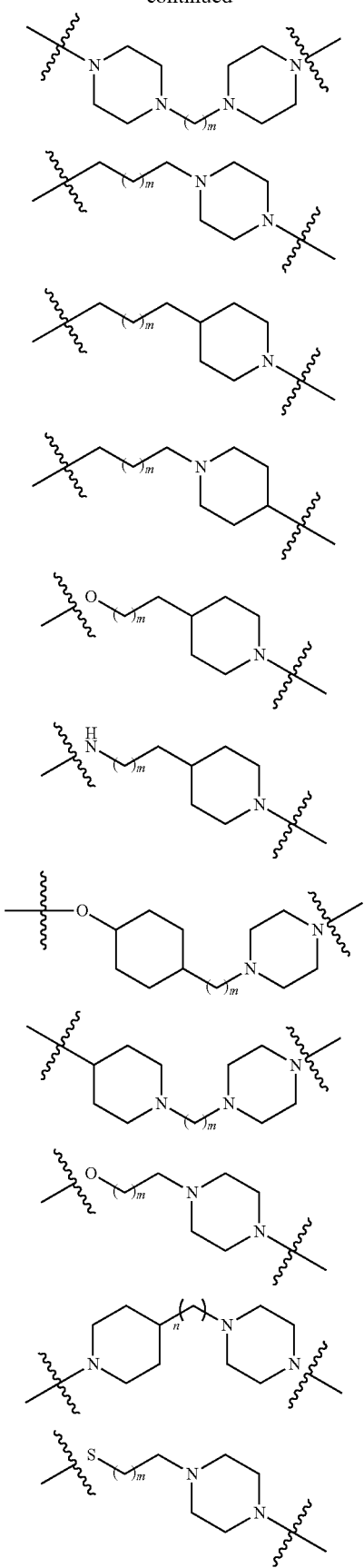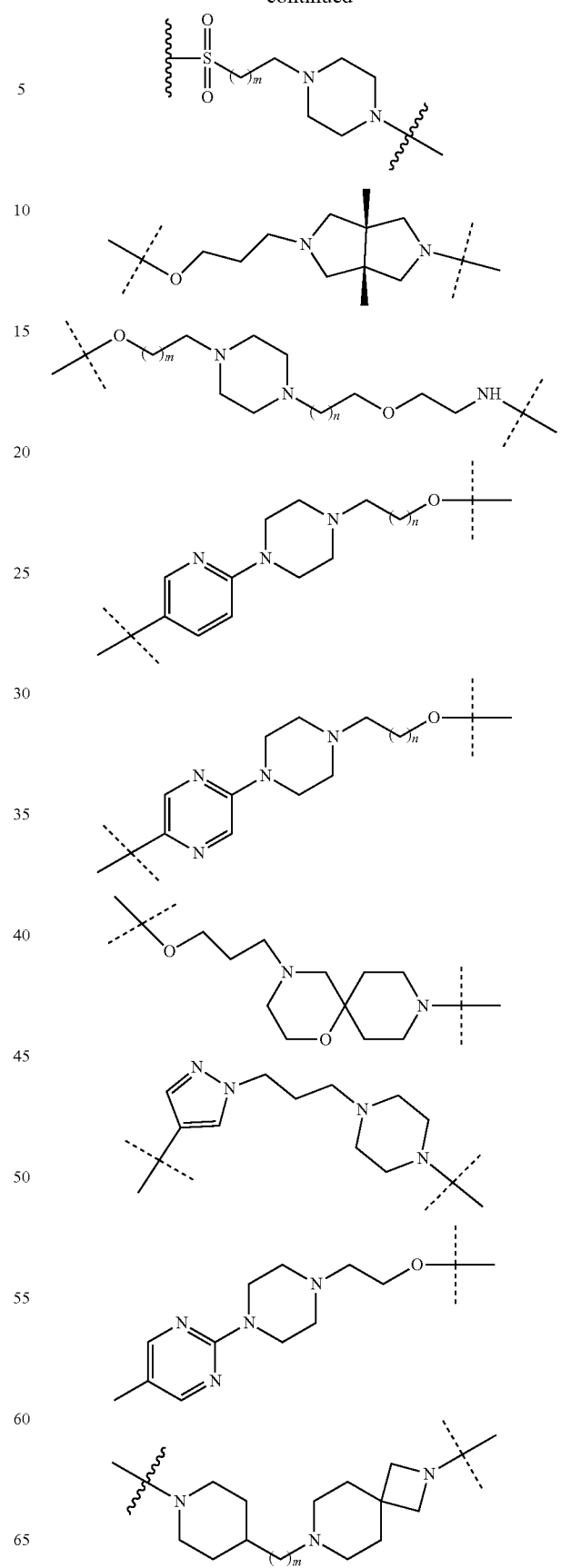

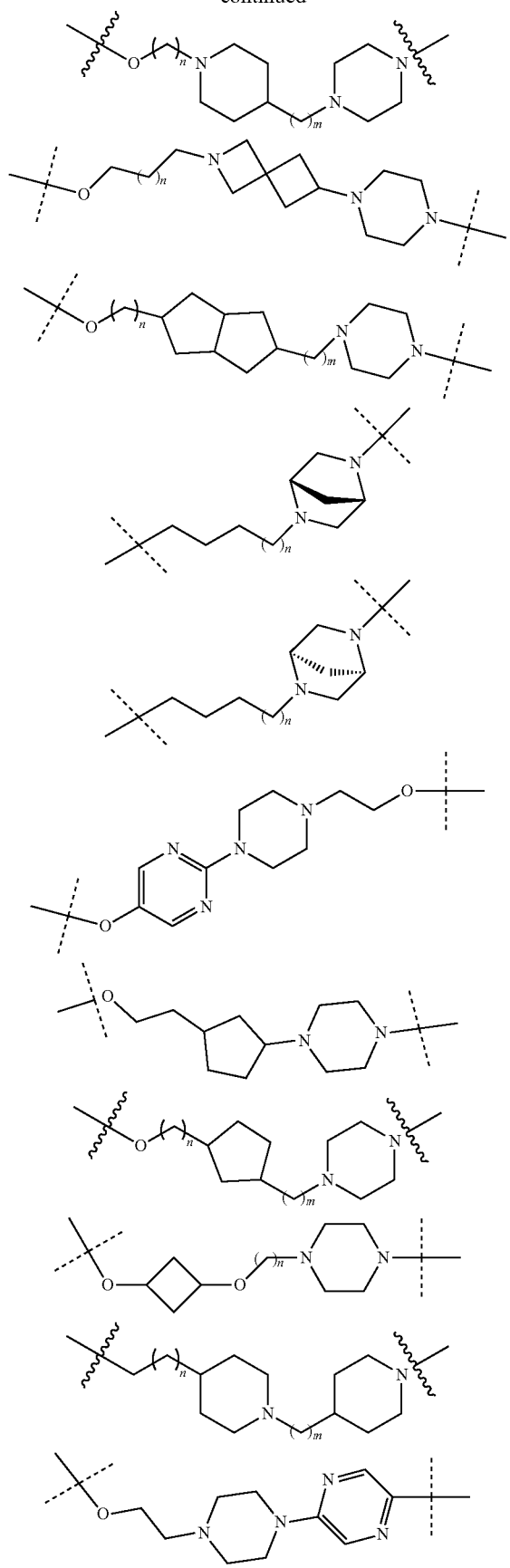
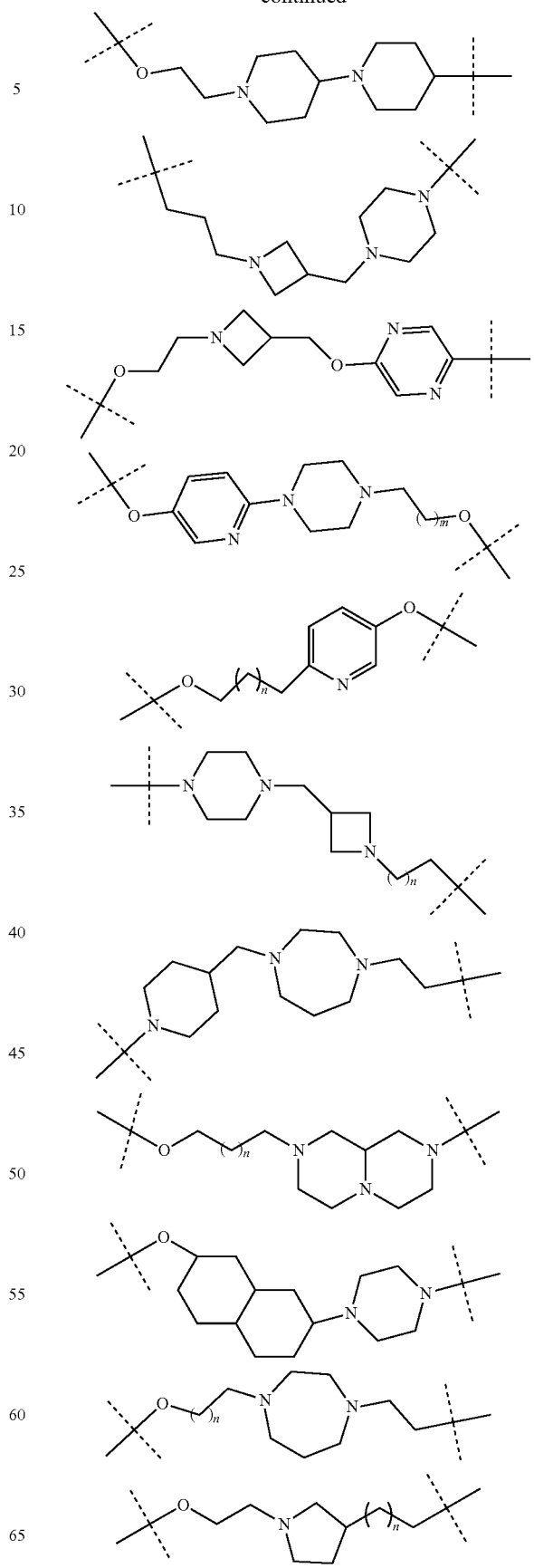

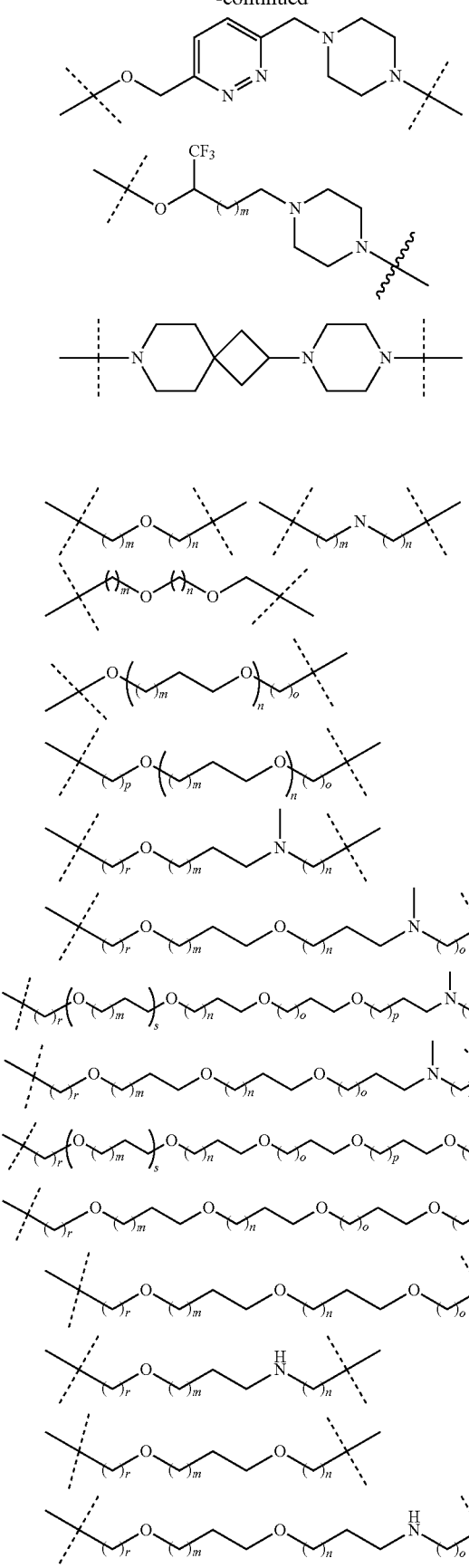
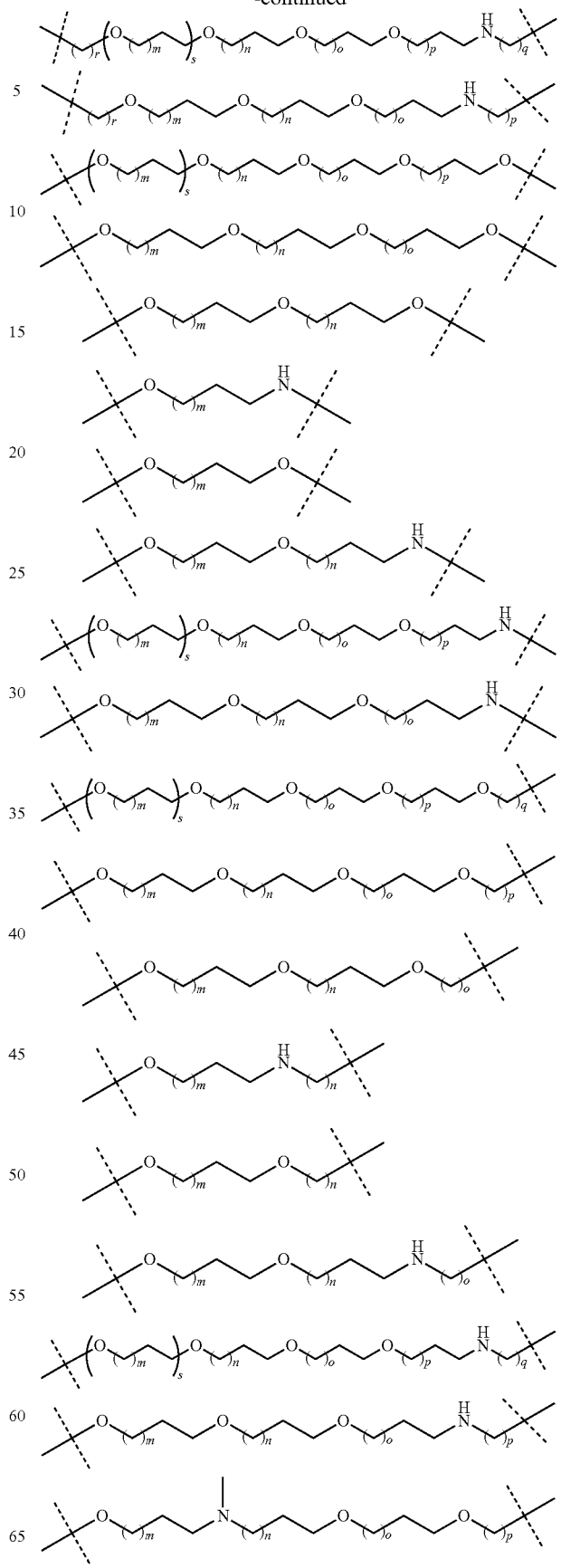

275
-continued
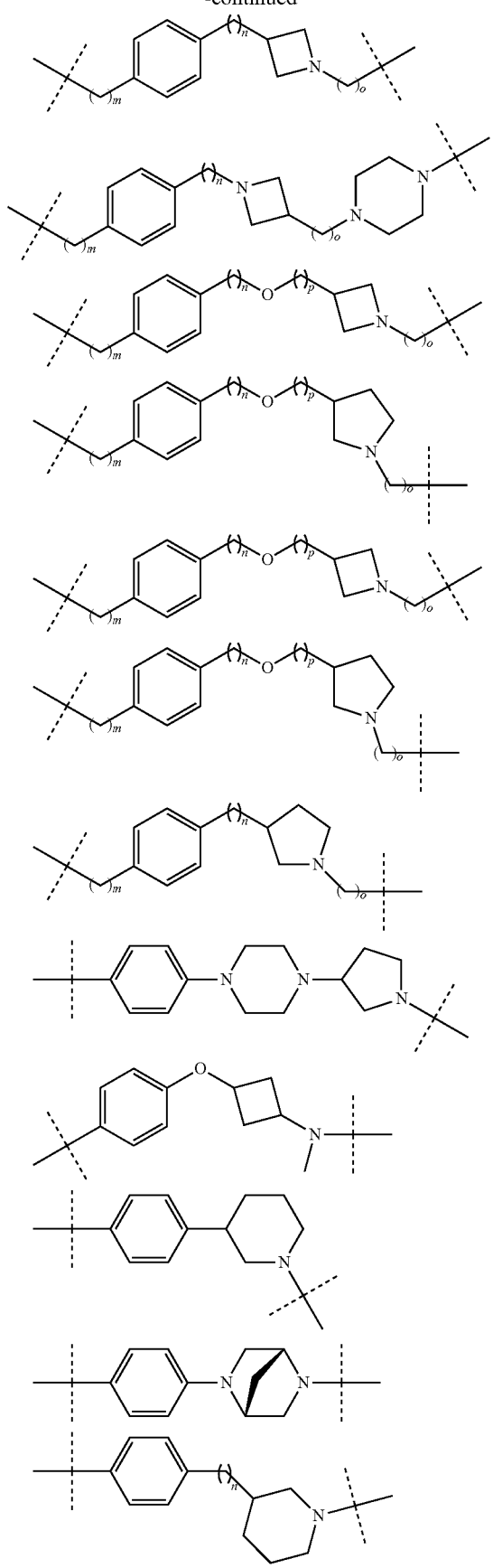
276
-continued
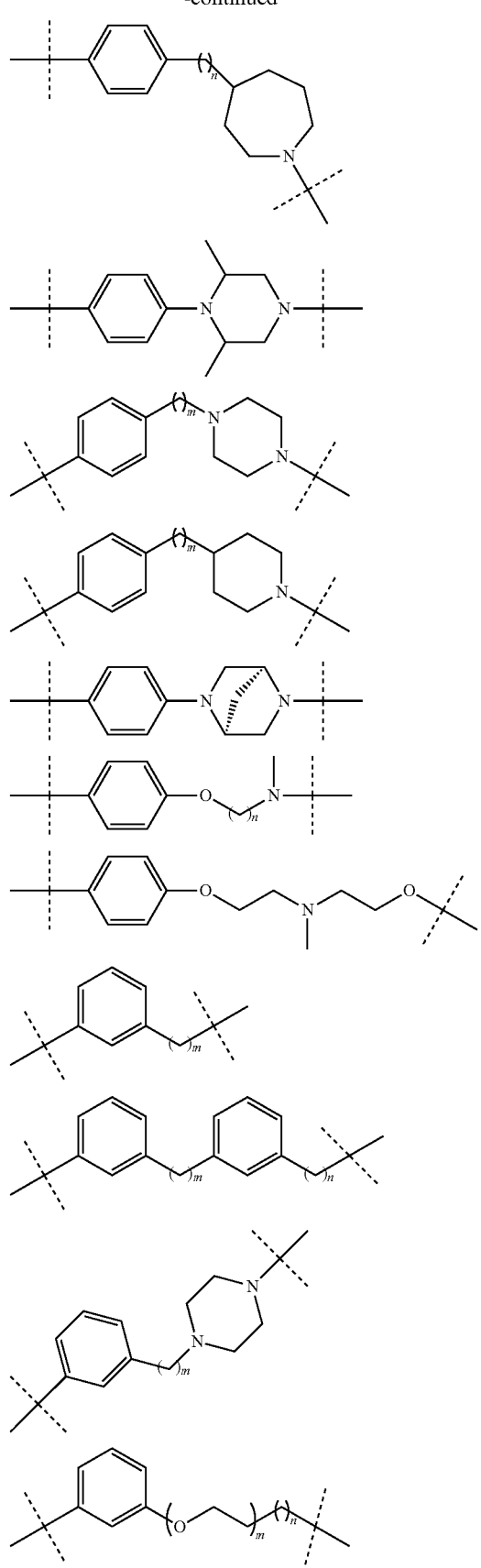

277
-continued
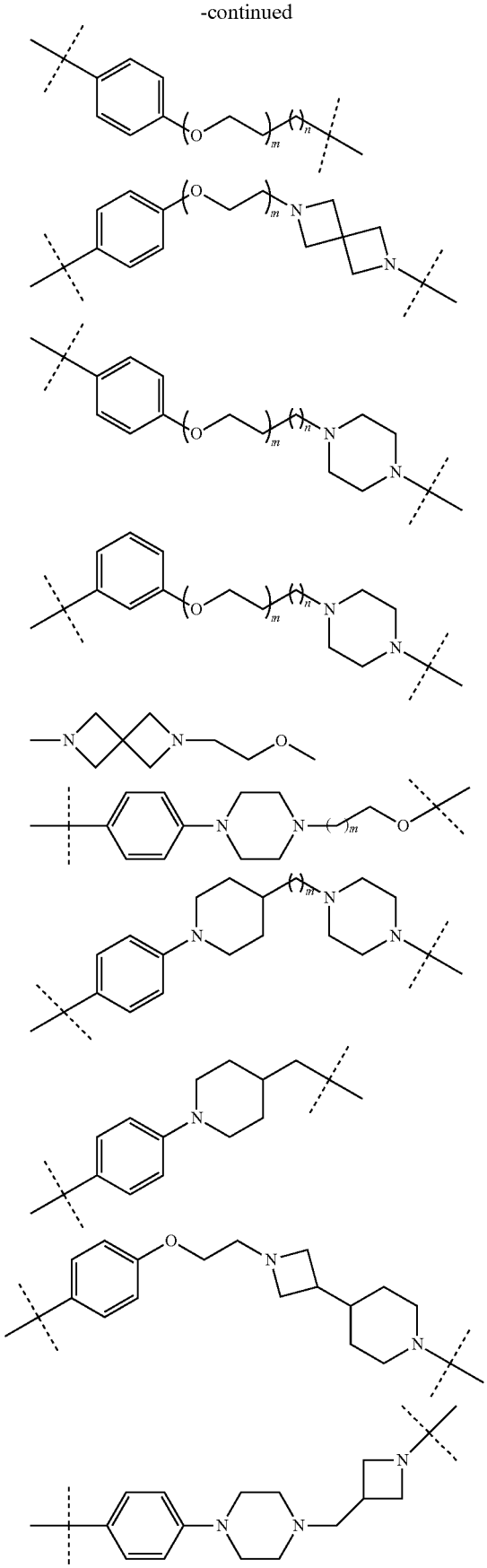
278
-continued
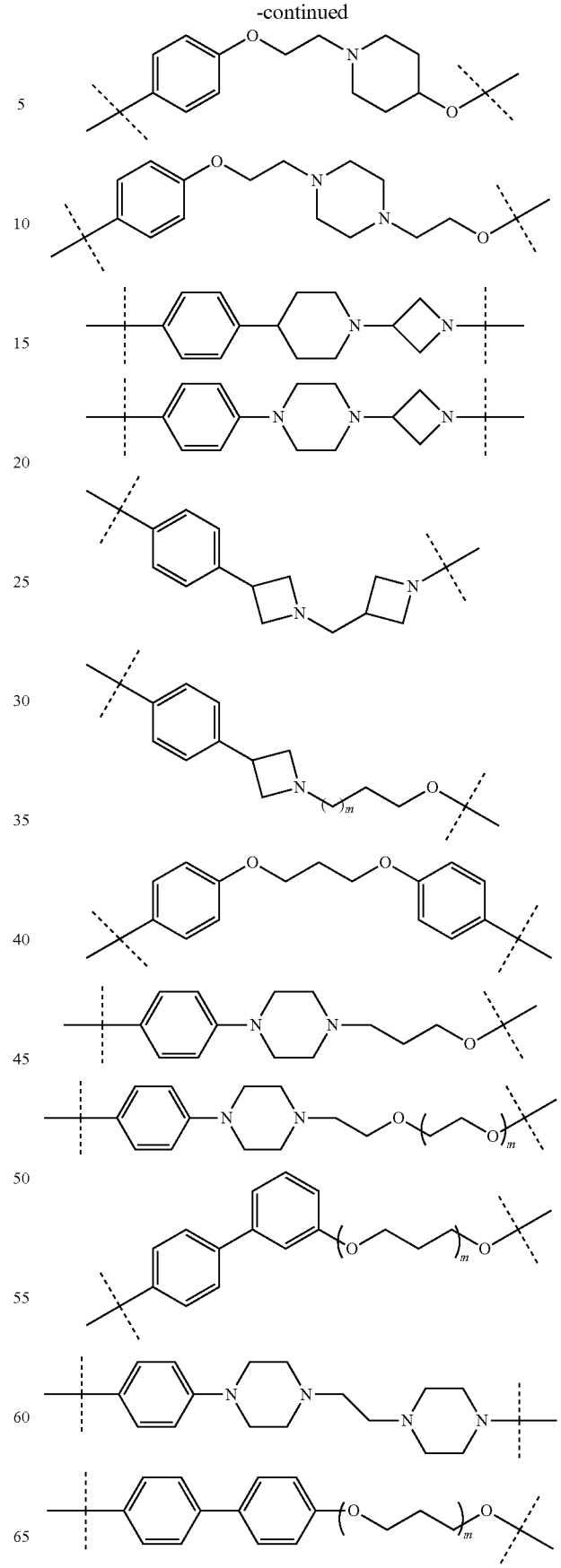

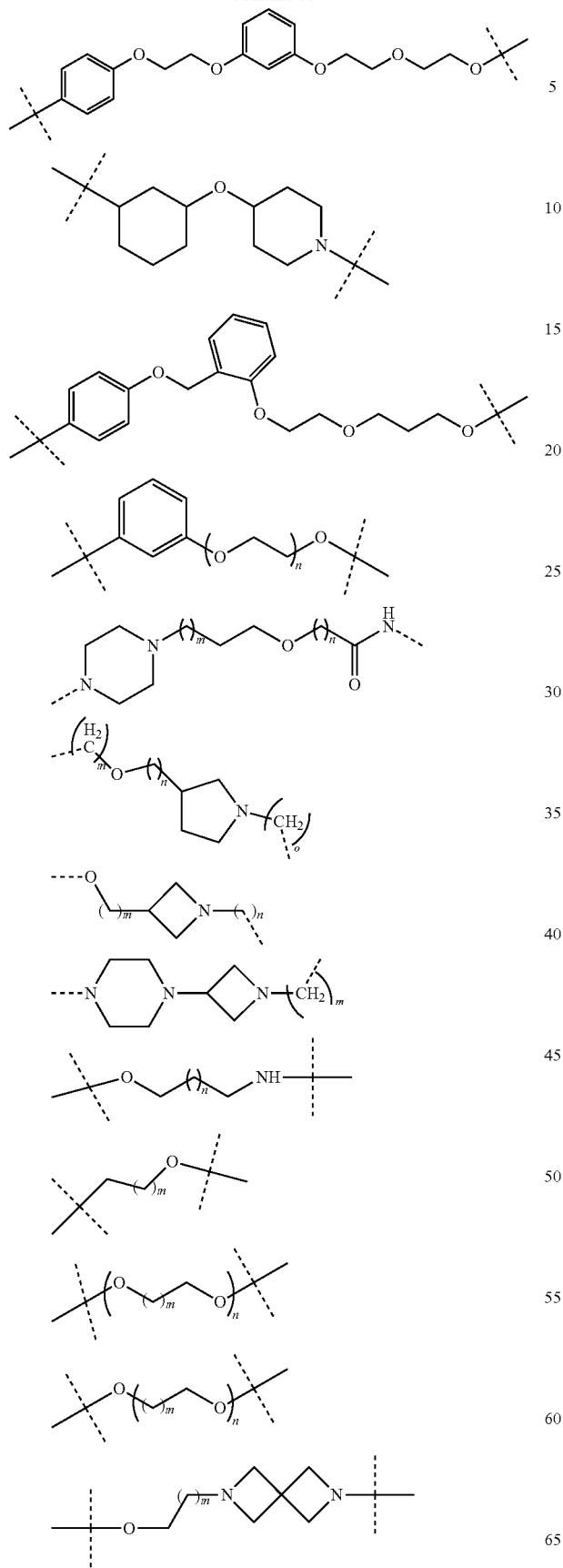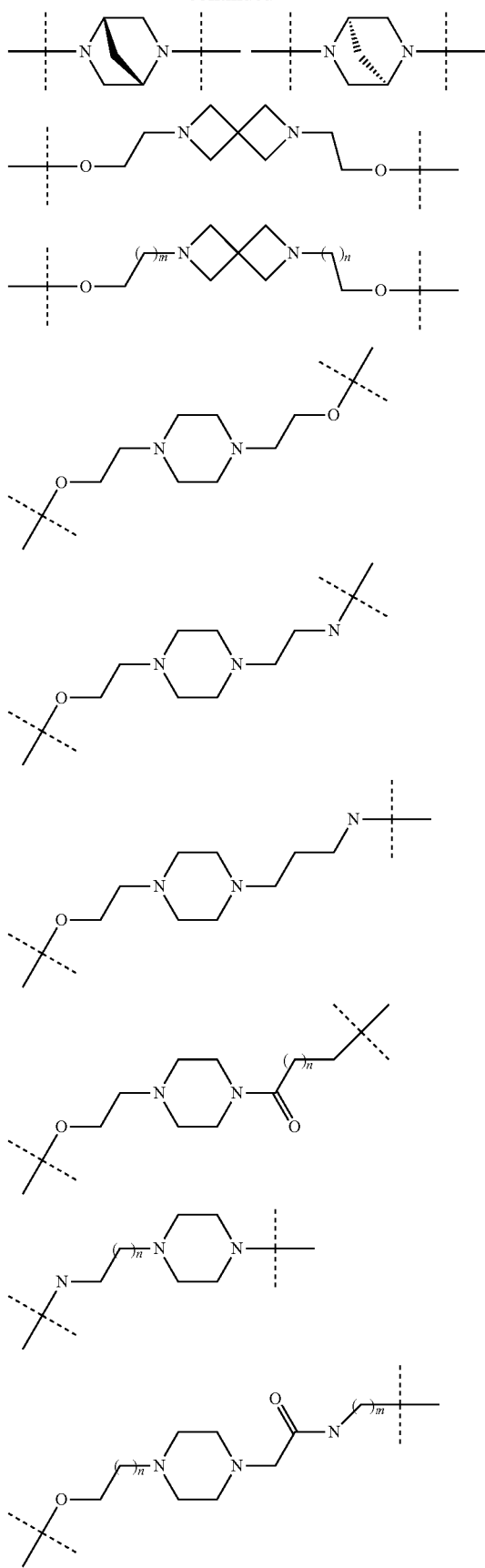

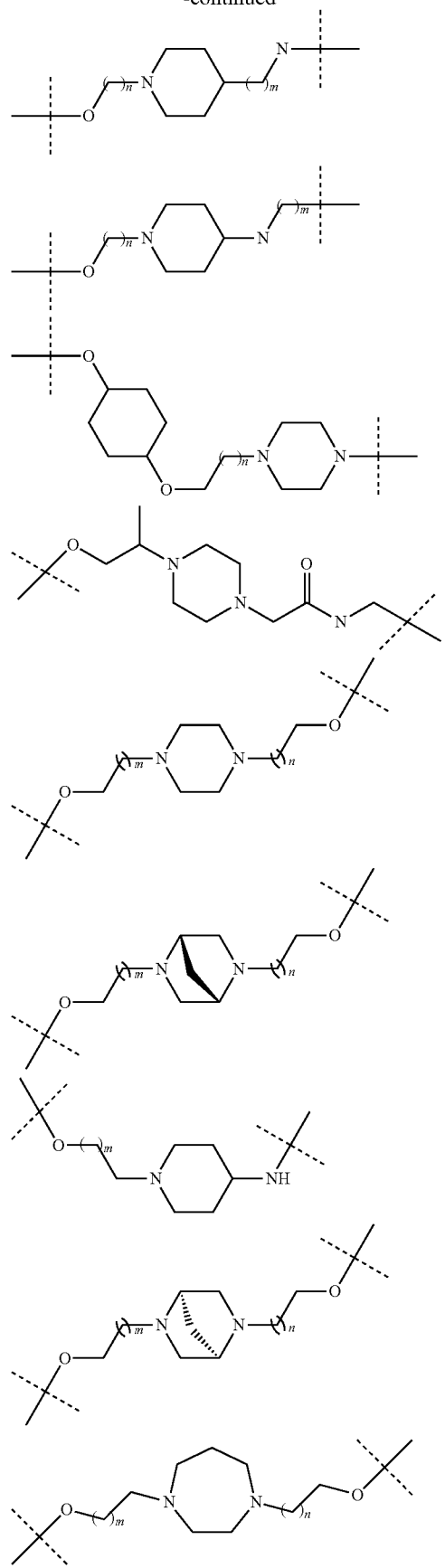
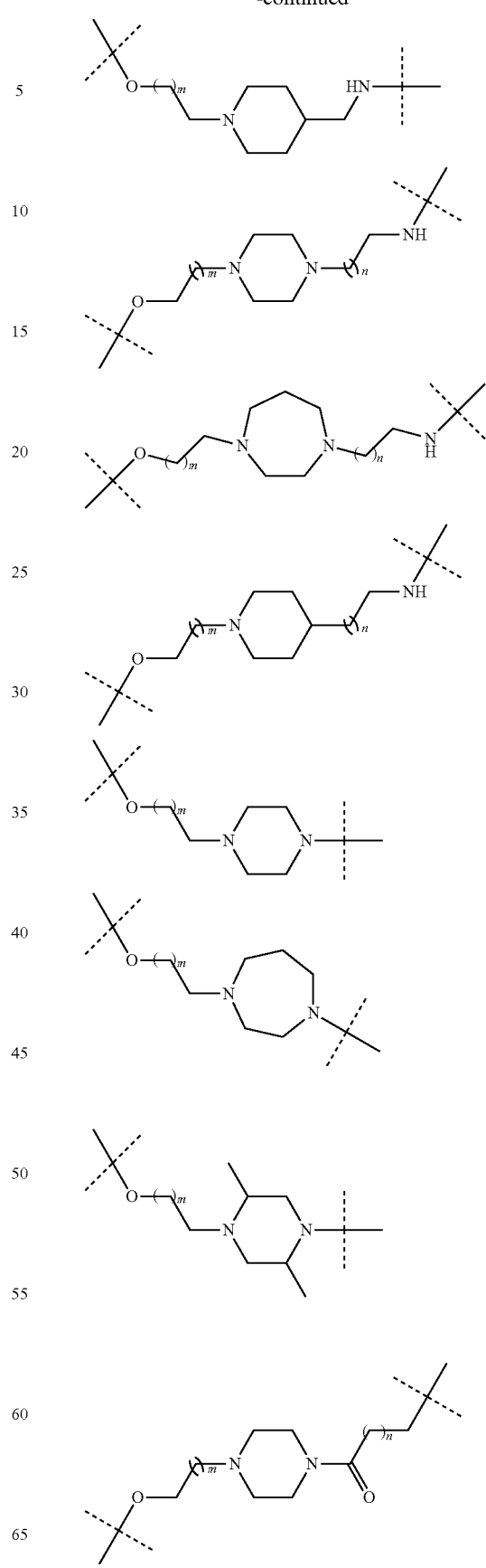

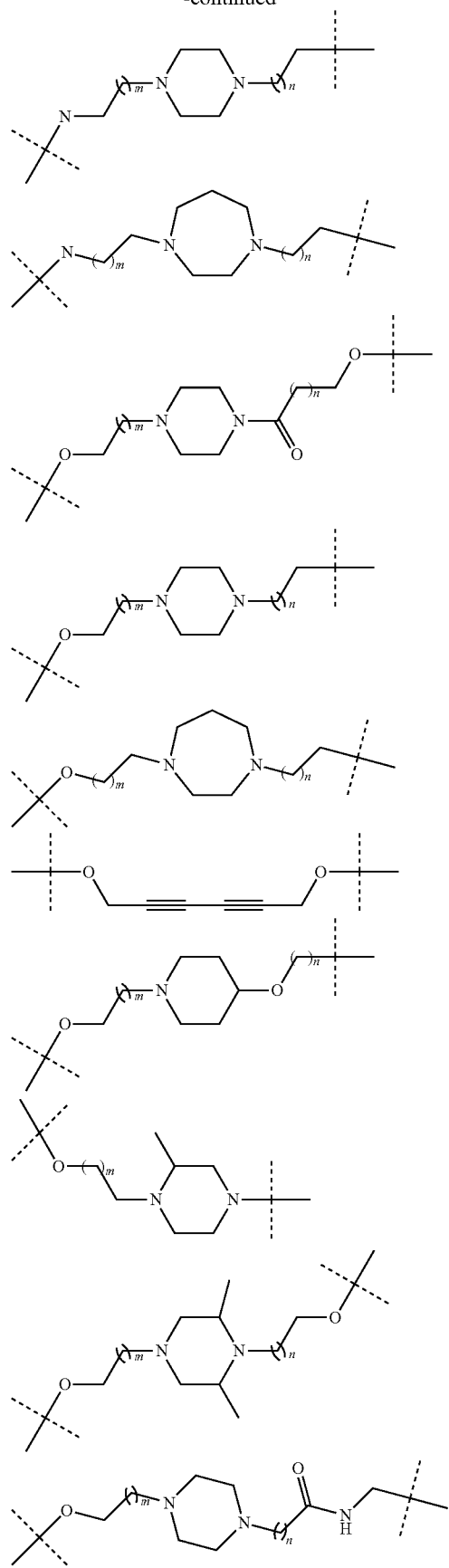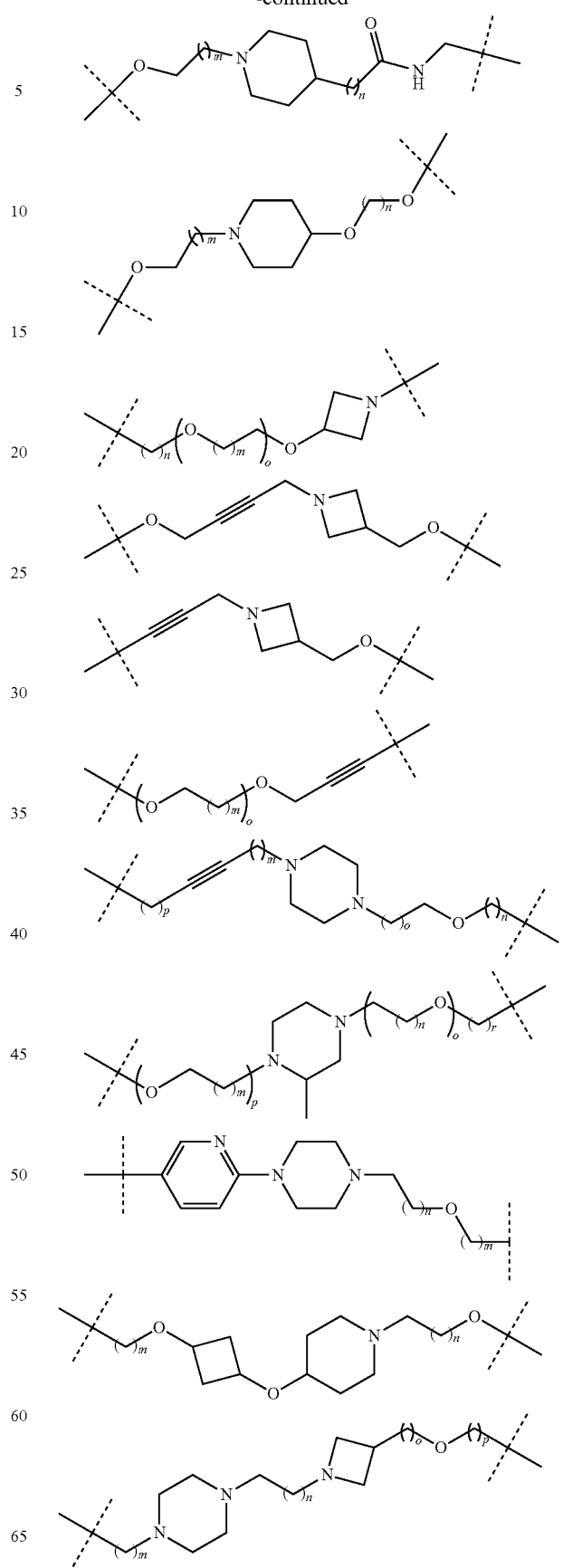

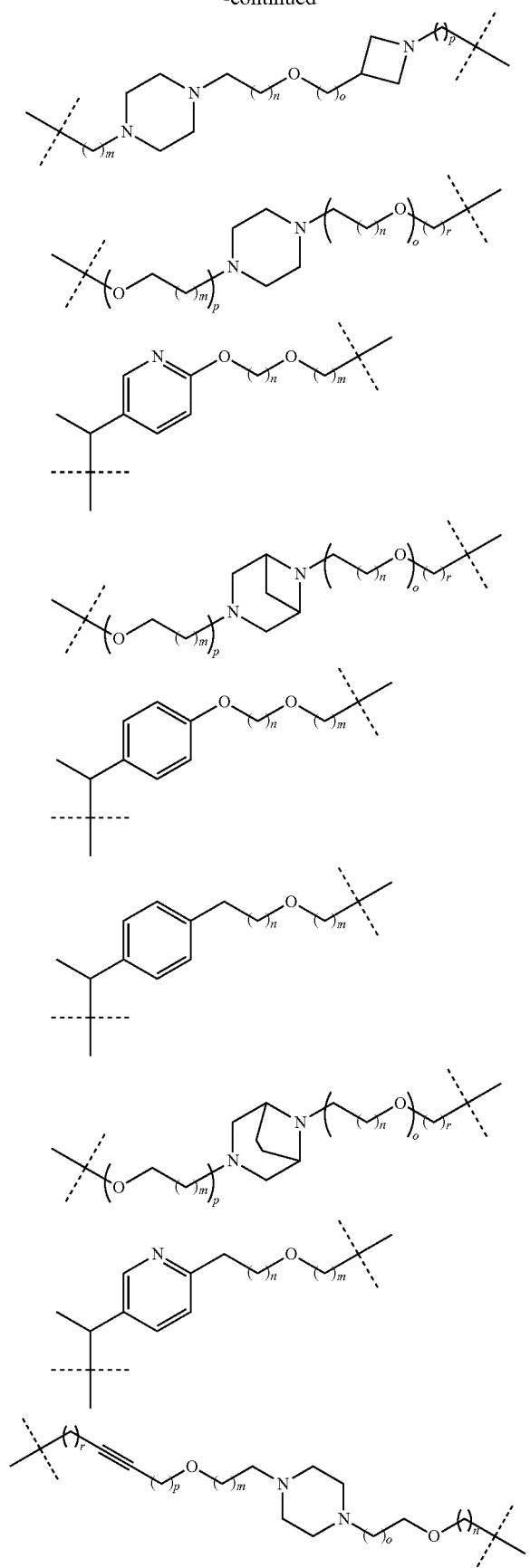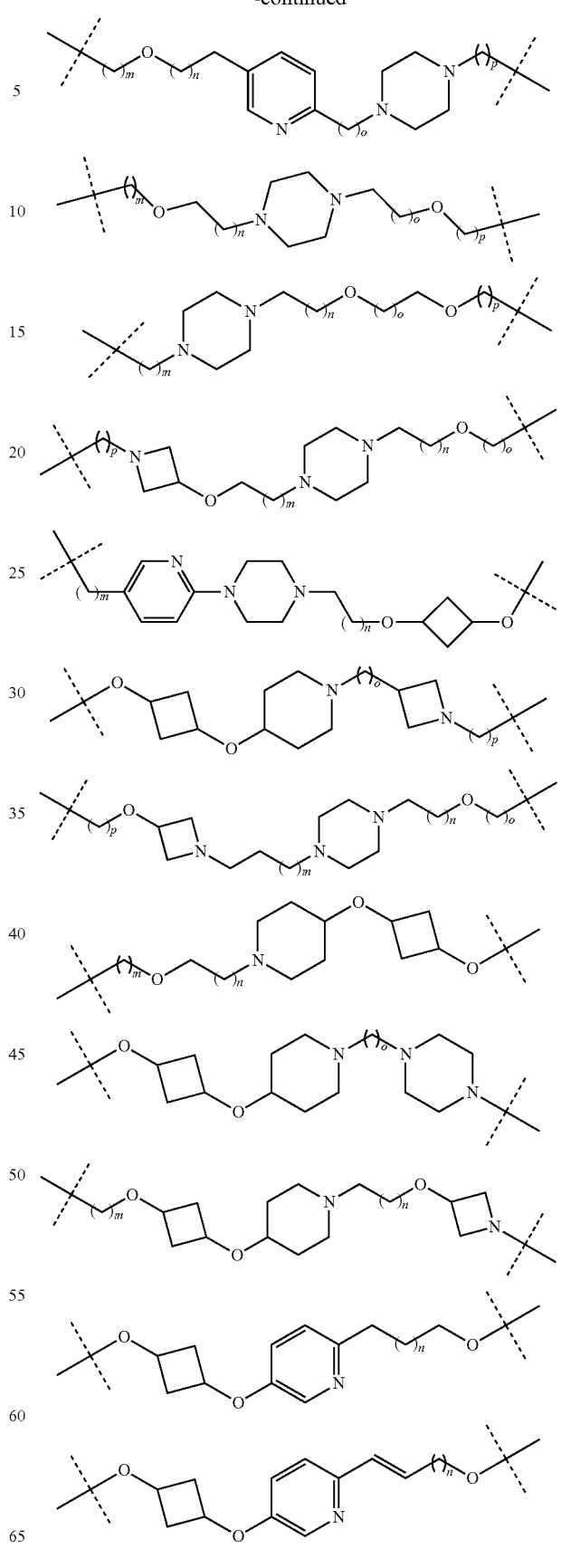

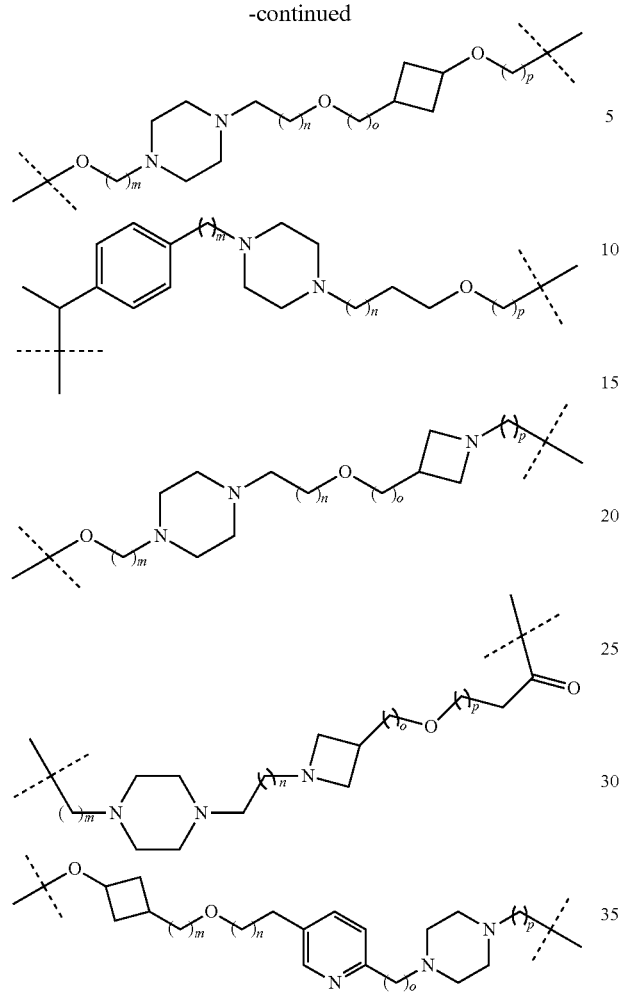
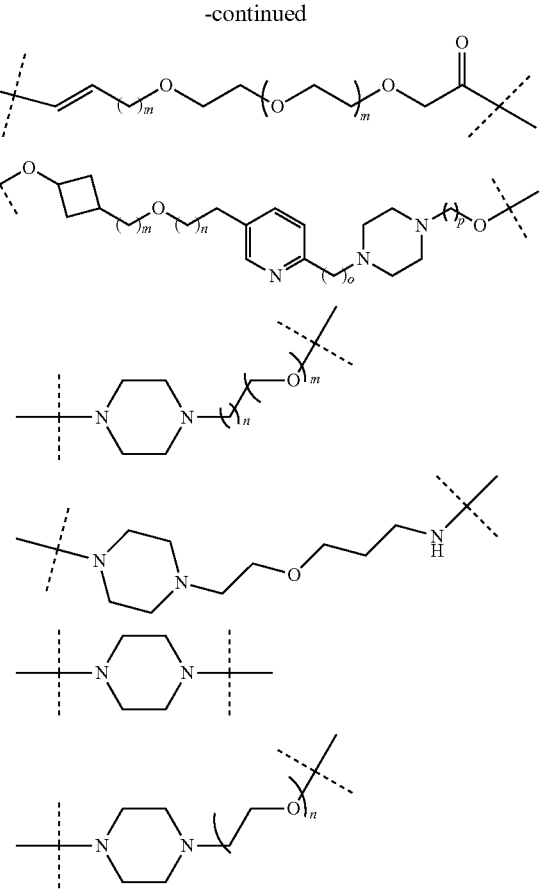
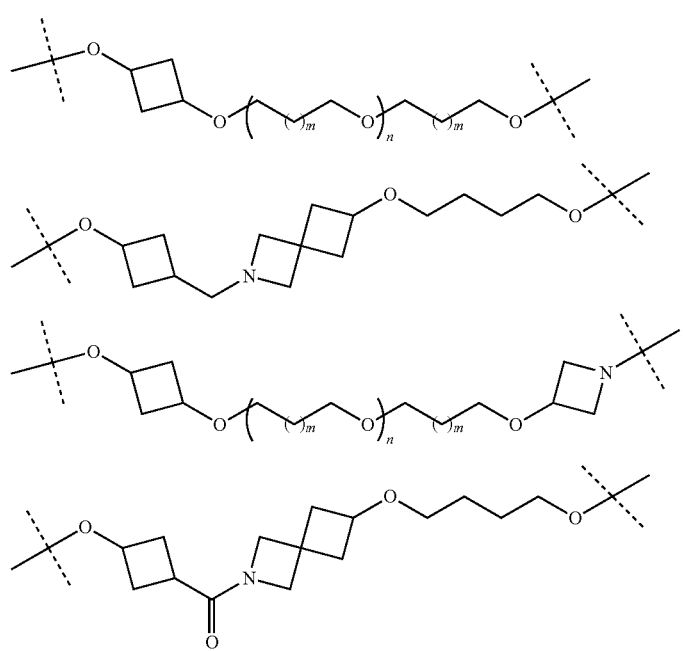

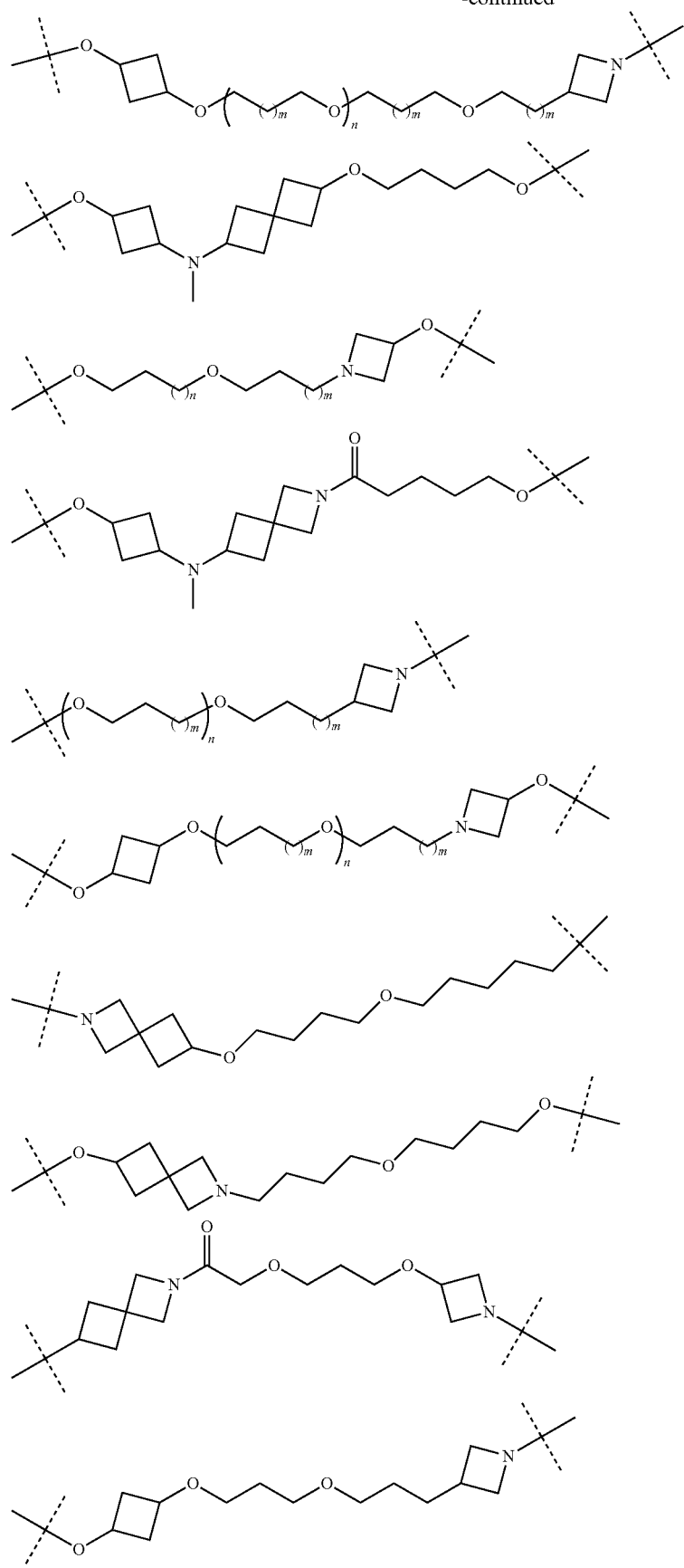

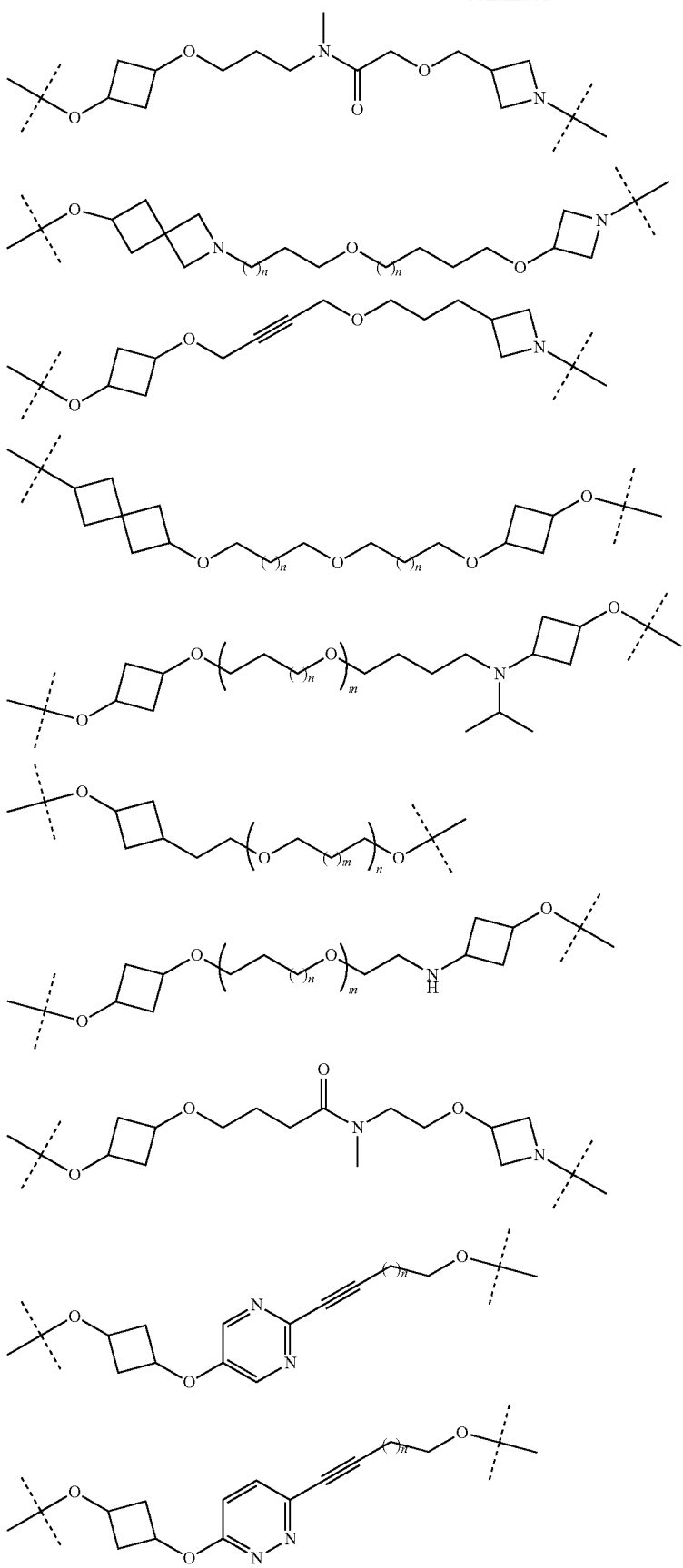

-continued
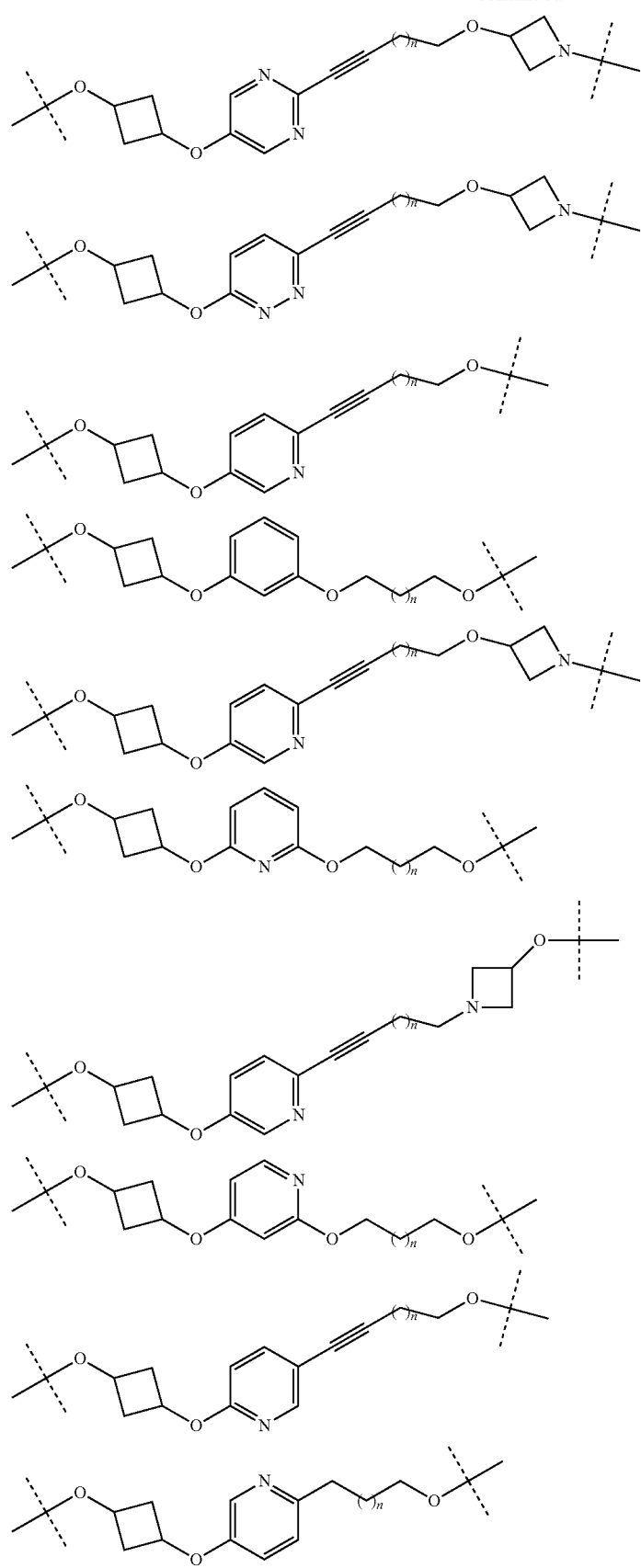

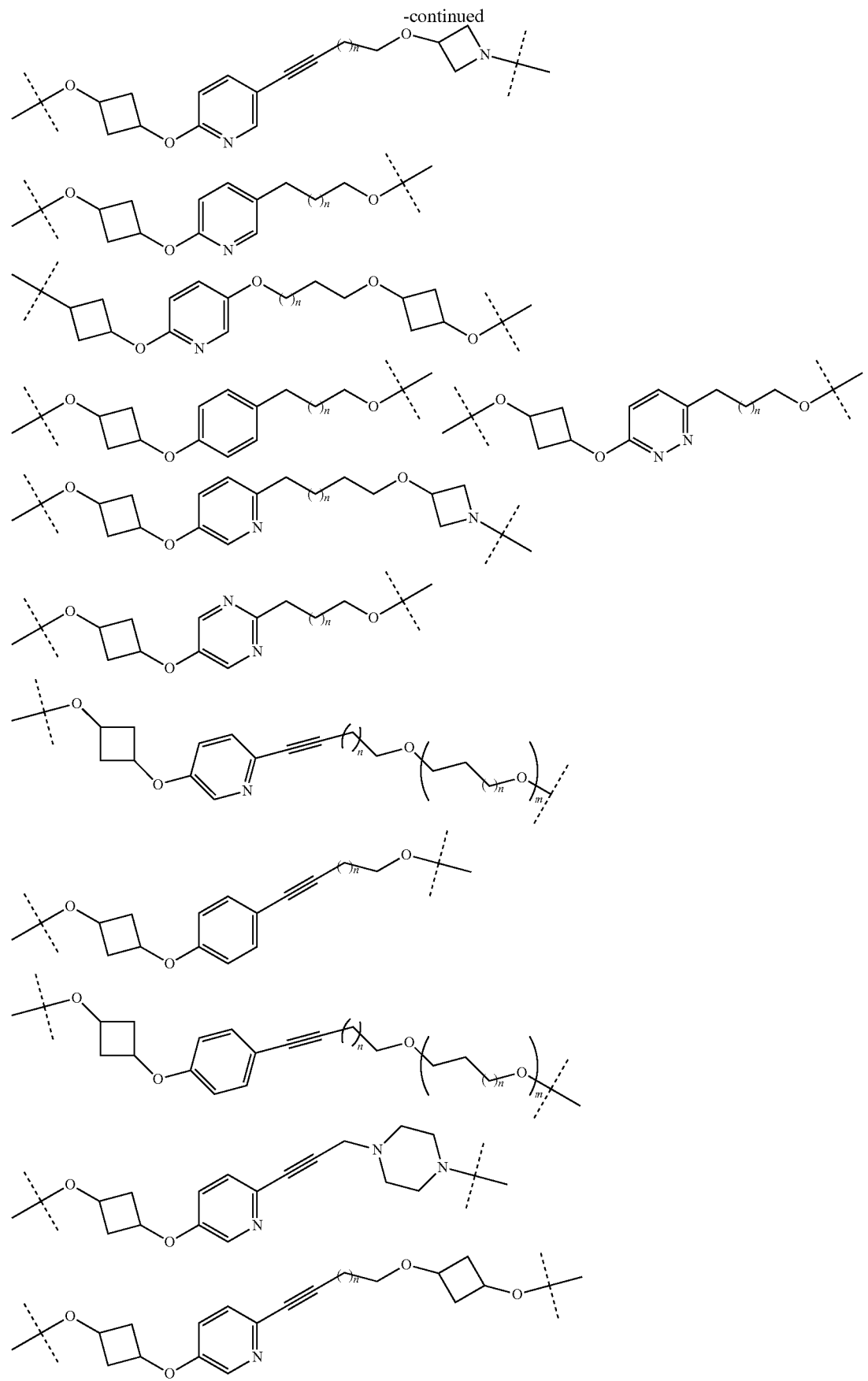

-continued
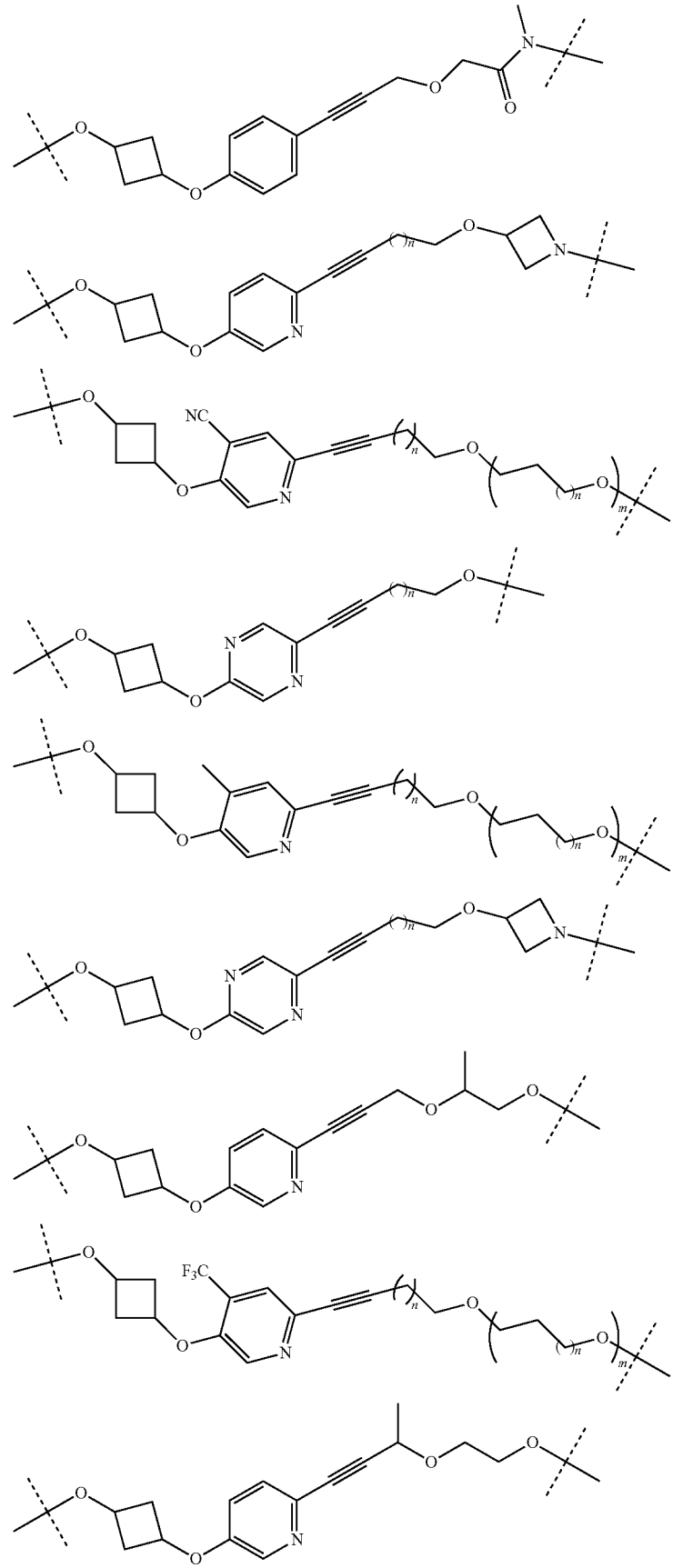

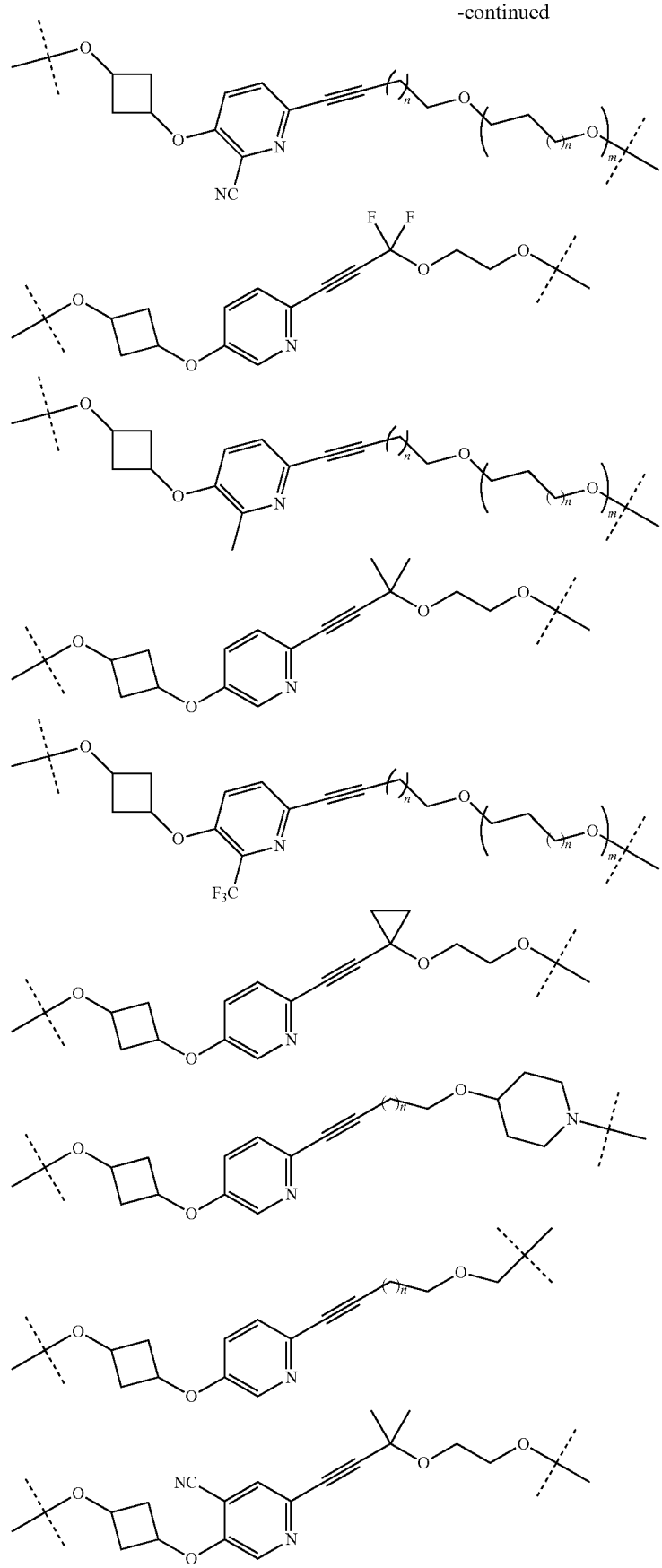

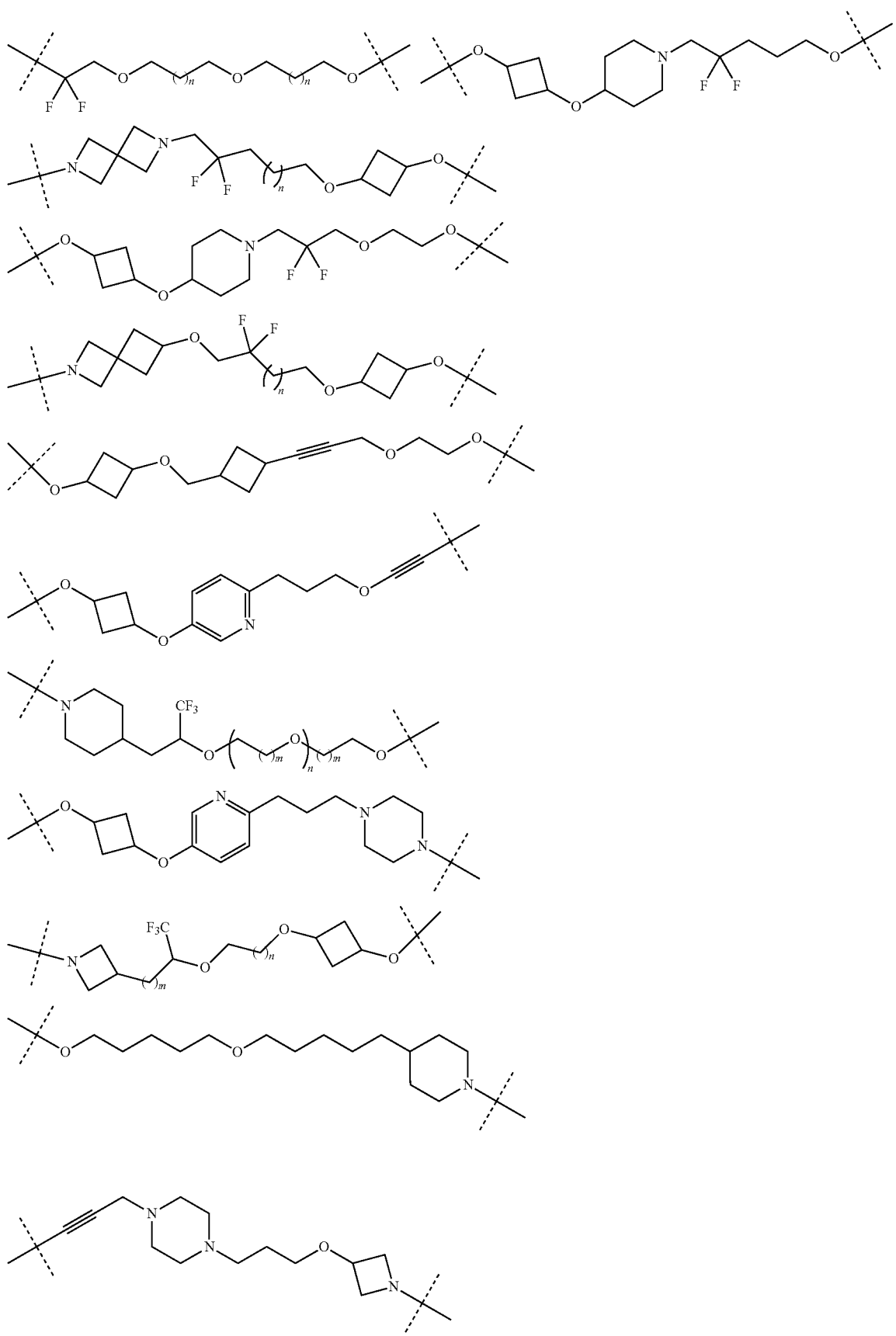

-continued
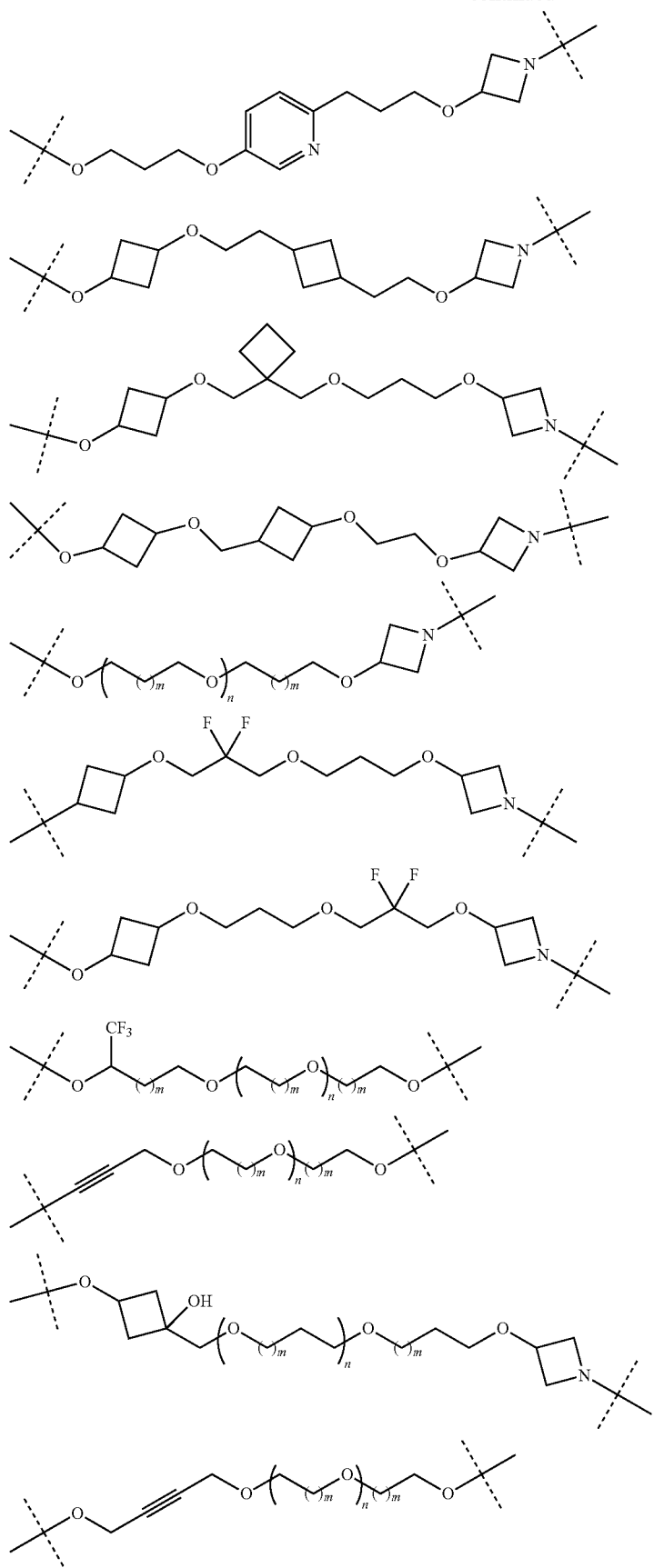

-continued
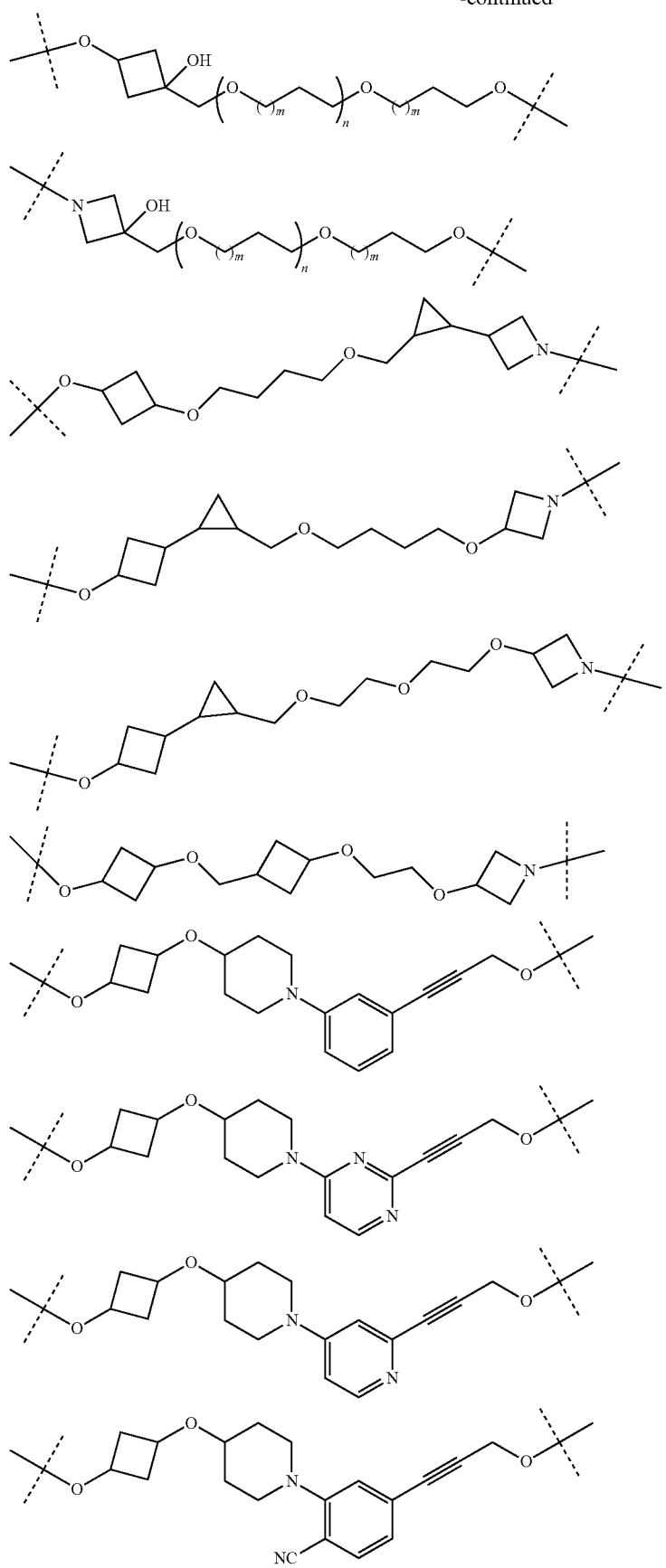

-continued
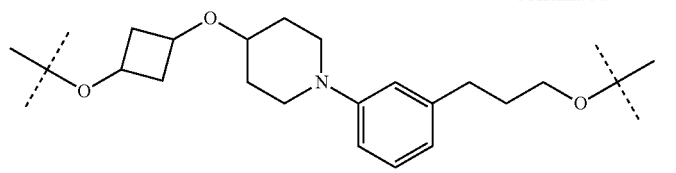
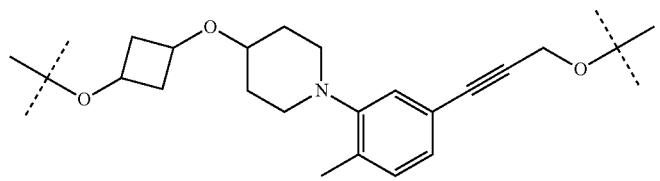
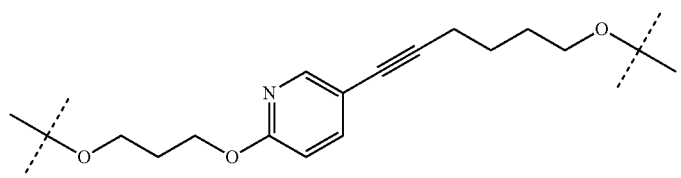
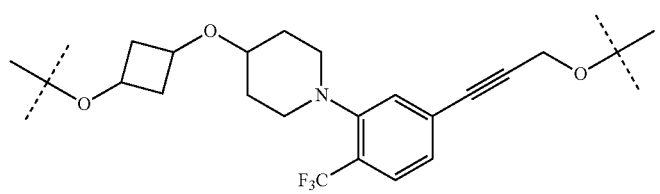
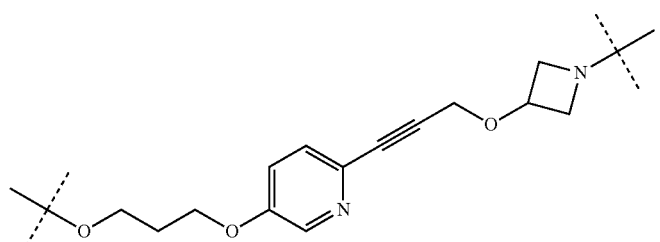
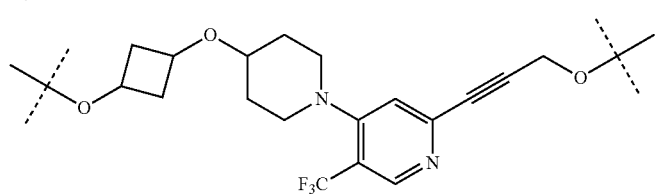
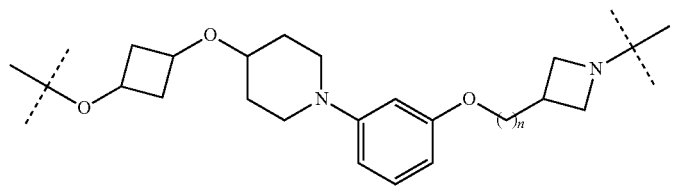
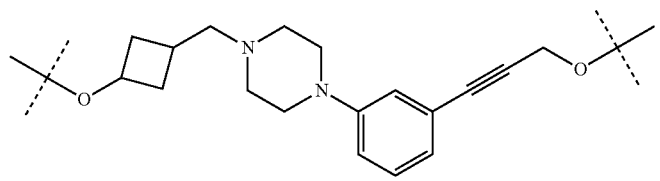
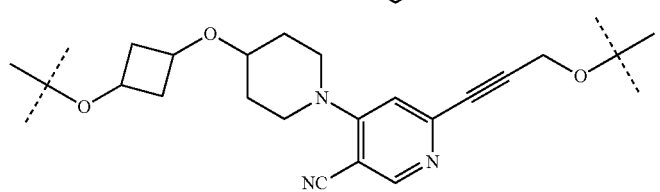

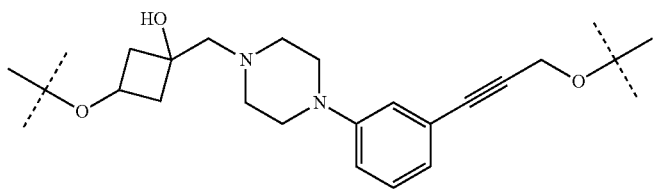
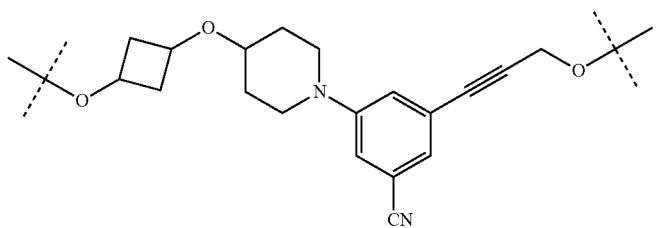
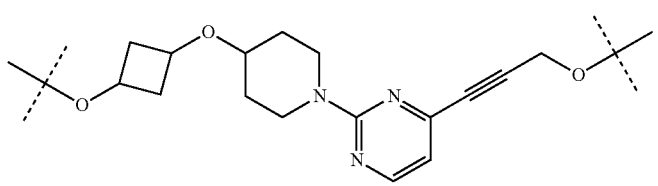
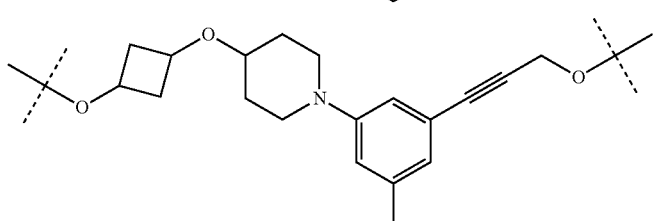
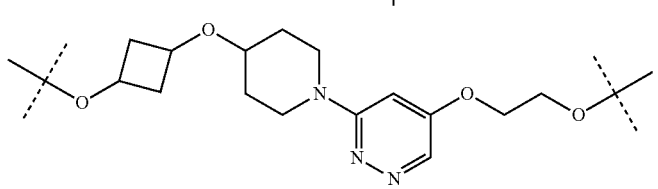
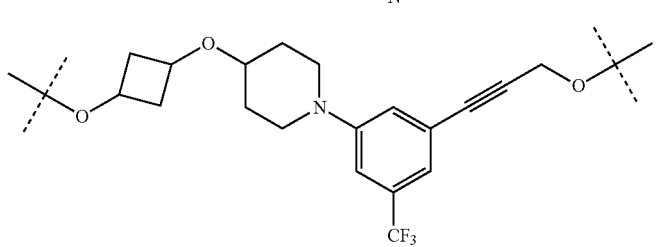
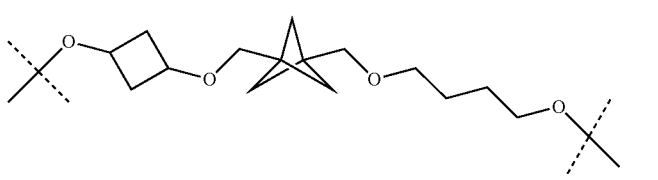
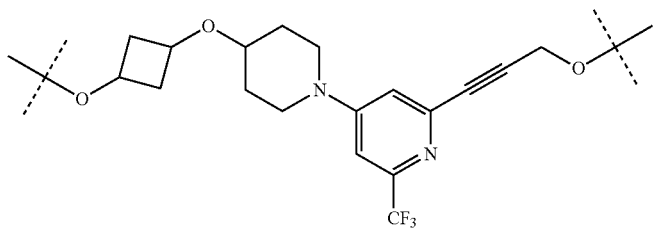

-continued
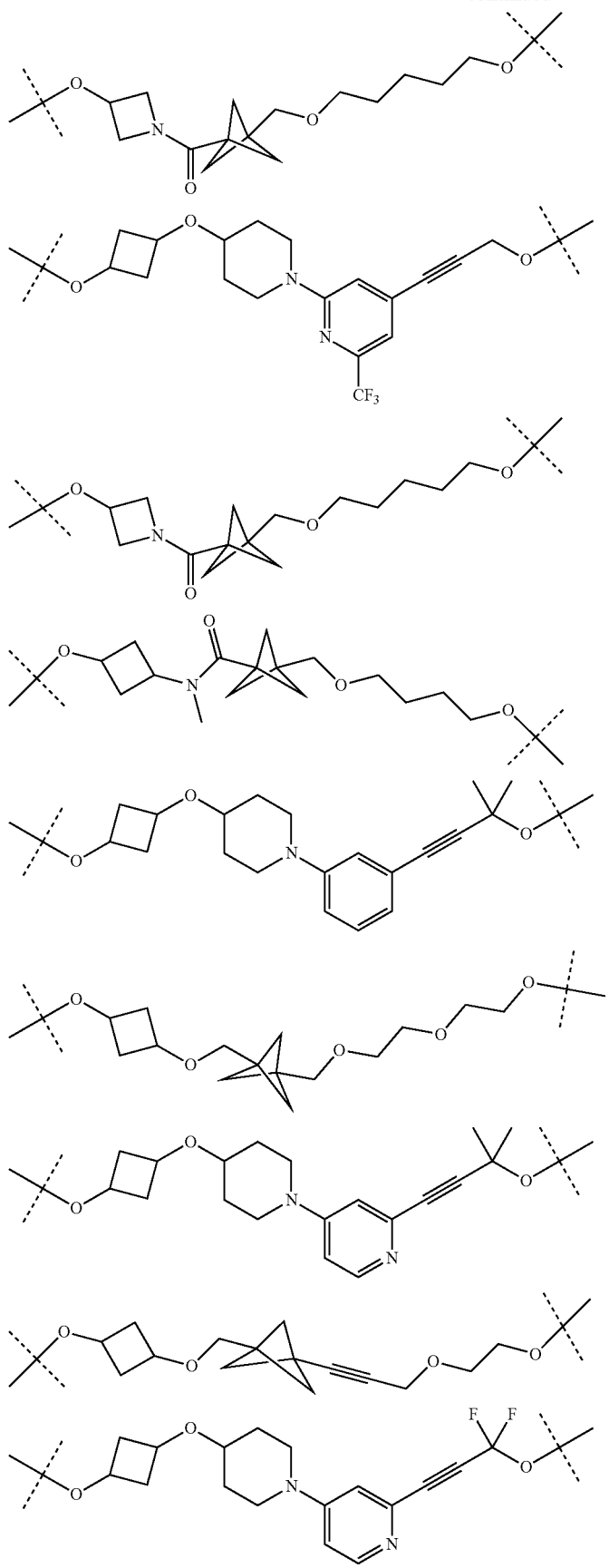

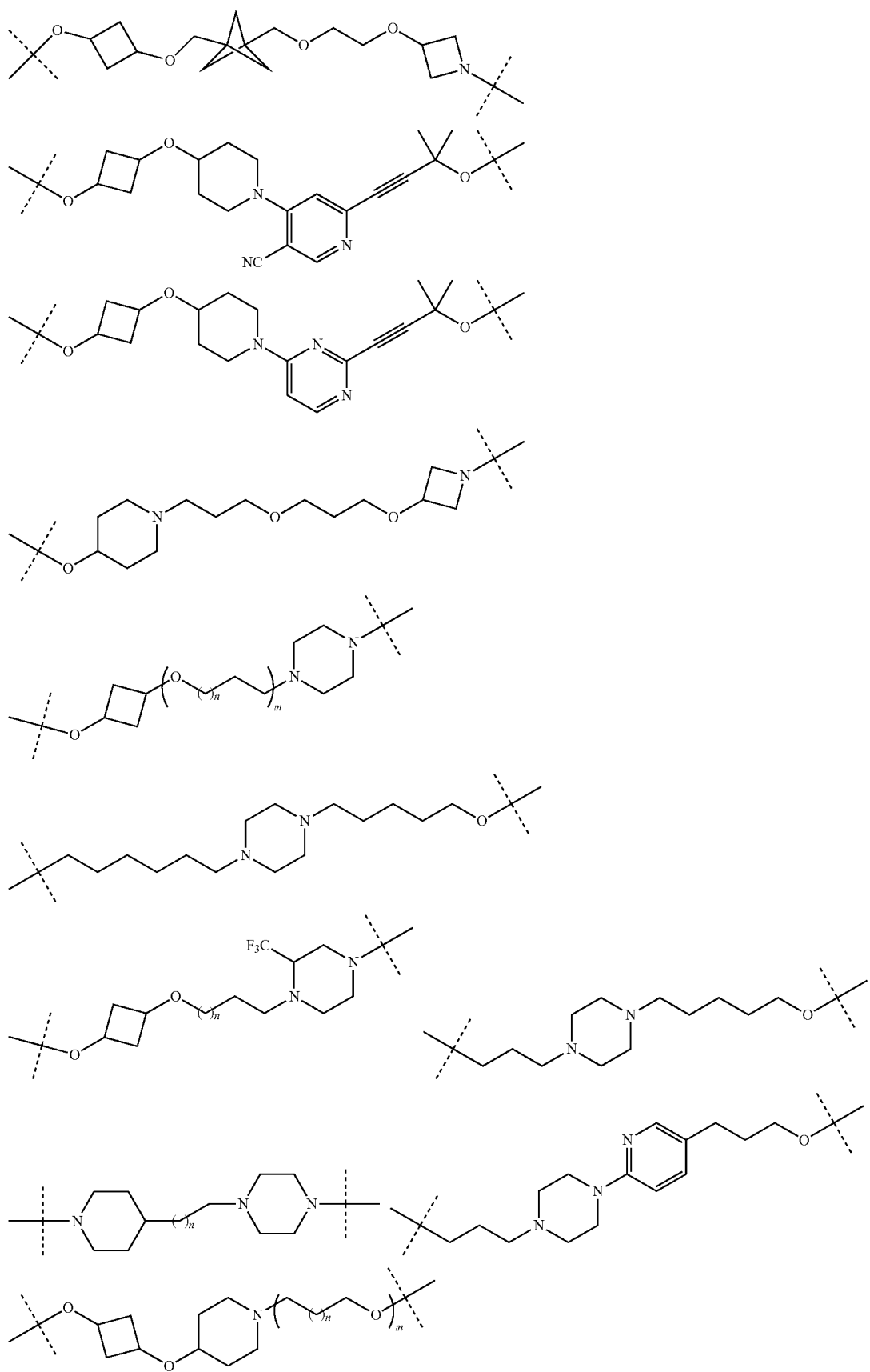

-continued
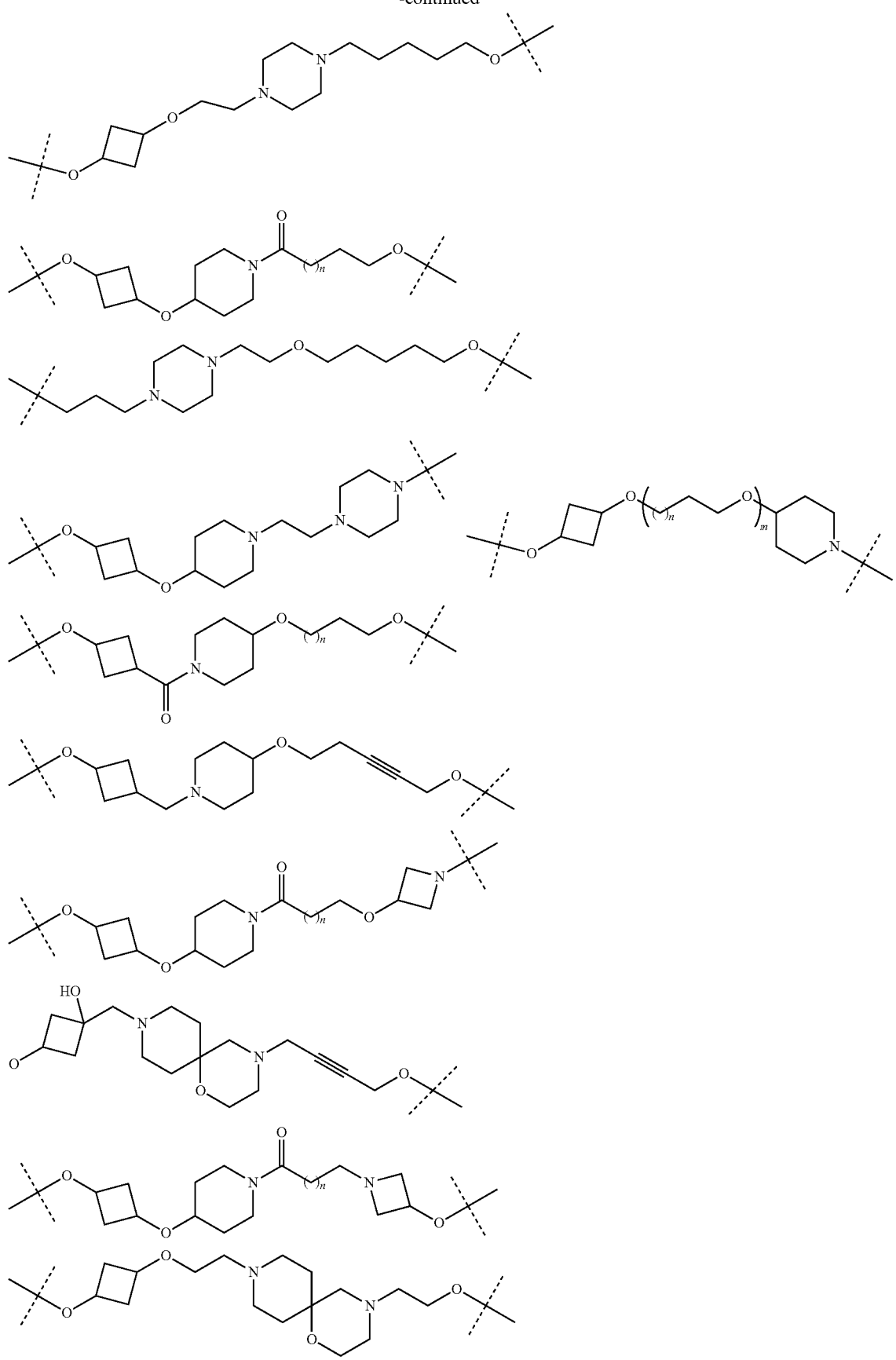

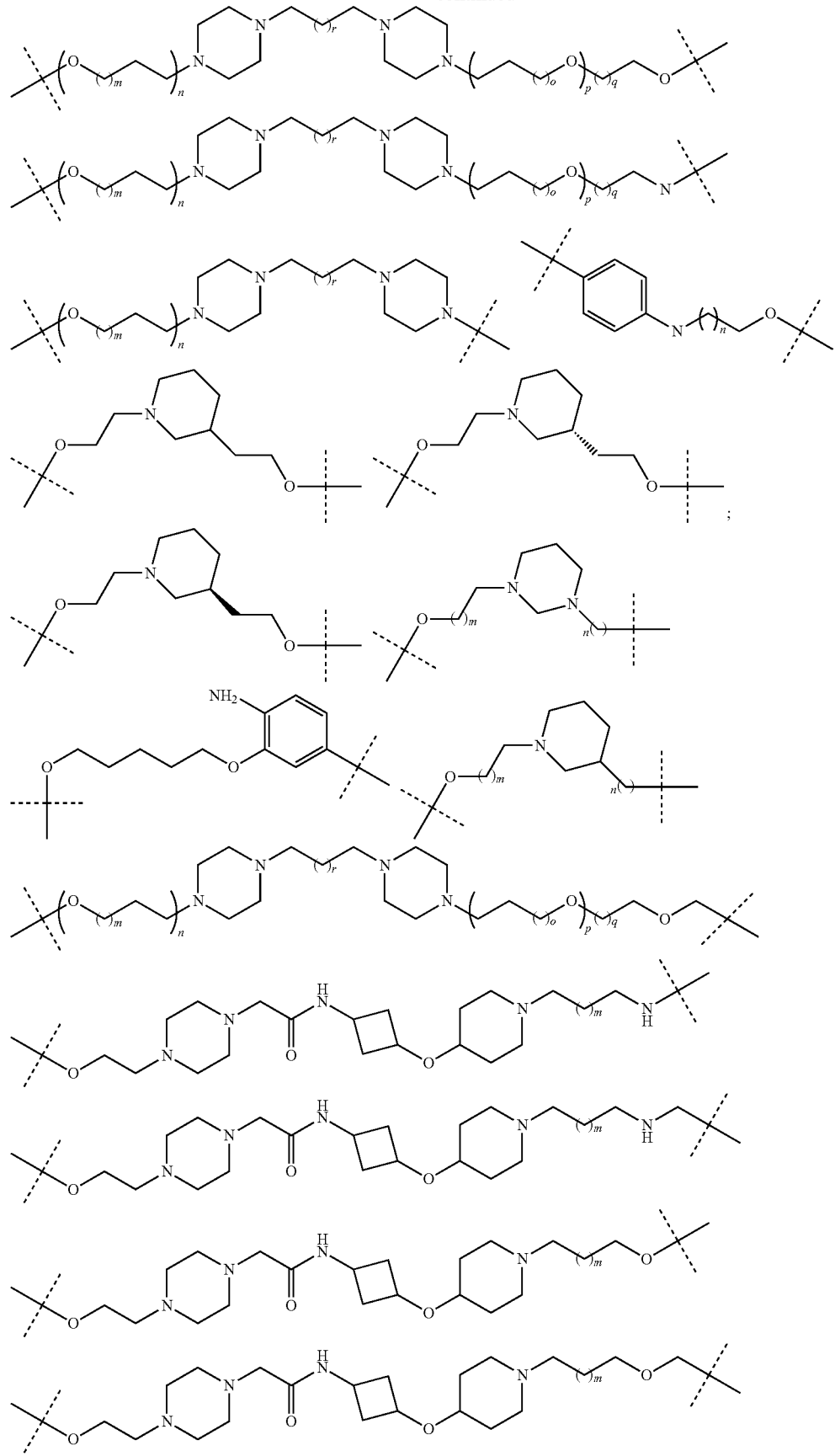

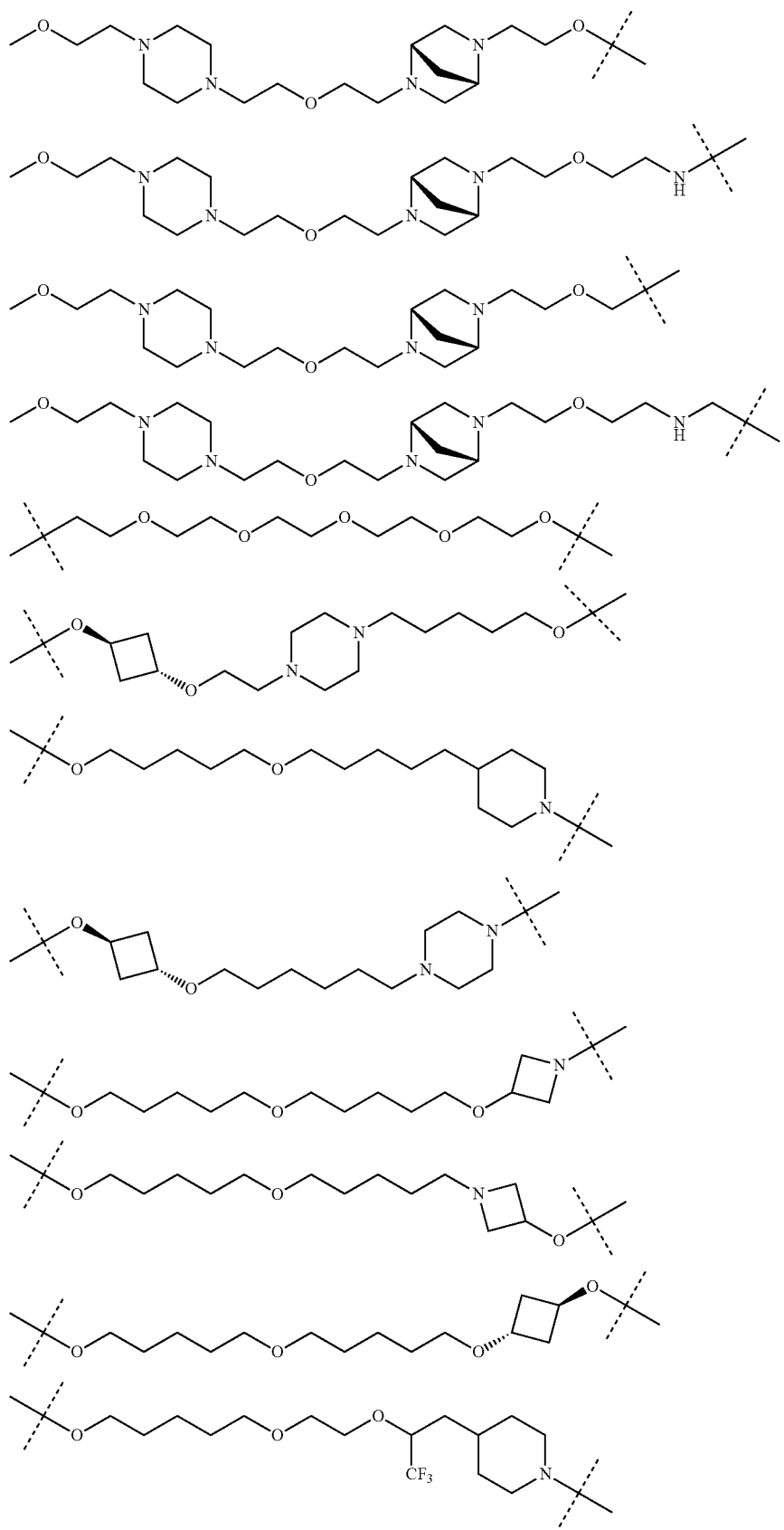

-continued
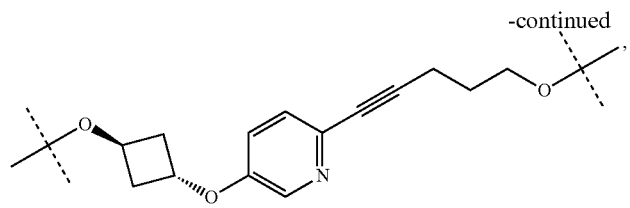
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of linker (L) is selected from the group consisting of:
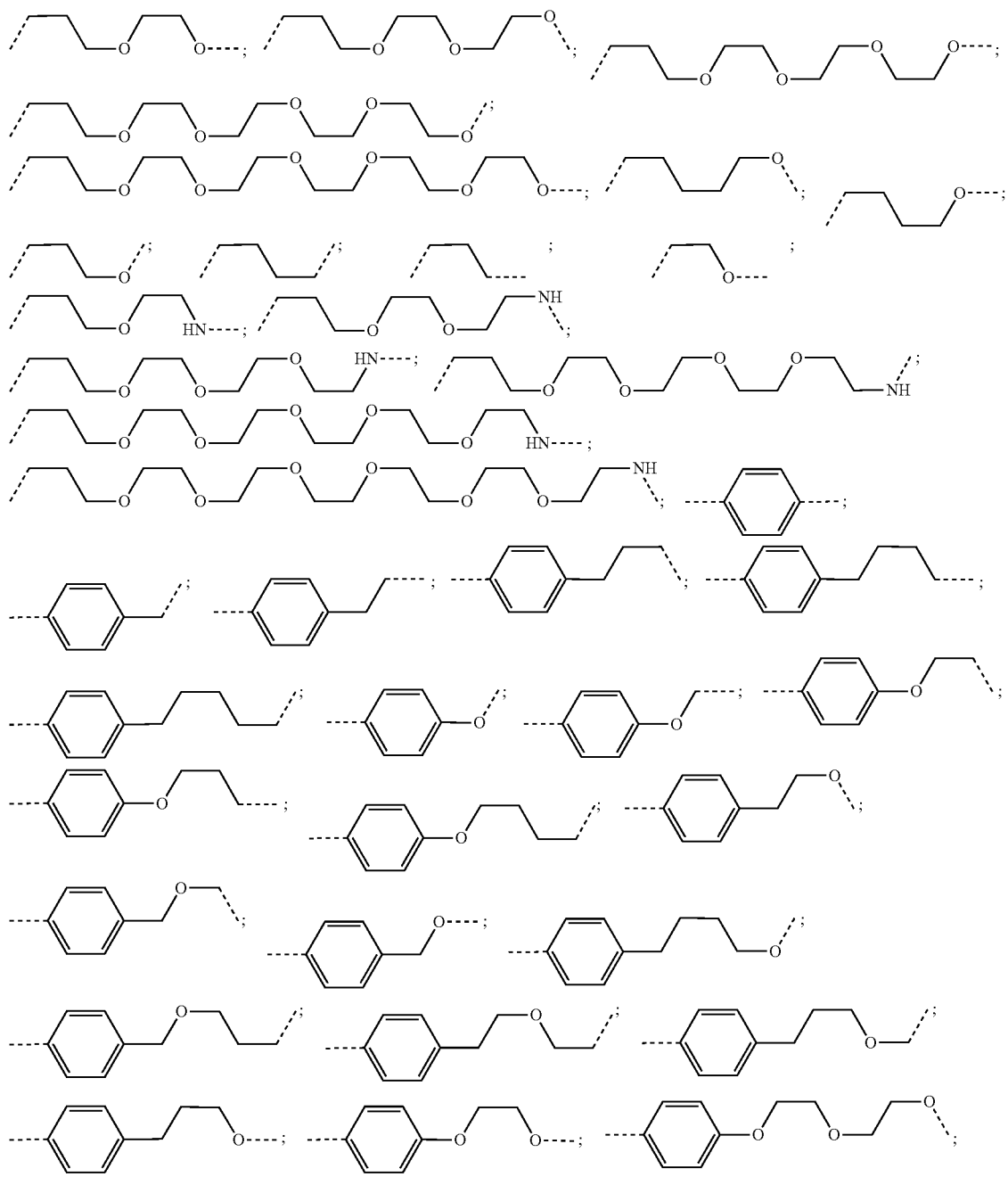

-continued
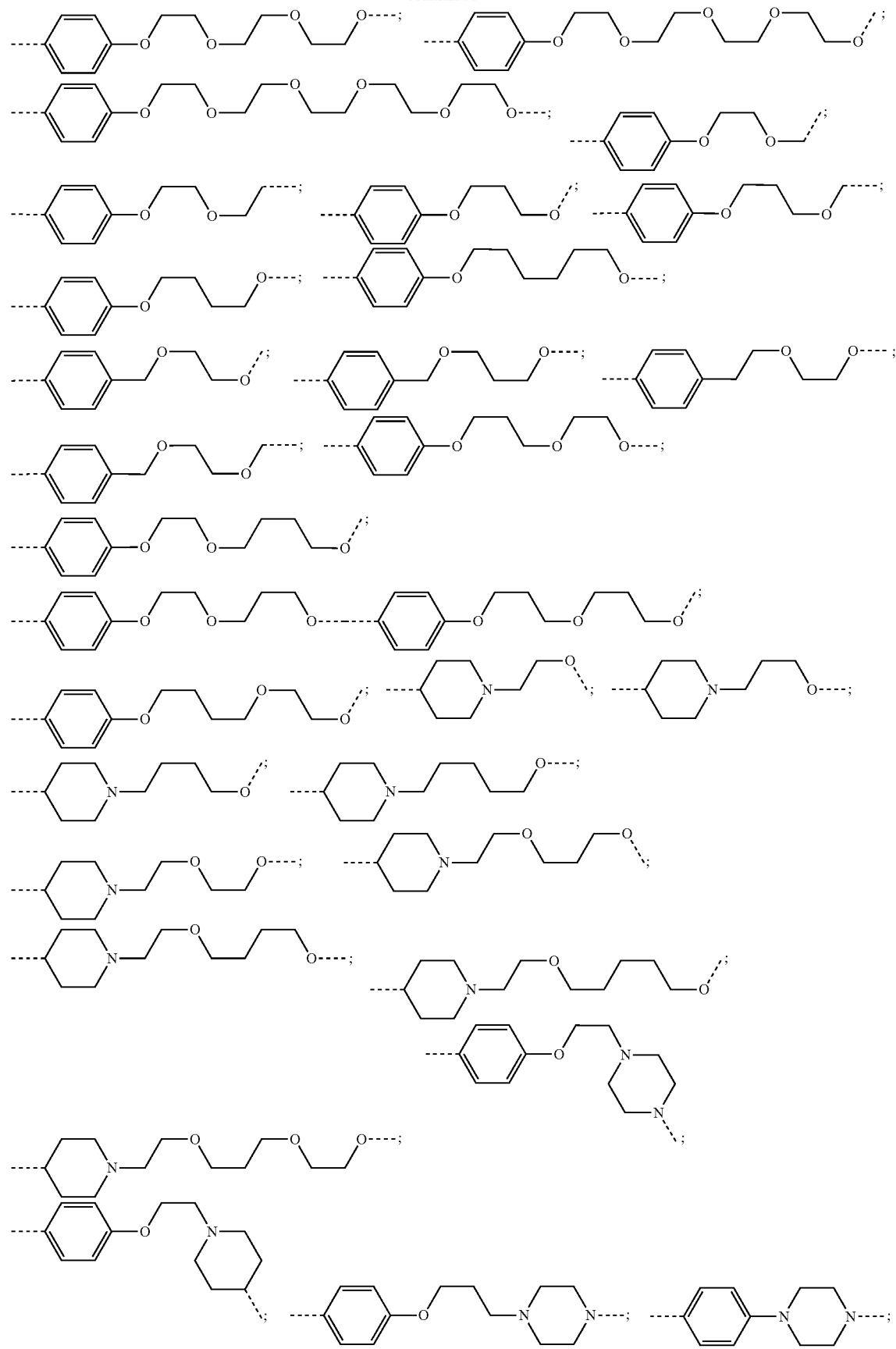

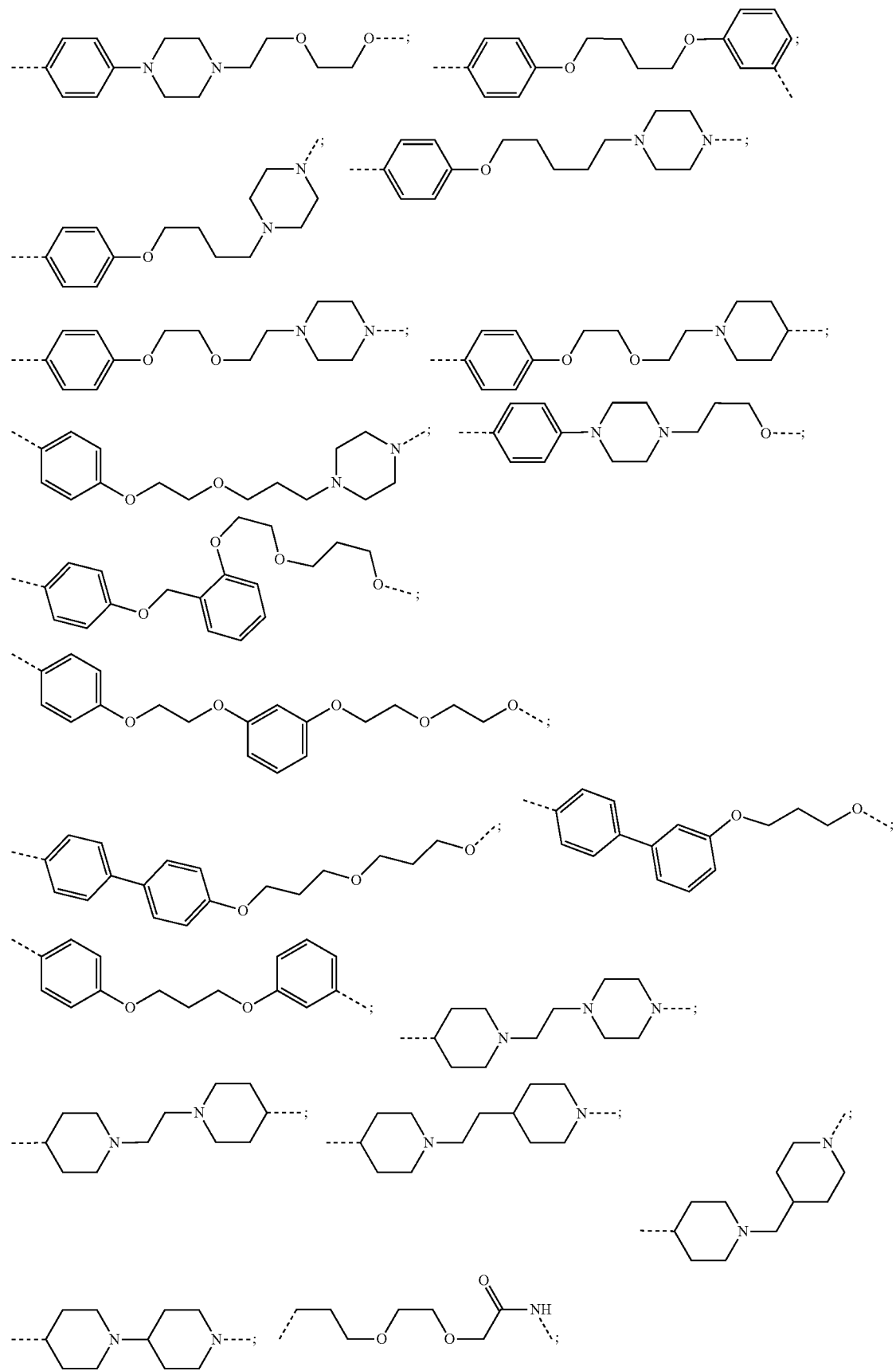

327 328
-continued
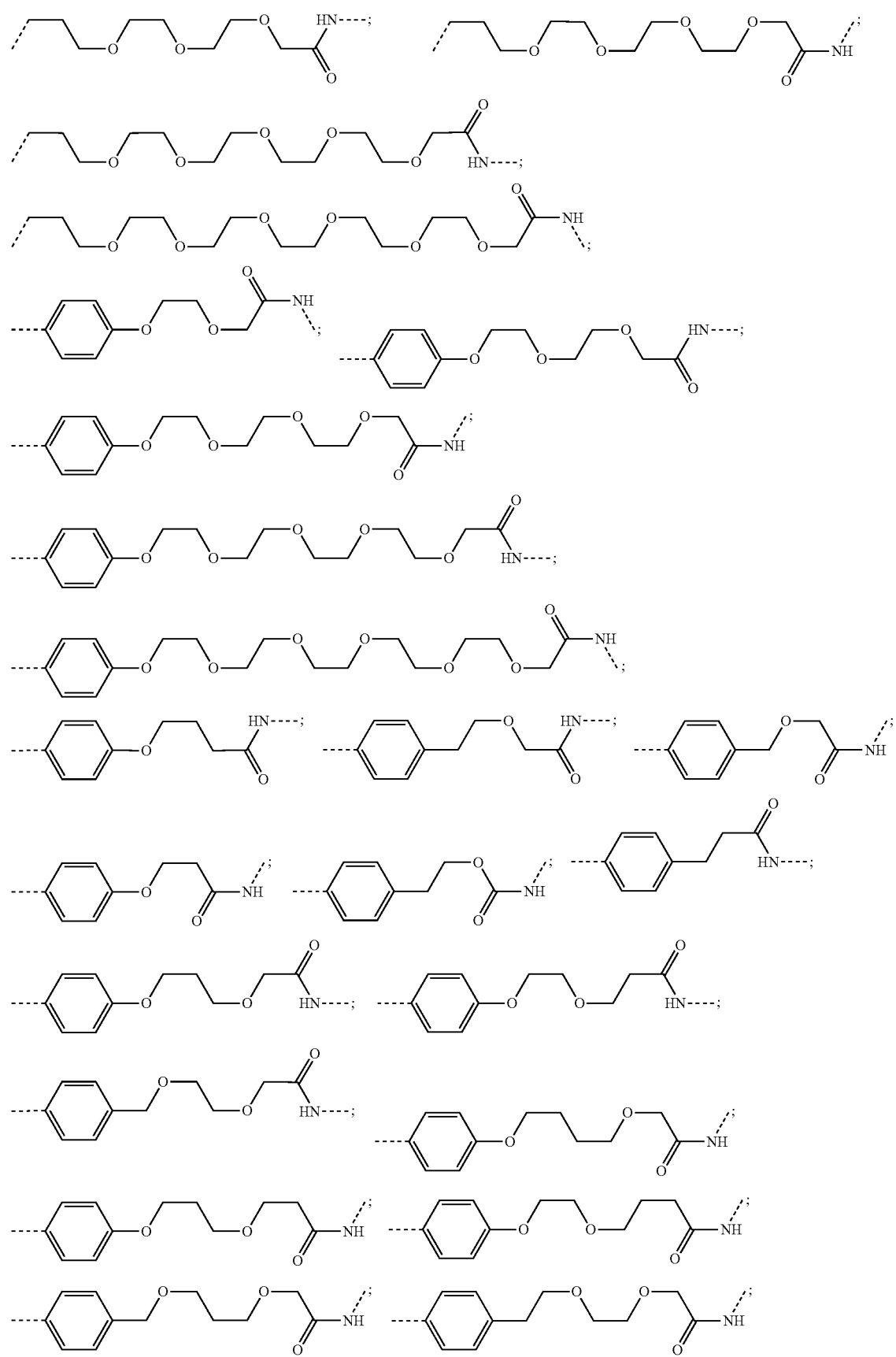

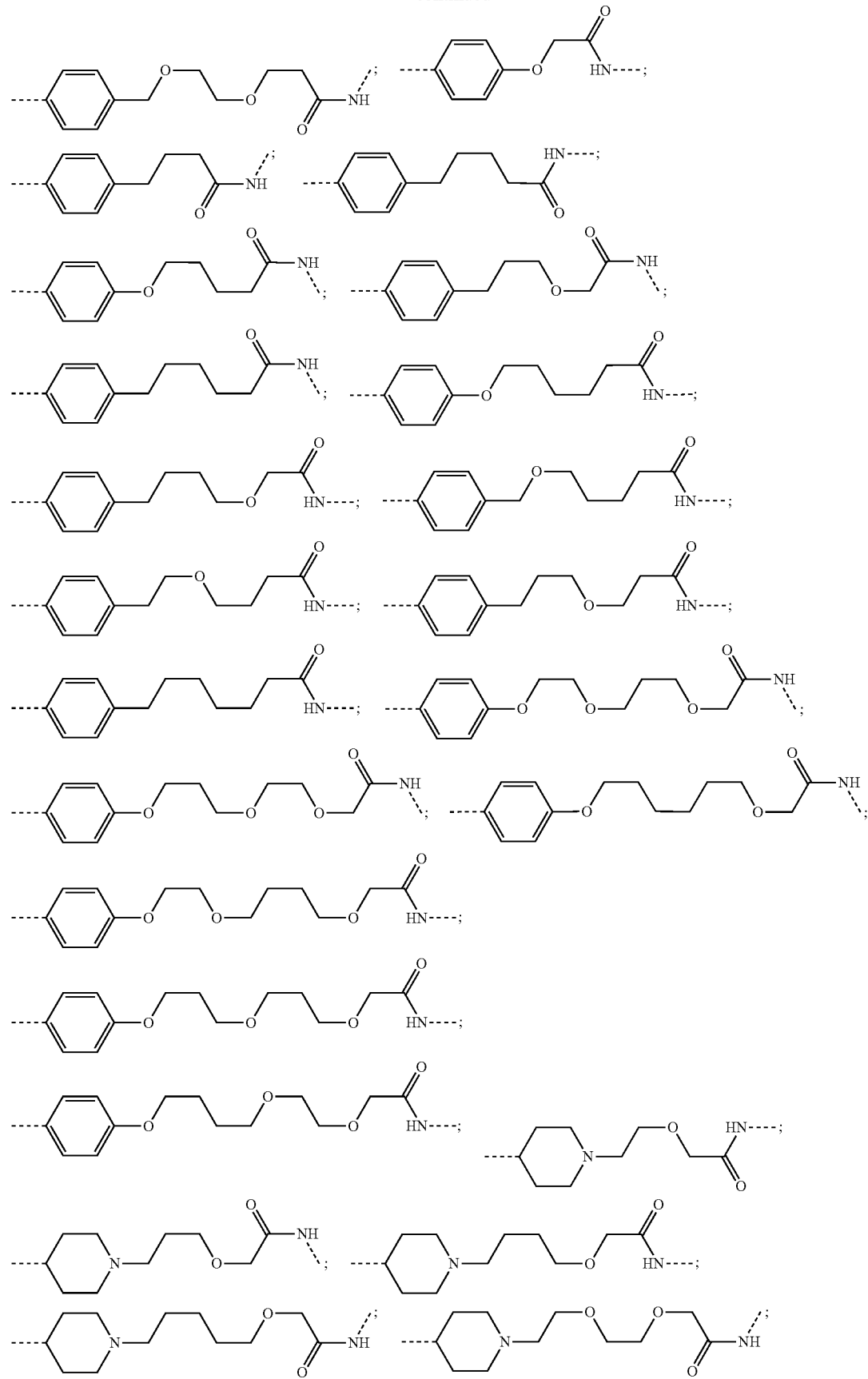

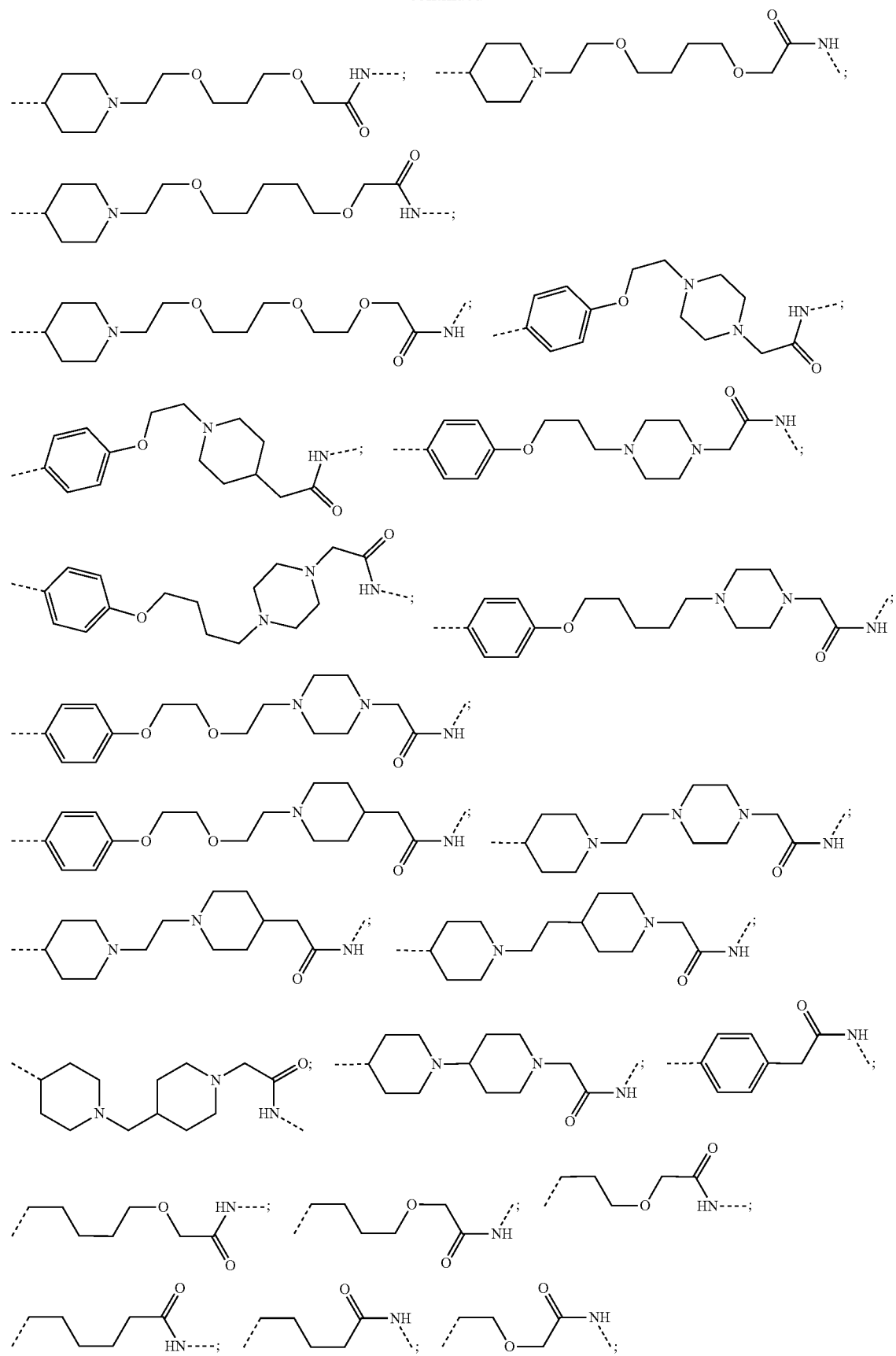

-continued
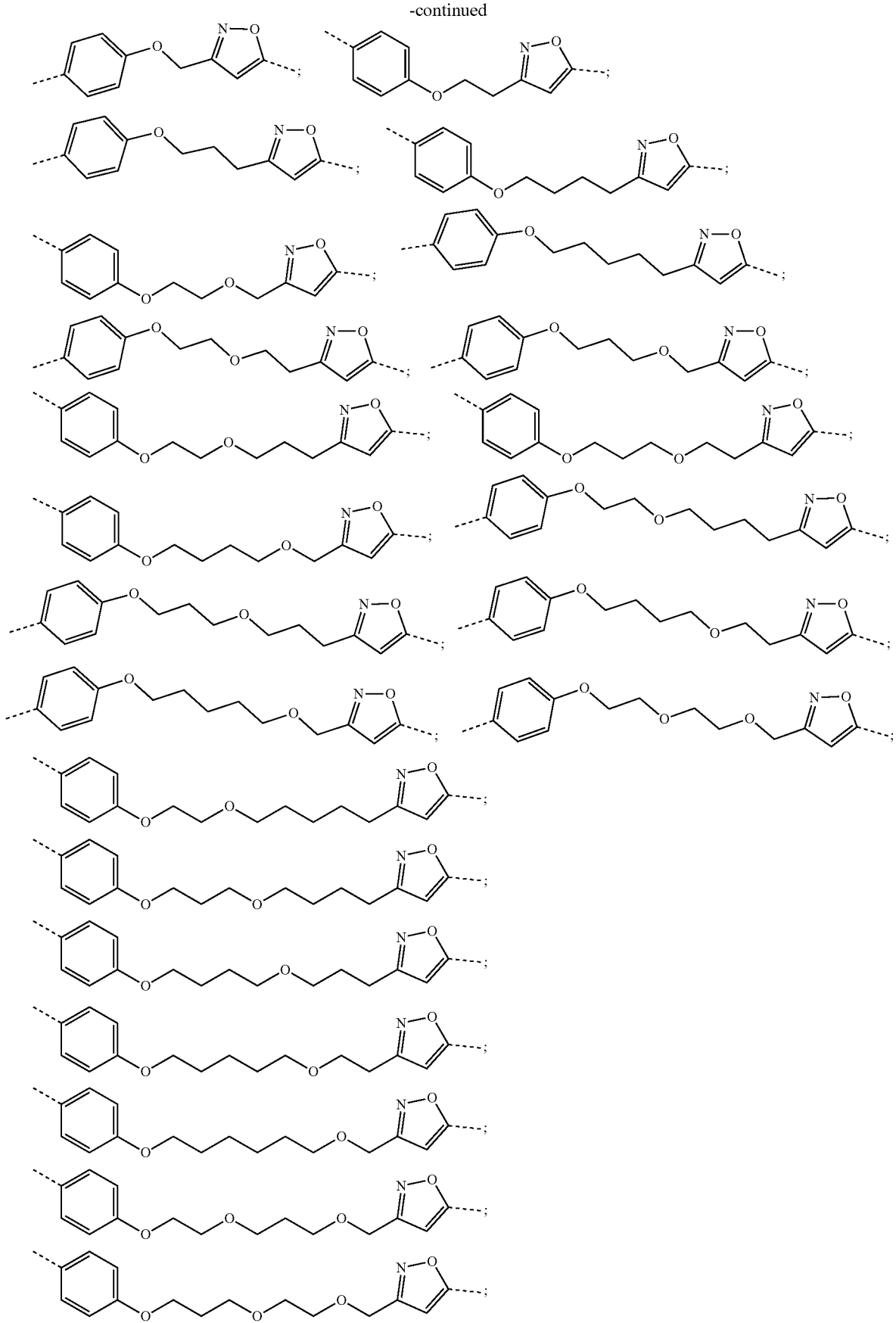

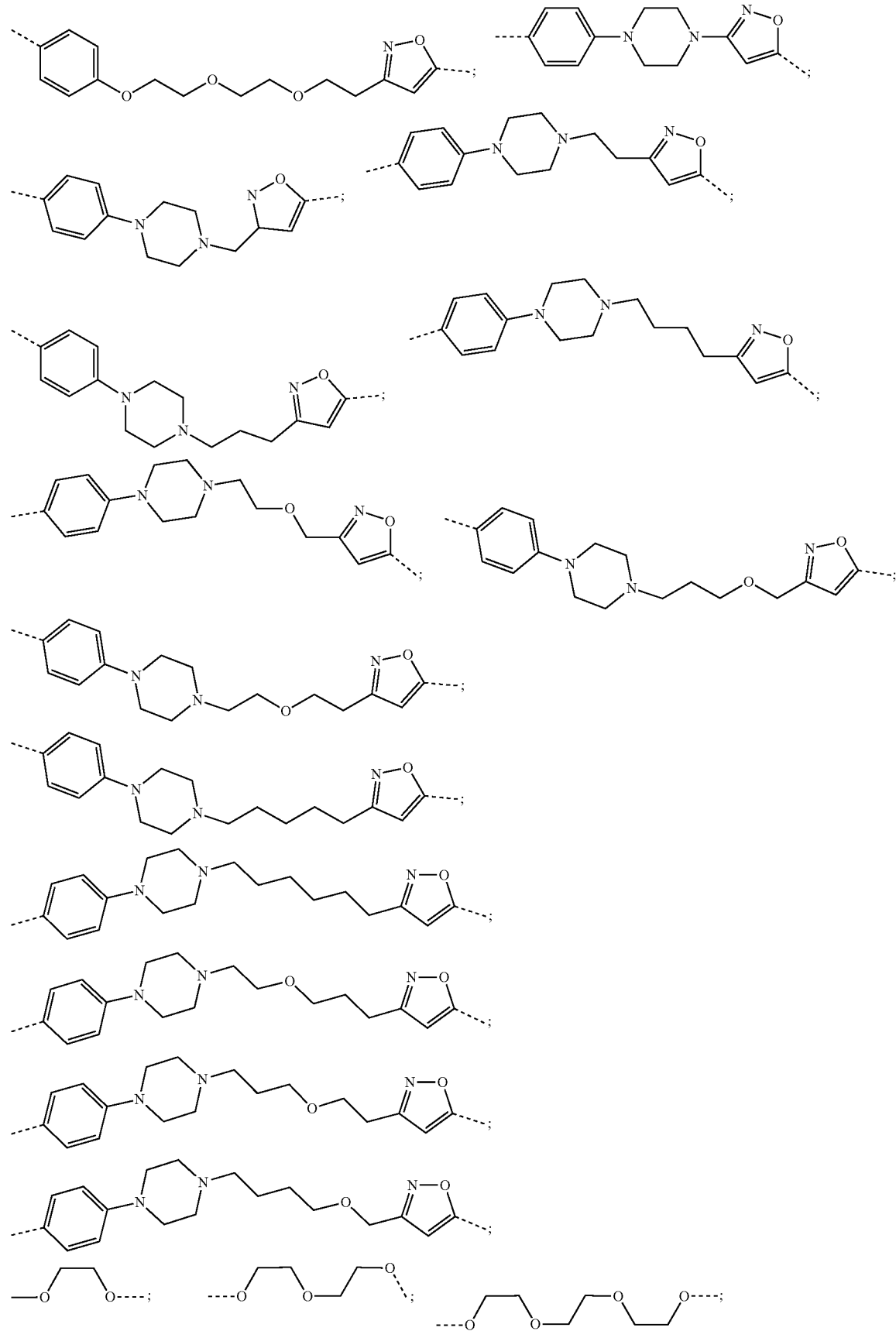

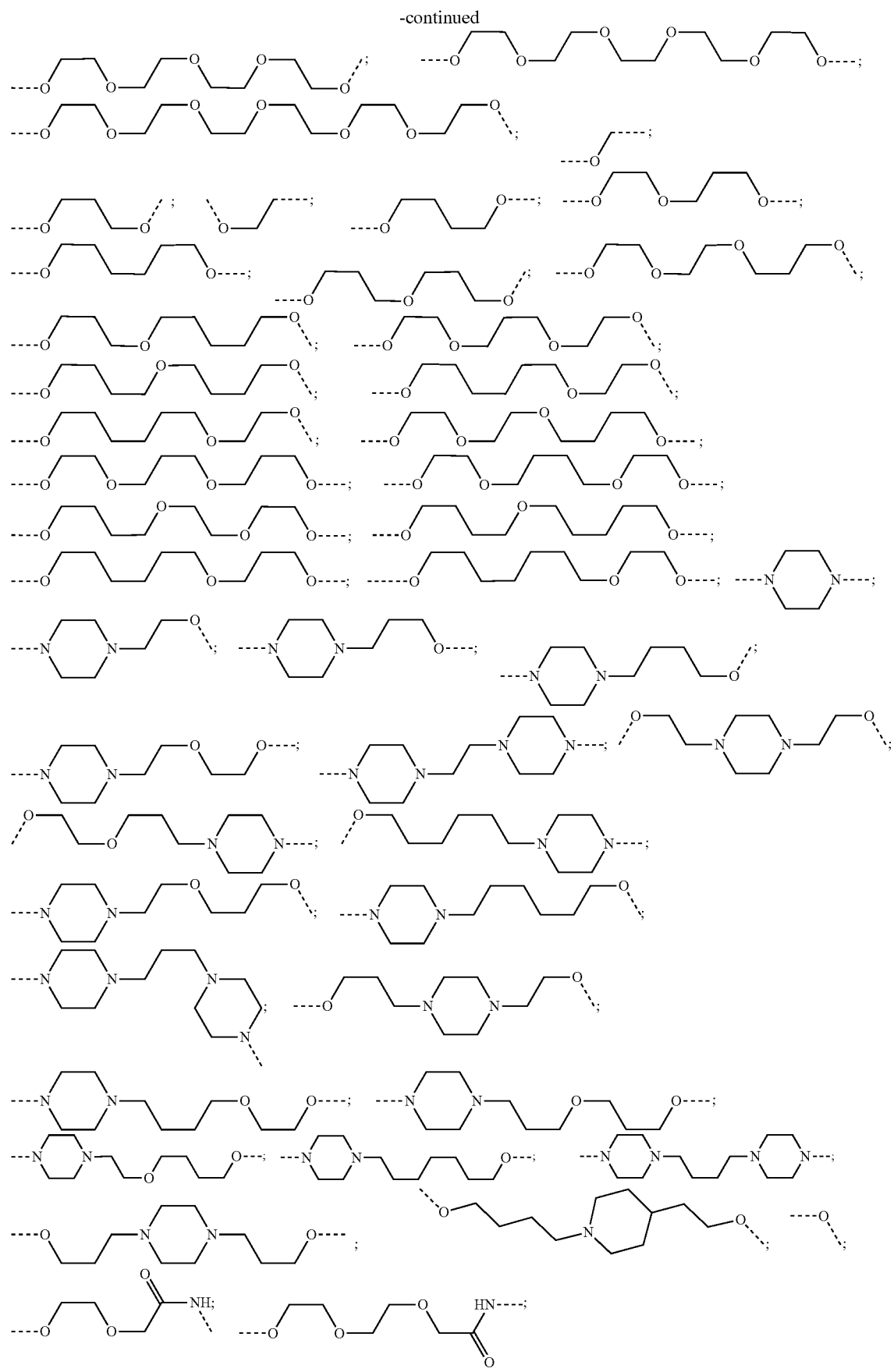

-continued
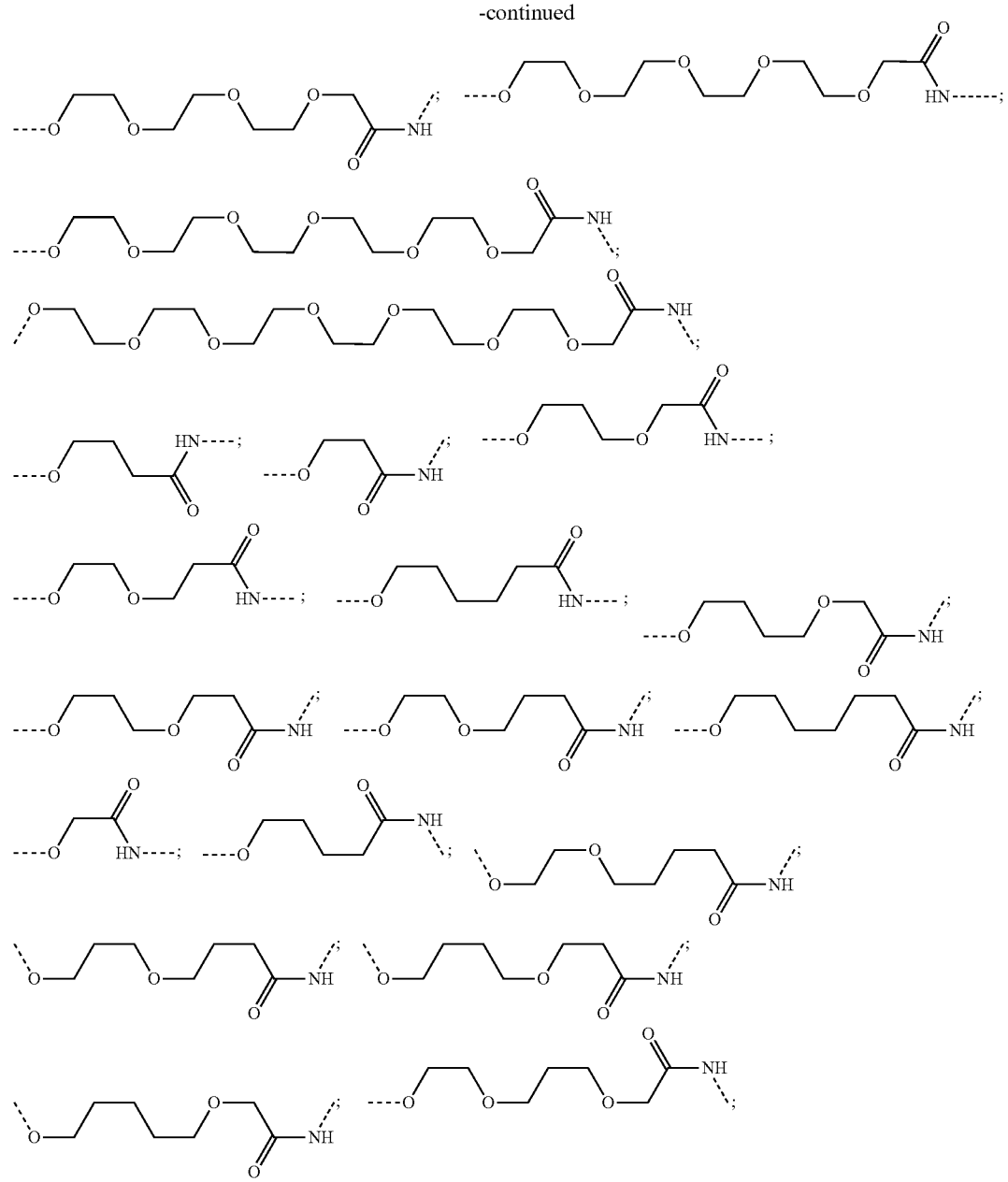
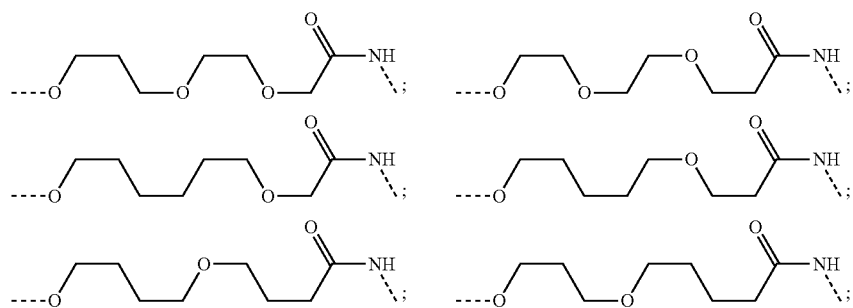

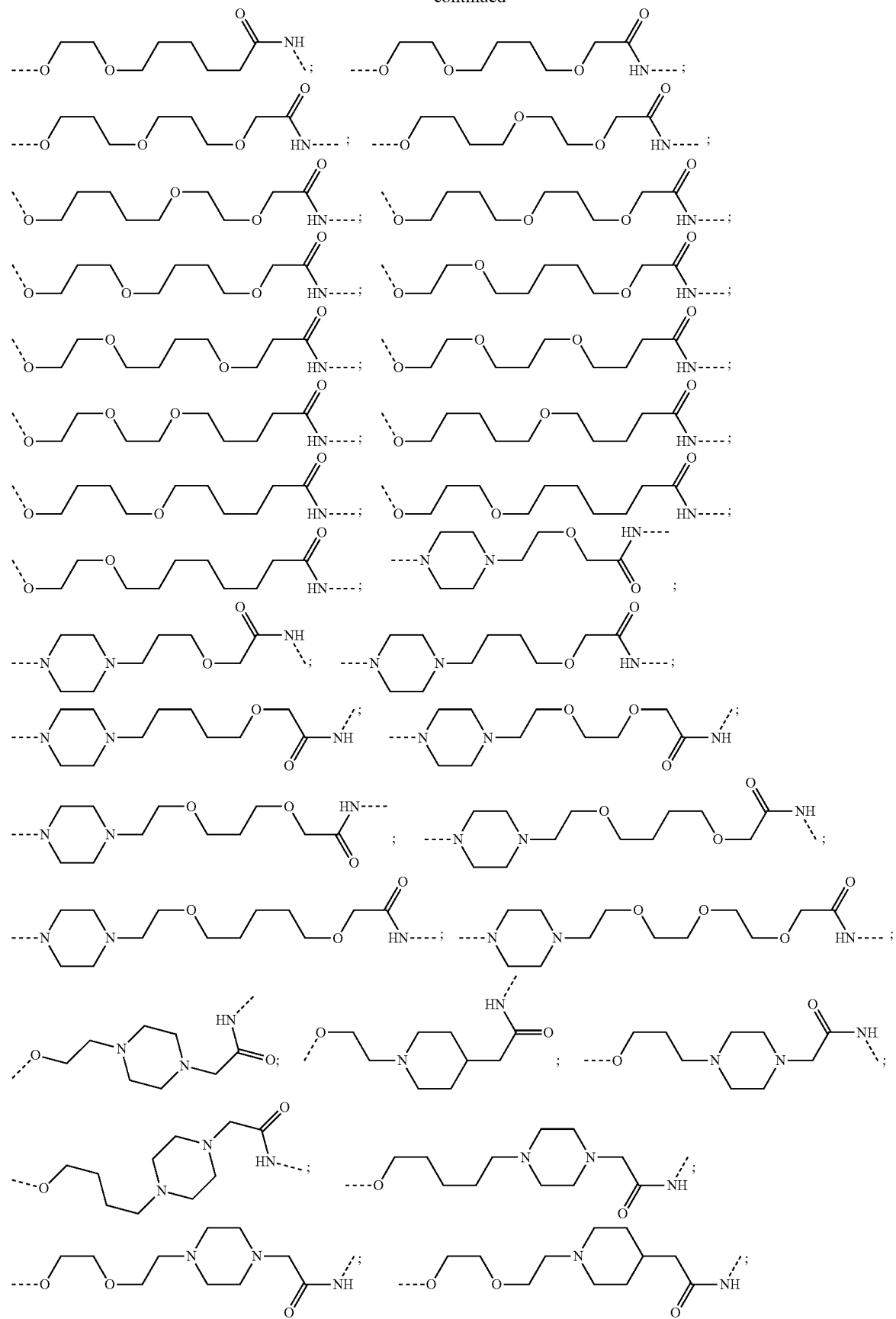

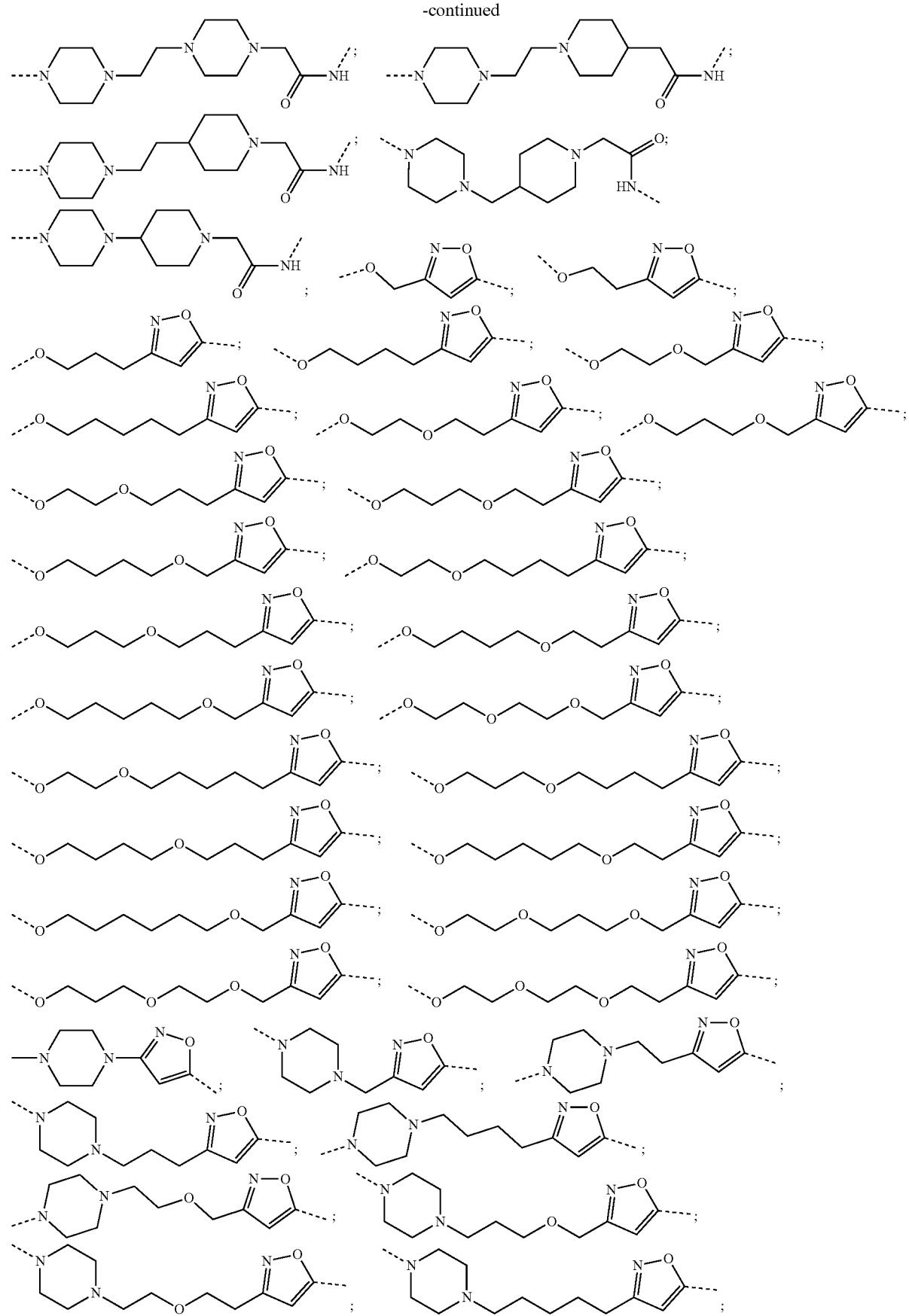

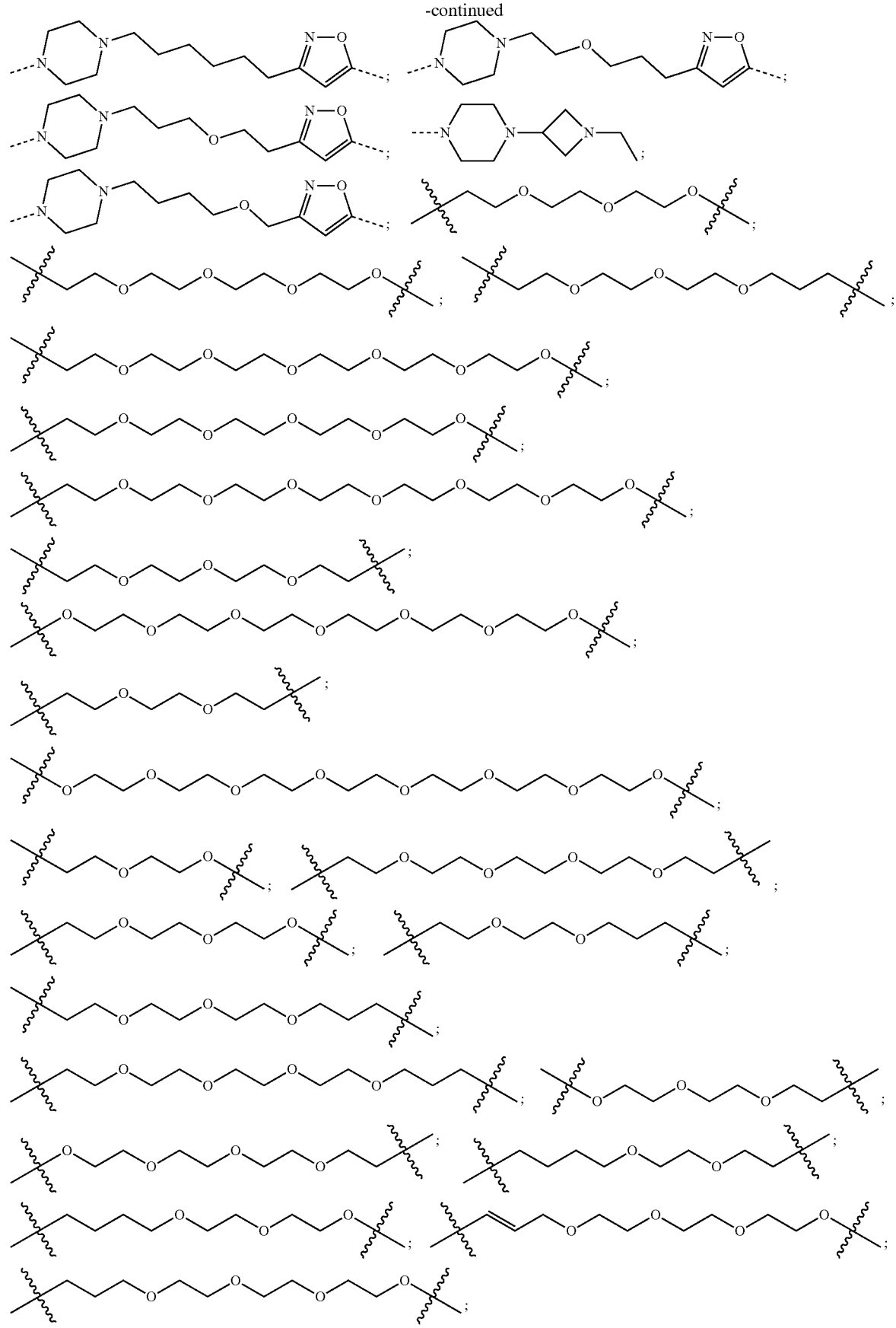

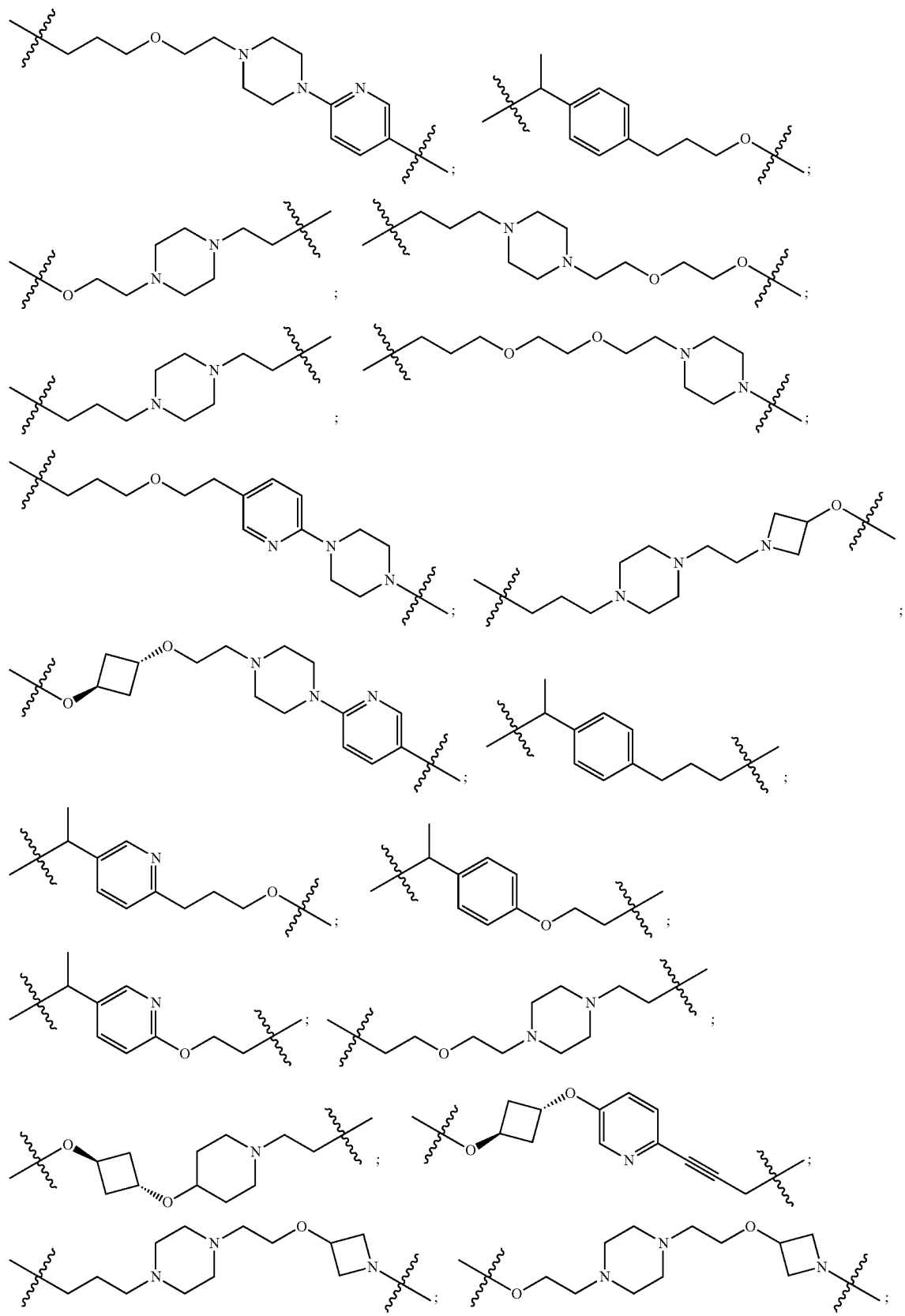

-continued
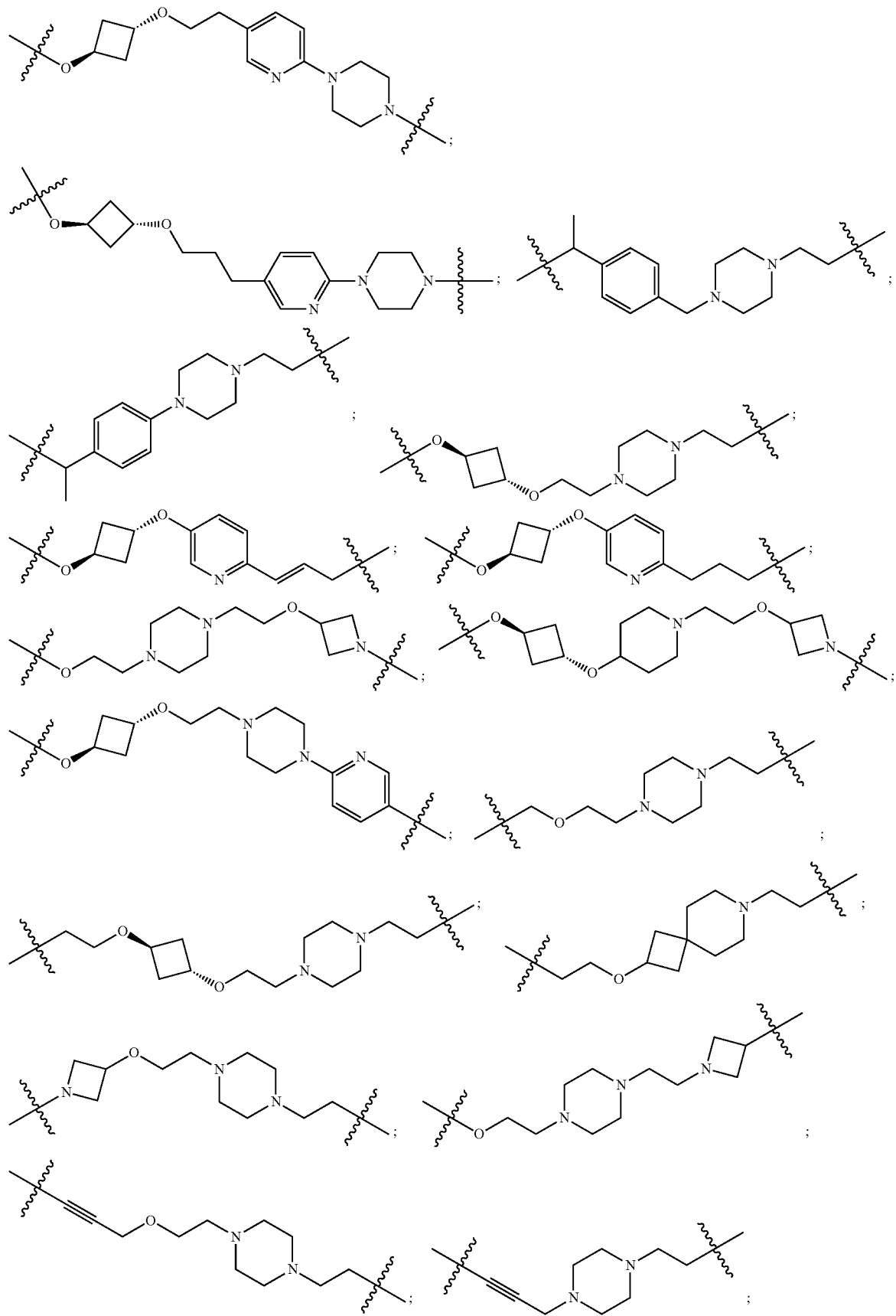

-continued
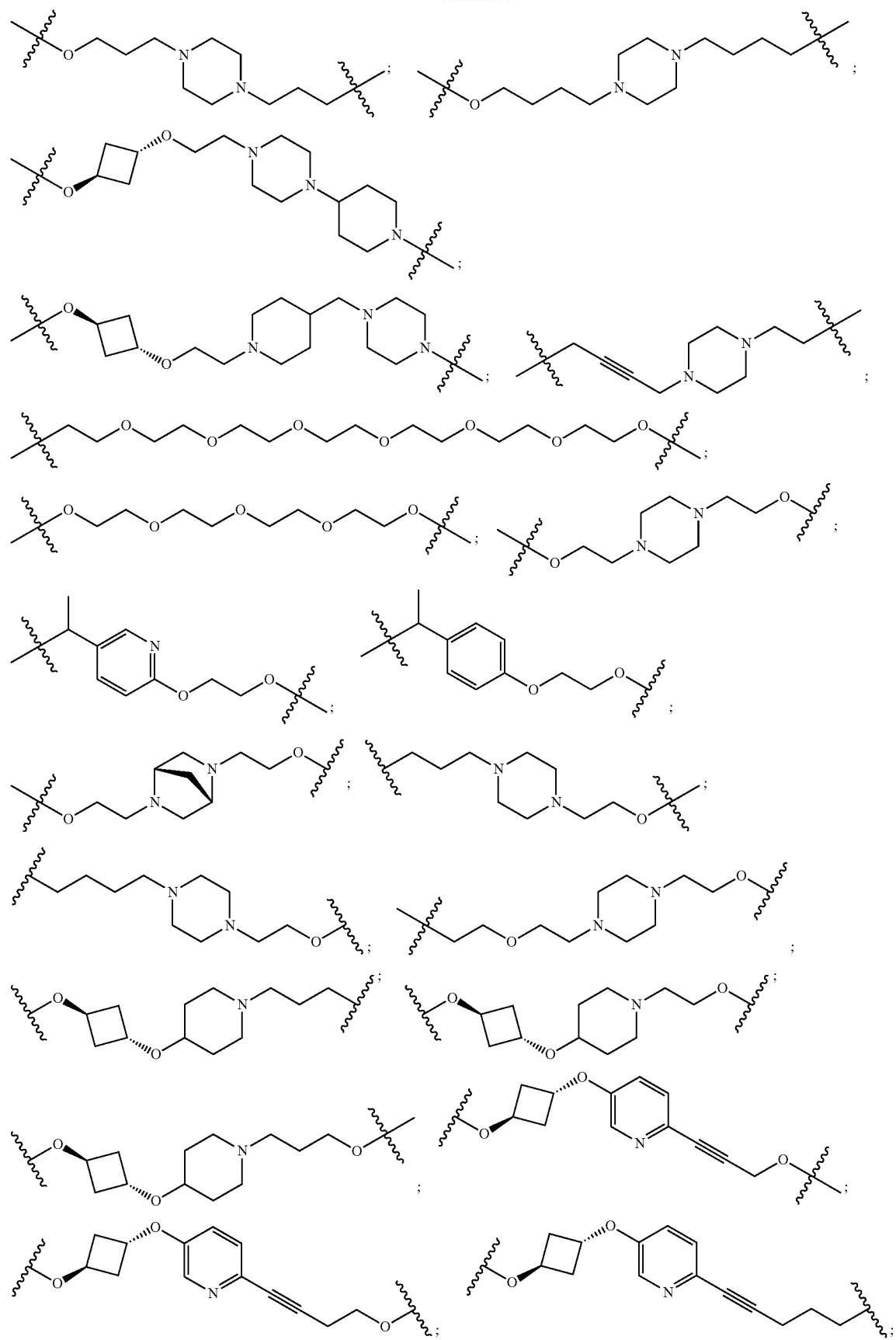

-continued
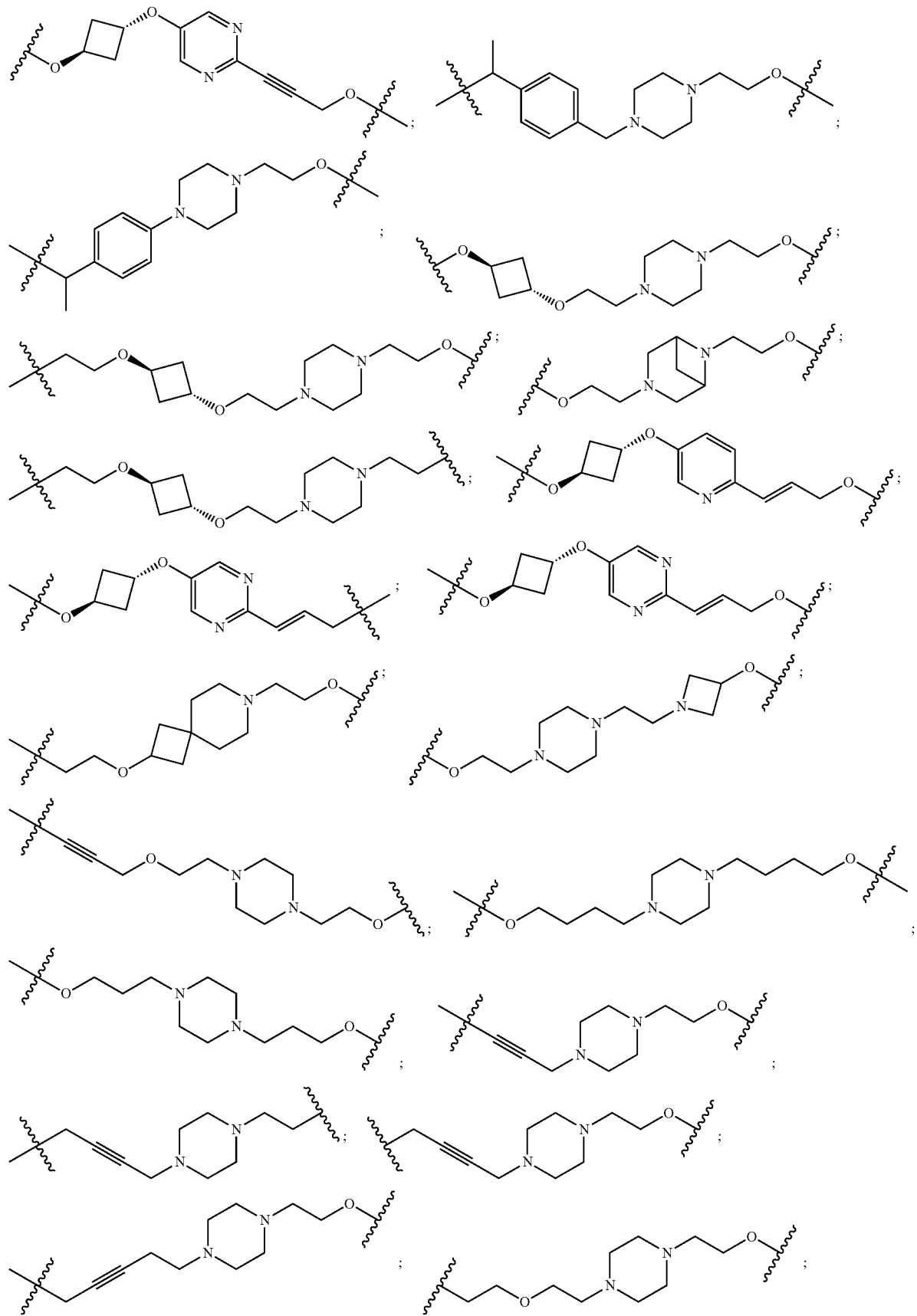

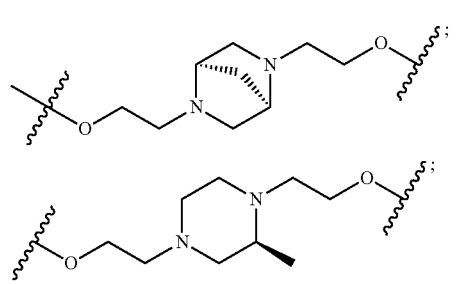
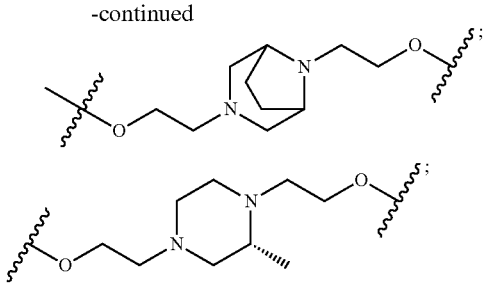
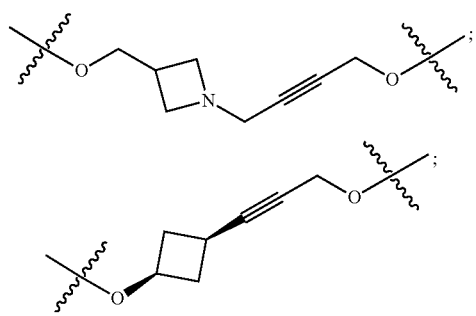
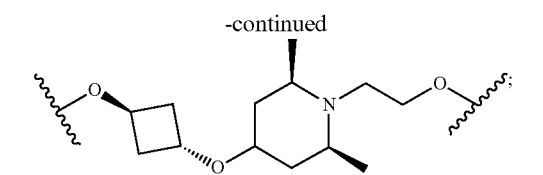
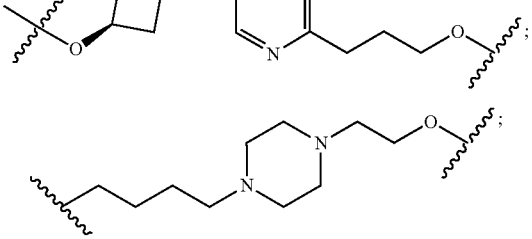
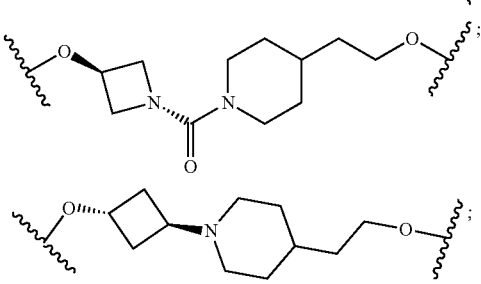
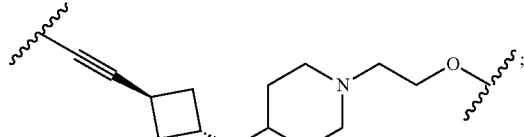
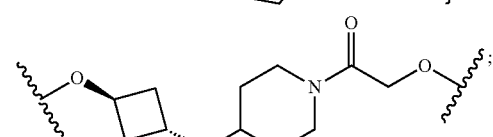
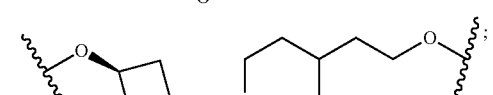
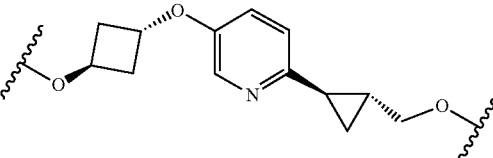
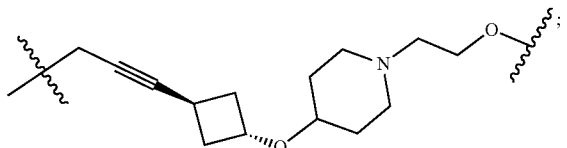
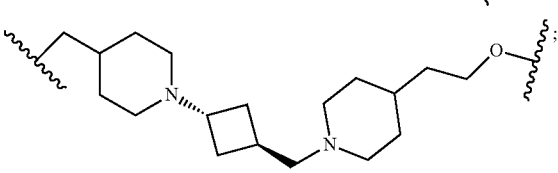
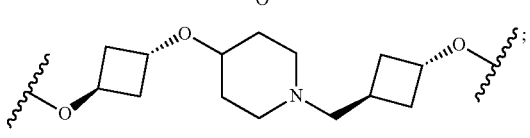
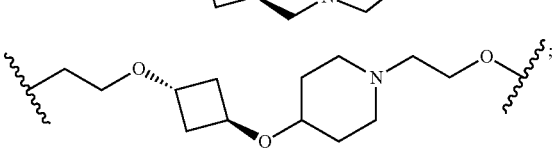

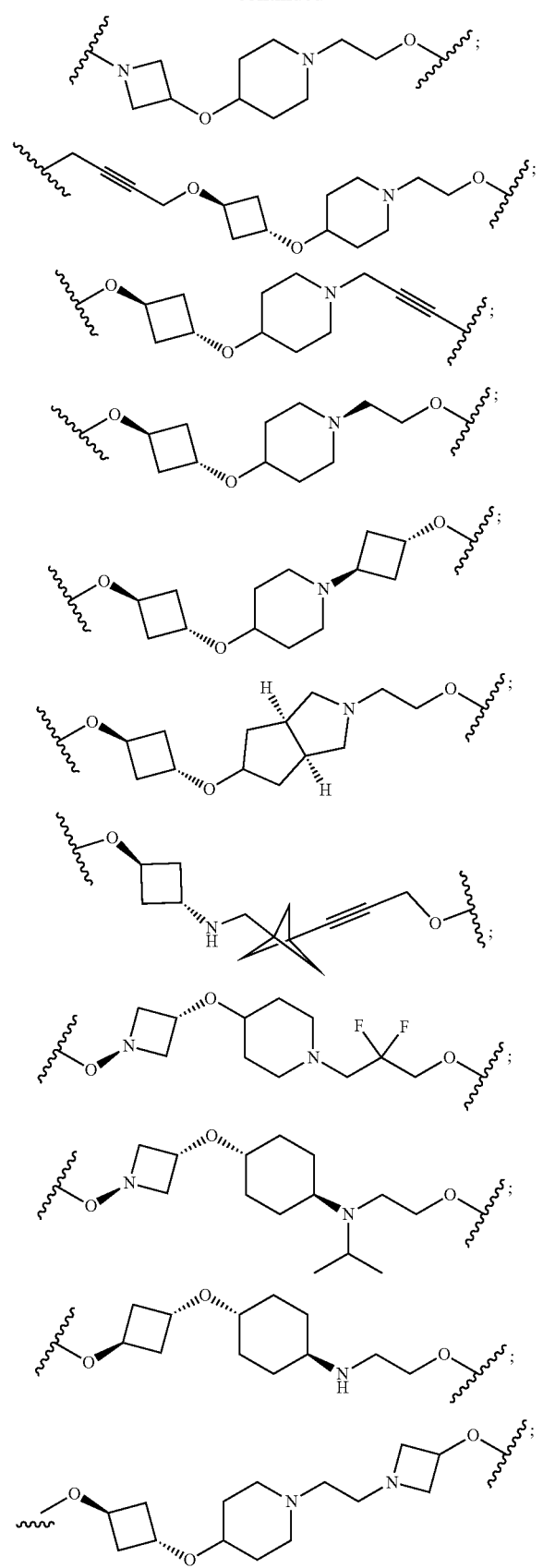
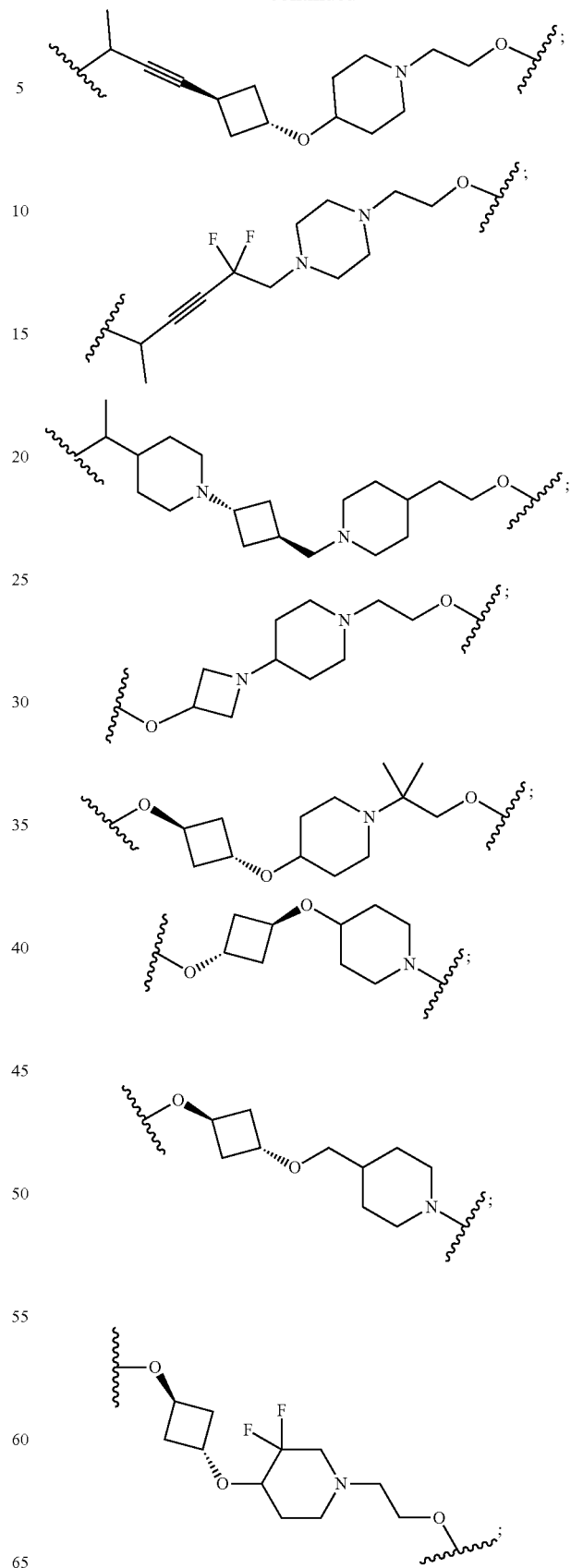

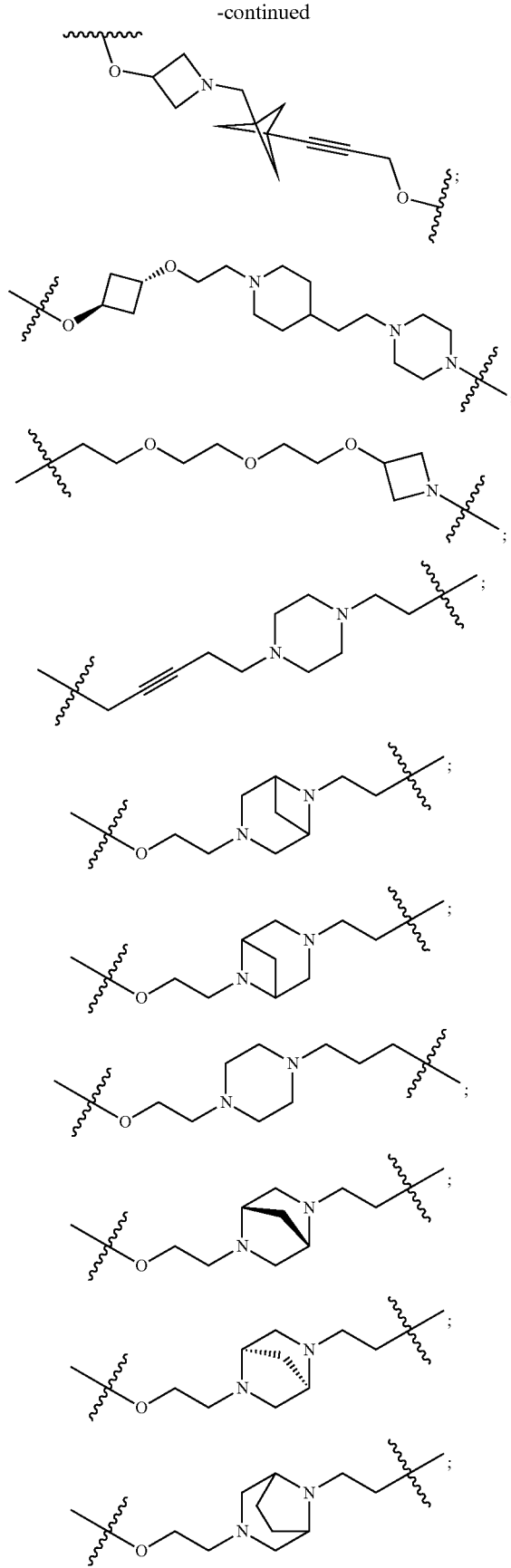
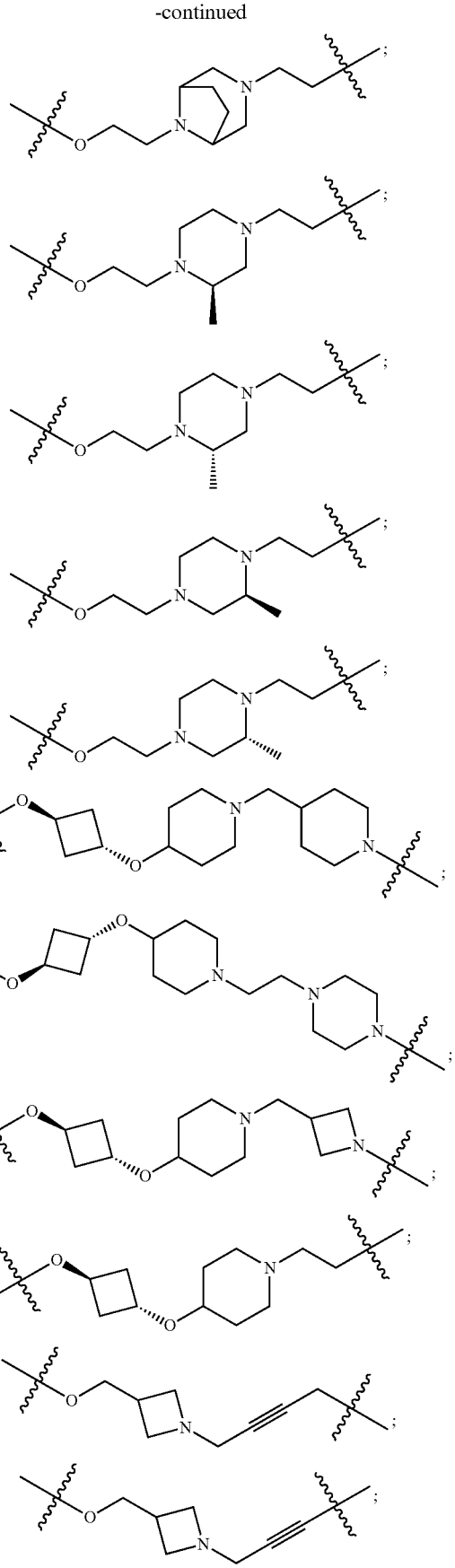

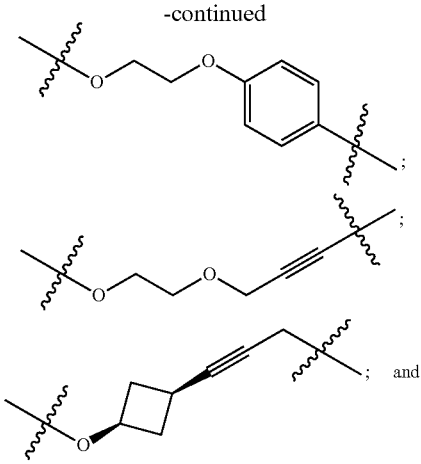

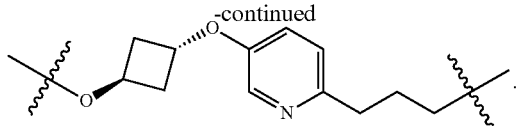

In any aspect or embodiment described herein, the linker unit or linker (L) comprises a group represented by a structure selected from the group consisting of:

—O—(CH$_2$)$_m$—O(CH$_2$)$_n$—O(CH$_2$)$_o$—O(CH$_2$)$_p$—O(CH$_2$)$_q$—O(CH$_2$)$_r$—O(CH$_2$)$_s$—O(CH$_2$)$_t$—;

—O—(CH$_2$)$_m$—O(CH$_2$)$_n$—O(CH$_2$)$_o$—O(CH$_2$)$_p$—O(CH$_2$)$_q$—O(CH$_2$)$_r$—O(CH$_2$)$_s$—O—;

—(CH$_2$)$_m$—O(CH$_2$)$_n$—O(CH$_2$)$_o$—O(CH$_2$)$_p$—O(CH$_2$)$_q$—O(CH$_2$)$_t$—O(CH$_2$)$_s$—O(CH$_2$)$_t$—;

—CH=CH(CH$_2$)$_m$—O(CH$_2$)$_n$—O(CH$_2$)$_o$—O(CH$_2$)$_p$—O(CH$_2$)$_q$—O(CH$_2$)$_r$—O(CH$_2$)$_s$—O(CH$_2$)$_t$—;

—O(CH$_2$)$_n$NCH$_3$C(=O)(CH$_2$)$_m$—;

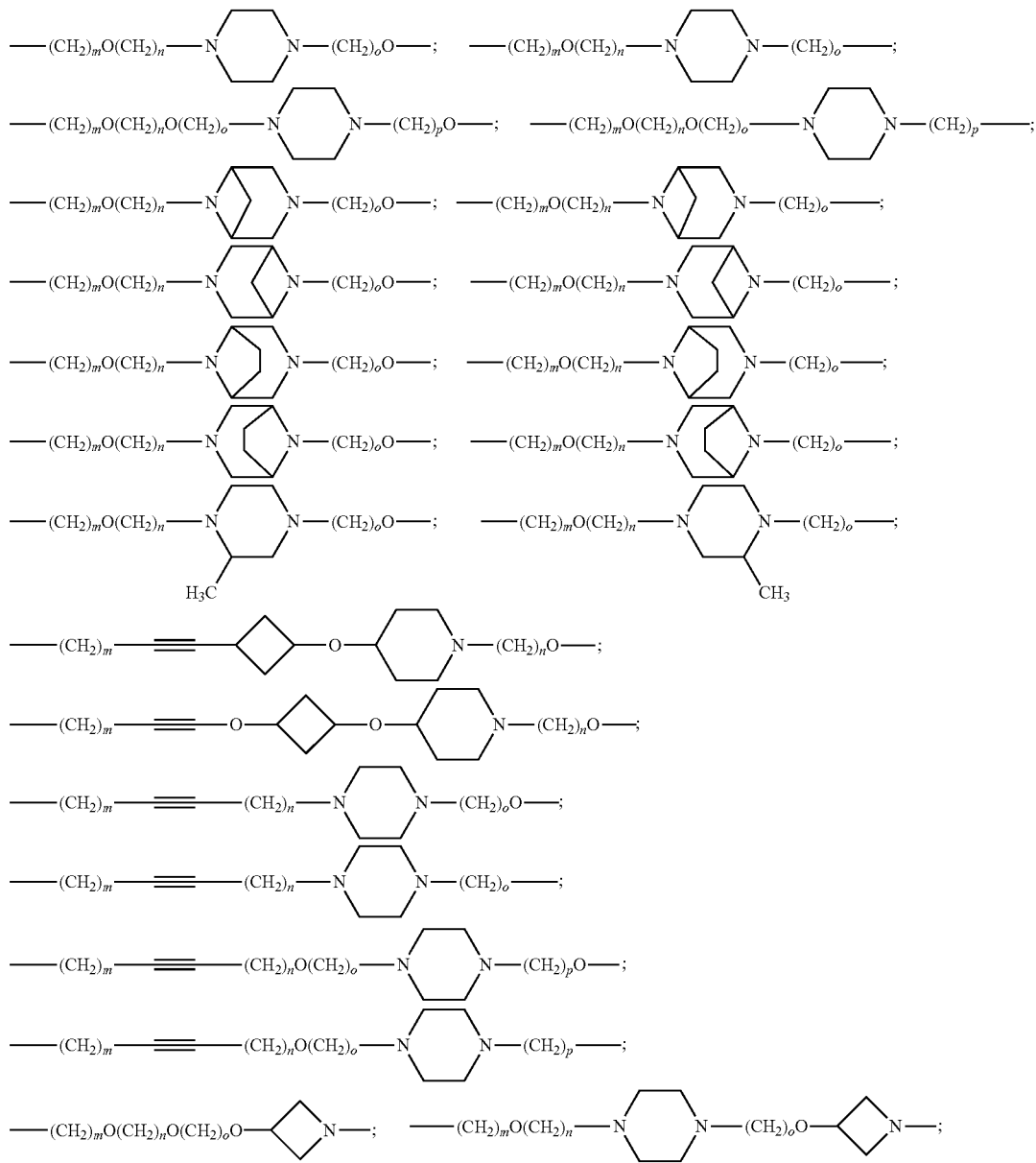

-continued
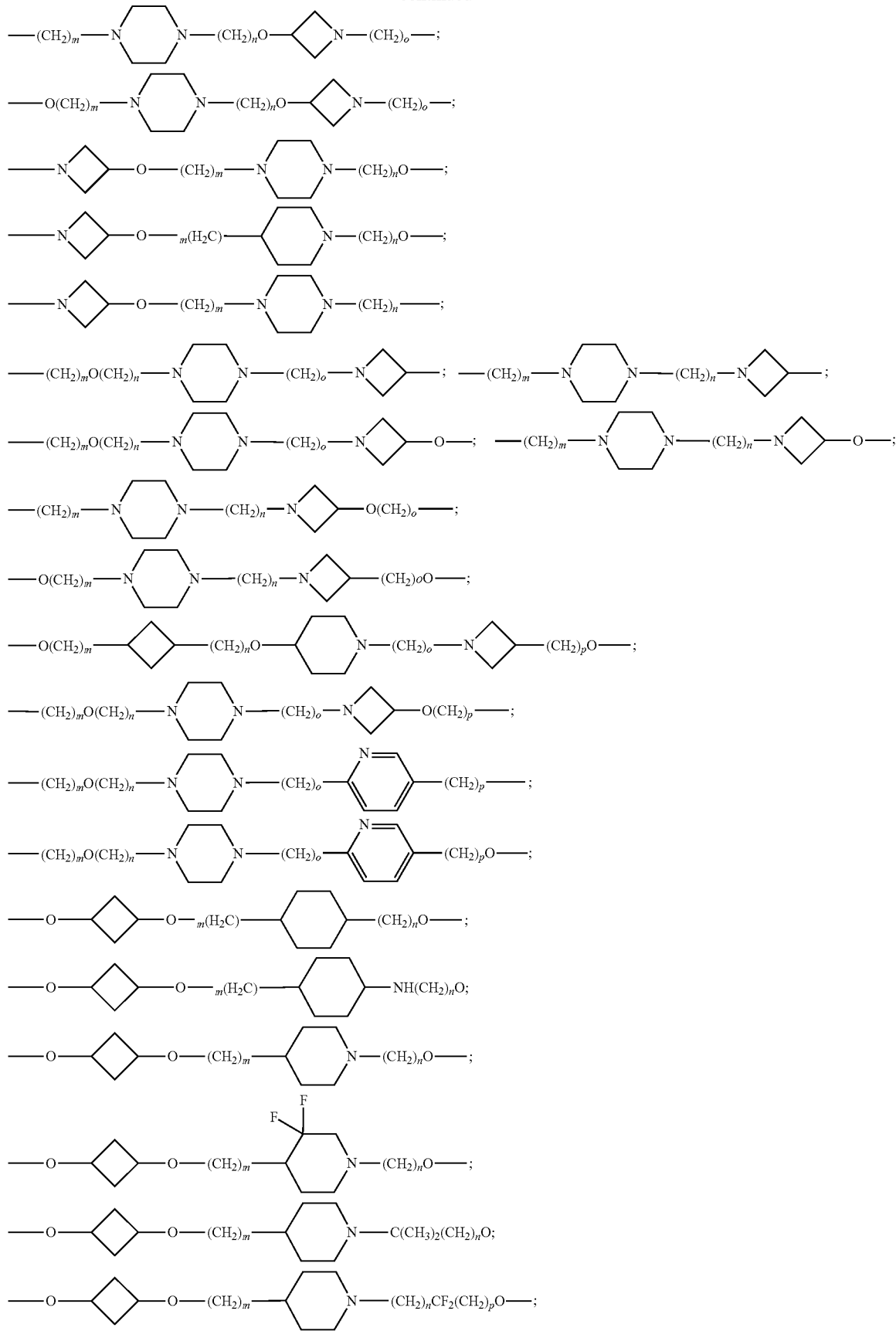

-continued
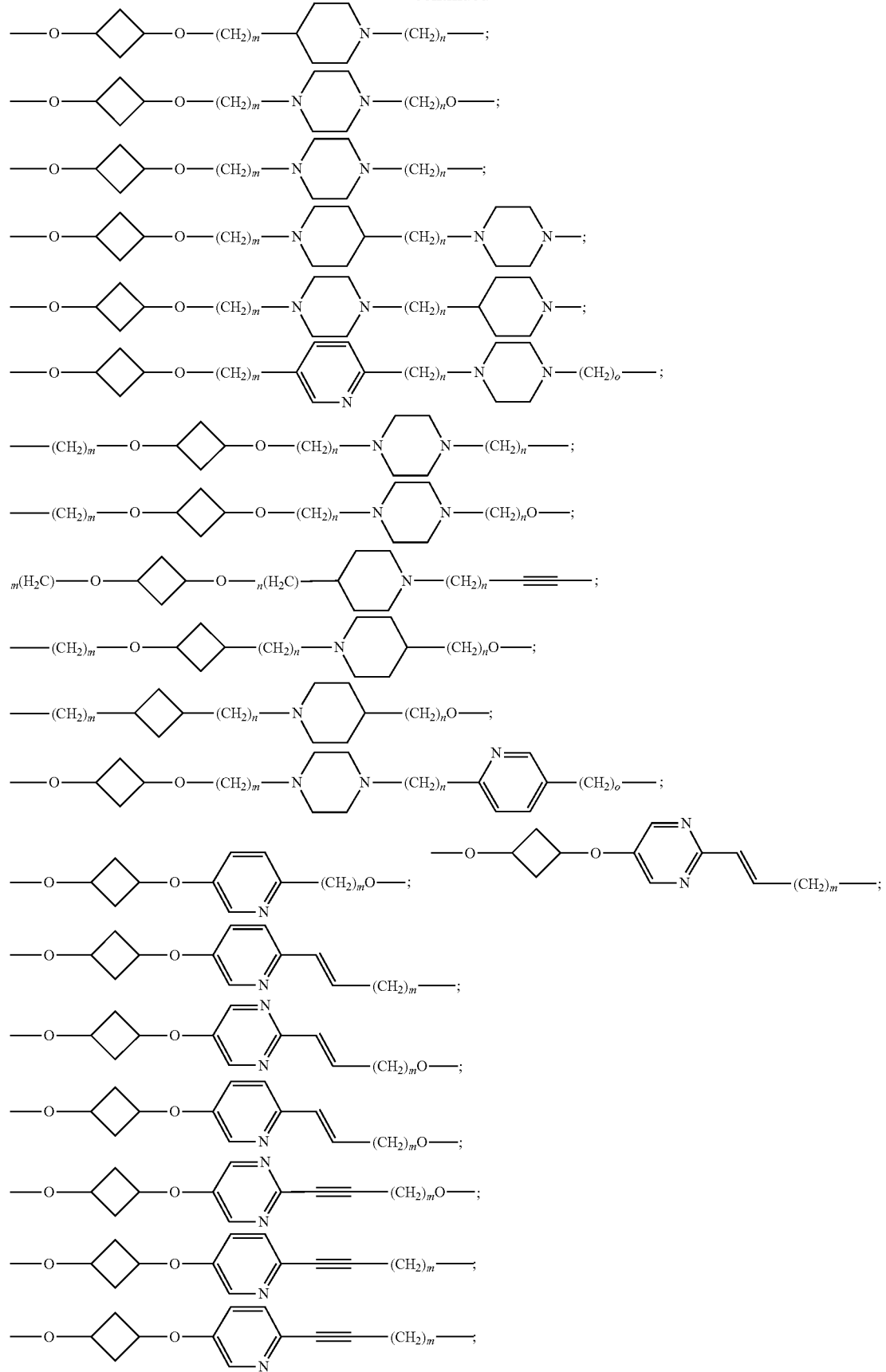

-continued
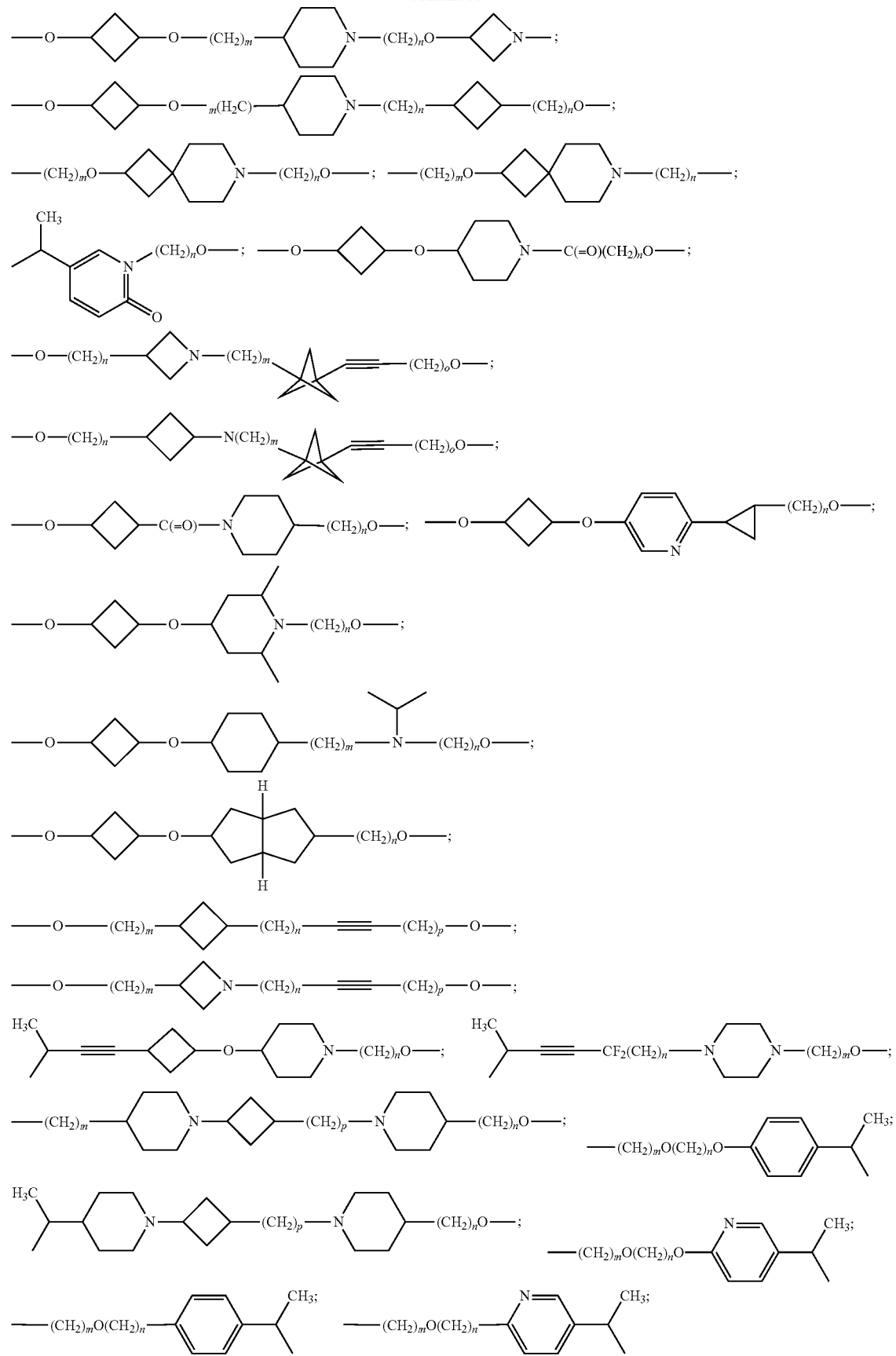

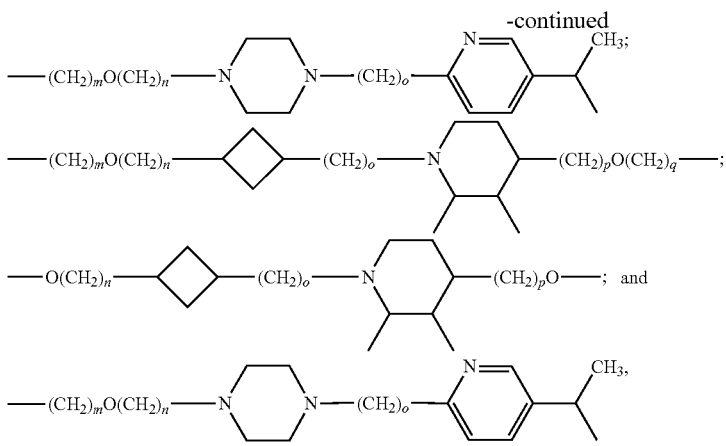

wherein m, n, o, p, q, r, s and t are each independently selected from the integers 0, 1, 2, 3 and 4.

In any aspect or embodiment described herein, the linker (L) is selected from the group consisting of:

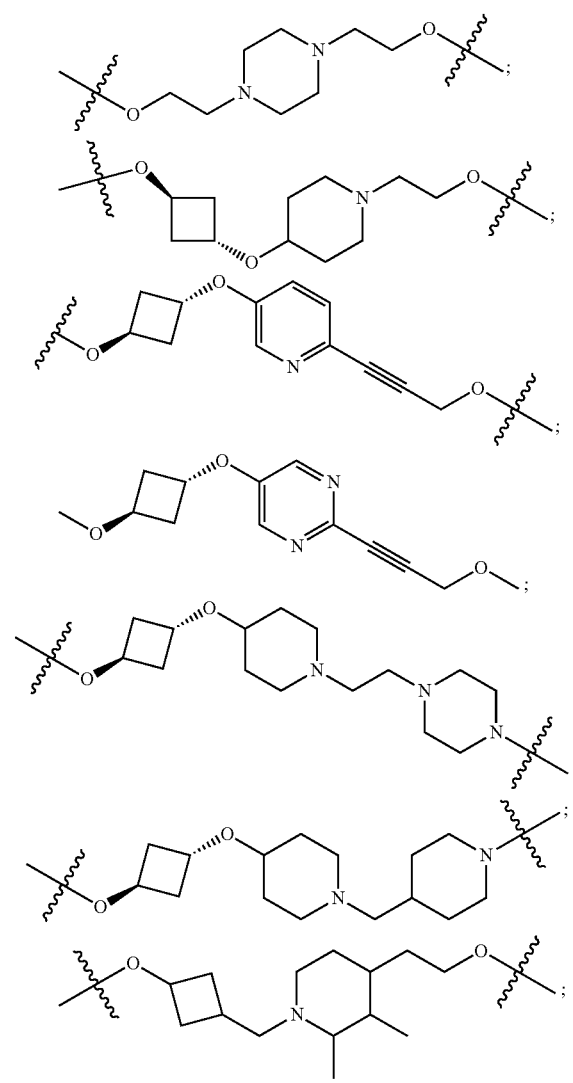

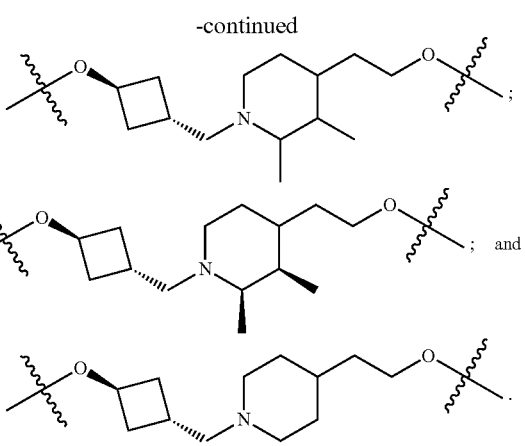

In any aspect or embodiment described herein, the linker (L) comprises a structure selected from, but not limited to the structure shown below, where a dashed line indicates the attachment point to the PTM or ULM moieties:

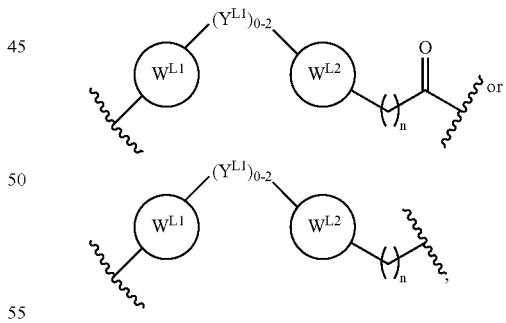

wherein:
$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;
$Y^{L1}$ is each independently a bond, optionally substituted linear or branched $C_1$-$C_6$ alkyl and optionally one or more C atoms are replaced with O; or optionally substituted linear or branched $C_1$-$C_6$ alkoxy;
n is 0-10; and ↘ indicates the attachment point to the PTM or ULM moieties.

In any aspect or embodiment described herein, the linker (L) comprises a structure selected from, but not limited to the structure shown below, where a dashed line indicates the attachment point to the PTM or ULM moieties:

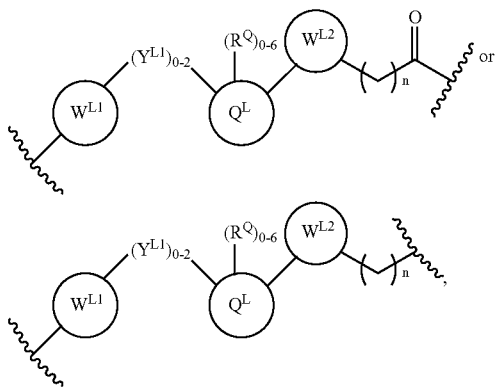

wherein:
- $W^{L1}$ and $W^{L2}$ are each independently absent, aryl, heteroaryl, cyclic, heterocyclic, $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
- $Y^{L1}$ is each independently a bond, $NR^{YL1}$, O, S, $NR^{YL2}$, $CR^{YL1}R^{YL2}$, C=O, C=S, SO, $SO_2$, optionally substituted linear or branched $C_1$-$C_6$ alkyl and optionally one or more C atoms are replaced with O; optionally substituted linear or branched $C_1$-$C_6$ alkoxy;
- $Q^L$ is a 3-6 membered alicyclic or aromatic ring with 0-4 heteroatoms, optionally bridged, optionally substituted with 0-6 $R^Q$, each $R^Q$ is independently H, optionally substitute linear or branched $C_{1-6}$ alkyl (e.g., optionally substituted by 1 or more halo, $C_{1-6}$ alkoxyl), or 2 $R^Q$ groups taken together with the atom they are attached to, form a 3-8 membered ring system containing 0-2 heteroatoms;
- $R^{YL1}$, $R^{YL2}$ are each independently H, OH, optionally substituted linear or branched $C_{1-6}$ alkyl (e.g., optionally substituted by 1 or more halo, $C_{1-6}$ alkoxyl), or $R^1$, $R^2$ together with the atom they are attached to, form a 3-8 membered ring system containing 0-2 heteroatoms;
- n is 0-10; and ↘ indicates the attachment point to the PTM or ULM moieties.

In any aspect or embodiment described herein, the linker group is optionally substituted (poly)ethyleneglycol having between 1 and about 100 ethylene glycol units (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc., ethylene glycol units), between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any aspect or embodiment described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In any aspect or embodiment described herein, the present disclosure is directed to a compound which comprises a PTM group as described above, which binds to a target protein or polypeptide (e.g., BCL6), which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In any aspect or embodiment described herein, the linker group L is a group comprising one or more covalently connected structural units independently selected from the group consisting of:

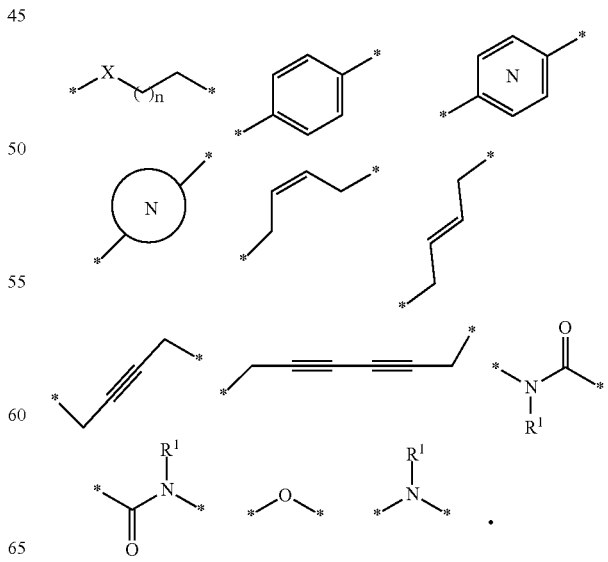

The X is selected from the group consisting of O, N, S, S(O) and SO$_2$; n is integer from 1 to 5; R$^{Z1}$ is hydrogen or alkyl,

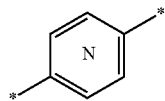

is a mono- or bicyclic aryl or heteroaryl optionally substituted with 1-3 substituents selected from alkyl, halogen, haloalkyl, hydroxy, alkoxy or cyano;

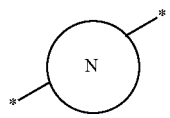

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the grou consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present dislcosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosore. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: Hsp90 inhibitors, kinase inhibitors, BCL6 inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is lymphoma, B-cell non-Hodgkin lymphomas, large B-cell lymphoma, Burkitt's lymphoma, follicular lymphoma, intravascular large B-cell lymphoma, B-cell leukemia, B-cell acute lymphoblastic leukemia, chronic myeloid leukemia, non-small cell lung cancer.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM and/or CLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFRlm, TNFR2, NADPH oxidase, BcllBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, BCL6, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvyl-shikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. The compositions described below exemplify some of the members of the small molecule target proteins. Exemplary protein target moieties according to the present disclosure include, haloalkane halogenase inhibitors, Hsp90 inhibitors, kinase inhibitors, BCL6 inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM is a small molecule that binds BCL6. For example, in any aspect or embodiment described herein, the PTM is represented by the chemical structure PTMI, PTMII, PTMIII, or PTMIV:

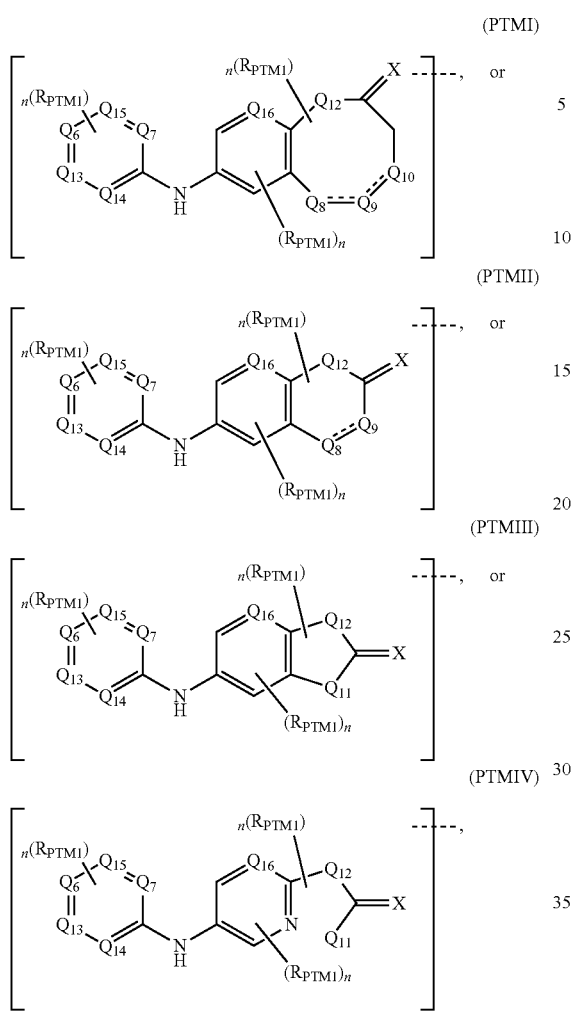

wherein:
each $R_{PTM1}$ is independently: H; halogen (e.g., Cl or F); —CN; —OH; —NO$_2$; —NH$_2$; optionally substituted linear or branched alkyl (e.g., optionally substituted linear or branched C1-C6 alkyl or optionally substituted linear or branched C1-C4 alkyl or C1-C8 alkyl optionally substituted with OH or an isopropyl group); O-optionally substituted linear or branched C1-C4 alkyl; an optionally substituted C1-C4 alkynyl; an optionally substituted C1-C4 alkyne; optionally substituted linear or branched hydroxyalkyl (e.g., optionally substituted linear or branched C1-C7 hydroxyalkyl); optionally substituted alkylcycloalkyl (e.g., includes optionally substituted C1-C6 alkyl, optionally substituted C3-C10 cycloalkyl; or both); optionally substituted alkyl-aryl (e.g., includes an optionally substituted linear or branched C1-C6 alkyl, an optionally substituted 5-10 member heteroaryl, or both); optionally substituted alkyl-heteroaryl (e.g., includes an optionally substituted linear or branched C1-C6 alkyl, an optionally substituted 5-10 member heteroaryl, or both); optionally substituted alkyl-heteroaryl (e.g., includes a C1-C6 alkyl, an optionally substituted 5 or 6 member heteroaryl, optionally substituted with a C1-C4 alkyl; the heteroaryl is selected from oxazol-4-yl, 1,3,4-triazol-2-yl, and imidazole-1-yl; or combination thereor); optionally substituted —NH-alkyl-heteroaryl (e.g., an optionally substituted linear or branched C1-C5 alkyl, an optionally substituted 5-8 member heteroaryl, optionally substituted with a C1-C4 alkyl, N—CH$_2$-pyrazol-4-yl, or a combination thereof); optionally substituted alkoxy (e.g., an optionally substituted linear or branched C1-C6 alkyl or —OCH3); optionally substituted O-heterocyclyl (e.g., includes an optionally substituted 3-12 or 4-7 member heterocyclyl; an optionally substituted heterocycloalkyl; an optionally substituted C$_{3-12}$ monocyclic or bicyclic heterocycloakly; optionally substituted with at least one OH, C1-C5 alkyl (such as a methyl), =O, NH$_2$, or a combination thereof; or a combination thereof); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof); optionally substituted

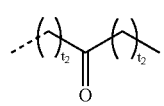

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5);
optionally substituted

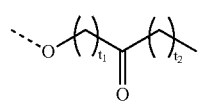

(e.g., optionally substituted with a linear or branched C1-C4 alkyl; —O(CH$_2$)$_u$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and x is independently selected from 1, 2, 3, 4 or 5); optionally substituted

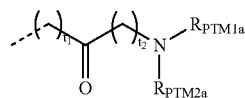

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

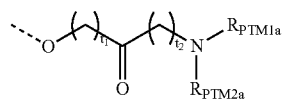

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_u$CH((CH$_2$)$_x$CH$_3$)(CH$_2$)$_w$CO(CH$_2$)$_v$NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted

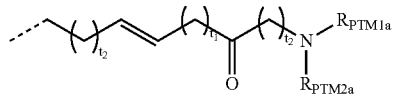

(e.g., optionally substituted with a linear or branched C1-C4 alkyl; —(CH$_2$)$_u$CHCH(CH$_2$)$_w$CO(CH$_2$)$_v$NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

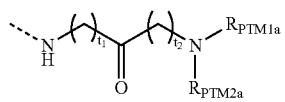

(e.g., optionally substituted with a linear or branched C1-C4 alkyl; —NH—(CH$_2$)$_u$CO(CH$_2$)$_v$NR$_{PTM1a}$R$_{PTM2a}$ or —NH—CH$_2$CONR$_{PTM1a}$R$_{PTM2a}$, wherein each u and v is independently selected from 1, 2, 3, 4 or 5); fluoroalkoxy (e.g., a mono-, bi- and/or tri-fluoroalkoxy); optionally substituted monocylic or bicyclic cyclocalkyl (e.g., an optionally substituted 3-12 member cycloalkyl; optionally substituted with at least one of OH, =O, liniear or branched C1-C6 alkyl (such as a methyl, ethyl, or butyl), or NH$_2$; or a combination thereof); optionally substituted hydroxycycloalkyl; optionally substituted aryl (e.g., an optionally substitute C5-C10 aryl, an optionally substituted 5-7 member aryl; optionally substituted with at least one halogen or C1-C3 alkyl (e.g, methyl or ethyl); or a combination thereof), optionally substituted heteroaryl (e.g., an optionally substituted 5-10 or member heteroaryl, an optionally substituted 5-7 member heteroaryl; an optionally substituted 5-member heteroaryl; optionally substituted with at least one halogen or C1-C3 alkyl (e.g, methyl or ethyl); or a combination thereof) optionally linked to Q$_6$, Q$_7$, Q$_8$, Q$_9$, Q$_{10}$, Q$_{11}$, Q$_{12}$, Q$_{13}$, Q$_{14}$, or Q$_{15}$ via a C or N-atom of the heteroaryl (e.g., at least one of optionally linked to Q$_{16}$, optionally linked via an optionally substituted —(CH$_2$)$_u$O(CH$_2$)$_v$O(CH$_2$)$_x$—, or a combination thereof); optionally substituted monocyclic or bicyclic heterocyclyl (e.g., an optionally substituted 3-12 member heterocyclyl; an C3-C12 monocylcic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with OH, a linear or branched C1-C5 alkyl (a methyl, ethyl, or butyl group) or NH$_2$) optionally linked to Q$_6$, Q$_7$, Q$_8$, Q$_9$, Q$_{10}$, Q$_{11}$, Q$_{12}$, Q$_{13}$, Q$_{14}$, or Q$_{15}$ via a C or N atom of the heterocyclyl (e.g., at least one of optionally linked to Q$_{16}$, optionally linked via an optionally substituted —(CH$_2$)$_u$O(CH$_2$)$_v$O(CH$_2$)$_x$—, or both);

each t$_1$ is independently selected from 1, 2, 3, 4, or 5;
each t$_2$ is independently is independently selected from 0, 1, 2, 3, 4, or 5;
each R$_{PTM1a}$ and R$_{PTM2a}$ are independently H, optionally substituted C1-C4 alkyl (e.g., a CH$_3$ or CH$_2$CH$_3$), optionally substituted C1-C4 alkoxy (e.g., —OCH$_2$ or —CH$_2$CH$_3$), CH$_2$OCH$_3$ or R$_{PTM1a}$ and R$_{PTM2a}$ are joined together form a 3-10 member ring;

Q$_6$, Q$_7$, Q$_8$, Q$_9$, Q$_{10}$, Q$_{11}$, Q$_{12}$, Q$_{13}$, Q$_{14}$, and Q$_{15}$ are each independently N, O, or C, each optionally substituted with one or more independently selected R$_{PTM1}$ (e.g., 1, 2, or 3 independently selected R$_{PTM1}$, depending upon valency);

Q$_{16}$ is CH;

X is O, S, or CH$_2$;

 is a single bond or a double bond;

n is an integer from 0 to 10; and

⸍⸍ of the PTM indicates the point of attachment with a chemical linker group or a ULM.

In any aspect or embodiment described herein, at least one R$_{PMT1}$ of PTMI, PTMII, PTMIII, PTMIV, or the associated location of other PTM structures described herein is modified to be covalently linked to a linker group (L) or a ULM. In any aspect or embodiment described herein, at least one of Q$_6$-Q$_{15}$ of PTMI, PTMII, PTMIII, PTMIV, or the associated location of other PTM structures described herein is modified to be covalently linked to a chemical linker group (L) or a ULM.

In any aspect or embodiment described herein, the X of the PTM (e.g., PTMI, PTMII, PTMIII, PTMIV, or the associated location of other PTM structures described herein) is O.

In any aspect or embodiment described herein, the PTM is selected from:

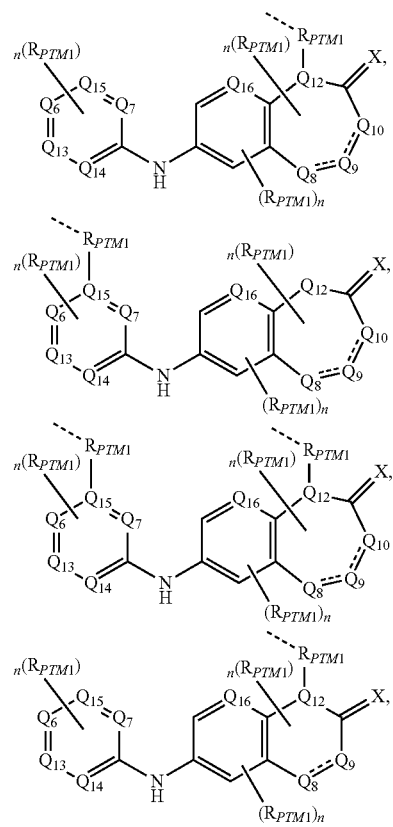

381
-continued
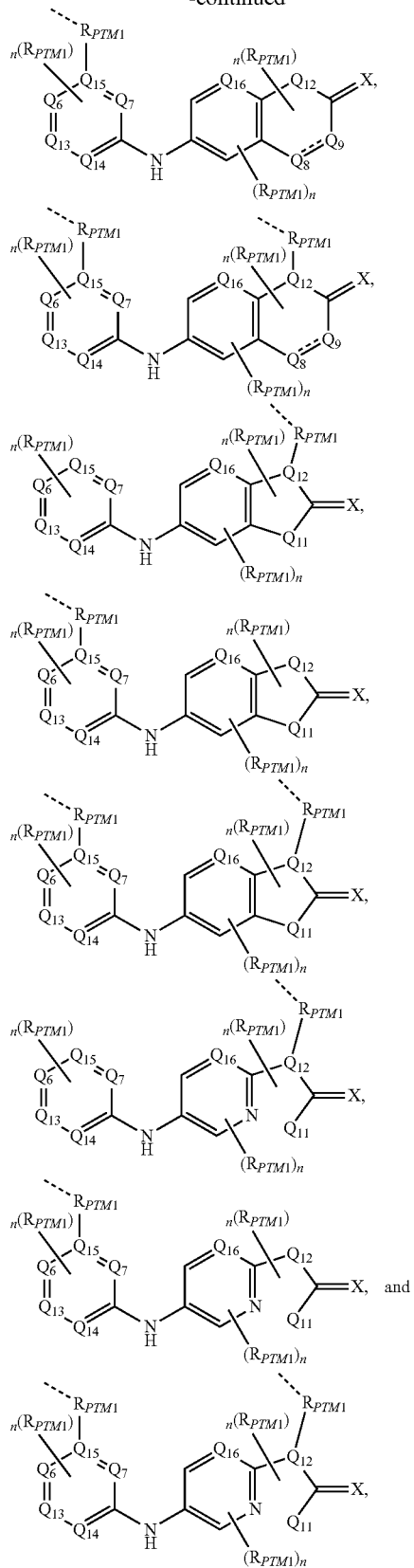
wherein the ⌐⌐ of the PTM indicates the point of attachment with a chemical linker group (L) or a ULM.
382
In any aspect or embodiment described herein, the PTM is selected from:
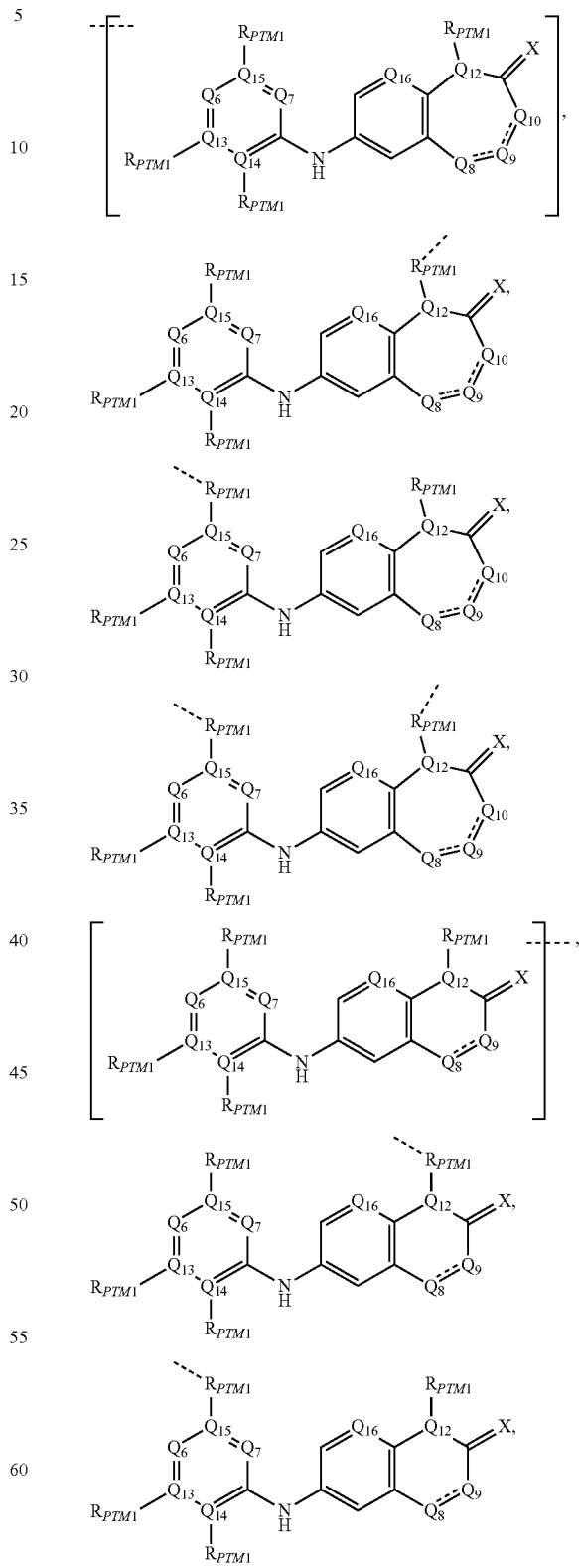

-continued
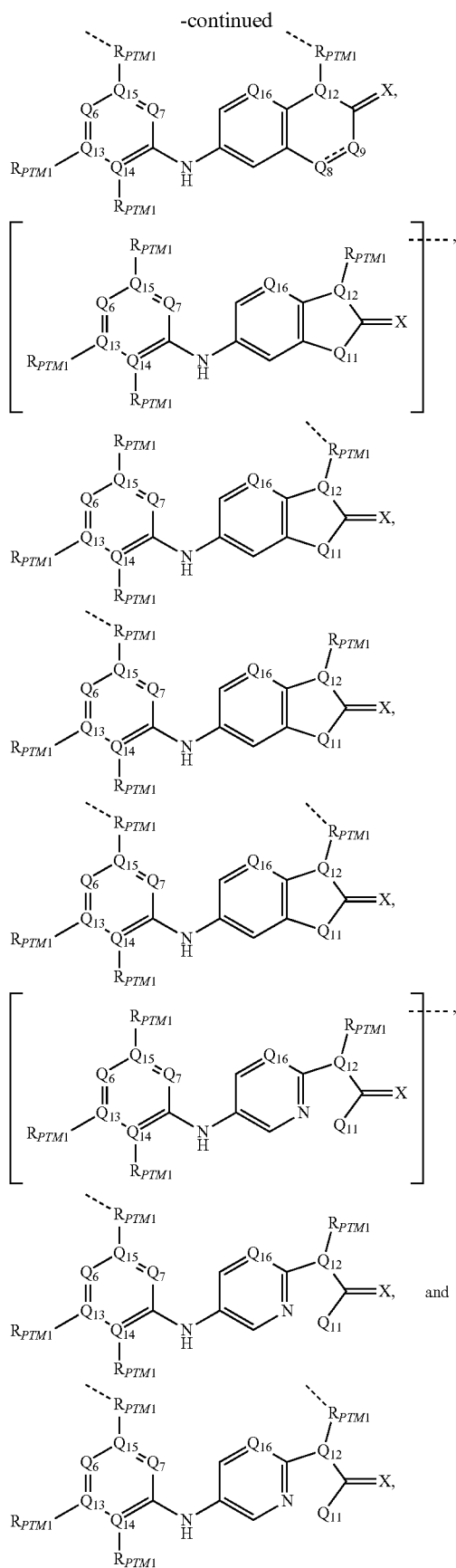
wherein the ⌇ of the PTM indicates the point of attachment with a chemical linker group (L) or a ULM.
In any aspect or embodiment described herein, at least one $R_{PTM1}$ is selected from
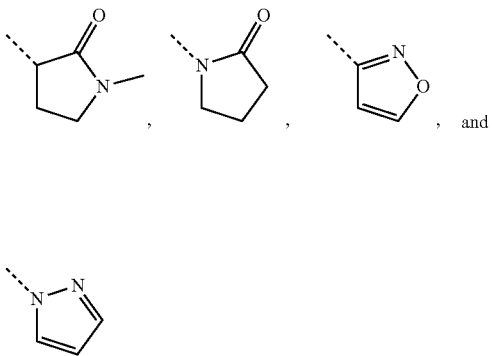
, and

.
In any aspect or embodiment described herein, the PTM has the chemical structure:
(PTMIa1)
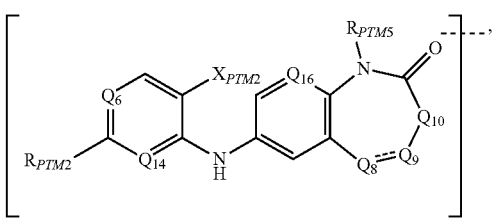
(PTMIa2)
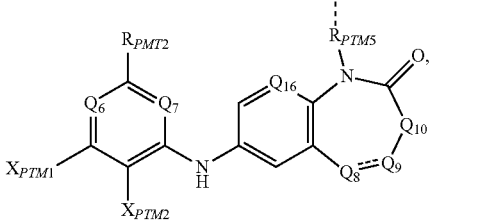
(PTMIb1)
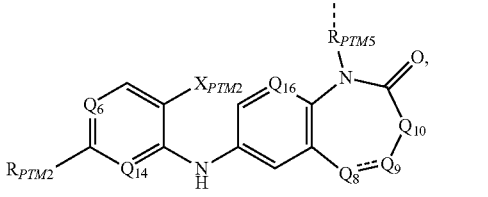
(PTMIb2)

(PTMIc1)
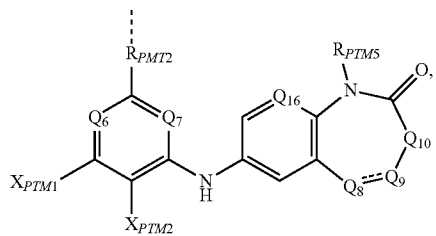
(PTMIc2)
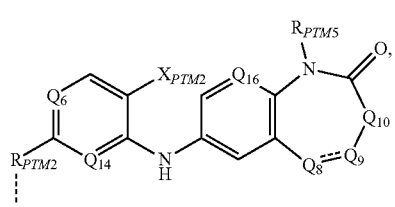
(PTMId1)
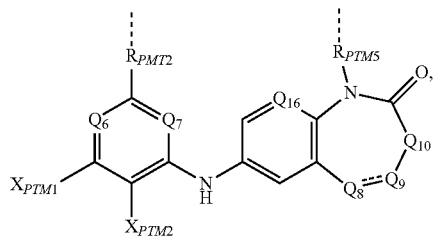
(PTMId2)
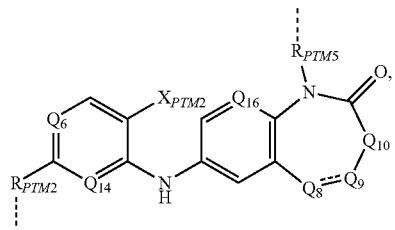
(PTMIIa1)

(PTMIIa2)

(PTMIIa3)
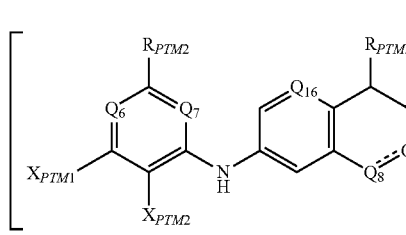
(PTMIIb1)
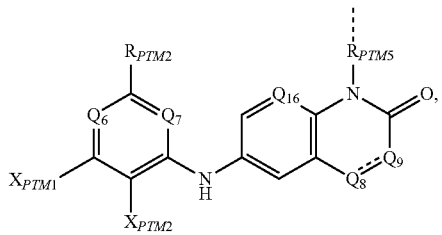
(PTMIIb2)
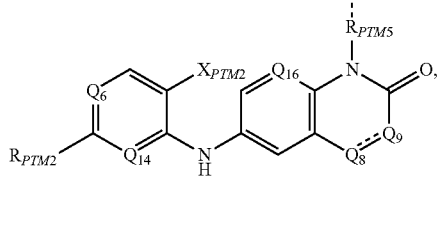
(PTMIIb3)
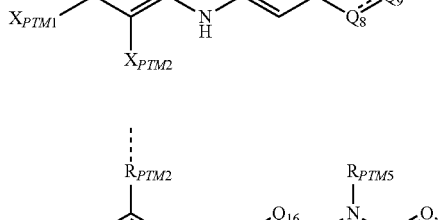
(PTMIIc1)
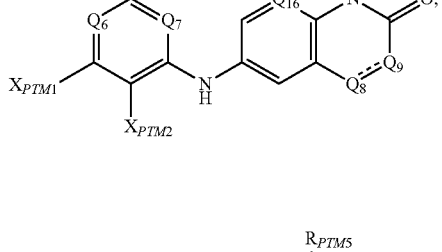
(PTMIIc2)
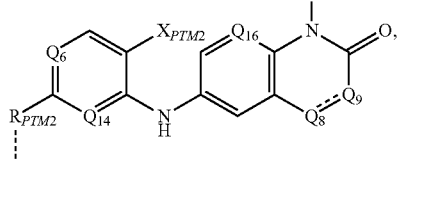
(PTMIIc3)
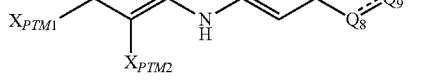

(PTMIId1)
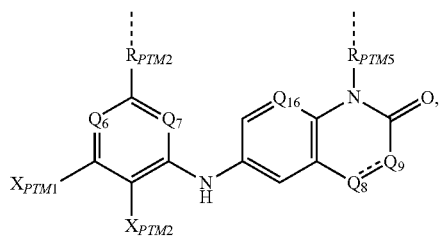
(PTMIId2)
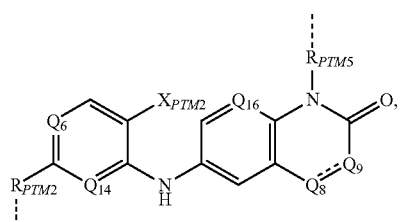
(PTMIId3)
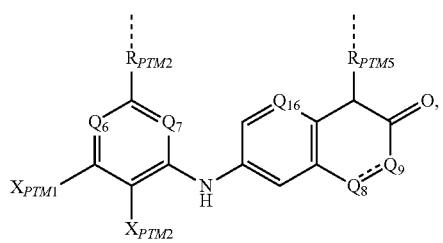
(PTMIIIa1)
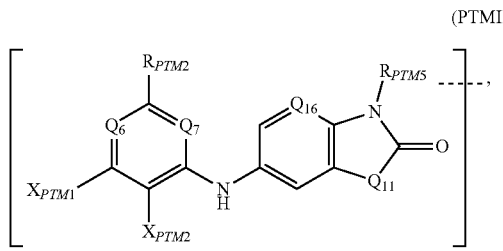
(PTMIIIa2)
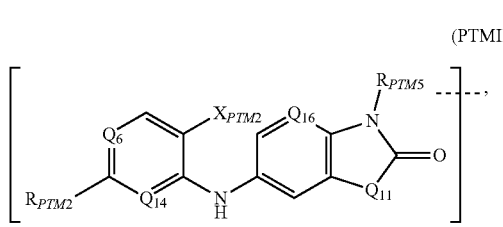
(PTMIIIb1)
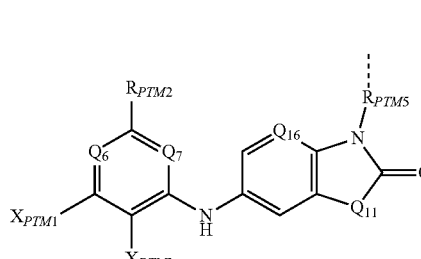
(PTMIIIb2)
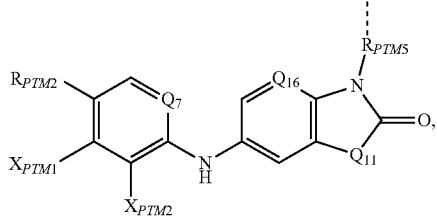
(PTMIIIb3)
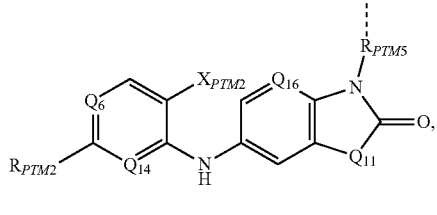
(PTMIIIc1)
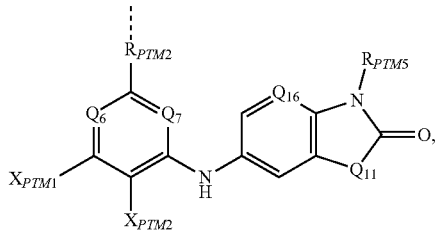
(PTMIIIc2)
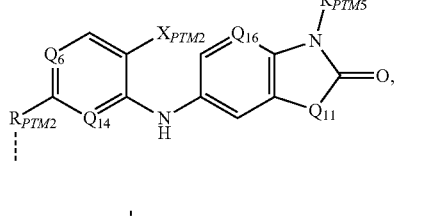
(PTMIIId1)
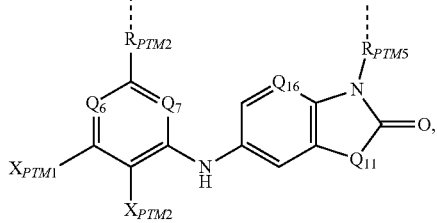
(PTMIIId2)
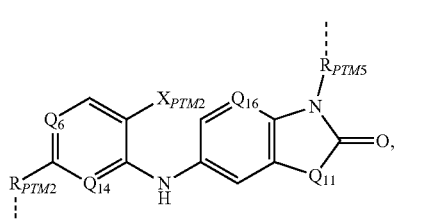
(PTMIVa1)
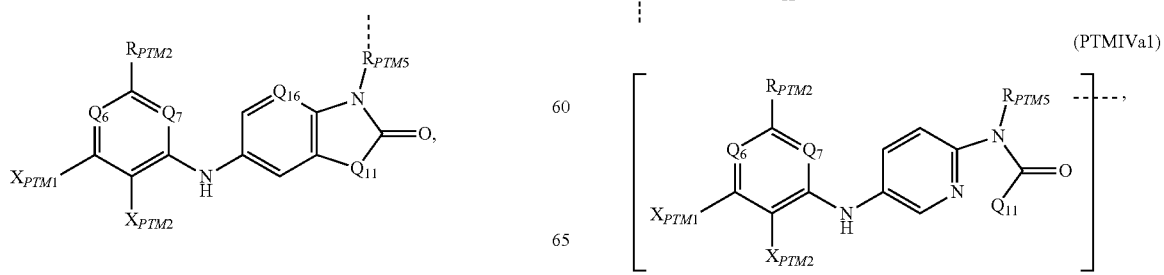

-continued

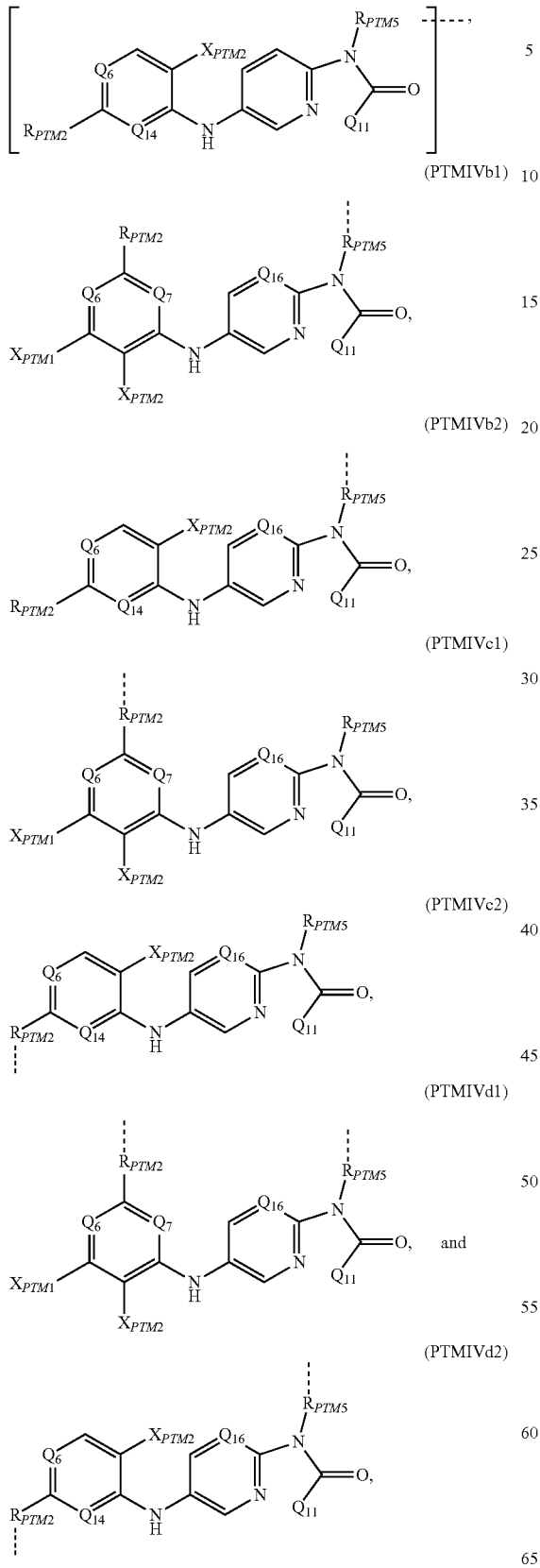

(PTMIVa2)
(PTMIVb1)
(PTMIVb2)
(PTMIVc1)
(PTMIVc2)
(PTMIVd1)
(PTMIVd2)

wherein:
$R_{PTM5}$ is H, optionally substituted linear or branched alkyl (e.g., optionally substituted linear or branched C1-C6 alkyl or isopropyl group or C1-C4 alkyl-NH(C1-C3 alkyl) or C1-C4 alkyl-N(C1-C3 alkyl)$_2$), optionally substituted -alkyl-aryl (e.g., optionally substituted C1-C6 alkyl, optionally substituted C5-C10 aryl, or both), optionally substituted -alkyl-heteroaryl (e.g., optionally substituted $C_1$-$C_6$ alkyl, optionally substituted C5-C10 heteroaryl, or both), optionally substituted aryl (e.g., optionally substituted C5-C10 aryl), optionally substituted heteroaryl (e.g., optionally substituted C5-C10 heteroaryl), optionally substituted cycloalkyl (e.g., optionally substituted C3-C10 cyclalkyl), optionally substituted -alkyl-cycloalkyl (e.g., optionally substituted C1-C6 alkyl, optionally substituted C3-C10 cycloalkyl, or both), optionally substitute heterocyclyl (e.g., optionally substituted C3-C10 heterocyclyl);

$Q_6$ is N, CH, C(NO$_2$), or C(CN);
$Q_7$ and $Q_{14}$ are each independently N or CH;
$X_{PTM1}$ is H or F;
$X_{PTM2}$ is H, Cl, F, or CN;

 of $Q_8$ and $Q_9$ is a single bond, a double bond, or absent when $Q_8$ is absent;

when $Q_8$ is absent,  is absent and $Q_{10}$ is absent;
when $Q_8$ and $Q_9$ are connected by a single bond:
  $Q_8$ is CH$_2$, O, CH(R$_{PTM3}$), N(R$_{PTM3}$), or N(CH$_3$); and
  $Q_9$ is CH$_2$, O, CH(R$_{PTM3}$), N(R$_{PTM3}$), N(CH$_3$), N(CH$_2$CH$_2$CONHCH$_3$), or N(CH$_2$CH$_2$COCH$_3$);
when $Q_8$ and $Q_9$ are connected by a double bond:
  $Q_8$ is CH, C(R$_{PTM3}$), N(R$_{PTM3}$), N, or optionally substituted C(NH-alkyl-heteroaryl) (such as a optionally substituted C1-C5 alky, an optionally substituted 5-7 member heteroaryl, or both);
  $Q_9$ is CH, C(R$_{PTM3}$), N, or N(R$_{PTM3}$); and
$R_{PTM3}$ is: —OH; optionally substitute linear or branched alkyl, optionally substituted alkoxy (e.g., optionally substituted with a linear or branched C1-C4 alkyl or —OCH$_3$); optionally substituted

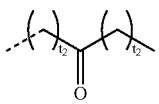

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5); optionally substituted

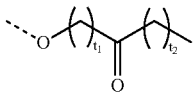

(e.g., optionally substituted with a linear or branched C1-C4 alkyl; —O(CH$_2$)$_u$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and x is independently selected from 1, 2, 3, 4 or 5); optionally substituted

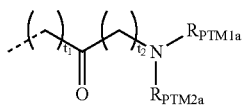

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

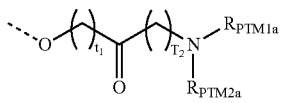

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_u$CH((CH$_2$)$_x$CH$_3$)(CH$_2$)$_w$CO(CH$_2$)$_v$NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted

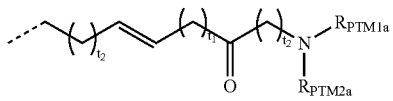

(e.g., optionally substituted with a linear or branched C1-C4 alkyl; —(CH$_2$)$_u$CHCH(CH$_2$)$_w$CO(CH$_2$)$_v$NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

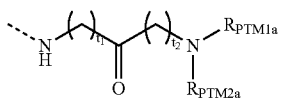

(e.g., optionally substituted with a linear or branched C1-C4 alkyl; —NH—(CH$_2$)$_u$CO(CH$_2$)$_v$NR$_{PTM1a}$R$_{PTM2a}$ or —NH—CH$_2$CONR$_{PTM1a}$R$_{PTM2a}$, wherein each u and v is independently selected from 1, 2, 3, 4 or 5); optionally substituted -alkyl-heteroaryl (e.g, optionally substituted with a C1-C4 alkyl; —(CH$_2$)$_{t2}$-optionally substituted 5 or 6 member heteroaryl; the heteroaryl is selected from oxazol-4-yl, 1,3,4-triazol-2-yl, and imidazole-1-yl; and combination thereos); optionally substituted —NH-alkyl-heteroaryl (e.g., optionally substituted with a C1-C4 alkyl, or combination thereof, —NH—(CH$_2$)$_{t2}$-optionally substituted 5 or 6 member heteroaryl, N—CH$_2$-pyrazol-4-yl); optionally substituted alkyl-cycloalkyl or alkyl-heterocycloalkyl (e.g., optionally substituted with a C1-C4 alkyl, —(CH$_2$)$_{t2}$-an optionally substituted 3-6 member cycloalkyl or heterocycloalkyl); optionally substituted —NH-alkyl-cycloalkyl or —NH-alkyl-heterocycloalkyl (e.g., optionally substituted with C1-C4 alkyl, —NH—(CH$_2$)$_{t2}$-optionally substituted 3-6 member cycloalkyl or heterocycloalkyl); optionally substituted —O-cycloalkyl or —O-heterocycloalkyl (e.g., optionally substituted 3-5 member cycloalky or heterocycloalkyl; —O-(oxetan-3-yl)); optionally substituted —O-alkyl-cycloalkyl or —O-alkyl-heterocycloalkyl (e.g., O—(CH$_2$)$_{t2}$— optionally substituted 3-5 member cycloalkyl or heterocycloalkyl; optionally substituted with at least one of =O, OH, and C1-C4 alkyl,); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof);

each R$_{PTM1a}$ and R$_{PTM2a}$ are independently H, optionally substituted C1-C4 alkyl (e.g., a CH$_3$ or CH$_2$CH$_3$), optionally substituted C$_1$-C$_4$ alkoxy (e.g., —OCH$_2$ or —CH$_2$CH$_3$), CH$_2$OCH$_3$ or R$_{PTM1a}$ and R$_{PTM2a}$ are joined together form a 3-10 member ring;

each t$_1$ is independently selected from 1, 2, 3, 4, or 5; and each t$_2$ is independently is independently selected from 0, 1, 2, 3, 4, or 5;

Q$_{10}$ is absent or CH$_2$;

Q$_{11}$ is CH$_2$, CHR$_{PMT3}$, or NR$_{PMT4}$;

R$_{PTM4}$ is a linear or branched C1-C8 alkyl optionally substituted with OH;

R$_{PMT2}$ is H, OH, CN, optionally substituted linear or branched C1-C4 alkyl, optionally substituted —NH$_2$ (e.g., —N(C1-C3 alkyl) or —NH(C1-C3 alkyl)), O-optionally substituted linear or branched C1-C4 alkyl, an optionally substituted C1-C4 alkynyl, an optionally substituted C1-C4 alkyne, an optionally substituted monocylic or bicyclic C3-C12 heterocyclyl (e.g., an optionally substituted C3-C12 monocyclic or bicyclic heterocycloalkyl, such as an C3-C12 monocylcic or bicyclic heterocycloalkyl, azetidine1-yl, azetidine1-yl-3-ol, pyrrolidin-1-yl, piperidin-1yl, piperazin-1-yl, or morpholin-4-yl, homopiperazin-1-yl,

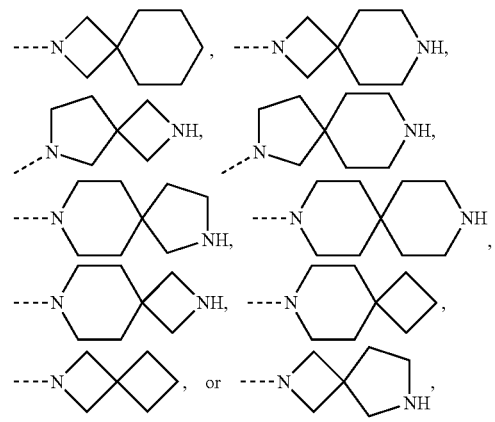

each optionally substituted with one or more of OH, a linear or branched C1-C5 alkyl or NH$_2$), or an optionally substituted —O—C$_{3-12}$ monocylic or bicyclic heterocyclyl (e.g., an optionally substituted —O—C$_{3-12}$ monocyclic or bicyclic heterocycloalkyl, such as —O—C$_{3-12}$ monocylcic or bicyclic heterocycloalkyl optionally substituted with at least one OH, a linear or branched C1-C5 alkyl or NH$_2$), or an optionally substituted C3-C12 member ring (e.g., an optionally substituted C3-C12 non-aryl membered ring optionally substituted with one or more of OH, linear or branched C1-C5 alkyl, or NH$_2$), wherein when R$_{PTM2}$ is a ring structure it is optionally covalently linked to Q$_{16}$ via a C or N of the R$_{PTM2}$ ring; and the ⚯ of the PTM indicates the point of attachment with a chemical linker group (L) or a ULM.

In any aspect or embodiment described herein, at least one (e.g., 1, 2, or 3) of $R_{PTM1}$, $R_{PTM2}$, $Q_6$, $Q_7$, $Q_8$, $Q_9$, $Q_{10}$, $X_{PTM1}$, $X_{PTM2}$ of PTMI, PTMII, PTMIII, PTMIV, or the associated location of other PTM structures described herein is directly or indirectly covalently linked to a ULM or a chemical linker group (L).

In any aspect or embodiment described herein, the $R_{PTM2}$ or the corresponding location of a PTM described herein (e.g. PTMI, PTMII, PTMIII, PTMIV, and derivatives thereof) may be substituted with one or more groups selected from: OH, linear or branched C1-C5 alkyl, or $NH_2$.

In any aspect or embodiment described herein, the $R_{PTM5}$ or the corresponding location of any PTM described herein (e.g. PTMI, PTMII, PTMIII, PTMIV, and derivatives thereof) is: H, optionally substituted linear or branched alkyl (e.g., optionally substituted linear or branched C1-C6 alkyl or C1-C4 alkyl-NH(C1-C3 alkyl) or C1-C4 alkyl-N(C1-C3 alkyl)$_2$), optionally substituted -alkyl-aryl (e.g., optionally substituted C1-C6 alkyl, optionally substituted C5-C10 aryl, or both), optionally substituted -alkyl-heteroaryl (e.g., optionally substituted C1-C6 alkyl, optionally substituted C5-C10 heteroaryl, or both), optionally substituted aryl (e.g., optionally substituted C5-C10 aryl), optionally substituted heteroaryl (e.g., optionally substituted C5-C10 heteroaryl), optionally substituted cycloalkyl (e.g., optionally substituted C3-C10 cyclalkyl), optionally substituted -alkyl-cycloalkyl (e.g., optionally substituted C1-C6 alkyl, optionally substituted C3-C10 cycloalkyl, or both), optionally substitute heterocyclyl (e.g., optionally substituted C3-C10 heterocyclyl).

In any aspect or embodiment described herein, the $R_{PTM5}$ or the corresponding location of a PTM described herein (e.g. PTMI, PTMII, PTMIII, PTMIV, and derivatives thereof) is selected from H, methyl, $CFH_2$, $CF_2H$, ethyl, propyl, isopropyl, cyclopropyl, butyl, pentyl, hexyl, —$CH_2CH_2OCH_3$, —$CH_2CH(CH_3)_2$, —$CH_2CHN(CH_3)_2$, —$CH_2$-cyclopropyl, —$CH_2$—$CH_2$-cyclopropyl,

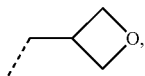 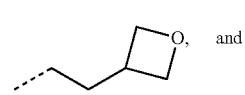 and

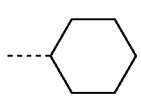

In any aspect or embodiment described herein, the $X_{PTM1}$ or the corresponding location of any PTM described herein (e.g. PTMI, PTMII, PTMIII, PTMIV, and derivatives thereof) is H or F.

In any aspect or embodiment described herein, the $X_{PTM2}$ or the corresponding location of any PTM described herein (e.g. PTMI, PTMII, PTMIII, PTMIV, and derivatives thereof is H, Cl, F, or CN.

In any aspect or embodiment described herein, the $R_{PTM2}$ or the corresponding location of a PTM described herein (e.g. PTMI, PTMII, PTMIII, PTMIV, and derivatives thereof) is selected from: H, OH, ethyl, $NH_2$, —$N(CH_3)_2$,

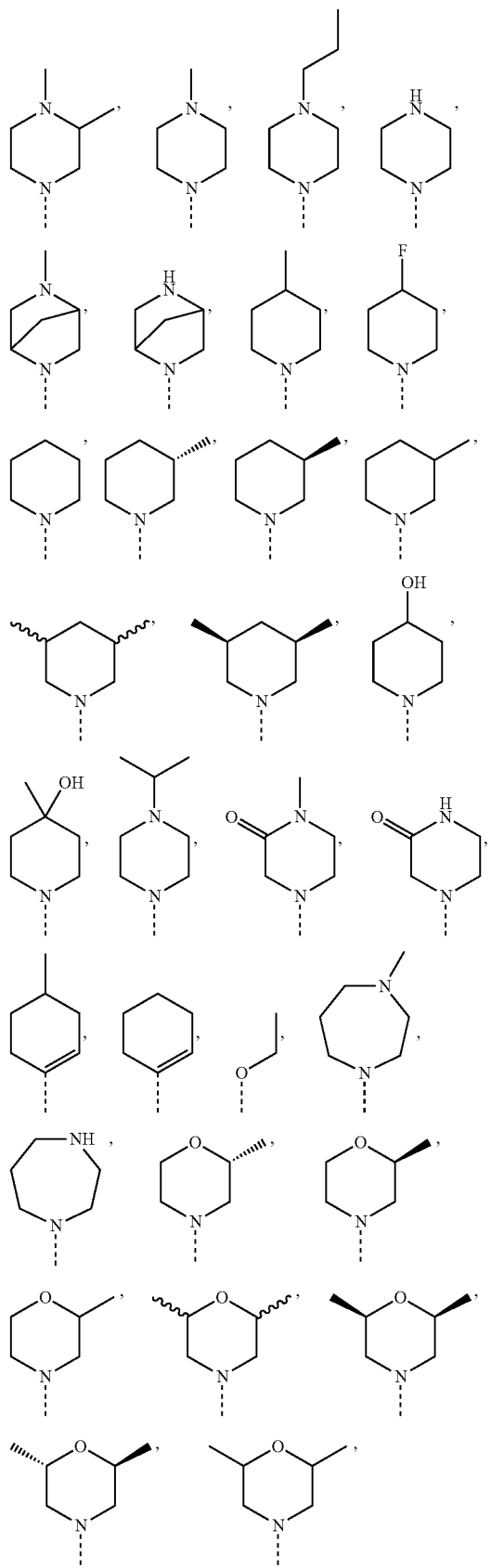

-continued

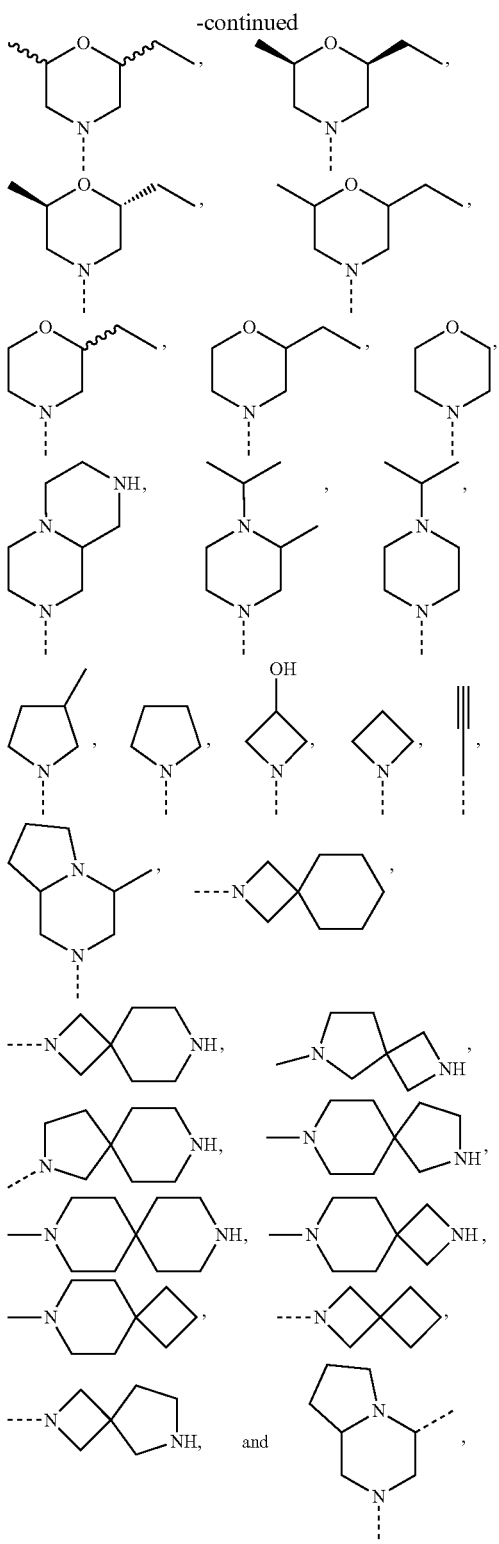

wherein ⌇ represents a bond that may be stereospecific ((R) or (S)) or non-stereospecific.

In any aspect or embodiment described herein, the $R_{PTM3}$ or the corresponding location of any PTM described herein (e.g. PTMI, PTMII, PTMIII, PTMIV, and derivatives thereof) is: OH; optionally substitute linear or branched alkyl, optionally substituted alkoxy (e.g., optionally substituted with a linear or branched C1-C4 alkyl or —OCH$_3$); optionally substituted

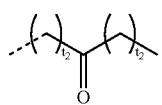

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5); optionally substituted

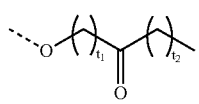

(e.g., optionally substituted with a linear or branched C1-C4 alkyl; —O(CH$_2$)$_u$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and x is independently selected from 1, 2, 3, 4 or 5); optionally substituted

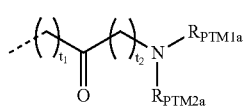

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

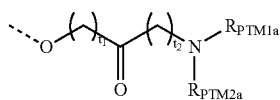

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_u$CH((CH$_2$)$_x$CH$_3$)(CH$_2$)$_w$CO(CH$_2$)$_v$NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted


(e.g., optionally substituted with a linear or branched C$_1$-C$_4$ alkyl; —(CH$_2$)$_u$CHCH(CH$_2$)$_w$CO(CH$_2$)$_v$NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

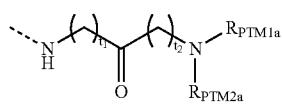

(e.g., optionally substituted with a linear or branched C1-C4 alkyl; —NH—$(CH_2)_u$CO$(CH_2)_v$NR$_{PTM1a}$R$_{PTM2a}$ or —NH—$CH_2$CONR$_{PTM1a}$R$_{PTM2a}$, wherein each u and v is independently selected from 1, 2, 3, 4 or 5); optionally substituted -alkyl-heteroaryl (e.g, optionally substituted with a C1-C4 alkyl; —$(CH_2)_{t2}$-optionally substituted 5 or 6 member heteroaryl; the heteroaryl is selected from oxazol-4-yl, 1,3,4-triazol-2-yl, and imidazole-1-yl; and combination thereos); optionally substituted —NH-alkyl-heteroaryl (e.g., optionally substituted with a C1-C4 alkyl, or combination thereof, —NH—$(CH_2)_{t2}$-optionally substituted 5 or 6 member heteroaryl, N—$CH_2$-pyrazol-4-yl); optionally substituted alkyl-cycloalkyl or alkyl-heterocycloalkyl (e.g., optionally substituted with a C1-C4 alkyl, —$(CH_2)_{t2}$-an optionally substituted 3-6 member cycloalkyl or heterocycloalkyl); optionally substituted —NH-alkyl-cycloalkyl or —NH-alkyl-heterocycloalkyl (e.g., optionally substituted with C1-C4 alkyl, —NH—$(CH_2)_{t2}$-optionally substituted 3-6 member cycloalkyl or heterocycloalkyl); optionally substituted —O-cycloalkyl or —O-heterocycloalkyl (e.g., optionally substituted 3-5 member cycloalky or heterocycloalkyl; —O-(oxetan-3-yl)); optionally substituted —O-alkyl-cycloalkyl or —O-alkyl-heterocycloalkyl (e.g., O—$(CH_2)_{t2}$— optionally substituted 3-5 member cycloalkyl or heterocycloalkyl; optionally substituted with at least one of =O, OH, and C1-C4 alkyl,); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof).

In any aspect or embodiment described herein, the R$_{PTM3}$ or the corresponding location of any PTM described herein (e.g. PTMI, PTMII, PTMIII, PTMIV, and derivatives thereof) is selected from:

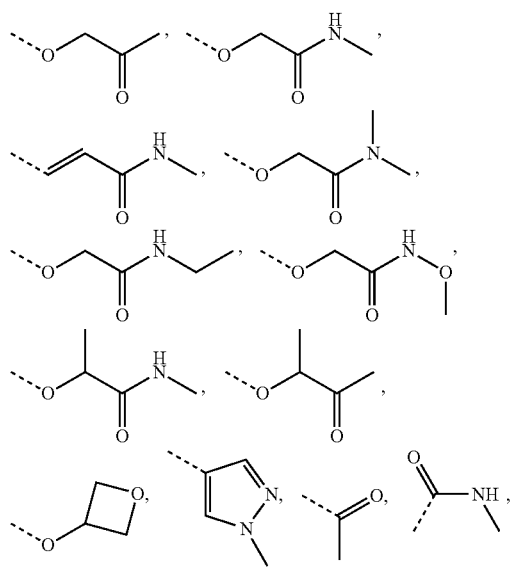

wherein: ∽ represents a bond that may be stereospecific ((R) or (S)) or non-stereospecific; and X$_{PTM3}$ is selected from $CH_2$, O, and S.

In any aspect or embodiment described herein, the R$_{PTM4}$ or the corresponding location of any PTM described herein (e.g. PTMI, PTMII, PTMIII, PTMIV, and derivatives thereof) is a linear or branched C1-C8 alkyl optionally substituted with OH.

In any aspect or embodiment described herein, the R$_{PMT2}$ or the corresponding location of any PTM described herein (e.g. PTMI, PTMII, PTMIII, PTMIV, and derivatives thereof) is H, OH, CN, optionally substituted linear or branched C1-C4 alkyl, optionally substituted —$NH_2$ (e.g., —N(C1-C3 alkyl) or —NH(C1-C3 alkyl) or —N$(CH_3)_2$), O-optionally substituted linear or branched C1-C4 alkyl, an optionally substituted C1-C4 alkynyl, an optionally substituted C1-C4 alkyne, an optionally substituted monocylic or bicyclic C3-C12 heterocyclyl (e.g., an optionally substituted C3-C12 monocyclic or bicyclic heterocycloalkyl, such as an C3-C12 monocylcic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with one or more of OH, a linear or branched C1-C5 alkyl or NH$_2$), or an optionally substituted —O—C$_{3-12}$ monocylic or bicyclic heterocyclyl (e.g., an optionally substituted —O—C$_{3-12}$ monocyclic or bicyclic heterocycloalkyl, such as —O—C$_{3-12}$ monocylcic or bicyclic heterocycloalkyl optionally substituted with at least one OH, a linear or branched C1-C5 alkyl or NH$_2$), or an optionally substituted C3-C12 member ring (e.g., an optionally substituted C3-C12 non-aryl membered ring optionally substituted with one or more of OH, linear or branched C1-C5 alkyl, or NH$_2$), wherein when R$_{PTM2}$ is a ring structure it is optionally covalently linked to Q$_{16}$ via a C or N of the R$_{PTM2}$ ring.

In any aspect or embodiment described herein, the PTM is represented by a chemical structure selected from:

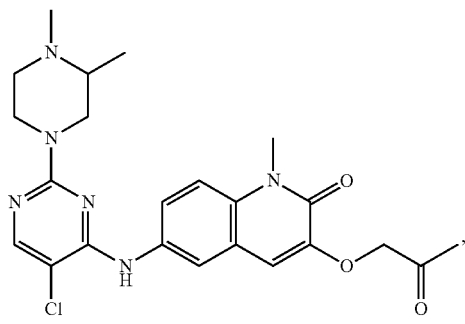

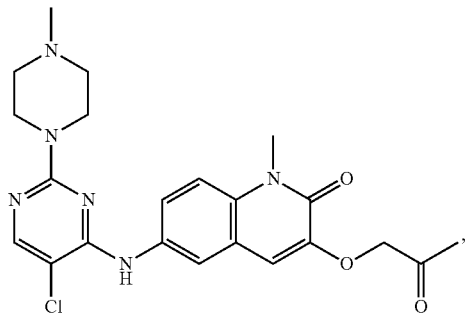

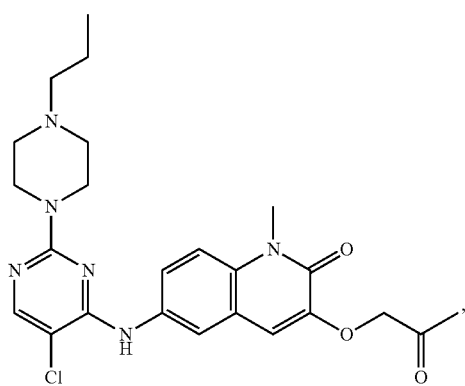

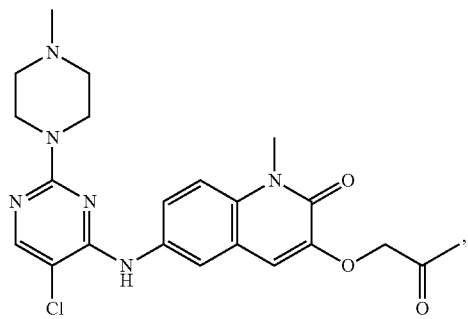

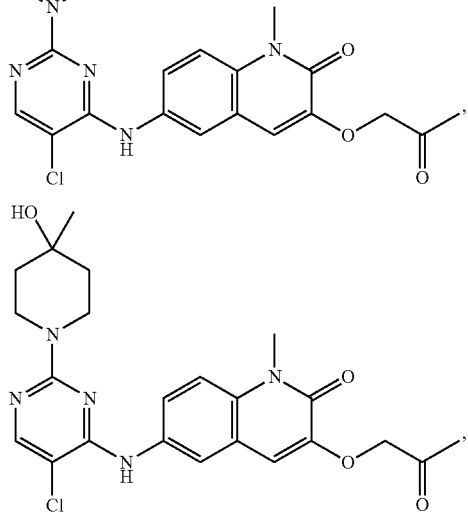

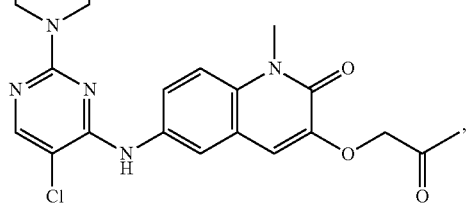

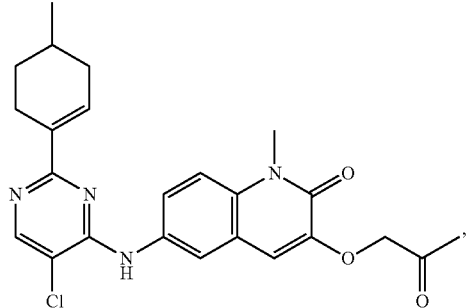

401
-continued
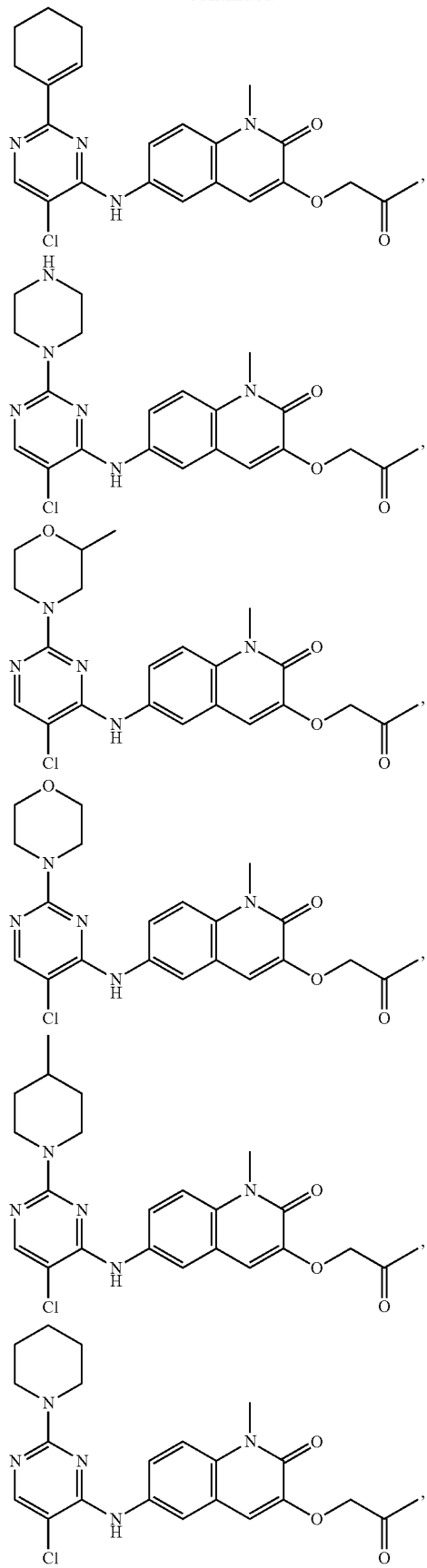
402
-continued
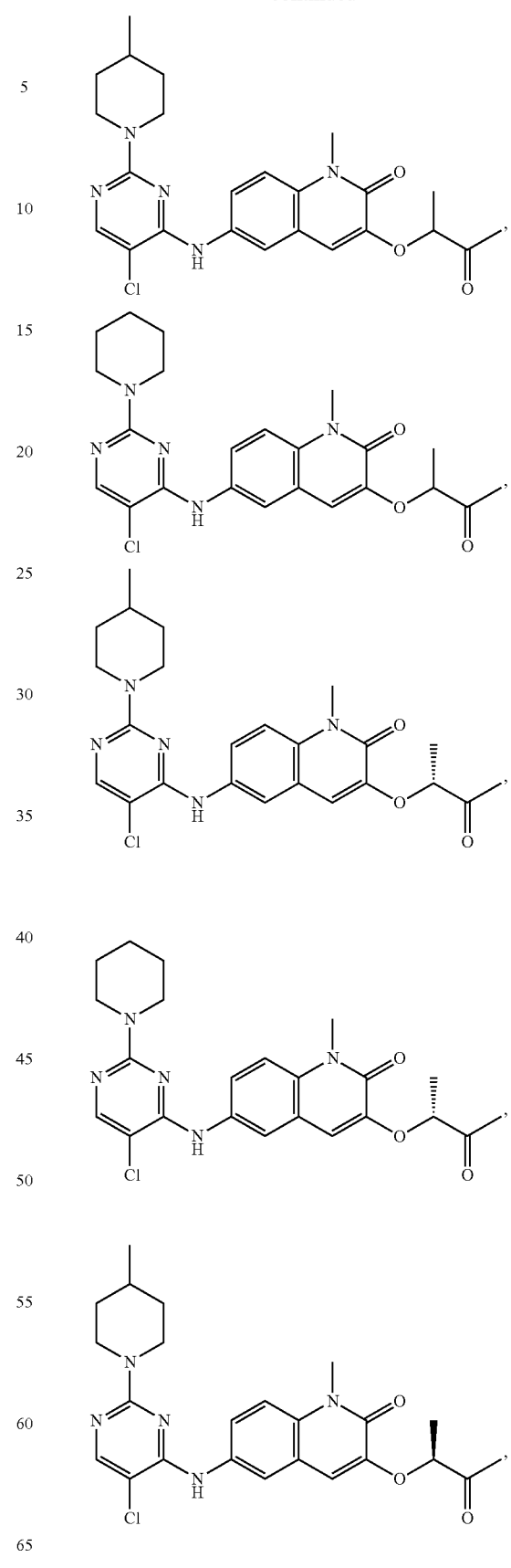

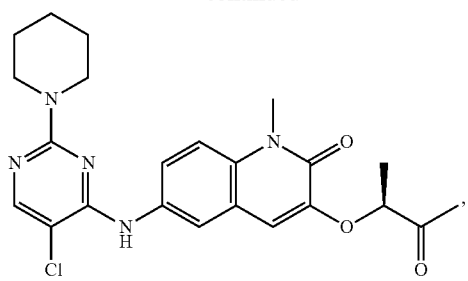
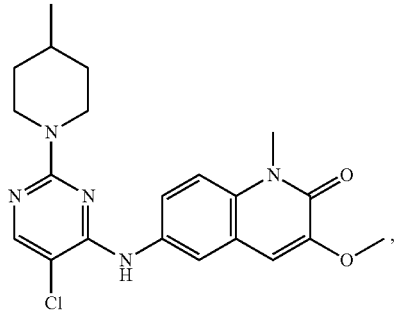
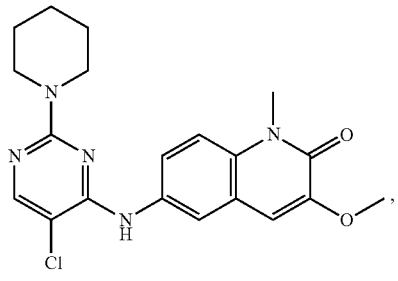
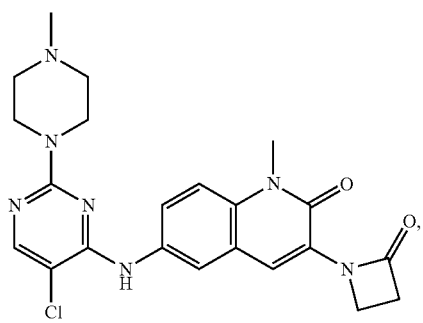
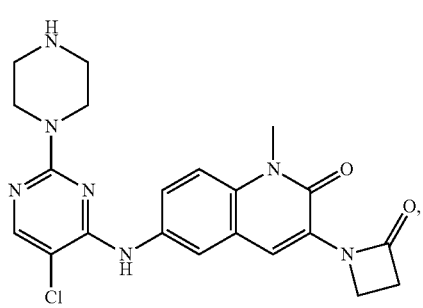
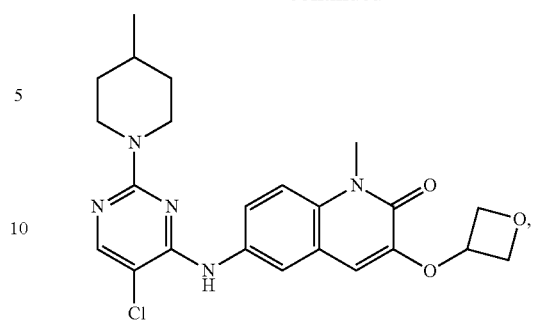
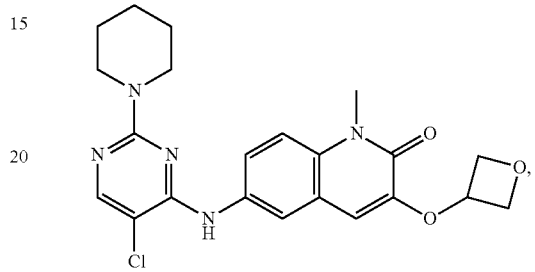
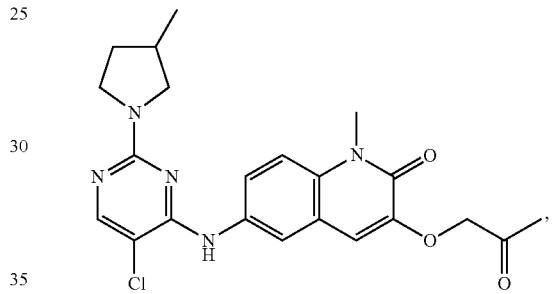
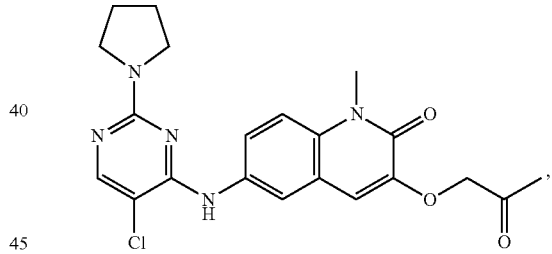
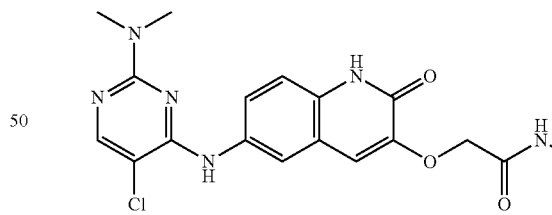
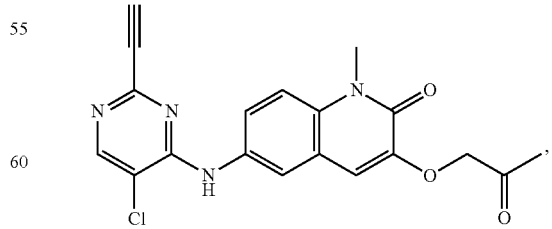

405
-continued
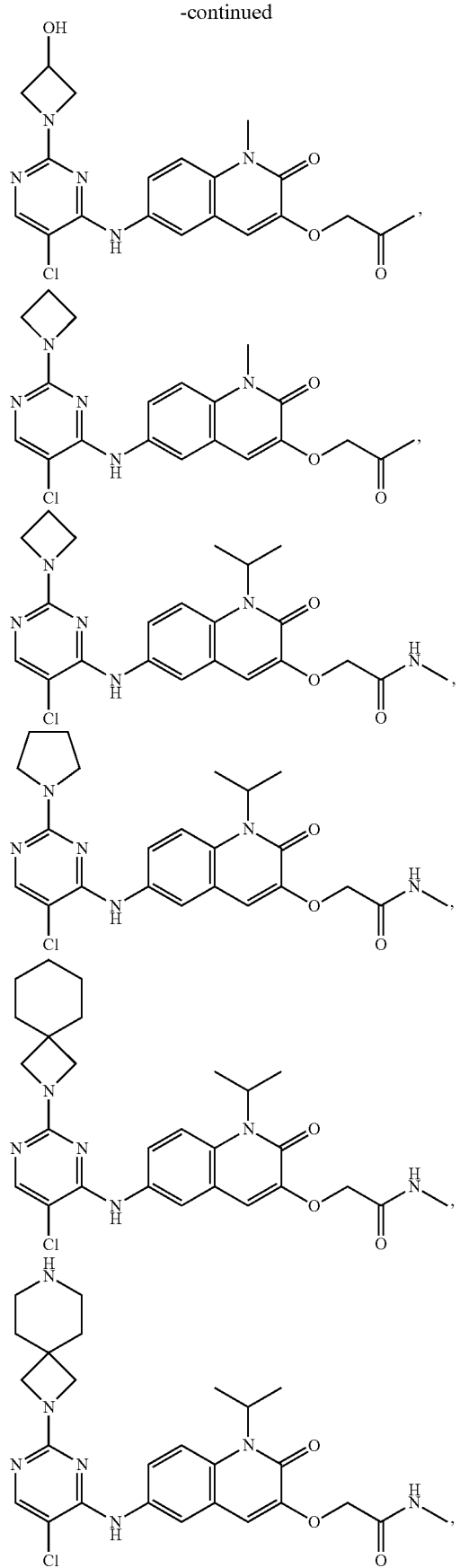
406
-continued
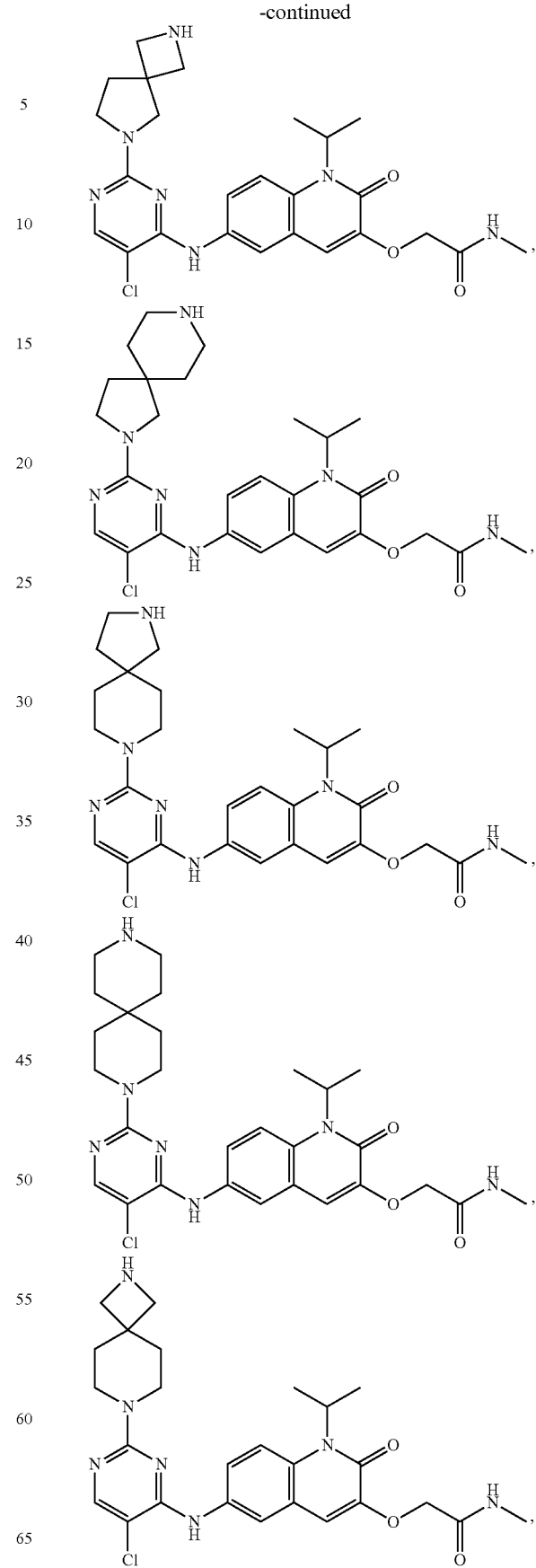

407
-continued
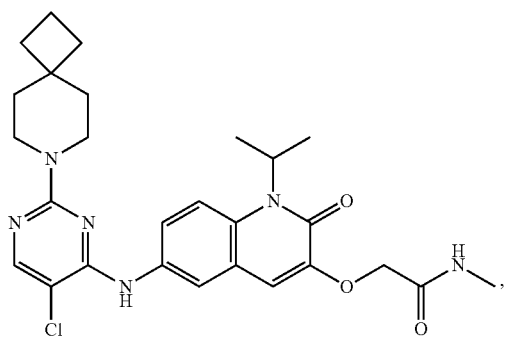
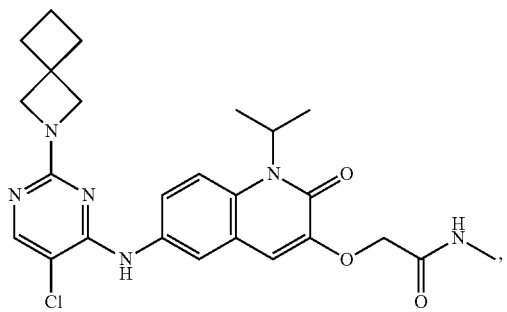
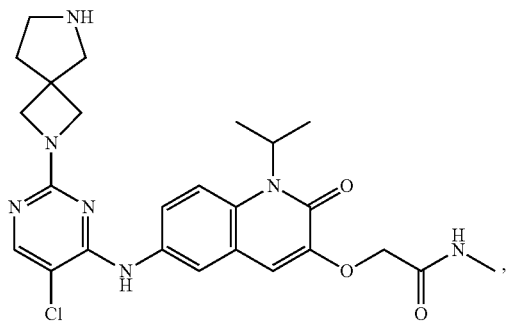
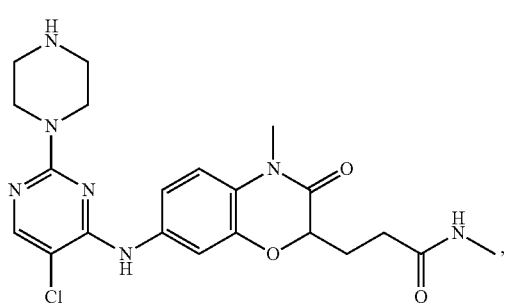
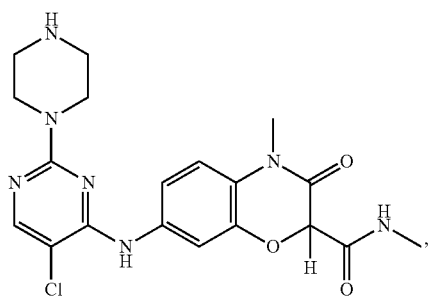
408
-continued
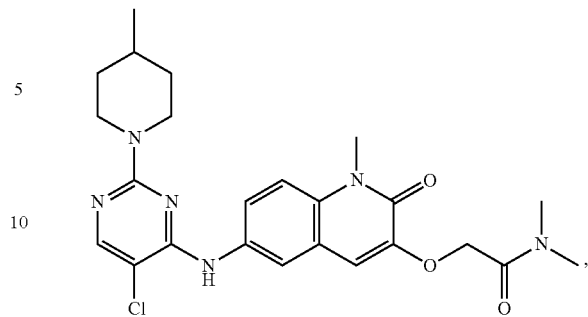

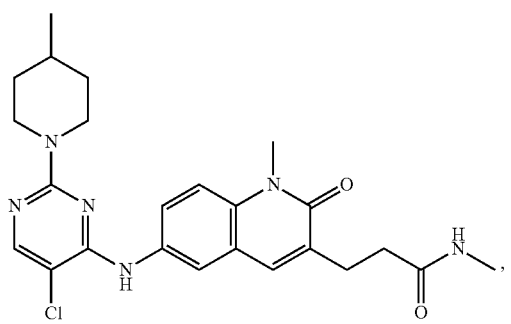
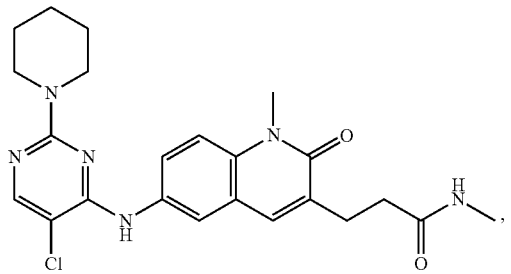
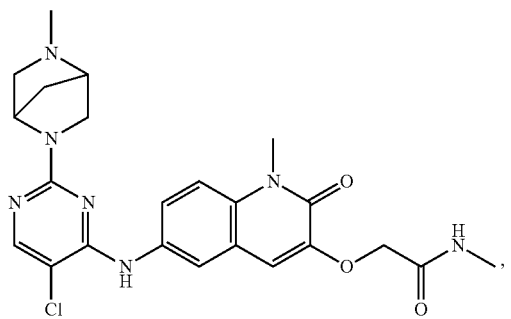
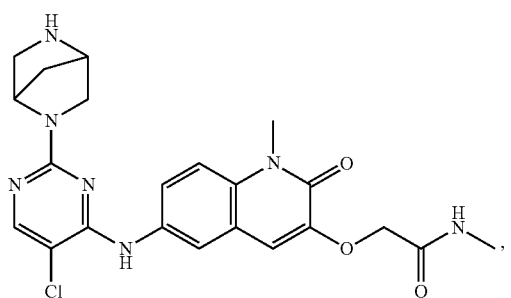
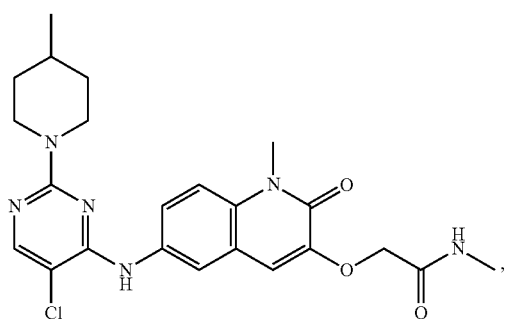
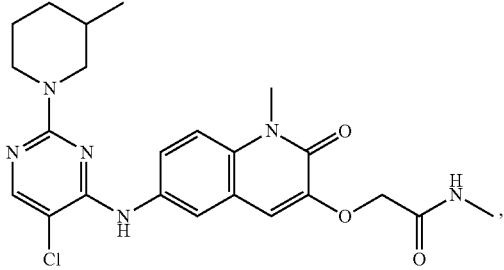
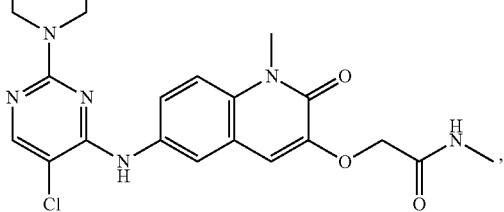
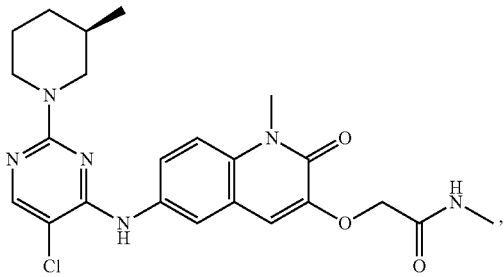
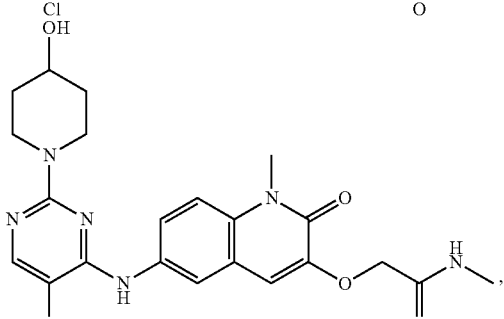
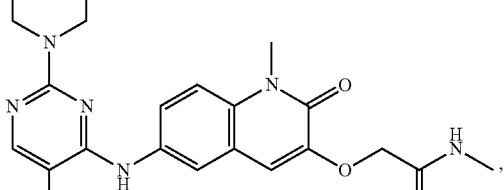
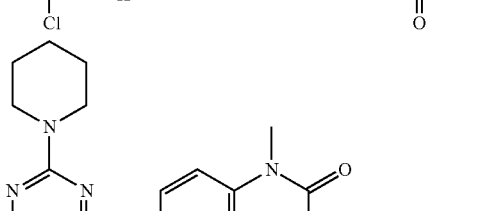
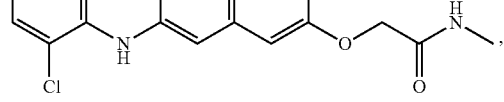

411
-continued
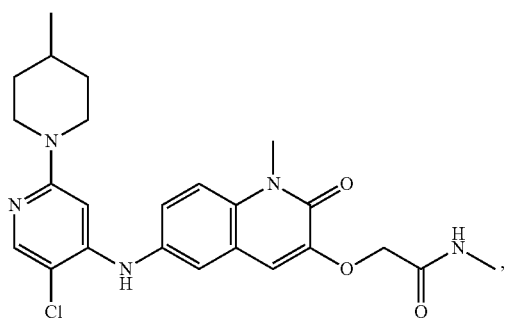
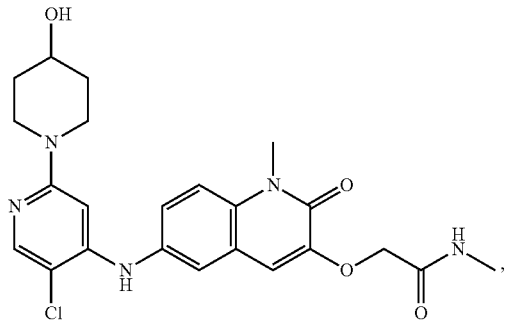
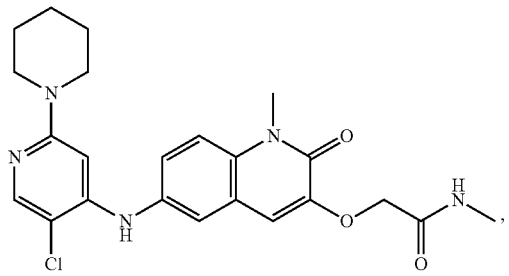
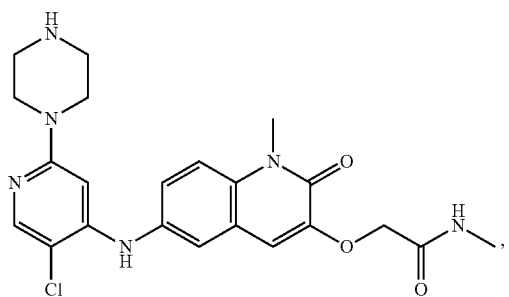
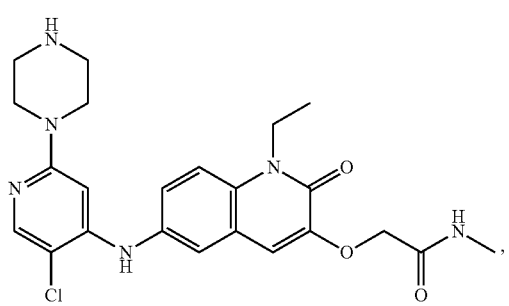
412
-continued
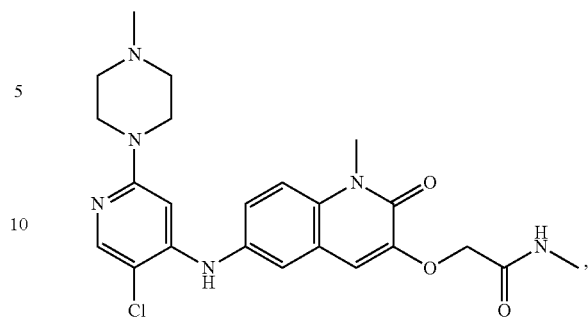
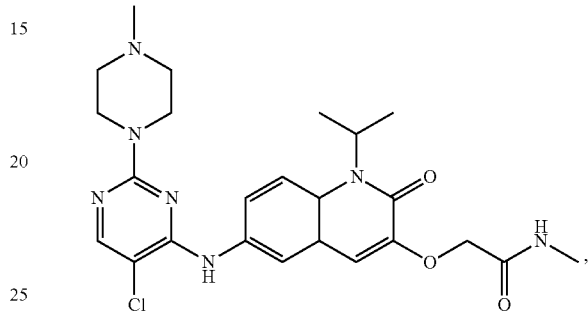
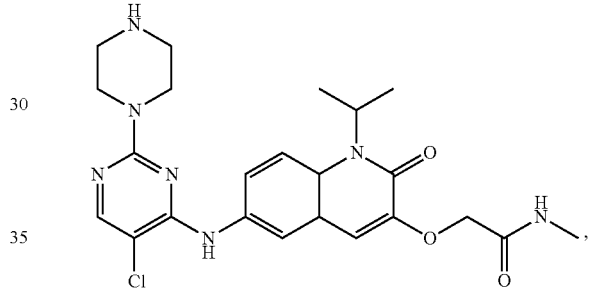
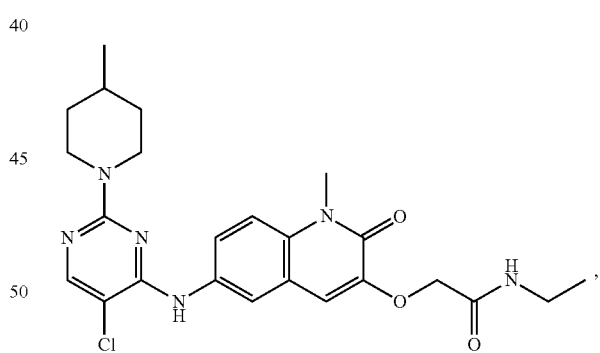
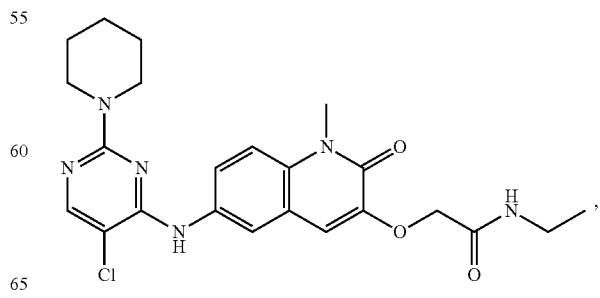

413
-continued
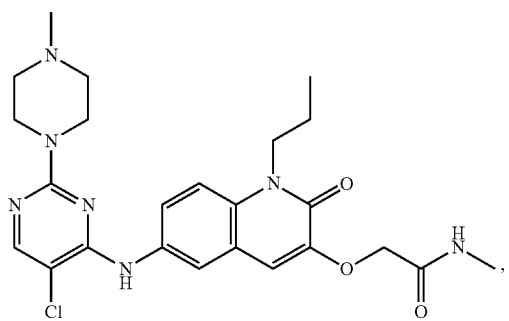
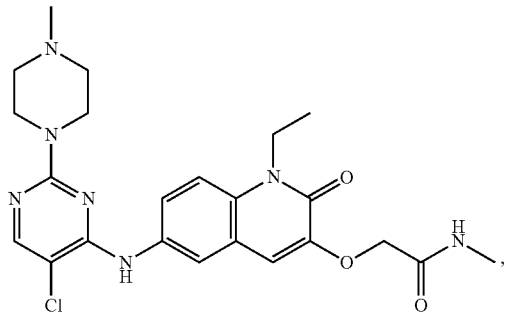
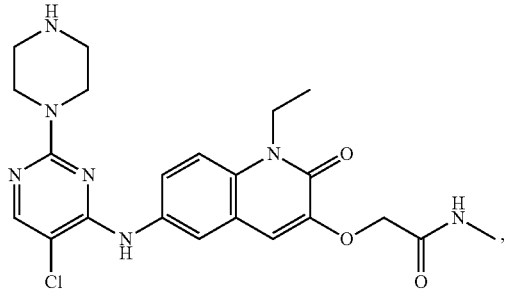
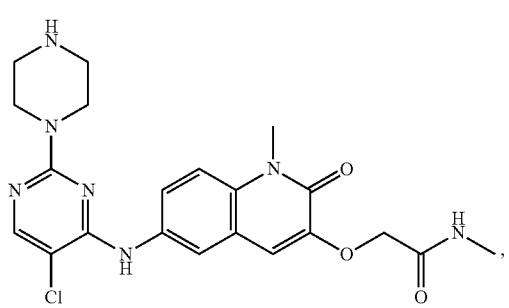
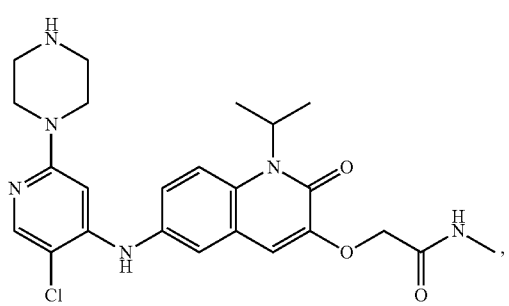
414
-continued
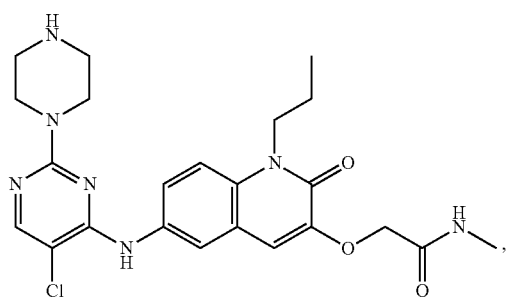
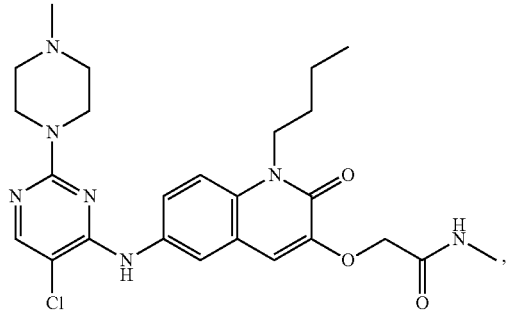
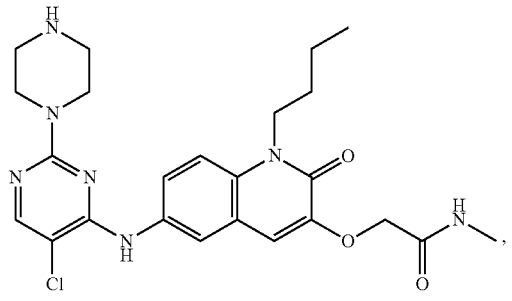
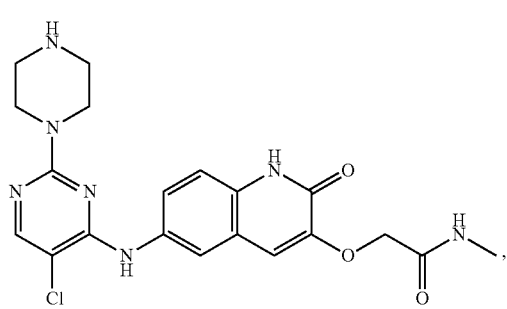
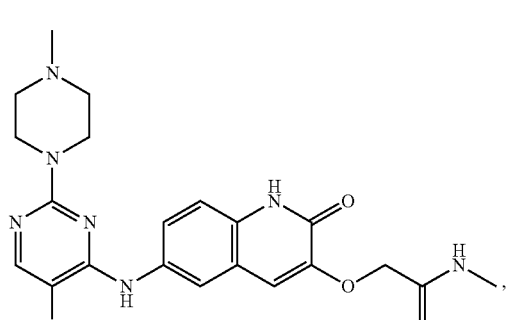

415
-continued
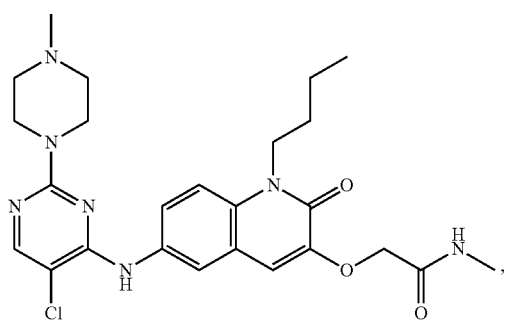
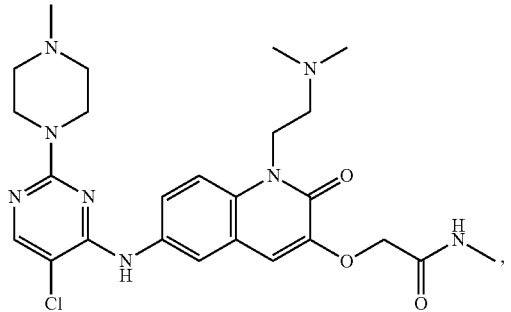
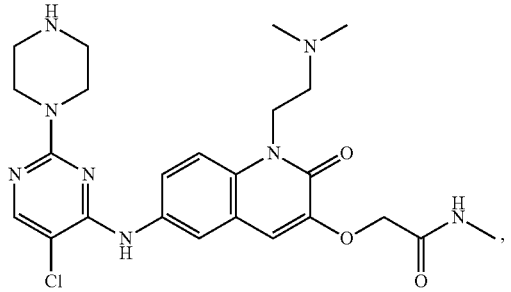
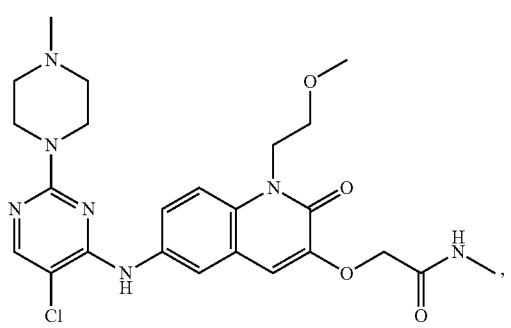
416
-continued
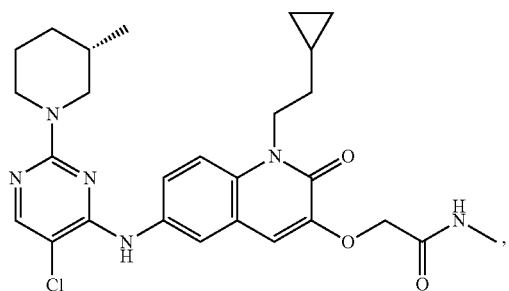
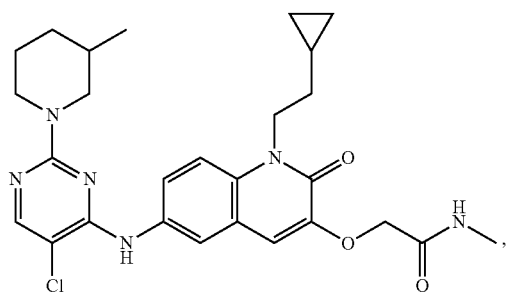
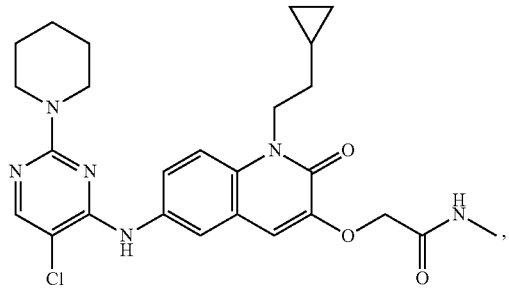
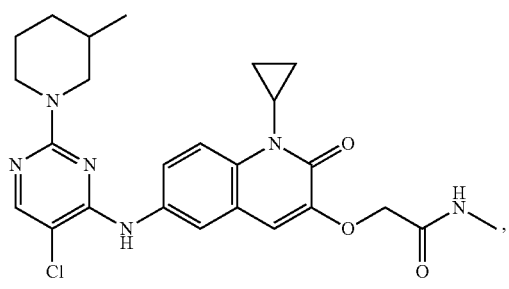
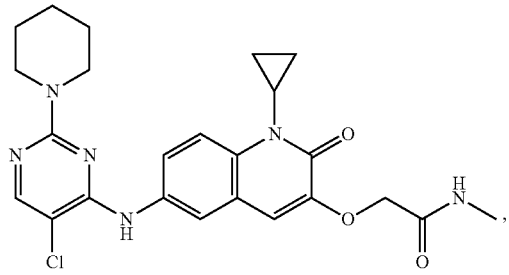

417
-continued
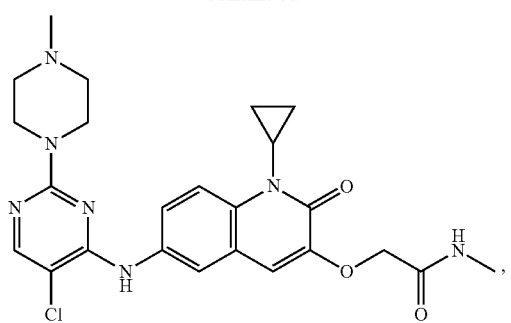
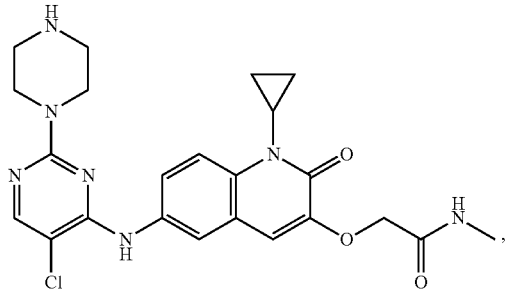
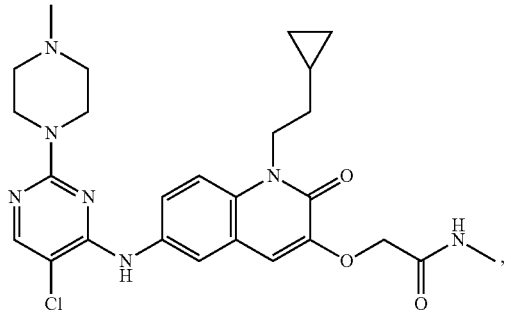
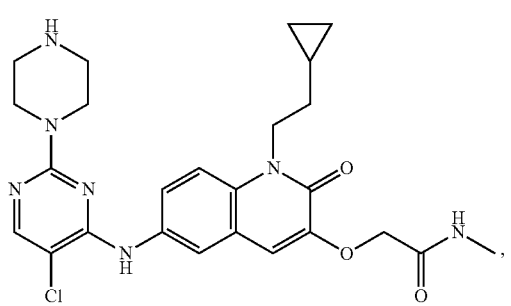
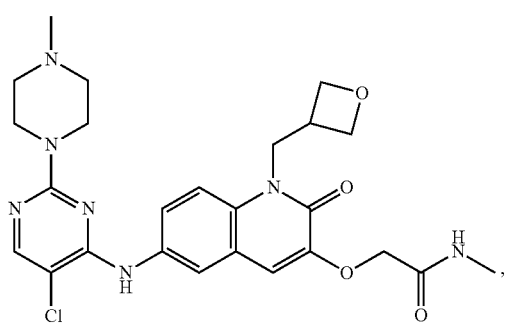
418
-continued
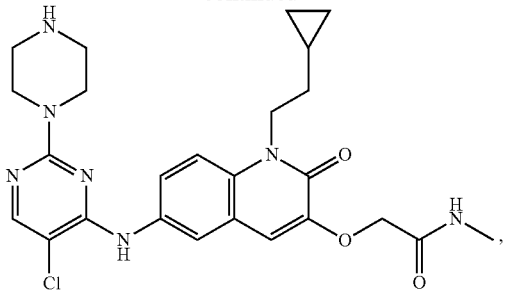
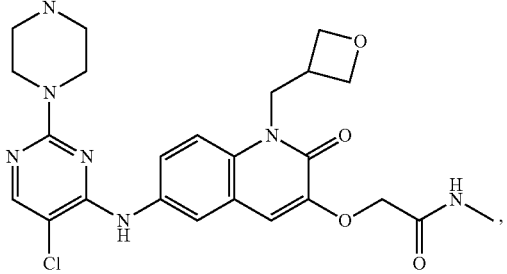

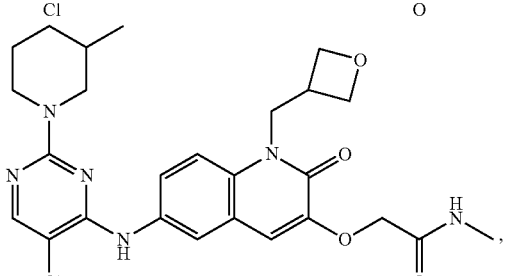
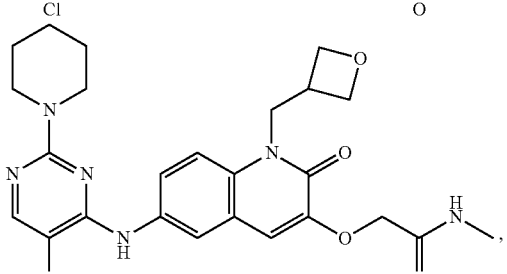
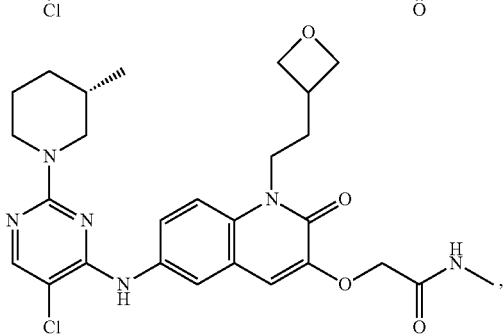

419
-continued
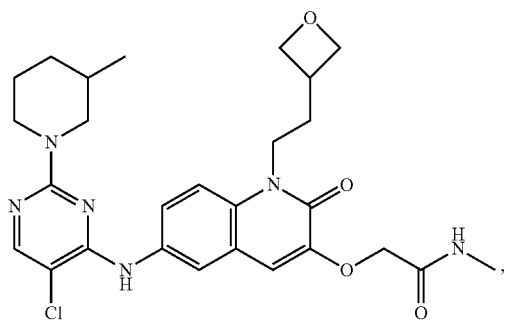
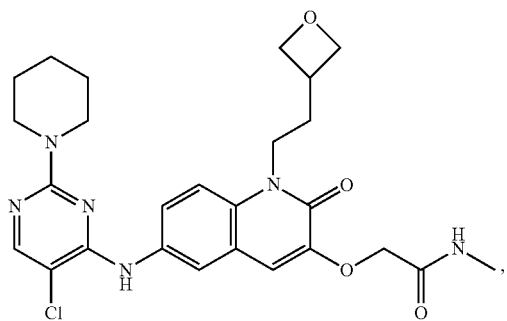
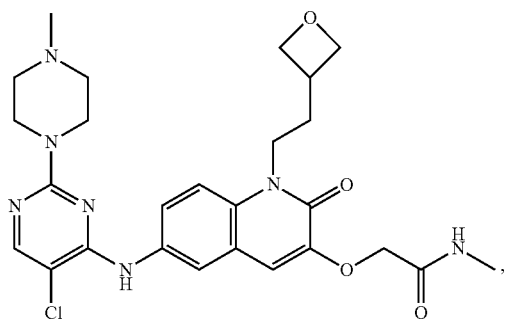
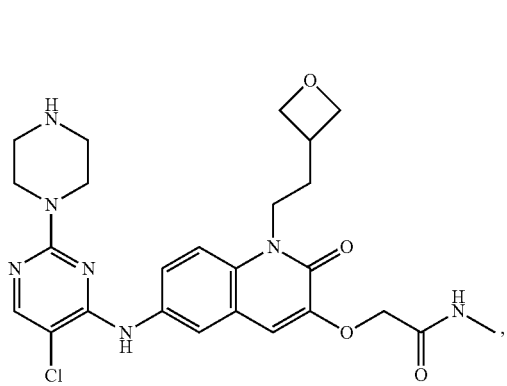
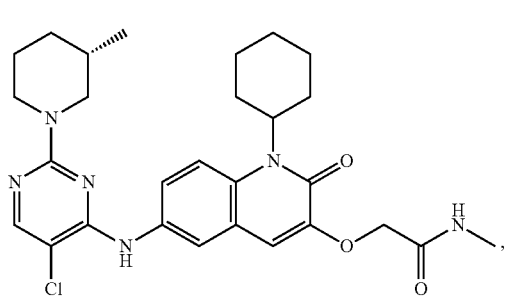
420
-continued
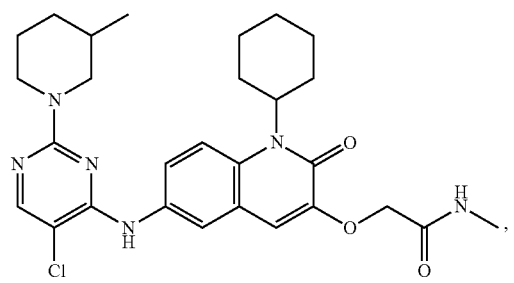
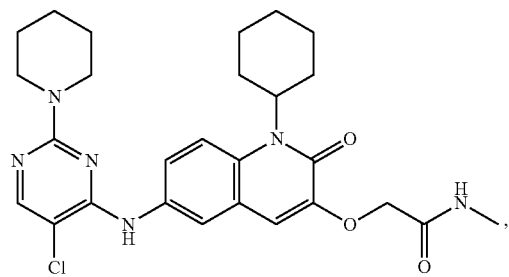
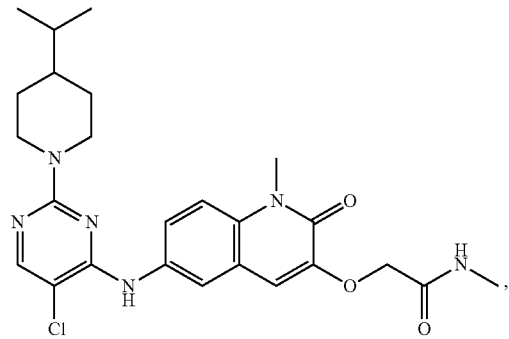
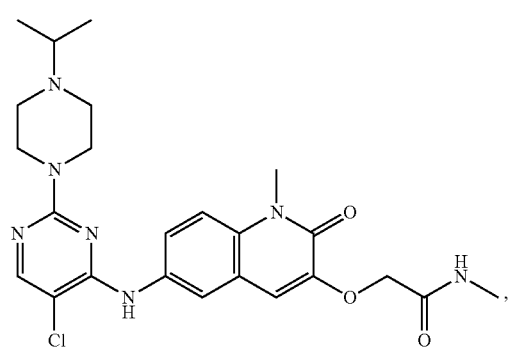
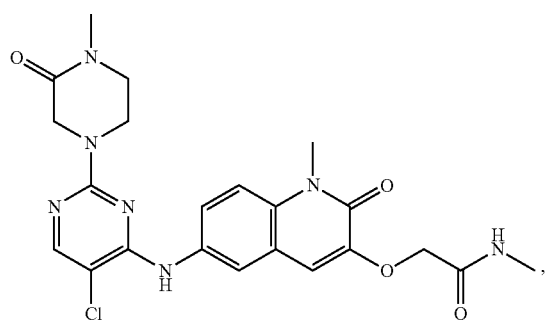

421
-continued
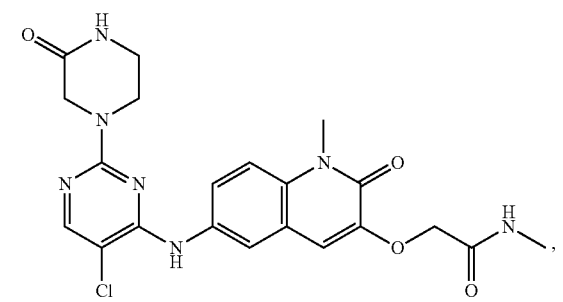
422
-continued
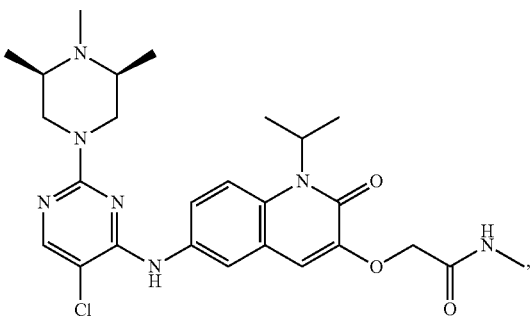
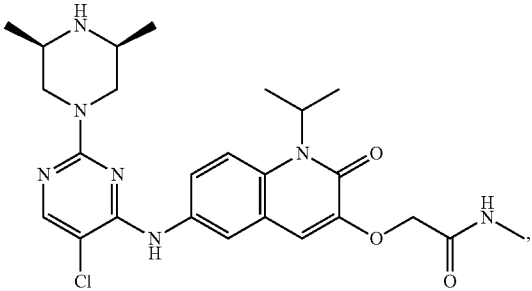
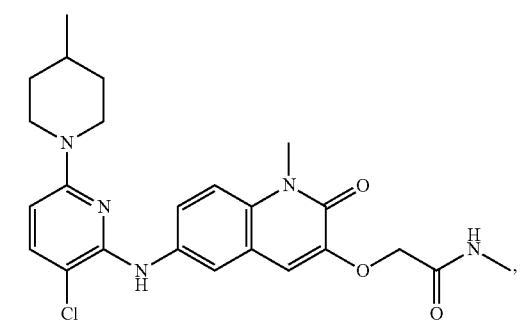
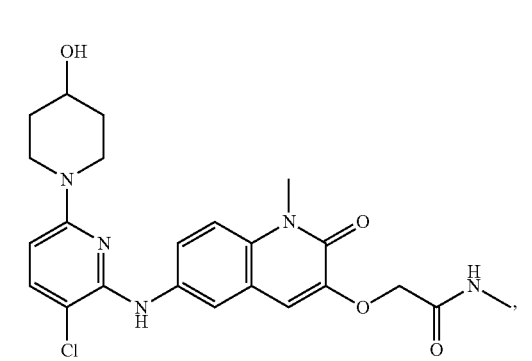
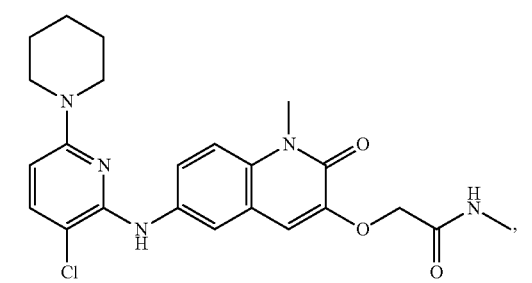

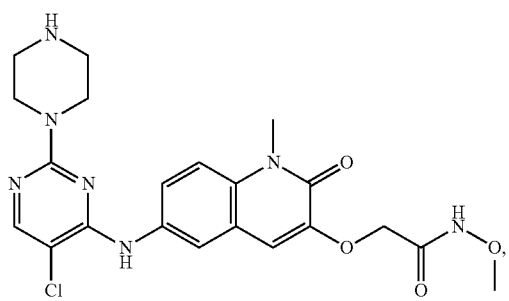
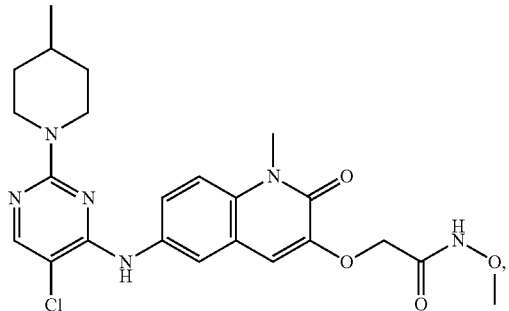
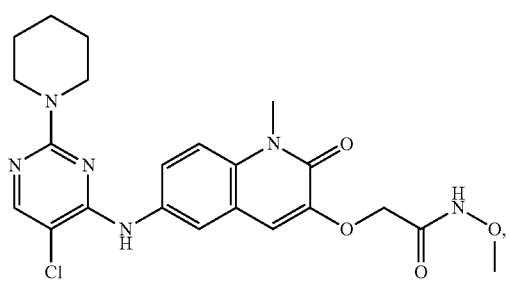
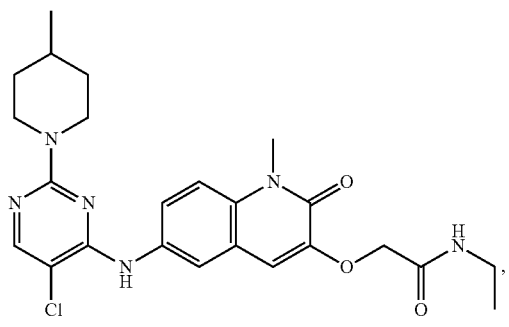
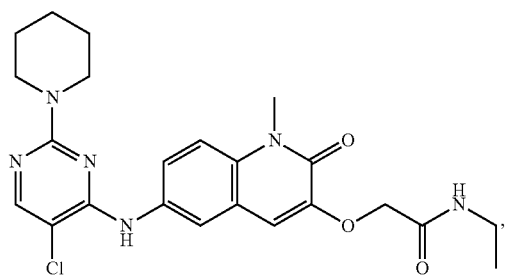
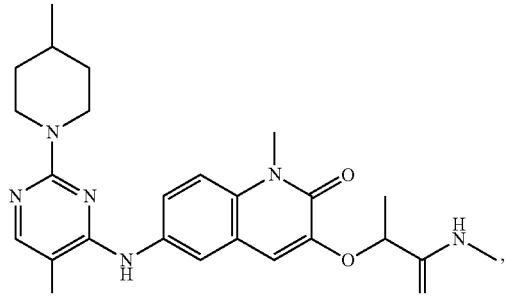
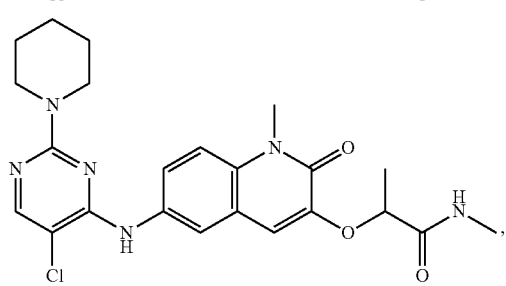
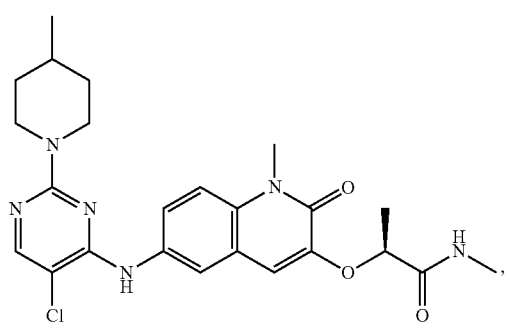
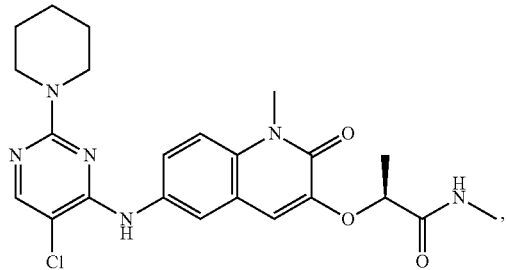

425
-continued
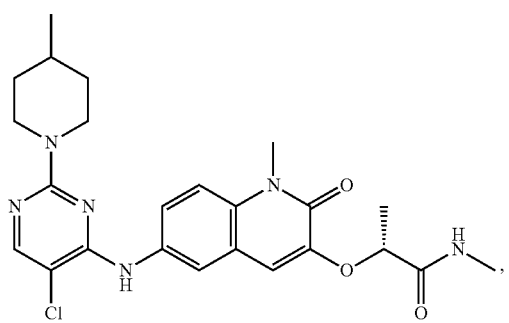
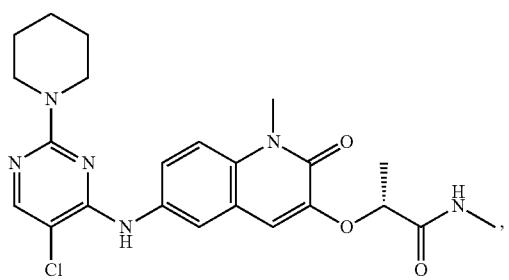
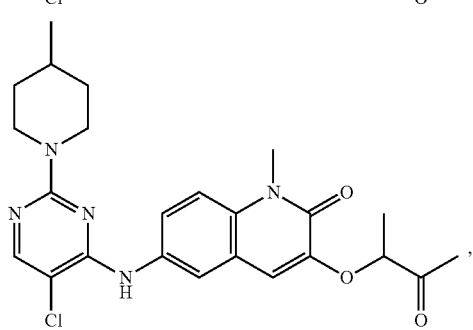
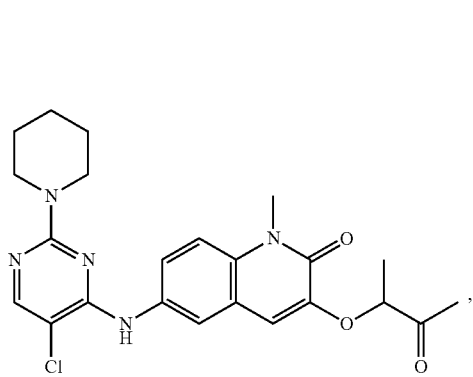
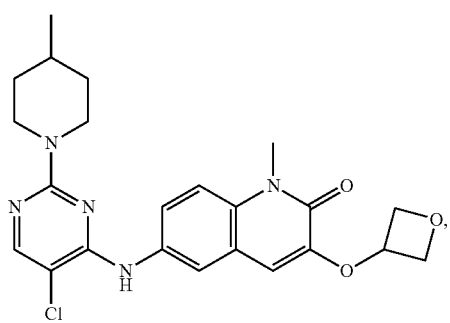
426
-continued
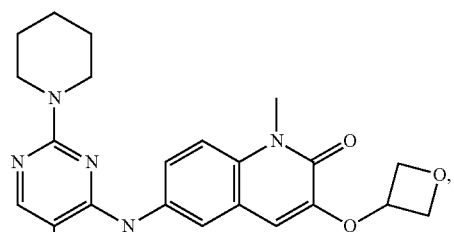
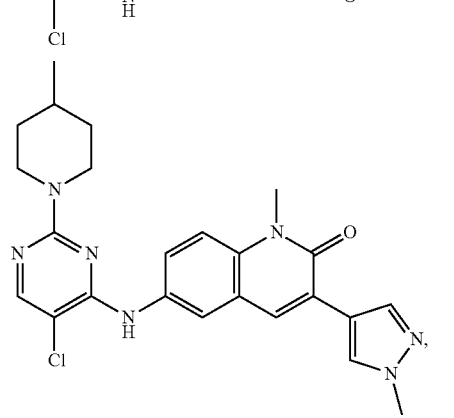
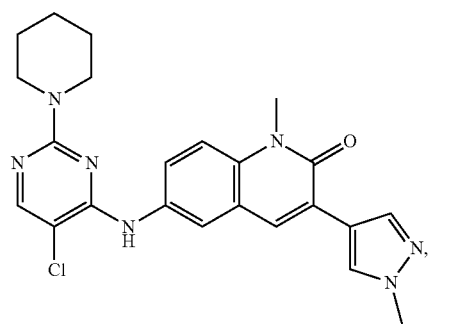
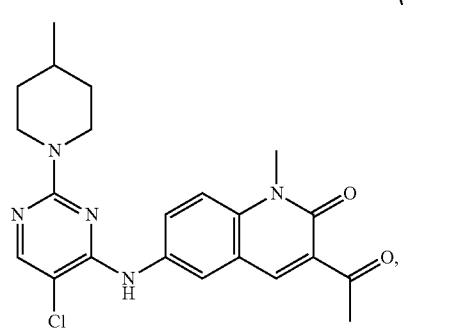
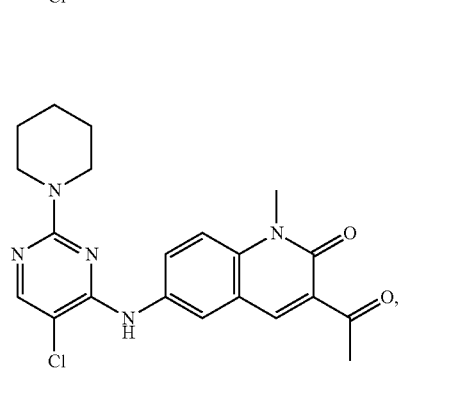

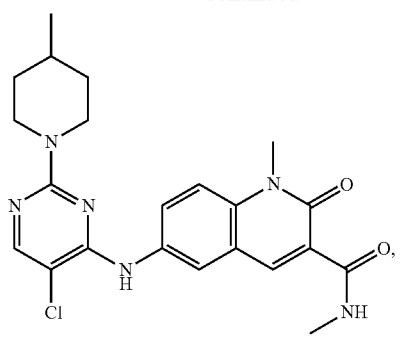
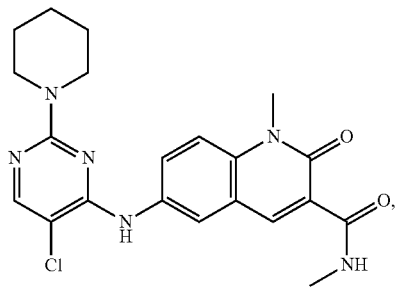
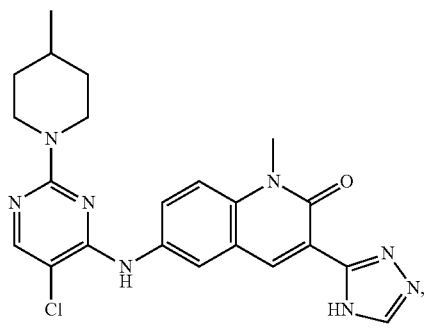
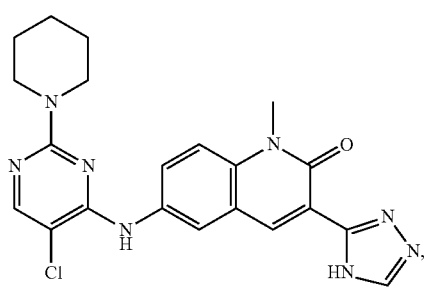
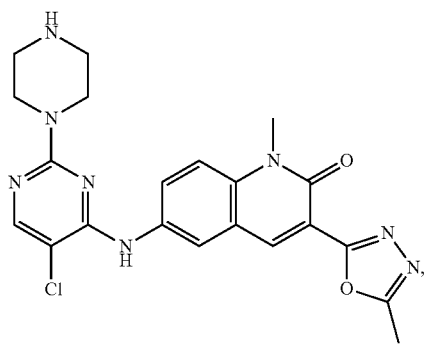
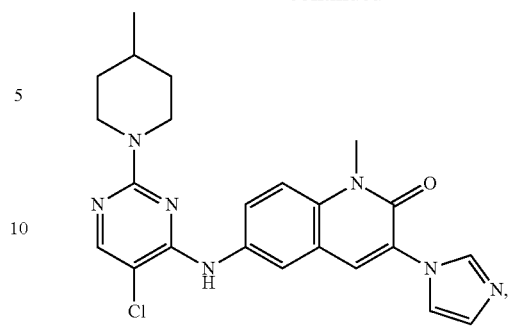
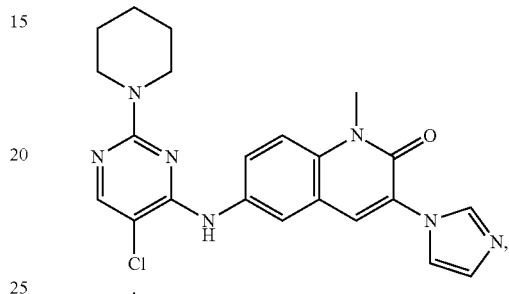
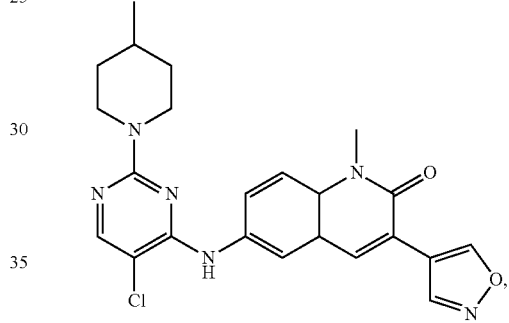
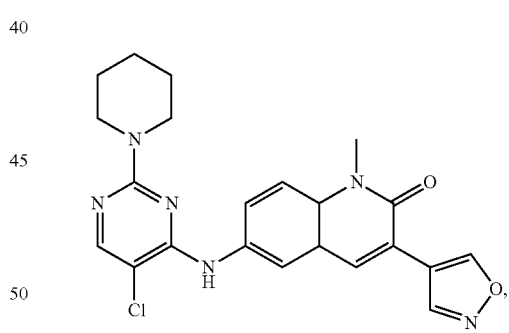
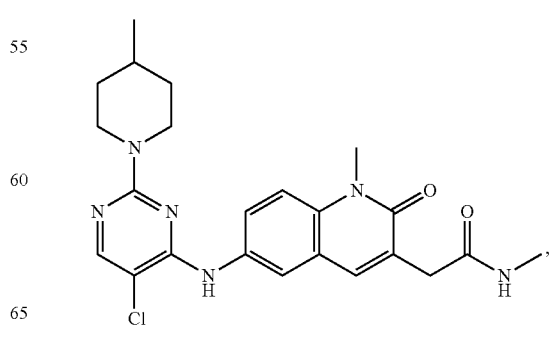

429
-continued
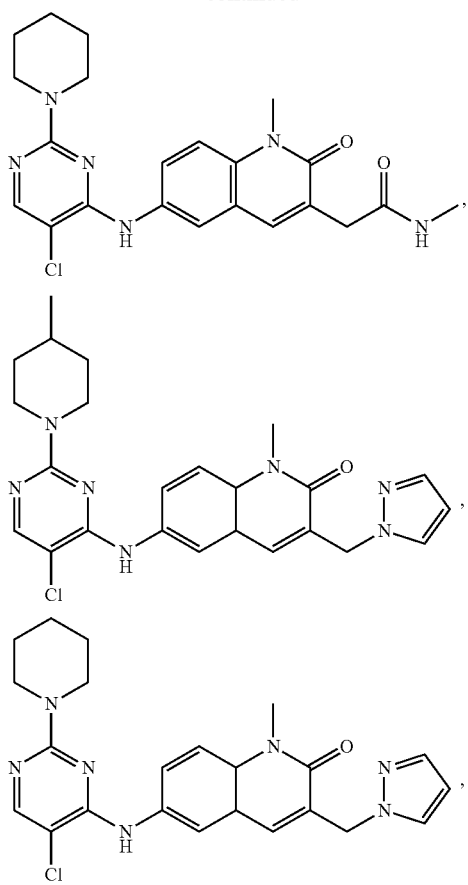
430
-continued
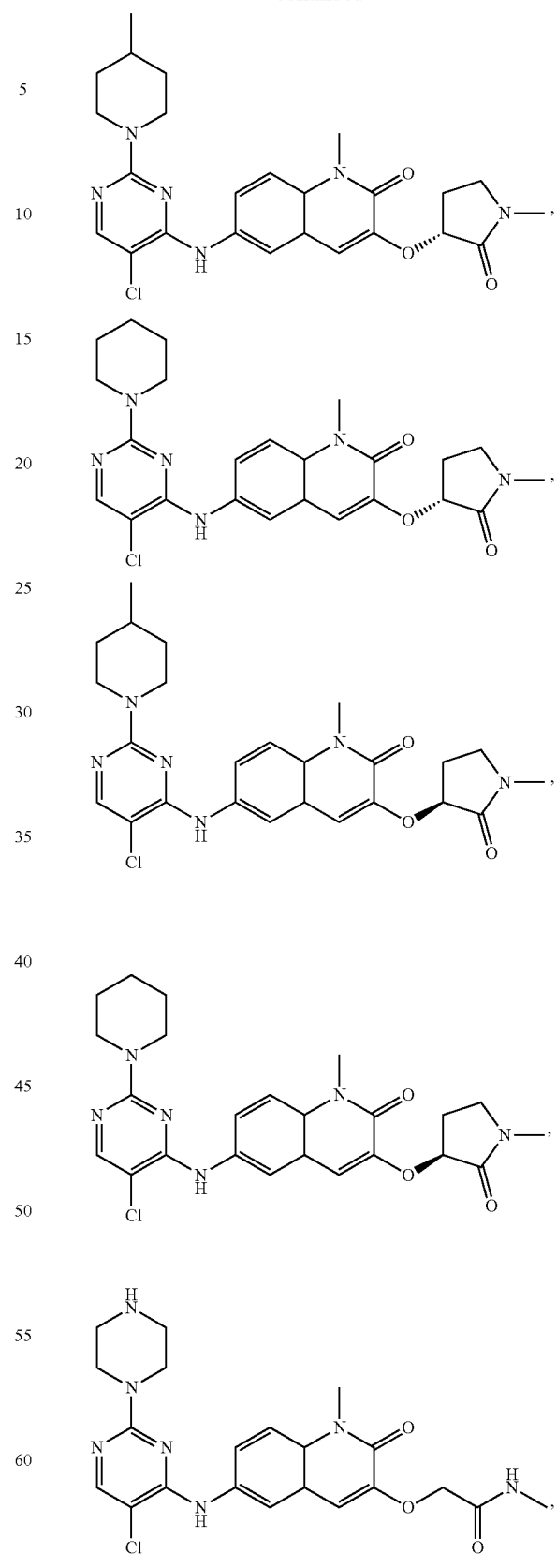

431
-continued
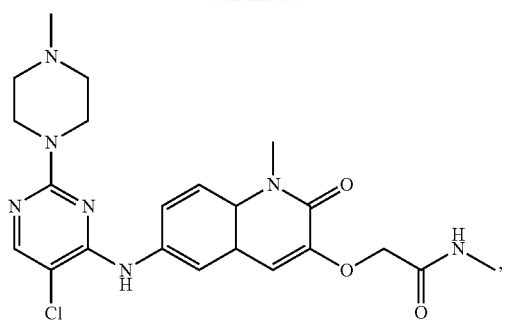
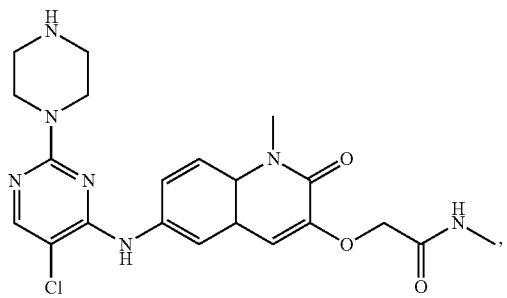
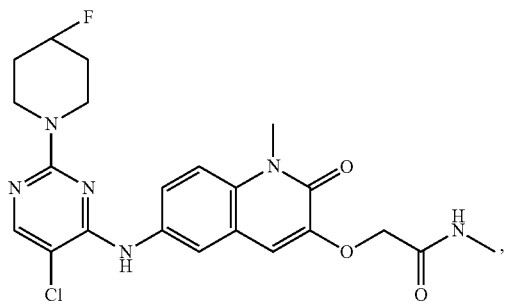
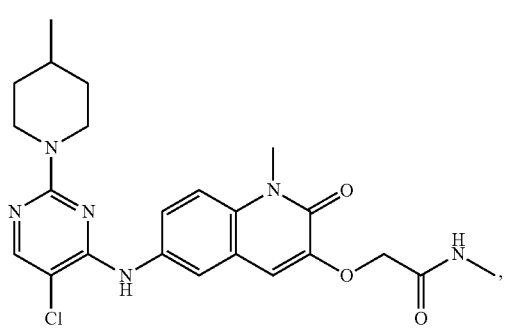
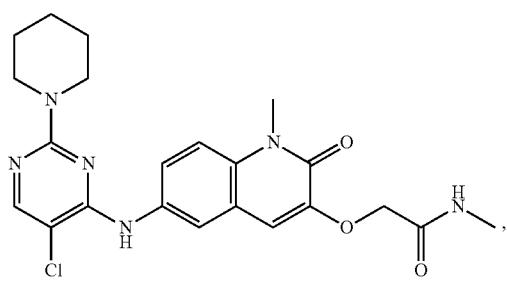
432
-continued
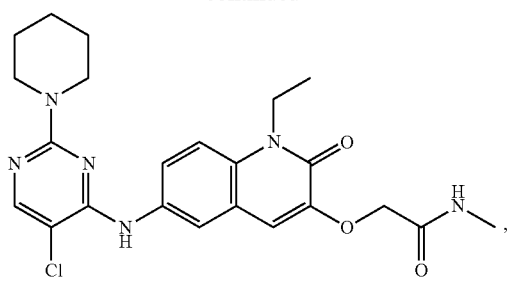
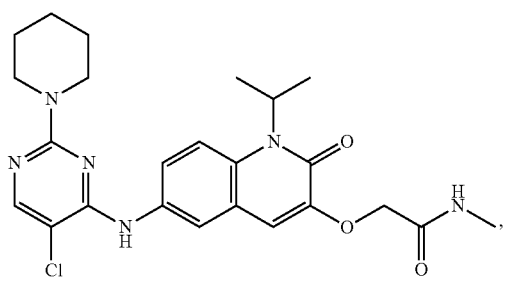
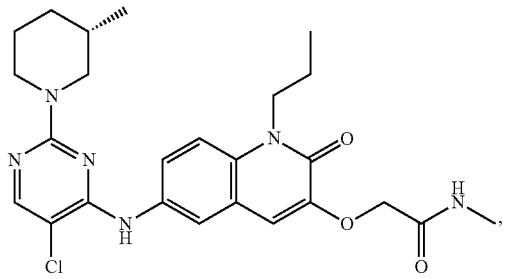
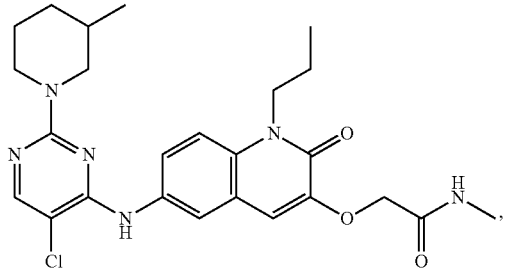
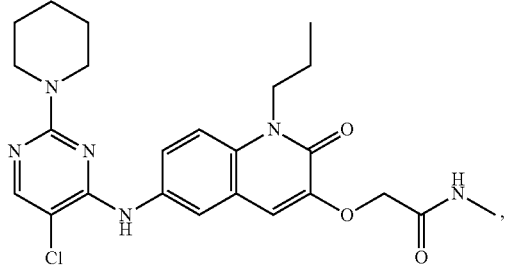
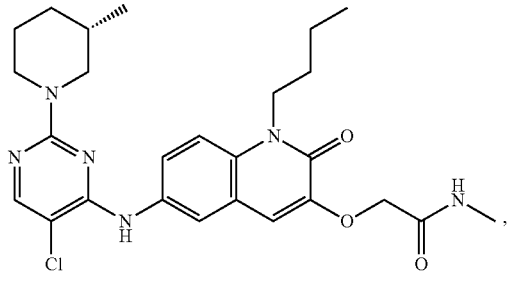

433
-continued
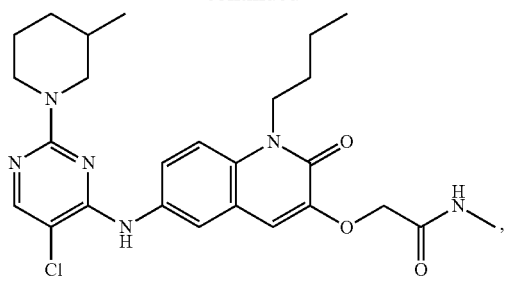
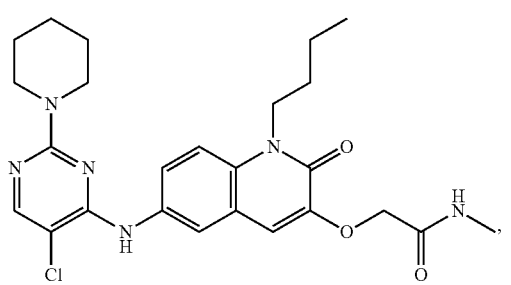
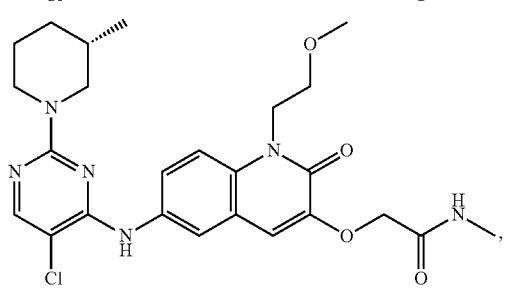
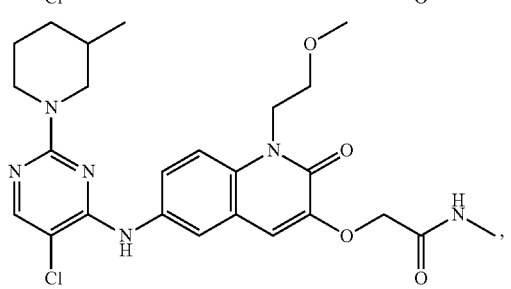
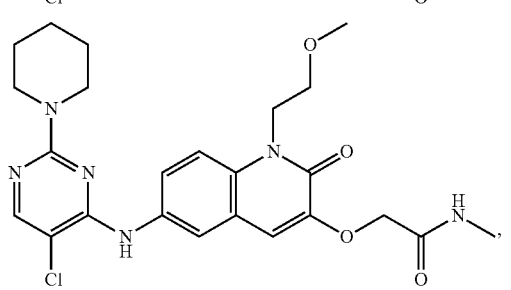
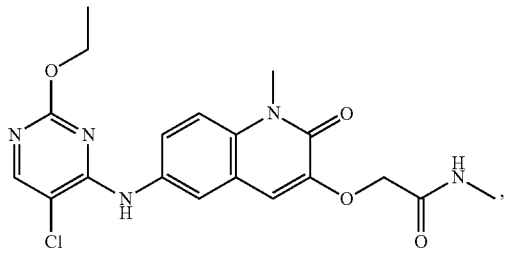
434
-continued
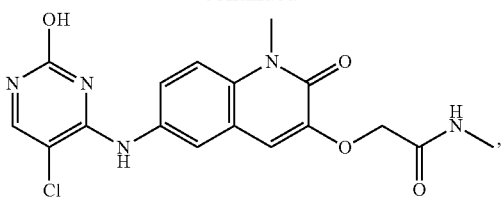
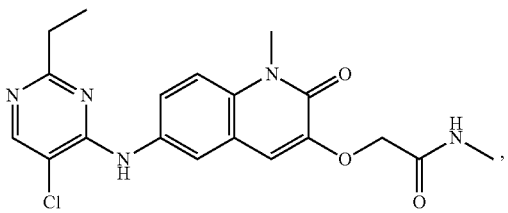
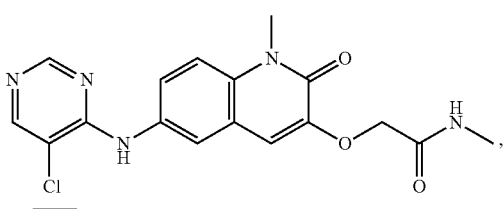
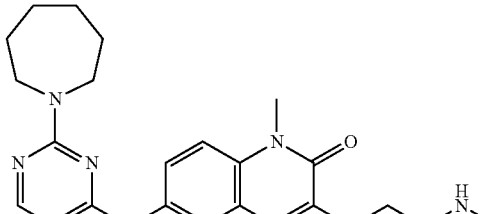
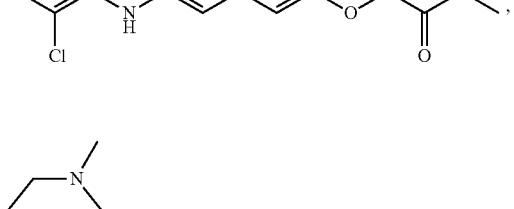
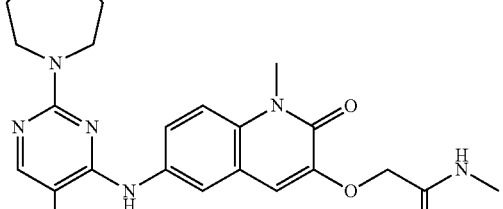
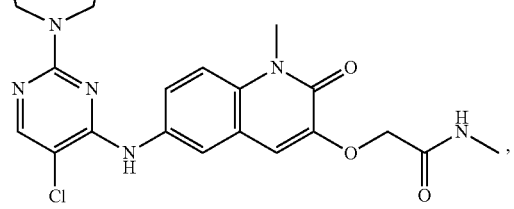

435
-continued
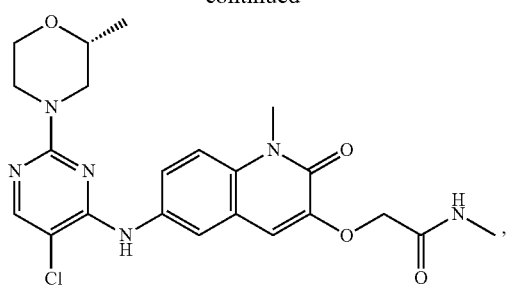
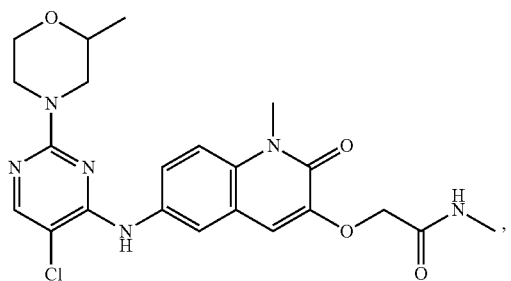
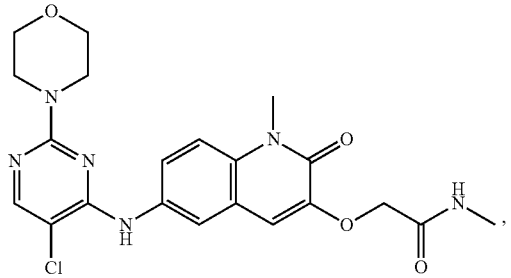
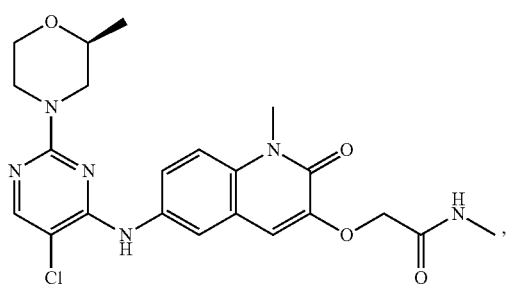
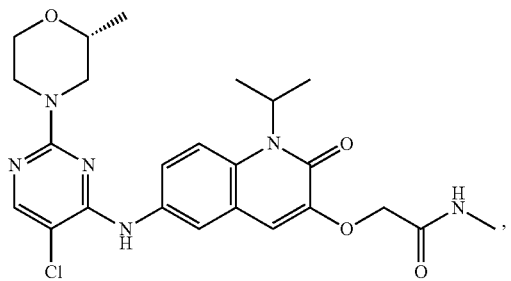
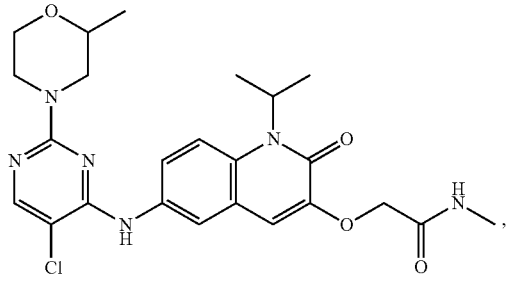
436
-continued
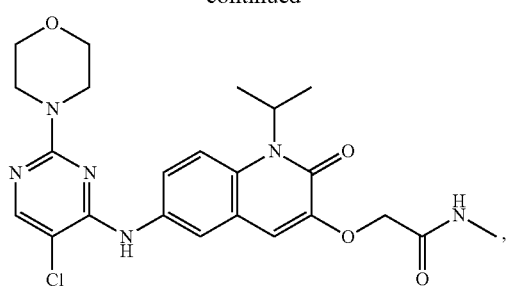
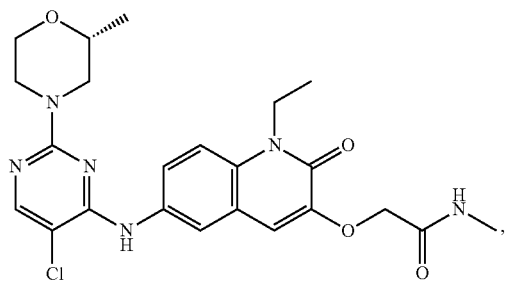
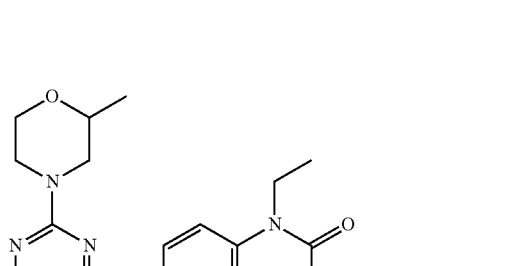
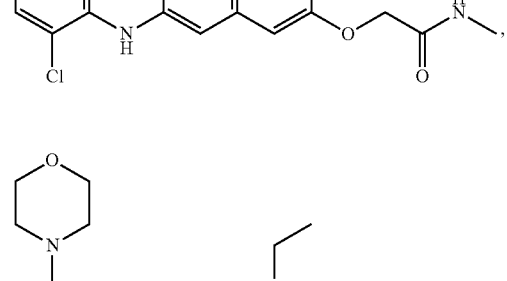
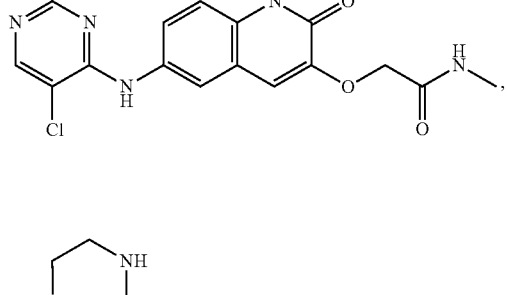
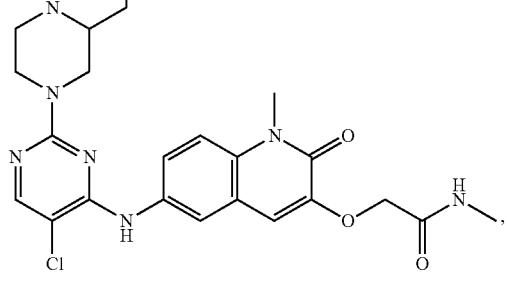

437
-continued
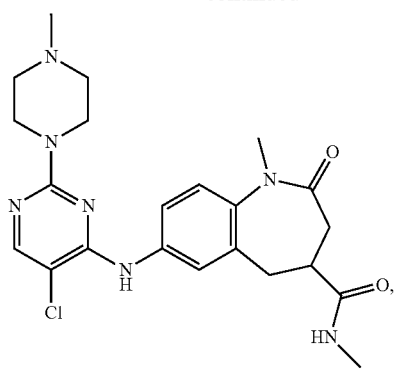
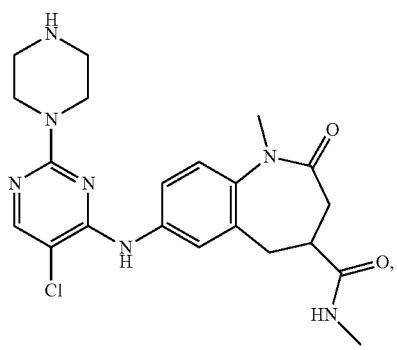
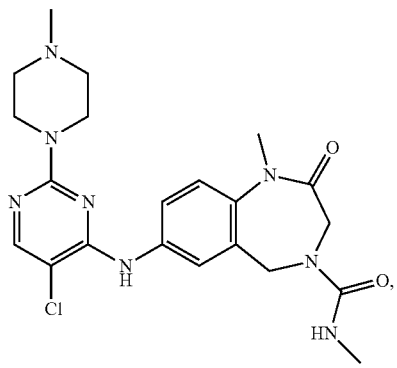
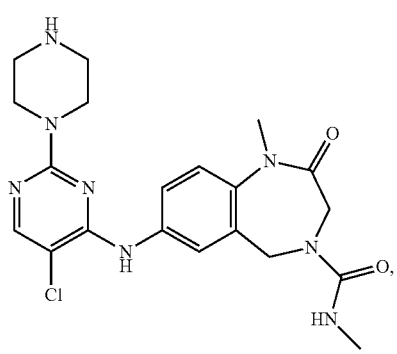
438
-continued
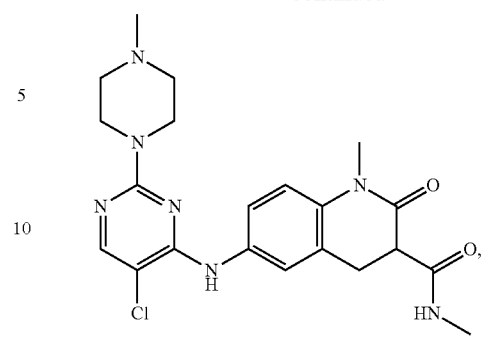
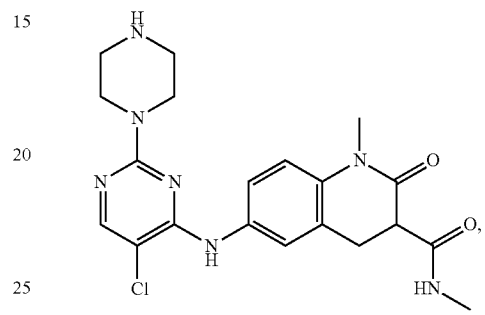
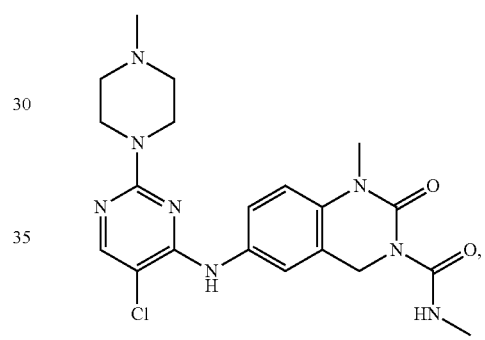
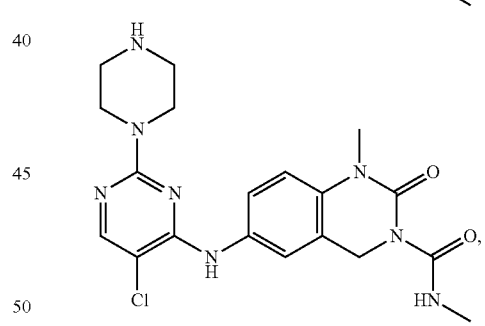
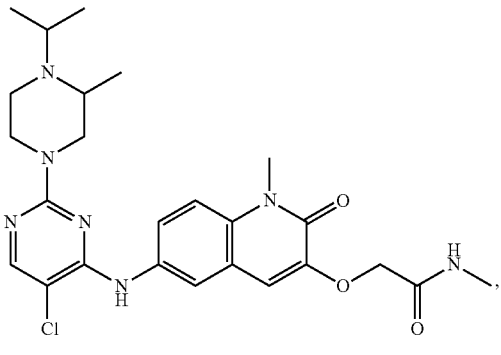

439
-continued
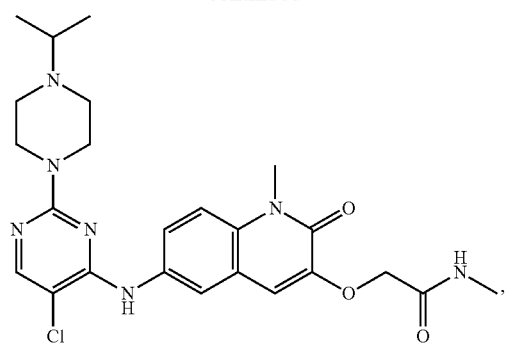
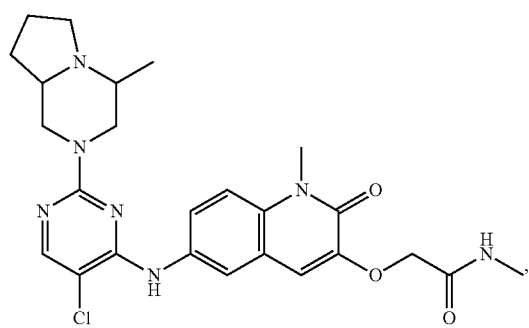
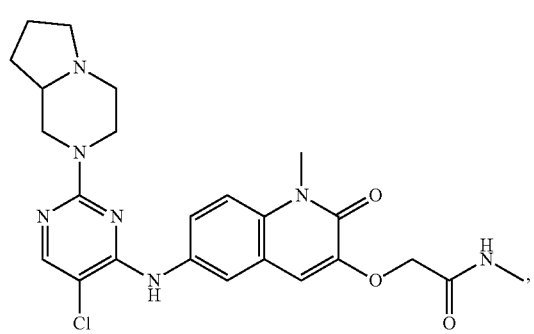
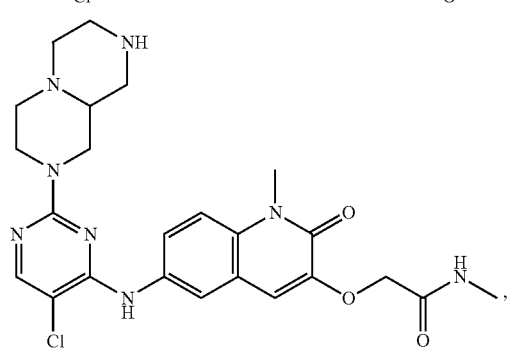
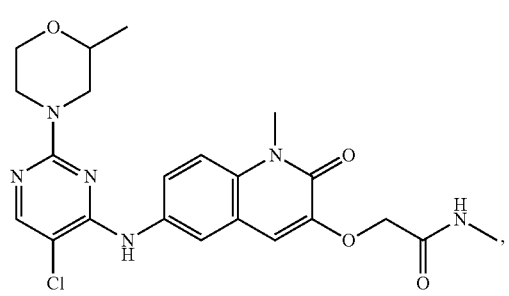
440
-continued
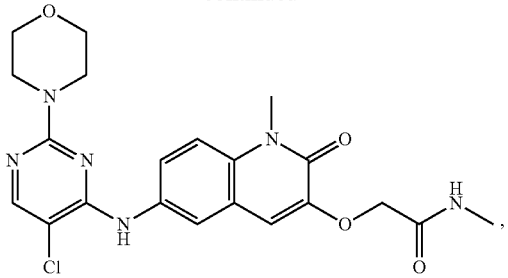
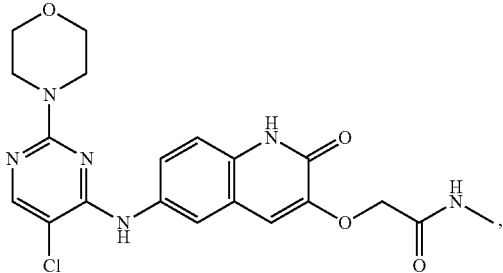
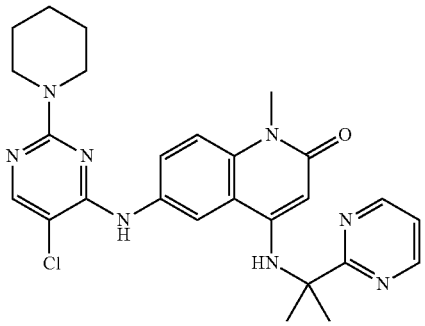
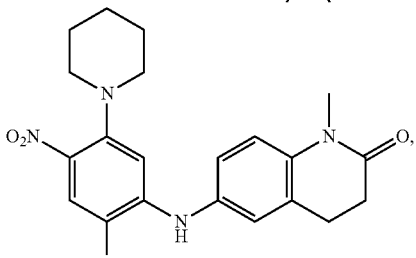
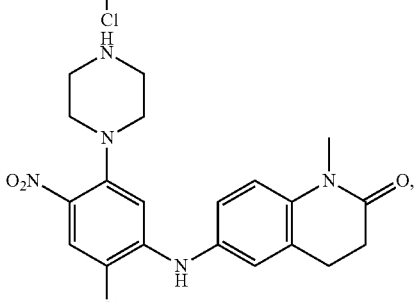
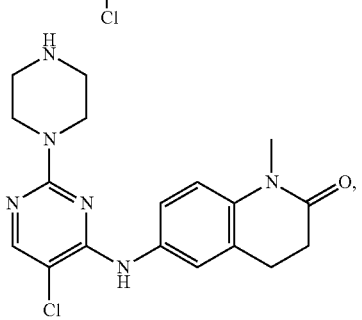

441
-continued
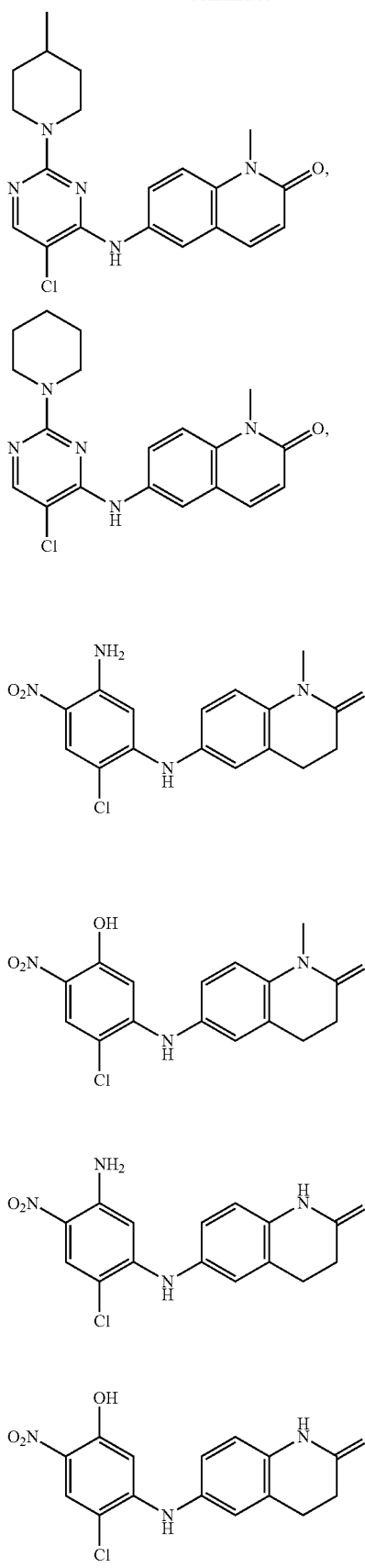
442
-continued
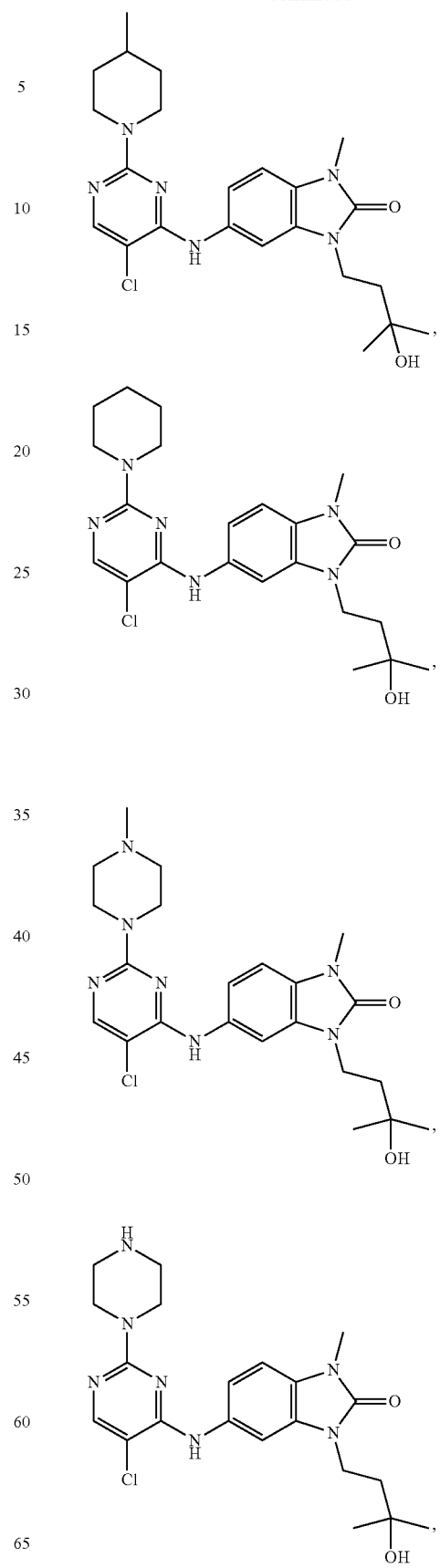

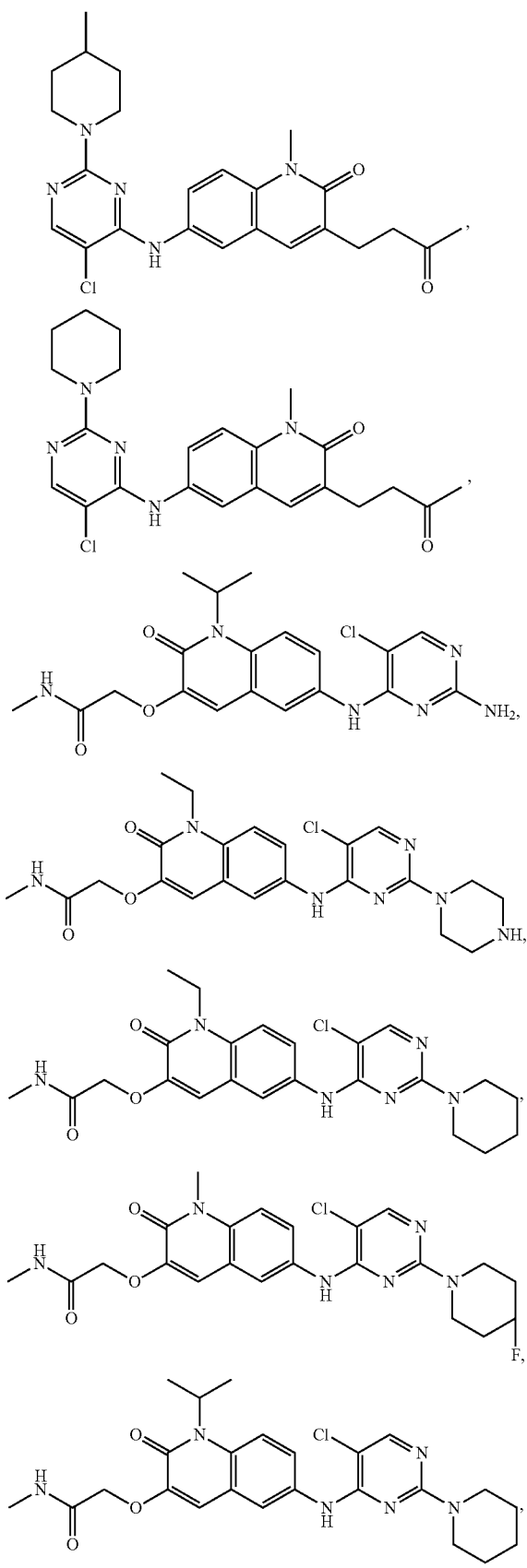
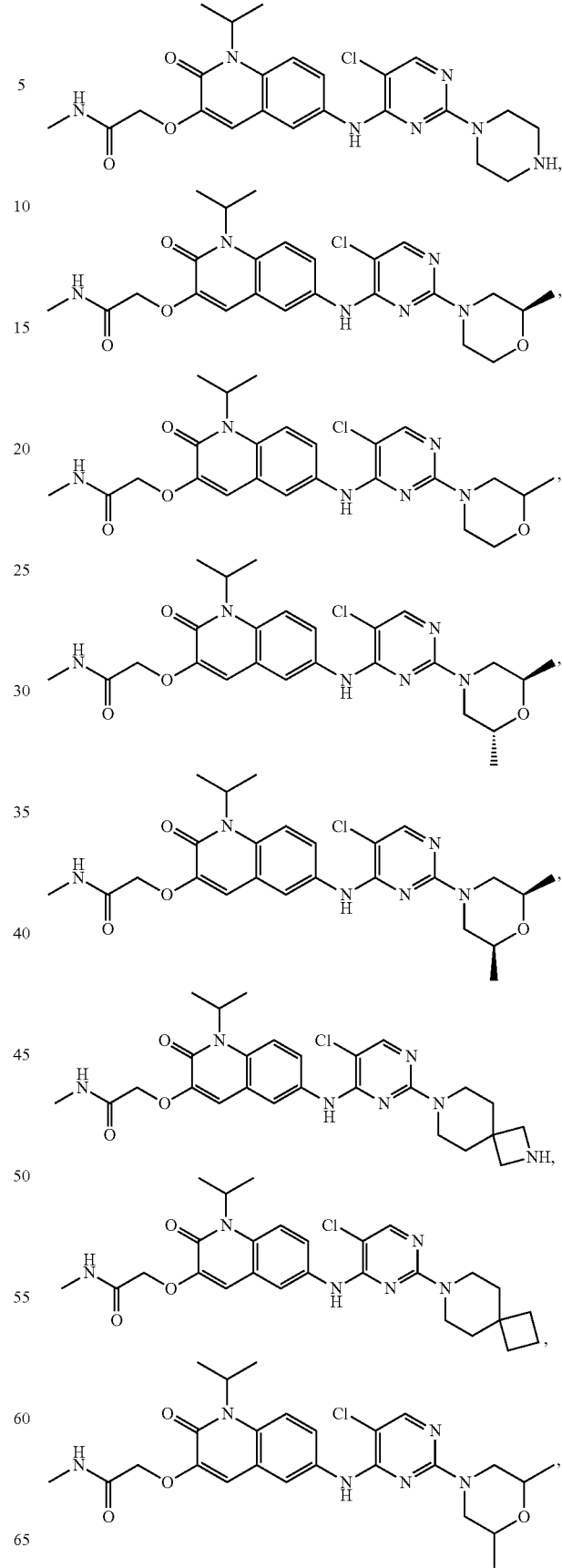

-continued
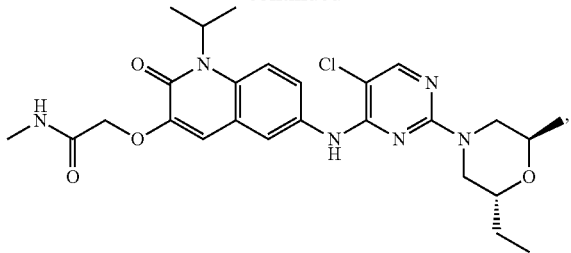
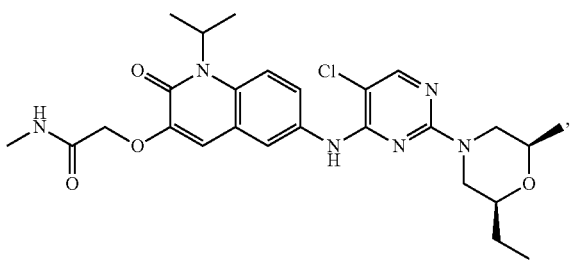
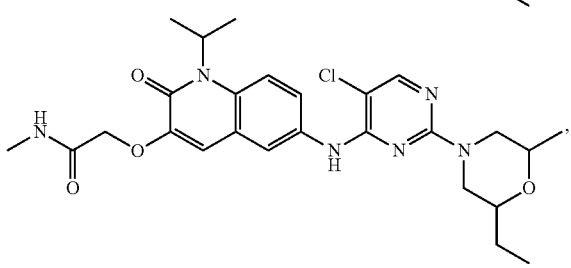
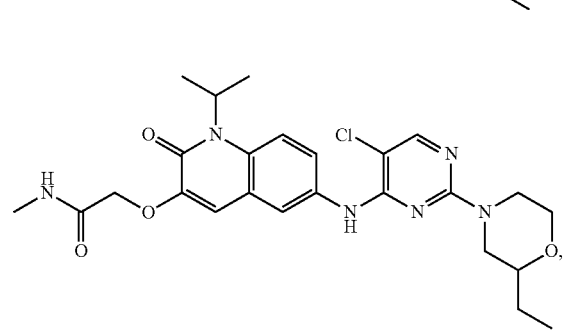
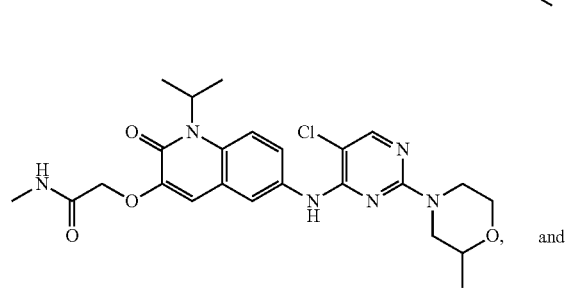, and
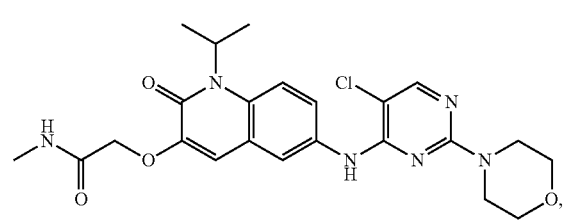
wherein ⌇ represents a bond that may be stereospecific ((R) or (S)) or non-stereospecific.
In any aspect or embodiment described herein, the PTM is selected from:
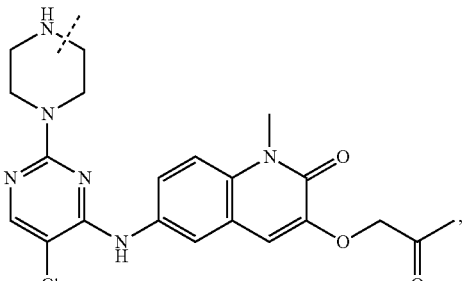
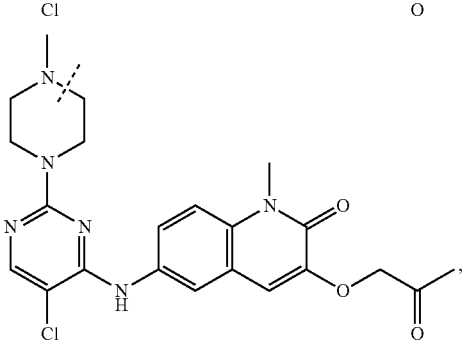
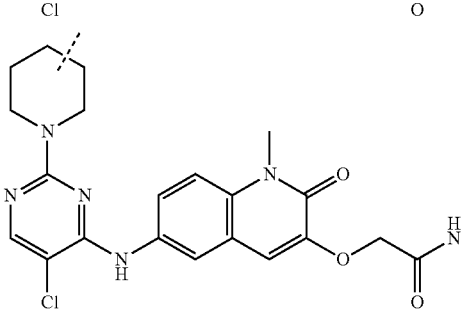
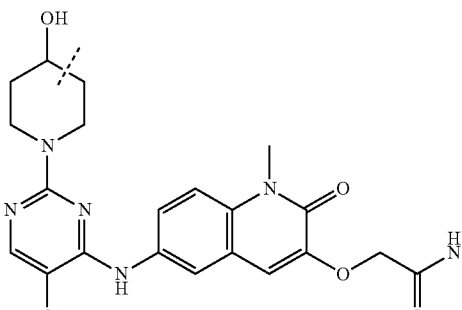
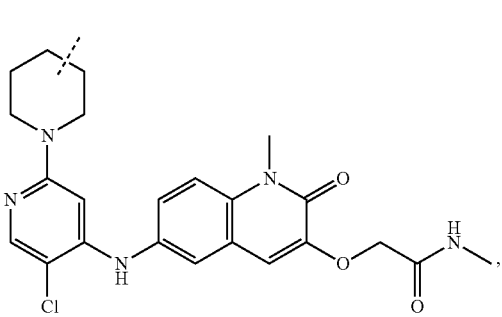

447
-continued
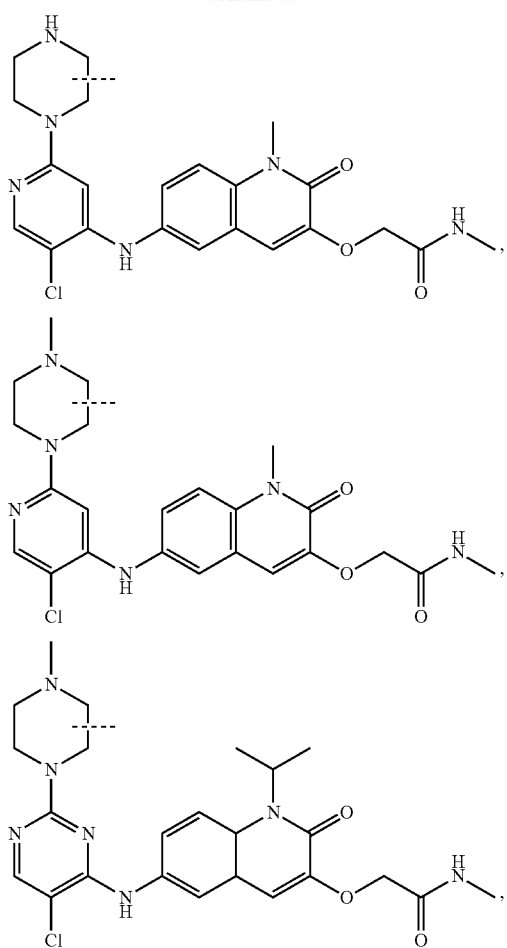
448
-continued
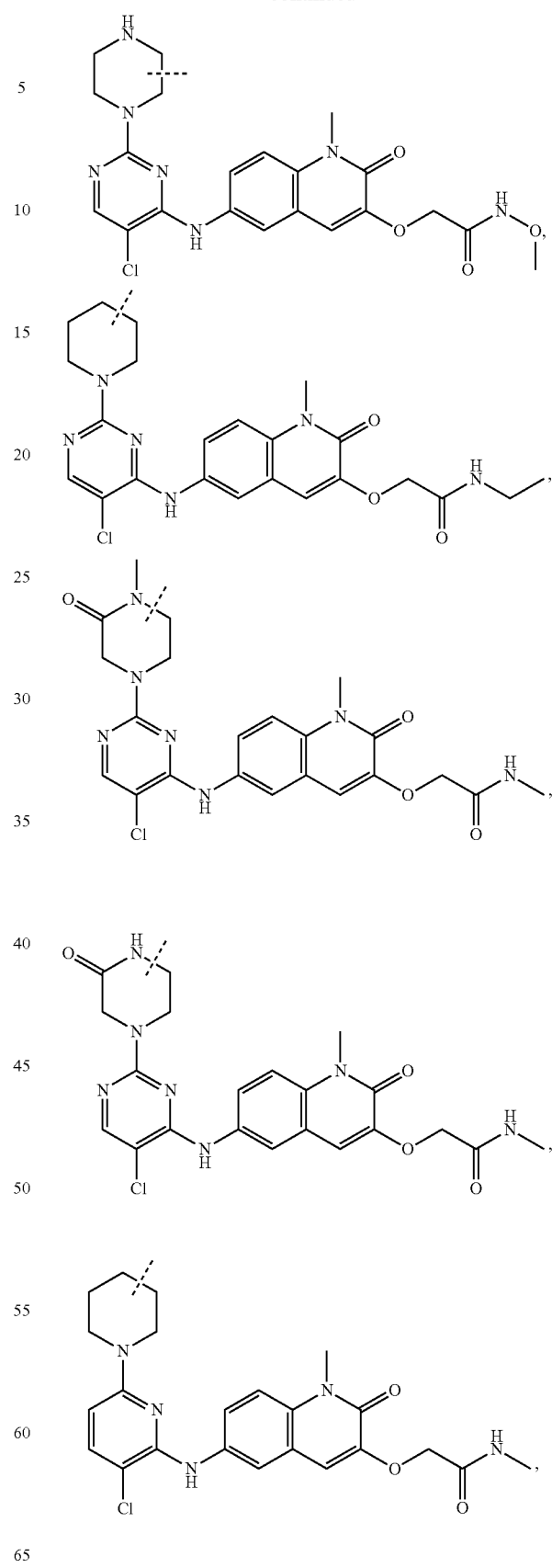

449
-continued
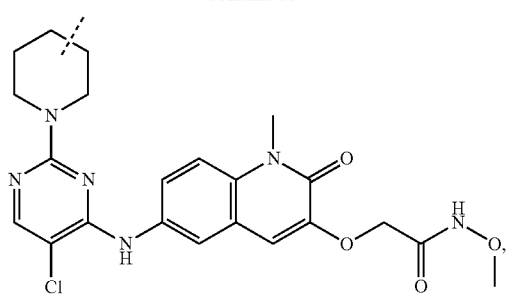
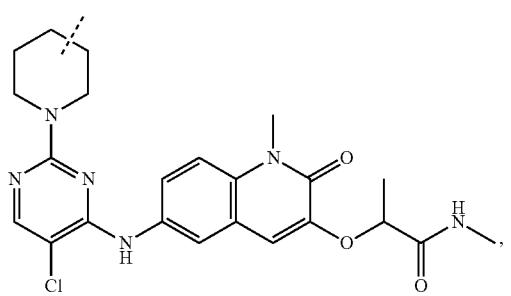
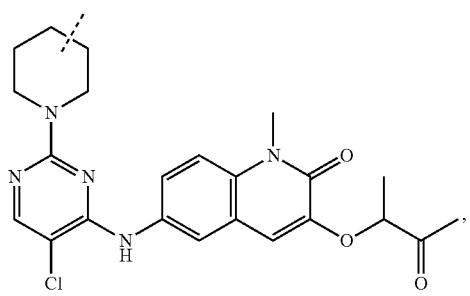
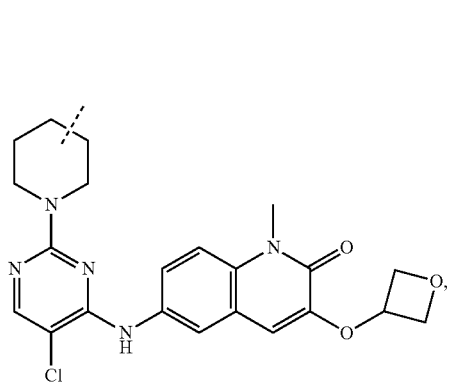
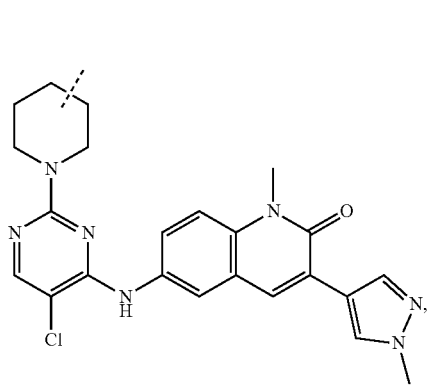
450
-continued
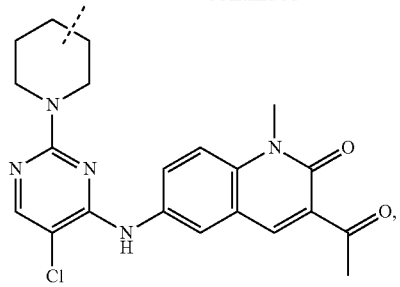
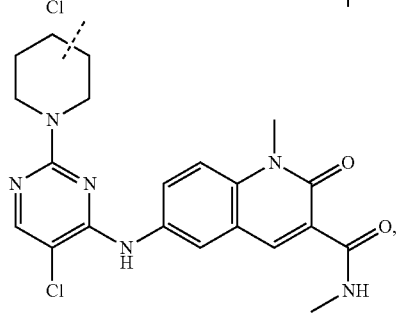
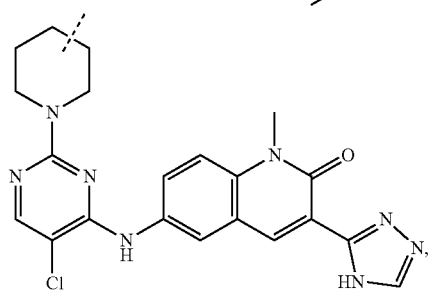
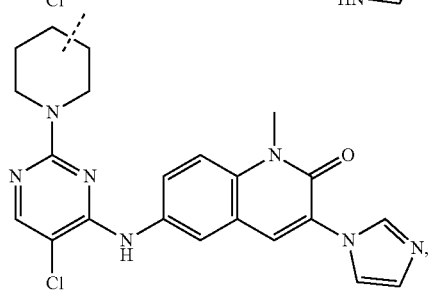
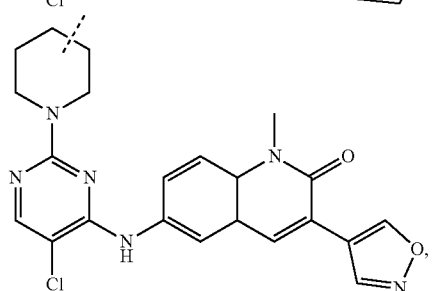
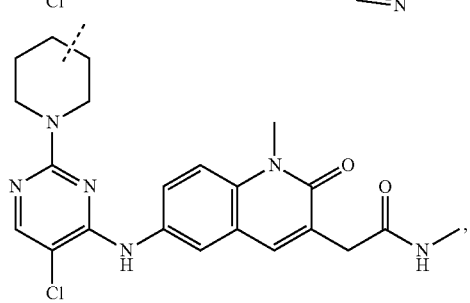

451
-continued
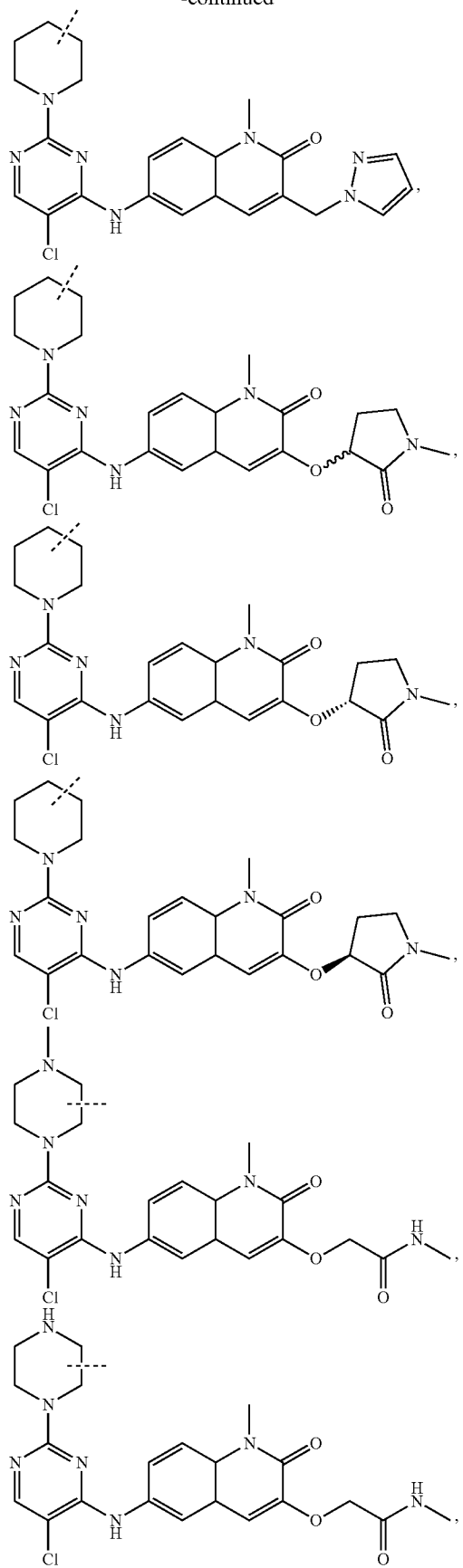
452
-continued
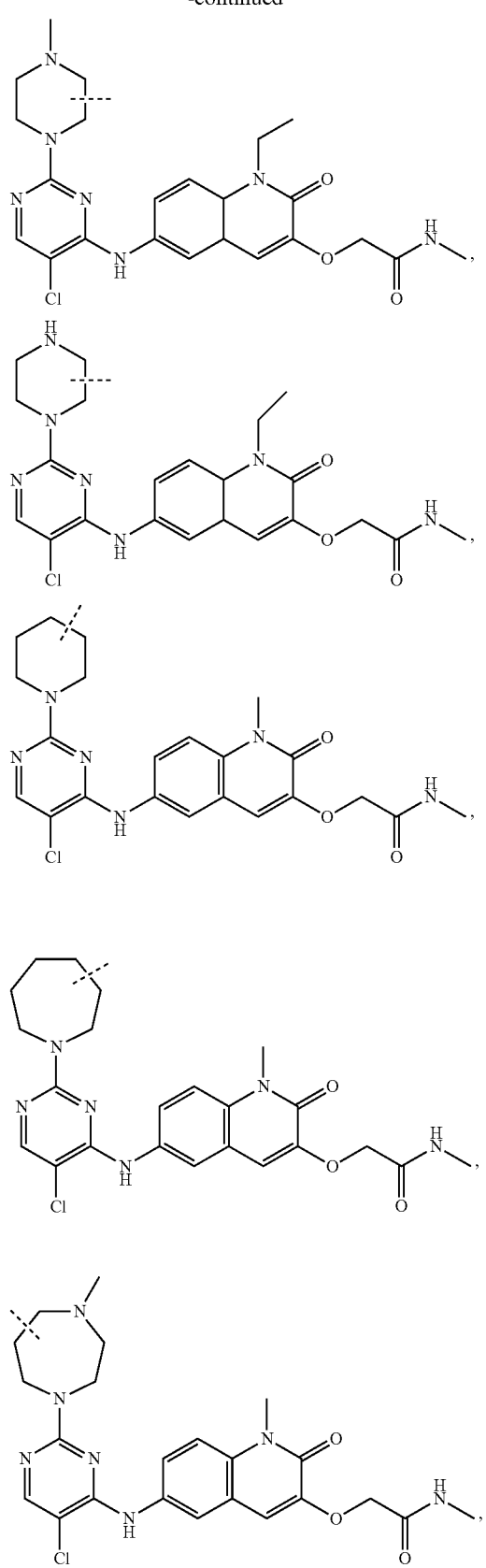

-continued
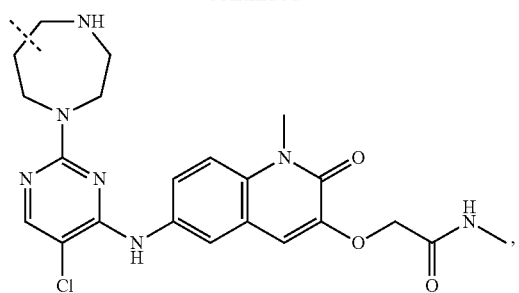
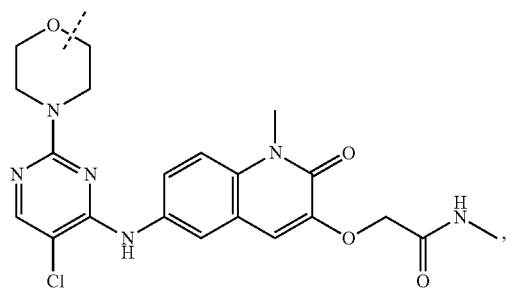
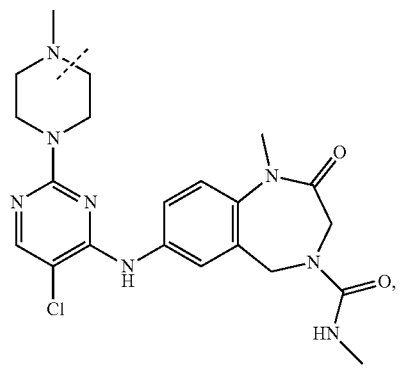
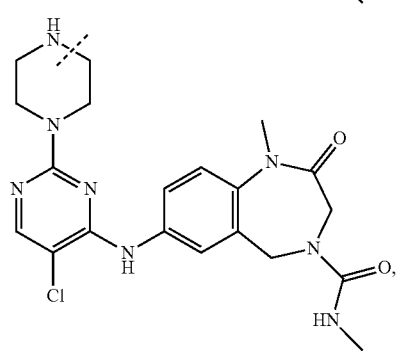
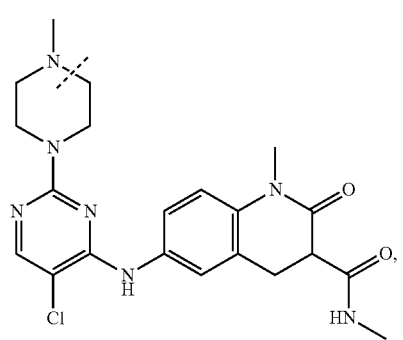
-continued
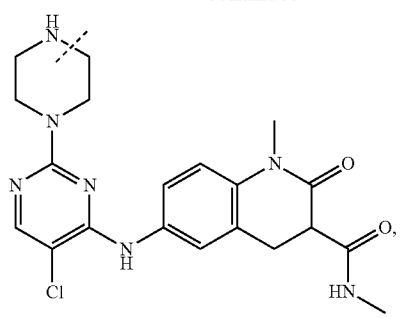
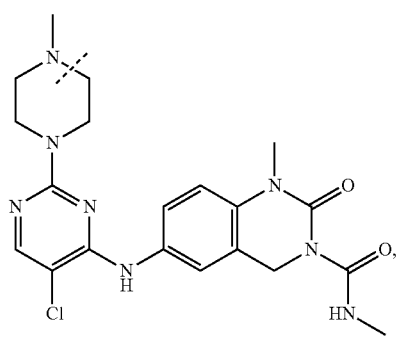
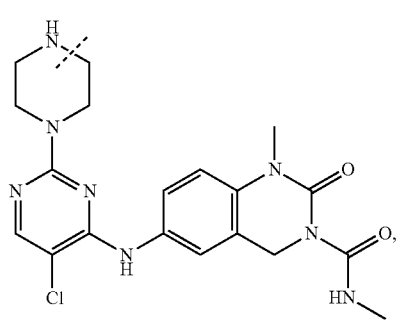
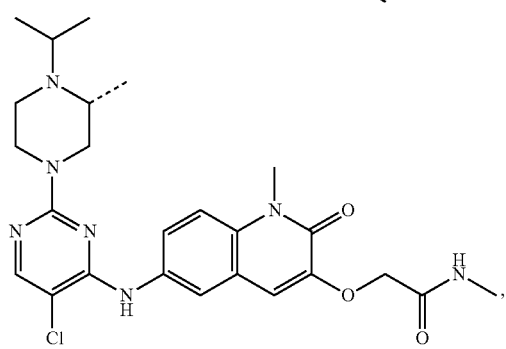
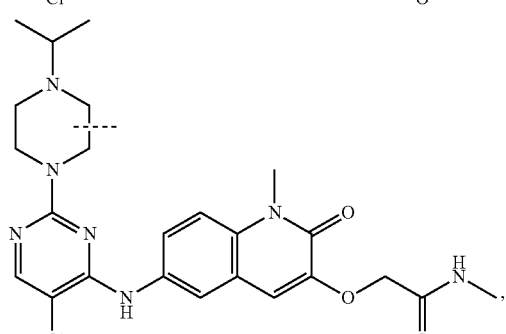

-continued
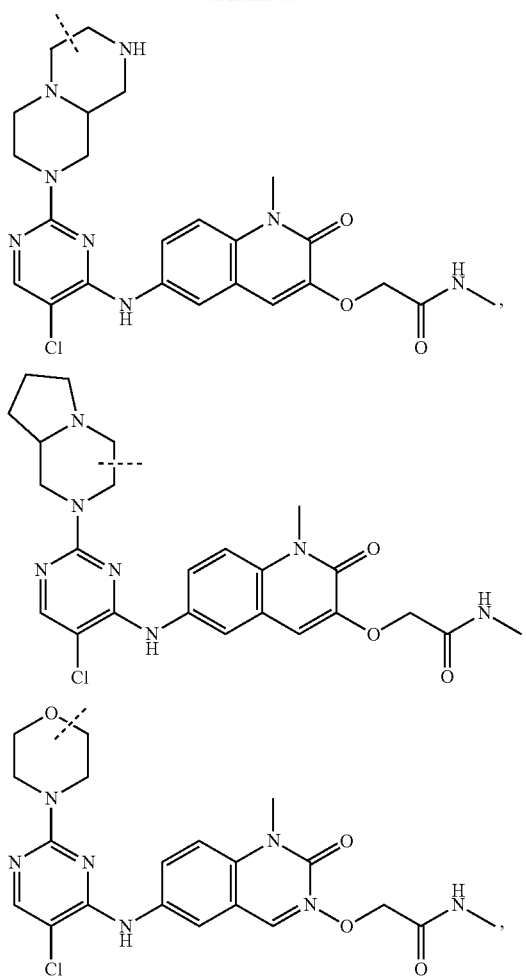
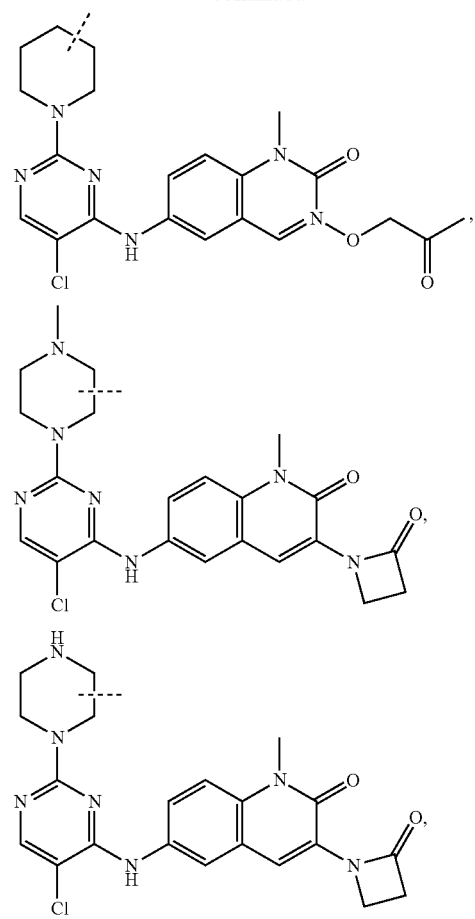
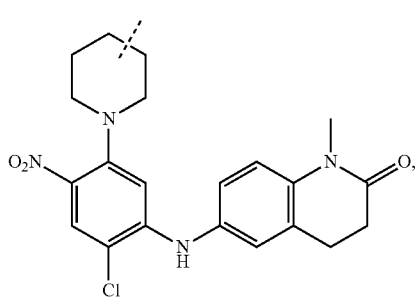
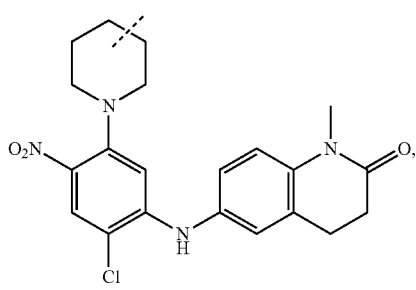
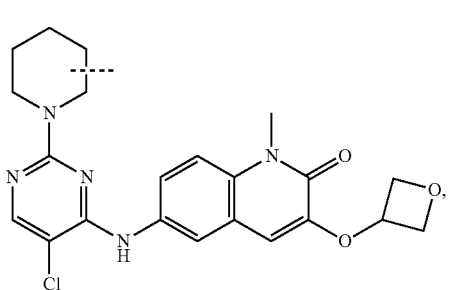

457
-continued
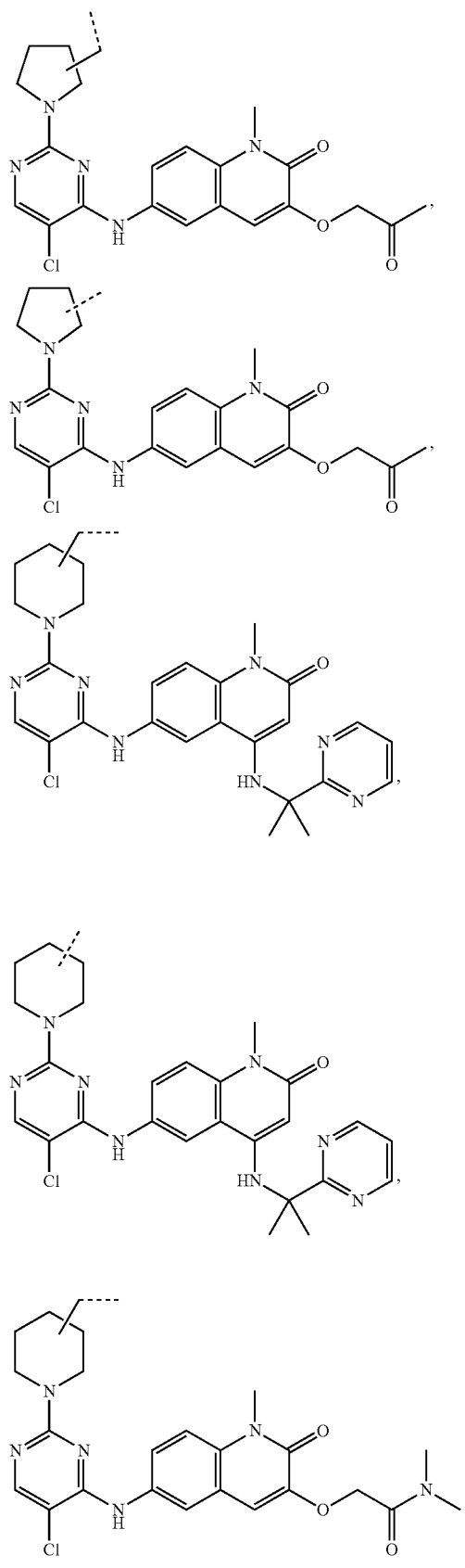
458
-continued
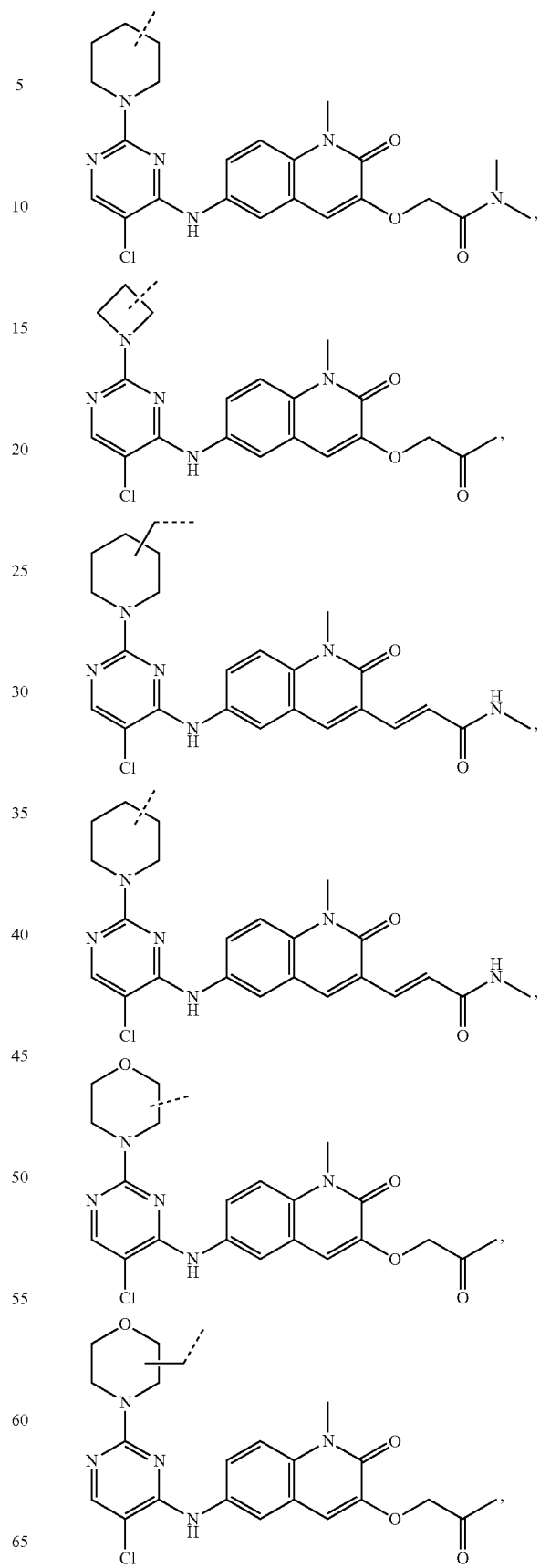

459
-continued
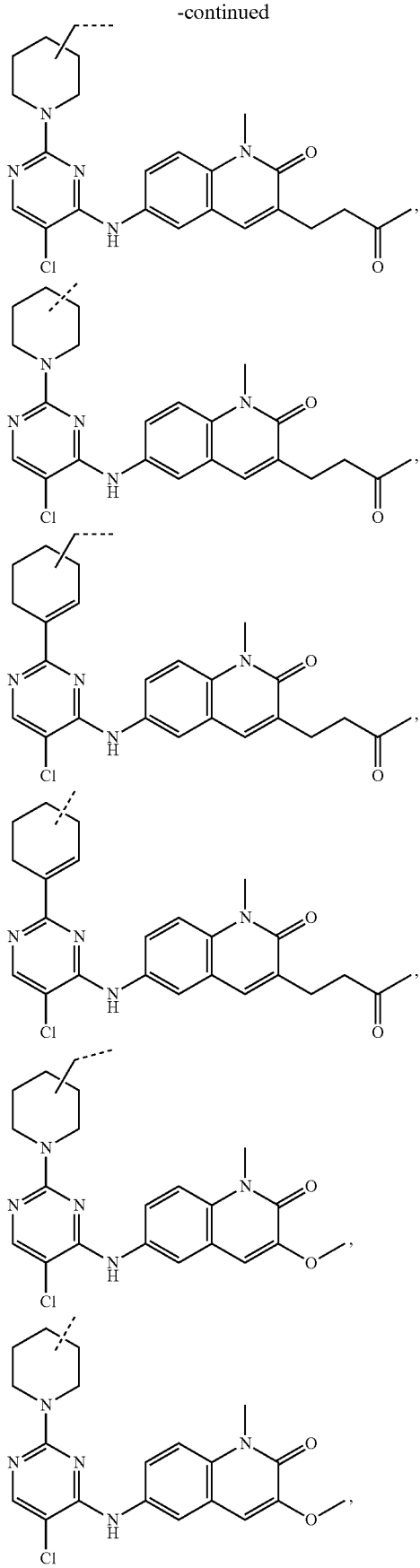
460
-continued
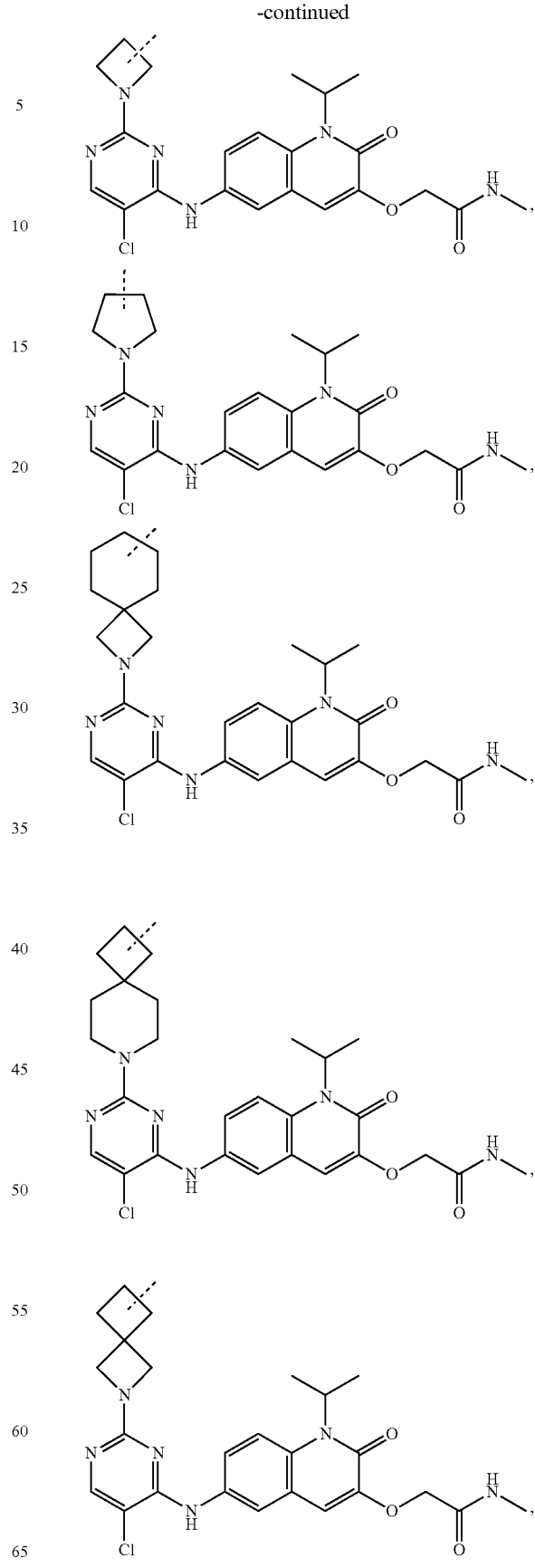

461
-continued
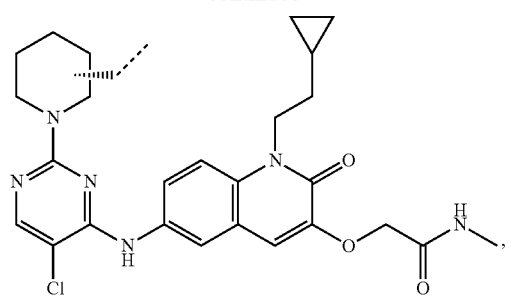
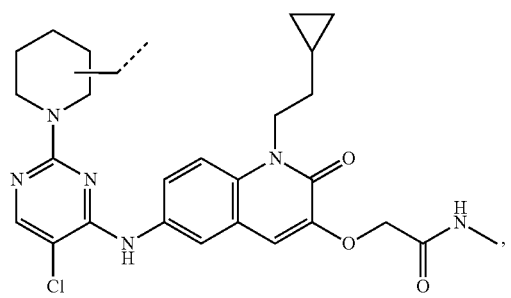
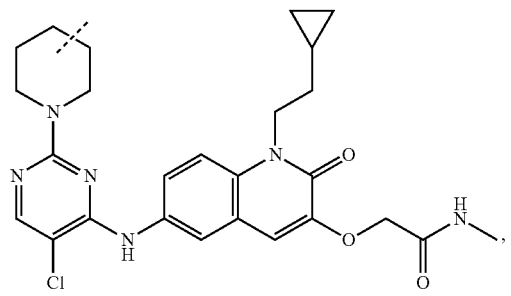
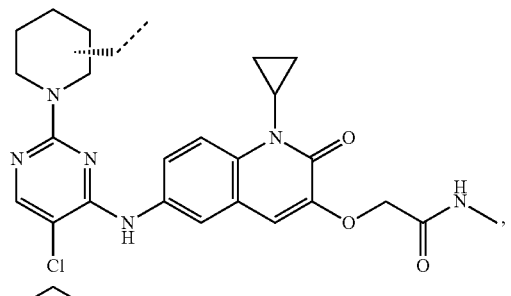
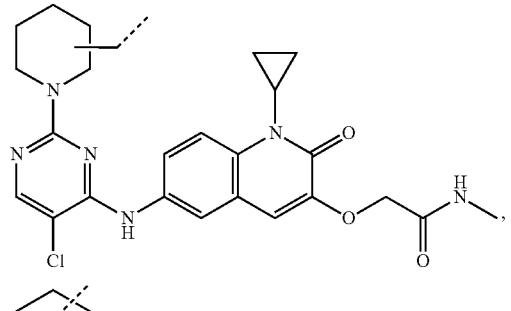
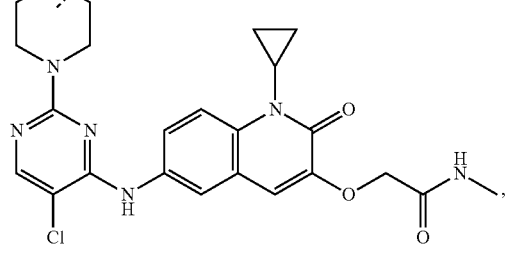
462
-continued
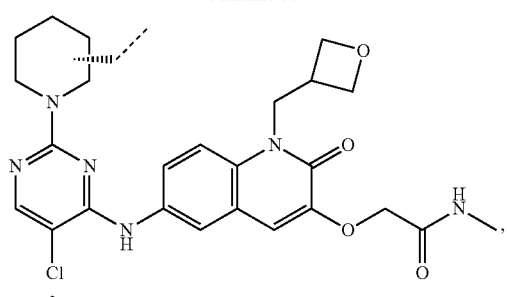
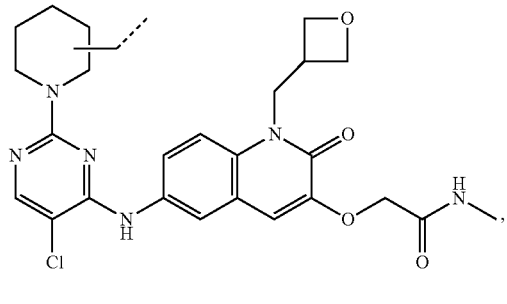
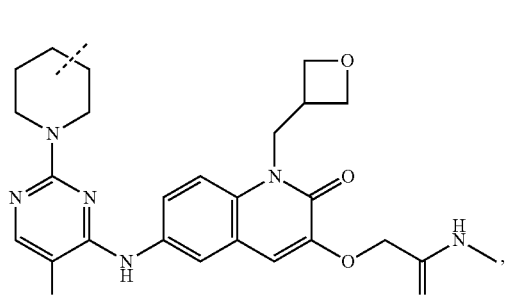

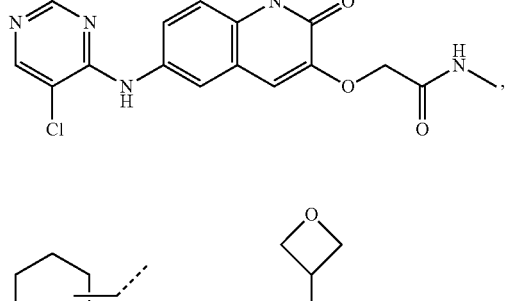
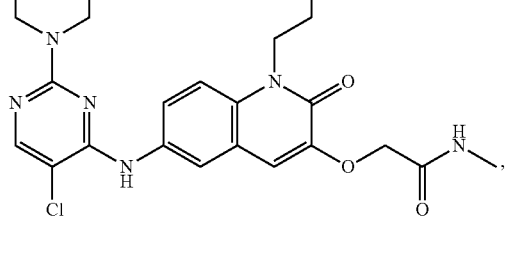

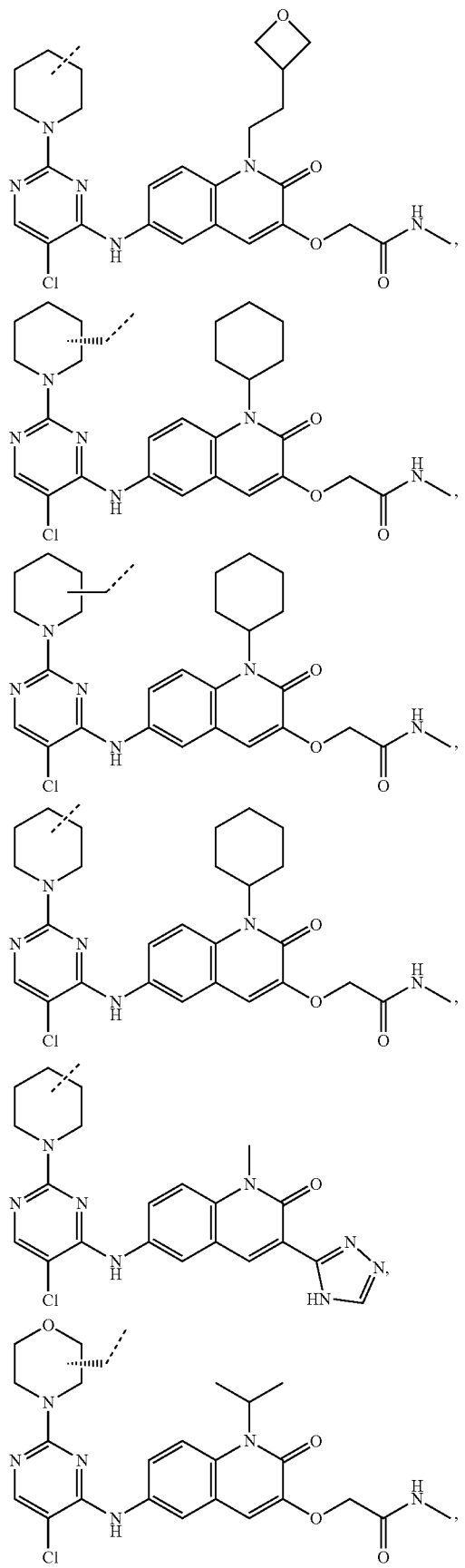
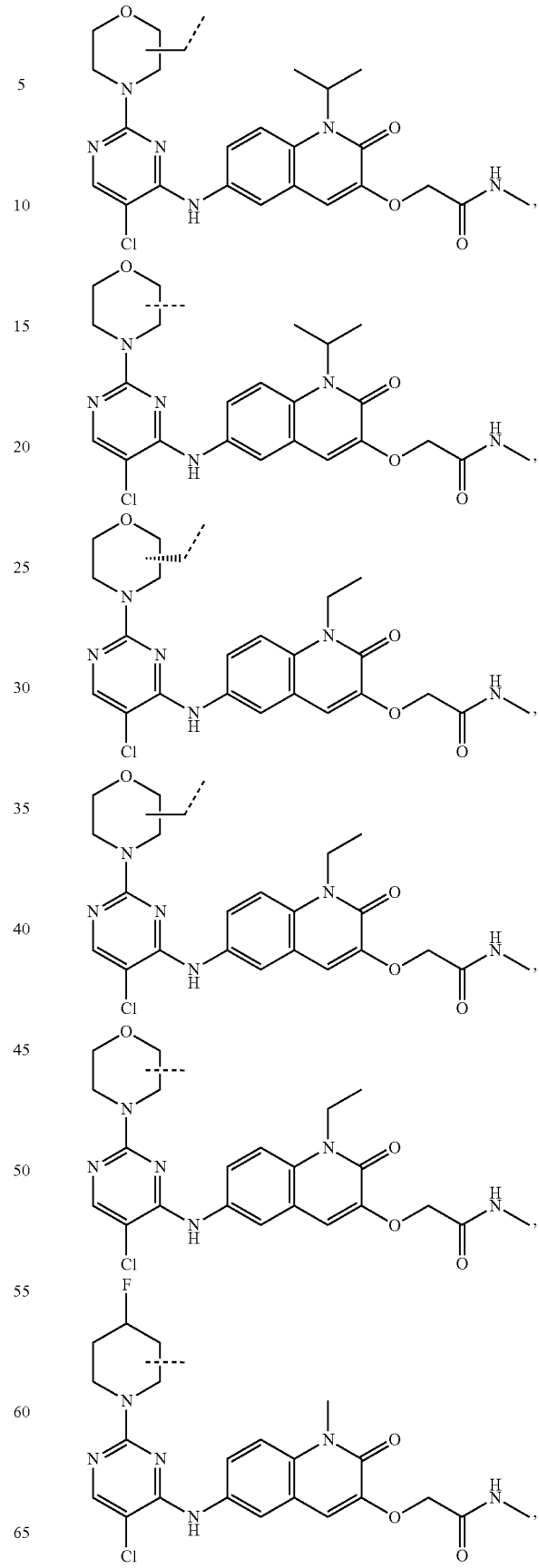

465
-continued
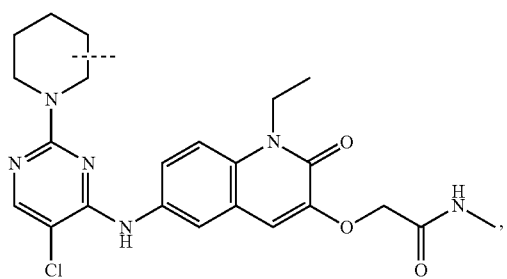
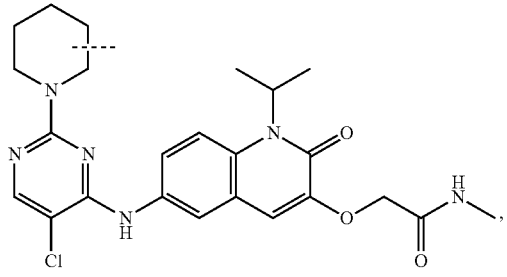
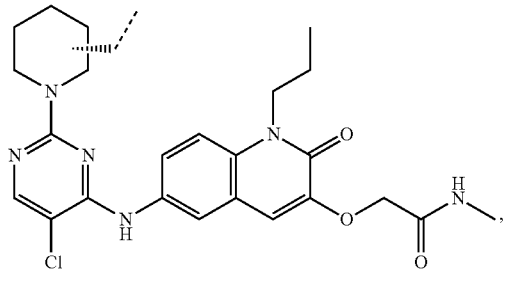
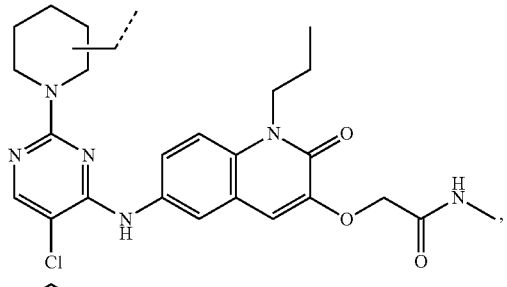
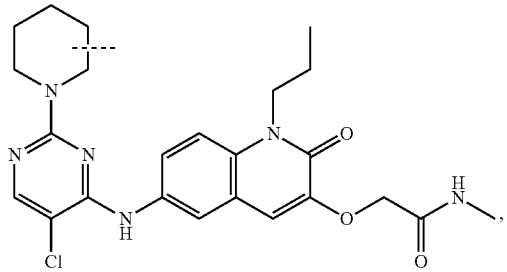
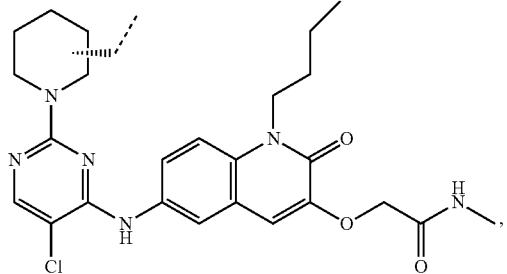
466
-continued
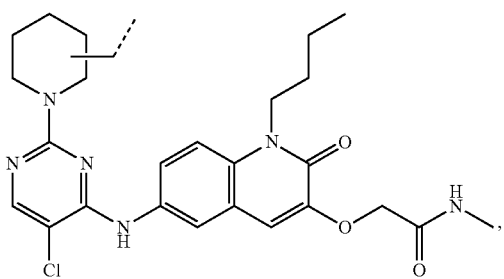
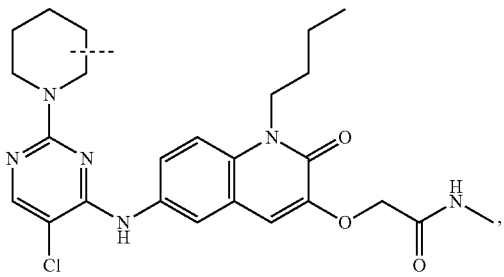
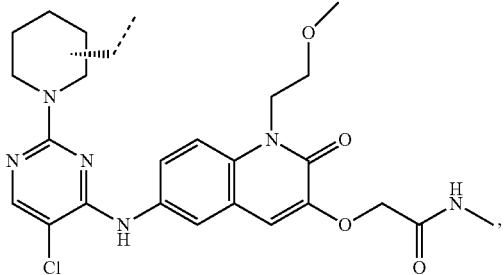
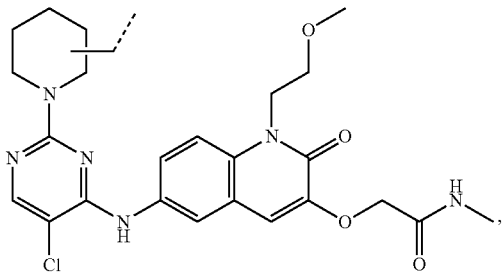
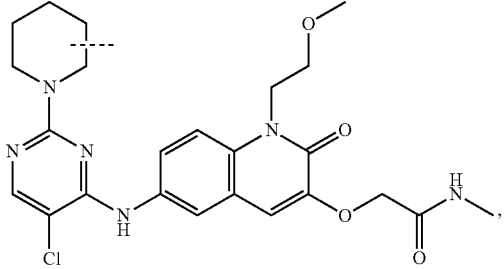
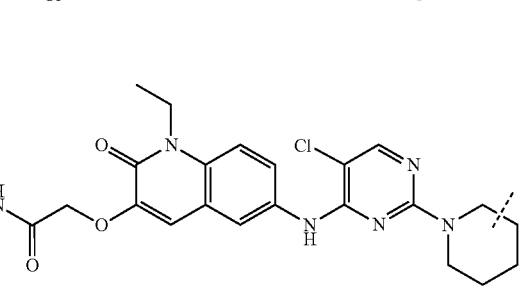

467
-continued
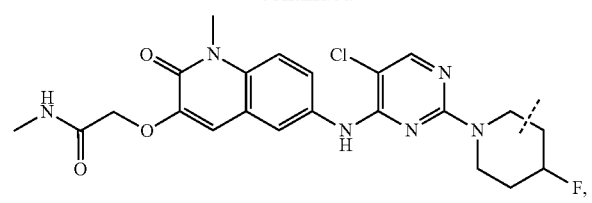
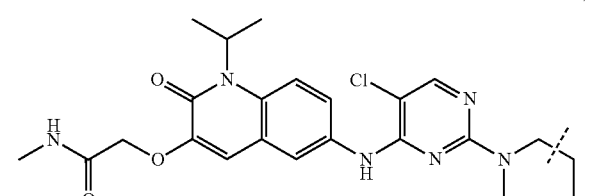
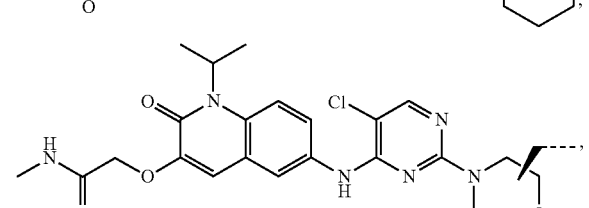
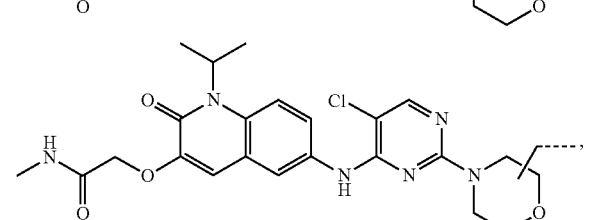

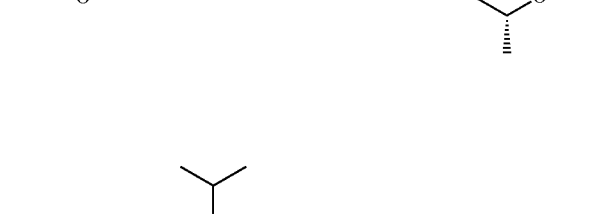
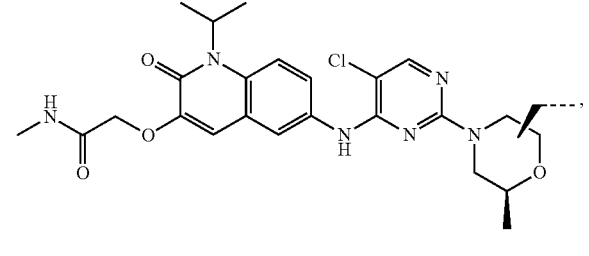
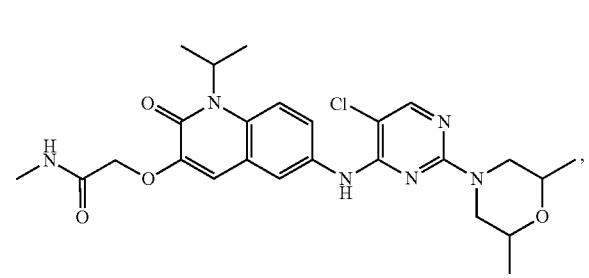
468
-continued
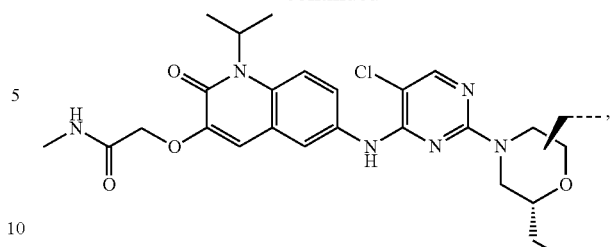

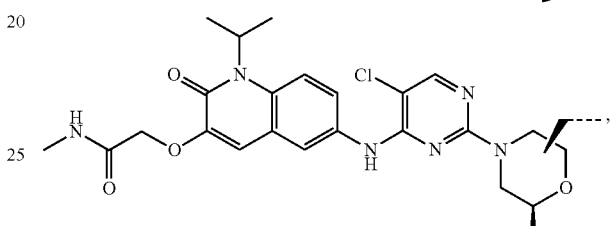
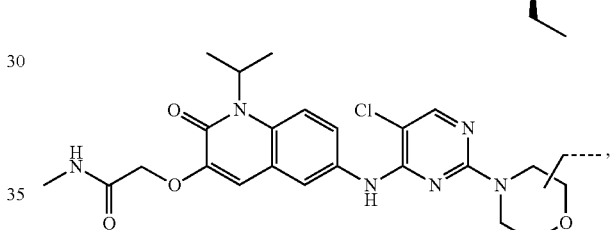
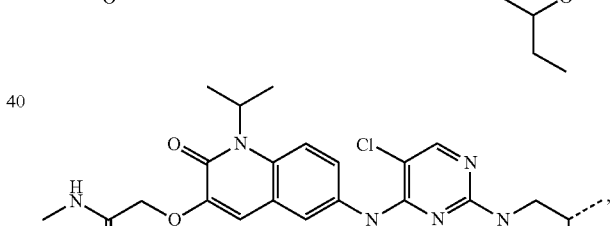
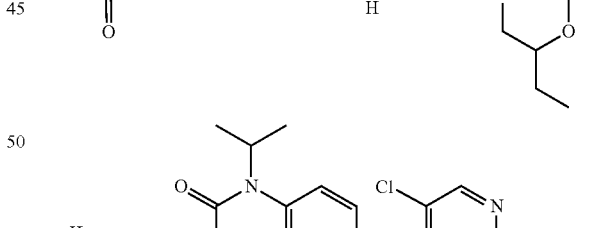
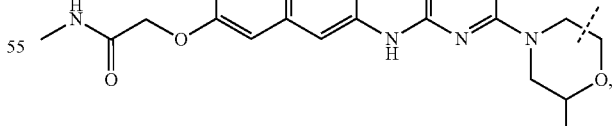
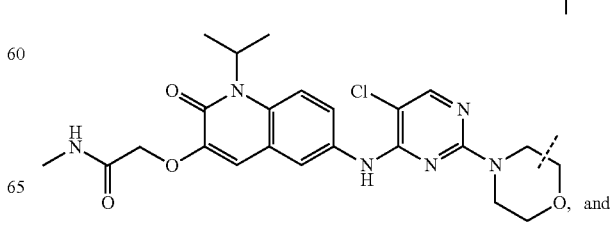
, and

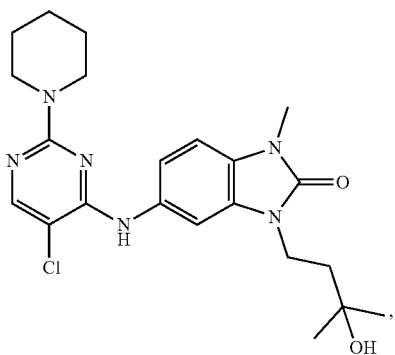
wherein --- of the PTM indicates the point of attachment with a linker group (L) or a ULM; and ⌇ represents a bond that may be stereospecific ((R) or (S)) or non-stereospecific.
In any aspect or embodiment described herein, the PTM is selected from:
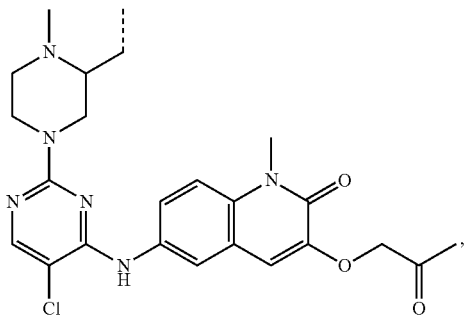
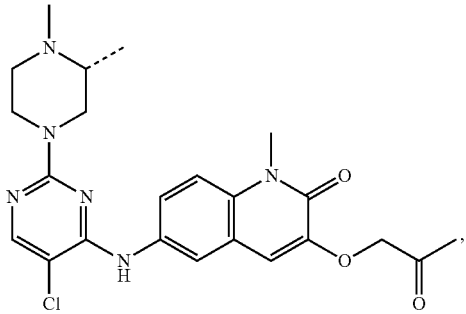
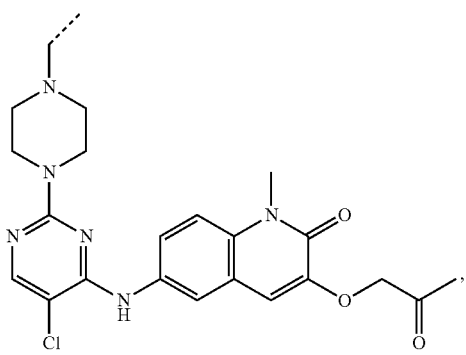
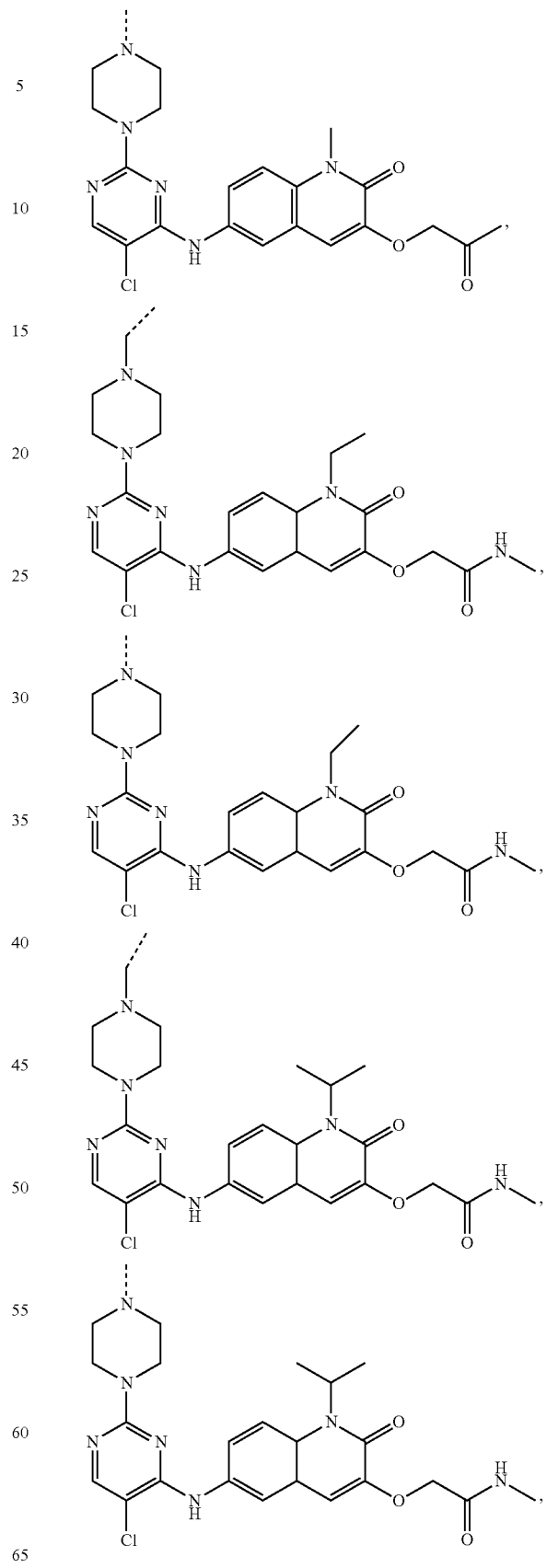

471
-continued
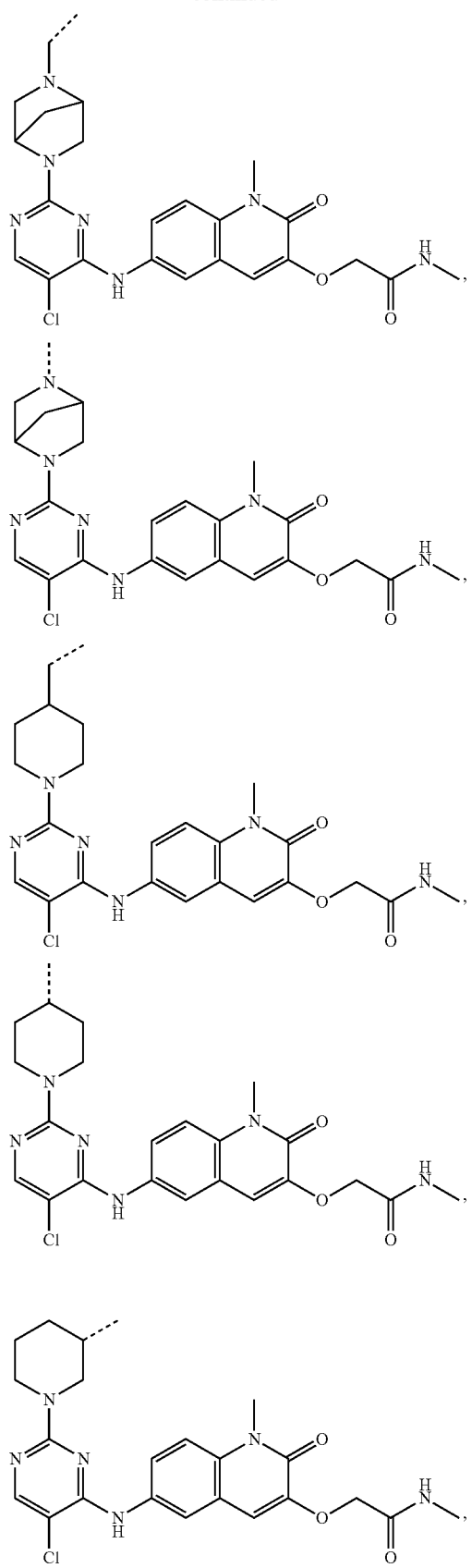
472
-continued
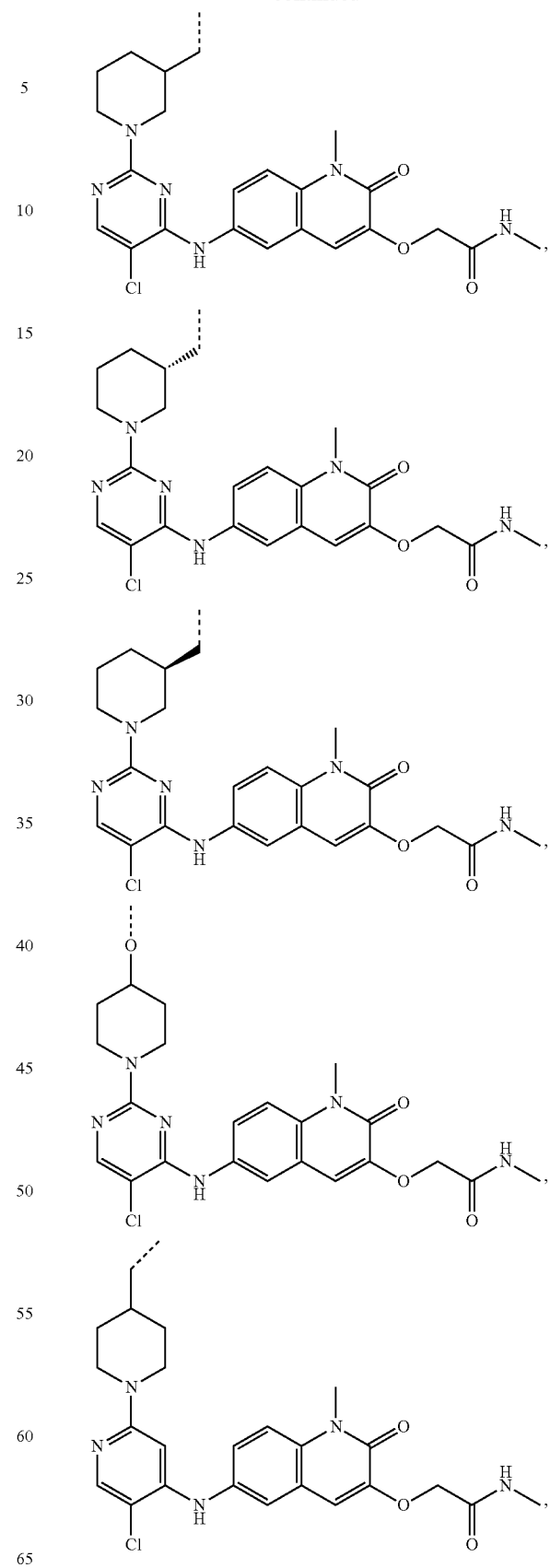

473
-continued
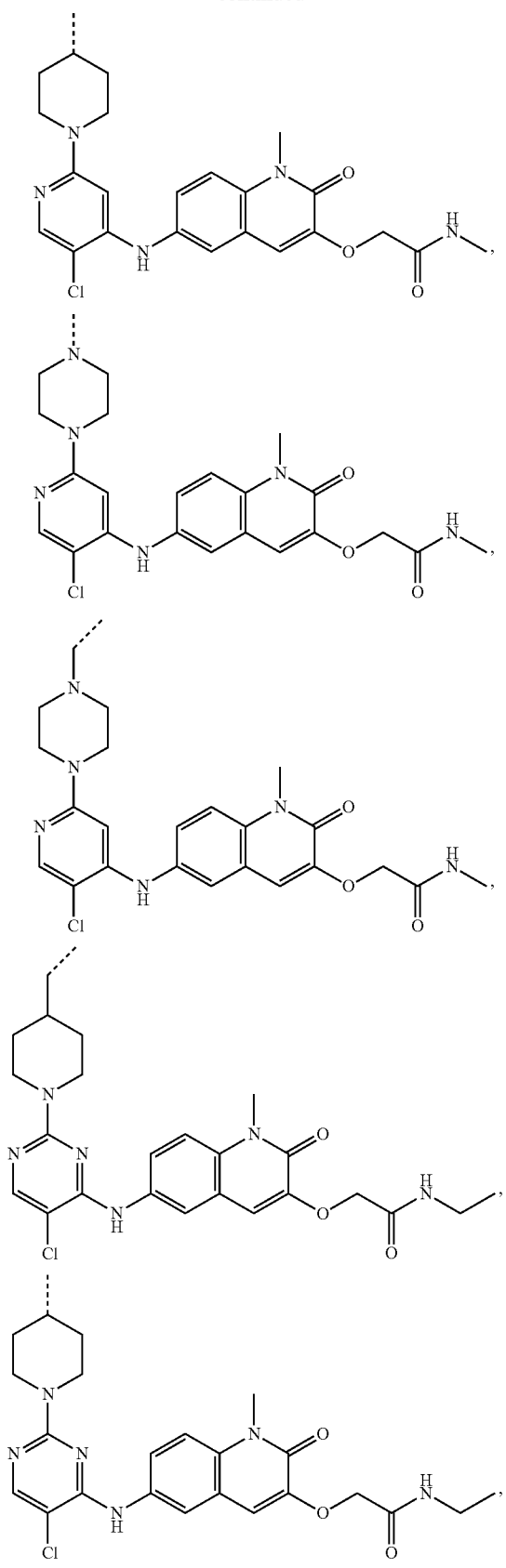
474
-continued
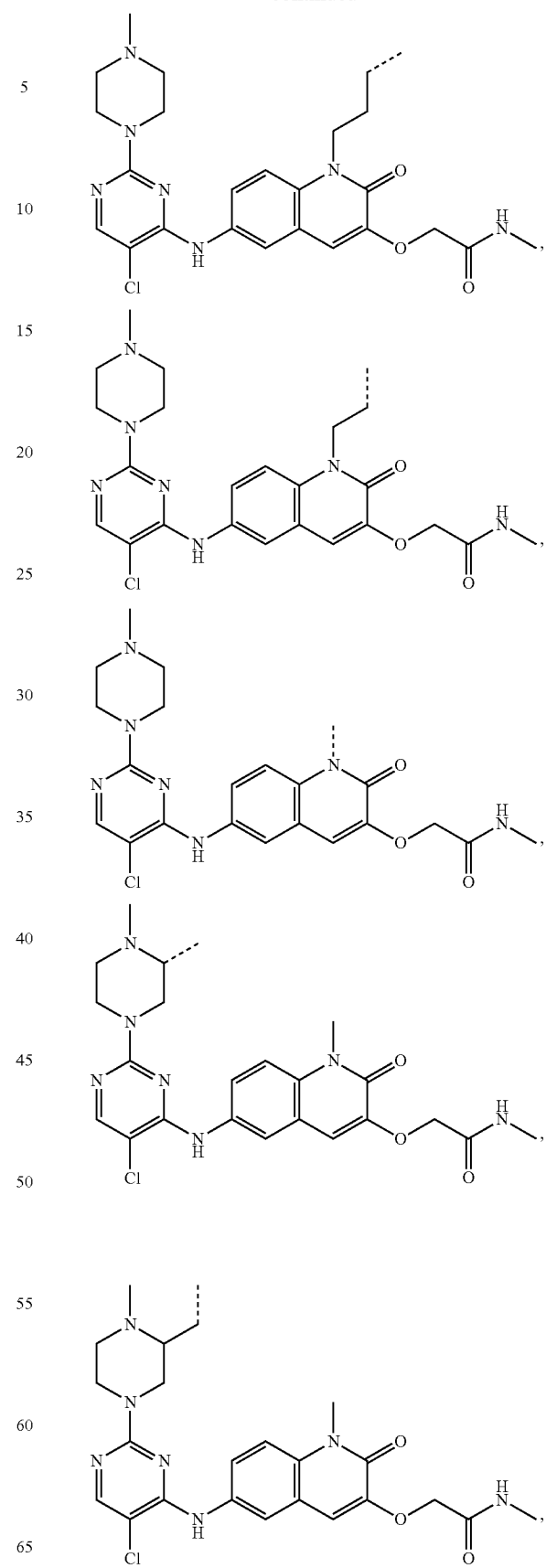

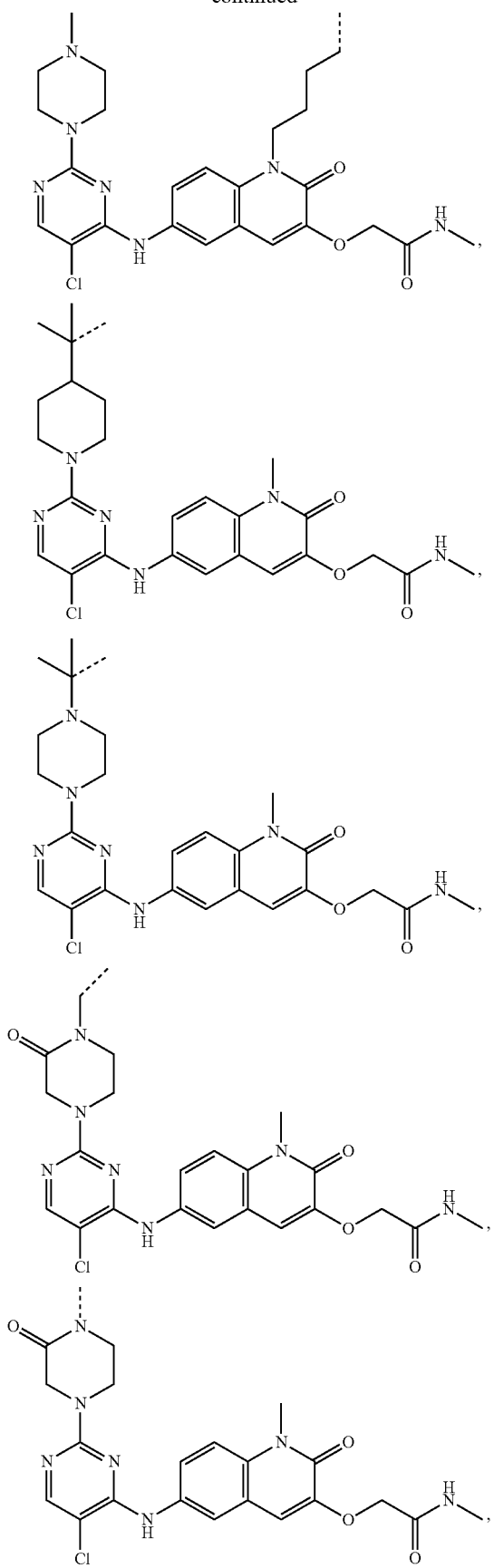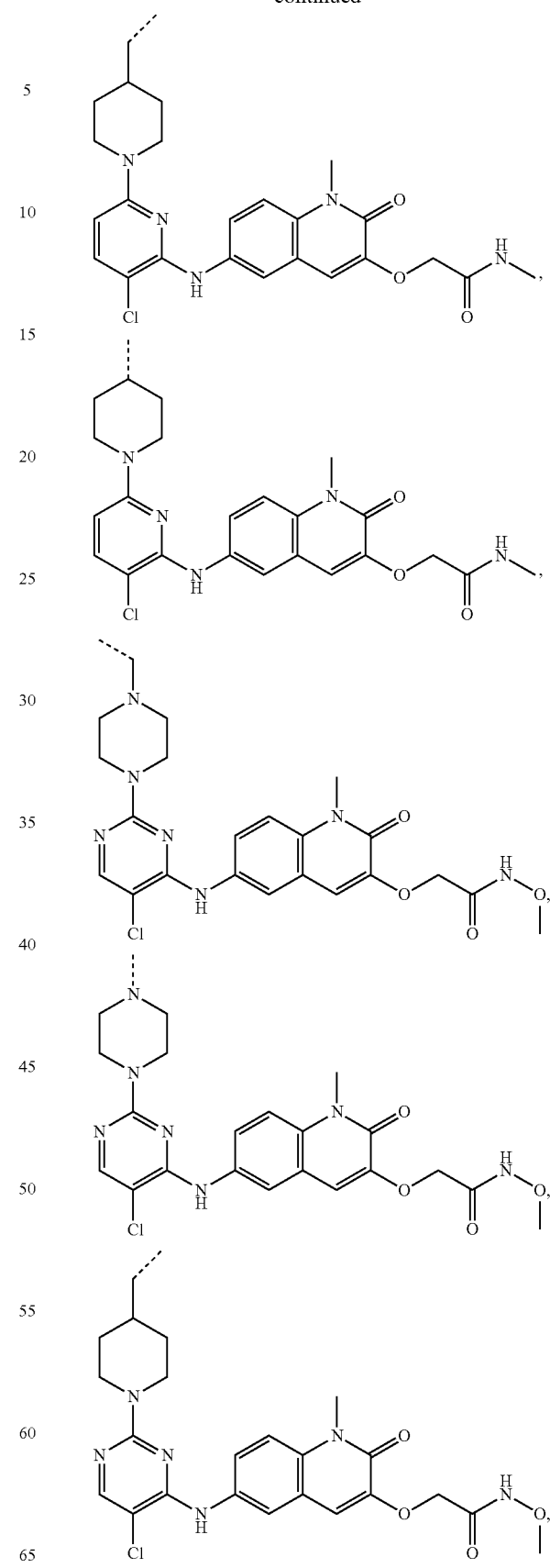

477
-continued
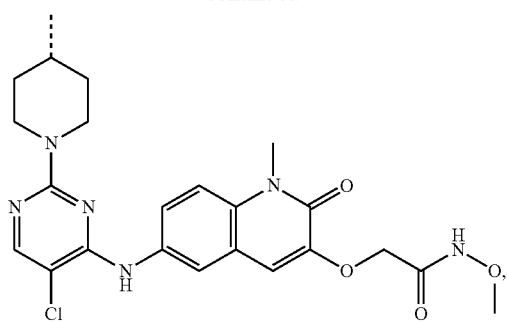
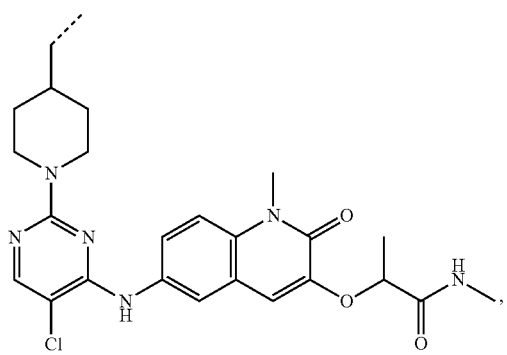
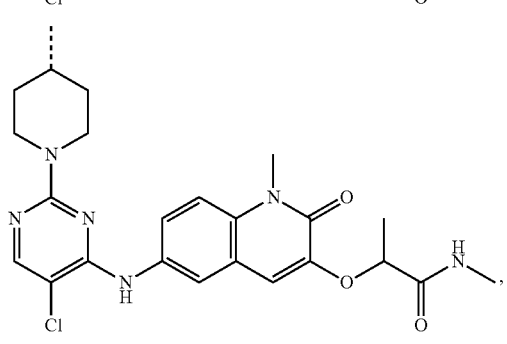
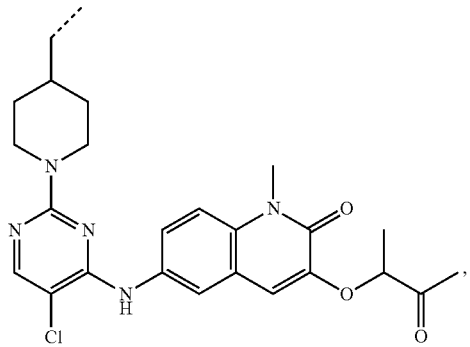
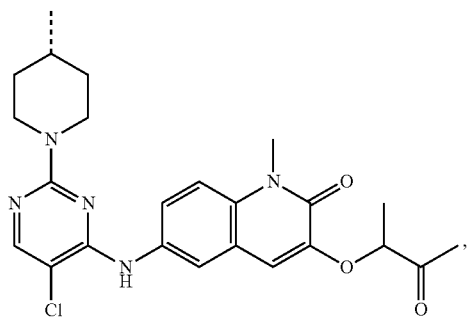
478
-continued
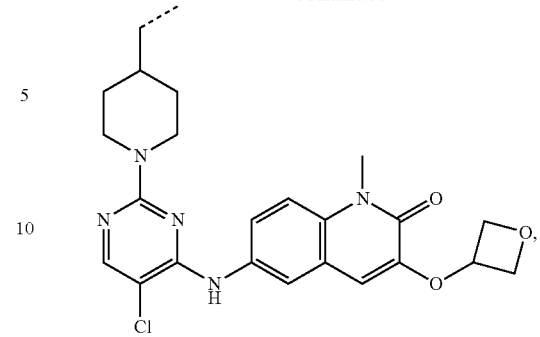
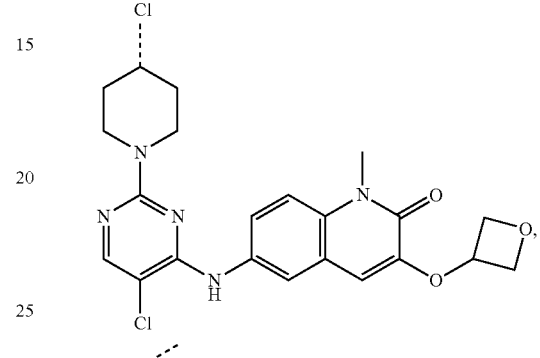
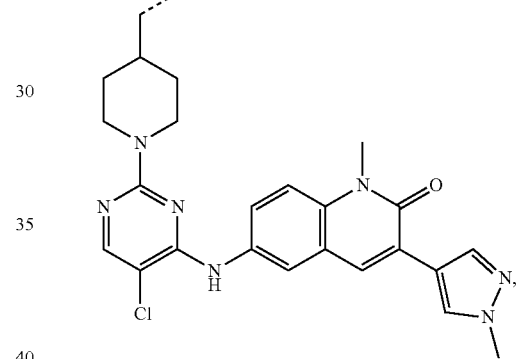
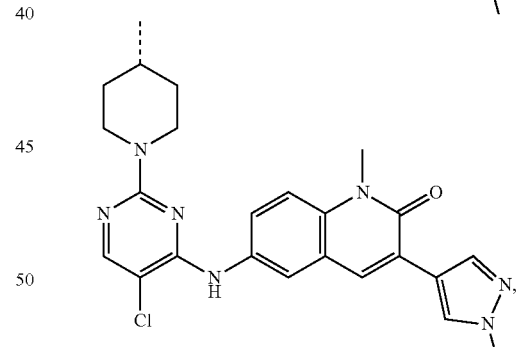
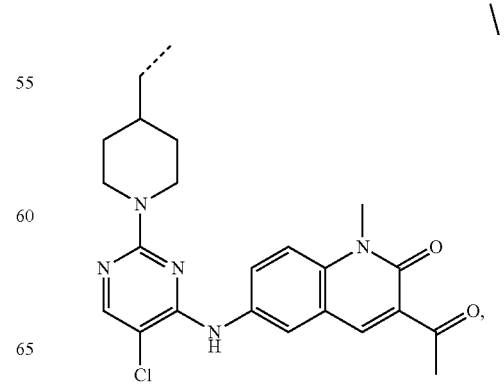

479
-continued
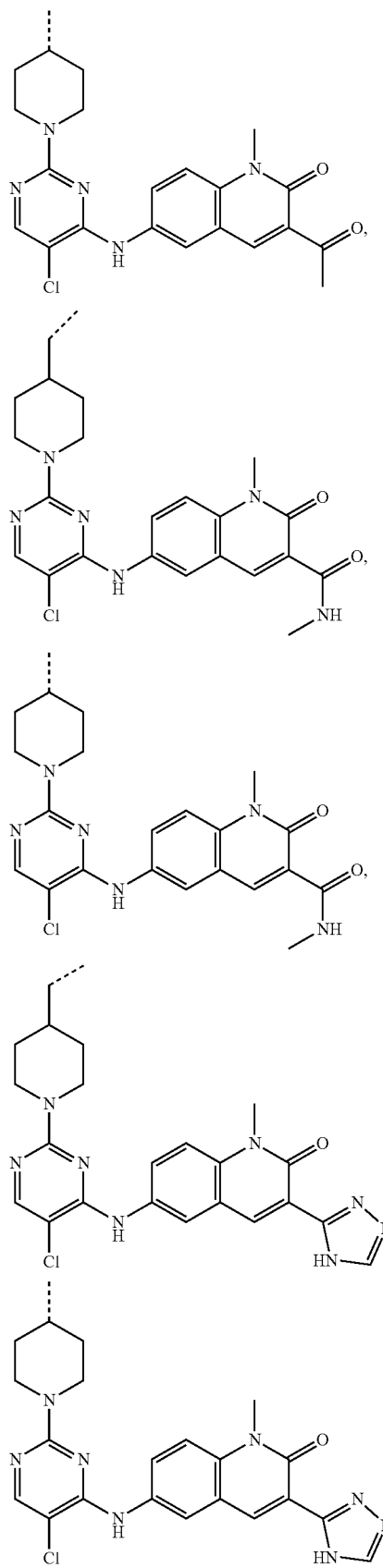
480
-continued
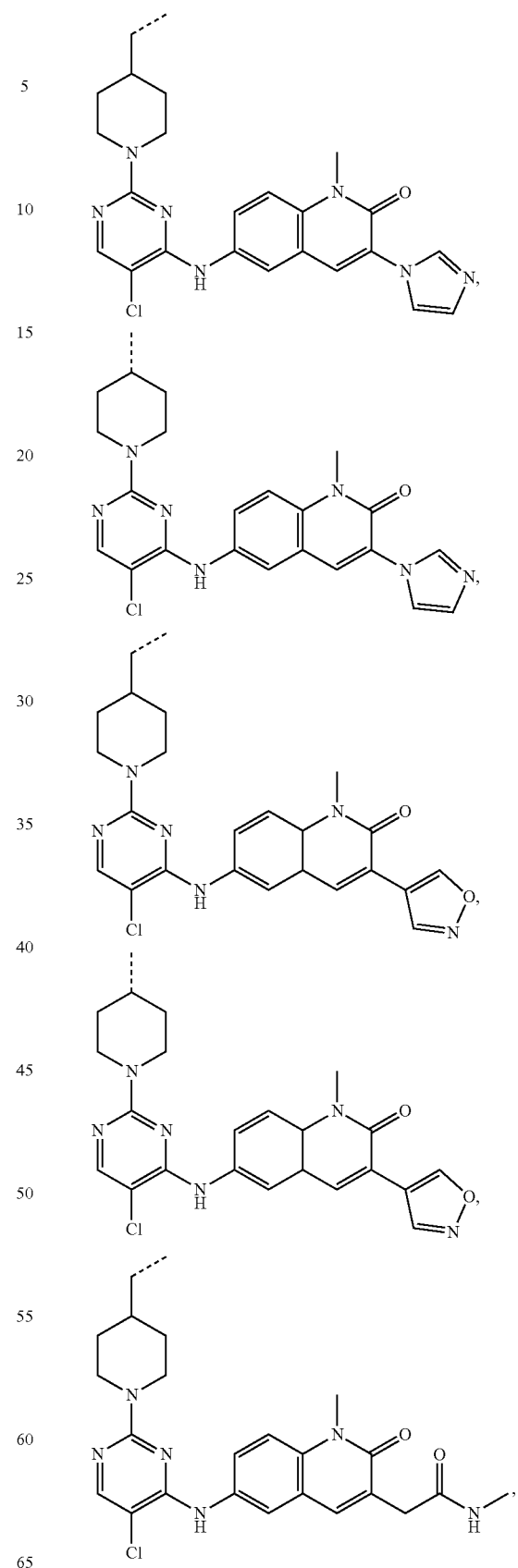

481
-continued
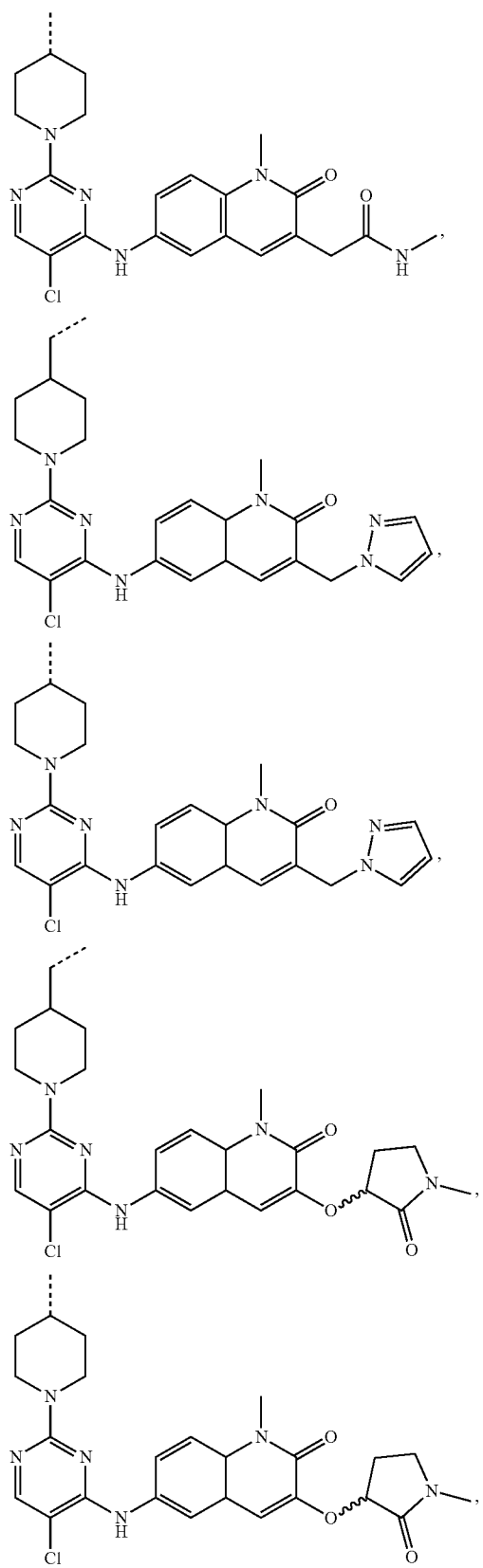
482
-continued
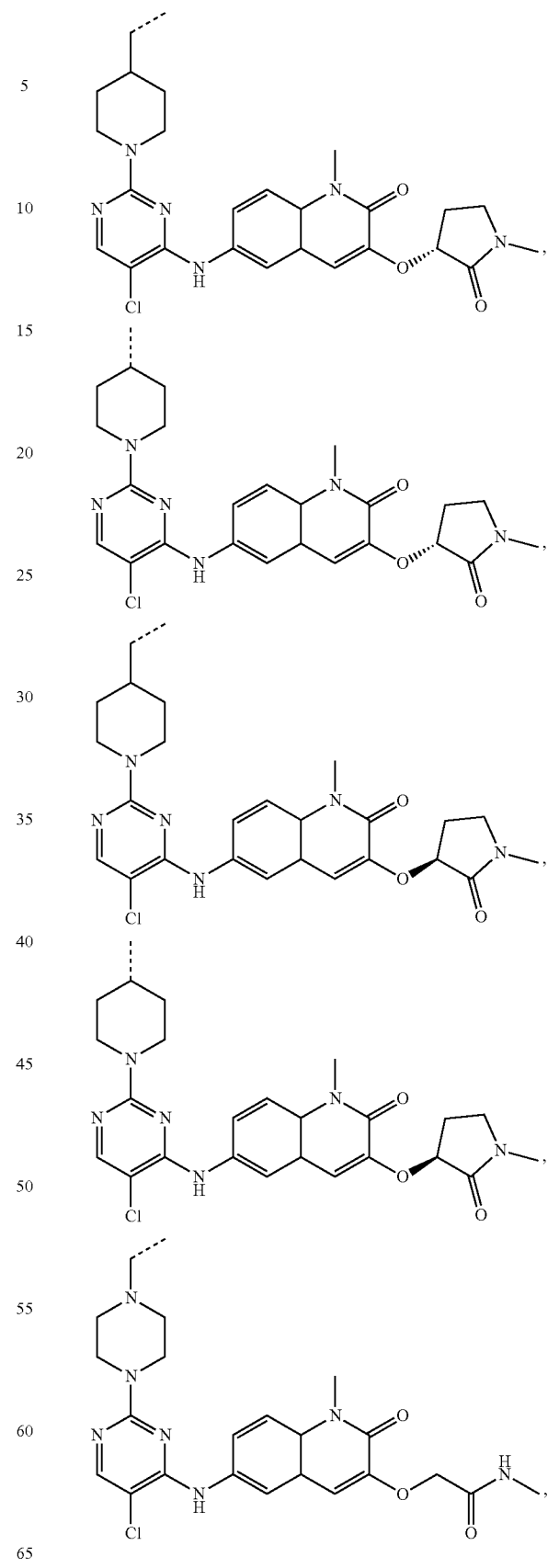

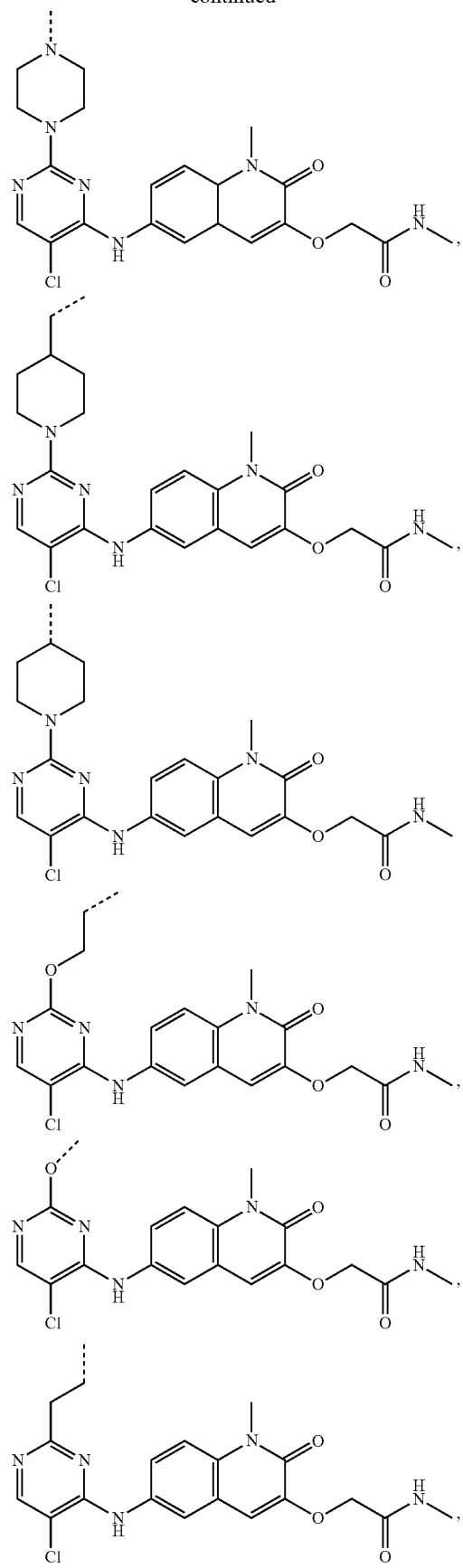
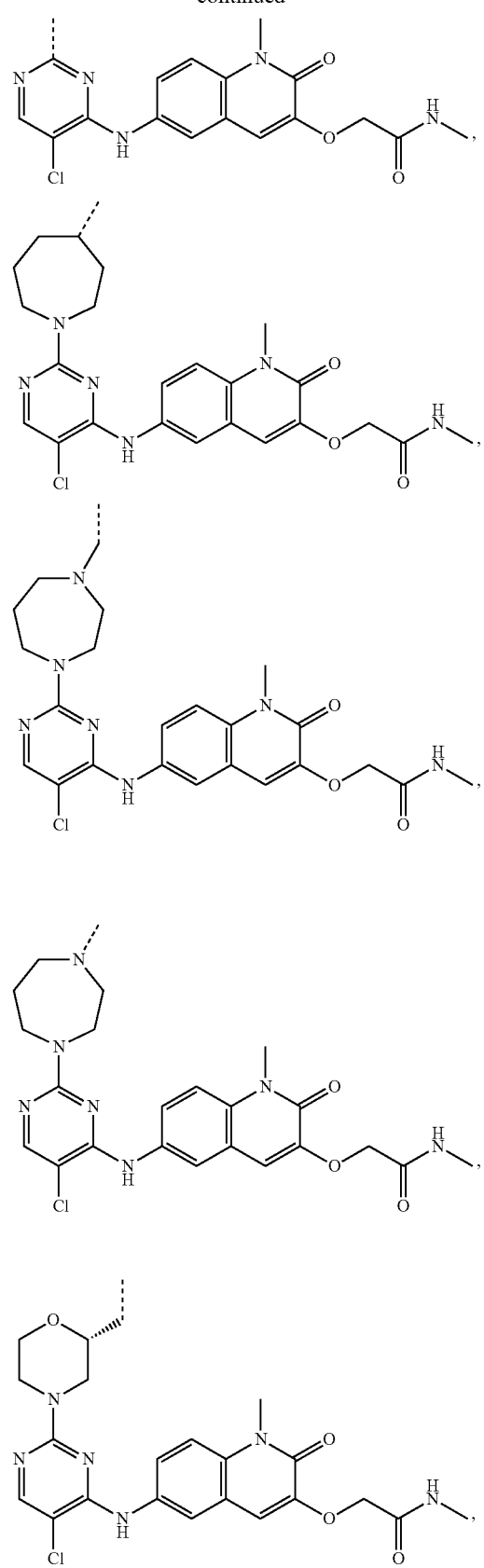

485
-continued
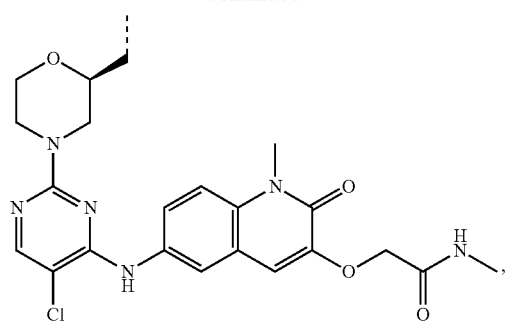
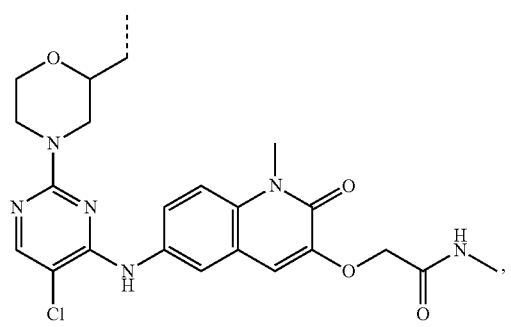
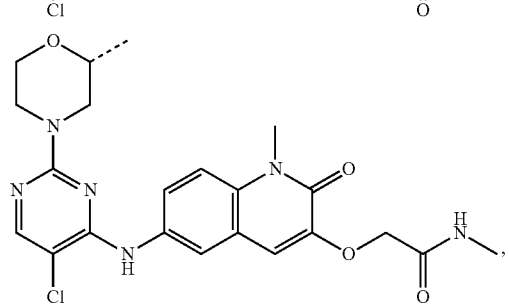
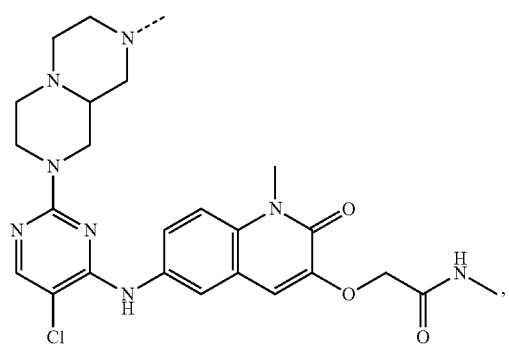
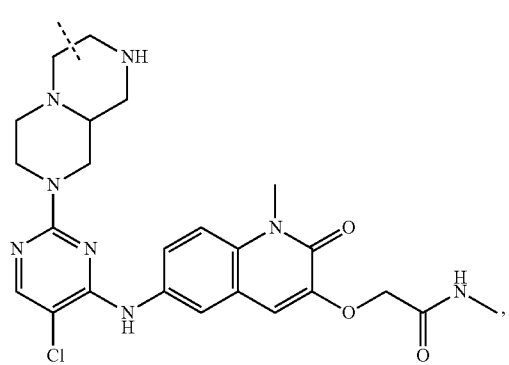
486
-continued
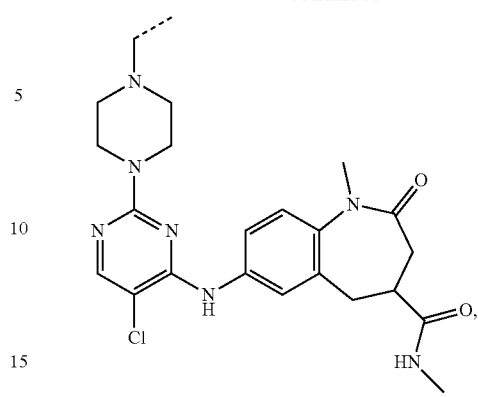
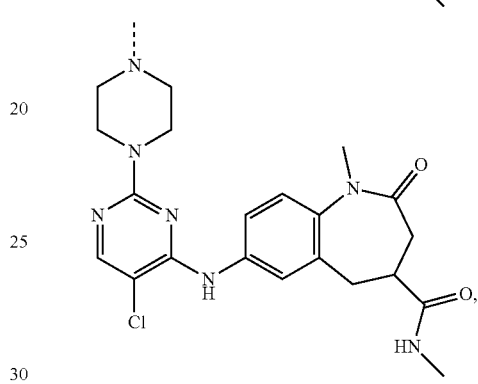
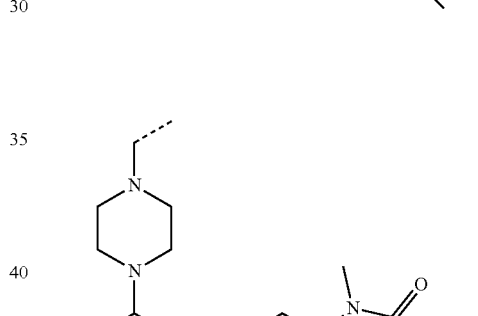
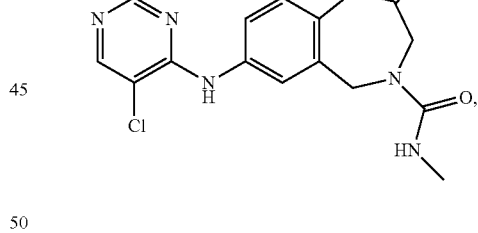
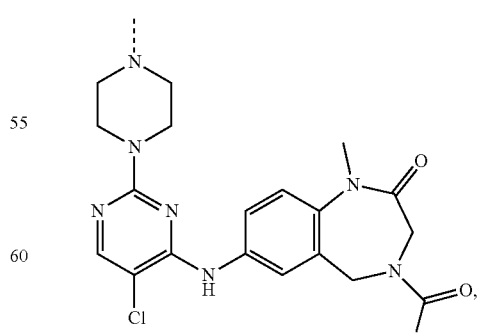

487
-continued
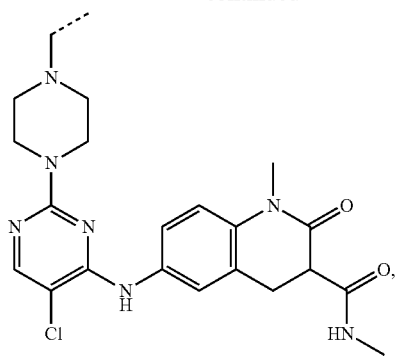
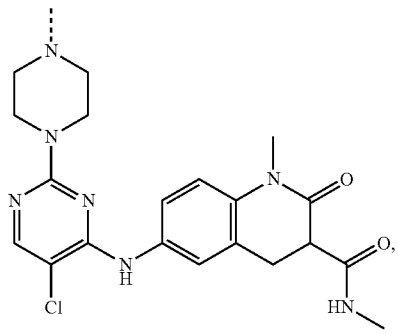
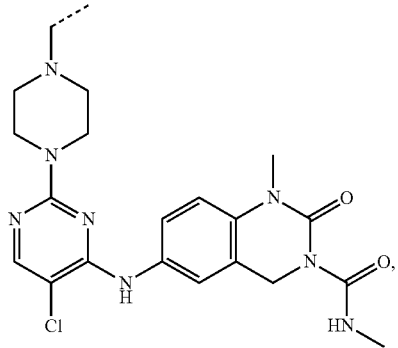
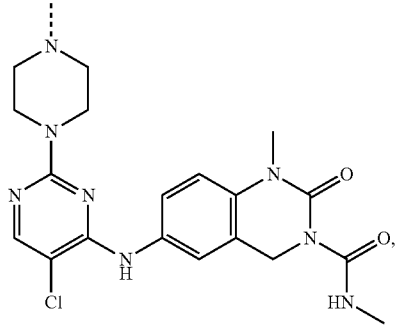
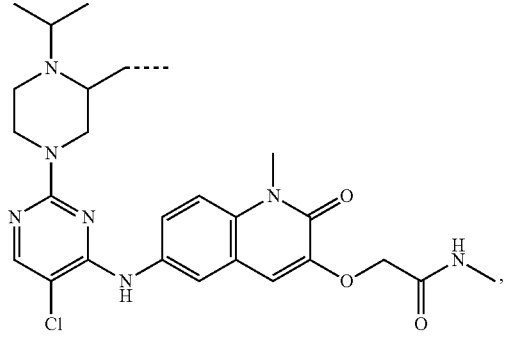
488
-continued
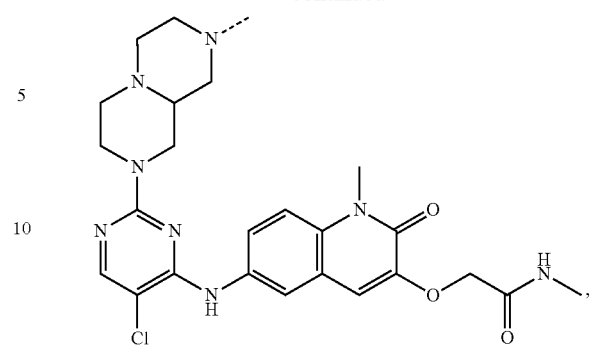
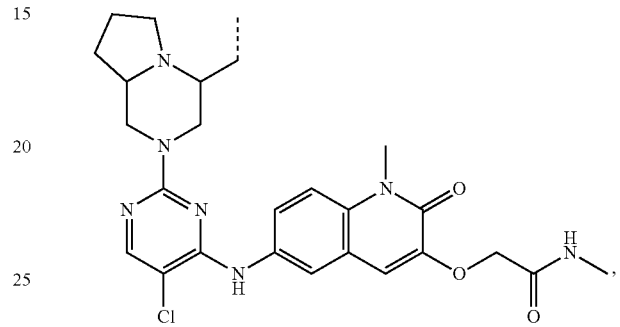
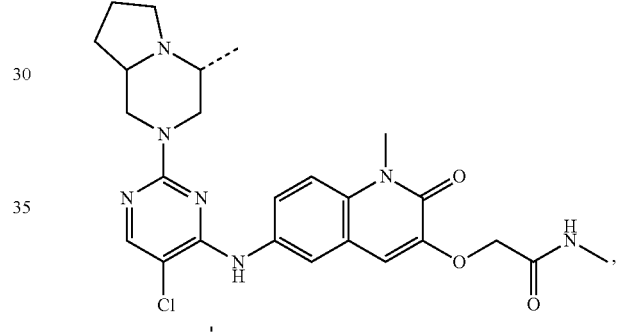
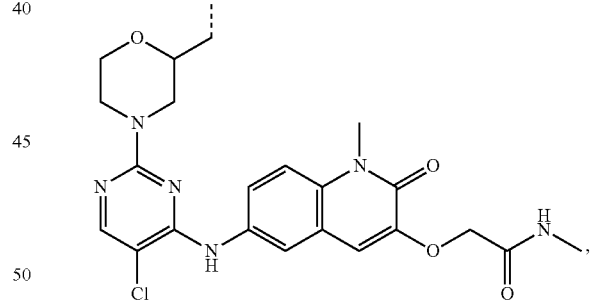
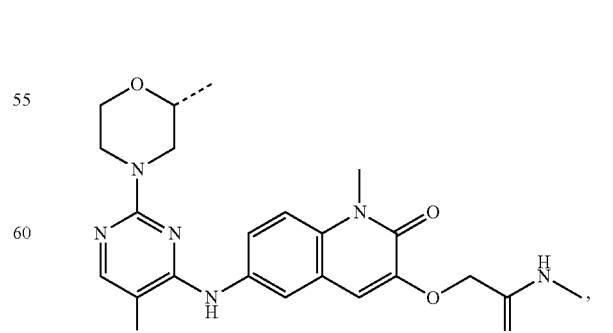

489
-continued
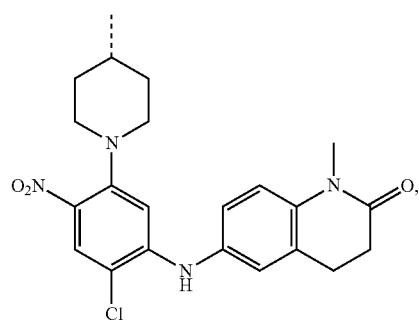
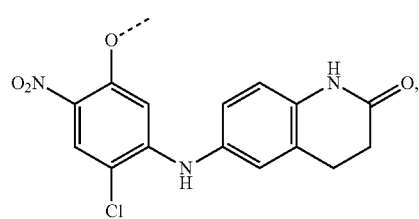
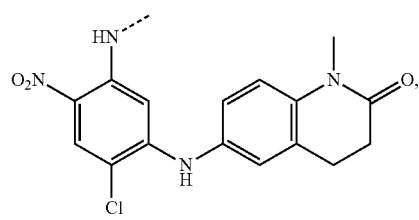
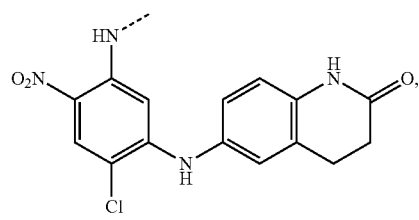
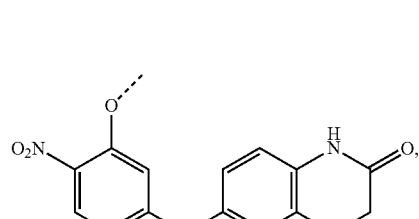
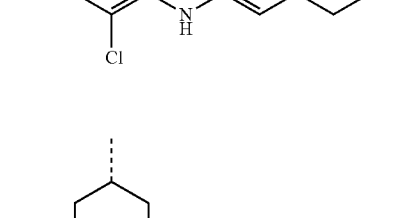
490
-continued
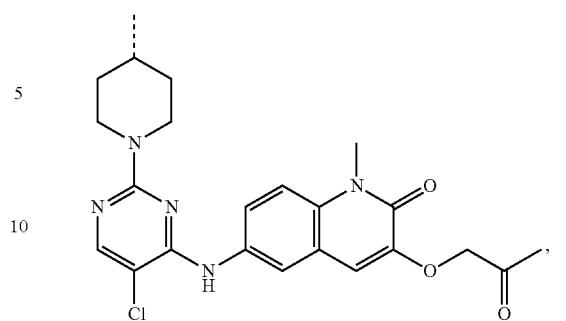
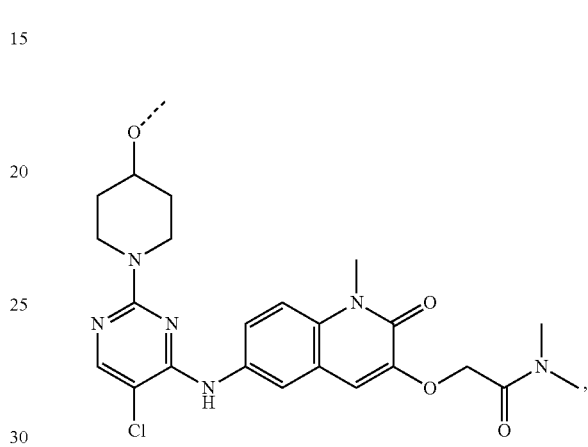
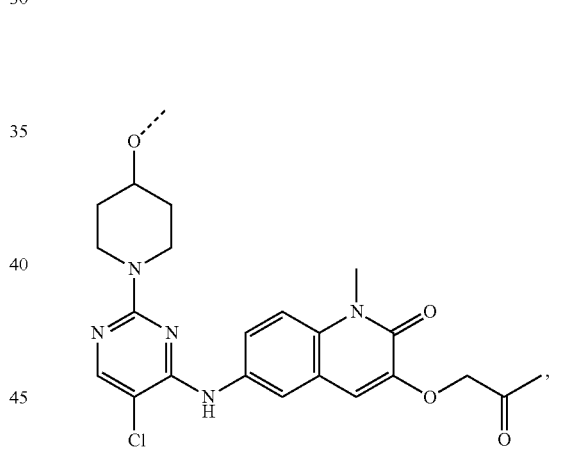
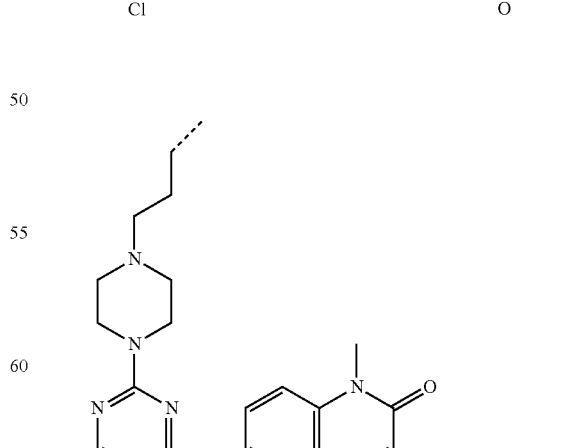

491
-continued
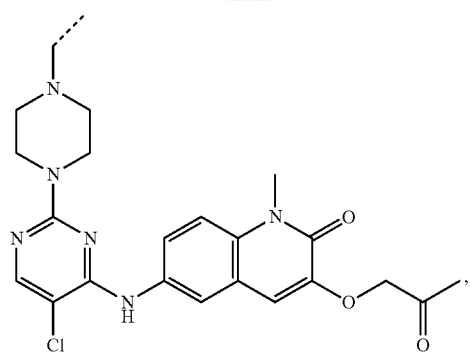
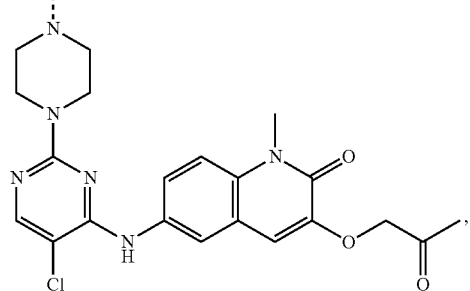
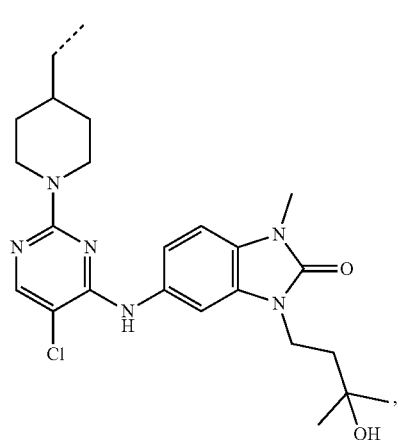
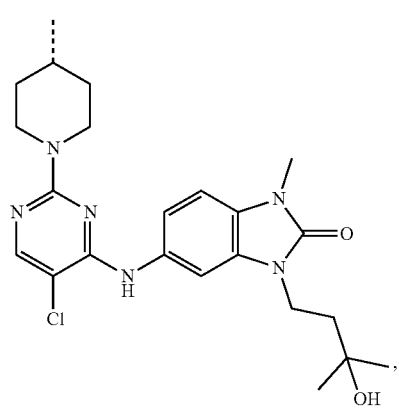
492
-continued
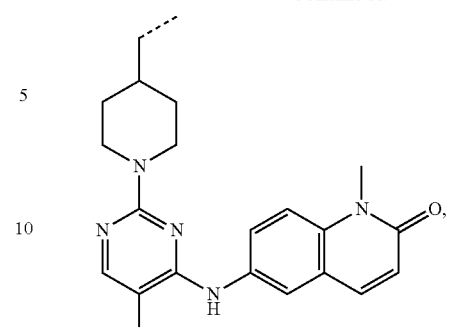
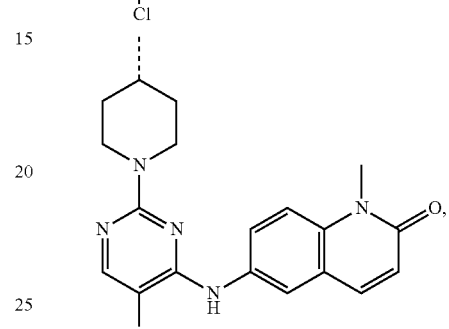
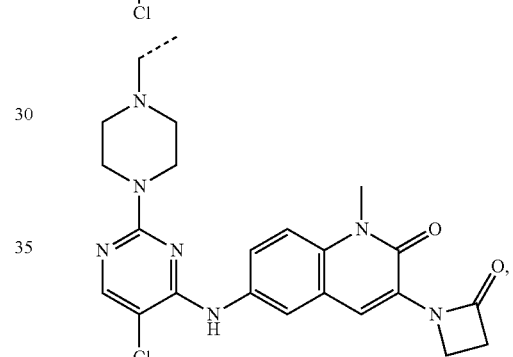
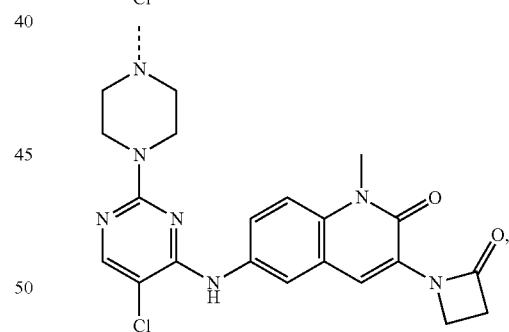
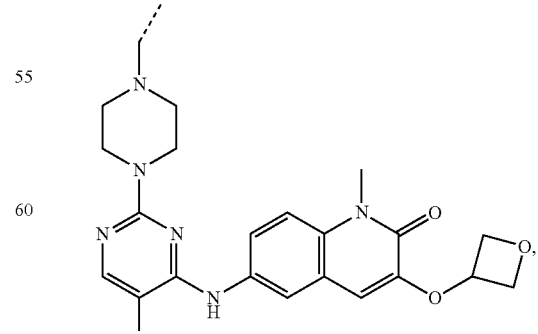

493
-continued
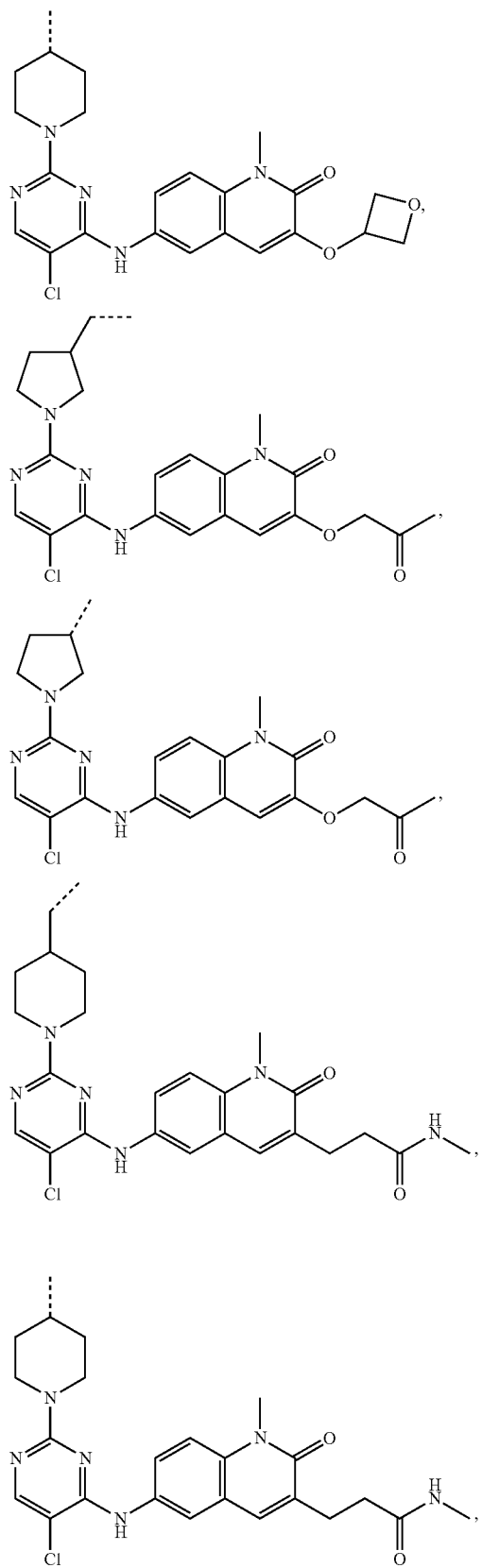
494
-continued
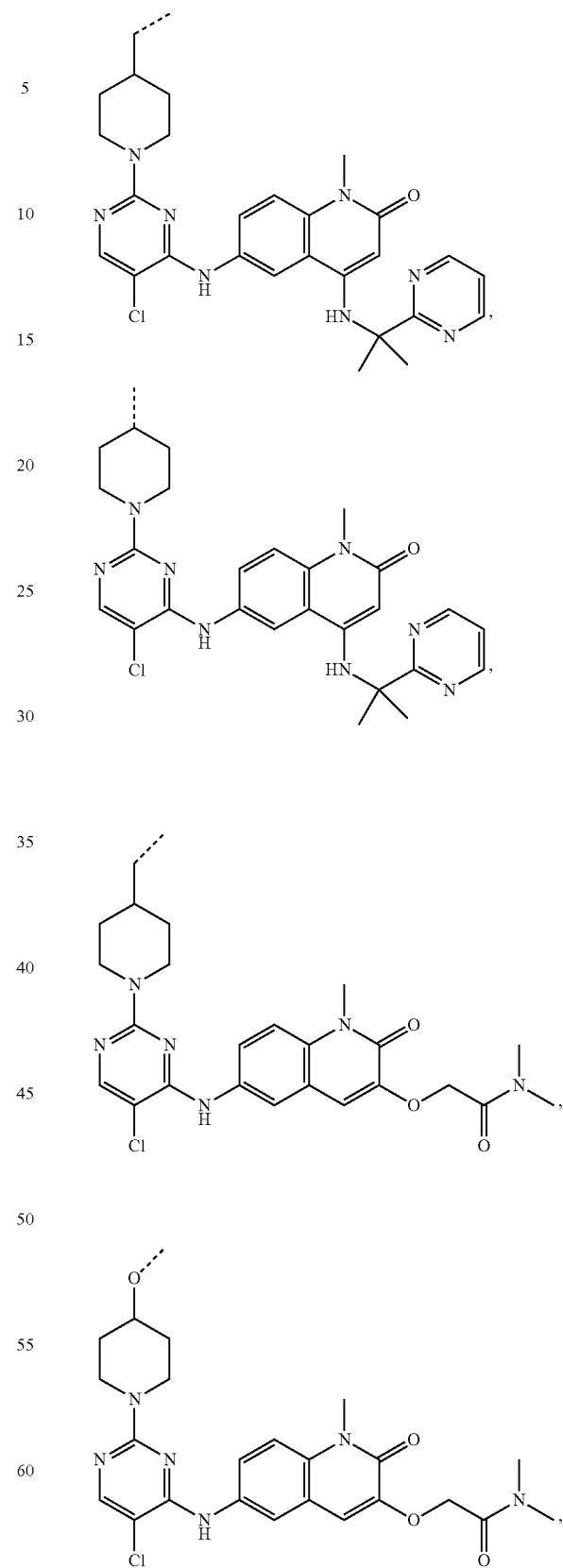

495
-continued
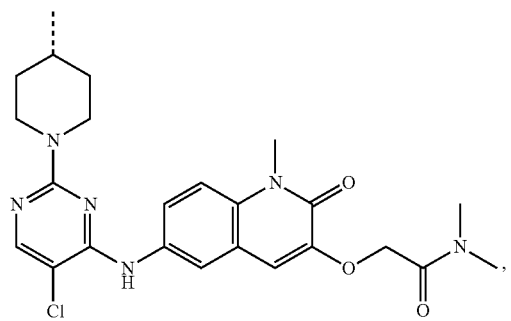
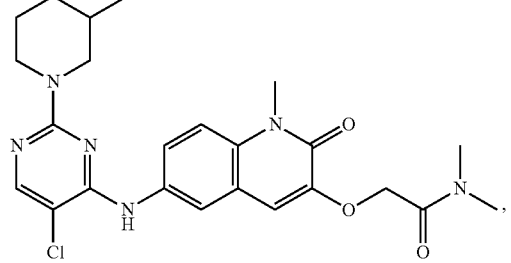
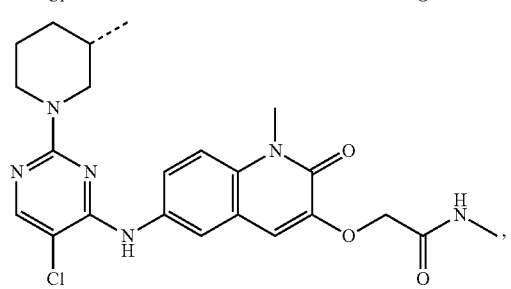
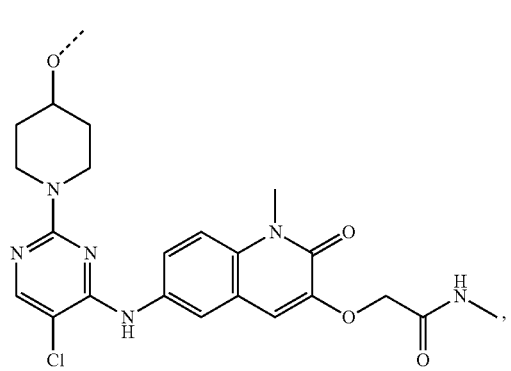
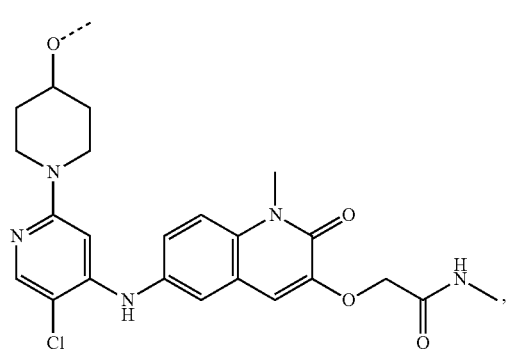
496
-continued
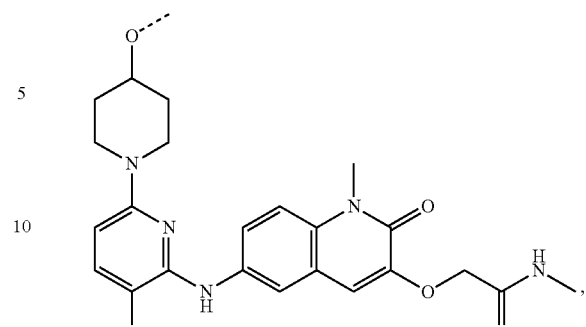
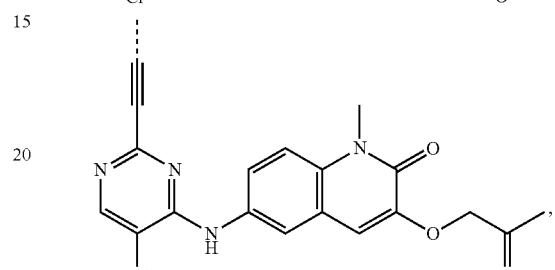
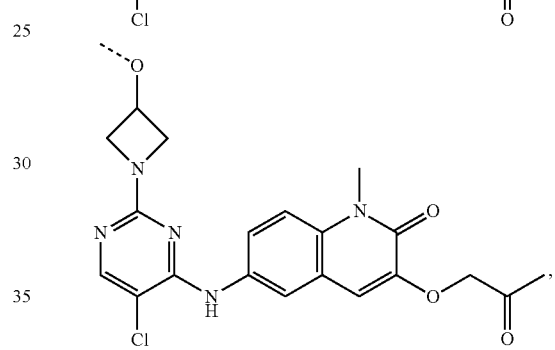
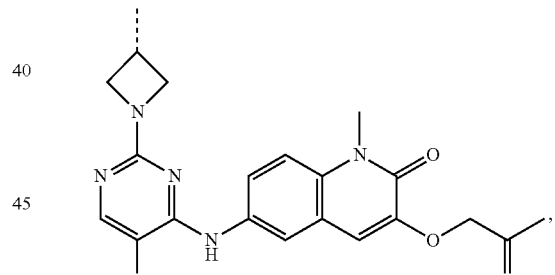
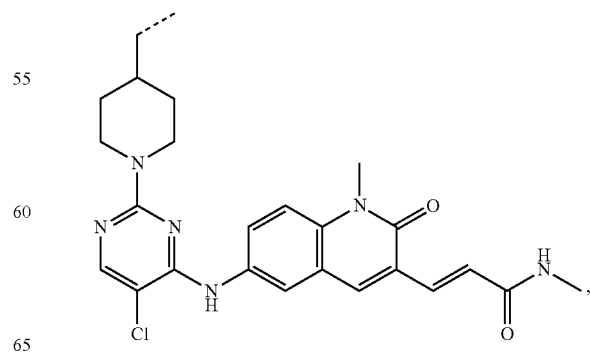

497
-continued
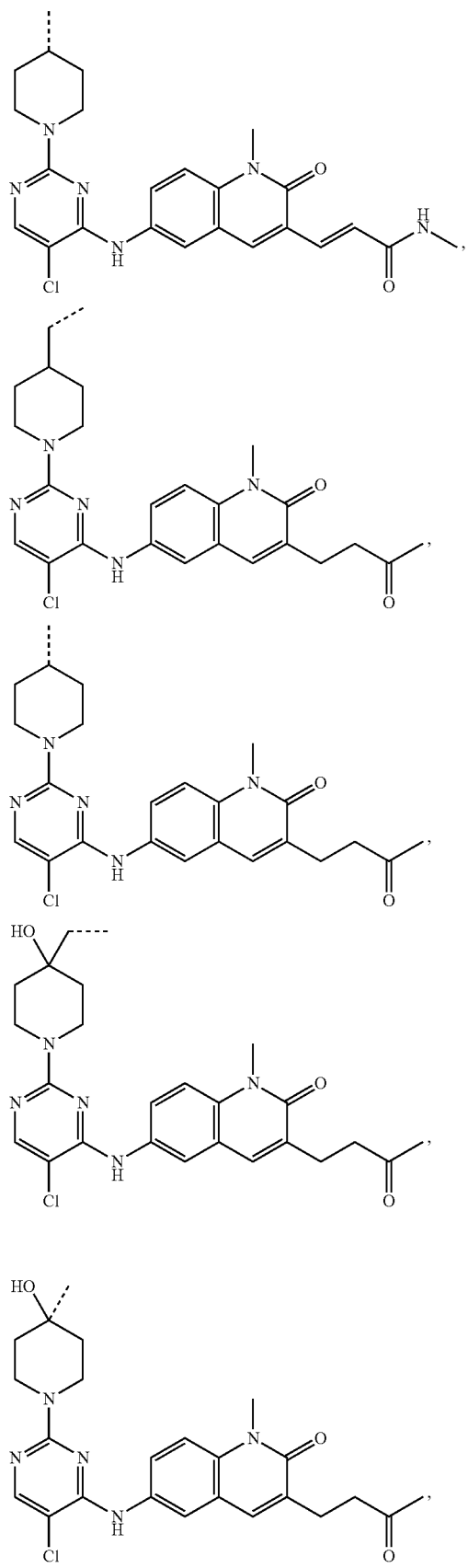
498
-continued
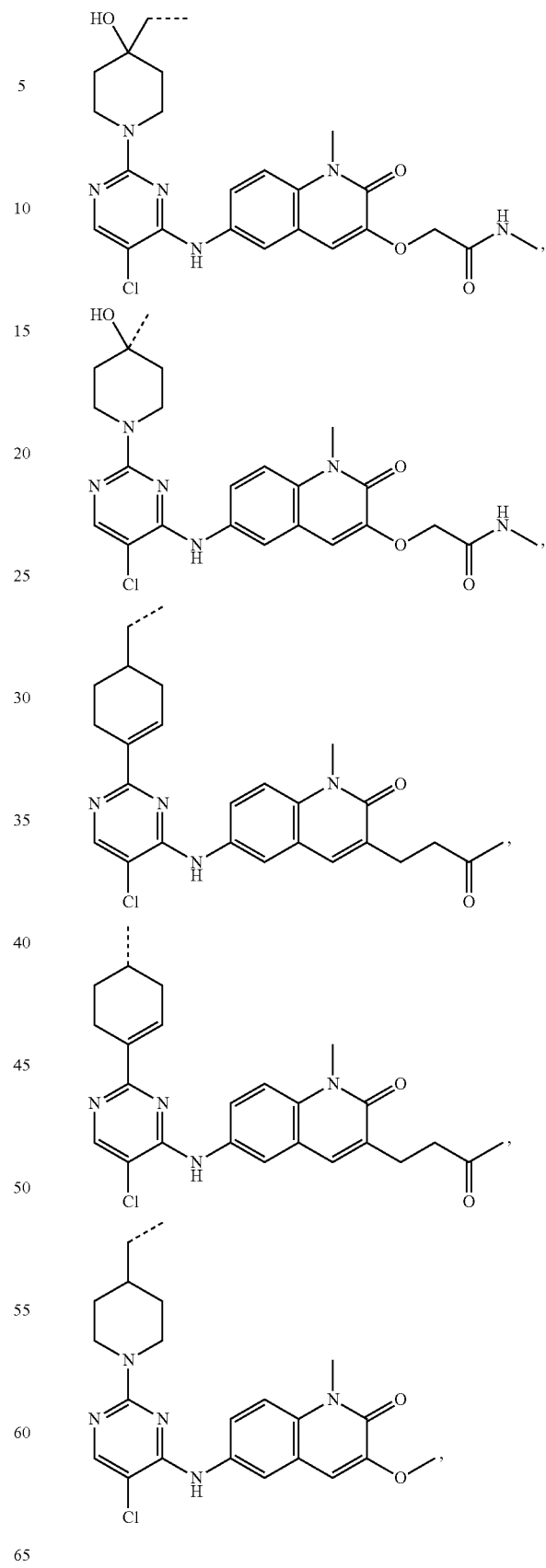

499
-continued
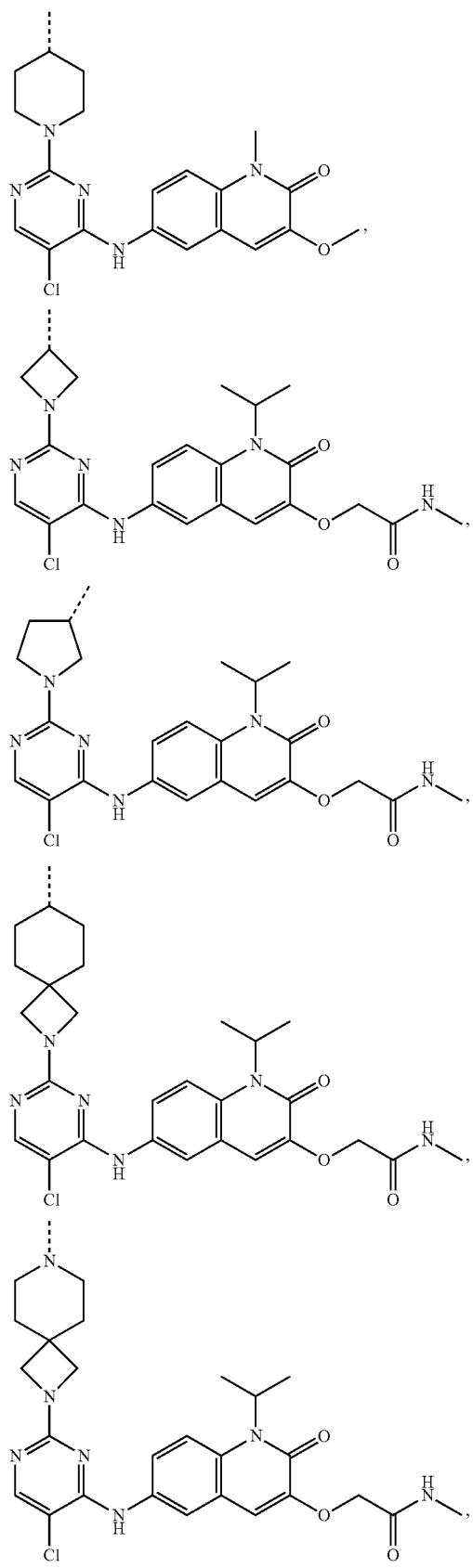
500
-continued
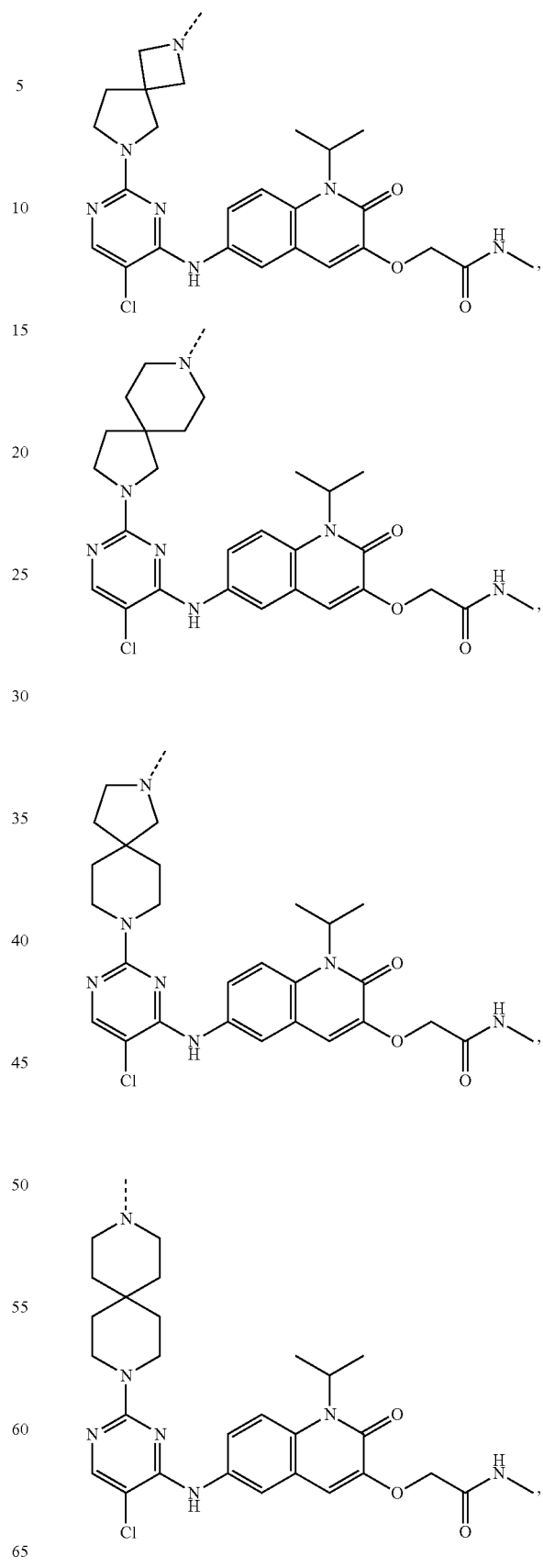

501
-continued
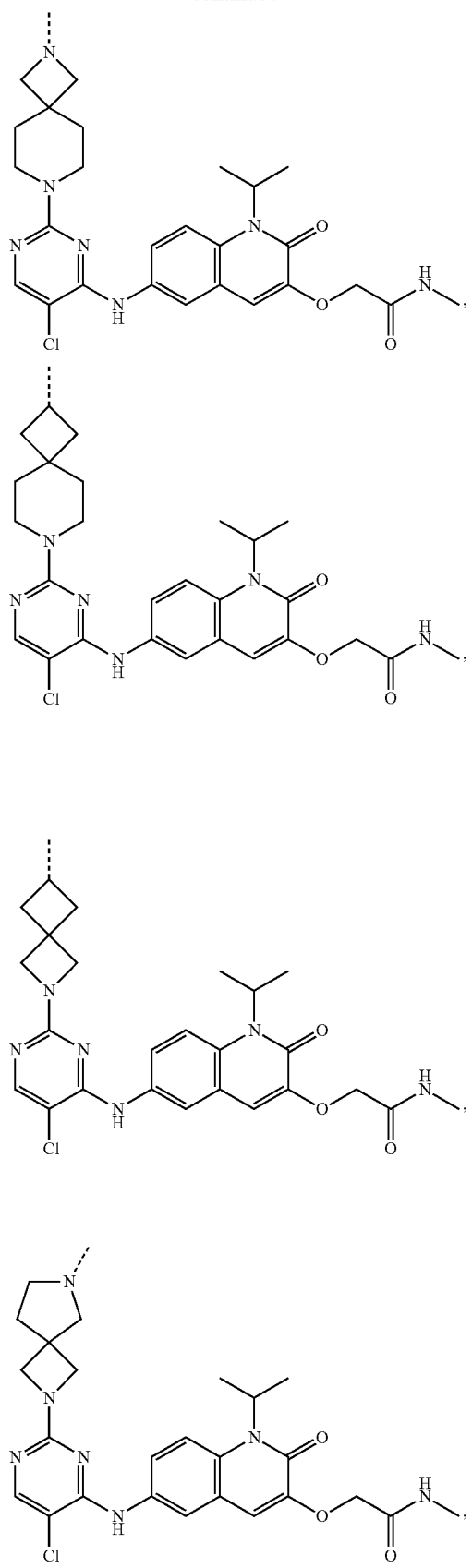
502
-continued
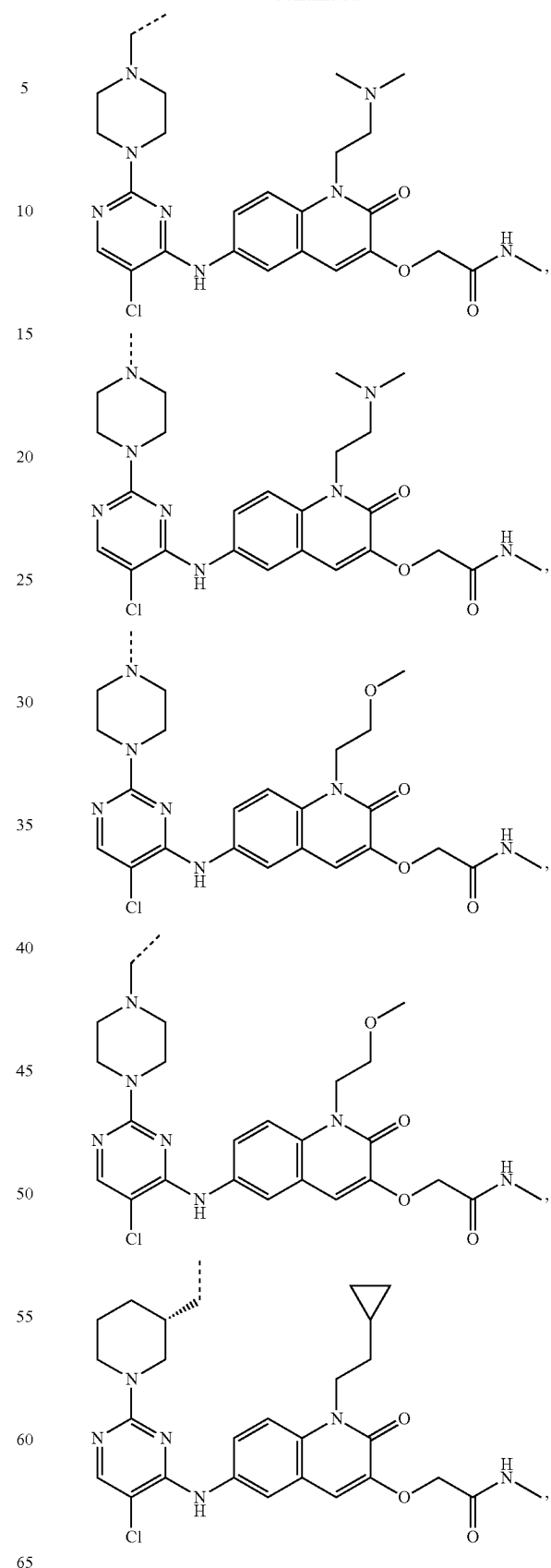

503
-continued
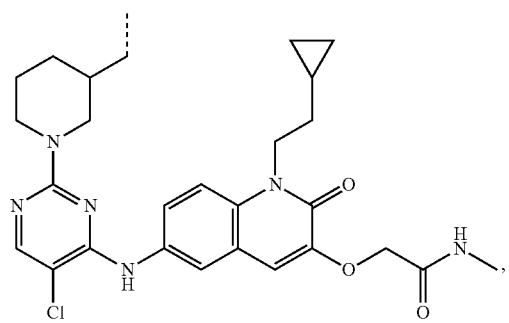
,
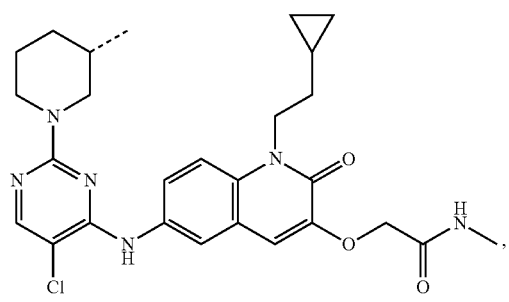
,
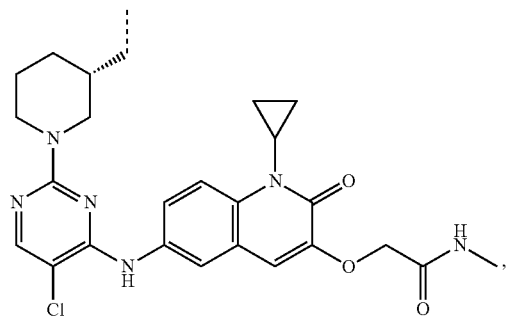
,
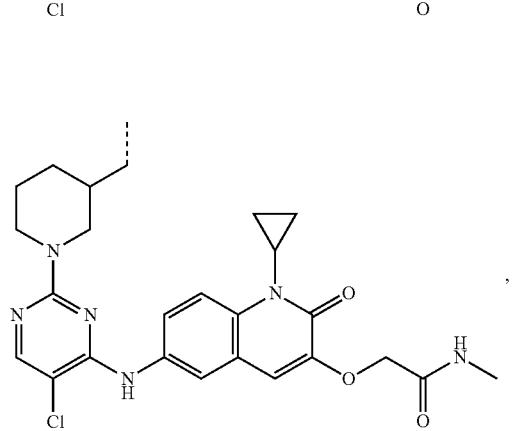
,
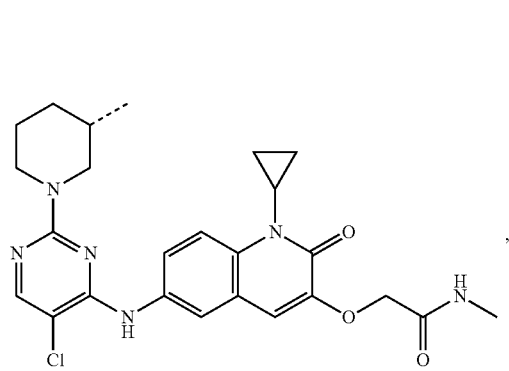
,
504
-continued
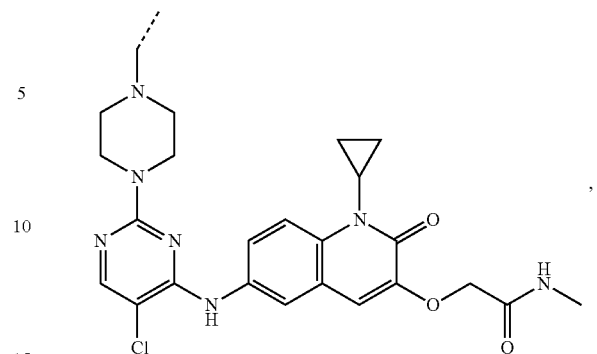
,
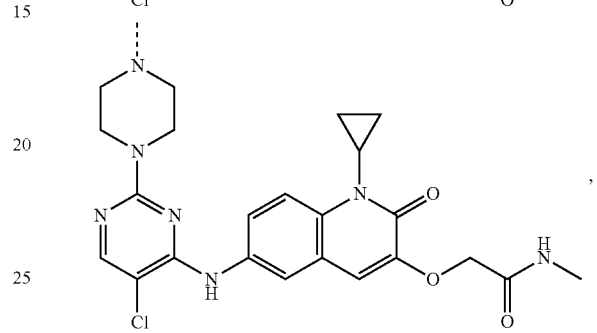
,
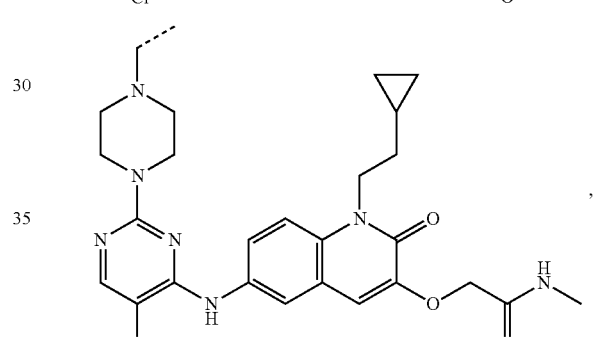
,
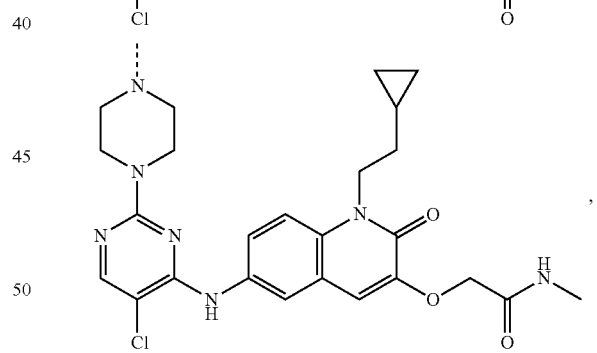
,
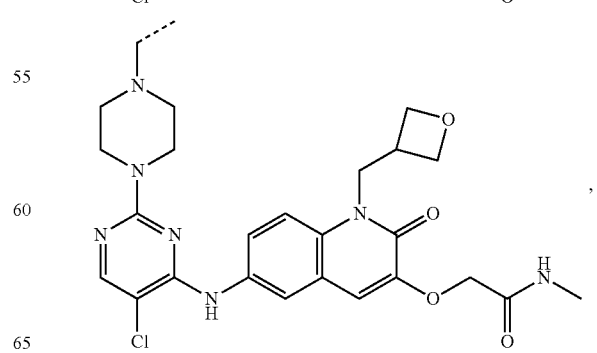
, 505
-continued
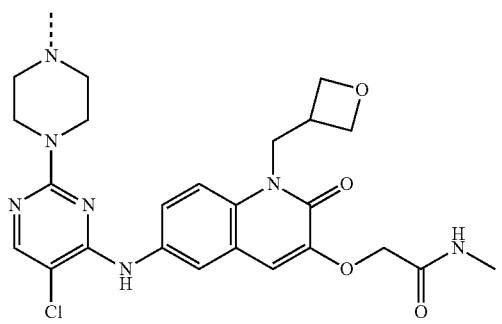
,
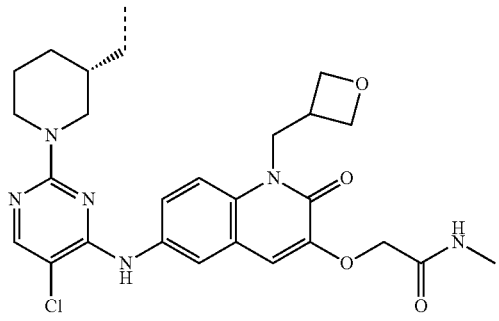
,
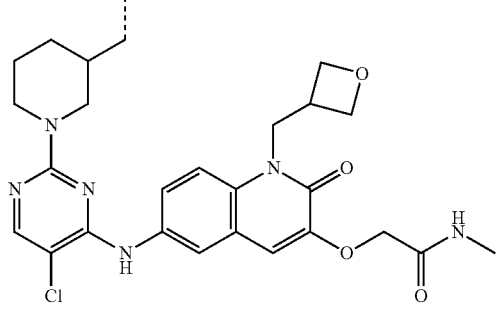
,
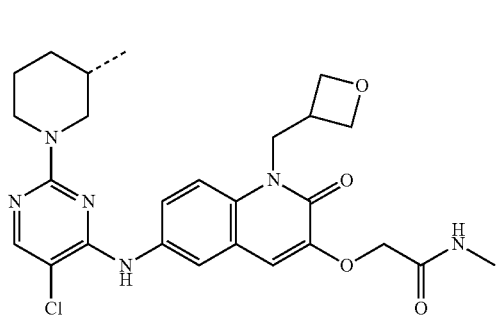
,
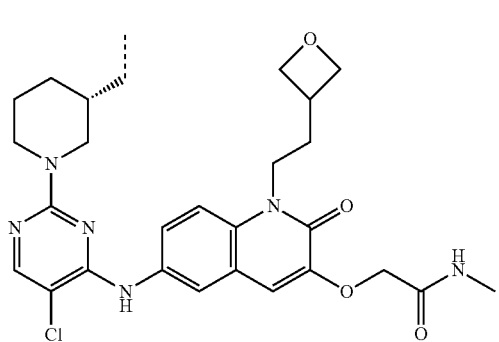
,
506
-continued
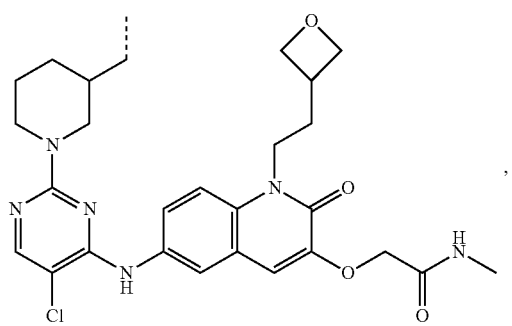
,
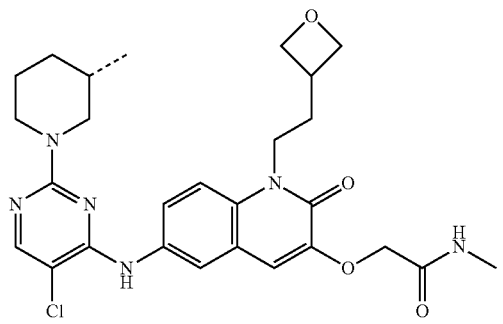
,
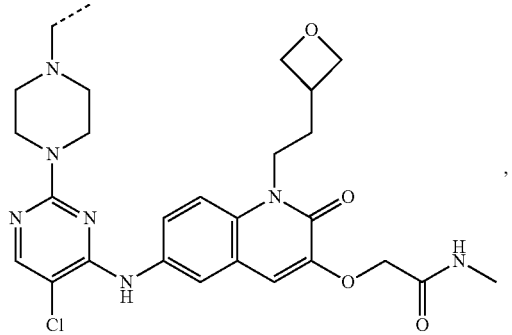
,
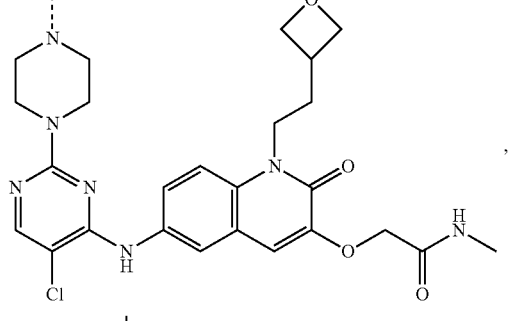
,
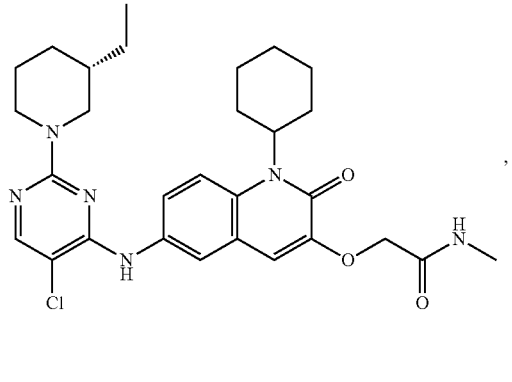
,

507
-continued
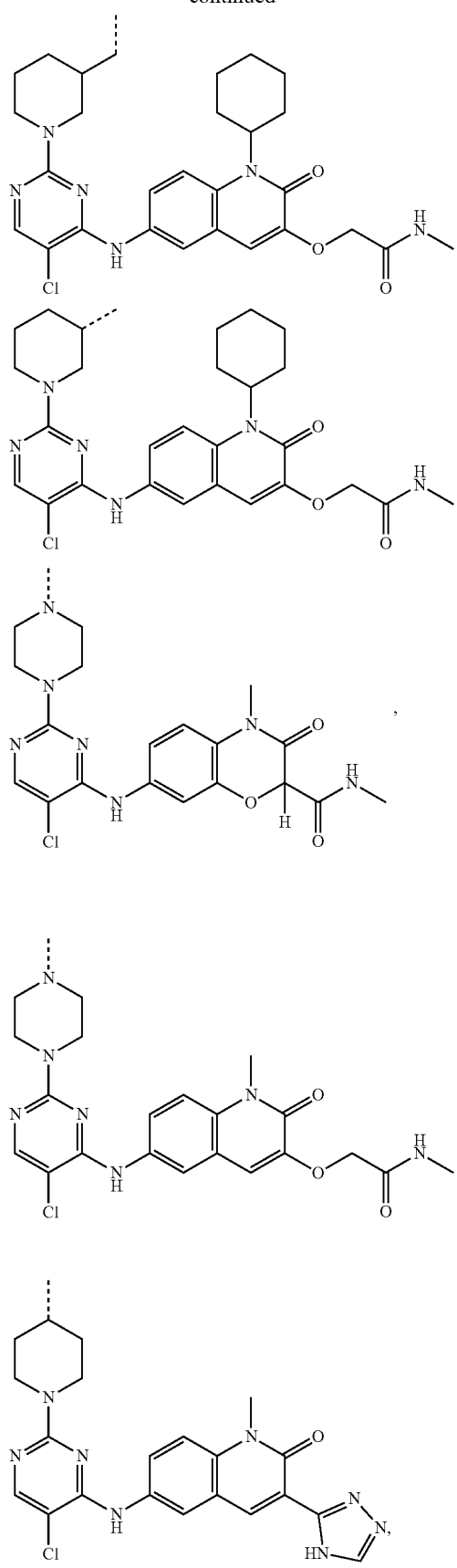
508
-continued
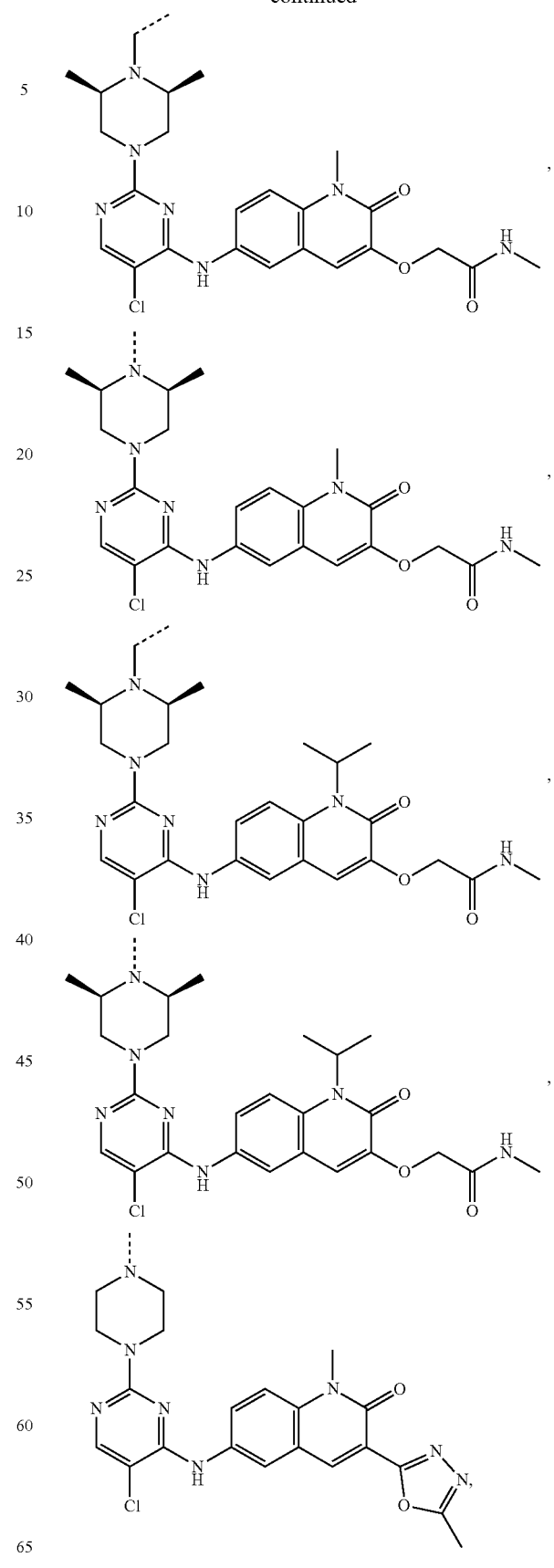

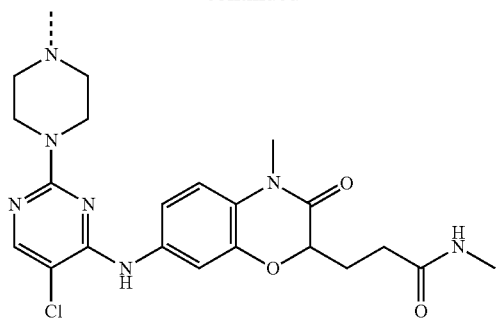
,
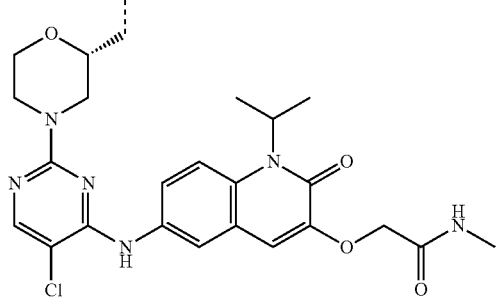
,
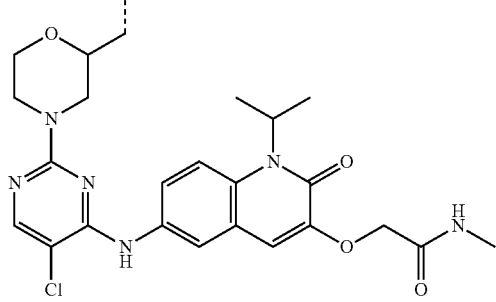
,
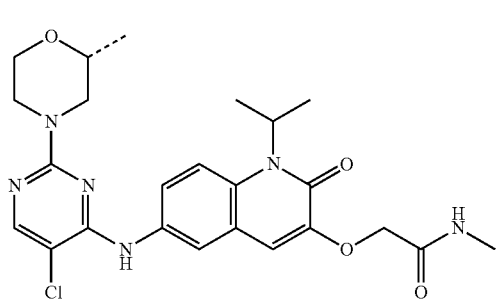
,
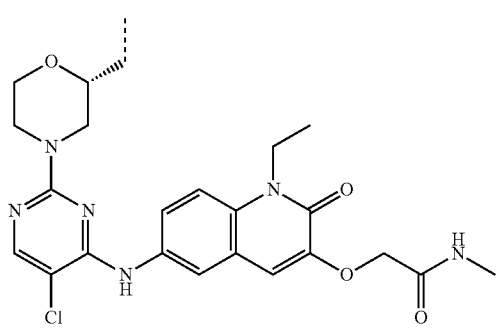
,
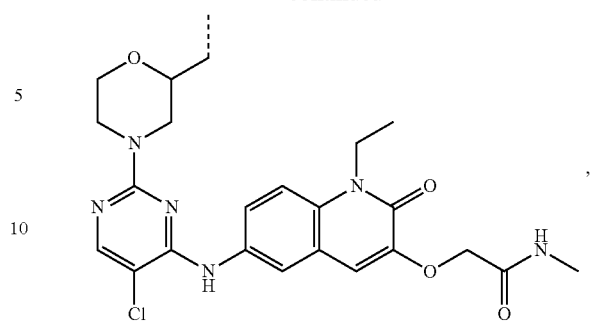
,
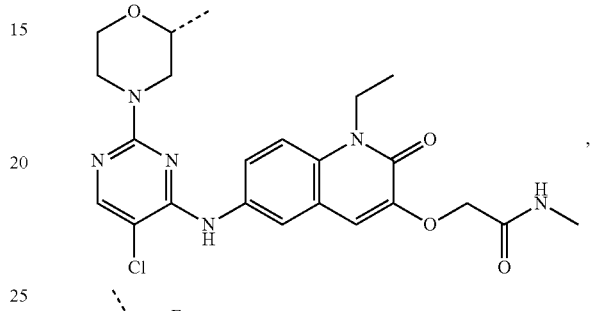
,
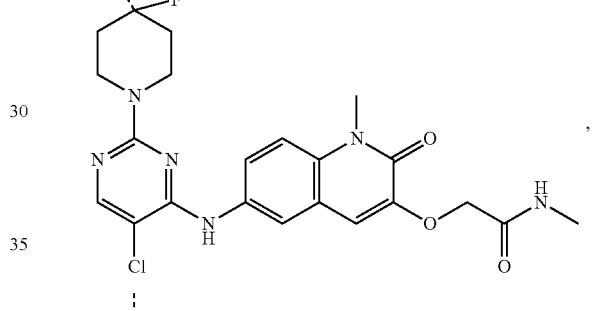
,

,
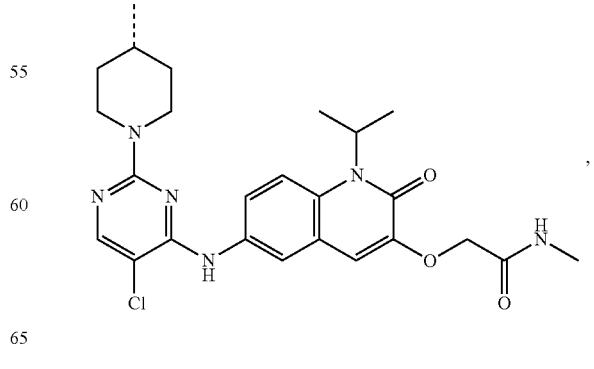
,

| 511 -continued | 512 -continued |
|---|---|
| 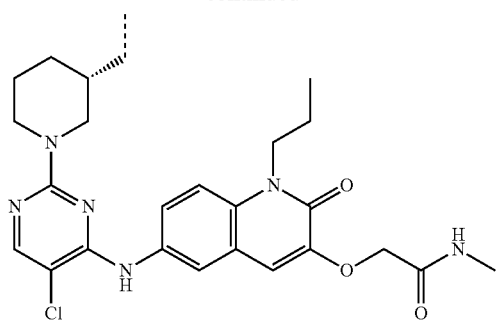 | 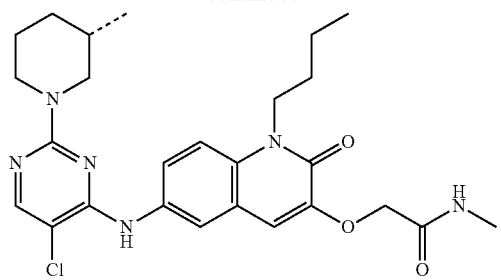 |
| 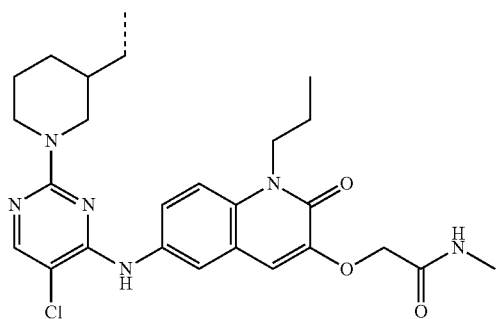 | 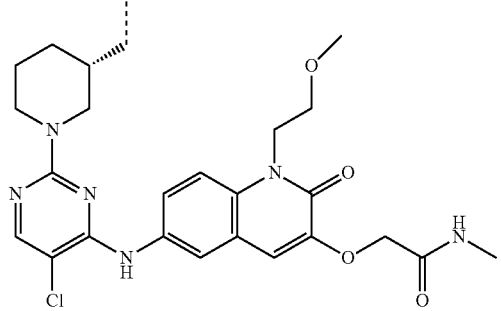 |
| 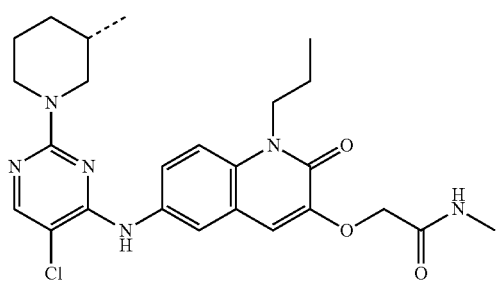 | 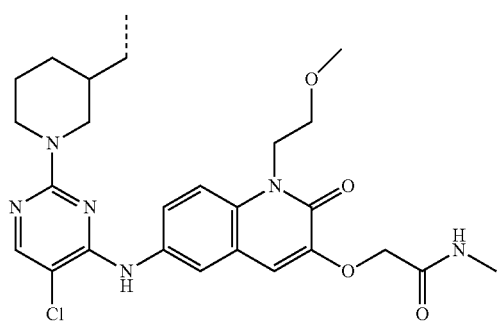 |
| 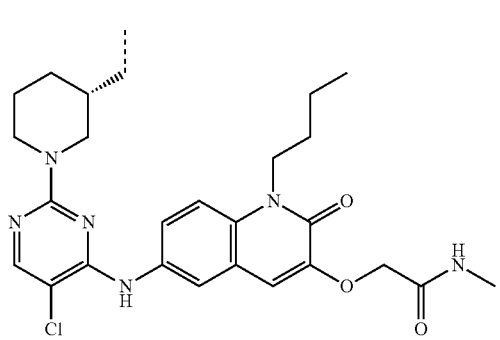 | 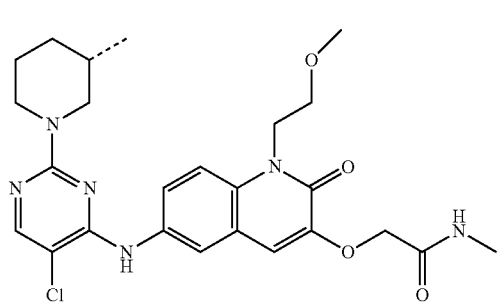 |
| 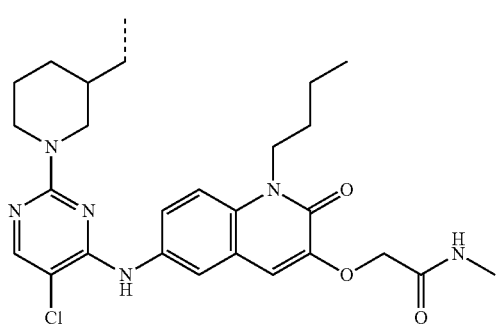 | 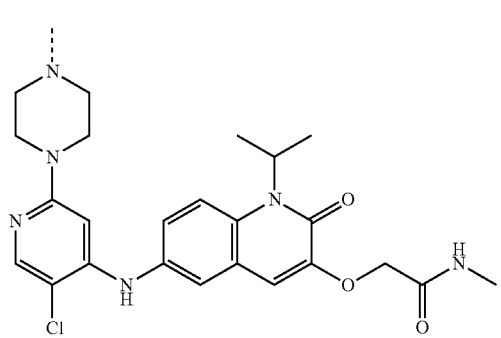 |

513
-continued
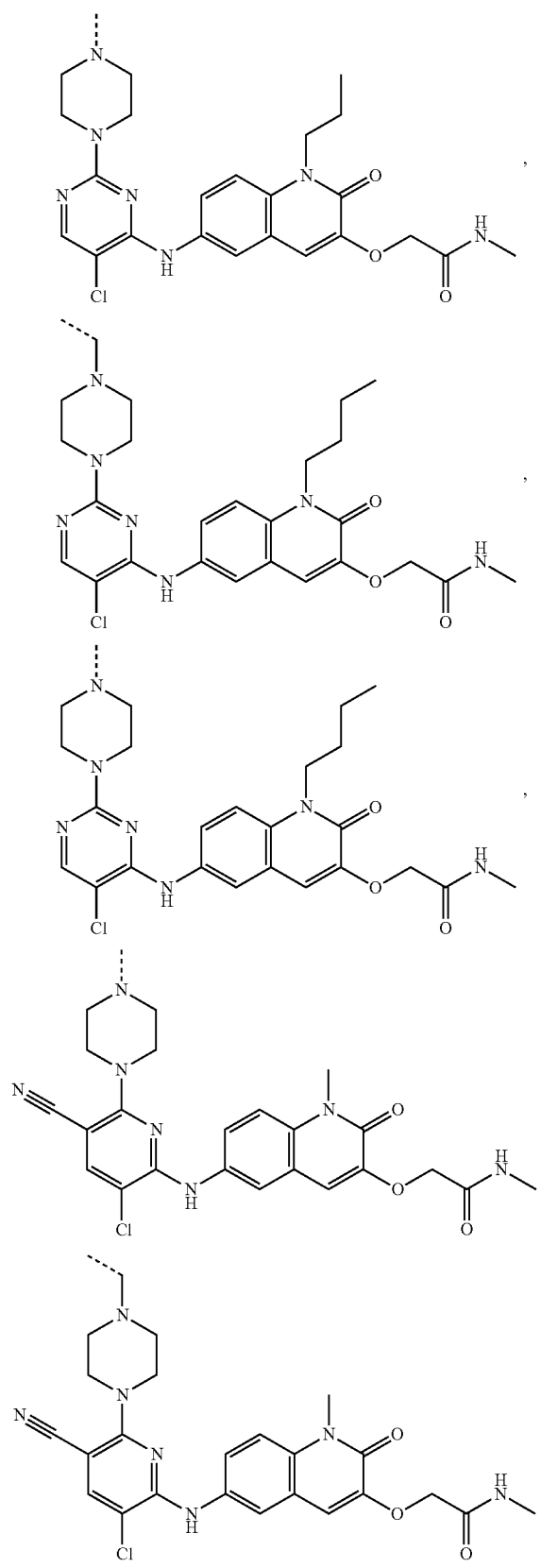
514
-continued
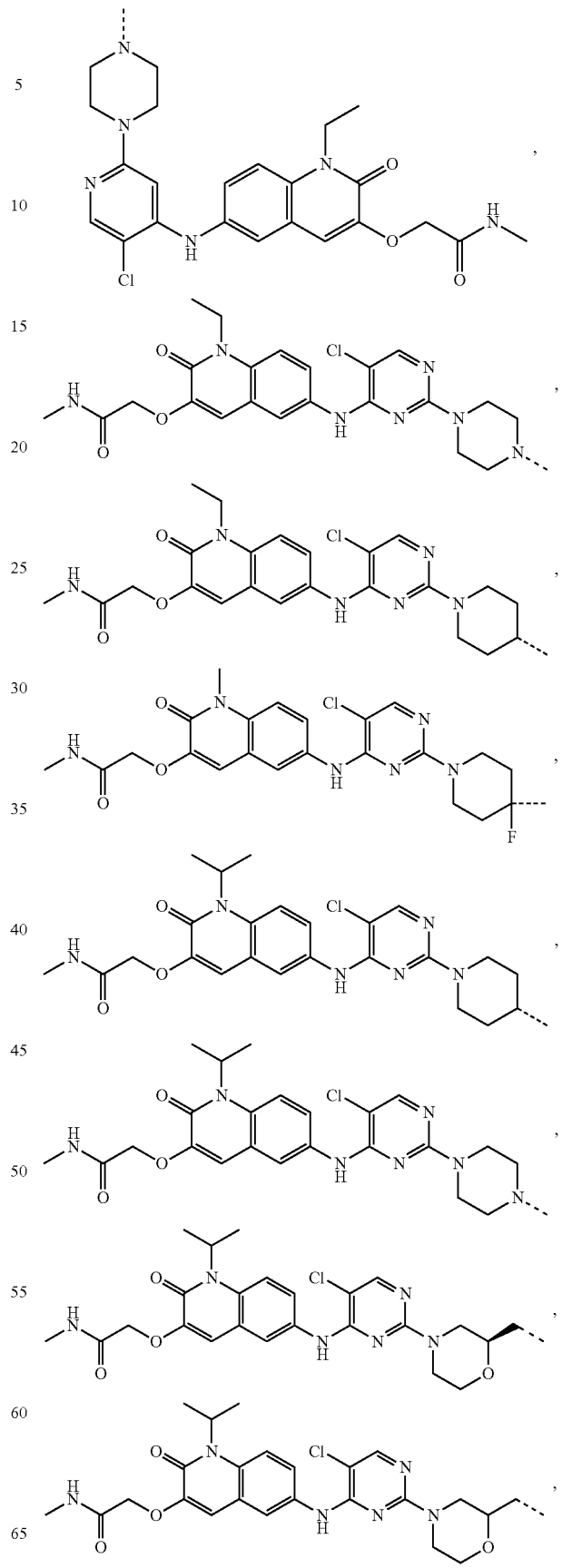

515
-continued
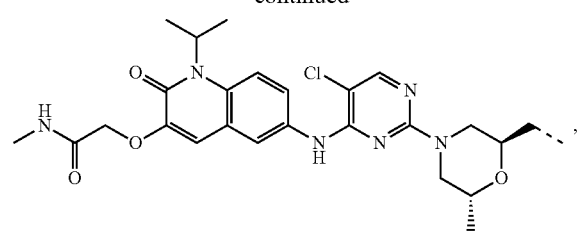
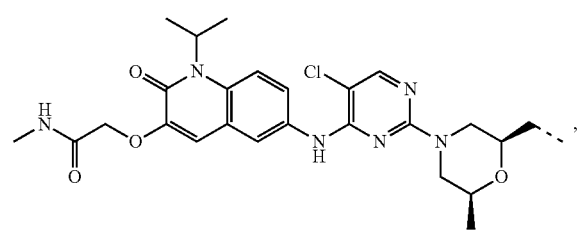
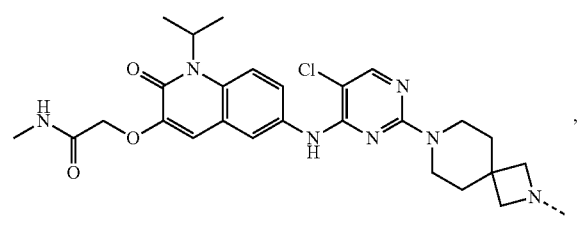
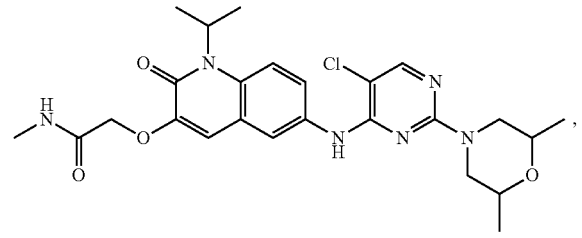
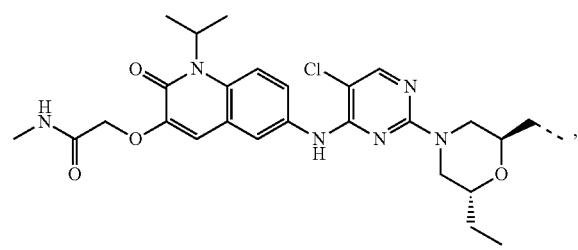
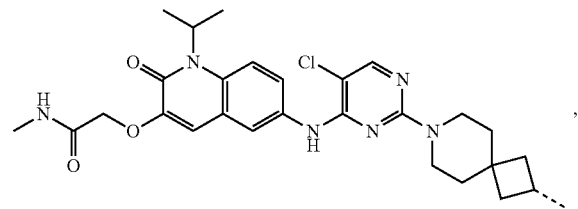
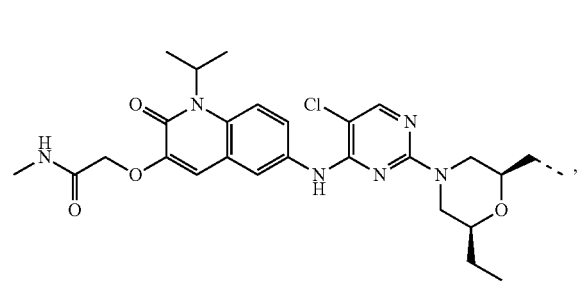
516
-continued
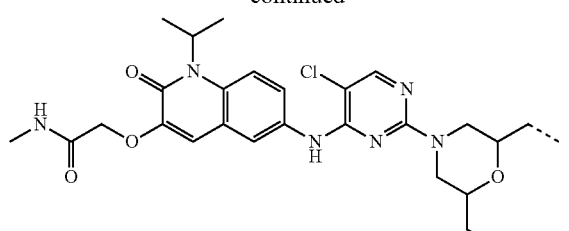
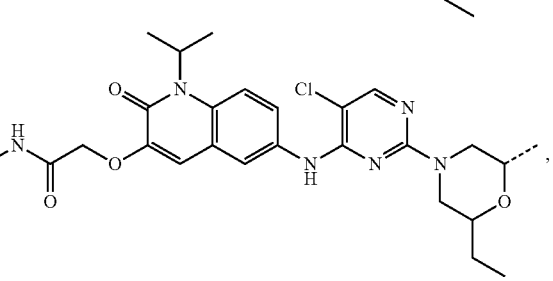
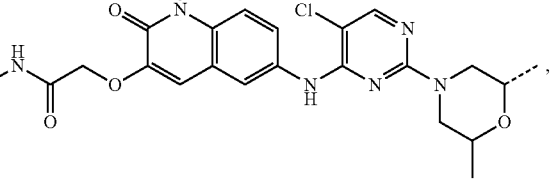
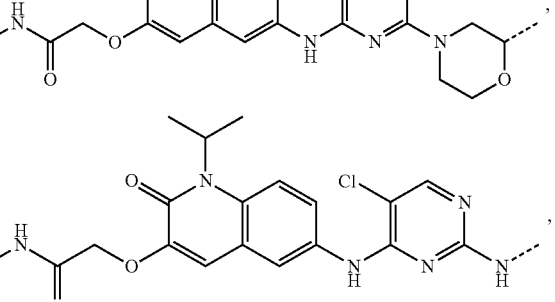
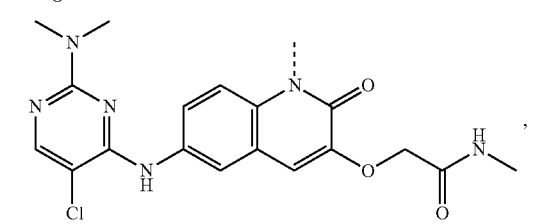
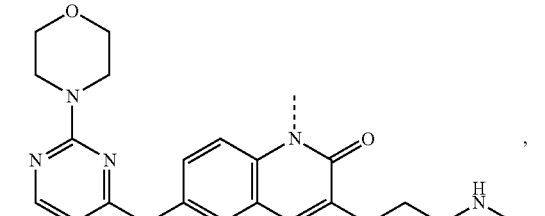

517
-continued
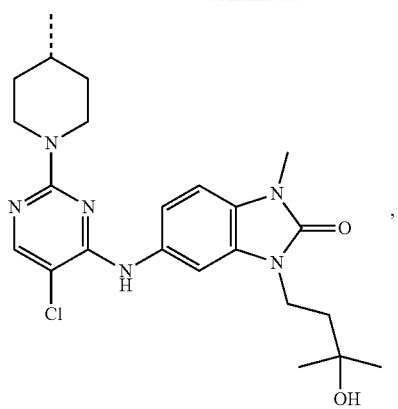
,
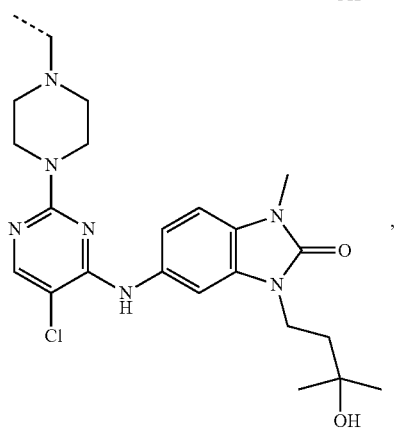
,
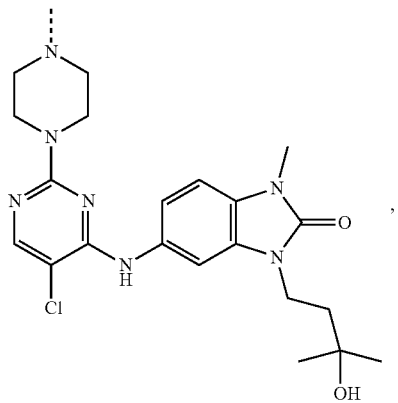
,
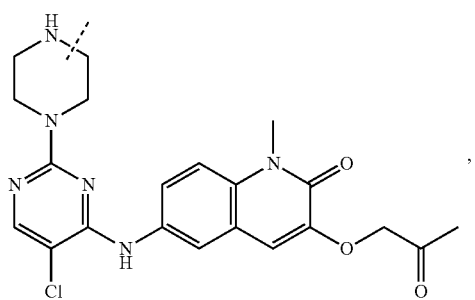
,
518
-continued
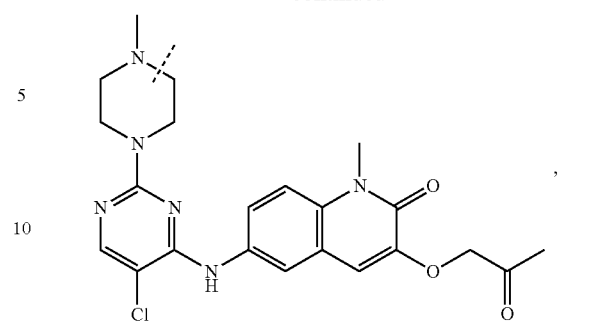
,
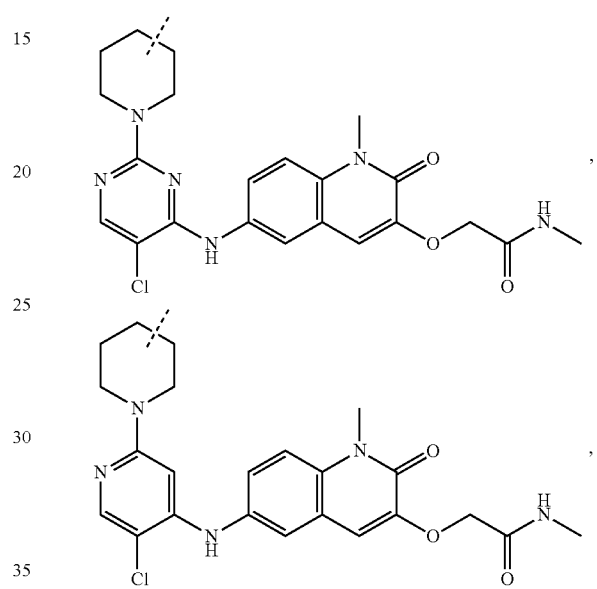
,
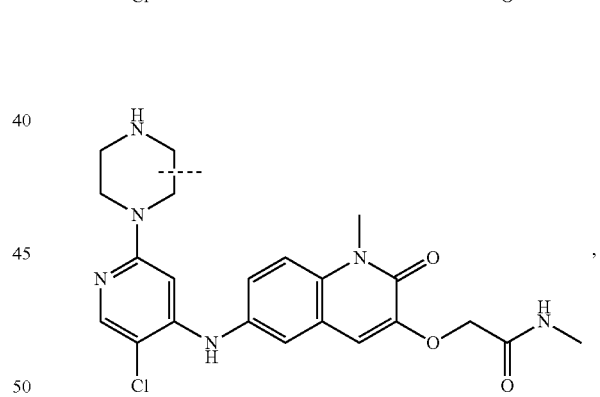
,
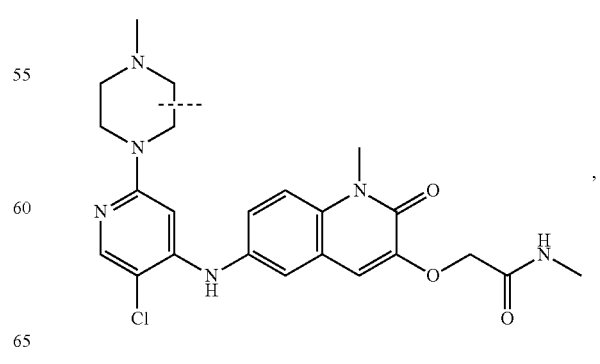
, 519
-continued
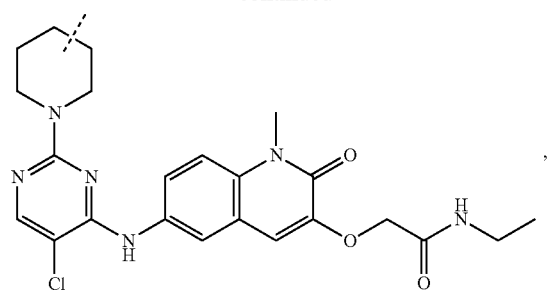
,
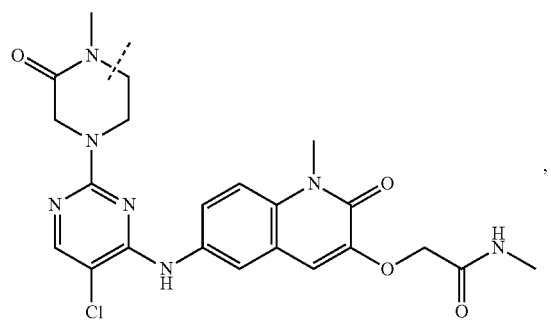
,
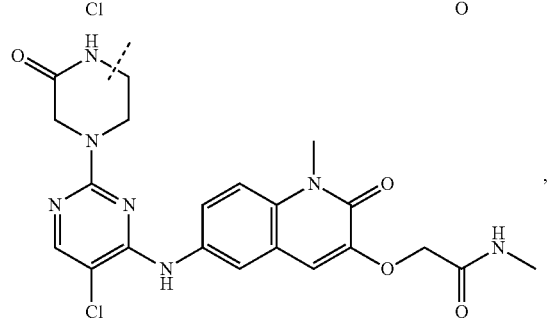
,
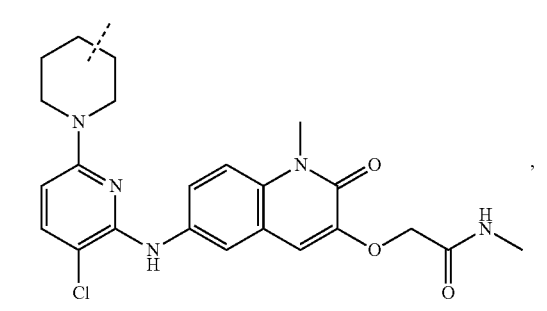
,
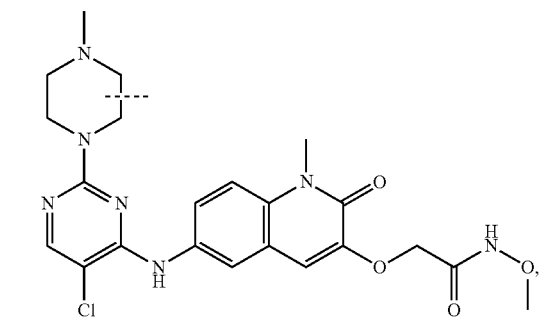
,
520
-continued
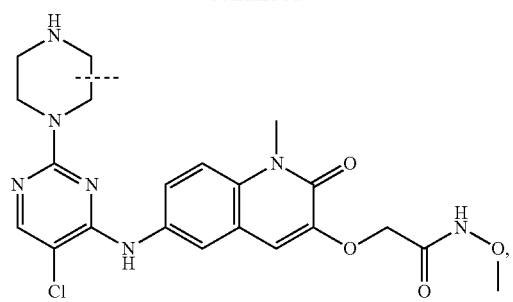
,
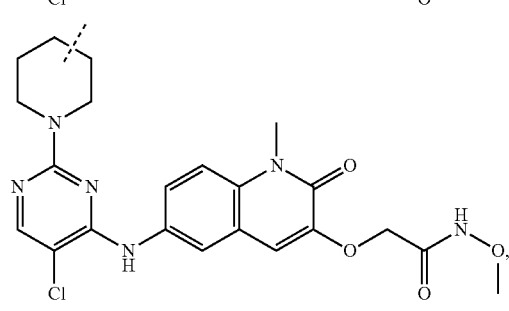
,
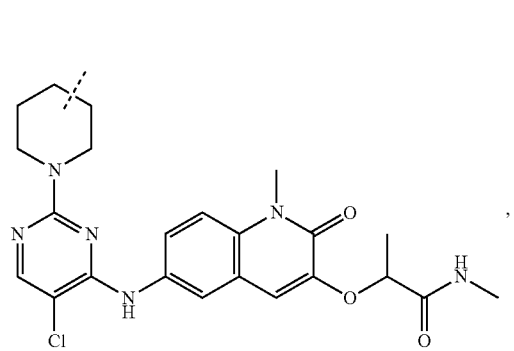
,
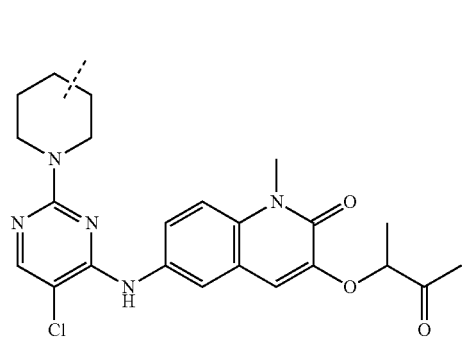
,
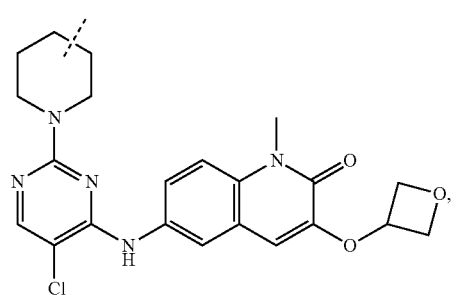
, 521
-continued
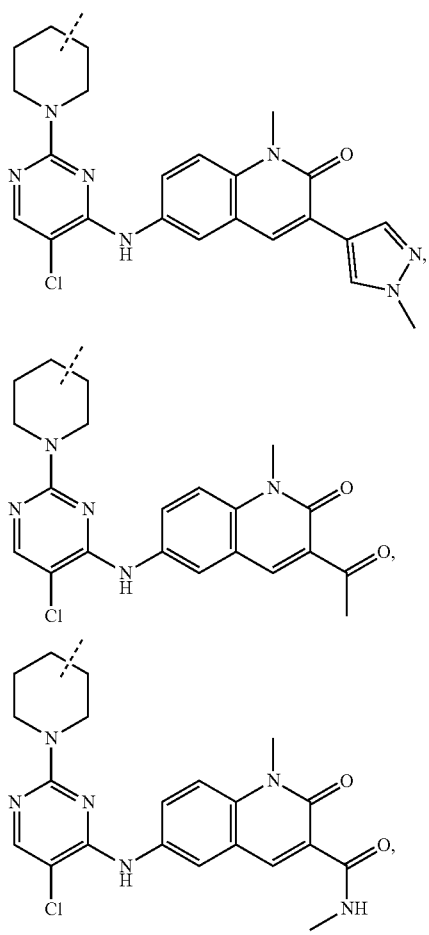
522
-continued
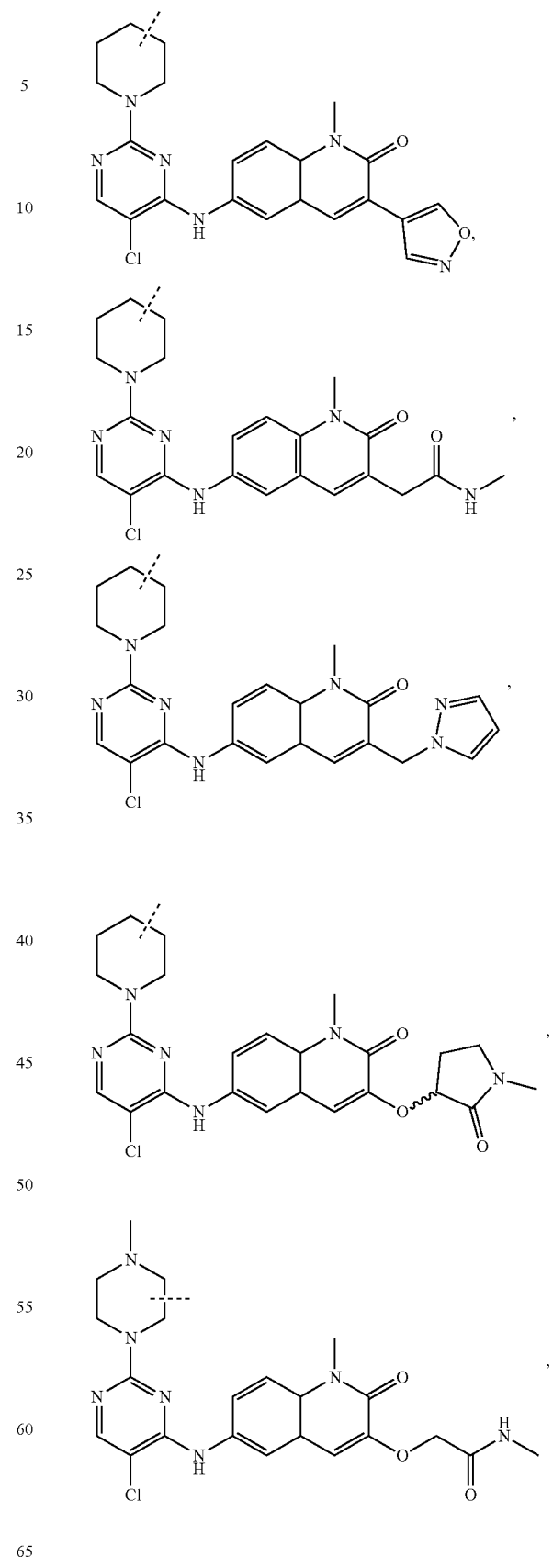

523
-continued
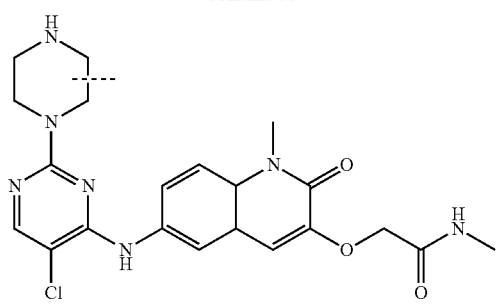,
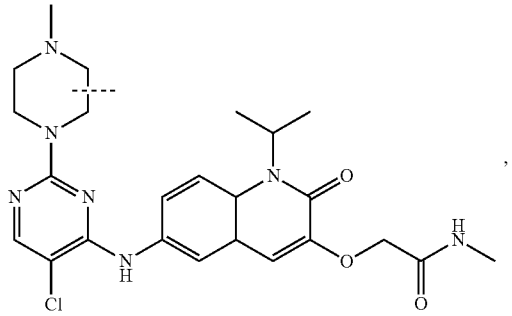,
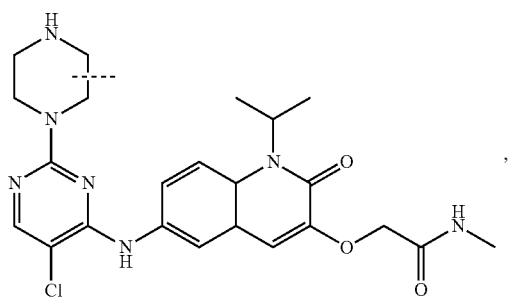,
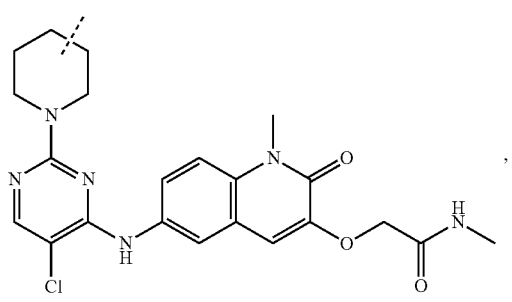,
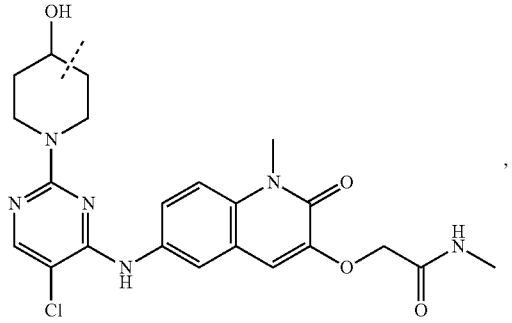,
524
-continued
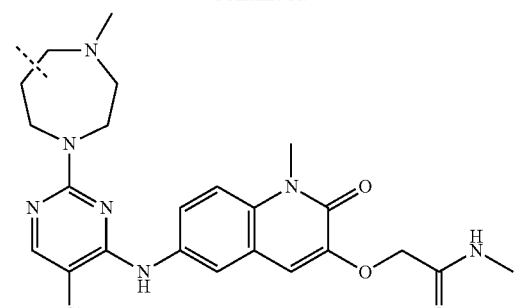,
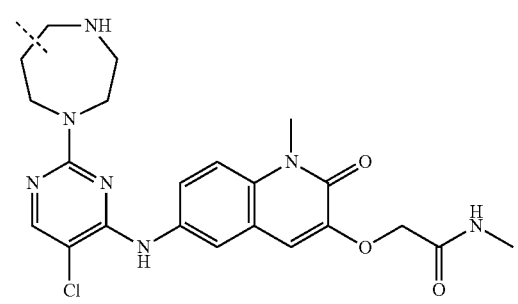,
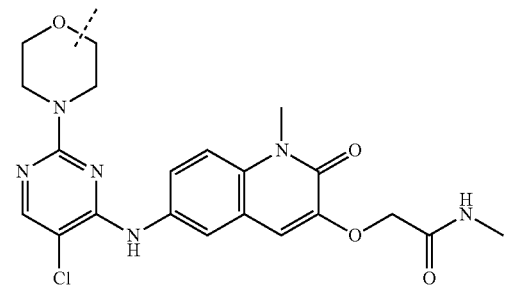,
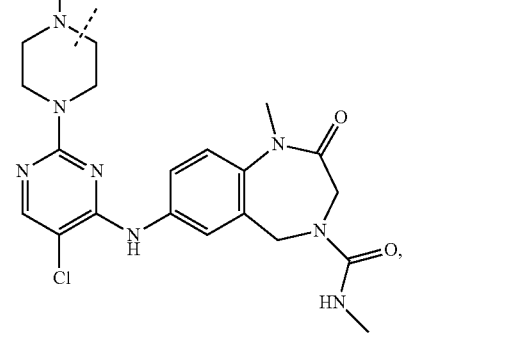,
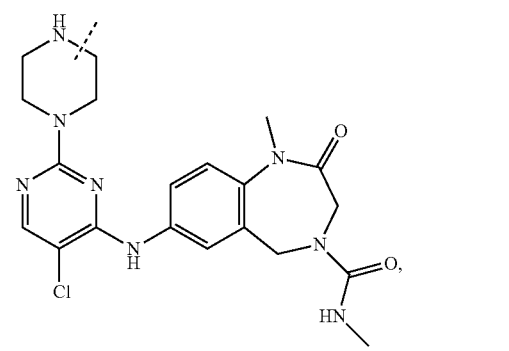, 525
-continued
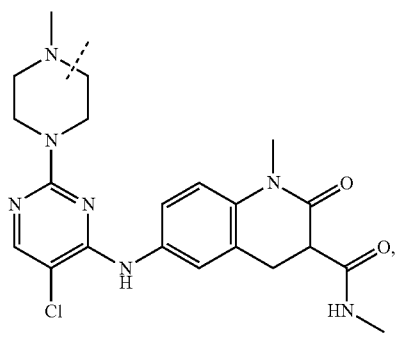
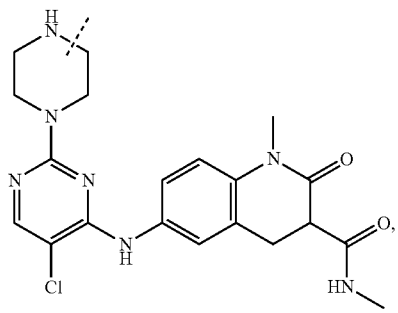
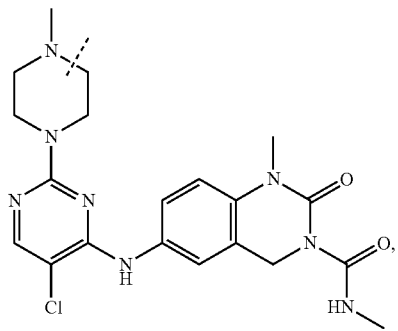
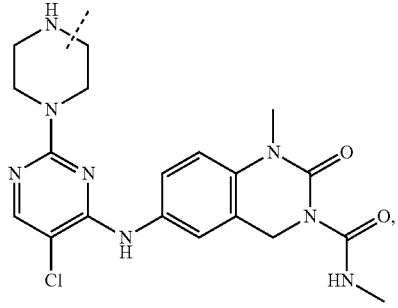
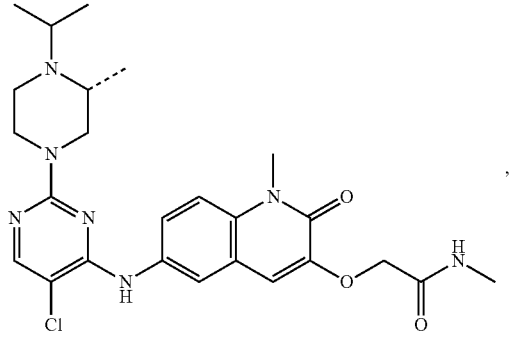
526
-continued
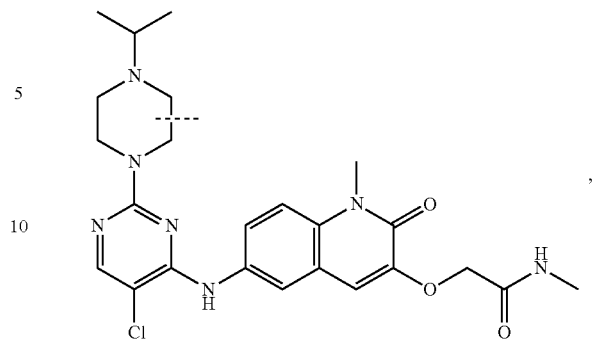
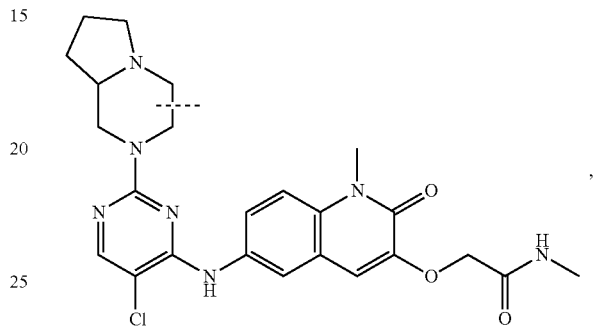
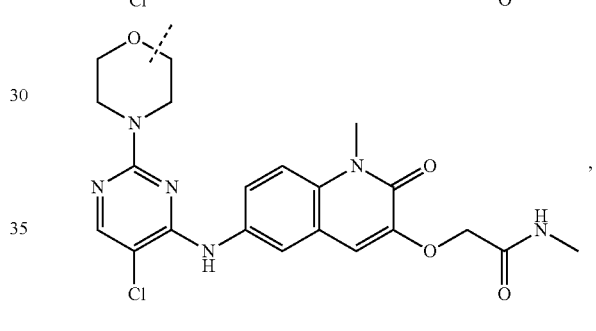
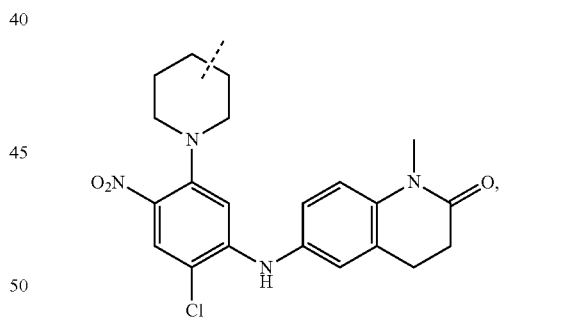
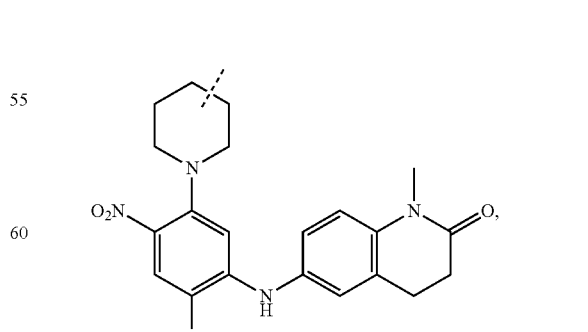

527
-continued
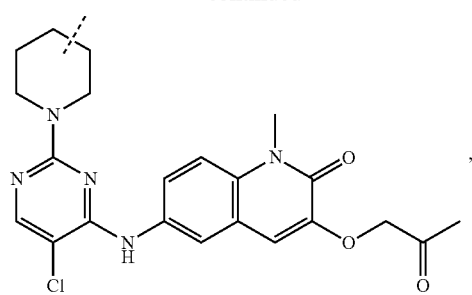
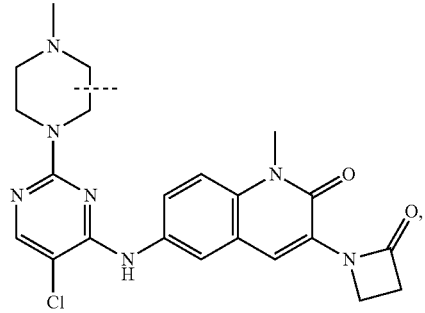
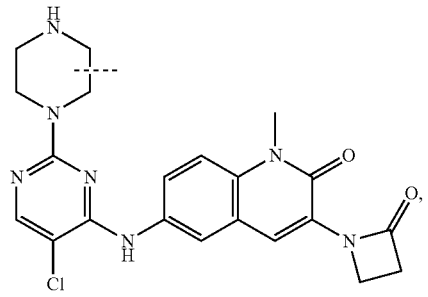
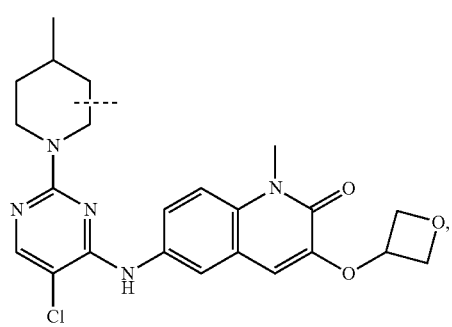
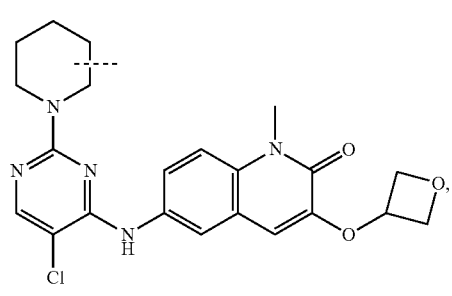
528
-continued
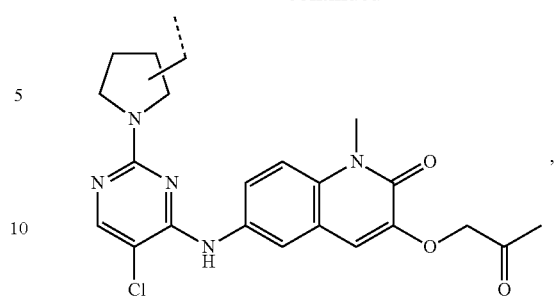
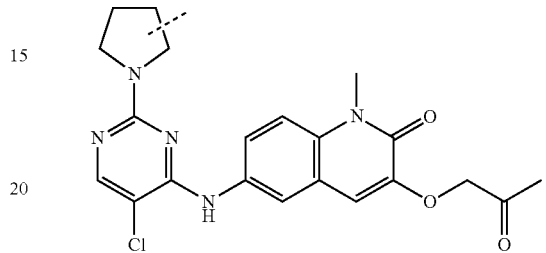
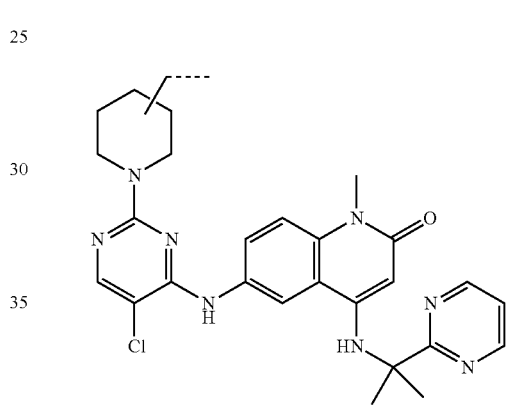
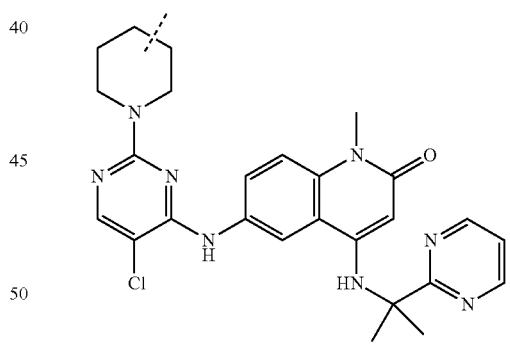
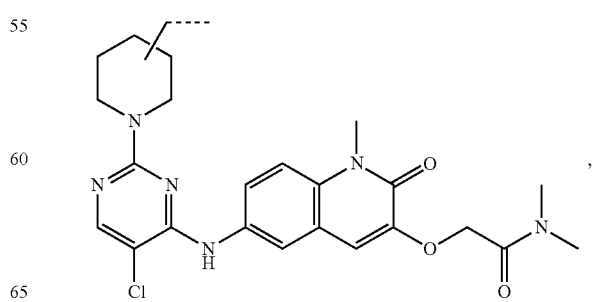

529
-continued
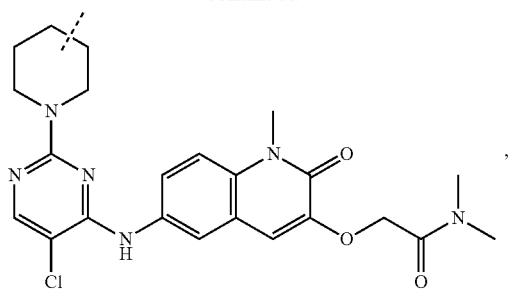,
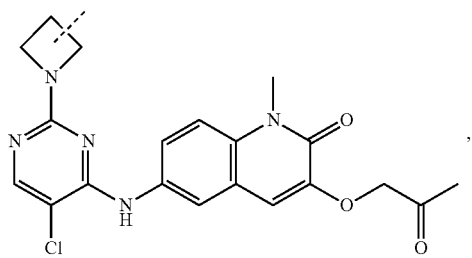,
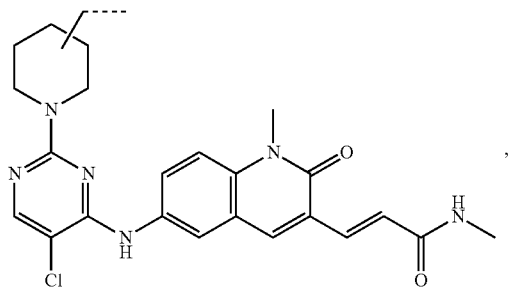,
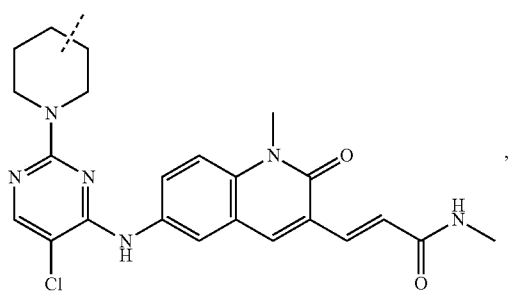,
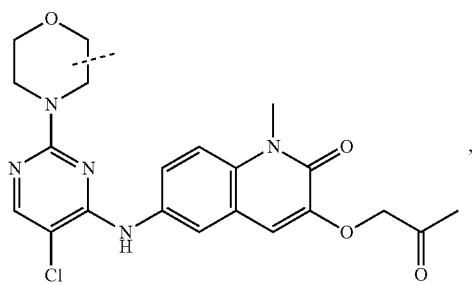,
,
530
-continued
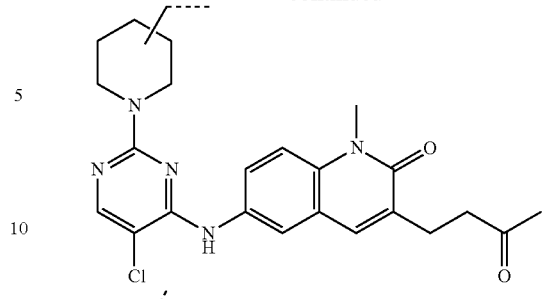,
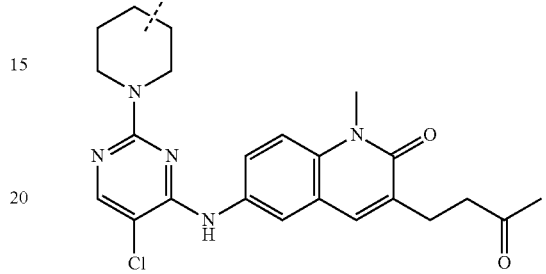,
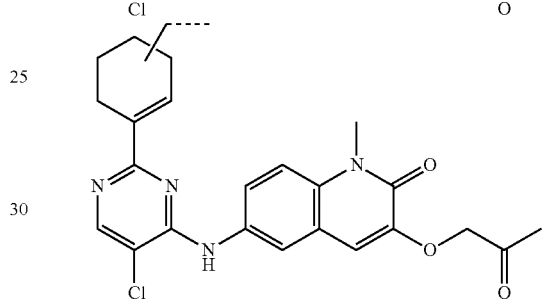,
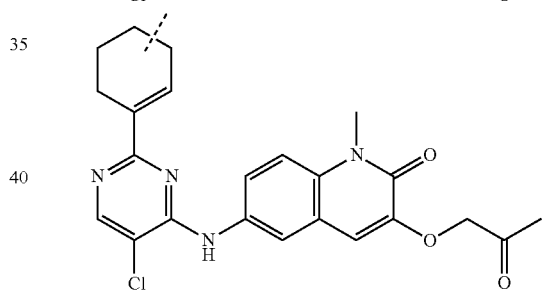,
,
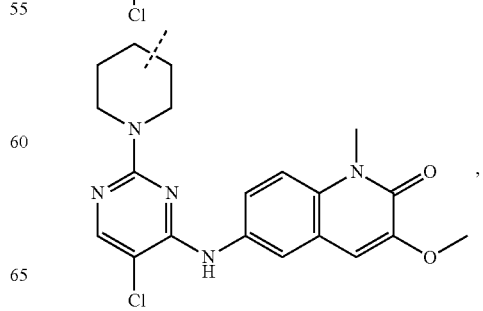, 531
-continued
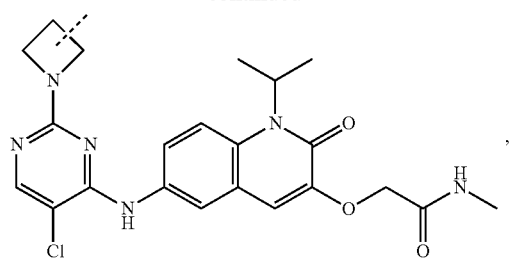
,
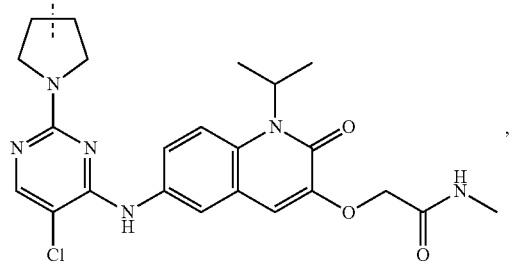
,
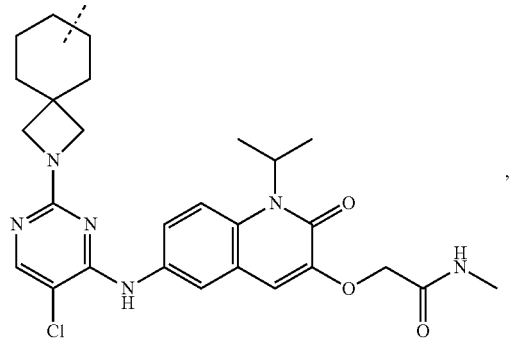
,
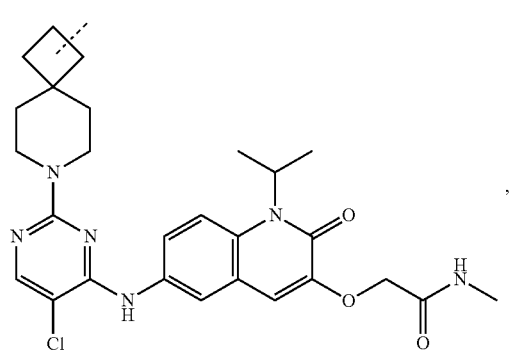
,
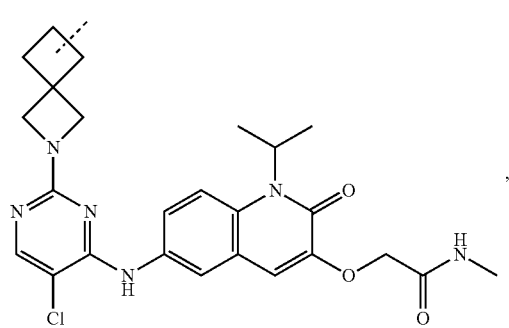
,
532
-continued
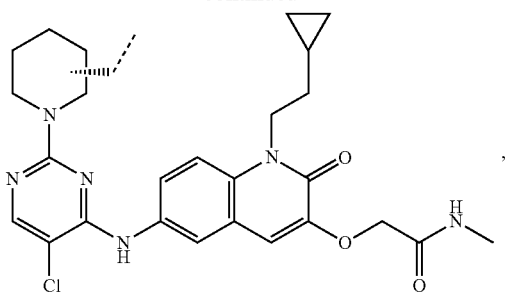
,
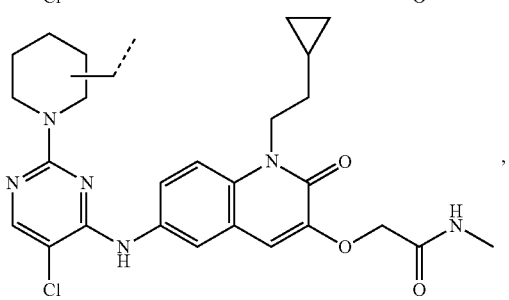
,
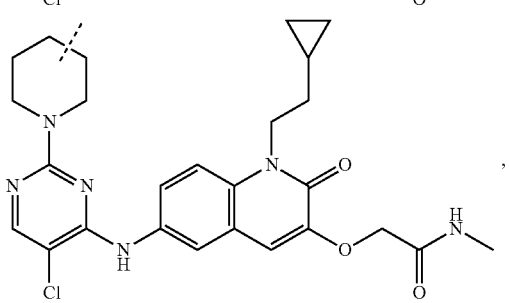
,
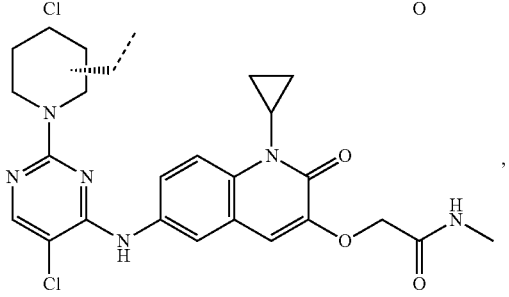
,
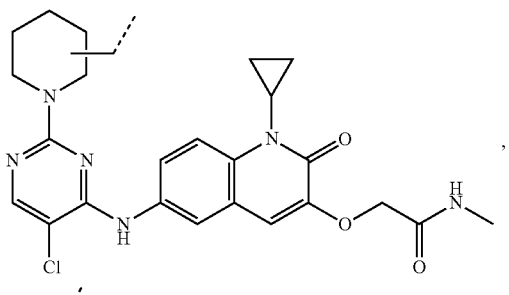
,
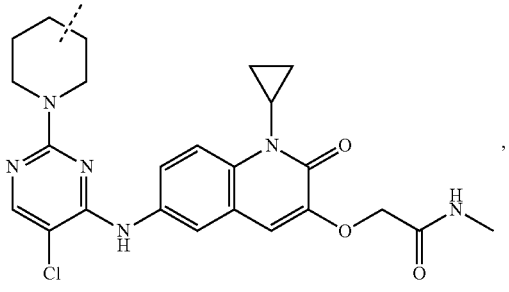
, 533
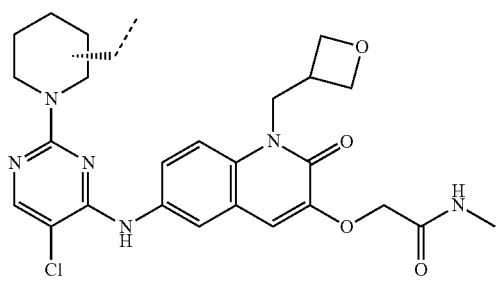,
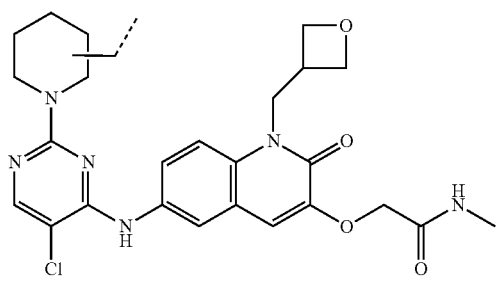,
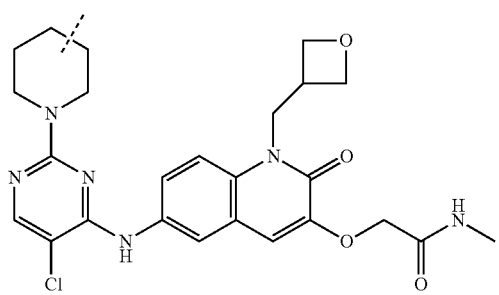,
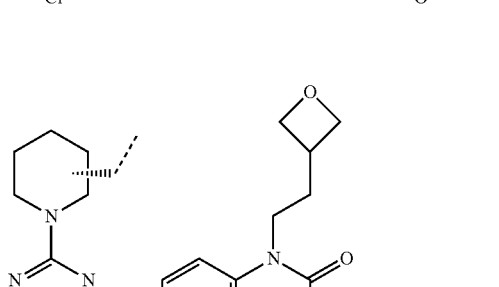,
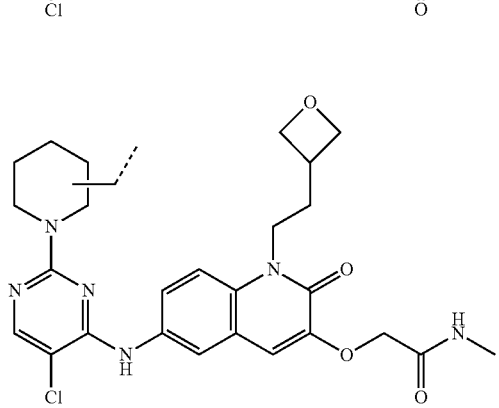,
534
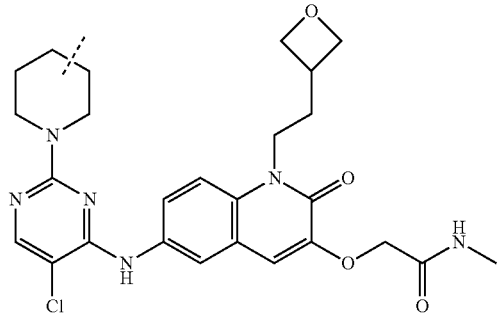,
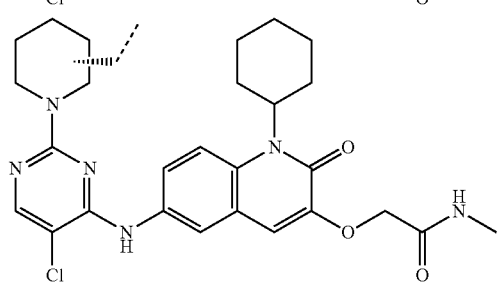,
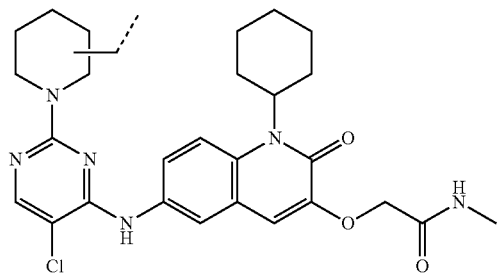,
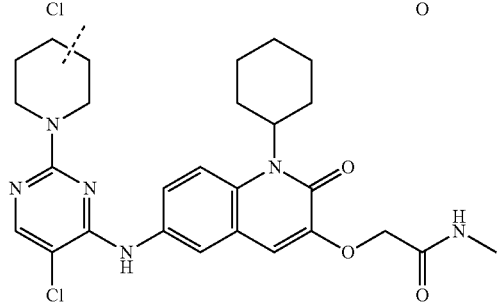,
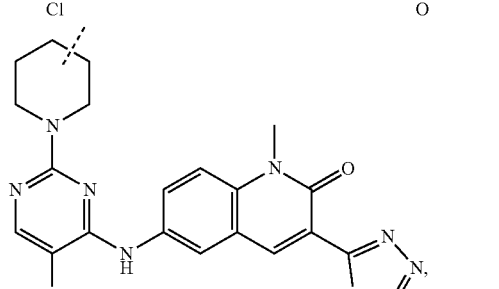,
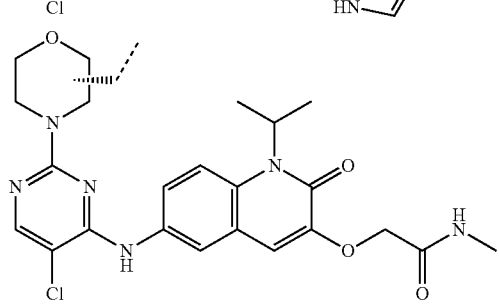, 535
-continued
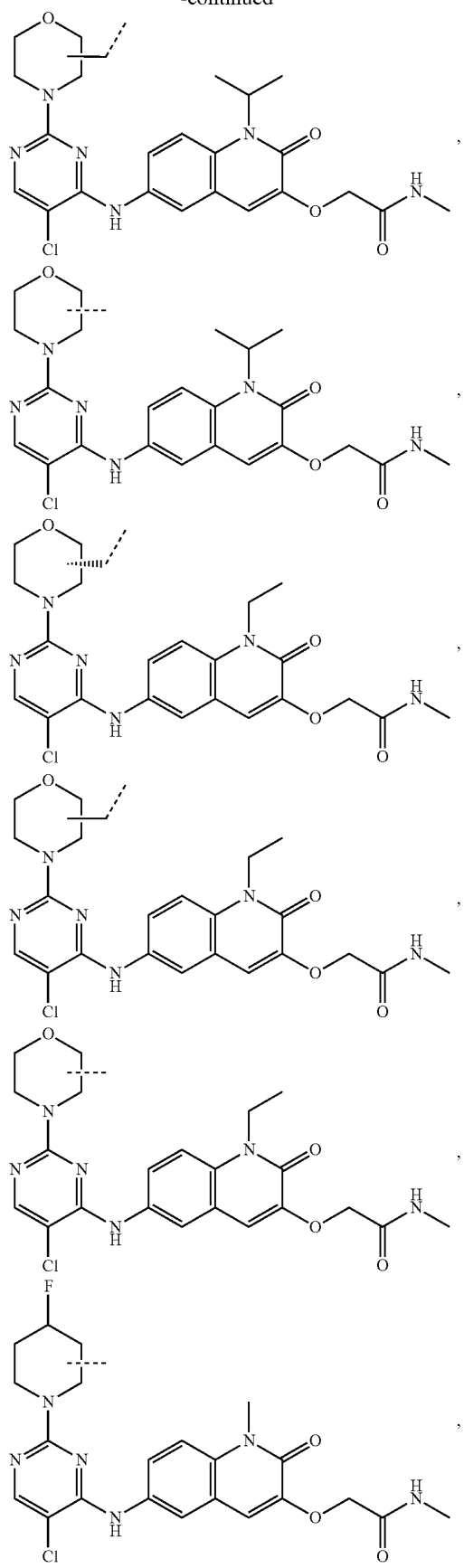
536
-continued
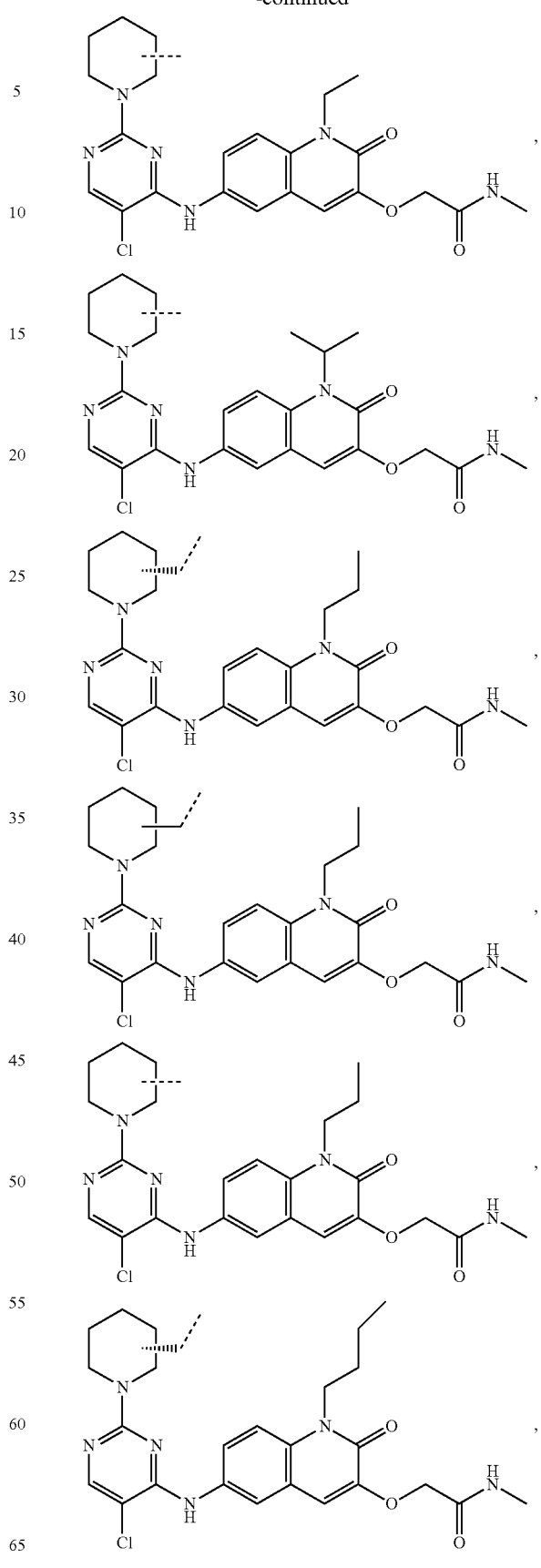

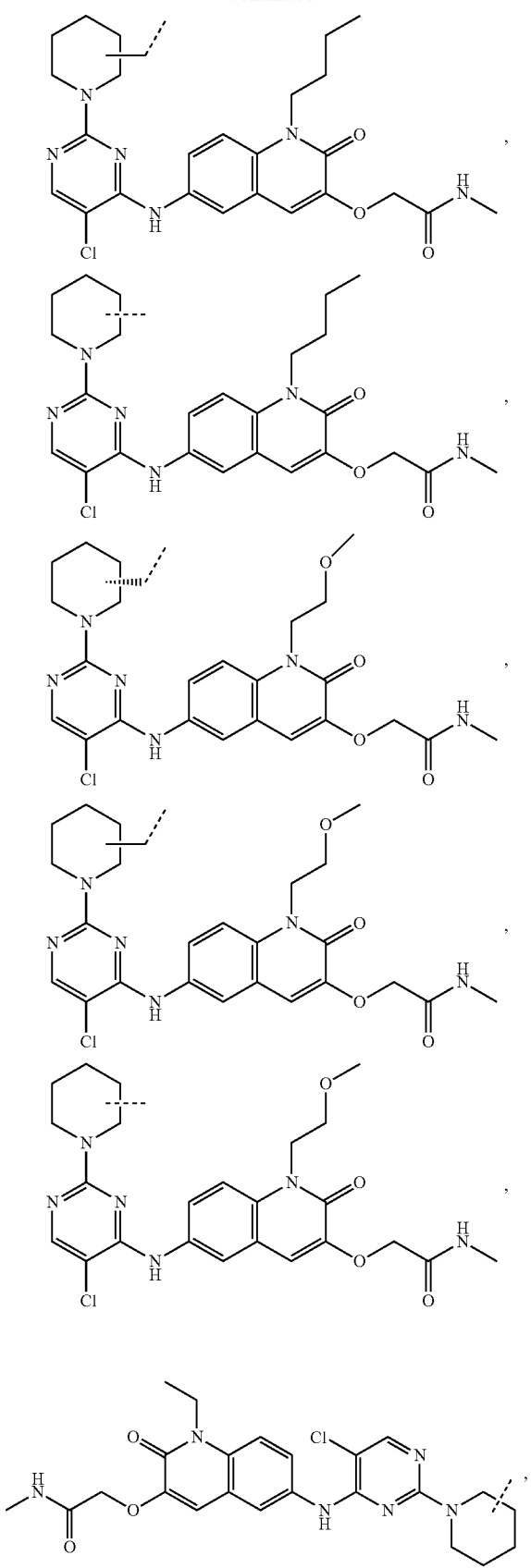

539
-continued
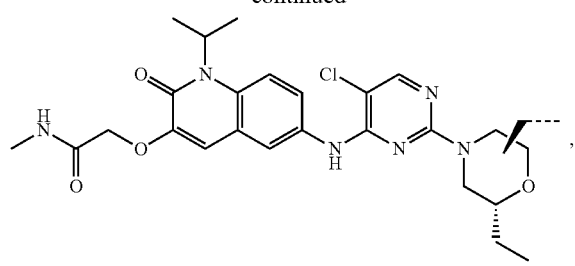,
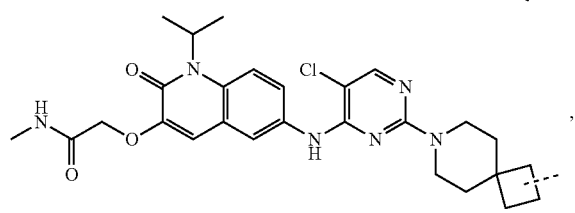,
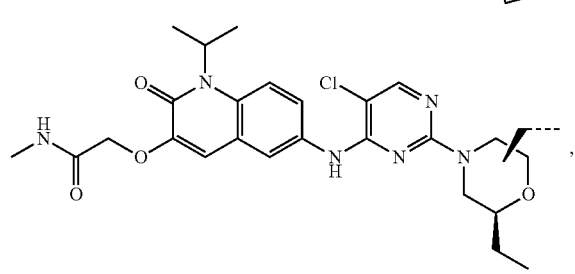,
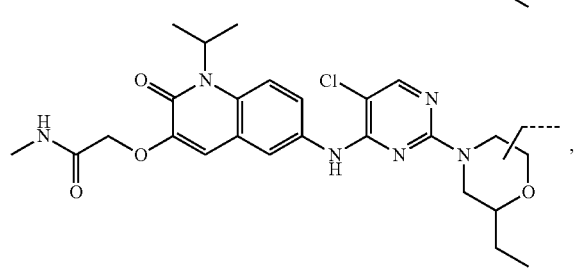,
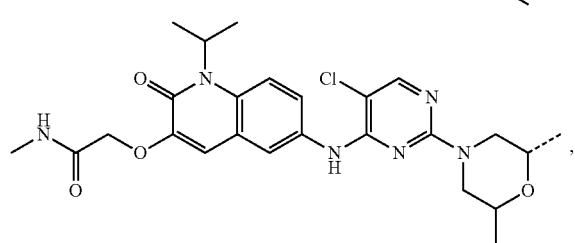,
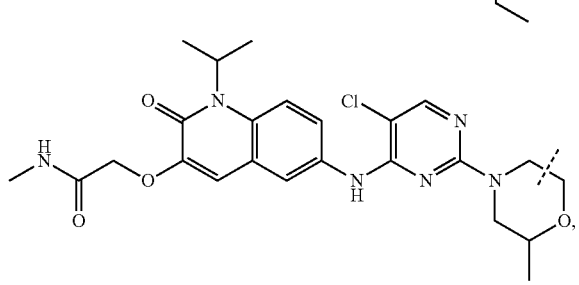,
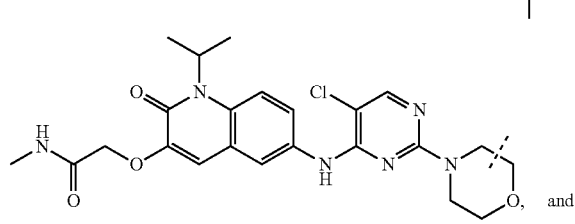, and
540
-continued
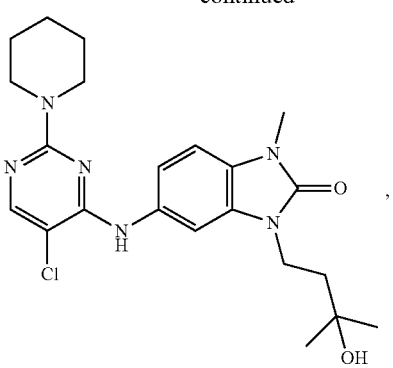,
wherein ⸺ of the PTM indicates the point of attachment with a linker group (L) or a ULM, and ⌇ represents a bond that may be stereospecific ((R) or (S)) or non-stereospecific.
In any aspect or embodiment described herein, the PTM is selected from:
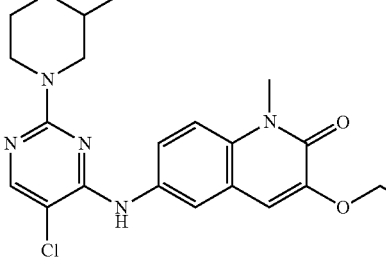,
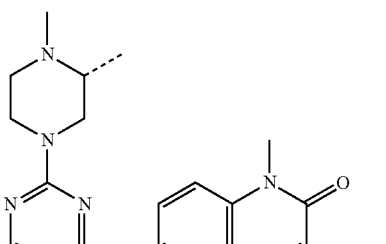,
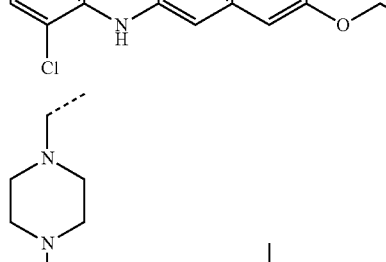,
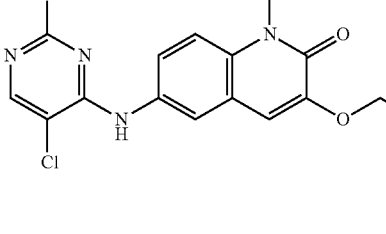, 541
-continued
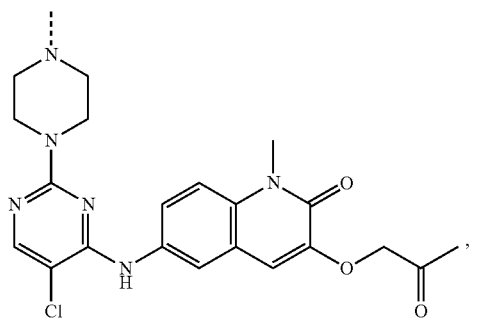
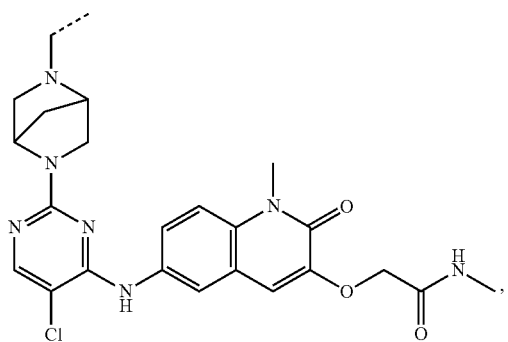
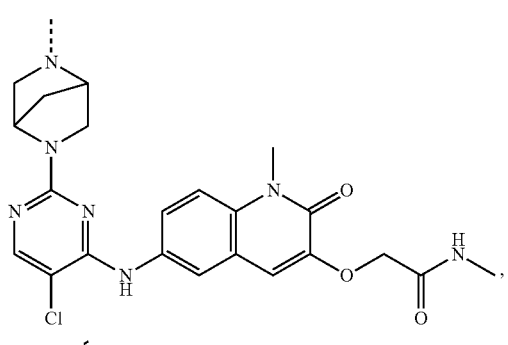
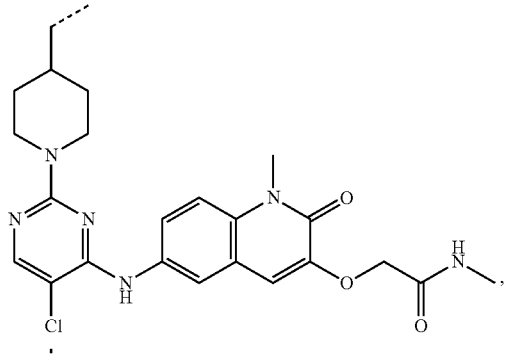
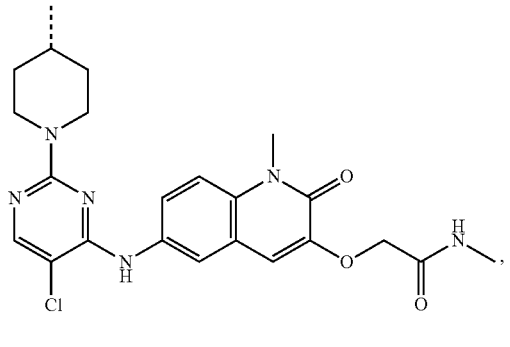
542
-continued
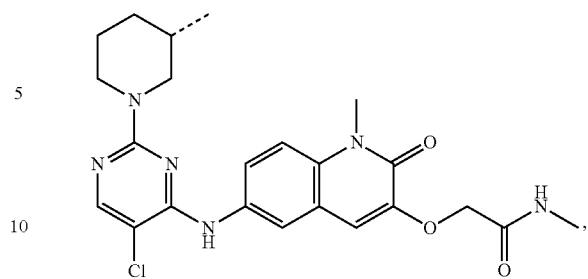
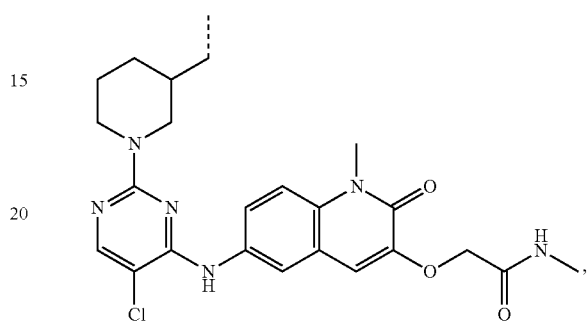
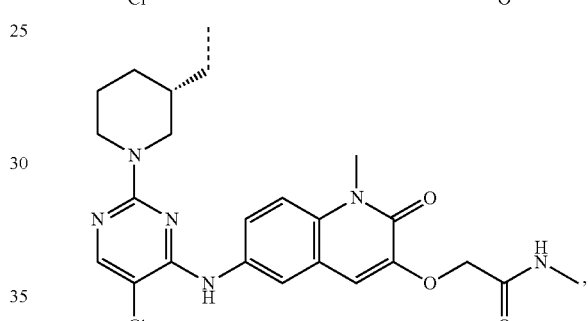
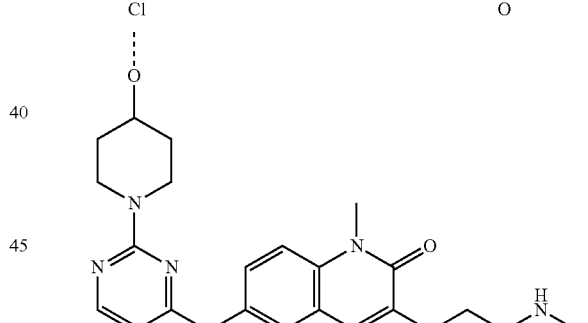
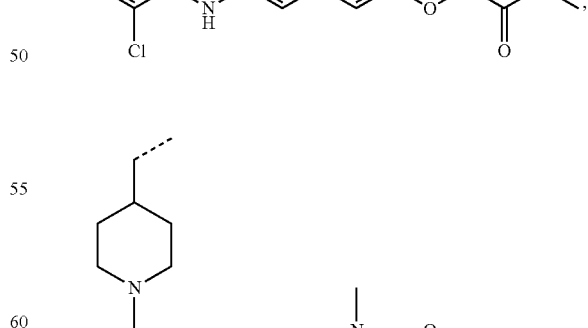
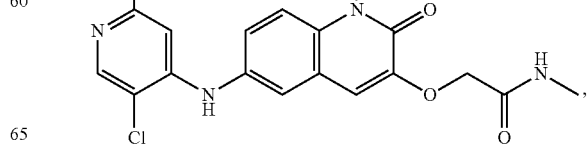

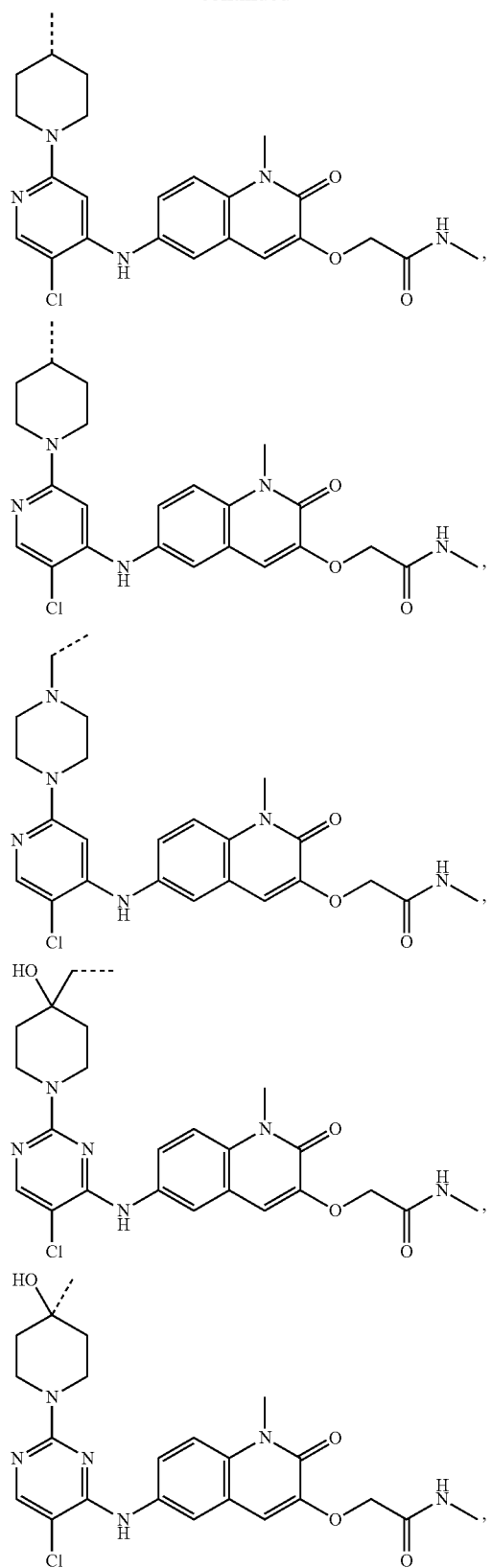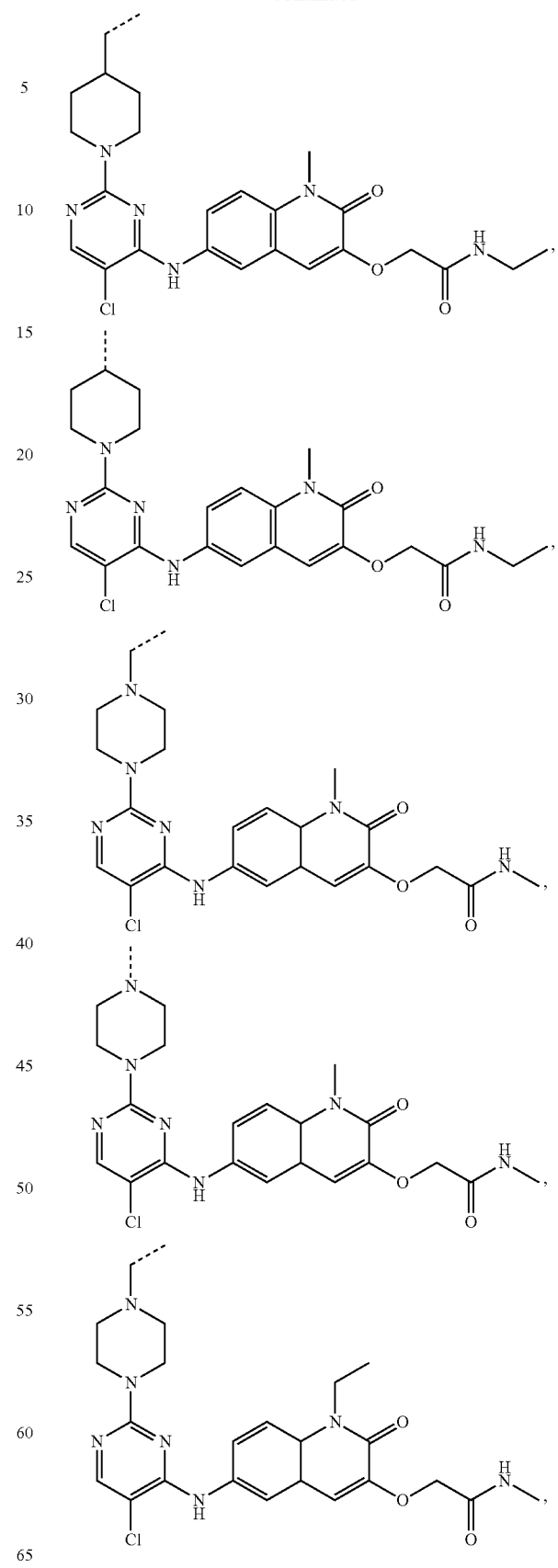

545
-continued
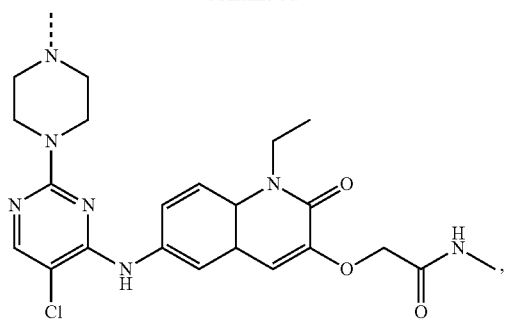
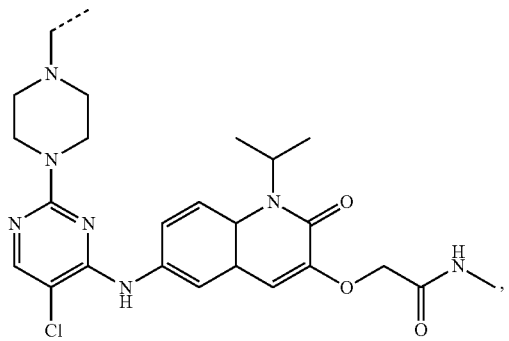
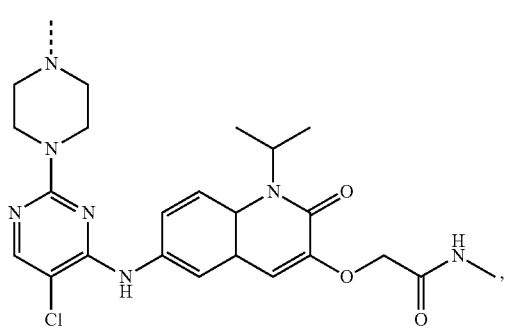
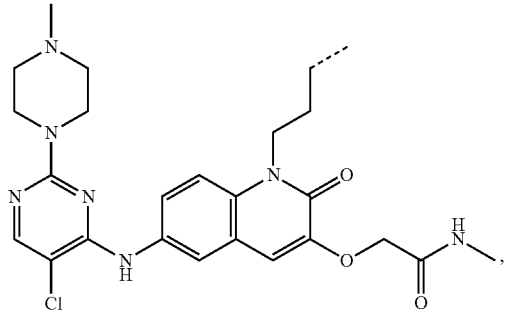
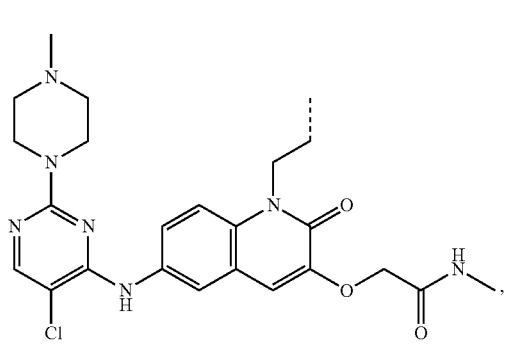
546
-continued
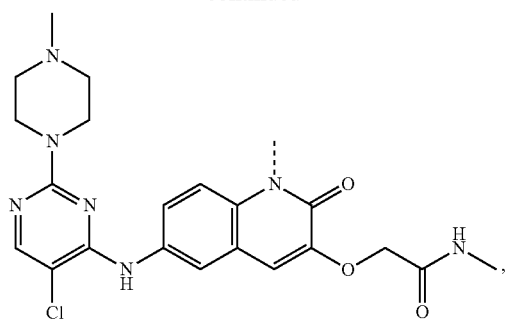
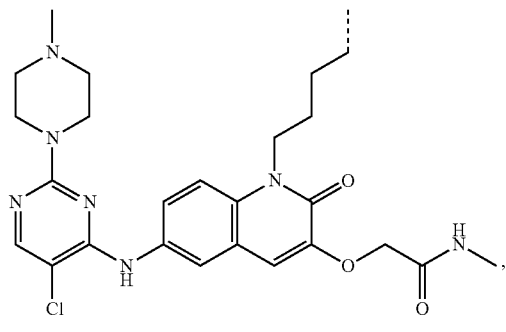
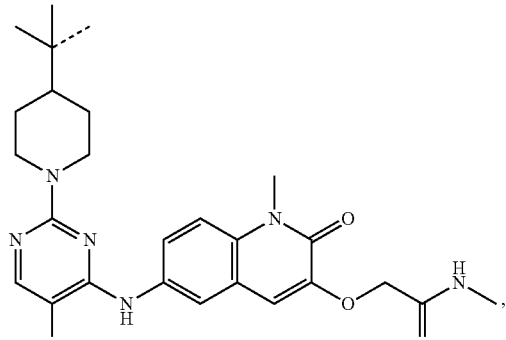
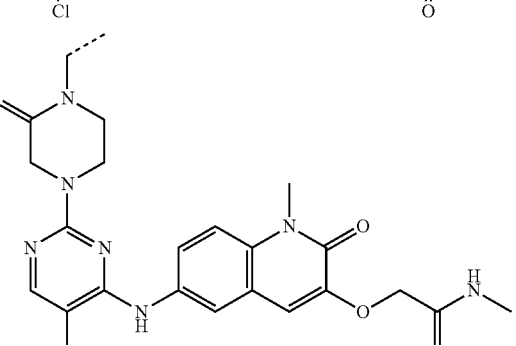

547
-continued
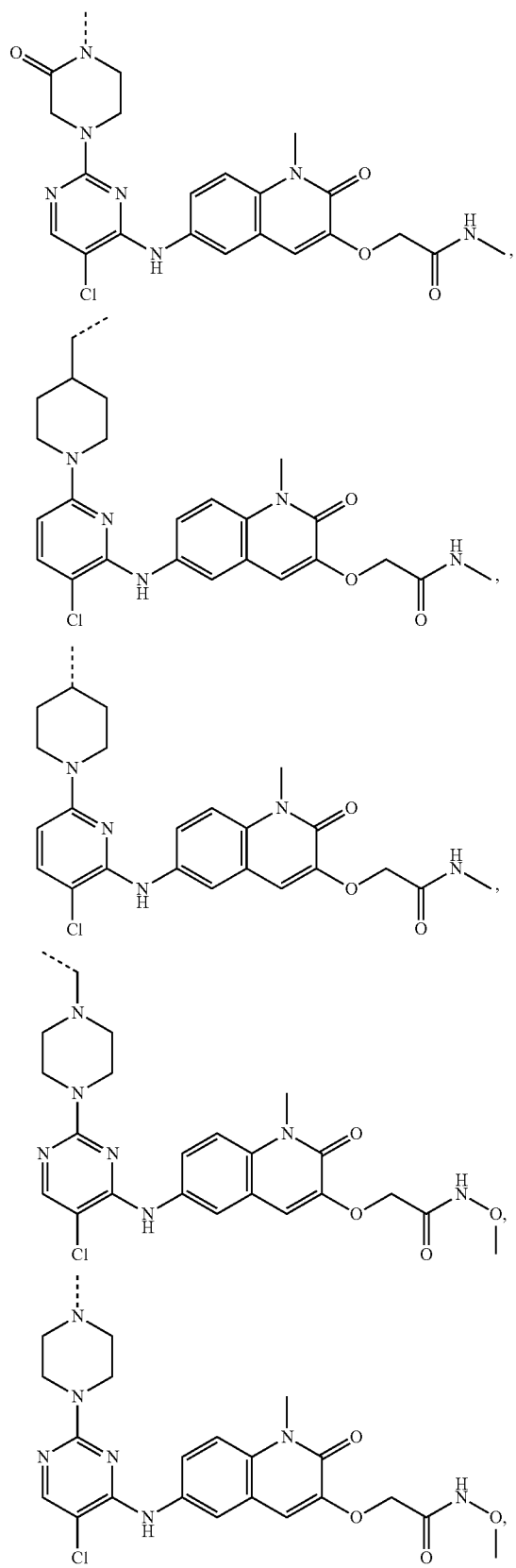
548
-continued
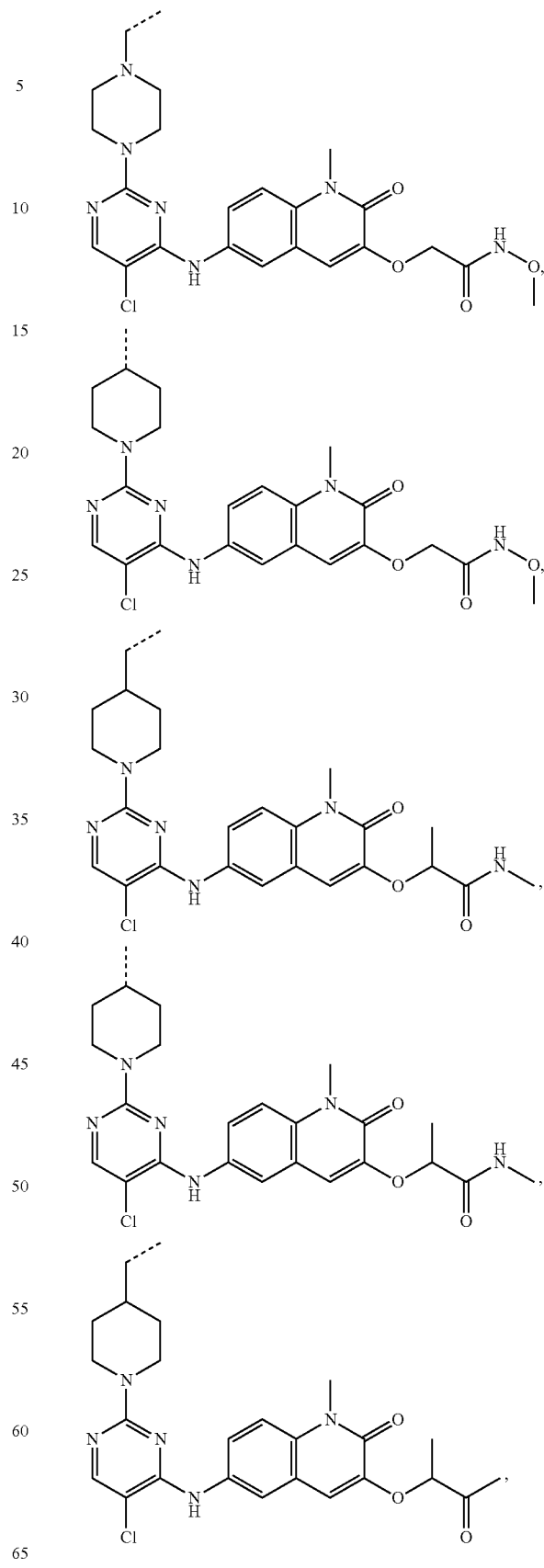

549
-continued
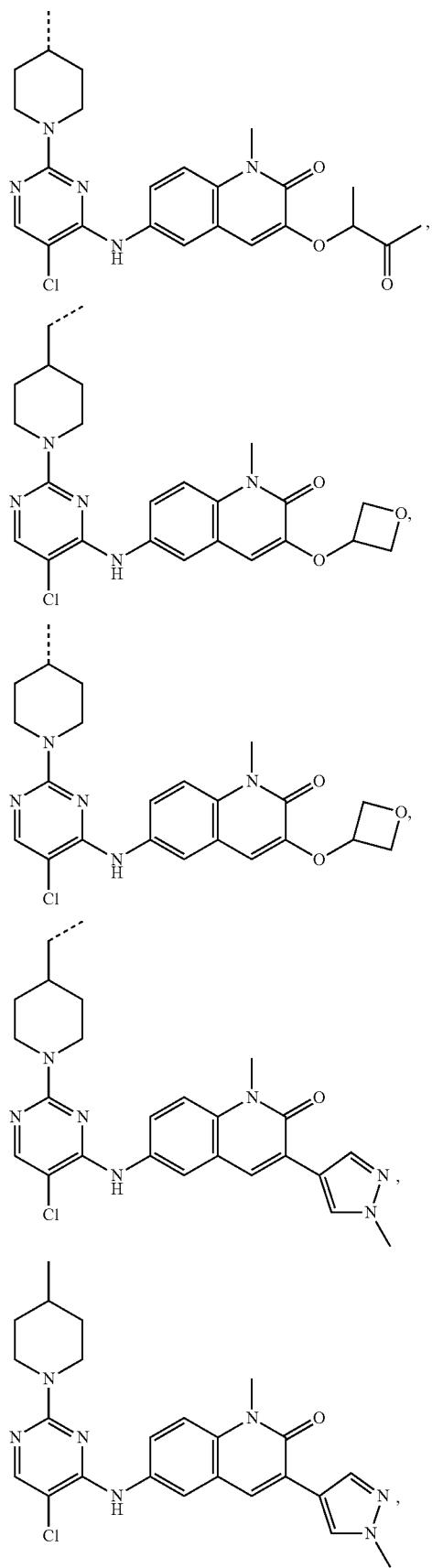
550
-continued
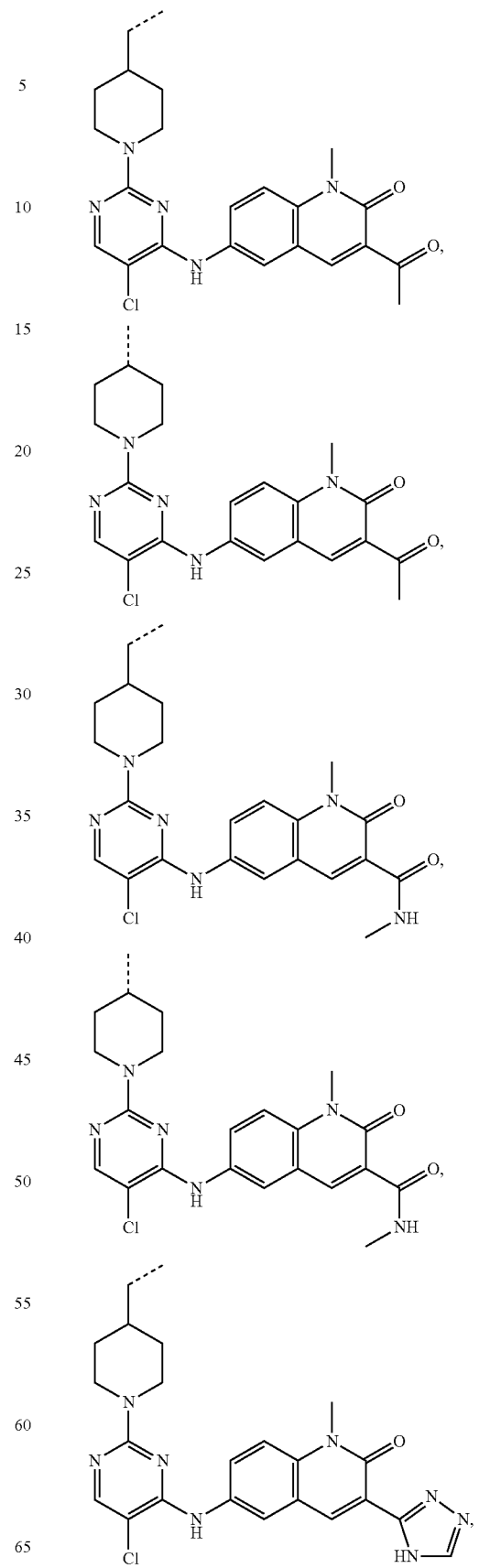

551
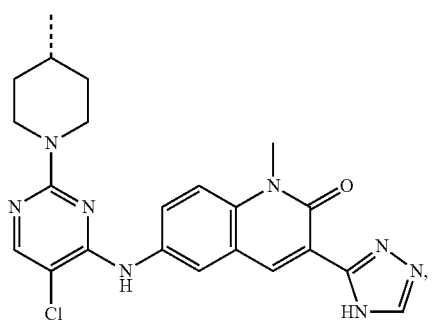
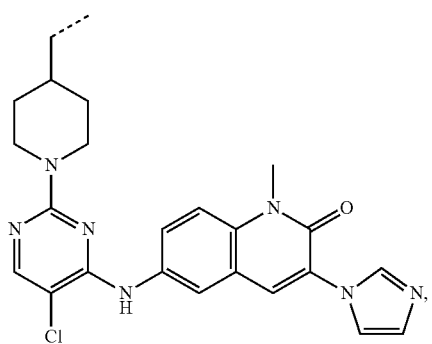
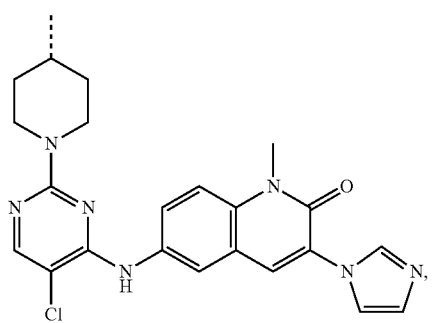
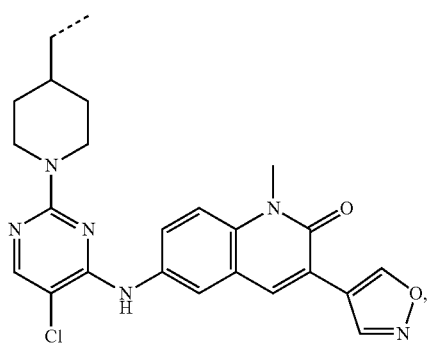
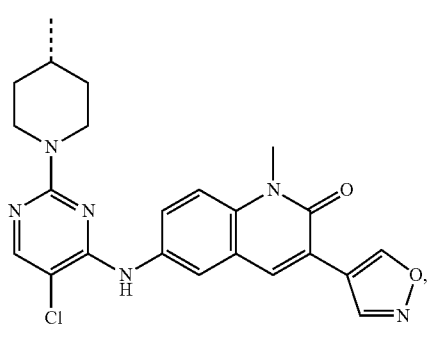
552
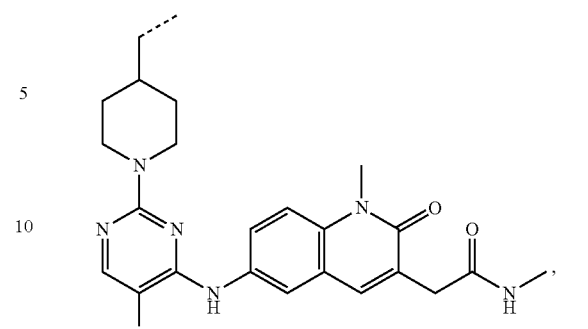
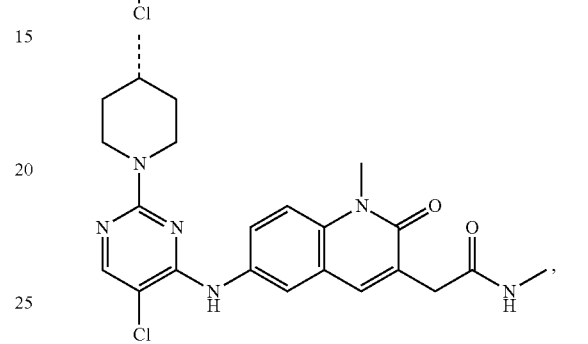
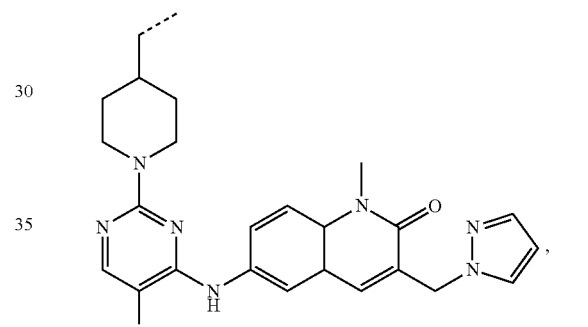
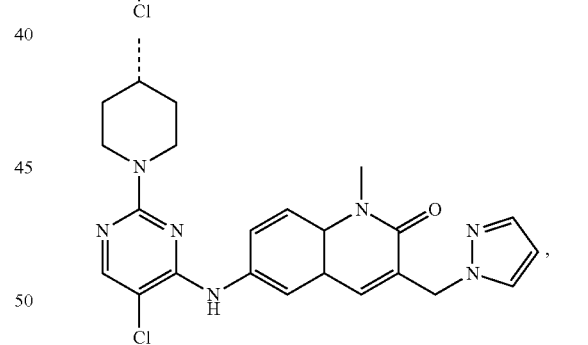
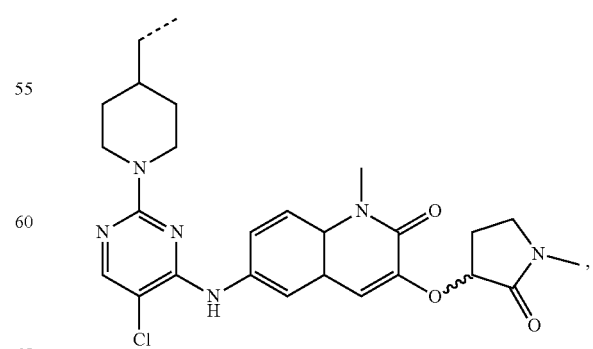

553
-continued
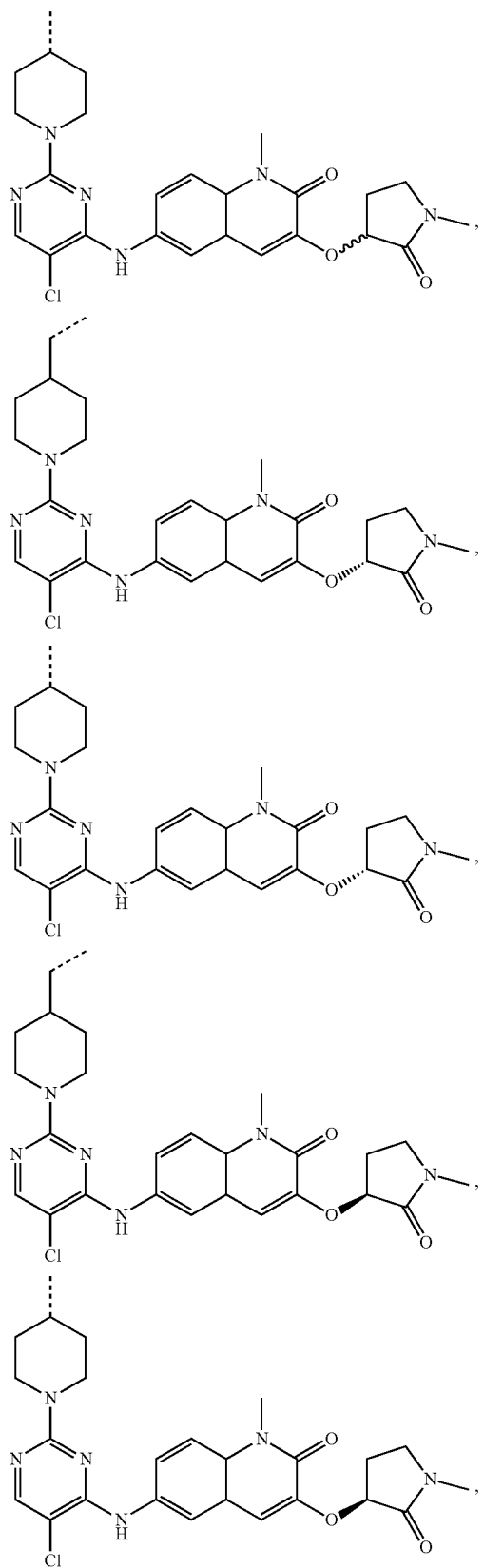
554
-continued
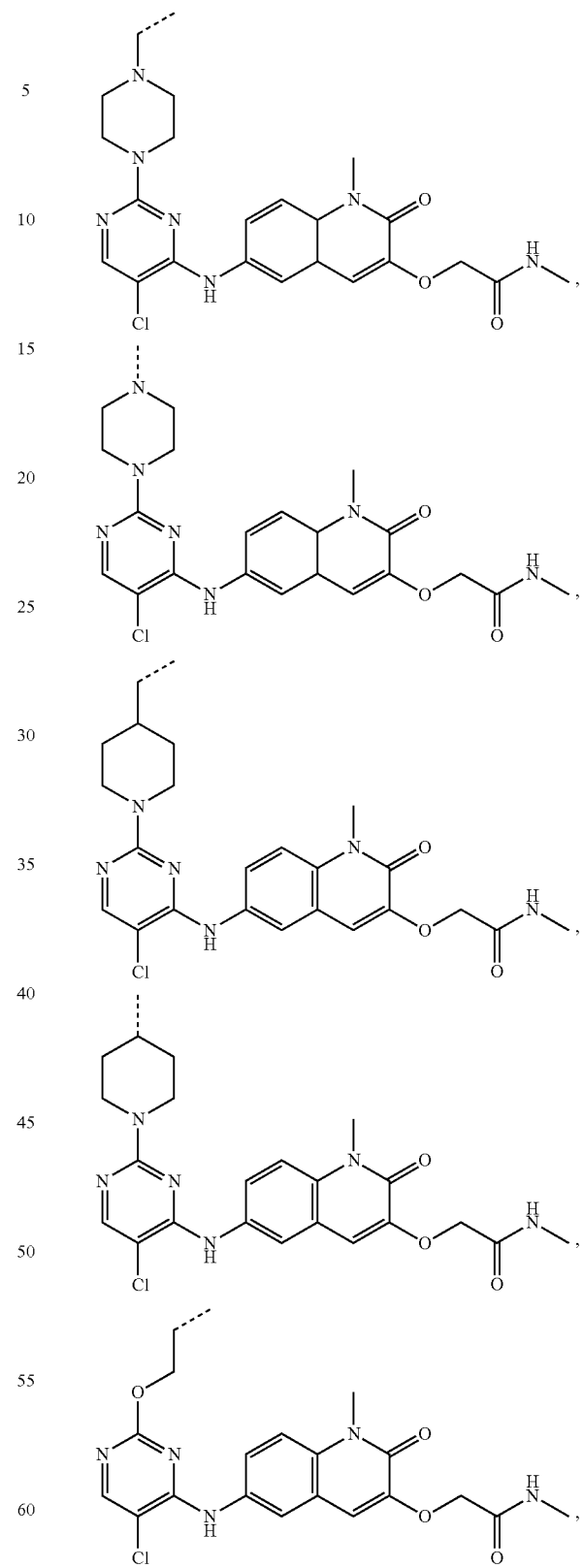

555
-continued
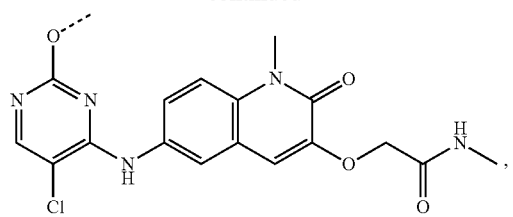
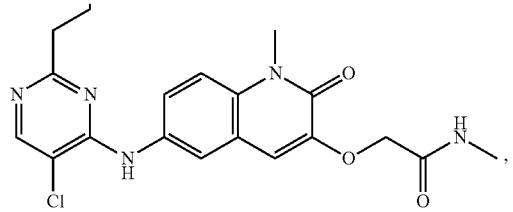
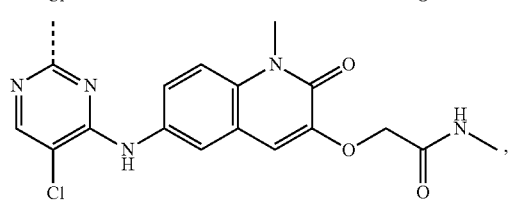
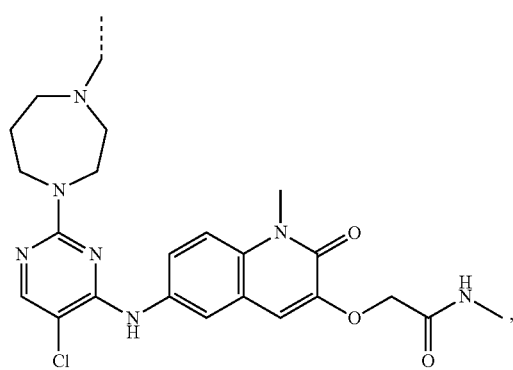
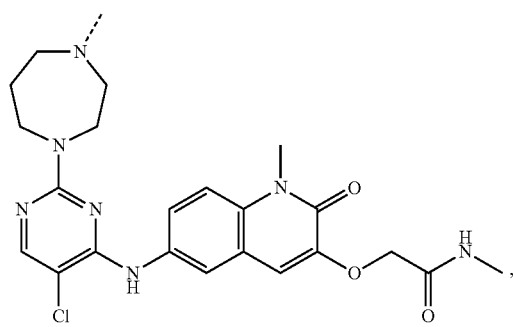
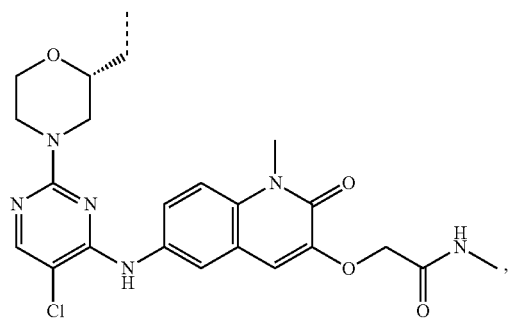
556
-continued
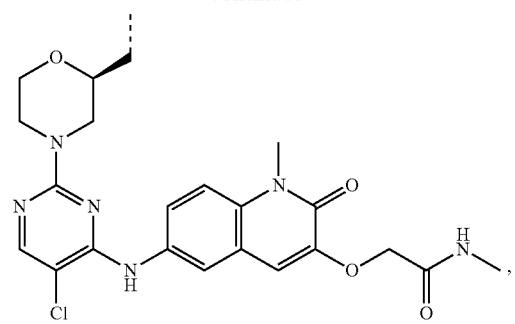
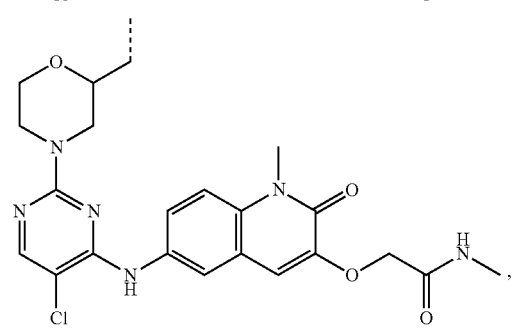
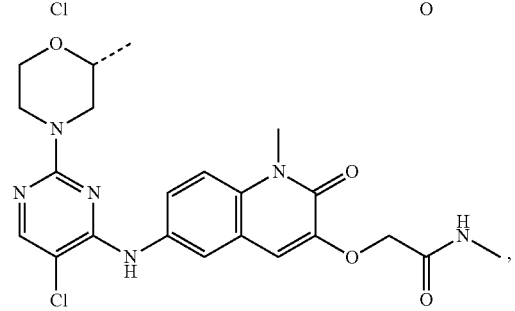
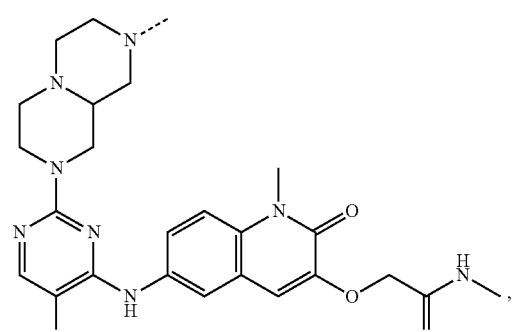
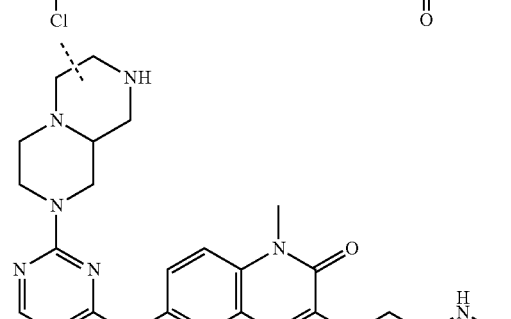

557
-continued
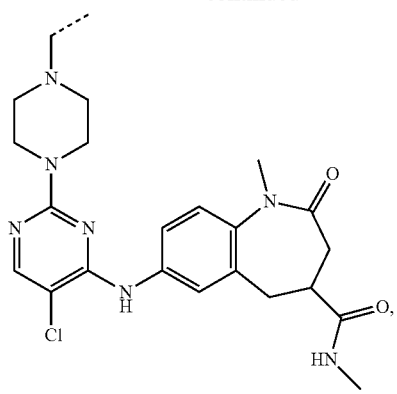
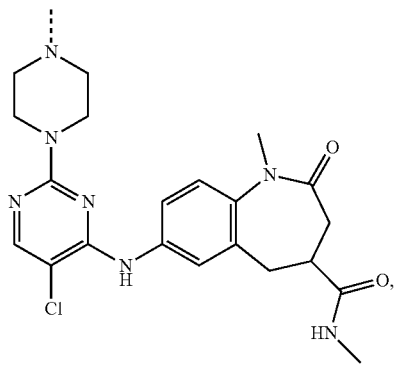
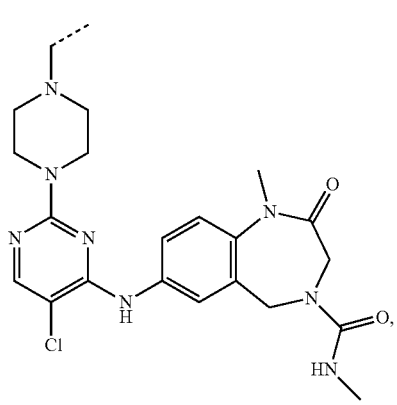
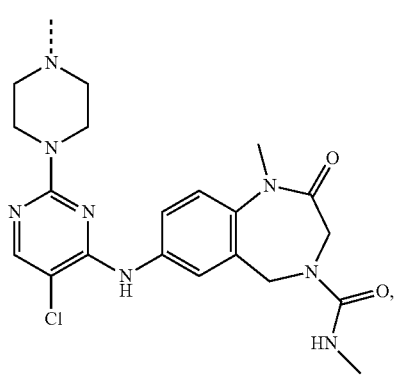
558
-continued
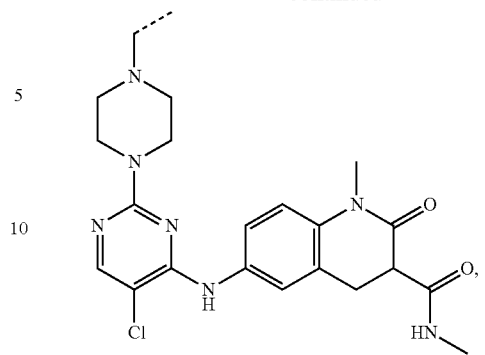
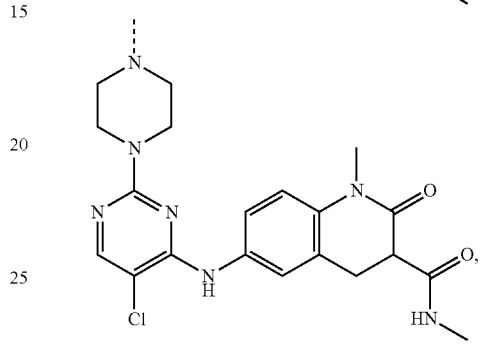
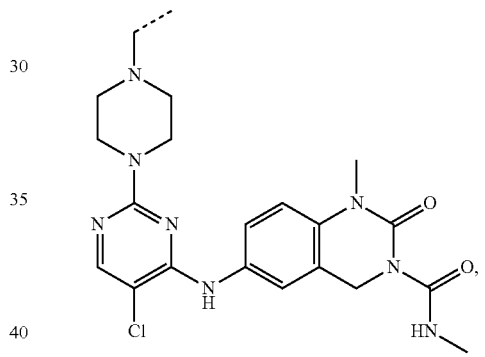
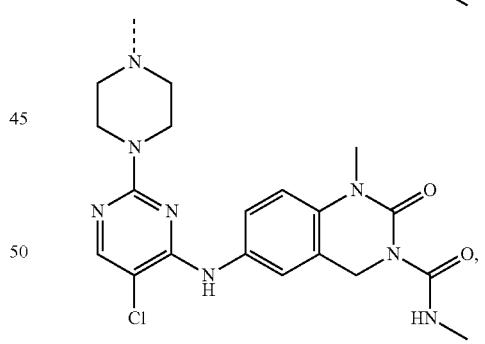
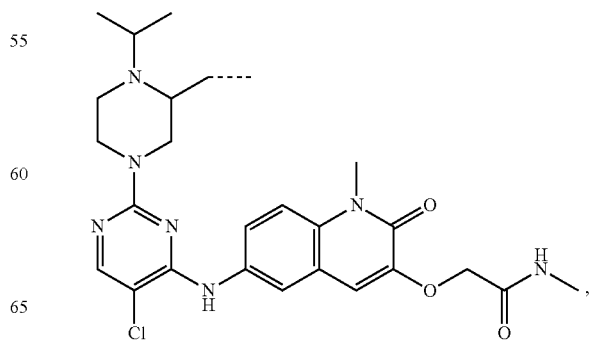

559
-continued
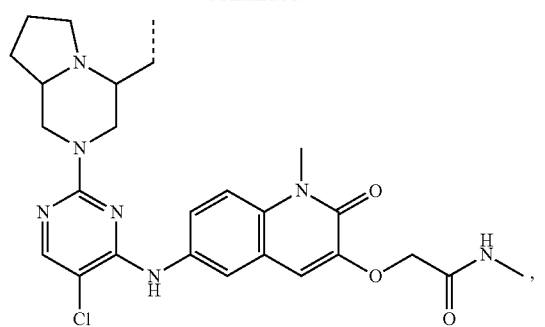
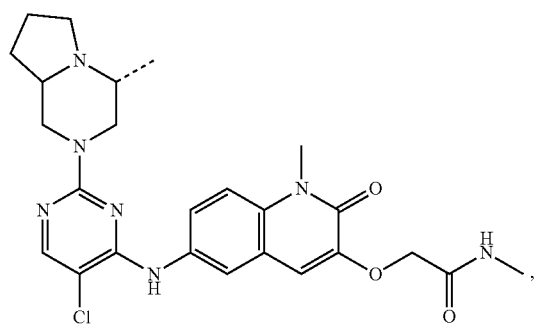
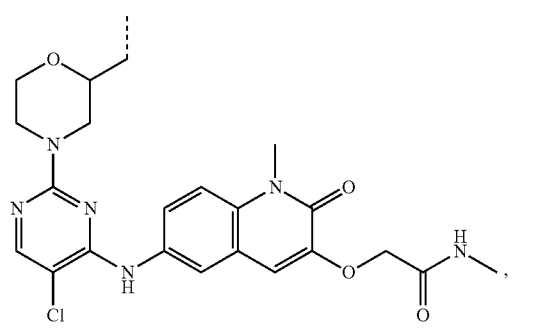
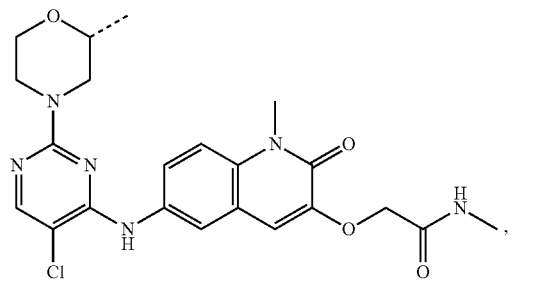
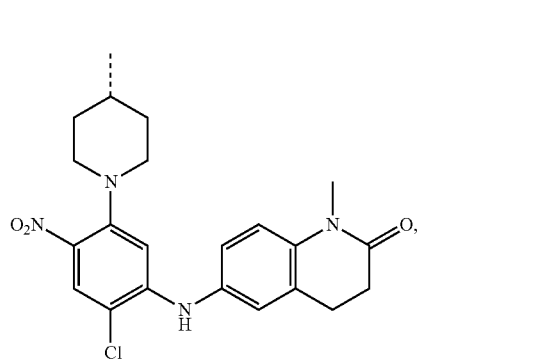
560
-continued
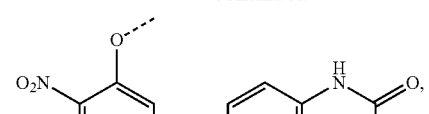

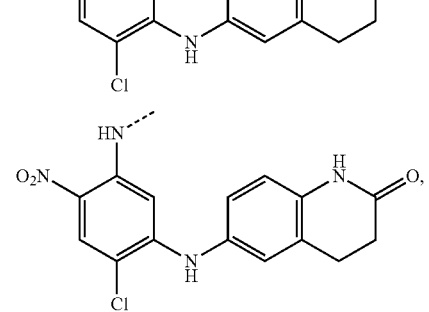
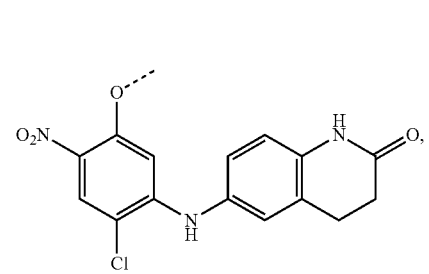
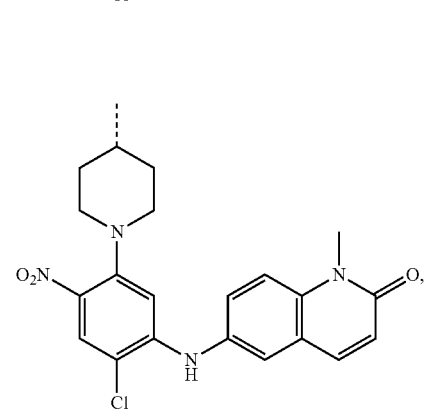
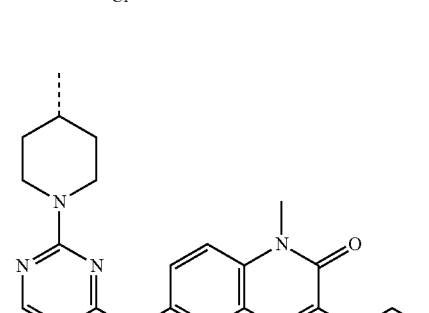

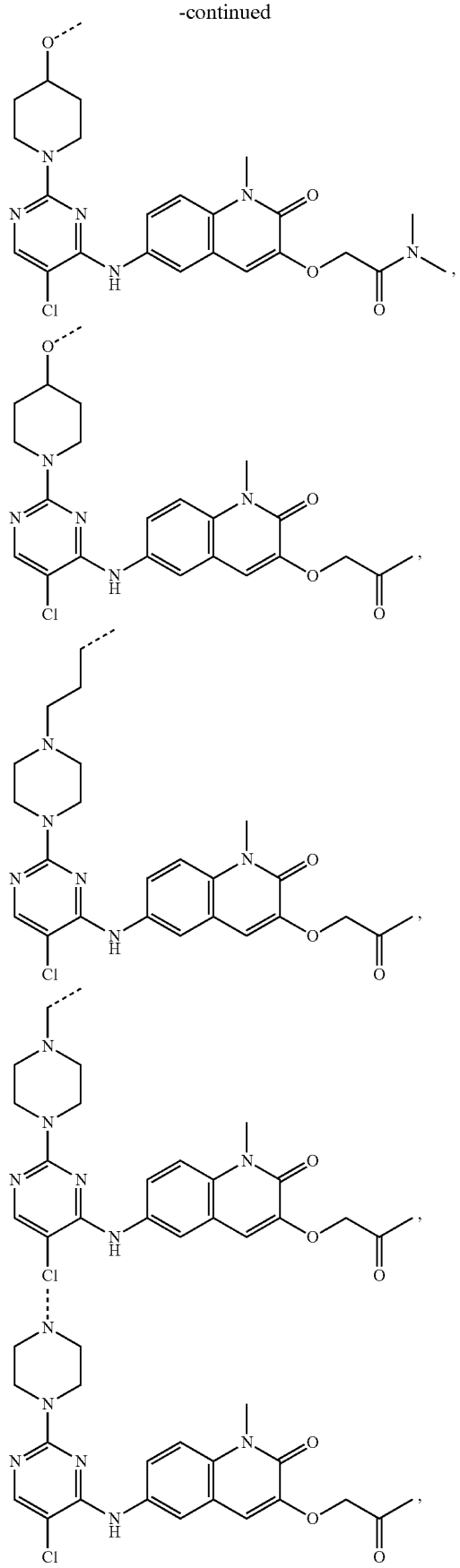
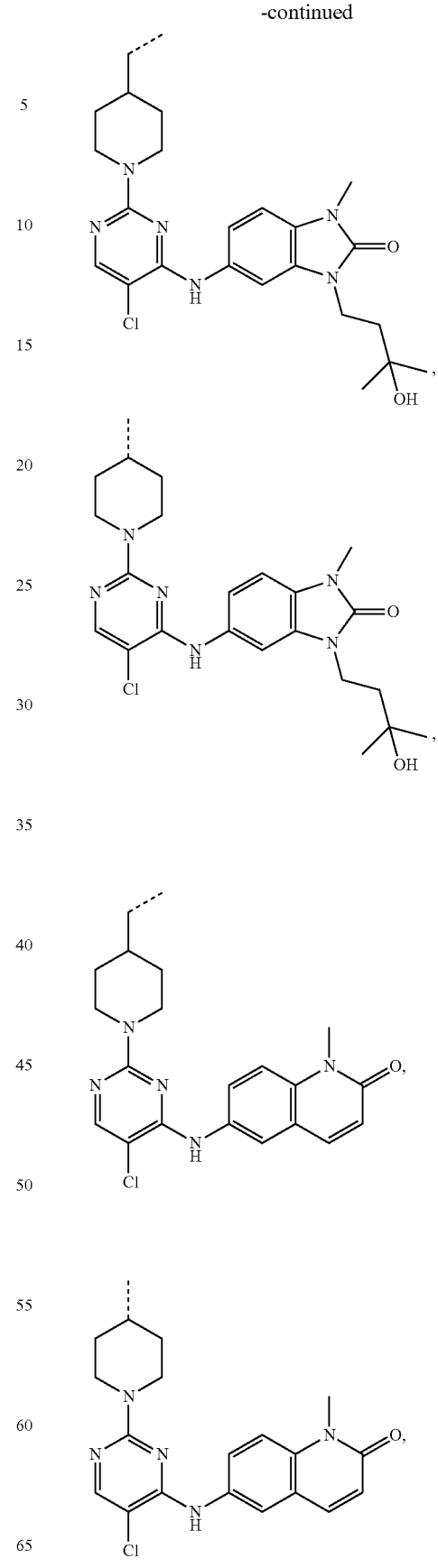

563
-continued
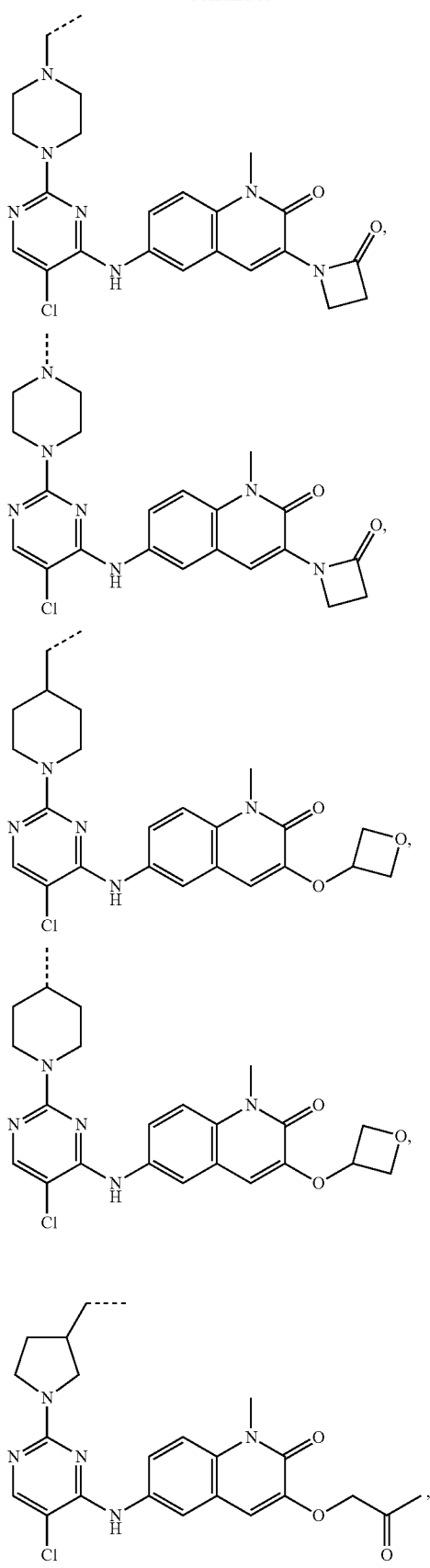
564
-continued
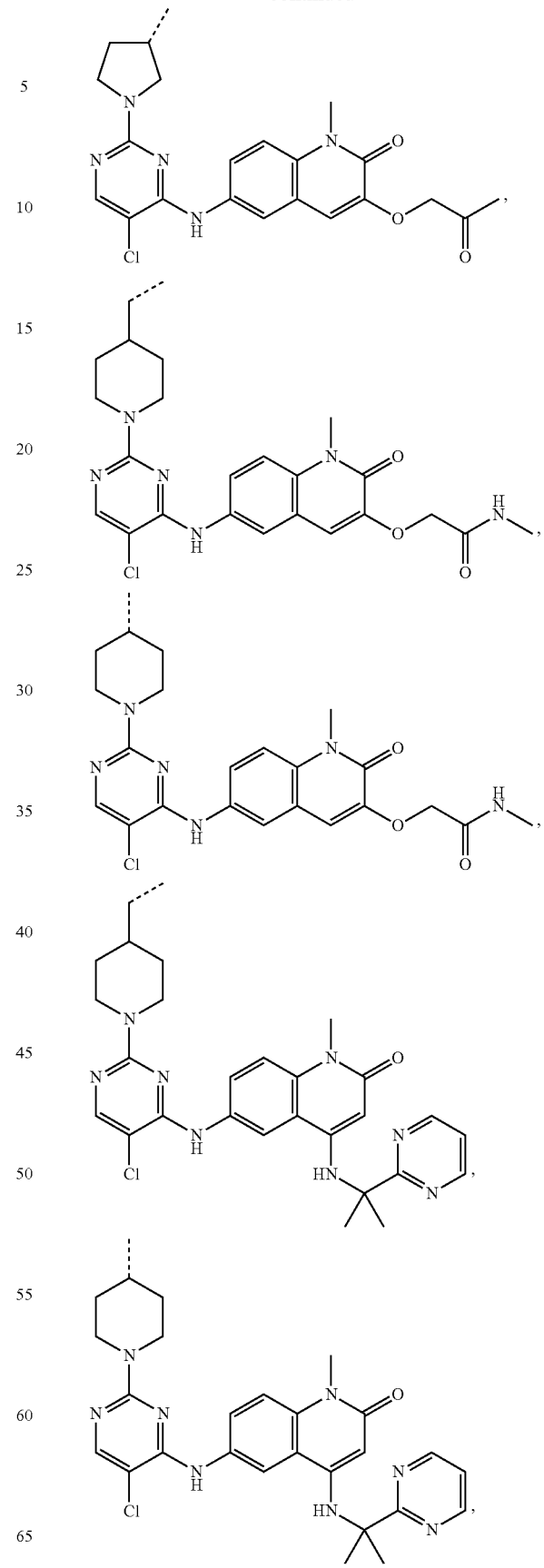

565
-continued
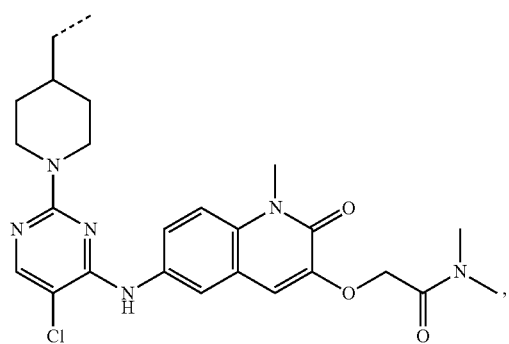
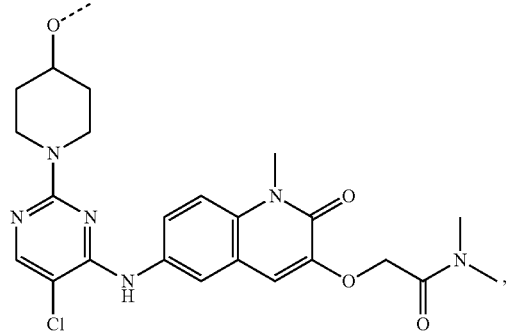
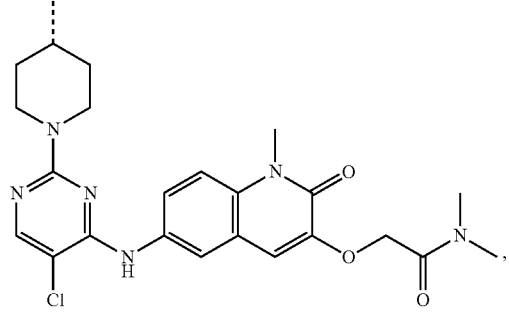
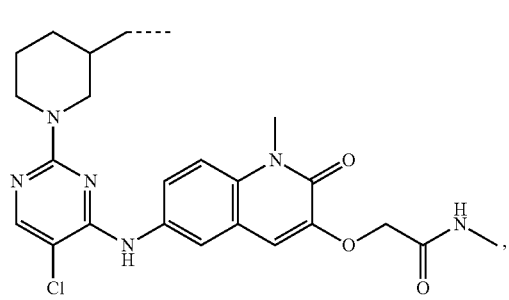
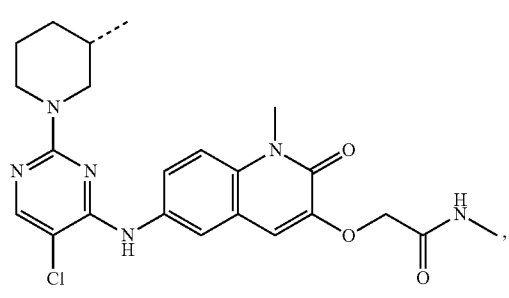
566
-continued
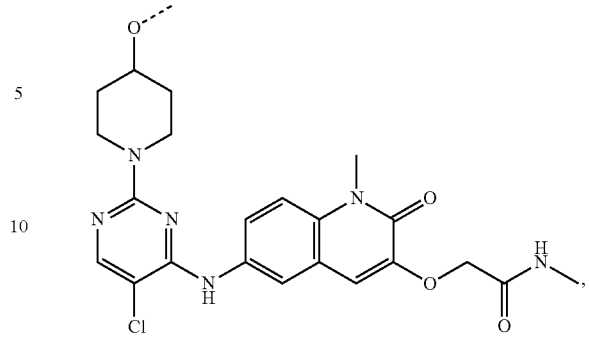
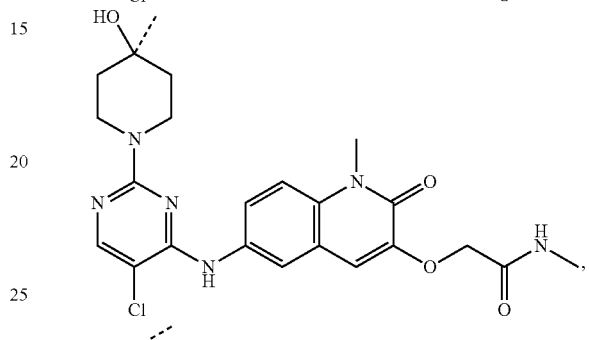
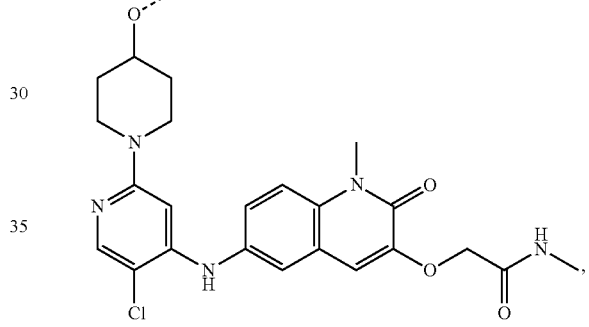
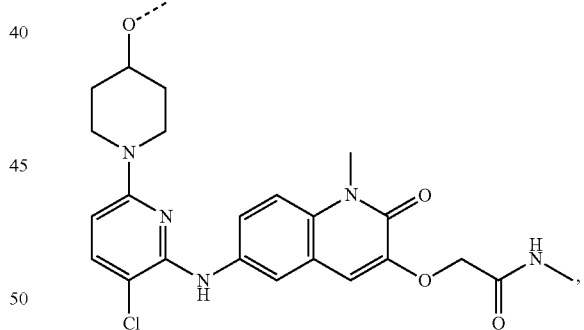
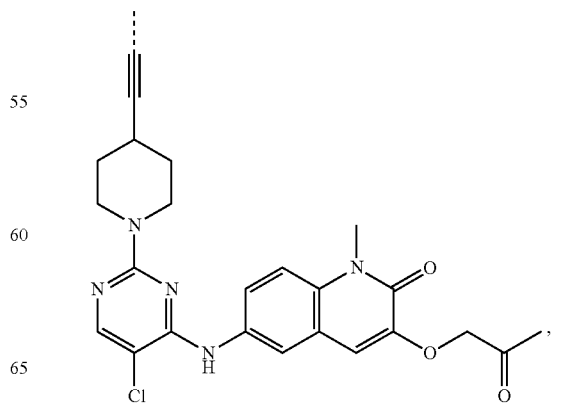

567
-continued
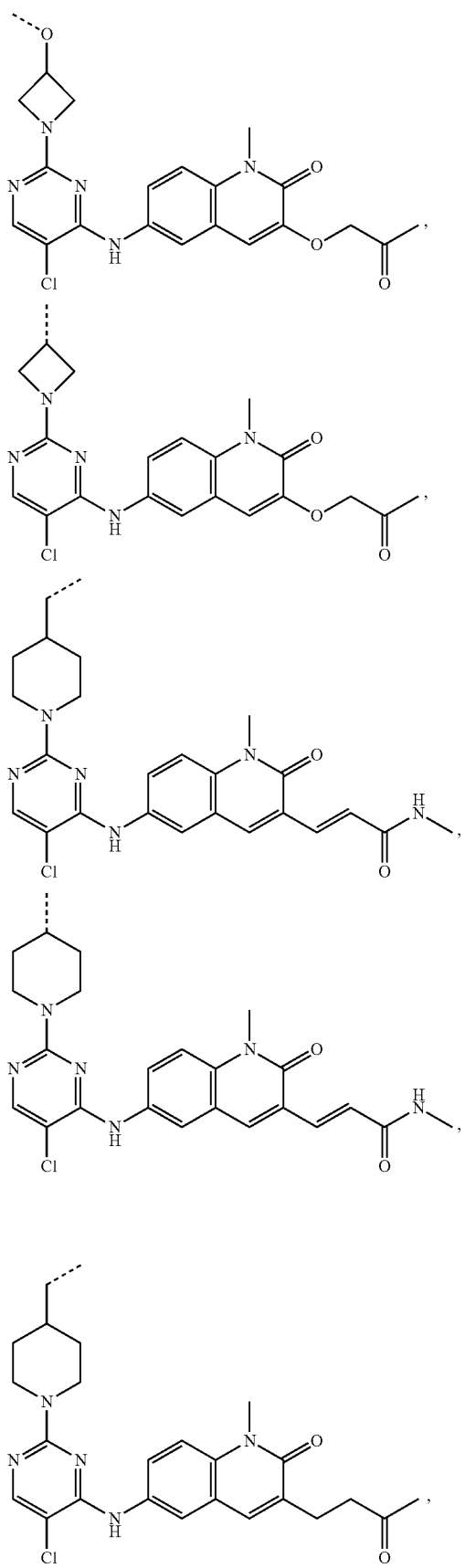
568
-continued
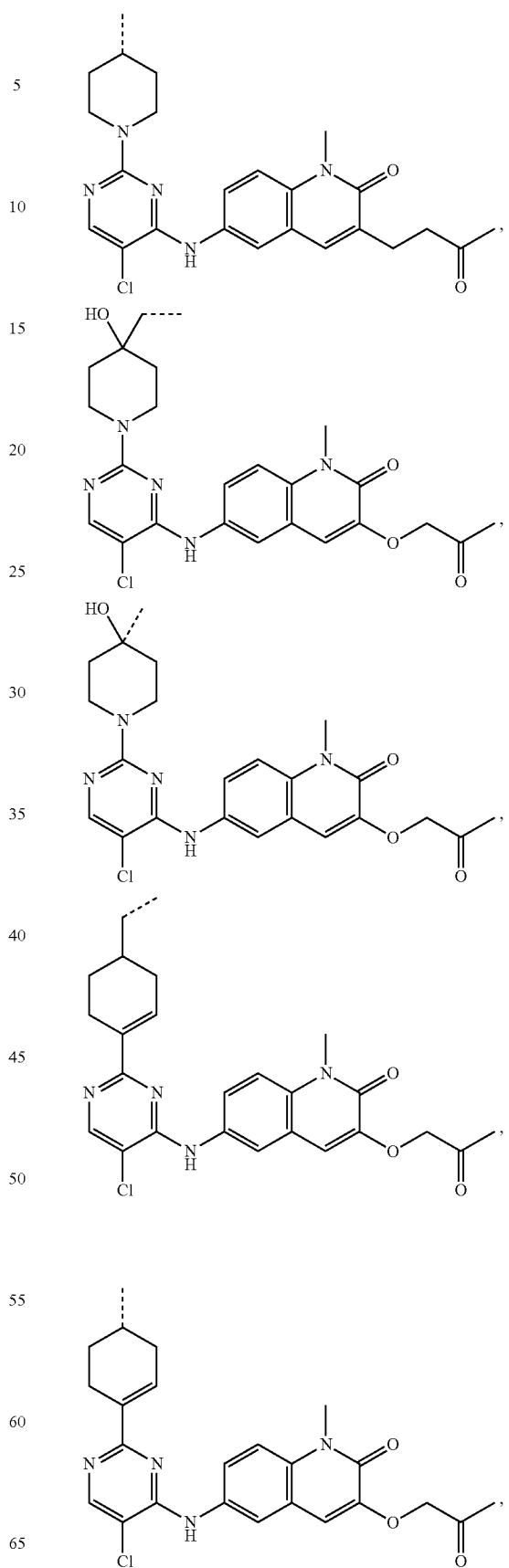

569
-continued
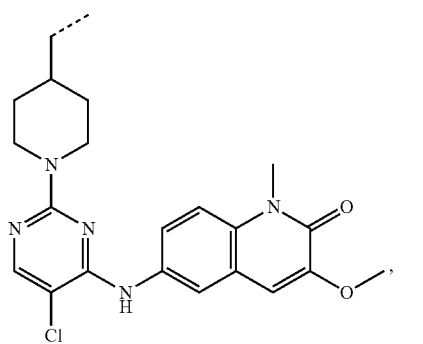
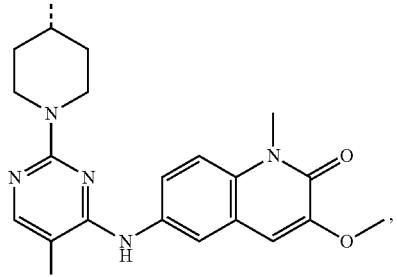
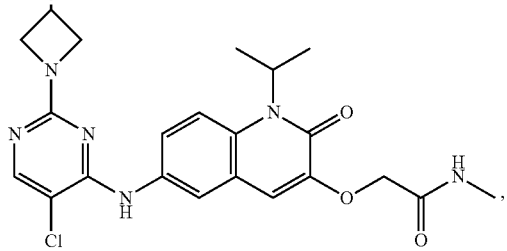
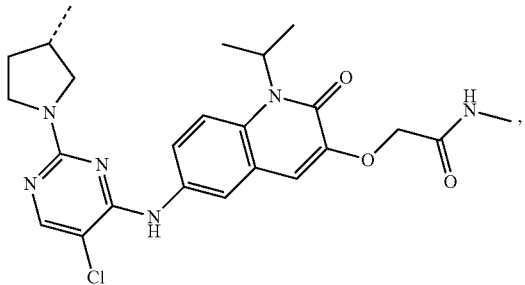
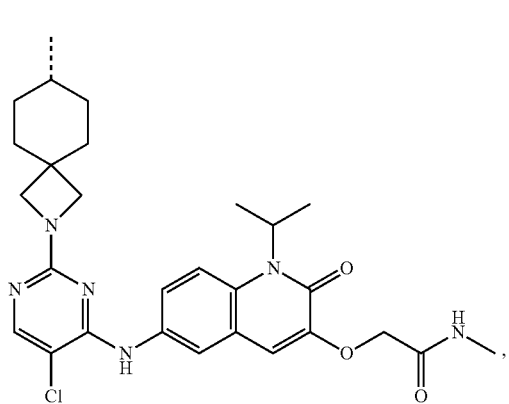
570
-continued
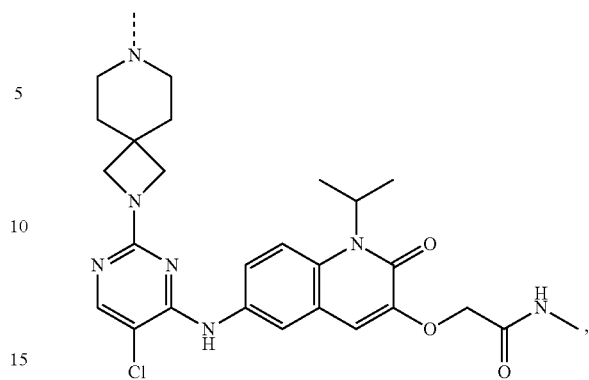
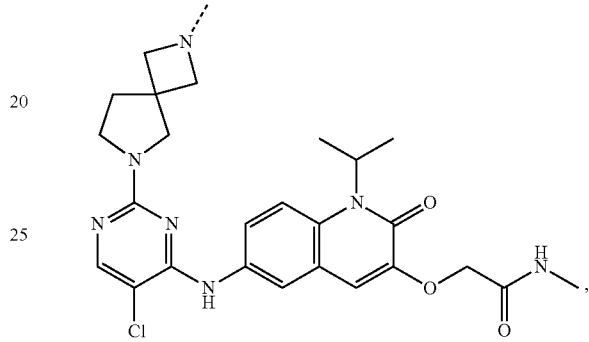
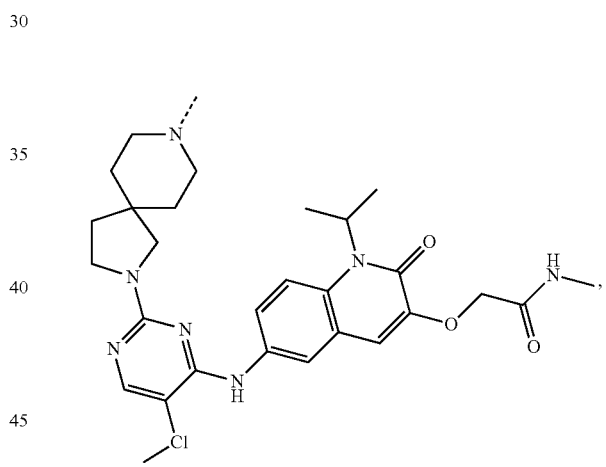

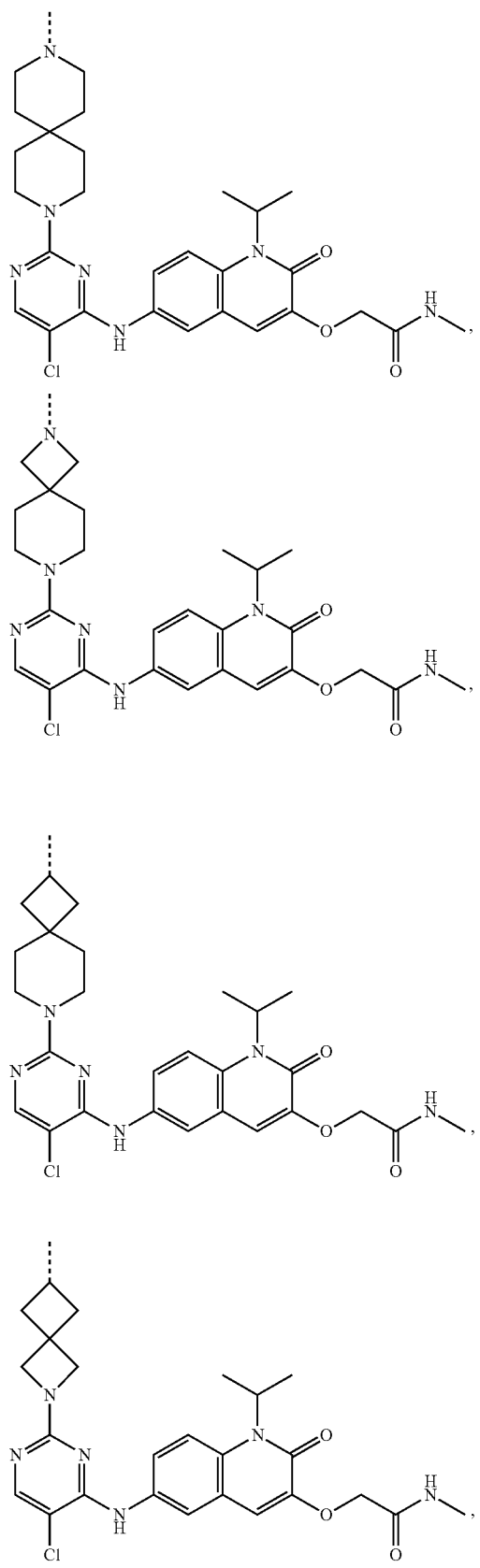
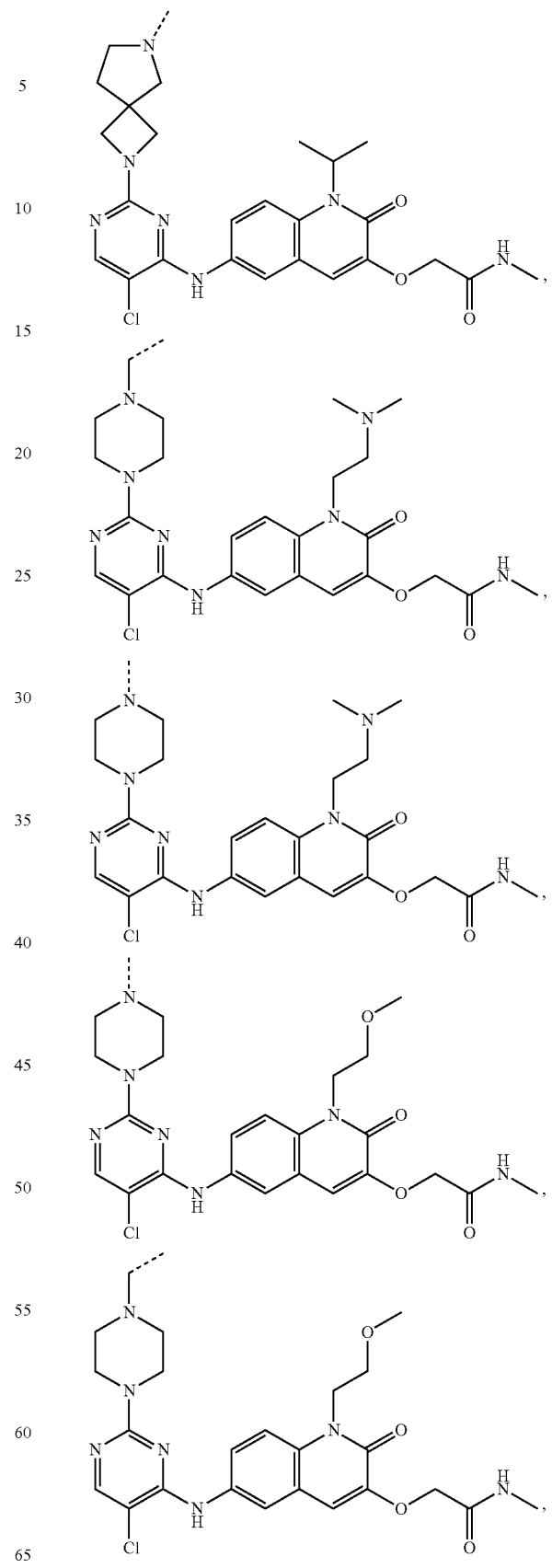

573
-continued
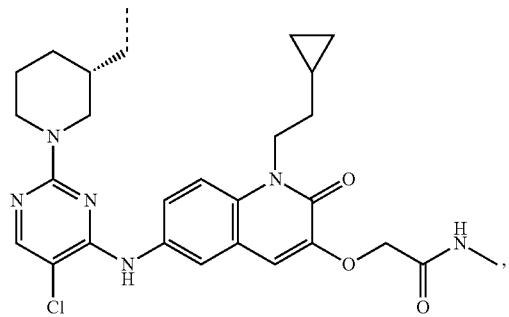
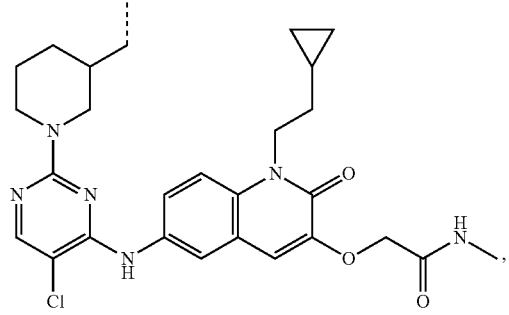
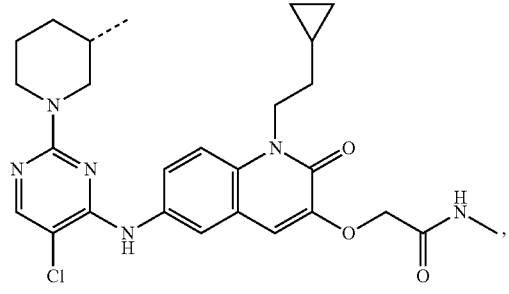
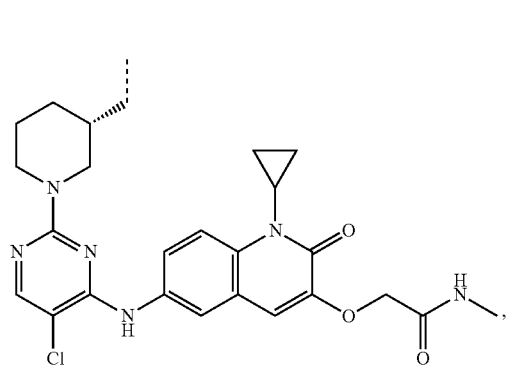
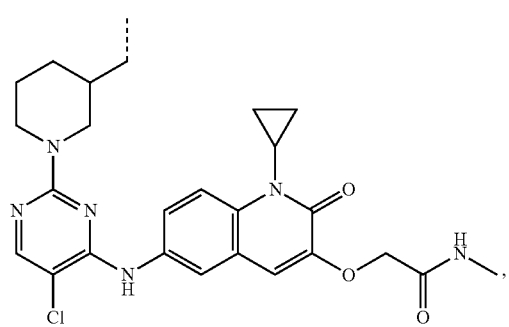
574
-continued
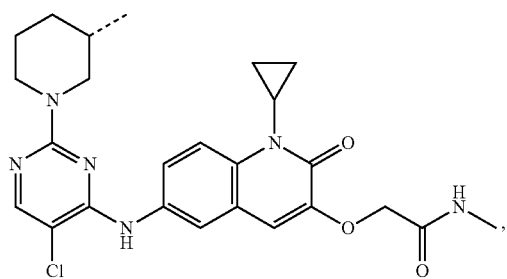
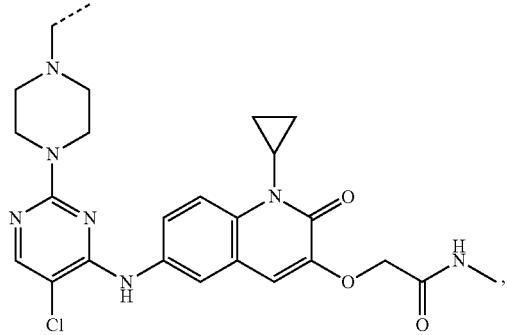
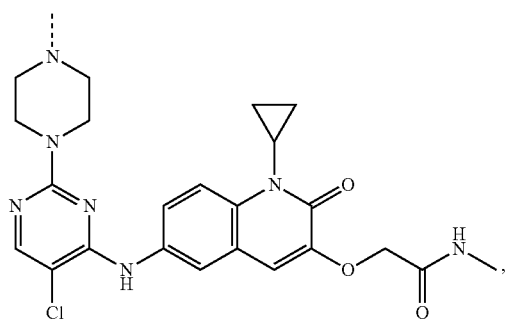
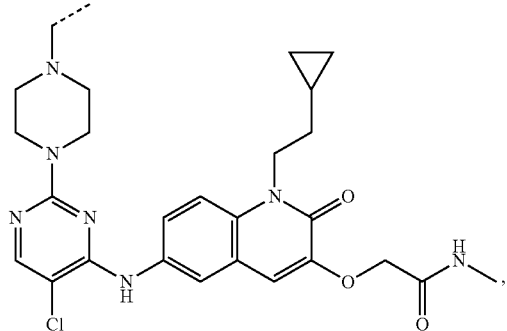
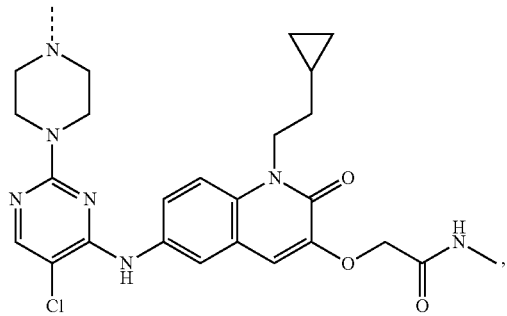

575
-continued
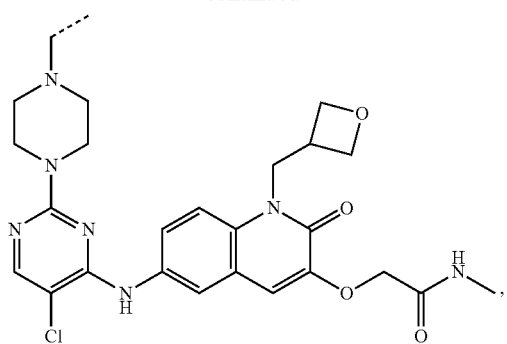
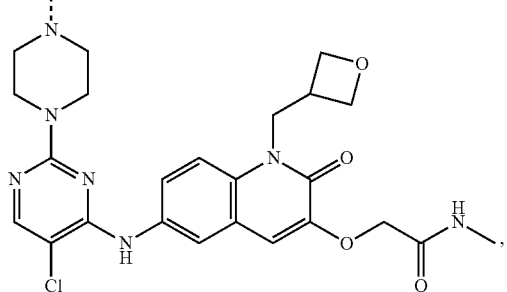
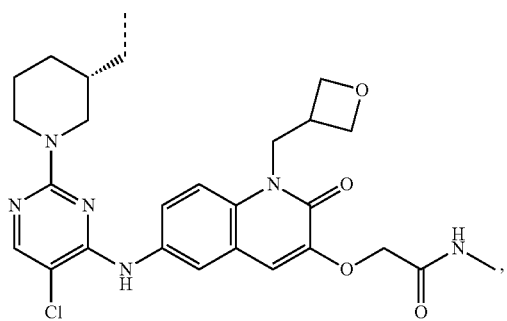
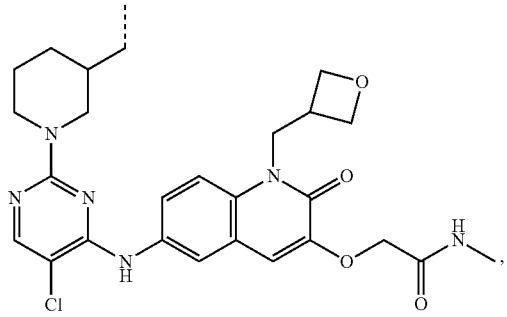
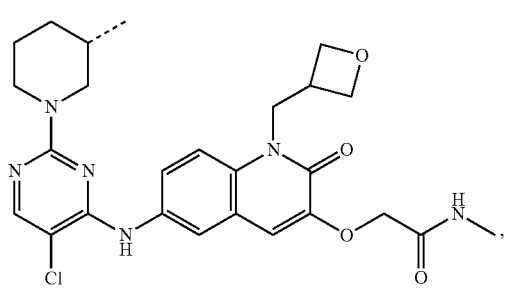
576
-continued
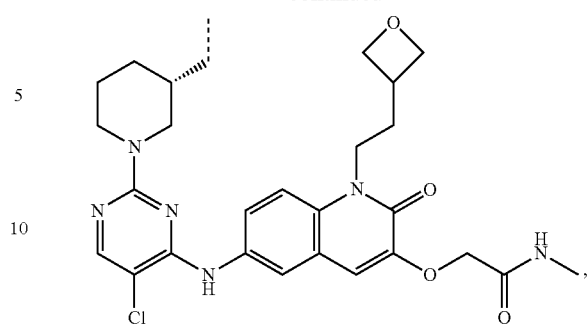
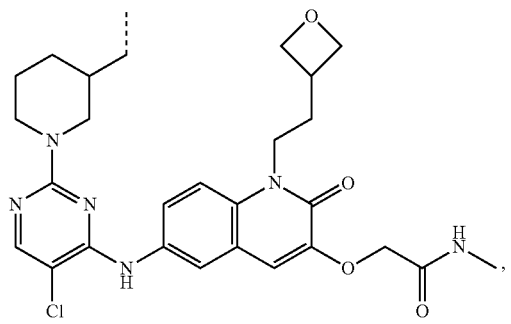
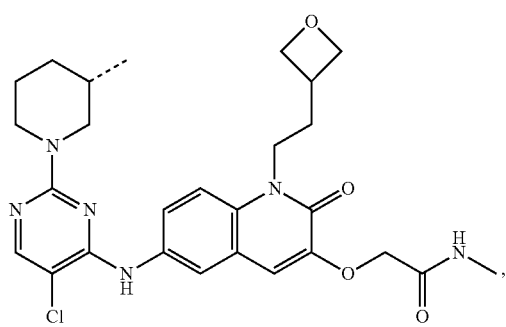
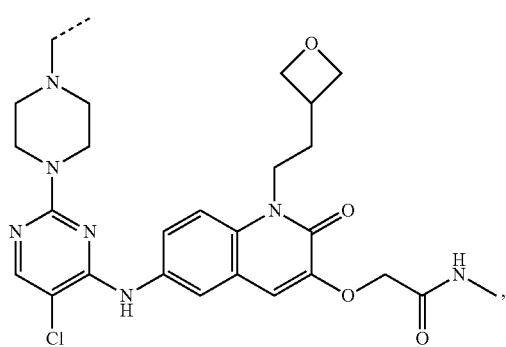
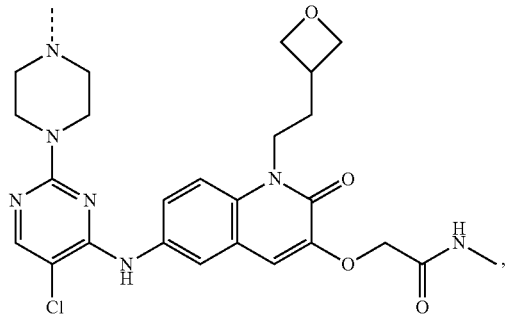

577
-continued
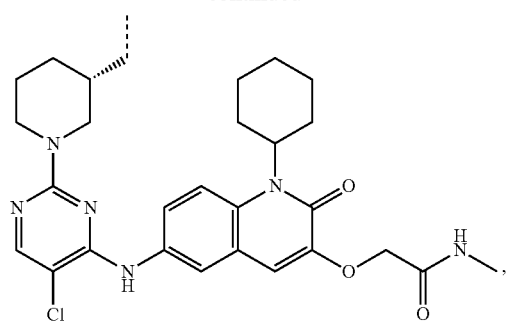
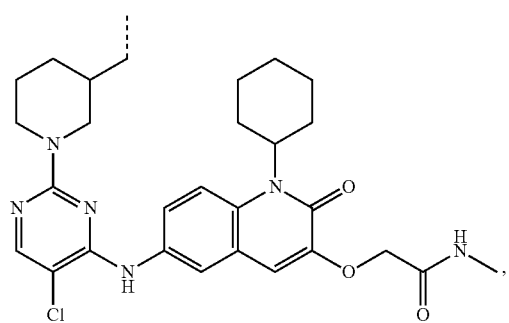
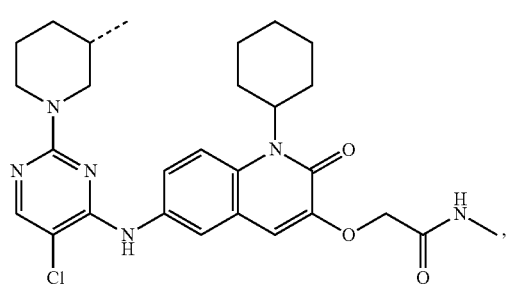
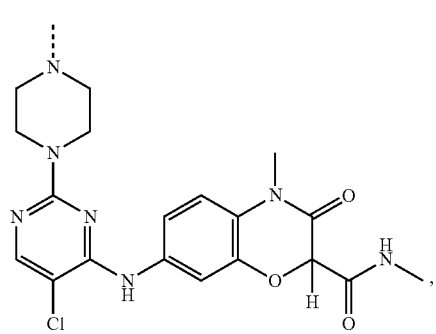
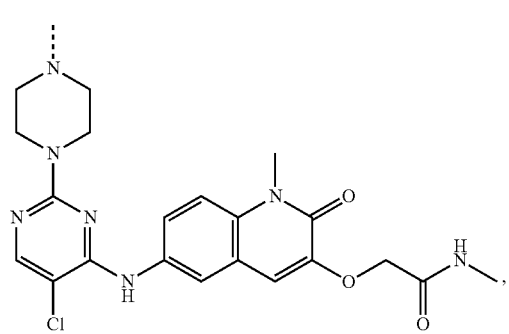
578
-continued
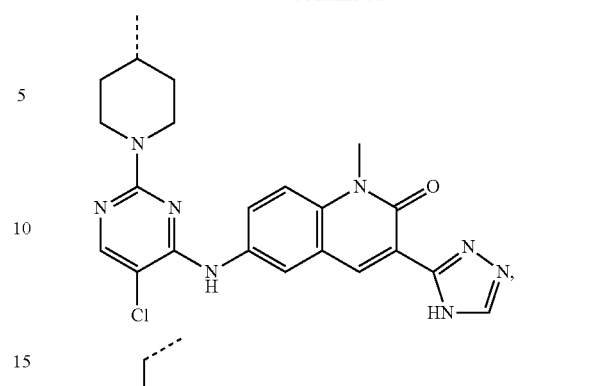
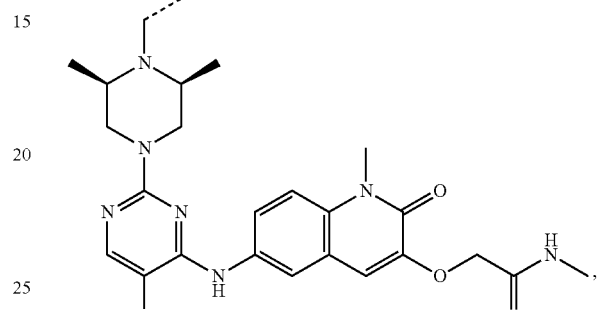
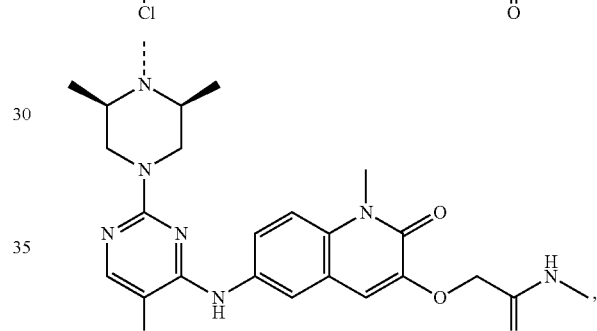
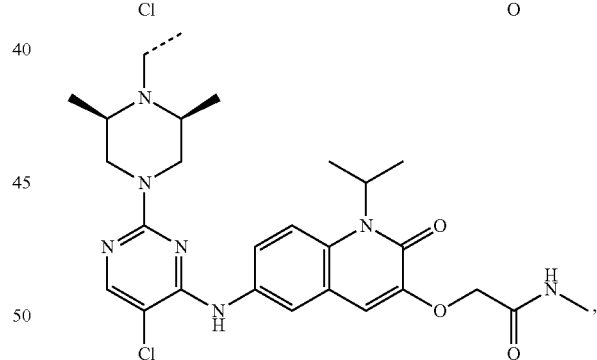
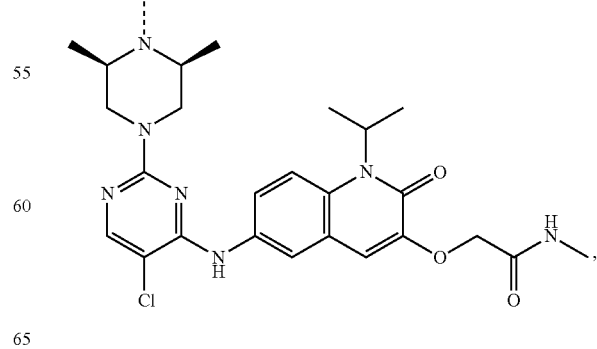

579
-continued
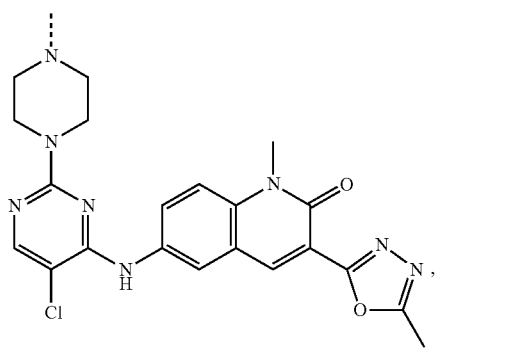
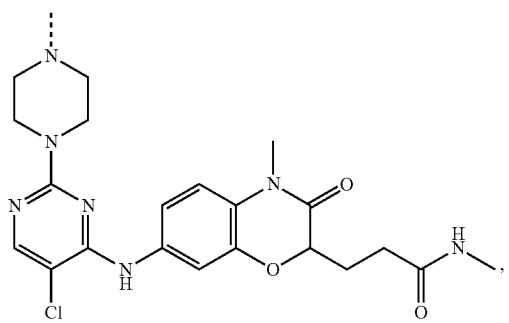
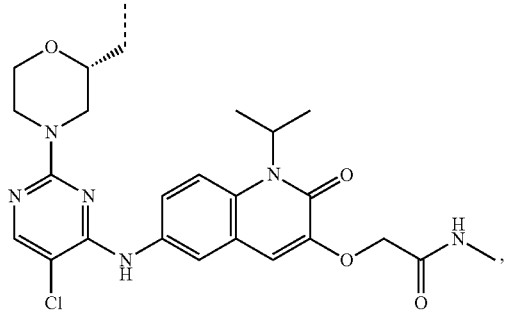
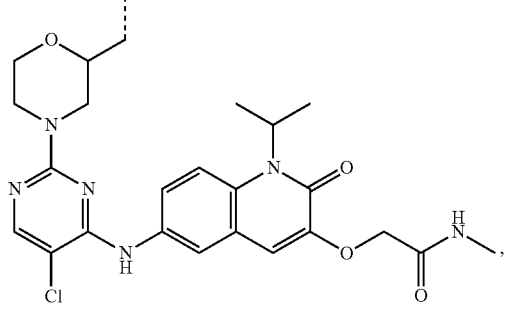
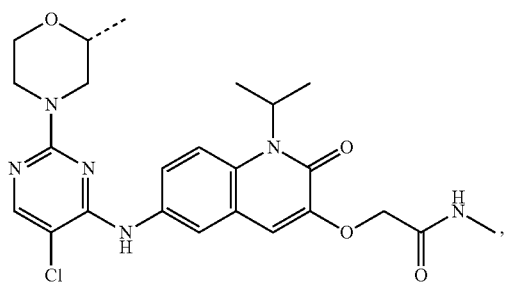
580
-continued
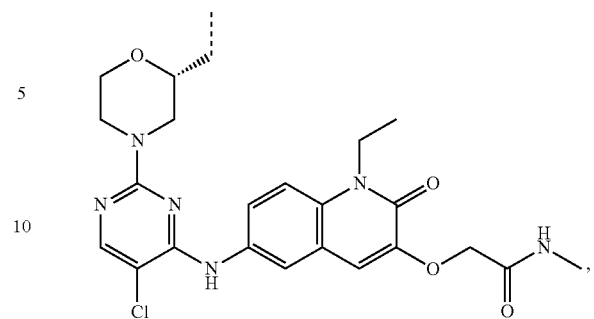
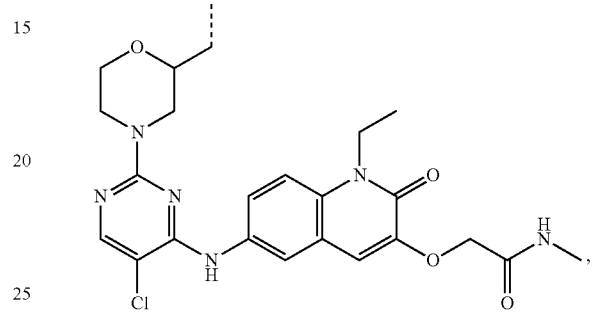
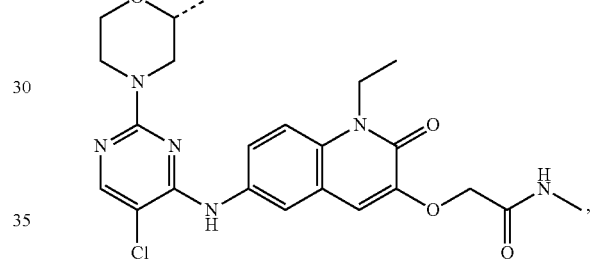
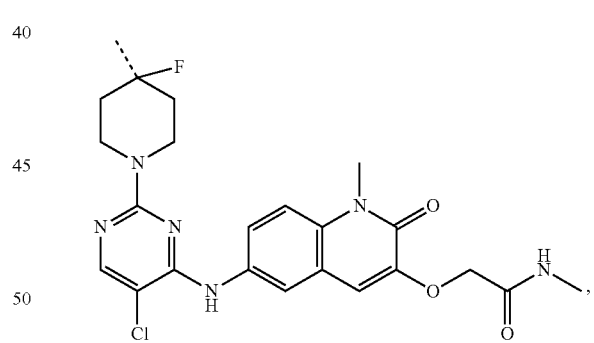
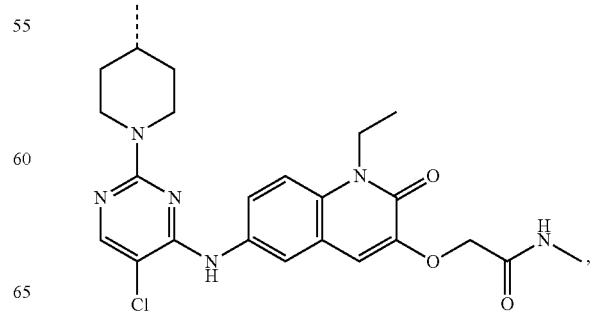

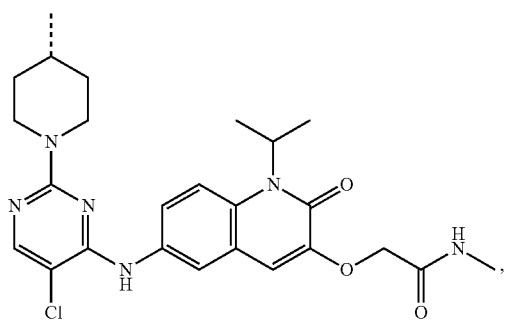
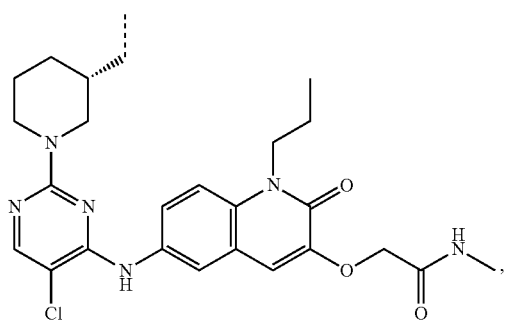
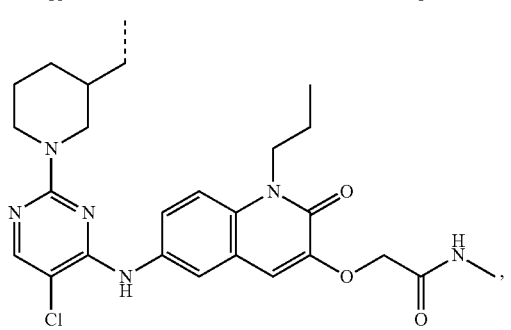
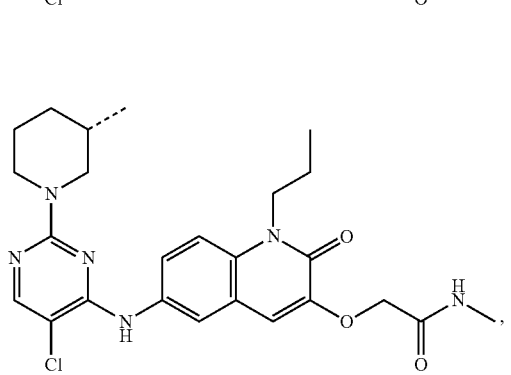
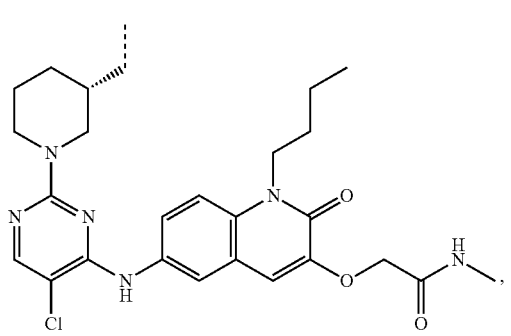
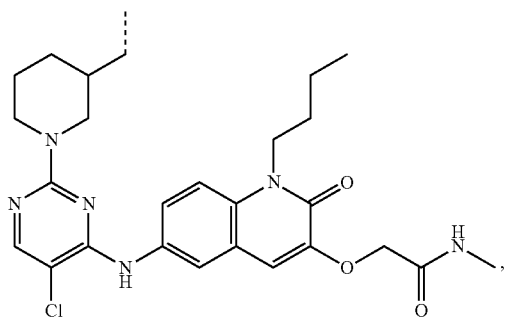
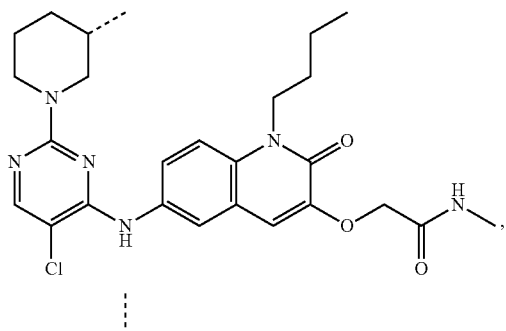
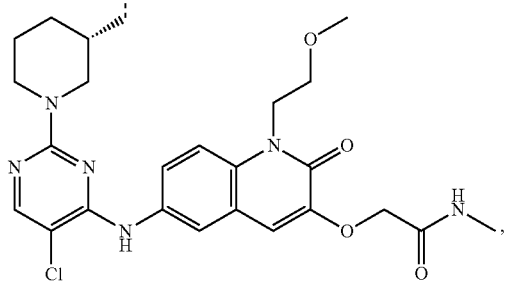
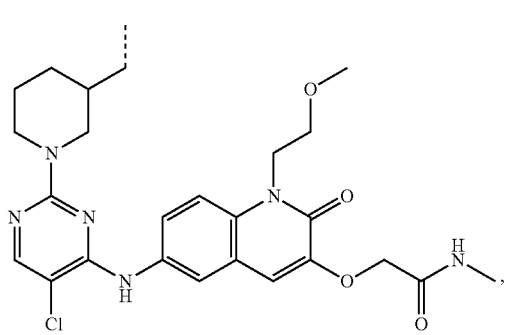
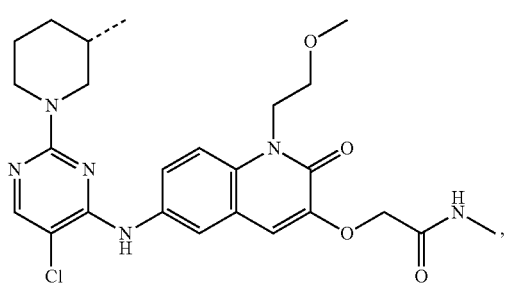

583
-continued
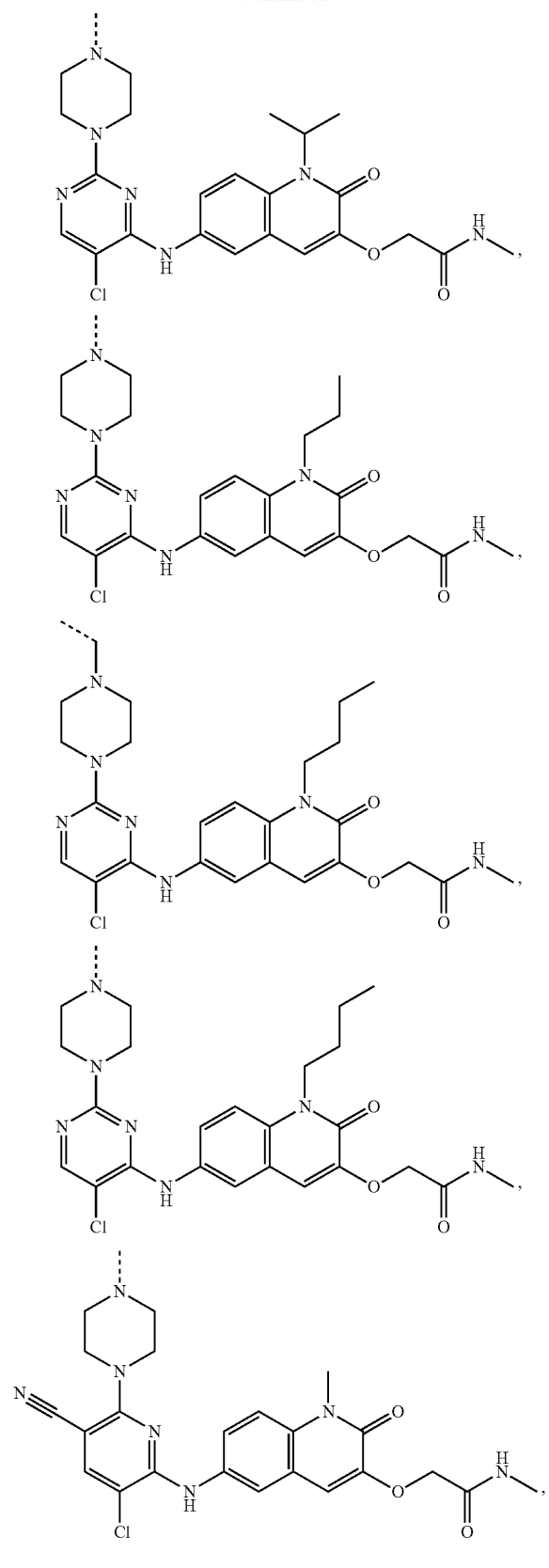
584
-continued
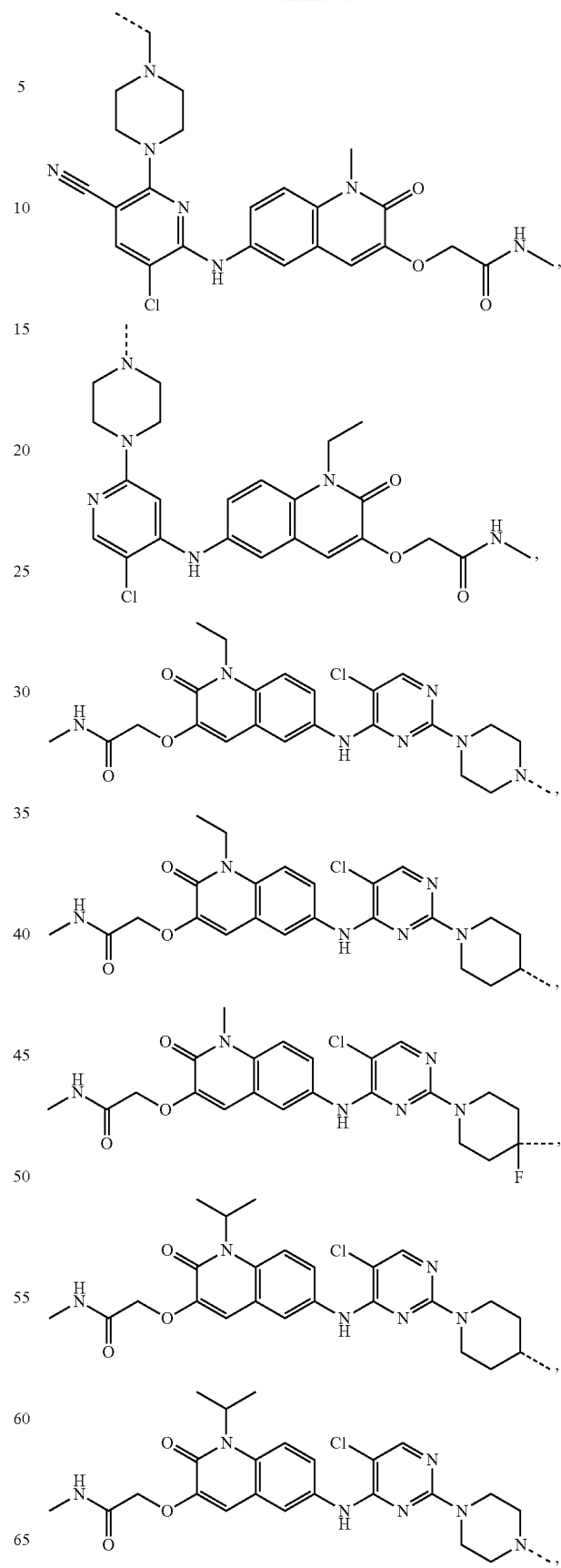

585
-continued

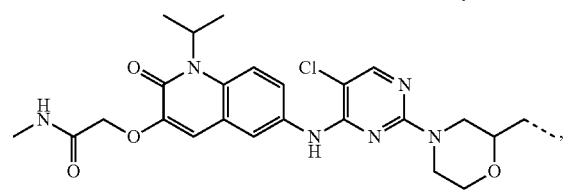
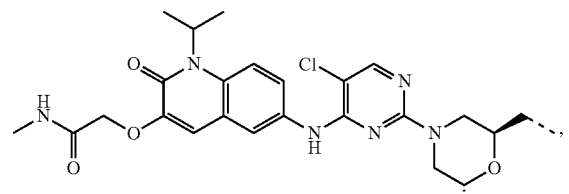
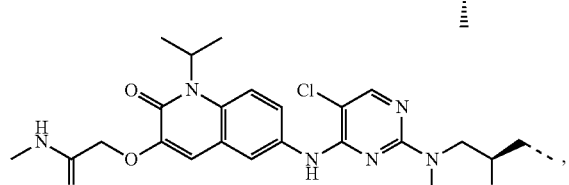
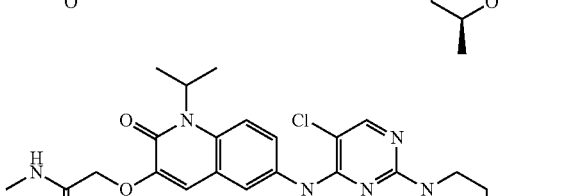
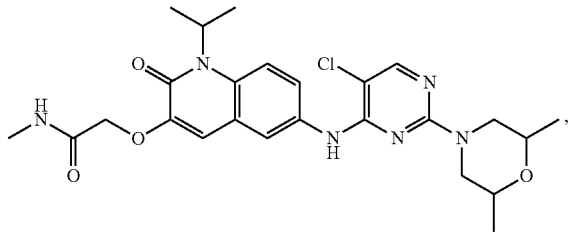
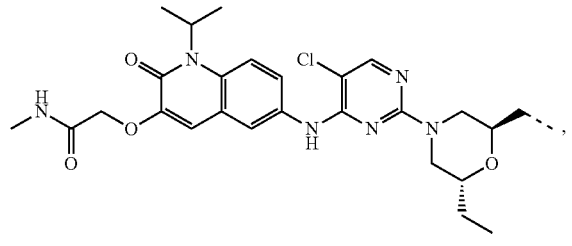
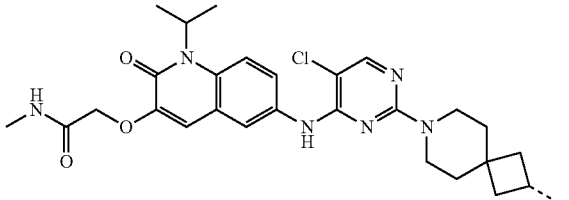
586
-continued
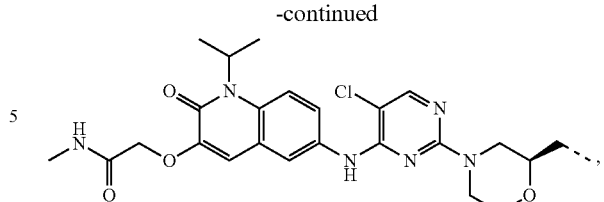
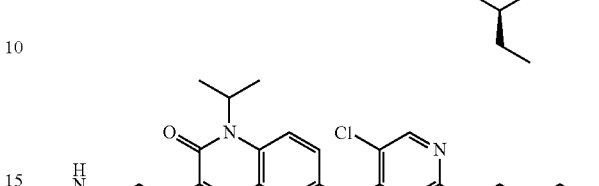
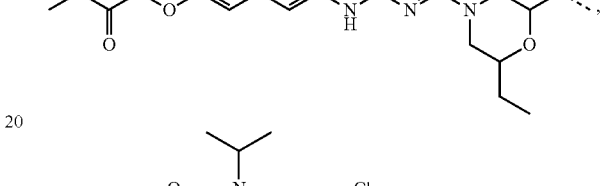
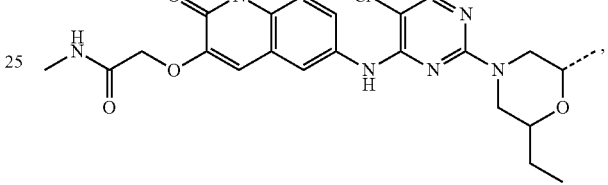
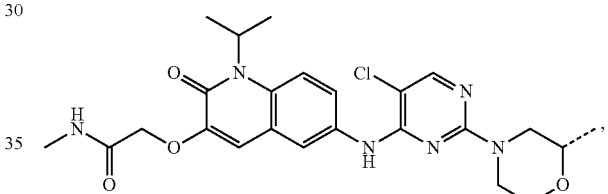
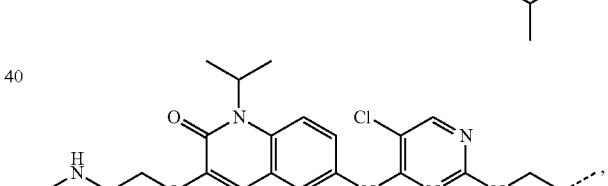
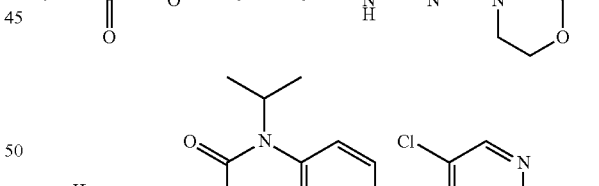
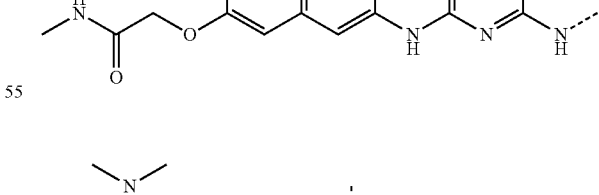
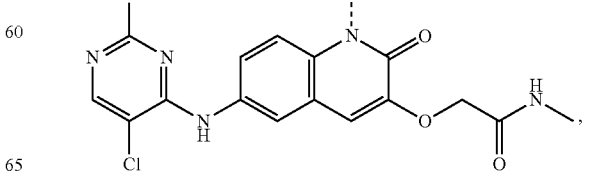

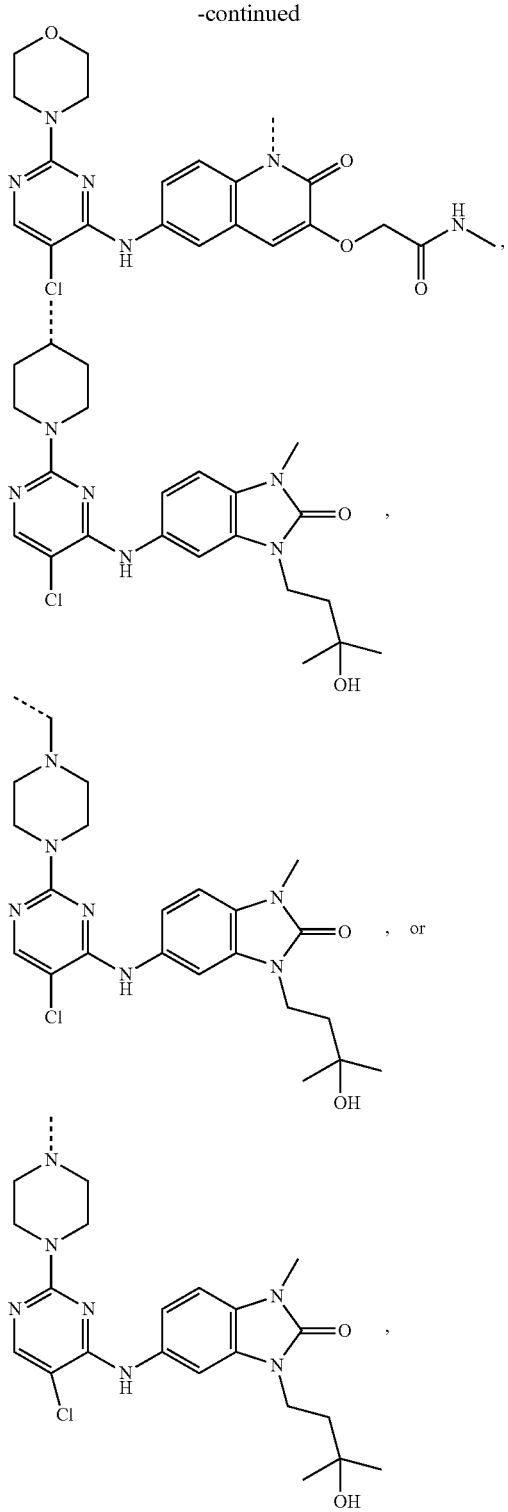

wherein -·- of the PTM indicates the point of attachment with a linker group (L) or a ULM, and ⌇ represents a bond that may be stereospecific ((R) or (S)) or non-stereospecific.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, as described herein among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon and/or VHL) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, renal cell carcinomas, bladder cancer, bowel cancer, breast cancer, cervical cancer, colon cancer, esophageal cancer, cancer of the head, kidney cancer, liver cancer, lung cancer, neck cancer, ovarian cancer, pancreatic cancer, prostate cancer, stomach cancer; leukemia; benign lymphoma, malignant lymphoma, Burkitt's lymphoma, Non-Hodgkin's lymphoma, benign melanoma, malignant melanomas, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas, prostate cancer, uterine cancer, testicular cancer, thyroid cancer, astrocytoma, stomach cancer, melanoma, carcinosarcoma, Hodgkin's disease, Wilms' tumor, teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, follicular lymphoma, intravascular large B-cell lymphoma, B-cell leukemia, chronic myeloid leukemia, non-small cell lung cancer.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucleoeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC 125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2- indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative}, N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. VLMs and/or CLMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

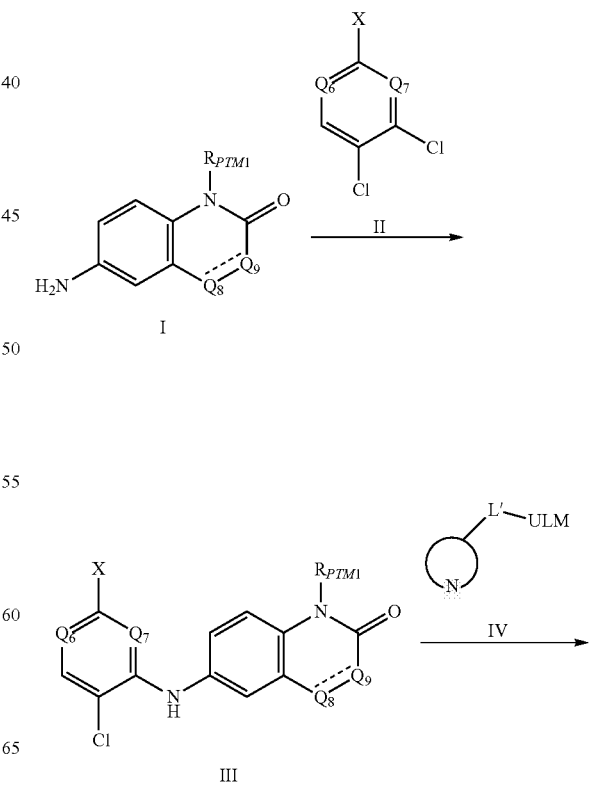

Scheme 1

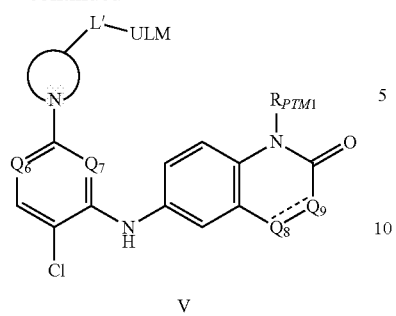

V

A compound of formula I (commercially available or readily prepared using standard reaction techniques known to one skilled in the art) may be reacted with a compound of formula II (also commercially available or readily prepared by the skilled artisan) in a solvent such as DMSO or DMF, with a base such as triethylamine or DIEA and with heating to produce a compound of formula III. In this case the X on compound II can be a leaving group such as a halogen and Q6 and Q7 are such that the selective displacement shown here is favored. Non-limiting examples are where X=Cl and $Q_6$ and $Q_7$ are both N. Compounds of formula III can generate a heterobifunctional degradative compound of formula V by reaction with a compound of formula IV by heating in a solvent such as DMSO, in the presence of a base such as DIEA. Compounds of formula IV are advanced building blocks where the ULM, linker and part of the PTM form a complete subunit. Wherein

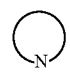

represents a 4-8 member cyclic amine or spirocyclic amine (any 2-ring combination from 4,4; 4,5; 4,6; 5,4; 5,5; 5,6; 6,4; 6,5; and 6,6) optionally including a second N if >2 carbons are between them. L' can be a bond, linker, or part of linker.

Scheme 2

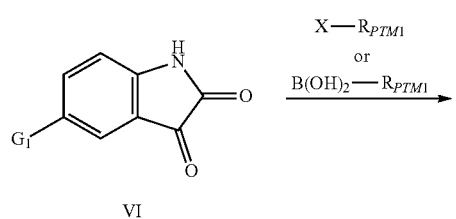

VI

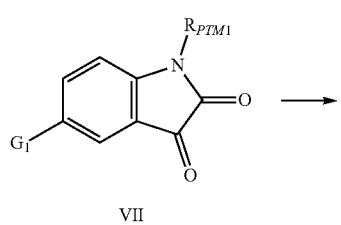

VII

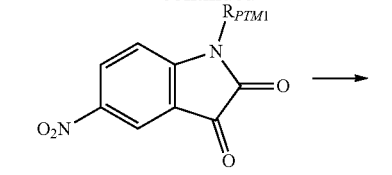

VIII

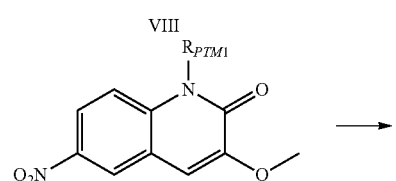

IX

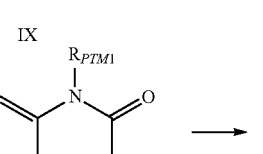

X

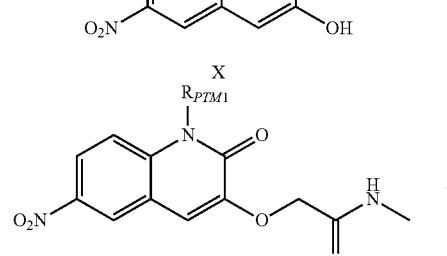

XI

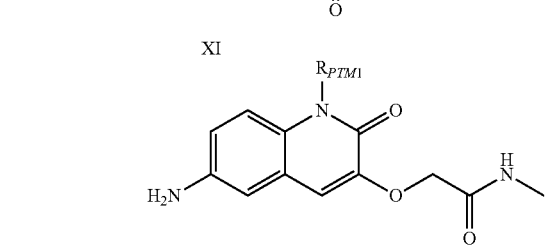

I

Certain compounds of formula I in Scheme I have a double bond between $Q_8$ and $Q_9$ and have $Q_8$=CH and $Q_9$=COCH$_2$CONHCH$_3$. These can be prepared using procedures found and/or adapted from Kerres et al., 2017, Cell Reports 20, 2860-2875 and are shown in Scheme II. When $G_1$ is NO$_2$, a compound of formula VI can be dissolved in a solvent such as DMF, treated with a base such as, but not limited to, K$_2$CO$_3$ and alkylated with an R$_{PTM1}$-X. In this case X can be a leaving group such as, but not limited to, iodo or bromo. Generally, R$_{PTM1}$-X are commercially available or readily prepared by someone skilled in the art. Alternatively, the boronic acid analogue of R$_{PTM1}$ can be employed to form a compound of formula VI using the Chan-Lam coupling reaction (for a review see Chen et al., 2020, Advanced Synthesis and Catalysis 62 (16), 3311-3331) wherein the boronic acid and compound of formula VI are combined with a copper salt such as Cu(OAc)$_2$, a base such as Na$_2$CO$_3$ in a solvent such as DCE and heated. In this case it may be preferable to have $G_1$=H and conduct a nitration as shown in the third step of scheme 2 using KNO$_3$ under acidic conditions. The skilled artisan will realize that the nitration step is skipped when alkylating a 5-nitroisatin (VI with $G_1$=NO$_2$) with R$_{PTM1}$-X as compounds of formula VIII are generated directly. Compounds of formula VIII can be reacted with TMS-diazomethane under basic conditions (See Duplantier et al., 2009, *J. Med. Chem.* 52, 3576-3585 and references cited therein) to give the ring expanded compounds of formula IX. The hydroxy group of compounds of formula X can be unmasked by treating compounds of formula IX with BBr$_3$. Compounds of formula I can me obtained in 2 additional steps by alkylation of the hydroxy group of X with a 2-haloacetamide followed by reduction of the nitro group. Numerous methods are available to the skilled artisan to effect the nitro reduction.

compound of formula XV. Heating this compound with BrettPhos Palladacycle Gen4 in a mixture of dioxane, water and KOH can furnish a compound of formula X. The final two steps are as shown in Scheme 2.

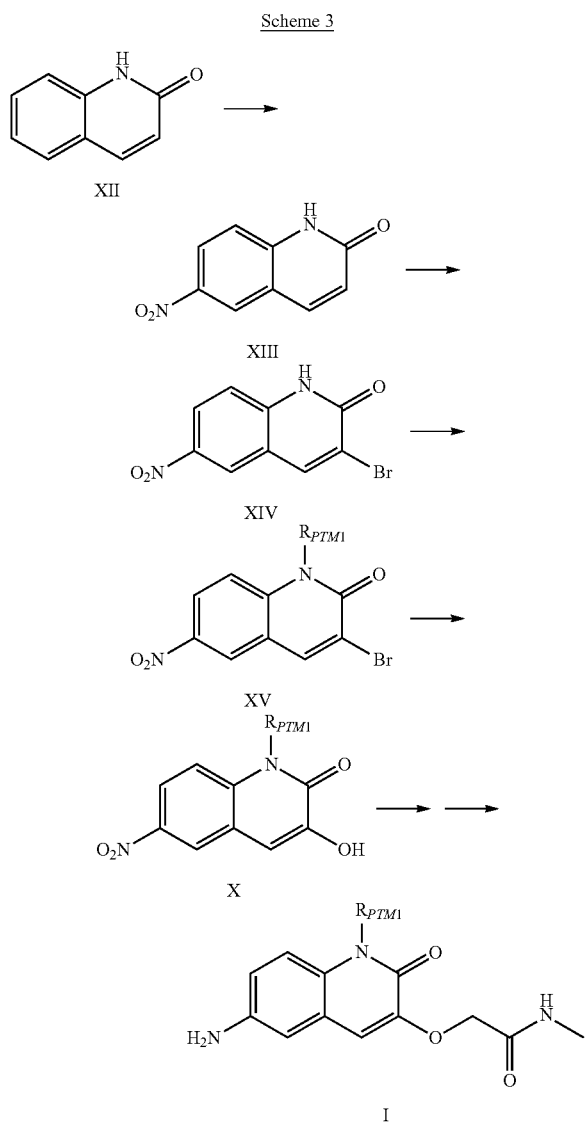

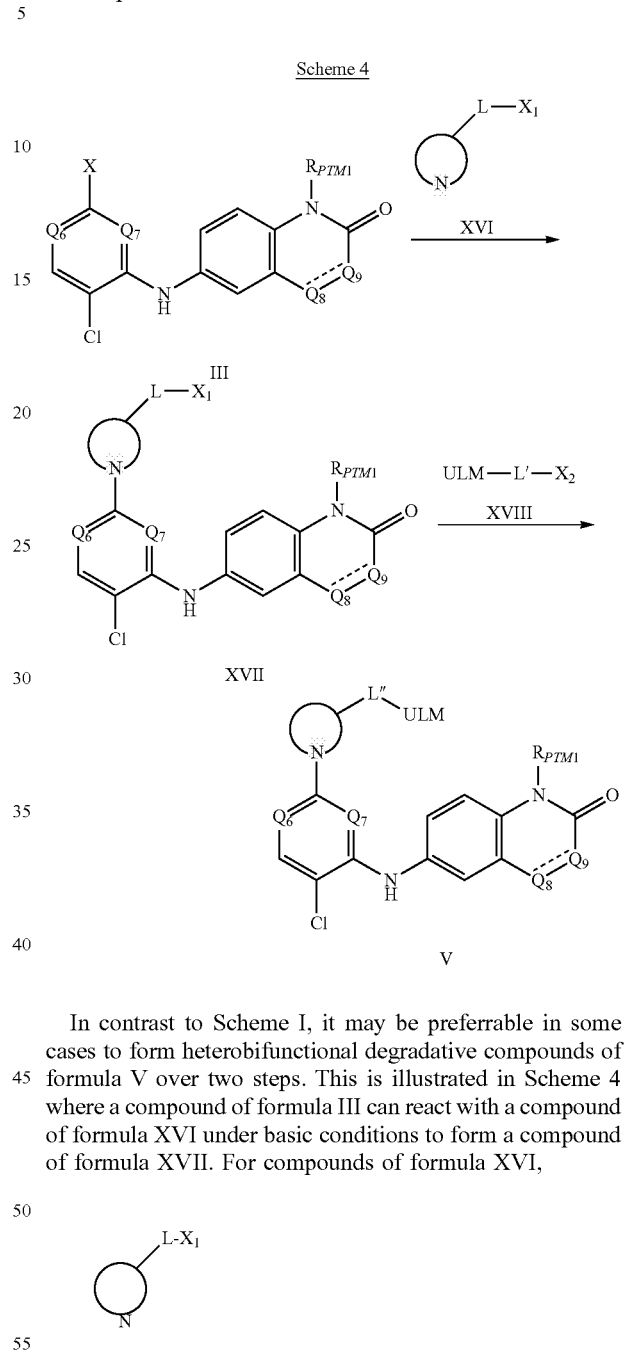

In contrast to Scheme I, it may be preferrable in some cases to form heterobifunctional degradative compounds of formula V over two steps. This is illustrated in Scheme 4 where a compound of formula III can react with a compound of formula XVI under basic conditions to form a compound of formula XVII. For compounds of formula XVI, represents a 4-8 member cyclic amine or spirocyclic amine (any 2-ring combination from 4,4; 4,5; 4,6; 5,4; 5,5; 5,6; 6,4; 6,5; and 6,6) optionally including a second N if >2 carbons are between them. L can be null, a bond, linker, or part of linker. L" represents the linker formed after a compound of formula XVII and a compound of formula XVIII are connected and contain all or some of L and L'. If L is null, X$_1$ can represent the aforementioned second, endocyclic secondary amine, or, if L=bond, linker or part of a linker, then X$_1$ can be an exocyclic amine (primary, secondary and optionally part of 4-8 member ring or 2-ring spirocycle as Compounds of formula I from Scheme 1 where there is a double bond between Q$_8$ and Q$_9$ and have Q$_8$=CH and Q$_9$=COCH$_2$CONHCH$_3$ can also be obtained using the approach shown in Scheme 3. Compounds of formula XII (commercially available or readily prepared by methods known to one skilled in the art) can be treated with nitric acid in sulfuric acid to form compounds of formula XIII Heating a compound of formula XIII in a mixture of sodium bromate/HBr can afford a compound of formula XIV. Similarly, as in Scheme 2, a compound of formula XIV can be alkylated with R$_{PTM1}$-X under basic conditions to afford a mentioned above) or an alcohol. If $X_1$ is an amine or alcohol, the skilled artisan will understand that, as part of a compound of formula XVII, this can act as a nucleophile in a subsequent reaction (Scheme 12) with a compound of formula XVIII to generate a heterobifunctional degradative compound of formula V. In this case, compounds of formula XVIII have $X_2$ as a leaving group of which non-limiting examples are halo or tosylate and compounds of formula V are formed under conditions well known to the skilled artisan such as combining XVII and XVIII in a solvent in the presence of a suitable base either with or without heating. Additionally, when $X_1$ is an amine, $X_2$ can be an aldehyde and compounds of formula V are formed under reductive alkylation conditions (Scheme 10). A non-limiting example of this is performing the reaction in MeOH in the presence of a mild reducing agent such as $Na(AcO)_3BH$ and a catalytic amount of acid. The skilled artisan will also understand that when $X_1$ is an alcohol it can also be further activated as a sulfonate ester, such as tosylate, mesylate or the like. In this case, $X_2$ of XVIII can be an amine or an alcohol and the compound of formula V can be formed under suitably basic condition known to the skilled artisan. If either $X_1$ or $X_2$ are alcohols or amines, there may a protecting group attached such as TBDMS or BOC respectively and these will need to be removed to complete transformation to V. Additionally, if $X_1$ is an alcohol, a compound of formula XVII can react with a compound of formula XVIII under Mitsunobu conditions when L1 of XVIII is a bond and $X_2$ is a phenolic hydroxy group. A non-limiting example of Mitsunobu reaction conditions would be treating a cooled solution of a compound of formula VII and a compound of formula VIII in THF with DIAD and $PH_3P$ (Scheme 15).

Compounds of formula XVII from Scheme 4 (where $Q_6=C-NO_2$ and $Q_7=C-H$) can also be formed as described in T. Yasui et al., 2017, *Bioorganic & Medicinal Chemistry* 25, 4876-4886 and shown in Scheme 5. The commercially available compound of formula XIX, wherein X is a halogen such as Cl, Br or I, can be reacted with an amine or alcohol (in a solvent such as DMF, in the presence of a base such DIEA or NaH respectively) to form compounds of formula XX. Compounds of formula VII can be prepared from compounds of formula XX by Pd catalyzed amination with a compound of formula I. A non-limiting example of these conditions are heating a solution of compounds of formula XX and I in anhydrous DME in the presence a palladium catalyst such as $Pd_2(dba)_3$, a ligand such as BINAP and a base such as $K_2CO_3$ under an inert atmosphere of a gas such as argon.

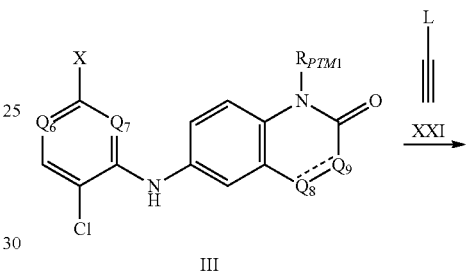

Scheme 6

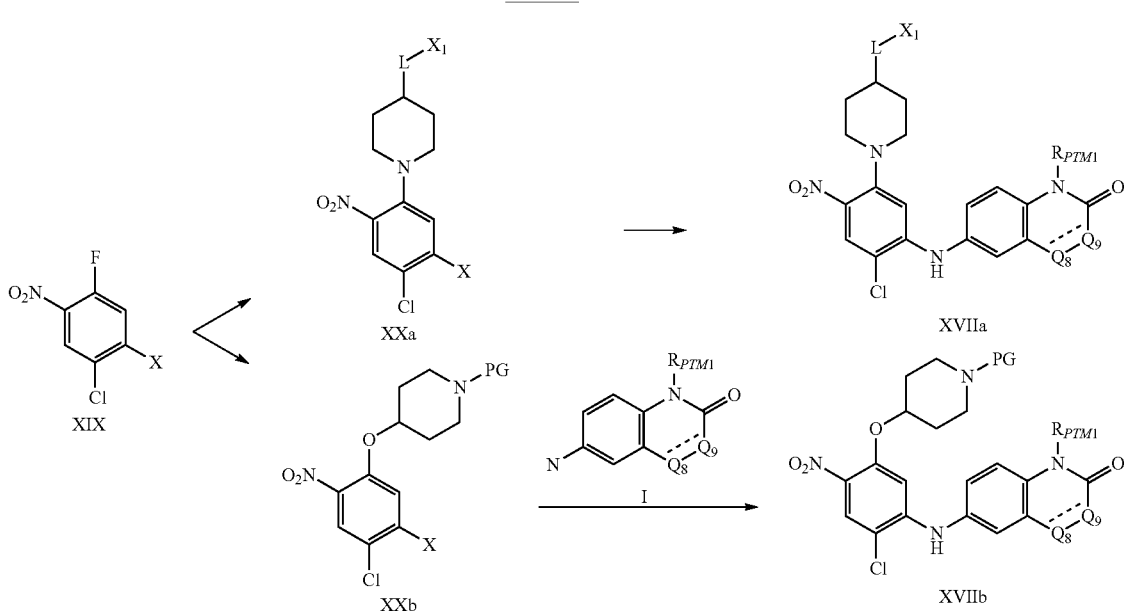

Scheme 5

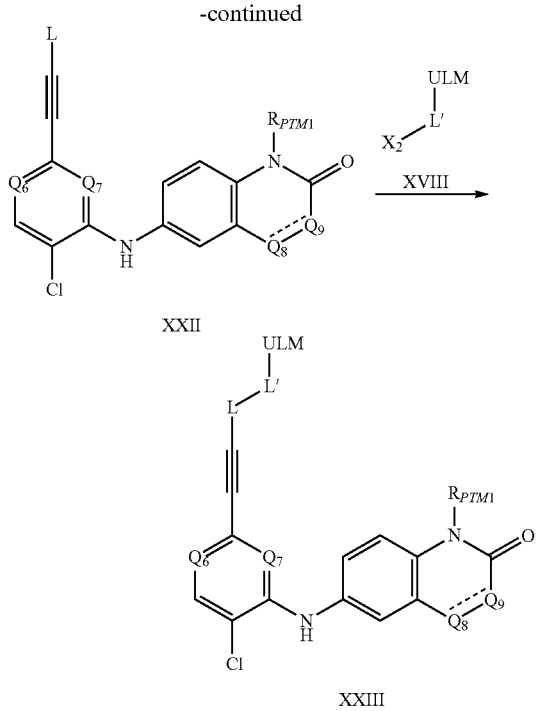

Certain compounds of the invention can be prepared as shown in Scheme 6. In this case, the PTM attaches to the linker-ULM subunit through an alkyne. The alkyne-containing moiety XXI is installed using the Sonogashira reaction. A typical but non-limiting example of these conditions is to heat a solution of a formula III and formula XXI compounds in anhydrous DMF under an inert atmosphere in the presence of TEA, CuI and Pd(PPh)$_3$ to form a compound of formula XXII. L represents a linker, or fragment of a linker either of which may bear a protecting group such as BOC if L contains an amine. The skilled artisan will understand that this protecting will need to be removed before completing the transformation to a heterobifunctional degradative compound of formula XXIII. In compounds of formula XVIII, X$_2$ can be a leaving group such as, but not limited to, halo or tosylate and L' can be a linker or fragment of a linker. Thus a de-protected compound of formula XXII can react with a compound of formula XVIII to prepare a heterobifunctional degradative compound of formula XXIII The skilled artisan will recognize that compounds of formula XXII can alternatively contain an electrophile or leaving group on L and that X$_2$ of a compound of formula XVIII could be a nucleophile such as an amine.

Scheme 7

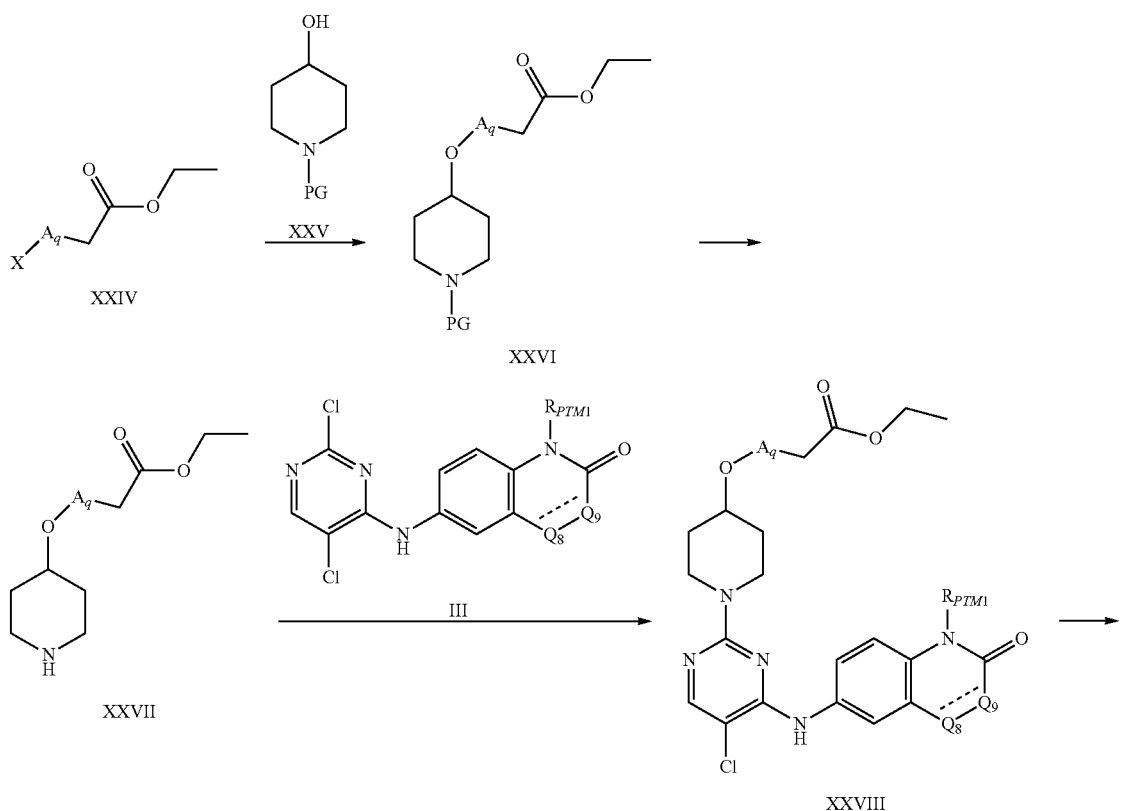

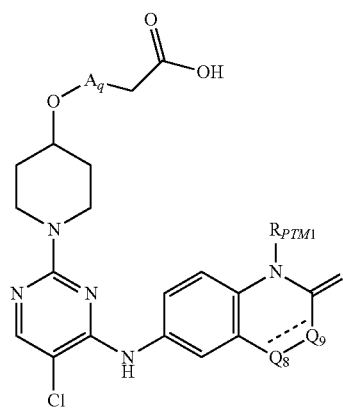

XXIX

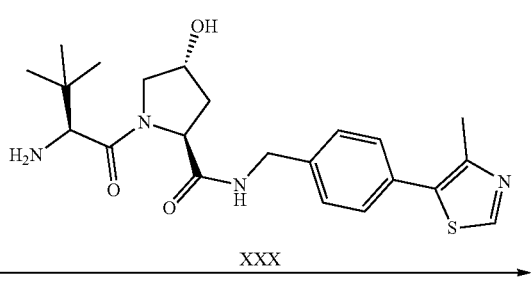

XXX

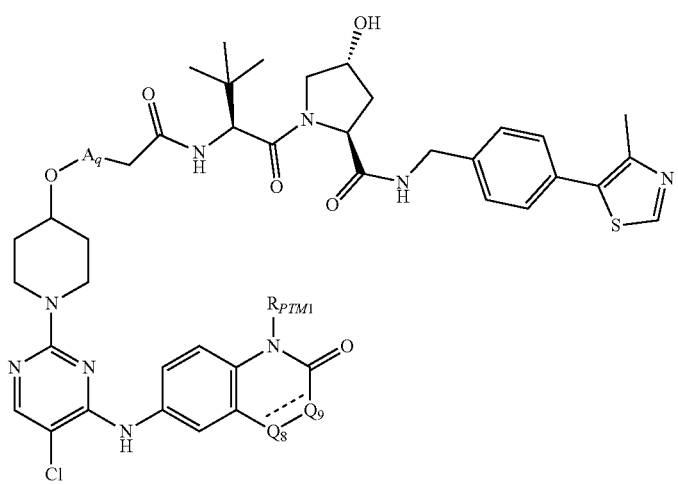

XXXI

Certain compounds of the invention have a VHL ligand as their ULM and these compounds can be prepared as shown in Scheme 7. A compound of formula XXIV (commercially available or readily prepared using standard reaction techniques known to one skilled in the art) may be reacted with a compound XXV under basic conditions, e.g. NaH and a suitable solvent such as DMF to produce a compound of formula XXVI. PG is a suitable protecting group, e.g. tert-butoxycarbonyl. A compound of formula XXVI may be converted to a compound of formula XXVII using conditions suitable for the removal of a protecting group, e.g. hydrogen chloride in 1,4-dioxane in dichloromethane when PG is tert-butoxycarbonyl. A compound of formula XXVII may then be reacted with a compound of formula III (where $Q_6=Q_7=N$, $X=Cl$) under basic conditions, e.g. DIEA base or equivalent, in a suitable solvent such as DMSO and with heating to afford a compound of formula XXVIII. Compounds of formula III can be prepared as described in Schemes 1-3. The ester functionality of compounds of formula XXVIII can be hydrolyzed with a base, e.g. NaOH or LiOH in a suitable solvent mixture such as 1:1 MeOH:water or 1:1:1 THF:MeOH:water to form a compound of formula XXIX. A heterobifunctional degradative compound of formula XXXI can be prepared by subjecting a compound of formula XXIX and a compound of formula XXX to amide coupling conditions, e.g. HOBt, EDCI, with a suitable base such as DIEA and a suitable solvent such as DMF. Compounds of formula XXX are well exemplified in the literature enabling their preparation by the skilled practitioner.

Scheme 8

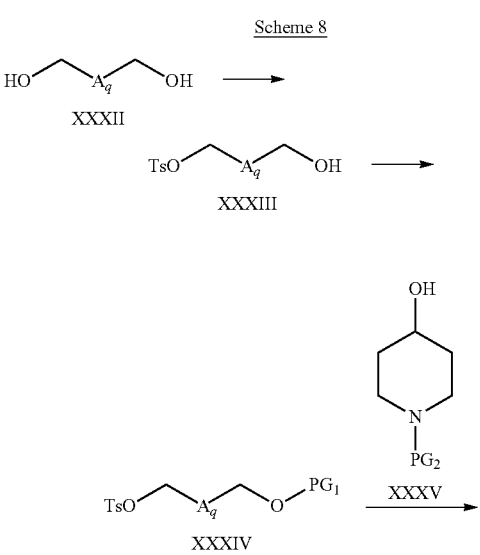

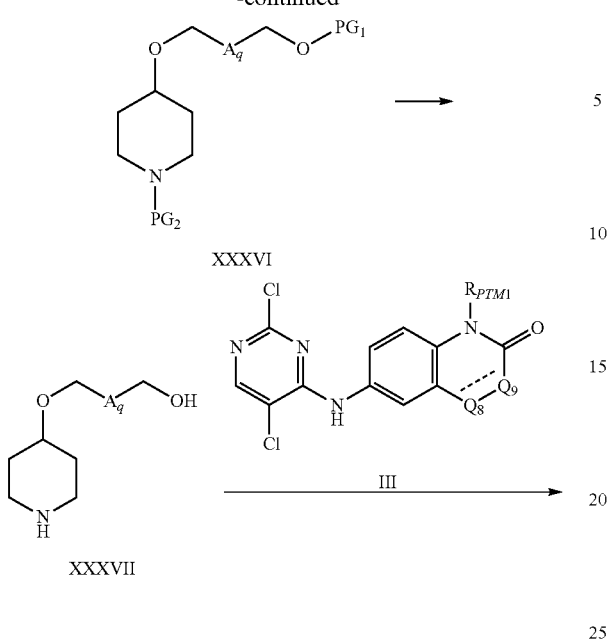

XXXVI

XXXVII

XXXVIII

XXXIX

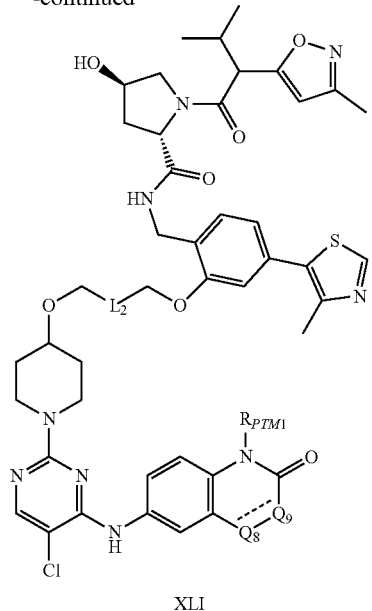

XLI

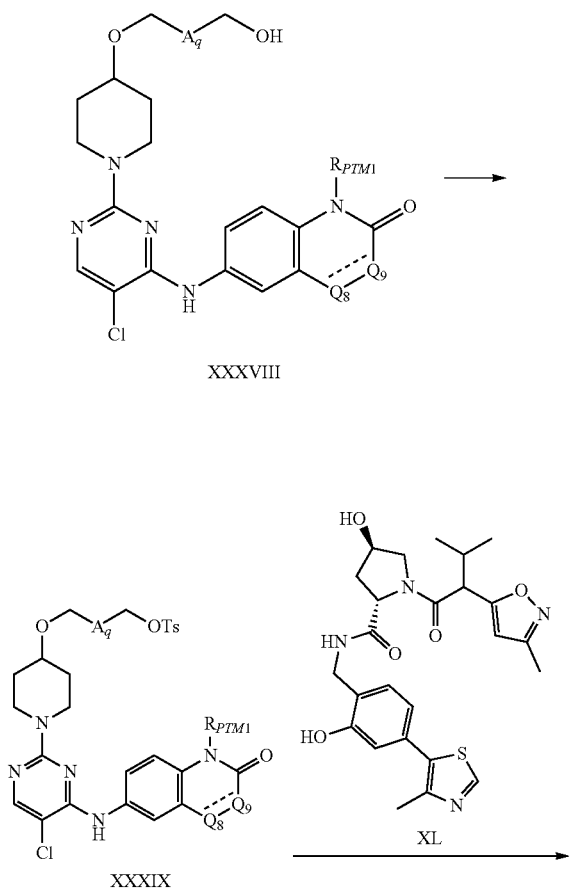

XL

Other compounds of the invention where a VHL ligand is the ULM can be represented by a compound of formula XLI in Scheme 8. These compounds can be prepared by converting a compound of formula XXXII (commercially available or readily prepared using standard reaction techniques known to one skilled in the art) to a mono-tosylate ester XXXIII by the method of Bouzide, et. al. [Tet. Lett. 2001, 42, 8781-8783] with tosyl chloride, $Ag_2O$ and KI in a suitable solvent such as DCM. Monoester XXX can be protected on the other hydroxy group with a suitable protecting group, e.g. THP. The protected monoester XXXIV can be reacted with a compound of formula XXXV to prepare a compound of formula XXXVI in the presence of base, e.g. NaH and in a suitable solvent, e.g. DMF. A compound of formula XXXVIII can be prepared by first removing the protecting groups of XXXVI under acidic conditions, e.g. 4M HCl in dioxane, and heating the product (a compound of formula XXXVII) with a compound of formula III (where $Q_6=Q_7=N$, X=Cl) in the presence of a base, e.g. DIEA and in a suitable solvent, e.g. DMSO. A heterobifunctional degradative compound of formula XLI can be prepared by first activating the hydroxy group of a compound of formula XXXVIII as the tosylate ester under suitable conditions e.g. tosyl chloride and DMAP in pyridine to prepare a compound of formula XXXIX. Then, a compound of formula XXXIX and a compound of formula XL can be heated in the presence of a base, e.g $K_2CO_3$, in a suitable solvent, e.g. DMF, to prepare a heterobifunctional degradative compound of formula XLI.

Scheme 9

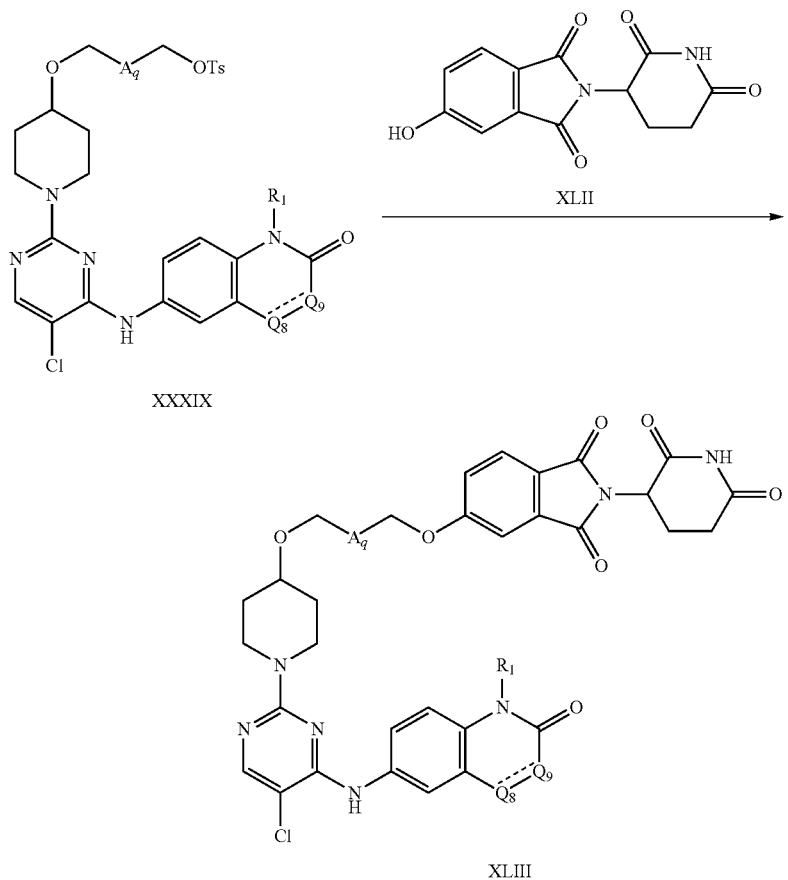

Degrader molecules where that have a cereblon ligand as the ULM can prepared as shown in Scheme 9. A compound of formula XLII (commercially available or readily prepared by one skilled in the art) can react with a compound of formula XXXIX under basic conditions, e.g. $K_2CO_3$, DMF, heat to furnish a heterobifunctional degradative compound of formula XLIII.

Scheme 10

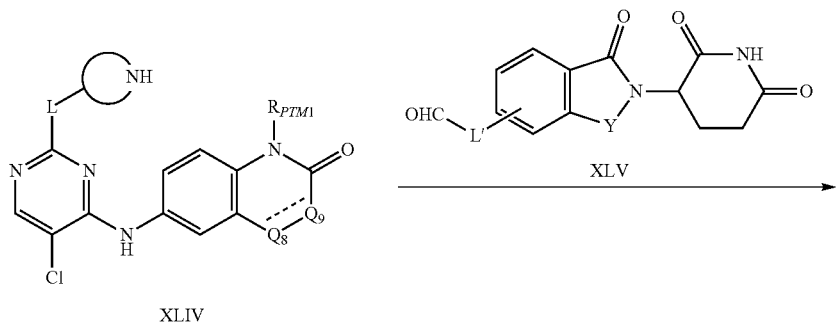

-continued

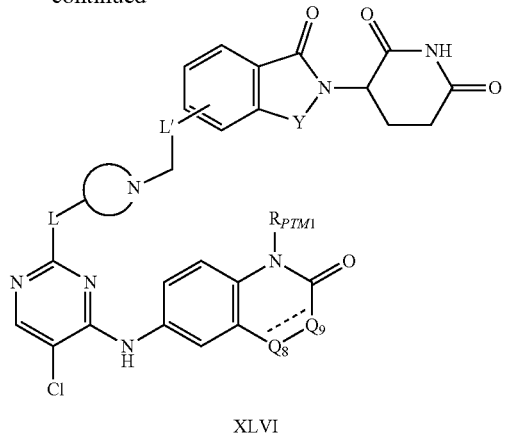

XLVI

Other examples where the ULM is a cereblon ligand can be prepare as shown in Scheme 10. For compounds of formula XLIV, L is bond, or an acyclic, cyclic or heterocyclic part of the PTM optionally including a linker or part of a linker and

is a 4-8 member cyclic amine or spirocyclic amine (any 2-ring combination from 4,4; 4,5; 4,6; 5,4; 5,5; 5,6; 6,4; 6,5; and 6,6) optionally including a second N if >2 carbons are between them. To form a heterobifunctional degradative compound of formula XLIV, reductive alkylation conditions are used e.g. sodium triacetoxyborohydride, acetic acid, dichloromethane, methanol, 30° C., with a compound of formula XLIV and a compound of XLV. The compound of formula XLV has Y=CO or CH, L' is null or a linker or a part of a linker and can be prepared by methods readily available to the skilled artisan.

Scheme 11

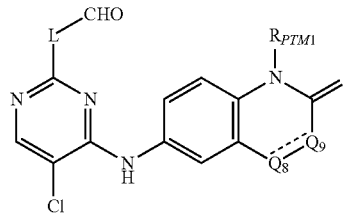

XLVII

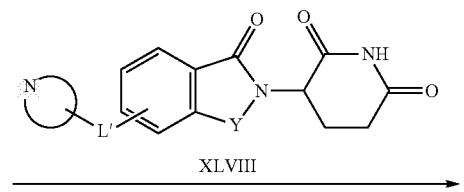

XLVIII

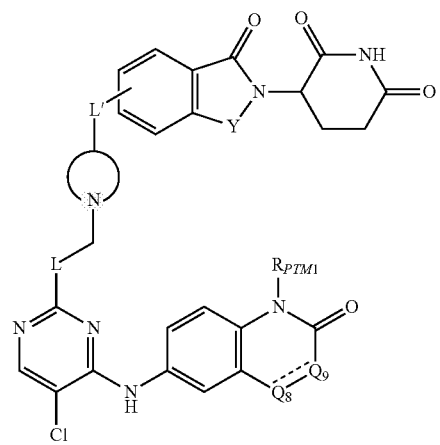

XLIX

In some cases, the reactivity illustrated in Scheme 10 can be reversed. As shown in Scheme 11, a compound of formula XLVII can be reductively alkylated onto a compound of formula XLVIII to form heterobifunctional degradative compounds of formula XLIX. Here L can be a bond, an acyclic, cyclic, heterocyclic or spiro-heterocyclic PTM moiety and L' can be a bond, a linker or part of a linker and

is a 4-8 member cyclic amine or spirocyclic amine (any 2-ring combination from 4,4; 4,5; 4,6; 5,4; 5,5; 5,6; 6,4; 6,5; and 6,6) optionally including a second N if >2 carbons are between them.

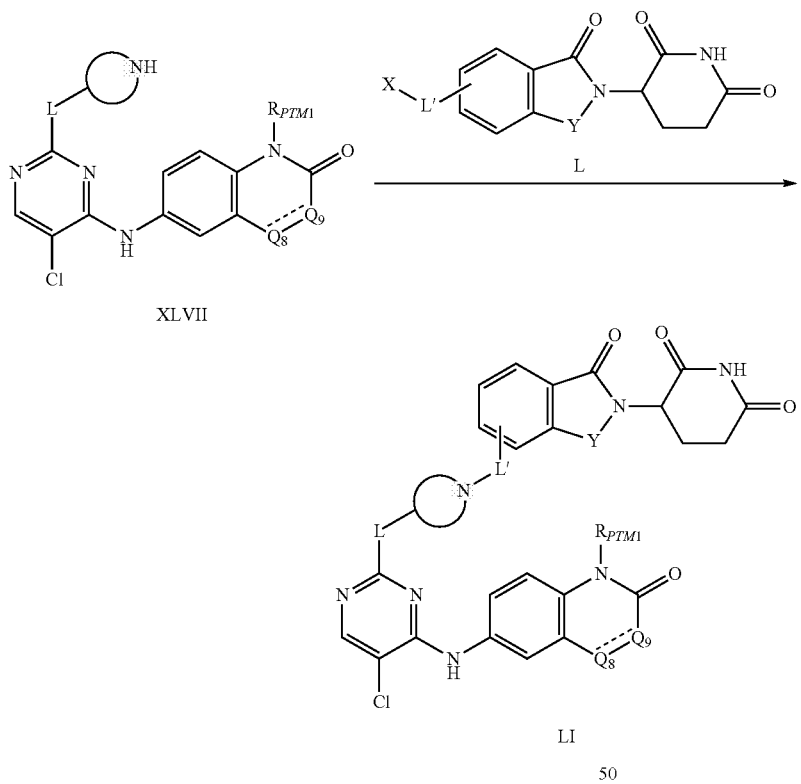

In other cases, a heterobifunctional degradative compound can be formed through a nucleophilic substitution reaction as shown in Scheme 12. Here the L and

are as previously described for a compound of formula XLVII. For the compound of formula L, Y is either CO or CH, L' can be a linker or part of a linker and X is a leaving group such as, but not limited to bromo or O-Tosylate. In certain cases apparent to the skilled praticioner, L' can also be null when X is F. A heterobifunctional degradative compound of formula LI can be formed by combining compounds of formula XLVII and L in solvent such as DMSO, in the presence of a base, eg. DIEA and with or without heating as needed.

Scheme 13

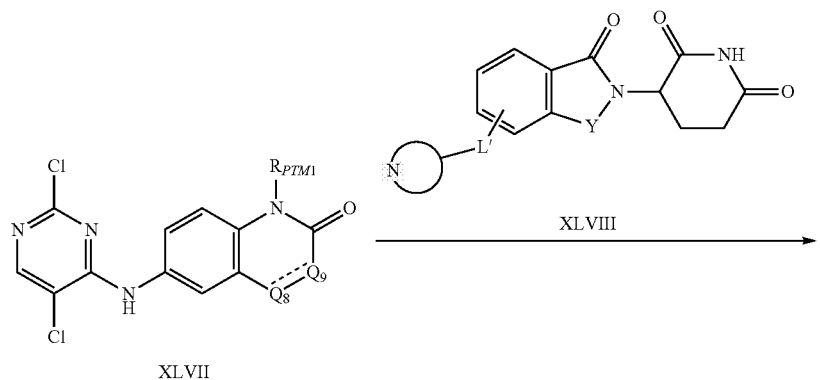

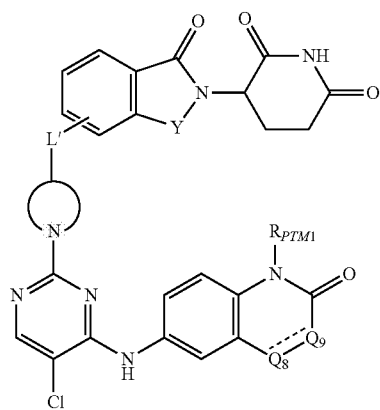

In other cases it may be preferable to form a heterobifunctional degradative compound of formula LII using a compound of XLVIII where the cereblon ligand, linker and PTM moiety form a complete subunit as shown in Scheme 13. Conditions of this reaction usually require a solvent such as DMSO, a base such as DIEA and heating. Compounds of formula XLVIII can be prepared by methods known and available to the skilled artisan.

Scheme 14

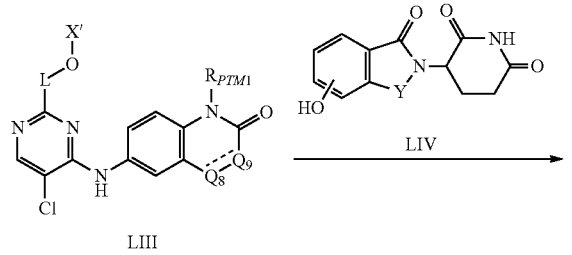

-continued

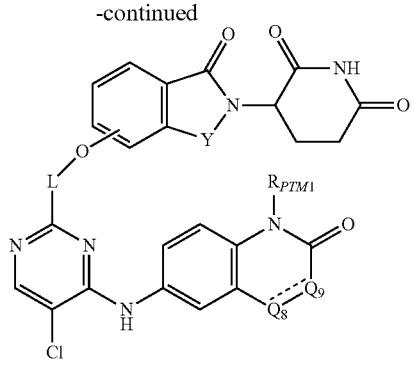

Degrader molecules of formula LV can be formed through the coupling of compounds of formula LIII, where L is an acyclic, cyclic, heterocyclic or spiro-heterocyclic moiety as previous described and X' is either H or a sulfonate moiety which with O forms an active ester such as tosylate. When X'=H, a compound of formula LV can be formed using the Mitsunobu reaction as previously described. When O—X' together are a sulfonate ester, the compound of formula LIII can be reacted with a compound of formula LIV in the presence a base such as $K_2CO_3$ in a solvent such as DMF.

Scheme 15

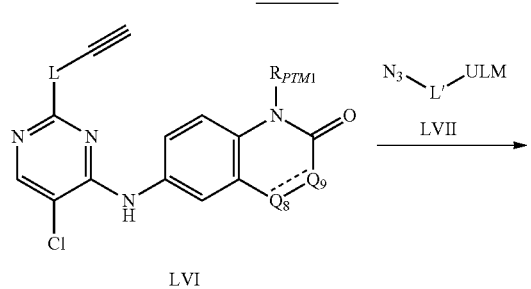

LVI

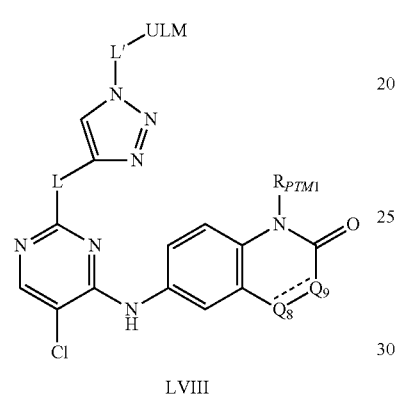

LVIII

Heterobifunctional compounds of formula LVIII can be prepared using Click Chemistry (for a review, see Thirumurigan et al., 2013, *Chem. Rev.* 113, 7, 4905-4979) from a compound of formula LVI where L is a is an acyclic, cyclic, heterocyclic or spiro-heterocyclic moiety as previous described terminating in an alkynyl group and a compound of formula LVII in which a linker (L') terminating in an azido group has been appended to a ULM via methods well know to the skilled artisan. A non-limiting example of click chemistry conditions are stirring a DMSO solution of compounds of formula LVI and LVII in the presence of CuI and DIEA.

Synthetic Procedures

Step 1: Preparation of 2-(2,6-dioxopiperidin-3-yl)-5-hydroxyisoindoline-1,3-dione

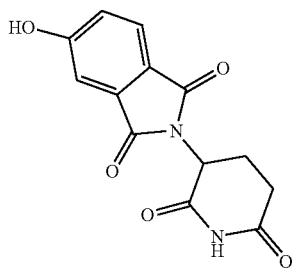 [SMILES: O=C1CCC(N2C(=O)c3ccc(O)cc3C2=O)C(=O)N1]

A solution of 3-aminopiperidine-2,6-dione (4.1 g, 24.7 mmol, 1.50 eq, HCl salt) in acetic acid (45 mL) was charged with sodium acetate (4.1 g, 49.4 mmol, 3.00 eq), then the mixture was stirred at 25° C. for 1 hour. Then 4-hydroxyphthalic acid (3.0 g, 16.5 mmol, 1.00 eq) was added into the mixture and heated to 120° C., stirred for additional 11 hours. The mixture was concentrated and then poured into water (20 mL), and then filtered. The crude product was purified by column chromatography (dichloromethane:methanol=50:1 to 10:1) to afford 2-(2,6-dioxo-3-piperidyl)-5-hydroxy-isoindoline-1,3-dione (3.9 g, 14.3 mmol, 86% yield) as a colorless solid. LC/MS (ESI) m/z: 275 [M+1]$^+$; $^1$H-NMR (400 MHz, CDCl$_3$) δ 11.19-10.94 (m, 2H), 7.75 (d, J=8.0 Hz, 1H), 7.20-7.08 (m, 2H), 5.08 (dd, J=5.2, 12.8 Hz, 1H), 3.34 (br s, 1H), 2.95-2.81 (m, 1H), 2.64-2.55 (m, 1H), 2.08-1.98 (m, 1H).

Synthesis of 6-((2,5-dichloropyrimidin-4-yl)amino)-1-methyl-3-(2-oxopropoxy)quinolin-2(1H)-one (Intermediate Used to Prepare Exemplary Compounds 179, 164, 187, 165, 169, and 170)

Step 1: Preparation of 1-methyl-5-nitroindoline-2,3-dione

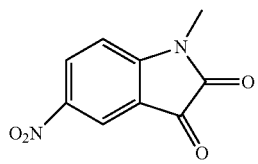

To a mixture of 5-nitroindoline-2,3-dione (5 g, 26.04 mmol), K$_2$CO$_3$ (14.1 g, 29.94 mmol) in DMF (10.0 mL) was added CH$_3$I (4.1 g, 28.64 mmol) dropwise. The mixture was stirred at room temperature for 3 hours. After quenched with H$_2$O (20 mL), the mixture was extracted with ethyl acetate (100 mL). The organic phase was concentrated under vacuum to afford the desired product (2.2 g) as a black solid. LC/MS (ESI) m/z: 207.1 [M+1]$^+$.

Step 2: Preparation of 3-hydroxy-1-methyl-6-nitroquinolin-2(1H)-one

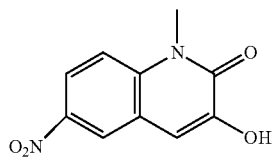 [SMILES: Cn1c(=O)c(O)cc2cc([N+](=O)[O-])ccc21]

To a solution of 1-methyl-5-nitroindoline-2,3-dione (100 mg, 0.485 mmol), TMSCH$_2$N$_2$ (110.8 mg, 0.971 mmol) in DCM (10 mL) at 0° C. was added Sc(OTf)$_3$ (24.1 mg, 0.0485 mmol) dropwise. The mixture was stirred at room temperature for 3 hours. After quenched with H$_2$O (5 mL), the mixture was extracted with ethyl acetate (50 mL). The organic phase was concentrated under vacuum to afford the desired product (50 mg) as a colorless oil. LC/MS (ESI) m/z: 221.1 [M+1]$^+$.

Step 3: Preparation of 1-methyl-6-nitro-3-(2-oxopropoxy)quinolin-2(1H)-one

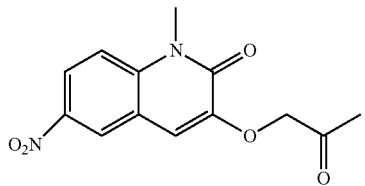

Into a 100 mL round-bottom flask, was placed 3-hydroxy-1-methyl-6-nitro-1,2-dihydroquinolin-2-one (600.0 mg, 2.7 mmol, 1.0 equiv), K₂CO₃ (1.1 g, 0.1 mmol, 3.0 equiv), 1-bromopropan-2-one (441.8 mg, 3.2 mmol, 1.2 equiv) in DMF (5 mL). The resulting mixture was stirred for 2 hours at room temperature. The reaction was then quenched by the addition of 20 mL water. The resulting mixture was extracted with ethyl acetate (20 mL×2). The combined organic layer was dried over anhydrous sodium sulfate and concentrated under reduced pressure. The residue was applied onto a silica gel column eluting with ethyl acetate/petroleum ether (1:1). This resulted in 295.0 mg (39%) of 1-methyl-6-nitro-3-(2-oxopropoxy)-1,2-dihydroquinolin-2-one as a yellow solid. LC/MS (ESI) m/z: 277.05 [M+1]⁺.

Step 4: Preparation of 6-amino-1-methyl-3-(2-oxopropoxy)quinolin-2(1H)-one

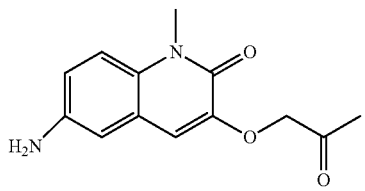 [SMILES: CC(=O)COc1cc2cc([N+](=O)[O-])ccc2n(C)c1=O]

In a 100 mL round bottom flask, to a solution of 1-methyl-6-nitro-3-(2-oxopropoxy)-1,2-dihydroquinolin-2-one (295.0 mg, 1.1 mmol, 1.0 equiv) in MeOH (3 mL) and DMF (3 mL) was added Pd/C (10%, 20.0 mg) under nitrogen atmosphere. The flask was then vacuumed and flushed with hydrogen. The reaction mixture was hydrogenated at 40° C. for 2 hours under hydrogen atmosphere using a hydrogen balloon, then filtered through a Celite pad. The filtrate was concentrated under reduced pressure. This resulted in 245.0 mg (93%) of 6-amino-1-methyl-3-(2-oxopropoxy)-1,2-dihydroquinolin-2-one as a yellow solid.

Step 5: Preparation of 6-((2,5-dichloropyrimidin-4-yl)amino)-1-methyl-3-(2-oxopropoxy)quinolin-2(1H)-one

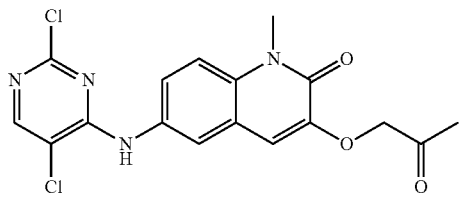 [SMILES: CC(=O)COc1cc2cc(Nc3nc(Cl)ncc3Cl)ccc2n(C)c1=O]

Into a 20 mL sealed tube, was placed 6-amino-1-methyl-3-(2-oxopropoxy)-1,2-dihydroquinolin-2-one (245.0 mg, 0.9 mmol, 1.0 equiv), DIEA (385.4 mg, 2.9 mmol, 3.0 equiv), 2,4,5-trichloropyrimidine (181.3 mg, 0.9 mmol, 1.0 equiv) in DMF (3 mL). The resulting mixture was stirred for 2 hours at 100° C. in an oil bath. The reaction was then quenched by the addition of 20 mL water. The resulting mixture was extracted with ethyl acetate (20 mL×2). The combined organic layer was dried over anhydrous sodium sulfate and concentrated under reduced pressure. The residue was applied onto a silica gel column eluting with ethyl acetate. This resulted in 210.0 mg (54%) of 6-[(2,5-dichloropyrimidin-4-yl)amino]-1-methyl-3-(2-oxopropoxy)-1,2-dihydroquinolin-2-one as a yellow solid. LC/MS (ESI) m/z: 393.00 [M+1]⁺.

Synthesis of 2-(2,6-dioxopiperidin-3-yl)-5-fluoroisoindoline-1,3-dione (Intermediate used to prepare Exemplary Compounds 26, 164, 187, 165, 169 and 170)

Step 1: Preparation of 2-(2,6-dioxopiperidin-3-yl)-5-fluoroisoindoline-1,3-dione

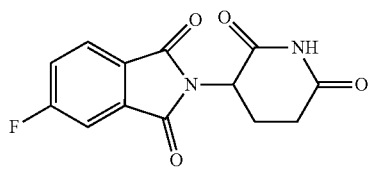 [SMILES: O=C1CCC(N2C(=O)c3ccc(F)cc3C2=O)C(=O)N1]

A mixture of 4-fluorophthalic acid (1.0 g, 5.4 mmol) and CDI (1,1'-carbonyldiimidazole) (1.9 mg, 11.9 mmol) in acetonitrile (20 ml) was stirred at room temperature for 1 hour. To the stirred solution was added 3-aminopiperidine-2,6-dione hydrochloride (894 mg, 5.4 mmol). The mixture was stirred at 70° C. overnight. The cooled reaction mixture was concentrated under reduced pressure to give a crude residue which was stirred in water (30 ml) for 1 hour. The mixture was filtered to give the crude residue which was dried in oven at 50° C. to afford 2-(2,6-dioxopiperidin-3-yl)-5-fluoroisoindoline-1,3-dione (1.4 g, yield 90%) as off-white solid. LC/MS (ESI) m/z: 277.1 [M+1]⁺; ¹H-NMR (400 MHz, DMSO-d₆) δ 2.03-2.11 (m, 1H), 2.50-2.63 (m, 2H), 2.85-2.94 (m, 1H), 5.15-5.20 (m, 1H), 7.66-7.78 (m, 1H), 7.86 (dd, J=7.6, 2.4 Hz, 1H), 8.02 (dd, J=8.4, 4.4 Hz, 1H), 11.16 (s, 1H).

Synthesis of 2-((6-((2,5-dichloropyrimidin-4-yl)amino)-1-methyl-2-oxo-1,2-dihydroquinolin-3-yl)oxy)-N-methylacetamide (Intermediate Used to Prepare Exemplary Compounds 26, 191, 51, 56, and 104)

Step 1: Preparation of N-methyl-2-((1-methyl-6-nitro-2-oxo-1,2-dihydroquinolin-3-yl)oxy)acetamide

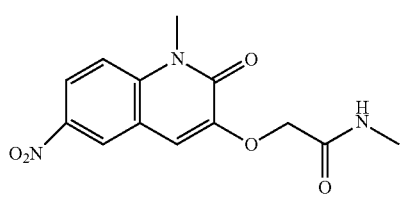

A mixture of 3-hydroxy-1-methyl-6-nitroquinolin-2(1H)-one (727 mg, 3.30 mmol), 2-bromo-N-methylacetamide (604.7 mg, 4.03 mmol), $Cs_2CO_3$ (2.15 g, 6.58 mmol) in DMF (10 mL) was stirred at room temperature for 12 hours. The reaction was quenched with MeOH (20 mL). The mixture was filtered through Celite, and the filtrate was concentrated to give the product (220 mg) as a colorless oil. LC/MS (ESI) m/z: 292.1 [M+1]$^+$.

Step 2: Preparation of 2-((6-amino-1-methyl-2-oxo-1,2-dihydroquinolin-3-yl)oxy)-N-methylacetamide

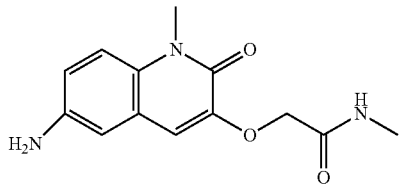 [SMILES: CNC(=O)COc1cc2cc([N+](=O)[O-])ccc2n(C)c1=O]

A mixture of N-methyl-2-((1-methyl-6-nitro-2-oxo-1,2-dihydroquinolin-3-yl)oxy)acetamide (220 mg, 0.75 mmol), Pd/C (100 mg) in MeOH/DMF (10 mL) was stirred at rt for 3 hours under $H_2$. The mixture was filtered through Celite, and the filtrate was concentrated to give the product (150 mg) as a black solid. LC/MS (ESI) m/z: 262.2 [M+23]$^+$.

Step 3: Preparation of 2-((6-((2,5-dichloropyrimidin-4-yl)amino)-1-methyl-2-oxo-1,2-dihydroquinolin-3-yl)oxy)-N-methylacetamide

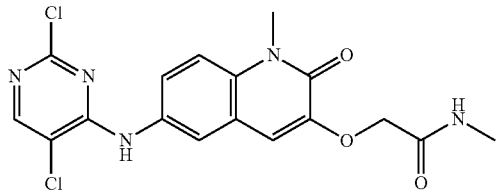 [SMILES: CNC(=O)COc1cc2cc(Nc3nc(Cl)ncc3Cl)ccc2n(C)c1=O]

To a solution of 2-((6-amino-1-methyl-2-oxo-1,2-dihydroquinolin-3-yl)oxy)-N-methylacetamide (100 mg, 0.38 mmol) and 2,4,5-trichloropyrimidine (83 mg, 0.46 mmol) in DMF (4 mL) and MeOH (4 mL) was added triethylamine (77.4 mg, 0.76 mmol) and the mixture was heated to 70° C. for 12 hours. After cooling to room temperature, the reaction mixture was concentrated in vacuo and the residue taken up in water. The resulting precipitate was collected by filtration, was washed with $Et_2O$ and dried in vacuo to give the product (140 mg). LC/MS (ESI) m/z: 408.1 [M+1]$^+$.

Synthesis of 2-(2,6-dioxopiperidin-3-yl)-4-hydroxyisoindoline-1,3-dione (Intermediate Used to Prepare Exemplary Compound 191)

Step 1: Preparation of 2-(2,6-dioxopiperidin-3-yl)-4-hydroxyisoindoline-1,3-dione

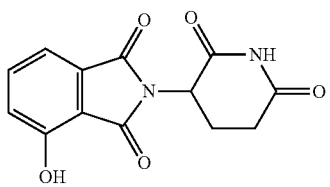 [SMILES: O=C1CCC(N2C(=O)c3cccc(O)c3C2=O)C(=O)N1]

Into a 100-mL round-bottom flask, was placed a solution of 4-hydroxy-1,3-dihydro-2-benzofuran-1,3-dione (1 g, 6.09 mmol, 1.00 equiv) in HOAc (30 mL), 3-aminopiperidine-2,6-dione hydrogen chloride (1.1 g, 6.71 mmol, 1.10 equiv), NaOAc (750 mg, 9.15 mmol, 1.50 equiv). The resulting solution was stirred for 12 hours at 120° C. The reaction mixture was cooled. The resulting mixture was concentrated under vacuum. The resulting solution was diluted with 100 mL of water. The resulting solution was extracted with 3×100 mL of dichloromethane and the organic layers combined. The resulting mixture was washed with 1×20 mL of brine. The mixture was dried over anhydrous sodium sulfate. The residue was applied onto a silica gel column with dichloromethane/methanol (20:1). This resulted in 350 mg (21%) of 2-(2,6-dioxopiperidin-3-yl)-4-hydroxy-2,3-dihydro-1H-isoindole-1,3-dione as a white solid. LC/MS (ESI) m/z: 273 [M−1]$^+$; $^1$H-NMR (300 MHz, DMSO-d$_6$) δ 11.154 (b, 1H), 11.139 (s, 1H), 7.692-7.625 (m, 1H), 7.325-7.234 (m, 2H), 5.100-5.039 (m, 1H), 2.947-2.825 (m, 1H), 2.611-2.445 (m, 2H), 2.036-2.002 (m, 1H).

Synthesis of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (Intermediate Used to Prepare Exemplary Compound 51)

Step 1: Preparation of 4-(4-methylthiazol-5-yl)benzonitrile

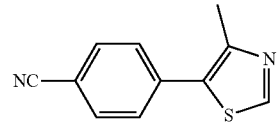

Into a 1-L round-bottom flask purged and maintained with an inert atmosphere of nitrogen, was placed a solution of 4-bromobenzonitrile (20 g, 109.88 mmol, 1.00 equiv) in DMA (250 mL), 4-methyl-1,3-thiazole (21.88 g, 220.67 mmol, 2.00 equiv), Pd(OAc)$_2$ (743 mg, 3.31 mmol, 0.03 equiv) and KOAc (21.66 g, 220.71 mmol, 2.00 equiv). The resulting solution was stirred for 5 hours at 150° C. The reaction mixture was cooled with a water/ice bath and diluted with 1 L of water. The resulting solution was extracted with 3×300 mL of ethyl acetate. The combined organic layers were washed with 3×300 mL of water and 1×300 mL of brine, then dried over anhydrous sodium sulfate and concentrated under vacuum. The residue was purified on combi-flash with ethyl acetate/petroleum ether (1:100-1:5). This resulted in 20 g (91%) of 4-(4-methyl-1,3-thiazol-5-yl)benzonitrile as a beige solid.

Step 2: Preparation of (4-(4-methylthiazol-5-yl)phenyl)methanamine

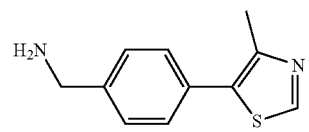

Into a 3-L 3-necked round-bottom flask purged and maintained with an inert atmosphere of nitrogen, was placed 4-(4-methyl-1,3-thiazol-5-yl)benzonitrile (35 g, 174.77 mmol, 1.00 equiv) in tetrahydrofuran (1000 mL). This was followed by the addition of LiAlH₄ (20 g, 526.32 mmol, 3.00 equiv) in portions at 0° C. in 10 minutes. The resulting solution was stirred for 3 hours at 60° C. in an oil bath. The reaction was cooled to 0° C. with a water/ice bath, then quenched by the addition of 20 mL of water, 20 mL of NaOH (15%) and 60 mL of water. The resulting solution was diluted with 200 mL of ethyl acetate. The solids were filtered out. The filtrate was dried over anhydrous sodium sulfate and concentrated under vacuum. The residue was applied onto a silica gel column with dichloromethane/methanol (10:1). This resulted in 20 g (56%) of [4-(4-methyl-1,3-thiazol-5-yl)phenyl]methanamine as yellow oil.

Step 3: Preparation of tert-butyl (2S,4R)-4-hydroxy-2-((4-(4-methylthiazol-5-yl)benzyl)carbamoyl)pyrrolidine-1-carboxylate

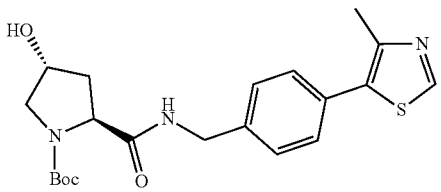 [SMILES: Cc1ncsc1-c1ccc(CNC(=O)[C@@H]2C[C@@H](O)CN2C(=O)OC(C)(C)C)cc1]

Into a 50-mL round-bottom flask, was placed (2S,4R)-1-[(tert-butoxy)carbonyl]-4-hydroxypyrrolidine-2-carboxylic acid (2.7 g, 11.68 mmol, 1.20 equiv) in N,N-dimethylformamide (30 mL), DIEA (2.52 g, 19.50 mmol, 1.20 equiv), HATU (4.47 g, 11.76 mmol, 1.20 equiv), [4-(4-methyl-1,3-thiazol-5-yl)phenyl]methanamine (2 g, 9.79 mmol, 1.00 equiv). The resulting solution was stirred overnight at 25° C. The reaction was then quenched by the addition of 20 mL of water and extracted with 3×20 mL of ethyl acetate. The organic layers combined, dried over anhydrous sodium sulfate and concentrated under vacuum. The residue was applied onto a silica gel column with dichloromethane/methanol (20:1). This resulted in 1 g (24%) of tert-butyl (2S,4R)-4-hydroxy-2-([[4-(4-methyl-1,3-thiazol-5-yl)phenyl]methyl]carbamoyl)pyrrolidine-1-carboxylate as a yellow solid.

Step 4: Preparation of (2S,4R)-4-hydroxy-N-(4-(4-methylthiazol-5-yl)benzyl)pyrrolidine-2-carboxamide hydrochloride

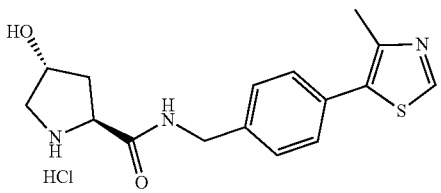 [SMILES: Cc1ncsc1-c1ccc(CNC(=O)[C@@H]2C[C@@H](O)CN2)cc1 ; Cl]

Into a 1000-mL round-bottom flask, was placed tert-butyl (2S,4R)-4-hydroxy-2-([[4-(4-methyl-1,3-thiazol-5-yl)phenyl]methyl]carbamoyl)pyrrolidine-1-carboxylate (45 g, 107.78 mmol, 1.00 equiv), a solution of hydrogen chloride (13.44 L) in dioxane (300 mL). The resulting solution was stirred for 2 hours at 20° C. The solids were collected by filtration. This resulted in 37.3 g (98%) of (2S,4R)-4-hydroxy-N-[[4-(4-methyl-1,3-thiazol-5-yl)phenyl]methyl]pyrrolidine-2-carboxamide hydrochloride as a yellow solid.

Step 5: Preparation of tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate

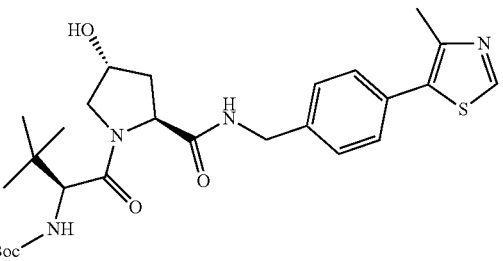

Into a 1000-mL round-bottom flask, was placed (2S)-2-[[(tert-butoxy)carbonyl]amino]-3,3-dimethylbutanoic acid (15.73 g, 68.01 mmol, 1.20 equiv) in N,N-dimethylformamide (500 mL), DIEA (29.2 g, 225.94 mmol, 4.00 equiv), HATU (25.9 g, 68.12 mmol, 1.20 equiv) and (2S,4R)-2-amino-5-chloro-4-hydroxy-N-[[4-(4-methyl-1,3-thiazol-5-yl)phenyl]methyl]pentanamide (20 g, 56.52 mmol, 1.00 equiv). The resulting solution was stirred 16 hours at 20° C. The reaction was then quenched by the addition of 200 mL of water and extracted with 3×100 mL of ethyl acetate. The combined organic layers were dried over anhydrous sodium sulfate and concentrated under vacuum. The residue was applied onto a silica gel column with ethyl acetate/petroleum ether (2:1). This resulted in 15.2 g (51%) of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate as a yellow solid.

Step 6: Preparation of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride

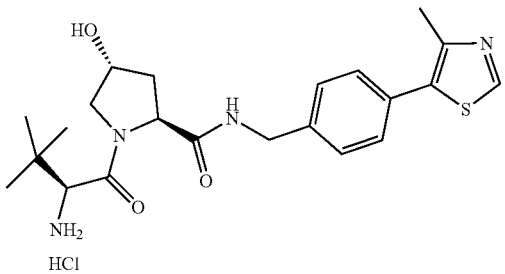 [SMILES: Cc1ncsc1-c1ccc(CNC(=O)[C@@H]2C[C@@H](O)CN2C(=O)[C@@H](N)C(C)(C)C)cc1 ; Cl]

Into a 500-mL round-bottom flask, was placed tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol, 1.00 equiv) in dioxane (20 mL) and a solution of hydrogen chloride (3.584 L) in dioxane (80 mL). The resulting solution was stirred for 2 h at 25° C. The solids were collected by filtration. This resulted in 5.1 g (48%) of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride as a yellow solid. LC/MS (ESI) m/z: 431 [M+1]$^+$; $^1$H-NMR (400 MHz, CD$_3$OD) δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H).

Synthesis of (2S,4R)-4-hydroxy-N-(2-hydroxy-4-(4-methylthiazol-5-yl)benzyl)-1-(3-methyl-2-(3-methyl-isoxazol-5-yl)butanoyl)pyrrolidine-2-carboxamide (Intermediate Used to Prepare Exemplary Compound 56)

Step 1: Preparation of 2-(3-methylisoxazol-5-yl)acetic acid

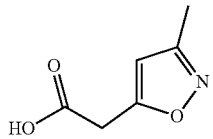

To a solution of 3,5-dimethylisoxazole (15 g, 154.46 mmol, 15 mL, 1 eq) in tetrahydrofuran (150 mL) was added n-butyllithium (2.5 M, 77 mL, 1.25 eq) dropwise at −78° C. under nitrogen, the mixture was stirred at −55° C. for 30 minutes, and then carbon dioxide was bubbled into the mixture for 30 minutes, the mixture was stirred at 25° C. for 1 hours. The mixture was quenched by saturated ammonium chloride solution (50 mL) the mixture was extracted with ethyl acetate (50 mL). The aqueous phase was adjusted with aqueous hydrochloric acid solution (2 M) until pH=2, the mixture was extracted with ethyl acetate (50 mL, three times), the organic phase was dried by anhydrous sodium sulfate, filtered and the filtrate was concentrated to give 2-(3-methylisoxazol-5-yl)acetic acid (10 g, 70.86 mmol, 46% yield) as a brown solid. $^1$H-NMR (400 MHz, DMSO-d$_6$) δ 12.74 (br s, 1H), 6.24 (s, 1H), 3.83 (s, 2H), 2.20 (s, 3H).

Step 2: Preparation of methyl 2-(3-methylisoxazol-5-yl)acetate

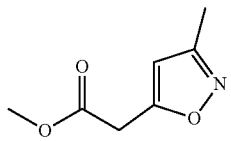

To a solution of 2-(3-methylisoxazol-5-yl)acetic acid (10 g, 70.86 mmol, 1 eq) in methanol (100 mL) was added thionyl chloride (12.65 g, 106.29 mmol, 7.71 mL, 1.5 eq) at 0° C., and the mixture was stirred at 50° C. for 4 hours. The mixture was concentrated to give crude product. This crude was diluted with ethyl acetate (200 mL) and washed by water (200 mL), and then saturated sodium bicarbonate aqueous solution (50 mL) and then brine (50 mL), the organic phase was dried by anhydrous, filtered and the filtrate was condensed to give methyl 2-(3-methylisoxazol-5-yl)acetate (10 g, 64.45 mmol, 91% yield) as a brown oil. $^1$H-NMR (400 MHz, CDCl$_3$) δ 6.11 (s, 1H), 3.80 (s, 2H), 3.76 (s, 3H), 2.30 (s, 3H).

Step 3: Preparation of methyl 3-methyl-2-(3-methylisoxazol-5-yl)butanoate

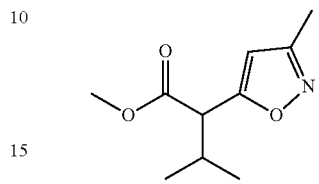

To a solution of methyl 2-(3-methylisoxazol-5-yl)acetate (10 g, 64.45 mmol, 1 eq) in tetrahydrofuran (100 mL) was added sodium hydride (3.87 g, 96.68 mmol, 60% purity, 1.5 eq) at 0° C. and then 2-iodopropane (13.15 g, 77.34 mmol, 7.74 mL, 1.2 eq) was added at 0° C., the mixture was stirred at 25° C. for 2 hours. Additional 2-iodopropane (2.55 g, 15.00 mmol, 1.5 mL) was added and the mixture was stirred at 25° C. for 10 hours. The mixture was quenched by aqueous hydrochloric acid solution (1 M, 300 mL) and the mixture was extracted with ethyl acetate (200 mL, three times), the organic phase was dried by anhydrous sodium sulfate, filtered and the filtrate was concentrated to give methyl 3-methyl-2-(3-methylisoxazol-5-yl)butanoate (13 g) as a brown oil.

Step 4: Preparation of 3-methyl-2-(3-methylisoxazol-5-yl)butanoic acid

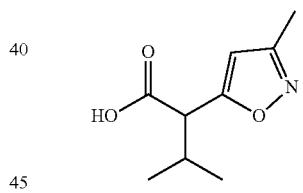

To a solution of methyl 3-methyl-2-(3-methylisoxazol-5-yl)butanoate (12.7 g, 64.39 mmol, 1 eq) in methanol (90 mL) and water (60 mL) was added sodium hydroxide (12.88 g, 321.96 mmol, 5 eq), the mixture was stirred at 25° C. for 2 hours. The mixture was concentrated to removed methanol, and then the residue was diluted with water (200 mL) and extracted with ethyl acetate (200 mL), the aqueous phase was adjusted by aqueous hydrochloric acid solution (2 M) until pH=3, and then the mixture was extracted with dichloromethane (200 mL, three times), the organic phase was dried by anhydrous sodium sulfate, filtered and the filtrate was concentrated to give crude product as a brown oil, this crude was purified by flash prep-HPLC, the fraction of acetonitrile was removed and the residue was extracted with dichloromethane (300 mL×5), the organic phase was dried by anhydrous sodium sulfate, filtered and the filtrate was concentrated to give product 3-methyl-2-(3-methylisoxazol-5-yl)butanoic acid (7.5 g, 40.94 mmol, 63% yield) as white solid. $^1$H-NMR (400 MHz, DMSO-d$_6$) δ 6.26 (s, 1H), 3.58 (d, J=8.7 Hz, 1H), 2.33-2.23 (m, 1H), 2.21 (s, 3H), 0.95 (d, J=6.7 Hz, 3H), 0.82 (d, J=6.8 Hz, 3H).

Step 5: Preparation of 2-hydroxy-4-(4-methylthiazol-5-yl)benzonitrile

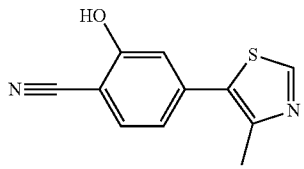

To a solution of 4-bromo-2-hydroxy-benzonitrile (15 g, 75.75 mmol, 1 eq) and 4-methylthiazole (20.28 g, 204.53 mmol, 19 mL, 2.7 eq) in N-methyl pyrrolidone (150 mL) was added potassium acetate (22.30 g, 227.25 mmol, 3 eq) and palladium acetate (1.70 g, 7.58 mmol, 0.1 eq)), the mixture stirred at 110° C. under nitrogen for 6 hours. The mixture was quenched with water (500 mL), the aqueous phase was extracted with ethyl acetate (300 mL×3). The combined organic phase was washed with brine (200 mL, twice), dried with anhydrous sodium sulfate, filtered and concentrated under vacuum and then methyl tertiary butyl ether (500 mL) was added to the mixture and the organic phase was washed with water (100 mL) and brine (100 mL, twice). The residue was purified by silica gel column chromatography (petroleum ether/ethyl acetate=3/1 to 1/1). Compound 2-hydroxy-4-(4-methylthiazol-5-yl)benzonitrile (11 g, 50.87 mmol, 67% yield) was obtained as a yellow solid.

Step 6: Preparation of 2-(aminomethyl)-5-(4-methylthiazol-5-yl)phenol

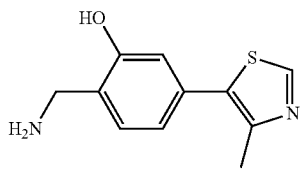

To a solution of 2-hydroxy-4-(4-methylthiazol-5-yl)benzonitrile (11 g, 50.87 mmol, 1 eq) in tetrahydrofuran (150 mL) was added lithium aluminum hydride (7.72 g, 203.46 mmol, 4 eq) at 0° C., the mixture was stirred at 50° C. for 3 hours. The mixture was quenched by water (8 mL) at 0° C., and then 15% sodium hydroxide aqueous solution (8 mL) and then water (8 mL), anhydrous sodium sulfate (30 g) was added, the mixture was stirred at 25° C. for 30 minutes, filtered and the solid was added dichloromethane/methanol (4/1, 50 mL), the mixture was stirred at 25° C. for 1 hours, filtered and the filtrate combined was concentrated to give 2-(aminomethyl)-5-(4-methylthiazol-5-yl)phenol (7 g, 31.78 mmol, 62% yield) as a brown solid. $^1$H-NMR (400 MHz, DMSO-d$_6$) δ 8.82 (s, 1H), 6.90 (d, J=7.5 Hz, 1H), 6.52 (d, J=1.6 Hz, 1H), 6.25 (dd, J=1.7, 7.5 Hz, 1H), 3.59 (s, 2H), 2.41 (s, 3H).

Step 7: Preparation of tert-butyl (2S,4R)-4-hydroxy-2-((2-hydroxy-4-(4-methylthiazol-5-yl)benzyl)carbamoyl)pyrrolidine-1-carboxylate

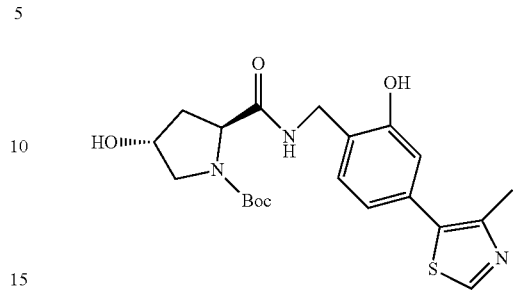

To a solution of 2-(aminomethyl)-5-(4-methylthiazol-5-yl)phenol (7 g, 31.78 mmol, 1 eq) and (2S,4R)-1-tert-butoxycarbonyl-4-hydroxy-pyrrolidine-2-carboxylic acid (7.35 g, 31.78 mmol, 1 eq) in dimethylformamide (70 mL) was added diisopropylethylamine (12.32 g, 95.33 mmol, 16.60 mL, 3 eq) and then HATU (13.29 g, 34.95 mmol, 1.1 eq), the mixture was stirred at 25° C. for 2 hours. Additional (2S,4R)-1-tert-butoxycarbonyl-4-hydroxy-pyrrolidine-2-carboxylic acid (7.35 g, 31.78 mmol, 1 eq) and HATU (12.08 g, 31.78 mmol, 1 eq) was added, the mixture was stirred at 25° C. for 5 hours. The mixture was diluted with water (300 mL) and extracted with ethyl acetate (300 mL, twice), the organic phase was dried by anhydrous sodium sulfate, filtered and the filtrate was concentrated to give crude product as a brown oil, this crude was dissolved in tetrahydrofuran/water (2/1, 150 mL) and lithium hydroxide (3 g) was added, the mixture was stirred at 25° C. for 1 hour. The mixture was diluted with water (300 mL) and adjusted with aqueous hydrochloric acid solution (0.5 M) until pH=7, the mixture was extracted with ethyl acetate (300 mL, twice), the organic phase was dried by anhydrous sodium sulfate, filtered and filtrate was concentrated to give crude product, this crude product was purified by silica gel chromatography (2-10% methnal in dichloromethane) to give tert-butyl (2S,4R)-4-hydroxy-2-[[2-hydroxy-4-(4-methylthiazol-5-yl)phenyl]methylcarbamoyl]pyrrolidine-1-carboxylate (6.9 g, 15.92 mmol, 50% yield) as a yellow oil. LC/MS (ESI) m/z: 434.1 [M+1]$^+$.

Step 8: Preparation of (2S,4R)-4-hydroxy-N-(2-hydroxy-4-(4-methylthiazol-5-yl)benzyl)pyrrolidine-2-carboxamide

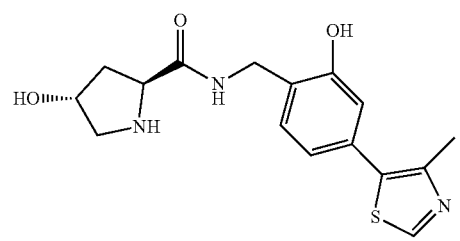 [SMILES: Cc1ncsc1-c1ccc(CNC(=O)[C@@H]2C[C@@H](O)CN2)c(O)c1]

To a solution of tert-butyl (2S,4R)-4-hydroxy-2-[[2-hydroxy-4-(4-methylthiazol-5-yl)phenyl]methylcarbamoyl] pyrrolidine-1-carboxylate (6.9 g, 15.92 mmol, 1 eq) in methanol (30 mL) was added hydrochloric/dioxane (4 M, 30 mL, 7.54 eq), the mixture was stirred at 25° C. for 20 minutes. The mixture was concentrated to give product as a yellow solid, this crude product was triturated by ethyl acetate and petroleum ether (1:1, 20 mL), the mixture was filtered and the solid was dried by rotary evaporator to give product (2S,4R)-4-hydroxy-N-[[2-hydroxy-4-(4-methylthiazol-5-yl)phenyl]methyl]pyrrolidine-2-carboxamide (4.83 g, 13.06 mmol, 82% yield, hydrochloric acid) as a yellow solid. $^1$H-NMR (400 MHz, DMSO-d$_6$) δ 10.03 (br s, 1H), 9.11-8.95 (m, 2H), 8.66 (br s, 1H), 7.20 (d, J=7.9 Hz, 1H), 7.04 (d, J=1.3 Hz, 1H), 6.90 (dd, J=1.7, 7.8 Hz, 1H), 4.44 (br s, 1H), 4.40-4.26 (m, 3H), 3.41-3.27 (m, 1H), 3.13-3.02 (m, 1H), 2.46 (s, 3H), 2.33 (br dd, J=7.5, 12.7 Hz, 1H), 1.96-1.85 (m, 1H), 1.33-1.24 (m, 1H).

Step 9: Preparation of (2S,4R)-4-hydroxy-N-(2-hydroxy-4-(4-methylthiazol-5-yl)benzyl)-1-(3-methyl-2-(3-methylisoxazol-5-yl)butanoyl)pyrrolidine-2-carboxamide

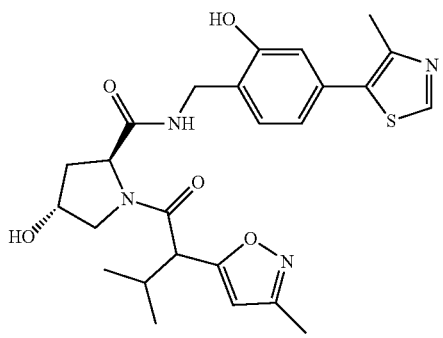 [SMILES: Cc1cc(C(C(=O)N2C[C@H](O)C[C@H]2C(=O)NCc2ccc(-c3scnc3C)cc2O)C(C)C)on1]

To a solution of (2S,4R)-4-hydroxy-N-[[2-hydroxy-4-(4-methylthiazol-5-yl)phenyl]methyl]pyrrolidine-2-carboxamide (4.83 g, 13.06 mmol, 1 eq, hydrochloride) in dimethylformamide (60 mL) was added diisopropylethylamine (5.06 g, 39.18 mmol, 6.82 mL, 3 eq), and then 3-methyl-2-(3-methylisoxazol-5-yl)butanoic acid (2.39 g, 13.06 mmol, 1 eq) and HATU (5.46 g, 14.36 mmol, 1.1 eq) was added, the mixture was stirred at 25° C. for 2 hours. The mixture was diluted with water (200 mL) and extracted with ethyl acetate (300 mL, twice), the organic phase was dried by anhydrous sodium sulfate, filtered and the filtrate was concentrated to give crude product. This crude product was purified by prep-HPLC, the fraction of acetonitrile was removed, and the residue was extracted with dichloromethane (300 mL×5), the organic phase was dried by anhydrous sodium sulfate, filtered and the filtrate was concentrated to give product (2S,4R)-4-hydroxy-N-[[2-hydroxy-4-(4-methylthiazol-5-yl)phenyl]methyl]-1-[3-methyl-2-(3-methylisoxazol-5-yl)butanoyl]pyrrolidine-2-carboxamide (4.0 g, 8.02 mmol, 61% yield) as a white solid. $^1$H-NMR (400 MHz, CD$_3$OD) δ 8.85 (s, 1H), 7.39-7.23 (m, 1H), 6.98-6.86 (m, 2H), 6.31-6.06 (m, 1H), 4.65-4.28 (m, 4H), 3.94-3.48 (m, 3H), 2.52-2.45 (m, 3H), 2.42-2.31 (m, 1H), 2.26-2.15 (m, 4H), 2.13-2.03 (m, 1H), 1.08-1.01 (m, 3H), 0.92-0.81 (m, 3H).

Synthesis of 2-(2-((2-(2,6-dioxopiperidin-3-yl)-1,3-dioxoisoindolin-5-yl)oxy)ethoxy)acetaldehyde (Intermediate Used to Prepare Exemplary Compound 74)

Step 1: Preparation of 2-(2,6-dioxopiperidin-3-yl)-5-(2-(2-hydroxyethoxy)ethoxy)isoindoline-1,3-dione

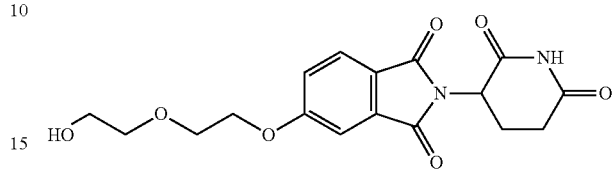

To a solution of tert-butyl 3-hydroxy-3-(phenylethynyl)pyrrolidine-1-carboxylate (2 g, 7.29 mmol) in THF (10 mL) were added sodium 2,2'-oxydiethanol (959 mg, 8.75 mmol), DIAD (5.9 g, 29.16 mmol) and Ph$_3$P (7.65 g, 29.16 mmol) under N$_2$. The mixture was stirred at rt for 1 hour. The mixture was quenched with water (15 mL), extracted with EA (15 mL). The combined filtrate was concentrated to afford the crude product, which was purified by chromatography column with PE:EA=10:1~3:1 to yield the desired product (1.2 g, 45.4% yield) as a yellow solid. LC/MS (ESI) m/z: 363.1 [M+1]$^+$.

Step 2: Preparation of 2-(2-((2-(2,6-dioxopiperidin-3-yl)-1,3-dioxoisoindolin-5-yl)oxy)ethoxy)acetaldehyde

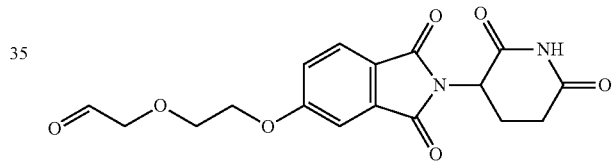

A solution of 2-(2,6-dioxopiperidin-3-yl)-5-(2-(2-hydroxyethoxy)ethoxy)isoindoline-1,3-dione (300 mg, 0.83 mmol) in MeCN (10 mL) was added IBX (278 mg, 0.99 mmol) at rt. The mixture was heated to 80° C. for 2 h. The mixture was filtered and concentrated to afford the product (300 mg) as a yellow oil. LC/MS (ESI) m/z: 361.2 [M+1]$^+$.

Synthesis of 2-(2,6-dioxopiperidin-3-yl)-5-(piperazin-1-yl)isoindoline-1,3-dione hydrochloride (Intermediate Used to Prepare Exemplary Compound 104)

Step 1: Preparation of tert-butyl 4-(2-(2,6-dioxopiperidin-3-yl)-1,3-dioxoisoindolin-5-yl)piperazine-1-carboxylate

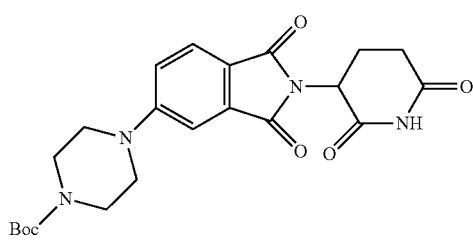 [SMILES: CC(C)(C)OC(=O)N1CCN(c2ccc3c(c2)C(=O)N(C2CCC(=O)NC2=O)C3=O)CC1]

To a solution of 2-(2,6-dioxopiperidin-3-yl)-5-fluoroisoindoline-1,3-dione (10 g, 36.2 mmol) in NMP (70 mL) was added tert-butyl piperazine-1-carboxylate (13.47 g, 72.5 mmol) and DIPEA (18.6 g, 14.5 mmol). The resulting mixture was stirred at 90° C. for 16 hours. After cooling to rt, the reaction was quenched with water (100 mL), and the mixture was extracted with EtOAc (300 mL×2). The combined organic layers were dried over $Na_2SO_4$, filtered and concentrated under reduced pressure. The residue was purified by silica gel column chromatography (PE/EA=100~2/1) to afford the desired product (14 g, 31.67 mmol, 87.5% yield) as a light yellow solid. $^1$H-NMR (400 MHz, $CDCl_3$) δ 7.97 (s, 1H), 7.71 (d, J=8.0 Hz, 1H), 7.27 (s, 1H), 7.05 (d, J=8.4 Hz, 1H), 4.92-4.96 (m, 1H), 3.60-3.61 (m, 4H), 3.40-3.41 (m, 4H), 2.72-2.92 (m, 3H), 2.12-2.15 (m, 1H), 1.49 (s, 9H).

Step 2: Preparation of 2-(2,6-dioxopiperidin-3-yl)-5-(piperazin-1-yl)isoindoline-1,3-dione hydrochloride

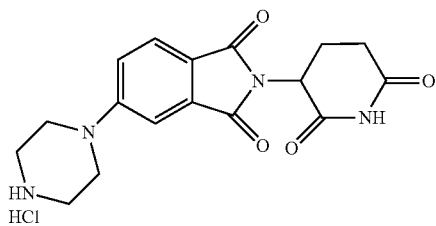 [SMILES: O=C1CCC(N2C(=O)c3ccc(N4CCNCC4)cc3C2=O)C(=O)N1 ; Cl]

To a solution of tert-butyl 4-(2-(2,6-dioxopiperidin-3-yl)-1,3-dioxoisoindolin-5-yl)piperazine-1-carboxylate (14 g, 31.67 mmol) in dioxane (50 mL) was added 5N HCl in dioxane (30 mL, 150 mmol) at 25° C. After stirring for 3 hours, the solvent was removed under reduced pressure to afford the desired product 2-(2,6-dioxopiperidin-3-yl)-5-(piperazin-1-yl)isoindoline-1,3-dione hydrochloride as a yellow solid (12 g, 31.67 mmol, 100% yield). LC/MS (ESI) m/z: 343.1 [M+1]$^+$; $^1$H-NMR (400 MHz, $CDCl_3$) δ 7.76 (d, J=8.8 Hz, 1H), 7.47 (s, 1H), 7.35 (dd, J=8.4, 2.0 Hz, 1H), 5.07-5.11 (m, 1H), 3.69-3.72 (m, 4H), 3.39-3.41 (m, 4H), 2.82-2.91 (m, 1H), 2.66-2.76 (m, 2H), 2.10-2.13 (m, 1H).

Synthesis of 5-((4-(5-chloro-4-((1-methyl-2-oxo-3-(2-oxopropoxy)-1,2-dihydroquinolin-6-yl)amino)pyrimidin-2-yl)morpholin-2-yl)methoxy)-2-(2,6-dioxopiperidin-3-yl)isoindoline-1,3-dione
(Exemplary Compound 179)

Step 1: Preparation of tert-butyl 2-((tosyloxy)methyl)morpholine-4-carboxylate

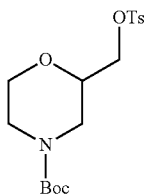

Into a 100-mL round-bottom flask, was placed tert-butyl 2-(hydroxymethyl)morpholine-4-carboxylate (3300 mg, 15.19 mmol, 1.0 equiv), p-toluenesulfonyl chloride (4343 mg, 22.8 mmol, 1.5 equiv), DMAP (186 mg, 1.5 mmol, 0.1 equiv), Et3N (4611 mg, 45.6 mmol, 3.0 equiv) in DCM (30 ml). The resulting solution was stirred for 2 h at room temperature. The reaction was then quenched by the addition of 40 mL of water/ice. The resulting solution was extracted with (40 mL×3) of dichloromethane. The combined organic layer was washed with (40 mL×3) of brine, dried over anhydrous sodium sulfate and concentrated under vacuum. The residue was applied onto a silica gel column with ethyl acetate/petroleum ether (4/6). This resulted in 5.2 g (92%) of tert-butyl 2-[[(4-methylbenzenesulfonyl)oxy]methyl]morpholine-4-carboxylate as yellow oil. LC/MS (ESI) m/z: 372 [M+1]$^+$.

Step 2: Preparation of tert-butyl 2-(((2-(2,6-dioxopiperidin-3-yl)-1,3-dioxoisoindolin-5-yl)oxy)methyl)morpholine-4-carboxylate

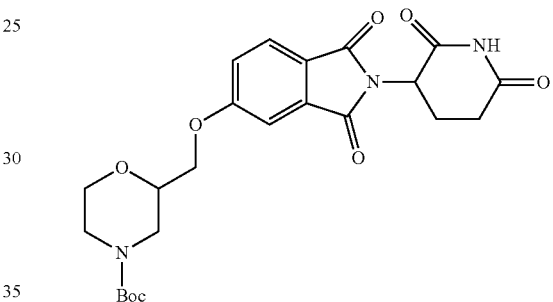

Into a 30-mL sealed tube, was placed tert-butyl 2-[[(4-methylbenzenesulfonyl)oxy]methyl]morpholine-4-carboxylate (1113 mg, 3.0 mmol, 1.0 equiv), $K_2CO_3$ (828 mg, 6.0 mmol, 2.0 equiv), 2-(2,6-dioxopiperidin-3-yl)-5-hydroxyisoindole-1,3-dione (822 mg, 3.0 mmol, 1.0 equiv) in DMF (15 mL). The resulting solution was stirred for 2 hours at 70° C. in an oil bath. The solids were filtered out and the filtrate was concentrated under reduced pressure. The crude product was purified by Prep-HPLC. This resulted in 754 mg (53%) of tert-butyl 2-([[2-(2,6-dioxopiperidin-3-yl)-1,3-dioxoisoindol-5-yl]oxy]methyl)morpholine-4-carboxylate as a light yellow solid. LC/MS (ESI) m/z: 418 [M−55]$^+$.

Step 3: Preparation of 2-(2,6-dioxopiperidin-3-yl)-5-(morpholin-2-ylmethoxy)isoindoline-1,3-dione

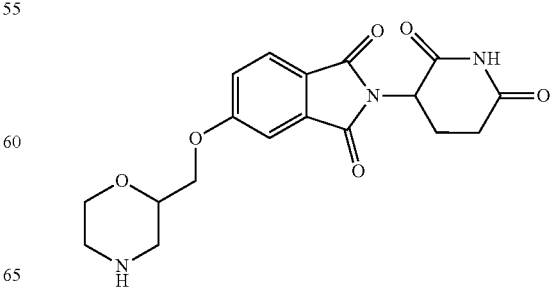

Into a 20-mL vial, was placed tert-butyl 2-([[2-(2,6-dioxopiperidin-3-yl)-1,3-dioxoisoindol-5-yl]oxy]methyl)morpholine-4-carboxylate (473 mg, 2.3 mmol, 1.0 equiv) in 1,4-dioxane (5 ml) and hydrogen chloride (4 M in dioxaen, 4.5 ml). The resulting solution was stirred overnight at room temperature and then concentrated under reduced pressure. This resulted in 377 mg of 2-(2,6-dioxopiperidin-3-yl)-5-(morpholin-2-ylmethoxy)isoindole-1,3-dione as a white solid. LC/MS (ESI) m/z: 374 [M+1]$^+$.

Step 4: Preparation of 5-((4-(5-chloro-4-((1-methyl-2-oxo-3-(2-oxopropoxy)-1,2-dihydroquinolin-6-yl)amino)pyrimidin-2-yl)morpholin-2-yl)methoxy)-2-(2,6-dioxopiperidin-3-yl)isoindoline-1,3-dione

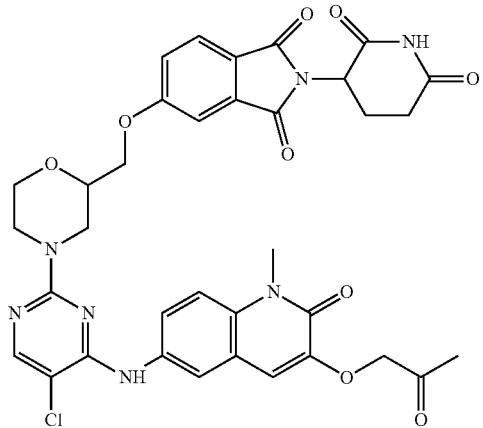 [SMILES: CC(=O)COc1cc2cc(Nc3nc(N4CCOC(COc5ccc6c(c5)C(=O)N(C5CCC(=O)NC5=O)C6=O)C4)ncc3Cl)ccc2n(C)c1=O]

Into a 10-mL sealed tube, was placed 2-(2,6-dioxopiperidin-3-yl)-5-(morpholin-2-ylmethoxy)isoindole-1,3-dione (340 mg, 0.9 mmol, 1.0 equiv), DIEA (588.5 mg, 4.6 mmol, 5.0 equiv), 6-[(2,5-dichloropyrimidin-4-yl)amino]-1-methyl-3-(2-oxopropoxy)quinolin-2-one (358 mg, 0.9 mmol, 1.0 equiv) in DMSO (3 mL). The resulting solution was stirred for 3 h at 100° C. in an oil bath. The crude product was purified by Prep-HPLC. This resulted in 60 mg (9%) of 5-[[4-(5-chloro-4-[[1-methyl-2-oxo-3-(2-oxopropoxy)quinolin-6-yl]amino]pyrimidin-2-yl)morpholin-2-yl]methoxy]-2-(2,6-dioxopiperidin-3-yl)isoindole-1,3-dione as a white solid. LC/MS (ESI) m/z: 730 [M+1]$^+$; $^1$H-NMR (400 MHz, DMSO-d$_6$) δ 11.10 (s, 1H), 8.93 (s, 1H), 8.09 (s, 1H), 7.89 (d, J=2.5 Hz, 1H), 7.79 (d, J=8.2 Hz, 1H), 7.74-7.61 (m, 1H), 7.44 (d, J=8.7 Hz, 2H), 7.30 (d, J=8.3 Hz, 1H), 7.08 (s, 1H), 5.11 (dd, J=13.1, 5.4 Hz, 1H), 4.80 (s, 2H), 4.44 (d, J=12.7 Hz, 1H), 4.37-4.07 (m, 3H), 3.93 (d, J=11.4 Hz, 1H), 3.83 (s, 1H), 3.63 (s, 3H), 3.55 (t, J=11.4 Hz, 1H), 2.91 (dt, J=41.1, 11.4 Hz, 3H), 2.73-2.53 (m, 2H), 2.14 (s, 3H), 2.05 (d, J=10.9 Hz, 1H).

Synthesis of 2-((6-((5-chloro-2-(4-((1-(2-(2,6-dioxopiperidin-3-yl)-1,3-dioxoisoindolin-5-yl)piperidin-4-yl)methyl)piperazin-1-yl)pyrimidin-4-yl)amino)-1-methyl-2-oxo-1,2-dihydroquinolin-3-yl)oxy)-N-methylacetamide (Exemplary Compound 26)

Step 1: Preparation of tert-butyl 4-((1-(2-(2,6-dioxopiperidin-3-yl)-1,3-dioxoisoindolin-5-yl)piperidin-4-yl)methyl)piperazine-1-carboxylate

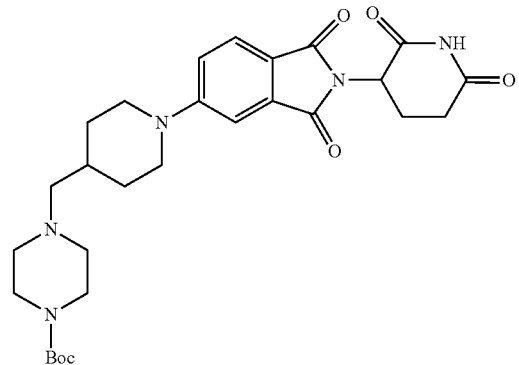 [SMILES: CC(C)(C)OC(=O)N1CCN(CC2CCN(c3ccc4c(c3)C(=O)N(C3CCC(=O)NC3=O)C4=O)CC2)CC1]

Into a 30 mL sealed tube, was placed tert-butyl 4-(piperidin-4-ylmethyl)piperazine-1-carboxylate (600 mg, 2.117 mmol, 1.0 equiv), 2-(2,6-dioxopiperidin-3-yl)-5-fluoroisoindole-1,3-dione (584.77 mg, 2.117 mmol, 1.0 equiv), DIEA (820.83 mg, 6.351 mmol, 3.0 equiv) in DMSO (20 ml). The resulting mixture was stirred for 4 hours at 100° C. in an oil bath. The crude product was purified by Prep-HPLC. This resulted in 520 mg of tert-butyl 4-([1-[2-(2,6-dioxopiperidin-3-yl)-1,3-dioxoisoindol-5-yl]piperidin-4-yl]methyl)piperazine-1-carboxylate as a yellow green solid. LC/MS (ESI) m/z: 540.25 [M+1]$^+$.

Step 2: Preparation of 2-(2,6-dioxopiperidin-3-yl)-5-(4-(piperazin-1-ylmethyl)piperidin-1-yl)isoindoline-1,3-dione

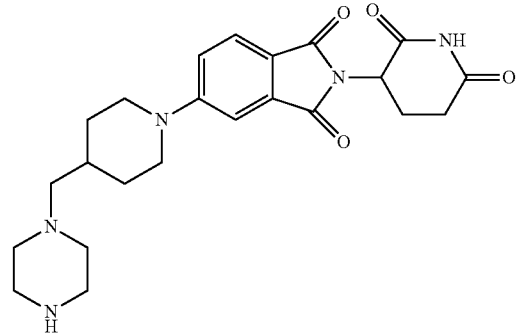 [SMILES: O=C1CCC(N2C(=O)c3ccc(N4CCC(CN5CCNCC5)CC4)cc3C2=O)C(=O)N1]

Into a 50 mL round-bottom flask, was placed tert-butyl 4-([1-[2-(2,6-dioxopiperidin-3-yl)-1,3-dioxoisoindol-5-yl]piperidin-4-yl]methyl)piperazine-1-carboxylate (520 mg, 0.964 mmol, 1.0 equiv) in DCM (15 ml), to which hydrogen chloride in 1,4-dioxane solution (4.0 M, 15 mL) was added.

637

The resulting mixture was stirred for 2 hours at room temperature. Then the mixture was concentrated under reduced pressure. This resulted in 400 mg of 2-(2,6-dioxopiperidin-3-yl)-5-[4-(piperazin-1-ylmethyl)piperidin-1-yl] isoindole-1,3-dione as a yellow powder. LC/MS (ESI) m/z: 440.20 [M+1]⁺.

Step 3: Preparation of 2-((6-((5-chloro-2-(4-((1-(2-(2,6-dioxopiperidin-3-yl)-1,3-dioxoisoindolin-5-yl)piperidin-4-yl)methyl)piperazin-1-yl)pyrimidin-4-yl)amino)-1-methyl-2-oxo-1,2-dihydroquinolin-3-yl)oxy)-N-methylacetamide

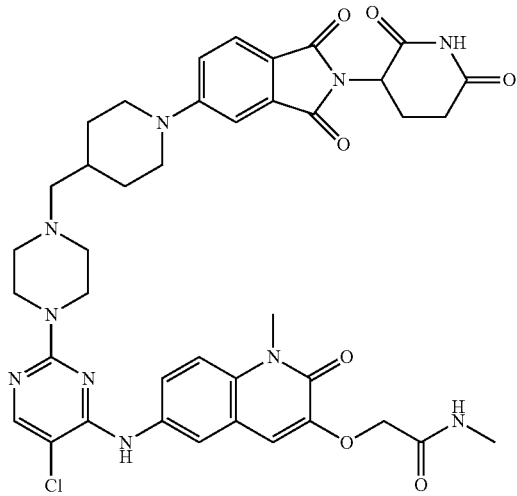 [SMILES: CNC(=O)COc1cc2cc(Nc3nc(N4CCN(CC5CCN(c6ccc7c(c6)C(=O)N(C6CCC(=O)NC6=O)C7=O)CC5)CC4)ncc3Cl)ccc2n(C)c1=O]

Into a 30 mL sealed tube, was placed 2-(2,6-dioxopiperidin-3-yl)-5-[4-(piperazin-1-ylmethyl)piperidin-1-yl]isoindole-1,3-dione (200 mg, 0.455 mmol, 1.0 equiv), 2-([6-[(2,5-dichloropyrimidin-4-yl)amino]-1-methyl-2-oxoquinolin-3-yl]oxy)-N-methylacetamide (185.8 mg, 0.455 mmol, 1.0 equiv), DIEA (176.43 mg, 1.365 mmol, 3.0 equiv) in DMSO (20 ml). The resulting mixture was stirred for 4 hours at 100° C. in an oil bath. The crude product was purified by Prep-HPLC. This resulted in 52.0 mg of 2-[[6-([5-chloro-2-[4-([1-[2-(2,6-dioxopiperidin-3-yl)-1,3-dioxoisoindol-5-yl]piperidin-4-yl]methyl) piperazin-1-yl]pyrimidin-4-yl] amino)-1-methyl-2-oxoquinolin-3-yl]oxy]-N-methylacetamide as a yellow solid. LC/MS (ESI) m/z: 811.30 [M+1]⁺; ¹H-NMR (400 MHz, DMSO-d₆) δ 11.05 (s, 1H), 8.83 (s, 1H), 8.05 (s, 1H), 8.00-7.95 (m, 2H), 7.80-7.70 (m, 1H), 7.70-7.60 (m, 1H), 7.55-7.45 (m, 1H), 7.40-7.30 (m, 1H), 7.30-7.20 (m, 1H), 7.15-7.05 (m, 1H), 5.10-5.00 (m, 1H), 4.65 (s, 2H), 4.15-4.00 (m, 2H), 3.75-3.65 (m, 3H), 3.65-3.60 (m, 4H), 3.05-2.85 (m, 3H), 2.70-2.60 (m, 4H), 2.60-2.55 (m, 1H), 2.45-2.34 (m, 4H), 2.25-2.15 (m, 2H), 2.10-2.00 (m, 1H), 2.00-1.80 (m, 3H), 1.30-1.10 (m, 2H).

638

Synthesis of 5-(3-(2-(1-(5-chloro-4-((1-methyl-2-oxo-3-(2-oxopropoxy)-1,2-dihydroquinolin-6-yl)amino)pyrimidin-2-yl)piperidin-4-yl)ethoxy)azetidin-1-yl)-2-(2,6-dioxopiperidin-3-yl)isoindoline-1,3-dione (Exemplary Compound 164)

Step 1: Preparation of tert-butyl 4-(2-(tosyloxy)ethyl)piperidine-1-carboxylate

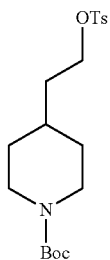

Into a 500-mL round-bottom flask, was placed tert-butyl 4-(2-hydroxyethyl)piperidine-1-carboxylate (10 g, 43.607 mmol, 1.00 equiv), DCM (300 mL). This was followed by the addition of TsCl (10 g, 52.453 mmol, 1.20 equiv) and TEA (13.00 g, 128.471 mmol, 2.95 equiv) with stirring at room temperature. Then DMAP (550 mg, 4.502 mmol, 0.10 equiv) was added. The resulting solution was stirred for 16 hours at room temperature. The reaction was then quenched by the addition of water. The resulting solution was extracted with dichloromethane (120 mL×3) and the combined organic layer was washed with brine (150 mL), dried over anhydrous sodium sulfate and concentrated under reduced pressure. The residue was applied onto a silica gel column with ethyl acetate/petroleum ether (6:4). This resulted in 16.4 g (98%) of tert-butyl 4-[2-[(4-methylbenzenesulfonyl)oxy]ethyl]piperidine-1-carboxylate as a solid. LC/MS (ESI) m/z: 328.05 [M−55]⁺.

Step 2: Preparation of tert-butyl 4-(2-((1-((benzyloxy)carbonyl)azetidin-3-yl)oxy)ethyl)piperidine-1-carboxylate

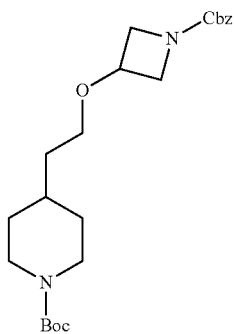 [SMILES: CC(C)(C)OC(=O)N1CCC(CCOC2CN(C(=O)OCc3ccccc3)C2)CC1]

To a solution of benzyl 3-hydroxyazetidine-1-carboxylate (2.75 g, 13.270 mmol, 1.02 equiv) in DMF (50 ml) was added sodium hydride (60% in oil, 750 mg, 18.752 mmol, 1.44 equiv) at 0° C. under the nitrogen atmosphere. The mixture was stirred for 30 minutes at 0° C. Then tert-butyl 4-[2-[(4-methylbenzenesulfonyl)oxy]ethyl]piperidine-1-carboxylate (5 g, 13.038 mmol, 1.00 equiv) in DMF (10 mL)

was added. The mixture was allowed to warm up to room temperature and stirred at 45° C. for 2 hours. The reaction mixture was quenched by water and the resulting mixture was extracted with ethyl acetate (80 mL×3). The combined organic layer was washed with brine (100 mL), dried over anhydrous sodium sulfate and concentrated under reduced pressure. The crude product was purified by Prep-HPLC. This resulted in 2.7 g (49%) of tert-butyl 4-[2-([1-[(benzyloxy)carbonyl]azetidin-3-yl]oxy)ethyl]piperidine-1-carboxylate as light yellow oil. LC/MS (ESI) m/z: 441.20 [M+23]$^+$.

Step 3: Preparation of tert-butyl 4-(2-(azetidin-3-yloxy)ethyl)piperidine-1-carboxylate

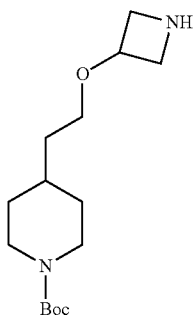 [SMILES: CC(C)(C)OC(=O)N1CCC(CCOC2CNC2)CC1]

To a solution of tert-butyl 4-[2-([1-[(benzyloxy)carbonyl]azetidin-3-yl]oxy)ethyl]piperidine-1-carboxylate (2.60 g, 6.212 mmol, 1.00 equiv) in MeOH (120 mL) was added Pd(OH)$_2$/C (10%, 500 mg) under nitrogen atmosphere in a 250 mL round bottom flask. The flask was then vacuumed and flushed with hydrogen. The reaction mixture was hydrogenated at room temperature in an oil bath for 2 hours under hydrogen atmosphere using a hydrogen balloon, then filtered through a Celite pad and the filtrate was concentrated under reduced pressure. This resulted in 1.56 g (88%) of tert-butyl 4-[2-(azetidin-3-yloxy)ethyl]piperidine-1-carboxylate as light yellow oil.

Step 4: Preparation of tert-butyl 4-(2-((1-(2-(2,6-dioxopiperidin-3-yl)-1,3-dioxoisoindolin-5-yl)azetidin-3-yl)oxy)ethyl)piperidine-1-carboxylate

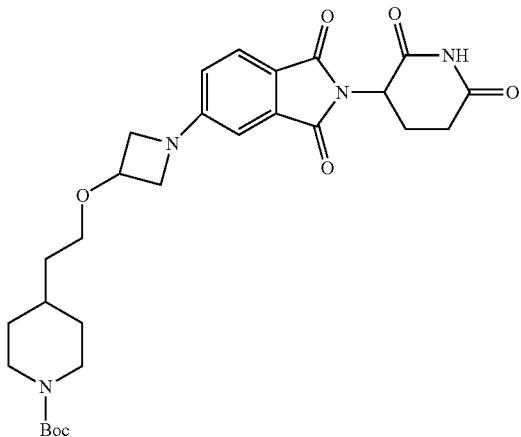 [SMILES: CC(C)(C)OC(=O)N1CCC(CCOC2CN(c3ccc4c(c3)C(=O)N(C3CCC(=O)NC3=O)C4=O)C2)CC1]

Into a 25-mL sealed tube purged and maintained with an inert atmosphere of nitrogen, was placed tert-butyl 4-[2-(azetidin-3-yloxy)ethyl]piperidine-1-carboxylate (200 mg, 0.703 mmol, 1.00 equiv), 2-(2,6-dioxopiperidin-3-yl)-5-fluoroisoindole-1,3-dione (384 mg, 1.390 mmol, 1.98 equiv) and DMSO (4 mL). This was followed by the addition of DIEA (0.50 mL) drop wise. The resulting solution was stirred for 2 hours at 120° C. in an oil bath. The reaction mixture was cooled and diluted with of water. The resulting solution was extracted with ethyl acetate (20 mL×3), The combined organic layer was washed with brine (30 mL), dried over anhydrous sodium sulfate and concentrated under reduced pressure. The residue was applied onto a silica gel column with dichloromethane/methanol (13:1). This resulted in 268 mg (70%) of tert-butyl 4-[2-([1-[2-(2,6-dioxopiperidin-3-yl)-1,3-dioxoisoindol-5-yl]azetidin-3-yl]oxy)ethyl]piperidine-1-carboxylate as a yellow solid. LC/MS (ESI) m/z: 485.15 [M−55]$^+$.

Step 5: Preparation of 2-(2,6-dioxopiperidin-3-yl)-5-(3-(2-(piperidin-4-yl)ethoxy)azetidin-1-yl)isoindoline-1,3-dione

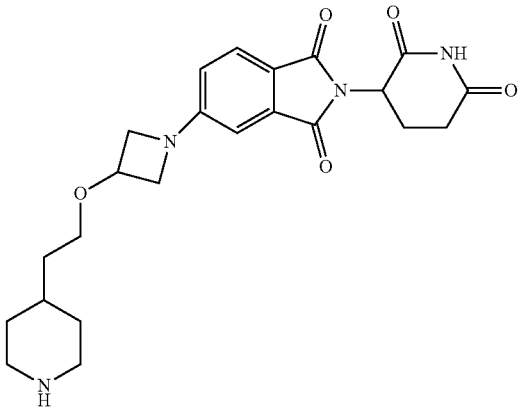 [SMILES: O=C1CCC(N2C(=O)c3ccc(N4CC(OCCC5CCNCC5)C4)cc3C2=O)C(=O)N1]

To a solution of tert-butyl 4-[2-([1-[2-(2,6-dioxopiperidin-3-yl)-1,3-dioxoisoindol-5-yl]azetidin-3-yl]oxy)ethyl]piperidine-1-carboxylate (152 mg, 0.281 mmol, 1.00 equiv) in DCM (6 mL), was added TFA (0.50 mL) in a 25 mL round bottom flask. The resulting solution was stirred for 30 min at room temperature. The resulting mixture was concentrated. This resulted in 134 mg (86%) of 2-(2,6-dioxopiperidin-3-yl)-5-[3-[2-(piperidin-4-yl)ethoxy]azetidin-1-yl] isoindole-1,3-dione; trifluoroacetic acid as yellow oil. LC/MS (ESI) m/z: 441.20 [M+1]$^+$.

Step 6: Preparation of 5-(3-(2-(1-(5-chloro-4-((1-methyl-2-oxo-3-(2-oxopropoxy)-1,2-dihydroquinolin-6-yl)amino)pyrimidin-2-yl)piperidin-4-yl)ethoxy)azetidin-1-yl)-2-(2,6-dioxopiperidin-3-yl)isoindoline-1,3-dione

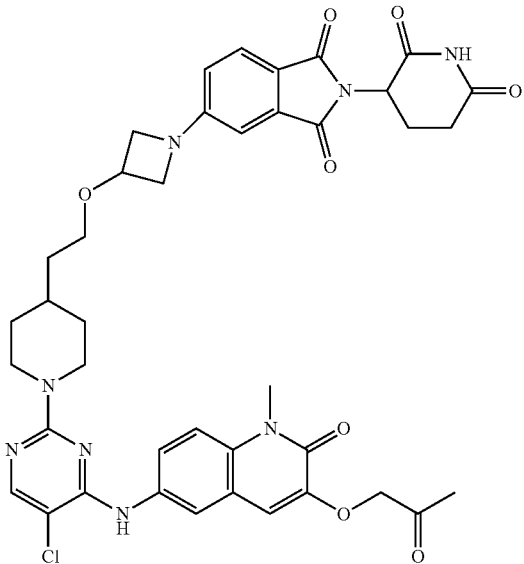 [SMILES: CC(=O)COc1cc2cc(Nc3nc(N4CCC(CCOC5CN(c6ccc7c(c6)C(=O)N(C6CCC(=O)NC6=O)C7=O)C5)CC4)ncc3Cl)ccc2n(C)c1=O]

To a solution of 2-(2,6-dioxopiperidin-3-yl)-5-[3-[2-(piperidin-4-yl)ethoxy]azetidin-1-yl]isoindole-1,3-dione hydrochloride (134 mg, 0.281 mmol, 1.00 equiv) in DMSO (4 mL), was added 6-[(2,5-dichloropyrimidin-4-yl)amino]-1-methyl-3-(2-oxopropoxy)quinolin-2-one (110 mg, 0.280 mmol, 1.00 equiv) in a 25 mL sealed tube purged and maintained with an inert atmosphere of nitrogen, then DIEA (0.70 mL) was added. The resulting solution was stirred for 2 hours at 120° C. in an oil bath. The resulting mixture was concentrated. The crude product was purified by Prep-HPLC. This resulted in 22.3 mg (10%) of 5-(3-[2-[1-(5-chloro-4-[[1-methyl-2-oxo-3-(2-oxopropoxy)quinolin-6-yl]amino]pyrimidin-2-yl)piperidin-4-yl]ethoxy]azetidin-1-yl)-2-(2,6-dioxopiperidin-3-yl)isoindole-1,3-dione as a yellow solid. LC/MS (ESI) m/z: 797.30 [M+1]⁺; ¹H-NMR (300 MHz, DMSO-d₆) δ 11.06 (br, 1H), 8.81 (br, 1H), 8.02 (s, 1H), 7.89-7.88 (m, 1H), 7.72-7.63 (m, 2H), 7.46-7.43 (d, J=9 Hz, 1H), 7.02 (s, 1H), 6.80 (s, 1H), 6.67-6.64 (d, J=8.4 Hz, 1H), 5.08-5.02 (m, 1H), 4.90 (s, 2H), 4.47-4.44 (m, 3H), 4.27-4.22 (m, 2H), 3.86-3.82 (m, 2H), 3.66 (s, 3H), 3.49-3.45 (m, 2H), 2.92-2.77 (m, 3H), 2.60-2.54 (m, 2H), 2.19 (s, 3H), 2.07-1.99 (m, 1H), 1.71-1.67 (m, 3H), 1.50-1.48 (m, 2H), 1.09-1.05 (m, 2H).

Synthesis of 5-(4-((1-(5-chloro-4-((1-methyl-2-oxo-3-(2-oxopropoxy)-1,2-dihydroquinolin-6-yl)amino)pyrimidin-2-yl)-4-hydroxypiperidin-4-yl)methyl)piperazin-1-yl)-2-(2,6-dioxopiperidin-3-yl)isoindoline-1,3-dione (Exemplary Compound 187)

Step 1: Preparation of tert-butyl 4-hydroxy-4-(methoxy(methyl)carbamoyl)piperidine-1-carboxylate

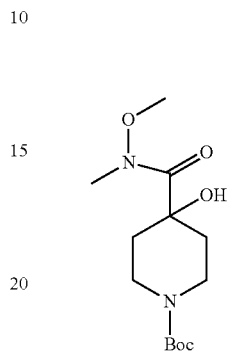

To a stirred solution of 1-(tert-butoxycarbonyl)-4-hydroxypiperidine-4-carboxylic acid (1.90 g, 7.746 mmol, 1.00 equiv) and N,O-dimethylhydroxylamine hydrochloride (0.91 g, 9.330 mmol, 1.20 equiv) in DMF (5.0 mL) were added DIEA (3.10 mL, 17.797 mmol, 3.00 equiv) and BOP (4.11 g, 9.293 mmol, 1.20 equiv) in portions at room temperature. The resulting mixture was stirred for 30 minutes at room temperature and then was quenched with water (30 mL). The resulting mixture was extracted with EtOAc (30 mL×3). The combined organic layer was washed with brine (50 mL×3) dried over anhydrous sodium sulfate and concentrated under reduced pressure and concentrated under vacuum. The residue was purified by silica gel column chromatography, eluted with PE/EtOAc (5:1) tert-butyl 4-hydroxy-4-[methoxy(methyl)carbamoyl]piperidine-1-carboxylate (1.1 g, 49.3%) as a solid. LC/MS (ESI) m/z: 289.17 [M+1]⁺.

Step 2: Preparation of tert-butyl 4-formyl-4-hydroxypiperidine-1-carboxylate

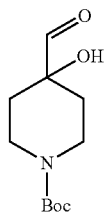

Into a 250-mL 3-necked round-bottom flask purged and maintained with an inert atmosphere of nitrogen, was placed a solution of tert-butyl 4-hydroxy-4-[methoxy(methyl)carbamoyl]piperidine-1-carboxylate (810.00 mg, 2.809 mmol, 1.00 equiv) in THF (50 mL). After cooled to −78° C., DIBA1-H (1M in THF) (6.00 mL, 2.0 equiv) was added dropwise over 5 minute period and the resulting mixture was stirred for 2 hours at −78° C. The reaction was then quenched by the addition of water (0.5 mL), 15% NaOH (0.5 mL) and water (0.6 mL) at −78° C. The solution was stirred at room temperature for 15 minutes. The solids were filtered out and the resulting mixture was extracted with ethyl acetate (30 mL×3). The combined organic layer was washed with brine (30 mL), dried over anhydrous sodium sulfate and concentrated under reduced pressure. This resulted in tert-butyl 4-formyl-4-hydroxypiperidine-1-carboxylate (589 mg, 91.45%) as light yellow oil. LC/MS (ESI) m/z: 230.13 [M+1]⁺.

Step 3: Preparation of benzyl 4-((1-(tert-butoxycarbonyl)-4-hydroxypiperidin-4-yl)methyl)piperazine-1-carboxylate

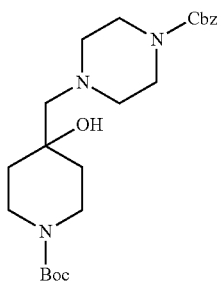 [SMILES: CC(C)(C)OC(=O)N1CCC(O)(CN2CCN(C(=O)OCc3ccccc3)CC2)CC1]

A solution of tert-butyl 4-formyl-4-hydroxypiperidine-1-carboxylate (191.00 mg, 0.833 mmol, 1.00 equiv) and benzyl piperazine-1-carboxylate (183.50 mg, 0.833 mmol, 1.00 equiv) in DCE (10.0 ml). The resulting mixture was stirred for 30 minutes at room temperature. To the above mixture was added NaBH(AcO)₃ (529.68 mg, 2.499 mmol, 3.00 equiv) at room temperature. The resulting mixture was stirred for additional 1 h at room temperature. The reaction was quenched by the addition of water (20 mL) at room temperature and the resulting mixture was extracted with EtOAc (20 mL×3). The combined organic layers were washed with brine (30 mL), dried over anhydrous sodium sulfate and concentrated under reduced pressure. The residue was purified by silica gel column chromatography, eluted with dichloromethane/methanol (10:1) to afford benzyl 4-[[1-(tert-butoxycarbonyl)-4-hydroxypiperidin-4-yl]methyl]piperazine-1-carboxylate (217 mg, 60.1%) as a solid. LC/MS (ESI) m/z: 444.26 [M+1]⁺.

Step 4: Preparation of tert-butyl 4-hydroxy-4-(piperazin-1-ylmethyl)piperidine-1-carboxylate

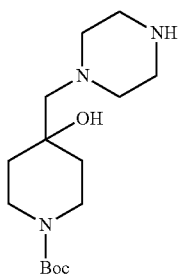 [SMILES: CC(C)(C)OC(=O)N1CCC(O)(CN2CCNCC2)CC1]

To a solution of benzyl 4-[[1-(tert-butoxycarbonyl)-4-hydroxypiperidin-4-yl]methyl]piperazine-1-carboxylate (217.00 mg, 1.00 equiv) in isopropyl alcohol (10.0 mL) was added Pd/C (30.00 mg, 2.00 equiv) under nitrogen atmosphere. The resulting mixture was stirred for 2 hours at room temperature under nitrogen atmosphere. The mixture was hydrogenated at room temperature for 2 h under hydrogen atmosphere using a hydrogen balloon, filtered through a Celite pad and concentrated under reduced pressure. This resulted in tert-butyl 4-hydroxy-4-(piperazin-1-ylmethyl)piperidine-1-carboxylate (37.1 mg, 50.1%) as a solid. LC/MS (ESI) m/z: 230.22 [M+1]⁺.

Step 5: Preparation of tert-butyl 4-((4-(2-(2,6-dioxopiperidin-3-yl)-1,3-dioxoisoindolin-5-yl)piperazin-1-yl)methyl)-4-hydroxypiperidine-1-carboxylate

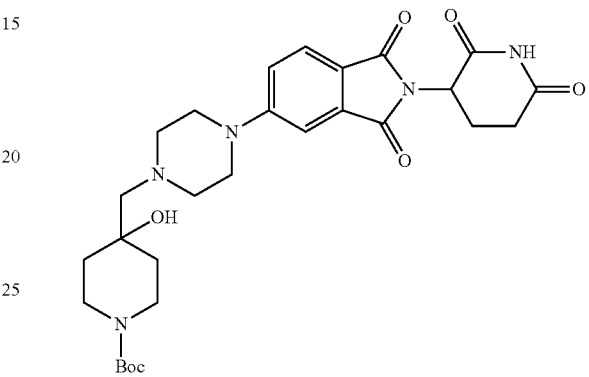

To a stirred solution of tert-butyl 4-hydroxy-4-(piperazin-1-ylmethyl)piperidine-1-carboxylate (37.10 mg, 0.124 mmol, 1.00 equiv) and 2-(2,6-dioxopiperidin-3-yl)-5-fluoroisoindole-1,3-dione (34.23 mg, 0.124 mmol, 1.00 equiv) in DMSO (1.50 mL, 0.019 mmol, 0.15 equiv) was added DIEA (48.04 mg, 0.372 mmol, 3.00 equiv) at room temperature. The resulting mixture was stirred for 2 hours at 100° C. under nitrogen atmosphere. The reaction was then quenched by the addition of water (20 mL) at room temperature. The resulting mixture was extracted with EtOAc (200 mL×3). The combined organic layers were washed with brine (30 mL×3), dried over anhydrous sodium sulfate and concentrated under reduced pressure. The mixture was concentrated under vacuum to afford tert-butyl 4-([4-[2-(2,6-dioxopiperidin-3-yl)-1,3-dioxoisoindol-5-yl]piperazin-1-yl] methyl)-4-hydroxypiperidine-1-carboxylate (67.1 mg, 97.5%) as a white solid. LC/MS (ESI) m/z: 556.27 [M+1]⁺.

Step 6: Preparation of 2-(2,6-dioxopiperidin-3-yl)-5-(4-((4-hydroxypiperidin-4-yl)methyl)piperazin-1-yl)isoindoline-1,3-dione

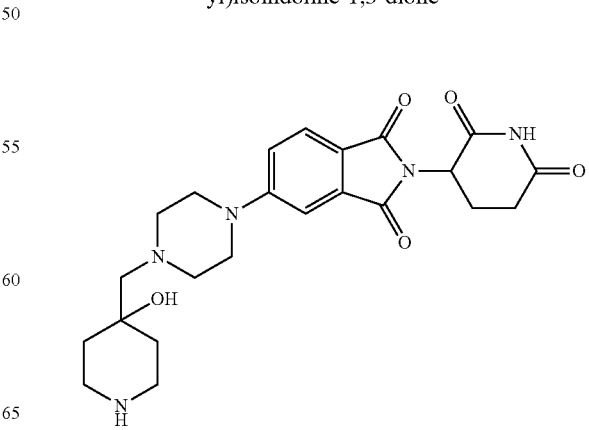

To a stirred solution of tert-butyl 4-([4-[2-(2,6-dioxopiperidin-3-yl)-1,3-dioxoisoindol-5-yl]piperazin-1-yl]methyl)-4-hydroxypiperidine-1-carboxylate (58.00 mg, 1.00 equiv) and in HCl (gas) in 1,4-dioxane (5.00 mL) dropwise at room temperature under nitrogen atmosphere. The resulting mixture was stirred for 30 minutes at room temperature under nitrogen atmosphere. The reaction was filter to give 2-(2,6-dioxopiperidin-3-yl)-5-[4-[(4-hydroxypiperidin-4-yl)methyl]piperazin-1-yl]isoindole-1,3-dione (35.0 mg, 74.5%) as a solid. LC/MS (ESI) m/z: 456.27 [M+1]$^+$.

Step 7: Preparation of 5-(4-((1-(5-chloro-4-((1-methyl-2-oxo-3-(2-oxopropoxy)-1,2-dihydroquinolin-6-yl)amino)pyrimidin-2-yl)-4-hydroxypiperidin-4-yl)methyl)piperazin-1-yl)-2-(2,6-dioxopiperidin-3-yl)isoindoline-1,3-dione

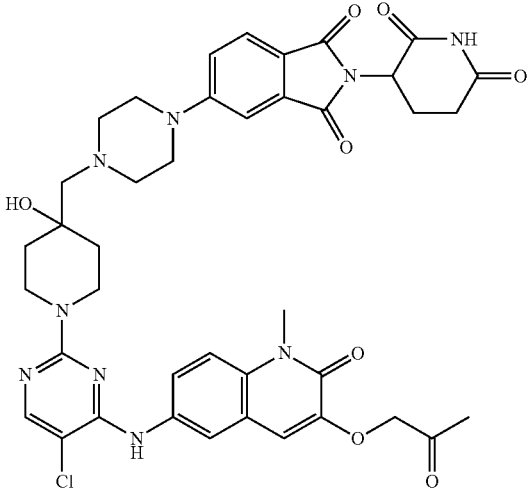 [SMILES: CC(=O)COc1cc2cc(Nc3nc(N4CCC(O)(CN5CCN(c6ccc7c(c6)C(=O)N(C6CCC(=O)NC6=O)C7=O)CC5)CC4)ncc3Cl)ccc2n(C)c1=O]

To a stirred solution of 2-(2,6-dioxopiperidin-3-yl)-5-[4-[(4-hydroxypiperidin-4-yl)methyl]piperazin-1-yl]isoindole-1,3-dione (196.30 mg, 0.431 mmol, 1.00 equiv) and 6-[(2,5-dichloropyrimidin-4-yl)amino]-1-methyl-3-(2-oxopropoxy)quinolin-2-one (169.45 mg, 0.431 mmol, 1 equiv) in DMSO (3.00 mL, 42.236 mmol, 98.01 equiv) was added DIEA (167.09 mg, 1.293 mmol, 3 equiv) dropwise at room temperature under nitrogen atmosphere. The resulting mixture was stirred for 2 hours at 100° C. nitrogen atmosphere. The residue was purified by reverse flash chromatography. This resulted in (31.0 mg, 8.9%) 5-(4-[[1-(5-chloro-4-[[1-methyl-2-oxo-3-(2-oxopropoxy)quinolin-6-yl]amino]pyrimidin-2-yl)-4-hydroxypiperidin-4-yl]methyl]piperazin-1-yl)-2-(2,6-dioxopiperidin-3-yl)isoindole-1,3-dione as a yellow solid. LC/MS (ESI) m/z: 812.35 [M+1]$^+$; $^1$H-NMR (400 MHz, DMSO-d$_6$) δ 11.06 (s, 1H), 8.78 (s, 1H), 8.03 (s, 1H), 7.88 (d, J=2.5 Hz, 1H), 7.73 (d, J=9.1 Hz, 2H), 7.66 (d, J=8.5 Hz, 1H), 7.46 (d, J=9.1 Hz, 1H), 7.31 (s, 1H), 7.04 (s, 1H), 5.06 (m, 1H), 4.89 (s, 2H), 4.26 (d, J=5.8 Hz, 1H), 4.08 (s, 2H), 3.67 (s, 3H), 3.41 (s, 4H), 2.86 (d, J=12.4 Hz, 1H), 2.66 (s, 5H), 2.60 (s, 3H), 2.32 (d, J=8.4 Hz, 3H), 2.03 (s, 1H), 1.52 (s, 4H), 1.39 (s, 2H).

Synthesis of 2-((6-((5-chloro-2-((3S)-3-4(2-(2,6-dioxopiperidin-3-yl)-1,3-dioxoisoindolin-4-yl)oxy)methyl)piperidin-1-yl)pyrimidin-4-yl)amino)-1-methyl-2-oxo-1,2-dihydroquinolin-3-yl)oxy)-N-methylacetamide (Exemplary Compound 191)

Step 1: Preparation of (S)-2-((6-((5-chloro-2-(3-(hydroxymethyl)piperidin-1-yl)pyrimidin-4-yl)amino)-1-methyl-2-oxo-1,2-dihydroquinolin-3-yl)oxy)-N-methylacetamide

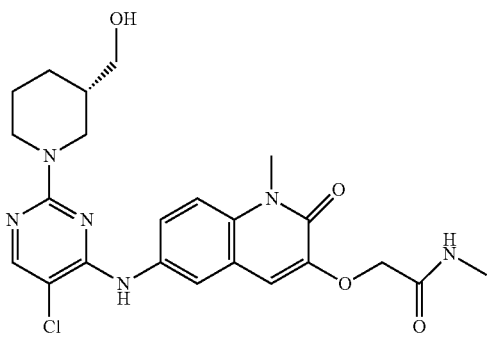 [SMILES: CNC(=O)COc1cc2cc(Nc3nc(N4CCC[C@H](CO)C4)ncc3Cl)ccc2n(C)c1=O]

A mixture of 2-((6-((2,5-dichloropyrimidin-4-yl)amino)-1-methyl-2-oxo-1,2-dihydroquinolin-3-yl)oxy)-N-methylacetamide (100 mg, 0.24 mmol). piperidin-4-ylmethanol (34 mg, 0.294 mmol) and triethyl amine (99.2 mg, 0.98 mmol) in DMSO (5 mL) was stirred at 100° C. for 1 hour. After cooling to room temperature, the mixture was quenched with H$_2$O. The mixture was filtered and the precipitate was collected. The solid was dried under vacuum to afford the desired product (100 mg) as a yellow solid. LC/MS (ESI) m/z: 487.2 [M+1]$^+$.

Step 2: Preparation of 2-((6-((5-chloro-2-((3S)-3-(((2-(2,6-dioxopiperidin-3-yl)-1,3-dioxoisoindolin-4-yl)oxy)methyl)piperidin-1-yl)pyrimidin-4-yl)amino)-1-methyl-2-oxo-1,2-dihydroquinolin-3-yl)oxy)-N-methylacetamide

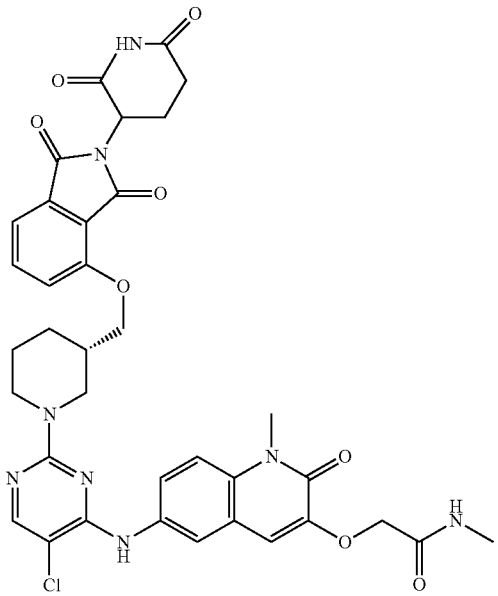 [SMILES: CNC(=O)COc1cc2cc(Nc3nc(N4CCC[C@H](COc5cccc6c5C(=O)N(C5CCC(=O)NC5=O)C6=O)C4)ncc3Cl)ccc2n(C)c1=O]

A suspension mixture of (S)-2-((6-((5-chloro-2-(3-(hydroxymethyl)piperidin-1-yl)pyrimidin-4-yl)amino)-1-methyl-2-oxo-1,2-dihydroquinolin-3-yl)oxy)-N-methylacetamide (100 mg, 0.20 mmol), 2-(2,6-dioxopiperidin-3-yl)-4-hydroxyisoindoline-1,3-dione (55 mg, 0.20 mmol) and PPh₃ (65 mg, 0.48 mmol) in THF (5 mL) was heated to 80° C., then DIAD (98 mg, 0.48 mmol) was added dropwise. The mixture was stirred at 80° C. for 10 minutes. After cooling to room temperature, the reaction was quenched with H₂O, and the mixture was extracted with ethyl acetate (20 mL×2). The organic phase was concentrated under vacuum. The residue was purified by prep-HPLC to afford the desired product (30 mg) as a white solid. LC/MS (ESI) m/z: 743.2 [M+1]⁺; ¹H-NMR (400 MHz, DMSO-d₆) δ 11.08 (s, 1H), 9.09 (s, 1H), 8.08 (s, 1H), 7.89 (m, 2H), 7.79-7.72 (m, 2H), 7.45-7.42 (m, 3H), 7.11 (s, 1H), 5.08-5.03 (m, 1H), 4.56-4.51 (m, 2H), 4.43-4.35 (m, 1H), 4.26-4.18 (m, 2H), 4.15-4.14 (m, 3H), 3.61 (s, 3H), 3.01-2.89 (m, 2H), 2.86-2.82 (m, 1H), 2.65-2.53 (m, 3H), 2.01-1.93 (m, 3H), 1.75 (m, 1H), 1.52-1.50 (m, 2H).

Synthesis of (2S,4R)-1-((S)-2-(tert-butyl)-14-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-4-oxo-6,9,12-trioxa-3-azatetradecanoyl)-4-hydroxy-N-(4-(4-methylthiazol-5-yl)benzyl)pyrrolidine-2-carboxamide (Exemplary Compound 51)

Step 1: Preparation of 2-(2-(2-(benzyloxy)ethoxy)ethoxy)ethyl 4-methylbenzenesulfonate

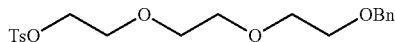 [SMILES: Cc1ccc(S(=O)(=O)OCCOCCOCCOCc2ccccc2)cc1]

Into a 250-mL round-bottom flask, was placed 2-[2-[2-(benzyloxy)ethoxy]ethoxy]ethan-1-ol (7.0 g, 29.130 mmol, 1 equiv) in DCM (100 mL), to which was added TsCl (6.7 g, 35.143 mmol, 1.21 equiv), TEA (4 mL, 28.778 mmol, 0.99 equiv) and DMAP (360 mg, 2.947 mmol, 0.10 equiv) at room temperature. The resulting solution was stirred for 2 hours at room temperature. The mixture was concentrated under vacuum and the residue was applied onto a silica gel column eluting with ethyl acetate/petroleum ether (1:1). This resulted in 11.4 g (99.21%) of 2-[2-[2-(benzyloxy)ethoxy]ethoxy]ethyl 4-methylbenzene-1-sulfonate as colorless oil. LC/MS (ESI) m/z: 394.95 [M+1]⁺.

Step 2: Preparation of tert-butyl 4-(2-(2-(2-(benzyloxy)ethoxy)ethoxy)ethoxy)piperidine-1-carboxylate

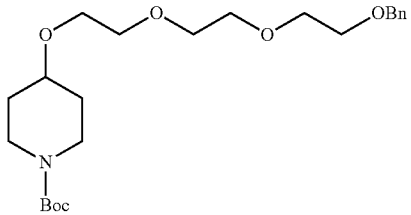 [SMILES: CC(C)(C)OC(=O)N1CCC(OCCOCCOCCOCc2ccccc2)CC1]

Into a 250-mL round-bottom flask purged and maintained with an inert atmosphere of nitrogen, was placed 2-[2-[2-(benzyloxy)ethoxy]ethoxy]ethyl 4-methylbenzene-1-sulfonate (5.0 g, 1.1 equiv) in DMF (100 mL), to which was added NaH (60%, 1.0 g, 2.0 equiv) in portions at 0° C. The resulting mixture was stirred for 10 min and then was added by tert-butyl 4-hydroxypiperidine-1-carboxylate (2.32 g, 1 equiv) slowly at 0° C. The reaction mixture was stirred for 16 h at 50° C. in an oil bath. The reaction was then quenched by the addition of 100 mL water/ice. The resulting mixture was extracted with ethyl acetate (150 mL×3) and the organic layers were combined, washed with brine, dried over anhydrous sodium sulfate and concentrated. The residue was applied onto a silica gel column eluting with ethyl acetate/petroleum ether (1:2). This resulted in 3.09 g (63.29%) of tert-butyl 4-(2-[2-[2-(benzyloxy)ethoxy]ethoxy]ethoxy)piperidine-1-carboxylate as colorless oil.

Step 3: Preparation of tert-butyl 4-(2-(2-(2-hydroxyethoxy)ethoxy)ethoxy)piperidine-1-carboxylate

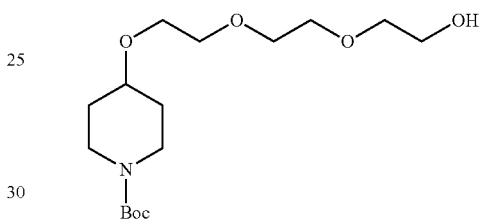

In a 100-ml round bottom flask, to a solution of tert-butyl 4-(2-[2-[2-(benzyloxy)ethoxy]ethoxy]ethoxy)piperidine-1-carboxylate (3.09 g, 7.295 mmol, 1 equiv) in MeOH (30 mL) was added Pd/C (10%, 2.0 g) under nitrogen atmosphere. The flask was then vacuumed and flushed with hydrogen. The reaction mixture was hydrogenated at room temperature for 2 hours under hydrogen atmosphere using a hydrogen balloon, then filtered through a Celite pad and concentrated under reduced pressure. This resulted in 2.5 g (82.78%) of tert-butyl 4-[2-[2-(2-hydroxyethoxy)ethoxy]ethoxy]piperidine-1-carboxylate as colorless oil. LC/MS (ESI) m/z: 334.05 [M+1]⁺.

Step 4: Preparation of tert-butyl 4-((11-oxo-3,6,9,12-tetraoxatetradecyl)oxy)piperidine-1-carboxylate

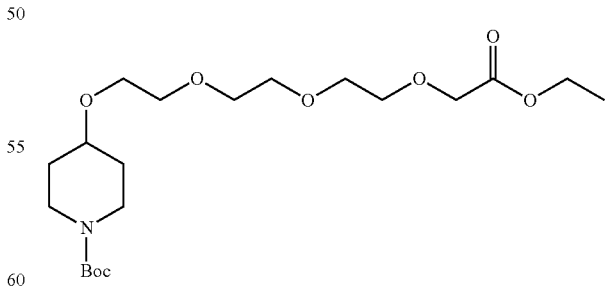

Into a 100-mL round-bottom flask, was placed a solution of tert-butyl 4-[2-[2-(2-hydroxyethoxy)ethoxy]ethoxy]piperidine-1-carboxylate (720 mg, 2.159 mmol, 1 equiv) in DCM (35 mL). This was followed by the addition of N₂CH₂COOEt (510 mg, 4.392 mmol, 2.03 equiv) dropwise with stirring at 0° C. in 10 minutes. To this was added BF₃.

Et₂O (0.5 mL) dropwise with stirring at 0° C. in 5 minutes. The resulting solution was stirred for 2 h at room temperature. The residue was applied onto a silica gel column eluting with ethyl acetate/petroleum ether (1:5). This resulted in 220 mg (24%) of tert-butyl 4-(2-[2-[2-(2-ethoxy-2-oxoethoxy)ethoxy]ethoxy]ethoxy)piperidine-1-carboxylate as colorless oil. LC/MS (ESI) m/z: 442.15 [M+23]⁺.

Step 5: Preparation of ethyl 2-(2-(2-(2-(piperidin-4-yloxy)ethoxy)ethoxy)ethoxy)acetate

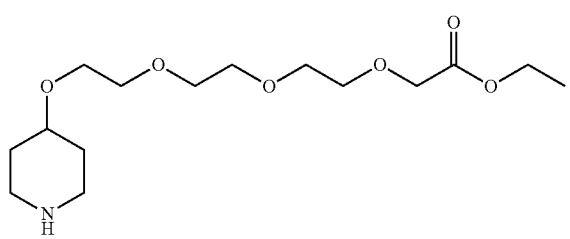 [SMILES: CCOC(=O)COCCOCCOCCOC1CCNCC1]

Into a 100-mL round-bottom flask, was placed tert-butyl 4-(2-[2-[2-(2-ethoxy-2-oxoethoxy)ethoxy]ethoxy]ethoxy)piperidine-1-carboxylate (220 mg, 0.524 mmol, 1 equiv) and HCl in 1,4-dioxane (20 mL, 4M). The resulting solution was stirred for 1 hour at room temperature. The resulting mixture was concentrated under reduced pressure. This resulted in 255 mg of ethyl 2-(2-[2-[2-(piperidin-4-yloxy)ethoxy]ethoxy]ethoxy)acetate hydrochloride as light yellow oil. LC/MS (ESI) m/z: 320.00 [M+1]⁺.

Step 6: Preparation of ethyl 2-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)ethoxy)acetate

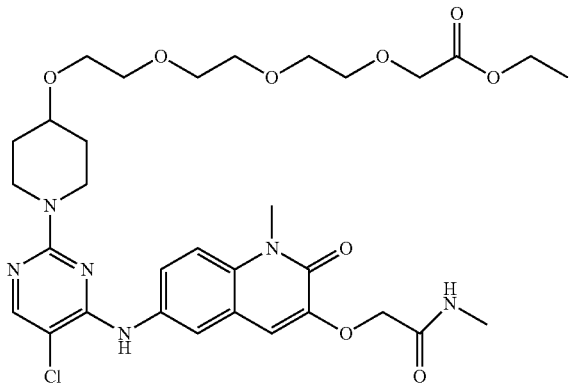 [SMILES: CCOC(=O)COCCOCCOCCOC1CCN(c2ncc(Cl)c(Nc3ccc4c(c3)cc(OCC(=O)NC)c(=O)n4C)n2)CC1]

Into a 25-mL sealed tube purged and maintained with an inert atmosphere of nitrogen, was placed ethyl 2-(2-[2-[2-(piperidin-4-yloxy)ethoxy]ethoxy]ethoxy)acetate hydrochloride (94 mg, 0.32 mmol, 1.2 equiv), 2-([6-[(2,5-dichloropyrimidin-4-yl)amino]-1-methyl-2-oxo-1,2-dihydroquinolin-3-yl]oxy)-N-methylacetamide (88 mg, 0.3 mmol, 1 equiv), DIEA (1.5 mL) in DMSO (10 mL). The resulting solution was stirred for 12 h at 100° C. in an oil bath. The resulting solution was extracted with 2×100 mL of ethyl acetate. The resulting mixture was washed with 2×100 ml of brine and concentrated under reduced pressure. The residue was applied onto a silica gel column eluting with dichloromethane/methanol (10:1). This resulted in 49 mg (33%) of ethyl 2-(2-[2-[2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethoxy]ethoxy]ethoxy)acetate as a yellow solid. LC/MS (ESI) m/z: 691.15 [M+1]⁺.

Step 7: Preparation of 2-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)ethoxy)acetic acid

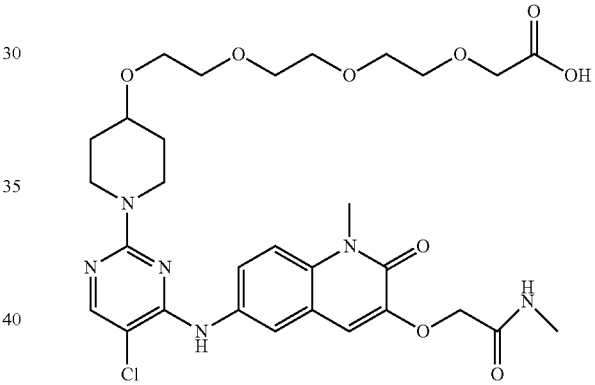

Into a 50-mL round-bottom flask, was placed ethyl 2-(2-[2-[2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethoxy]ethoxy]ethoxy)acetate (39 mg, 0.03 mmol, 1 equiv) in MeOH (5 mL) and sodium hydroxide (10 mg, 0.15 mmol, 5 equiv) in H₂O (5 mL). The resulting solution was stirred for 1 hour at room temperature. The pH value of the solution was adjusted to 6-7 with HCl (aq) (2 mol/L). The solids were filtered out and the filtrate was concentrated under reduced pressure. This resulted in 50 mg of 2-(2-[2-[2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethoxy]ethoxy]ethoxy)acetic acid as a yellow solid. LC/MS (ESI) m/z: 663.30 [M+1]⁺.

Step 8: Preparation of (2S,4R)-1-((S)-2-(tert-butyl)-14-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-4-oxo-6,9,12-trioxa-3-azatetradecanoyl)-4-hydroxy-N-(4-(4-methylthiazol-5-yl)benzyl)pyrrolidine-2-carboxamide

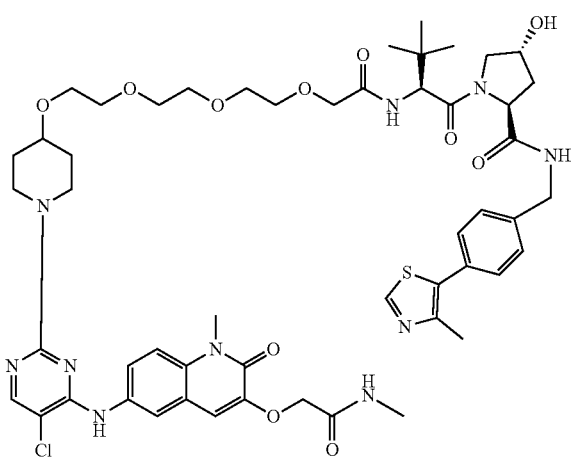 [SMILES: CNC(=O)COc1cc2cc(Nc3nc(N4CCC(OCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O]

Into a 50-mL round-bottom flask, was placed 2-(2-[2-[2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethoxy]ethoxy]ethoxy)acetic acid (80 mg, 0.121 mmol, 1 equiv), DIEA (1.0 mL), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (52 mg, 0.121 mmol, 1.00 equiv), BOP (65 mg, 0.147 mmol, 1.22 equiv) in DMF (15 mL). The resulting solution was stirred for 1 hour at room temperature. The resulting solution was extracted with 2×100 mL of ethyl acetate. The resulting mixture was washed with 2×20 ml of brine and concentrated under reduced pressure. The residue was applied onto a silica gel column eluting with dichloromethane/methanol (10:1). This resulted in 22.4 mg (17%) of (2S,4R)-1-[(2S)-2-[2-(2-[2-[2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethoxy]ethoxy]ethoxy)acetamido]-3,3-dimethylbutanoyl]-4-hydroxy-N-[[4-(4-methyl-1,3-thiazol-5-yl)phenyl]methyl]pyrrolidine-2-carboxamide as a white solid. LC/MS (ESI) m/z: 1075.35/1077.35 [M+1]⁺; ¹H-NMR (300 MHz, DMSO-d₆) δ 8.96 (s, 1H), 8.83 (s, 1H), 8.58 (s, 1H), 8.03 (s, 1H), 7.93 (m, 1H), 7.74 (m, 1H), 7.51-7.40 (m, 1H), 7.38 (s, 6H), 7.10 (s, 1H), 5.14 (s, 1H), 4.57 (s, 3H), 4.43 (s, 1H), 4.35 (s, 2H), 4.26 (s, 1H), 4.02 (s, 1H), 3.95 (s, 2H), 3.67 (s, 4H), 3.55 (m, 14H), 3.23 (s, 2H), 2.65 (m, 3H), 2.43 (s, 4H), 1.81 (s, 1H), 1.37 (s, 3H), 1.23 (s, 2H), 0.92 (s, 9H).

Synthesis of (2S,4R)—N-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)-4-(4-methylthiazol-5-yl)benzyl)-4-hydroxy-1-(3-methyl-2-(3-methylisoxazol-5-yl)butanoyl)pyrrolidine-2-carboxamide (Exemplary Compound 56)

Step 1: Preparation of tert-butyl 4-(2-((tetrahydro-2H-pyran-2-yl)oxy)ethoxy)piperidine-1-carboxylate

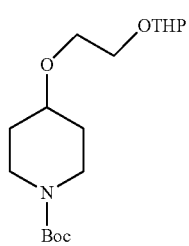

Into a 250-mL round-bottom flask, was placed tert-butyl 4-hydroxypiperidine-1-carboxylate (10 g, 49.685 mmol, 1 equiv) in dimethylformamide (10 mL), this was followed by the addition of sodium hydride (60%, 8.0 g, 198.742 mmol, 4 equiv) at 10° C. under nitrogen atmosphere. After stirred for 30 minutes at 25° C., 2-(2-bromoethoxy)oxane (15.58 g, 74.516 mmol, 1.5 equiv) was added dropwise into at 10° C. under nitrogen atmosphere. The resulting solution was stirred for 16 hours at 90° C. in an oil bath. The resulting solution was extracted with ethyl acetate (3×40 mL). The resulting mixture was washed with brine (20 mL), dried over anhydrous sodium sulfate and concentrated under reduced pressure. The residue was applied onto a silica gel column eluting with ethyl acetate/petroleum ether (1:1). This resulted in 2.11 g (13%) of tert-butyl 4-[2-(oxan-2-yloxy)ethoxy]piperidine-1-carboxylate as a yellow liquid. LC/MS (ESI) m/z: 330.15 [M+1]⁺.

Step 2: Preparation of 2-(piperidin-4-yloxy)ethan-1-ol

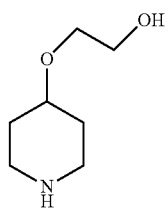

Into a 100-mL round-bottom flask, was placed tert-butyl 4-[2-(oxan-2-yloxy)ethoxy]piperidine-1-carboxylate (2.11 g, 6.405 mmol, 1 equiv) in dioxane (20 mL) and hydrogen chloride (37% aqueous solution, 20 mL). The resulting solution was stirred for 16 hours at room temperature. The reaction was concentrated under reduced pressure. This resulted in 1.25 g of 2-(piperidin-4-yloxy)ethan-1-ol hydrochloride as a solid. LC/MS (ESI) m/z: 146.15 [M+1]+.

Step 3: Preparation of 2-(((6-((5-chloro-2-(4-(2-hydroxyethoxy)piperidin-1-yl)pyrimidin-4-yl)amino)-1-methyl-2-oxo-1,2-dihydroquinolin-3-yl)oxy)-N-methylacetamide

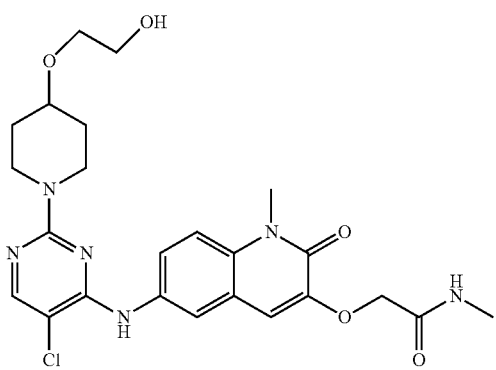

Into a 30-mL sealed tube, was placed 2-([6-[(2,5-dichloropyrimidin-4-yl)amino]-1-methyl-2-oxo-1,2-dihydroquinolin-3-yl]oxy)-N-methylacetamide (468 mg, 1.14 mmol, 1 equiv), 2-(piperidin-4-yloxy)ethan-1-ol (166 mg, 1.148 mmol, 1 equiv), diisopropylethylamine (2 mL) in dimethyl sulfoxide (5 mL). The resulting solution was stirred for 16 hours at 100° C. in an oil bath. The resulting solution was extracted with ethyl acetate (3×40 mL). The resulting mixture was washed with brine (20 mL), dried over anhydrous sodium sulfate and concentrated under reduced pressure. The residue was applied onto a silica gel column eluting with dichloromethane/methanol (10/1). This resulted in 351 mg (59%) of 2-[[6-([5-chloro-2-[4-(2-hydroxyethoxy)piperidin-1-yl]pyrimidin-4-yl]amino)-1-methyl-2-oxo-1,2-dihydroquinolin-3-yl]oxy]-N-methylacetamide as a light yellow solid. LC/MS (ESI) m/z: 517.25 [M+1]+.

Step 4: Preparation of 2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethyl 4-methylbenzenesulfonate

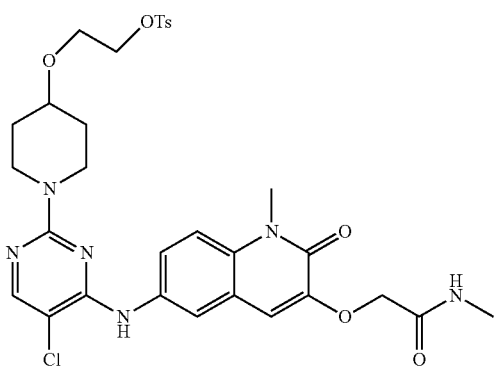 [SMILES: CNC(=O)COc1cc2cc(Nc3nc(N4CCC(OCCO)CC4)ncc3Cl)ccc2n(C)c1=O]

Into a 25-mL round-bottom flask, was placed 2-[[6-([5-chloro-2-[4-(2-hydroxyethoxy)piperidin-1-yl]pyrimidin-4-yl]amino)-1-methyl-2-oxo-1,2-dihydroquinolin-3-yl]oxy]-N-methylacetamide (340 mg, 0.658 mmol, 1.00 equiv) in dichloromethane (10 mL), TEA (199 mg, 1.973 mmol, 3.00 equiv), TsCl (188 mg, 0.986 mmol, 1.50 equiv), dimethylaminopyridine (8 mg, 0.066 mmol, 0.1 equiv). The resulting solution was stirred for 3 hours at room temperature. The reaction was then quenched by the addition of water (10 mL). The resulting solution was extracted with dichloromethane (3×30 mL). The resulting mixture was washed with brine (20 mL), dried over anhydrous sodium sulfate and concentrated under reduced pressure. The residue was applied onto a silica gel column eluting with dichloromethane/methanol (10/1). This resulted in 379 mg (86%) of 2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethyl 4-methylbenzene-1-sulfonate as a yellow solid. LC/MS (ESI) m/z: 671.10 [M+1]+.

Step 5: Preparation of (2S,4R)—N-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)-4-(4-methylthiazol-5-yl)benzyl)-4-hydroxy-1-(3-methyl-2-(3-methylisoxazol-5-yl)butanoyl)pyrrolidine-2-carboxamide

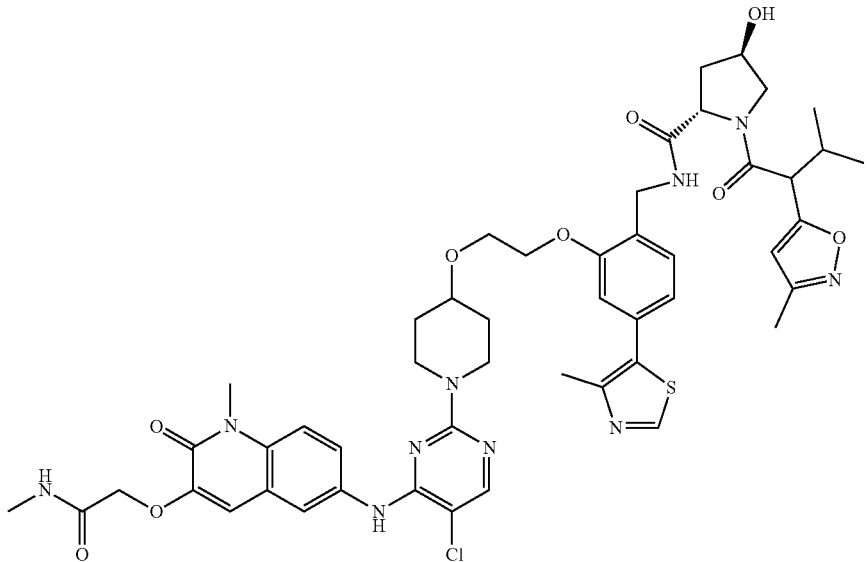 [SMILES: CNC(=O)COc1cc2cc(Nc3nc(N4CCC(OCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O]

Into a 30-mL sealed tube, was placed 2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethyl 4-methylbenzene-1-sulfonate (100 mg, 0.149 mmol, 1.00 equiv), (2S,4R)-4-hydroxy-N-(2-hydroxy-4-(4-methylthiazol-5-yl)benzyl)-1-(3-methyl-2-(3-methylisoxazol-5-yl)butanoyl)pyrrolidine-2-carboxamide (81 mg, 0.164 mmol, 1.10 equiv), $K_2CO_3$ (61 mg, 0.447 mmol, 3.00 equiv) in dimethylformamide (5 mL). The resulting solution was stirred for 3 h at 70° C. in an oil bath. The crude product was purified by Prep-HPLC. This resulted in 15 mg (10%) of (2S,4R)-N-([2-[2-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)ethoxy]-4-(4-methyl-1,3-thiazol-5-yl)phenyl]methyl)-4-hydroxy-1-[2-(3-methyl-1,2-oxazol-5-yl)butanoyl]pyrrolidine-2-carboxamide as a light yellow solid. LC/MS (ESI) m/z: 997.15/999.15 [M+1]$^+$; $^1$H-NMR (400 MHz, DMSO-d$_6$) δ 8.99 (s, 1H), 8.09-8.00 (m, 4H), 7.59-7.57 (m, J=8.8 Hz, 1H), 7.52-7.45 (d, J=8.8 Hz, 1H), 7.37-7.34 (d, J=8.8 Hz, 2H), 7.22 (s, 2H), 7.13-7.09 (m, 1H), 7.09-7.06 (m, 2H), 7.05-7.00 (m, 1H), 6.22 (s, 1H), 4.59 (s, 1H), 4.39-4.21 (m, 6H), 4.03 (s, 3H), 3.96-3.82 (m, 4H), 3.79-3.74 (m, 1H), 3.77-3.69 (m, 6H), 3.10 (s, 3H), 2.70-2.65 (m, 2H), 2.52-2.46 (m, 4H), 2.21 (s, 3H), 2.20-2.11 (m, 2H), 2.10-2.00 (m, 1H), 2.00-1.82 (m, 4H), 1.57-1.45 (m, 3H), 1.35-1.20 (m, 3H), 1.02-0.90 (m, 3H), 0.90-0.74 (m, 3H).

Synthesis of 5-(2-(2-(4-(4-chloro-2-nitro-5-((2-oxo-1,2,3,4-tetrahydroquinolin-6-yl)amino)phenoxy)piperidin-1-yl)ethoxy)ethoxy)-2-(2,6-dioxopiperidin-3-yl)isoindoline-1,3-dione (Exemplary Compound 74)

Step 1: Preparation of tert-butyl 4-(4,5-dichloro-2-nitrophenoxy)piperidine-1-carboxylate

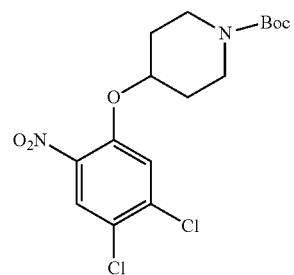 [SMILES: CC(C)(C)OC(=O)N1CCC(Oc2cc(Cl)c(Cl)cc2[N+](=O)[O-])CC1]

A mixture of tert-butyl 4-hydroxypiperidine-1-carboxylate (481 mg, 2.9 mmol), NaH (115 mg, 3.48 mmol) in DMF (10.0 mL) was stirred at room temperature for 1 hour. Then 1,2-dichloro-4-fluoro-5-nitrobenzene (500 mg, 2.9 mmol) was added dropwise. The mixture was stirred at RT for 3 h. $H_2O$ (10 mL) was added and the mixture was extracted with ethyl acetate (30 mL). The organic phase was concentrated under vacuum. The residue was applied onto a silica gel column to afford desired product (320 mg) as a yellow oil.

Step 2: Preparation of 6-amino-3,4-dihydroquinolin-2(1H)-one

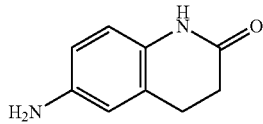

A solution of 6-nitro-3,4-dihydroquinolin-2(1H)-one (2 g, 10.4 mmol), Pd/C (300 mg) in ethyl acetate (10 mL) was stirred at rt for 3 h under $H_2$. The mixture was filtered through a Celite pad, and the filtrate was concentrated to give the product (1.4 g) as a white solid. LC/MS (ESI) m/z: 163.2 $[M+23]^+$.

Step 3: Preparation of tert-butyl 4-(4-chloro-2-nitro-5-((2-oxo-1,2,3,4-tetrahydroquinolin-6-yl)amino)phenoxy)piperidine-1-carboxylate

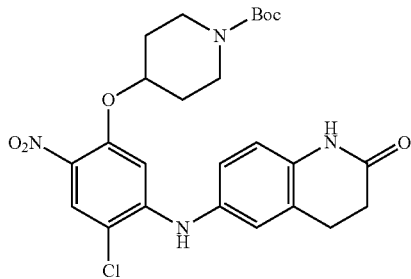 [SMILES: CC(C)(C)OC(=O)N1CCC(Oc2cc(Nc3ccc4c(c3)CCC(=O)N4)c(Cl)cc2[N+](=O)[O-])CC1]

A mixture of tert-butyl 4-(4,5-dichloro-2-nitrophenoxy)piperidine-1-carboxylate (182 mg, 0.465 mmol), 6-amino-3,4-dihydroquinolin-2(1H)-one (75.4 mg, 0.465 mmol), $Pd_2(dba)_3$ (21.3 mg, 0.023 mmol), BINAP (28.9 mg, 0.046 mmol), $K_2CO_3$ (229.6 mg, 0.70 mmol) in DME (3 mL) was stirred at 100° C. for 12 hours. After quenched with $H_2O$, the mixture was extracted with ethyl acetate (10 mL×2). The organic phase was concentrated under vacuum. The organic phase was concentrated under vacuum and purified by Pre-TLC to afford the desired product (210 mg) as a yellow solid.

Step 4: Preparation of 6-((2-chloro-4-nitro-5-(piperidin-4-yloxy)phenyl)amino)-3,4-dihydroquinolin-2(1H)-one

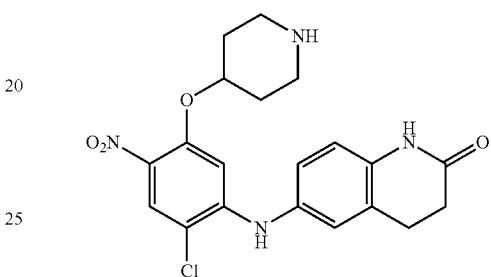

A mixture of tert-butyl 4-(4-chloro-2-nitro-5-((2-oxo-1,2,3,4-tetrahydroquinolin-6-yl)amino)phenoxy)piperidine-1-carboxylate (200 mg, 0.386 mmol) in DCM/TFA (3 mL/3 mL) was stirred at RT for 2 h. The organic phase was concentrated under vacuum to afford the desired product (150 mg) as a yellow solid. LC/MS (ESI) m/z: 417.2 $[M+23]^+$.

Step 4: Preparation of 5-(2-(2-(4-(4-chloro-2-nitro-5-((2-oxo-1,2,3,4-tetrahydroquinolin-6-yl)amino)phenoxy)piperidin-1-yl)ethoxy)ethoxy)-2-(2,6-dioxopiperidin-3-yl)isoindoline-1,3-dione

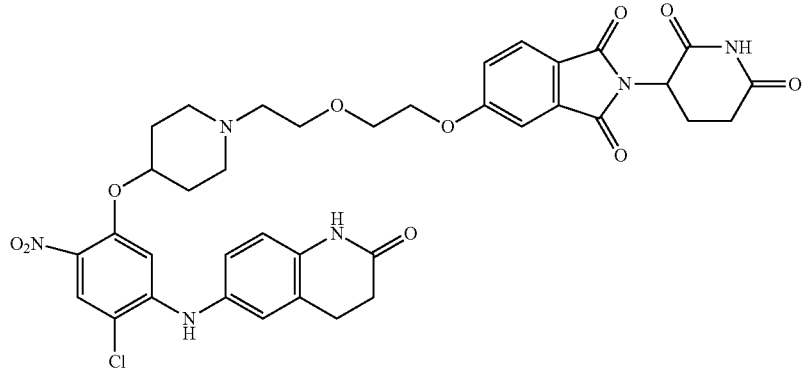 [SMILES: O=C1CCC(N2C(=O)c3ccc(OCCOCCN4CCC(Oc5cc(Nc6ccc7c(c6)CCC(=O)N7)c(Cl)cc5[N+](=O)[O-])CC4)cc3C2=O)C(=O)N1]

A solution of 6-((2-chloro-4-nitro-5-(piperidin-4-yloxy)phenyl)amino)-3,4-dihydroquinolin-2(1H)-one (200 mg, 0.26 mmol), 2-(2-((2-(2,6-dioxopiperidin-3-yl)-1,3-dioxoisoindolin-5-yl)oxy)ethoxy)acetaldehyde (160 mg, 0.30 mmol) and CH₃COONa (30 mg, 0.188 mmol) in DCM/EtOH was stirred at 40° C. for 1 hour. Then added NaBH₃CN (40 mg, 0.52 mmol) to the mixture. After quenched with water, the mixture was taken up EA (10 mL), washed with brine three times. The organic phase was dried over anhydrous sodium sulfate and concentrated under vacuum. The residue was purified by prep-HPLC to afford the desired product (42 mg) as a yellow solid. LC/MS (ESI) m/z: 761.3 [M+1]⁺; ¹H-NMR (400 MHz, DMSO-d₆) δ 11.11 (s, 1H), 10.17 (s, 1H), 9.68-9.57 (s, 1H), 8.52-8.46 (s, 1H), 8.12-8.09 (s, 1H), 7.83-7.81 (m, 1H), 7.44 (s, 1H), 7.34-7.32 (m, 1H), 7.16 9 (s, 1H), 7.13-7.10 (m, 1H), 6.88-6.86 (m, 1H), 6.56-6.52 (m, 1H), 5.13-5.09 (m, 1H), 4.35 (s, 2H), 3.85 (s, 4H), 3.34 (m, 3H), 3.14-2.93 (m, 2H), 2.93-2.84 (m, 3H), 2.66-2.50 (m, 1H), 2.47-2.43 (m, 2H), 2.20-2.17 (m, 1H), 2.05-1.98 (m, 4H), 1.91-1.75 (m, 1H), 1.52-1.50 (m, 1H).

Synthesis of 2-((6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylacetamide (Exemplary Compound 104)

Step 1: Preparation of tert-butyl 4-formylpiperidine-1-carboxylate

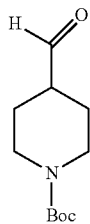

To a solution of tert-butyl 4-(hydroxymethyl)piperidine-1-carboxylate (500 mg, 2.3 mmol) in acetonitrile (10.0 mL) was added IBX (1.3 g, 4.6 mmol) in portions. The mixture was stirred at 80° C. for 2 h. The mixture was filtered through a Celite pad and the filtrate was concentrated to give the product (300 mg) as a yellow oil.

Step 2: Preparation of tert-butyl 4-((4-(2-(2,6-dioxopiperidin-3-yl)-1,3-dioxoisoindolin-5-yl)piperazin-1-yl)methyl)piperidine-1-carboxylate

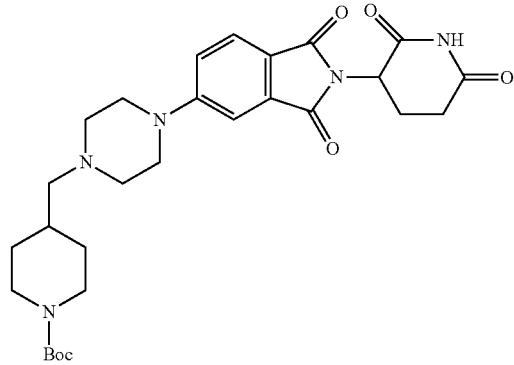 [SMILES: CC(C)(C)OC(=O)N1CCC(CN2CCN(c3ccc4c(c3)C(=O)N(C3CCC(=O)NC3=O)C4=O)CC2)CC1]

A mixture of tert-butyl 4-formylpiperidine-1-carboxylate (200 mg, 0.94 mmol), 2-(2,6-dioxopiperidin-3-yl)-5-(piperazin-1-yl)isoindoline-1,3-dione (385 mg, 1.12 mmol), CH₃COONa (38 mg, 0.42 mmol), CH₃COOH (28 mg, 0.42 mmol) in DCM/EtOH (3 mL) was stirred at 40° C. for 1 hour. Then NaBH₃CN (58.9 mg, 0.94 mmol) was added dropwise. The mixture was stirred at 40° C. for 12 hours. After quenched with H₂O (20 mL), the mixture was extracted with ethyl acetate (10 mL). The organic phase was concentrated under vacuum and purified by prep-TLC to afford the desired product (120 mg) as a yellow solid. LC/MS (ESI) m/z: 484.3 [M−55]⁺.

Step 3: Preparation of 2-(2,6-dioxopiperidin-3-yl)-5-(4-(piperidin-4-ylmethyl)piperazin-1-yl)isoindoline-1,3-dione

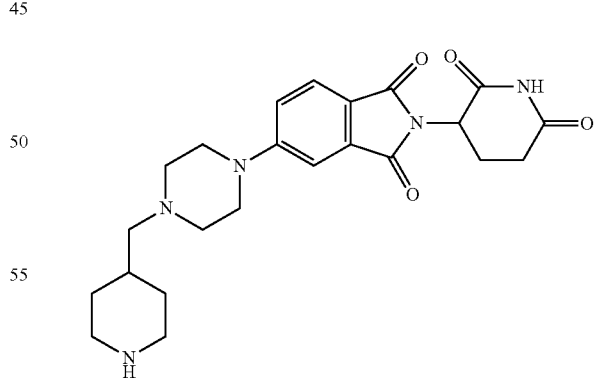

A mixture of tert-butyl 4-((4-(2-(2,6-dioxopiperidin-3-yl)-1,3-dioxoisoindolin-5-yl)piperazin-1-yl)methyl)piperidine-1-carboxylate (120 mg, 0.22 mmol) in DCM/TFA (3 mL) was stirred at room temperature for 2 hours. The organic phase was concentrated under vacuum to afford the desired product (100 mg) as a yellow oil. LC/MS (ESI) m/z: 440.2 [M+23]⁺.

Step 4: Preparation of 2-((6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylacetamide

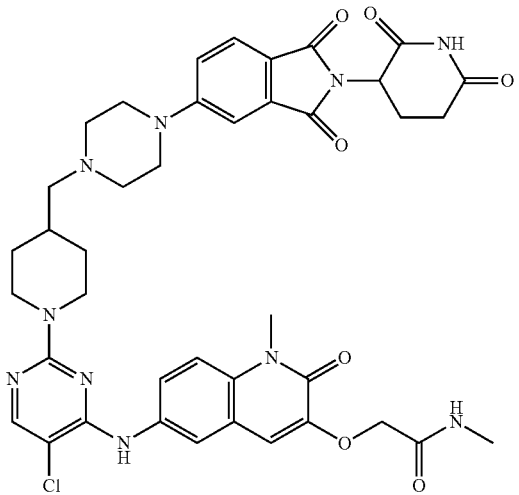 [SMILES: CNC(=O)COc1cc2cc(Nc3nc(N4CCC(CN5CCN(c6ccc7c(c6)C(=O)N(C6CCC(=O)NC6=O)C7=O)CC5)CC4)ncc3Cl)ccc2n(C)c1=O]

A mixture of 2-(2,6-dioxopiperidin-3-yl)-5-(4-(piperidin-4-ylmethyl)piperazin-1-yl)isoindoline-1,3-dione (114 mg, 0.26 mmol), 2-((6-((2,5-dichloropyrimidin-4-yl)amino)-1-methyl-2-oxo-1,2-dihydroquinolin-3-yl)oxy)-N-methylacetamide (96 mg, 0.24 mmol) and TEA (131 mg, 1.29 mmol) in DMSO (1.0 mL) was stirred at 100° C. for 1 hour. After cooling to room temperature, the mixture was quenched with H$_2$O, and the mixture was extracted with ethyl acetate (20 mL×2). The organic phase was concentrated under vacuum. The residue was purified by prep-HPLC to afford the desired product (31 mg) as a white solid. LC/MS (ESI) m/z: 811.4 [M+1]$^+$; $^1$H-NMR (400 MHz, DMSO-d$_6$) δ 11.09 (s, 1H), 9.01 (s, 1H), 8.08 (m, 1H), 7.98-7.93 (m, 2H), 7.77-7.72 (m, 2H), 7.49-7.45 (m, 2H), 7.37-7.35 (m, 1H), 7.11 (m, 1H), 5.11-5.07 (m, 1H), 4.59 (s, 2H), 4.47-4.44 (m, 2H), 4.22-4.19 (m, 2H), 3.67 (s, 3H), 3.63-3.60 (m, 2H), 3.35-3.29 (m, 2H), 3.17-3.08 (m, 4H), 2.96-2.90 (m, 3H), 2.66-2.61 (m, 5H), 2.27-2.16 (m, 1H), 2.04-2.01 (m, 1H), 1.79-1.76 (m, 2H), 1.21-1.15 (m, 2H).

Synthesis of 5-(6-(((1-(5-chloro-4-((1-methyl-2-oxo-3-(2-oxopropoxy)-1,2-dihydroquinolin-6-yl)amino)pyrimidin-2-yl)piperidin-4-yl)methyl)-2,6-diazaspiro[3.3]heptan-2-yl)-2-(2,6-dioxopiperidin-3-yl)isoindoline-1,3-dione (Exemplary Compound 165)

Step 1: Preparation of tert-butyl 6-(2-(2,6-dioxopiperidin-3-yl)-1,3-dioxoisoindolin-5-yl)-2,6-diazaspiro[3.3]heptane-2-carboxylate

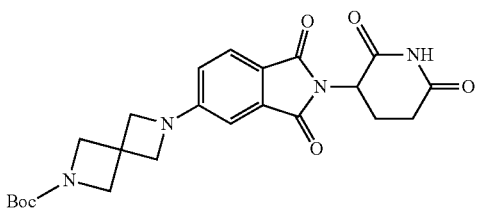 [SMILES: CC(C)(C)OC(=O)N1CC2(C1)CN(c1ccc3c(c1)C(=O)N(C1CCC(=O)NC1=O)C3=O)C2]

Into a 20-mL sealed tube, was placed 2-(2,6-dioxopiperidin-3-yl)-5-fluoroisoindole-1,3-dione (500 mg, 1.810 mmol, 1.00 equiv), DMSO (5 mL), DIEA (1.20 mL), tert-butyl 2,6-diazaspiro[3.3]heptane-2-carboxylate (430 mg, 2.172 mmol, 1.20 equiv). The resulting solution was stirred for 2 hours at 120° C. in an oil bath. The reaction mixture was cooled. The reaction was then quenched by the addition of 50 mL of water. The resulting solution was extracted with 3×50 mL of ethyl acetate. The combined organic layer was washed with 1×30 ml of brine and concentrated under reduced pressure. The residue was applied onto a silica gel column eluting with ethyl acetate/petroleum ether (2:3). This resulted in 541 mg (66%) of tert-butyl 6-[2-(2,6-dioxopiperidin-3-yl)-1,3-dioxoisoindol-5-yl]-2,6-diazaspiro[3.3]heptane-2-carboxylate as a light yellow solid. LC/MS (ESI) m/z: 455.15 [M+1]$^+$.

Step 2: Preparation of 2-(2,6-dioxopiperidin-3-yl)-5-(2,6-diazaspiro[3.3]heptan-2-yl)isoindoline-1,3-dione

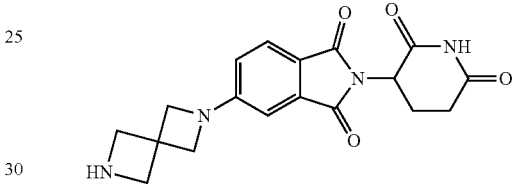

Into a 50-mL round-bottom flask, was placed tert-butyl 6-[2-(2,6-dioxopiperidin-3-yl)-1,3-dioxoisoindol-5-yl]-2,6-diazaspiro[3.3]heptane-2-carboxylate (541 mg, 1.192 mmol, 1.00 equiv) in dichloromethane (15 mL) and TFA (3 mL). The resulting solution was stirred for 2 hours at room temperature. The resulting mixture was concentrated. This resulted in 503 mg (93%) of 542,6-diazaspiro[3.3]heptan-2-yl]2-(2,6-dioxopiperidin-3-yl)isoindole-1,3-dione TFA salt as a light yellow solid. LC/MS (ESI) m/z: 355.05 [M+1]$^+$.

Step 3: Preparation of tert-butyl 4-((6-(2-(2,6-dioxopiperidin-3-yl)-1,3-dioxoisoindolin-5-yl)-2,6-diazaspiro[3.3]heptan-2-yl)methyl)piperidine-1-carboxylate

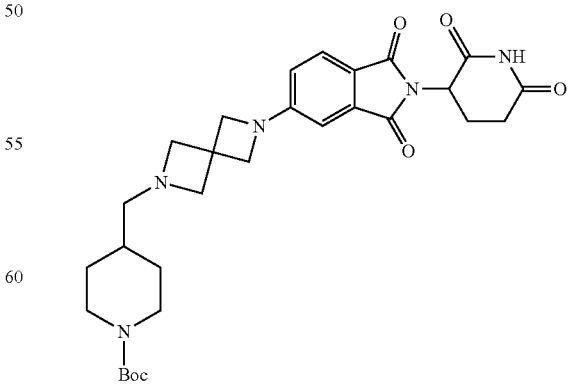

Into a 50-mL round-bottom flask, was placed 5-[2,6-diazaspiro[3.3]heptan-2-yl]-2-(2,6-dioxopiperidin-3-yl)

isoindole-1,3-dione TFA (500 mg, 1.105 mmol, 1.00 equiv), DIEA was added to adjust the PH to 8. This was followed by the addition of dichloromethane (20 mL). To this was added tert-butyl 4-formylpiperidine-1-carboxylate (361.00 mg, 1.693 mmol, 1.53 equiv). After stirred for 30 minutes at room temperature, to the mixture was added NaBH(OAc)$_3$ (450 mg, 2.123 mmol, 1.92 equiv) at room temperature. The resulting solution was stirred for 4 hr at room temperature. The reaction was then quenched by the addition of 100 mL of water, extracted with 3×50 mL of dichloromethane, washed with 1×30 of brine, dried over anhydrous sodium sulfate and concentrated. The residue was applied onto a silica gel column eluting with dichloromethane/methanol (10:1). This resulted in 451.7 mg (74%) of tert-butyl 4-([6-[2-(2,6-dioxopiperidin-3-yl)-1,3-dioxoisoindol-5-yl]-2,6-diazaspiro[3.3]heptan-2-yl]methyl)piperidine-1-carboxylate as a light yellow solid. LC/MS (ESI) m/z: 552.25 [M+1]$^+$.

Step 4: Preparation of 2-(2,6-dioxopiperidin-3-yl)-5-(6-(piperidin-4-ylmethyl)-2,6-diazaspiro[3.3]heptan-2-yl)isoindoline-1,3-dione

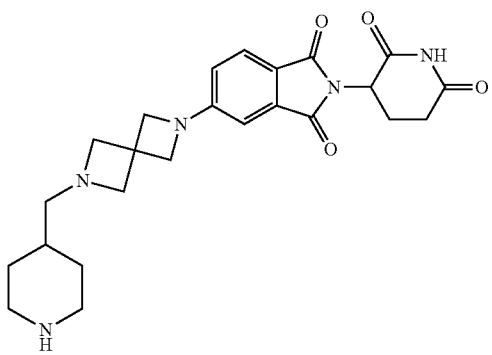 [SMILES: O=C1CCC(N2C(=O)c3ccc(N4CC5(CN(CC6CCNCC6)C5)C4)cc3C2=O)C(=O)N1]

Into a 100-mL round-bottom flask, was placed tert-butyl 4-([6-[2-(2,6-dioxopiperidin-3-yl)-1,3-dioxoisoindol-5-yl]-2,6-diazaspiro[3.3]heptan-2-yl]methyl)piperidine-1-carboxylate (451 mg, 0.819 mmol, 1 equiv) in dichloromethane (30 mL) and TFA (6 mL). The resulting solution was stirred for 2 hours at room temperature. The resulting mixture was concentrated. This resulted in 432 mg (96%) of 2-(2,6-dioxopiperidin-3-yl)-5-[6-(piperidin-4-ylmethyl)-2,6-diazaspiro[3.3]heptan-2-yl]isoindole-1,3-dione TFA salt as a light yellow solid. The TFA salt was adjusted to 8 by DIEA in DMF, and remove the salt by Prep-HPLC. After lyophilization, this resulted in 2-(2,6-dioxopiperidin-3-yl)-5-[6-(piperidin-4-ylmethyl)-2,6-diazaspiro[3.3]heptan-2-yl]isoindole-1,3-dione 256 mg (51%) a light yellow solid. LC/MS (ESI) m/z: 452.15 [M+1]$^+$.

Step 5: Preparation of 5-(6-((1-(5-chloro-4-((1-methyl-2-oxo-3-(2-oxopropoxy)-1,2-dihydroquinolin-6-yl)amino)pyrimidin-2-yl)piperidin-4-yl)methyl)-2,6-diazaspiro[3.3]heptan-2-yl)-2-(2,6-dioxopiperidin-3-yl)isoindoline-1,3-dione

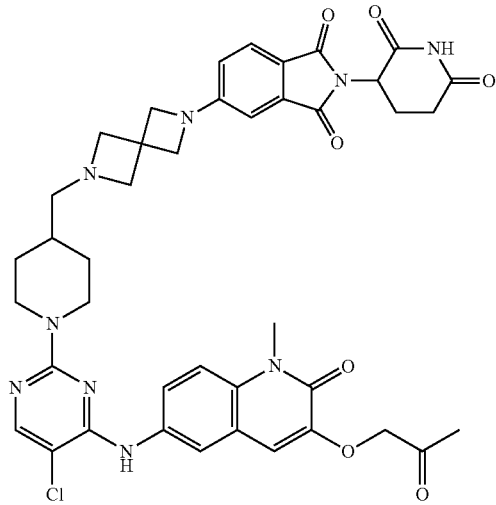 [SMILES: CC(=O)COc1cc2cc(Nc3nc(N4CCC(CN5CC6(C5)CN(c5ccc7c(c5)C(=O)N(C5CCC(=O)NC5=O)C7=O)C6)CC4)ncc3Cl)ccc2n(C)c1=O]

Into a 20-mL round-bottom flask, was placed 2-(2,6-dioxopiperidin-3-yl)-5-[6-(piperidin-4-ylmethyl)-2,6-diazaspiro[3.3]heptan-2-yl]isoindole-1,3-dione (352 mg, 0.780 mmol, 1.00 equiv), 6-[(2,5-dichloropyrimidin-4-yl)amino]-1-methyl-3-(2-oxopropoxy)quinolin-2-one (256 mg, 0.651 mmol, 0.84 equiv), DMSO (5 mL), DIEA (252 mg, 1.950 mmol, 2.50 equiv). The resulting solution was stirred for 2 hours at 120° C. in an oil bath. The reaction mixture was cooled and quenched by the addition of 50 mL of water. The resulting solution was extracted with 3×50 mL of ethyl acetate. The combined organic layer was concentrated under reduced pressure. The crude product was purified by Prep-HPLC. This resulted in 9.5 mg (2%) of 5-(6-[[1-(5-chloro-4-[[1-methyl-2-oxo-3-(2-oxopropoxy)quinolin-6-yl]amino]pyrimidin-2-yl)piperidin-4-yl]methyl]-2,6-diazaspiro[3.3]heptan-2-yl)-2-(2,6-dioxopiperidin-3-yl)isoindoline-1,3-dione as a light yellow solid. LC/MS (ESI) m/z: 808.30/810.30 [M+1]$^+$; $^1$H-NMR (400 MHz, DMSO-d$_6$) δ 11.05 (s, 1H), 8.87 (s, 1H), 8.03 (s, 1H), 7.88 (s, 1H), 7.65-7.63 (m, 2H), 7.45 (d, J=9.2 Hz, 1H), 7.03 (s, 1H), 6.83 (s, 1H), 6.76-6.72 (m, 1H), 5.31 (s, 1H), 5.11-5.02 (m, 1H), 4.91 (s, 2H), 4.65-4.62 (m, 2H), 4.11 (s, 3H), 3.67 (s, 3H), 2.95-2.73 (m, 4H), 2.21 (s, 4H), 2.03-1.97 (m, 3H), 1.71-1.68 (m, 2H), 1.52-1.50 (m, 1H), 1.33-1.31 (m, 8H), 1.13-1.01 (m, 2H).

Synthesis of 5-(4-((1-(5-chloro-4-((1-methyl-2-oxo-3-(2-oxopropoxy)-1,2-dihydroquinolin-6-yl)amino)pyrimidin-2-yl)piperidin-4-yl)(methyl)amino)piperidin-1-yl)-2-(2,6-dioxopiperidin-3-yl)isoindoline-1,3-dione (Exemplary Compound 169)

Step 1: Preparation of benzyl 4-((1-(tert-butoxycarbonyl)piperidin-4-yl)(methyl)amino)piperidine-1-carboxylate

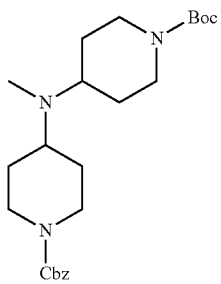 [SMILES: CN(C1CCN(C(=O)OCc2ccccc2)CC1)C1CCN(C(=O)OC(C)(C)C)CC1]

Into a 50-mL round-bottom flask, was placed tert-butyl 4-(methylamino)piperidine-1-carboxylate (2 g, 9.332 mmol, 1.00 equiv), benzyl 4-oxopiperidine-1-carboxylate (2.39 g, 10.266 mmol, 1.10 equiv), DCM (20 mL). The resulting solution was stirred for 30 minutes at room temperature, Na(OAc)₃BH (1.68 g, 27.997 mmol, 3.00 equiv) was added. The resulting solution was allowed to react, with stirring, for an additional 1 hour at room temperature. The solids were filtered out and the filtrate was concentrated under reduced pressure. This resulted in 2.6 g (65%) of tert-butyl 4-([1-[(benzyloxy)carbonyl]piperidin-4-yl](methyl)amino)piperidine-1-carboxylate as colorless oil. LC/MS (ESI) m/z: 432.25 [M+1]⁺.

Step 2: Preparation of benzyl 4-(methyl(piperidin-4-yl)amino)piperidine-1-carboxylate

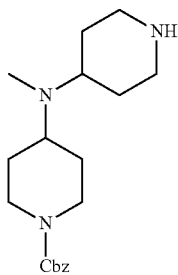 [SMILES: CN(C1CCNCC1)C1CCN(C(=O)OCc2ccccc2)CC1]

To a stirred solution tert-butyl 4-([1-[(benzyloxy)carbonyl]piperidin-4-yl](methyl)amino)piperidine-1-carboxylate (2.6 g, 6.024 mmol, 1.00 equiv) in 1,4-dioxane (10 mL) was added 10 mL of hydrogen chloride in 1,4-dioxane (4 M) at room temperature. The resulting mixture was stirred for 30 minutes at room temperature and then concentrated under vacuum. This resulted in benzyl 4-[methyl(piperidin-4-yl)amino]piperidine-1-carboxylate (1.5 g, 75%) as a yellow solid. LC/MS (ESI) m/z: 332.20 [M+1]⁺.

Step 3: Preparation of benzyl 4-((1-(2-(2,6-dioxopiperidin-3-yl)-1,3-dioxoisoindolin-5-yl)piperidin-4-yl)(methyl)amino)piperidine-1-carboxylate

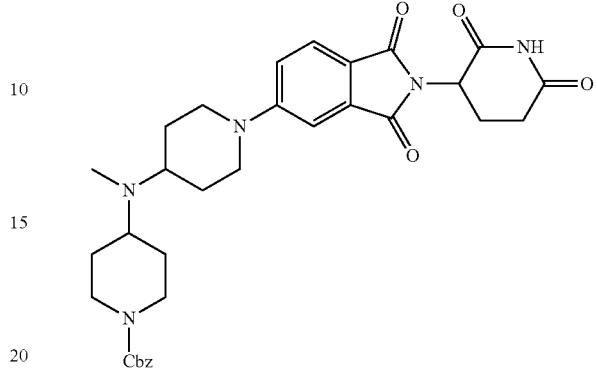

To a stirred mixture of benzyl 4-[methyl(piperidin-4-yl)amino]piperidine-1-carboxylate (300 mg, 0.905 mmol, 1.0 equiv) and 2-(2,6-dioxopiperidin-3-yl)-5-fluoroisoindole-1,3-dione (250 mg, 0.905 mmol, 1.00 equiv) in 8 mL DMSO was added DIEA (350 mg, 2.715 mmol, 3.00 equiv). The reaction mixture was stirred overnight at 100° C. in an oil bath and then concentrated under reduced pressure. The residue was purified by reverse flash chromatography. This resulted in benzyl 4-([1-[2-(2,6-dioxopiperidin-3-yl)-1,3-dioxoisoindol-5-yl]piperidin-4-yl](methyl)amino)piperidine-1-carboxylate (335 mg, 63%) as a yellow solid. LC/MS (ESI) m/z: 588.25 [M+1]⁺.

Step 4: Preparation of 2-(2,6-dioxopiperidin-3-yl)-5-(4-(methyl(piperidin-4-yl)amino)piperidin-1-yl)isoindoline-1,3-dione

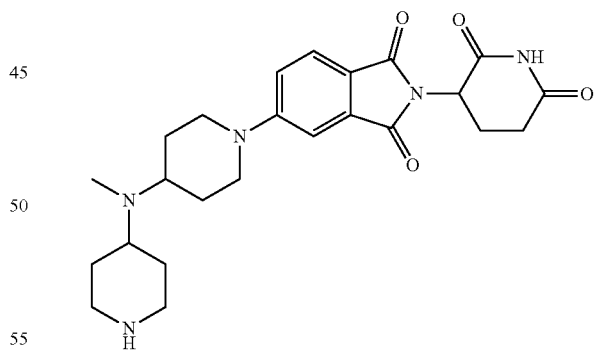

A solution of benzyl 4-([1-[2-(2,6-dioxopiperidin-3-yl)-1,3-dioxoisoindol-5-yl]piperidin-4-yl](methyl)amino)piperidine-1-carboxylate (335 mg, 0.570 mmol, 1.00 equiv) and Pd/C in i-PrOH (15 mL) was stirred for 3 h at 40° C. under hydrogen atmosphere. The precipitated solids were collected by filtration and washed with THF. The resulting mixture was concentrated under vacuum. This resulted in 2-(2,6-dioxopiperidin-3-yl)-5-[4-[methyl(piperidin-4-yl)amino]piperidin-1-yl]isoindole-1,3-dione (209 mg, 81%) as a yellow solid. LC/MS (ESI) m/z: 454.25 [M+1]⁺.

Step 5: Preparation of 5-(4-((1-(5-chloro-4-((1-methyl-2-oxo-3-(2-oxopropoxy)-1,2-dihydroquinolin-6-yl)amino)pyrimidin-2-yl)piperidin-4-yl)(methyl)amino)piperidin-1-yl)-2-(2,6-dioxopiperidin-3-yl)isoindoline-1,3-dione

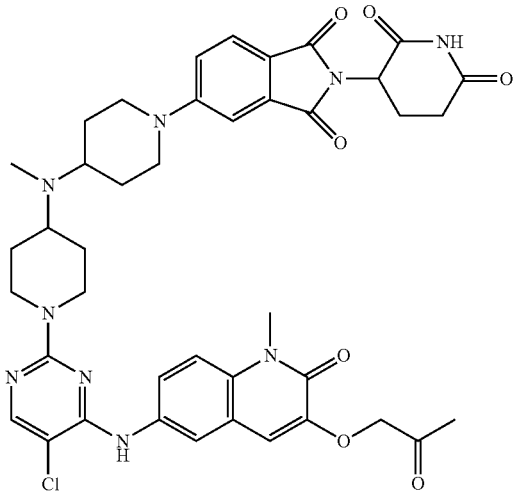 [SMILES: CC(=O)COc1cc2cc(Nc3nc(N4CCC(N(C)C5CCN(c6ccc7c(c6)C(=O)N(C6CCC(=O)NC6=O)C7=O)CC5)CC4)ncc3Cl)ccc2n(C)c1=O]

To a stirred solution of 2-(2,6-dioxopiperidin-3-yl)-5-[4-[methyl(piperidin-4-yl)amino]piperidin-1-yl]isoindole-1,3-dione (110 mg, 0.243 mmol, 1.00 equiv) and 6-[(2,5-dichloropyrimidin-4-yl)amino]-1-methyl-3-(2-oxopropoxy)quinolin-2-one (95.37 mg, 0.243 mmol, 1.00 equiv) in DMSO (4 mL) was added DIEA (62.69 mg, 0.485 mmol, 2.00 equiv). The reaction mixture was stirred overnight at 100° C. in an oil bath. The reaction mixture was direactly purified by Prep-HPLC. This resulted in 5-(4-[[1-(5-chloro-4-[[1-methyl-2-oxo-3-(2-oxopropoxy)quinolin-6-yl]amino]pyrimidin-2-yl]piperidin-4-yl](methyl)amino]piperidin-1-yl)-2-(2,6-dioxopiperidin-3-yl)isoindole-1,3-dione (34.2 mg, 17%) as a yellow solid. LC/MS (ESI) m/z: 810.35 [M+1]⁺; ¹H-NMR (400 MHz, DMSO-$d_6$) δ 11.08 (s, 1H), 8.83 (s, 1H), 8.04 (s, 1H), 7.91 (s, 1H), 7.72-7.66 (m, 2H), 7.47 (d, J=9.0 Hz, 1H), 7.32-7.24 (m, 2H), 7.05 (s, 1H), 5.08 (d, J=12.4 Hz, 1H), 4.92 (s, 2H), 4.52 (d, J=12.6 Hz, 2H), 4.07 (d, J=13.2 Hz, 2H), 3.68 (s, 3H), 3.03-2.98 (m, 2H), 2.83-2.72 (m, 5H), 2.60 (m, 2H) 2.20-2.15 (m, 6H), 2.03 (s, 1H), 1.76-1.71 (m, 4H), 1.53-1.41 (m, 4H).

Synthesis of 5-(4-((1-(5-chloro-4-((1-methyl-2-oxo-3-(2-oxopropoxy)-1,2-dihydroquinolin-6-yl)amino)pyrimidin-2-yl)piperidin-4-yl)oxy)piperidin-1-yl)-2-(2,6-dioxopiperidin-3-yl)isoindoline-1,3-dione (Exemplary Compound 170)

Step 1: Preparation of tert-butyl 4-(pyridin-4-yloxy)piperidine-1-carboxylate

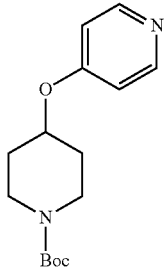 [SMILES: CC(C)(C)OC(=O)N1CCC(Oc2ccncc2)CC1]

Into a 500-mL round-bottom flask, was placed PPh₃ (41.4 g, 157.7 mmol, 1.5 equiv) in THF (300 mL), to which DIAD (31.9 g, 157.7 mmol, 1.5 equiv) was added. Then 4-hydroxypyridine (10 g, 105.1 mmol, 1.0 equiv) and tert-butyl 4-hydroxypiperidine-1-carboxylate (21.2 g, 105.1 mmol, 1.0 equiv) were added respectively at 0° C. The mixture was allowed to warm up to room temperature and stirred overnight. Then the mixture was concentrated under reduced pressure. The residue was applied onto a silica gel column eluting with ethyl acetate/petroleum ether (1:1). This resulted in 29.0 g (99%) of tert-butyl 4-(pyridin-4-yloxy)piperidine-1-carboxylate as a yellow solid. LC/MS (ESI) m/z: 279.20 [M+1]⁺.

Step 2: Preparation of 1-benzyl-4-((1-(tert-butoxycarbonyl)piperidin-4-yl)oxy)pyridin-1-ium bromide

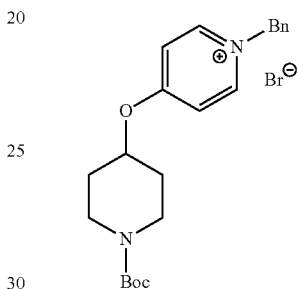

Into a 500-mL round-bottom flask, was placed tert-butyl 4-(pyridin-4-yloxy)piperidine-1-carboxylate (28 g, 100.6 mmol, 1.0 equiv) in DCM (400 mL), to which benzyl bromide (51.6 g, 301.7 mmol, 3.0 equiv) was added. The resulting mixture was stirred overnight at room temperature. Then the mixture was concentrated and the solid were collected by filtration. This resulted in 14.3 g (38.47%) of 1-benzyl-4-[[1-(tert-butoxycarbonyl)piperidin-4-yl]oxy]pyridin-1-ium as a white solid. LC/MS (ESI) m/z: 369.20 [M+1]⁺.

Step 3: Preparation of tert-butyl 4-((1-benzyl-1,2,3,6-tetrahydropyridin-4-yl)oxy)piperidine-1-carboxylate

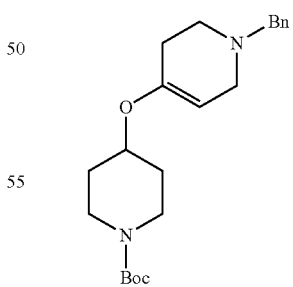

Into a 500-mL round-bottom flask, was placed 1-benzyl-4-[[1-(tert-butoxycarbonyl)piperidin-4-yl]oxy]pyridin-1-ium (14.3 g, 38.7 mmol, 1.0 equiv) in methanol (400 mL), to which NaBH₄ (4.3 g, 116.2 mmol, 3.0 equiv) was added. The resulting mixture was stirred for 3 hours at room temperature. Then the mixture was extracted with dichloromethane (200 mL×2). The organic layers were combined

Step 4: Preparation of tert-butyl 4-(piperidin-4-yloxy)piperidine-1-carboxylate

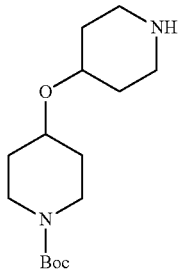

To a solution of tert-butyl 4-[(1-benzyl-3,6-dihydro-2H-pyridin-4-yl)oxy]piperidine-1-carboxylate (12.0 g, 32.2 mmol, 1.0 equiv) in isopropyl alcohol (300 mL) was added Pd/C (10%, 1.0 g) under nitrogen atmosphere in a 500 mL round bottom flask. The flask was then vacuumed and flushed with hydrogen. The reaction mixture was hydrogenated at 35° C. in an oil bath overnight under hydrogen atmosphere using a hydrogen balloon, then filtered through a Celite pad and the filtrate was concentrated under reduced pressure. This resulted in 8.2 g (89.50%) of tert-butyl 4-(piperidin-4-yloxy)piperidine-1-carboxylate as a white solid.

Step 5: Preparation of tert-butyl 4-((1-(2-(2,6-dioxopiperidin-3-yl)-1,3-dioxoisoindolin-5-yl)piperidin-4-yl)oxy)piperidine-1-carboxylate

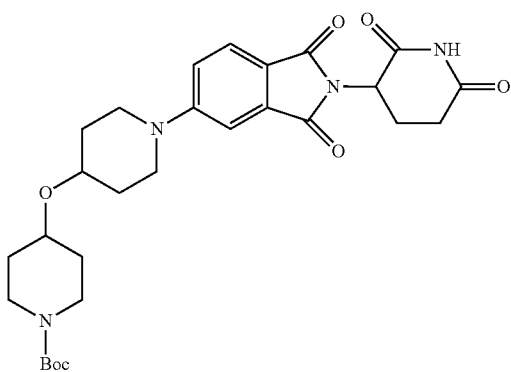 [SMILES: CC(C)(C)OC(=O)N1CCC(OC2CCN(c3ccc4c(c3)C(=O)N(C3CCC(=O)NC3=O)C4=O)CC2)CC1]

Into a 30-mL sealed tube, was placed tert-butyl 4-(piperidin-4-yloxy)piperidine-1-carboxylate (500 mg, 1.7 mmol, 1.0 equiv), 2-(2,6-dioxopiperidin-3-yl)-5-fluoroisoindole-1,3-dione (509.9 mg, 1.8 mmol, 1.05 equiv), DIEA (681.7 mg, 5.3 mmol, 3.0 equiv) in DMF (20 mL). The resulting mixture was stirred for 2 hours at 100° C. in an oil bath. Then the mixture was diluted with 20 mL of water and extracted with ethyl acetate (20 mL×2). The organic layers were combined and concentrated under reduced pressure. The residue was applied onto a silica gel column eluting with ethyl acetate/petroleum ether (2:1). This resulted in 880 mg (92.6%) of tert-butyl 4-([1-[2-(2,6-dioxopiperidin-3-yl)-1,3-dioxoisoindol-5-yl]piperidin-4-yl]oxy)piperidine-1-carboxylate as a yellow solid. LC/MS (ESI) m/z: 541.35 [M+1]⁺.

Step 6: Preparation of 2-(2,6-dioxopiperidin-3-yl)-5-(4-(piperidin-4-yloxy)piperidin-1-yl)isoindoline-1,3-dione

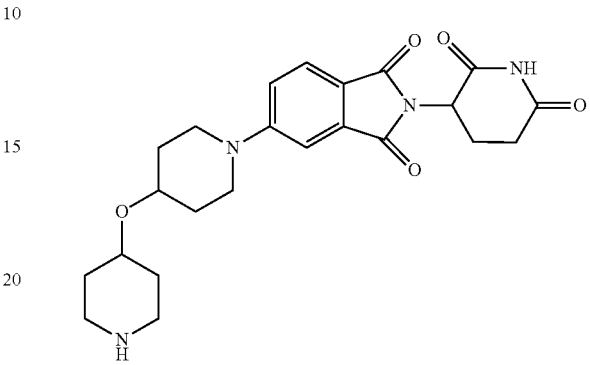

Into a 100-mL round-bottom flask, was placed tert-butyl 4-([1-[2-(2,6-dioxopiperidin-3-yl)-1,3-dioxoisoindol-5-yl] piperidin-4-yl]oxy)piperidine-1-carboxylate (880 mg, 1.628 mmol, 1.00 equiv) in DCM (30 mL), to which TFA (10 mL) was added. The resulting mixture was stirred for 2 hours at room temperature. The mixture was concentrated under reduced pressure. This resulted in 700.0 mg (97.6%) of 2-(2,6-dioxopiperidin-3-yl)-5-[4-(piperidin-4-yloxy)piperidin-1-yl]isoindole-1,3-dione as yellow oil. LC/MS (ESI) m/z: 441.20 [M+1]⁺.

Step 7: Preparation of 5-(4-((1-(5-chloro-4-((1-methyl-2-oxo-3-(2-oxopropoxy)-1,2-dihydroquinolin-6-yl)amino)pyrimidin-2-yl)piperidin-4-yl)oxy)piperidin-1-yl)-2-(2,6-dioxopiperidin-3-yl)isoindoline-1,3-dione

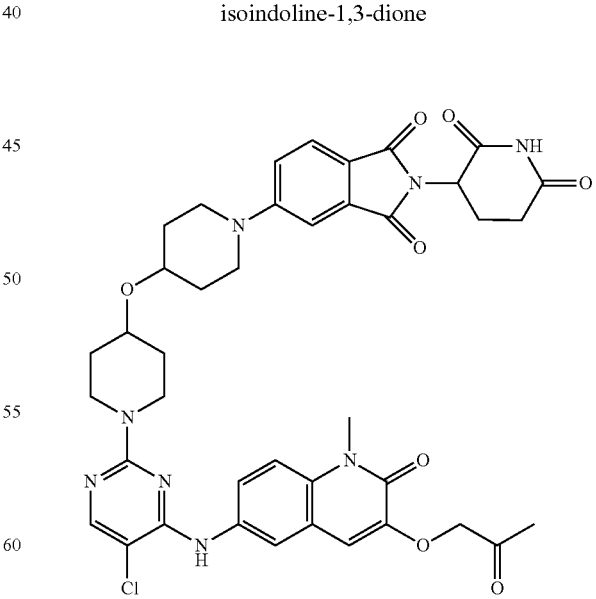

Into a 10-mL sealed tube, was placed 2-(2,6-dioxopiperidin-3-yl)-5-[4-(piperidin-4-yloxy)piperidin-1-yl]isoindole-1,3-dione (210 mg, 0.5 mmol, 1.3 equiv), 6-[(2,5-dichloropyrimidin-4-yl)amino]-1-methyl-3-(2-oxopropoxy)

quinolin-2-one (150 mg, 0.4 mmol, 1.0 equiv) and DIEA (194.0 mg, 1.5 mmol, 3.0 equiv) in DMF (5 mL). The resulting mixture was stirred for 2 hours at 70° C. in an oil bath. The reaction mixture was directly purified by Prep-HPLC. This resulted in 40.7 mg (13.4%) of 5-(4-[[1-(5-chloro-4-[[1-methyl-2-oxo-3-(2-oxopropoxy)quinolin-6-yl]amino]pyrimidin-2-yl)piperidin-4-yl]oxy]piperidin-1-yl)-2-(2,6-dioxopiperidin-3-yl)isoindole-1,3-dione as a yellow solid. LC/MS (ESI) m/z: 797.30 [M+1]$^+$; $^1$H-NMR (400 MHz, DMSO-d$_6$) δ 11.06 (s, 1H), 8.83 (s, 1H), 8.03 (s, 1H), 7.89 (s, 1H), 7.73-7.62 (m, 2H), 7.45 (d, J=9.1 Hz, 1H), 7.33-7.24 (m, 2H), 7.03 (s, 1H), 5.10-5.02 (m, 1H), 4.95-4.83 (m, 2H), 4.15-4.02 (m, 2H), 3.78-3.66 (m, 7H), 2.95-2.81 (m, 2H), 2.63-2.51 (m, 2H), 2.19-2.23 (m, 3H), 2.03-1.98 (m, 2H), 1.90-1.80 (m, 4H), 1.50-1.36 (m, 5H), 1.31-1.24 (m, 1H).

Synthesis of 2-((6-((5-chloro-2-(4-(2-(1-(2-(2,6-dioxopiperidin-3-yl)-1,3-dioxoisoindolin-5-yl)piperidin-4-yl)propan-2-yl)piperazin-1-yl)pyrimidin-4-yl)amino)-1-methyl-2-oxo-1,2-dihydroquinolin-3-yl)oxy)-N-methylacetamide (Exemplary Compound 205)

Step 1: Preparation of benzyl 3,4-dihydroxypyrrolidine-1-carboxylate

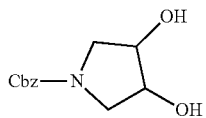 [SMILES: O=C(OCc1ccccc1)N1CC(O)C(O)C1]

Into a 500-mL round-bottom flask, was placed a solution of benzyl 2,5-dihydro-1H-pyrrole-1-carboxylate (10.15 g, 50.0 mmol, 1.00 equiv) and N-methylmorpholine-N-oxide (5.85 g, 50.00 mmol, 50.00 equiv) in $^t$BuOH (60.0 mL) and tetrahydrofuran (130.0 mL), to which tetraoxoosmium (130.0 mg in 3 mL $^t$BuOH, 0.51 mmol, 0.01 equiv) was added. The resulting mixture was stirred for 16 hours at room temperature. The resulting mixture was concentrated under reduced pressure. The residue was applied onto a silica gel column with ethyl acetate/petroleum ether (1:1). This resulted in 10.1 g (85%) of benzyl 3,4-dihydroxypyrrolidine-1-carboxylate as a white solid. LC/MS (ESI) m/z: 238.05 [M+1]$^+$.

Step 2: Preparation of benzyl bis(2-oxoethyl)carbamate

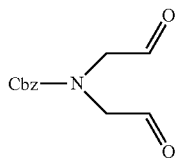

Into a 250-mL round-bottom flask, was placed a solution of benzyl 3,4-dihydroxypyrrolidine-1-carboxylate (10.1 g, 42.3 mmol, 1.00 equiv) in THF (100 mL), to which a solution of NaIO$_4$ (13.7 g, 63.4 mmol, 1.50 equiv) in water (20 mL) was added. The resulting mixture was stirred for 30 min at room temperature. The resulting solution was extracted with ethyl acetate (50 mL×2) and the organic layers combined and concentrated under reduced pressure. This resulted in 9.4 g (95%) of benzyl N,N-bis(2-oxoethyl)carbamate as colorless oil. LC/MS (ESI) m/z: 236.05 [M+1]$^+$.

Step 3: Preparation of benzyl 4-(2-(1-(tert-butoxycarbonyl)piperidin-4-yl)propan-2-yl)piperazine-1-carboxylate

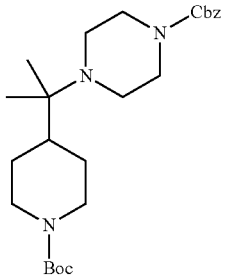 [SMILES: CC(C)(C)OC(=O)N1CCC(C(C)(C)N2CCN(C(=O)OCc3ccccc3)CC2)CC1]

Into a 100 mL round-bottom flask, was placed a solution of benzyl N,N-bis(2-oxoethyl)carbamate (4.7 g, 20.0 mmol, 2.0 equiv) and tert-butyl 4-(2-aminopropan-2-yl)piperidine-1-carboxylate (2.4 g, 10.0 mmol, 1.0 equiv) in MeOH (30 mL). The PH of the mixture was adjusted to 5 with HOAc (0.5 mL, 8.7 mmol, 38.8 equiv). After stirred for 2 hours at room temperature, borane/2-methylpyridine (2.1 g, 20.0 mmol, 2.0 equiv) was added. The reaction mixture was stirred for 16 h at room temperature and then quenched by the addition of water. The resulting mixture was extracted with dichloromethane (50 mL×3), and the combined organic layer was washed with brine (50 mL×3), dried over anhydrous sodium sulfate and concentrated under reduced pressure. The residue was applied onto a silica gel column eluting with ethyl acetate/hexane (1:3). This resulted in 770 mg (17%) of benzyl 4-[2-[1-(tert-butoxycarbonyl)piperidin-4-yl]propan-2-yl]piperazine-1-carboxylate as a white solid. LC/MS (ESI) m/z: 446.35 [M+1]$^+$.

Step 4: Preparation of tert-butyl 4-(2-(piperazin-1-yl)propan-2-yl)piperidine-1-carboxylate

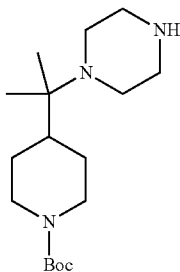 [SMILES: CC(C)(C)OC(=O)N1CCC(C(C)(C)N2CCNCC2)CC1]

To a solution of benzyl 4-[2-[1-(tert-butoxycarbonyl)piperidin-4-yl]propan-2-yl]piperazine-1-carboxylate (770.0 mg, 1.7 mmol, 1.0 equiv) in isopropyl alcohol (40 mL), was added Pd(OH)$_2$/C (10%, 37 mg) under nitrogen atmosphere in a 100 mL round bottom flask. The flask was then vacuumed and flushed with hydrogen. The reaction mixture was hydrogenated at room temperature overnight under hydrogen atmosphere using a hydrogen balloon, then filtered through a Celite pad and the filtrate was concentrated under reduced pressure. This resulted in 516 mg (98%) of tert-butyl 4-[2-(piperazin-1-yl)propan-2-yl]piperidine-1-carboxylate as a yellow solid. LC/MS (ESI) m/z: 312.35 [M+1]$^+$.

Step 5: Preparation of tert-butyl 4-(2-(4-(5-chloro-4-((1-methyl-3-(2-(methylamino)-2-oxoethoxy)-2-oxo-1,2-dihydroquinolin-6-yl)amino)pyrimidin-2-yl)piperazin-1-yl)propan-2-yl)piperidine-1-carboxylate

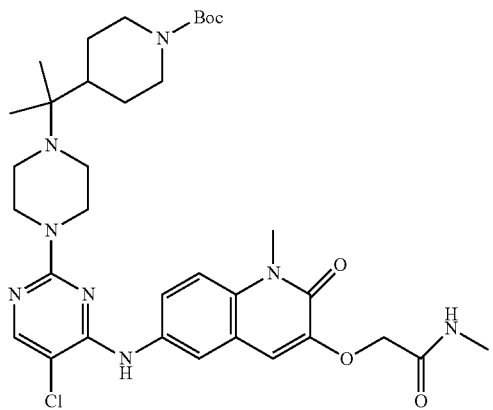 [SMILES: CNC(=O)COc1cc2cc(Nc3nc(N4CCN(C(C)(C)C5CCN(C(=O)OC(C)(C)C)CC5)CC4)ncc3Cl)ccc2n(C)c1=O]

Into a 30 mL sealed tube, was placed 1-[2-(piperidin-4-yl)propan-2-yl]piperazine (400.0 mg, 1.3 mmol, 1.0 equiv), 2-([6-[(2,5-dichloropyrimidin-4-yl)amino]-1-methyl-2-oxoquinolin-3-yl]oxy)-N-methylacetamide (523.0 mg, 1.3 mmol, 1.0 equiv) and DIEA (666.0 mg, 5.2 mmol, 4.0 equiv) in DMF (10 mL). The resulting mixture was stirred for 3 h at 100° C. in an oil bath. The reaction was then quenched by the addition of 150 mL of water/ice. The solids were collected by filtration and purified by a silica gel column eluting with dichloromethane/methanol (10:1). This resulted in 320.0 mg (36%) of tert-butyl 4-(2-[4-[5-chloro-4-(([1-methyl-3-[(methylcarbamoyl)methoxy]-2-oxoquinolin-6-yl]amino)pyrimidin-2-yl]piperazin-1-yl]propan-2-yl)piperidine-1-carboxylate as a yellow solid. LC/MS (ESI) m/z: 683.40 [M+1]$^+$.

Step 6: Preparation of 2-((6-((5-chloro-2-(4-(2-(piperidin-4-yl)propan-2-yl)piperazin-1-yl)pyrimidin-4-yl)amino)-1-methyl-2-oxo-1,2-dihydroquinolin-3-yl)oxy)-N-methylacetamide

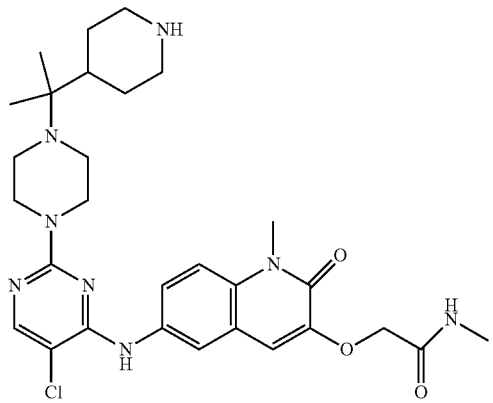 [SMILES: CNC(=O)COc1cc2cc(Nc3nc(N4CCN(C(C)(C)C5CCNCC5)CC4)ncc3Cl)ccc2n(C)c1=O]

Into a 100 mL round-bottom flask, was placed tert-butyl 4-(2-[4-[5-chloro-4-(([1-methyl-3-[(methylcarbamoyl)methoxy]-2-oxoquinolin-6-yl]amino)pyrimidin-2-yl]piperazin-1-yl]propan-2-yl)piperidine-1-carboxylate (300.0 mg, 0.4 mmol, 1.0 equiv) in DCM, to which hydrogen chloride in 1,4-dioxane solution (4.0 M, 5 mL) was added. The resulting mixture was stirred for 2 hours at room temperature and concentrated under reduced pressure. This resulted in 180.0 mg (77%) of 2-([6-[(5-chloro-2-[4-[2-(piperidin-4-yl)propan-2-yl]piperazin-1-yl]pyrimidin-4-yl)amino]-1-methyl-2-oxoquinolin-3-yl]oxy)-N-methylacetamide as a yellow solid. LC/MS (ESI) m/z: 583.40 [M+1]$^+$.

Step 7: Preparation of 2-((6-((5-chloro-2-(4-(2-(1-(2-(2,6-dioxopiperidin-3-yl)-1,3-dioxoisoindolin-5-yl)piperidin-4-yl)propan-2-yl)piperazin-1-yl)pyrimidin-4-yl)amino)-1-methyl-2-oxo-1,2-dihydroquinolin-3-yl)oxy)-N-methylacetamide

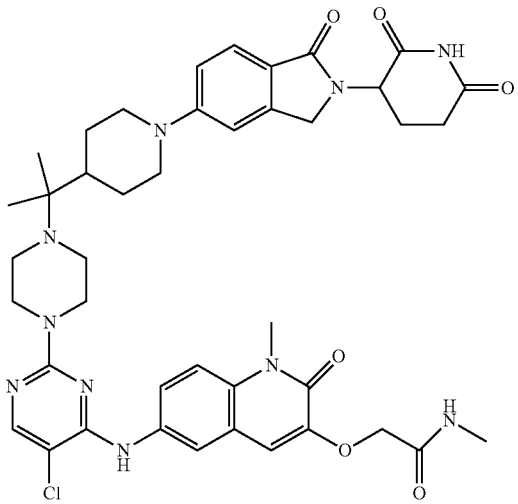 [SMILES: CNC(=O)COc1cc2cc(Nc3nc(N4CCN(C(C)(C)C5CCN(c6ccc7c(c6)CN(C6CCC(=O)NC6=O)C7=O)CC5)CC4)ncc3Cl)ccc2n(C)c1=O]

Into a 10 mL sealed tube, was placed 2-([6-[(5-chloro-2-[4-[2-(piperidin-4-yl)propan-2-yl]piperazin-1-yl]pyrimidin-4-yl)amino]-1-methyl-2-oxoquinolin-3-yl]oxy)-N-methylacetamide (150.0 mg, 0.3 mmol, 1.0 equiv), 2-(2,6-dioxopiperidin-3-yl)-5-fluoroisoindole-1,3-dione (67.0 mg, 0.3 mmol, 1.0 equiv) and DIEA (155.0 mg, 1.2 mmol, 4.0 equiv) in DMSO (2 mL). The resulting mixture was stirred for 3 hours at 100° C. in an oil bath. The crude product was purified by Prep-HPLC. This resulted in 33.7 mg (15%) of 2-[[6-([5-chloro-2-[4-[2-[1-[2-(2,6-dioxopiperidin-3-yl)-1,3-dioxoisoindol-5-yl]piperidin-4-yl]propan-2-yl]piperazin-1-yl]pyrimidin-4-yl]amino)-1-methyl-2-oxoquinolin-3-yl]oxy]-N-methylacetamide as a yellow solid. LC/MS (ESI) m/z: 839.35 [M+1]$^+$; $^1$H-NMR (300 MHz, DMSO-d$_6$) δ 11.06 (s, 1H), 8.83 (s, 1H), 8.03 (s, 1H), 7.99-7.82 (m, 2H), 7.85-7.71 (m, 1H), 7.71-7.62 (m, 1H), 7.53-7.41 (m, 1H), 7.33-7.28 (m, 1H), 7.28-7.19 (m, 1H), 7.11 (s, 1H), 5.11-5.00 (m, 1H), 4.56 (s, 2H), 4.19-4.01 (m, 2H), 3.71-3.50 (m, 9H), 2.99-2.80 (m, 3H), 2.70-2.61 (m, 4H), 2.03-1.77 (m, 5H), 1.34-1.18 (s, 3H), 0.85 (s, 7H).

Synthesis of 2-((6-((5-chloro-2-(4-((1-(2-(2,6-di-oxopiperidin-3-yl)-1,3-dioxoisoindolin-4-yl)piperidin-4-yl)methyl)piperazin-1-yl)pyrimidin-4-yl)amino)-1-methyl-2-oxo-1,2-dihydroquinolin-3-yl)oxy)-N-methylacetamide (Exemplary Compound 209)

Step 1: Preparation of benzyl 4-((1-(tert-butoxycarbonyl)piperidin-4-yl)methyl)piperazine-1-carboxylate

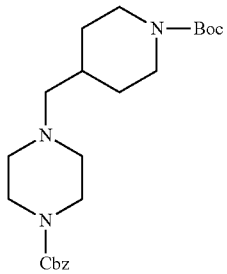 [SMILES: CC(C)(C)OC(=O)N1CCC(CN2CCN(C(=O)OCc3ccccc3)CC2)CC1]

To a solution of tert-butyl 4-(hydroxymethyl)piperidine-1-carboxylate (2 g, 9.3 mmol) in MeCN (20 mL) was added IBX (3.1 g, 11.2 mmol) at r.t. After stirred at 80° C. for 2 h. The mixture was filtered and concentrated. Then the crude was dissolved in EA (80 mL), washed with Na₂CO₃ solution (80 mL). The organic phase was concentrated to desired crude product as a yellow oil. To a solution of the crude product in DCM:EtOH=1:1 (20 mL) were added benzyl piperazine-1-carboxylate (3.07 g, 13.9 mmol) and NaBH₃CN (1.75 g, 27.9 mmol) at r.t. Then stirred at r.t for 2 h. The mixture was concentrated to give the crude product, which was purified by chromatography column with PE:EA=10:1~3:1 to give the product (1.5 g, 70% purity) as a yellow oil. LC/MS (ESI) m/z: 418.3 [M+1]⁺.

Step 2: Preparation of benzyl 4-(piperidin-4-ylmethyl)piperazine-1-carboxylate

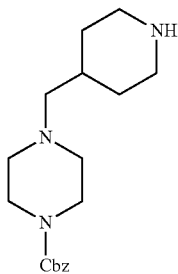 [SMILES: O=C(OCc1ccccc1)N1CCN(CC2CCNCC2)CC1]

A solution of benzyl 4-((1-(tert-butoxycarbonyl)piperidin-4-yl)methyl)piperazine-1-carboxylate (1.5 g, 3.6 mmol) in HCl/dioxane (10 mL) was stirred at r.t for 1 h. The mixture was concentrated to afford the desired product (0.8 g) as a yellow oil. LC/MS (ESI) m/z: 318.2 [M+1]⁺.

Step 3: Preparation of benzyl 4-((1-(2-(2,6-dioxopiperidin-3-yl)-1,3-dioxoisoindolin-4-yl)piperidin-4-yl)methyl)piperazine-1-carboxylate

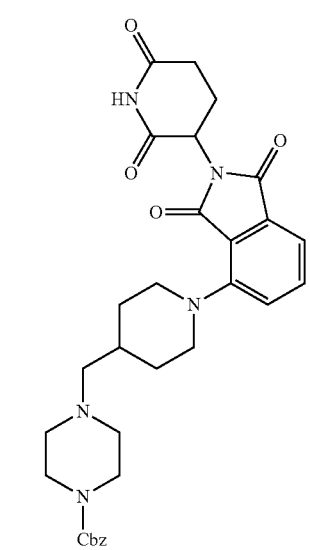 [SMILES: O=C1CCC(N2C(=O)c3cccc(N4CCC(CN5CCN(C(=O)OCc6ccccc6)CC5)CC4)c3C2=O)C(=O)N1]

To a solution of benzyl 4-(piperidin-4-ylmethyl)piperazine-1-carboxylate (0.8 g, 2.52 mmol) in DMAC (5 mL) were added 2-(2,6-dioxopiperidin-3-yl)-4-fluoroisoindoline-1,3-dione (580 mg, 2.1 mmol) and DIEA (677 mg, 5.25 mmol) at room temperature. After the mixture was stirred at 120° C. for 3 hours, the mixture was quenched with water (30 mL), extracted with EA (50 mL), concentrated, purified by flash to desired product (800 mg, 80% purity) as a yellow oil. LC/MS (ESI) m/z: 574.3 [M+1]⁺.

Step 4: Preparation of 2-(2,6-dioxopiperidin-3-yl)-4-(4-(piperazin-1-ylmethyl)piperidin-1-yl)isoindoline-1,3-dione

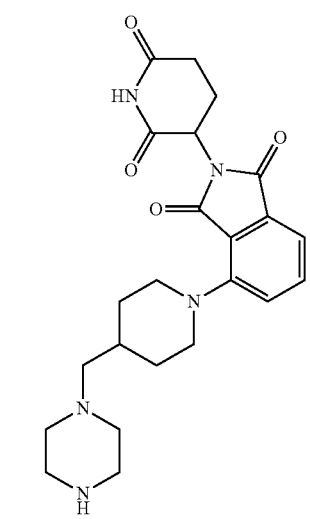 [SMILES: O=C1CCC(N2C(=O)c3cccc(N4CCC(CN5CCNCC5)CC4)c3C2=O)C(=O)N1]

A solution of benzyl 4-((1-(2-(2,6-dioxopiperidin-3-yl)-1,3-dioxoisoindolin-4-yl)piperidin-4-yl)methyl)piperazine-1-carboxylate (320 mg, 0.558 mmol) in MeOH (20 mL) was added 10% Pd/C (20 mg) at room temperature. Then the mixture was stirred at room temperature under $H_2$ for 2 hours. The mixture was filtered and concentrated to afford the product (240 mg, 95% yield) as a yellow oil. LC/MS (ESI) m/z: 440.2 $[M+1]^+$.

Step 5: Preparation of 2-((6-((5-chloro-2-(4-((1-(2-(2,6-dioxopiperidin-3-yl)-1,3-dioxoisoindolin-4-yl)piperidin-4-yl)methyl)piperazin-1-yl)pyrimidin-4-yl)amino)-1-methyl-2-oxo-1,2-dihydroquinolin-3-yl)oxy)-N-methylacetamide

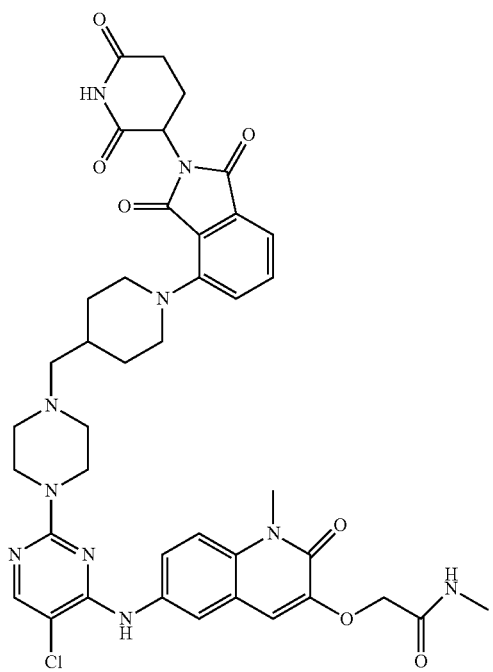 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(C)c1=O]

To a solution of 6-((2,5-dichloropyrimidin-4-yl)amino)-1,4-dimethylquinoxaline-2,3(1H,4H)-dione (100 mg, 0.245 mmol) in DMSO (3 mL) were added 2-(2,6-dioxo piperidin-3-yl)-4-(4-(piperazin-1-ylmethyl)piperidin-1-yl)isoindoline-1,3-dione (130 mg, 0.295 mmol) and DIEA (158 mg, 1.23 mmol) at room temperature. The mixture was stirred at 100° C. for 3 hours. The mixture was purified by prep-HPLC to afford the desired product (36 mg, 18.1% yield) as a yellow solid. LC/MS (ESI) m/z: 811.3 $[M+1]^+$; $^1$H-NMR (400 MHz, DMSO-$d_6$) δ 11.08 (s, 1H), 9.07 (s, 1H), 8.15 (s, 1H), 8.00-7.88 (m, 2H), 7.75-7.67 (m, 2H), 7.53-7.45 (m, 1H), 7.39-7.32 (m, 2H), 7.17 (s, 1H), 5.13-5.05 (m, 1H), 4.59 (s, 2H), 4.57-4.42 (m, 2H), 3.80-3.63 (m, 5H), 3.63-3.52 (m, 2H), 3.39-3.25 (m, 2H), 3.18-3.02 (m, 4H), 2.97-2.82 (m, 3H), 2.70-2.52 (m, 5H), 2.13-1.99 (m, 2H), 1.91-1.82 (m, 2H), 1.57-1.42 (m, 2H).

Synthesis of 2-((6-((5-chloro-2-(4-((4-(2-(2,6-dioxopiperidin-3-yl)-1,3-dioxoisoindolin-4-yl)piperazin-1-yl)methyl)-4-hydroxypiperidin-1-yl)pyrimidin-4-yl)amino)-1-methyl-2-oxo-1,2-dihydroquinolin-3-yl)oxy)-N-methylacetamide
(Exemplary Compound 253)

Step 1: Preparation of tert-butyl 4-((4-(2-(2,6-dioxopiperidin-3-yl)-1,3-dioxoisoindolin-4-yl)piperazin-1-yl)methyl)-4-hydroxypiperidine-1-carboxylate

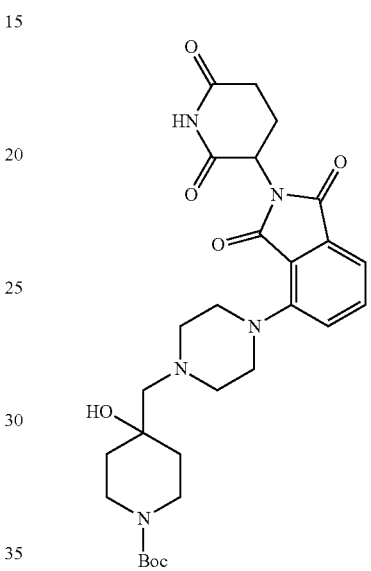

To a stirred solution of tert-butyl 4-hydroxy-4-(piperazin-1-ylmethyl)piperidine-1-carboxylate (497.00 mg, 1.660 mmol, 1.00 equiv) and 2-(2,6-dioxopiperidin-3-yl)-4-fluoroisoindole-1,3-dione (458.50 mg, 1.660 mmol, 1 equiv) in DMSO (5 mL) was added DIEA (643.59 mg, 4.980 mmol, 3.0 equiv) drop wise at room temperature under nitrogen atmosphere. The resulting mixture was stirred for 3 hours at 120° C. nitrogen atmosphere. The residue was purified by reverse flash chromatography to afford tert-butyl 4-([4-[2-(2,6-dioxopiperidin-3-yl)-1,3-dioxoisoindol-4-yl]piperazin-1-yl]methyl)-4-hydroxypiperidine-1-carboxylate (403 mg, 43%) as a yellow solid. LC/MS (ESI) m/z: 556.30 $[M+1]^+$.

Step 2: Preparation of 2-(2,6-dioxopiperidin-3-yl)-4-(4-((4-hydroxypiperidin-4-yl)methyl)piperazin-1-yl)isoindoline-1,3-dione

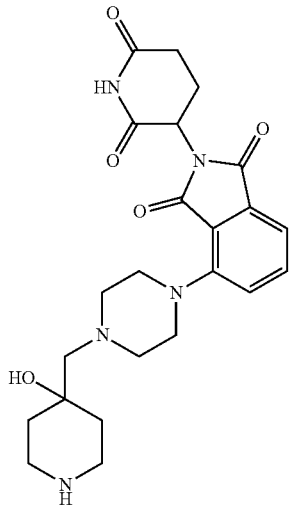 [SMILES: O=C1CCC(N2C(=O)c3cccc(N4CCN(CC5(O)CCNCC5)CC4)c3C2=O)C(=O)N1]

To a stirred solution of tert-butyl 4-([4-[2-(2,6-dioxopiperidin-3-yl)-1,3-dioxoisoindol-4-yl]piperazin-1-yl]methyl)-4-hydroxypiperidine-1-carboxylate (280.00 mg, 0.504 mmol, 1.00 equiv) in 1,4-dioxane was added HCl (gas) in 1,4-dioxane (15 mL, 4 M) drop wise at room temperature under nitrogen atmosphere. The resulting mixture was stirred for 30 min at room temperature under nitrogen atmosphere. The reaction was concentrated under reduced pressure to give 2-(2,6-dioxopiperidin-3-yl)-4-[4-[(4-hydroxypiperidin-4-yl)methyl]piperazin-1-yl]isoindole-1,3-dione hydrochloride (220.5 mg, 89%) as a solid. LC/MS (ESI) m/z: 456.20 [M+1]$^+$.

Step 3: Preparation of 2-((6-((5-chloro-2-(4-((4-(2-(2,6-dioxopiperidin-3-yl)-1,3-dioxoisoindolin-4-yl)piperazin-1-yl)methyl)-4-hydroxypiperidin-1-yl)pyrimidin-4-yl)amino)-1-methyl-2-oxo-1,2-dihydroquinolin-3-yl)oxy)-N-methylacetamide

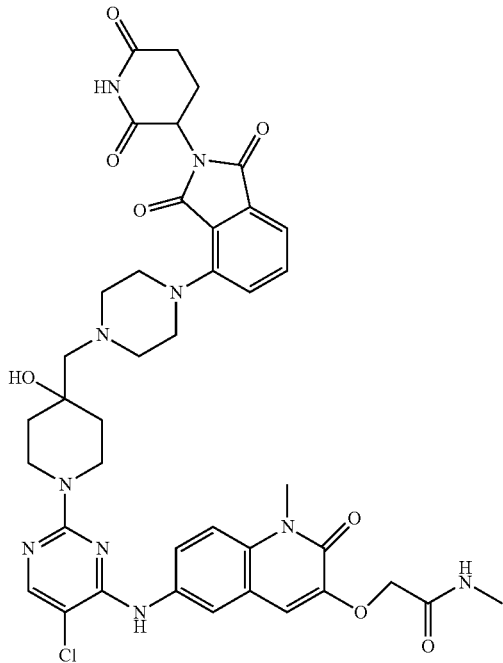 [SMILES: CNC(=O)COc1cc2cc(Nc3nc(N4CCC(O)(CN5CCN(c6cccc7c6C(=O)N(C6CCC(=O)NC6=O)C7=O)CC5)CC4)ncc3Cl)ccc2n(C)c1=O]

To a stirred solution of 2-(2,6-dioxopiperidin-3-yl)-4-[4-[(4-hydroxypiperidin-4-yl)methyl]piperazin-1-yl]isoindole-1,3-dione hydrochloride (229.5 mg, 1.2 equiv) and 2-([6-[(2,5-dichloropyrimidin-4-yl)amino]-1-methyl-2-oxoquinolin-3-yl]oxy)-N-methylacetamide (170.3 mg, 1.00 equiv) in DMSO (6 mL) was added DIEA (162.0 mg, 3.0 equiv) at room temperature under nitrogen atmosphere. The resulting mixture was stirred for 2 hours at 100° C. nitrogen atmosphere. The residue was purified by reverse flash chromatography to afford 2-[[6-([5-chloro-2-[4-([4-[2-(2,6-dioxopiperidin-3-yl)-1,3-dioxoisoindol-4-yl]piperazin-1-yl]methyl)-4-hydroxypiperidin-1-yl]pyrimidin-4-yl]amino)-1-methyl-2-oxoquinolin-3-yl]oxy]-N-methylacetamide (56.6 mg, 17%) as a yellow solid. LC/MS (ESI) m/z: 827.25 [M+1]$^+$; $^1$H-NMR (400 MHz, DMSO-d$_6$) δ 11.08 (s, 1H), 8.81 (s, 1H), 8.03 (s, 1H), 7.96 (d, J=4.6 Hz, 1H), 7.90 (d, J=2.4 Hz, 1H), 7.77 (d, J=9.0 Hz, 1H), 7.69 (t, J=7.8 Hz, 1H), 7.48 (d, J=9.2 Hz, 1H), 7.37-7.28 (m, 2H), 7.12 (s, 1H), 5.08 (m, 1H), 4.57 (s, 2H), 4.27 (s, 1H), 4.11 (s, 2H), 3.68 (s, 3H), 3.23-3.21 (m, 5H), 2.85-2.81 (m, 2H), 2.73-2.63 (m, 8H), 2.58 (d, J=17.2 Hz, 2H), 2.34 (s, 2H), 1.52 (s, 4H).

Synthesis of 2-((6-((5-chloro-2-(4-(2-((1-(2-(2,6-dioxopiperidin-3-yl)-1,3-dioxoisoindolin-4-yl)azetidin-3-yl)oxy)ethyl)piperidin-1-yl)pyrimidin-4-yl)amino)-1-methyl-2-oxo-1,2-dihydroquinolin-3-yl)oxy)-N-methylacetamide (Exemplary Compound 254)

Step 1: Preparation of tert-butyl 4-(2-((1-(2-(2,6-dioxopiperidin-3-yl)-1,3-dioxoisoindolin-4-yl)azetidin-3-yl)oxy)ethyl)piperidine-1-carboxylate

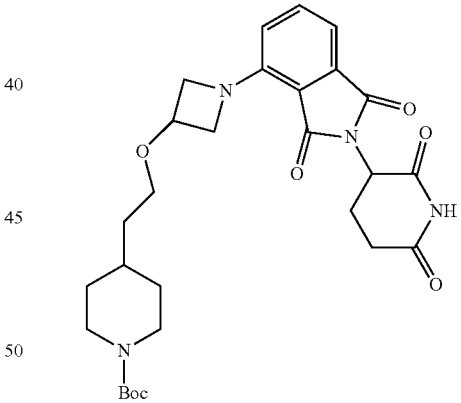

Into a 30 mL sealed tube, was placed tert-butyl 4-[2-(azetidin-3-yloxy)ethyl]piperidine-1-carboxylate (500.0 mg, 1.8 mmol, 1.0 equiv), 2-(2,6-dioxopiperidin-3-yl)-4-fluoroisoindole-1,3-dione (486.0 mg, 1.8 mmol, 1.0 equiv) and DIEA (908.0 mg, 7.0 mmol, 4.0 equiv) in DMSO (15 mL). The resulting mixture was stirred for 1.5 hours at 100° C. in an oil bath. The resulting solution was extracted with ethyl acetate (100 mL×3) and the organic layers combined. The residue was applied onto a silica gel column eluting with ethyl acetate/petroleum ether (1:1). This resulted in 440 mg (45%) of tert-butyl 4-[2-([1-[2-(2,6-dioxopiperidin-3-yl)-1,3-dioxoisoindol-4-yl]azetidin-3-yl]oxy)ethyl]piperidine-1-carboxylate as a yellow solid. LC/MS (ESI) m/z: 541.30 [M+1]$^+$.

Step 2: Preparation of 2-(2,6-dioxopiperidin-3-yl)-4-(3-(2-(piperidin-4-yl)ethoxy)azetidin-1-yl)isoindoline-1,3-dione

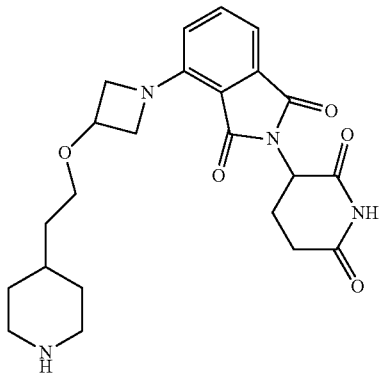 [SMILES: O=C1CCC(N2C(=O)c3cccc(N4CC(OCCC5CCNCC5)C4)c3C2=O)C(=O)N1]

Into a 100 mL round-bottom flask, was placed tert-butyl 4-[2-([1-[2-(2,6-dioxopiperidin-3-yl)-1,3-dioxoisoindol-4-yl]azetidin-3-yl]oxy)ethyl]piperidine-1-carboxylate (200.0 mg, 0.4 mmol, 1.0 equiv) in DCM (30 mL). This was followed by the addition of trimethylsilyl triflate (98.6 mg, 0.4 mmol, 1.2 equiv) dropwise with stirring at 0° C. The resulting mixture was stirred for 2 hours at room temperature. The resulting mixture was concentrated under reduced pressure. This resulted in 150.0 mg (93%) of 2-(2,6-dioxopiperidin-3-yl)-4-[3-[2-(piperidin-4-yl)ethoxy]azetidin-1-yl]isoindole-1,3-dione as a yellow solid. LC/MS (ESI) m/z: 441.20 [M+1]$^+$.

Step 3: Preparation of 2-((6-((5-chloro-2-(4-(2-((1-(2-(2,6-dioxopiperidin-3-yl)-1,3-dioxoisoindolin-4-yl)azetidin-3-yl)oxy)ethyl)piperidin-1-yl)pyrimidin-4-yl)amino)-1-methyl-2-oxo-1,2-dihydroquinolin-3-yl)oxy)-N-methylacetamide

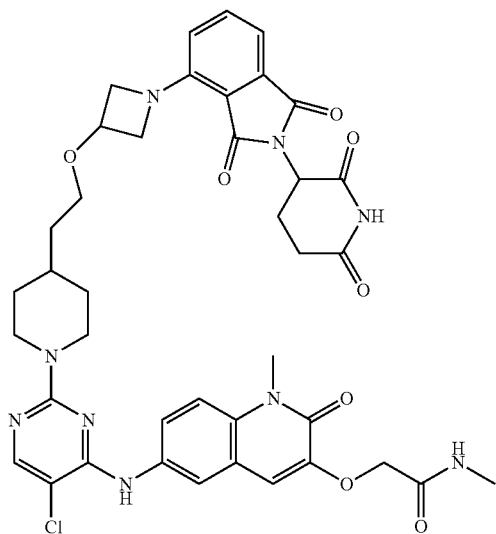 [SMILES: CNC(=O)COc1cc2cc(Nc3nc(N4CCC(CCOC5CN(c6cccc7c6C(=O)N(C6CCC(=O)NC6=O)C7=O)C5)CC4)ncc3Cl)ccc2n(C)c1=O]

Into a 10 mL sealed tube, was placed 2-(2,6-dioxopiperidin-3-yl)-4-[3-[2-(piperidin-4-yl)ethoxy]azetidin-1-yl]isoindole-1,3-dione (100.0 mg, 0.2 mmol, 1.0 equiv), 2-([6-[(2,5-dichloropyrimidin-4-yl)amino]-1-methyl-2-oxoquinolin-3-yl]oxy)-N-methylacetamide (92.5 mg, 0.2 mmol, 1.0 equiv) and DIEA (117.0 mg, 0.9 mmol, 4.0 equiv) in DMSO (5 mL). The resulting solution was stirred for 4 hours at 100° C. in an oil bath. The crude product was purified by Prep-HPLC. This resulted in 75.0 mg (41%) of 2-([6-[(5-chloro-2-[4-[2-([1-[2-(2,6-dioxopiperidin-3-yl)-1,3-dioxoisoindol-4-yl]azetidin-3-yl]oxy)ethyl]piperidin-1-yl]pyrimidin-4-yl)amino]-1-methyl-2-oxoquinolin-3-yl]oxy)-N-methylacetamide as a yellow solid. LC/MS (ESI) m/z: 812.25 [M+1]$^+$; $^1$H-NMR (400 MHz, DMSO-d$_6$) δ 11.06 (s, 1H), 8.80 (s, 1H), 8.01 (s, 1H), 8.01-7.87 (m, 2H), 7.87-7.69 (m, 1H), 7.69-7.58 (m, 1H), 7.58-7.31 (m, 1H), 7.06 (s, 1H), 6.85-6.72 (m, 1H), 6.70-6.51 (m, 1H), 5.13-4.85 (m, 1H), 4.56 (s, 2H), 4.55-4.37 (m, 3H), 4.31-4.09 (m, 2H), 3.99-3.77 (m, 2H), 3.65 (s, 3H), 3.53-3.40 (m, 2H), 2.98-2.71 (m, 3H), 2.71-2.52 (m, 4H), 2.13-1.87 (m, 1H), 1.77-1.58 (m, 3H), 1.58-1.35 (m, 2H), 1.31-1.25 (m, 2H), 1.18-0.90 (m, 2H).

Exemplary Synthesis of 2-([6-[(5-chloro-2-[4-[(14-[[2-(3-methyl-2,6-dioxopiperidin-3-yl)-1-oxo-3H-isoindol-5-yl]oxy]-3,6,9,12-tetraoxatetradecan-1-yl)oxy]piperidin-1-yl]pyrimidin-4-yl)amino]-1-methyl-2-oxoquinolin-3-yl]oxy)-N-methylacetamide (Exemplary Compound 84)

Step 1: Synthesis of 14-[(4-methylbenzenesulfonyl)oxy]-3,6,9,12-tetraoxatetradecan-1-ol

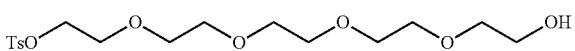 [SMILES: Cc1ccc(S(=O)(=O)OCCOCCOCCOCCOCCO)cc1]

Into a 500-mL round-bottom flask, was placed 3,6,9,12-tetraoxatetradecane-1,14-diol (9.53 g, 39.995 mmol, 1 equiv) in dichloromethane (200 mL), to which was added Ag$_2$O (13.90 g, 59.982 mmol, 1.50 equiv) and TsCl (7.78 g, 40.808 mmol, 1.02 equiv) at 0° C. in a water/ice bath. Then KI (1.33 g, 8.012 mmol, 0.20 equiv) was added. The resulting mixture was stirred for 2 hr at room temperature. The solids were filtered out and the filtrate was concentrated under vacuum. The residue was applied onto a silica gel column eluting with dichloromethane/methanol (12/1). This resulted in 9.61 g (61.22%) of 14-[(4-methylbenzenesulfonyl)oxy]-3,6,9,12-tetraoxatetradecan-1-ol as a light yellow oil. MS (ES$^+$): m/z 392.95[MH$^+$]

Step 2: Synthesis of 14-((tetrahydro-2H-pyran-2-yl)oxy)-3,6,9,12-tetraoxatetradecyl 4-methylbenzenesulfonate

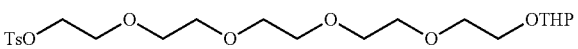

Into a 250-mL round-bottom flask, was placed 14-[(4-methylbenzenesulfonyl)oxy]-3,6,9,12-tetraoxatetradecan-1-ol (9.22 g, 23.493 mmol, 1 equiv) in dichloromethane (150 mL), to which was added DHP (2.17 g, 25.798 mmol, 1.10 equiv) and PPTS (1.18 g, 4.696 mmol, 0.20 equiv) in sequence. The resulting mixture was stirred for 16 hr at room temperature. The mixture was quenched by 100 mL water and extracted with ethyl acetate (50 mL×3). The organic layers were combined, washed with brine, dried over anhy-

Step 3: Synthesis of tert-butyl 4-((14-((tetrahydro-2H-pyran-2-yl)oxy)-3,6,9,12-tetraoxatetradecyl)oxy)piperidine-1-carboxylate

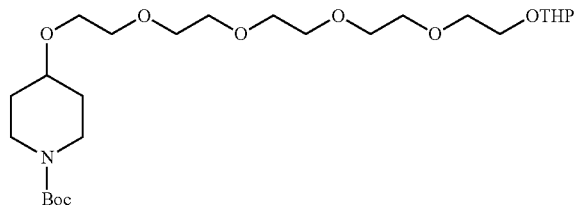

Into a 250-mL round-bottom flask purged and maintained with an inert atmosphere of nitrogen, was placed tert-butyl 4-hydroxypiperidine-1-carboxylate (3.62 g, 17.986 mmol, 1.20 equiv) in DMF (70 mL), to which was added NaH (1.2 g, 30.003 mmol, 2.00 equiv, 60%) in portions at 0° C. The resulting mixture was stirred for 0.5 hr at room temperature. To this was added 14-((tetrahydro-2H-pyran-2-yl)oxy)-3,6,9,12-tetraoxatetradecyl 4-methylbenzenesulfonate (7.15 g, 15.003 mmol, 1 equiv) in portions at room temperature. The reaction mixture was allowed to stir for additional 3 hr at 60° C. in an oil bath. The reaction mixture was cooled to room temperature and then was quenched by the addition of 200 mL water. The resulting mixture was extracted with ethyl acetate (3×120 mL) and the organic layers were combined, washed with brine (2×150 mL), dried over anhydrous sodium sulfate and concentrated under vacuum. The residue was applied onto a silica gel column eluting with ethyl acetate/petroleum ether (2/3). This resulted in 5.46 g (72%) of the title compound as a light yellow oil. MS (ES⁺): m/z 528.15 [MNa⁺]

Step 4: Synthesis of 14-(piperidin-4-yloxy)-3,6,9,12-tetraoxatetradecan-1-ol hydrochloride

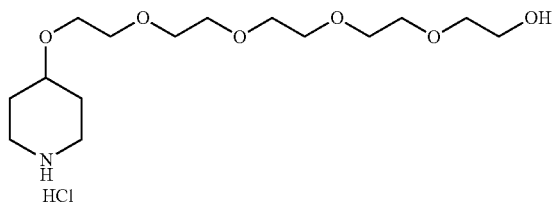 [SMILES: OCCOCCOCCOCCOCCOC1CCNCC1 ; Cl]

Into a 100-mL round-bottom flask, was placed tert-butyl 4-((14-((tetrahydro-2H-pyran-2-yl)oxy)-3,6,9,12-tetraoxatetradecyl)oxy)piperidine-1-carboxylate (1.93 g, 3.817 mmol, 1 equiv) in dioxane (20 mL), to which was added hydrogen chloride solution (4M in dioxane, 20 mL). The resulting solution was stirred for 1 hr at room temperature. The mixture was concentrated under vacuum to afford the title compound as 1.72 g of a crude yellow oil. MS (ES⁺): m/z 322.00 [MH⁺]

Step 5: Synthesis of 2-([6-[(5-chloro-2-[4-[(14-hydroxy-3,6,9,12-tetraoxatetradecan-1-yl)oxy]piperidin-1-yl]pyrimidin-4-yl)amino]-1-methyl-2-oxo-1,2-dihydroquinolin-3-yl]oxy)-N-methylacetamide

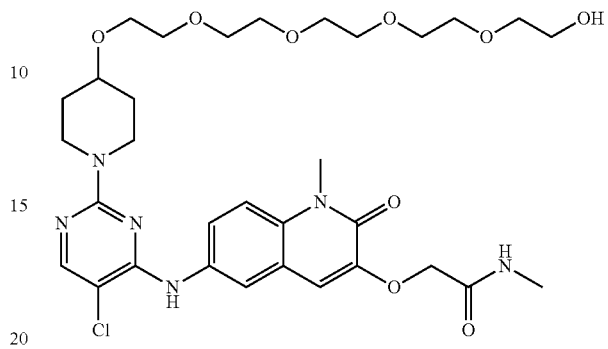

Into a 100-mL round-bottom flask purged and maintained with an inert atmosphere of nitrogen, was placed 2-([6-[(2,5-dichloropyrimidin-4-yl)amino]-1-methyl-2-oxo-1,2-dihydroquinolin-3-yl]oxy)-N-methylacetamide (1.30 g, 3.184 mmol, 1 equiv), 14-(piperidin-4-yloxy)-3,6,9,12-tetraoxatetradecan-1-ol hydrochloride (1.72 g, 3.820 mmol, 1.20 equiv), DIEA (5 mL, 28.706 mmol, 9.01 equiv) in DMSO (50 mL). The resulting mixture was stirred for 4 hr at 100° C. in an oil bath. The reaction mixture was cooled to room temperature and diluted with 300 mL water. The resulting mixture was extracted with ethyl acetate (200 mL×3) and the organic layers were combined, washed with brine, dried over anhydrous sodium sulfate and concentrated. The residue was applied onto a silica gel column eluting with dichloromethane/methanol (12/1). This resulted in 1.83 g (83%) of the title compound as a yellow solid. MS (ES⁺): m/z 693.10/695.10 [MH⁺]

Step 6: Synthesis of 14-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)-3,6,9,12-tetraoxatetradecan-1-yl 4-methylbenzene-1-sulfonate

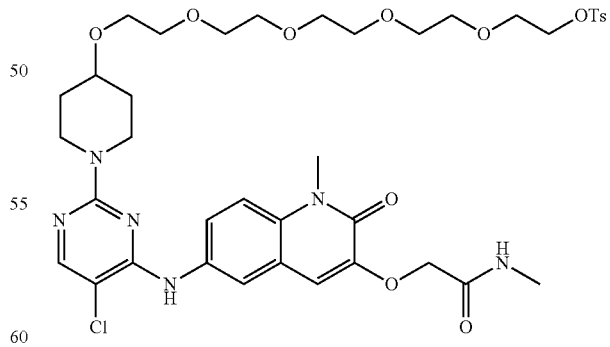

Into a 100-mL round-bottom flask, was placed 2-([6-[(5-chloro-2-[4-[(14-hydroxy-3,6,9,12-tetraoxatetradecan-1-yl)oxy]piperidin-1-yl]pyrimidin-4-yl)amino]-1-methyl-2-oxo-1,2-dihydroquinolin-3-yl]oxy)-N-methylacetamide (600 mg, 0.866 mmol, 1 equiv) in dichloromethane (20 mL), to which was added TEA (879 mg, 8.687 mmol, 10.04 equiv), 4-methylbenzene-1-sulfonyl chloride (827 mg, 4.338 mmol, 5.01 equiv) and DMAP (21 mg, 0.172 mmol, 0.20 equiv) at room temperature. The resulting solution was stirred for 12 hr at room temperature. The reaction was then quenched by the addition of 30 mL water. The resulting mixture was extracted with dichloromethane (3×30 mL) and the organic layers were combined, washed with brine, dried over anhydrous sodium sulfate and concentrated. The residue was applied onto a silica gel pre-TLC eluting with dichloromethane/methanol (10:1). This resulted in 610 mg (83.17%) of 14-([1-[5-chloro-4-([1-methyl-3-[(methylcarbamoyl)methoxy]-2-oxo-1,2-dihydroquinolin-6-yl]amino)pyrimidin-2-yl]piperidin-4-yl]oxy)-3,6,9,12-tetraoxatetradecan-1-yl 4-methylbenzene-1-sulfonate as a yellow solid. MS (ES$^+$): m/z 847.10/849.10 [MH$^+$]

Step 7: Synthesis of methyl 4-[(tert-butyldimethylsilyl)oxy]-2-methylbenzoate

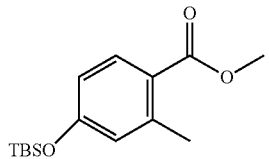 [SMILES: COC(=O)c1ccc(O[Si](C)(C)C(C)(C)C)cc1C]

Into a 250-mL round-bottom flask, was placed methyl 4-hydroxy-2-methylbenzoate (5 g, 30.09 mmol, 1.00 equiv), dichloromethane (70 mL), tert-Butyldimethylsilyl chloride (5 g), imidazole (5 g). The resulting solution was stirred for 4 h at 25° C. The resulting solution was diluted with water (50 mL). The resulting solution was extracted with dichloromethane (50 mL×3) and the organic layers combined. The resulting mixture was washed with saturated sodium chloride aqueous solution (40 mL×2). The mixture was dried over anhydrous sodium sulfate and concentrated under vacuum. This resulted in 7.5 g (89%) of methyl 4-[(tert-butyldimethylsilyl)oxy]-2-methylbenzoate as yellow oil. MS (ES$^+$): m/z 281.05 [MH$^+$].

Step 8: Synthesis methyl 2-(bromomethyl)-4-[(tert-butyldimethylsilyl)oxy]benzoate

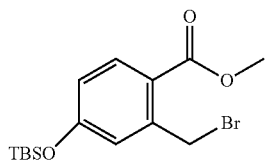 [SMILES: COC(=O)c1ccc(O[Si](C)(C)C(C)(C)C)cc1CBr]

Into a 250-mL round-bottom flask, was placed methyl 4-[(tert-butyldimethylsilyl)oxy]-2-methylbenzoate (7.1 g, 25.32 mmol, 1.00 equiv), carbontetrachloride (150 mL), N-bromosuccinimide (4.7 g, 26.41 mmol, 1.04 equiv), 2,2'-azobisisobutyronitrile (500 mg, 3.04 mmol, 0.12 equiv). The resulting solution was stirred for 3 h at 70° C. The resulting mixture was washed with saturated sodium thiosulfate solution (200 mL). The resulting solution was extracted with ethyl acetate (50 mL×3) and the organic layers combined and dried over anhydrous sodium sulfate and concentrated under vacuum. The residue was applied onto a silica gel column with ethyl acetate/petroleum ether (1:10). This resulted in 8.1 g (89%) of methyl 2-(bromomethyl)-4-[(tert-butyldimethylsilyl)oxy]benzoate as light yellow oil. MS (ES$^+$): m/z 358.90/360.90 [MH$^+$]

Step 9: Synthesis of ethyl 2-[(E)-(phenylmethylidene)amino]propanoate

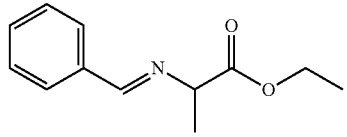

Into a 250-mL round-bottom flask, was placed ethyl 2-aminopropanoate hydrochloride (5.0 g, 32.55 mmol, 1.00 equiv), dichloromethane (50 mL), magnesium sulfate (3.0 g). This was followed by the addition of triethylamine (6.0 mL, 1.35 equiv) dropwise with stirring, after stirred 30 min. To this was added benzaldehyde (3.29 mL, 1.00 equiv) dropwise with stirring. The resulting solution was stirred overnight at room temperature. The solids were filtered out, washed with dichloromethane (50 mL). The resulting mixture was concentrated under vacuum. The resulting mixture was washed with ethyl acetate/petroleum ether=(1/2) (100 mL). The solids were filtered out. The filtrate was concentrated under vacuum. This resulted in 6.43 g (96%) of ethyl 2-[(E)-(phenylmethylidene)amino]propanoate as colorless oil.

Step 10: Synthesis of 3-methyl-3-[(E)-(phenylmethylidene) amino] piperidine-2, 6-dione

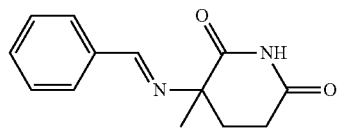

Into a 250-mL 3-necked round-bottom flask purged and maintained with an inert atmosphere of nitrogen, was placed ethyl 2-[(E)-(phenylmethylidene)amino]propanoate (5.43 g, 26.46 mmol, 1.00 equiv), tetrahydrofuran (50 mL), prop-2-enamide (2.82 g, 39.67 mmol, 1.50 equiv). This was followed by the addition of t-BuOK (3.26 g, 29.05 mmol, 1.10 equiv) in portions at 0° C., after stirred 30 min at 0° C. To this was added NH$_4$Cl (1.54 g, 28.79 mmol, 1.10 equiv) in portions at 0° C. The resulting solution was stirred for 20 min at 0° C. The reaction was then quenched by the addition of water/ice (50 mL). The resulting solution was extracted with ethyl acetate (200 mL) and the organic layers combined. The resulting mixture was washed with sodium chloride (30 mL). The mixture was dried over anhydrous sodium sulfate and concentrated under vacuum. This resulted in 5.6 g (92%) of 3-methyl-3-[(E)-(phenylmethylidene) amino] piperidine-2, 6-dione as a white solid. MS (ES$^+$): m/z 230.90 [MH$^+$]

Step 11: Synthesis of 3-amino-3-methylpiperidine-2,6-dione hydrochloride

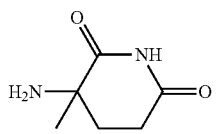

Into a 250-mL round-bottom flask, was placed 3-methyl-3-[(E)-(phenylmethylidene) amino] piperidine-2,6-dione (6.0 g, 26.06 mmol, 1.00 equiv), THF (20 mL). This was followed by the addition of hydrogen chloride (4M) in dioxane (100 mL) dropwise with stirring at 0° C. The resulting solution was stirred for 5 h at room temperature. The resulting mixture was concentrated under vacuum. This resulted in 4.3 g (92%) of 3-amino-3-methylpiperidine-2,6-dione hydrochloride as a white solid.

Step 12: Synthesis of 3-(5-hydroxy-1-oxo-3H-isoindol-2-yl)-3-methylpiperidine-2,6-dione

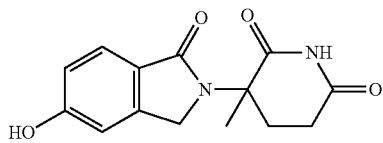 [SMILES: CC1(N2Cc3cc(O)ccc3C2=O)CCC(=O)NC1=O]

Into a 50-mL round-bottom flask, was placed a solution of methyl 2-(bromomethyl)-4-[(tert-butyldimethylsilyl)oxy]benzoate (1.06 g, 2.800 mmol, 1.00 equiv), DIEA (1085 mg, 8.399 mmol, 3.00 equiv), 3-amino-3-methylpiperidine-2,6-dione hydrochloride (400 mg, 2.240 mmol, 0.80 equiv) in CH$_3$CN (20 mL). The resulting solution was stirred overnight at 60° C. in an oil bath. Then 10 ml of HOAc was added, and the mixture was heated to 80° C. and stirred for additional 1 h. The mixture was cooled to room temperature and filtered. The filtrate was concentrated under vacuum. This resulted in 410 mg (53%) of 3-(5-hydroxy-1-oxo-3H-isoindol-2-yl)-3-methylpiperidine-2,6-dione as a white solid. MS (ES$^+$): m/z 275.05 [MH$^+$]

Step 13: 2-([6-[(5-chloro-2-[4-[(14-[[2-(3-methyl-2,6-dioxopiperidin-3-yl)-1-oxo-3H-isoindol-5-yl]oxy]-3,6,9,12-tetraoxatetradecan-1-yl)oxy]piperidin-1-yl]pyrimidin-4-yl)amino]-1-methyl-2-oxoquinolin-3-yl]oxy)-N-methylacetamide Into a 10-mL sealed tube purged and maintained with an inert atmosphere of nitrogen, was placed 14-([1-[5-chloro-4-([1-methyl-3-[(methylcarbamoyl)methoxy]-2-oxoquinolin-6-yl]amino)pyrimidin-2-yl]piperidin-4-yl]oxy)-3,6,9,12-tetraoxatetradecan-1-yl 4-methylbenzenesulfonate (100 mg, 0.118 mmol, 1.00 equiv), K$_2$CO$_3$ (48.93 mg, 0.354 mmol, 3.00 equiv), 3-(5-hydroxy-1-oxo-3H-isoindol-2-yl)-3-methylpiperidine-2,6-dione (25.89 mg, 0.094 mmol, 0.8 equiv) in DMF (4 mL). The resulting solution was stirred for 4 h at 70° C. in an oil bath. The reaction mixture was purified by Prep-HPLC with the following conditions: Column; mobile phase, Water (10 mmol/L NH$_4$HCO$_3$) and CH$_3$CN (25% PhaseB up to 55% in 8 min); Detector, uv. This resulted in 23 mg (21%) of 2-([6-[(5-chloro-2-[4-[(14-[[2-(3-methyl-2,6-dioxopiperidin-3-yl)-1-oxo-3H-isoindol-5-yl]oxy]-3,6,9,12-tetraoxatetradecan-1-yl)oxy]piperidin-1-yl]pyrimidin-4-yl)amino]-1-methyl-2-oxoquinolin-3-yl]oxy)-N-methylacetamide as a white solid. 1H NMR (300 MHz, DMSO-d6) δ 10.84 (s, 1H), 8.85 (s, 1H), 8.05 (s, 1H), 7.96 (m, 2H), 7.75 (m, 1H), 7.50 (m, 2H), 7.13 (d, J=6.0 Hz, 2H), 7.03 (m, 1H), 4.59 (s, 4H), 4.14 (m, 2H), 4.04 (s, 2H), 3.76 (m, 6H), 3.68 (s, 6H), 3.54 (m, 9H), 3.30 (m, 3H), 2.62 (s, 6H), 1.90 (s, 3H), 1.87 (s, 3H), 1.83 (s, 2H); LC-MS (ES$^+$): m/z 949.30 [MH$^+$]

Exemplary Synthesis of 5-((1r,3r)-3-(((1-(4-chloro-5-((1-methyl-2-oxo-1,2,3,4-tetrahydroquinolin-6-yl)amino)-2-nitrophenyl)piperidin-4-yl)methyl)(methyl)amino)cyclobutoxy)-2-(2,6-dioxopiperidin-3-yl)isoindoline-1,3-dione (Exemplary Compound 85)

Step 1: Preparation of tert-butyl((1r,3r)-3-((2-(2,6-dioxopiperidin-3-yl)-1,3-dioxoisoindolin-5-yl)oxy)cyclobutyl)(methyl)carbamate

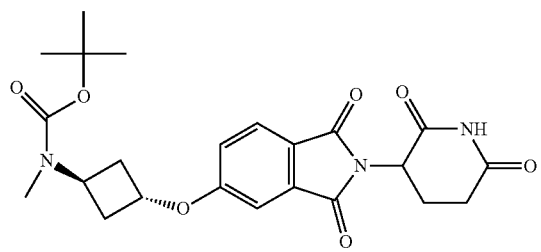

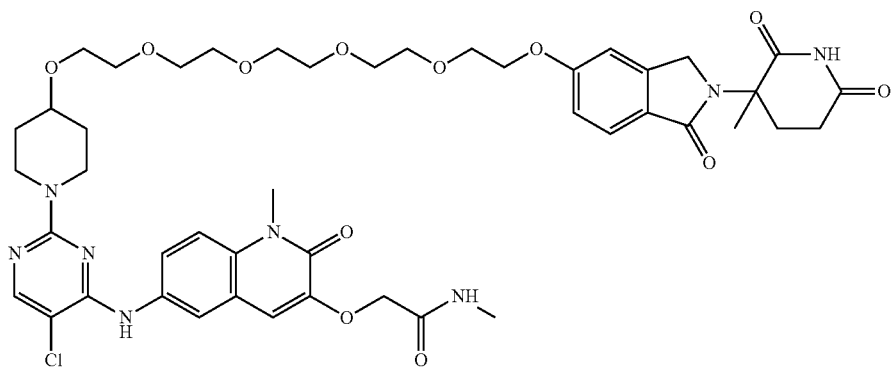 [SMILES: CNC(=O)COc1cc2cc(Nc3nc(N4CCC(OCCOCCOCCOCCOCCOc5ccc6c(c5)CN(C5(C)CCC(=O)NC5=O)C6=O)CC4)ncc3Cl)ccc2n(C)c1=O]

A solution of tert-butyl ((1s,3s)-3-hydroxycyclobutyl)(methyl)carbamate [prepared according to procedures found in WO2016187723A1] (50 mg, 0.25 mmol), 2-(2,6-dioxopiperidin-3-yl)-5-hydroxyisoindoline-1,3-dione (69 mg, 0.25 mmol), PPh$_3$ (131 mg, 0.5 mmol) in THF (1 mL) was stirred at 80° C. for 5 min. Then the mixture was added DIAD (101 mg, 0.5 mmol). The mixture was stirred at 80° C. for 15 min. The reaction was diluted with water (3 mL) and extracted with DCM (10 mL). The organic phase was concentrated under vacuum. The residue was purified by column chromatography (MeOH:DCM=1:50-1:10) to afford 45 mg of the title compound. MS (ES$^+$): m/z 402.1 [M−55]$^+$ Step 2: Preparation of 2-(2,6-dioxopiperidin-3-yl)-5-(((1r,3r)-3-(methylamino)cyclobutoxy)isoindoline-1,3-dione

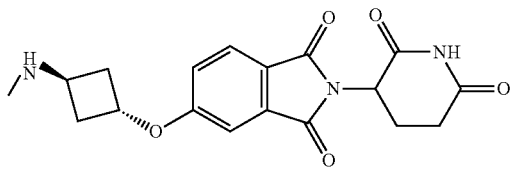 [SMILES: CN[C@H]1C[C@H](Oc2ccc3c(c2)C(=O)N(C2CCC(=O)NC2=O)C3=O)C1]

To a solution of tert-butyl((1,3r)-3-((2-(2,6-dioxopiperidin-3-yl)-1,3-dioxoisoindolin-5-yl)oxy)cyclobutyl)(methyl)carbamate (200 mg, 0.437 mmol) in DCM (3 mL) was added TFA (2 mL). The mixture was stirred at rt for 0.5 h. The organic phase was concentrated under vacuum to afford the desired product as 177 mg of a colorless oil. MS (ES$^+$): m/z 358.2 [M+1]$^+$ Step 3: Preparation of (1-(4,5-Dichloro-2-nitrophenyl)piperidin-4-yl)methanol

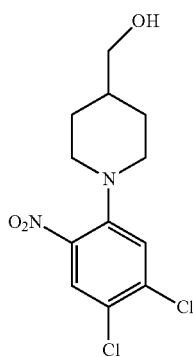 [SMILES: O=[N+]([O-])c1cc(Cl)c(Cl)cc1N1CCC(CO)CC1]

To a mixture of 1,2-dichloro-4-fluoro-5-nitrobenzene (210 mg, 1.0 mmol), piperidin-4-ylmethanol (138 mg, 1.2 mmol) in DMF (2.5 mL) was added DIPEA (258 mg, 2.0 mmol). The reaction was stirred at RT for 1 h. The reaction was quenched with water (5 mL) and extracted with DCM (2×20 mL). The organic phase was concentrated to afford the title product as 310 mg of a yellow oil, which was used into next reaction without further purification. MS (ES+): m/z 305.1 [M+1]$^+$.

Step 4: preparation of 6-((2-Chloro-5-(4-(hydroxymethyl)piperidin-1-yl)-4-nitrophenyl)amino)-1-methyl-3,4-dihydroquinolin-2(1H)-one

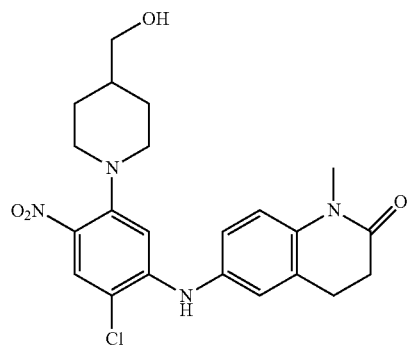 [SMILES: CN1C(=O)CCc2cc(Nc3cc(N4CCC(CO)CC4)c([N+](=O)[O-])cc3Cl)ccc21]

A mixture of (1-(4,5-Dichloro-2-nitrophenyl)piperidin-4-yl)methanol (300 mg, 1.0 mmol), 6-amino-1-methyl-3,4-dihydroquinolin-2(1H)-one (176 mg, 1.0 mmol), Pd$_2$(dba)$_3$ (91.6 mg, 0.1 mmol), BINAP (125 mg, 0.2 mmol), Cs$_2$CO$_3$ (489 mg, 1.5 mmol) in DME (4 mL) was stirred at 120° C. for 10 h. After quenching with H$_2$O, the mixture was extracted with ethyl acetate (10 mL×2). The organic phase was concentrated under vacuum and purified by silica gel column to afford the desired product as 410 mg of a yellow solid. LCMS: (ES$^+$): m/z 445.1 [M+1]$^+$ Step 5: 1-(4-Chloro-5-((1-methyl-2-oxo-1,2,3,4-tetrahydroquinolin-6-yl)amino)-2-nitrophenyl)piperidine-4-carbaldehyde

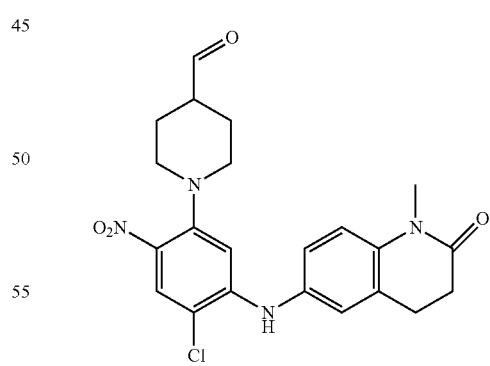

A mixture of 6-((2-Chloro-5-(4-(hydroxymethyl)piperidin-1-yl)-4-nitrophenyl)amino)-1-methyl-3,4-dihydroquinolin-2(1H)-one (100 mg, 0.23 mmol), IBX (94 mg, 0.34 mmol) in CH$_3$CN (3 mL) was stirred at 80° C. for 0.5 h. The mixture was filtered and the filtrate was concentrated under reduced pressure to afford the desired crude product as 102 mg of a yellow solid. MS (ES$^+$): m/z 443.2 [M+1]$^+$ Step 6: Preparation of 5-((1r,3r)-3-(((1-(4-chloro-5-((1-methyl-2-oxo-1,2,3,4-tetrahydroquinolin-6-yl)amino)-2-nitrophenyl)piperidin-4-yl)methyl)(methyl)amino) cyclobutoxy)-2-(2,6-dioxopiperidin-3-yl)isoindoline-1,3-dione

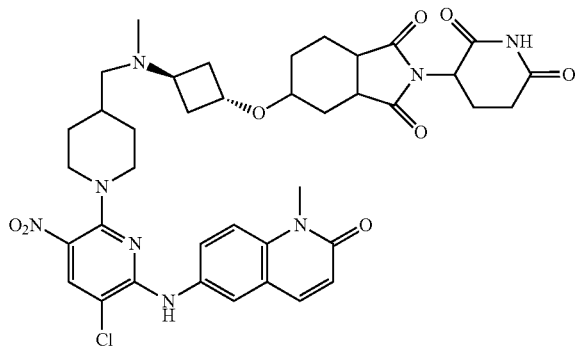 [SMILES: Cn1c(=O)ccc2cc(Nc3nc(N4CCC(CN(C)[C@H]5C[C@H](OC6CCC7C(=O)N(C8CCC(=O)NC8=O)C(=O)C7C6)C5)CC4)c([N+](=O)[O-])cc3Cl)ccc21]

A solution of 2-(2,6-dioxopiperidin-3-yl)-5-((1r,3r)-3-(methylamino)cyclobutoxy)isoindoline-1,3-dione (177 mg, 0.495 mmol), 2-(2,6-dioxopiperidin-3-yl)-5-((1r,3r)-3-(methylamino)cyclobutoxy)isoindoline-1,3-dione (182 mg, 0.412 mmol), HOAc (1 drops) in EtOH/DCM (2 ml:2 ml) was stirred at R, T for 30 min. Then the mixture was added NaBH(OAc)$_3$ (351 mg, 1.648 mmol). The mixture was stirred at RT for 3 h. The reaction was diluted with water (3 mL) and extracted with DCM (10 mL). The organic phase was concentrated and purified by prep-HPLC with the following conditions (Welch Ultimate XB-C18, 21.2*250 mm 5 um), eluted with H$_2$O in CH$_3$CN containing 0.05% TFA). The product containing prep-HPLC fraction was lyophilized to dryness to afford the desired product as 45 mg of a white solid. $^1$H NMR (400 MHz, CD$_3$OD) δ: 8.14 (s, 1H), 7.83 (d, J=8.4 Hz, 1H), 7.29 (s, 1H), 7.20-7.25 (m, 2H), 7.15-7.19 (m, 2H), 5.06-5.13 (m, 1H), 5.00-5.15 (m, 1H), 4.06-4.18 (m, 1H), 3.38 (s, 3H), 3.20-3.26 (m, 2H), 2.89-2.96 (m, 3H), 2.80-2.87 (m, 5H), 2.60-2.79 (m, 8H), 2.07-2.16 (m, 1H), 1.75-1.97 (m, 3H), 1.65 (d, J=7.2 Hz, 2H), 1.45-1.61 (m, 2H). MS (ES$^+$): m/z 784.3

Exemplary Synthesis of 2-(6-(5-chloro-2-(4-(4-(3-(2-(2-(2-(2,6-dioxopiperidin-3-yl)-1-oxoisoindolin-5-yloxy)ethoxy)ethoxy)propoxy)phenyl)piperidin-1-yl)pyrimidin-4-ylamino)-1-methyl-2-oxo-1,2-dihydroquinolin-3-yloxy)-N-methylacetamide (Exemplary Compound 89)

Step 1: Synthesis of 2-(2-(benzyloxy)ethoxy)ethyl 4-methylbenzenesulfonate

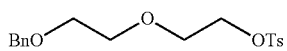

To a stirred solution of 2-[2-(benzyloxy)ethoxy]ethanol (3 g, 15.287 mmol, 1.00 equiv) and TEA (2.32 g, 22.93 mmol, 1.50 equiv) in DCM (20 mL) was added DMAP (0.37 g, 3.057 mmol, 0.20 equiv) and TsCl (4.37 g, 22.930 mmol, 1.50 equiv) dropwise at room temperature. The reaction was quenched with water (20 mL) at room temperature. The aqueous layer was extracted with CH$_2$Cl$_2$ (3×20 mL). The residue was purified by silica gel column chromatography, eluted with PE/EtOAc (5:1) to afford 2-[2-(benzyloxy)ethoxy]ethyl 4-methylbenzenesulfonate (2.89 g, 54%) as a colorless oil. MS (ES+): m/z 368.15[MH$^+$].

Step 2: Synthesis of 3-(2-(2-(benzyloxy)ethoxy)ethoxy)propan-1-ol

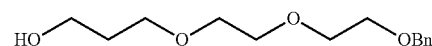 [SMILES: OCCCOCCOCCOCc1ccccc1]

To a solution of 1,3-propandiol (0.94 g, 12.37 mmol, 1.50 equiv) in DMF (20 mL) was added sodium hydride (60% in oil, 800 mg, 12.37 mmol, 1.50 equiv) at 0 degrees. The mixture was stirred for 15 min, then 2-[2-(benzyloxy)ethoxy]ethyl 4-methylbenzenesulfonate (2.89 g, 8.247 mmol, 1.00 equiv) was added and the mixture was allowed to warm to RT and stirred overnight. The reaction mixture was quenched by water and extracted with DCM (3×25 mL). The residue was purified by silica gel column chromatography, eluted with PE/EtOAc (2:1) to afford 3-[2-[2-(benzyloxy)ethoxy]ethoxy]propan-1-ol (1.86 g, 89%) as a colorless oil. MS (ES+): m/z 255.10[MH$^+$].

Step 3: Synthesis of 3-(2-(2-(benzyloxy)ethoxy)ethoxy)propyl 4-methylbenzenesulfonate

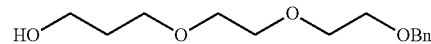 [SMILES: OCCCOCCOCCOCc1ccccc1]

To a stirred solution of 3-[2-[2-(benzyloxy)ethoxy]ethoxy]propan-1-ol (1.86 g, 7.313 mmol, 1.00 equiv) and TEA (1.11 g, 10.970 mmol, 1.50 equiv) in DCM (20 mL) were added DMAP (0.18 g, 1.463 mmol, 0.20 equiv) and TsCl (2.09 g, 10.970 mmol, 1.50 equiv) dropwise at room temperature. The reaction was quenched with water (20 mL) at room temperature. The aqueous layer was extracted with CH2Cl2 (3×20 mL). The combined organic layer was concentrated under reduced pressure. The residue was purified by silica gel column chromatography, eluted with PE/EtOAc (4:1) to afford 3-[2-[2-(benzyloxy)ethoxy]ethoxy]propyl 4-methylbenzenesulfonate (1.92 g, 64%) as a colorless oil. MS (ES+): m/z 426.15[MH+].

Step 4: Synthesis of tert-butyl 4-(4-(3-(2-(2-(benzyloxy)ethoxy)ethoxy)propoxy)phenyl)-5,6-dihydropyridine-1(2H)-carboxylate

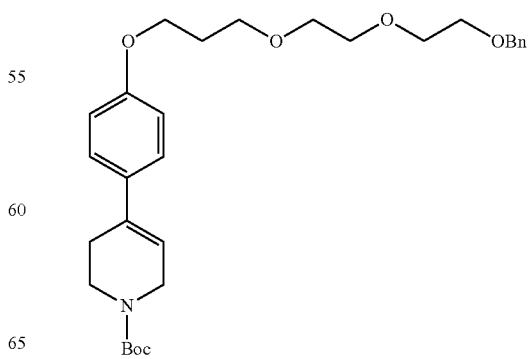

To a stirred solution of 3-[2-[2-(benzyloxy)ethoxy]ethoxy]propyl 4-methylbenzenesulfonate (500 mg, 1.224 mmol, 1.00 equiv) and tert-butyl 4-(4-hydroxyphenyl)-3,6-dihydro-2H-pyridine-1-carboxylate (337 mg, 1.224 mmol, 1.00 equiv) in MeCN (8 mL) was added $K_2CO_3$ (507 mg, 3.672 mmol, 3.00 equiv) under nitrogen atmosphere. The reaction mixture was stirred overnight at 70 degrees in an oil bath and then concentrated under reduced pressure. The residue was purified by reverse flash chromatography with the following conditions: column, C18 silica gel; mobile phase, ACN in water, 65% to 85% gradient in 15 min; detector, UV 254 nm. This resulted in tert-butyl 4-[4-(3-[2-[2-(benzyloxy)ethoxy]ethoxy]propoxy)phenyl]-3,6-dihydro-2H-pyridine-1-carboxylate (362 mg, 58%) as a colorless oil.

Step 5: Synthesis of tert-butyl 4-(4-(3-(2-(2-hydroxyethoxy)ethoxy)propoxy)phenyl)piperidine-1-carboxylate

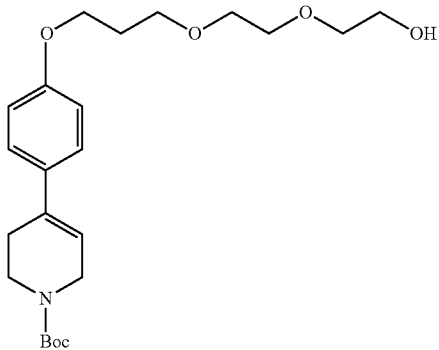

To a solution of tert-butyl 4-[4-(3-[2-[2-(benzyloxy)ethoxy]ethoxy]propoxy)phenyl]-3,6-dihydro-2H-pyridine-1-carboxylate (362 mg, 0.708 mmol, 1.00 equiv) in (10 mL) MeOH was added Pd/C (10%, 0.12 g) under nitrogen atmosphere in a 50 mL round-bottom flask. The mixture was hydrogenated at room temperature for 3 h under hydrogen atmosphere using a hydrogen balloon, filtered through a Celite pad and the filtrated was concentrated under reduced pressure. This resulted in tert-butyl 4-(4-[3-[2-(2-hydroxyethoxy)ethoxy]propoxy]phenyl)piperidine-1-carboxylate (281 mg, 94%) as a colorless oil. MS (ES+): m/z 441.20 [MH+].

Step 6: Synthesis of 2-(2-(3-(4-(piperidin-4-yl)phenoxy)propoxy)ethoxy)ethanol

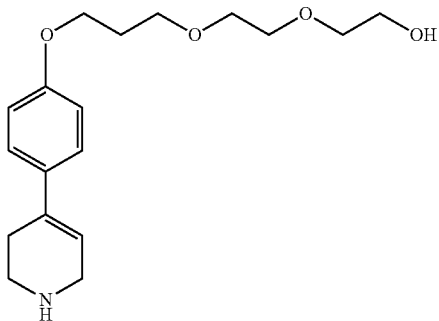

To a solution of tert-butyl 4-(4-[3-[2-(2-hydroxyethoxy)ethoxy]propoxy]phenyl)piperidine-1-carboxylate (281 mg, 0.663 mmol, 1.00 equiv) in dioxane (5 ml) was added HCl in dioxane (4.0M, 2 ml). After stirred for 1 h at room temperature, the resulting mixture was concentrated under reduced pressure. This resulted in 211 mg (98%) 2-(2-[3-[4-(piperidin-4-yl)phenoxy]propoxy]ethoxy)ethanol as a colorless oil. (ES+): m/z 324.15[MH+]

Step 7: Synthesis of 2-(6-(5-chloro-2-(4-(4-(3-(2-(2-hydroxyethoxy)ethoxy)propoxy)phenyl)piperidin-1-yl)pyrimidin-4-ylamino)-1-methyl-2-oxo-1,2-dihydroquinolin-3-yloxy)-N-methylacetamide

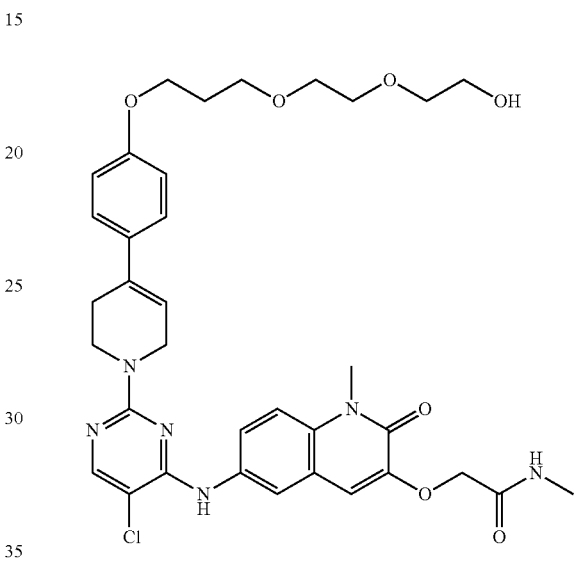

To a stirred solution of 2-(2-[3-[4-(piperidin-4-yl)phenoxy]propoxy]ethoxy)ethanol (206 mg, 0.637 mmol, 1.0 equiv) and 2-([6-[(2,5-dichloropyrimidin-4-yl)amino]-1-methyl-2-oxoquinolin-3-yl]oxy)-N-methylacetamide (260 mg, 0.637 mmol, 1.0 equiv) in DMSO (5 mL) was added DIEA (164 mg, 1.274 mmol, 2.0 equiv). The reaction mixture was stirred overnight at 100 degrees in an oil bath. The resulting mixture was concentrated under reduced pressure. The residue was purified by reverse flash chromatography with the following conditions: column, C18 silica gel; mobile phase, ACN in water, 50% to 70% gradient in 20 min; detector, UV 254 nm. This resulted in 2-[[6-([5-chloro-2-[4-(4-[3-[2-(2-hydroxyethoxy)ethoxy]propoxy]phenyl)piperidin-1-yl]pyrimidin-4-yl]amino)-1-methyl-2-oxoquinolin-3-yl]oxy]-N-methylacetamide (197 mg, 45%) as a white solid. MS (ES+): m/z 695.20[MH+].

Step 8: Synthesis of 2-(2-(3-(4-(1-(5-chloro-4-(1-methyl-3-(2-(methylamino)-2-oxoethoxy)-2-oxo-1,2-dihydroquinolin-6-ylamino)pyrimidin-2-yl)piperidin-4-yl)phenoxy)propoxy)ethoxy)ethyl 4-methylbenzenesulfonate

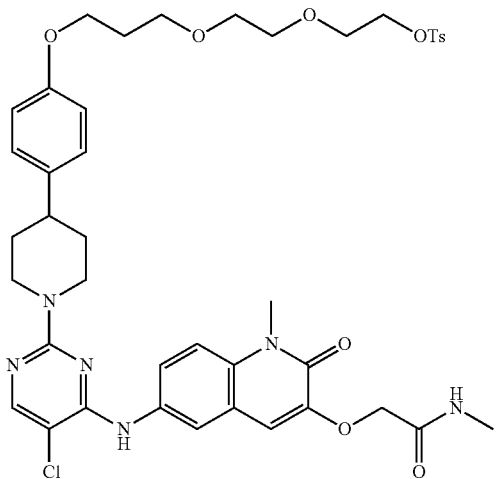

To a stirred solution of 2-[[6-([5-chloro-2-[4-(4-[3-[2-(2-hydroxyethoxy)ethoxy]propoxy]phenyl)piperidin-1-yl]pyrimidin-4-yl]amino)-1-methyl-2-oxoquinolin-3-yl]oxy]-N-methylacetamide (182 mg, 0.262 mmol, 1.00 equiv) and TEA (105 mg, 1.047 mmol, 4.0 equiv) in DCM (10 mL) were added DMAP (6.4 mg, 0.052 mmol, 0.20 equiv) and TsCl (199 mg, 1.047 mmol, 4.0 equiv). The reaction mixture was stirred overnight at room temperature. The reaction was quenched with water. The aqueous layer was extracted with CH$_2$Cl$_2$ (3×10 mL). The combined organic layer was concentrated under reduced pressure. The residue was purified by Prep-TLC (CH2Cl2/MeOH 13:1) to afford the title compound as 120 mg of a white solid (54%). MS (ES$^+$): m/z 849.25 [MH$^+$].

Step 9: Synthesis of 2-((6-((5-chloro-2-(4-(4-(3-(2-(2-((2-(2,6-dioxopiperidin-3-yl)-1-oxoisoindolin-5-yl)oxy)ethoxy)ethoxy)propoxy)phenyl)piperidin-1-yl)pyrimidin-4-yl)amino)-1-methyl-2-oxo-1,2-dihydroquinolin-3-yl)oxy)-N-methylacetamide To a stirred solution of 2-(2-(3-(4-(1-(5-chloro-4-(1-methyl-3-(2-(methylamino)-2-oxoethoxy)-2-oxo-1,2-dihydroquinolin-6-ylamino)pyrimidin-2-yl)piperidin-4-yl)phenoxy)propoxy)ethoxy)ethyl 4-methylbenzenesulfonate (120 mg, 0.141 mmol, 1.00 equiv) and 3-(5-hydroxy-1-oxo-3H-isoindol-2-yl)piperidine-2,6-dione (36 mg, 0.141 mmol, 1.0 equiv) in DMF (5 mL) was added K$_2$CO$_3$ (58 mg, 0.424 mmol, 3.0 equiv). The reaction mixture was stirred overnight at 70 degrees in an oil bath. The reaction mixture was directly purified by Prep-HPLC with the following conditions: Column: XBridge Prep OBD C18 Column, 30Åf?150 mm 5 um; Mobile Phase A: Water (10 MMOL/L NH4HCO3+0.1% NH3·H2O), Mobile Phase B: ACN; Flow rate:60 mL/min; Gradient: 43 B to 55 B in 10 min; 254 nm. This resulted in 21.5 mg (16%) of the title product as a white solid. $^1$H NMR (400 MHz, DMSO-d6, ppm):δ 10.95 (s, 1H), 8.83 (s, 1H), 8.06 (s, 1H), 7.92 (m, 2H), 7.77 (m, 1H), 7.60 (d, J=8.4 Hz, 1H), 7.47 (d, J=9.2 Hz, 1H), 7.18-7.08 (m, 4H), 7.03 (m, 1H), 6.82-6.51 (m, 2H), 5.06 (m, 1H), 4.63 (d, J=12.9 Hz, 2H), 4.55 (s, 2H), 4.37 (d, J=17.1 Hz, 1H), 4.25 (d, J=7.2 Hz, 1H), 4.15 (m, 2H), 3.97 (t, J=6.3 Hz, 2H), 3.79-3.72 (m, 2H), 3.66 (s, 3H), 3.59 (m, 2H), 3.53 (m, 4H), 2.89 (t, J=12.8 Hz, 3H), 2.70 (s, 1H), 2.61 (m, 4H), 2.00-1.85 (m, 3H), 1.77 (d, J=12.7 Hz, 2H), 1.51 (t, J=12.1 Hz, 2H), 1.24 (s, 1H). MS (ES+): m/z 937.45[

Exemplary Synthesis of 2-[[6-([5-chloro-2-[4-(2-[4-[(4-[2-[2-(2,6-dioxopiperidin-3-yl)-1-oxo-3H-isoindol-5-yl]ethynyl]phenyl)methyl]piperazin-1-yl]ethoxy)piperidin-1-yl]pyrimidin-4-yl]amino)-1-methyl-2-oxoquinolin-3-yl]oxy]-N-methylacetamide (Exemplary Compound 119)

Step 1: 1. Synthesis of 3-[1-oxo-5-[2-(trimethylsilyl)ethynyl]-3H-isoindol-2-yl]piperidine-2,6-dione

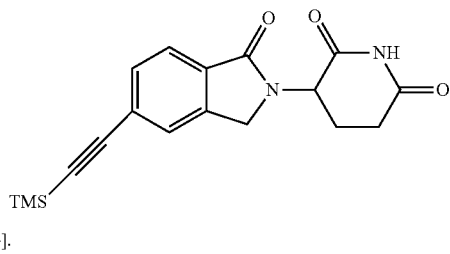

MH+].

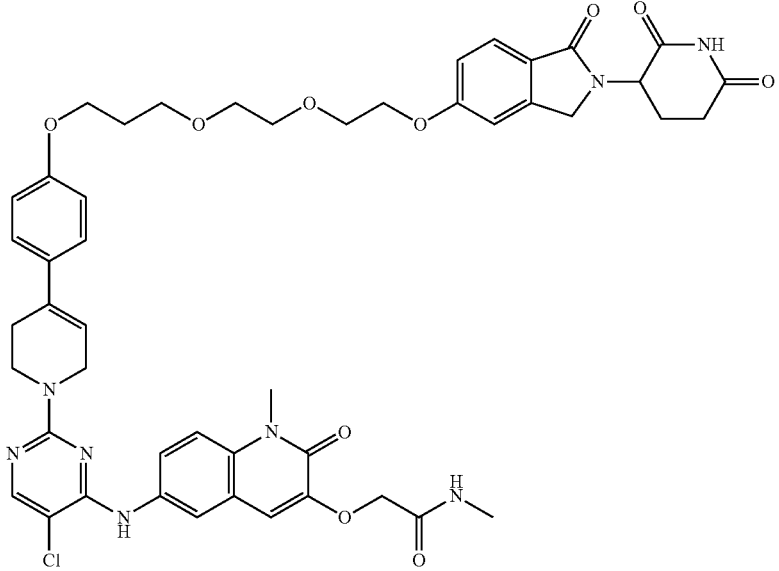

Into a 30-mL sealed tube, was placed 3-(5-bromo-1-oxo-3H-isoindol-2-yl)piperidine-2,6-dione (680.00 mg, 2.11 mmol), DMF (10 mL), Pd(PPh3)2Cl2 (148 mg, 0.211 mmol), CuI (40 mg, 0.211 mmol), DIEA (1.2 mL), trimethylsilylacetylene (1.03 g, 10.56 mmol, 5 equiv). The resulting solution was stirred for 1 overnight at 65° C. in an oil bath. The crude product was purified by Flash-Prep-HPLC with the following conditions: Column, C18 silica gel; mobile phase: CH3CN/H2O=0 increasing to =95 within 34 min; Detector 25/220 nm. Product was obtained and concentrated. This resulted in 258 mg (36%) of 3-[1-oxo-5-[2-(trimethylsilyl)ethynyl]-3H-isoindol-2-yl]piperidine-2,6-dione as a brown solid.

Step 2: 2. Synthesis of 3-(5-ethynyl-1-oxo-3H-isoindol-2-yl)piperidine-2,6-dione

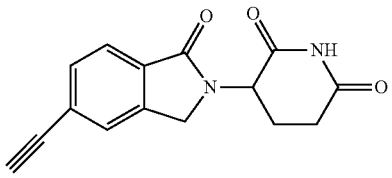 [SMILES: C#Cc1ccc2c(c1)CN(C1CCC(=O)NC1=O)C2=O]

Into a 100-mL round-bottom flask, was placed 3-[1-oxo-5-[2-(trimethylsilyl)ethynyl]-3H-isoindol-2-yl]piperidine-2,6-dione (258.00 mg, 0.758 mmol, 1.00 equiv), THF (10 mL), TBAF (0.76 mL, 0.76 mmol, 1 equiv, 1 M in THF). The resulting solution was stirred for 3 hr at room temperature. The resulting solution was extracted with 3×50 mL of ethyl acetate. The washed with 2×20 mL of NH4Cl aq. The resulting mixture was concentrated. This resulted in 234 mg (crude) of 3-(5-ethynyl-1-oxo-3H-isoindol-2-yl)piperidine-2,6-dione as a yellow solid.

Step 3: Synthesis of tert-butyl 4-[(4-iodophenyl)methyl]piperazine-1-carboxylate

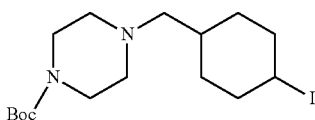 [SMILES: CC(C)(C)OC(=O)N1CCN(CC2CCC(I)CC2)CC1]

Into a 250-mL round-bottom flask, was placed 4-iodobenzaldehyde (5.0 g, 0.02 mol), DCM (50.0 mL), tert-butyl piperazine-1-carboxylate (4.1 g, 0.02 mol), HOAc (0.5 mL). This was followed by the addition of NaBH(OAc)3 (13.70 g, 0.06 mol, 3.0 equiv). The resulting solution was stirred for 2 hr at 30° C. in an oil bath. The reaction was then quenched by the addition of 50 mL of water, extracted with 3×50 mL of dichloromethane, washed with 3×40 mL of NaCl(aq), dried over anhydrous sodium sulfate and concentrated. This resulted in 5.2 g of tert-butyl 4-[(4-iodophenyl)methyl]piperazine-1-carboxylate as yellow oil which was used directly in the next step.

Step 4: Synthesis of 1-[(4-iodophenyl)methyl]piperazine

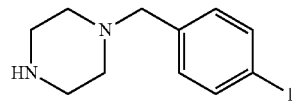

Into a 250-mL round-bottom flask, was placed a solution of tert-butyl 4-[(4-iodophenyl)methyl]piperazine-1-carboxylate (2.0 g, 5.0 mmol) in dioxane (20 mL) and hydrogen chloride (4 M in dioxane, 10 mL). The resulting solution was stirred overnight at 20° C. The resulting mixture was concentrated. This resulted in 2.5 g of 1-[(4-iodophenyl)methyl]piperazine as a white solid.

Step 5: Synthesis of tert-butyl 4-(2-hydroxyethoxy)piperidine-1-carboxylate

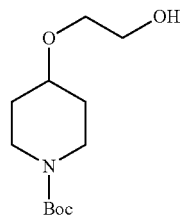 [SMILES: CC(C)(C)OC(=O)N1CCC(OCCO)CC1]

Into a 250-mL round-bottom flask, was placed tert-butyl 4-[2-(benzyloxy)ethoxy]piperidine-1-carboxylate (3.0 g, 8.943 mmol) in MeOH (15.00 mL) and Pd/C (0.95 g, 8.943 mmol). The resulting solution was stirred overnight at 40° C. in an oil bath under the hydrogen atmosphere. The solids were filtered out. The resulting mixture was concentrated. This resulted in 2.35 g (crude) of tert-butyl 4-(2-hydroxyethoxy)piperidine-1-carboxylate as a black solid.

Step 6: Synthesis of tert-butyl 4-[2-[(4-methylbenzenesulfonyl)oxy]ethoxy]piperidine-1-carboxylate

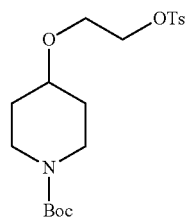 [SMILES: Cc1ccc(S(=O)(=O)OCCOC2CCN(C(=O)OC(C)(C)C)CC2)cc1]

Into a 100-mL round-bottom flask, was placed tert-butyl 4-(2-hydroxyethoxy)piperidine-1-carboxylate (500 mg, 2.038 mmol), DCM (10 mL), TEA (0.85 mL, 8.399 mmol), DMAP (24.9 mg, 0.204 mmol), TsCl (582.85 mg, 3.057 mmol). The resulting solution was stirred for 3 hr at room temperature. The resulting solution was extracted with 3×20 mL of dichloromethane dried over anhydrous sodium sulfate. The residue was applied onto a silica gel column with ethyl acetate/petroleum ether (0/70). This resulted in 647 mg (79%) of tert-butyl 4-[2-[(4-methylbenzenesulfonyl)oxy]ethoxy]piperidine-1-carboxylate as a yellow liquid. MS (ESI+): m/z=400.2 [MH+].

Step 7: Synthesis of tert-butyl 4-(2-[4-[(4-iodophenyl)methyl]piperazin-1-yl]ethoxy)piperidine-1-carboxylate

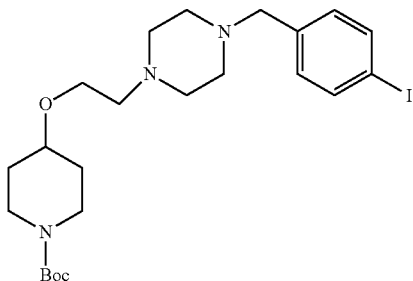 [SMILES: CC(C)(C)OC(=O)N1CCC(OCCN2CCN(Cc3ccc(I)cc3)CC2)CC1]

Into a 30-mL sealed tube purged and maintained with an inert atmosphere of nitrogen, was placed 1-[(4-iodophenyl)methyl]piperazine (466 mg, 1.38 mmol,), CH$_3$CN (10 mL), K$_2$CO$_3$ (635.0 mg, 4.6 mmol), tert-butyl 4-[2-[(4-methylbenzenesulfonyl)oxy]ethoxy]piperidine-1-carboxylate (460 mg, 1.15 mmol), NaI (173.0 mg, 1.15 mmol). The resulting solution was stirred for overnight at 70 degrees in an oil bath. The solids were filtered out and the filtrate was concentrated under reduced pressure. The residue was applied onto a silica gel column with chloroform/methanol (15:1). This resulted in 670 mg of tert-butyl 4-(2-[4-[(4-iodophenyl)methyl]piperazin-1-yl]ethoxy)piperidine-1-carboxylate as yellow oil. MS(ES$^+$): m/z=530.15 [MH$^+$].

Step 8: Synthesis of tert-butyl 4-(2-[4-[(4-[2-[2-(2,6-dioxopiperidin-3-yl)-1-oxo-3H-isoindol-5-yl]ethynyl]phenyl)methyl]piperazin-1-yl]ethoxy)piperidine-1-carboxylate

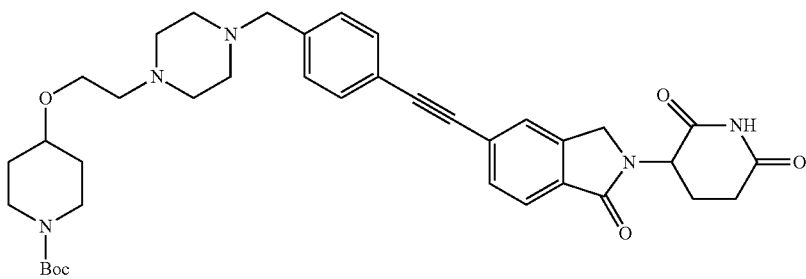 [SMILES: CC(C)(C)OC(=O)N1CCC(OCCN2CCN(Cc3ccc(C#Cc4ccc5c(c4)CN(C4CCC(=O)NC4=O)C5=O)cc3)CC2)CC1]

Into a 30-mL sealed tube purged and maintained with an inert atmosphere of nitrogen, was placed 3-(5-ethynyl-1-oxo-3H-isoindol-2-yl)piperidine-2,6-dione (120 mg, 0.45 mmol), CuI (11.5 mg, 0.06 mmol) in DMF (5 mL), the mixture was stirred for 10 min at room temperature, tert-butyl 4-(2-[4-[(4-iodophenyl)methyl]piperazin-1-yl]ethoxy)piperidine-1-carboxylate (160 mg, 0.30 mmol), Pd(PPh$_3$)$_2$Cl$_2$ (105 mg, 0.15 mmol) and TEA (2.5 mL) was added respectively. The resulting solution was stirred for 4 hr at 65° C. in an oil bath. The solids were filtered out and the filtrate was concentrated under reduced pressure. The crude product was purified by Prep-HPLC with the following conditions: Column, C18 silica gel; mobile phase, 5 mMNH$_4$HCO$_3$(aq)/ACN=100/0 increasing to 5 mMNH$_4$HCO$_3$(aq)/ACN=30/70 within 35 min; Detector, 254 nm. This resulted in 70 mg of tert-butyl 4-(2-[4-[(4-[2-[2-(2,6-dioxopiperidin-3-yl)-1-oxo-3H-isoindol-5-yl]ethynyl]phenyl)methyl]piperazin-1-yl]ethoxy)piperidine-1-carboxylate as a yellow solid. MS (ES$^+$): m/z=670.30 [MH$^+$].

Step 9: Synthesis of 3-(1-oxo-5-[2-[4-([4-[2-(piperidin-4-yloxy)ethyl]piperazin-1-yl]methyl)phenyl]ethynyl]-3H-isoindol-2-yl)piperidine-2,6-dione

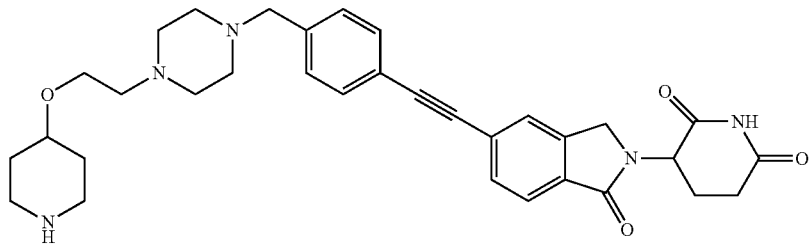 [SMILES: O=C1CCC(N2Cc3cc(C#Cc4ccc(CN5CCN(CCOC6CCNCC6)CC5)cc4)ccc3C2=O)C(=O)N1]

Into a 10-mL vial, was placed tert-butyl 4-(2-[4-[(4-[2-[2-(2,6-dioxopiperidin-3-yl)-1-oxo-3H-isoindol-5-yl]ethynyl]phenyl)methyl]piperazin-1-yl]ethoxy)piperidine-1-carboxylate (60 mg, 0.09 mmol, 1.0 equiv) in DCM (5.0 mL) and trifluoroacetic acid (1.5 mL). The resulting solution was stirred for 60 min at room temperature. The resulting mixture was concentrated under vacuum. This resulted in 120 mg of 3-(1-oxo-5-[2-[4-([4-[2-(piperidin-4-yloxy)ethyl]piperazin-1-yl]methyl)phenyl]ethynyl]-3H-isoindol-2-yl)piperidine-2,6-dione as brown oil. MS (ES+): m/z=570.25 [MH+]. Step 10: Synthesis of 2-[[6-([5-chloro-2-[4-(2-[4-[(4-[2-[2-(2,6-dioxopiperidin-3-yl)-1-oxo-3H-isoindol-5-yl]ethynyl]phenyl)methyl]piperazin-1-yl]ethoxy)piperidin-1-yl]pyrimidin-4-yl]amino)-1-methyl-2-oxoquinolin-3-yl]oxy]-N-methylacetamide

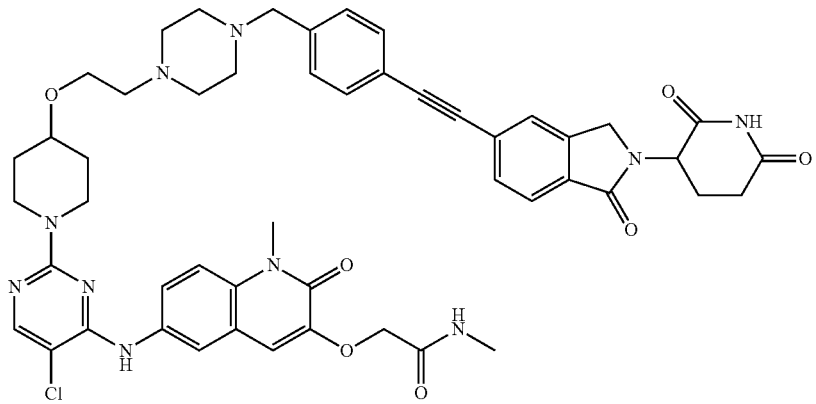 [SMILES: CNC(=O)COc1cc2cc(Nc3nc(N4CCC(OCCN5CCN(Cc6ccc(C#Cc7ccc8c(c7)CN(C7CCC(=O)NC7=O)C8=O)cc6)CC5)CC4)ncc3Cl)ccc2n(C)c1=O]

Into a 10-mL sealed tube, was placed 3-(1-oxo-5-[2-[4-([4-[2-(piperidin-4-yloxy)ethyl]piperazin-1-yl]methyl)phenyl]ethynyl]-3H-isoindol-2-yl)piperidine-2,6-dione (120 mg, 0.2 mmol), DMSO (5 mL), DIEA (0.5 mL), 2-([6-[(2,5-dichloropyrimidin-4-yl)amino]-1-methyl-2-oxoquinolin-3-yl]oxy)-N-methylacetamide (81.4 mg, 0.2 mmol). The resulting solution was stirred for 4 hr at 100° C. in an oil bath. The crude product was purified by Prep-HPLC with the following conditions: Column, C18 silica gel; mobile phase, 5 mM NH4HCO3(aq)/ACN=100/0 increasing to 5 mM NH4HCO3(aq)/ACN=20/80 within 20 min; Detector, UV. This resulted in 8 mg of 2-[[6-([5-chloro-2-[4-(2-[4-[(4-[2-[2-(2,6-dioxopiperidin-3-yl)-1-oxo-3H-isoindol-5-yl]ethynyl]phenyl)methyl]piperazin-1-yl]ethoxy)piperidin-1-yl]pyrimidin-4-yl]amino)-1-methyl-2-oxoquinolin-3-yl]oxy]-N-methylacetamide as a brown solid. $^1$H NMR (400 MHz, DMSO-d6): δ 10.97 (s, 1H), 8.79 (s, 1H), 8.01 (s, 1H), 7.95-7.86 (m, 2H), 7.73 (dd, J=16.6, 8.8 Hz, 3H), 7.64 (d, J=7.9 Hz, 1H), 7.51 (d, J=7.7 Hz, 2H), 7.44 (d, J=9.1 Hz, 1H), 7.33 (d, J=7.8 Hz, 2H), 7.08 (s, 1H), 5.10 (dd, J=13.3, 5.1 Hz, 1H), 4.58-4.31 (m, 4H), 4.00 (d, J=12.9 Hz, 2H), 3.64 (s, 3H), 3.54-3.42 (m, 5H), 3.22 (s, 2H), 2.89 (ddd, J=17.9, 13.2, 5.3 Hz, 1H), 2.63 (d, J=4.6 Hz, 4H), 2.45-2.30 (m, 10H), 2.00 (d, J=12.0 Hz, 1H), 1.80 (d, J=12.6 Hz, 2H), 1.36 (d, J=9.1 Hz, 2H), 1.21 (s, 1H). MS (ES+): m/z=941.30 [MH+].

Exemplary Synthesis of 2-([6-[(5-chloro-2-[3-[4-(1-[3-[2-(2,6-dioxopiperidin-3-yl)-1-oxo-3H-isoindol-5-yl]-3-hydroxypropyl]piperidin-4-yl)phenoxymethyl]piperidin-1-yl]pyrimidin-4-yl)amino]-1-methyl-2-oxoquinolin-3-yl]oxy)-N-methylacetamide (Exemplary Compound 127)

Step 1: Synthesis of 3-(5-bromo-1-oxo-2,3-dihydro-1H-isoindol-2-yl)piperidine-2,6-dione

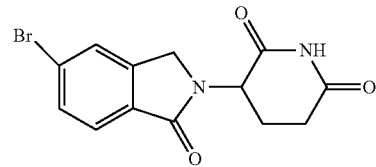 [SMILES: O=C1CCC(N2Cc3cc(Br)ccc3C2=O)C(=O)N1]

To a mixture of methyl 4-bromo-2-(bromomethyl)benzoate (10.0 g, 32.47 mmol, 1 equiv) and 3-aminopiperidine-2,6-dione hydrochloride (1.2 g, 39.21 mmol, 1.20 equiv) in DMF (40 mL) was added Et3N (11.3 mL, 81.30 mmol, 2.50 equiv) dropwise. The reaction mixture was stirred for 16 hr at room temperature. 50 mL HOAc was added and stirring continued at 120° C. for 2 h. The reaction was cooled and diluted with water (500 mL). The resulting solid was filtered, washed with water (100 mL) and further dried under high vacuum. This resulted in 6.95 g (66%) of 3-(5-bromo-1-oxo-2,3-dihydro-1H-isoindol-2-yl)piperidine-2,6-dione as a light pale solid. MS (ES+): m/z 323 [M+H+].

Step 2: Synthesis of 3-[5-(3,3-diethoxyprop-1-yn-1-yl)-1-oxo-3H-isoindol-2-yl]piperidine-2,6-dione

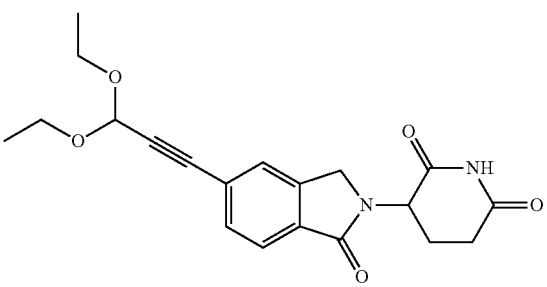 [SMILES: CCOC(C#Cc1ccc2c(c1)CN(C1CCC(=O)NC1=O)C2=O)OCC]

Into a 30-mL sealed tube, was placed 3-(5-bromo-1-oxo-3H-isoindol-2-yl)piperidine-2,6-dione (2.00 g, 6.19 mmol, 1.00 equiv), DMF (15.00 mL), CuI (0.12 g, 0.619 mmol, 0.10 equiv), DIEA (2.40 g, 18.57 mmol, 3.00 equiv), Pd(PPh$_3$)$_2$Cl$_2$ (0.43 g, 0.62 mmol, 0.10 equiv), 3,3-diethoxypropyne (1.19 g, 9.28 mmol, 1.50 equiv). The resulting solution was stirred for 3 h at 65° C. in an oil bath. The reaction was then quenched by the addition of water (20 mL). The resulting solution was extracted with ethyl acetate (2×40 mL). The resulting mixture was washed with brine (1×20 ml). The mixture was dried over anhydrous sodium sulfate. The residue was applied onto a silica gel column eluting with dichloromethane/methanol (10/1). The collected fractions were combined and concentrated under vacuum. This resulted in 1.2 g (52%) of 3-[5-(3,3-diethoxyprop-1-yn-1-yl)-1-oxo-3H-isoindol-2-yl]piperidine-2,6-dione as a yellow solid. MS (ES+): m/z 371.05 [MH+].

Step 3: Synthesis of 3-[2-(2,6-dioxopiperidin-3-yl)-1-oxo-3H-isoindol-5-yl]prop-2-ynal

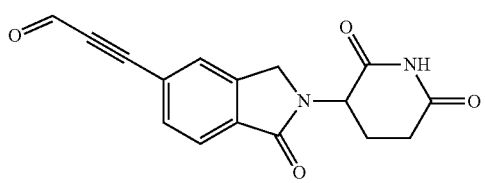 [SMILES: O=CC#Cc1ccc2c(c1)CN(C1CCC(=O)NC1=O)C2=O]

Into a 50-mL round-bottom flask, was placed 3-[5-(3,3-diethoxyprop-1-yn-1-yl)-1-oxo-3H-isoindol-2-yl]piperidine-2,6-dione (200.00 mg, 0.540 mmol, 1.00 equiv), THF (5.00 mL), H$_2$SO$_4$ (5.00 mL, 1 mol/L). The resulting solution was stirred for 2 h at room temperature. The reaction was then quenched by the addition of 10 mL of water. The pH value of the solution was adjusted to 8 with sat.aq Na$_2$CO$_3$. The resulting solution was extracted with dichloromethane (2×20 mL) concentrated under vacuum. This resulted in 121 mg (75%) of 3-[2-(2,6-dioxopiperidin-3-yl)-1-oxo-3H-isoindol-5-yl]prop-2-ynal as a yellow solid. MS (ES+): m/z 315.1 [MH+].

Step 4: Synthesis of tert-butyl 4-(4-hydroxyphenyl)piperidine-1-carboxylate

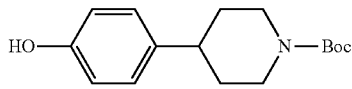

Into a 100-mL round-bottom flask, was placed 4-(piperidin-4-yl)phenol hydrochloride (5. g, 23.47 mmol, 1.00 equiv) in dichloromethane (50 mL). TEA (7.11 g, 70.42 mmol, 3.0 equiv), (Boc)$_2$O (5.63 g, 25.82 mmol, 1.10 equiv) were added into at room temperature. The resulting solution was stirred for 3 h at room temperature. The reaction was then quenched by the addition of water (100 mL). The resulting solution was extracted with dichloromethane (3×50 mL). The resulting mixture was washed with brine (2×20 mL). The mixture was dried over anhydrous sodium sulfate. The residue was applied onto a silica gel column eluting with ethyl acetate/petroleum ether (1/1). This resulted in 2.3 g (35%) of tert-butyl 4-(4-hydroxyphenyl)piperidine-1-carboxylate as a white solid. MS (ES+): m/z 222.05/263.05 [M−60+].

Step 5: Synthesis of benzyl 3-((methylsulfonyloxy)methyl)piperidine-1-carboxylate

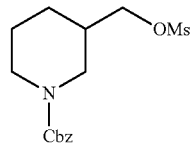

Into a 100-mL round-bottom flask purged and maintained with an inert atmosphere of nitrogen, was placed benzyl 3-(hydroxymethyl)piperidine-1-carboxylate (2.85 g, 11.432 mmol, 1.00 equiv) in DCM (30 mL). This was followed by the addition of TEA (2.31 g, 22.828 mmol, 2.00 equiv), MsCl (1.44 g, 12.571 mmol, 1.10 equiv) dropwise with stirring at 0° C. To the mixture was added DMAP (139 mg, 1.143 mmol, 0.10 equiv) at 0° C. The resulting solution was stirred for 2 hr at room temperature. The reaction was then quenched by the addition of 100 mL of water, extracted with 3×30 mL of dichloromethane, washed with 1×30 ml of brine, dried over anhydrous sodium sulfate and concentrated. This resulted in 3.6 g (96%) of benzyl 3-[(methanesulfonyloxy)methyl]piperidine-1-carboxylate as light yellow oil. MS (ES+): m/z 328.00 [MH+].

Step 6: Synthesis of tert-butyl 4-[4-([1-[(benzyloxy)carbonyl]piperidin-3-yl]methoxy)phenyl]piperidine-1-carboxylate

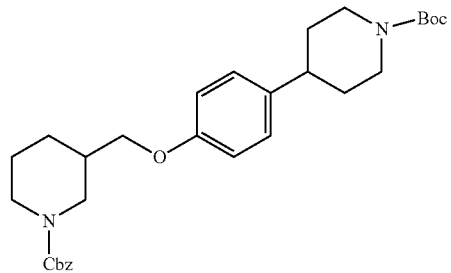 [SMILES: CC(C)(C)OC(=O)N1CCC(c2ccc(OCC3CCCN(C(=O)OCc4ccccc4)C3)cc2)CC1]

Into a 100-mL round-bottom flask, was placed tert-butyl 4-(4-hydroxyphenyl)piperidine-1-carboxylate (1.50 g, 5.408 mmol, 1.00 equiv), DMF (15 mL), K$_2$CO$_3$ (2.24 g, 16.208 mmol, 3.00 equiv), benzyl 3-[(methanesulfonyloxy)methyl]piperidine-1-carboxylate (2.12 g, 6.475 mmol, 1.20 equiv). The resulting solution was stirred for 2 hr at 85° C. in an oil bath. The reaction was then quenched by the addition of 100 mL of water/ice. The resulting solution was extracted with 3×100 mL of ethyl acetate and the organic layers combined. The resulting mixture was washed with 1×50 ml of water and 1×50 mL of brine. The mixture was dried over anhydrous sodium sulfate and concentrated. The residue was applied onto a silica gel column eluting with ethyl acetate/petroleum ether (1:1). This resulted in 2.5 g (91%) of tert-butyl 4-[4-([1-[(benzyloxy)carbonyl]piperidin-3-yl]methoxy)phenyl]piperidine-1-carboxylate as a light yellow solid. MS (ES+): m/z 531.25 [MNa+].

Step 7: Synthesis of tert-butyl 4-[4-(piperidin-3-ylmethoxy)phenyl]piperidine-1-carboxylate

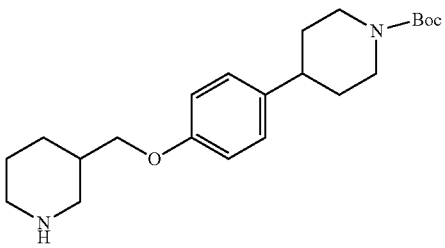 [SMILES: CC(C)(C)OC(=O)N1CCC(c2ccc(OCC3CCCNC3)cc2)CC1]

Into a 100-mL round-bottom flask, was placed benzyl 4-(4-[[1-(tert-butoxycarbonyl)piperidin-3-yl]methoxy]phenyl)piperidine-1-carboxylate (750 mg, 1.474 mmol, 1.00 equiv) in EA (30 mL). Pd(OH)₂/C (10%, 0.1 g) was added into under nitrogen atmosphere. The flask was then vacuumed and flushed with hydrogen. The reaction mixture was hydrogenated for 4 hr at room temperature using a hydrogen balloon, then filtered through a Celite pad and the filtrate was concentrated under reduced pressure. This resulted in 502 mg (91%) of tert-butyl 3-[4-(piperidin-4-yl)phenoxymethyl]piperidine-1-carboxylate as a light grey solid. MS (ES⁺): m/z 375.20 [MH⁺].

Step 8: Synthesis of tert-butyl 4-[4-([1-[5-chloro-4-([1-methyl-3-[(methylcarbamoyl)methoxy]-2-oxoquinolin-6-yl]amino)pyrimidin-2-yl]piperidin-3-yl]methoxy)phenyl]piperidine-1-carboxylate

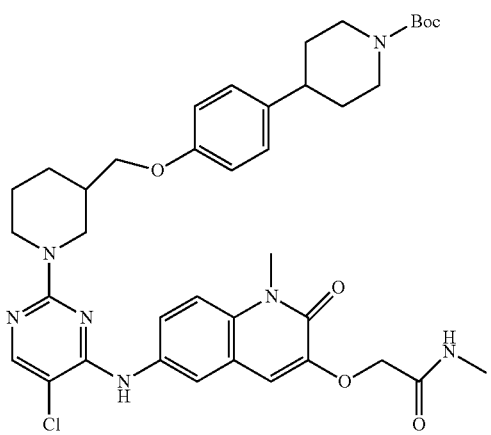 [SMILES: CNC(=O)COc1cc2cc(Nc3nc(N4CCCC(COc5ccc(C6CCN(C(=O)OC(C)(C)C)CC6)cc5)C4)ncc3Cl)ccc2n(C)c1=O]

Into a 25-mL round-bottom flask, was placed tert-butyl 4-[4-(piperidin-3-ylmethoxy)phenyl]piperidine-1-carboxylate (200 mg, 0.534 mmol, 1.00 equiv), 2-([6-[(2,5-dichloropyrimidin-4-yl)amino]-1-methyl-2-oxoquinolin-3-yl]oxy)-N-methylacetamide (327.01 mg, 0.801 mmol, 1.50 equiv), diisopropylethylamine (206.66 mg, 1.602 mmol, 3 equiv) in dimethylsulfoxide (10 mL). The resulting solution was stirred for 2 h at 100° C. in an oil bath. The reaction was then quenched by the addition of water (50 mL). The resulting solution was extracted with ethyl acetate (3×30 mL). The resulting mixture was washed with brine (2×20 mL). The mixture was dried over anhydrous sodium sulfate. The residue was applied onto a silica gel column with ethyl acetate/petroleum ether (1/1). The residue was applied onto a silica gel column with dichloromethane/methanol (1:10). This resulted in 301.7 mg (76%) of tert-butyl 4-[4-([1-[5-chloro-4-([1-methyl-3-[(methylcarbamoyl)methoxy]-2-oxoquinolin-6-yl]amino)pyrimidin-2-yl]piperidin-3-yl]methoxy)phenyl]piperidine-1-carboxylate as an off-white solid. MS (ES⁺): m/z 746.35 [MH⁺].

Step 9: Synthesis of 2-([6-[(5-chloro-2-[3-[4-(piperidin-4-yl)phenoxymethyl]piperidin-1-yl]pyrimidin-4-yl)amino]-1-methyl-2-oxoquinolin-3-yl]oxy)-N-methylacetamide

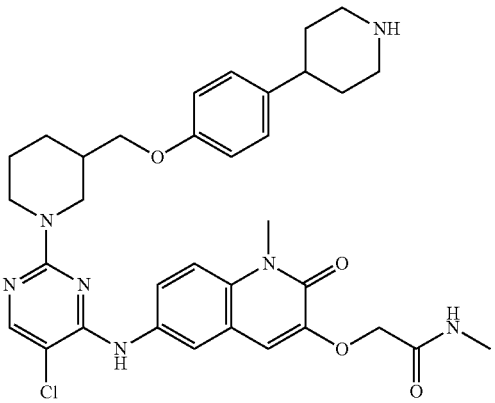 [SMILES: CNC(=O)COc1cc2cc(Nc3nc(N4CCCC(COc5ccc(C6CCNCC6)cc5)C4)ncc3Cl)ccc2n(C)c1=O]

Into a 25-mL round-bottom flask, was placed tert-butyl 4-[4-([1-[5-chloro-4-([1-methyl-3-[(methylcarbamoyl)methoxy]-2-oxoquinolin-6-yl]amino)pyrimidin-2-yl]piperidin-3-yl]methoxy)phenyl]piperidine-1-carboxylate (301.7 mg, 0.405 mmol, 1.00 equiv) and hydrogen chloride (4 M in dioxane, 15 mL). The resulting solution was stirred for 2 h at room temperature. The resulting mixture was concentrated under vacuum. This resulted in 276 mg (100%) of 2-(6-(5-chloro-2-(3-((4-(piperidin-4-yl)phenoxy)methyl)piperidin-1-yl)pyrimidin-4-ylamino)-1-methyl-2-oxo-1,2-dihydroquinolin-3-yloxy)-N-methylacetamide hydrogen chloride salt as a light yellow solid. MS (ES⁺): m/z 646.25 [MH⁺].

Step 10: Synthesis of 2-([6-[(5-chloro-2-[3-[4-(1-[3-[2-(2,6-dioxopiperidin-3-yl)-1-oxo-3H-isoindol-5-yl]-3-hydroxypropyl]piperidin-4-yl)phenoxymethyl]piperidin-1-yl]pyrimidin-4-yl)amino]-1-methyl-2-oxoquinolin-3-yl]oxy)-N-methylacetamide

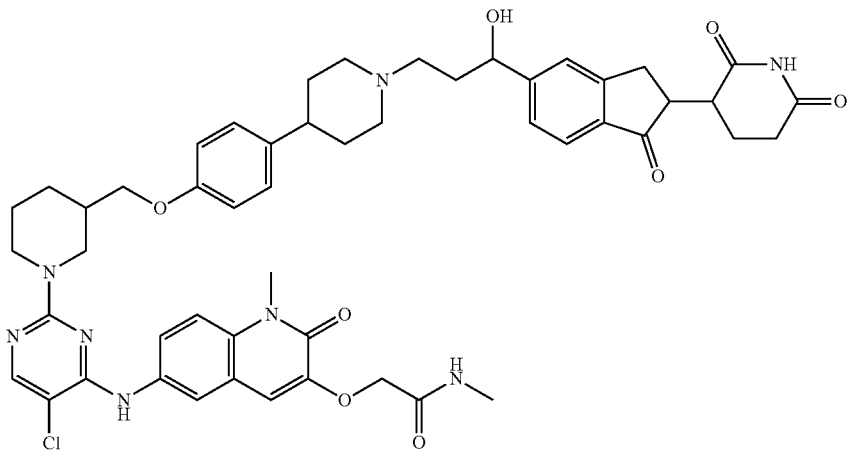 [SMILES: CNC(=O)COc1cc2cc(Nc3nc(N4CCCC(COc5ccc(C6CCN(CCC(O)c7ccc8c(c7)CC(C7CCC(=O)NC7=O)C8=O)CC6)cc5)C4)ncc3Cl)ccc2n(C)c1=O]

Into a 50-mL round-bottom flask, was placed 3-[2-(2,6-dioxopiperidin-3-yl)-1-oxo-3H-isoindol-5-yl]prop-2-ynal (100 mg, 0.338 mmol, 1.00 equiv), dichloromethane (15 mL), HOAc (40.54 mg, 0.675 mmol, 2.00 equiv), 2-([6-[(5-chloro-2-[3-[4-(piperidin-4-yl)phenoxymethyl]piperidin-1-yl]pyrimidin-4-yl)amino]-1-methyl-2-oxoquinolin-3-yl]oxy)-N-methylacetamide (261.72 mg, 0.405 mmol, 1.20 equiv), NaBH$_3$CN (63.63 mg, 1.013 mmol, 3.00 equiv). The resulting solution was stirred for overnight at 35° C. in an oil bath. The reaction was then quenched by the addition of water (20 mL). The resulting solution was extracted with dichloromethane (2×40 mL), and dried over anhydrous sodium sulfate. The residue was applied onto a silica gel column with dichloromethane/methanol (10/1). The crude product was purified by Prep-HPLC with the following conditions: Column, XBridge Shield RP18 OBD Column: 5 um, 19*150 mm; mobile phase, Water (10 mmol/L NH$_4$HCO$_3$) and acetonitrile (34% acetonitrile to 66% in 8 min); Detector, uv. This resulted in 11.7 mg (4%) of 2-([6-[(5-chloro-2-[3-[4-(1-[3-[2-(2,6-dioxopiperidin-3-yl)-1-oxo-3H-isoindol-5-yl]-3-hydroxypropyl]piperidin-4-yl)phenoxymethyl]piperidin-1-yl]pyrimidin-4-yl)amino]-1-methyl-2-oxoquinolin-3-yl]oxy)-N-methylacetamide as a white solid. $^1$H-NMR (400 MHz, DMSO-d6) δ 10.97 (s, 1H), 8.82 (s, 1H), 8.04 (s, 1H), 7.89 (s, 2H), 7.80-7.78 (d, J=8.4 Hz, 1H), 7.69-7.67 (d, J=7.6 Hz, 1H), 7.59 (s, 1H), 7.50-7.48 (d, J=8.0 Hz, 2H), 7.43-7.41 (d, J=8.0 Hz, 1H), 7.14 (s, 1H), 7.07-7.05 (d, J=8.0 Hz, 2H), 6.75 (s, 2H), 5.31-5.04 (m, 1H), 4.80 (s, 1H), 4.59-4.24 (m, 6H), 3.89-3.72 (m, 2H), 3.61 (s, 1H), 2.96-2.71 (m, 5H), 2.66-2.62 (m, 4H), 2.46-2.31 (m, 4H), 2.03-1.76 (m, 8H), 1.72-1.69 (m, 4H), 1.58-1.24 (m, 4H); MS (ES$^+$): m/z 946.30/948.30 [MH$^+$].

Exemplary Synthesis of 2-((6-((5-Chloro-2-(4-((1-(2-(2-((2-(2,6-dioxopiperidin-3-yl)-1,3-dioxoisoindolin-5-yl)oxy)ethoxy)ethyl)-1H-1,2,3-triazol-4-yl)methyl)piperidin-1-yl)pyrimidin-4-yl) amino)-1-methyl-2-oxo-1,2-dihydroquinolin-3-yl)oxy)-N-methylacetamide (Exemplary Compound 130)

Step 1: Synthesis of tert-butyl 4-(prop-2-yn-1-yl)piperidine-1-carboxylate

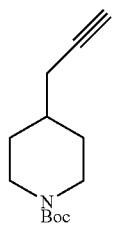

To a solution of tert-butyl 4-(((tosyloxy)methyl)piperidine-1-carboxylate (13 g, 35.2 mmol) in dry DMSO (100 mL) was added Lithium acetylide ethylenediamine complex (8.1 g, 88.1 mmol). The solution was warmed to 35° C. and stirred for 16 h. Quenched with H$_2$O, extracted with MTBE, dried and concentrated to afford the desired crude product tert-butyl 4-(prop-2-yn-1-yl)piperidine-1-carboxylate (6 g), which was used in next step directly. $^1$H NMR (400 MHz, CDCl$_3$): δ 4.05-4.20 (m, 2H), 3.49 (d, J=6.0 Hz, 2H), 2.65-2.78 (m, 2H), 2.10-2.20 (m, 1H), 1.60-1.80 (m, 3H), 1.46 (s, 9H), 1.10-1.20 (m, 2H).

Step 2: Synthesis of 4-(prop-2-yn-1-yl)piperidine hydrochloride

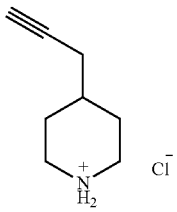

To a solution of tert-butyl 4-(prop-2-yn-1-yl)piperidine-1-carboxylate (2 g, 8.97 mmol) in MeOH (15 mL) was added CH₃COCl (5 mL) at 0° C. The solution was warmed to 25° C. and stirred for 1 h. Concentrated to afford the desired crude product 4-(prop-2-yn-1-yl)piperidine hydrochloride (1.7 g crude), which was used in next step directly

Step 3: Synthesis of 2-((6-((5-chloro-2-(4-(prop-2-yn-1-yl)piperidin-1-yl)pyrimidin-4-yl)amino)-1-methyl-2-oxo-1,2-dihydroquinolin-3-yl)oxy)-N-methylacetamide

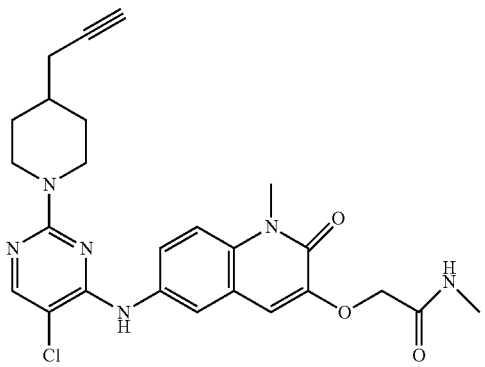 [SMILES: C#CCC1CCN(c2ncc(Cl)c(Nc3ccc4c(c3)cc(OCC(=O)NC)c(=O)n4C)n2)CC1]

To a solution of 2-((6-((2,5-dichloropyrimidin-4-yl)amino)-1-methyl-2-oxo-1,2-dihydroquinolin-3-yl)oxy)-N-methylacetamide (1.1 g, 2.70 mmol) in DMSO (20 ml) were added 4-(prop-2-yn-1-yl)piperidine hydrochloride (518 mg, 3.24 mmol) and DIEA (1.75 g, 13.5 mmol). After stirring at 100° C. for 2 h, the reaction mixture was poured into ice-water, filtered and dried to afford 1.3 g of the desired product. MS (ES⁺): m/z 495.2 [M+1]⁺

Step 4: Synthesis of 2-(2-(2-azidoethoxy)ethoxy)ethanol

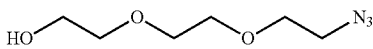 [SMILES: [N-]=[N+]=NCCOCCOCCO]

To a solution of 2-(2-(2-hydroxyethoxy)ethoxy)ethyl 4-methylbenzenesulfonate (6 g, 19.7 mmol) in DMF (30 mL) was added NaN₃ (1.45 g, 21.7 mmol). After stirred at 80° C. for 2 h, the mixture was cooled to room temperature and used in the next step without further purification.

Step 5: Synthesis of 2-(2-(2-azidoethoxy)ethoxy)ethyl methanesulfonate

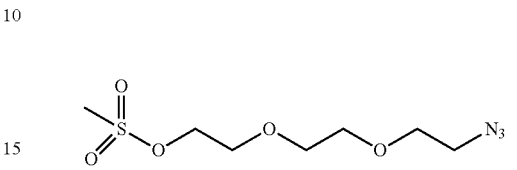

To a solution of 2-(2-(2-azidoethoxy)ethoxy)ethanol (the reaction mixture) in DMF/DCM (60 mL, 1/1, v/v) was added TEA (5.4 g, 5.34 mmol) and MsCl (3.0 g, 26.7 mmol). The mixture was stirred at r.t for 1 h. The mixture was quenched with H₂O (35 mL) and extracted with DCM (30 mL*3). The combined organic layers were dried over anhydrous sodium sulfate, filtered and concentrated to afford the crude product (5.4 g).

Step 6: Synthesis of 5-(2-(2-(2-azidoethoxy)ethoxy)ethoxy)-2-(2,6-dioxopiperidin-3-yl)isoindoline-1,3-dione

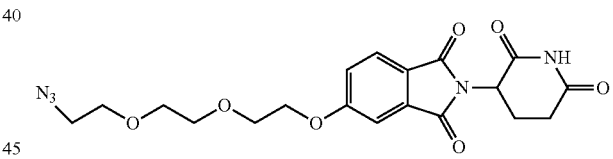

To a solution of crude 2-(2-(2-azidoethoxy)ethoxy)ethyl methanesulfonate (5.4 g, 21.3 mmol) in DMF (30 mL) was added 2-(2,6-dioxopiperidin-3-yl)-5-hydroxyisoindoline-1,3-dione (6.4 g, 23.45 mmol) and K₂CO₃ (5.9 g, 42.6 mmol). The mixture was stirred at 60° C. for 20 h. The mixture was diluted with H₂O (35 mL) and extracted with EA (40 mL*3). The combined organic layers were dried over anhydrous sodium sulfate, filtered and concentrated. The residue was purified by prep-HPLC to afford the desired product as a yellow solid (4.1 g, 49.4%). ¹H NMR (400 MHz, CD₃OD): δ 7.79 (d, J=8.4 Hz, 1H), 7.43 (d, J=1.6 Hz, 1H), 7.33 (dd, J=8.4 Hz, 2.0 Hz, 1H), 5.12-5.08 (m, 1H), 4.31 (t, J=4.4 Hz, 2H), 3.90 (t, J=4.4 Hz, 2H), 3.73-3.65 (m, 6H), 3.35 (t, J=4.8 Hz, 2H), 2.88-2.82 (m, 1H), 2.78-2.70 (m, 2H), 2.16-2.13 (m, 1H). MS (ES+): m/z 432.2 [M+1]⁺, Step 7: 2-((6-((5-chloro-2-(4-((1-(2-(2-(2-((2-(2,6-dioxopiperidin-3-yl)-1,3-dioxoisoindolin-5-yl)oxy)ethoxy)ethoxy)ethyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide

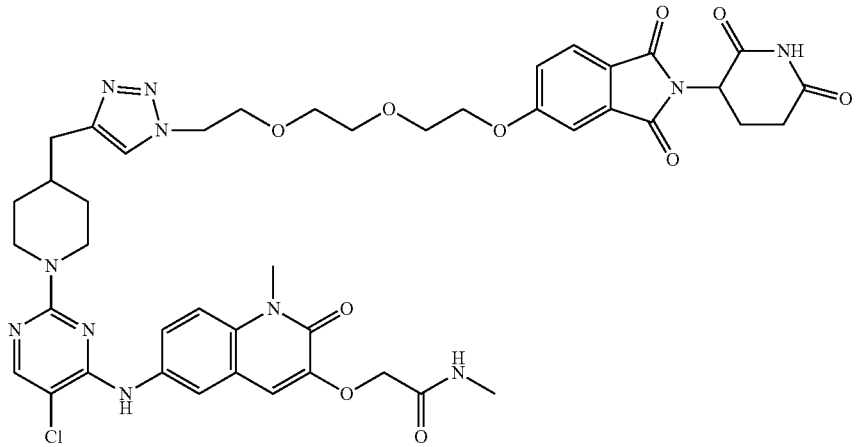 [SMILES: CNC(=O)COc1cc2cc(Nc3nc(N4CCC(Cc5cn(CCOCCOCCOc6ccc7c(c6)C(=O)N(C6CCC(=O)NC6=O)C7=O)nn5)CC4)ncc3Cl)ccc2n(C)c1=O]

To a solution of 5-(2-(2-(2-azidoethoxy)ethoxy)ethoxy)-2-(2,6-dioxopiperidin-3-yl)isoindoline-1,3-dione (100 mg, 0.23 mmol) in DMSO (2 ml) was added 2-((6-((5-chloro-2-(4-(prop-2-yn-1-yl)piperidin-1-yl)pyrimidin-4-yl)amino)-1-methyl-2-oxo-1,2-dihydroquinolin-3-yl)oxy)-N-methylacetamide (113.62 mg, 0.23 mmol), DIEA (0.2 mL) and CuI (10 mg, 0.05 mmol). After stirring at 30° C. for 3 h under $N_2$, the reaction mixture was filtered. Purified by pre-TLC first and then by prep-HPLC to afford the desired product 2-((6-((5-chloro-2-(4-((1-(2-(2-(2-((2-(2,6-dioxopiperidin-3-yl)-1,3-dioxoisoindolin-5-yl)oxy)ethoxy)ethoxy)ethyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide (33.5 mg) as white solid. $^1$HNMR (400 MHz, $CD_3OD$): δ 8.03 (s, 1H), 7.81 (m, 1H), 7.80 (s, 1H), 7.73 (m, 1H), 7.70 (m, 1H), 7.59 (d, J=9.2 Hz, 1H), 7.28 (s, 1H), 7.21 (s, 1H), 7.18 (d, J=8.4 Hz, 1H), 5.07 (m, 1H), 4.57 (s, 2H), 4.53 (m, 2H), 4.09 (m, 2H), 3.86 (m, 2H), 3.82 (s, 3H), 3.72 (m, 2H), 3.60 (s, 4H), 3.03 (m, 2H), 2.86 (m, 4H), 2.74 (m, 2H), 2.68 (m, 2H), 2.18 (m, 3H), 1.95 (m, 1H), 1.75 (m, 2H), 1.22 (m, 2H). MS: (ES$^+$): m/z 926.5 [M+1]$^+$ Exemplary Synthesis of 5-(4-((1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidin-4-yl)methyl)piperazin-1-yl)-2-(2,6-dioxopiperidin-3-yl)isoindoline-1,3-dione (Exemplary Compound 149)

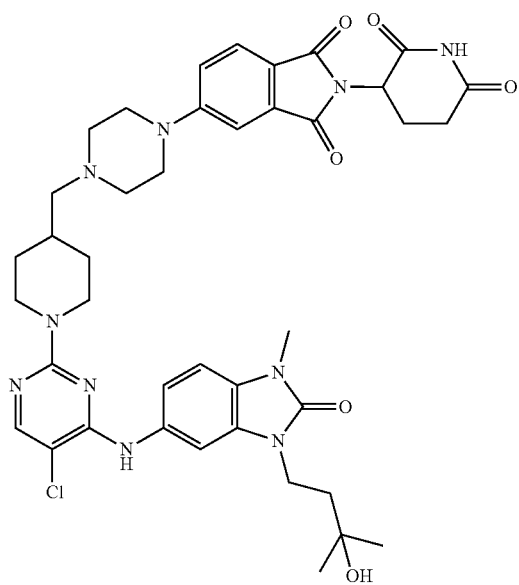 [SMILES: Cn1c(=O)n(CCC(C)(C)O)c2cc(Nc3nc(N4CCC(CN5CCN(c6ccc7c(c6)C(=O)N(C6CCC(=O)NC6=O)C7=O)CC5)CC4)ncc3Cl)ccc21]

A mixture of 5-((2,5-dichloropyrimidin-4-yl)amino)-3-(3-hydroxy-3-methylbutyl)-1-methyl-1,3-dihydro-2H-benzo[d]imidazol-2-one (WO2018215801, 100 mg, 0.40 mmol), 2-(2,6-dioxopiperidin-3-yl)-5-(4-(piperidin-4-ylmethyl)piperazin-1-yl)isoindoline-1,3-dione (194 mg, 0.44 mmol) and triethyl amine (202 mg, 2 mmol) in DMSO (1.0 mL) was stirred at 100° C. for 1 h. After cooling to room temperature the mixture was quenched with H₂O, and the mixture was extracted with ethyl acetate (20 mL×2). The organic phase was concentrated under vacuum. The residue was purified by prep-HPLC with the following conditions (1#-Pre-HPLC-011 (Waters)): Column, SunFire Prep C18, 19*150 mm 5 um; mobile phase, water and acetonitrile (20.0% acetonitrile up to 71.0% in 8 min, up to 100.0% in 2 min, down to 20.0% in 1 min); Detector, UV 254&220 nm to afford the desired product (30 mg) as a white solid. ¹HNMR (400 MHz, DMSO-d₆): δ 11.07 (s, 1H), 8.65 (s, 1H), 7.99 (s, 1H), 7.67-7.66 (m, 1H), 7.43 (s, 1H), 7.33 (m, 1H), 7.28-7.23 (m, 2H), 7.10-7.08 (m, 1H), 5.09-5.04 (m, 1H), 4.49-4.42 (m, 3H), 3.88-3.84 (m, 2H), 3.42 (s, 3H), 3.32 (m, 4H), 2.84-2.78 (m, 3H), 2.60-2.50 (m, 2H), 2.49-2.47 (m, 3H), 2.16 (m, 1H), 2.02-2.00 (m, 1H), 1.75-1.68 (m, 5H), 1.16 (s, 6H), 1.03-1.00 (m, 2H). MS: (ES+): m/z 799.3 [M+1]⁺.

Exemplary Synthesis of 5-[(1-[[1-(5-chloro-4-[[1-methyl-2-oxo-3-(2-oxopropoxy)quinolin-6-yl]amino]pyrimidin-2-yl)pyrrolidin-3-yl]methyl]piperidin-4-yl)oxy]-2-(2,6-dioxopiperidin-3-yl)isoindole-1,3-dione (Exemplary Compound 154)

Step 1: Synthesis of tert-butyl 4-[[2-(2,6-dioxopiperidin-3-yl)-1,3-dioxoisoindol-5-yl]oxy]piperidine-1-carboxylate

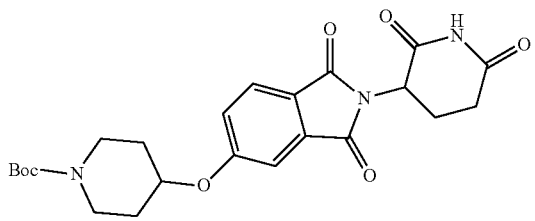 [SMILES: CC(C)(C)OC(=O)N1CCC(Oc2ccc3c(c2)C(=O)N(C2CCC(=O)NC2=O)C3=O)CC1]

Into a 30-mL sealed tube purged and maintained with an inert atmosphere of nitrogen, was placed PPh₃ (980 mg, 3.736 mmol, 1.50 equiv) and DIAD (750 mg, 3.709 mmol, 1.49 equiv) in THF (6 mL). This was followed by the addition of tert-butyl 4-hydroxypiperidine-1-carboxylate (500 mg, 2.484 mmol, 1.00 equiv) in THF (2 mL) and 2-(2,6-dioxopiperidin-3-yl)-5-hydroxyisoindole-1,3-dione (683 mg, 2.491 mmol, 1.00 equiv) respectively. The resulting solution was stirred for 3 h at 60° C. in an oil bath. The resulting mixture was concentrated. The crude product was purified by Prep-HPLC with the following conditions: Column, C18 silica gel; mobile phase, MeCN:H₂O (0.5% NH₄O₃)=1:9 increasing to MeCN:H₂O (0.5% NH₄O₃)=6:4 within 35 min; Detector, 254 nm. This resulted in 625 mg (55%) of tert-butyl 4-[[2-(2,6-dioxopiperidin-3-yl)-1,3-dioxoisoindol-5-yl]oxy]piperidine-1-carboxylate as a yellow solid. MS (ES+): m/z 402.05 [MH⁺–56].

Step 2: 2. Synthesis of 2-(2,6-dioxopiperidin-3-yl)-5-(piperidin-4-yloxy)isoindole-1,3-dione hydrochloride

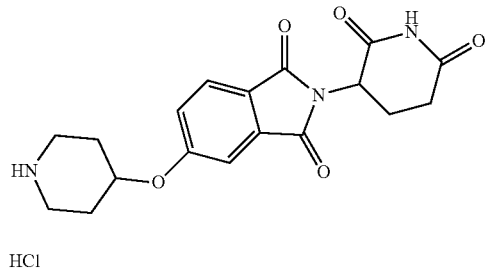 [SMILES: O=C1CCC(N2C(=O)c3ccc(OC4CCNCC4)cc3C2=O)C(=O)N1 ; Cl]

Into a 50-mL round-bottom flask, was placed tert-butyl 4-[[2-(2,6-dioxopiperidin-3-yl)-1,3-dioxoisoindol-5-yl]oxy]piperidine-1-carboxylate (625 mg, 1.366 mmol, 1.00 equiv) and dioxane (3 mL). This was followed by the addition of HCl (gas) in 1,4-dioxane (10 mL) drop wise with stirring at room temperature. The resulting solution was stirred for 30 min at room temperature and then concentrated. This resulted in 531 mg (98%) of 2-(2,6-dioxopiperidin-3-yl)-5-(piperidin-4-yloxy)isoindole-1,3-dione hydrochloride as a light yellow solid. MS (ES+): m/z 358.15 [MH⁺].

Step 3: Synthesis of tert-butyl 3-[(4-[[2-(2,6-dioxopiperidin-3-yl)-1,3-dioxoisoindol-5-yl]oxy]piperidin-1-yl)methyl]pyrrolidine-1-carboxylate

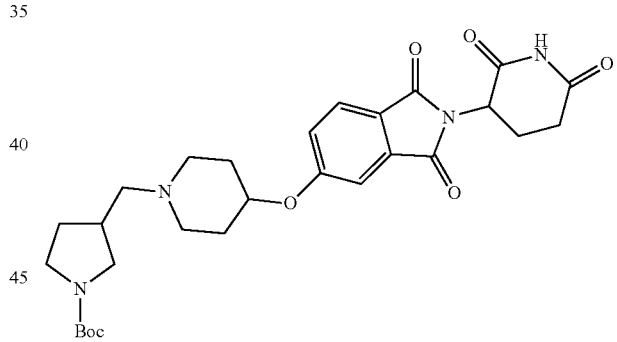

Into a 50-mL round-bottom flask, was placed 2-(2,6-dioxopiperidin-3-yl)-5-(piperidin-4-yloxy)isoindole-1,3-dione hydrochloride (530 mg, 1.346 mmol, 1.00 equiv) and DIEA (0.3 mL) in dichloromethane (20 mL). To this was added a solution of tert-butyl 3-formylpyrrolidine-1-carboxylate (270 mg, 1.355 mmol, 1.01 equiv) in dichloromethane (5 mL) drop wise at 0° C. in 10 min. The pH of the mixture was adjusted to 5 with HOAc (0.30 mL). After stirred for 1 hours at room temperature, NaBH(OAc)₃ (570 mg, 2.689 mmol, 2.00 equiv) was added. The resulting solution was stirred for 2 h at room temperature. The reaction was then quenched by the addition of water. The resulting solution was extracted with dichloromethane (50 mL×3). The combined organic layer was washed with brine (70 mL), dried over anhydrous sodium sulfate and concentrated under reduced pressure. The residue was applied onto a silica gel column with dichloromethane/methanol (13:1). This resulted in 575 mg (79%) of tert-butyl 3-[(4-[[2-(2,6- dioxopiperidin-3-yl)-1,3-dioxoisoindol-5-yl]oxy]piperidin-1-yl)methyl]pyrrolidine-1-carboxylate as a yellow solid. MS (ES+): m/z 541.25 [MH+].

Step 4: Synthesis of 2-(2,6-dioxopiperidin-3-yl)-5-((1-(pyrrolidin-3-ylmethyl)piperidin-4-yl)oxy)isoindoline-1,3-dione hydrochloride

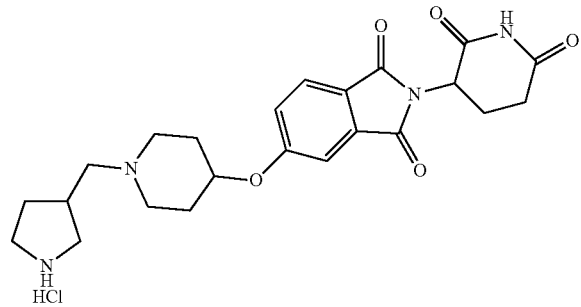 [SMILES: O=C1CCC(N2C(=O)c3ccc(OC4CCN(CC5CCNC5)CC4)cc3C2=O)C(=O)N1 ; Cl]

Into a 50-mL round-bottom flask, was placed tert-butyl 4-[[2-(2,6-dioxopiperidin-3-yl)-1,3-dioxoisoindol-5-yl]oxy]piperidine-1-carboxylate (575 mg, 1.257 mmol, 1.00 equiv) in dioxane (10 mL). This was followed by the addition of HCl (4M in 1,4-dioxane, 1.50 mL) dropwise with stirring at room temperature. The resulting solution was stirred for 30 min at room temperature and then concentrated under reduced pressure. This resulted in 449 mg (99%) of the title compound as an off-white solid. MS (ES+): m/z 441.20 [MH+].

Step 5: 5. Synthesis of 5-[(1-[[1-(5-chloro-4-[[1-methyl-2-oxo-3-(2-oxopropoxy)quinolin-6-yl]amino]pyrimidin-2-yl)pyrrolidin-3-yl]methyl]piperidin-4-yl)oxy]-2-(2,6-dioxopiperidin-3-yl)isoindole-1,3-dione

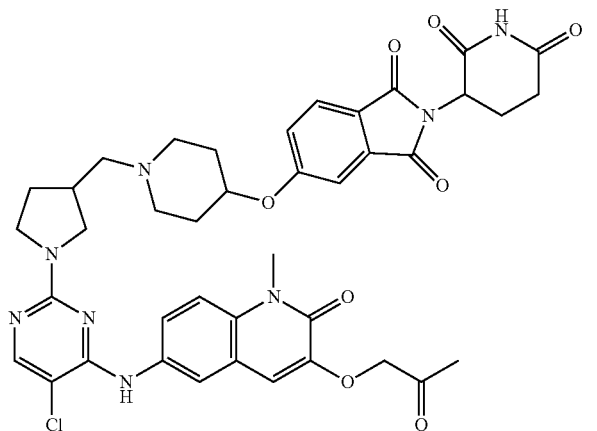 [SMILES: CC(=O)COc1cc2cc(Nc3nc(N4CCC(CN5CCC(Oc6ccc7c(c6)C(=O)N(C6CCC(=O)NC6=O)C7=O)CC5)C4)ncc3Cl)ccc2n(C)c1=O]

Into a 25-mL sealed tube purged and maintained with an inert atmosphere of nitrogen, was placed 6-[(2,5-dichloropyrimidin-4-yl)amino]-1-methyl-3-(2-oxopropoxy)quinolin-2-one (160 mg, 0.407 mmol, 1.00 equiv), 2-(2,6-dioxopiperidin-3-yl)-5-[[1-(pyrrolidin-3-ylmethyl)piperidin-4-yl]oxy]isoindole-1,3-dione hydrochloride (195 mg, 0.409 mmol, 1.00 equiv), DMSO (5 mL). This was followed by the addition of DIEA (0.70 mL) drop wise. The resulting solution was stirred for 2 h at 110° C. in an oil bath under the inert atmosphere of nitrogen. The reaction mixture was cooled and diluted with water. The resulting solution was extracted with ethyl acetate (50 mL×3). The combined organic layer was washed with brine (80 mL), dried over anhydrous sodium sulfate and concentrated under reduced pressure. The crude product was purified by Prep-HPLC with the following conditions: Column, C18 silica gel; mobile phase, MeCN:H$_2$O (0.5% TFA)=0:100 increasing to MeCN:H$_2$O (0.5% TFA)=21:79 within 13 min; Detector, 254 nm. This resulted in 24 mg (7%) of 5-[(1-[[1-(5-chloro-4-[[1-methyl-2-oxo-3-(2-oxopropoxy)quinolin-6-yl]amino]pyrimidin-2-yl)pyrrolidin-3-yl]methyl]piperidin-4-yl)oxy]-2-(2,6-dioxopiperidin-3-yl)isoindole-1,3-dione as an off-white solid. $^1$HNMR (400 MHz, DMSO, ppm) δ11.08 (br, 1H), 8.72 (br, 1H), 8.04-8.02 (m, 2H), 7.87-7.81 (m, 2H), 7.45-7.35 (m, 3H), 7.08 (s, 1H), 5.13-5.09 (m, 1H), 4.89 (s, 2H), 4.70-4.69 (m, 1H), 3.66-3.60 (m, 4H), 3.55-3.50 (m, 1H), 3.41-3.38 (m, 1H), 3.13-3.11 (m, 1H), 2.89-2.86 (m, 1H), 2.72-2.67 (m, 2H), 2.62-2.58 (m, 2H), 2.49-2.43 (m, 1H), 2.36-2.29 (m, 4H), 2.21 (s, 3H), 2.07-1.96 (m, 4H), 1.67-1.62 (m, 3H). MS (ES+): m/z 797.30 [MH+].

Exemplary Synthesis of 5-(4-((1-(5-chloro-4-((1-methyl-2-oxo-4-((2-(pyrimidin-2-yl)propan-2-yl)amino)-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione (Exemplary Compound 156)

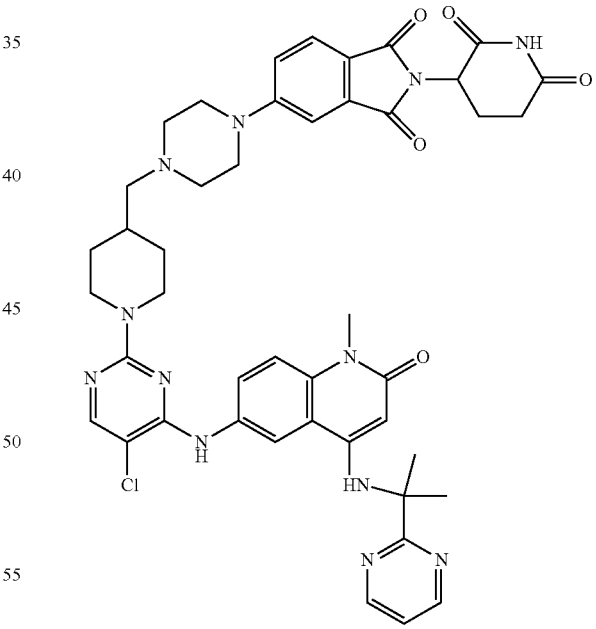

A mixture of 6-((2,5-dichloropyrimidin-4-yl)amino)-1-methyl-4-((2-(pyrimidin-2-yl)propan-2-yl)amino)quinolin-2(1H)-one (WO2018215798, 70 mg, 0.15 mmol), 2-(2,6-dioxopiperidin-3-yl)-5-(4-(piperidin-4-ylmethyl)piperazin-1-yl)isoindoline-1,3-dione (81 mg, 0.18 mmol) and triethyl amine (77 mg, 0.76 mmol) in DMSO (1.0 mL) was stirred at 100° C. for 1 h. After cooling to room temperature the mixture was diluted with H$_2$O and extracted with ethyl acetate (20 mL×2). The organic phase was concentrated under vacuum. The residue was purified by prep-HPLC with the following conditions (1#-Pre-HPLC-011 (Waters)): Column, SunFire Prep C18, 19*150 mm Sum; mobile phase, water and acetonitrile (20.0% acetonitrile up to 71.0% in 8 min, up to 100.0% in 2 min, down to 20.0% in 1 min); Detector, UV 254&220 nm to afford the desired product as 23 mg of a white solid. $^1$HNMR (400 MHz, DMSO-$d_6$): δ 11.09 (s, 1H), 9.39 (s, 1H), 8.92 (s, 1H), 8.82-8.81 (m, 2H), 8.39 (s, 1H), 8.08 (s, 1H), 7.77-7.75 (m, 2H), 7.48 (m, 1H), 7.41-7.34 (m, 3H), 6.78 (s, 1H), 5.11-5.07 (m, 1H), 4.71 (s, 1H), 4.57-4.46 (m, 2H), 4.28-4.18 (m, 2H), 3.59-3.56 (m, 2H), 3.40 (s, 3H), 3.33-3.27 (m, 2H), 3.14-3.06 (m, 4H), 2.91-2.85 (m, 3H), 2.66-2.61 (m, 1H), 2.38-2.32 (m, 1H), 2.10-2.01 (m, 2H), 1.77 (m, 7H), 1.17-1.10 (m, 2H). MS: (ES+): m/z 859.4 [M+1]$^+$ Exemplary Synthesis of 2-([6-[(5-chloro-2-[3-[4-(1-[3-[2-(2,6-dioxopiperidin-3-yl)-1-oxo-3H-isoindol-5-yl]prop-2-yn-1-yl]piperidin-4-yl)phenoxymethyl]piperidin-1-yl]pyrimidin-4-yl)amino]-1-methyl-2-oxoquinolin-3-yl]oxy)-N-methylacetamide (Exemplary Compound 167)

Step 1: of benzyl 4-(4-[[1-(tert-butoxycarbonyl)piperidin-3-yl]methoxy]phenyl)piperidine-1-carboxylate

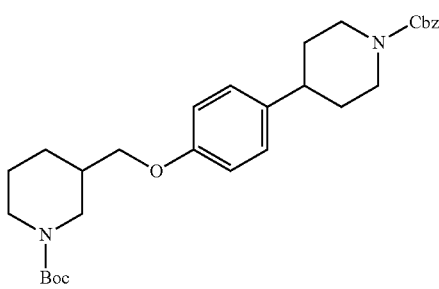 [SMILES: CC(C)(C)OC(=O)N1CCCC(COc2ccc(C3CCN(C(=O)OCc4ccccc4)CC3)cc2)C1]

Into a 100-mL round-bottom flask, was placed benzyl 4-(4-hydroxyphenyl)piperidine-1-carboxylate (1.37 g, 4.400 mmol, 1.00 equiv), Dimethyl Formamide (15 mL), K$_2$CO$_3$ (1.82 g, 13.199 mmol, 3 equiv), tert-butyl 3-[(methanesulfonyloxy)methyl]piperidine-1-carboxylate (1.55 g, 5.283 mmol, 1.20 equiv). The resulting solution was stirred for 3 h at 85° C. in an oil bath. The reaction was then quenched by the addition of water (20 mL). The resulting solution was extracted with ethyl acetate (2×20 mL). The resulting mixture was washed with brine (2×20 mL). The mixture was dried over anhydrous sodium sulfate. The residue was applied onto a silica gel column with ethyl acetate/petroleum ether (1/1). The collected fractions were combined and concentrated under vacuum. This resulted in 1.43 g (63.9%) of benzyl 4-(4-[[1-(tert-butoxycarbonyl)piperidin-3-yl]methoxy]phenyl)piperidine-1-carboxylate as a yellow solid. MS (ES$^+$): m/z 531.30 [MH$^+$].

Step 2: Synthesis of tert-butyl 3-[4-(piperidin-4-yl)phenoxymethyl]piperidine-1-carboxylate

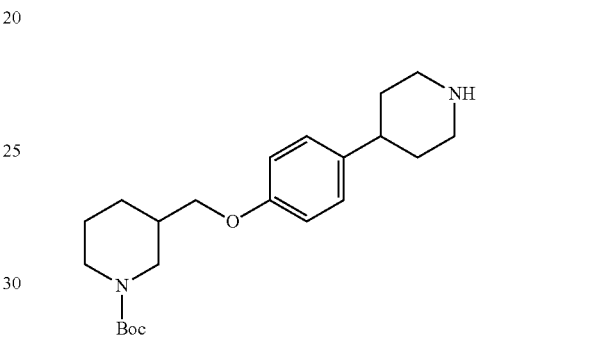

Into a 100-mL round-bottom flask, was placed benzyl 4-(4-[[1-(tert-butoxycarbonyl)piperidin-3-yl]methoxy]phenyl)piperidine-1-carboxylate (750 mg, 1.474 mmol, 1.00 equiv) in ethyl acetate (30 mL) and Pd(OH)$_2$/C (100 mg, 0.712 mmol, 0.48 equiv). The resulting solution was stirred for 4 h at room temperature under hydrogen atmosphere. The solids were filtered out. The resulting mixture was concentrated under vacuum. This resulted in 500 mg (90%) of tert-butyl 3-[4-(piperidin-4-yl)phenoxymethyl]piperidine-1-carboxylate as a light grey solid. MS (ES$^+$): m/z 375.00 [MH$^+$].

Step 3: Synthesis of tert-butyl 3-[4-(1-[3-[2-(2,6-dioxopiperidin-3-yl)-1-oxo-3H-isoindol-5-yl]prop-2-yn-1-yl]piperidin-4-yl)phenoxymethyl]piperidine-1-carboxylate

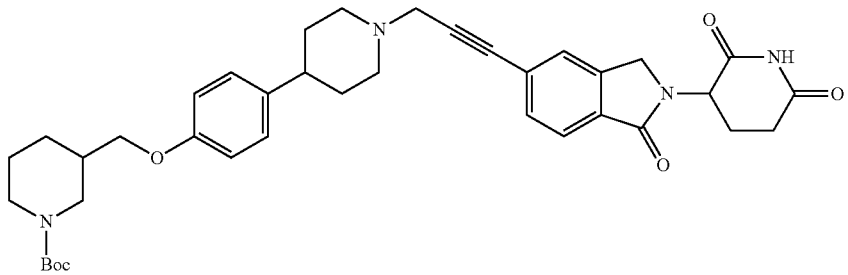 [SMILES: CC(C)(C)OC(=O)N1CCCC(COc2ccc(C3CCN(CC#Cc4ccc5c(c4)CN(C4CCC(=O)NC4=O)C5=O)CC3)cc2)C1]

Into a 100-mL round-bottom flask, was placed tert-butyl 3-[4-(piperidin-4-yl)phenoxymethyl]piperidine-1-carboxylate (177 mg, 0.473 mmol, 1.00 equiv), dichloromethane (10 mL), 3-[2-(2,6-dioxopiperidin-3-yl)-1-oxo-3H-isoindol-5-yl]prop-2-ynal (140.02 mg, 0.473 mmol, 1 equiv). The resulting solution was stirred for 3 h at 35° C. in an oil bath. To this was added NaBH₃CN (89.10 mg, 1.418 mmol, 3 equiv). The resulting solution was stirred for 3 h at 35° C. in an oil bath. The resulting solution was extracted with dichloromethane (3×20 mL). The resulting mixture was washed with brine (3×20 mL). The mixture was dried over anhydrous sodium sulfate and concentrated. The residue was applied onto a silica gel column with ethyl acetate/petroleum ether (1/1). This resulted in 146 mg (47%) of tert-butyl 3-[4-(1-[3-[2-(2,6-dioxopiperidin-3-yl)-1-oxo-3H-isoindol-5-yl]prop-2-yn-1-yl]piperidin-4-yl)phenoxymethyl]piperidine-1-carboxylate as a brown solid. MS (ES⁺): m/z 655.35 [MH⁺].

Step 4: Synthesis of 3-[1-oxo-5-(3-[4-[4-(piperidin-3-ylmethoxy)phenyl]piperidin-1-yl]prop-1-yn-1-yl)-3H-isoindol-2-yl]piperidine-2,6-dione

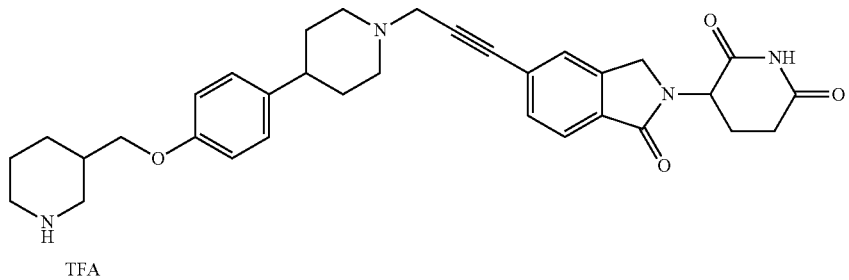 [SMILES: O=C1CCC(N2Cc3cc(C#CCN4CCC(c5ccc(OCC6CCCNC6)cc5)CC4)ccc3C2=O)C(=O)N1]

Into a 50-mL round-bottom flask, was placed tert-butyl 3-[4-(1-[3-[2-(2,6-dioxopiperidin-3-yl)-1-oxo-3H-isoindol-5-yl]prop-2-yn-1-yl]piperidin-4-yl)phenoxymethyl]piperidine-1-carboxylate (130 mg, 0.199 mmol, 1.00 equiv) in dichloromethane (15 mL) and TFA (5 mL). The resulting solution was stirred for 3 h at room temperature. The resulting mixture was concentrated. This resulted in 108 mg (crude) of 3-[1-oxo-5-(3-[4-[4-(piperidin-3-ylmethoxy)phenyl]piperidin-1-yl]prop-1-yn-1-yl)-3H-isoindol-2-yl]piperidine-2,6-dione as a yellow solid.

LC-MS (ES⁺): m/z 555.3 [MH⁺]

Step 5: Synthesis of 2-([6-[(5-chloro-2-[3-[4-(1-[3-[2-(2,6-dioxopiperidin-3-yl)-1-oxo-3H-isoindol-5-yl]prop-2-yn-1-yl]piperidin-4-yl)phenoxymethyl]piperidin-1-yl]pyrimidin-4-yl)amino]-1-methyl-2-oxoquinolin-3-yl]oxy)-N-methylacetamide

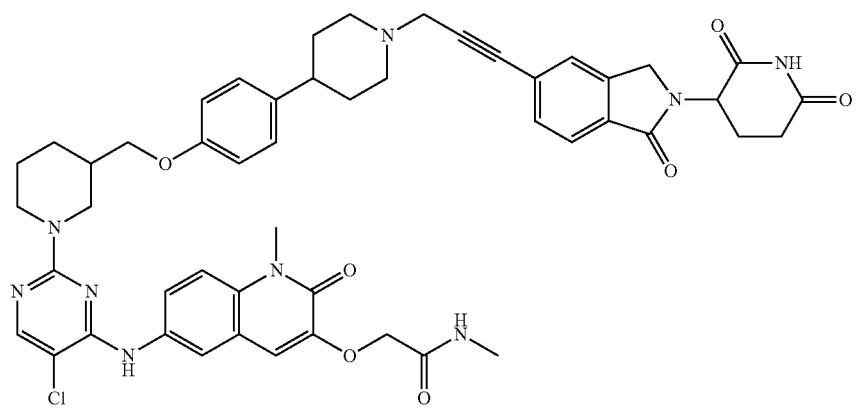 [SMILES: CNC(=O)COc1cc2cc(Nc3nc(N4CCCC(COc5ccc(C6CCN(CC#Cc7ccc8c(c7)CN(C7CCC(=O)NC7=O)C8=O)CC6)cc5)C4)ncc3Cl)ccc2n(C)c1=O]

Into a 50-mL round-bottom flask, was placed 3-[1-oxo-5-(3-[4-[4-(piperidin-3-ylmethoxy)phenyl]piperidin-1-yl]prop-1-yn-1-yl)-3H-isoindol-2-yl]piperidine-2,6-dione (102 mg, 0.184 mmol, 1.00 equiv), Dimethylsulfoxide (5 mL), Diisopropylethylamine (0.10 mL, 0.574 mmol, 3.12 equiv), 2-([6-[(2,5-dichloropyrimidin-4-yl)amino]-1-methyl-2-oxo-quinolin-3-yl]oxy)-N-methylacetamide (75 mg, 0.184 mmol, 1.00 equiv). The resulting solution was stirred for 5 h at 100° C. in an oil bath. The resulting mixture was concentrated under vacuum. The reaction was then quenched by the addition of water (20 mL). The resulting solution was extracted with dichloromethane (2×10 mL), and dried over anhydrous sodium sulfate. The residue was applied onto a silica gel column with dichloromethane/methanol (10/1). The crude product was purified by Prep-HPLC with the following conditions: Column, XBridge Shield RP18 OBD Column, 5 um, 19*150 mm; mobile phase, Water (10 MMOL/L NH$_4$HCO$_3$) and acetonitrile (38% acetonitrile to 62% in 8 min); Detector, uv. This resulted in 36.4 mg (21.37%) of 2-([6-[(5-chloro-2-[3-[4-(1-[3-[2-(2,6-dioxopiperidin-3-yl)-1-oxo-3H-isoindol-5-yl]prop-2-yn-1-yl]piperidin-4-yl)phenoxymethyl]piperidin-1-yl]pyrimidin-4-yl)amino]-1-methyl-2-oxoquinolin-3-yl]oxy)-N-methylacetamide as a brown solid. $^1$H NMR (400 MHz, DMSO-d6) δ 11.00 (s, 1H), 8.90 (s, 1H), 8.31-7.33 (m, 8H), 7.3-6.98 (m, 3H), 6.6 (s, 1H), 5.20 (s, 1H), 4.9-4.19 (m, 6H), 3.99-3.48 (m, 7H), 3.05-2.78 (m, 5H), 2.72-2.59 (m, 4H), 2.42-2.19 (m, 5H), 2.09-1.59 (m, 5H), 1.50-1.02 (m, 3H). MS (ES$^+$): m/z 926.25 [MH$^+$].

Exemplary Synthesis of 5-([3-[2-(5-chloro-4-[[1-methyl-2-oxo-3-(2-oxopropoxy)quinolin-6-yl]amino]pyrimidin-2-yl)ethynyl]piperidin-1-yl]methyl)-2-(2,6-dioxopiperidin-3-yl)isoindole-1,3-dione (Exemplary Compound 173)

Step 1: Synthesis of tert-butyl 3-[2-(5-chloro-4-[[1-methyl-2-oxo-3-(2-oxopropoxy)quinolin-6-yl]amino]pyrimidin-2-yl)ethynyl]piperidine-1-carboxylate

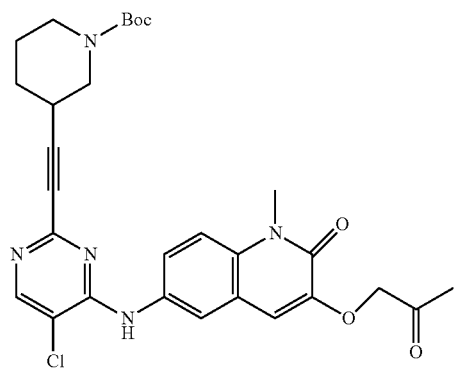 [SMILES: CC(=O)COc1cc2cc(Nc3nc(C#CC4CCCN(C(=O)OC(C)(C)C)C4)ncc3Cl)ccc2n(C)c1=O]

tert-butyl 3-ethynylpiperidine-1-carboxylate (638 mg, 3.0 mmol, 5.00 equiv) was added to a stirred solution of 6-[(2,5-dichloropyrimidin-4-yl)amino]-1-methyl-3-(2-oxopropoxy)quinolin-2-one (240 mg, 0.6 mmol, 1.00 equiv), CuI (35 mg, 0.18 mmol, 0.30 equiv), TEA (2. mL, 19.7 mmol, 23.6 equiv), Pd(PPh$_3$)$_2$Cl$_2$ (42.8 mg, 0.06 mmol, 0.10 equiv), PPh$_3$ (32.0 mg, 0.12 mmol, 0.20 equiv) in DMF (5 mL) under nitrogen atmosphere. The resulting mixture was heated to 100° C. for 2 hr before evaporation. The product was isolated by Prep-HPLC with the following conditions: Column, C18 silica gel; mobile phase, ACN/NH$_4$HCO$_3$=0 increasing to ACN/NH$_4$HCO$_3$=60. This resulted in 250 mg (71%) of tert-butyl 3-[2-(5-chloro-4-[[1-methyl-2-oxo-3-(2-oxopropoxy)quinolin-6-yl]amino]pyrimidin-2-yl)ethynyl]piperidine-1-carboxylate as a white solid. MS (ES$^+$): m/z 566.20 [MH$^+$].

Step 2: 2. Synthesis of 6-([5-chloro-2-[2-(piperidin-3-yl)ethynyl]pyrimidin-4-yl]amino)-1-methyl-3-(2-oxopropoxy)quinolin-2-one hydrochloride

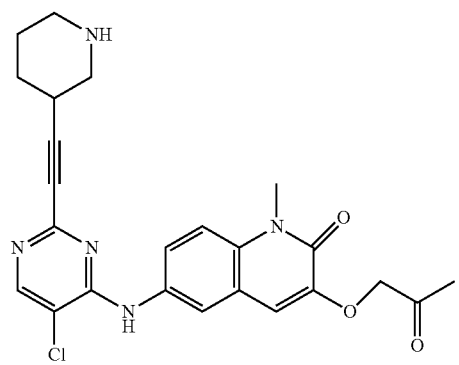 [SMILES: CC(=O)COc1cc2cc(Nc3nc(C#CC4CCCNC4)ncc3Cl)ccc2n(C)c1=O]

Into a 100-mL round-bottom flask, was placed a solution of tert-butyl 4-[2-(5-chloro-4-[[1-methyl-2-oxo-3-(2-oxo-propoxy)quinolin-6-yl]amino]pyrimidin-2-yl)ethynyl]piperidine-1-carboxylate (250 mg, 0.442 mmol, 1.00 equiv) in dioxane (2 ml) and hydrogen chloride (4M in dioxane, 5 mL). The resulting solution was stirred for 1 h at room temperature and concentrated under reduced pressure. This resulted in 250 mg (crude) of 4-(3-methoxyprop-1-yn-1-yl)piperidine hydrochloride as a white solid. MS (ES$^+$): m/z 466.20 [MH$^+$].

Step 3: Synthesis of 2-(2,6-dioxopiperidin-3-yl)-5-methylisoindole-1,3-dione

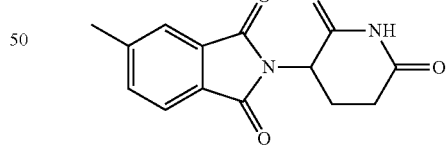

Into a 50-mL round-bottom flask, was placed 5-methyl-2-benzofuran-1,3-dione (300 mg, 1.85 mmol, 1.0 equiv), HOAc (20 mL), 3-aminopiperidine-2,6-dione hydrochloride (365 mg, 2.22 mmol, 1.2 equiv), and NaOAc (607 mg, 7.40 mmol, 4.0 equiv). The resulting mixture was stirred for 2 hr at 120 degrees C. in an oil bath. The reaction mixture was cooled to room temperature, and then quenched by the addition of 50 mL of water. The solids were collected by filtration, and then dried under vacuum. This resulted in 433 mg (86%) of 2-(2,6-dioxopiperidin-3-yl)-5-methylisoindole-1,3-dione as a grey solid.

Step 4: Synthesis of 5-(bromomethyl)-2-(2,6-dioxopiperidin-3-yl)isoindole-1,3-dione

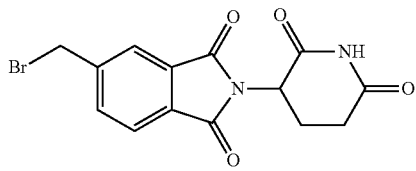 [SMILES: O=C1CCC(N2C(=O)c3ccc(CBr)cc3C2=O)C(=O)N1]

Into a 25-mL round-bottom flask purged and maintained with an inert atmosphere of nitrogen, was placed 2-(2,6-dioxopiperidin-3-yl)-5-methylisoindole-1,3-dione (200 mg, 0.74 mmoL, 1.0 equiv), acetonitrile (10 mL), NBS (144 mg, 0.81 mmoL, 1.1 equiv), and AIBN (24 mg, 0.15 mmol, 0.2 equiv). The resulting mixture was stirred for 2 hr at 85 degrees C. in an oil bath. The reaction mixture was cooled to room temperature, and then concentrated under vacuum. The residue was diluted with 10 mL of EA. The solids were collected by filtration. This resulted in 141 mg (55%) of 5-(bromomethyl)-2-(2,6-dioxopiperidin-3-yl)isoindole-1,3-dione as a white solid.

Step 5: Synthesis of 5-([3-[2-(5-chloro-4-[[1-methyl-2-oxo-3-(2-oxopropoxy)quinolin-6-yl]amino]pyrimidin-2-yl)ethynyl]piperidin-1-yl]methyl)-2-(2,6-dioxopiperidin-3-yl)isoindole-1,3-dione

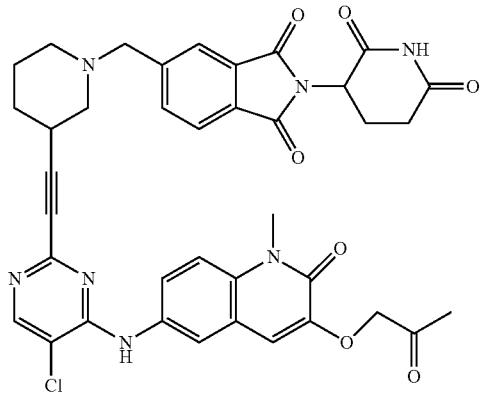 [SMILES: CC(=O)COc1cc2cc(Nc3nc(C#CC4CCCN(Cc5ccc6c(c5)C(=O)N(C5CCC(=O)NC5=O)C6=O)C4)ncc3Cl)ccc2n(C)c1=O]

Into a 25-mL round-bottom flask, was placed 6-([5-chloro-2-[2-(piperidin-3-yl)ethynyl]pyrimidin-4-yl]amino)-1-methyl-3-(2-oxopropoxy)quinolin-2-one hydrochloride (108 mg, 0.22 mmol, 1.0 equiv), 5-(bromomethyl)-2-(2,6-dioxopiperidin-3-yl)isoindole-1,3-dione (113 mg, 0.32 mmol, 1.5 equiv), DMSO (2 mL), and DIEA (1.5 mL). The resulting mixture was stirred for 1 hr at room temperature. The product was isolated by Flash-Prep-HPLC with the following conditions (IntelFlash-1): Column, C18 (330 g); mobile phase, CH$_3$CN/NH$_4$HCO$_3$ (aq, c=10 mmol/L)=(0 to 40:60 within 30 min). This resulted in 21.2 mg (13.4%) of 5-([3-[2-(5-chloro-4-[[1-methyl-2-oxo-3-(2-oxopropoxy)quinolin-6-yl]amino]pyrimidin-2-yl)ethynyl]piperidin-1-yl]methyl)-2-(2,6-dioxopiperidin-3-yl)isoindole-1,3-dione as a white solid. $^1$H NMR (300 MHz, DMSO-d$_6$) δ (ppm): 11.13 (s, 1H), 9.27 (s, 1H), 8.37 (s, 1H), 7.82 (d, J=6.5 Hz, 3H), 7.72 (d, J=2.4 Hz, 1H), 7.67-7.57 (m, 1H), 7.47 (d, J=9.1 Hz, 1H), 7.11 (s, 1H), 5.15-5.09 (m, 1H), 4.88 (s, 2H), 3.72 (s. 1H), 3.67 (d, J=9.6 Hz, 2H), 2.96-2.78 (m, 2H), 2.62-2.57 (m, 3H), 2.39-2.18 (m, 6H), 2.06-2.02 (m, 1H), 1.89-1.65 (m, 3H), 1.49-1.21 (m, 3H). MS (ES$^+$): m/z 736.20 [MH$^+$].

Exemplary Synthesis of 5-(4-((4-(5-chloro-4-((1-methyl-2-oxo-3-(2-oxopropoxy)-1,2-dihydroquinolin-6-yl)amino)pyrimidin-2-yl)-3,6-dihydropyridin-1(2H)-yl)methyl)piperidin-1-yl)-2-(2,6-dioxopiperidin-3-yl)isoindoline-1,3-dione (Exemplary Compound 188)

Step 1: Synthesis of tert-butyl 4-(5-chloro-4-[[1-methyl-2-oxo-3-(2-oxopropoxy)quinolin-6-yl]amino]pyrimidin-2-yl)-3,6-dihydro-2H-pyridine-1-carboxylate

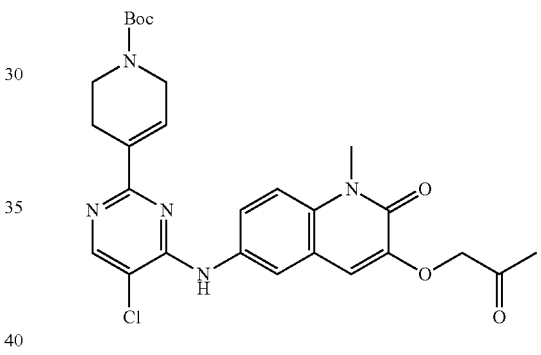

Into a 20-mL sealed tube purged and maintained with an inert atmosphere of nitrogen, was placed 6-[(2,5-dichloropyrimidin-4-yl)amino]-1-methyl-3-(2-oxopropoxy)quinolin-2-one (300 mg, 0.7 mmol, 1.0 equiv), tert-butyl 4-(4,4,5,5-tetramethyl-1,3,2-dioxaborolan-2-yl)-3,6-dihydro-2H-pyridine-1-carboxylate (235.9 mg, 0.7 mmol, 1.0 equiv), K$_2$CO$_3$ (316.3 mg, 2.3 mmol, 3.0 equiv), Pd(dppf)Cl$_2$ (111.6 mg, 0.15 mmol, 0.2 equiv), dioxane (5.0 mL) and H$_2$O (1.0 mL). The resulting mixture was stirred for 2 hours at 90° C. in an oil bath. Then the mixture was diluted with 50 mL of water and extracted with ethyl acetate (50 mL×2). The combined organic layer was washed with brine (50 mL×3), dried over anhydrous sodium sulfate and concentrated under reduced pressure. The residue was applied onto a silica gel column eluting with ethyl acetate/petroleum ether (1:0). This resulted in 140 mg (33%) of tert-butyl 4-(5-chloro-4-[[1-methyl-2-oxo-3-(2-oxopropoxy)quinolin-6-yl]amino]pyrimidin-2-yl)-3,6-dihydro-2H-pyridine-1-carboxylate as a yellow solid. MS (ES$^+$): m/z 540.20 [MH$^+$].

Step 2: Synthesis of 6-[[5-chloro-2-(1,2,3,6-tetrahydropyridin-4-yl)pyrimidin-4-yl]amino]-1-methyl-3-(2-oxopropoxy)quinolin-2-one

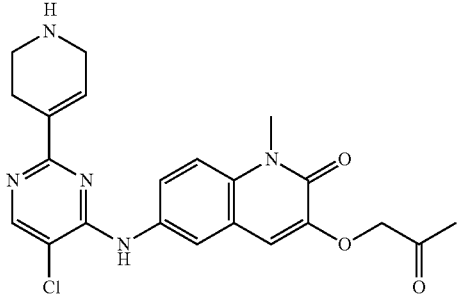

Into a 100-mL round-bottom flask, was placed tert-butyl 4-(5-chloro-4-[[1-methyl-2-oxo-3-(2-oxopropoxy)quinolin-6-yl]amino]pyrimidin-2-yl)-3,6-dihydro-2H-pyridine-1-carboxylate (140 mg, 0.259 mmol, 1.0 equiv) in DCM (10 mL), to which hydrogen chloride in 1,4-dioxane solution (4.0 M, 5 mL) was added. The resulting mixture was stirred for 2 hours at room temperature. Then the mixture was concentrated under reduced pressure. This resulted in 100.0 mg (87.69%) of 6-[[5-chloro-2-(1,2,3,6-tetrahydropyridin-4-yl)pyrimidin-4-yl]amino]-1-methyl-3-(2-oxopropoxy)quinolin-2-one as a yellow solid. MS (ES$^+$): m/z 440.25 [MH$^+$].

Step 3: Synthesis of 5-[4-(dimethoxymethyl)piperidin-1-yl]-2-(2,6-dioxopiperidin-3-yl)isoindole-1,3-dione

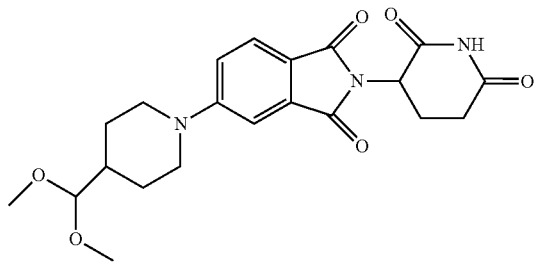 [SMILES: COC(OC)C1CCN(c2ccc3c(c2)C(=O)N(C2CCC(=O)NC2=O)C3=O)CC1]

Into a 30-mL sealed tube purged and maintained with an inert atmosphere of nitrogen, was placed 4-(dimethoxymethyl)piperidine (300 mg, 1.9 mmol, 1.0 equiv), DMSO (20.0 mL), 2-(2,6-dioxopiperidin-3-yl)-5-fluoroisoindole-1,3-dione (520.4 mg, 1.9 mmol, 1.0 equiv), DIEA (730.5 mg, 5.7 mmol, 3.0 equiv). The resulting mixture was stirred for 2 hours at 110° C. in an oil bath. Then the mixture was diluted with 30 mL of water and extracted with ethyl acetate (30 mL×2). The combined organic layer was washed with brine (30 mL×3), dried over anhydrous sodium sulfate and concentrated under reduced pressure. The residue was applied onto a silica gel column eluting with ethyl acetate/petroleum ether (1:0). This resulted in 750.0 mg (95.9%) of 5-[4-(dimethoxymethyl)piperidin-1-yl]-2-(2,6-dioxopiperidin-3-yl)isoindole-1,3-dione as a yellow solid. MS (ES$^+$): m/z 416.25[MH$^+$].

Step 4: Synthesis of 1-[2-(2,6-dioxopiperidin-3-yl)-1,3-dioxoisoindol-5-yl]piperidine-4-carbaldehyde

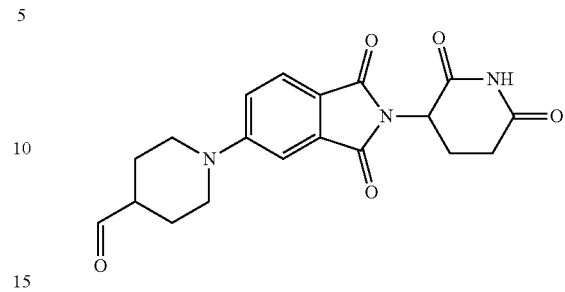

Into a 100-mL round-bottom flask, was placed 5-[4-(dimethoxymethyl)piperidin-1-yl]-2-(2,6-dioxopiperidin-3-yl)isoindole-1,3-dione (750 mg, 1.8 mmol, 1.00 equiv) in THF (20 mL), then H$_2$SO$_4$ (1M, 20 mL) was added. The resulting mixture was stirred for 6 hours at 60° C. in an oil bath. Then the pH value of the mixture was adjusted to 7 with NH$_4$HCO$_3$. The mixture was extracted with ethyl acetate (30 mL×2). The combined organic layer was washed with brine (30 mL×3), dried over anhydrous sodium sulfate and concentrated under reduced pressure. This resulted in 660.0 mg (92.8%) of 1-[2-(2,6-dioxopiperidin-3-yl)-1,3-dioxoisoindol-5-yl]piperidine-4-carbaldehyde as a yellow solid. MS (ES$^+$): m/z 370.20[MH$^+$].

Step 5: Synthesis of 5-(4-[[4-(5-chloro-4-[[1-methyl-2-oxo-3-(2-oxopropoxy)quinolin-6-yl]amino]pyrimidin-2-yl)-3,6-dihydro-2H-pyridin-1-yl]methyl]piperidin-1-yl)-2-(2,6-dioxopiperidin-3-yl)isoindole-1,3-dione

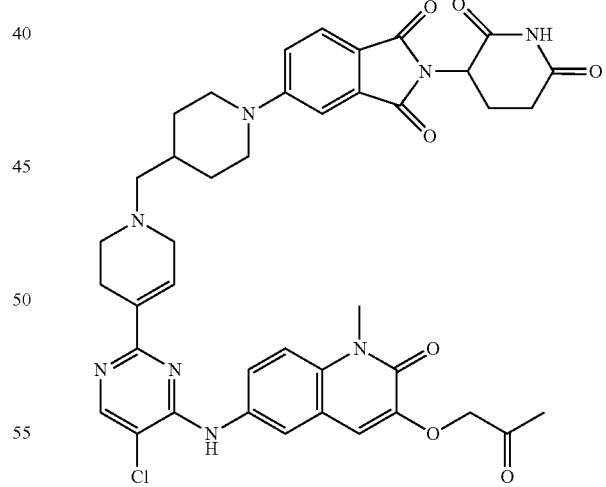

Into a 100-mL round-bottom flask, was placed a solution of 6-[[5-chloro-2-(1,2,3,6-tetrahydropyridin-4-yl)pyrimidin-4-yl]amino]-1-methyl-3-(2-oxopropoxy)quinolin-2-one (70.0 mg, 0.16 mmol, 1.0 equiv) and DIEA (1.0 mL) in DCE (20 mL). This was followed by the addition of 1-[2-(2,6-dioxopiperidin-3-yl)-1,3-dioxoisoindol-5-yl]piperidine-4-carbaldehyde (176.3 mg, 0.5 mmol, 3.0 equiv) at room temperature. The PH of the mixture was adjusted to 5 with HOAc (0.50 mL). After stirred for 2 hours at room temperature, NaBH(OAC)₃ (134.9 mg, 0.6 mmol, 4.00 equiv) was added. The reaction mixture was stirred for 2 hours at room temperature and then quenched by the addition of water. The resulting mixture was extracted with dichloromethane (50 mL×3), and the combined organic layer was washed with brine (50 mL×3), dried over anhydrous sodium sulfate and concentrated under reduced pressure. The crude product was purified by Prep-HPLC with the following conditions: Column, X select CSH OBD Column 30*150 mm Sum, n; mobile phase, undefined and undefined (20% Phase B up to 40% in 10 min); Detector, UV. This resulted in 33 mg (26%) of 5-(4-[[4-(5-chloro-4-[[1-methyl-2-oxo-3-(2-oxopropoxy)quinolin-6-yl]amino]pyrimidin-2-yl)-3,6-dihydro-2H-pyridin-1-yl]methyl]piperidin-1-yl)-2-(2,6-dioxopiperidin-3-yl)isoindole-1,3-dione as a yellow solid. ¹H NMR (400 MHz, DMSO-d₆, ppm): δ 11.06 (s, 1H), 9.14 (s, 1H), 8.42 (s, 1H), 8.00 (d, J=2.4 Hz, 1H), 7.78-7.74 (m, 1H), 7.65 (d, J=8.5 Hz, 1H), 7.49 (d, J=9.1 Hz, 1H), 7.30 (d, J=2.3 Hz, 1H), 7.23-7.19 (m, 1H), 7.12 (s, 1H), 6.99 (d, J=4.0 Hz, 1H), 5.08-5.02 (m, 1H), 4.92 (s, 2H), 4.08-4.02 (m, 2H), 3.68 (s, 3H), 3.15-3.10 (m, 2H), 2.97-2.81 m, 3H), 2.60-2.51 (m, 5H), 2.30-2.25 (m, 2H), 2.20 (s, 3H), 2.10-1.97 (m, 1H), 1.95-1.93 (m, 1H), 1.90-1.80 (m, 2H), 1.26-1.10 (m, 3H); MS (ES⁺): m/z 793.25[MH⁺].

Exemplary Synthesis of 5-(2-[3-[2-(5-chloro-4-[[1-methyl-2-oxo-3-(2-oxopropoxy)quinolin-6-yl]amino]pyrimidin-2-yl)ethynyl]piperidin-1-yl]ethoxy)-2-(2,6-dioxopiperidin-3-yl)isoindole-1,3-dione (Exemplary Compound 189)

Step 1: Synthesis of 5-(2,2-dihydroxyethoxy)-2-(2,6-dioxopiperidin-3-yl)isoindole-1,3-dione

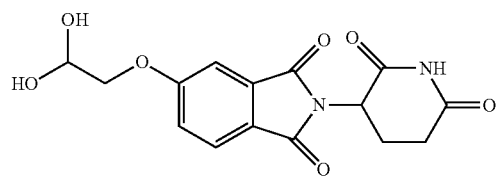 [SMILES: O=C1CCC(N2C(=O)c3ccc(OCC(O)O)cc3C2=O)C(=O)N1]

Into a 8-mL sealed tube purged and maintained with an inert atmosphere of nitrogen, was placed 5-(2,2-dimethoxyethoxy)-2-(2,6-dioxopiperidin-3-yl)isoindole-1,3-dione (300 mg, 0.828 mmol, 1.00 equiv), amberlyst(R) a-26(OH) (10 mg) in acetone (2.5 mL)/H₂O (0.50 mL). The resulting solution was stirred overnight at 70° C. in an oil bath. The solids were removed by filtration and the filtrate was concentrated under vacuum. This resulted in 270 mg (97.55%) of 5-(2,2-dihydroxyethoxy)-2-(2,6-dioxopiperidin-3-yl)isoindole-1,3-dione as a white crude solid. MS (ES⁺): m/z 335.15 [MH⁺].

Step 2: Synthesis of tert-butyl 3-[2-(5-chloro-4-[[1-methyl-2-oxo-3-(2-oxopropoxy)quinolin-6-yl]amino]pyrimidin-2-yl)ethynyl]piperidine-1-carboxylate

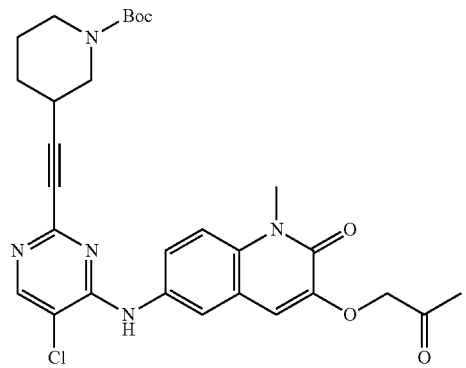 [SMILES: CC(=O)COc1cc2cc(Nc3nc(C#CC4CCCN(C(=O)OC(C)(C)C)C4)ncc3Cl)ccc2n(C)c1=O]

tert-Butyl 3-ethynylpiperidine-1-carboxylate (638 mg, 3.0 mmol, 5.00 equiv) was added to a stirred solution of 6-[(2,5-dichloropyrimidin-4-yl)amino]-1-methyl-3-(2-oxopropoxy)quinolin-2-one (240 mg, 0.6 mmol, 1.00 equiv), CuI (35 mg, 0.18 mmol, 0.30 equiv), TEA (2. mL, 19.7 mmol, 23.6 equiv), Pd(PPh₃)₂Cl₂ (42.8 mg, 0.06 mmol, 0.10 equiv), PPh₃ (32.0 mg, 0.12 mmol, 0.20 equiv) in DMF (5 mL) under nitrogen atmosphere. The resulting mixture was heated to 100° C. for 2 hr before evaporation. The product was isolated by Prep-HPLC with the following conditions: Column, C18 silica gel; mobile phase, ACN/NH₄HCO₃=0 increasing to ACN/NH₄HCO₃=60. This resulted in 250 mg (71%) of tert-butyl 3-[2-(5-chloro-4-[[1-methyl-2-oxo-3-(2-oxopropoxy)quinolin-6-yl]amino]pyrimidin-2-yl)ethynyl]piperidine-1-carboxylate as a white solid. MS (ES⁺): m/z 566.20 [MH⁺].

Step 3: Synthesis of 6-([5-chloro-2-[2-(piperidin-3-yl)ethynyl]pyrimidin-4-yl]amino)-1-methyl-3-(2-oxopropoxy)quinolin-2-one hydrochloride

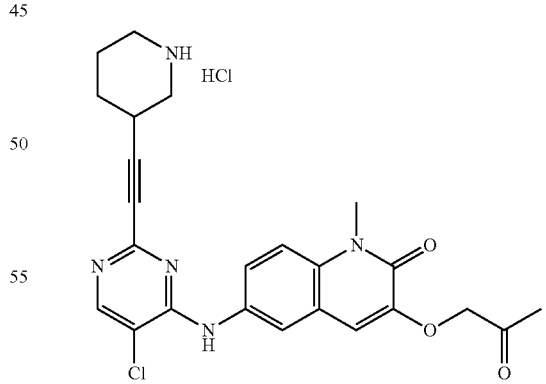

Into a 100-mL round-bottom flask, was placed a solution of tert-butyl 4-[2-(5-chloro-4-[[1-methyl-2-oxo-3-(2-oxopropoxy)quinolin-6-yl]amino]pyrimidin-2-yl)ethynyl]piperidine-1-carboxylate (250 mg, 0.442 mmol, 1.00 equiv) in dioxane (2 ml) and hydrogen chloride (4M in dioxane, 5 mL). The resulting solution was stirred for 1 h at room temperature and concentrated under reduced pressure. This resulted in 250 mg (crude) of 4-(3-methoxyprop-1-yn-1-yl) piperidine hydrochloride as a white solid. MS (ES⁺): m/z 466.20 [MH⁺].

Synthesis of 5-(2-[3-[2-(5-chloro-4-[[1-methyl-2-oxo-3-(2-oxopropoxy)quinolin-6-yl]amino]pyrimidin-2-yl)ethynyl]piperidin-1-yl]ethoxy)-2-(2,6-dioxopiperidin-3-yl)isoindole-1,3-dione

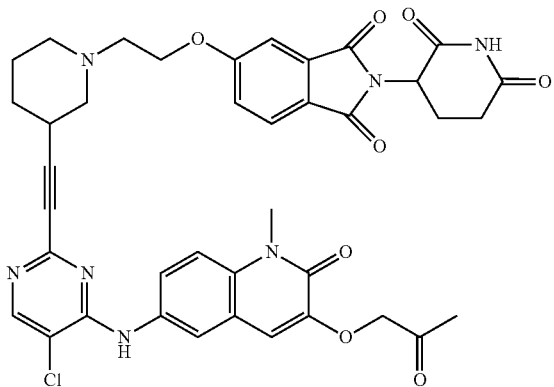 [SMILES: CC(=O)COc1cc2cc(Nc3nc(C#CC4CCCN(CCOc5ccc6c(c5)C(=O)N(C5CCC(=O)NC5=O)C6=O)C4)ncc3Cl)ccc2n(C)c1=O]

Into a 100-mL round-bottom flask, was placed 5-(2,2-dihydroxyethoxy)-2-(2,6-dioxopiperidin-3-yl)isoindole-1,3-dione (110.0 mg, 0.328 mmol, 1.10 equiv), 6-([5-chloro-2-[2-(piperidin-3-yl)ethynyl]pyrimidin-4-yl]amino)-1-methyl-3-(2-oxopropoxy)quinolin-2-one hydrochloride (150 mg, 0.299 mmol, 1.00 equiv), DIEA (0.50 mL, 2.871 mmol, 9.61 equiv), AcOH (0.5 mL, 8.327 mmol, 29.23 equiv), NaBH(OAc)₃ (190 mg, 0.896 mmol, 3.00 equiv) in DCE (10 mL). The resulting solution was stirred for 3 hr at 30° C. The product was isolated by Prep-HPLC with the following conditions: Column, C18 silica gel; mobile phase, ACN/NH₄HCO₃=0 increasing to ACN/NH₄HCO₃=40. This resulted in 23.3 mg (10%) of the title product as a white solid. ¹H NMR (400 MHz, DMSO-d₆) δ 11.08 (s, 1H), 9.27 (s, 1H), 8.37 (s, 1H), 7.79 (d, J=8.3 Hz, 1H), 7.73 (d, J=2.4 Hz, 1H), 7.63 (dd, J=9.0, 2.4 Hz, 1H), 7.49 (d, J=9.0 Hz, 1H), 7.44 (d, J=2.2 Hz, 1H), 7.34 (dd, J=8.3, 2.3 Hz, 1H), 7.13 (s, 1H), 5.11 (dd, J=12.8, 5.3 Hz, 1H), 4.90 (s, 2H), 4.28 (t, J=5.8 Hz, 2H), 3.67 (s, 3H), 2.91 (s, 2H), 2.87 (s, 3H), 2.27 (s, 2H), 2.19 (s, 4H), 2.04 (d, J=14.9 Hz, 1H), 1.87 (s, 1H), 1.63 (s, 1H), 1.49 (s, 1H), 1.36 (d, J=11.3 Hz, 1H), 1.24 (s, 1H), 0.94 (t, J=7.1 Hz, 1H). MS (ES⁺): m/z 766.30 [MH⁺].

Exemplary Synthesis of 5-[[4-(5-chloro-4-[[1-methyl-2-oxo-3-(2-oxopropoxy)quinolin-6-yl]amino]pyrimidin-2-yl)-1-methylpiperazin-2-yl]methoxy]-2-(2,6-dioxopiperidin-3-yl)isoindole-1,3-dione (Exemplary Compound 194)

Step 1: Synthesis of (1-methylpiperazin-2-yl)methanol

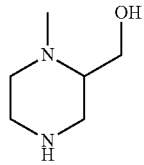

Into a 250-mL round-bottom flask, was placed tert-butyl 2-(hydroxymethyl)piperazine-1-carboxylate (5.00 g, 23.15 mmol, 1.00 equiv), THF (100 mL) under nitrogen atmosphere. LiAlH₄ (3.96 g, 104.18 mmol, 4.5 equiv) was carefully added in batches. The resulting solution was stirred for 5 h at 60° C. in an oil bath. The reaction mixture was cooled rt, quenched with water and concentrated. The residue was applied onto a silica gel column eluting with dichloromethane/MeOH (10/1). This resulted in 3.6 g (40%) of (1-methylpiperazin-2-yl)methanol as a yellow solid. MS (ES⁺): m/z 131.28 [MH⁺].

Step 2: Synthesis of tert-butyl 3-(hydroxymethyl)-4-methylpiperazine-1-carboxylate

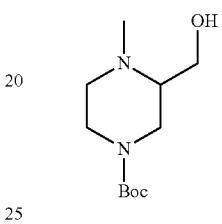

Into a 250-mL round-bottom flask, was placed (1-methylpiperazin-2-yl)methanol (3.60 g, 27.652 mmol, 1.00 equiv), H₂O (6 mL), THF (25 mL), Et₃N (8.4 g, 82.956 mmol, 3.00 equiv), (Boc)₂O (7.85 g, 35.947 mmol, 1.3 equiv). The resulting solution was stirred for 5 h at room temperature. The resulting solution was extracted with ethyl acetate (3×50 mL). The resulting mixture was washed with brine (3×10 mL). The mixture was dried over anhydrous sodium sulfate. The residue was applied onto a silica gel column eluting with ethyl acetate/petroleum ether (1/2). This resulted in 2.42 g (38%) of tert-butyl 3-(hydroxymethyl)-4-methylpiperazine-1-carboxylate as a yellow liquid. MS (ES⁺): m/z 231.15 [MH⁺].

Step 3: Synthesis of tert-butyl 4-methyl-3-[[(4-methylbenzenesulfonyl)oxy]methyl]piperazine-1-carboxylate

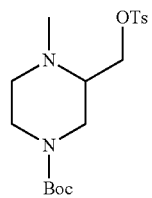 [SMILES: Cc1ccc(S(=O)(=O)OCC2CN(C(=O)OC(C)(C)C)CCN2C)cc1]

Into a 50-mL round-bottom flask, was placed tert-butyl 3-(hydroxymethyl)-4-methylpiperazine-1-carboxylate (1.00 g, 4.329 mmol, 1.00 equiv), dichloromethane (20 mL), TEA (1.3 g, 12.987 mmol, 3 equiv), TsCl (1.23 g, 6.494 mmol, 1.50 equiv), DMAP (53.05 mg, 0.434 mmol, 0.1 equiv). The resulting solution was stirred for 3 h at room temperature. The resulting solution was extracted with dichloromethane (3×30 mL). The resulting mixture was washed with brine (1×10 mL). The mixture was dried over anhydrous sodium sulfate. The residue was applied onto a silica gel column eluting with ethyl acetate/petroleum ether (1/5). The collected fractions were combined and concentrated. This resulted in 350 mg (21%) of tert-butyl 4-methyl-3-[[(4- methylbenzenesulfonyl)oxy]methyl]piperazine-1-carboxylate as yellow oil. MS (ES+): m/z 385.20 [MH+]

Step 4: Synthesis of tert-butyl 3-([[2-(2,6-dioxopiperidin-3-yl)-1,3-dioxoisoindol-5-yl]oxy]methyl)-4-methylpiperazine-1-carboxylate

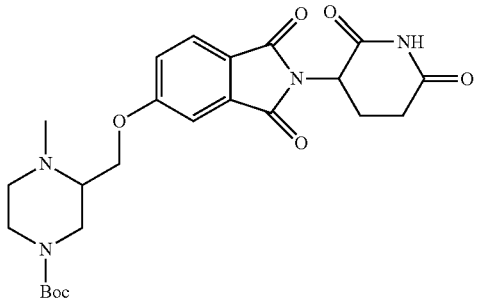 [SMILES: CN1CCN(C(=O)OC(C)(C)C)CC1COc1ccc2c(c1)C(=O)N(C1CCC(=O)NC1=O)C2=O]

Into a 10-mL sealed tube, was placed O-[(1-methylpiperazin-2-yl)methyl]-1-sulfanylidene (3H) (324.00 mg, 1.972 mmol, 1.00 equiv), DMF (10 mL), 2-(2,6-dioxopiperidin-3-yl)-5-hydroxyisoindole-1,3-dione (540.92 mg, 1.972 mmol, 1 equiv), K$_2$CO$_3$ (817.82 mg, 5.917 mmol, 3.00 equiv). The resulting solution was stirred for 3 h at 70° C. in an oil bath. The crude product was purified by Flash-Prep-HPLC with the following conditions: Column, C18 silica gel; mobile phase (water/CH$_3$CN)=10% CH$_3$CN increasing to =50% CH$_3$CN within 36 min; Detector: UV. The product was obtained and concentrated. This resulted in 89 mg (9%) of tert-butyl 3-([[2-(2,6-dioxopiperidin-3-yl)-1,3-dioxoisoindol-5-yl]oxy]methyl)-4-methylpiperazine-1-carboxylate as a yellow solid. MS (ES+): m/z 487.25 [MH+].

Step 5: 2-(2,6-dioxopiperidin-3-yl)-5-[(1-methylpiperazin-2-yl)methoxy]isoindole-1,3-dione hydrochloride

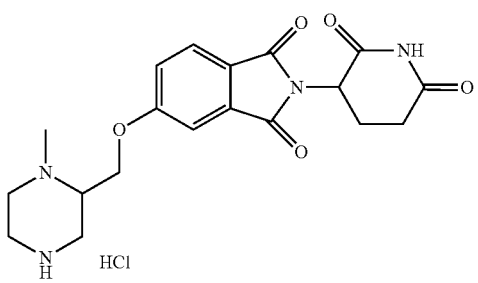 [SMILES: CN1CCNCC1COc1ccc2c(c1)C(=O)N(C1CCC(=O)NC1=O)C2=O ; Cl]

Into a 50-mL round-bottom flask, was placed tert-butyl 3-([[2-(2,6-dioxopiperidin-3-yl)-1,3-dioxoisoindol-5-yl]oxy]methyl)-4-methylpiperazine-1-carboxylate (80.00 mg, 0.164 mmol, 1.00 equiv), hydrogen chloride in dioxane (8 mL, 4 M). The resulting solution was stirred for 3 h at room temperature. The resulting mixture was concentrated. This resulted in 80 mg (crude) of 2-(2,6-dioxopiperidin-3-yl)-5-[(1-methylpiperazin-2-yl)methoxy]isoindole-1,3-dione hydrochloride as a yellow solid. MS (ES+): m/z 387.15 [MH+].

Step 6: Synthesis of 5-[[4-(5-chloro-4-[[1-methyl-2-oxo-3-(2-oxopropoxy)quinolin-6-yl]amino]pyrimidin-2-yl)-1-methylpiperazin-2-yl]methoxy]-2-(2,6-dioxopiperidin-3-yl)isoindole-1,3-dione

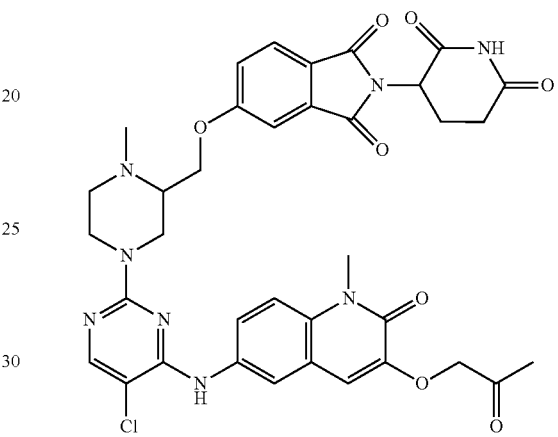

Into a 10-mL sealed tube, was placed 2-(2,6-dioxopiperidin-3-yl)-5-[(1-methylpiperazin-2-yl)methoxy]isoindole-1,3-dione hydrochloride (80.00 mg, crude), DMSO (6 mL), DIEA (0.30 mL), 6-[(2,5-dichloropyrimidin-4-yl)amino]-1-methyl-3-(2-oxopropoxy)quinolin-2-one (89.27 mg, 0.227 mmol, 1.20 equiv). The resulting solution was stirred for 2 h at 100° C. The crude product was purified by Prep-HPLC with the following conditions: Column: Xselect CSH OBD Column 30*150 mm Sum; Mobile Phase A: Water (0.1% FA), Mobile Phase B: ACN; Flow rate: 60 mL/min; Gradient: 7% B to 28% B in 9 min; 254 nm; RT1:9.17; This resulted in 7.9 mg (6%) of 5-[[4-(5-chloro-4-[[1-methyl-2-oxo-3-(2-oxopropoxy)quinolin-6-yl]amino]pyrimidin-2-yl)-1-methylpiperazin-2-yl]methoxy]-2-(2,6-dioxopiperidin-3-yl)isoindole-1,3-dione as a yellow solid. $^1$H NMR (400 MHz, DMSO-d6) δ 8.28 (s, 1H), 8.00 (s, 1H), 7.84 (s, 1H), 7.64-7.62 (m, 2H), 7.41-7.39 (m, 1H), 7.11-6.98 (m, 3H), 5.06 (dd, J=12.8, 5.4 Hz, 1H), 4.73-4.65 (m, 3H), 4.35-4.29 (m, 3H), 3.58 (s, 3H), 3.20-3.09 (m, 2H), 2.92-2.76 (m, 2H), 2.63-2.53 (m, 3H), 2.41-2.37 (m, 5H), 2.33-2.15 (m, 4H); MS (ES+): m/z 743.05/745.05 [MH+].

Exemplary Synthesis of 2-((6-((5-Chloro-2-((2S)-2-(((2-(2,6-dioxopiperidin-3-yl)-1,3-dioxoisoindolin-5-yl)oxy)methyl)morpholino)pyrimidin-4-yl)amino)-1-methyl-2-oxo-1,2-dihydroquinolin-3-yl)oxy)-N-methylacetamide (Exemplary Compound 228)

Step 1: Synthesis of Tert-butyl (2S)-2-(((2-(2,6-dioxopiperidin-3-yl)-1,3-dioxoisoindolin-5-yl)oxy)methyl)morpholine-4-carboxylate

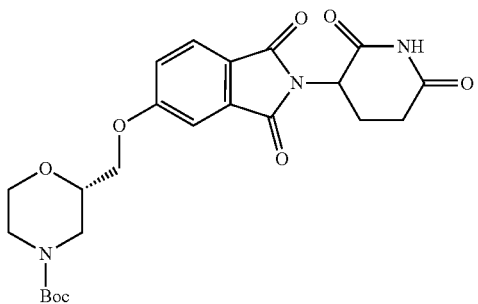 [SMILES: CC(C)(C)OC(=O)N1CCO[C@H](COc2ccc3c(c2)C(=O)N(C2CCC(=O)NC2=O)C3=O)C1]

To a solution of tert-butyl (S)-2-(hydroxymethyl)morpholine-4-carboxylate (500 mg, 2.3 mmol) in TEA/DCM (1/10, 20 mL) was added MsCl (530 mg, 4.6 mmol) dropwised at 0° C. After stirring for 2 h, TLC showed it was completed. The reaction was quenched with aq. NaHCO$_3$, taken up with DCM, washed with brine, dried, concentrated to afford crude desired product of tert-butyl (S)-2-(((methylsulfonyl) oxy)methyl)morpholine-4-carboxylate (527 mg, crdue) as a light oil, which was used into next reaction without further purification.

A mixture of tert-butyl (S)-2-(((methylsulfonyl) oxy)methyl)morpholine-4-carboxylate (527 mg, crude, 2.3 mmol), 2-(2,6-dioxopiperidin-3-yl)-5-hydroxyisoindoline-1,3-dione (819, 3.0 mmol) and K$_2$CO$_3$ (640 mg, 4.6 mmol) in DMF (30 mL) was heated to 80° C. overnight. The reaction was taken up with EA (100 mL), washed with brine, dried, concentrated. The crude material was purified by column chromatography eluting with DCM/EA (10~1/1) to afford desired product as 412 mg of a light yellow solid. $^1$HNMR (400 MHz, CDCl$_3$): δ 8.03 (s, 1H), 7.79 (d, J=8.0 Hz, 1H), 7.37 (s, 1H), 7.22-7.24 (m, 1H), 4.95-4.98 (m, 1H), 4.11-4.18 (m, 3H), 3.83-3.97 (m, 3H), 3.61-3.62 (m, 1H), 2.83-3.01 (m, 4H), 2.15-2.16 (m, 1H), 1.48 (s, 9H).

Step 2: Synthesis of 2-(2,6-Dioxopiperidin-3-yl)-5-(((S)-morpholin-2-yl)methoxy)isoindoline-1,3-dione hydrochloride

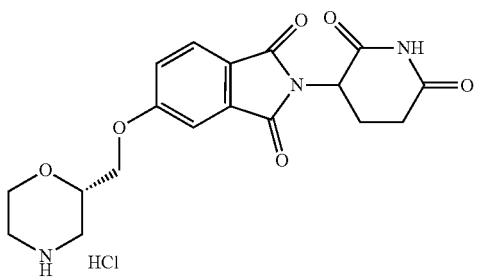 [SMILES: O=C1CCC(N2C(=O)c3ccc(OC[C@@H]4CNCCO4)cc3C2=O)C(=O)N1 ; Cl]

A mixture of tert-butyl (2S)-2-(((2-(2,6-dioxopiperidin-3-yl)-1,3-dioxoisoindolin-5-yl)oxy)methyl)morpholine-4-carboxylate (412 mg, 0.87 mmol) in HCl/dioxane (4M, 5 mL) was stirred at rt for 3 h. LCMS showed it was completed. The solvent was removed under vacuum to afford desired product of 2-(2,6-dioxopiperidin-3-yl)-5-(((S)-morpholin-2-yl)methoxy)isoindoline-1,3-dione hydrochloride (322 mg) as a white solid. MS (ES$^+$): m/z, 374.1[M+1]$^+$.

Step 3: 2-((6-((5-Chloro-2-((2S)-2-(((2-(2,6-dioxopiperidin-3-yl)-1,3-dioxoisoindolin-5-yl)oxy)methyl)morpholino)pyrimidin-4-yl)amino)-1-methyl-2-oxo-1,2-dihydroquinolin-3-yl)oxy)-N-methylacetamide

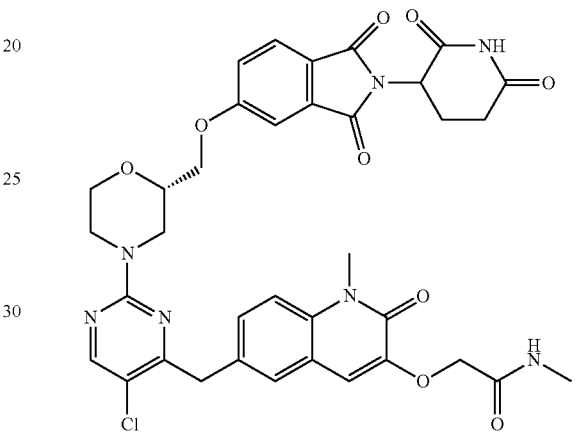

A mixture of 2-(2,6-dioxopiperidin-3-yl)-5-(((S)-morpholin-2-yl)methoxy) isoindoline-1,3-dione hydrochloride (115 mg, 0.28 mmol) and 2-((6-((2,5-dichloropyrimidin-4-yl)amino)-1-methyl-2-oxo-1,2-dihydroquinolin-3-yl)oxy)-N-methylacetamide (103 mg, 0.25 mmol) in DIEA/DMSO (1/10, 5 mL) was stirred at 100° C. for 3 h. The solvent was removed in vacuo and the residue was purified by prep-HPLC to afford desired product as 22 mg of a white solid. $^1$HNMR (400 MHz, DMSO-d$_6$): δ 11.12 (s, 1H), 8.96 (s, 1H), 8.12 (s, 1H), 7.93-7.96 (m, 2H), 7.75-7.79 (m, 2H), 7.18-7.49 (m, 4H), 5.11-5.14 (m, 1H), 4.49 (br, 3H), 4.28 (br, 3H), 3.85-3.87 (m, 2H), 3.66 (s, 3H), 3.45-3.49 (m, 2H), 2.86-3.04 (m, 3H), 2.65-2.53 (m, 3H), 1.99-2.08 (m, 2H). MS: (ES$^+$): m/z 745.1 [M]$^+$.

Exemplary Synthesis of 2-[[6-([5-chloro-2-[4-([6-[2-(2,6-dioxopiperidin-3-yl)-1,3-dioxoisoindol-5-yl]-2,6-diazaspiro[3.3]heptan-2-yl]methyl)piperidin-1-yl]pyrimidin-4-yl]amino)-1-methyl-2-oxoquinolin-3-yl]oxy]-N-methylacetamide (Exemplary Compound 248)

Step 1: Synthesis of tert-butyl 6-([1-[(benzyloxy)carbonyl]piperidin-4-yl]methyl)-2,6-diazaspiro[3.3]heptane-2-carboxylate

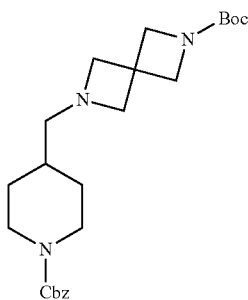 [SMILES: CC(C)(C)OC(=O)N1CC2(CN(CC3CCN(C(=O)OCc4ccccc4)CC3)C2)C1]

Into a 50-mL round-bottom flask, was placed tert-butyl 2,6-diazaspiro[3.3]heptane-2-carboxylate (2.00 g, 10.087 mmol, 1.00 equiv), DCE (30 mL), to which was added benzyl 4-formylpiperidine-1-carboxylate (4.99 g, 20.175 mmol, 2 equiv), NaBH(OAc)$_3$ (6.41 g, 30.262 mmol, 3 equiv). The resulting solution was stirred for 12 hr at 25° C. The reaction was then quenched by the addition of 20 mL of water. The resulting solution was extracted with 3×30 mL of dichloromethane and the organic layers combined and dried over anhydrous sodium sulfate. The solids were filtered out. The resulting mixture was concentrated under vacuum. The crude product was purified by Flash-Prep-HPLC with the following conditions: Column: silica gel: mobile phase: PE:EA=100:0 increasing to PE:EA=70:30 within 30 min; Detector: UV. This resulted in 2.5 g (58%) of tert-butyl 6-([1-[(benzyloxy)carbonyl]piperidin-4-yl]methyl)-2,6-diazaspiro[3.3]heptane-2-carboxylate as light yellow oil. LC-MS (ES$^+$): m/z 430.2 [M+H$^+$].

Step 2: Synthesis of tert-butyl 6-(piperidin-4-ylmethyl)-2,6-diazaspiro[3.3]heptane-2-carboxylate

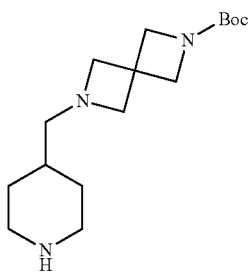 [SMILES: CC(C)(C)OC(=O)N1CC2(CN(CC3CCNCC3)C2)C1]

Into a 50-mL round-bottom flask, was placed tert-butyl 6-([1-[(benzyloxy)carbonyl]piperidin-4-yl]methyl)-2,6-diazaspiro[3.3]heptane-2-carboxylate (1.00 g, 2.328 mmol, 1.00 equiv), methanol (20 mL), to which was added Pd/C (100.00 mg, 0.940 mmol, 0.40 equiv) under nitrogen atmosphere. The flask was evacuated and flushed with hydrogen. The reaction mixture was hydrogenated at room temperature for 16 hours under hydrogen atmosphere using a hydrogen balloon, then filtered through a Celite pad and concentrated under reduced pressure. This resulted in 503 mg (73%) of tert-butyl 6-(piperidin-4-ylmethyl)-2,6-diazaspiro[3.3]heptane-2-carboxylate as light yellow oil.

Step 3: Synthesis of tert-butyl 6-([1-[5-chloro-4-([1-methyl-3-[(methylcarbamoyl)methoxy]-2-oxoquinolin-6-yl]amino)pyrimidin-2-yl]piperidin-4-yl]methyl)-2,6-diazaspiro[3.3]heptane-2-carboxylate

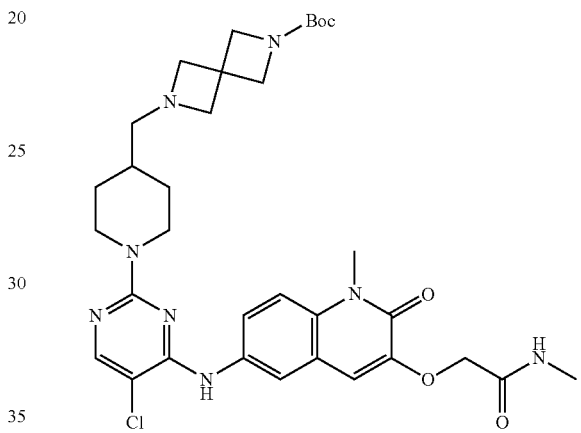

Into a 100-mL round-bottom flask, was placed 2-([6-[(2,5-dichloropyrimidin-4-yl)amino]-1-methyl-2-oxoquinolin-3-yl]oxy)-N-methylacetamide (300.00 mg, 0.735 mmol, 1.00 equiv), DMSO (5 mL), to which was added DIEA (284.93 mg, 2.205 mmol, 3.00 equiv), tert-butyl 6-(piperidin-4-ylmethyl)-2,6-diazaspiro[3.3]heptane-2-carboxylate (260.52 mg, 0.882 mmol, 1.20 equiv). The resulting solution was stirred for 3 hr at 100° C. The crude product was purified by Flash-Prep-HPLC with the following conditions: Column: C18 silica gel; mobile phase: H$_2$O:ACN=100:0 increasing to H2O:ACN=60:40 within 50 min; Detector: UV. This resulted in 400 mg (82%) of tert-butyl 6-([1-[5-chloro-4-([1-methyl-3-[(methylcarbamoyl)methoxy]-2-oxoquinolin-6-yl]amino)pyrimidin-2-yl]piperidin-4-yl]methyl)-2,6-diazaspiro[3.3]heptane-2-carboxylate as a light yellow solid. MS (ES$^+$): m/z 667.4 [M+H$^+$].

Step 4: Synthesis of 2-[(6-[[5-chloro-2-(4-[2,6-diaz-aspiro[3.3]heptan-2-ylmethyl]piperidin-1-yl)pyrimidin-4-yl]amino]-1-methyl-2-oxoquinolin-3-yl)oxy]-N-methylacetamide

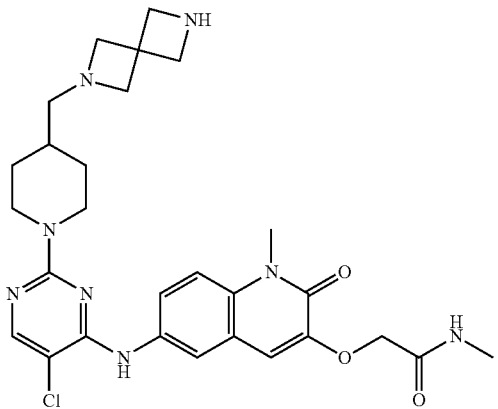 [SMILES: CNC(=O)COc1cc2cc(Nc3nc(N4CCC(CN5CC6(CNC6)C5)CC4)ncc3Cl)ccc2n(C)c1=O]

Into a 50-mL round-bottom flask, was placed tert-butyl 6-([1-[5-chloro-4-([1-methyl-3-[(methylcarbamoyl)methoxy]-2-oxoquinolin-6-yl]amino)pyrimidin-2-yl]piperidin-4-yl]methyl)-2,6-diazaspiro[3.3]heptane-2-carboxylate (200.00 mg, 0.300 mmol, 1.00 equiv), DCM (20 mL), to which was added TFA (5 mL). The resulting solution was stirred for 2 hr at 25° C. The resulting mixture was concentrated under vacuum. This resulted in 160 mg (crude) of 2-[(6-[[5-chloro-2-(4-[2,6-diazaspiro[3.3]heptan-2-ylmethyl]piperidin-1-yl)pyrimidin-4-yl]amino]-1-methyl-2-oxoquinolin-3-yl)oxy]-N-methylacetamide as light yellow oil Step 5: Synthesis of 2-[[6-([5-chloro-2-[4-([6-[2-(2,6-dioxopiperidin-3-yl)-1,3-dioxoisoindol-5-yl]-2,6-diazaspiro[3.3]heptan-2-yl]methyl)piperidin-1-yl]pyrimidin-4-yl]amino)-1-methyl-2-oxoquinolin-3-yl]oxy]-N-methylacetamide

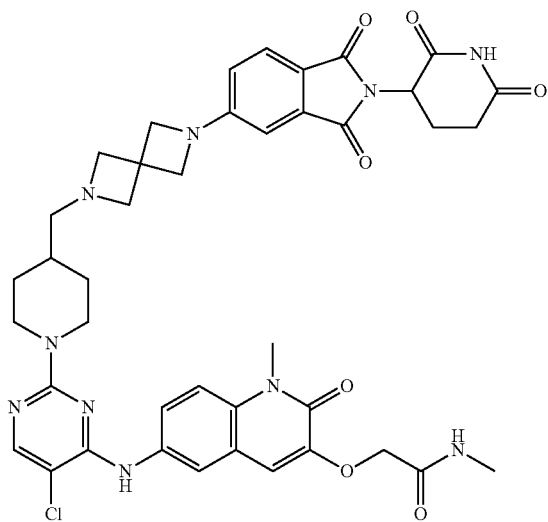 [SMILES: CNC(=O)COc1cc2cc(Nc3nc(N4CCC(CN5CC6(C5)CN(c5ccc7c(c5)C(=O)N(C5CCC(=O)NC5=O)C7=O)C6)CC4)ncc3Cl)ccc2n(C)c1=O]

Into a 50-mL round-bottom flask, was placed 2-[(6-[[5-chloro-2-(4-[2,6-diazaspiro[3.3]heptan-2-ylmethyl]piperidin-1-yl)pyrimidin-4-yl]amino]-1-methyl-2-oxoquinolin-3-yl)oxy]-N-methylacetamide (140.00 mg, 0.247 mmol, 1.00 equiv), DMSO (5 mL), to which was added DIEA (95.72 mg, 0.741 mmol, 3.00 equiv), 2-(2,6-dioxopiperidin-3-yl)-5-fluoroisoindole-1,3-dione (81.83 mg, 0.296 mmol, 1.20 equiv). The resulting solution was stirred for 2 hr at 100° C. The crude product was purified by Flash-Prep-HPLC with the following conditions: Column, C18 silica gel; mobile phase, H$_2$O:ACN=100:0 increasing to H2O:ACN=60:40 within 40 min; Detector: UV. This resulted in 49 mg (24%) of 2-[[6-([5-chloro-2-[4-([6-[2-(2,6-dioxopiperidin-3-yl)-1,3-dioxoisoindol-5-yl]-2,6-diazaspiro[3.3]heptan-2-yl]methyl)piperidin-1-yl]pyrimidin-4-yl]amino)-1-methyl-2-oxoquinolin-3-yl]oxy]-N-methylacetamide as a light yellow solid. $^1$H NMR (300 MHz, DMSO-d6) δ 11.09 (s, 1H), 8.84 (s, 1H), 8.13-7.88 (m, 3H), 7.83-7.72 (m, 1H), 7.68-7.58 (m, 1H), 7.53-7.43 (m, 1H), 7.21-7.06 (s, 1H), 6.80 (s, 1H), 6.66 (s, 1H), 5.07 (m, 1H), 4.73-4.38 (m, 5H), 4.25-4.00 (s, 5H), 3.83-3.63 (s, 5H), 3.02-2.60 (m, 8H), 2.35-2.18 (s, 2H), 2.15-1.92 (m, 1H), 1.85-1.43 (m, 3H), 1.14-0.87 (m, 2H). MS (ES$^+$): m/z 823.40 [M+H$^+$].

Exemplary Synthesis of 2-[[6-([5-chloro-2-[4-([1-[2-(2,6-dioxopiperidin-3-yl)-1,3-dioxoisoindol-5-yl]piperidin-4-yl]methyl)piperazin-1-yl]pyrimidin-4-yl]amino)-1-isopropyl-2-oxoquinolin-3-yl]oxy]-N-methylacetamide (Exemplary Compound 263)

Step 1: Synthesis of 1-isopropyl-5-nitro-indoline-2,3-dione

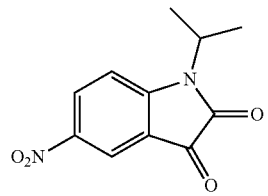 [SMILES: CC(C)N1C(=O)C(=O)c2cc([N+](=O)[O-])ccc21]

To a mixture of 5-nitroindoline-2,3-dione (5.00 g, 26.02 mmol, 1.00 eq) in N,N-dimethylformamide (50 mL) was added potassium carbonate (7.19 g, 52.05 mmol, 2.00 eq) and 2-iodopropane (6.64 g, 39.04 mmol, 3.90 mL, 1.50 eq). The mixture was stirred at 25° C. for 48 h. The mixture was poured into water (300 mL) and extracted with ethyl acetate (50 mL×3). The organic layer was washed with brine (100 mL), dried over anhydrous sodium sulfate, filtered and concentrated under reduced pressure to give 1-isopropyl-5-nitro-indoline-2,3-dione (4.00 g, 17.08 mmol, 66% yield) as yellow solid, which was used in next step directly. H NMR (400 MHz, DMSO-d6) δ=8.46 (dd, J=8.8, 2.4 Hz, 1H), 8.21 (d, J=2.4 Hz, 1H), 7.52 (d, J=8.8 Hz, 1H), 4.60-4.45 (m, 1H), 1.46 (d, J=6.8 Hz, 6H).

Step 2: Synthesis of 1-isopropyl-3-methoxy-6-nitro-quinolin-2-one

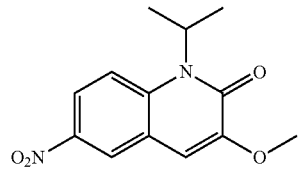 [SMILES: COc1cc2cc([N+](=O)[O-])ccc2n(C(C)C)c1=O]

To a stirred solution of 1-isopropyl-5-nitro-indoline-2,3-dione (25.00 g, 106.74 mmol, 1.00 eq) in ethanol (400 mL) was added triethylamine (234.83 mmol, 33 mL, 2.20 eq) followed by TMS-diazomethane in hexane (2 M, 117 mL, 2.20 eq) at 25° C. After stirring for 12 hours at 25° C. the reaction mixture was poured into water (1500 mL) and extracted with dichloromethane (500 mL×3). The organic layers were combined and concentrated under reduced pressure. The residue was stirred in a mixture of ethyl acetate (50 mL) and petroleum ether (500 mL) at 25° C. for 2 h then filtered. The filter cake was dried under reduced pressure to give 1-isopropyl-3-methoxy-6-nitro-quinolin-2-one as a yellow solid (45.00 g, crude). LCMS (ESI) m/z: 263.1 [M+1]$^+$. $^1$H NMR (400 MHz, DMSO-d6) δ=8.59 (d, J=2.8 Hz, 1H), 8.17 (dd, J=9.6, 2.8 Hz, 1H), 7.52 (d, J=9.6 Hz, 1H), 7.49 (s, 1H), 5.45-5.28 (m, 1H), 3.84 (s, 3H), 1.55 (d, J=6.8 Hz, 6H).

Step 3: Synthesis of 3-hydroxy-1-isopropyl-6-nitro-quinolin-2-one

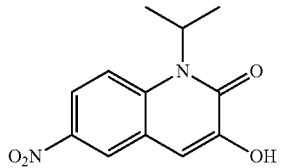 [SMILES: CC(C)n1c(=O)c(O)cc2cc([N+](=O)[O-])ccc21]

A solution of boron tribromide (46.14 mmol, 4.5 mL, 1.10 eq) in dichloromethane (40 mL) was added, dropwise, to a mixture of 1-isopropyl-3-methoxy-6-nitro-quinolin-2-one (11.00 g, 41.94 mmol, 1.00 eq) in 400 mL dichloromethane at 0° C. After stirring at 0° C. for 2 h, the mixture was poured into saturated sodium bicarbonate (1000 mL) and extracted with dichloromethane (500 mL×3). The organic layers were combined, washed with brine (100 mL), dried over anhydrous sodium sulfate and concentrated under reduced pressure. The residue was stirred with a mixture of ethyl acetate (50 mL), petroleum ether (500 mL) and acetonitrile (50 mL) at 25° C. for 12 h then filtered. The filtrate was concentrated under reduced pressure to give 3-hydroxy-1-isopropyl-6-nitro-quinolin-2-one (28.00 g, 112.80 mmol, 90% yield) as brown solid. LCMS (ESI) m/z: 280.2 [M+23]$^+$. $^1$H NMR (400 MHz, DMSO-d6) δ=9.95 (s, 1H), 8.54 (d, J=2.8 Hz, 1H), 8.14 (dd, J=9.2, 2.4 Hz, 1H), 7.92 (d, J=9.2 Hz, 1H), 7.33 (s, 1H), 5.58-5.14 (m, 1H), 1.59 (d, J=6.8 Hz, 6H).

Step 4: Synthesis of 2-[(1-isopropyl-6-nitro-2-oxo-3-quinolyl)oxy]-N-methyl-acetamide

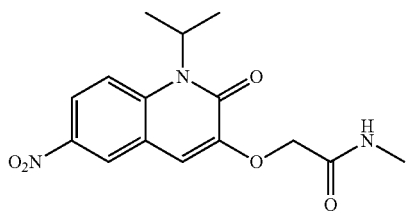 [SMILES: CNC(=O)COc1cc2cc([N+](=O)[O-])ccc2n(C(C)C)c1=O]

This compound was prepared analogously to 2-[(6-amino-1-ethyl-2-oxo-3-quinolyl)oxy]-N-methyl-acetamide. LCMS (ESI) m/z: 320.1 [M+1]$^+$. $^1$H NMR (400 MHz, DMSO-d6) δ=8.60 (d, J=2.8 Hz, 1H), 8.21 (dd, J=9.6, 2.8 Hz, 1H), 8.01-7.88 (m, 2H), 7.48 (s, 1H), 5.70-5.15 (m, 1H), 4.57 (s, 2H), 2.68 (d, J=4.8 Hz, 3H), 1.58 (d, J=7.2 Hz, 6H).

Step 5: Synthesis of 2-[(6-amino-1-isopropyl-2-oxoquinolin-3-yl)oxy]-N-methylacetamide

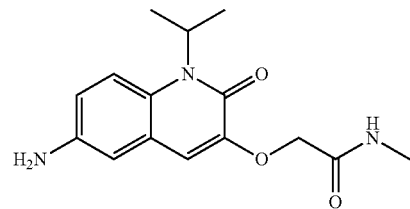

2-[(1-isopropyl-6-nitro-2-oxoquinolin-3-yl)oxy]-N-methylacetamide (300.00 mg, 0.94 mmol, 1.00 equiv) was added to a 50-mL round-bottom flask under nitrogen and taken up in DMF (15 mL) and MeOH (15 mL). After adding Pd/C (30.00 mg, 0.28 mmol, 0.30 equiv) the flask was evacuated and flushed with hydrogen. The mixture was allowed to stir for 4 hours at rt then filtered through a Celite pad and concentrated under reduced pressure to afford 253 mg of 2-[(6-amino-1-isopropyl-2-oxoquinolin-3-yl)oxy]-N-methylacetamide as a light yellow solid (92%). LC-MS (ES$^+$): m/z 290.00 [M+H$^+$], $t_R$=0.59 min (1.20 minute run).

Step 6: Synthesis of 2-([6-[(2,5-dichloropyrimidin-4-yl)amino]-1-isopropyl-2-oxoquinolin-3-yl]oxy)-N-methylacetamide

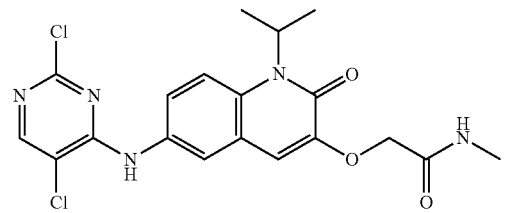 [SMILES: CNC(=O)COc1cc2cc(Nc3nc(Cl)ncc3Cl)ccc2n(C(C)C)c1=O]

Into a 50-mL round-bottom flask, DIEA (268.01 mg, 2.07 mmol, 3 equiv), 2,4,5-trichloropyrimidine (152.14 mg, 0.83 mmol, 1.2 equiv) was added to a mixture of 2-[(6-amino-1-isopropyl-2-oxoquinolin-3-yl)oxy]-N-methylacetamide (200.00 mg, 0.69 mmol, 1.00 equiv), DMSO (5 mL). The resulting solution was stirred for 2 hr at 100° C. The crude product was purified by Flash-Prep-HPLC with the following conditions: Column, C18 silica gel; mobile phase, H2O:ACN=100:0 increasing to H2O:ACN=60:40 within 30 min; Detector: 254 nm. To afford 183 mg (60%) of 2-([6-[(2,5-dichloropyrimidin-4-yl)amino]-1-isopropyl-2-oxoquinolin-3-yl]oxy)-N-methylacetamide as a light yellow solid. LC-MS (ES+): m/z 436.00 [M+H+], tR=0.81 min (1.20 minute run).

741

Step 7: Synthesis of 2-[[6-([5-chloro-2-[4-([1-[2-(2,6-dioxopiperidin-3-yl)-1,3-dioxoisoindol-5-yl]piperidin-4-yl]methyl)piperazin-1-yl]pyrimidin-4-yl]amino)-1-isopropyl-2-oxoquinolin-3-yl]oxy]-N-methylacetamide

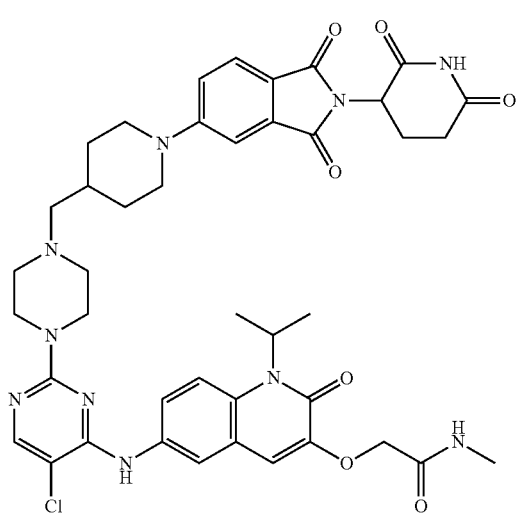 [SMILES: CNC(=O)COc1cc2cc(Nc3nc(N4CCN(CC5CCN(c6ccc7c(c6)C(=O)N(C6CCC(=O)NC6=O)C7=O)CC5)CC4)ncc3Cl)ccc2n(C(C)C)c1=O]

Into a 100-mL round-bottom flask, was placed 2-([6-[(2,5-dichloropyrimidin-4-yl)amino]-1-isopropyl-2-oxoquinolin-3-yl]oxy)-N-methylacetamide (300 mg, 0.68 mmol, 1.00 equiv), DMSO (25 mL), to which was added DIEA (2 mL), 2-(2,6-dioxopiperidin-3-yl)-5-[4-(piperazin-1-ylmethyl)piperidin-1-yl]isoindole-1,3-dione (454 mg, 1.02 mmol, 1.50 equiv). The resulting solution was stirred for 2 hr at 100 degrees C. The crude product was purified by Flash-Prep-HPLC with the following conditions: Column, C18; mobile phase, $H_2O$:ACN=100:0 increasing to $H_2O$:ACN=20:80 within 40 min; Detector: 254/220 nm. This resulted in 315 mg (55%) of 2-[[6-([5-chloro-2-[4-([1-[2-(2,6-dioxopiperidin-3-yl)-1,3-dioxoisoindol-5-yl]piperidin-4-yl]methyl)piperazin-1-yl]pyrimidin-4-yl]amino)-1-isopropyl-2-oxoquinolin-3-yl]oxy]-N-methylacetamide as a light yellow solid. $^1$HNMR (400 MHz, DMSO-d6) δ 11.09 (s, 1H), 8.87 (s, 1H), 8.06 (s, 1H), 7.96 (m, 2H), 7.75-7.63 (m, 3H), 7.32 (m, 1H), 7.23 (m, 1H), 7.03 (s, 1H), 5.37 (b, 1H), 5.07 (m, 1H), 4.56 (s, 2H), 4.05-4.03 (m, 2H), 3.64 (s, 4H), 3.03-2.82 (m, 3H), 2.67-2.64 (m, 3H), 2.63-2.53 (m, 1H), 2.46-2.34 (m, 5H), 2.18 (s, 2H), 2.03-2.00 (m, 2H), 1.84-1.81 (m, 2H), 1.58 (d, J=6.8 Hz, 6H), 1.20-1.18 (m, 2H); LC-MS (ES$^+$): m/z 839.30/841.30 [M+H$^+$].

742

Exemplary Synthesis of 2-[[6-([5-chloro-2-[4-(2-[1-[2-(2,6-dioxopiperidin-3-yl)-1,3-dioxoisoindol-4-yl]piperidin-4-yl]propan-2-yl)piperazin-1-yl]pyrimidin-4-yl]amino]-1-methyl-2-oxoquinolin-3-yl]oxy]-N-methylacetamide (Exemplary Compound 266)

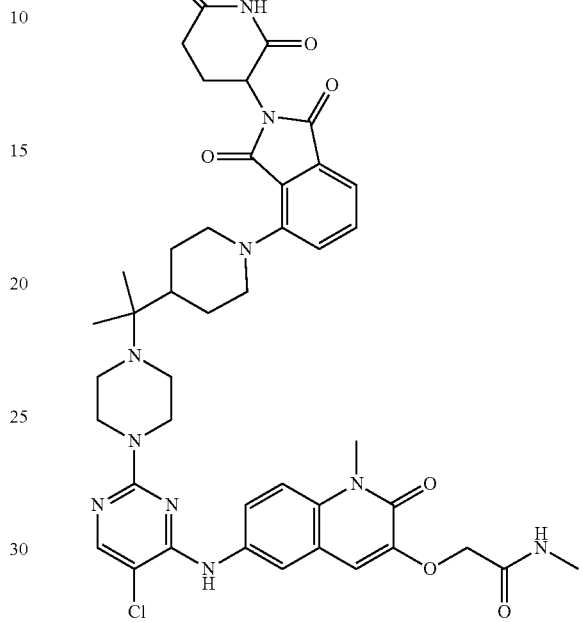

Into a 30-mL sealed tube, was placed 2-([6-[(5-chloro-2-[4-[2-(piperidin-4-yl)propan-2-yl]piperazin-1-yl]pyrimidin-4-yl)amino]-1-methyl-2-oxoquinolin-3-yl]oxy)-N-methylacetamide (150.00 mg, 0.257 mmol, 1.00 equiv), 2-(2,6-dioxopiperidin-3-yl)-4-fluoroisoindole-1,3-dione (106.00 mg, 0.384 mmol, 1.49 equiv) and DIEA (1.00 mL, 0.008 mmol, 0.03 equiv) in DMSO (10.00 mL). The resulting mixture was stirred for 2 hours at 110° C. in an oil bath. The crude product was purified by Prep-HPLC with the following conditions: Column, C18 silica gel; mobile phase, water ($NH_4HCO_3$)/ACN=0% increasing to water ($NH_4HCO_3$)/ACN=60% within 30 min; Detector, 254/220 nm. This resulted in 46.8 mg (21.68%) of 2-[[6-([5-chloro-2-[4-(2-[1-[2-(2,6-dioxopiperidin-3-yl)-1,3-dioxoisoindol-4-yl]piperidin-4-yl]propan-2-yl)piperazin-1-yl]pyrimidin-4-yl]amino)-1-methyl-2-oxoquinolin-3-yl]oxy]-N-methylacetamide as a yellow solid. $^1$H NMR (300 MHz, DMSO-d$_6$, ppm): δ 11.08 (s, 1H), 8.82 (s, 1H), 8.04 (s, 1H), 7.94-7.93 (m, 2H), 7.79-7.76 (m, 1H), 7.70-7.64 (m, 1H), 7.48 (d, J=9.0 Hz, 1H), 7.33-7.30 (m, 2H), 7.14 (s, 1H), 5.12-5.06 (m, 1H), 4.58 (s, 2H), 3.79-3.75 (m, 2H), 3.68 (s, 3H), 3.61 (s, 4H), 3.29 (s, 2H), 2.94-2.79 (m, 3H), 2.66-2.62 (m, 4H), 2.59-2.57 (m, 3H), 2.07-1.95 (m, 1H), 1.90-1.72 (m, 3H), 1.55-1.31 (m, 2H), 0.89 (s, 6H); LC-MS (ES$^+$): m/z 839.25/841.25[MH$^+$].

Exemplary Synthesis of 2-[[6-([5-chloro-2-[4-([4-[2-(2,6-dioxopiperidin-3-yl)-1,3-dioxoisoindol-5-yl]piperidin-1-yl]methyl)piperidin-1-yl]pyrimidin-4-yl]amino)-1-methyl-2-oxoquinolin-3-yl]oxy]-N-methylacetamide (Exemplary Compound 289)

Step 1: Synthesis of tert-butyl 4-[2-(2,6-dioxopiperidin-3-yl)-1,3-dioxoisoindol-5-yl]-3,6-dihydro-2H-pyridine-1-carboxylate

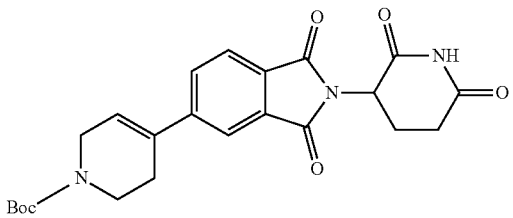

Into a 250-mL round-bottom flask purged and maintained with an inert atmosphere of nitrogen, was placed 5-bromo-2-(2,6-dioxopiperidin-3-yl)isoindole-1,3-dione (1.0 g, 2.96 mmol, 1.0 equiv), tert-butyl 4-(4,4,5,5-tetramethyl-1,3,2-dioxaborolan-2-yl)-3,6-dihydro-2H-pyridine-1-carboxylate (1.8 g, 5.9 mmol, 2.0 equiv), dioxane, K$_2$CO$_3$ (1.23 g, 8.9 mmol, 3 equiv), Pd(dppf)Cl$_2$ (217.0 mg, 0.29 mmol, 0.1 equiv). The resulting solution was stirred for 3 h at 100° C. The reaction mixture was cooled to room temperature with a water bath. The reaction was then quenched by the addition of water. The resulting solution was extracted with ethyl acetate (100 mL). The resulting mixture was washed with brine. The mixture was dried over anhydrous sodium sulfate and concentrated. The residue was applied onto a silica gel column with ethyl acetate/petroleum ether (1:5). This resulted in 1.2 g (92%) of tert-butyl 4-[2-(2,6-dioxopiperidin-3-yl)-1,3-dioxoisoindol-5-yl]-3,6-dihydro-2H-pyridine-1-carboxylate as a solid. MS (ES$^+$): m/z 340.15[MH$^+$].

Step 2: Synthesis of tert-butyl 4-[2-(2,6-dioxopiperidin-3-yl)-1,3-dioxoisoindol-5-yl]piperidine-1-carboxylate

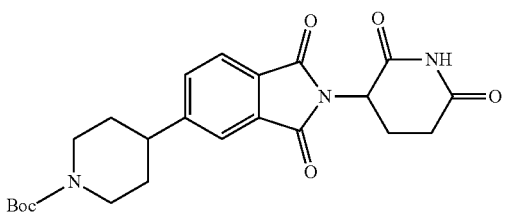 [SMILES: CN1CCC(c2ccc3c(c2)C(=O)N(C2CCC(=O)NC2=O)C3=O)CC1 ; "Boc"]

To a solution of tert-butyl 4-[2-(2,6-dioxopiperidin-3-yl)-1,3-dioxoisoindol-5-yl]-3,6-dihydro-2H-pyridine-1-carboxylate (1.00 g, 2.3 mmol, 1.0 equiv) in EA (50 mL) was added Pd/C (242.16 mg) under nitrogen atmosphere in a 200 mL of round-bottom flask. The mixture was hydrogenated at room temperature overnight under hydrogen atmosphere using a hydrogen balloon, filtered through a Celite pad and concentrated under reduced pressure. This afforded tert-butyl 4-[2-(2,6-dioxopiperidin-3-yl)-1,3-dioxoisoindol-5-yl]piperidine-1-carboxylate (1 g, 99%). MS (ES$^+$): m/z 442.10[MH$^+$].

Step 3: Synthesis of 2-(2,6-dioxopiperidin-3-yl)-5-(piperidin-4-yl)isoindole-1,3-dione

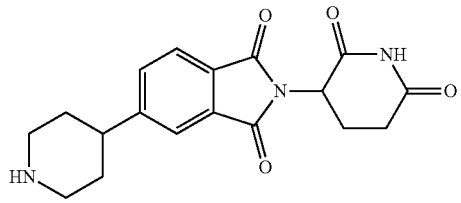 [SMILES: O=C1CCC(N2C(=O)c3ccc(C4CCNCC4)cc3C2=O)C(=O)N1]

Into a 100-mL round-bottom flask purged and maintained with an inert atmosphere of nitrogen, was placed tert-butyl 4-[2-(2,6-dioxopiperidin-3-yl)-1,3-dioxoisoindol-5-yl]piperidine-1-carboxylate (900 mg, 2.05 mmol, 1.0 equiv), dioxane (20.0 mL), 4M HCl in 1,4-dioxane (10.0 mL). The resulting solution was stirred for 1 h at room temperature. The resulting mixture was concentrated. This resulted in 651 mg (93.55%) of 2-(2,6-dioxopiperidin-3-yl)-5-(piperidin-4-yl)isoindole-1,3-dione as a solid. MS (ES$^+$): m/z 342.10 [MH$^+$].

Step 4: 2-[[6-([5-chloro-2-[4-([4-[2-(2,6-dioxopiperidin-3-yl)-1,3-dioxoisoindol-5-yl]piperidin-1-yl]methyl)piperidin-1-yl]pyrimidin-4-yl]amino)-1-methyl-2-oxoquinolin-3-yl]oxy]-N-methylacetamide

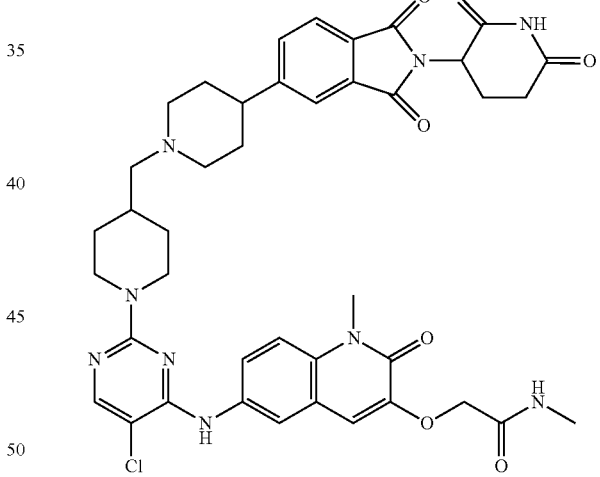

Into a 250 mL round-bottom flask were added 2-(2,6-dioxopiperidin-3-yl)-5-(piperidin-4-yl)isoindole-1,3-dione (300 mg, 0.88 mmol, 1.0 equiv) and DIEA (0.5 mL) in DCE (100 mL) at room temperature. Then added 2-[(6-[[5-chloro-2-(4-formylpiperidin-1-yl)pyrimidin-4-yl]amino]-1-methyl-2-oxoquinolin-3-yl)oxy]-N-methylacetamide (426.17 mg, 0.88 mmol, 1.0 equiv) and AcOH (63.3 mg, 1.1 mmol, 1.2 equiv) was stirred for 2 h at room temperature. Then added sodium triacetoxyborohydride (279.39 mg, 1.32 mmol, 1.5 equiv). The resulting mixture was stirred for 3 h at room temperature under nitrogen atmosphere. The reaction was quenched with water at room temperature. The resulting mixture was extracted with EtOAc (70 mL). The combined organic layers were washed with water (10 mL), dried over anhydrous Na$_2$SO$_4$. After filtration, the filtrate was concentrated under reduced pressure. The crude product was purified by Prep-HPLC with the following conditions: Column, XBridge Prep OBD C$_{18}$ Column, 30 Ã,Â,ÃfÂ 150 mm 5 um; mobile phase, water (10 MMOL/L NH$_4$HCO$_3$) and acetonitrile (42% Phase B up to 72% in 8 min); Detector, 254 nm uv. This resulted in 2-[[6-([5-chloro-2-[4-([4-[2-(2, 6-dioxopiperidin-3-yl)-1,3-dioxoisoindol-5-yl]piperidin-1-yl]methyl)piperidin-1-yl]pyrimidin-4-yl]amino)-1-methyl-2-oxoquinolin-3-yl]oxy]-N-methylacetamide (47.7 mg, 6.70%). $^1$HNMR (300 MHz, DMSO-d$_6$, ppm) 11.11 (s, 1H), 8.81 (s, 1H), 8.02 (s, 1H), 7.98-7.87 (m, 2H), 7.85-7.71 (m, 4H), 7.46 (d, J=9.2 Hz, 1H), 7.09 (s, 1H), 5.12 (dd, J=12.7, 5.5 Hz, 1H), 4.51 (d, J=32.8 Hz, 4H), 3.66 (s, 3H), 2.95 (d, J=10.9 Hz, 2H), 2.82 (t, J=12.9 Hz, 3H), 2.65 (d, J=4.6 Hz, 4H), 2.54 (s, 1H), 2.16 (s, 2H), 2.05-1.89 (m, 3H), 1.75 (s, 7H), 1.22 (s, 1H), 1.01 (d, J=12.5 Hz, 2H). MS (ES$^+$): m/z 810.31[MH$^+$].

Exemplary Synthesis of 3-[4-([4-[5-chloro-4-([1-ethyl-3-[(methylcarbamoyl)methoxy]-2-oxoquinolin-6-yl]amino)pyrimidin-2-yl]piperazin-1-yl]methyl)piperidin-1-yl]-N-(2,6-dioxopiperidin-3-yl)-2-fluorobenzamide (Exemplary Compound 295)

Step 1: 1. Synthesis of tert-butyl 4-([1-[2-fluoro-3-(methoxycarbonyl)phenyl]piperidin-4-yl]methyl)piperazine-1-carboxylate

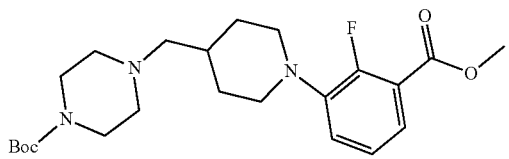 [SMILES: COC(=O)c1cccc(N2CCC(CN3CCN(C(=O)OC(C)(C)C)CC3)CC2)c1F]

Into a 250-mL round-bottom flask purged and maintained with an inert atmosphere of nitrogen, was placed methyl 3-bromo-2-fluorobenzoate (1.0 g, 4.3 mmol, 1.0 equiv), tert-butyl 4-(piperidin-4-ylmethyl)piperazine-1-carboxylate (1.22 g, 4.3 mmol, 1.00 equiv), Cs$_2$CO$_3$ (4.2 g, 12.8 mmol, 3.0 equiv), RuPhosPd (0.63 g, 0.86 mmol, 0.2 equiv), tetrahydrofuran (15 mL). The resulting solution was stirred overnight at 90° C. After work-up, the residue was applied onto a silica gel column with ethyl acetate/petroleum ether (1:2). This resulted in 480 mg (25.7%) of tert-butyl 4-([1-[2-fluoro-3-(methoxycarbonyl)phenyl]piperidin-4-yl]methyl)piperazine-1-carboxylate as a yellow solid. MS (ES$^+$): m/z 436.30[MH$^+$].

Step 2: Synthesis of 3-(4-[[4-(tert-butoxycarbonyl)piperazin-1-yl]methyl]piperidin-1-yl)-2-fluorobenzoic acid

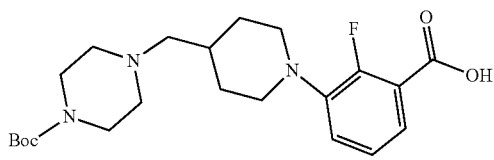 [SMILES: CC(C)(C)OC(=O)N1CCN(CC2CCN(c3cccc(C(=O)O)c3F)CC2)CC1]

Into a 50-mL sealed tube purged and maintained with an inert atmosphere of nitrogen, was placed tert-butyl 4-([1-[2-fluoro-3-(methoxycarbonyl)phenyl]piperidin-4-yl]methyl)piperazine-1-carboxylate (850.0 mg, 1.9 mmol, 1.0 equiv), dioxane (20 mL), sodium hydroxide (312.2 mg, 7.8 mmol, 4.0 equiv) in water (4 mL). The resulting solution was stirred for overnight at 60° C. The residue was applied onto a silica gel column with ethyl acetate/petroleum ether (1:2). This resulted in 890 mg (crude) of 3-(4-[[4-(tert-butoxycarbonyl)piperazin-1-yl]methyl]piperidin-1-yl)-2-fluorobenzoic acid as a yellow solid. MS (ES$^+$): m/z 422.30[MH$^+$].

Step 3: Synthesis of tert-butyl 4-[(1-[3-[(2,6-dioxopiperidin-3-yl)carbamoyl]-2-fluorophenyl]piperidin-4-yl)methyl]piperazine-1-carboxylate

Into a 30-mL sealed tube purged and maintained with an inert atmosphere of nitrogen, was placed 3-(4-[[4-(tert-butoxycarbonyl)piperazin-1-yl]methyl]piperidin-1-yl)-2-fluorobenzoic acid (890.0 mg, 2.1 mmol, 1.0 equiv), 3-aminopiperidine-2,6-dione (541.0 mg, 4.2 mmol, 2.0 equiv), DIEA (5.0 mL), dimethylformamide (5.0 mL), BOP (1120.6 mg, 2.5 mmol, 1.2 equiv). The resulting solution was stirred for 3 h at room temperature. The product was isolated by Flash-Prep-HPLC with the following conditions: Column, C18 silica gel; mobile phase, acetonitrile/water (NH$_4$HCO$_3$) =0 increasing to acetonitrile/water (NH$_4$HCO$_3$)=75 in 20 min. This resulted in 500 mg (44.5%) of tert-butyl 4-[(1-[3-[(2,6-dioxopiperidin-3-yl)carbamoyl]-2-fluorophenyl]piperidin-4-yl)methyl]piperazine-1-carboxylate as a white solid. MS (ES$^+$): m/z 532.25[MH$^+$].

Step 4: Synthesis of N-(2,6-dioxopiperidin-3-yl)-2-fluoro-3-[4-(piperazin-1-ylmethyl)piperidin-1-yl]benzamide hydrochloride

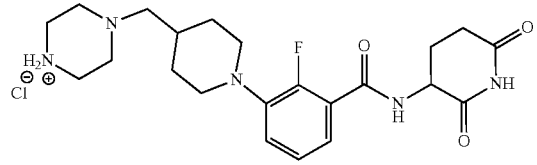 [SMILES: Cl ; O=C1CCC(NC(=O)c2cccc(N3CCC(CN4CCNCC4)CC3)c2F)C(=O)N1]

Into a 100-mL round-bottom flask, was placed tert-butyl 4-[(1-[3-[(2,6-dioxopiperidin-3-yl)carbamoyl]-2-fluorophenyl]piperidin-4-yl)methyl]piperazine-1-carboxylate (400.0 mg, 1 equiv), dioxane (4.0 mL), hydrogen chloride (4.0 mL). The resulting solution was stirred for 2 h at room temperature and concentrated under reduced pressure to afford 464 mg (crude) of N-(2,6-dioxopiperidin-3-yl)-2-fluoro-3-[4-(piperazin-1-ylmethyl)piperidin-1-yl]benzamide as a white solid. MS (ES$^+$): m/z 432.20[MH$^+$].

Step 5: 5. Synthesis of 3-[4-([4-[5-chloro-4-([1-ethyl-3-[(methylcarbamoyl)methoxy]-2-oxoquinolin-6-yl]amino)pyrimidin-2-yl]piperazin-1-yl]methyl)piperidin-1-yl]-N-(2,6-dioxopiperidin-3-yl)-2-fluorobenzamide

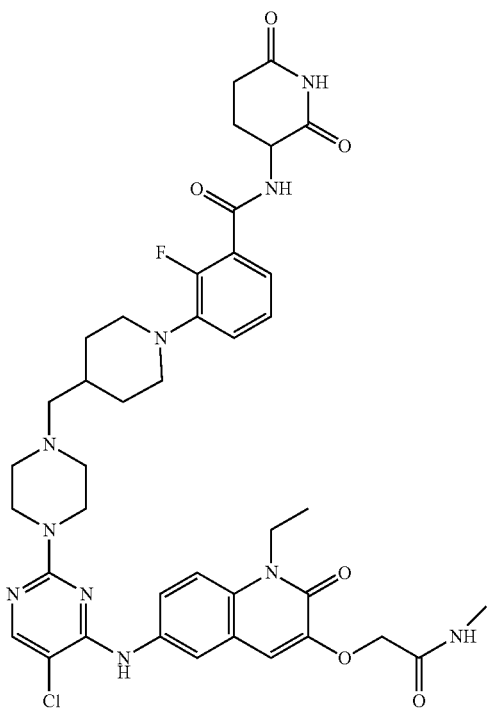 [SMILES: CCn1c(=O)c(OCC(=O)NC)cc2cc(Nc3nc(N4CCN(CC5CCN(c6cccc(C(=O)NC7CCC(=O)NC7=O)c6F)CC5)CC4)ncc3Cl)ccc21]

Into a 30-mL sealed tube purged and maintained with an inert atmosphere of nitrogen, was placed N-(2,6-dioxopiperidin-3-yl)-2-fluoro-3-[4-(piperazin-1-ylmethyl)piperidin-1-yl]benzamide (205.0 mg, 0.47 mmol, 2.0 equiv), 2-([6-[(2,5-dichloropyrimidin-4-yl)amino]-1-ethyl-2-oxoquinolin-3-yl]oxy)-N-methylacetamide (100.0 mg, 0.24 mmol, 1.0 equiv), DMSO (5.0 mL), DIEA (2.0 mL). The resulting solution was stirred for 2 h at 100° C. The product was isolated by Flash-Prep-HPLC with the following conditions: Column, C18 silica gel; mobile phase, acetonitrile/water (NH$_4$HCO$_3$)=0 increasing to acetonitrile/water (NH$_4$HCO$_3$)=80 in 20 min. This resulted in 44.3 mg (23.0%) of 3-[4-([4-[5-chloro-4-([1-ethyl-3-[(methylcarbamoyl)methoxy]-2-oxoquinolin-6-yl]amino)pyrimidin-2-yl]piperazin-1-yl]methyl)piperidin-1-yl]-N-(2,6-dioxopiperidin-3-yl)-2-fluorobenzamide as a white solid. $^1$H NMR (300 MHz, DMSO-d$_6$, ppm) δ10.83 (s, 1H), 8.84 (s, 1H), 8.55-8.50 (m, 1H), 8.05 (s, 1H), 7.97-7.96 (d, J=2.4 Hz, 2H), 7.72-7.50 (m, 2H), 7.15-7.09 (m, 4H), 4.80-4.71 (m, 1H) 4.57 (s, 2H), 4.32-4.30 (m, 2H), 3.64-3.60 (m, 4H), 3.05-2.55 (m, 7H), 2.49-2.39 (m, 5H), 2.22-1.95 (m, 4H), 1.82-1.65 (m, 3H), 1.25-1.21 (m, 6H). MS (ES$^+$): m/z 817.25[MH$^+$].

Exemplary Synthesis of 2-[[6-[[5-chloro-2-[4-[[2-[2-(2,6-dioxo-3-piperidyl)-1,3-dioxo-isoindolin-5-yl]-2-azaspiro[3.3]heptan-6-yl]oxy]-1-piperidyl]pyrimidin-4-yl]amino]-1-ethyl-2-oxo-3-quinolyl]oxy]-N-methyl-acetamide (Exemplary Compound 303)

Step 1: Step 1: Synthesis of 6-nitro-1H-quinolin-2-one Synthesis of 3-bromo-1-ethyl-6-nitroquinolin-2-one

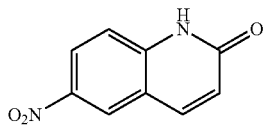 [SMILES: O=c1ccc2cc([N+](=O)[O-])ccc2[nH]1]

To a mixture of 1H-quinolin-2-one (3.50 g, 24.11 mmol, 1.00 eq) in concentrated sulfuric acid (15 mL) was added dropwise concentrated nitric acid (11.11 mmol, 0.5 mL, 0.46 eq) at 0° C. The mixture was stirred at 0° C. for 3 h. Then to the mixture was added nitric acid (22.22 mmol, 1 mL, 0.92 eq). The reaction mixture was stirred at 0° C. for 1 h. LCMS showed the reaction was completed. Then the reaction mixture was poured into ice water (100 mL). The precipitate that formed was filtered and washed with water (100 mL). The solid was concentrated under reduced pressure to give 6-nitro-1H-quinolin-2-one (2.50 g, 13.15 mmol, 55% yield) as a yellow solid, which was used in next step directly. LC/MS (ESI) m/z: 191.2 [M+1]$^+$. $^1$H NMR: (400 MHz, DMSO-d$_6$) δ=8.67 (s, 1H), 8.31 (dd, J=9.2, 2.4 Hz, 1H), 8.11 (d, J=9.6 Hz, 1H), 7.44 (d, J=9.2 Hz, 1H), 6.66 (d, J=9.6 Hz, 1H).

Step 2: Synthesis of 3-bromo-6-nitro-1H-quinolin-2-one

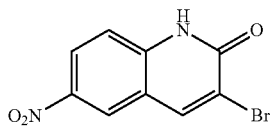 [SMILES: O=c1[nH]c2ccc([N+](=O)[O-])cc2cc1Br]

To a suspension of 6-nitro-1H-quinolin-2-one (12.00 g, 63.11 mmol, 1.00 eq), sodium bromate (12.38 g, 82.04 mmol, 1.30 eq) and water (100 mL) was added hydrogen bromide (2120 mmol, 240 mL, 48% purity, 33.62 eq) and the reaction mixture was heated at 100° C. for 4 h. LCMS showed the reaction was completed. Then the reaction mixture was poured into ice water (300 mL). The mixture was filtered. The filter cake was concentrated under reduced pressure to give 3-bromo-6-nitro-1H-quinolin-2-one (15.00 g, 55.75 mmol, 88% yield) as a yellow solid, which was used in next step directly. LC/MS (ESI) m/z: 269.0 [M+1]$^+$. $^1$H NMR: (400 MHz, DMSO-d$_6$) δ=12.77 (brs, 1H), 8.76 (s, 1H), 8.68 (d, J=2.8 Hz, 1H), 8.34 (dd, J=9.6, 2.8 Hz, 1H), 7.47 (d, J=9.2 Hz, 1H).

Step 3: Synthesis of 3-bromo-1-ethyl-6-nitro-quinolin-2-one

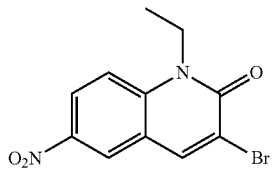 [SMILES: CCn1c(=O)c(Br)cc2cc([N+](=O)[O-])ccc21]

To a solution of 3-bromo-6-nitro-1H-quinolin-2-one (6.00 g, 22.30 mmol, 1.00 eq) in N,N'-dimethyformamide (50 mL) was added potassium carbonate (10.90 g, 78.86 mmol, 3.54 eq) and iodoethane (44.60 mmol, 3.57 mL, 2.00 eq). The reaction was stirred at 25° C. for 0.5 h. LCMS showed the reaction was complete. Then the reaction mixture was poured into ice water (100 mL) and filtered. The filter cake was treated with a solution of petroleum ether (300 mL) and ethyl acetate (30 mL). The mixture was stirred at 25° C. for 0.5 h and filtered. The filter cake was collected and dried under reduced pressure to give 3-bromo-1-ethyl-6-nitro-quinolin-2-one (4.00 g, 13.46 mmol, 30% yield) as a yellow solid, which was used in next step directly. LCMS (ESI) m/z: 299.0 [M+1]$^+$. $^1$H NMR: (400 MHz, DMSO-d6) δ=8.79-8.74 (m, 2H), 8.42 (dd, J=9.6, 2.8 Hz, 1H), 7.83 (d, J=9.6 Hz, 1H), 4.39 (q, J=7.2 Hz, 2H), 1.26 (t, J=7.2 Hz, 3H).

Step 4: Synthesis of 1-ethyl-3-hydroxy-6-nitro-quinolin-2-one

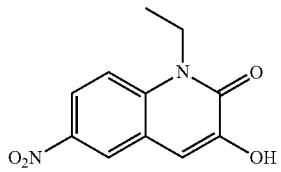 [SMILES: CCn1c(=O)c(O)cc2cc([N+](=O)[O-])ccc21]

To a solution of 3-bromo-1-ethyl-6-nitro-quinolin-2-one (3.00 g, 10.10 mmol, 1.00 eq) in dioxane (50 mL) and water (100 mL) was added potassium hydroxide (1.70 g, 30.29 mmol, 3.00 eq) and methanesulfonato(2-dicyclohexylphosphino-3,6-dimethoxy-2',4',6'-tri-i-propyl-1,1'-biphenyl)(2'-amino-1,1'-biphenyl-2-yl)palladium (II) (0.92 g, 1.01 mmol, 0.10 eq). The mixture was heated under nitrogen atmosphere at 100° C. for 12 h. The reaction mixture was concentrated under reduced pressure. The residue was adjusted pH=6 with hydrochloric acid (1 M) and the mixture was filtered. The filter cake was concentrated under reduced pressure to give 1-ethyl-3-hydroxy-6-nitro-quinolin-2-one (2.20 g, 9.39 mmol, 93% yield) as a yellow solid. LCMS: (ESI) m/z: 235.1 [M+1]$^+$. $^1$H NMR (400 MHz, DMSO-d6) δ=10.10 (s, 1H), 8.59 (s, 1H), 8.21 (dd, J=9.6, 2.8 Hz, 1H), 7.75 (d, J=9.2 Hz, 1H), 7.38 (s, 1H), 4.40 (q, J=7.2 Hz, 2H), 1.26 (t, J=7.2 Hz, 3H).

Step 5: Synthesis of 2-[(1-ethyl-6-nitro-2-oxo-3-quinolyl)oxy]-N-methyl-acetamide

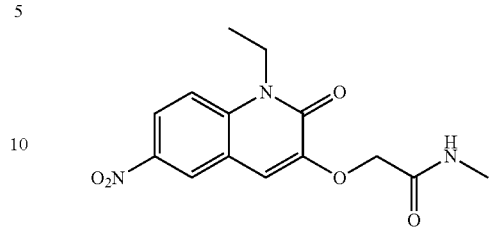

To a solution of 1-ethyl-3-hydroxy-6-nitro-quinolin-2-one (1.00 g, 4.27 mmol, 1.00 eq) in acetonitrile (5 mL) was added potassium carbonate (1.77 g, 12.81 mmol, 3.00 eq) and 2-bromo-N-methyl-acetamide (0.65 g, 4.27 mmol, 1.00 eq). The reaction was stirred at 80° C. for 0.5 h. To the mixture was added water (50 mL). The mixture was filtered. The filter cake was concentrated under reduced pressure to give 2-[(1-ethyl-6-nitro-2-oxo-3-quinolyl)oxy]-N-methyl-acetamide (1.20 g, 3.93 mmol, 92% yield) as a yellow solid. LCMS (ESI) m/z: 328.2 [M+23]$^+$. HNMR (400 MHz, DMSO-d6) δ=8.64 (d, J=2.8 Hz, 1H), 8.27 (dd, J=9.2, 2.8 Hz, 1H), 7.96 (d, J=3.6 Hz, 1H), 7.77 (d, J=9.6 Hz, 1H), 7.53 (s, 1H), 4.60 (s, 2H), 4.38 (q, J=7.2 Hz, 2H), 2.68 (d, J=4.8 Hz, 3H), 1.26 (t, J=7.2 Hz, 3H).

Step 6: 2-[(6-amino-1-ethyl-2-oxo-3-quinolyl)oxy]-N-methyl-acetamide

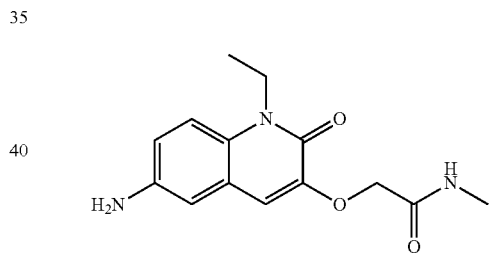

To a mixture of 2-[(1-ethyl-6-nitro-2-oxo-3-quinolyl)oxy]-N-methyl-acetamide (1.00 g, 3.28 mmol, 1.00 eq) in tetrahydrofuran (25 mL) and methanol (30 mL) was added palladium on carbon (0.15 g, 10% purity). The mixture was stirred under 1 atmosphere of hydrogen atmosphere at 25° C. for 12 h. Then the reaction mixture was filtered. The filtrate was concentrated under reduced pressure to give 2-[(6-amino-1-ethyl-2-oxo-3-quinolyl)oxy]-N-methyl-acetamide (1.00 g, crude) as a yellow solid, which was used in next step directly without further purification. LCMS (ESI) m/z: 276.1 [M+1]$^+$. $^1$H NMR (400 MHz, DMSO-d6) δ=7.99 (d, J=4.0 Hz, 1H), 7.25 (d, J=8.8 Hz, 1H), 7.04 (s, 1H), 6.81 (dd, J=9.2, 2.8 Hz, 1H), 6.71 (d, J=2.8 Hz, 1H), 5.06 (s, 2H), 4.51 (s, 2H), 4.24 (q, J=7.2 Hz, 2H), 2.67 (d, J=4.8 Hz, 3H), 1.20 (t, J=7.2 Hz, 3H).

Step 6: Synthesis of 2-[[6-[(2,5-dichloropyrimidin-4-yl)amino]-1-ethyl-2-oxo-3-quinolyl]oxy]-N-methyl-acetamide

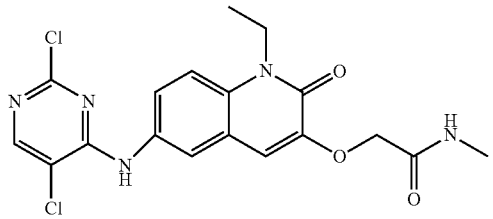 [SMILES: CCn1c(=O)c(OCC(=O)NC)cc2cc(Nc3nc(Cl)ncc3Cl)ccc21]

To a mixture of 2-[(6-amino-1-ethyl-2-oxo-3-quinolyl)oxy]-N-methyl-acetamide (1.00 g, 3.63 mmol, 1.00 eq) and diisopropylethylamine (10.90 mmol, 1.90 mL, 3.00 eq) in dimethylsulfoxide (30 mL) was added 2,4,5-trichloropyrimidine (1.33 g, 7.26 mmol, 2.00 eq). The mixture was stirred at 100° C. for 1 h, poured into ice water (50 mL) and filtered. The filter cake was treated with a solution of petroleum ether (50 mL) and ethyl acetate (10 mL) and filtered to give 2-[[6-[(2,5-dichloropyrimidin-4-yl)amino]-1-ethyl-2-oxo-3-quinolyl]oxy]-N-methyl-acetamide (1.20 g, 2.84 mmol, 78% yield) as a white solid, which was used in next step directly. LCMS (ESI) m/z: 422.3 [M+1]$^+$. $^1$H NMR (400 MHz, DMSO-d6) δ=9.66 (s, 1H), 8.39 (s, 1H), 7.97 (d, J=4.0 Hz, 1H), 7.77 (d, J=2.4 Hz, 1H), 7.68 (dd, J=9.6, 2.4 Hz, 1H), 7.59 (d, J=9.2 Hz, 1H), 7.23 (s, 1H), 4.59 (s, 2H), 4.35 (q, J=7.2 Hz, 2H), 2.68 (d, J=4.8 Hz, 3H), 1.25 (t, J=7.2 Hz, 3H).

Step 7: Synthesis of tert-butyl 6-(4-pyridyloxy)-2-azaspiro[3.3]heptane-2-carboxylate

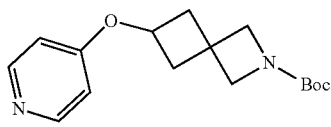 [SMILES: CC(C)(C)OC(=O)N1CC2(CC(Oc3ccncc3)C2)C1]

To a solution of pyridin-4-ol (223 mg, 2.34 mmol, 1.00 eq), tert-butyl 6-hydroxy-2-azaspiro[3.3]heptane-2-carboxylate (500 mg, 2.34 mmol, 1.00 eq) and triphenylphosphine (800 mg, 3.05 mmol, 1.30 eq) in tetrahydrofuran (10 mL) was added diisopropyl azodicarboxylate (616 mg, 3.05 mmol, 0.6 mL, 1.30 eq) dropwise at 25° C. After the addition was completed, the mixture was stirred at 60° C. for 12 hours. The reaction mixture was evaporated under reduced pressure to get a residue which was purified by silica gel column chromatography (Petroleum ether/Ethyl acetate=3/1 to 0/1). The product tert-butyl 6-(4-pyridyloxy)-2-azaspiro[3.3]heptane-2-carboxylate (500 mg, 1.72 mmol, 73% yield) was obtained as a white solid. $^1$HNMR (400 MHz, CDCl$_3$) δ: 8.42 (d, J=6.0 Hz, 2H), 6.69 (d, J=1.6 Hz, 4.8 Hz, 2H), 4.64-4.61 (m, 1H), 3.99 (s, 2H), 3.94 (s, 2H), 2.76-2.71 (m, 2H), 2.38-2.33 (m, 2H), 1.44 (s, 9H). MS (ESI) m/z: 291.2 [M+1]$^+$.

Step 8: Synthesis of 6-(1-benzylpyridin-1-ium-4-yl)oxy-2-azaspiro[3.3]heptane-2-carboxylate

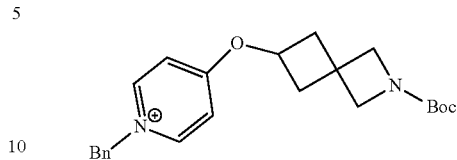

To a solution of tert-butyl 6-(4-pyridyloxy)-2-azaspiro[3.3]heptane-2-carboxylate (4.2 g, 14.46 mmol, 1.00 eq) in acetonitrile (50 mL) was added benzyl bromide (2.72 g, 15.91 mmol, 1.9 mL, 1.10 eq). The mixture was stirred at 80° C. for 12 hours. White precipitate was formed when the mixture was cooled to 25° C. The mixture was filtered and the filtrate cake was collected, washed by acetonitrile (50 mL), dried under reduced pressure to get the crude product. The crude product tert-butyl 6-(1-benzylpyridin-1-ium-4-yl)oxy-2-azaspiro[3.3]heptane-2-carboxylate (5 g, crude) was obtained as a white solid.

Step 9: Synthesis of tert-butyl 6-[(1-benzyl-3,6-dihydro-2H-pyridin-4-yl)oxy]-2-azaspiro[3.3]heptane-2-carboxylate

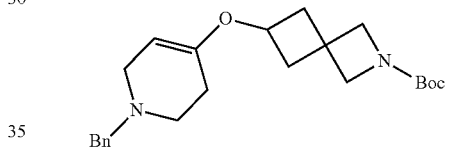

To a solution of tert-butyl 6-(1-benzylpyridin-1-ium-4-yl)oxy-2-azaspiro[3.3]heptane-2-carboxylate (2.50 g, 6.55 mmol, 1.00 eq) in methanol (30 mL) was added sodium borohydride (1.49 g, 39.32 mmol, 6.00 eq) at 20° C. and the mixture was stirred at 20° C. for 12 h. The mixture was diluted with water (60 mL) and extracted with ethyl acetate (60 mL×3). The organic layers were washed with saturated sodium bicarbonate solution (60 mL), washed with brine (60 mL), dried over sodium sulfate, filtered and concentrated under reduced pressure to give a residue which was purified by column chromatography (petroleum ether/ethyl acetate=8/1 to 0/1) to give tert-butyl 6-[(1-benzyl-3,6-dihydro-2H-pyridin-4-yl)oxy]-2-azaspiro[3.3]heptane-2-carboxyl-ate (500 mg, 1.30 mmol, 20% yield) as a white solid. $^1$HNMR (400 MHz, DMSO-d$_6$) δ: 7.16-7.40 (m, 5H), 4.44 (s, 1H), 4.20-4.30 (m, 1H), 3.75-3.88 (m, 4H), 3.52 (s, 2H), 2.83-2.91 (m, 2H), 2.52-2.60 (m, 4H), 2.00-2.13 (m, 4H), 1.36 (s, 9H).

Step 10: Synthesis of tert-butyl 6-(4-piperidyloxy)-2-azaspiro[3.3]heptane-2-carboxylate

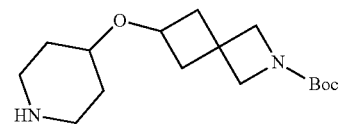 [SMILES: CC(C)(C)OC(=O)N1CC2(CC(OC3CCNCC3)C2)C1]

To a solution of tert-butyl 6-[(1-benzyl-3,6-dihydro-2H-pyridin-4-yl)oxy]-2-azaspiro[3.3]heptane-2-carboxylate (500 mg, 1.30 mmol, 1.00 eq) in methanol (20 mL) was added palladium on carbon (500 mg, 10% purity) under hydrogen (hydrogen balloon, 15 psi) at 20° C. and the mixture was stirred at 20° C. for 12 h. Thin layer chromatography (petroleum ether/ethyl acetate=1/1) showed the reaction was completed. The mixture was filtered and the filtrate was concentrated under reduced pressure to give tert-butyl 6-(4-piperidyloxy)-2-azaspiro[3.3]heptane-2-carboxylate (350 mg, 1.18 mmol, 91% yield) as a colorless oil. $^1$HNMR (400 MHz, DMSO-$d_6$) δ: 3.85-3.96 (m, 1H), 3.63-3.84 (m, 4H), 3.15-3.29 (m, 2H), 2.81-2.90 (m, 1H), 2.50-2.77 (m, 2H), 2.31-2.44 (m, 3H), 2.02-1.65 (m, 4H), 1.36 (s, 9H), 1.25-1.13 (m, 1H). MS (ESI) m/z: 241.3 [M−56]$^+$.

Step 11: Synthesis of tert-butyl 6-[[1-[5-chloro-4-[[1-ethyl-3-[2-(methylamino)-2-oxo-ethoxy]-2-oxo-6-quinolyl]amino]pyrimidin-2-yl]-4-piperidyl]oxy]-2-azaspiro[3.3]heptane-2-carboxylate

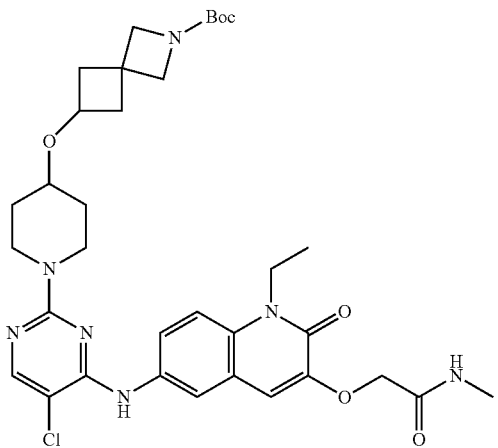 [SMILES: CCn1c(=O)c(OCC(=O)NC)cc2cc(Nc3nc(N4CCC(OC5CC6(C5)CN(C(=O)OC(C)(C)C)C6)CC4)ncc3Cl)ccc21]

To a solution of tert-butyl 6-(4-piperidyloxy)-2-azaspiro[3.3]heptane-2-carboxylate (300 mg, 1.01 mmol, 1.00 eq) in dimethylsulfoxide (4 mL) was added diisopropylethylamine (392 mg, 3.04 mmol, 3.00 eq) and 2-[[6-[(2,5-dichloropyrimidin-4-yl)amino]-1-ethyl-2-oxo-3-quinolyl]oxy]-N-methyl-acetamide (299 mg, 0.7 mmol, 0.70 eq) at 110° C. and the mixture was stirred at 110° C. for 1 h. LCMS showed that the reaction was completed. The mixture was filtered and the filtrate was purified by preparative high performance liquid chromatography (column: Phenomenex Synergi C18 150*25*10 um; mobile phase: [water (0.225% FA)-ACN]; B %: 37%-70%, 11 min) to give tert-butyl 6-[[1-[5-chloro-4-[[1-ethyl-3-[2-(methylamino)-2-oxo-ethoxy]-2-oxo-6-quinolyl]amino]pyrimidin-2-yl]-4-piperidyl]oxy]-2-azaspiro[3.3]heptane-2-carboxylate (300 mg, 0.44 mmol, 43% yield) as a white solid. MS (ESI) m/z: 682.3 [M]$^+$.

Step 11: Synthesis of 2-[[6-[[2-[4-(2-azaspiro[3.3]heptan-6-yloxy)-1-piperidyl]-5-chloro-pyrimidin-4-yl]amino]-1-ethyl-2-oxo-3-quinolyl]oxy]-N-methyl-acetamide trifluoroacetate

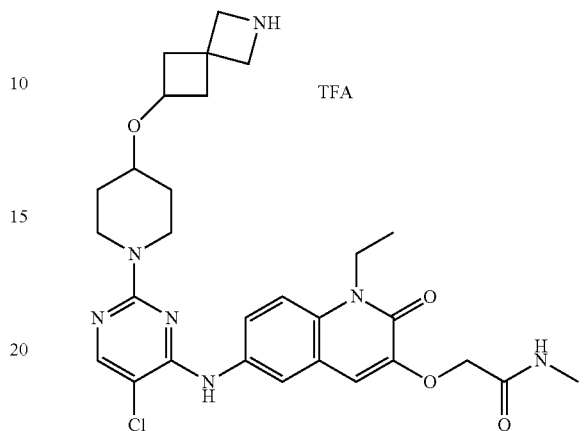

To a solution of tert-butyl 6-[[1-[5-chloro-4-[[1-ethyl-3-[2-(methylamino)-2-oxo-ethoxy]-2-oxo-6-quinolyl]amino]pyrimidin-2-yl]-4-piperidyl]oxy]-2-azaspiro[3.3]heptane-2-carboxylate (100 mg, 0.15 mmol, 1.00 eq) in dichloromethane (5 mL) was added trifluoroacetic acid (770 mg, 6.75 mmol, 0.5 mL, 46.07 eq) and the mixture was stirred at 20° C. for 0.5 h. LCMS showed the reaction was completed. The mixture was concentrated under reduced pressure to give 2-[[6-[[2-[4-(2-azaspiro[3.3]heptan-6-yloxy)-1-piperidyl]-5-chloro-pyrimidin-4-yl]amino]-1-ethyl-2-oxo-3-quinolyl]oxy]-N-methyl-acetamide (100 mg, 0.14 mmol, 98% yield, trifluoroacetic acid) as a light yellow oil. MS (ESI) m/z: 582.3 [M]$^+$.

Step 12: Synthesis of 2-[[6-[[5-chloro-2-[4-[[2-[2-(2,6-dioxo-3-piperidyl)-1,3-dioxo-isoindolin-5-yl]-2-azaspiro[3.3]heptan-6-yl]oxy]-1-piperidyl]pyrimidin-4-yl]amino]-1-ethyl-2-oxo-3-quinolyl]oxy]-N-methyl-acetamide

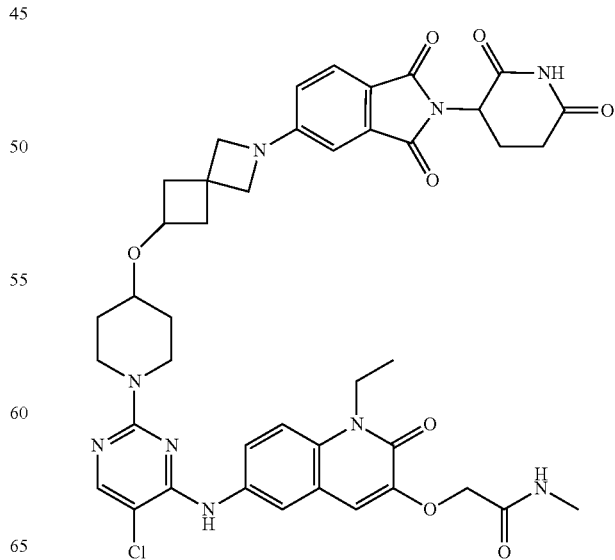

To a solution of 2-(2,6-dioxo-3-piperidyl)-5-fluoro-isoindoline-1,3-dione (44 mg, 0.16 mmol, 1.10 eq) in dimethylsulfoxide (3 mL) were added 2-[[6-[[2-[4-(2-azaspiro[3.3]heptan-6-yloxy)-1-piperidyl]-5-chloro-pyrimidin-4-yl]amino]-1-ethyl-2-oxo-3-quinolyl]oxy]-N-methyl-acetamide (100 mg, 1.00 eq, trifluoroacetic acid) and diisopropylethylamine (93 mg, 0.72 mmol, 5.00 eq) at 100° C. and the mixture was stirred at 100° C. for 5 h. The mixture was filtered and the filtrate was purified by preparative high performance liquid chromatography (column: Phenomenex Luna C18 150*25 mm*10 um; mobile phase: [water (0.225% FA)-ACN]; B %: 30%-60%, 10 min) to give 2-[[6-[[5-chloro-2-[4-[[2-[2-(2,6-dioxo-3-piperidyl)-1,3-dioxo-isoindolin-5-yl]-2-azaspiro[3.3]heptan-6-yl]oxy]-1-piperidyl]pyrimidin-4-yl]amino]-1-ethyl-2-oxo-3-quinolyl]oxy]-N-methyl-acetamide (77.4 mg, 0.09 mmol, 62% yield, 97% purity) as a yellow solid. MS (ESI) m/z: 838.3 [M]$^+$. $^1$HNMR (400 MHz, DMSO-$d_6$) δ: 11.07 (s, 1H), 8.85 (s, 1H), 8.05 (s, 1H), 7.96-8.02 (m, 2H), 7.73 (dd, J=2.4, 9.2 Hz, 1H), 7.63 (d, J=8.4 Hz, 1H), 7.53 (d, J=9.2 Hz, 1H), 7.09 (s, 1H), 6.75 (d, J=2.0 Hz, 1H), 6.62 (dd, J=2.0, 8.4 Hz, 1H), 5.06 (dd, J=5.2, 12.8 Hz, 1H), 4.58 (s, 2H), 4.29-4.37 (m, 2H), 4.05-4.13 (m, 3H), 3.97-4.05 (m, 4H), 3.50-3.59 (m, 1H), 3.21-3.29 (m, 3H), 2.82-2.95 (m, 1H), 2.67 (d, J=4.8 Hz, 3H), 2.54-2.61 (m, 3H), 2.10-2.16 (m, 2H), 1.97-2.05 (m, 1H), 1.79-1.87 (m, 2H), 1.33-1.43 (m, 2H), 1.25 (t, J=7.2 Hz, 3H).

Exemplary Synthesis of 2-[[6-([5-chloro-2-[(3S)-3-([[2-(2,6-dioxopiperidin-3-yl)-1,3-dioxoisoindol-4-yl]oxy]methyl)piperidin-1-yl]pyrimidin-4-yl]amino)-1-cyclopropyl-2-oxoquinolin-3-yl]oxy]-N-methylacetamide (Exemplary Compound 336)

Step 1: Synthesis of 1-cyclopropylindole-2,3-dione

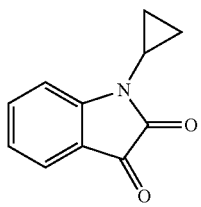 [SMILES: O=C1C(=O)N(C2CC2)c2ccccc21]

Into a 500-mL round-bottom flask purged and maintained with an inert atmosphere of nitrogen, was placed isatin (2.94 g, 19.982 mmol, 1.00 equiv), cyclopropylboronic acid (3.43 g, 39.964 mmol, 2.00 equiv), Na$_2$CO$_3$ (4.24 g, 39.964 mmol, 2.00 equiv), Cu(OAc)$_2$ (3.63 g, 19.982 mmol, 1.00 equiv), DCE (60.00 mL). The resulting solution was stirred for 2 h at 70° C. The reaction was quenched with sat. NH4Cl (aq.) at 0° C. The resulting mixture was extracted with CH2Cl2 (3×100 mL). The combined organic layers were washed with brine (1×100 mL), dried over anhydrous Na2SO4. After filtration, the filtrate was concentrated under reduced pressure. The residue was purified by silica gel column chromatography, eluted with PE/EtOAc (5:1) to afford 1-cyclopropylindole-2,3-dione (2.75 g, 74%) as a yellow solid.

Step 2: Synthesis of 1-cyclopropyl-5-nitroindole-2,3-dione

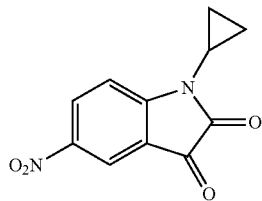 [SMILES: O=C1C(=O)N(C2CC2)c2ccc([N+](=O)[O-])cc21]

Into a 250-mL round-bottom flask, was placed 1-cyclopropylindole-2,3-dione (2.70 g, 14.423 mmol, 1.00 equiv), H$_2$SO$_4$ (40.00 mL), potassiooxy nitrite (2.19 g, 21.661 mmol, 1.50 equiv). The resulting solution was stirred for 2 h at 0° C. in a water/ice bath. The reaction was then quenched by the addition of 50 mL of brine (aq.). The resulting solution was extracted with ethyl acetate (3×100 mL), washed with brine (2×50 mL), dried over anhydrous sodium sulfate and concentrated under vacuum. This resulted in 3.65 g (109%) of 1-cyclopropyl-5-nitroindole-2,3-dione as a yellow solid.

Steps 3-7: Synthesis of 2-([1-cyclopropyl-6-[(2,5-dichloropyrimidin-4-yl)amino]-2-oxoquinolin-3-yl]oxy)-N-methylacetamide

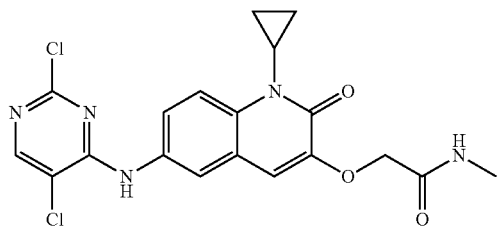 [SMILES: CNC(=O)COc1cc2cc(Nc3nc(Cl)ncc3Cl)ccc2n(C2CC2)c1=O]

The title compound was prepared from 1-cyclopropyl-5-nitroindole-2,3-dione using Steps 2-6 in Example 263 resulting in 420 mg (97%) of 2-([1-cyclopropyl-6-[(2,5-dichloropyrimidin-4-yl)amino]-2-oxoquinolin-3-yl]oxy)-N-methylacetamide as a yellow solid. MS (ES$^+$): m/z 434.05 [MH$^+$].

Step 8: Synthesis of tert-butyl (3S)-3-[[(4-methylbenzenesulfonyl)oxy]methyl]piperidine-1-carboxylate

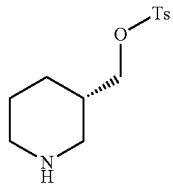 [SMILES: Cc1ccc(S(=O)(=O)OC[C@H]2CCCNC2)cc1]

A solution of tert-Butyl (3S)-3-(hydroxymethyl)piperidine-1-carboxylate (5.0 g, 23 mmol, 1.0 equiv) in DCM (100 mL) was treated with TsCl (6.6 g, 34.5 mmol, 1.5 equiv), Et$_3$N (7.00 g, 69 mmol, 3.0 equiv), DMAP (0.3 g, 2.3 mmol, 0.1 equiv) and stirred for 2 h at room temperature. The reaction was then quenched by the addition of NH₄Cl aq solution, extracted with dichloromethane. The organic layers combined, dried over anhydrous sodium sulfate, concentrated in vacuo and purified by column chromatography eluting with 0 to 60% EtOAc in pet. Ether. This afforded 6.8 g (84%) tert-butyl (3S)-3-[[(4-methylbenzenesulfonyl)oxy] methyl]piperidine-1-carboxylate as a yellow solid. MS (ES⁺): m/z 270.15 [MH⁺].

Step 9: Synthesis of tert-butyl (3S)-3-([[2-(2,6-dioxopiperidin-3-yl)-1,3-dioxoisoindol-4-yl]oxy] methyl)piperidine-1-carboxylate

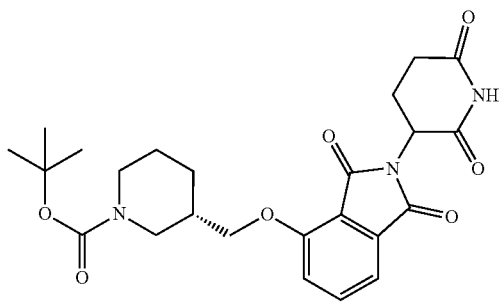 [SMILES: CC(C)(C)OC(=O)N1CCC[C@H](COc2cccc3c2C(=O)N(C2CCC(=O)NC2=O)C3=O)C1]

Into a 250-mL round-bottom flask, was placed tert-butyl (3S)-3-[[(4-methylbenzenesulfonyl)oxy]methyl]piperidine-1-carboxylate (6.8 g, 18 mmol, 1.0 equiv), 2-(2,6-dioxopiperidin-3-yl)-4-hydroxyisoindole-1,3-dione (6.0 g, 21.6 mmol, 1.2 equiv), K₂CO₃ (3.8 g, 27 mmol, 1.5 equiv), DMF (100 mL). The resulting solution was stirred for 2 h at 70° C. The reaction solution was poured in to water/ice, the product precipitated. This resulted of 6.6 g (76%) tert-butyl (3S)-3-([[2-(2,6-dioxopiperidin-3-yl)-1,3-dioxoisoindol-4-yl]oxy]methyl)piperidine-1-carboxylate as yellow solids. MS (ES⁺): m/z 472.25 [MH⁺].

Step 10: Synthesis of 2-(2,6-dioxopiperidin-3-yl)-4-[(3S)-piperidin-3-ylmethoxy]isoindole-1,3-dione hydrochloride

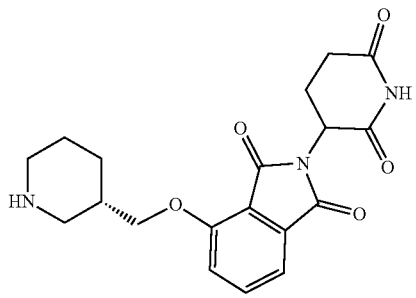 [SMILES: O=C1CCC(N2C(=O)c3cccc(OC[C@H]4CCCNC4)c3C2=O)C(=O)N1]

tert-butyl N-[(2S)-3-[[2-(2,6-dioxopiperidin-3-yl)-1,3-dioxoisoindol-4-yl]oxy]-2-methylpropyl]carbamate (1.0 g) was taken up in 1,4-dioxane (10 mL) and treated with 5 mL of 4M HCl in 1,4-dioxane. The resulting solution was stirred for 2 h at room temperature. The resulting mixture was concentrated under vacuum to obtain 900 mg of 2-(2,6-dioxopiperidin-3-yl)-4-[(3S)-piperidin-3-ylmethoxy] isoindole-1,3-dione HCl as a yellow solid. MS (ES⁺): m/z 372.05 [MH⁺].

Step 11: Synthesis of 2-[[6-([5-chloro-2-[(3S)-3-([[2-(2,6-dioxopiperidin-3-yl)-1,3-dioxoisoindol-4-yl]oxy]methyl)piperidin-1-yl]pyrimidin-4-yl]amino)-1-cyclopropyl-2-oxoquinolin-3-yl]oxy]-N-methylacetamide

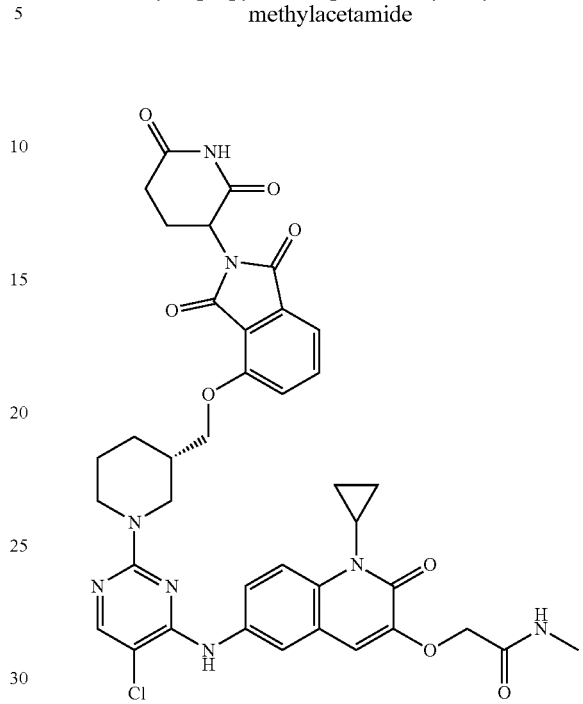

Into a 10-mL sealed tube purged and maintained with an inert atmosphere of nitrogen, was placed 2-([1-cyclopropyl-6-[(2,5-dichloropyrimidin-4-yl)amino]-2-oxoquinolin-3-yl] oxy)-N-methylacetamide (87.00 mg, 0.200 mmol, 1.00 equiv), DMSO (3.0 mL), DIEA (1 mL), 2-(2,6-dioxopiperidin-3-yl)-4-[(3S)-piperidin-3-ylmethoxy]isoindole-1,3-dione (133.92 mg, 0.361 mmol, 1.80 equiv). The resulting solution was stirred for 3 h at 100° C. in an oil bath. The crude product was purified by Flash-Prep-HPLC with the following conditions: mobile phase, acetonitrile/water (10 mmol/L NH₄HCO₃)=0/100 increasing to acetonitrile/water (10 mmol/LNH₄HCO₃)=60/40 within 30 min. to afford 53.8 mg (39%) of 2-[[6-([5-chloro-2-[(3S)-3-([[2-(2,6-dioxopiperidin-3-yl)-1,3-dioxoisoindol-4-yl]oxy]methyl)piperidin-1-yl]pyrimidin-4-yl]amino)-1-cyclopropyl-2-oxoquinolin-3-yl]oxy]-N-methylacetamide as a yellow solid. ¹H NMR (300 MHz, DMSO-d₆, ppm) δ11.08 (s, 1H), 8.82 (s, 1H), 8.03 (s, 1H), 7.88-7.81 (m, 2H), 7.78-7.72 (m, 3H), 7.47-7.44 (m, 2H), 7.06 (s, 1H), 5.07-5.01 (m, 1H), 4.48 (s, 3H), 4.32 (d, J=13.1 Hz, 1H), 4.21-4.14 (m, 1H), 4.11-4.03 (m, 1H), 2.97-2.94 (m, 4H), 2.66 (d, J=4.2 Hz, 4H), 1.97-1.96 (m, 3H), 1.74 (s, 1H), 1.49 (s, 2H), 1.24 (s, 3H), 0.74 (s, 2H). MS (ES+): m/z 769.10 [MH⁺].

Exemplary Synthesis of 2-[[6-[[5-chloro-2-[4-[[2-[2-(2,6-dioxo-3-piperidyl)-1,3-dioxo-isoindolin-5-yl]-2,7-diazaspiro[3.5]nonan-7-yl]methyl]-1-piperidyl]pyrimidin-4-yl]amino]-1-isopropyl-2-oxo-3-quinolyl]oxy]-N-methyl-acetamide (Exemplary Compound 372)

Step 1: Synthesis of tert-butyl 2-[2-(2,6-dioxo-3-piperidyl)-1,3-dioxo-isoindolin-5-yl]-2,7-diazaspiro[3.5]nonane-7-carboxylate

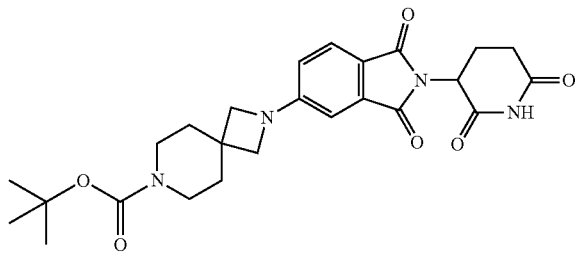 [SMILES: CC(C)(C)OC(=O)N1CCC2(CC1)CN(c1ccc3c(c1)C(=O)N(C1CCC(=O)NC1=O)C3=O)C2]

To a solution of 2-(2,6-dioxo-3-piperidyl)-5-fluoro-isoindoline-1,3-dione (1 g, 3.62 mmol, 1 eq) and N,N-diisopropylethylamine (1.40 g, 10.86 mmol, 3 eq) in dimethyl sulfoxide (8 mL) was added tert-butyl 2,7-diazaspiro[3.5]nonane-7-carboxylate (1.05 g, 3.98 mmol, 1.1 eq, HCl). The solution was heated to 120° C. for 1 hr. TLC (dichloromethane:methanol=20:1) showed reaction was complete. Reaction was quenched with water (80 mL) and extracted with ethyl acetate (30 mL×3). The organic layer was washed with brine (50 mL) and dried over sodium sulfate. Filtered and filtrate was concentrated in vacuum. Crude product was triturated in ethyl acetate: petroleum oil (40 mL, v/v=1:1) to afford product as yellow green solid. tert-butyl 2-[2-(2,6-dioxo-3-piperidyl)-1,3-dioxo-isoindolin-5-yl]-2,7-diazaspiro[3.5]nonane-7-carboxylate (1.4 g, 2.90 mmol, 80% yield) was obtained as a yellow green solid. $^1$HNMR: EW4821-1059-P1A (400 MHz, CHLOROFORM-d) δ: 8.08 (s, 1H), 7.65 (d, J=8.2 Hz, 1H), 6.79 (d, J=2.0 Hz, 1H), 6.53 (dd, J=2.2, 8.4 Hz, 1H), 4.94 (dd, J=5.4, 12.4 Hz, 1H), 3.78 (s, 4H), 3.52-3.33 (m, 4H), 2.98-2.63 (m, 3H), 2.16-2.09 (m, 1H), 1.86-1.77 (m, 4H), 1.47 (s, 9H)

Step 2: Synthesis of 5-(2,7-diazaspiro[3.5]nonan-2-yl)-2-(2,6-dioxo-3-piperidyl) isoindoline-1,3-dione

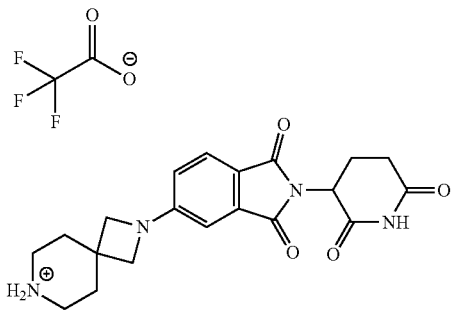 [SMILES: O=C([O-])C(F)(F)F ; O=C1CCC(N2C(=O)c3ccc(N4CC5(CC[NH2+]CC5)C4)cc3C2=O)C(=O)N1]

To a solution of tert-butyl 2-[2-(2,6-dioxo-3-piperidyl)-1,3-dioxo-isoindolin-5-yl]-2,7-diazaspiro[3.5]nonane-7-carboxylate (400 mg, 0.828 mmol, 1 eq) in dichloromethane (5 mL) was added trifluoroacetic acid (1.54 g, 13.51 mmol, 16.29 eq), The solution was stirred at 20° C. for 1 hr. LCMS showed reaction was complete. Solvent was removed in vacuum to afford product, which was used in next step without purification. 5-(2,7-diazaspiro[3.5]nonan-2-yl)-2-(2,6-dioxo-3-piperidyl) isoindoline-1,3-dione (400 mg, 0.805 mmol, 97% yield, TFA salt) was obtained as a yellow solid. MS (ESI) m/z: 383.3 [M+1]$^+$.

Step 3: Synthesis of tert-butyl 4-[[2-[2-(2,6-dioxo-3-piperidyl)-1,3-dioxo-isoindolin-5-yl]-2,7-diazaspiro[3.5]nonan-7-yl]methyl]piperidine-1-carboxylate

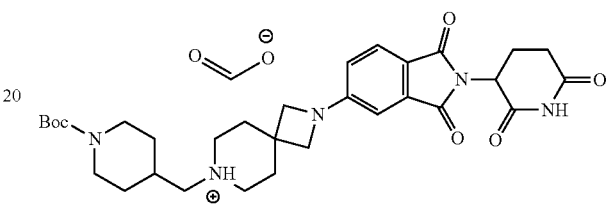

5-(2,7-diazaspiro[3.5]nonan-2-yl)-2-(2,6-dioxo-3-piperidyl)isoindoline-1,3-dione (200 mg, 0.40 mmol, 1.00 eq, trifluoroacetic salt) in dichloromethane (5 mL) was added diisopropylethylamine (104 mg, 0.81 mmol, 0.14 mL, 2.00 eq) and tert-butyl 4-formylpiperidine-1-carboxylate (86 mg, 0.40 mmol, 1.00 eq). The mixture was stirred at 20° C. for 0.5 h. Then to the mixture was added sodium triacetoxyborohydride (213 mg, 1.01 mmol, 2.50 eq) and stirred at 20° C. for 11.5 h. LCMS showed the reaction was completed. The mixture was filtered and the filtrate was concentrated under reduced pressure to give a residue which was purified by preparative high performance liquid chromatography (column: Phenomenex luna C18 150*40 mm* 15 um; mobile phase: [water (0.1% TFA)-ACN]; B %: 16%-46%, 10 min) to give tert-butyl 4-[[2-[2-(2,6-dioxo-3-piperidyl)-1,3-dioxo-isoindolin-5-yl]-2,7-diazaspiro[3.5]nonan-7-yl]methyl]piperidine-1-carboxylate (200 mg, 0.32 mmol, 79% yield, formate salt) as a green solid. MS (ESI) m/z: 580.2 [M+1]$^+$.

Step 4: Synthesis of 2-(2,6-dioxo-3-piperidyl)-5-[7-(4-piperidylmethyl)-2,7-diazaspiro[3.5]nonan-2-yl]isoindoline-1,3-dione

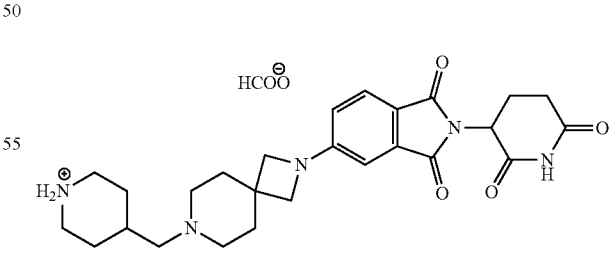

To a solution of tert-butyl 4-[[2-[2-(2,6-dioxo-3-piperidyl)-1,3-dioxo-isoindolin-5-yl]-2,7-diazaspiro[3.5]nonan-7-yl]methyl]piperidine-1-carboxylate (200 mg, 0.32 mmol, 1.00 eq, formate) in dichloromethane (8 mL) was added trifluoroacetic acid (1.54 g, 13.51 mmol, 1.00 mL, 42.25 eq) and stirred at 20° C. for 0.5 h. LCMS showed the reaction was completed. The mixture was concentrated under reduced pressure to give a residue. The residue was purified by preparative high performance liquid chromatography (column: Phenomenex Synergi C18 150*25*10 um; mobile phase: [water (0.225% FA)-ACN]; B %: 0%-22%, 12 min) to give 2-(2,6-dioxo-3-piperidyl)-5-[7-(4-piperidylmethyl)-2,7-diazaspiro[3.5]nonan-2-yl]isoindoline-1,3-dione (150 mg, 0.29 mmol, 89% yield, formate) as a yellow solid. $^1$H NMR (400 MHz, DMSO-$d_6$) δ: 11.08 (s, 1H), 8.64-8.40 (m, 1H), 8.15 (s, 1H), 7.67 (d, J=8.4 Hz, 1H), 6.78 (d, J=2.0 Hz, 1H), 6.66 (dd, J=2.0, 8.4 Hz, 1H), 5.06 (dd, J=5.4, 12.8 Hz, 1H), 3.82 (s, 4H), 3.32-3.26 (m, 5H), 2.92-2.83 (m, 4H), 2.63-2.52 (m, 4H), 2.05-1.77 (m, 8H), 1.36-1.26 (m, 2H). MS (ESI) m/z: 480.3 [M+1]$^+$.

Step 5: 2-[[6-[[5-chloro-2-[4-[[2-[2-(2,6-dioxo-3-piperidyl)-1,3-dioxo-isoindolin-5-yl]-2,7-diazaspiro [3.5]nonan-7-yl]methyl]-1-piperidyl]pyrimidin-4-yl] amino]-1-isopropyl-2-oxo-3-quinolyl]oxy]-N-methyl-acetamide

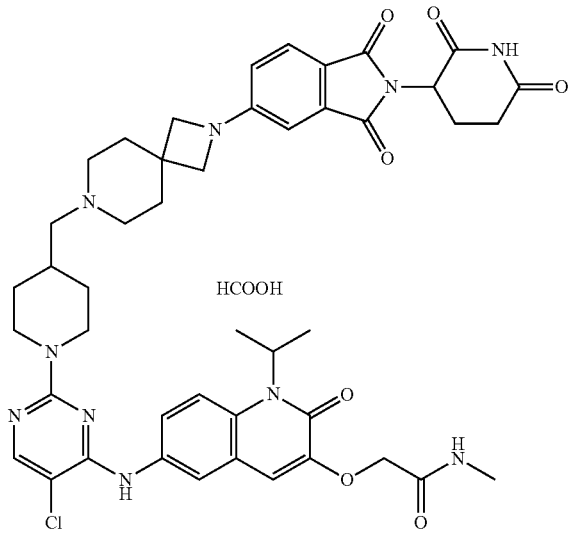 [SMILES: CNC(=O)COc1cc2cc(Nc3nc(N4CCC(CN5CCC6(CC5)CN(c5ccc7c(c5)C(=O)N(C5CCC(=O)NC5=O)C7=O)C6)CC4)ncc3Cl)ccc2n(C(C)C)c1=O ; "HCOOH"]

To a solution of 2-(2,6-dioxo-3-piperidyl)-5-[7-(4-piperidylmethyl)-2,7-diazaspiro[3.5]nonan-2-yl]isoindoline-1,3-dione (100 mg, 0.19 mmol, 1.00 eq, formate) in dimethylsulfoxide (2 mL) was added diisopropylethylamine (98.36 mg, 0.76 mmol, 0.13 mL, 4.00 eq) and 2-[[6-[(2,5-dichloropyrimidin-4-yl)amino]-1-isopropyl-2-oxo-3-quinolyl] oxy]-N-methyl-acetamide (83 mg, 0.19 mmol, 1.00 eq) at 120° C. The mixture was stirred at 120° C. for 0.5 h. LCMS showed the reaction was completed. The mixture was filtered. The filtrate was purified by preparative high performance liquid chromatography (column: Phenomenex Synergi C18 150*25*10 um; mobile phase: [water (0.225% FA)-ACN]; B %: 18%-38%, 10 min) to give 2-[[6-[[5-chloro-2-[4-[[2-[2-(2,6-dioxo-3-piperidyl)-1,3-dioxo-isoindolin-5-yl]-2,7-diazaspiro[3.5]nonan-7-yl]methyl]-1-piperidyl]pyrimidin-4-yl]amino]-1-isopropyl-2-oxo-3-quinolyl]oxy]-N-methyl-acetamide (43.7 mg, 0.05 mmol, 24% yield, 96% purity, formate) as a yellow solid. $^1$H NMR (400 MHz, DMSO-$d_6$) δ: 11.07 (s, 1H), 8.80 (s, 1H), 8.20 (s, 1H), 8.04 (s, 1H), 8.00-7.93 (m, 2H), 7.76-7.67 (m, 2H), 7.64 (d, J=8.0 Hz, 1H), 7.02 (s, 1H), 6.78 (d, J=2.0 Hz, 1H), 6.65 (dd, J=2.0, 8.4 Hz, 1H), 5.05 (dd, J=5.4, 12.8 Hz, 1H), 4.54 (s, 2H), 4.50 (br d, J=11.6 Hz, 2H), 3.75 (s, 4H), 2.91-2.79 (m, 3H), 2.68 (d, J=4.8 Hz, 3H), 2.66-2.52 (m, 3H), 2.40-2.22 (m, 4H), 2.12 (d, J=6.4 Hz, 2H), 2.06-1.96 (m, 1H), 1.85-1.70 (m, 7H), 1.58 (d, J=6.8 Hz, 6H), 1.12-0.96 (m, 2H). MS (ESI) m/z: 879.3 [M+1]$^+$.

Exemplary Synthesis of 2-[[6-([5-chloro-2-[4-([4-[2-(2,6-dioxopiperidin-3-yl)-1,3-dioxoisoindol-4-yl] piperidin-1-yl]methyl)piperidin-1-yl]pyrimidin-4-yl] amino)-1-isopropyl-2-oxoquinolin-3-yl]oxy]-N-methylacetamide (Exemplary Compound 386)

Step 1: Synthesis of tert-butyl 4-[2-(2,6-dioxopiperidin-3-yl)-1,3-dioxoisoindol-4-yl]-3,6-dihydro-2H-pyridine-1-carboxylate

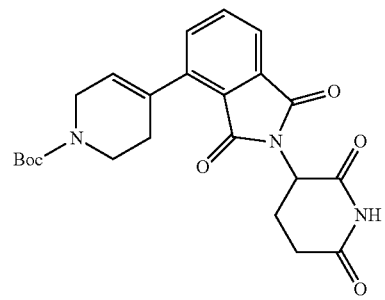 [SMILES: CC(C)(C)OC(=O)N1CC=C(c2cccc3c2C(=O)N(C2CCC(=O)NC2=O)C3=O)CC1]

Into a 250-mL round-bottom flask purged and maintained with an inert atmosphere of nitrogen, was placed 4-bromo-2-(2,6-dioxopiperidin-3-yl)isoindole-1,3-dione (2.00 g, 5.93 mmol, 1.00 equiv), tert-butyl 4-(4,4,5,5-tetramethyl-1,3,2-dioxaborolan-2-yl)-3,6-dihydro-2H-pyridine-1-carboxylate (1834.37 mg, 5.93 mmol, 1 equiv), K$_2$CO$_3$ (1639.79 mg, 11.86 mmol, 2 equiv), Pd(dppf)Cl$_2$ (434.08 mg, 0.59 mmol, 0.1 equiv), dioxane (20 mL, 226.97 mmol, 39.79 equiv). The resulting solution was stirred for 3 h at 100° C. The reaction mixture was cooled to room temperature with a water bath. The reaction was then quenched by the addition of 100 mL of water. The resulting solution was extracted with ethyl acetate. The resulting mixture was washed with brine. The mixture was dried over anhydrous sodium sulfate. The residue was applied onto a silica gel column with ethyl acetate/hexane (1:1). This resulted in 2.3 g (88%) of tert-butyl 4-[2-(2,6-dioxopiperidin-3-yl)-1,3-dioxoisoindol-4-yl]-3,6-dihydro-2H-pyridine-1-carboxylate as a solid. MS (ES+): m/z 440 [MH$_+$].

Step 2: Synthesis of tert-butyl 4-[2-(2,6-dioxopiperidin-3-yl)-1,3-dioxoisoindol-4-yl]piperidine-1-carboxylate

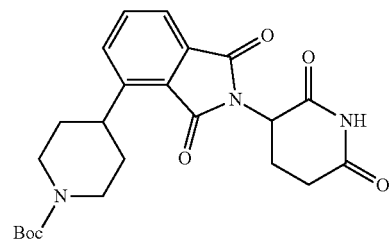 [SMILES: CC(C)(C)OC(=O)N1CCC(c2cccc3c2C(=O)N(C2CCC(=O)NC2=O)C3=O)CC1]

To a solution of tert-butyl 4-[2-(2,6-dioxopiperidin-3-yl)-1,3-dioxoisoindol-4-yl]-3,6-dihydro-2H-pyridine-1-carboxylate (2.10 g, 4.77 mmol, 1.00 equiv) in tetrahydrofuran (50 mL) was added Pd/C (1.50 g, 14.09 mmol, 2.95 equiv) under nitrogen atmosphere in a 250 mL round-bottom flask. The mixture was hydrogenated at room temperature for 3 h under hydrogen atmosphere using a hydrogen balloon, filtered through a Celite pad and the filtrate concentrated under reduced pressure. This afford tert-butyl 4-[2-(2,6-dioxopiperidin-3-yl)-1,3-dioxoisoindol-4-yl]piperidine-1-carboxylate (1.9 g, 90.1%) as a solid. MS (ES+): m/z 442 [MH$^+$].

Step 3: Synthesis of 2-(2,6-dioxopiperidin-3-yl)-4-(piperidin-4-yl)isoindole-1,3-dione

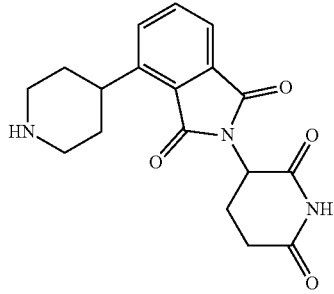 [SMILES: O=C1CCC(N2C(=O)c3cccc(C4CCNCC4)c3C2=O)C(=O)N1]

Into a 100-mL round-bottom flask purged and maintained with an inert atmosphere of nitrogen, was placed tert-butyl 4-[2-(2,6-dioxopiperidin-3-yl)-1,3-dioxoisoindol-4-yl]piperidine-1-carboxylate (400.00 mg, 0.90 mmol, 1.00 equiv), dioxane (19.96 mg, 0.22 mmol, 0.25 equiv), hydrogen chloride (9.91 mg, 0.27 mmol, 0.30 equiv). The resulting solution was stirred for 3 hr at room temperature. The resulting mixture was concentrated under vacuum. This resulted in 300 mg (97.00%) of 2-(2,6-dioxopiperidin-3-yl)-4-(piperidin-4-yl)isoindole-1,3-dione as a white solid. MS (ES+): m/z 342 [MH$^+$].

Step 4: Synthesis of 2-[[6-([5-chloro-2-[4-([4-[2-(2,6-dioxopiperidin-3-yl)-1,3-dioxoisoindol-4-yl]piperidin-1-yl]methyl)piperidin-1-yl]pyrimidin-4-yl]amino)-1-isopropyl-2-oxoquinolin-3-yl]oxy]-N-methylacetamide

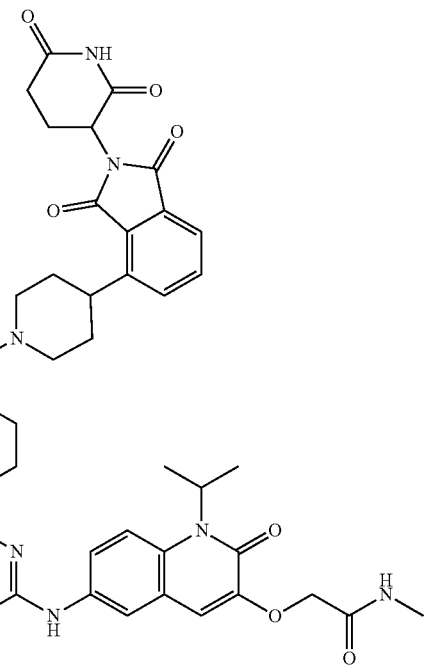

Into a 50-mL round-bottom flask purged and maintained with an inert atmosphere of nitrogen, was placed 2-(2,6-dioxopiperidin-3-yl)-4-(piperidin-4-yl)isoindole-1,3-dione (100.00 mg, 0.29 mmol, 1.00 equiv), 2-[(6-[[5-chloro-2-(4-formylpiperidin-1-yl)pyrimidin-4-yl]amino]-1-isopropyl-2-oxoquinolin-3-yl)oxy]-N-methylacetamide (150.28 mg, 0.29 mmol, 1 equiv), DCE (10 mL), HOAc (1.76 mg, 0.02 mmol, 0.1 equiv), after the reaction solution was stirred at rt for 3 h, added NaBH(OAc)3 (124.17 mg, 0.58 mmol, 2 equiv). The resulting solution was stirred for 1 hr at room temperature. The residue was purified by reverse flash chromatography with the following conditions: column, C18 silica gel; mobile phase, acetonitrile/water (10 mmol/L NH4HCO3), 10% to 50% gradient in 10 min; detector, UV 254 nm. This resulted in 56.2 mg (22.84%) of 2-[[6-([5-chloro-2-[4-([4-[2-(2,6-dioxopiperidin-3-yl)-1,3-dioxoisoindol-4-yl]piperidin-1-yl]methyl)piperidin-1-yl]pyrimidin-4-yl]amino)-1-isopropyl-2-oxoquinolin-3-yl]oxy]-N-methylacetamide as a white solid. $^1$H NMR (300 MHz, DMSO-$d_6$, ppm) δ11.12 (s, 1H), 8.79 (s, 1H), 8.03 (s, 1H), 7.95 (s, 2H), 7.85-7.70 (m, 5H), 7.02 (s, 1H), 5.16-5.10 (m, 2H), 4.54-4.48 (m, 4H), 2.98-2.81 (m, 5H), 2.73-2.63 (m, 4H), 2.56 (s, 1H), 2.18-2.10 (m, 2H), 2.06-1.93 (m, 3H), 1.77-1.66 (m, 6H), 1.57 (d, J=6.9 Hz, 6H), 1.23 (s, 2H), 1.07-1.02 (m, 2H). MS (ES+): m/z 838.30 [MH$^+$].

Exemplary Synthesis of 2-[[6-[[5-chloro-2-[4-[(3R,5S)-5-[[2-(2,6-dioxo-3-piperidyl)-1,3-dioxo-isoindolin-5-yl]oxymethyl]-1-methyl-pyrrolidin-3-yl]piperazin-1-yl]pyrimidin-4-yl]amino]-1-ethyl-2-oxo-3-quinolyl]oxy]-N-methyl-acetamide (Exemplary Compound 371)

Step 1: Synthesis of benzyl 3,4-dihydroxypyrrolidine-1-carboxylate

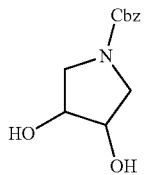

To a solution of benzyl 2,5-dihydropyrrole-1-carboxylate (5.00 g, 24.60 mmol, 1.00 eq) in tertiary butanol (60 mL) and water (50 mL) were added tripotassium; hexacyanoiron (3-) (20.25 g, 61.50 mmol, 16.88 mL, 2.50 eq), potassium carbonate (8.50 g, 61.50 mmol, 2.50 eq), methanesulfonamide (2.34 g, 24.60 mmol, 1.00 eq) and potassium osmate (91 mg, 0.25 mmol, 0.01 eq) at 0° C. The mixture was stirred at 0° C. for 5 h. Thin layer chromatography (dichloromethane:methanol=20:1) showed the reaction was completed. The reaction mixture was quenched with saturated sodium sulfite (60 mL). The residue was diluted with water (50 mL) and extracted with ethyl acetate (60 mL×2). The combined organic phase was washed with saturated brine (60 mL×2), dried with anhydrous sodium sulfate, filtered and concentrated under reduced pressure to give colorless oil. The oil was triturated with 60 mL of 5:1 petroleum ether:ethyl acetate and filtered. The filter cake was dried under reduced pressure to give benzyl 3,4-dihydroxypyrrolidine-1-carboxylate (5.00 g, 21.07 mmol, 86% yield) as a white solid. ¹H NMR: (400 MHz, DMSO-d₆) δ: 7.41-7.27 (m, 5H), 5.07 (s, 2H), 4.94 (d, J=4.4 Hz, 2H), 4.11-3.91 (m, 2H), 3.50-3.39 (m, 2H), 3.26-3.11 (m, 2H).

Step 2: Synthesis of benzyl N,N-bis(2-oxoethyl)carbamate

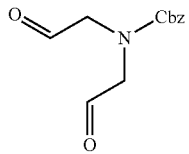 [SMILES: O=CCN(CC=O)C(=O)OCc1ccccc1]

To a solution of benzyl 3,4-dihydroxypyrrolidine-1-carboxylate (2.50 g, 10.54 mmol, 1.00 eq) in tetrahydrofuran (15 mL) was added a solution of sodium periodate (3.38 g, 15.81 mmol, 875.85 uL, 1.50 eq) in water (4 mL) at 20° C. The mixture was stirred at 20° C. for 0.5 h. The reaction mixture was quenched with saturated sodium sulfite (80 mL). The residue was diluted with water (50 mL) and extracted with ethyl acetate (50 mL×2). The combined organic phase was washed with brine (50 mL×2), dried over anhydrous sodium sulfate, filtered and concentrated under reduced pressure to give benzyl N,N-bis(2-oxoethyl)carbamate (2.20 g, 9.35 mmol, 89% yield) as a colorless oil, which was used in next step directly.

Step 3: Synthesis of 1-(tert-butyl) 2-methyl (2S,4R)-4-(4-((benzyloxy)carbonyl) piperazin-1-yl)pyrrolidine-1,2-dicarboxylate

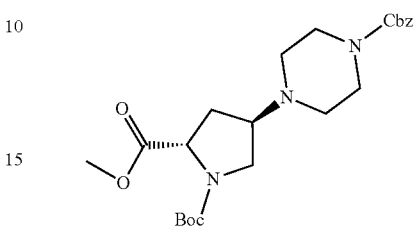

To a solution of 1-(tert-butyl)-2-methyl (2S,4R)-4-aminopyrrolidine-1,2-dicarboxylate (1.80 g, 7.37 mmol, 1.00 eq) in methanol (100 mL) was added benzyl N,N-bis(2-oxoethyl)carbamate (2.08 g, 8.84 mmol, 1.20 eq) at 20° C. The mixture was stirred at 20° C. for 1 h. Then to the mixture was added borane, 2-methylpyridine (3.13 g, 29.27 mmol, 3.97 eq) and stirred at 20° C. for 12 h. The mixture was quenched with water (150 mL) and then concentrated under reduced pressure to give a residue. The residue was extracted with ethyl acetate (80 mL). The organic layer was washed with brine, dried over sodium sulfate and then concentrated under reduced pressure to give a residue. The residue was purified by column chromatography (petroleum ether:ethyl acetate=5:1 to 0:1) to give the title compound as (2.40 g, 73% yield) of a colorless oil. ¹H NMR (400 MHz, DMSO-d₆ δ: 7.43-7.27 (m, 5H), 5.07 (s, 2H), 4.31-4.20 (m, 1H), 3.69-3.58 (m, 4H), 3.38 (s, 3H), 3.31 (s, 1H), 3.14-3.00 (m, 1H), 2.96-2.81 (m, 1H), 2.44-2.36 (m, 2H), 2.35-2.27 (m, 2H), 2.16-2.03 (m, 2H), 1.44-1.28 (m, 9H).

Step 4: Synthesis of benzyl 4-[(3R,5S)-1-tert-butoxycarbonyl-5-(hydroxymethyl)pyrrolidin-3-yl]piperazine-1-carboxylate

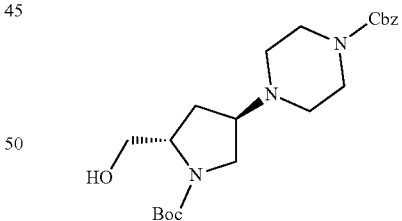

To a solution of 1-(tert-butyl)-2-methyl (2S,4R)-4-(4-benzyloxycarbonylpiperazin-1-yl)pyrrolidine-1,2-dicarboxylate (2.20 g, 4.92 mmol, 1.00 eq) in tetrahydrofuran (30 mL) was added lithium borohydride (535 mg, 24.58 mmol, 5.00 eq) at 0° C. The mixture was stirred at 0° C. for 3 h. LCMS showed the reaction was completed. The mixture was quenched with water (100 mL) and extracted with ethyl acetate (50 mL). The organic layer was washed with water (30 mL), brine (30 mL), dried over sodium sulfate and then concentrated under reduced pressure to give a residue. The residue was purified by column chromatography (petroleum ether:ethyl acetate=5:1 to 0:1) to give benzyl 4-[(3R,5S)-1-tert-butoxycarbonyl-5-(hydroxymethyl)pyrrolidin-3-yl]piperazine-1-carboxylate (2.00 g, 4.77 mmol, 97% yield) as a colorless oil. $^1$H NMR (400 MHz, DMSO-$d_6$) δ: 7.51-7.13 (m, 5H), 5.08 (s, 2H), 4.82-4.67 (m, 1H), 3.82-3.66 (m, 1H), 3.46-3.36 (m, 5H), 3.32-3.20 (m, 2H), 3.05-2.99 (m, 1H), 2.98-2.85 (m, 1H), 2.44-2.35 (m, 2H), 2.34-2.24 (m, 2H), 2.16-2.01 (m, 1H), 1.79-1.61 (m, 1H), 1.39 (s, 9H). MS (ESI) m/z: 420.2 [M+1]$^+$ Step 5: Synthesis of benzyl 4-[(3R,5S)-1-tert-butoxycarbonyl-5-[[2-(2,6-dioxo-3-piperidyl)-1,3-dioxo-isoindolin-5-yl]oxymethyl]pyrrolidin-3-yl]piperazine-1-carboxylate

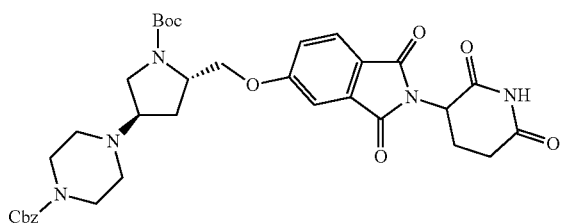 [SMILES: CC(C)(C)OC(=O)N1C[C@H](N2CCN(C(=O)OCc3ccccc3)CC2)C[C@H]1COc1ccc2c(c1)C(=O)N(C1CCC(=O)NC1=O)C2=O]

To a solution of benzyl 4-[(3R,5S)-1-tert-butoxycarbonyl-5-(hydroxymethyl)pyrrolidin-3-yl]piperazine-1-carboxylate (1.50 g, 3.58 mmol, 1.00 eq) in tetrahydrofuran (20 mL) were added 2-(2,6-dioxo-3-piperidyl)-5-hydroxy-isoindoline-1,3-dione (981 mg, 3.58 mmol, 1.00 eq) and triphenylphosphine (1.41 g, 5.36 mmol, 1.50 eq) at 20° C. under nitrogen. Then to the mixture was added dropwise diisopropyl azodicarboxylate (1.08 g, 5.36 mmol, 1.04 mL, 1.50 eq) at 20° C. The mixture was warmed to 70° C. and stirred at 70° C. for 10 h. The mixture was concentrated under reduced pressure to give a residue. The residue was purified by preparative high performance liquid chromatography (column: Phenomenex luna C18 250*50 mm*10 um; mobile phase: [water (0.225% FA)-ACN]; B %: 20%-45%, 20 min) to give benzyl 4-[(3R,5S)-1-tert-butoxycarbonyl-5-[[2-(2,6-dioxo-3-piperidyl)-1,3-dioxo-isoindolin-5-yl]oxymethyl] pyrrolidin-3-yl]piperazine-1-carboxylate (800 mg, 33% yield) as a white solid. MS (ESI) m/z: 676.4[M+1]$^+$.

Step 6: Synthesis of benzyl 4-[(3R,5S)-5-[[2-(2,6-dioxo-3-piperidyl)-1,3-dioxo-isoindolin-5-yl]oxymethyl]pyrrolidin-3-yl]piperazine-1-carboxylate

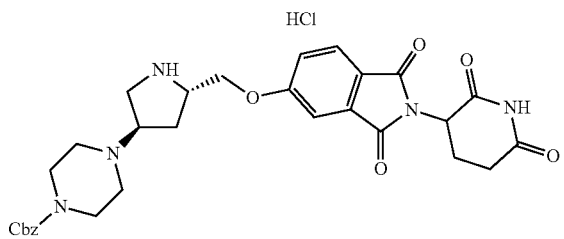 [SMILES: Cl ; O=C1CCC(N2C(=O)c3ccc(OC[C@@H]4C[C@@H](N5CCN(C(=O)OCc6ccccc6)CC5)CN4)cc3C2=O)C(=O)N1]

To a solution of benzyl 4-[(3R,5S)-1-tert-butoxycarbonyl-5-[[2-(2,6-dioxo-3-piperidyl)-1,3-dioxo-isoindolin-5-yl] oxymethyl]pyrrolidin-3-yl]piperazine-1-carboxylate (770 mg, 1.14 mmol, 1.00 eq) in dichloromethane (16 mL) was added hydrochloric acid/dioxane (4 M, 6.00 mL, 21.06 eq) at 20° C. The mixture was stirred at 20° C. for 0.5 h. then concentrated under reduced pressure to give benzyl 4-[(3R,5S)-5-[[2-(2,6-dioxo-3-piperidyl)-1,3-dioxo-isoindolin-5-yl]oxymethyl]pyrrolidin-3-yl]piperazine-1-carboxylate (750 mg, crude, hydrochloric salt) as a white solid. MS (ESI) m/z: 576.4[M+1]$^+$.

Step 7: Synthesis of benzyl 4-[(3R,5S)-5-[[2-(2,6-dioxo-3-piperidyl)-1,3-dioxo-isoindolin-5-yl]oxymethyl]-1-methyl-pyrrolidin-3-yl]piperazine-1-carboxylate

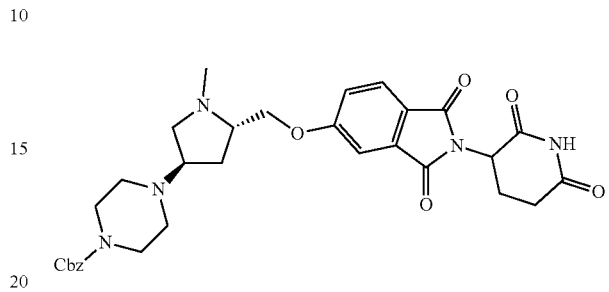

To a solution of benzyl 4-[(3R,5S)-5-[[2-(2,6-dioxo-3-piperidyl)-1,3-dioxo-isoindolin-5-yl]oxymethyl]pyrrolidin-3-yl]piperazine-1-carboxylate (280 mg, 0.41 mmol, 1.00 eq, trifluoroacetic salt) in dimethyl formamide (4 mL) was added diisopropylethylamine (105 mg, 0.81 mmol, 0.14 mL, 2.00 eq) and formaldehyde (329 mg, 4.06 mmol, 0.30 mL, 10.00 eq). The mixture was stirred at 20° C. for 0.5 h. Then to the mixture was added sodium triacetoxyborohydride (215 mg, 1.02 mmol, 2.50 eq) and then stirred for 0.5 h at 20° C. The mixture was quenched with water (20 mL) and extracted with ethyl acetate (2×20 mL). The organic layers were washed with water (40 mL), brine (2×40 mL), dried over sodium sulfate and concentrated under reduced pressure to give benzyl4-[(3R,5S)-5-[[2-(2,6-dioxo-3-piperidyl)-1,3-dioxo-isoindolin-5-yl]oxymethyl]-1-methyl-pyrrolidin-3-yl]piperazine-1-carboxylate (220 mg, 0.37 mmol, 92% yield) as a light yellow oil. MS (ESI) m/z: 590.3[M+1]$^+$.

Step 8: Synthesis of 2-(2,6-dioxo-3-piperidyl)-5-[[(2S,4R)-1-methyl-4-piperazin-1-yl-pyrrolidin-2-yl]methoxy]isoindoline-1,3-dione

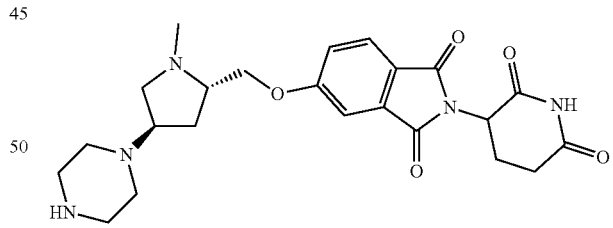

To a solution of benzyl 4-[(3R,5S)-5-[[2-(2,6-dioxo-3-piperidyl)-1,3-dioxo-isoindolin-5-yl]oxymethyl]-1-methyl-pyrrolidin-3-yl]piperazine-1-carboxylate (220 mg, 0.37 mmol, 1.00 eq) in trifluoroethanol (15 mL) was added palladium on carbon (100 mg, 10% purity) under hydrogen (15 psi). The mixture was stirred at 20° C. for 1 h. LCMS showed that the reaction was completed. The mixture was filtered and the filtrate was concentrated under reduced pressure to give 2-(2,6-dioxo-3-piperidyl)-5-[[(2S,4R)-1-methyl-4-piperazin-1-yl-pyrrolidin-2-yl]methoxy]isoindoline-1,3-dione (160 mg, 0.35 mmol, 94% yield) as a colorless oil, which was used in next step directly. MS (ESI) m/z: 456.4 [M+1]$^+$.

Step 9: Synthesis of 2-[[6-[[5-chloro-2-[4-[(3R,5S)-5-[[2-(2,6-dioxo-3-piperidyl)-1,3-dioxo-isoindolin-5-yl]oxymethyl]-1-methyl-pyrrolidin-3-yl]piperazin-1-yl]pyrimidin-4-yl]amino]-1-ethyl-2-oxo-3-quinolyl]oxy]-N-methyl-acetamide formate salt

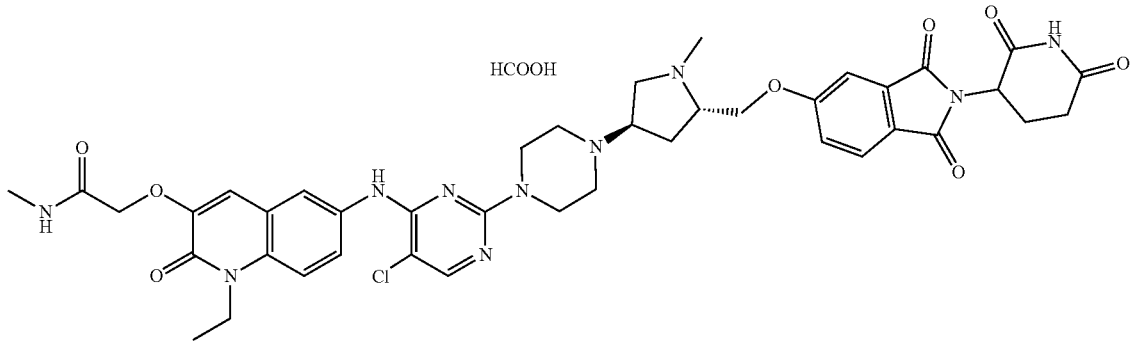 [SMILES: CCn1c(=O)c(OCC(=O)NC)cc2cc(Nc3nc(N4CCN([C@@H]5C[C@@H](COc6ccc7c(c6)C(=O)N(C6CCC(=O)NC6=O)C7=O)N(C)C5)CC4)ncc3Cl)ccc21 ; "HCOOH"]

To a solution of 2-(2,6-dioxo-3-piperidyl)-5-[[(2S,4R)-1-methyl-4-piperazin-1-yl-pyrrolidin-2-yl]methoxy]isoindoline-1,3-dione (150 mg, 0.33 mmol, 1.00 eq) in dimethylsulfoxide (4 mL) was added diisopropylethylamine (128 mg, 0.99 mmol, 0.17 mL, 3.00 eq) and 2-[[6-[(2,5-dichloropyrimidin-4-yl)amino]-1-ethyl-2-oxo-3-quinolyl]oxy]-N-methyl-acetamide (139 mg, 0.33 mmol, 1.00 eq) at 120° C. The mixture was stirred at 120° C. for 1 h. LCMS showed that the reaction was completed. The mixture was filtered. The filtrate was purified by preparative high performance liquid chromatography (column: Phenomenex Synergi C18 150*25*10 um; mobile phase: [water (0.225% FA)-ACN]; B %: 13%-33%, 10 min) to give 2-[[6-[[5-chloro-2-[4-[(3R,5S)-5-[[2-(2,6-dioxo-3-piperidyl)-1,3-dioxo-isoindolin-5-yl]oxymethyl]-1-methyl-pyrrolidin-3-yl]piperazin-1-yl]pyrimidin-4-yl]amino]-1-ethyl-2-oxo-3-quinolyl]oxy]-N-methyl-acetamide (52.1 mg, 17% yield, 93% purity, formate) as a yellow solid. $^1$H NMR (400 MHz, DMSO-$d_6$) δ: 11.11 (s, 1H), 8.86 (s, 1H), 8.23 (s, 1H), 8.06 (s, 1H), 8.00-7.92 (m, 2H), 7.86-7.70 (m, 2H), 7.57-7.50 (m, 1H), 7.46-7.32 (m, 1H), 7.19-7.10 (m, 2H), 5.23-5.04 (m, 1H), 4.58 (s, 2H), 4.37-4.28 (m, 2H), 4.18-4.03 (m, 1H), 3.63-3.62 (m, 2H), 3.36-3.32 (m, 1H), 3.16-3.04 (m, 2H), 3.04-2.81 (m, 2H), 2.80-2.71 (m, 2H), 2.66 (d, J=4.4 Hz, 3H), 2.64-2.54 (m, 2H), 2.43-2.29 (m, 5H), 2.26 (d, J=3.2 Hz, 1H), 2.22-2.16 (m, 1H), 2.12-1.96 (m, 2H), 1.95-1.84 (m, 1H), 1.78-1.68 (m, 1H), 1.24 (t, J=6.8 Hz, 3H). MS (ESI) m/z: 841.3 [M+1]$^+$.

Exemplary Synthesis of 2-[[6-[[5-chloro-2-[(2S,6R)-2-[[2-(2,6-dioxo-3-piperidyl)-1,3-dioxo-isoindolin-5-yl]oxymethyl]-6-methyl-morpholin-4-yl]pyrimidin-4-yl]amino]-1-isopropyl-2-oxo-3-quinolyl]oxy]-N-methyl-acetamide (Exemplary Compound 383)

Step 1: Synthesis of (2S)-1-amino-3-benzyloxy-propan-2-ol

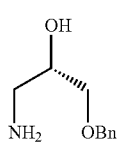

A solution of (2S)-2-(benzyloxymethyl)oxirane (10.00 g, 60.90 mmol) in ammonium hydroxide (200 mL) was stirred at 25° C. for 16 h then concentrated under reduced. The residue was purified by preparative high performance liquid chromatography (column: Phenomenex luna c18 250 mm*100 mm*10 um; mobile phase: [water (0.225% FA)-ACN]; B %: 2ACN %-20ACN %, 5 min) to give (2S)-1-amino-3-benzyloxy-propan-2-ol (10.60 g, 96% yield) as a colorless oil. $^1$H NMR (400 MHz, CDCl3) δ: 7.24-7.40 (m, 5H), 4.53 (s, 2H), 3.69-3.80 (m, 1H), 3.42-3.52 (m, 2H), 2.75-2.85 (m, 1H), 2.65-2.74 (m, 1H). MS (ESI) m/z: 182.1 [M+1]$^+$.

Step 2: Synthesis of (2R)-N-[(2S)-3-benzyloxy-2-hydroxy-propyl]-2-chloro-propanamide

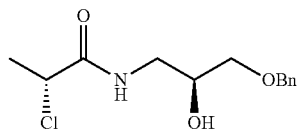 [SMILES: C[C@@H](Cl)C(=O)NC[C@H](O)COCc1ccccc1]

To a solution of (2S)-1-amino-3-benzyloxy-propan-2-ol (4.00 g, 22.07 mmol) in ethanol (70 mL) was added methyl (2R)-2-chloropropanoate (3.25 g, 26.49 mmol, 2.82 mL). The mixture was stirred at 80° C. for 12 hours then concentrated under reduced pressure to move ethanol. Then the residue was washed with water (50 mL) and extracted with ethyl acetate (20 mL×2). The organic layer was concentrated under reduced pressure to give the residue which was purified by column chromatography on silica gel (petroleum ether/ethyl acetate=5/1 to 3/1) to give (2R)-N-[(2S)-3-benzyloxy-2-hydroxy-propyl]-2-chloro-propanamide (1.00 g, 17% yield) as an off white oil. $^1$H NMR (400 MHz, DMSO-$d_6$) δ: 8.17 (br t, J=5.6 Hz, 1H), 7.23-7.41 (m, 5H), 5.02 (d, J=5.2 Hz, 1H), 4.54 (q, J=6.8 Hz, 1H), 4.49 (s, 2H), 3.66-3.77 (m, 1H), 3.36 (s, 1H), 3.27 (dt, J=13.2, 5.6 Hz, 1H), 3.01-3.11 (m, 1H), 1.50 (d, J=6.8 Hz, 3H). MS (ESI) m/z: 272.1 [M+1]$^+$.

Step 3: Synthesis of (2R,6S)-6-(benzyloxymethyl)-2-methyl-morpholin-3-one

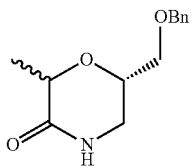

To a mixture of (2R)—N-[(2S)-3-benzyloxy-2-hydroxypropyl]-2-chloro-propanamide (2.50 g, 9.20 mmol) and sodium hydride (736 mg, 18.40 mmol, 60% purity) in tetrahydrofuran (200 mL) was degassed and purged with nitrogen for 3 times. The mixture was stirred at 0° C. for 1 hr then at rt for an additional hour then quenched with water (200 mL) and extracted with ethyl acetate (200 mL). The organic layer was washed with brine (200 mL), dried over sodium sulfate and concentrated under reduced pressure to give a residue which was purified by column chromatography on silica gel (dichloromethane:methanol=50:1-20:1) to give (2R,6S)-6-(benzyloxymethyl)-2-methyl-morpholin-3-one (1.54 g, 71% yield) as a colorless oil. $^1$H NMR (400 MHz, CDCl$_3$) δ: 7.29-7.42 (m, 5H), 6.40-6.61 (m, 1H), 4.54-4.64 (m, 2H), 3.94-4.49 (m, 1H), 3.94-4.19 (m, 1H), 3.61-3.69 (m, 1H), 3.48-3.59 (m, 1H), 3.31-3.46 (m, 2H), 1.47-1.55 (m, 3H). MS (ESI) m/z: 236.1 [M+1]$^+$.

Step 4: Synthesis of (2S)-2-((benzyloxy)methyl)-6-methylmorpholine

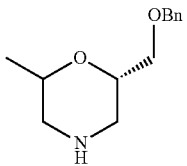 [SMILES: CC1CNC[C@@H](COCc2ccccc2)O1]

To a solution of (2R,6S)-6-(benzyloxymethyl)-2-methyl-morpholin-3-one (1.54 g, 6.55 mmol) in tetrahydrofuran (50 mL) was added lithium aluminum hydride (497 mg, 13.09 mmol). The mixture was stirred at 25° C. for 2.5 h then quenched with a 5% NaOH solution until bubbling ceased. The mixture was filtered and concentrated under reduced pressure to give (2S)-2-((benzyloxy)methyl)-6-methylmorpholine (1.33 g, 92% yield) as a white solid, which was used in next step without further purification. MS (ESI) m/z: 222.1 [M+1]$^+$.

Step 5: Synthesis of tert-butyl (2S,6R)-2-(benzyloxymethyl)-6-methyl-morpholine-4-carboxylate and tert-butyl (2S,6S)-2-(benzyloxymethyl)-6-methyl-morpholine-4-carboxylate

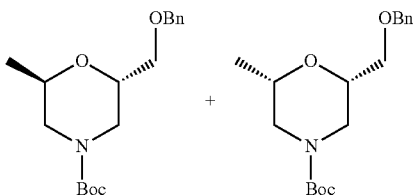 [SMILES: C[C@@H]1CN(C(=O)OC(C)(C)C)C[C@@H](COCc2ccccc2)O1 ; C[C@H]1CN(C(=O)OC(C)(C)C)C[C@@H](COCc2ccccc2)O1]

To a solution of (2S)-2-((benzyloxy)methyl)-6-methylmorpholine (1.33 g, 6.01 mmol) and triethylamine (1.82 g, 18.03 mmol) in dichloromethane (10 mL) was added di-tert-butyldicarbonate (2.62 g, 12.02 mmol). The mixture was stirred at 25° C. for 10 h. LCMS showed that the reaction was completed. The mixture was concentrated under reduced pressure to give the residue. The residue was purified by preparative high performance liquid chromatography (column: Phenomenex luna C18 150*40 mm*15 um; mobile phase: [water (0.225% FA)-ACN]; B %: 57%-77%, 11 min) to give tert-butyl (2S,6R)-2-(benzyloxymethyl)-6-methyl-morpholine-4-carboxylate (700 mg, 36% yield) $^1$H NMR (400 MHz, DMSO-d$_6$) δ: 7.21-7.43 (m, 5H), 4.50 (s, 2H), 3.73-3.97 (m, 2H), 3.36-3.56 (m, 4H), 2.76-3.12 (m, 1H), 1.41-1.56 (m, 1H), 1.39 (s, 9H), 1.07 (d, J=6.4 Hz, 3H), MS (ESI) m/z: 222.2 [M−100+1]$^+$ and tert-butyl (2S,6S)-2-(benzyloxymethyl)-6-methyl-morpholine-4-carboxylate (410 mg, 21% yield) $^1$H NMR (400 MHz, DMSO-d$_6$) δ: 7.43-7.24 (m, 5H), 4.50 (s, 2H), 3.95-3.71 (m, 2H), 3.62-3.52 (m, 1H), 3.51-3.38 (m, 3H), 2.66-2.53 (m, 1H), 2.50-2.35 (m, 1H), 1.41 (s, 9H), 1.08 (d, J=6.4 Hz, 3H) as off white oils.

Step 6: Synthesis of tert-butyl (2S,6R)-2-(hydroxymethyl)-6-methyl-morpholine-4-carboxylate

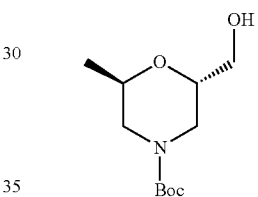

To a solution of tert-butyl (2S,6R)-2-(benzyloxymethyl)-6-methyl-morpholine-4-carboxylate (600 mg, 1.87 mmol) in methanol (5 mL) was added palladium on activated carbon catalyst (60 mg, 10% purity). The mixture was stirred at 25° C. for 10 h under 1 atm. of hydrogen. The mixture was filtered to give tert-butyl (2S,6R)-2-(hydroxymethyl)-6-methyl-morpholine-4-carboxylate (470 mg, crude) as an off-white oil, which was used in next step directly. MS (ESI) m/z: 132.1 [M−100+1]$^+$.

Step 7: Synthesis of tert-butyl (2R,6S)-2-methyl-6-(p-tolylsulfonyloxymethyl)morpholine-4-carboxylate

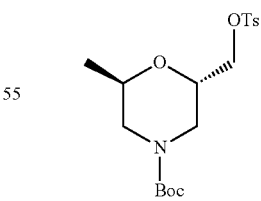

To a solution of tert-butyl (2S,6R)-2-(hydroxymethyl)-6-methyl-morpholine-4-carboxylate (470 mg, 2.03 mmol) in dichloromethane (5 mL) was added triethylamine (617 mg, 6.10 mmol), 4-dimethylaminopyridine (25 mg, 0.20 mmol) and p-toluenesulfonyl chloride (388 mg, 2.03 mmol). The mixture was stirred at 25° C. for 3 h. then quenched with water (50 mL). The organic layer was washed with brine (50 mL), dried over sodium sulfate and concentrated under reduced pressure to give a crude residue which was purified by column chromatography on silica gel (petroleum ether/ethyl acetate=20:1~10:1~5:1) to give tert-butyl (2R,6S)-2-methyl-6-(p-tolylsulfonyloxymethyl)morpholine-4-carboxylate (550 mg, 70% yield) as a colorless oil. MS (ESI) m/z: 286.0 [M−100+1]+.

Step 8: Synthesis of (2S,6R)-2-[[2-(2,6-dioxo-3-piperidyl)-1,3-dioxo-isoindolin-5-yl]oxymethyl]-6-methyl-morpholine-4-carboxylate

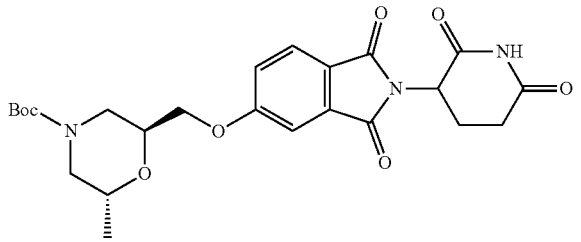 [SMILES: C[C@@H]1CN(C(=O)OC(C)(C)C)C[C@@H](COc2ccc3c(c2)C(=O)N(C2CCC(=O)NC2=O)C3=O)O1]

To a solution of tert-butyl (2R,6S)-2-methyl-6-(p-tolylsulfonyloxymethyl)morpholine-4-carboxylate (200 mg, 0.52 mmol) and 2-(2,6-dioxo-3-piperidyl)-5-hydroxy-isoindoline-1,3-dione (156 mg, 0.57 mmol) in N,N-dimethylformamide (5 mL) was added potassium carbonate (215 mg, 1.56 mmol). The mixture was stirred at 70° C. for 10 h. The mixture was quenched with water (30 mL) and extracted with ethyl acetate (20 mL). The organic layer was washed with brine (50 mL), dried over anhydrous sodium sulfate and concentrated under reduced pressure to give the residue. The residue was purified by preparative high performance liquid chromatography (column: Phenomenex Synergi C18 150*25*10 um; mobile phase: [water (0.225% FA)-ACN]; B %: 36%-66%, 10 min) to give tert-butyl (2S,6R)-2-[[2-(2,6-dioxo-3-piperidyl)-1,3-dioxo-isoindolin-5-yl]oxymethyl]-6-methyl-morpholine-4-carboxylate (20 mg, 8% yield) as a white solid. MS (ESI) m/z: 510.1 [M+23]+.

Step 9: Synthesis of 2-(2,6-dioxo-3-piperidyl)-5-[[(2S,6R)-6-methylmorpholin-2-yl]methoxy]isoindoline-1,3-dione

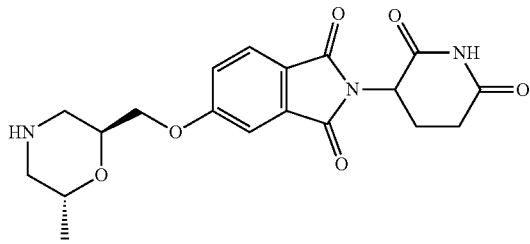 [SMILES: C[C@@H]1CNC[C@@H](COc2ccc3c(c2)C(=O)N(C2CCC(=O)NC2=O)C3=O)O1]

To a solution of tert-butyl (2S,6R)-2-[[2-(2,6-dioxo-3-piperidyl)-1,3-dioxo-isoindolin-5-yl]oxymethyl]-6-methyl-morpholine-4-carboxylate (20 mg, 0.04 mmol) in dichloromethane (2 mL) was added hydrochloric acid/dioxane (4 M, 1 mL). The mixture was stirred at 25° C. for 20 minutes then concentrated under reduced pressure to give 2-(2,6-dioxo-3-piperidyl)-5-[[(2S,6R)-6-methylmorpholin-2-yl]methoxy]isoindoline-1,3-dione (17 mmol, 98% yield, hydrochloric salt) as a white solid, which was used in next step directly. MS (ESI) m/z: 388.3 [M+1]+.

Step 10: Synthesis of 2-[[6-[[5-chloro-2-[(2S,6R)-2-[[2-(2,6-dioxo-3-piperidyl)-1,3-dioxo-isoindolin-5-yl]oxymethyl]-6-methyl-morpholin-4-yl]pyrimidin-4-yl]amino]-1-isopropyl-2-oxo-3-quinolyl]oxy]-N-methyl-acetamide

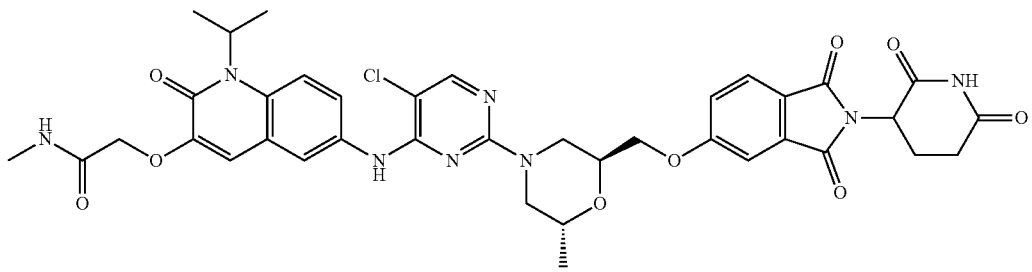 [SMILES: CNC(=O)COc1cc2cc(Nc3nc(N4C[C@@H](COc5ccc6c(c5)C(=O)N(C5CCC(=O)NC5=O)C6=O)O[C@H](C)C4)ncc3Cl)ccc2n(C(C)C)c1=O]

To a solution of 2-[[6-[(2,5-dichloropyrimidin-4-yl)amino]-1-isopropyl-2-oxo-3-quinolyl]oxy]-N-methyl-acetamide (21 mg, 0.05 mmol) and 2-(2,6-dioxo-3-piperidyl)-5-[[(2S,6R)-6-methylmorpholin-2-yl]methoxy]isoindoline-1,3-dione (17 mg, 0.04 mmol) hydrochloric salt) in dimethylsulfoxide (1 mL) was added diisopropylethylamine (26 mg, 0.02 mmol). The mixture was stirred at 120° C. for 2 h. LCMS showed the reaction was completed. The mixture was filtered to give the residue. The residue was purified by preparative high performance liquid chromatography (column: Phenomenex Synergi C18 150*25*10 um; mobile phase: [water (0.225% FA)-ACN]; B %: 36%-60%, 8 min) to give 2-[[6-[[5-chloro-2-[(2S,6R)-2-[[2-(2,6-dioxo-3-piperidyl)-1,3-dioxo-isoindolin-5-yl]oxymethyl]-6-methyl-morpholin-4-yl]pyrimidin-4-yl]amino]-1-isopropyl-2-oxo-3-quinolyl]oxy]-N-methyl-acetamide (14 mg, 45% yield) as a white solid. 1H NMR (400 MHz, DMSO-d6) δ: 11.12 (s, 1H), 9.16-8.85 (m, 1H), 8.08 (s, 1H), 7.99-7.83 (m, 2H), 7.80-7.57 (m, 3H), 7.38 (br d, J=1.6 Hz, 1H), 7.30-7.11 (m, 1H), 7.06 (s, 1H), 5.11 (br dd, J=5.2, 12.4 Hz, 2H), 4.49 (br s, 2H), 4.37-4.17 (m, 3H), 4.11-3.86 (m, 3H), 3.82-3.58 (m, 2H), 3.24-3.16 (m, 1H), 2.95-2.82 (m, 1H), 2.66 (br d, J=4.4 Hz, 3H), 2.58 (br s, 1H), 2.13-1.97 (m, 1H), 1.55 (br d, J=6.4 Hz, 6H), 1.14 (br d, J=6.0 Hz, 3H). MS (ESI) m/z: 787.3 [M+1]+.

Exemplary Synthesis of 2-([6-[(5-chloro-2-[4-[(1r,3r)-3-[4-[2-(2,6-dioxopiperidin-3-yl)-1,3-dioxoisoindol-5-yl]piperidin-1-yl]cyclobutoxy]piperidin-1-yl]pyrimidin-4-yl)amino]-1-isopropyl-2-oxoquinolin-3-yl]oxy)-N-methylacetamide (Exemplary Compound 403)

Step 1: Synthesis of 1. Synthesis of tert-butyl 4-[(1R,3R)-3-[4-[2-(2,6-dioxopiperidin-3-yl)-1,3-dioxoisoindol-5-yl]piperidin-1-yl]cyclobutoxy]piperidine-1-carboxylate

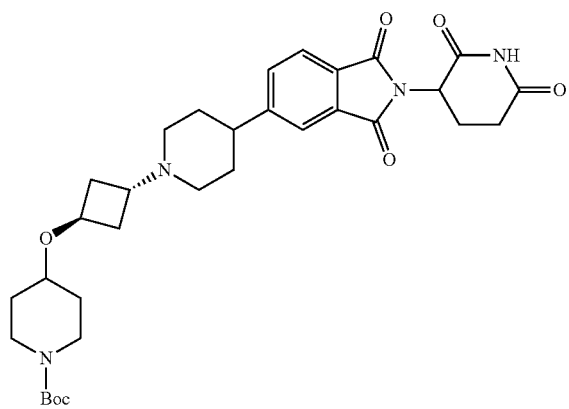 [SMILES: CC(C)(C)OC(=O)N1CCC(O[C@H]2C[C@H](N3CCC(c4ccc5c(c4)C(=O)N(C4CCC(=O)NC4=O)C5=O)CC3)C2)CC1]

Into a 20-mL sealed tube purged and maintained with an inert atmosphere of nitrogen, was placed 2-(2,6-dioxopiperidin-3-yl)-5-(piperidin-4-yl)isoindole-1,3-dione (200 mg, 0.6 mmol, 1.0 equiv), DMF (20 ml), DIEA (227 mg, 1.8 mmol, 3.0 equiv), tert-butyl 4-[(1S,3S)-3-[(4-nitrobenzenesulfonyl)oxy]cyclobutoxy]piperidine-1-carboxylate (WO2018102725, 267.5 mg, 0.6 mmol, 1.0 equiv). The resulting solution was stirred for 36 h at 65° C. in an oil bath. The crude product was purified by Flash-Prep-HPLC with the following conditions: Column, C18 silica gel; mobile phase, acetonitrile/water=10 increasing to acetonitrile/water=70 within 25 min; Detector, 254 nm. This resulted in 60 mg (17%) of tert-butyl 4-[(1R,3R)-3-[4-[2-(2,6-dioxopiperidin-3-yl)-1,3-dioxoisoindol-5-yl]piperidin-1-yl]cyclobutoxy]piperidine-1-carboxylate as yellow oil. MS (ES$^+$): m/z 595.30 [MH$^+$].

Step 2: Synthesis of 2-(2,6-dioxopiperidin-3-yl)-5-[1-[(1r,3r)-3-(piperidin-4-yloxy)cyclobutyl]piperidin-4-yl]isoindole-1,3-dione

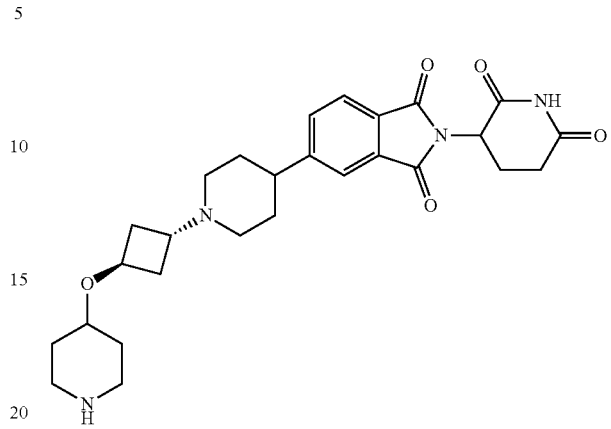

Into a 25-mL round-bottom flask, was placed tert-butyl 4-[(1r,3r)-3-[4-[2-(2,6-dioxopiperidin-3-yl)-1,3-dioxoisoindol-5-yl]piperidin-1-yl]cyclobutoxy]piperidine-1-carboxylate (60 mg, 0.1 mmol, 1.0 equiv), DCM (10 mL), TFA (3 mL). The resulting solution was stirred for 2 h at room temperature. The resulting mixture was concentrated. This resulted in 55 mg (99%) of 2-(2,6-dioxopiperidin-3-yl)-5-[1-[(1r,3r)-3-(piperidin-4-yloxy)cyclobutyl]piperidin-4-yl]isoindole-1,3-dione as yellow oil. LC-MS (ES$^+$): m/z 495.30 [MH$^+$].

Step 3: Synthesis of 2-([6-[(5-chloro-2-[4-[(1r,3r)-3-[4-[2-(2,6-dioxopiperidin-3-yl)-1,3-dioxoisoindol-5-yl]piperidin-1-yl]cyclobutoxy]piperidin-1-yl]pyrimidin-4-yl)amino]-1-isopropyl-2-oxoquinolin-3-yl]oxy)-N-methylacetamide

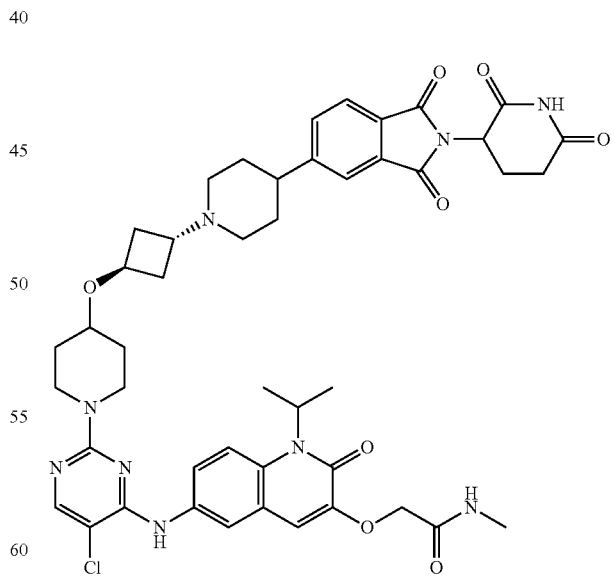

To a stirred solution of 2-(2,6-dioxopiperidin-3-yl)-5-[1-[(1r,3r)-3-(piperidin-4-yloxy) cyclobutyl]piperidin-4-yl] isoindole-1,3-dione (50.0 mg, 0.1 mmol, 1.0 equiv) and 2-([6-[(2,5-dichloropyrimidin-4-yl)amino]-1-isopropyl-2-oxoquinolin-3-yl]oxy)-N-methylacetamide (31.0 mg, 0.1 mmol, 0.7 equiv) in DMSO (3 mL) was added DIEA (79 mg) at room temperature. The result in g mixture was stirred for 2 h at 100° C. The residue was purified by reverse flash chromatography with the following conditions: column, C18 silica gel; mobile phase, acetonitrile/water (10 mmol/L NH$_4$HCO$_3$), 0% to 55% gradient in 30 min; detector, UV 254 nm. To afford 2-([6-[(5-chloro-2-[4-[(1r,3r)-3-[4-[2-(2,6-dioxopiperidin-3-yl)-1,3-dioxoisoindol-5-yl]piperidin-1-yl]cyclobutoxy]piperidin-1-yl]pyrimidin-4-yl)amino]-1-isopropyl-2-oxoquinolin-3-yl]oxy)-N-methylacetamide (21 mg, 23%) as a yellow solid. $^1$H NMR (400 MHz, DMSO-d$_6$, ppm): δ 11.11 (s, 1H), 8.82 (s, 1H), 8.04 (s, 1H), 8.04-7.99 (m, 2H), 7.8 5 (s, 1H), 7.83-7.78 (m, 2H), 7.76-7.69 (m, 2H), 7.03 (s, 1H), 5.50-5.20 (m, 1H), 5.19-5.12 (m, 1H), 4.54 (s, 2H), 4.25-4.01 (m, 3H), 3.55 (s, 1H), 3.25-3.10 (m, 3H), 3.00 (s, 2H), 2.90 (s, 1H), 2.89-2.80 (m, 1H), 2.79-2.69 (m, 3H), 2.60-2.52 (m, 1H), 2.15 (s, 2H), 2.10-1.99 (m, 3H), 1.92-1.78 (m, 6H), 1.76-1.69 (m, 2H), 1.56 (s, 6H), 1.48-1.32 (m, 2H), 1.21 (s, 1H). LC-MS (ES$^+$): m/z 894.25, [MH$^+$].

Exemplary Synthesis of 2-([6-[(5-chloro-2-[4-[(1r,3r)-3-[4-[2-(2,6-dioxopiperidin-3-yl)-1,3-dioxoisoindol-4-yl]piperidin-1-yl]cyclobutoxy]piperidin-1-yl]pyrimidin-4-yl)amino]-1-isopropyl-2-oxoquinolin-3-yl]oxy)-N-methylacetamide (Exemplary Compound 409)

Step 1: Synthesis of tert-butyl 4-[(1R,3R)-3-[4-[2-(2,6-dioxopiperidin-3-yl)-1,3-dioxoisoindol-4-yl]piperidin-1-yl]cyclobutoxy]piperidine-1-carboxylate

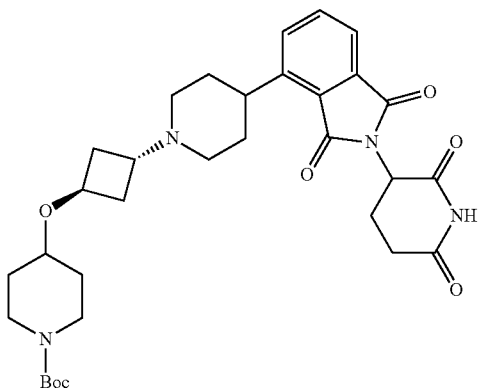 [SMILES: CC(C)(C)OC(=O)N1CCC(O[C@H]2C[C@H](N3CCC(c4cccc5c4C(=O)N(C4CCC(=O)NC4=O)C5=O)CC3)C2)CC1]

Into a 20-mL sealed tube, was placed 2-(2,6-dioxopiperidin-3-yl)-4-(piperidin-4-yl)isoindole-1,3-dione (300 mg, 0.8 mmol, 1 equiv), tert-butyl 4-[(1S,3S)-3-[(4-nitrobenzenesulfonyl)oxy]cyclobutoxy]piperidine-1-carboxylate (WO2018102725, 401 mg, 0.8 mmol, 1 equiv), DMF (10 mL), DIEA (1 mL). The resulting solution was stirred for 48 h at 65° C. The crude product was purified by Flash-Prep-HPLC with the following conditions: Column, C18 silica gel; mobile phase, acetonitrile/water (10 mmol/L NH$_4$HCO$_3$)=0 increasing to acetonitrile/water (10 mmol/L NH$_4$HCO$_3$)=60 within 30 min; Detector, 220 nm. This resulted in 100 mg (19.13%) of tert-butyl 4-[(1r,3r)-3-[4-[2-(2,6-dioxopiperidin-3-yl)-1,3-dioxoisoindol-4-yl]piperidin-1-yl]cyclobutoxy]piperidine-1-carboxylate as a solid. MS (ES+): m/z 595.3, [MH$^+$].

Step 2: Synthesis of 2-(2,6-dioxopiperidin-3-yl)-4-[1-[(1R, 3R)-3-(piperidin-4-yloxy)cyclobutyl]piperidin-4-yl]isoindole-1,3-dione

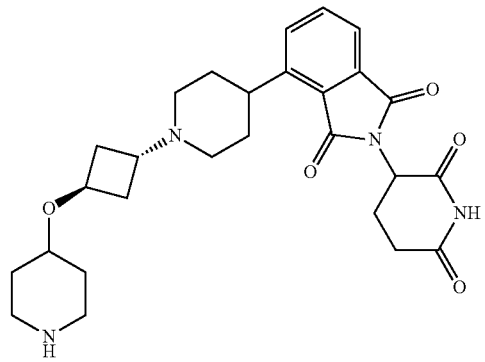 [SMILES: O=C1CCC(N2C(=O)c3cccc(C4CCN([C@H]5C[C@H](OC6CCNCC6)C5)CC4)c3C2=O)C(=O)N1]

Into a 50-mL round-bottom flask, was placed tert-butyl 4-[(1R,3R)-3-[4-[2-(2,6-dioxopiperidin-3-yl)-1,3-dioxoisoindol-4-yl]piperidin-1-yl]cyclobutoxy]piperidine-1-carboxylate (100 mg, 0.16 mmol, 1 equiv), trifluoroacetaldehyde (0.5 mL), DCM (1 mL). The resulting solution was stirred for 1 h at room temperature. The resulting mixture was concentrated. This resulted in 83 mg (99%) of 2-(2,6-dioxopiperidin-3-yl)-4-[1-[(1R,3R)-3-(piperidin-4-yloxy)cyclobutyl]piperidin-4-yl]isoindole-1,3-dione as a solid. MS (ES+): m/z 495.25[MH$^+$].

Step 3: 6. Synthesis of 2-([6-[(5-chloro-2-[4-[(1R, 3R)-3-[4-[2-(2,6-dioxopiperidin-3-yl)-1,3-dioxoisoindol-4-yl]piperidin-1-yl]cyclobutoxy]piperidin-1-yl]pyrimidin-4-yl)amino]-1-isopropyl-2-oxoquinolin-3-yl]oxy)-N-methylacetamide

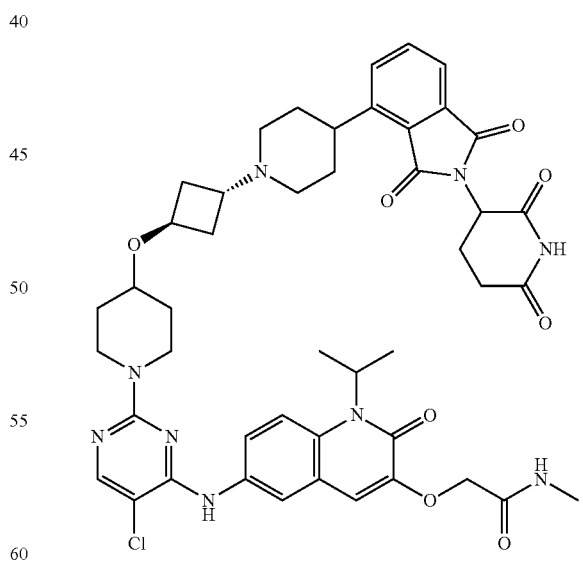

Into a 10-mL sealed tube, was placed 2-(2,6-dioxopiperidin-3-yl)-4-[1-[(1R,3R)-3-(piperidin-4-yloxy)cyclobutyl]piperidin-4-yl]isoindole-1,3-dione (83 mg, 1.5 equiv), 2-([6-[(2,5-dichloropyrimidin-4-yl)amino]-1-isopropyl-2-oxoquinolin-3-yl]oxy)acetamide (48 mg, 1.0 equiv), DIEA (0.5 mL), DMSO (3 mL). The resulting solution was stirred for 3 h at 100° C. The crude product was purified by Flash-Prep-HPLC with the following conditions: Column, C18 silica gel; mobile phase, acetonitrile/water (10 mmol/L $NH_4HCO_3$)=0 increasing to acetonitrile/water (10 mmol/L $NH_4HCO_3$)=60 within 30 min; Detector, 254 nm. This resulted in 50 mg (49%) of 2-([6-[(5-chloro-2-[4-[(1r,3r)-3-[4-[2-(2,6-dioxopiperidin-3-yl)-1,3-dioxoisoindol-4-yl]piperidin-1-yl]cyclobutoxy]piperidin-1-yl]pyrimidin-4-yl)amino]-1-isopropyl-2-oxoquinolin-3-yl]oxy)-N-methyl acetamide as a solid. $^1$H NMR (300 MHz, DMSO-$d_6$, ppm) 610.15 (s, 1H), 8.87 (s, 1H), 8.03 (m, 3H), 7.68-8.03 (m, 5H), 7.03 (s, 1H), 5.11-5.18 (m, 1H), 4.54 (s, 2H), 4.01-4.35 (m, 3H), 2.49-3.13 (m, 10H), 2.26-2.27 (m, 3H), 1.78-2.49 (m, 6H), 1.55-1.78 (m, 8H), 1.45-1.48 (m, 6H), 1.27-1.47 (m, 2H). MS (ES+): m/z 894.25 [MH$^+$].

Exemplary Synthesis of 2-[[6-([5-chloro-2-[4-([1-[2-(2,6-dioxopiperidin-3-yl)-1-oxo-3H-isoindol-4-yl]piperidin-4-yl]methyl)piperazin-1-yl]pyrimidin-4-yl]amino)-1-isopropyl-2-oxoquinolin-3-yl]oxy]-N-methylacetamide (Exemplary Compound 423)

Step 1: Synthesis of tert-butyl 4-([1-[2-(2,6-dioxopiperidin-3-yl)-1-oxo-3H-isoindol-4-yl]piperidin-4-yl]methyl)piperazine-1-carboxylate

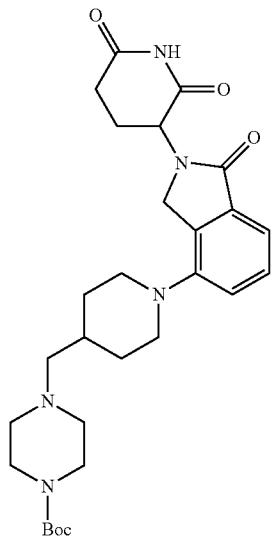 [SMILES: CC(C)(C)OC(=O)N1CCN(CC2CCN(c3cccc4c3CN(C3CCC(=O)NC3=O)C4=O)CC2)CC1]

Into a 20-mL sealed tube purged and maintained with an inert atmosphere of nitrogen, was placed tert-butyl 4-(piperidin-4-ylmethyl)piperazine-1-carboxylate (407 mg, 1.2 equiv), 3-(7-bromo-1-oxo-3H-isoindol-2-yl)piperidine-2,6-dione (386 mg, 1.00 equiv), $Cs_2CO_3$ (782 mg, 2.0 equiv), Pd-PEPPSI-IPentCl 2-methylpyridine (o-picoline (50 mg, 0.05 equiv), DMF (5 mL). The resulting solution was stirred for overnight at 80° C. in an oil bath. The solids were filtered out. The crude product was purified by Flash-Prep-HPLC with the following conditions: Column, $C_{18}$ silica gel; mobile phase, ACN/water (5 mM $NH_4HCO_3$)=0/100 increasing to ACN/water (5 mM $NH_4HCO_3$)=60/40 within 30 min. Product was obtained and concentrated under vacuum. This resulted in 215 mg (34.24%) of tert-butyl 4-([1-[2-(2,6-dioxopiperidin-3-yl)-1-oxo-3H-isoindol-4-yl]piperidin-4-yl]methyl)piperazine-1-carboxylate as a white solid Step 2: Synthesis of 3-[1-oxo-4-[4-(piperazin-1-ylmethyl)piperidin-1-yl]-3H-isoindol-2-yl]piperidine-2,6-dione

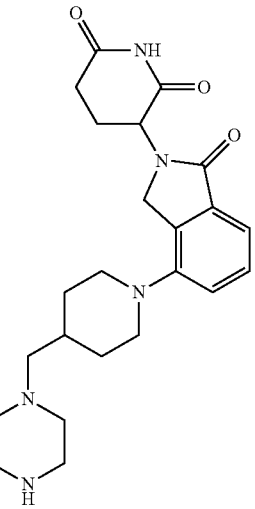

Into a 50-mL round-bottom flask, was placed tert-butyl 4-([1-[2-(2,6-dioxopiperidin-3-yl)-1-oxo-3H-isoindol-4-yl]piperidin-4-yl]methyl)piperazine-1-carboxylate (215.00 mg), DCM (5.00 mL), trifluoroacetaldehyde (1.00 mL). The resulting solution was stirred for 2 h at room temperature. The resulting mixture was concentrated under vacuum. This resulted in 240 mg of 3-[1-oxo-4-[4-(piperazin-1-ylmethyl)piperidin-1-yl]-3H-isoindol-2-yl]piperidine-2,6-dione as yellow oil.

Step 3: Synthesis of 2-[[6-([5-chloro-2-[4-([1-[2-(2,6-dioxopiperidin-3-yl)-1-oxo-3H-isoindol-4-yl]piperidin-4-yl]methyl)piperazin-1-yl]pyrimidin-4-yl]amino)-1-isopropyl-2-oxoquinolin-3-yl]oxy]-N-methylacetamide

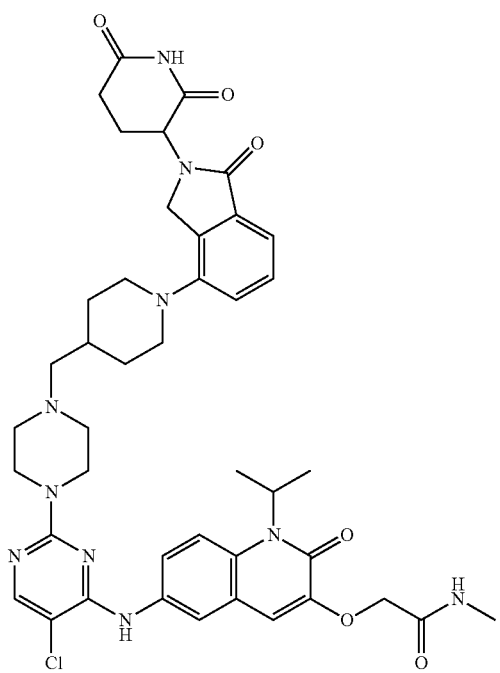 [SMILES: CNC(=O)COc1cc2cc(Nc3nc(N4CCN(CC5CCN(c6cccc7c6CN(C6CCC(=O)NC6=O)C7=O)CC5)CC4)ncc3Cl)ccc2n(C(C)C)c1=O]

Into a 10-mL sealed tube purged and maintained with an inert atmosphere of nitrogen, was placed 3-[1-oxo-4-[4-(piperazin-1-ylmethyl)piperidin-1-yl]-3H-isoindol-2-yl]piperidine-2,6-dione (170.00 mg, 2.0 equiv), 2-([6-[(2,5-dichloropyrimidin-4-yl)amino]-1-isopropyl-2-oxoquinolin-3-yl]oxy)-N-methylacetamide (87.00 mg, 1.0 equiv), DMSO (3 mL), DIEA (1 mL). The resulting solution was stirred for 2 h at 100° C. in an oil bath. The crude product was purified by Flash-Prep-HPLC with the following conditions: Column, C18 silica gel; mobile phase, ACN/water (5 mM NH$_4$HCO$_3$)=0/100 increasing to ACN/water (5 mM NH$_4$HCO$_3$)=60/40 within 30 min. This resulted in 69 mg of 2-[[6-([5-chloro-2-[4-([1-[2-(2,6-dioxopiperidin-3-yl)-1-oxo-3H-isoindol-4-yl]piperidin-4-yl]methyl)piperazin-1-yl]pyrimidin-4-yl]amino)-1-isopropyl-2-oxoquinolin-3-yl]oxy]-N-methylacetamide as an off-white solid. $^1$H NMR (300 MHz, DMSO-d6) δ 10.98 (s, 1H), 8.85 (s, 1H), 8.06 (s, 1H), 7.97 (s, 2H), 7.71 (s, 2H), 7.44-7.41 (m, 1H), 7.30 (d, J=7.2 Hz, 1H), 7.16 (d, J=7.5 Hz, 1H), 7.05 (s, 1H), 5.32 (s, 1H), 5.15-5.11 (m, 1H), 4.56 (s, 2H), 4.44 (d, J=17.1 Hz, 1H), 4.30 (d, J=17.4 Hz, 1H), 3.66 (s, 4H), 3.39-3.33 (m, 2H), 2.98-2.83 (m, 1H), 2.79-2.72 (m, 2H), 2.75 (d, J=9.0 Hz, 4H), 2.69-2.63 (m, 1H), 2.47 (s, 4H), 2.08-1.99 (m, 1H), 1.88-1.83 (m, 3H), 1.58 (d, J=6.9 Hz, 6H), 1.38-1.16 (m, 2H). LC-MS (ES+): m/z 825.30 [MH+].

Exemplary Synthesis of 2-[[6-([5-chloro-2-[4-([2-[2-(2,6-dioxopiperidin-3-yl)-1,3-dioxoisoindol-5-yl]-2-azaspiro[3.5]nonan-7-yl]methyl)piperazin-1-yl]pyrimidin-4-yl]amino)-1-isopropyl-2-oxoquinolin-3-yl]oxy]-N-methylacetamide (Exemplary Compound 451)

Step 1: Synthesis of tert-butyl 7-[4-[(benzyloxy)carbonyl]piperazine-1-carbonyl]-2-azaspiro[3.5]nonane-2-carboxylate

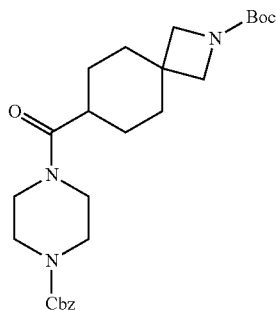 [SMILES: CC(C)(C)OC(=O)N1CC2(CCC(C(=O)N3CCN(C(=O)OCc4ccccc4)CC3)CC2)C1]

Into a 50-mL round-bottom flask purged and maintained with an inert atmosphere of nitrogen, was placed 2-(tert-butoxycarbonyl)-2-azaspiro[3.5]nonane-7-carboxylic acid (270 mg, 1.002 mmol, 1.00 equiv), DMF (5 mL), DIEA (0.5 mL), benzyl piperazine-1-carboxylate (220.81 mg, 1.000 mmol, 1.00 equiv), T$_3$P (1594.80 mL, 5.010 mmol, 5.00 equiv). The resulting solution was stirred for overnight at room temperature. The reaction was then quenched by the addition of 20 mL of water/ice. The resulting solution was extracted with dichloromethane (3×40 mL,) washed with brine (50 mL), dried over anhydrous sodium sulfate and concentrated under vacuum. The crude product was purified by Flash-Prep-HPLC with the following conditions: Column, C$_{18}$ silica gel; mobile phase, ACN/water (5 mM NH$_4$HCO$_3$)=0/100 increasing to ACN/water (5 mM NH$_4$HCO$_3$)=60/40 within 30 min. Product was obtained and concentrated under vacuum. This resulted in 244 mg (52%) of tert-butyl 7-[4-[(benzyloxy)carbonyl]piperazine-1-carbonyl]-2-azaspiro[3.5]nonane-2-carboxylate as a white solid.

Step 2: Synthesis of tert-butyl 7-([4-[(benzyloxy)carbonyl]piperazin-1-yl]methyl)-2-azaspiro[3.5]nonane-2-carboxylate

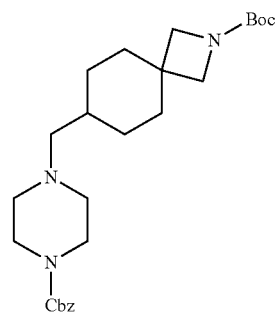 [SMILES: CC(C)(C)OC(=O)N1CC2(CCC(CN3CCN(C(=O)OCc4ccccc4)CC3)CC2)C1]

Into a 20-mL sealed tube purged and maintained with an inert atmosphere of nitrogen, was placed Zn(OAc)$_2$ (1099 mg, 5.988 mmol, 4.00 equiv), tetrahydrofuran (10 mL), triethoxysilane (984 mg, 5.988 mmol, 4.00 equiv), tert-butyl 7-[4-[(benzyloxy)carbonyl]piperazine-1-carbonyl]-2-azaspiro[3.5]nonane-2-carboxylate (706 mg, 1.497 mmol, 1.00 equiv). The resulting solution was stirred for overnight at 30° C. in an oil bath. The reaction was then quenched by the addition of 10 mL of 1M MeOH. The resulting solution was extracted with ethyl acetate (3×50 mL), washed with brine (50 mL), dried over anhydrous sodium sulfate and concentrated under vacuum. This resulted in 660 mg (96.34%) of tert-butyl 7-([4-[(benzyloxy)carbonyl]piperazin-1-yl]methyl)-2-azaspiro[3.5]nonane-2-carboxylate as a white solid.

Step 3: Synthesis of tert-butyl 7-(piperazin-1-ylmethyl)-2-azaspiro[3.5]nonane-2-carboxylate

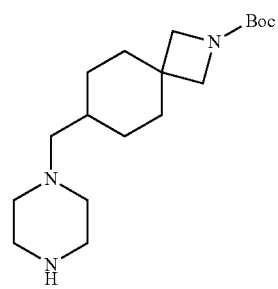 [SMILES: CC(C)(C)OC(=O)N1CC2(CCC(CN3CCNCC3)CC2)C1]

Into a 100-mL round-bottom flask, was placed tert-butyl 7-([4-[(benzyloxy)carbonyl]piperazin-1-yl]methyl)-2-azaspiro[3.5]nonane-2-carboxylate (660 mg, 1.442 mmol, 1.00 equiv), isopropyl alcohol (10.00 mL), Pd(OH)$_2$/C (300 mg) under nitrogen atmosphere The flask was then vacuumed and flushed with hydrogen. The reaction mixture was hydrogenated at 35° C. for 4 hours under hydrogen atmosphere using a hydrogen balloon, then filtered through a Celite pad and concentrated under reduced pressure. This resulted in 620 mg of tert-butyl 7-(piperazin-1-ylmethyl)-2-azaspiro[3.5]nonane-2-carboxylate as yellow oil.

Step 4: Synthesis of tert-butyl 7-([1-[5-chloro-4-([1-isopropyl-3-[(methylcarbamoyl)methoxy]-2-oxoquinolin-6-yl]amino)pyrimidin-2-yl]piperidin-4-yl]methyl)-2-azaspiro[3.5]nonane-2-carboxylate

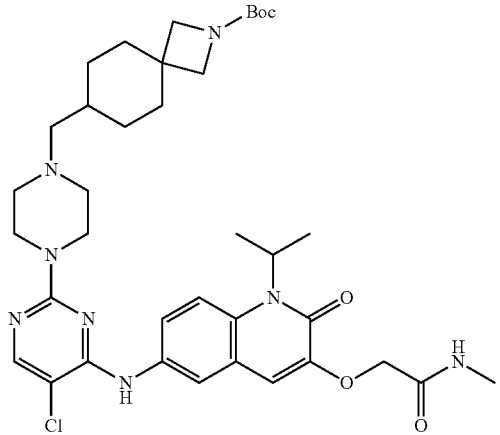 [SMILES: CNC(=O)COc1cc2cc(Nc3nc(N4CCN(CC5CCC6(CC5)CN(C(=O)OC(C)(C)C)C6)CC4)ncc3Cl)ccc2n(C(C)C)c1=O]

Into a 20-mL sealed tube purged and maintained with an inert atmosphere of nitrogen, was placed tert-butyl 7-(piperazin-1-ylmethyl)-2-azaspiro[3.5]nonane-2-carboxylate (600 mg, 1.855 mmol, 1.00 equiv), 2-([6-[(2,5-dichloropyrimidin-4-yl)amino]-1-isopropyl-2-oxoquinolin-3-yl]oxy)-N-methylacetamide (647 mg, 1.484 mmol, 0.80 equiv), DMSO (5 mL), DIEA (1 mL). The resulting solution was stirred for 4 h at 100° C. The crude product was purified by Flash-Prep-HPLC with the following conditions: Column, C18 silica gel; mobile phase, ACN/water (5 mM $NH_4HCO_3$)=0/100 increasing to ACN/water (5 mM $NH_4HCO_3$)=60/40 within 30 min. Product was obtained and concentrated under vacuum. This resulted in 820 mg (61%) of tert-butyl 7-([1-[5-chloro-4-([1-isopropyl-3-[(methylcarbamoyl)methoxy]-2-oxoquinolin-6-yl]amino)pyrimidin-2-yl]piperidin-4-yl]methyl)-2-azaspiro[3.5]nonane-2-carboxylate as a yellow solid.

Step 5: Synthesis of 2-[(6-[[2-(4-[2-azaspiro[3.5]nonan-7-ylmethyl]piperidin-1-yl)-5-chloropyrimidin-4-yl]amino]-1-isopropyl-2-oxoquinolin-3-yl)oxy]-N-methylacetamide

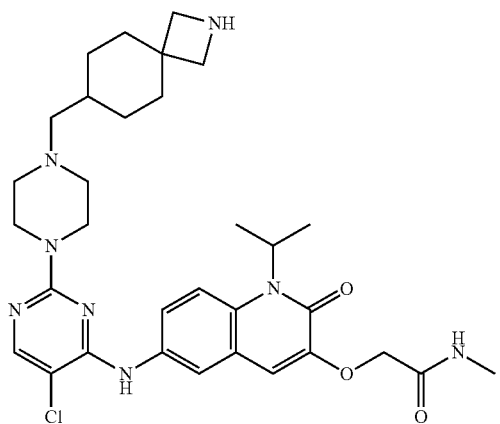 [SMILES: CNC(=O)COc1cc2cc(Nc3nc(N4CCN(CC5CCC6(CC5)CNC6)CC4)ncc3Cl)ccc2n(C(C)C)c1=O]

Into a 100-mL round-bottom flask, was placed tert-butyl 7-([1-[5-chloro-4-([1-isopropyl-3-[(methylcarbamoyl)methoxy]-2-oxoquinolin-6-yl]amino)pyrimidin-2-yl]piperidin-4-yl]methyl)-2-azaspiro[3.5]nonane-2-carboxylate (360 mg, 0.498 mmol, 1.00 equiv), DCM (10 mL), TFA (3 mL). The resulting solution was stirred for 1 h at room temperature. The resulting mixture was concentrated under vacuum. This resulted in 400 mg (crude) of 2-[(6-[[2-(4-[2-azaspiro[3.5]nonan-7-ylmethyl]piperidin-1-yl)-5-chloropyrimidin-4-yl]amino]-1-isopropyl-2-oxoquinolin-3-yl)oxy]-N-methylacetamide as yellow oil.

Step 6: Synthesis of 2-[[6-([5-chloro-2-[4-([2-[2-(2,6-dioxopiperidin-3-yl)-1,3-dioxoisoindol-5-yl]-2-azaspiro[3.5]nonan-7-yl]methyl)piperazin-1-yl]pyrimidin-4-yl]amino)-1-isopropyl-2-oxoquinolin-3-yl]oxy]-N-methylacetamide

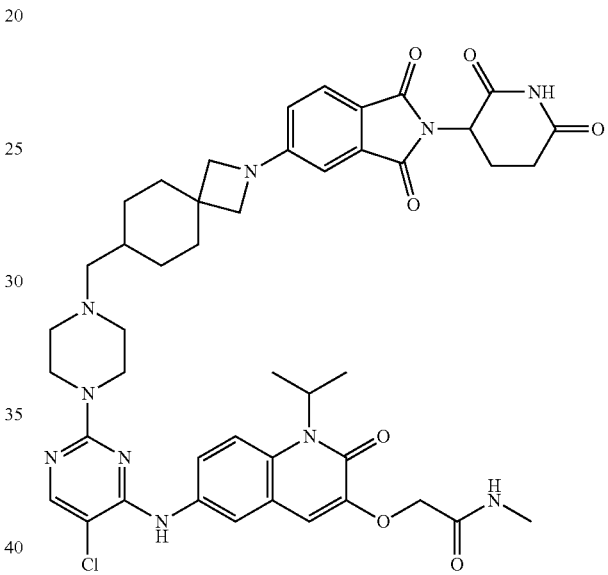

Into a 10-mL sealed tube purged and maintained with an inert atmosphere of nitrogen, was placed 2-[(6-[[2-(4-[2-azaspiro[3.5]nonan-7-ylmethyl]piperidin-1-yl)-5-chloropyrimidin-4-yl]amino]-1-isopropyl-2-oxoquinolin-3-yl)oxy]-N-methylacetamide (155 mg, 0.249 mmol, 1.00 equiv), 2-(2,6-dioxopiperidin-3-yl)-5-fluoroisoindole-1,3-dione (68.81 mg, 0.249 mmol, 1.00 equiv), DMSO (5 mL), DIEA (0.5 mL). The resulting solution was stirred for 2 h at 100° C. in an oil bath. The crude product was purified by Flash-Prep-HPLC with the following conditions: Column, $C_{18}$ silica gel; mobile phase, ACN/water (5 mM $NH_4HCO_3$)=0/100 increasing to ACN/water (5 mM $NH_4HCO_3$)=60/40 within 30 min. Product was obtained and concentrated under vacuum. This resulted in 67.4 mg (31%) of 2-[[6-([5-chloro-2-[4-([2-[2-(2,6-dioxopiperidin-3-yl)-1,3-dioxoisoindol-5-yl]-2-azaspiro[3.5]nonan-7-yl]methyl)piperazin-1-yl]pyrimidin-4-yl]amino)-1-isopropyl-2-oxoquinolin-3-yl]oxy]-N-methylacetamide as a yellow solid. $^1$H NMR (300 MHz, DMSO-d6) δ 11.08 (s, 1H), 8.85 (s, 1H), 8.03 (d, J=31.8, 3H), 7.71-7.62 (m, 3H), 7.04 (s, 1H), 6.77 (s, 1H), 6.65-6.62 (m, 1H), 5.35 (s, 1H), 5.09-5.05 (m, 1H), 4.56 (s, 1H), 3.74-3.65 (m, 8H), 2.89-2.85 (m, 1H), 2.69 (s, 4H), 2.38 (s, 4H), 2.12-1.88 (m, 5H), 1.72 (s, 2H), 1.59-1.40 (m, 10H), 1.05-0.88 (m, 2H). MS (ES$^+$): m/z 879.25 [MH$^+$].

Exemplary Synthesis of 2-[[6-([5-chloro-2-[4-([2-[2-(2,6-dioxopiperidin-3-yl)-1,3-dioxoisoindol-4-yl]-2-azaspiro[3.5]nonan-7-yl]methyl)piperazin-1-yl]pyrimidin-4-yl]amino)-1-isopropyl-2-oxoquinolin-3-yl]oxy]-N-methylacetamide (Exemplary Compound 452)

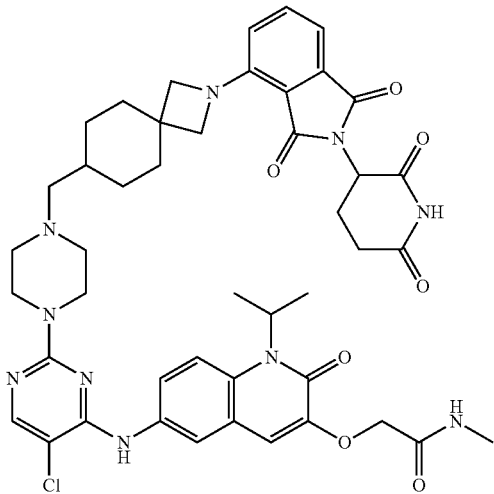 [SMILES: CNC(=O)COc1cc2cc(Nc3nc(N4CCN(CC5CCC6(CC5)CN(c5cccc7c5C(=O)N(C5CCC(=O)NC5=O)C7=O)C6)CC4)ncc3Cl)ccc2n(C(C)C)c1=O]

Into a 10-mL sealed tube purged and maintained with an inert atmosphere of nitrogen, was placed 2-[(6-[[2-(4-[2-azaspiro[3.5]nonan-7-ylmethyl]piperidin-1-yl)-5-chloropyrimidin-4-yl]amino]-1-isopropyl-2-oxoquinolin-3-yl)oxy]-N-methylacetamide (155 mg, 0.249 mmol, 1.00 equiv), 2-(2,6-dioxopiperidin-3-yl)-4-fluoroisoindole-1,3-dione (68.81 mg, 0.249 mmol, 1.00 equiv), DMSO (5 mL), DIEA (0.5 mL). The resulting solution was stirred for 2 h at 100° C. The crude product was purified by Flash-Prep-HPLC with the following conditions: Column, $C_{18}$ silica gel; mobile phase, ACN/water (5 mM $NH_4HCO_3$)=0/100 increasing to ACN/water (5 mM $NH_4HCO_3$)=60/40 within 30 min. Product was obtained and concentrated under vacuum. This resulted in 66 mg (30%) of 2-[[6-([5-chloro-2-[4-([2-[2-(2,6-dioxopiperidin-3-yl)-1,3-dioxoisoindol-4-yl]-2-azaspiro[3.5]nonan-7-yl]methyl)piperazin-1-yl]pyrimidin-4-yl]amino)-1-isopropyl-2-oxoquinolin-3-yl]oxy]-N-methylacetamide as a yellow solid.

1H NMR (300 MHz, DMSO-d6) δ 11.08 (s, 1H), 8.84 (s, 1H), 8.01 (d, J=25.2, 3H), 7.74-7.67 (m, 2H), 7.57-7.51 (m, 1H), 7.10-7.04 (m, 2H), 6.76 (d, J=8.4, 1H), 5.35 (s, 1H), 5.08-5.02 (m, 1H), 4.57 (s, 2H), 3.90-3.84 (m, 4H), 3.74-3.65 (m, 8H), 3.64 (s, 4H), 2.90-2.82 (m, 1H), 2.69-2.51 (m, 5H), 2.36 (s, 4H), 2.12-1.70 (m, 7H), 1.70-1.43 (m, 9H), 0.97-0.90 (m, 2H). LC-MS (ES$^+$): m/z 879.30 [MH$^+$].

Exemplary Synthesis of 2-[(6-[[5-chloro-2-(4-[[(3R,5S)-5-([[2-(2,6-dioxopiperidin-3-yl)-1,3-dioxoisoindol-5-yl]oxy]methyl)-1-methylpyrrolidin-3-yl]oxy]piperidin-1-yl)pyrimidin-4-yl]amino]-1-isopropyl-2-oxoquinolin-3-yl)oxy]-N-methylacetamide (Exemplary Compound 463)

Step 1: Synthesis of 1-tert-butyl 2-methyl (2S,4R)-4-(pyridin-4-yloxy)pyrrolidine-1,2-dicarboxylate

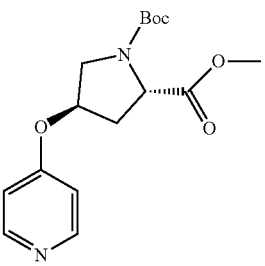 [SMILES: COC(=O)[C@@H]1C[C@@H](Oc2ccncc2)CN1C(=O)OC(C)(C)C]

Into a 250-mL round-bottom flask purged and maintained with an inert atmosphere of nitrogen, was placed 1-tert-butyl 2-methyl (2S,4S)-4-hydroxypyrrolidine-1,2-dicarboxylate (20 g, 81.5 mmol), Toluene (120 mL), 4-hydroxypyridine (9.31 g, 97.9 mmol), PPh$_3$ (32.08 g, 122.3 mmol), DIAD (24.73 g, 122.3 mmol). The resulting solution was stirred for 3 hr at 100° C. The reaction was quenched by the addition of 100 mL of water and extracted with 3×150 mL of ethyl acetate. The combined organic layers were washed with 200 ml of brine, dried over anhydrous sodium sulfate and concentrated under vacuum. The residue was applied onto a silica gel column with ethyl acetate/petroleum ether (1:3). This resulted in 17 g (65%) of 1-tert-butyl 2-methyl (2S,4R)-4-(pyridin-4-yloxy)pyrrolidine-1,2-dicarboxylate as white oil. MS (ES+): m/z 323.1 [MH+].

Step 2: Synthesis of 1-benzyl-4-[[(3R,5S)-1-(tert-butoxycarbonyl)-5-(methoxycarbonyl)pyrrolidin-3-yl]oxy]pyridin-1-ium

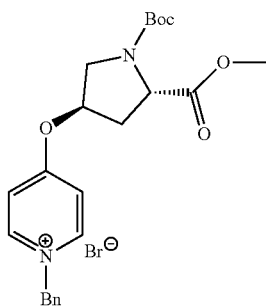 [SMILES: COC(=O)[C@@H]1C[C@@H](Oc2cc[n+](Cc3ccccc3)cc2)CN1C(=O)OC(C)(C)C ; [Br-]]

Into a 500-mL round-bottom flask, was placed 1-tert-butyl 2-methyl (2S,4R)-4-(pyridin-4-yloxy)pyrrolidine-1,2-dicarboxylate (15.00 g, 46.5 mmol), DCM (200 mL) and benzyl bromide (9.55 g, 55.8 mmol). The resulting solution was stirred for 3 hr at room temperature then quenched by the addition of 200 mL of water. The resulting mixture was extracted with 3×150 mL of dichloromethane and the combined organic layers were washed with 200 ml of brine, dried over anhydrous sodium sulfate and concentrated under vacuum. The residue was applied onto a silica gel column with dichloromethane/methanol (10:1). This resulted in 10.2 g (53%) of 1-benzyl-4-[[(3R,5S)-1-(tert-butoxycarbonyl)-5-(methoxycarbonyl)pyrrolidin-3-yl]oxy]pyridin-1-ium as an off-white solid. MS (ES+): m/z 413.2 [MH].

Step 3: Synthesis of -tert-butyl 2-methyl (2S,4R)-4-[(1-benzyl-3,6-dihydro-2H-pyridin-4-yl)oxy]pyrrolidine-1,2-dicarboxylate

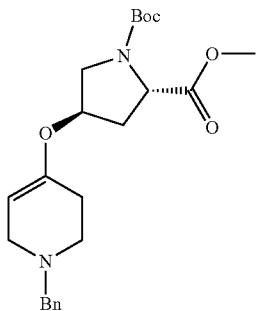 [SMILES: COC(=O)[C@@H]1C[C@@H](OC2=CCN(Cc3ccccc3)CC2)CN1C(=O)OC(C)(C)C]

Sodium borohydride (0.98 g, 26.6 mmol) was added to a solution of 1-benzyl-4-[[(3R,5S)-1-(tert-butoxycarbonyl)-5-(methoxycarbonyl)pyrrolidin-3-yl]oxy]pyridin-1-ium (10 g, 24.2 mmol) in MeOH (120 mL). The resulting solution was stirred for 2 hr at room temperature then quenched by the addition of 100 mL of water. The pH value of the solution was adjusted to 7-8 with NH₄Cl. The resulting solution was extracted with 2×150 mL of dichloromethane and the combined organic layers were washed with 200 ml of brine, dried over anhydrous sodium sulfate, filtered and concentrated in vacuo. The residue was applied onto a silica gel column with ethyl acetate/petroleum ether (1:2). This resulted in 6.1 g (61%) of 1-tert-butyl 2-methyl (2S,4R)-4-[(1-benzyl-3,6-dihydro-2H-pyridin-4-yl)oxy]pyrrolidine-1,2-dicarboxylate as off-white oil. MS (ES+): m/z 417.1 [MH+].

Step 4: Synthesis of [(2S,4R)-4-[(1-benzyl-3,6-dihydro-2H-pyridin-4-yl)oxy]-1-methylpyrrolidin-2-yl]methanol

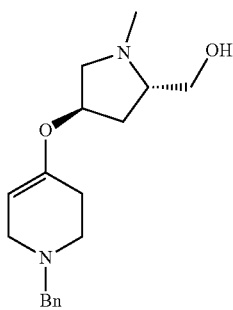 [SMILES: CN1C[C@H](OC2=CCN(Cc3ccccc3)CC2)C[C@H]1CO]

Lithium aluminum hydride (2.77 g, 75 mmol) was added to a solution of 1-tert-butyl 2-methyl (2S,4R)-4-[(1-benzyl-3,6-dihydro-2H-pyridin-4-yl)oxy]pyrrolidine-1,2-dicarboxylate (5.20 g, 12.484 mmol, 1.00 equiv) in THF (100 mL, 1234.299 mmol). The resulting mixture was stirred for 2 hr at 65° C. in an oil bath. The reaction was then quenched by the addition of 3 mL of water. The pH value of the solution was adjusted to 7-8 with NaOH (6 mol/L). The solids were filtered out. The resulting mixture was concentrated under vacuum. This resulted in 3.1 g (82%) of [(2S,4R)-4-[(1-benzyl-3,6-dihydro-2H-pyridin-4-yl)oxy]-1-methylpyrrolidin-2-yl]methanol as off-white oil. MS (ES+): m/z 303.0 [MH+].

Step 5: Synthesis of [(2S,4R)-1-methyl-4-(piperidin-4-yloxy)pyrrolidin-2-yl]methanol

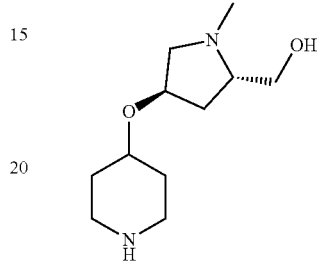

To a solution of [(2S,4R)-4-[(1-benzyl-3,6-dihydro-2H-pyridin-4-yl)oxy]-1-methylpyrrolidin-2-yl]methanol (3 g) in 100 mL MeOH was added Pd/C (10%, 500 mg) under nitrogen atmosphere. The flask was evacuated and flushed with hydrogen. The reaction mixture stirred for 5 hours and then filtered through a Celite pad and concentrated under reduced pressure to afford 1.8 g (85%) of [(2S,4R)-1-methyl-4-(piperidin-4-yloxy)pyrrolidin-2-yl]methanol as off-white oil. MS (ES+): m/z 215.0 [MH+].

Step 6: Synthesis of tert-butyl 4-[[(3R,5S)-5-(hydroxymethyl)-1-methylpyrrolidin-3-yl]oxy]piperidine-1-carboxylate

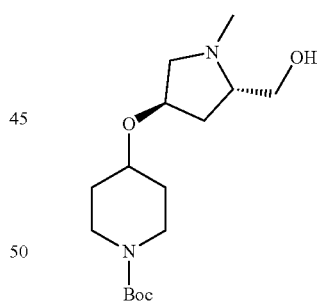

A mixture of [(2S,4R)-1-methyl-4-(piperidin-4-yloxy)pyrrolidin-2-yl]methanol (1.50 g, 6.999 mmol, 1.00 equiv), di-tert-butyl dicarbonate (1.83 g, 8.385 mmol, 1.20 equiv), sodium carbonate (1.50 g, 13.998 mmol, 2 equiv), THF (30 mL) and H₂O (10 mL) was stirred for 2 hr at room temperature. The mixture was diluted with 30 mL of water and extracted with 3×50 mL of ethyl acetate. The combined organic were washed with 100 ml of brine, dried over anhydrous sodium sulfate, filtered and concentrated in vacuo. The residue was applied onto a silica gel column with ethyl acetate/petroleum ether (1:2). This resulted in 1.2 g (54%) of tert-butyl 4-[[(3R,5S)-5-(hydroxymethyl)-1-methylpyrrolidin-3-yl]oxy]piperidine-1-carboxylate as a off-white solid. MS (ES+): m/z 315.2 [MH+].

789

Step 7: Synthesis of dimethyl 4-(((2S,4R)-4-((1-(tert-butoxycarbonyl)piperidin-4-yl)oxy)-1-methylpyrrolidin-2-yl)methoxy)phthalate and dimethyl 4-(((3R,5R)-5-((1-(tert-butoxycarbonyl)piperidin-4-yl)oxy)-1-methylpiperidin-3-yl)oxy)phthalate

790

Step 8: Synthesis of 4-(((2S,4R)-4-((1-(tert-butoxycarbonyl)piperidin-4-yl)oxy)-1-methylpyrrolidin-2-yl)methoxy)phthalic acid and 4-(((3R,5R)-5-((1-(tert-butoxycarbonyl)piperidin-4-yl)oxy)-1-methylpiperidin-3-yl)oxy)phthalic acid

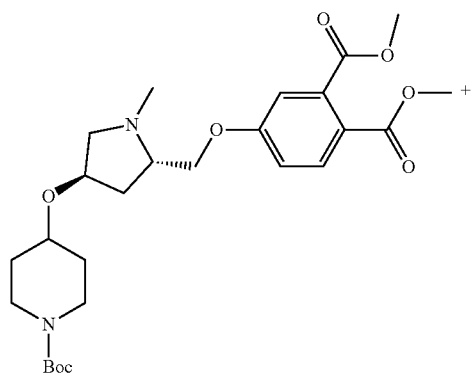

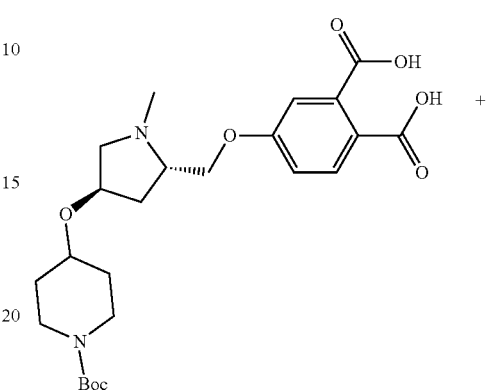

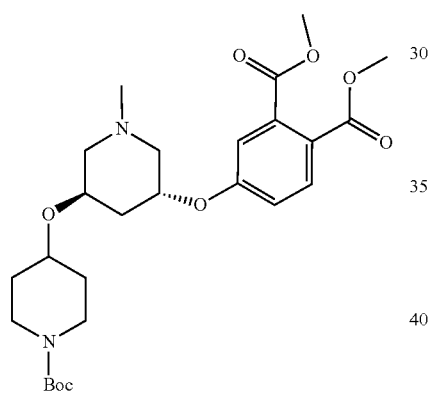

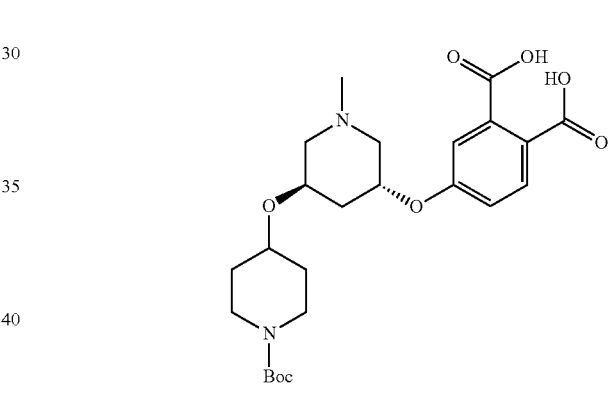

A mixture of tert-butyl 4-[[(3R,5S)-5-(hydroxymethyl)-1-methylpyrrolidin-3-yl]oxy]piperidine-1-carboxylate (1 g, 3.2 mmol), 1,2-dimethyl 4-hydroxyphthalate (0.8 g, 3.8 mmol), PPh$_3$ (1.25 g, 4.8 mmol), DIAD (0.96 g, 4.8 mmol) in 30 mL toluene was stirred for 3 hr at 100° C. in an oil bath. The reaction diluted with 30 mL of water and extracted with 3×50 mL of ethyl acetate. The combined organic layers were washed with 70 ml of brine, dried over anhydrous sodium sulfate, filtered and concentrated in vacuo. The residue was applied onto a silica gel column with ethyl acetate/petroleum ether (1:2). This resulted in 850 mg (53%) of a mixture of the title products as a light yellow solid. MS (ES+): m/z 507.3 [MH+].

The mixture from the previous step (850 mg, 1.678 mmol) was dissolved in MeOH (10 mL) and treated with a solution of LiOH (80 mg, 3.356 mmol) in H$_2$O (3 mL). The resulting solution was stirred for 2 hr at room temperature then diluted with 20 mL of water. The pH value of the solution was adjusted to 5-6 with HCl (1 mol/L). The solids were removed by filtration and the solution was concentrated in vacuo to afford a mixture of the two title products as 745 mg of an off white solid. MS (ES+): m/z 479.05 [MH+].

Step 9: Synthesis of tert-butyl 4-(((3R,5S)-5-(((2-(2,6-dioxopiperidin-3-yl)-1,3-dioxoisoindolin-5-yl)oxy)methyl)-1-methylpyrrolidin-3-yl)oxy)piperidine-1-carboxylate and tert-butyl 4-(((3R,5R)-5-((2-(2,6-dioxopiperidin-3-yl)-1,3-dioxoisoindolin-5-yl)oxy)-1-methylpiperidin-3-yl)oxy)piperidine-1-carboxylate

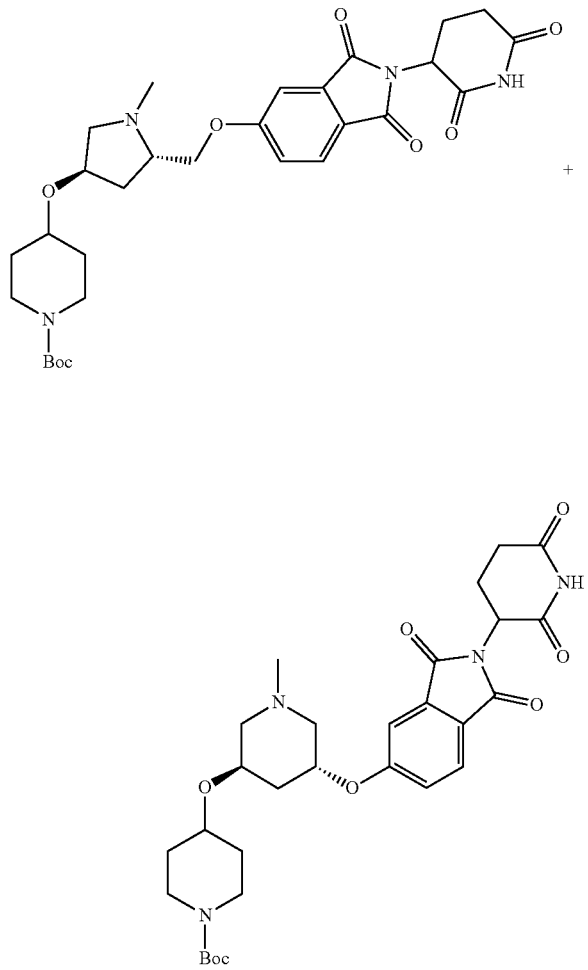

The product mixture from the previous step (382 mg, 2.320 mmol) in Pyridine (10 mL) was treated with 3-aminopiperidine-2,6-dione hydrochloride (1.5 g, 9.2 mmol). The resulting solution was stirred for 5 hr at 110° C. in an oil bath. The reaction was diluted with 20 mL of water and extracted with 3×30 mL of dichloromethane. The combined organic layers were washed with 50 ml of brine, dried over anhydrous sodium sulfate, filtered and concentrated under reduced pressure. The residue was applied onto a silica gel column with dichloromethane/methanol (1:1). The mixture was purified by Pre-HPLC: Column: XSelect CSH Prep C18 OBD Column, 5 um, 19*150 mm; Mobile Phase A: Water (10 mmol/L NH4HCO3), Mobile Phase B: ACN; Flow rate: 25 mL/min; Gradient: 45% B to 80% B in 10 min; This resulted in 180 mg of tert-butyl 4-[[(3R,5S)-5-([[2-(2,6-dioxopiperidin-3-yl)-1,3-dioxoisoindol-5-yl]oxy]methyl)-1-methylpyrrolidin-3-yl]oxy]piperidine-1-carboxylate as an off-white solid and 210 mg of tert-butyl 4-((3R,5R)-5-(2-(2,6-dioxopiperidin-3-yl)-1,3-dioxoisoindolin-5-yloxy)-1-methylpiperidin-3-yloxy)piperidine-1-carboxylate. MS (ES+): m/z 571.1 [MH+].

Step 10: Synthesis of 2-(2,6-dioxopiperidin-3-yl)-5-[[(2S,4R)-1-methyl-4-(piperidin-4-yloxy)pyrrolidin-2-yl]methoxy]isoindole-1,3-dione trifluoroacetate

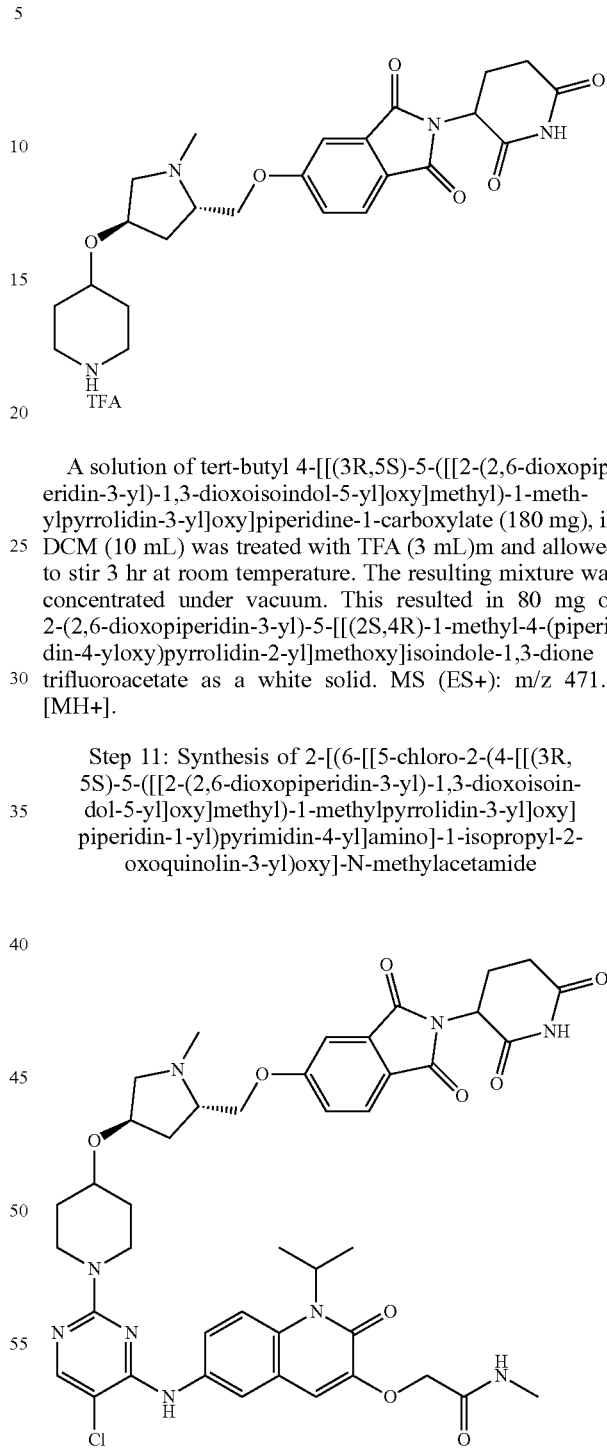

A solution of tert-butyl 4-[[(3R,5S)-5-([[2-(2,6-dioxopiperidin-3-yl)-1,3-dioxoisoindol-5-yl]oxy]methyl)-1-methylpyrrolidin-3-yl]oxy]piperidine-1-carboxylate (180 mg), in DCM (10 mL) was treated with TFA (3 mL)m and allowed to stir 3 hr at room temperature. The resulting mixture was concentrated under vacuum. This resulted in 80 mg of 2-(2,6-dioxopiperidin-3-yl)-5-[[(2S,4R)-1-methyl-4-(piperidin-4-yloxy)pyrrolidin-2-yl]methoxy]isoindole-1,3-dione trifluoroacetate as a white solid. MS (ES+): m/z 471.1 [MH+].

Step 11: Synthesis of 2-[(6-[[5-chloro-2-(4-[[(3R,5S)-5-([[2-(2,6-dioxopiperidin-3-yl)-1,3-dioxoisoindol-5-yl]oxy]methyl)-1-methylpyrrolidin-3-yl]oxy]piperidin-1-yl)pyrimidin-4-yl]amino]-1-isopropyl-2-oxoquinolin-3-yl)oxy]-N-methylacetamide

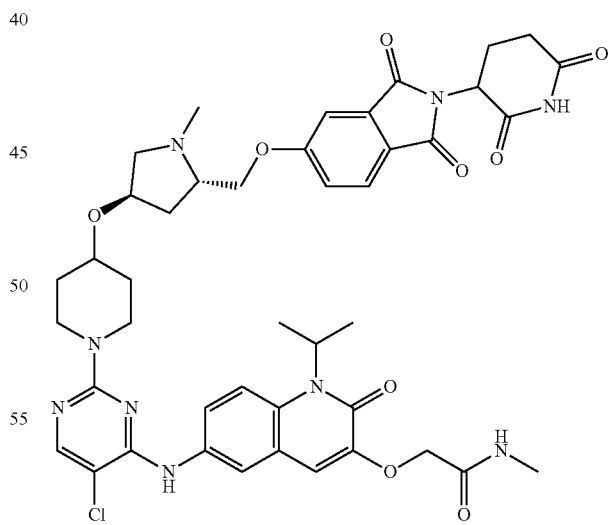

A mixture of 2-(2,6-dioxopiperidin-3-yl)-5-[[(2S,4R)-1-methyl-4-(piperidin-4-yloxy)pyrrolidin-2-yl]methoxy]isoindole-1,3-dione (100 mg, 0.21 mmol.), DMSO (5 mL), 2-([6-[(2,5-dichloropyrimidin-4-yl)amino]-1-isopropyl-2-oxoquinolin-3-yl]oxy)-N-methylacetamide (74.18 mg, 0.170 mmol) and DIEA (0.5 mL) in a 10-mL sealed tube was purged with nitrogen, sealed and stirred for 3 hr at 100° C.

in an oil bath. The reaction was diluted with 20 mL of water and extracted with 2×30 mL of ethyl acetate. The combined organic layers were washed with 50 ml of brine, dried over anhydrous sodium sulfate, filtered and concentrated in vacuo. The residue was applied onto a silica gel column with dichloromethane/methanol (10:1). This resulted in 43.7 mg (24%) of 2-[(6-[[5-chloro-2-(4-[[(3R,5S)-5-([[2-(2,6-dioxopiperidin-3-yl)-1,3-dioxoisoindol-5-yl]oxy]methyl)-1-methylpyrrolidin-3-yl]oxy]piperidin-1-yl)pyrimidin-4-yl]amino]-1-isopropyl-2-oxoquinolin-3-yl)oxy]-N-methylacetamide as a white solid. $^1$H NMR (300 MHz, DMSO-d$_6$) δ 11.11 (s, 1H), 8.82 (s, 1H), 8.03-7.94 (m, 3H), 7.91 (s, 1H), 7.84-7.81 (m, 1H), 7.68 (s, 1H), 7.44 (s, 1H), 7.37-7.34 (m, 1H), 7.02 (s, 1H), 5.24-5.20 (b, 1H), 5.14-5.11 (m, 1H), 4.54 (s, 2H), 4.21-4.07 (m, 4H), 3.57-3.55 (m, 1H), 3.35-3.28 (m, 4H), 2.97-2.94 (m, 2H), 2.87-2.83 (m, 3H), 2.77-2.74 (m, 2H), 2.33 (s, 3H), 2.26-2.23 (m, 1H), 2.06-2.03 (m, 1H), 1.95-1.90 (m, 4H), 1.61-1.60 (m, 6H), 1.47-1.40 (m, 2H). MS (ES+): m/z 870.40/872.40 [MH+].

Exemplary Synthesis of 2-[(6-[[5-chloro-2-(4-[[(3R,5R)-5-[[2-(2,6-dioxopiperidin-3-yl)-1,3-dioxoisoindol-5-yl]oxy]-1-methylpiperidin-3-yl]oxy]piperidin-1-yl)pyrimidin-4-yl]amino]-1-isopropyl-2-oxoquinolin-3-yl)oxy]-N-methylacetamide
(Exemplary Compound 464)

Step 1: Synthesis of 2-(2,6-dioxopiperidin-3-yl)-5-[[(3R,5R)-1-methyl-5-(piperidin-4-yloxy)piperidin-3-yl]oxy]isoindole-1,3-dione trifluoroacetate

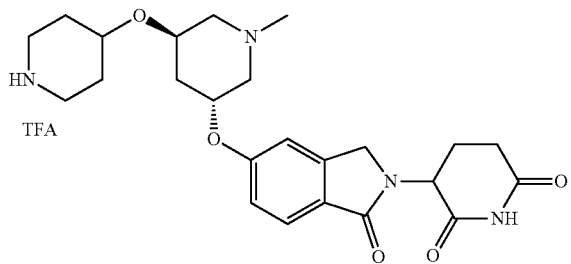 [SMILES: CN1C[C@H](Oc2ccc3c(c2)CN(C2CCC(=O)NC2=O)C3=O)C[C@@H](OC2CCNCC2)C1]

A solution of tert-butyl 4-[[(3R,5R)-5-[[2-(2,6-dioxopiperidin-3-yl)-1,3-dioxoisoindol-5-yl]oxy]-1-methylpiperidin-3-yl]oxy]piperidine-1-carboxylate (210 mg), in 10 mL DCM was treated with 3 mL TFA and allowed to stir for 3 hr at room temperature. The resulting mixture was concentrated under vacuum to afford 130 mg of 2-(2,6-dioxopiperidin-3-yl)-5-[[(3R,5R)-1-methyl-5-(piperidin-4-yloxy)piperidin-3-yl]oxy]isoindole-1,3-dione TFA salt as a light yellow solid. MS (ES+): m/z 471.1 [MH+].

Step 2: Synthesis 2-[(6-[[5-chloro-2-(4-[[(3R,5R)-5-[[2-(2,6-dioxopiperidin-3-yl)-1,3-dioxoisoindol-5-yl]oxy]-1-methylpiperidin-3-yl]oxy]piperidin-1-yl)pyrimidin-4-yl]amino]-1-isopropyl-2-oxoquinolin-3-yl)oxy]-N-methylacetamide

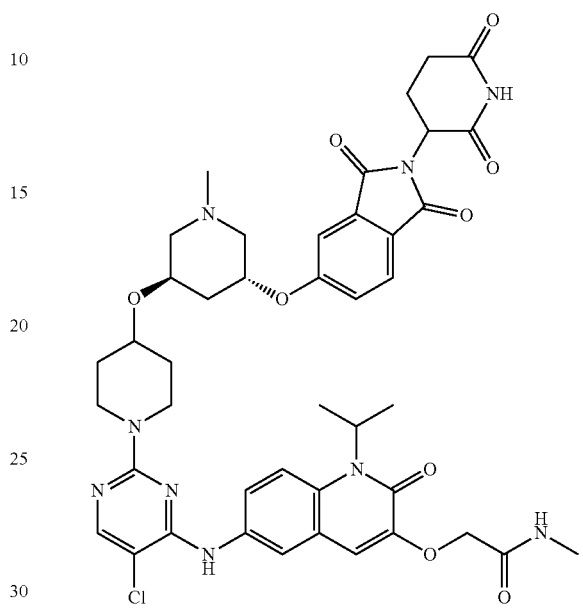

A mixture of 2-(2,6-dioxopiperidin-3-yl)-5-[[(3R,5R)-1-methyl-5-(piperidin-4-yloxy)piperidin-3-yl]oxy]isoindole-1,3-dione (80 mg, 0.170 mmol), DMSO (5 mL), 2-([6-[(2,5-dichloropyrimidin-4-yl)amino]-1-isopropyl-2-oxoquinolin-3-yl]oxy)-N-methylacetamide (59 mg, 0.136 mmol), and DIEA (0.5 mL) in a pressure tube was stirred for 3 hr at 100° C. under nitrogen. The reaction diluted with 20 mL of water and extracted with 2×30 mL of ethyl acetate. The combined organic layers were washed with 50 ml of brine, dried over anhydrous sodium sulfate, filtered and concentrated in vacuo. The residue was applied onto a silica gel column with dichloromethane/methanol (10:1). This resulted in 45.3 mg (31%) of 2-[(6-[[5-chloro-2-(4-[[(3R,5R)-5-[[2-(2,6-dioxopiperidin-3-yl)-1,3-dioxoisoindol-5-yl]oxy]-1-methylpiperidin-3-yl]oxy]piperidin-1-yl)pyrimidin-4-yl]amino]-1-isopropyl-2-oxoquinolin-3-yl)oxy]-N-methylacetamide as a white solid. $^1$H NMR (300 MHz, DMSO-d$_6$) δ 11.10 (s, 1H), 8.82 (s, 1H), 8.04 (s, 1H), 7.95 (s, 2H), 7.85-7.82 (m, 1H), 7.69 (s, 2H), 7.44-7.34 (m, 2H), 7.01 (s, 1H), 5.34-5.20 (b, 1H), 5.14-5.12 (m, 1H), 4.53 (s, 2H), 4.11-4.07 (m, 2H), 4.02-3.95 (m, 1H), 3.75-3.70 (m, 1H), 3.35-3.30 (m, 8H), 2.97-2.94 (m, 1H), 2.77-2.73 (m, 4H), 2.36-2.23 (m, 2H), 2.16-1.95 (m, 3H), 1.95-1.90 (m, 2H), 1.61-1.60 (m, 7H), 1.49-1.41 (m, 2H). MS (ES+): m/z 870.45/872.45 [MH+].

Exemplary Synthesis of 2-[[6-([5-chloro-2-[4-([2-[2-(2,6-dioxopiperidin-3-yl)-1,3-dioxoisoindol-5-yl]-2-azaspiro[3.5]nonan-7-yl]oxy)piperidin-1-yl]pyrimidin-4-yl]amino)-1-isopropyl-2-oxoquinolin-3-yl]oxy]-N-methylacetamide (Exemplary Compound 421)

Step 1: Synthesis of tert-butyl 7-(pyridin-4-yloxy)-2-azaspiro[3.5]nonane-2-carboxylate

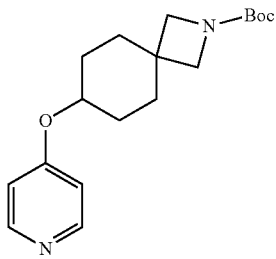 [SMILES: CC(C)(C)OC(=O)N1CC2(CCC(Oc3ccncc3)CC2)C1]

To a stirred solution of 4-hydroxypyridine (2 g, 20 mmol, 1.00 equiv, 95%) and tert-butyl 7-hydroxy-2-azaspiro[3.5]nonane-2-carboxylate (5.58 g, 22 mmol, 1.10 equiv) in THF (10 mL) was added PPh$_3$ (8.27 g, 30 mmol, 1.50 equiv) and DIAD (6.38 g, 30 mmol, 1.50 equiv) under nitrogen atmosphere. The resulting mixture was stirred for 16 h at 80° C. under a nitrogen atmosphere. The resulting mixture was concentrated under reduced pressure. The residue was purified by reverse flash chromatography with the following conditions: column, C18 silica gel; mobile phase, ACN in water, 10% to 50% gradient in 40 min; detector, UV 254 nm. This resulted in tert-butyl 7-(pyridin-4-yloxy)-2-azaspiro[3.5]nonane-2-carboxylate (1.5 g, 19%) as a white solid. MS (ES$^+$): m/z 319.2 [M+H$^+$].

Step 2: Synthesis of 1-benzyl-4-[[2-(tert-butoxycarbonyl)-2-azaspiro[3.5]nonan-7-yl]oxy]pyridin-1-ium

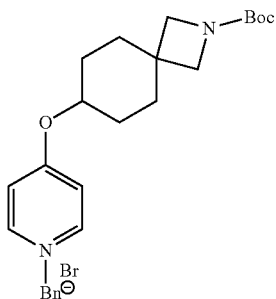

To a stirred solution of tert-butyl 7-(pyridin-4-yloxy)-2-azaspiro[3.5]nonane-2-carboxylate (1.50 g, 4.475 mmol, 1.00 equiv) in DCM (10 mL) was added BnBr (1.21 g, 6.721 mmol, 1.50 equiv). The resulting mixture was stirred for 3 h at room temperature. The resulting mixture was washed with 3×50 mL of PE. The precipitated solids were collected by filtration. This resulted in 1-benzyl-4-[[2-(tert-butoxycarbonyl)-2-azaspiro[3.5]nonan-7-yl]oxy]pyridin-1-ium (1.07 g, 27%) as a yellow solid. MS (ES$^+$): m/z 409.0 [M+H$^+$].

Step 3: Synthesis of tert-butyl 7-[(1-benzyl-3,6-dihydro-2H-pyridin-4-yl)oxy]-2-azaspiro[3.5]nonane-2-carboxylate

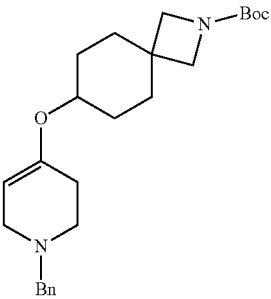 [SMILES: CC(C)(C)OC(=O)N1CC2(CCC(OC3=CCN(Cc4ccccc4)CC3)CC2)C1]

To a stirred solution of 1-benzyl-4-[[2-(tert-butoxycarbonyl)-2-azaspiro[3.5]nonan-7-yl]oxy]pyridin-1-ium bromide (1.00 g, 1.941 mmol, 1.00 equiv) in MeOH was added NaBH4 (0.12 g, 3.013 mmol, 1.55 equiv) The resulting mixture was stirred for 1 h at room temperature. The resulting mixture was concentrated under reduced pressure. The residue was purified by reverse flash chromatography with the following conditions: column, C18 silica gel; mobile phase, ACN in water, 10% to 50% gradient in 40 min; detector, UV 254 nm. This resulted in tert-butyl 7-[(1-benzyl-3,6-dihydro-2H-pyridin-4-yl)oxy]-2-azaspiro[3.5]nonane-2-carboxylate (702 mg, 79%) as a yellow solid. MS (ES$^+$): m/z 413.0 [M+H$^+$].

Step 4: Synthesis of tert-butyl 7-(piperidin-4-yloxy)-2-azaspiro[3.5]nonane-2-carboxylate

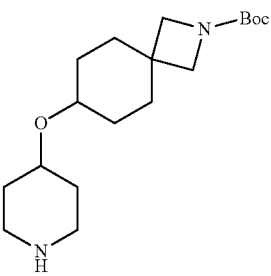 [SMILES: CC(C)(C)OC(=O)N1CC2(CCC(OC3CCNCC3)CC2)C1]

To a stirred solution of tert-butyl 7-[(1-benzyl-3,6-dihydro-2H-pyridin-4-yl)oxy]-2-azaspiro[3.5]nonane-2-carboxylate (702.00 mg, 1.612 mmol, 1.00 equiv) in MeOH was added Pd(OH)2/C (357 mg, 2.418 mmol, 1.50 equiv). The flask was then vacuumed and flushed with hydrogen. The reaction mixture was hydrogenated at room temperature for 3 hours under hydrogen atmosphere using a hydrogen balloon, then filtered through a Celite pad and concentrated under reduced pressure. This resulted in tert-butyl 7-(piperidin-4-yloxy)-2-azaspiro[3.5]nonane-2-carboxylate (605 mg, 92%) as a yellow solid. MS (ES$^+$): m/z 325.0 [M+H$^+$].

Step 5: Synthesis of tert-butyl 7-([1-[5-chloro-4-([1-isopropyl-3-[(methylcarbamoyl)methoxy]-2-oxoquinolin-6-yl]amino)pyrimidin-2-yl]piperidin-4-yl]oxy)-2-azaspiro[3.5]nonane-2-carboxylate

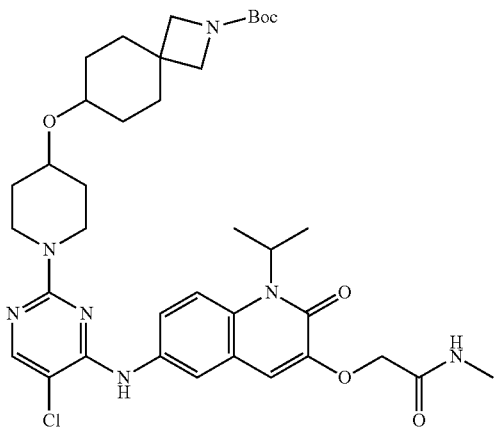 [SMILES: CNC(=O)COc1cc2cc(Nc3nc(N4CCC(OC5CCC6(CC5)CN(C(=O)OC(C)(C)C)C6)CC4)ncc3Cl)ccc2n(C(C)C)c1=O]

To a stirred solution of tert-butyl 7-(piperidin-4-yloxy)-2-azaspiro[3.5]nonane-2-carboxylate (600.00 mg, 1.757 mmol, 1.00 equiv, 95%) and 2-([6-[(2,5-dichloropyrimidin-4-yl)amino]-1-isopropyl-2-oxoquinolin-3-yl]oxy)-N-methylacetamide (645.43 mg, 1.405 mmol, 0.80 equiv) in DMSO (5 mL) was added DIEA (717 mg, 5.270 mmol, 3.00 equiv). The resulting mixture was stirred for 1 h at 100 degrees C. under nitrogen atmosphere. The residue was purified by reverse flash chromatography with the following conditions: column, C18 silica gel; mobile phase, ACN in water, 10% to 50% gradient in 30 min; detector, UV 254 nm. This resulted in tert-butyl 7-([1-[5-chloro-4-([1-isopropyl-3-[(methylcarbamoyl)methoxy]-2-oxoquinolin-6-yl]amino)pyrimidin-2-yl]piperidin-4-yl]oxy)-2-azaspiro[3.5]nonane-2-carboxylate (404 mg, 28%) as a yellow solid. MS (ES+): m/z 725.0 [M+H+].

Step 6: Synthesis of 2-[(6-[[2-(4-[2-azaspiro[3.5]nonan-7-yloxy]piperidin-1-yl)-5-chloropyrimidin-4-yl]amino]-1-isopropyl-2-oxoquinolin-3-yl)oxy]-N-methylacetamide

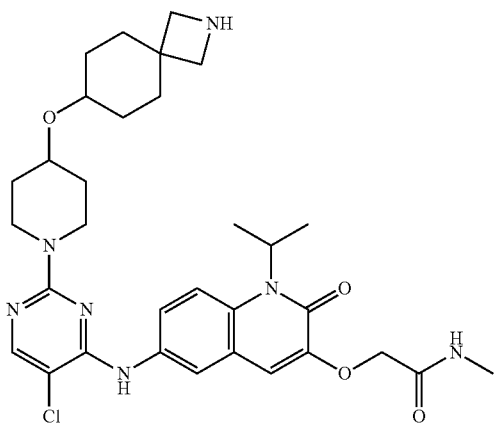

To a stirred solution of tert-butyl 7-([1-[5-chloro-4-([1-isopropyl-3-[(methylcarbamoyl)methoxy]-2-oxoquinolin-6-yl]amino)pyrimidin-2-yl]piperidin-4-yl]oxy)-2-azaspiro[3.5]nonane-2-carboxylate (400 mg, 0.525 mmol, 1.00 equiv) in DCM (20 mL) was added TFA (5 mL). The resulting mixture was stirred for 2 h at room temperature. The resulting mixture was concentrated under reduced pressure. This resulted in 2-[(6-[[2-(4-[2-azaspiro[3.5]nonan-7-yloxy]piperidin-1-yl)-5-chloropyrimidin-4-yl]amino]-1-isopropyl-2-oxoquinolin-3-yl)oxy]-N-methylacetamide (305 mg, 83%) as a yellow solid. MS (ES+): m/z 624.3 [M+H+].

Step 7: Synthesis of 2-[[6-([5-chloro-2-[4-([2-[2-(2,6-dioxopiperidin-3-yl)-1,3-dioxoisoindol-5-yl]-2-azaspiro[3.5]nonan-7-yl]oxy)piperidin-1-yl]pyrimidin-4-yl]amino)-1-isopropyl-2-oxoquinolin-3-yl]oxy]-N-methylacetamide

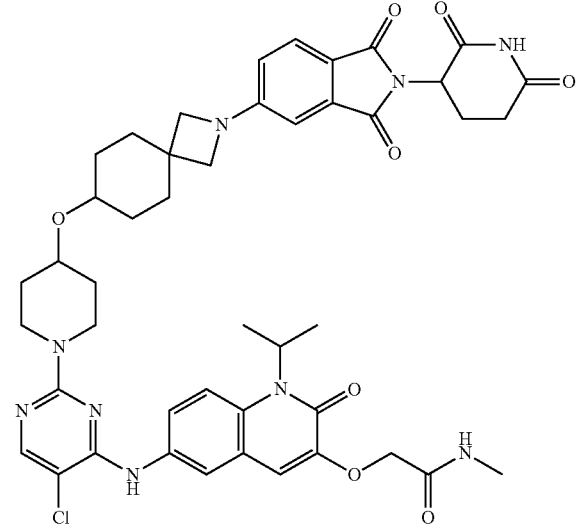

To a stirred solution of 2-[(6-[[2-(4-[2-azaspiro[3.5]nonan-7-yloxy]piperidin-1-yl)-5-chloropyrimidin-4-yl]amino]-1-isopropyl-2-oxoquinolin-3-yl)oxy]-N-methylacetamide (150 mg, 0.228 mmol, 1.00 equiv) and 2-(2,6-dioxopiperidin-3-yl)-5-fluoroisoindole-1,3-dione (99.57 mg, 0.342 mmol, 1.50 equiv) in DMSO was added DIEA (93.18 mg, 0.685 mmol, 3.00 equiv). The resulting mixture was stirred for 2 h at 100 degrees C. The residue was purified by reverse flash chromatography with the following conditions: column, C18 silica gel; mobile phase, ACN in water, 10% to 50% gradient in 40 min; detector, UV 254 nm. This resulted in 2-[[6-([5-chloro-2-[4-([2-[2-(2,6-dioxopiperidin-3-yl)-1,3-dioxoisoindol-5-yl]-2-azaspiro[3.5]nonan-7-yl]oxy)piperidin-1-yl]pyrimidin-4-yl]amino)-1-isopropyl-2-oxoquinolin-3-yl]oxy]-N-methylacetamide (36.4 mg, 17%) as a yellow solid. $^{1}$H NMR (300 MHz, DMSO-d6) δ 8.83 (s, 1H), 8.05 (s, 1H), 7.96 (s, 1H), 7.70 (s, 2H), 7.64 (d, J=8.3 Hz, 2H), 7.02 (s, 1H), 6.77 (d, J=2.1 Hz, 1H), 6.64 (d, J=10.1 Hz, 1H), 5.06 (m, 1H), 4.55 (s, 1H), 4.07 (s, 2H), 3.73 (d, J=6.9 Hz, 2H), 3.52 (s, 5H), 2.88 (s, 1H), 2.68 (d, J=4.5 Hz, 4H), 2.55 (s, 3H), 2.02 (s, 2H), 1.80 (s, 6H), 1.58 (d, J=6.8 Hz, 8H), 1.39 (d, J=10.7 Hz, 4H), 1.24 (s, 1H). LC-MS (ES+): m/z 880.35 [M+H+].

Exemplary Synthesis of 2-[(6-[[5-chloro-2-(dimethylamino)pyrimidin-4-yl]amino]-1-(2-[[2-(2,6-dioxopiperidin-3-yl)-1,3-dioxoisoindol-5-yl]oxy]ethyl)-2-oxoquinolin-3-yl)oxy]-N-methylacetamide (Exemplary Compound 470)

Step 1: Synthesis of 1,2-dimethyl 4-(2-bromoethoxy)phthalate

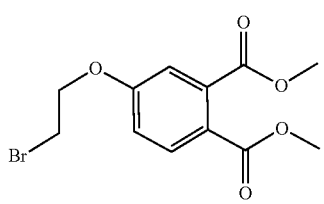 [SMILES: COC(=O)c1ccc(OCCBr)cc1C(=O)OC]

Into a 250-mL round-bottom flask purged and maintained with an inert atmosphere of nitrogen, was placed THF, PPh$_3$ (5.62 g, 21.410 mmol, 1.5 equiv), DEAD (3.73 g, 21.410 mmol, 1.5 equiv), 2-bromoethanol (2.68 g, 21.410 mmol, 1.5 equiv), 1,2-dimethyl 4-hydroxyphthalate (3.00 g, 14.273 mmol, 1.00 equiv). The resulting solution was stirred for 16 h at 60° C. in an oil bath. The resulting solution was extracted with ethyl acetate, dried over anhydrous sodium sulfate. The residue was applied onto a silica gel column with ethyl acetate/petroleum ether (7/3). This resulted in 4.5 g (99.41%) of 1,2-dimethyl 4-(2-bromoethoxy)phthalate as yellow oil.

Step 2: Synthesis of 1,2-dimethyl 4-[2-(5-nitro-2,3-dioxoindol-1-yl)ethoxy]phthalate

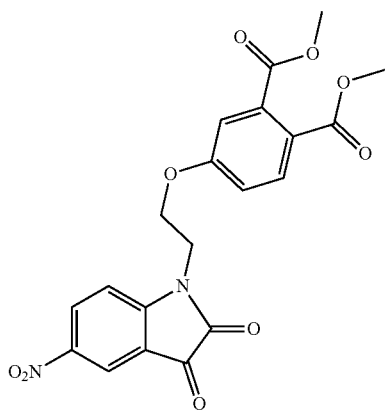 [SMILES: COC(=O)c1ccc(OCCN2C(=O)C(=O)c3cc([N+](=O)[O-])ccc32)cc1C(=O)OC]

Into a 100-mL round-bottom flask purged and maintained with an inert atmosphere of nitrogen, was placed 1H-indole-2,3-dione, 5-nitro-(1.26 g, 1.00 equiv), DMF (40 mL), Cs$_2$CO$_3$ (4.265 g, 2.0 equiv), 1,2-dimethyl 4-(2-bromoethoxy)phthalate (2.5 g, 1.2 equiv). The resulting solution was stirred for 48 h at room temperature. The solids were filtered out. The resulting solution was extracted with ethyl acetate. The resulting mixture was washed with NH$_4$Cl (aq.). The resulting mixture was concentrated. The crude product was purified by Flash-Prep-HPLC with the following conditions Column, C18 silica gel; mobile phase, acetonitrile/(10 mmol/L NH$_4$HCO$_3$) water=5 increasing to acetonitrile/water=60 within 25 min; Detector, 254 nm. This resulted in 1.58 g (56.24%) of 1,2-dimethyl 4-[2-(5-nitro-2,3-dioxoindol-1-yl)ethoxy]phthalate as yellow oil. MS (ES$^+$): m/z 447.0 [MNH$_4^+$].

Step 3: Synthesis of 1,2-dimethyl 4-[2-(3-methoxy-6-nitro-2-oxoquinolin-1-yl)ethoxy]phthalate

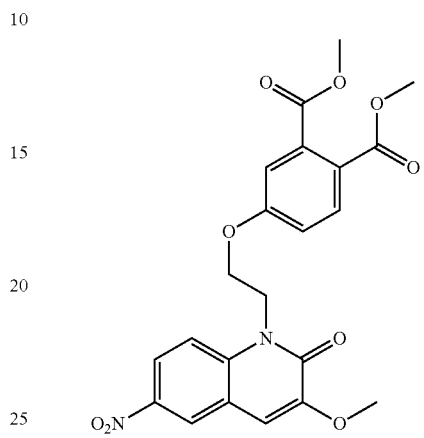

Into a 100-mL round-bottom flask purged and maintained with an inert atmosphere of nitrogen, was placed 1,2-dimethyl 4-[2-(5-nitro-2,3-dioxoindol-1-yl)ethoxy]phthalate (1.39 g, 3.245 mmol, 1.00 equiv), EtOH (50.00 mL), TEA (1.31 g, 12.966 mmol, 4.00 equiv), TMSCHN$_2$ (12.39 mL, 4.00 equiv). The resulting solution was stirred for 16 h at room temperature. The resulting mixture was concentrated. The residue was applied onto a silica gel column with ethyl acetate/petroleum ether (1/1). This resulted in 805 mg (54.35%) of 1,2-dimethyl 4-[2-(3-methoxy-6-nitro-2-oxoquinolin-1-yl)ethoxy]phthalate as a yellow solid. MS (ES$^+$): m/z 457.00 [MH$^+$].

Step 4: Synthesis of 4-[2-(3-hydroxy-6-nitro-2-oxoquinolin-1-yl)ethoxy]benzene-1,2-dicarboxylic acid

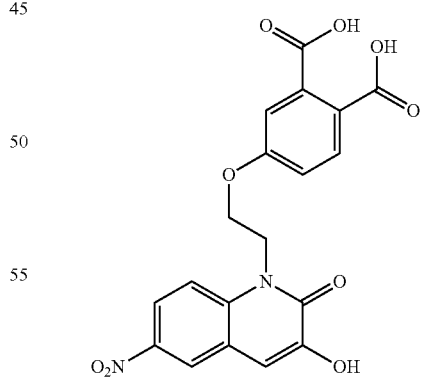

Into a 100-mL round-bottom flask purged and maintained with an inert atmosphere of nitrogen, was placed 1,2-dimethyl 4-[2-(3-methoxy-6-nitro-2-oxoquinolin-1-yl)ethoxy]phthalate (805.00 mg, 1.764 mmol, 1.00 equiv), DCM (20.00 mL). This was followed by the addition of boron tribromide (5.29 mL, 0.021 mmol, 0.01 equiv) dropwise with stirring at 0° C. The resulting solution was stirred for 4 h at room temperature. The product was precipitated by the addition of water. The solids was collected by filtration, This resulted in 750 mg (crude) of 4-[2-(3-hydroxy-6-nitro-2-oxoquinolin-1-yl)ethoxy]benzene-1,2-dicarboxylic acid as a yellow solid.

Step 5: Synthesis of 1,2-dimethyl 4-[2-(3-hydroxy-6-nitro-2-oxoquinolin-1-yl)ethoxy]phthalate

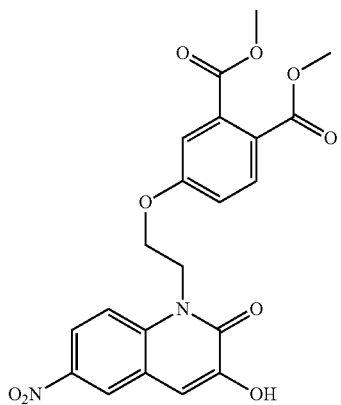 [SMILES: COC(=O)c1ccc(OCCn2c(=O)c(OC)cc3cc([N+](=O)[O-])ccc32)cc1C(=O)OC]

4-[2-(3-hydroxy-6-nitro-2-oxoquinolin-1-yl)ethoxy]benzene-1,2-dicarboxylic acid (750.00 mg, 1.810 mmol, 1.00 equiv), MeOH (20.00 mL), $H_2SO_4$ (0.50 mL, 0.005 mmol). The resulting solution was stirred for 16 h at 65° C. in an oil bath. The resulting mixture was concentrated. The resulting solution was extracted with ethyl acetate. The residue was applied onto a silica gel column with ethyl acetate/petroleum ether (7/3). This resulted in 780 mg (97.40%) of 1,2-dimethyl 4-[2-(3-hydroxy-6-nitro-2-oxoquinolin-1-yl)ethoxy]phthalate as a yellow solid.

Step 6: Synthesis of 1,2-dimethyl 4-(2-[3-[(methylcarbamoyl)methoxy]-6-nitro-2-oxoquinolin-1-yl]ethoxy)phthalate

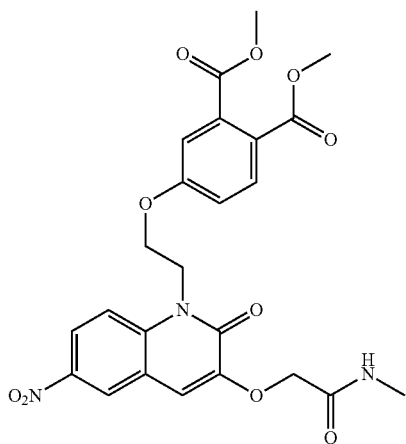 [SMILES: CNC(=O)COc1cc2cc(N)ccc2n(CCOc2ccc(C(=O)OC)c(C(=O)OC)c2)c1=O]

Into a 100-mL round-bottom flask, was placed 1,2-dimethyl 4-[2-(3-hydroxy-6-nitro-2-oxoquinolin-1-yl)ethoxy]phthalate (780.00 mg, 1.763 mmol, 1.00 equiv), DMF, $Cs_2CO_3$ (1148.96 mg, 3.526 mmol, 2.0 equiv), 2-bromo-N-methylacetamide (321.59 mg, 2.116 mmol, 1.2 equiv). The resulting solution was stirred for 2 h at room temperature. The product was precipitated by the addition of water. The solids were collected by filtration. This resulted in 560 mg (61.86%) of 1,2-dimethyl 4-(2-[3-[(methylcarbamoyl)methoxy]-6-nitro-2-oxoquinolin-1-yl]ethoxy)phthalate as a yellow solid. MS (ES+): m/z 514.0 [MH+]

Step 7: Synthesis of 1,2-dimethyl 4-(2-[6-amino-3-[(methylcarbamoyl)methoxy]-2-oxoquinolin-1-yl]ethoxy)phthalate

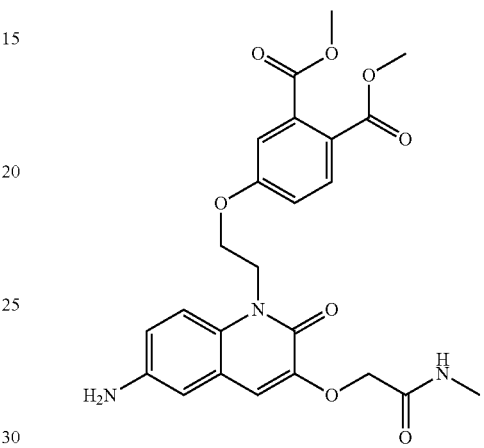

Into a 100-mL round-bottom flask, was placed 1,2-dimethyl 4-(2-[3-[(methylcarbamoyl)methoxy]-6-nitro-2-oxoquinolin-1-yl]ethoxy)phthalate (560.00 mg, 1.091 mmol, 1.00 equiv), dimethylformamide (15.00 mL), Pd/C (200 mg, 0.1 equiv), The mixture was hydrogenated at room temperature for 4 h under hydrogen atmosphere using a hydrogen balloon, filtered through a Celite pad and concentrated under reduced pressure. This resulted in 550 mg (95%) of 1,2-dimethyl 4-(2-[6-amino-3-[(methylcarbamoyl)methoxy]-2-oxoquinolin-1-yl]ethoxy)phthalate as a yellow solid. MS (ES+): m/z 484.20 [MH+].

Step 8: Synthesis of 1,2-dimethyl 4-(2-[6-[(2,5-dichloropyrimidin-4-yl)amino]-3-[(methylcarbamoyl)methoxy]-2-oxoquinolin-1-yl]ethoxy)phthalate

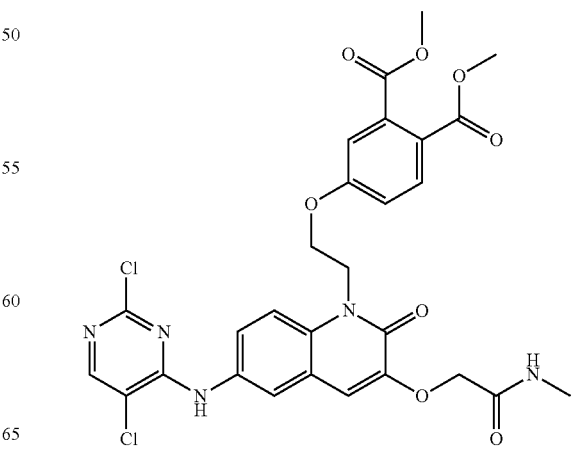

Into a 100-mL round-bottom flask, was placed 1,2-dimethyl 4-(2-[6-amino-3-[(methylcarbamoyl)methoxy]-2-oxoquinolin-1-yl]ethoxy)phthalate (550.00 mg, 1.138 mmol, 1.00 equiv), DMF, DIEA (441.08 mg, 3.413 mmol, 3.0 equiv), 2,4,5-trichloropyrimidine (208.66 mg, 1.138 mmol, 1.00 equiv). The resulting solution was stirred for 2 h at 80° C. in an oil bath. The product was precipitated by the addition of water. The solids were collected by filtration. This resulted in 560 mg (78.08%) of 1,2-dimethyl 4-(2-[6-[(2,5-dichloropyrimidin-4-yl)amino]-3-[(methylcarbamoyl)methoxy]-2-oxoquinolin-1-yl]ethoxy)phthalate as a yellow solid. MS (ES$^+$): m/z 630.90, 631.90 [MH$^+$].

Step 9: Synthesis of 1,2-dimethyl 4-[2-(6-[[5-chloro-2-(dimethylamino)pyrimidin-4-yl]amino]-3-[(methylcarbamoyl)methoxy]-2-oxoquinolin-1-yl)ethoxy]phthalate

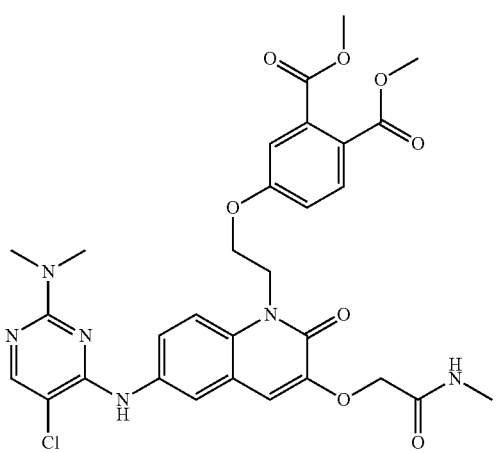 [SMILES: CNC(=O)COc1cc2cc(Nc3nc(N(C)C)ncc3Cl)ccc2n(CCOc2ccc(C(=O)OC)c(C(=O)OC)c2)c1=O]

Into a 10-mL sealed tube, was placed 1,2-dimethyl 4-(2-[6-[(2,5-dichloropyrimidin-4-yl)amino]-3-[(methylcarbamoyl)methoxy]-2-oxoquinolin-1-yl]ethoxy)phthalate (240.00 mg, 0.381 mmol, 1.00 equiv), DMSO, DIEA (147.60 mg, 1.142 mmol, 3.0 equiv), dimethylamine hydrochloride (62.08 mg, 0.761 mmol, 2.00 equiv). The resulting solution was stirred for 2 h at 80° C. in an oil bath. The product was precipitated by the addition of water. The solids were collected by filtration. This resulted in 220 mg (90.43%) of 1,2-dimethyl 4-[2-(6-[[5-chloro-2-(dimethylamino)pyrimidin-4-yl]amino]-3-[(methylcarbamoyl)methoxy]-2-oxoquinolin-1-yl)ethoxy]phthalate as a yellow solid. MS (ES$^+$): m/z 639.0 [MH$^+$].

Step 10: Synthesis of 4-[2-(6-[[5-chloro-2-(dimethylamino)pyrimidin-4-yl]amino]-3-[(methylcarbamoyl)methoxy]-2-oxoquinolin-1-yl)ethoxy]benzene-1,2-dicarboxylic acid

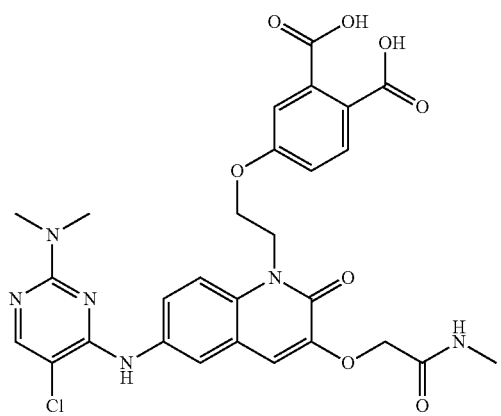 [SMILES: CNC(=O)COc1cc2cc(Nc3nc(N(C)C)ncc3Cl)ccc2n(CCOc2ccc(C(=O)O)c(C(=O)O)c2)c1=O]

Into a 50-mL round-bottom flask, was placed 1,2-dimethyl 4-[2-(6-[[5-chloro-2-(dimethylamino)pyrimidin-4-yl]amino]-3-[(methylcarbamoyl)methoxy]-2-oxoquinolin-1-yl)ethoxy]phthalate (220.00 mg, 0.344 mmol, 1.00 equiv), dioxane (10 mL), THF (2 ml), water (2 mL), caustic soda (55.08 mg, 1.377 mmol, 4.00 equiv). The resulting solution was stirred for 16 h at room temperature. The resulting mixture was concentrated. This resulted in 220 mg (crude) of 4-[2-(6-[[5-chloro-2-(dimethylamino)pyrimidin-4-yl]amino]-3-[(methylcarbamoyl)methoxy]-2-oxoquinolin-1-yl)ethoxy]benzene-1,2-dicarboxylic acid as a yellow solid. MS (ES$^+$): m/z 611.0 [MH$^+$].

Step 11: Synthesis of 2-[(6-[[5-chloro-2-(dimethylamino)pyrimidin-4-yl]amino]-1-(2-[[2-(2,6-dioxopiperidin-3-yl)-1,3-dioxoisoindol-5-yl]oxy]ethyl)-2-oxoquinolin-3-yl)oxy]-N-methylacetamide

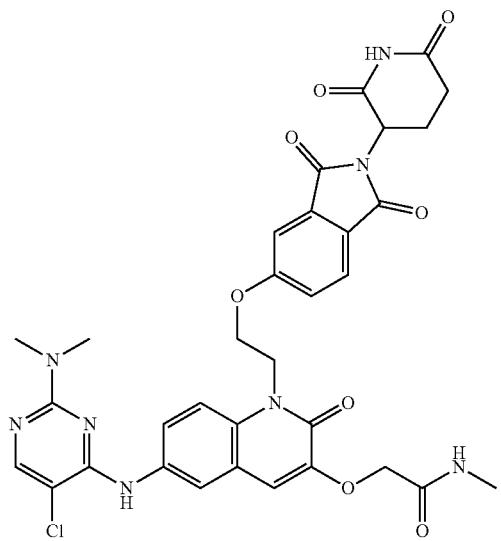 [SMILES: CNC(=O)COc1cc2cc(Nc3nc(N(C)C)ncc3Cl)ccc2n(CCOc2ccc3c(c2)C(=O)N(C2CCC(=O)NC2=O)C3=O)c1=O]

Into a 10-mL sealed tube purged and maintained with an inert atmosphere of nitrogen, was placed 4-[2-(6-[[5-chloro- 2-(dimethylamino)pyrimidin-4-yl]amino]-3-[(methylcarbamoyl)methoxy]-2-oxoquinolin-1-yl)ethoxy]benzene-1,2-dicarboxylic acid (220.00 mg, 0.360 mmol, 1.00 equiv), HOAc (5.0 mL), NaOAc (88.61 mg, 1.080 mmol, 3.0 equiv), 3-aminopiperidine-2,6-dione hydrochloride (177.79 mg, 1.080 mmol, 3.00 equiv). The resulting solution was stirred for 2 h at 120° C. in an oil bath. The resulting mixture was concentrated. The product was precipitated by the addition of water. The crude product was purified by Flash-Prep-HPLC with the following conditions (IntelFlash-1): Column, silica gel; mobile phase, DCM/MeOH=0 increasing to DCM/MeOH=5 within 20 min; Detector, 254 nm affording 27 mg (10.67%) of the title product as a white solid. $^1$H NMR (400 MHz, DMSO-$d_6$, ppm): δ11.11 (s, 1H), 8.92 (s, 1H), 8.06-7.99 (m, 3H), 7.84-7.80 (m, 2H), 7.69 (d, J=9.2 Hz 1H), 7.40 (d, J=2.0 Hz, 1H), 7.29-7.26 (m, 1H), 7.19 (s, 1H), 5.13-5.08 (m, 1H), 4.77-4.74 (m, 2H), 4.57-4.51 (m, 4H), 3.06 (s, 6H), 2.89-2.84 (m, 1H), 2.67 (d, J=4.8 Hz, 3H), 2.51-2.50 (m, 1H), 2.18-2.16 (m, 1H), 2.05-2.03 (m, 1H). MS (ES$^+$): m/z 703.10 [MH$^+$].

Exemplary Synthesis of 2-[[6-([5-chloro-2-[4-(1-[4-[2-(2,6-dioxopiperidin-3-yl)-1,3-dioxoisoindol-5-yl]piperidin-1-yl]cyclopropyl)piperidin-1-yl]pyrimidin-4-yl]amino)-1-methyl-2-oxoquinolin-3-yl]oxy]-N-methylacetamide (Exemplary Compound 482)

Step 1: 1. Synthesis of tert-butyl 4-(1-hydroxycyclopropyl)piperidine-1-carboxylate

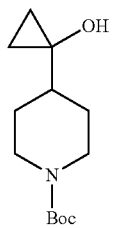

Into a 100-mL round-bottom flask, was placed 1-tert-butyl 4-ethyl piperidine-1,4-dicarboxylate (3 g, 11 mmol, 1. equiv), tetrahydrofuran (50 mL), Ti(Oi-Pr)$_4$ (1.13 mL, 3.777 mmol, 0.32 equiv) This was followed by the addition of EtMgBr (9.0. mL, 3 mol/L, 2.5 equiv) at 0° C. The resulting solution was stirred for 16 h at room temperature. The resulting solution was extracted with dichloromethane. The crude product was purified by Flash-Prep-HPLC with the following conditions: Column, C18 silica gel; mobile phase, acetonitrile/water (10 mmol/L NH$_4$HCO$_3$)=0 increasing to acetonitrile/water (10 mmol/L NH$_4$HCO$_3$)=60 within 30 min; Detector, 220 nm. This resulted in 1.8 g (63%) of tert-butyl 4-(1-hydroxycyclopropyl)piperidine-1-carboxylate as a solid. MS (ES+): m/z 186.00 [MH$^+$].

Step 2: Synthesis of tert-butyl 4-[1-(methanesulfonyloxy)cyclopropyl]piperidine-1-carboxylate

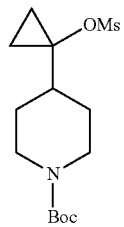 [SMILES: CC(C)(C)OC(=O)N1CCC(C2(OS(C)(=O)=O)CC2)CC1]

Into a 100-mL round-bottom flask, was placed tert-butyl 4-(1-hydroxycyclopropyl)piperidine-1-carboxylate (1.8 g, 7.5 mmol, 1 equiv), methanesulfonyl chloride (1.3 g, 11.25 mmo, 1.5 equiv), DCM (10 mL). This was followed by the addition of Et$_3$N (1.5 g, 1.5 mmol, 2 equiv) at 0° C. The resulting solution was stirred for 1 h at room temperature. The resulting solution was extracted with dichloromethane and the organic layers combined. This resulted in 2.3 g (96%) of tert-butyl 4-[1-(methanesulfonyloxy)cyclopropyl]piperidine-1-carboxylate as a solid. MS (ES$^+$): m/z 264.0 [MH$^+$]

Step 3: Synthesis of tert-butyl 4-(1-[4-[2-(2,6-dioxopiperidin-3-yl)-1,3-dioxoisoindol-5-yl]piperidin-1-yl]cyclopropyl)piperidine-1-carboxylate

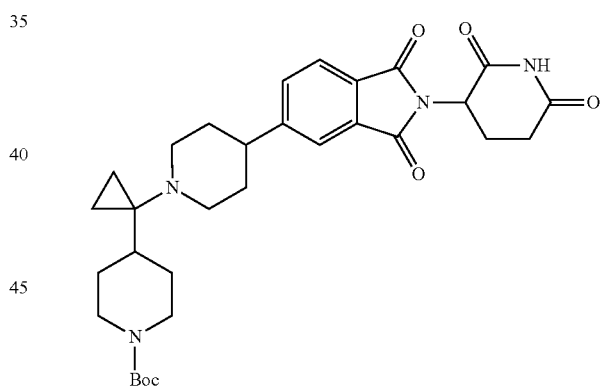

Into a 20-mL sealed tube, was placed 2-(2,6-dioxopiperidin-3-yl)-5-(piperidin-4-yl)isoindole-1,3-dione (1 g, 3 mmol, 1 equiv), tert-butyl 4-[1-(methanesulfonyloxy)cyclopropyl]piperidine-1-carboxylate (0.9 g, 3 mmol, 1 equiv), K$_2$CO$_3$ (0.8 g, 6 mmol, 2 equiv), NaI (0.4 g, 3 mmol, 1 equiv), acetonitrile (15 mL). The resulting solution was stirred for 3 days at 90° C. The crude product was purified by Flash-Prep-HPLC with the following conditions: Column, C18 silica gel; mobile phase, acetonitrile/water (10 mmol/L NH$_4$HCO$_3$)=0 increasing to acetonitrile/water (10 mmol/L NH$_4$HCO$_3$)=85 within 40; Detector, 254. This resulted in 150 mg (20%) of tert-butyl 4-(1-[4-[2-(2,6-dioxopiperidin-3-yl)-1,3-dioxoisoindol-5-yl]piperidin-1-yl]cyclopropyl)piperidine-1-carboxylate as a solid. MS (ES+): m/z 509.10 [MH+].

Step 4: Synthesis of 2-(2,6-dioxopiperidin-3-yl)-5-[1-[1-(piperidin-4-yl)cyclopropyl]piperidin-4-yl]isoindole-1,3-dione

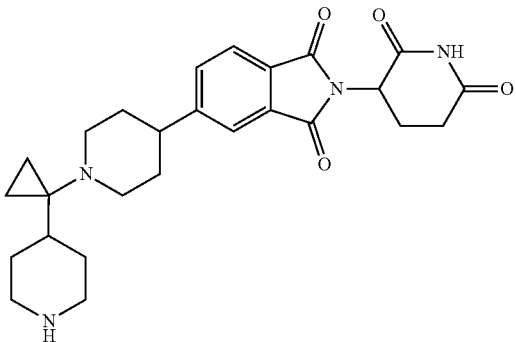 [SMILES: O=C1CCC(N2C(=O)c3ccc(C4CCN(C5(C6CCNCC6)CC5)CC4)cc3C2=O)C(=O)N1]

Into a 50-mL round-bottom flask, was placed tert-butyl 4-(1-[4-[2-(2,6-dioxopiperidin-3-yl)-1,3-dioxoisoindol-5-yl]piperidin-1-yl]cyclopropyl)piperidine-1-carboxylate (150 mg, 0.3 mmol, 1 equiv), DCM (5 mL), trifluoroacetic acid (0.5 mL). The resulting solution was stirred for 2 h at room temperature. The resulting mixture was concentrated under vacuum. This resulted in 130 mg (crude) of 2-(2,6-dioxopiperidin-3-yl)-5-[1-[1-(piperidin-4-yl)cyclopropyl]piperidin-4-yl]isoindole-1,3-dione as a solid. MS (ES$^+$): m/z 465.10 [MH$^+$].

Step 5: Synthesis of 2-[[6-([5-chloro-2-[4-(1-[4-[2-(2,6-dioxopiperidin-3-yl)-1,3-dioxoisoindol-5-yl]piperidin-1-yl]cyclopropyl)piperidin-1-yl]pyrimidin-4-yl]amino)-1-methyl-2-oxoquinolin-3-yl]oxy]-N-methylacetamide

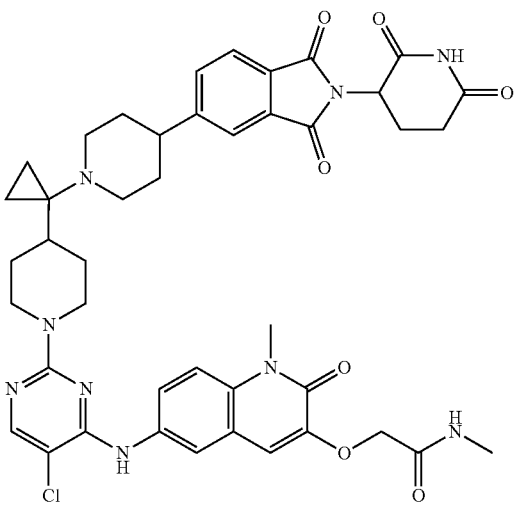

Into a 10-mL sealed tube, was placed 2-(2,6-dioxopiperidin-3-yl)-5-[1-[1-(piperidin-4-yl)cyclopropyl]piperidin-4-yl]isoindole-1,3-dione (46 mg, 1.5 equiv), 2-([6-[(2,5-dichloropyrimidin-4-yl)amino]-1-methyl-2-oxoquinolin-3-yl]oxy)-N-methylacetamide (27 mg, 1 equiv), DIEA (0.5 mL), DMSO (2 mL). The resulting solution was stirred for 2 h at 100° C. The crude product was purified by Flash-Prep-HPLC with the following conditions: Column, C18 silica gel; mobile phase, acetonitrile/water (10 mmol/L NH$_4$HCO$_3$)=0 increasing to acetonitrile/water (10 mmol/L NH$_4$HCO$_3$)=85 within 40; Detector, 254 nm. This resulted in 32.3 mg (58%) of 2-[[6-([5-chloro-2-[4-(1-[4-[2-(2,6-dioxopiperidin-3-yl)-1,3-dioxoisoindol-5-yl]piperidin-1-yl]cyclopropyl)piperidin-1-yl]pyrimidin-4-yl]amino)-1-methyl-2-oxoquinolin-3-yl]oxy]-N-methylacetamide as a solid. $^1$H NMR (300 MHz, DMSO-d$_6$, ppm) δ 11.11 (s, 1H), 8.88 (s, 1H), 8.06-7.95 (m, 2H), 7.86-7.84 (m, 1H), 7.79-7.77 (m, 2H), 7.76-7.75 (m, 1H), 7.50-7.47 (m, 1H), 7.12 (s, 1H), 6.44 (s, 1H), 5.17-5.16 (m, 1H), 4.96-4.88 (m, 1H), 4.61-4.58 (m, 2H), 3.94-3.90 (m, 1H), 3.68 (s, 2H), 2.96-2.92 (m, 4H), 2.90-2.86 (m, 4H), 2.81-2.74 (m, 4H), 2.55-2.52 (m, 1H), 2.32-2.28 (m, 1H), 2.06-1.94 (m, 3H), 1.81-1.56 (m, 5H), 1.40-1.34 (m, 5H), 1.341.30 (m, 1H). MS (ES+): m/z 858.35, [MH$^+$].

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

Specific Embodiments of the Present Disclosure

The present disclosure encompasses embodiments that may include features recited in other embodiments described herein. For example, where applicable, embodiments described herein may also include the features recited in any other embodiment (e.g., an embodiment that precedes or proceeds the embodiment) inclusively or in the alternative (e.g., an eighth embodiment may include the features recited in a first embodiment, as recited, and/or the features of any of the second through seventh embodiments). By way of further example, each of the articulated claims may also include the features recited in any of the other claims or embodiments described herein, except where the language indicates otherwise.

In certain embodiments, the description provides the following exemplary BCL6 bifunctional molecules (compounds of Table 1 or compounds 1-543), including salts, prodrugs, polymorphs, analogs, derivatives, and deuterated forms thereof:

Examples

Figure 2A:
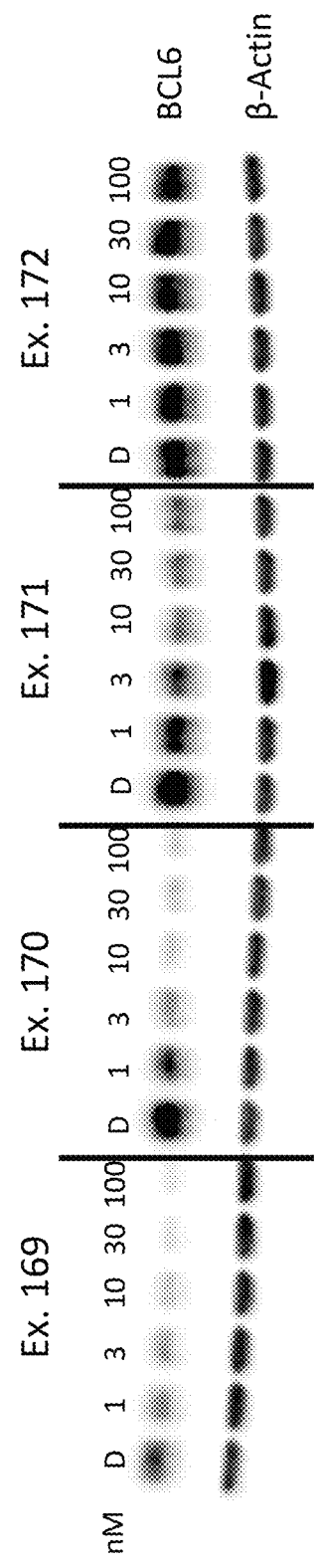
FIGS. 2A and 2B. (A) Western blot illustrating BCL6 protein degradation in Farage Cells 24 hours post treatment. Protein lysates were run on a 4-12% Bis Tris gel. BCL6 was detected with anti-BCL6 antibody (PG-B6P, sc-56625) at 1:500 O/N in 5% BSA-TBS-T and normalized to β-actin. Anti-β-actin antibody (CST, 8H10D10) was used at 1:10,000 in 5% BSA-TBS-T to detect β-actin. (B) Quantification of BCL6 protein quantity in the Western blots of FIG. 2A. Number above each bar indicates % of BCL6 degradation.
Figure 2B:
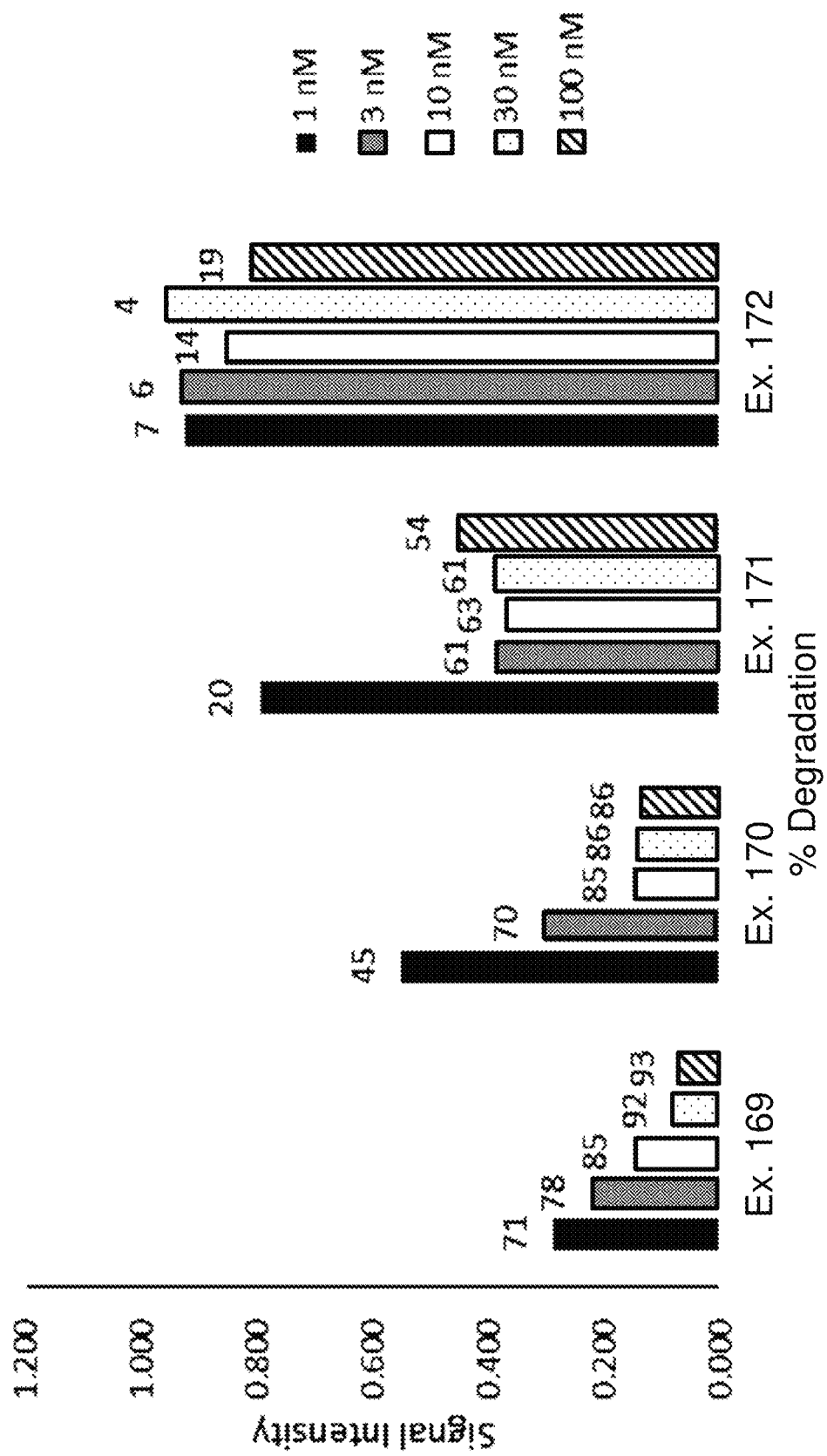

FIGS. 2A and 2B. (A) Western blot illustrating BCL6 protein degradation in Farage Cells 24 hours post treatment. Protein lysates were run on a 4-12% Bis Tris gel. BCL6 was detected with anti-BCL6 antibody (PG-B6P, sc-56625) at 1:500 O/N in 5% BSA-TBS-T and normalized to β-actin. Anti-β-actin antibody (CST, 8H10D10) was used at 1:10,000 in 5% BSA-TBS-T to detect β-actin. (B) Quantification of BCL6 protein quantity in the Western blots of FIG. 2A. Number above each bar indicates % of BCL6 degradation.

Protein Synthesis. BCL6 protein was expressed by transforming Invitrogen One Shot cells with GS63525 pET24a-His-SUMO-TEV-BCLm-Avitag plasmid following manufacturer's instructions. In addition, biotin at a final concentration of 50 μM, and IPTG at a final concentration of 1 mM was added to the culture and incubated at room temperature shaking overnight.

BCL6 TR-FRET Protocol

Assay buffer A: 50 mM HEPES pH 7.5, 125 mM NaCl, 0.01% TritonX.

Assay buffer B (made fresh): buffer A+1 mM Glutathione (or 0.5 mM DTT).

Assay buffer C (made fresh): buffer B+0.03% BSA.

Black Proxy plates, 96 well.

15 µl final reaction volumes (BCoR-Cy5 100 nM, SA-Eu 2 nM, BCL6-avitag 2 nM).

134 µM BCL6-Avitag-Biotin stock: made fresh by adding 2 µl of BCL6-Avitag-Biotin to 31.5 ml Buffer C.

1 mM BCoR-Cy5 peptide (LifeTein) stock in Dimethylformamide (DMF).

300 nM BCoR-Cy5 working stock: made fresh by adding 4.5 µl of the 1 mM BCoR-Cy5 peptide stock to 15 ml Buffer B.

10 µM Eu-Streptavidin (Lance Eu-W1024 Streptavidin, PerkinElmer) stock solution.

6 nM Eu-Streptavidin working stock: made fresh by adding 9 µl Eu-Streptavidin stock solution to 15 ml Buffer A.

Compounds were diluted to 10 mM. Twenty microliters of DMSO was aliquoted to each well of the microtiter plates. From the 10 mM compound stock, 8.7 ul was aliquoted to the 20 ul DMSO and 3-fold serial dilutions (12 pt 3-0.01 uM tritration plate, 96 well, 100% DMSO) performed. Five ul from the titration plate wells was aliquoted to 45 ul Buff C (Intermediate dilution plates, 10% DMSO).

Spot 1.5 µl compound titrations to 384-well plates in duplicate, and spot 3.5 µl [8.5 nM] BCL6-bio protein to each well. The plate was mix briefly, centrifuged, and incubated for 30 minutes at room temperature.

Mix 14 mls of BCoR-Cy5 [300 nM] and 14 mls [6 nM] Eu-Streptavidin. Spot 10 µl BCoR-Cy5/SA-Eu (1:1) mix to each well. The plates were incubated for 2 hours and then read on an Envision plate reader.

Immunofluorescence Protocol for High Cotent Imaging of BCL6

T47D cells were seeded in 100 µl volume of RPMI1640-10% FBS in a 96-well black/clear bottom plates for adherent lines (Corning #3904).

Day 1. T47D breast cancer epithelial cells were seeded at a density so that confluence is ~70-90% at endpoint. Cells were seeded at 7K/0.1 ml/well the morning prior to the addition of exemplary bifunctional degradation compounds.

Compound Treatment

Day 2. Prepare an 11 point 3-fold serial dilution of exemplary bifunctional compound in DMSO and aliquot an appropriate volume to cell growth media to generate a 2× final concentration of exemplary bifunctional compound. Add an equal volume (0.1 ml) of 2× exemplary bifunctional compound/media mix to previously plated cells, for a final top concentration in aqueous cell growth media of 0.1 or 1 µM. Incubate for 3 days at 37° C., 5% $CO_2$.

Day 5 Immunofluorescence. Discard cell media. Wash wells with 200 µl of room temperature phosphate-buffered saline (PBS). Prepared 4% paraformaldehyde (PFA) from 16% PFA (Electron Microscopy Sciences #15710) using 1×PBS. Fifty µl of 4% PF was added to each well and incubate for 15 minutes at room temperature to fix the cells. The PFA was aspirated and the cells washed twice with PBS (200 µl)).

Prepared 0.1% Triton X-100 in PBS using 10% triton X-100 stock. The cells were permeabilized by adding 100 ul of the 0.1% Triton X-100 in PBS to each well to permeabilize cells and incubating at room temperature for 15 minutes. Cells were washed twice with PBS.

Prepared 3% BSA/PBS (from Thermofisher #37515 Blocker BSA in TBS, 10%), and 100 ul was added to each well. The cells were incubated for at least 1 hour at room temperature.

Prepared 1% BSA/PBS using Blocker BSA/PBS, and the 3% BSA/PBS removed from the wells.

For no primary antibody controls, 50 µl 1% BSA/PBS was added.

Primary antibody (BCL6 Rb Ab, CST-14895, Cell Signaling) was diluted 1:300 in 1% BSA/PBS using Blocker BSA/PBS.

Fifty µl of primary antibody added to all remaining wells (i.e., all wells other than the primary antibody controls) and the cells were incubated overnight at 4° C. with slow orbital movement.

Day 6. Contents of the wells was removed and the cells washed four times with 200 ul PBS. 1% BSA/PBS was prepared using Blocker BSA in PBS.

Diluted secondary antibody goat anti-Rb IgG Alexa-488 1:1000, and cell mask-Alexa-647 1:3000 in 1% BSA/PBS in the same mix. Add 50 µl to each well and incubate at room temperature for 1 hour in the dark.

Cells were washed three times with 200 ul PBS, and then incubated for 10 minutes with 100 ul Hoechst dye at 1 µg/mL (20 mM stock) to stain cell nuclei. Wells were then washed with 200 µl PBS, and 100 ul of PBS was added to each well and the plate covered plate with a plastic opaque cover. Plates were stored at 4° C. and covered in aluminum foil until imaged.

Plates were equilibrated to room temperature prior to reading. The bottom of the plate was wiped with 70% isopropanol immediately prior to imaging.

Imaging:

10×, 4 fields/well, include Top hat smoothing in the analysis protocol.

Supplies/Reagents:

16% paraformaldehyde: Electron Microscopy Sciences #15710

Hoechst: Thermofisher #62249

Blocker BSA in PBS, 10%: Thermofisher #37515

Blocker BSA in TBS, 10%: Thermofisher #37520

Goat anti-rabbit or mouse AlexaFluor-488: Thermofisher #A11008

Cell mask deep red AlexaFluor-647: Thermofisher #C10046

Wash buffer, PBS: 20×PBS, Thermofisher

TABLE 1

Exemplary bifunctional compounds of the present disclosure

| Ex. # | Parent Mol Structure | Name |
|---|---|---|
| 1 | | |
| 2 | | |
| 3 | | |

TABLE 1-continued

Exemplary bifunctional compounds of the present disclosure

| Ex. # | Parent Mol Structure | Name |
|---|---|---|
| 4 | | |
| 5 | | |
| 6 | | |

TABLE 1-continued

Exemplary bifunctional compounds of the present disclosure

| Ex. # | Parent Mol Structure | Name |
|---|---|---|
| 7 | | |
| 8 | | |
| 9 | | 2-[(6-{[5-chloro-2-(4-{[(5R)-7-{2-[(3R)-2,6-dioxopiperidin-3-yl]-1-oxo-2,3-dihydro-1H-isoindol-5-yl}-2,7-diazaspiro[4.4]nonan-2-yl]methyl}piperidin-1-yl)pyrimidin-4-yl]amino}-2-oxo-1-(propan-2-yl)-1,2-dihydroquinolin-3-yl)oxy]-N-methylacetamide |

TABLE 1-continued
Exemplary bifunctional compounds of the present disclosure
| Ex. # | Parent Mol Structure | Name |
|---|---|---|
| 10 | 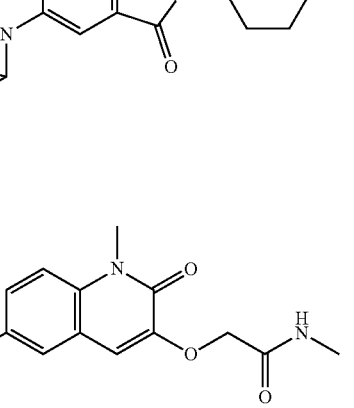 | |
| 11 | 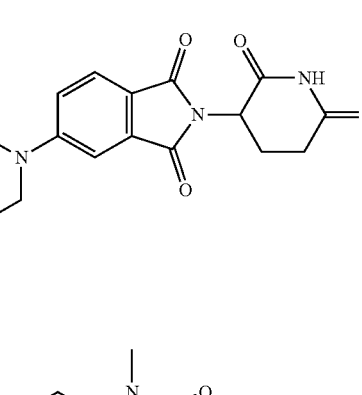 | |
| 12 | 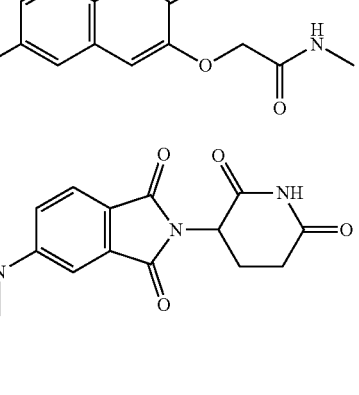 | |

TABLE 1-continued

Exemplary bifunctional compounds of the present disclosure

| Ex. # | Parent Mol Structure | Name |
|---|---|---|
| 13 | | |
| 14 | | |
| 15 | | |

TABLE 1-continued
Exemplary bifunctional compounds of the present disclosure
| Ex. # | Parent Mol Structure | Name |
|---|---|---|
| 16 | 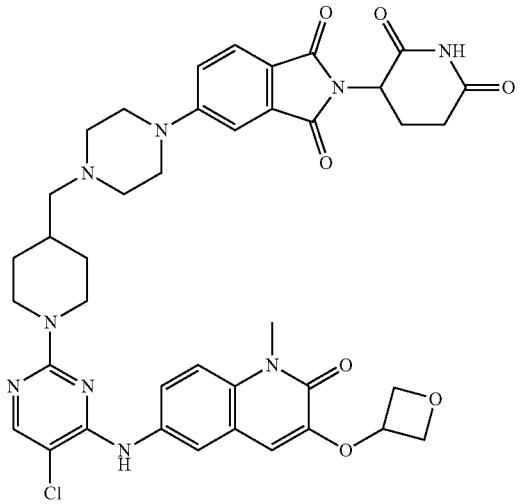 [SMILES: Cn1c(=O)c(OC2COC2)cc2cc(Nc3nc(N4CCC(CN5CCN(c6ccc7c(c6)C(=O)N(C6CCC(=O)NC6=O)C7=O)CC5)CC4)ncc3Cl)ccc21] | |
| 17 | 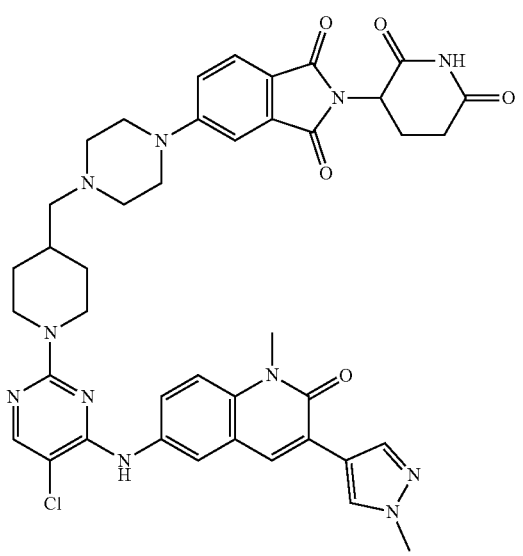 [SMILES: Cn1cc(-c2cc3cc(Nc4nc(N5CCC(CN6CCN(c7ccc8c(c7)C(=O)N(C7CCC(=O)NC7=O)C8=O)CC6)CC5)ncc4Cl)ccc3n(C)c2=O)cn1] | |
| 18 | 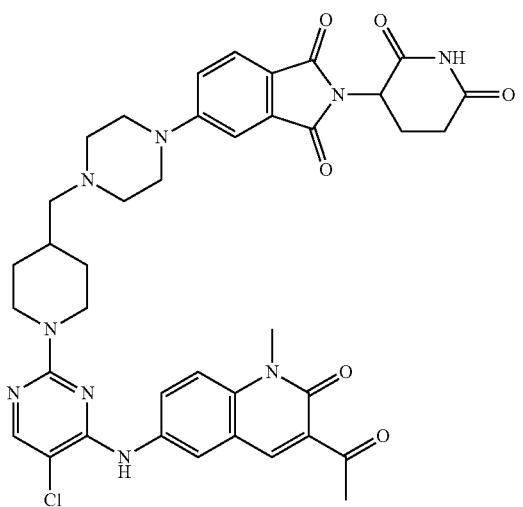 [SMILES: CC(=O)c1cc2cc(Nc3nc(N4CCC(CN5CCN(c6ccc7c(c6)C(=O)N(C6CCC(=O)NC6=O)C7=O)CC5)CC4)ncc3Cl)ccc2n(C)c1=O] | |

TABLE 1-continued

Exemplary bifunctional compounds of the present disclosure

| Ex. # | Parent Mol Structure | Name |
|---|---|---|
| 19 | | |
| 20 | | |
| 21 | | |

TABLE 1-continued

Exemplary bifunctional compounds of the present disclosure

| Ex. # | Parent Mol Structure | Name |
|---|---|---|
| 22 | | |
| 23 | | |
| 24 | | |

TABLE 1-continued

Exemplary bifunctional compounds of the present disclosure

| Ex. # | Parent Mol Structure | Name |
|---|---|---|
| 25 | | |
| 26 | | |
| 27 | | |

TABLE 1-continued

Exemplary bifunctional compounds of the present disclosure

| Ex. # | Parent Mol Structure | Name |
|---|---|---|
| 28 | | |
| 29 | | |
| 30 | | |

TABLE 1-continued
Exemplary bifunctional compounds of the present disclosure
| Ex. # | Parent Mol Structure | Name |
|---|---|---|
| 31 | 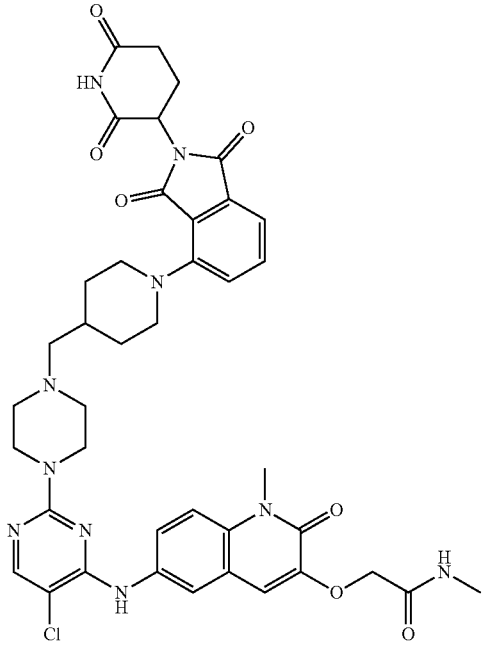 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(C)c1=O] | |
| 32 | 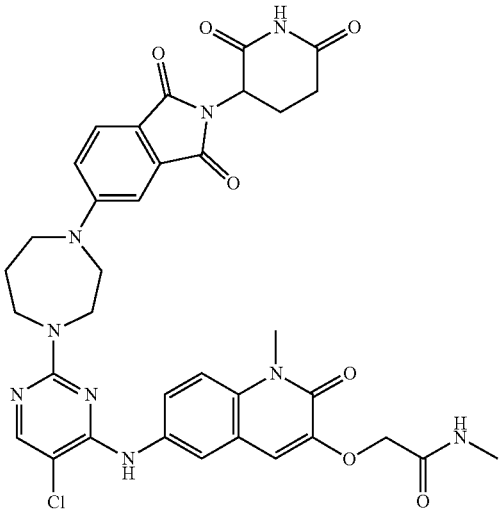 [SMILES: CNC(=O)COc1cc2cc(Nc3nc(N4CCCN(c5ccc6c(c5)C(=O)N(C5CCC(=O)NC5=O)C6=O)CC4)ncc3Cl)ccc2n(C)c1=O] | |

TABLE 1-continued

Exemplary bifunctional compounds of the present disclosure

| Ex. # | Parent Mol Structure | Name |
|---|---|---|
| 33 | | |
| 34 | | |
| 35 | | |

TABLE 1-continued

Exemplary bifunctional compounds of the present disclosure

| Ex. # | Parent Mol Structure | Name |
|---|---|---|
| 36 | | |
| 37 | | |
| 38 | | |

TABLE 1-continued

Exemplary bifunctional compounds of the present disclosure

| Ex. # | Parent Mol Structure | Name |
|---|---|---|
| 39 | | |
| 40 | | |
| 41 | | |

TABLE 1-continued

Exemplary bifunctional compounds of the present disclosure

| Ex. # | Parent Mol Structure | Name |
|---|---|---|
| 42 | | |
| 43 | | |
| 44 | | |

TABLE 1-continued
Exemplary bifunctional compounds of the present disclosure
| Ex. # | Parent Mol Structure | Name |
|---|---|---|
| 45 | 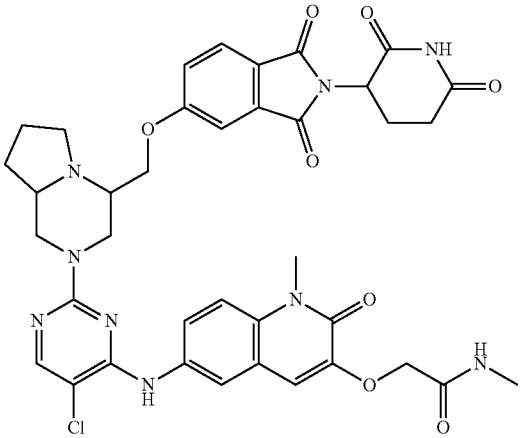 [SMILES: CNC(=O)COc1cc2cc(Nc3nc(N4CC5CCCN5C(COc5ccc6c(c5)C(=O)N(C5CCC(=O)NC5=O)C6=O)C4)ncc3Cl)ccc2n(C)c1=O] | |
| 46 | 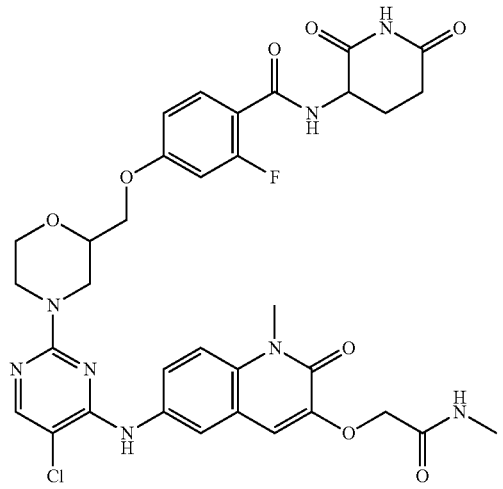 [SMILES: CNC(=O)COc1cc2cc(Nc3nc(N4CCOC(COc5ccc(C(=O)NC6CCC(=O)NC6=O)c(F)c5)C4)ncc3Cl)ccc2n(C)c1=O] | |
| 47 | 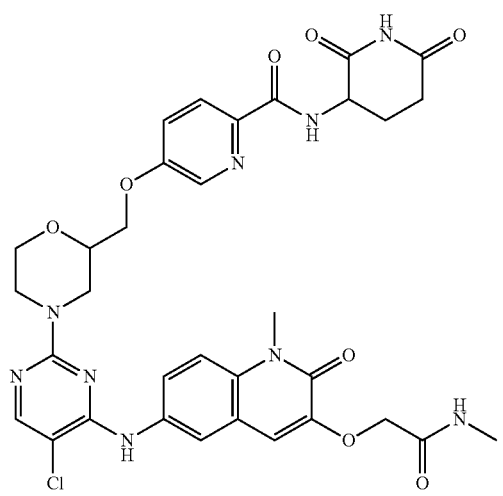 [SMILES: CNC(=O)COc1cc2cc(Nc3nc(N4CCOC(COc5ccc(C(=O)NC6CCC(=O)NC6=O)nc5)C4)ncc3Cl)ccc2n(C)c1=O] | |

TABLE 1-continued

Exemplary bifunctional compounds of the present disclosure

| Ex. # | Parent Mol Structure | Name |
|---|---|---|
| 48 | | |
| 49 | | (2S,4R)-N-(2-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)ethoxy)-4-(4-methylthiazol-5-yl)benzyl)-4-hydroxy-1-((S)-3-methyl-2-(3-methylisoxazol-5-yl)butanoyl)pyrrolidine-2-carboxamide |
| 50 | | (2S,4R)-N-(2-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide |

TABLE 1-continued

Exemplary bifunctional compounds of the present disclosure

| Ex. # | Parent Mol Structure | Name |
|---|---|---|
| 51 | | (2S,4R)-1-((S)-2-(tert-butyl)-14-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-4-oxo-6,9,12-trioxa-3-azatetradecanoyl)-4-hydroxy-N-(4-(4-methylthiazol-5-yl)benzyl)pyrrolidine-2-carboxamide |
| 52 | | 2-((6-((5-chloro-2-(4-(2-(2-(2-(2-(2,6-dioxopiperidin-3-yl)-1,3-dioxoisoindolin-5-yl)oxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 53 | | (2S,4R)-N-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)-4-(4-methylthiazol-5-yl)benzyl)-4-hydroxy-1-(3-methyl-2-(3-methylisoxazol-5-yl)butanoyl)pyrrolidine-2-carboxamide |

TABLE 1-continued

Exemplary bifunctional compounds of the present disclosure

| Ex. # | Parent Mol Structure | Name |
|---|---|---|
| 54 | | (2S,4R)-N-(2-(2-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)ethoxy)ethoxy)-4-(4-methylthiazol-5-yl)benzyl)-4-hydroxy-1-(3-methyl-2-(3-methylisoxazol-5-yl)butanoyl)pyrrolidine-2-carboxamide |
| 55 | | 2S,4R)-N-(2-((14-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-3,6,9,12-tetraoxatetradecyl)oxy)-4-(4-methylthiazol-5-yl)benzyl)-4-hydroxy-1-(3-methyl-2-(3-methylisoxazol-5-yl)butanoyl)pyrrolidine-2-carboxamide |
| 56 | | (2S,4R)-N-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)-4-(4-methylthiazol-5-yl)benzyl)-4-hydroxy-1-(3-methyl-2-(3-methylisoxazol-5-yl)butanoyl)pyrrolidine-2-carboxamide |

TABLE 1-continued

Exemplary bifunctional compounds of the present disclosure

| Ex. # | Parent Mol Structure | Name |
|---|---|---|
| 57 | | 2-((6-((5-chloro-2-(4-(2-(2-(2-((2-(2,6-dioxopiperidin-3-yl)-1,3-dioxoisoindolin-4-yl)amino)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 58 | | (2S,4R)-N-(2-((17-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-3,6,9,12,15-pentaoxaheptadecyl)oxy)-4-(4-methylthiazol-5-yl)benzyl)-4-hydroxy-1-(3-methyl-2-(3-methylisoxazol-5-yl)butanoyl)pyrrolidine-2-carboxamide |
| 59 | | 2-((6-((5-chloro-2-(4-(2-(2-(2-(2-((2-(2,6-dioxopiperidin-3-yl)-1-oxoisoindolin-5-yl)oxy)ethoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |

| Ex. # | Parent Mol Structure | Name |
|---|---|---|
| 60 | | 2-((6-((5-chloro-2-(4-(2-(2-(2-(2-(2-((2-(2,6-dioxopiperidin-3-yl)-1,3-dioxoisoindolin-5-yl)oxy)ethoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 61 | | 2-((6-((5-chloro-2-(4-(2-(2-((2-(2,6-dioxopiperidin-3-yl)-1-oxoisoindolin-5-yl)oxy)ethoxy)ethoxy)piperidin-1-yl)pyrimidin-4-yl)amino)-1-methyl-2-oxo-1,2-dihydroquinolin-3-yl)oxy)-N-methylacetamide |
| 62 | | 2-((6-((5-chloro-2-(4-((14-((2-(2,6-dioxopiperidin-3-yl)-1-oxoisoindolin-5-yl)oxy)-3,6,9,12-tetraoxatetradecyl)oxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 63 | | 2-((6-((5-chloro-2-(4-(2-(2-((2-(2,6-dioxopiperidin-3-yl)-1,3-dioxoisoindolin-5-yl)oxy)ethoxy)ethoxy)piperidin-1-yl)pyrimidin-4-yl)amino)-1-methyl-2-oxo-1,2-dihydroquinolin-3-yl)oxy)-N-methylacetamide |
| 64 | | 2-((6-((5-chloro-2-(4-((14-((2-(2,6-dioxopiperidin-3-yl)-1,3-dioxoisoindolin-5-yl)oxy)-3,6,9,12-tetraoxatetradecyl)oxy)piperidin-1-yl)pyrimidin-4-yl)amino)-1-methyl-2-oxo-1,2-dihydroquinolin-3-yl)oxy)-N-methylacetamide |
| 65 | | 2-((6-((5-chloro-2-(4-(2-(2-((2-(2,6-dioxopiperidin-3-yl)-1-oxoisoindolin-5-yl)oxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 66 | | 2-((6-((5-chloro-2-(4-(2-(2-(2-((2-(2,6-dioxopiperidin-3-yl)-1,3-dioxoisoindolin-4-yl)amino)ethoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 67 | 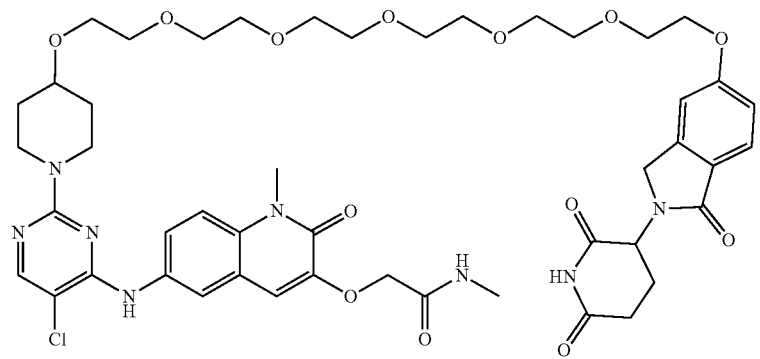 [SMILES: CNC(=O)COc1cc2cc(Nc3nc(N4CCC(OCCOCCOCCOCCOCCOCCOc5ccc6c(c5)CN(C5CCC(=O)NC5=O)C6=O)CC4)ncc3Cl)ccc2n(C)c1=O] | 2-((6-((5-chloro-2-(4-((17-((2-(2,6-dioxopiperidin-3-yl)-1-oxoisoindolin-5-yl)oxy)-3,6,9,12,15-pentaoxaheptadecyl)oxy)piperidin-1-yl)pyrimidin-4-yl)amino)-1-methyl-2-oxo-1,2-dihydroquinolin-3-yl)oxy)-N-methylacetamide |
| 68 | 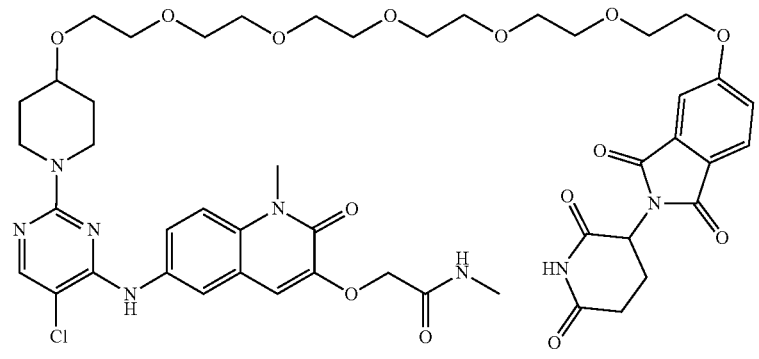 [SMILES: CNC(=O)COc1cc2cc(Nc3nc(N4CCC(OCCOCCOCCOCCOCCOCCOc5ccc6c(c5)C(=O)N(C5CCC(=O)NC5=O)C6=O)CC4)ncc3Cl)ccc2n(C)c1=O] | 2-((6-((5-chloro-2-(4-((17-((2-(2,6-dioxopiperidin-3-yl)-1,3-dioxoisoindolin-5-yl)oxy)-3,6,9,12,15-pentaoxaheptadecyl)oxy)piperidin-1-yl)pyrimidin-4-yl)amino)-1-methyl-2-oxo-1,2-dihydroquinolin-3-yl)oxy)-N-methylacetamide |
| 69 | 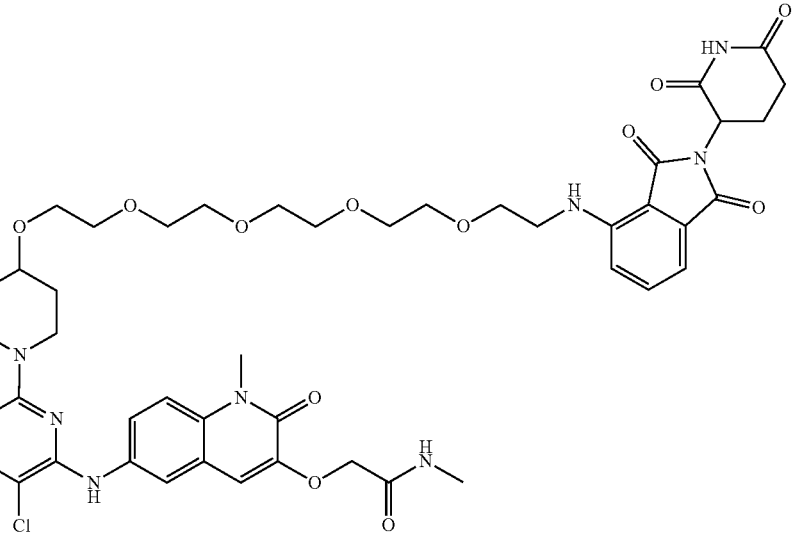 | 2-((6-((5-chloro-2-(4-((14-((2-(2,6-dioxopiperidin-3-yl)-1,3-dioxoisoindolin-4-yl)amino)-3,6,9,12-tetraoxatetradecyl)oxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 70 | | (2S,4R)-1-((S)-2-(2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)ethoxy)acetamido)-3,3-dimethylbutanoyl)-4-hydroxy-N-(4-(4-methylthiazol-5-yl)benzyl)pyrrolidine-2-carboxamide |
| 71 | | 2-((6-((5-chloro-2-(4-(2-((2-(2,6-dioxopiperidin-3-yl)-1-oxoisoindolin-5-yl)oxy)ethoxy)piperidin-1-yl)pyrimidin-4-yl)amino)-1-methyl-2-oxo-1,2-dihydroquinolin-3-yl)oxy)-N-methylacetamide |
| 72 | | 2-((6-((5-chloro-2-(4-(2-((2-(2,6-dioxopiperidin-3-yl)-1,3-dioxoisoindolin-5-yl)oxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 73 | | 5-(2-(2-(4-(4-chloro-5-((1-methyl-2-oxo-1,2,3,4-tetrahydroquinolin-6-yl)amino)-2-nitrophenoxy)piperidin-1-yl)ethoxy)ethoxy)-2-(2,6-dioxopiperidin-3-yl)isoindoline-1,3-dione |
| 74 | | 5-(2-(2-(4-(4-chloro-2-nitro-5-((2-oxo-1,2,3,4-tetrahydroquinolin-6-yl)amino)phenoxy)piperidin-1-yl)ethoxy)ethoxy)-2-(2,6-dioxopiperidin-3-yl)isoindoline-1,3-dione |
| 75 | | 2-((6-((5-chloro-2-(4-(2-(2-((2-(2,6-dioxopiperidin-3-yl)-1,3-dioxoisoindolin-4-yl)amino)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 76 | | 5-(2-(2-(4-(4-chloro-5-((1-methyl-2-oxo-1,2,3,4-tetrahydroquinolin-6-yl)amino)-2-nitrophenoxy)piperidin-1-yl)-2-oxoethoxy)ethoxy)-2-(2,6-dioxopiperidin-3-yl)isoindoline-1,3-dione |
| 77 | | 5-(4-((1-(4-chloro-5-((1-methyl-2-oxo-1,2,3,4-tetrahydroquinolin-6-yl)amino)-2-nitrophenyl)piperidin-4-yl)methyl)piperazin-1-yl)-2-(2,6-dioxopiperidin-3-yl)isoindoline-1,3-dione |
| 78 | | (2S,4R)-1-((S)-2-(tert-butyl)-17-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-4-oxo-6,9,12,15-tetraoxa-3-azaheptadecanoyl)-4-hydroxy-N-(4-(4-methylthiazol-5-yl)benzyl)pyrrolidine-2-carboxamide |

TABLE 1-continued

Exemplary bifunctional compounds of the present disclosure

| Ex. # | Parent Mol Structure | Name |
|---|---|---|
| 79 | | 5-(4-(4-chloro-5-((1-methyl-2-oxo-1,2,3,4-tetrahydroquinolin-6-yl)amino)-2-nitrophenoxy)-[1,4'-bipiperidin]-1'-yl)-2-(2,6-dioxopiperidin-3-yl)isoindoline-1,3-dione |
| 80 | | 2-((6-((5-chloro-2-(4-(2-((2-(2,6-dioxopiperidin-3-yl)-1,3-dioxoisoindolin-4-yl)amino)ethoxy)piperidin-1-yl)pyrimidin-4-yl)amino)-1-methyl-2-oxo-1,2-dihydroquinolin-3-yl)oxy)-N-methylacetamide |
| 81 | | 2-((6-((5-chloro-2-(4-((17-((2-(2,6-dioxopiperidin-3-yl)-1,3-dioxoisoindolin-4-yl)amino)-3,6,9,12,15-pentaoxaheptadecyl)oxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 82 | | (2S,4R)-1-((S)-2-(tert-butyl)-20-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-4-oxo-6,9,12,15,18-pentaoxa-3-azaicosanoyl)-4-hydroxy-N-(4-(4-methylthiazol-5-yl)benzyl)pyrrolidine-2-carboxamide |
| 83 | | (2S,4R)-1-((S)-2-(tert-butyl)-23-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)-4-oxo-6,9,12,15,18,21-hexaoxa-3-azatricosanoyl)-4-hydroxy-N-(4-(4-methylthiazol-5-yl)benzyl)pyrrolidine-2-carboxamide |
| 84 | | 2-((6-((5-chloro-2-(4-((14-((2-(3-methyl-2,6-dioxopiperidin-3-yl)-1-oxoisoindolin-5-yl)oxy)-3,6,9,12-tetraoxatetradecyl)oxy)piperidin-1-yl)pyrimidin-4-yl)amino)-1-methyl-2-oxo-1,2-dihydroquinolin-3-yl)oxy)-N-methylacetamide |
| 85 | | 5-((1r,3r)-3-(((1-(4-chloro-5-((1-methyl-2-oxo-1,2,3,4-tetrahydroquinolin-6-yl)amino)-2-nitrophenyl)piperidin-4-yl)methyl)(methyl)amino)cyclobutoxy)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 86 | | (2S,4R)-1-((S)-2-(2-(2-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)ethoxy)acetamido)-3,3-dimethylbutanoyl)-4-hydroxy-N-(4-(4-methylthiazol-5-yl)benzyl)pyrrolidine-2-carboxamide |
| 87 | | 2-((6-((5-chloro-2-(4-((14-((2-(1-methyl-2,6-dioxopiperidin-3-yl)-1-oxoisoindolin-5-yl)oxy)-3,6,9,12-tetraoxatetradecyl)oxy)piperidin-1-yl)pyrimidin-4-yl)amino)-1-methyl-2-oxo-1,2-dihydroquinolin-3-yl)oxy)-N-methylacetamide |
| 88 | | 2-((6-((5-chloro-2-(4-(3-(2-(2-(2-(2-((2-(2,6-dioxopiperidin-3-yl)-1-oxoisoindolin-5-yl)oxy)ethoxy)ethoxy)ethoxy)ethoxy)phenyl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 89 | | 2-((6-((5-chloro-2-(4-(4-(3-(2-(2-((2-(2,6-dioxopiperidin-3-yl)-1-oxoisoindolin-5-yl)oxy)ethoxy)ethoxy)propoxy)phenyl)piperidin-1-yl)pyrimidin-4-yl)amino)-1-methyl-2-oxo-1,2-dihydroquinolin-3-yl)oxy)-N-methylacetamide |
| 90 | | 2-((6-((5-chloro-2-(4-(2-(3-(2-(2-(2-((2-(2,6-dioxopiperidin-3-yl)-1-oxoisoindolin-5-yl)oxy)ethoxy)ethoxy)ethoxy)propoxy)phenyl)piperidin-1-yl)pyrimidin-4-yl)amino)-1-methyl-2-oxo-1,2-dihydroquinolin-3-yl)oxy)-N-methylacetamide |
| 91 | | 2-((6-((5-chloro-2-(4-(2-(2-(2-(2-((2-(2,6-dioxopiperidin-3-yl)-1-oxoisoindolin-5-yl)oxy)ethoxy)ethoxy)ethoxy)ethoxy)phenoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 92 | 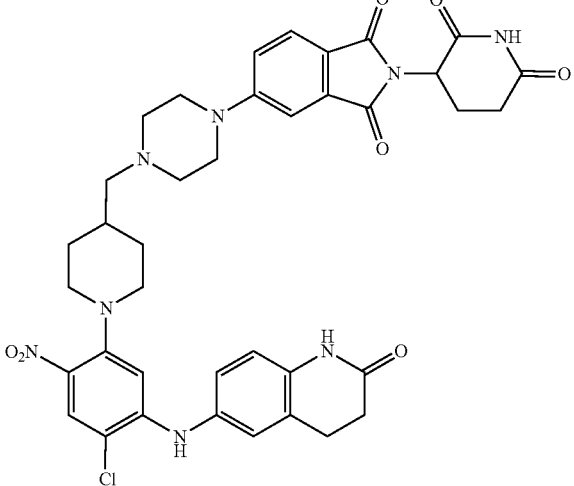 | 5-(4-((1-(4-chloro-2-nitro-5-((2-oxo-1,2,3,4-tetrahydroquinolin-6-yl)amino)phenyl)piperidin-4-yl)methyl)piperazin-1-yl)-2-(2,6-dioxopiperidin-3-yl)isoindoline-1,3-dione |
| 93 | 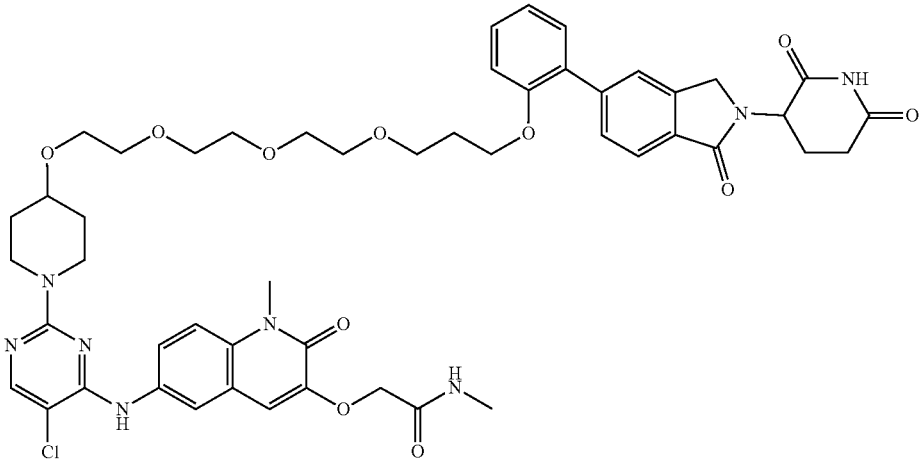 [SMILES: CNC(=O)COc1cc2cc(Nc3nc(N4CCC(OCCOCCOCCOCCCOc5ccccc5-c5ccc6c(c5)CN(C5CCC(=O)NC5=O)C6=O)CC4)ncc3Cl)ccc2n(C)c1=O] | 2-((6-((5-chloro-2-(4-(2-(2-(2-(3-(2-(2,6-dioxopiperidin-3-yl)-1-oxoisoindolin-5-yl)phenoxy)propoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 94 | 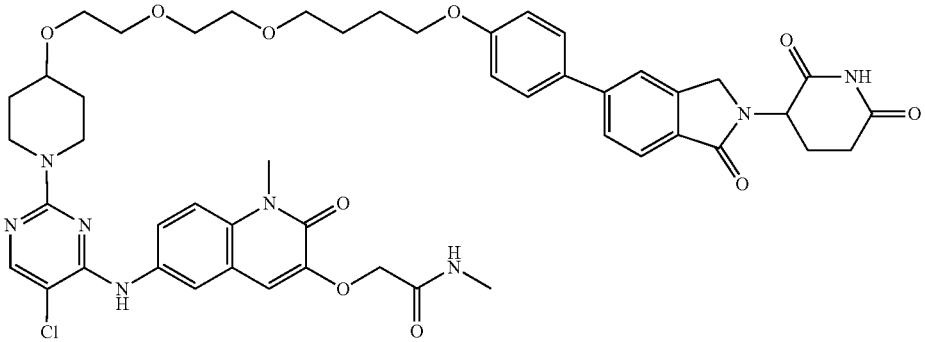 [SMILES: CNC(=O)COc1cc2cc(Nc3nc(N4CCC(OCCOCCOCCCCOc5ccc(-c6ccc7c(c6)CN(C6CCC(=O)NC6=O)C7=O)cc5)CC4)ncc3Cl)ccc2n(C)c1=O] | 2-((6-((5-chloro-2-(4-(2-(2-(4-(4-(2-(2,6-dioxopiperidin-3-yl)-1-oxoisoindolin-5-yl)phenoxy)butoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 95 |  | 2-((6-((5-chloro-2-(4-(3-(4-(2-(2-((2-(2,6-dioxopiperidin-3-yl)-1-oxoisoindolin-5-yl)oxy)ethoxy)ethoxy)butoxy)phenoxy)piperidin-1-yl)pyrimidin-4-yl)amino)-1-methyl-2-oxo-1,2-dihydroquinolin-3-yl)oxy)-N-methylacetamide |
| 96 |  | 2-((6-((5-chloro-2-(4-(4-(3-(2-(2-((2-(2,6-dioxopiperidin-3-yl)-1-oxoisoindolin-5-yl)oxy)ethoxy)ethoxy)propoxy)phenoxy)piperidin-1-yl)pyrimidin-4-yl)amino)-1-methyl-2-oxo-1,2-dihydroquinolin-3-yl)oxy)-N-methylacetamide |
| 97 |  | 2-((6-((5-chloro-2-(4-((3-((2-(2-(2-((2-(2,6-dioxopiperidin-3-yl)-1-oxoisoindolin-5-yl)oxy)ethoxy)ethoxy)ethoxy)methyl)benzyl)oxy)piperidin-1-yl)pyrimidin-4-yl)amino)-1-methyl-2-oxo-1,2-dihydroquinolin-3-yl)oxy)-N-methylacetamide |
| 98 |  | 3-(5-((14-((1-(5-chloro-4-((1-methyl-2-oxo-3-(2-oxopropoxy)-1,2-dihydroquinolin-6-yl)amino)pyrimidin-2-yl)piperidin-4-yl)oxy)-3,6,9,12-tetraoxatetradecyl)oxy)-1-oxoisoindolin-2-yl)piperidine-2,6-dione |

TABLE 1-continued

Exemplary bifunctional compounds of the present disclosure

| Ex. # | Parent Mol Structure | Name |
|---|---|---|
| 99 | | 2-((6-((5-chloro-2-(4-((14-((2-(2,6-dioxopiperidin-3-yl)-1-oxoisoindolin-5-yl)oxy)-3,6,9,12-tetraoxatetradecyl)oxy)piperidin-1-yl)pyrimidin-4-yl)amino)-1-methyl-2-oxo-1,2-dihydroquinolin-3-yl)oxy)-N,N-dimethylacetamide |
| 100 | | 2-((6-((5-chloro-2-(4-(2-(2-(2-(3-(2-((2-(2,6-dioxopiperidin-3-yl)-1-oxoisoindolin-5-yl)oxy)ethyl)phenoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 101 | | 2-((6-((5-chloro-2-(4-(((1r,4r)-4-((4-(2-(2,6-dioxopiperidin-3-yl)-1-oxoisoindolin-5-yl)piperazin-1-yl)methyl)cyclohexyl)(methyl)amino)piperidin-1-yl)pyrimidin-4-yl)amino)-1-methyl-2-oxo-1,2-dihydroquinolin-3-yl)oxy)-N-methylacetamide |
| 102 | | 2-((6-((5-chloro-2-(4-(((1s,4s)-4-((4-(2-(2,6-dioxopiperidin-3-yl)-1-oxoisoindolin-5-yl)piperazin-1-yl)methyl)cyclohexyl)(methyl)amino)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 103 | 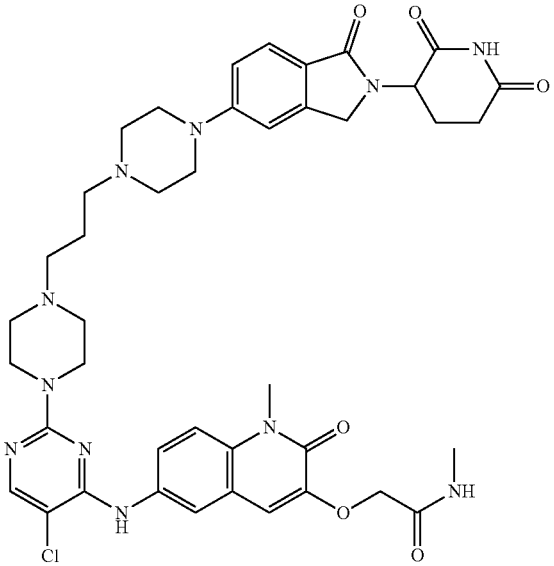 [SMILES: CNC(=O)COc1cc2cc(Nc3nc(N4CCN(CCCN5CCN(c6ccc7c(c6)CN(C6CCC(=O)NC6=O)C7=O)CC5)CC4)ncc3Cl)ccc2n(C)c1=O] | 2-((6-((5-chloro-2-(4-(3-(4-(2-(2,6-dioxopiperidin-3-yl)-1-oxoisoindolin-5-yl)piperazin-1-yl)propyl)piperazin-1-yl)pyrimidin-4-yl)amino)-1-methyl-2-oxo-1,2-dihydroquinolin-3-yl)oxy)-N-methylacetamide |
| 104 | 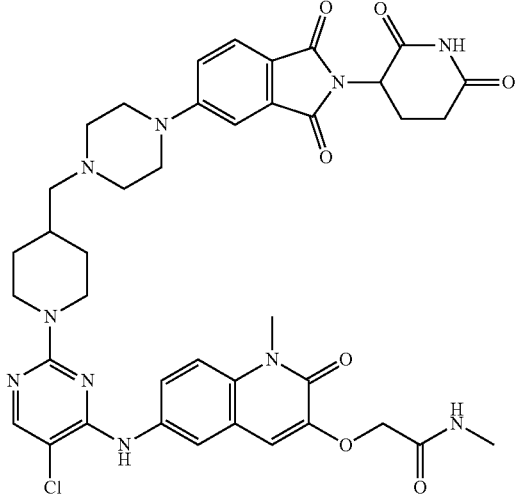 | 2-((6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylacetamide |
| 105 | 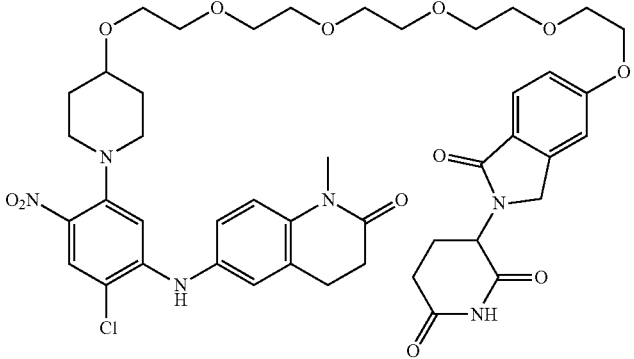 [SMILES: CN1C(=O)CCc2cc(Nc3cc(N4CCC(OCCOCCOCCOCCOCCOc5ccc6c(c5)CN(C5CCC(=O)NC5=O)C6=O)CC4)c([N+](=O)[O-])cc3Cl)ccc21] | 3-(5-((14-((1-(4-chloro-5-((1-methyl-2-oxo-1,2,3,4-tetrahydroquinolin-6-yl)amino)-2-nitrophenyl)piperidin-4-yl)oxy)-3,6,9,12-tetraoxatetradecyl)oxy)-1-oxoisoindolin-2-yl)piperidine-2,6-dione |

TABLE 1-continued

Exemplary bifunctional compounds of the present disclosure

| Ex. # | Parent Mol Structure | Name |
|---|---|---|
| 106 | | 2-((6-((5-chloro-2-(4-(1-(2-((2-(2,6-dioxopiperidin-3-yl)-1,3-dioxoisoindolin-5-yl)oxy)ethyl)-1H-1,2,3-triazol-4-yl)piperidin-1-yl)pyrimidin-4-yl)amino)-1-methyl-2-oxo-1,2-dihydroquinolin-3-yl)oxy)-N-methylacetamide |
| 107 | | 2-((6-((5-chloro-2-(4-(1-(2-(2-((2-(2,6-dioxopiperidin-3-yl)-1,3-dioxoisoindolin-5-yl)oxy)ethoxy)ethyl)-1H-1,2,3-triazol-4-yl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 108 | 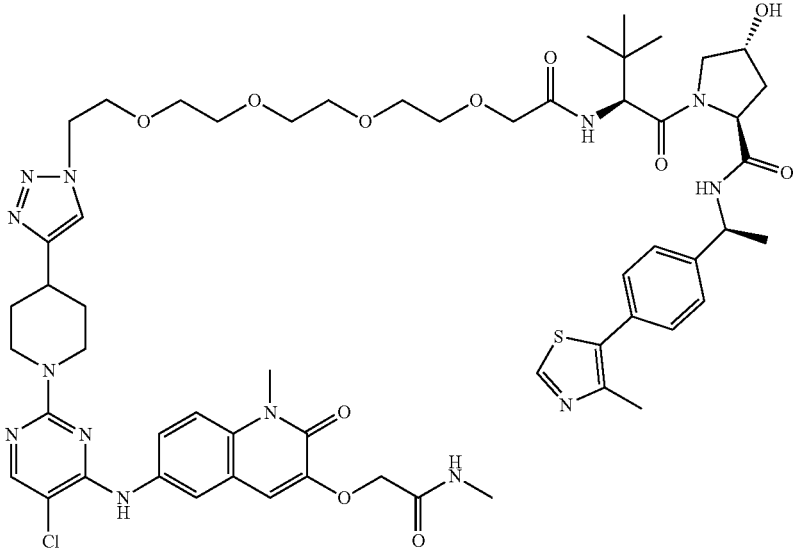 [SMILES: CNC(=O)COc1cc2cc(Nc3nc(N4CCC(c5cn(CCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] | (2S,4R)-1-((S)-2-(tert-butyl)-17-(4-(1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)-1H-1,2,3-triazol-1-yl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide |
| 109 | 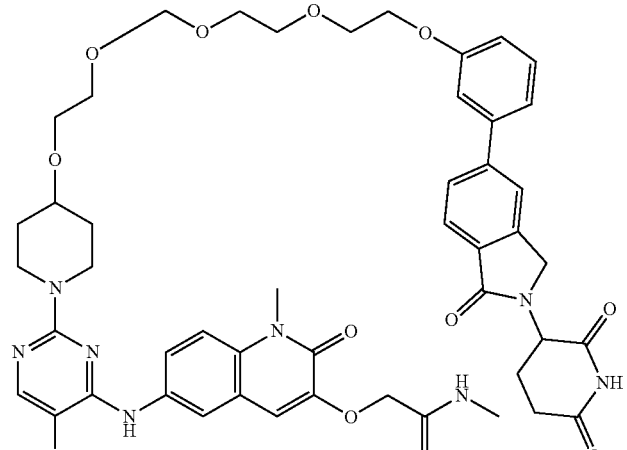 | 2-((6-((5-chloro-2-(4-(2-(2-(2-(2-(3-(2-(2,6-dioxopiperidin-3-yl)-1-oxoisoindolin-5-yl)phenoxy)ethoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 110 | 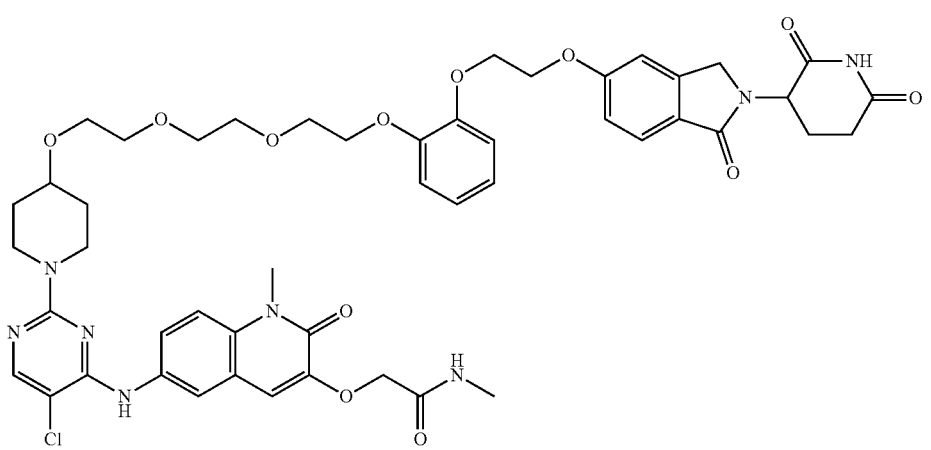 [SMILES: CNC(=O)COc1cc2cc(Nc3nc(N4CCC(OCCOCCOCCOc5ccccc5OCCOc5ccc6c(c5)CN(C5CCC(=O)NC5=O)C6=O)CC4)ncc3Cl)ccc2n(C)c1=O] | 2-((6-((5-chloro-2-(4-(2-(2-(2-(2-((2-(2-(2,6-dioxopiperidin-3-yl)-1-oxoisoindolin-5-yl)oxy)ethoxy)phenoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 111 | | 2-((6-((5-chloro-2-(4-(2-(2-(3-(2-(2-((2-(2,6-dioxopiperidin-3-yl)-1-oxoisoindolin-5-yl)oxy)ethyl)phenoxy)propoxy)ethoxy)ethoxy)piperidin-1-yl)pyrimidin-4-yl)amino)-1-methyl-2-oxo-1,2-dihydroquinolin-3-yl)oxy)-N-methylacetamide |
| 112 | | 2-((6-((5-chloro-2-(4-((1-(2-((2-(2,6-dioxopiperidin-3-yl)-1,3-dioxoisoindolin-5-yl)oxy)ethyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide |
| 113 | | 2-((6-((5-chloro-2-(4-((1-(2-(2-((2-(2,6-dioxopiperidin-3-yl)-1,3-dioxoisoindolin-5-yl)oxy)ethoxy)ethyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 114 | | (2S,4R)-1-((S)-2-(2-(2-(4-(1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)-1H-1,2,3-triazol-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 115 | | (2S,4R)-1-((S)-2-(2-(2-(2-(4-(1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)-1H-1,2,3-triazol-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary bifunctional compounds of the present disclosure

| Ex. # | Parent Mol Structure | Name |
|---|---|---|
| 116 | 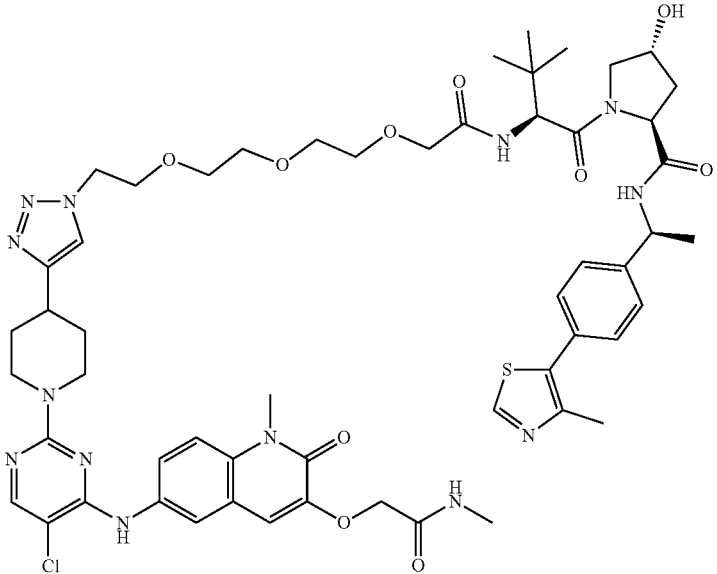 [SMILES: CNC(=O)COc1cc2cc(Nc3nc(N4CCC(c5cn(CCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] | (2S,4R)-1-((S)-2-(tert-butyl)-14-(4-(1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)-1H-1,2,3-triazol-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |
| 117 | 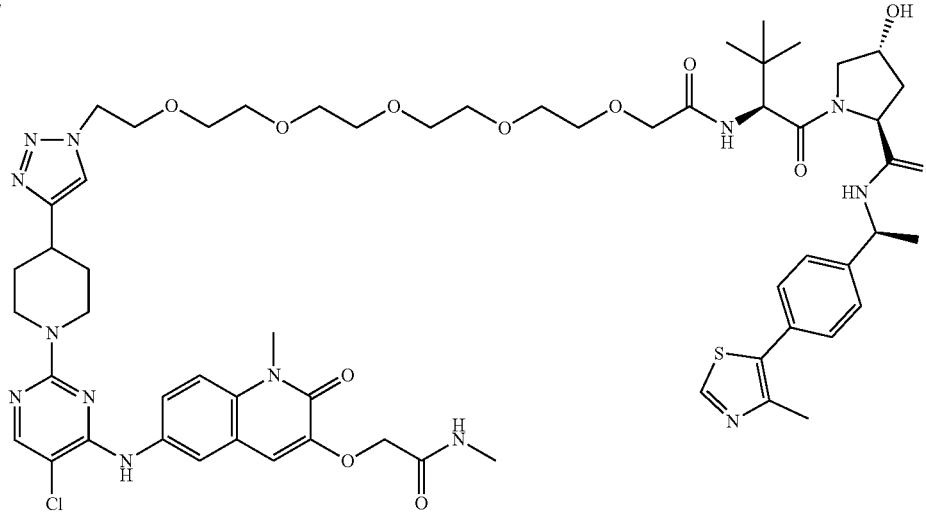 | (2S,4R)-1-((S)-2-(tert-butyl)-20-(4-(1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)-1H-1,2,3-triazol-1-yl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide |
| 118 | 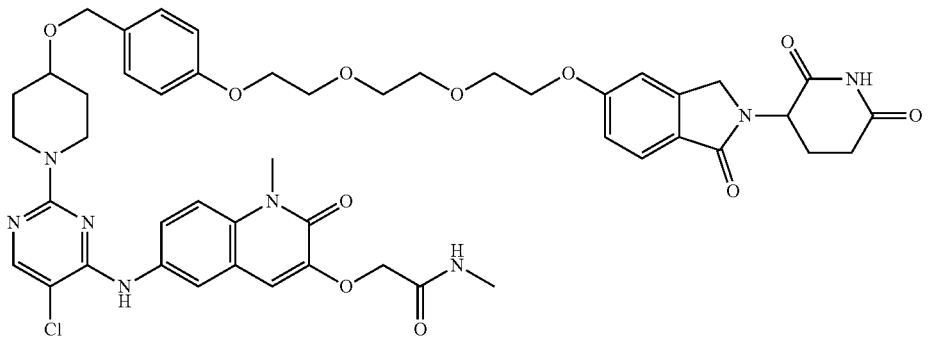 [SMILES: CNC(=O)COc1cc2cc(Nc3nc(N4CCC(OCc5ccc(OCCOCCOCCOc6ccc7c(c6)CN(C6CCC(=O)NC6=O)C7=O)cc5)CC4)ncc3Cl)ccc2n(C)c1=O] | 2-((6-((5-chloro-2-(4-((4-(2-(2-(2-((2-(2,6-dioxopiperidin-3-yl)-1-oxoisoindolin-5-yl)oxy)ethoxy)ethoxy)ethoxy)benzyl)oxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 119 | | 2-((6-((5-chloro-2-(4-(2-(4-(4-((2-(2-(2,6-dioxopiperidin-3-yl)-1-oxoisoindolin-5-yl)ethynyl)benzyl)piperazin-1-yl)ethoxy)piperidin-1-yl)pyrimidin-4-yl)amino)-1-methyl-2-oxo-1,2-dihydroquinolin-3-yl)oxy)-N-methylacetamide |
| 120 | | 2-((6-((5-chloro-2-(4-(1-(2-(2-(2-((2-(2,6-dioxopiperidin-3-yl)-1,3-dioxoisoindolin-5-yl)oxy)ethoxy)ethoxy)ethyl)-1H-1,2,3-triazol-4-yl)piperidin-1-yl)pyrimidin-4-yl)amino)-1-methyl-2-oxo-1,2-dihydroquinolin-3-yl)oxy)-N-methylacetamide |
| 121 | | 2-((6-((5-chloro-2-(4-(1-(14-((2-(2,6-dioxopiperidin-3-yl)-1,3-dioxoisoindolin-5-yl)oxy)-3,6,9,12-tetraoxatetradecyl)-1H-1,2,3-triazol-4-yl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 122 | | (2S,4R)-1-((S)-2-(2-(2-(4-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)methyl)-1H-1,2,3-triazol-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 123 | | (2S,4R)-1-((S)-2-(tert-butyl)-14-(4-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)methyl)-1H-1,2,3-triazol-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |

TABLE 1-continued

Exemplary bifunctional compounds of the present disclosure

| Ex. # | Parent Mol Structure | Name |
|---|---|---|
| 124 | 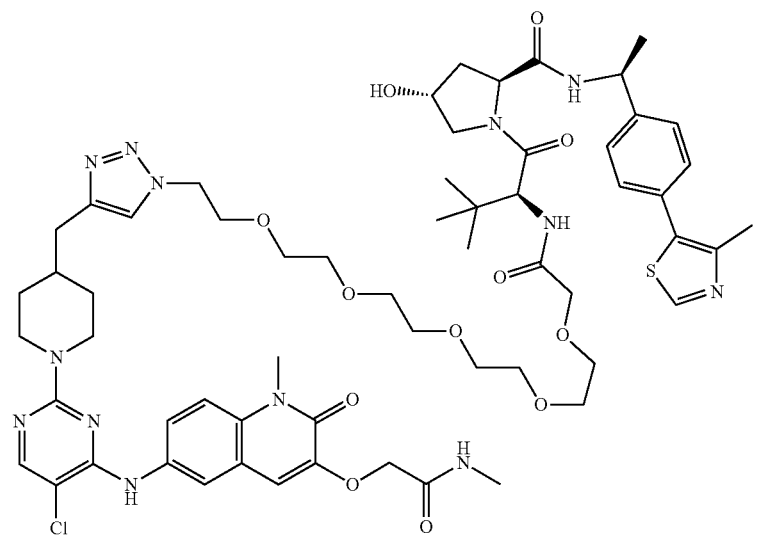 [SMILES: CNC(=O)COc1cc2cc(Nc3nc(N4CCC(Cc5cn(CCOCCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] | (2S,4R)-1-((S)-2-(tert-butyl)-20-(4-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)methyl)-1H-1,2,3-triazol-1-yl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide |
| 125 | 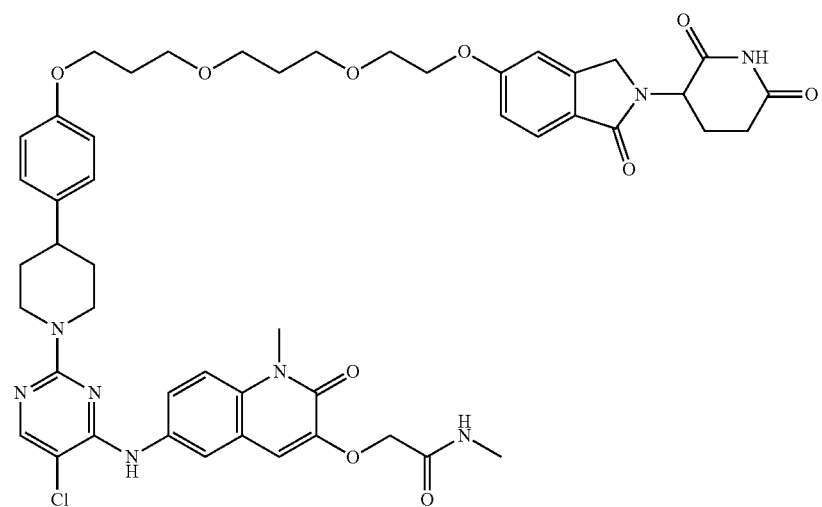 [SMILES: CNC(=O)COc1cc2cc(Nc3nc(N4CCC(c5ccc(OCCCOCCCOCCOc6ccc7c(c6)CN(C6CCC(=O)NC6=O)C7=O)cc5)CC4)ncc3Cl)ccc2n(C)c1=O] | 2-((6-((5-chloro-2-(4-(4-(3-(3-(2-((2-(2,6-dioxopiperidin-3-yl)-1-oxoisoindolin-5-yl)oxy)ethoxy)propoxy)propoxy)phenyl)piperidin-1-yl)pyrimidin-4-yl)amino)-1-methyl-2-oxo-1,2-dihydroquinolin-3-yl)oxy)-N-methylacetamide |
| 126 | 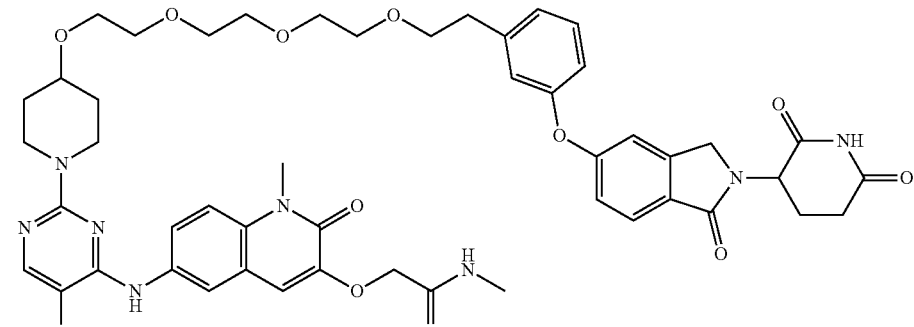 | 2-((6-((5-chloro-2-(4-(2-(2-(2-(2-(3-((2-(2,6-dioxopiperidin-3-yl)-1-oxoisoindolin-5-yl)oxy)phenethoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 127 | | 2-((6-((5-chloro-2-(3-((4-(1-(3-(2-(2,6-dioxopiperidin-3-yl)-1-oxoisoindolin-5-yl)-3-hydroxypropyl)piperidin-4-yl)phenoxy)methyl)piperidin-1-yl)pyrimidin-4-yl)amino)-1-methyl-2-oxo-1,2-dihydroquinolin-3-yl)oxy)-N-methylacetamide |
| 128 | | 3-(5-(4-(2-((1-(5-chloro-4-((1-methyl-2-oxo-3-(2-oxopropoxy)-1,2-dihydroquinolin-6-yl)amino)pyrimidin-2-yl)piperidin-4-yl)oxy)ethyl)piperazin-1-yl)-1-oxoisoindolin-2-yl)piperidine-2,6-dione |
| 129 | | 2-((6-((5-chloro-2-(4-(1-(2-(2-(2-(2-((2-(2,6-dioxopiperidin-3-yl)-1,3-dioxoisoindolin-5-yl)oxy)ethoxy)ethoxy)ethoxy)ethyl)-1H-1,2,3-triazol-4-yl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 130 | | 2-((6-((5-chloro-2-(4-((1-(2-(2-(2-((2-(2,6-dioxopiperidin-3-yl)-1,3-dioxoisoindolin-5-yl)oxy)ethoxy)ethoxy)ethyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide |
| 131 | | 2-((6-((5-chloro-2-(4-((1-(2-(2-(2-((2-(2,6-dioxopiperidin-3-yl)-1,3-dioxoisoindolin-5-yl)oxy)ethoxy)ethoxy)ethoxy)ethyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide |
| 132 | | 2-((6-((5-chloro-2-(4-((1-(14-((2-(2,6-dioxopiperidin-3-yl)-1,3-dioxoisoindolin-5-yl)oxy)-3,6,9,12-tetraoxatetradecyl)-1H-1,2,3-triazol-4-yl)methyl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 133 | | (2S,4R)-1-((S)-2-(2-(2-(2-(4-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)methyl)-1H-1,2,3-triazol-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 134 | | 2-((6-((5-chloro-2-(4-(2-(2-(2-(2-(2-((2-(2,6-dioxopiperidin-3-yl)-1-oxoisoindolin-5-yl)oxy)phenoxy)ethoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |
| 135 | | 2-((6-((5-chloro-2-(4-(2-(2-(2-((4-((2-(2,6-dioxopiperidin-3-yl)-1-oxoisoindolin-5-yl)oxy)benzyl)oxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 136 | | 2-((6-((5-chloro-2-(4-((2-(4-(2-(2-((2-(2,6-dioxopiperidin-3-yl)-1-oxoisoindolin-5-yl)oxy)ethoxy)ethoxy)butoxy)benzyl)oxy)piperidin-1-yl)pyrimidin-4-yl)amino)-1-methyl-2-oxo-1,2-dihydroquinolin-3-yl)oxy)-N-methylacetamide |
| 137 | | 3-(5-(4-(3-(4-(5-chloro-4-((1-methyl-2-oxo-3-(2-oxopropoxy)-1,2-dihydroquinolin-6-yl)amino)pyrimidin-2-yl)piperazin-1-yl)propyl)piperazin-1-yl)-1-oxoisoindolin-2-yl)piperidine-2,6-dione |
| 138 | | 2-((6-((5-chloro-2-(4-((1-((1-(4-((2-(2,6-dioxopiperidin-3-yl)-1-oxoisoindolin-5-yl)ethynyl)phenyl)piperidin-4-yl)methyl)piperidin-4-yl)(methyl)amino)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 139 | | 2-((6-((5-chloro-2-(4-(3-((2-(2,6-dioxopiperidin-3-yl)-1-oxoisoindolin-5-yl)oxy)propoxy)piperidin-1-yl)pyrimidin-4-yl)amino)-1-methyl-2-oxo-1,2-dihydroquinolin-3-yl)oxy)-N-methylacetamide |
| 140 | | 2-((6-((5-chloro-2-(4-(3-(3-((2-(2,6-dioxopiperidin-3-yl)-1-oxoisoindolin-5-yl)oxy)propoxy)propoxy)piperidin-1-yl)pyrimidin-4-yl)amino)-1-methyl-2-oxo-1,2-dihydroquinolin-3-yl)oxy)-N-methylacetamide |
| 141 | | (2S,4R)-N-(2-(3-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)propoxy)-4-(4-methylthiazol-5-yl)benzyl)-4-hydroxy-1-(3-methyl-2-(3-methylisoxazol-5-yl)butanoyl)pyrrolidine-2-carboxamide |

TABLE 1-continued

Exemplary bifunctional compounds of the present disclosure

| Ex. # | Parent Mol Structure | Name |
|---|---|---|
| 142 | | 2-((6-((5-chloro-2-(4-(4-((2-(2,6-dioxopiperidin-3-yl)-1-oxoisoindolin-5-yl)oxy)butoxy)piperidin-1-yl)pyrimidin-4-yl)amino)-1-methyl-2-oxo-1,2-dihydroquinolin-3-yl)oxy)-N-methylacetamide |
| 143 | | 2-((6-((5-chloro-2-(4-(2-(4-((3-(2-(2,6-dioxopiperidin-3-yl)-1-oxoisoindolin-5-yl)prop-2-yn-1-yl)oxy)-[1,4'-bipiperidin]-1'-yl)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 144 | 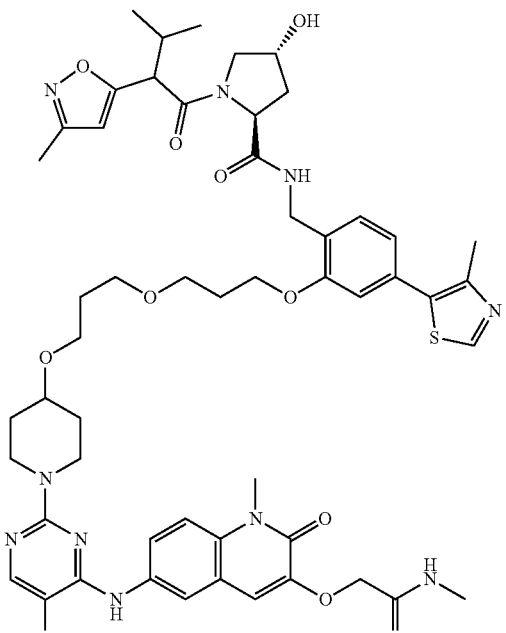 | (2S,4R)-N-(2-(3-(3-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)propoxy)propoxy)-4-(4-methylthiazol-5-yl)benzyl)-4-hydroxy-1-(3-methyl-2-(3-methylisoxazol-5-yl)butanoyl)pyrrolidine-2-carboxamide |
| 145 | 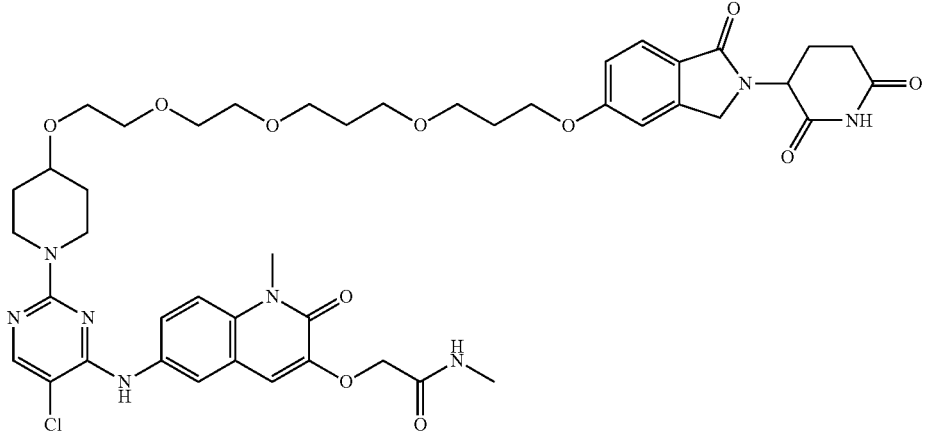 [SMILES: CNC(=O)COc1cc2cc(Nc3nc(N4CCC(OCCOCCOCCCOCCCOc5ccc6c(c5)CN(C5CCC(=O)NC5=O)C6=O)CC4)ncc3Cl)ccc2n(C)c1=O] | 2-((6-((5-chloro-2-(4-(2-(2-(3-(3-((2-(2,6-dioxopiperidin-3-yl)-1-oxoisoindolin-5-yl)oxy)propoxy)propoxy)ethoxy)ethoxy)piperidin-1-yl)pyrimidin-4-yl)amino)-1-methyl-2-oxo-1,2-dihydroquinolin-3-yl)oxy)-N-methylacetamide |
| 146 | 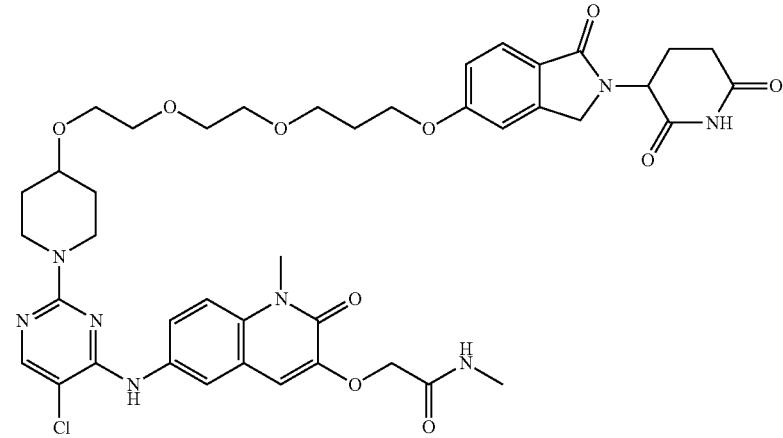 [SMILES: CNC(=O)COc1cc2cc(Nc3nc(N4CCC(OCCOCCOCCCOc5ccc6c(c5)CN(C5CCC(=O)NC5=O)C6=O)CC4)ncc3Cl)ccc2n(C)c1=O] | 2-((6-((5-chloro-2-(4-(2-(2-(3-((2-(2,6-dioxopiperidin-3-yl)-1-oxoisoindolin-5-yl)oxy)propoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 147 | 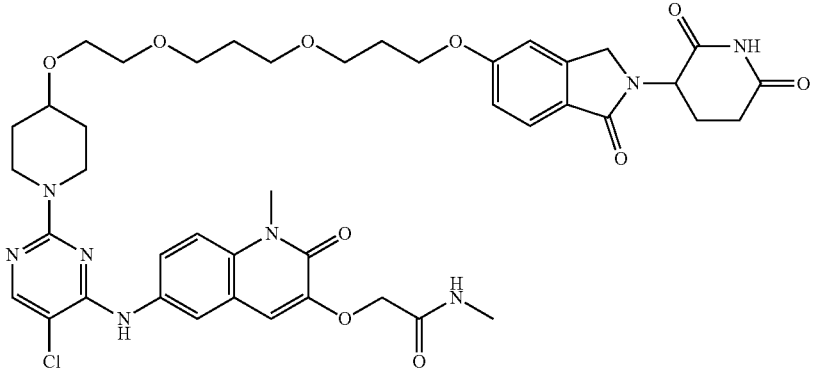 [SMILES: CNC(=O)COc1cc2cc(Nc3nc(N4CCC(OCCOCCCOCCCOc5ccc6c(c5)CN(C5CCC(=O)NC5=O)C6=O)CC4)ncc3Cl)ccc2n(C)c1=O] | 2-((6-((5-chloro-2-(4-(2-(3-(3-((2-(2,6-dioxopiperidin-3-yl)-1-oxoisoindolin-5-yl)oxy)propoxy)propoxy)ethoxy)piperidin-1-yl)pyrimidin-4-yl)amino)-1-methyl-2-oxo-1,2-dihydroquinolin-3-yl)oxy)-N-methylacetamide |
| 148 | 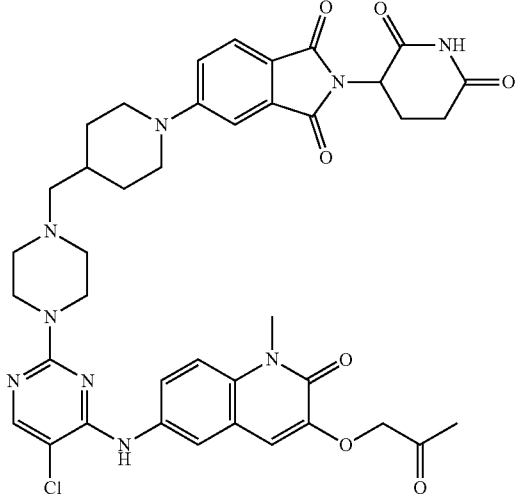 | 5-(4-((4-(5-chloro-4-((1-methyl-2-oxo-3-(2-oxopropoxy)-1,2-dihydroquinolin-6-yl)amino)pyrimidin-2-yl)piperazin-1-yl)methyl)piperidin-1-yl)-2-(2,6-dioxopiperidin-3-yl)isoindoline-1,3-dione |
| 149 | 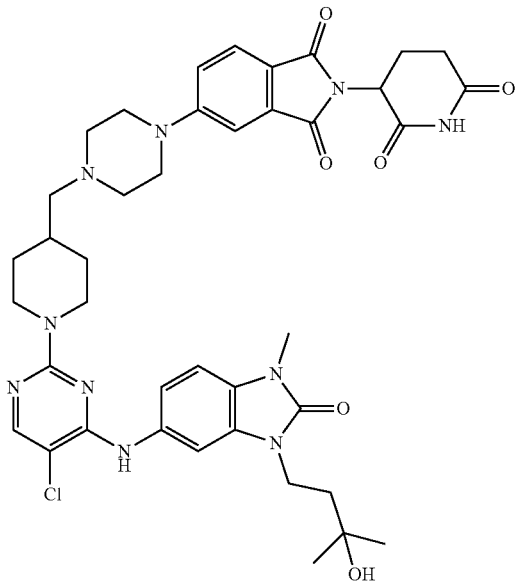 [SMILES: Cn1c(=O)n(CCC(C)(C)O)c2cc(Nc3nc(N4CCC(CN5CCN(c6ccc7c(c6)C(=O)N(C6CCC(=O)NC6=O)C7=O)CC5)CC4)ncc3Cl)ccc21] | 5-(4-((1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 150 | 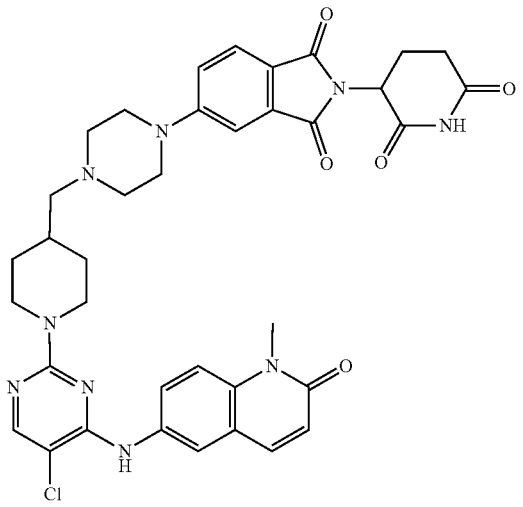 [SMILES: Cn1c(=O)ccc2cc(Nc3nc(N4CCC(CN5CCN(c6ccc7c(c6)C(=O)N(C6CCC(=O)NC6=O)C7=O)CC5)CC4)ncc3Cl)ccc21] | 5-(4-((1-(5-chloro-4-((1-methyl-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |
| 151 | 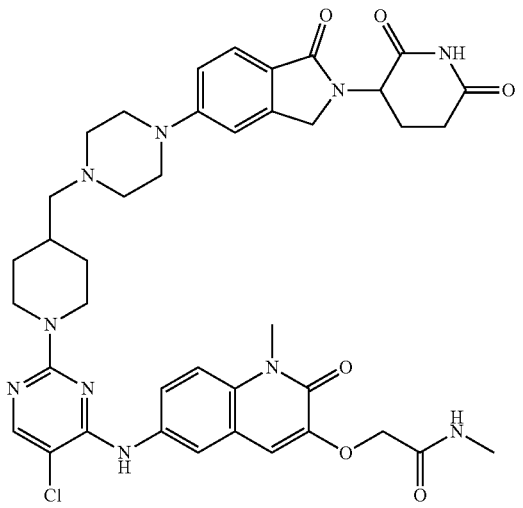 [SMILES: CNC(=O)COc1cc2cc(Nc3nc(N4CCC(CN5CCN(c6ccc7c(c6)CN(C6CCC(=O)NC6=O)C7=O)CC5)CC4)ncc3Cl)ccc2n(C)c1=O] | 2-((6-((5-chloro-2-(4-((4-(2-(2,6-dioxopiperidin-3-yl)-1-oxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylacetamide |
| 152 | 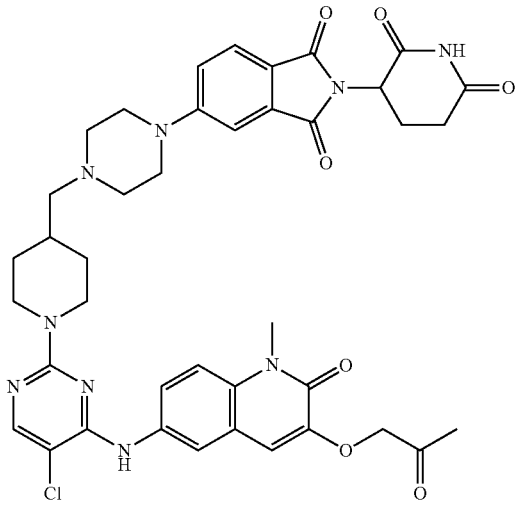 | 5-(4-((1-(5-chloro-4-((1-methyl-2-oxo-3-(2-oxopropoxy)-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 153 | 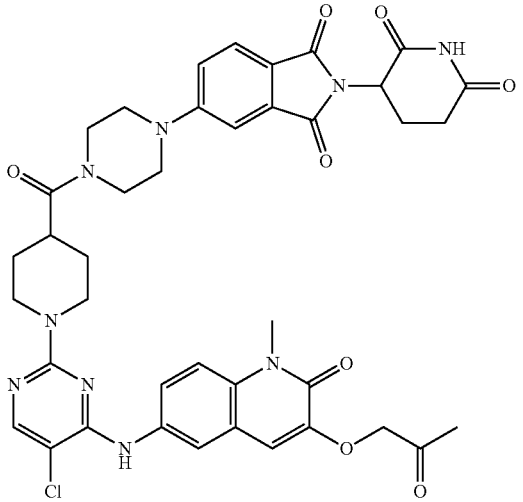 [SMILES: CC(=O)COc1cc2cc(Nc3nc(N4CCC(C(=O)N5CCN(c6ccc7c(c6)C(=O)N(C6CCC(=O)NC6=O)C7=O)CC5)CC4)ncc3Cl)ccc2n(C)c1=O] | 5-(4-(1-(5-chloro-4-((1-methyl-2-oxo-3-(2-oxopropoxy)-1,2-dihydroquinolin-6-yl)amino)pyrimidin-2-yl)piperidine-4-carbonyl)piperazin-1-yl)-2-(2,6-dioxopiperidin-3-yl)isoindoline-1,3-dione |
| 154 | 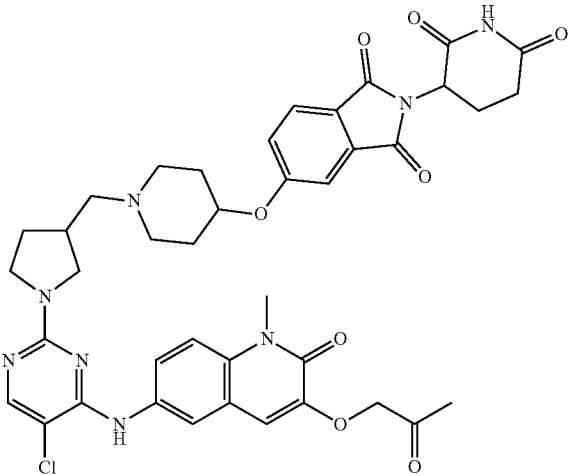 [SMILES: CC(=O)COc1cc2cc(Nc3nc(N4CCC(CN5CCC(Oc6ccc7c(c6)C(=O)N(C6CCC(=O)NC6=O)C7=O)CC5)C4)ncc3Cl)ccc2n(C)c1=O] | 5-((1-((1-(5-chloro-4-((1-methyl-2-oxo-3-(2-oxopropoxy)-1,2-dihydroquinolin-6-yl)amino)pyrimidin-2-yl)pyrrolidin-3-yl)methyl)piperidin-4-yl)oxy)-2-(2,6-dioxopiperidin-3-yl)isoindoline-1,3-dione |
| 155 | 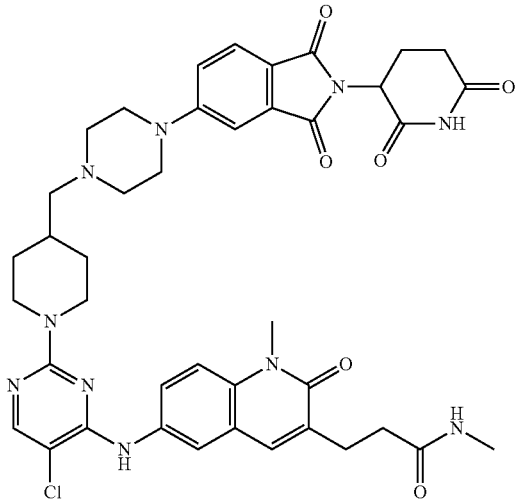 [SMILES: CNC(=O)CCc1cc2cc(Nc3nc(N4CCC(CN5CCN(c6ccc7c(c6)C(=O)N(C6CCC(=O)NC6=O)C7=O)CC5)CC4)ncc3Cl)ccc2n(C)c1=O] | 3-(6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)-N-methylpropanamide |

TABLE 1-continued

Exemplary bifunctional compounds of the present disclosure

| Ex. # | Parent Mol Structure | Name |
|---|---|---|
| 156 | 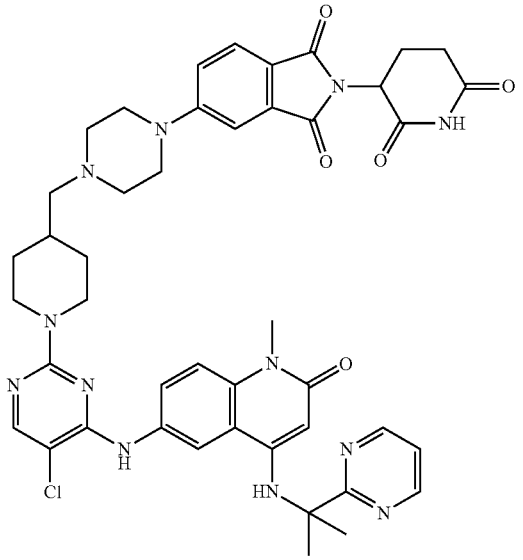 [SMILES: Cn1c(=O)cc(NC(C)(C)c2ncccn2)c2cc(Nc3nc(N4CCC(CN5CCN(c6ccc7c(c6)C(=O)N(C6CCC(=O)NC6=O)C7=O)CC5)CC4)ncc3Cl)ccc21] | 5-(4-((1-(5-chloro-4-((1-methyl-2-oxo-4-((2-(pyrimidin-2-yl)propan-2-yl)amino)-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |
| 157 | 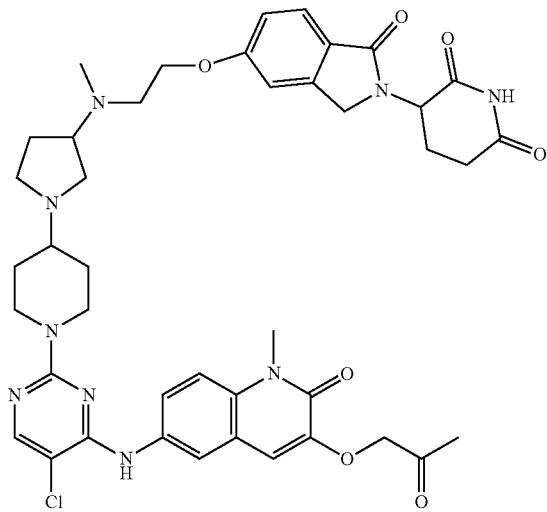 [SMILES: CC(=O)COc1cc2cc(Nc3nc(N4CCC(N5CCC(N(C)CCOc6ccc7c(c6)CN(C6CCC(=O)NC6=O)C7=O)C5)CC4)ncc3Cl)ccc2n(C)c1=O] | 3-(5-(2-((1-(1-(5-chloro-4-((1-methyl-2-oxo-3-(2-oxopropoxy)-1,2-dihydroquinolin-6-yl)amino)pyrimidin-2-yl)piperidin-4-yl)pyrrolidin-3-yl)(methyl)amino)ethoxy)-1-oxoisoindolin-2-yl)piperidine-2,6-dione |

TABLE 1-continued

Exemplary bifunctional compounds of the present disclosure

| Ex. # | Parent Mol Structure | Name |
|---|---|---|
| 158 | | 3-(5-(3-(3-(4-(5-chloro-4-((1-methyl-2-oxo-3-(2-oxopropoxy)-1,2-dihydroquinolin-6-yl)amino)pyrimidin-2-yl)piperazin-1-yl)pyrrolidin-1-yl)propoxy)-1-oxoisoindolin-2-yl)piperidine-2,6-dione |
| 159 | | (2S,4R)-N-(2-(4-((1-(5-chloro-4-((1-methyl-3-(2-(methylamino)-2-oxoethoxy)-2-oxo-1,2-dihydroquinolin-6-yl)amino)pyrimidin-2-yl)piperidin-4-yl)oxy)butoxy)-4-(4-methylthiazol-5-yl)benzyl)-4-hydroxy-1-(3-methyl-2-(3-methylisoxazol-5-yl)butanoyl)pyrrolidine-2-carboxamide |

TABLE 1-continued

Exemplary bifunctional compounds of the present disclosure

| Ex. # | Parent Mol Structure | Name |
|---|---|---|
| 160 | | 5-(4-(4-(5-chloro-4-((1-methyl-2-oxo-3-(2-oxopropoxy)-1,2-dihydroquinolin-6-yl)amino)pyrimidin-2-yl)piperazin-1-yl)piperidin-1-yl)-2-(2,6-dioxopiperidin-3-yl)isoindoline-1,3-dione |
| 161 | | 5-(3-(4-(5-chloro-4-((1-methyl-2-oxo-3-(2-oxopropoxy)-1,2-dihydroquinolin-6-yl)amino)pyrimidin-2-yl)piperazin-1-yl)piperidin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 162 | 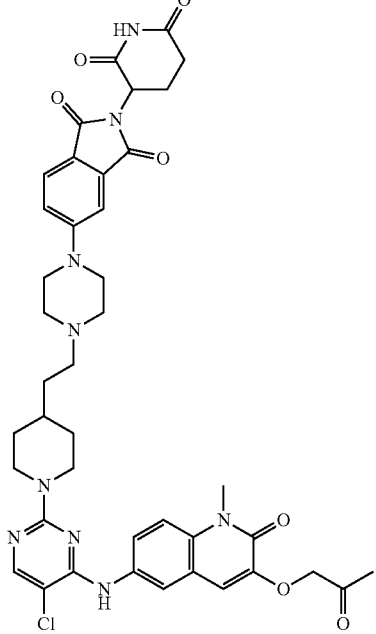 [SMILES: CC(=O)COc1cc2cc(Nc3nc(N4CCC(CCN5CCN(c6ccc7c(c6)C(=O)N(C6CCC(=O)NC6=O)C7=O)CC5)CC4)ncc3Cl)ccc2n(C)c1=O] | 5-(4-(2-(1-(5-chloro-4-((1-methyl-2-oxo-3-(2-oxopropoxy)-1,2-dihydroquinolin-6-yl)amino)pyrimidin-2-yl)piperidin-4-yl)ethyl)piperazin-1-yl)-2-(2,6-dioxopiperidin-3-yl)isoindoline-1,3-dione |
| 163 | 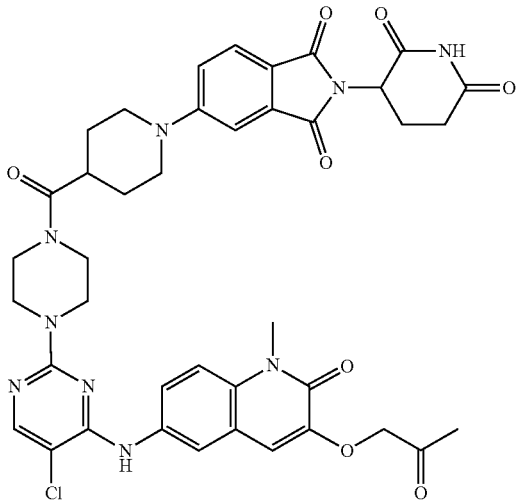 [SMILES: CC(=O)COc1cc2cc(Nc3nc(N4CCN(C(=O)C5CCN(c6ccc7c(c6)C(=O)N(C6CCC(=O)NC6=O)C7=O)CC5)CC4)ncc3Cl)ccc2n(C)c1=O] | 5-(4-(4-(5-chloro-4-((1-methyl-2-oxo-3-(2-oxopropoxy)-1,2-dihydroquinolin-6-yl)amino)pyrimidin-2-yl)piperazine-1-carbonyl)piperidin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 164 | 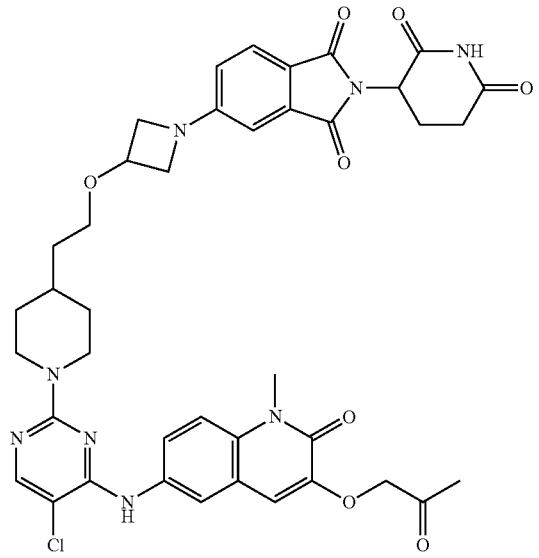 [SMILES: CC(=O)COc1cc2cc(Nc3nc(N4CCC(CCOC5CN(c6ccc7c(c6)C(=O)N(C6CCC(=O)NC6=O)C7=O)C5)CC4)ncc3Cl)ccc2n(C)c1=O] | 5-(3-(2-(1-(5-chloro-4-((1-methyl-2-oxo-3-(2-oxopropoxy)-1,2-dihydroquinolin-6-yl)amino)pyrimidin-2-yl)piperidin-4-yl)ethoxy)azetidin-1-yl)-2-(2,6-dioxopiperidin-3-yl)isoindoline-1,3-dione |
| 165 | 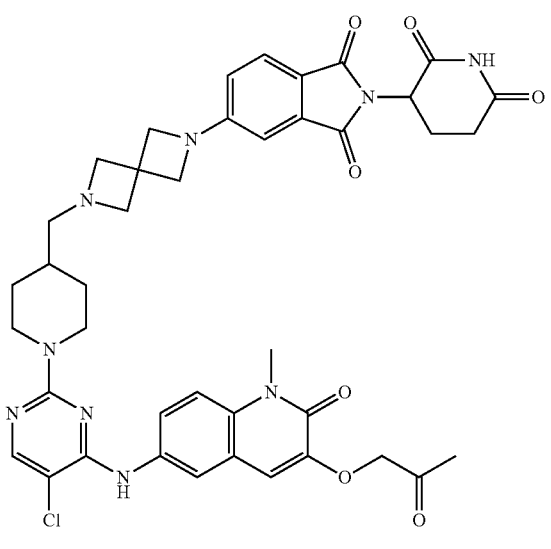 [SMILES: CC(=O)COc1cc2cc(Nc3nc(N4CCC(CN5CC6(C5)CN(c5ccc7c(c5)C(=O)N(C5CCC(=O)NC5=O)C7=O)C6)CC4)ncc3Cl)ccc2n(C)c1=O] | 5-(6-((1-(5-chloro-4-((1-methyl-2-oxo-3-(2-oxopropoxy)-1,2-dihydroquinolin-6-yl)amino)pyrimidin-2-yl)piperidin-4-yl)methyl)-2,6-diazaspiro[3.3]heptan-2-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 166 | | 2-((6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N,N-dimethylacetamide |
| 167 | | 2-((6-((5-chloro-2-(3-((4-(1-(3-(2-(2,6-dioxopiperidin-3-yl)-1-oxoisoindolin-5-yl)prop-2-yn-1-yl)piperidin-4-yl)phenoxy)methyl)piperidin-1-yl)pyrimidin-4-yl)amino)-1-methyl-2-oxo-1,2-dihydroquinolin-3-yl)oxy)-N-methylacetamide |
| 168 | | 2-((6-((5-chloro-2-(4-(2-(2-(2-(3-((2-(2,6-dioxopiperidin-3-yl)-1-oxoisoindolin-5-yl)oxy)propoxy)ethoxy)ethoxy)ethoxy)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 169 | | 5-(4-((1-(5-chloro-4-((1-methyl-2-oxo-3-(2-oxopropoxy)-1,2-dihydroquinolin-6-yl)amino)pyrimidin-2-yl)piperidin-4-yl)(methyl)amino)piperidin-1-yl)-2-(2,6-dioxopiperidin-3-yl)isoindoline-1,3-dione |
| 170 | | 5-(4-((1-(5-chloro-4-((1-methyl-2-oxo-3-(2-oxopropoxy)-1,2-dihydroquinolin-6-yl)amino)pyrimidin-2-yl)piperidin-4-yl)oxy)piperidin-1-yl)-2-(2,6-dioxopiperidin-3-yl)isoindoline-1,3-dione |
| 171 | | 5-(4-((5-chloro-4-((1-methyl-2-oxo-3-(2-oxopropoxy)-1,2-dihydroquinolin-6-yl)amino)pyrimidin-2-yl)ethynyl)piperidin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 172 | 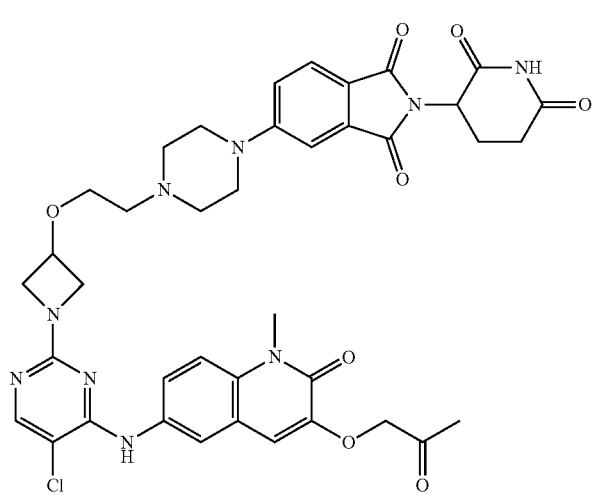 [SMILES: CC(=O)COc1cc2cc(Nc3nc(N4CC(OCCN5CCN(c6ccc7c(c6)C(=O)N(C6CCC(=O)NC6=O)C7=O)CC5)C4)ncc3Cl)ccc2n(C)c1=O] | 5-(4-(2-((1-(5-chloro-4-((1-methyl-2-oxo-3-(2-oxopropoxy)-1,2-dihydroquinolin-6-yl)amino)pyrimidin-2-yl)azetidin-3-yl)oxy)ethyl)piperazin-1-yl)-2-(2,6-dioxopiperidin-3-yl)isoindoline-1,3-dione |
| 173 | 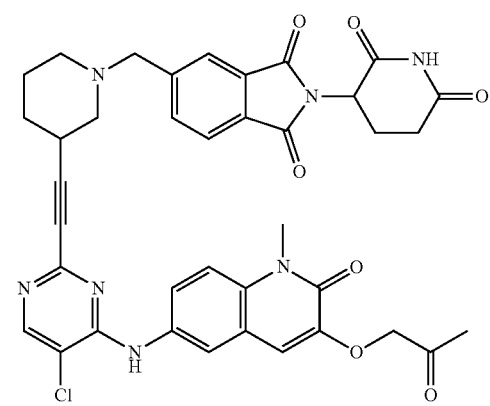 [SMILES: CC(=O)COc1cc2cc(Nc3nc(C#CC4CCCN(Cc5ccc6c(c5)C(=O)N(C5CCC(=O)NC5=O)C6=O)C4)ncc3Cl)ccc2n(C)c1=O] | 5-((3-((5-chloro-4-((1-methyl-2-oxo-3-(2-oxopropoxy)-1,2-dihydroquinolin-6-yl)amino)pyrimidin-2-yl)ethynyl)piperidin-1-yl)methyl)-2-(2,6-dioxopiperidin-3-yl)isoindoline-1,3-dione |
| 174 | 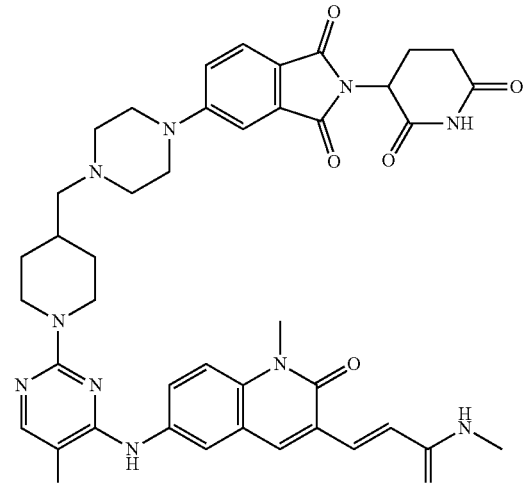 | (E)-3-(6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)-N-methylacrylamide |

TABLE 1-continued

Exemplary bifunctional compounds of the present disclosure

| Ex. # | Parent Mol Structure | Name |
|---|---|---|
| 175 | 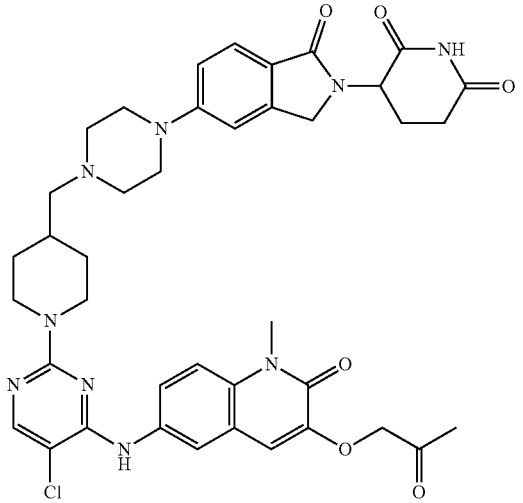 [SMILES: CC(=O)COc1cc2cc(Nc3nc(N4CCC(CN5CCN(c6ccc7c(c6)CN(C6CCC(=O)NC6=O)C7=O)CC5)CC4)ncc3Cl)ccc2n(C)c1=O] | 3-(5-(4-((1-(5-chloro-4-((1-methyl-2-oxo-3-(2-oxopropoxy)-1,2-dihydroquinolin-6-yl)amino)pyrimidin-2-yl)piperidin-4-yl)methyl)piperazin-1-yl)-1-oxoisoindolin-2-yl)piperidine-2,6-dione |
| 176 | 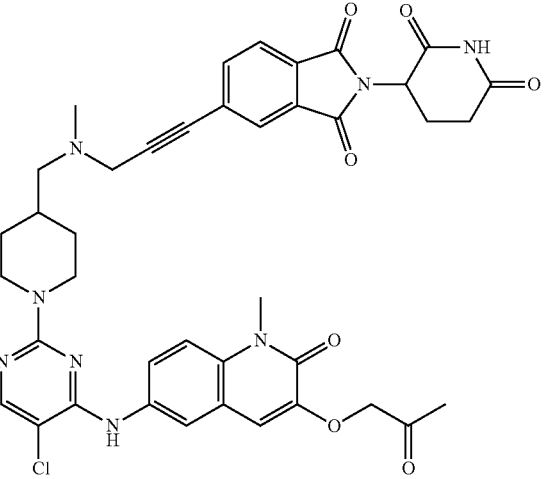 | 5-(3-(((1-(5-chloro-4-((1-methyl-2-oxo-3-(2-oxopropoxy)-1,2-dihydroquinolin-6-yl)amino)pyrimidin-2-yl)piperidin-4-yl)methyl)(methyl)amino)prop-1-yn-1-yl)-2-(2,6-dioxopiperidin-3-yl)isoindoline-1,3-dione |
| 177 | 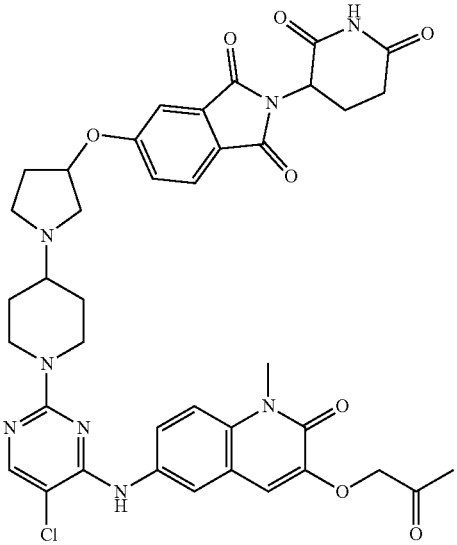 [SMILES: CC(=O)COc1cc2cc(Nc3nc(N4CCC(N5CCC(Oc6ccc7c(c6)C(=O)N(C6CCC(=O)NC6=O)C7=O)C5)CC4)ncc3Cl)ccc2n(C)c1=O] | 5-((1-(1-(5-chloro-4-((1-methyl-2-oxo-3-(2-oxopropoxy)-1,2-dihydroquinolin-6-yl)amino)pyrimidin-2-yl)piperidin-4-yl)pyrrolidin-3-yl)oxy)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 178 | | 5-(3-((1-(5-chloro-4-((1-methyl-2-oxo-3-(2-oxopropoxy)-1,2-dihydroquinolin-6-yl)amino)pyrimidin-2-yl)piperidin-4-yl)oxy)azetidin-1-yl)-2-(2,6-dioxopiperidin-3-yl)isoindoline-1,3-dione |
| 179 | | 5-((4-(5-chloro-4-((1-methyl-2-oxo-3-(2-oxopropoxy)-1,2-dihydroquinolin-6-yl)amino)pyrimidin-2-yl)morpholin-2-yl)methoxy)-2-(2,6-dioxopiperidin-3-yl)isoindoline-1,3-dione |
| 180 | | 5-(4-(2-((1-(5-chloro-4-((1-methyl-2-oxo-3-(2-oxopropoxy)-1,2-dihydroquinolin-6-yl)amino)pyrimidin-2-yl)pyrrolidin-3-yl)oxy)ethoxy)piperidin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 181 | | 5-(3-((5-chloro-4-((1-methyl-2-oxo-3-(2-oxopropoxy)-1,2-dihydroquinolin-6-yl)amino)pyrimidin-2-yl)ethynyl)piperidin-1-yl)-2-(2,6-dioxopiperidin-3-yl)isoindoline-1,3-dione |
| 182 | | 5-((1-(1-(5-chloro-4-((1-methyl-2-oxo-3-(2-oxopropoxy)-1,2-dihydroquinolin-6-yl)amino)pyrimidin-2-yl)piperidin-4-yl)pyrrolidin-2-yl)methoxy)-2-(2,6-dioxopiperidin-3-yl)isoindoline-1,3-dione |
| 183 | | 5-(4-((1-(5-chloro-4-((1-methyl-2-oxo-3-(2-oxopropoxy)-1,2-dihydroquinolin-6-yl)amino)pyrimidin-2-yl)azetidin-3-yl)oxy)piperidin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 184 | | 4-(4-((5-chloro-4-((1-methyl-2-oxo-3-(2-oxopropoxy)-1,2-dihydroquinolin-6-yl)amino)pyrimidin-2-yl)ethynyl)piperidin-1-yl)-2-(2,6-dioxopiperidin-3-yl)isoindoline-1,3-dione |
| 185 | | 5-((4-((5-chloro-4-((1-methyl-2-oxo-3-(2-oxopropoxy)-1,2-dihydroquinolin-6-yl)amino)pyrimidin-2-yl)ethynyl)piperidin-1-yl)methyl)-2-(2,6-dioxopiperidin-3-yl)isoindoline-1,3-dione |
| 186 | | 5-(4-((1-(5-chloro-4-((1-methyl-2-oxo-3-(3-oxobutyl)-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 187 | | 5-(4-((1-(5-chloro-4-((1-methyl-2-oxo-3-(2-oxopropoxy)-1,2-dihydroquinolin-6-yl)amino)pyrimidin-2-yl)-4-hydroxypiperidin-4-yl)methyl)piperazin-1-yl)-2-(2,6-dioxopiperidin-3-yl)isoindoline-1,3-dione |
| 188 | | 5-(4-((4-(5-chloro-4-((1-methyl-2-oxo-3-(2-oxopropoxy)-1,2-dihydroquinolin-6-yl)amino)pyrimidin-2-yl)-3,6-dihydropyridin-1(2H)-yl)methyl)piperidin-1-yl)-2-(2,6-dioxopiperidin-3-yl)isoindoline-1,3-dione |
| 189 | | 5-(2-(3-((5-chloro-4-((1-methyl-2-oxo-3-(2-oxopropoxy)-1,2-dihydroquinolin-6-yl)amino)pyrimidin-2-yl)ethynyl)piperidin-1-yl)ethoxy)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 190 | 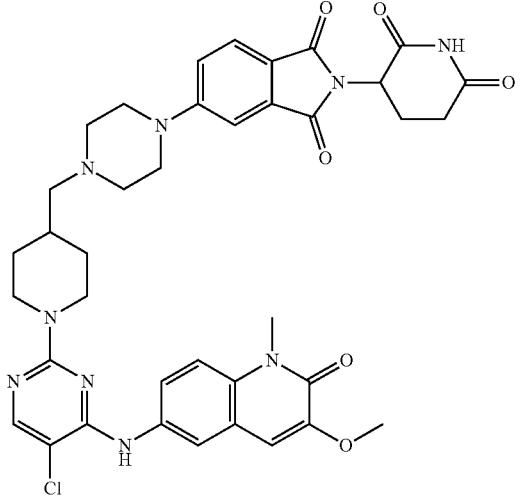 [SMILES: COc1cc2cc(Nc3nc(N4CCC(CN5CCN(c6ccc7c(c6)C(=O)N(C6CCC(=O)NC6=O)C7=O)CC5)CC4)ncc3Cl)ccc2n(C)c1=O] | 5-(4-((1-(5-chloro-4-((3-methoxy-1-methyl-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |
| 191 | 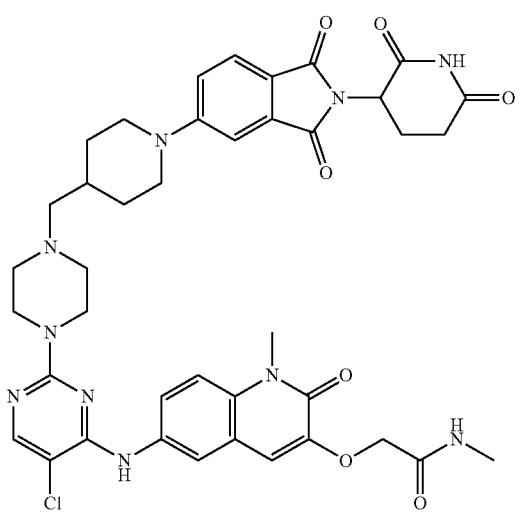 | 2-((6-((5-chloro-2-(4-((1-(2-(2,6-dioxopiperidin-3-yl)-1,3-dioxoisoindolin-5-yl)piperidin-4-yl)methyl)piperazin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 192 | | 2-((6-((5-chloro-2-((3S)-3-(((2-(2,6-dioxopiperidin-3-yl)-1,3-dioxoisoindolin-4-yl)oxy)methyl)piperidin-1-yl)pyrimidin-4-yl)amino)-1-methyl-2-oxo-1,2-dihydroquinolin-3-yl)oxy)-N-methylacetamide |
| 193 | | 2-{[6-({5-chloro-2-[4-({7-[2-(2,6-dioxopiperidin-3-yl)-1,3-dioxo-2,3-dihydro-1H-isoindol-4-yl]-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 194 | | 5-((4-(5-chloro-4-((1-methyl-2-oxo-3-(2-oxopropoxy)-1,2-dihydroquinolin-6-yl)amino)pyrimidin-2-yl)-1-methylpiperazin-2-yl)methoxy)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 195 | 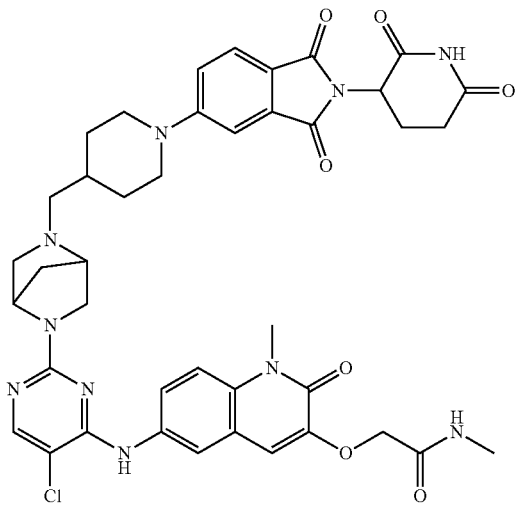 [SMILES: CNC(=O)COc1cc2cc(Nc3nc(N4CC5CC4CN5CC4CCN(c5ccc6c(c5)C(=O)N(C5CCC(=O)NC5=O)C6=O)CC4)ncc3Cl)ccc2n(C)c1=O] | 2-((6-((5-chloro-2-(5-((1-(2-(2,6-dioxopiperidin-3-yl)-1,3-dioxoisoindolin-5-yl)piperidin-4-yl)methyl)-2,5-diazabicyclo[2.2.1]heptan-2-yl)pyrimidin-4-yl)amino)-1-methyl-2-oxo-1,2-dihydroquinolin-3-yl)oxy)-N-methylacetamide |
| 196 | 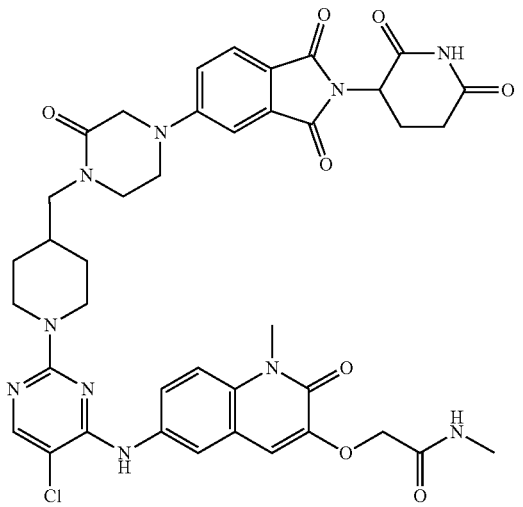 [SMILES: CNC(=O)COc1cc2cc(Nc3nc(N4CCC(CN5CCN(c6ccc7c(c6)C(=O)N(C6CCC(=O)NC6=O)C7=O)CC5=O)CC4)ncc3Cl)ccc2n(C)c1=O] | 2-((6-((5-chloro-2-(4-((4-(2-(2,6-dioxopiperidin-3-yl)-1,3-dioxoisoindolin-5-yl)-2-oxopiperazin-1-yl)methyl)piperidin-1-yl)pyrimidin-4-yl)amino)-1-methyl-2-oxo-1,2-dihydroquinolin-3-yl)oxy)-N-methylacetamide |
| 197 | 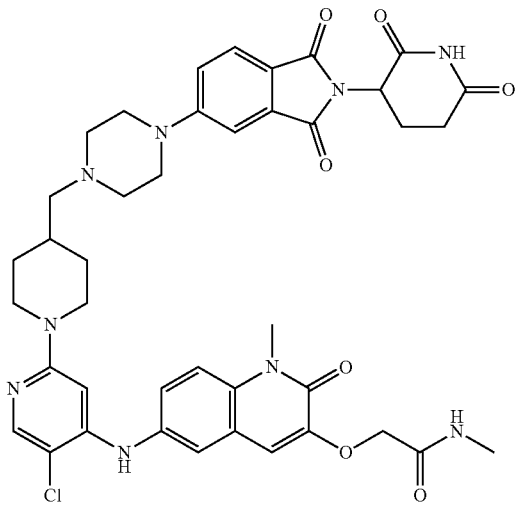 | 2-((6-((5-chloro-2-(4-((4-(2-(2,6-dioxopiperidin-3-yl)-1,3-dioxoisoindolin-5-yl)piperazin-1-yl)methyl)piperidin-1-yl)pyridin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 198 | 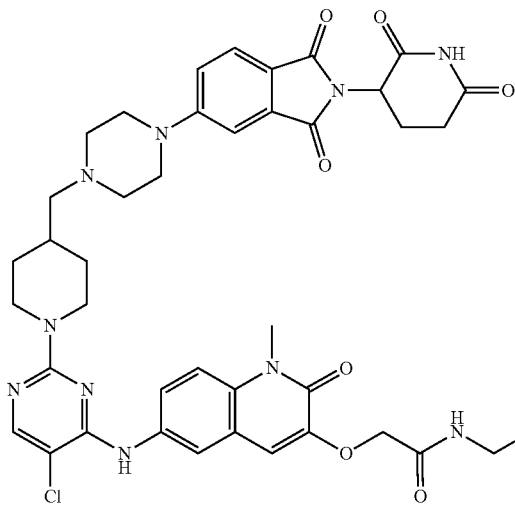 | 2-((6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-ethylacetamide |
| 199 | 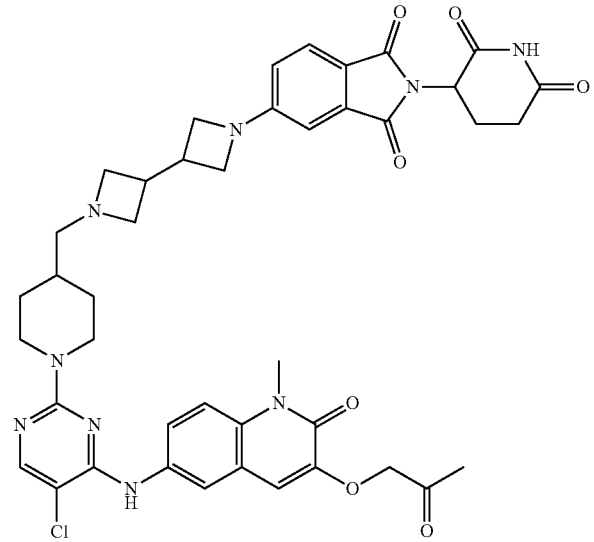 [SMILES: CC(=O)COc1cc2cc(Nc3nc(N4CCC(CN5CC(C6CN(c7ccc8c(c7)C(=O)N(C7CCC(=O)NC7=O)C8=O)C6)C5)CC4)ncc3Cl)ccc2n(C)c1=O] | 5-(1'-((1-(5-chloro-4-((1-methyl-2-oxo-3-(2-oxopropoxy)-1,2-dihydroquinolin-6-yl)amino)pyrimidin-2-yl)piperidin-4-yl)methyl)-[3,3'-biazetidin]-1-yl)-2-(2,6-dioxopiperidin-3-yl)isoindoline-1,3-dione |
| 200 | 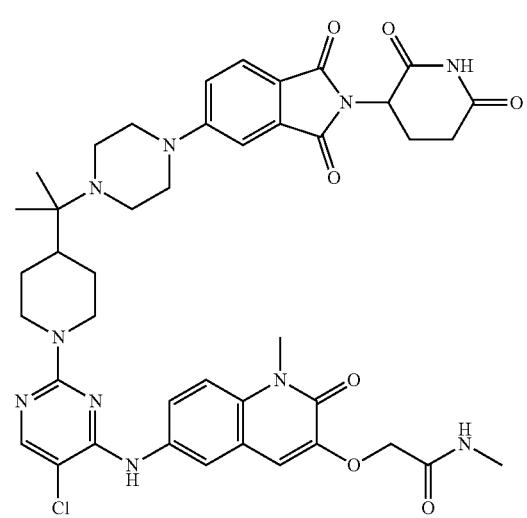 | 2-((6-((5-chloro-2-(4-(2-(4-(2-(2,6-dioxopiperidin-3-yl)-1,3-dioxoisoindolin-5-yl)piperazin-1-yl)propan-2-yl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 201 | 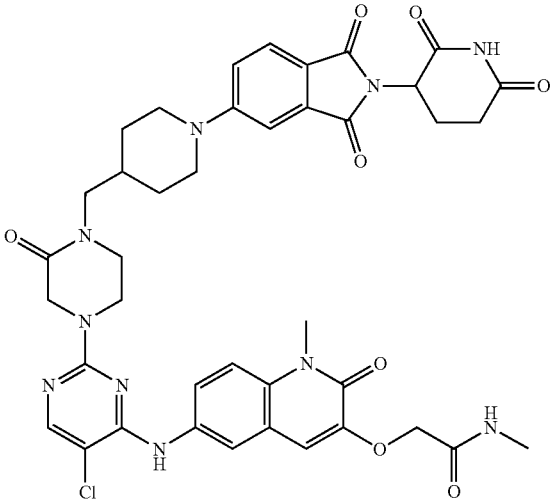 [SMILES: CNC(=O)COc1cc2cc(Nc3nc(N4CCN(CC5CCN(c6ccc7c(c6)C(=O)N(C6CCC(=O)NC6=O)C7=O)CC5)C(=O)C4)ncc3Cl)ccc2n(C)c1=O] | 2-((6-((5-chloro-2-(4-((1-(2-(2,6-dioxopiperidin-3-yl)-1,3-dioxoisoindolin-5-yl)piperidin-4-yl)methyl)-3-oxopiperazin-1-yl)pyrimidin-4-yl)amino)-1-methyl-2-oxo-1,2-dihydroquinolin-3-yl)oxy)-N-methylacetamide |
| 202 | 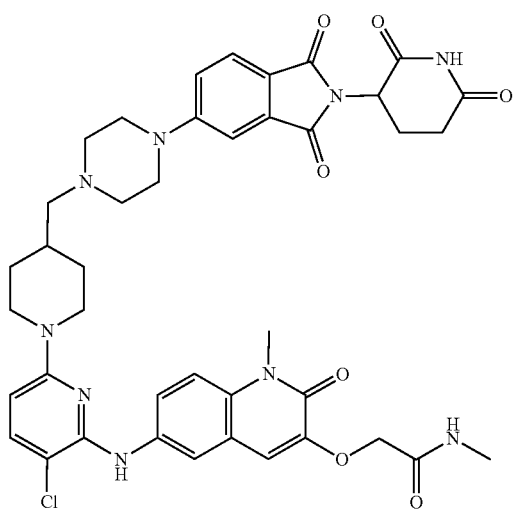 [SMILES: CNC(=O)COc1cc2cc(Nc3nc(N4CCC(CN5CCN(c6ccc7c(c6)C(=O)N(C6CCC(=O)NC6=O)C7=O)CC5)CC4)ccc3Cl)ccc2n(C)c1=O] | 2-((6-((3-chloro-6-(4-((4-(2-(2,6-dioxopiperidin-3-yl)-1,3-dioxoisoindolin-5-yl)piperazin-1-yl)methyl)piperidin-1-yl)pyridin-2-yl)amino)-1-methyl-2-oxo-1,2-dihydroquinolin-3-yl)oxy)-N-methylacetamide |
| 203 | 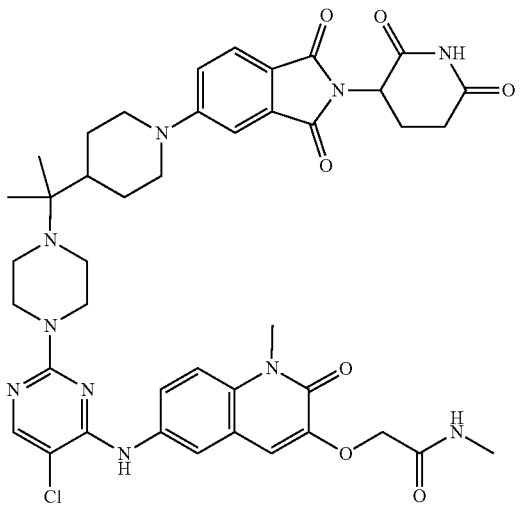 [SMILES: CNC(=O)COc1cc2cc(Nc3nc(N4CCN(C(C)(C)C5CCN(c6ccc7c(c6)C(=O)N(C6CCC(=O)NC6=O)C7=O)CC5)CC4)ncc3Cl)ccc2n(C)c1=O] | 2-((6-((5-chloro-2-(4-(2-(1-(2-(2,6-dioxopiperidin-3-yl)-1,3-dioxoisoindolin-5-yl)piperidin-4-yl)propan-2-yl)piperazin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 204 | 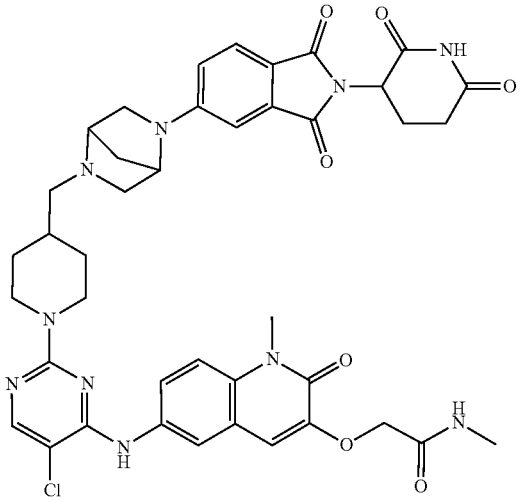 [SMILES: CNC(=O)COc1cc2cc(Nc3nc(N4CCC(CN5CC6CC5CN6c5ccc6c(c5)C(=O)N(C5CCC(=O)NC5=O)C6=O)CC4)ncc3Cl)ccc2n(C)c1=O] | 2-((6-((5-chloro-2-(4-((5-(2-(2,6-dioxopiperidin-3-yl)-1,3-dioxoisoindolin-5-yl)-2,5-diazabicyclo[2.2.1]heptan-2-yl)methyl)piperidin-1-yl)pyrimidin-4-yl)amino)-1-methyl-2-oxo-1,2-dihydroquinolin-3-yl)oxy)-N-methylacetamide |
| 205 | 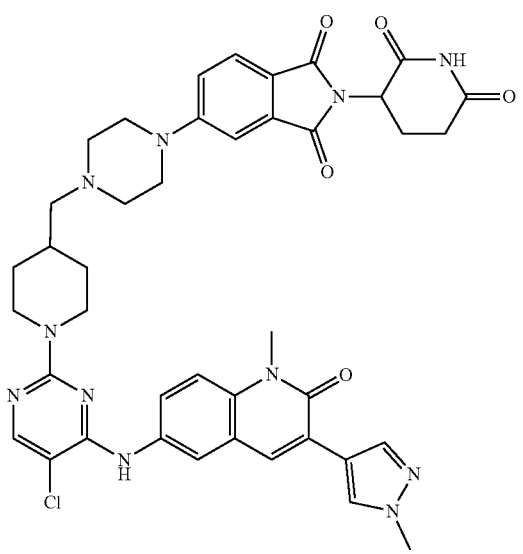 [SMILES: Cn1cc(-c2cc3cc(Nc4nc(N5CCC(CN6CCN(c7ccc8c(c7)C(=O)N(C7CCC(=O)NC7=O)C8=O)CC6)CC5)ncc4Cl)ccc3n(C)c2=O)cn1] | 5-(4-((1-(5-chloro-4-((1-methyl-3-(1-methyl-1H-pyrazol-4-yl)-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |
| 206 | 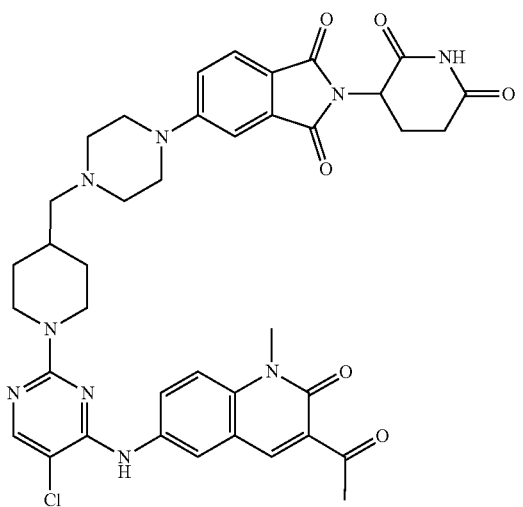 [SMILES: CC(=O)c1cc2cc(Nc3nc(N4CCC(CN5CCN(c6ccc7c(c6)C(=O)N(C6CCC(=O)NC6=O)C7=O)CC5)CC4)ncc3Cl)ccc2n(C)c1=O] | 5-(4-((1-(4-((3-acetyl-1-methyl-2-oxo-1,2-dihydroquinolin-6-yl)amino)-5-chloropyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 207 | 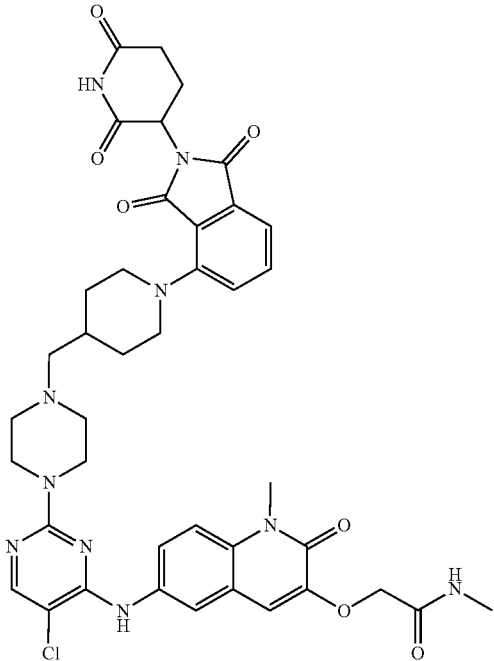 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(C)c1=O] | 2-((6-((5-chloro-2-(4-((1-(2-(2,6-dioxopiperidin-3-yl)-1,3-dioxoisoindolin-4-yl)piperidin-4-yl)methyl)piperazin-1-yl)pyrimidin-4-yl)amino)-1-methyl-2-oxo-1,2-dihydroquinolin-3-yl)oxy)-N-methylacetamide |
| 208 | 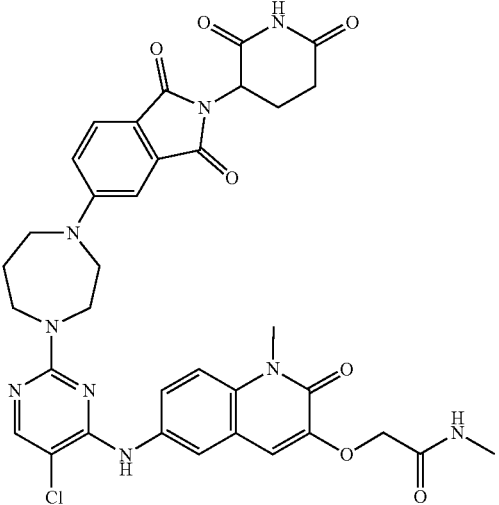 [SMILES: CNC(=O)COc1cc2cc(Nc3nc(N4CCCN(c5ccc6c(c5)C(=O)N(C5CCC(=O)NC5=O)C6=O)CC4)ncc3Cl)ccc2n(C)c1=O] | 2-((6-((5-chloro-2-(4-(2-(2,6-dioxopiperidin-3-yl)-1,3-dioxoisoindolin-5-yl)-1,4-diazepan-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 209 | | 2-((6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methoxyacetamide |
| 210 | | (R)-2-((6-((5-chloro-2-(4-((4-(2-((S)-2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylpropanamide |
| 211 | | (S)-2-((6-((5-chloro-2-(4-((4-(2-((S)-2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylpropanamide |

TABLE 1-continued

Exemplary bifunctional compounds of the present disclosure

| Ex. # | Parent Mol Structure | Name |
|---|---|---|
| 212 | 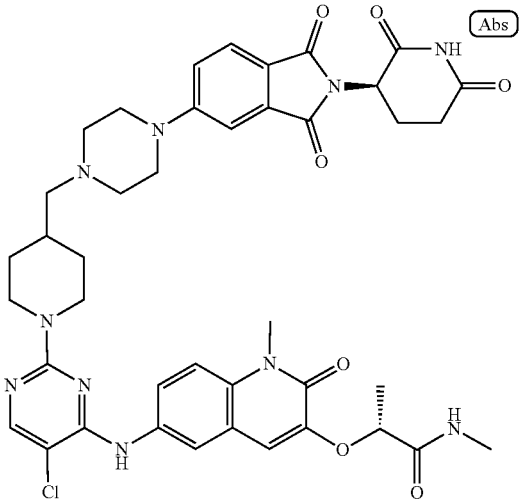 [SMILES: CNC(=O)[C@@H](C)Oc1cc2cc(Nc3nc(N4CCC(CN5CCN(c6ccc7c(c6)C(=O)N([C@@H]6CCC(=O)NC6=O)C7=O)CC5)CC4)ncc3Cl)ccc2n(C)c1=O] | (R)-2-((6-((5-chloro-2-(4-((4-(2-((R)-2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylpropanamide |
| 213 | 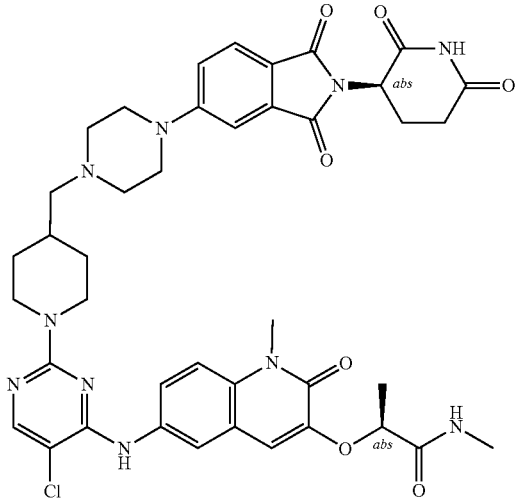 [SMILES: CNC(=O)[C@H](C)Oc1cc2cc(Nc3nc(N4CCC(CN5CCN(c6ccc7c(c6)C(=O)N([C@@H]6CCC(=O)NC6=O)C7=O)CC5)CC4)ncc3Cl)ccc2n(C)c1=O] | (S)-2-((6-((5-chloro-2-(4-((4-(2-((R)-2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)oxy)-N-methylpropanamide |
| 214 | 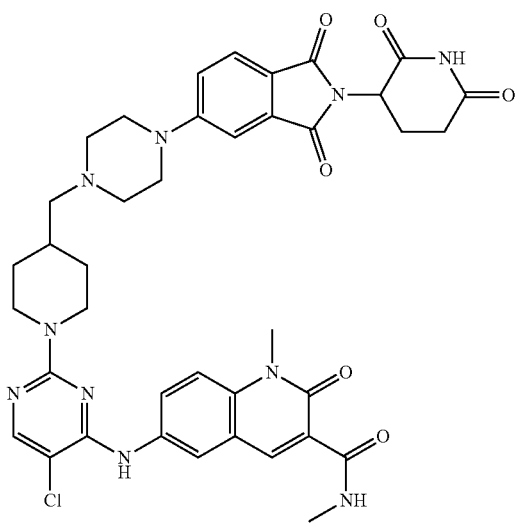 [SMILES: CNC(=O)c1cc2cc(Nc3nc(N4CCC(CN5CCN(c6ccc7c(c6)C(=O)N(C6CCC(=O)NC6=O)C7=O)CC5)CC4)ncc3Cl)ccc2n(C)c1=O] | 6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-N,1-dimethyl-2-oxo-1,2-dihydroquinoline-3-carboxamide |

TABLE 1-continued

Exemplary bifunctional compounds of the present disclosure

| Ex. # | Parent Mol Structure | Name |
|---|---|---|
| 215 | 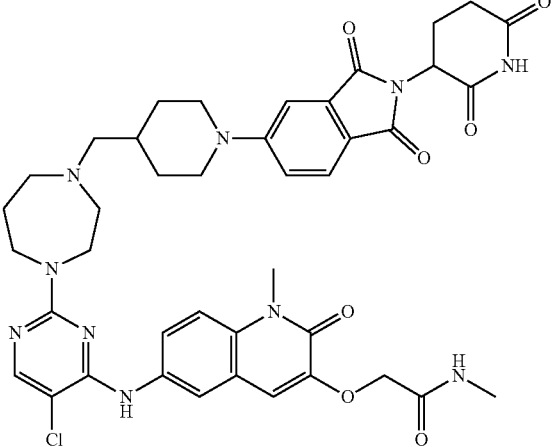 | 2-((6-((5-chloro-2-(4-((1-(2-(2,6-dioxopiperidin-3-yl)-1,3-dioxoisoindolin-5-yl)piperidin-4-yl)methyl)-1,4-diazepan-1-yl)pyrimidin-4-yl)amino)-1-methyl-2-oxo-1,2-dihydroquinolin-3-yl)oxy)-N-methylacetamide |
| 216 | 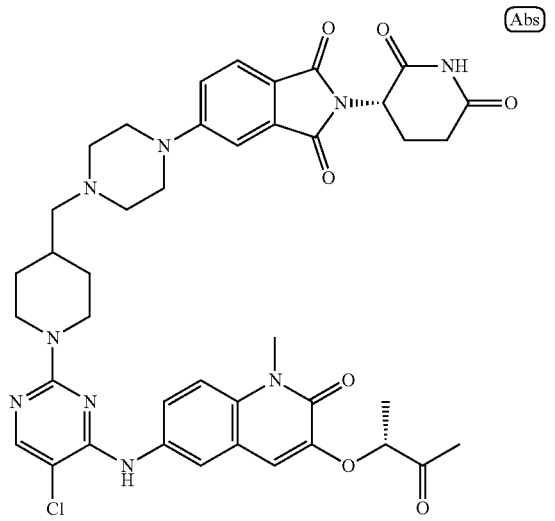 | 5-(4-((1-(5-chloro-4-((1-methyl-2-oxo-3-(((R)-3-oxobutan-2-yl)oxy)-1,2-dihydroquinolin-6-yl)amino)pyrimidin-2-yl)piperidin-4-yl)methyl)piperazin-1-yl)-2-((S)-2,6-dioxopiperidin-3-yl)isoindoline-1,3-dione |
| 217 | 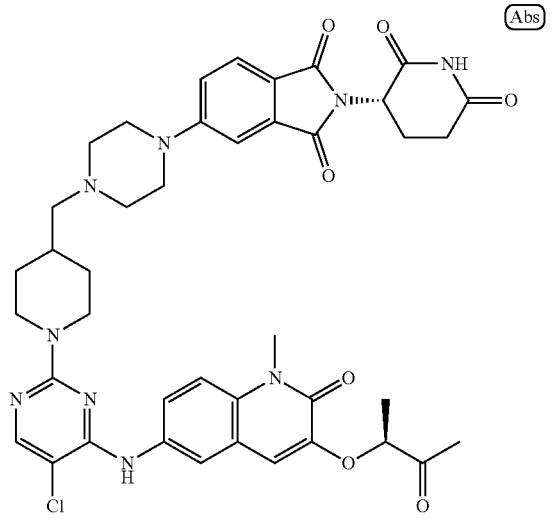 | 5-(4-((1-(5-chloro-4-((1-methyl-2-oxo-3-(((S)-3-oxobutan-2-yl)oxy)-1,2-dihydroquinolin-6-yl)amino)pyrimidin-2-yl)piperidin-4-yl)methyl)piperazin-1-yl)-2-((S)-2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 218 | 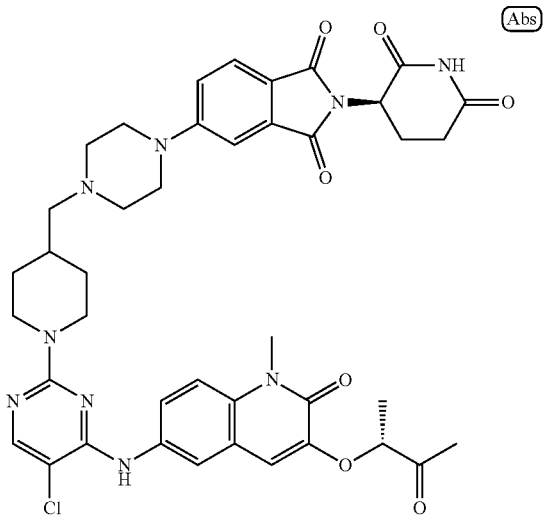 (Abs) | 5-(4-((1-(5-chloro-4-((1-methyl-2-oxo-3-(((R)-3-oxobutan-2-yl)oxy)-1,2-dihydroquinolin-6-yl)amino)pyrimidin-2-yl)piperidin-4-yl)methyl)piperazin-1-yl)-2-((R)-2,6-dioxopiperidin-3-yl)isoindoline-1,3-dione |
| 219 | 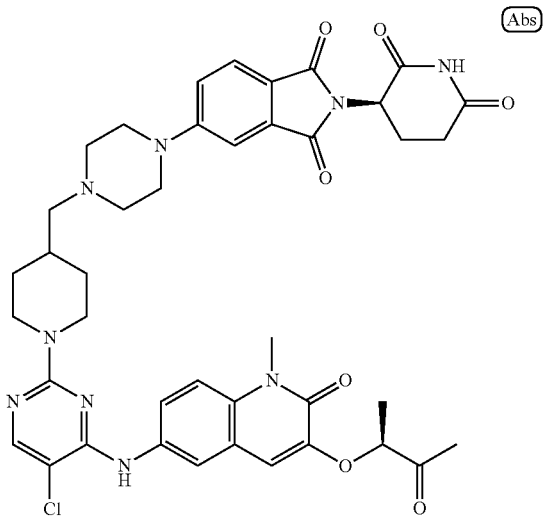 (Abs) | 5-(4-((1-(5-chloro-4-((1-methyl-2-oxo-3-(((S)-3-oxobutan-2-yl)oxy)-1,2-dihydroquinolin-6-yl)amino)pyrimidin-2-yl)piperidin-4-yl)methyl)piperazin-1-yl)-2-((R)-2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 220 | | 2-((6-((5-chloro-2-(4-(1-(2-(2,6-dioxopiperidin-3-yl)-1,3-dioxoisoindolin-4-yl)piperidin-4-yl)piperazin-1-yl)pyrimidin-4-yl)amino)-1-methyl-2-oxo-1,2-dihydroquinolin-3-yl)oxy)-N-methylacetamide |
| 221 | | 2-((6-((5-chloro-2-(4-((1-(2-(2,6-dioxopiperidin-3-yl)-1,3-dioxoisoindolin-5-yl)piperidin-4-yl)oxy)piperidin-1-yl)pyrimidin-4-yl)amino)-1-methyl-2-oxo-1,2-dihydroquinolin-3-yl)oxy)-N-methylacetamide |
| 222 | | 2-((6-((5-chloro-2-((2R)-2-(((2-(2,6-dioxopiperidin-3-yl)-1,3-dioxoisoindolin-5-yl)oxy)methyl)morpholino)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 223 | 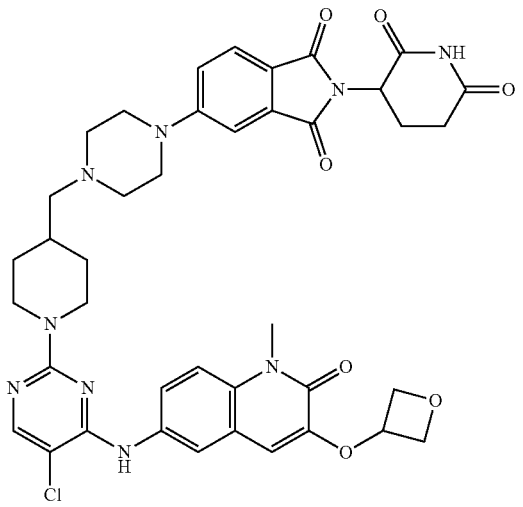 | 5-(4-((1-(5-chloro-4-((1-methyl-3-(oxetan-3-yloxy)-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |
| 224 | 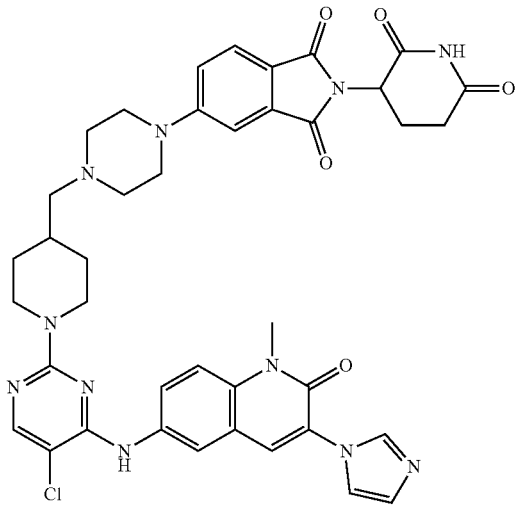 | 5-(4-((1-(4-((3-(1H-imidazol-1-yl)-1-methyl-2-oxo-1,2-dihydroquinolin-6-yl)amino)-5-chloropyrimidin-2-yl)piperidin-4-yl)methyl)piperazin-1-yl)-2-(2,6-dioxopiperidin-3-yl)isoindoline-1,3-dione |
| 225 | 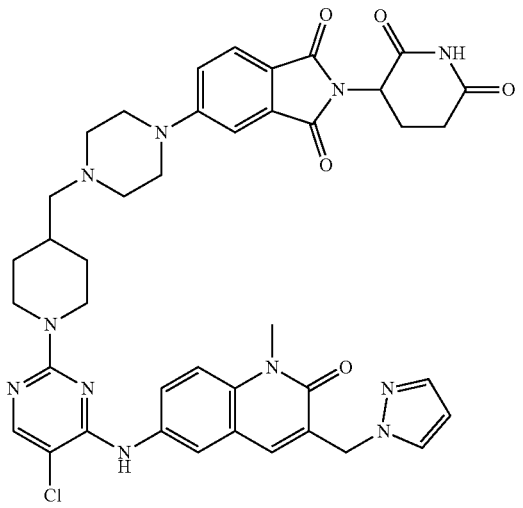 | 5-(4-((1-(4-((3-((1H-pyrazol-1-yl)methyl)-1-methyl-2-oxo-1,2-dihydroquinolin-6-yl)amino)-5-chloropyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 226 | | 2-((6-((5-chloro-2-(2-(((2-(2,6-dioxopiperidin-3-yl)-1,3-dioxoisoindolin-4-yl)oxy)methyl)morpholino)pyrimidin-4-yl)amino)-1-methyl-2-oxo-1,2-dihydroquinolin-3-yl)oxy)-N-methylacetamide |
| 227 | | 2-((6-((5-chloro-2-(4-((1-(2-(2,6-dioxopiperidin-3-yl)-1,3-dioxoisoindolin-5-yl)azetidin-3-yl)oxy)piperidin-1-yl)pyrimidin-4-yl)amino)-1-methyl-2-oxo-1,2-dihydroquinolin-3-yl)oxy)-N-methylacetamide |
| 228 | | 2-((6-((5-chloro-2-((2S)-2-(((2-(2,6-dioxopiperidin-3-yl)-1,3-dioxoisoindolin-5-yl)oxy)methyl)morpholino)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 229 | | 2-((6-((5-chloro-2-(4-(2-(4-(2-(2,6-dioxopiperidin-3-yl)-1,3-dioxoisoindolin-5-yl)piperazin-1-yl)ethyl)piperazin-1-yl)pyrimidin-4-yl)amino)-1-methyl-2-oxo-1,2-dihydroquinolin-3-yl)oxy)-N-methylacetamide |
| 230 | | 2-((6-((5-chloro-2-(4-(3-(4-(2-(2,6-dioxopiperidin-3-yl)-1,3-dioxoisoindolin-5-yl)piperazin-1-yl)propyl)piperazin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 231 | 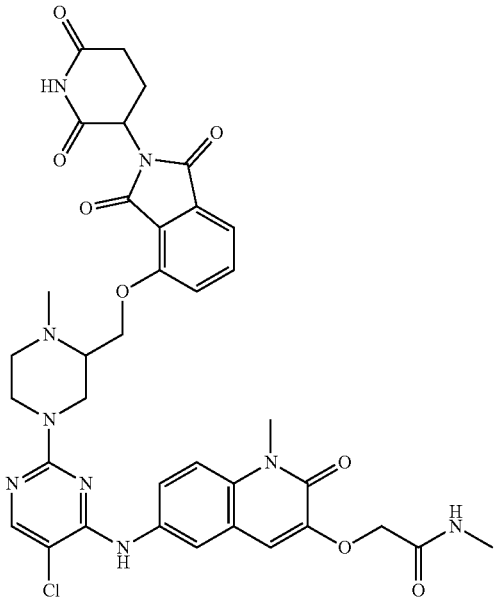 [SMILES: CNC(=O)COc1cc2cc(Nc3nc(N4CCN(C)C(COc5cccc6c5C(=O)N(C5CCC(=O)NC5=O)C6=O)C4)ncc3Cl)ccc2n(C)c1=O] | 2-((6-((5-chloro-2-(3-(((2-(2,6-dioxopiperidin-3-yl)-1,3-dioxoisoindolin-4-yl)oxy)methyl)-4-methylpiperazin-1-yl)pyrimidin-4-yl)amino)-1-methyl-2-oxo-1,2-dihydroquinolin-3-yl)oxy)-N-methylacetamide |
| 232 | 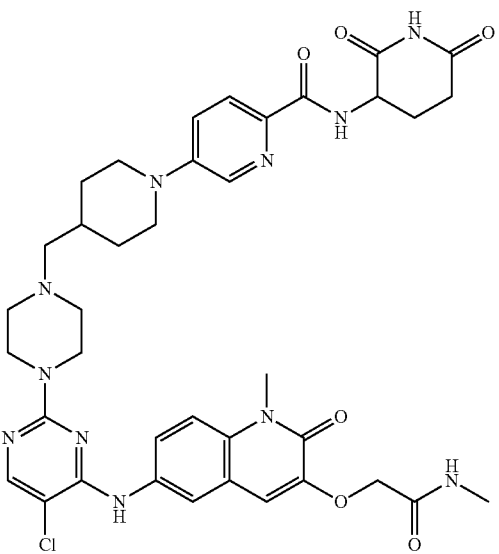 [SMILES: CNC(=O)COc1cc2cc(Nc3nc(N4CCN(CC5CCN(c6ccc(C(=O)NC7CCC(=O)NC7=O)nc6)CC5)CC4)ncc3Cl)ccc2n(C)c1=O] | 5-(4-((4-(5-chloro-4-((1-methyl-3-(2-(methylamino)-2-oxoethoxy)-2-oxo-1,2-dihydroquinolin-6-yl)amino)pyrimidin-2-yl)piperazin-1-yl)methyl)piperidin-1-yl)-N-(2,6-dioxopiperidin-3-yl)picolinamide |

TABLE 1-continued

Exemplary bifunctional compounds of the present disclosure

| Ex. # | Parent Mol Structure | Name |
|---|---|---|
| 233 | | 4-(4-((4-(5-chloro-4-((1-methyl-3-(2-(methylamino)-2-oxoethoxy)-2-oxo-1,2-dihydroquinolin-6-yl)amino)pyrimidin-2-yl)piperazin-1-yl)methyl)piperidin-1-yl)-N-(2,6-dioxopiperidin-3-yl)-2-fluorobenzamide |
| 234 | | 2-((6-((5-chloro-2-(8-(2-(2,6-dioxopiperidin-3-yl)-1,3-dioxoisoindolin-5-yl)octahydro-2H-pyrazino[1,2-a]pyrazin-2-yl)pyrimidin-4-yl)amino)-1-methyl-2-oxo-1,2-dihydroquinolin-3-yl)oxy)-N-methylacetamide |
| 235 | | 5-(4-((1-(5-chloro-4-((3-(isoxazol-4-yl)-1-methyl-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 236 | 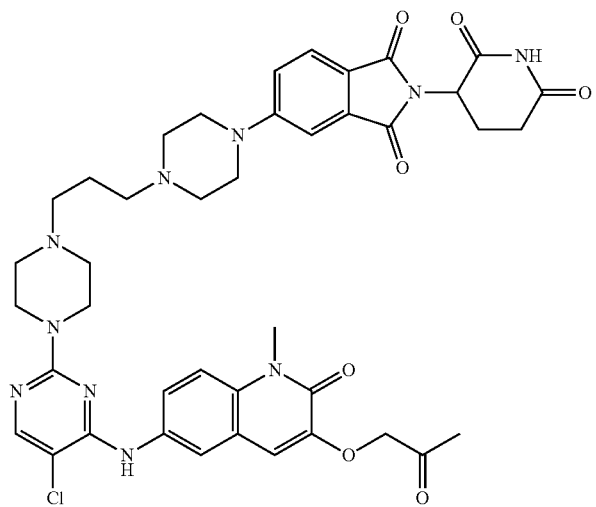 [SMILES: CC(=O)COc1cc2cc(Nc3nc(N4CCN(CCCN5CCN(c6ccc7c(c6)C(=O)N(C6CCC(=O)NC6=O)C7=O)CC5)CC4)ncc3Cl)ccc2n(C)c1=O] | 5-(4-(3-(4-(5-chloro-4-((1-methyl-2-oxo-3-(2-oxopropoxy)-1,2-dihydroquinolin-6-yl)amino)pyrimidin-2-yl)piperazin-1-yl)propyl)piperazin-1-yl)-2-(2,6-dioxopiperidin-3-yl)isoindoline-1,3-dione |
| 237 | 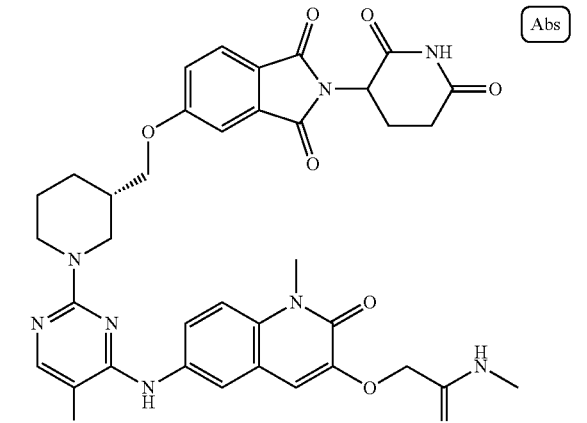 | 2-((6-((5-chloro-2-((3S)-3-(((2-(2,6-dioxopiperidin-3-yl)-1,3-dioxoisoindolin-5-yl)oxy)methyl)piperidin-1-yl)pyrimidin-4-yl)amino)-1-methyl-2-oxo-1,2-dihydroquinolin-3-yl)oxy)-N-methylacetamide |
| 238 | 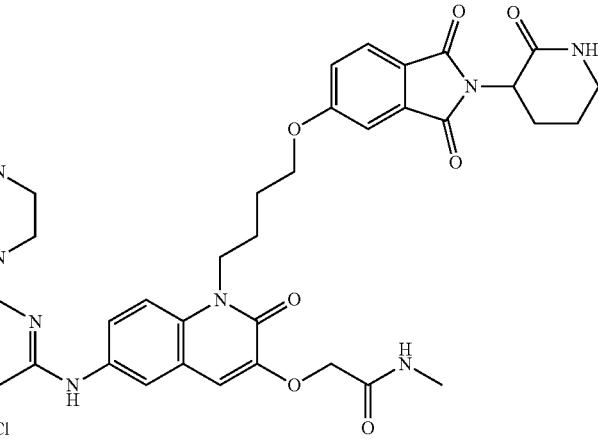 | 2-((6-((5-chloro-2-(4-methylpiperazin-1-yl)pyrimidin-4-yl)amino)-1-(4-((2-(2,6-dioxopiperidin-3-yl)-1,3-dioxoisoindolin-5-yl)oxy)butyl)-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 239 | | 2-(6-((5-chloro-2-(4-((4-(2-(2,6-dioxopiperidin-3-yl)-1,3-dioxoisoindolin-5-yl)piperazin-1-yl)methyl)piperidin-1-yl)pyrimidin-4-yl)amino)-1-methyl-2-oxo-1,2-dihydroquinolin-3-yl)-N-methylacetamide |
| 240 | | 2-((6-((5-chloro-2-(4-((1-(2-(2,6-dioxopiperidin-3-yl)-1,3-dioxoisoindolin-5-yl)-4-hydroxypiperidin-4-yl)methyl)piperazin-1-yl)pyrimidin-4-yl)amino)-1-methyl-2-oxo-1,2-dihydroquinolin-3-yl)oxy)-N-methylacetamide |
| 241 | | 2-((6-((5-chloro-2-(4-((1-(2-(2,6-dioxopiperidin-3-yl)-1,3-dioxoisoindolin-5-yl)piperidin-4-yl)oxy)azepan-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 242 | | 2-((6-((5-chloro-2-(4-((1-(2-(2,6-dioxopiperidin-3-yl)-1,3-dioxoisoindolin-5-yl)azepan-4-yl)oxy)piperidin-1-yl)pyrimidin-4-yl)amino)-1-methyl-2-oxo-1,2-dihydroquinolin-3-yl)oxy)-N-methylacetamide |
| 243 | | 4-(4-((4-(5-chloro-4-((1-methyl-3-(2-(methylamino)-2-oxoethoxy)-2-oxo-1,2-dihydroquinolin-6-yl)amino)pyrimidin-2-yl)piperazin-1-yl)methyl)piperidin-1-yl)-N-(2,6-dioxopiperidin-3-yl)-2-methoxybenzamide |
| 244 | | 2-((6-((5-chloro-2-(4-methylpiperazin-1-yl)pyrimidin-4-yl)amino)-1-(3-((2-(2,6-dioxopiperidin-3-yl)-1,3-dioxoisoindolin-5-yl)oxy)propyl)-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 245 | | 2-((6-((5-chloro-2-(4-((4-(2-(2,6-dioxopiperidin-3-yl)-1,3-dioxoisoindolin-5-yl)piperazin-1-yl)methyl)-4-hydroxypiperidin-1-yl)pyrimidin-4-yl)amino)-1-methyl-2-oxo-1,2-dihydroquinolin-3-yl)oxy)-N-methylacetamide |
| 246 | | 2-((6-((5-chloro-2-(4-((1-(2-(2,6-dioxopiperidin-3-yl)-1,3-dioxoisoindolin-5-yl)azetidin-3-yl)methyl)piperazin-1-yl)pyrimidin-4-yl)amino)-1-methyl-2-oxo-1,2-dihydroquinolin-3-yl)oxy)-N-methylacetamide |
| 247 | | 2-((6-((5-chloro-2-(4-(2-((1-(2-(2,6-dioxopiperidin-3-yl)-1,3-dioxoisoindolin-5-yl)azetidin-3-yl)oxy)ethyl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 248 | | 2-((6-((5-chloro-2-(4-((6-(2-(2,6-dioxopiperidin-3-yl)-1,3-dioxoisoindolin-5-yl)-2,6-diazaspiro[3.3]heptan-2-yl)methyl)piperidin-1-yl)pyrimidin-4-yl)amino)-1-methyl-2-oxo-1,2-dihydroquinolin-3-yl)oxy)-N-methylacetamide |
| 249 | | 5-(4-((4-(5-chloro-4-((1-methyl-2-oxo-3-(2-oxoazetidin-1-yl)-1,2-dihydroquinolin-6-yl)amino)pyrimidin-2-yl)piperazin-1-yl)methyl)piperidin-1-yl)-2-(2,6-dioxopiperidin-3-yl)isoindoline-1,3-dione |
| 250 | | 2-((6-((5-chloro-2-(4-((1-(2-(2,6-dioxopiperidin-3-yl)-1,3-dioxoisoindolin-5-yl)piperidin-4-yl)methyl)piperazin-1-yl)pyrimidin-4-yl)amino)-1-ethyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 251 | 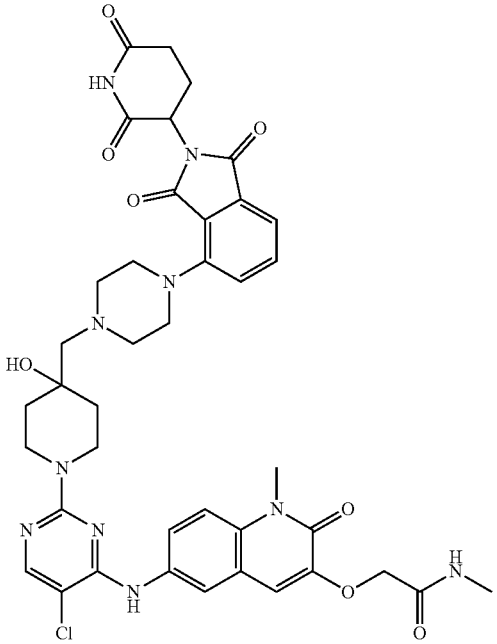 [SMILES: CNC(=O)COc1cc2cc(Nc3nc(N4CCC(O)(CN5CCN(c6cccc7c6C(=O)N(C6CCC(=O)NC6=O)C7=O)CC5)CC4)ncc3Cl)ccc2n(C)c1=O] | 2-((6-((5-chloro-2-(4-((4-(2-(2,6-dioxopiperidin-3-yl)-1,3-dioxoisoindolin-4-yl)piperazin-1-yl)methyl)-4-hydroxypiperidin-1-yl)pyrimidin-4-yl)amino)-1-methyl-2-oxo-1,2-dihydroquinolin-3-yl)oxy)-N-methylacetamide |
| 252 | 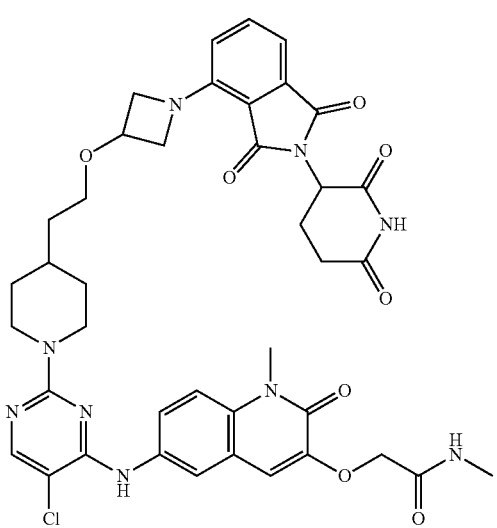 [SMILES: CNC(=O)COc1cc2cc(Nc3nc(N4CCC(CCOC5CN(c6cccc7c6C(=O)N(C6CCC(=O)NC6=O)C7=O)C5)CC4)ncc3Cl)ccc2n(C)c1=O] | 2-((6-((5-chloro-2-(4-(2-((1-(2-(2,6-dioxopiperidin-3-yl)-1,3-dioxoisoindolin-4-yl)azetidin-3-yl)oxy)ethyl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 253 | | 2-((6-((5-chloro-2-(4-((1-(2-(2,6-dioxopiperidin-3-yl)-1,3-dioxoisoindolin-5-yl)piperidin-4-yl)methyl)piperazin-1-yl)pyridin-4-yl)amino)-1-methyl-2-oxo-1,2-dihydroquinolin-3-yl)oxy)-N-methylacetamide |
| 254 | | 2-((6-((3,5-dichloro-6-(4-((1-(2-(2,6-dioxopiperidin-3-yl)-1,3-dioxoisoindolin-5-yl)piperidin-4-yl)methyl)piperazin-1-yl)pyridin-2-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 255 | 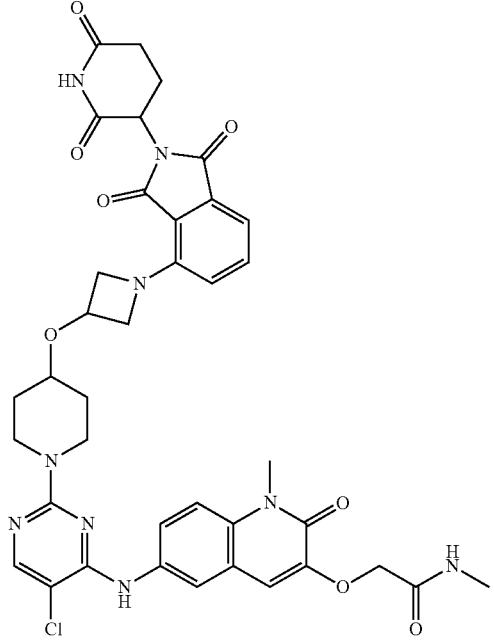 [SMILES: CNC(=O)COc1cc2cc(Nc3nc(N4CCC(OC5CN(c6cccc7c6C(=O)N(C6CCC(=O)NC6=O)C7=O)C5)CC4)ncc3Cl)ccc2n(C)c1=O] | 2-((6-((5-chloro-2-(4-((1-(2-(2,6-dioxopiperidin-3-yl)-1,3-dioxoisoindolin-4-yl)azetidin-3-yl)oxy)piperidin-1-yl)pyrimidin-4-yl)amino)-1-methyl-2-oxo-1,2-dihydroquinolin-3-yl)oxy)-N-methylacetamide |
| 256 | 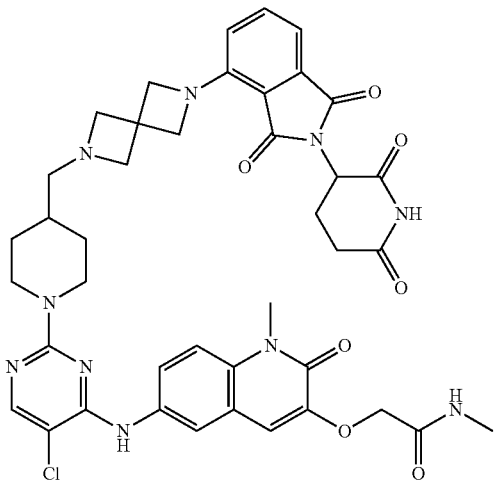 [SMILES: CNC(=O)COc1cc2cc(Nc3nc(N4CCC(CN5CC6(C5)CN(c5cccc7c5C(=O)N(C5CCC(=O)NC5=O)C7=O)C6)CC4)ncc3Cl)ccc2n(C)c1=O] | 2-((6-((5-chloro-2-(4-((6-(2-(2,6-dioxopiperidin-3-yl)-1,3-dioxoisoindolin-4-yl)-2,6-diazaspiro[3.3]heptan-2-yl)methyl)piperidin-1-yl)pyrimidin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 257 | | 5-(4-(2-(4-(5-chloro-4-((1-methyl-2-oxo-3-(2-oxopropoxy)-1,2-dihydroquinolin-6-yl)amino)pyrimidin-2-yl)piperazin-1-yl)propan-2-yl)piperidin-1-yl)-2-(2,6-dioxopiperidin-3-yl)isoindoline-1,3-dione |
| 258 | | 5-(4-((1-(5-chloro-4-((1-methyl-3-(((R)-1-methyl-2-oxopyrrolidin-3-yl)oxy)-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |
| 259 | | 5-(4-((1-(5-chloro-4-((1-methyl-3-(((S)-1-methyl-2-oxopyrrolidin-3-yl)oxy)-2-oxo-1,2-dihydroquinolin-6-yl)amino)pyrimidin-2-yl)piperidin-4-yl)methyl)piperazin-1-yl)-2-(2,6-dioxopiperidin-3-yl)isoindoline-1,3-dione |

TABLE 1-continued

Exemplary bifunctional compounds of the present disclosure

| Ex. # | Parent Mol Structure | Name |
|---|---|---|
| 260 | 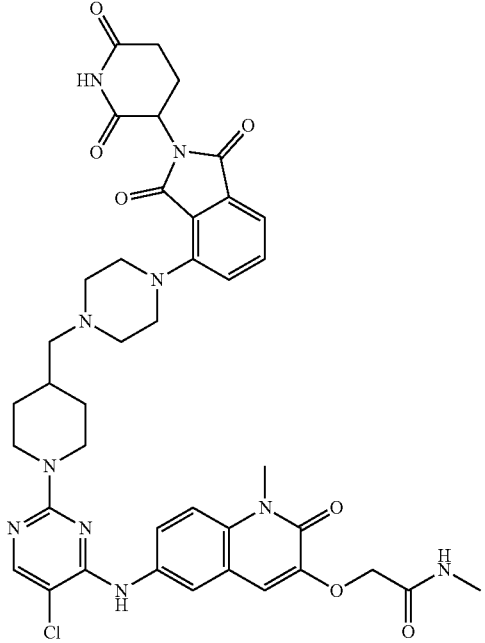 [SMILES: CNC(=O)COc1cc2cc(Nc3nc(N4CCC(CN5CCN(c6cccc7c6C(=O)N(C6CCC(=O)NC6=O)C7=O)CC5)CC4)ncc3Cl)ccc2n(C)c1=O] | 2-((6-((5-chloro-2-(4-((4-(2-(2,6-dioxopiperidin-3-yl)-1,3-dioxoisoindolin-4-yl)piperazin-1-yl)methyl)piperidin-1-yl)pyrimidin-4-yl)amino)-1-methyl-2-oxo-1,2-dihydroquinolin-3-yl)oxy)-N-methylacetamide |
| 261 | 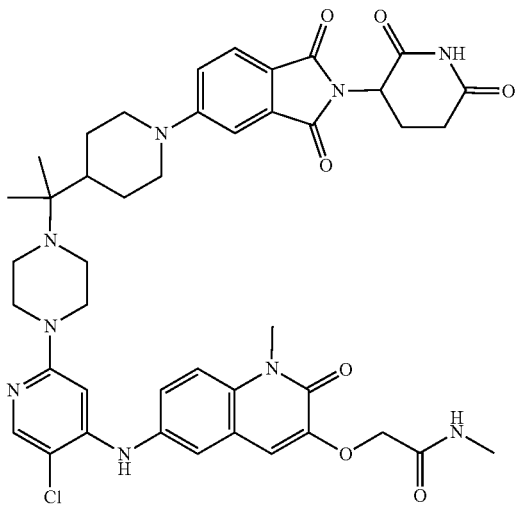 | 2-((6-((5-chloro-2-(4-(2-(1-(2-(2,6-dioxopiperidin-3-yl)-1,3-dioxoisoindolin-5-yl)piperidin-4-yl)propan-2-yl)piperazin-1-yl)pyridin-4-yl)amino)-1-methyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 262 | 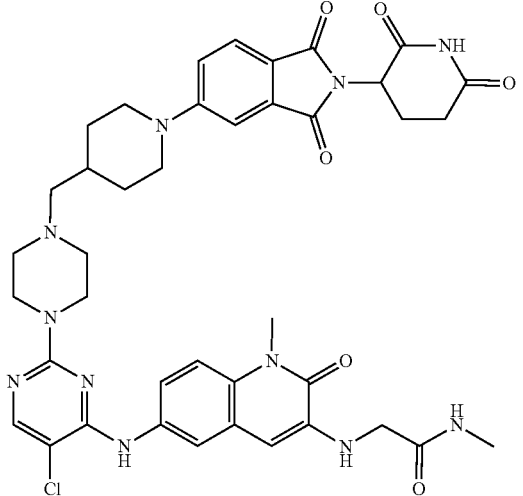 [SMILES: CNC(=O)CNc1cc2cc(Nc3nc(N4CCN(CC5CCN(c6ccc7c(c6)C(=O)N(C6CCC(=O)NC6=O)C7=O)CC5)CC4)ncc3Cl)ccc2n(C)c1=O] | 2-((6-((5-chloro-2-(4-((1-(2-(2,6-dioxopiperidin-3-yl)-1,3-dioxoisoindolin-5-yl)piperidin-4-yl)methyl)piperazin-1-yl)pyrimidin-4-yl)amino)-1-methyl-2-oxo-1,2-dihydroquinolin-3-yl)amino)-N-methylacetamide |
| 263 | 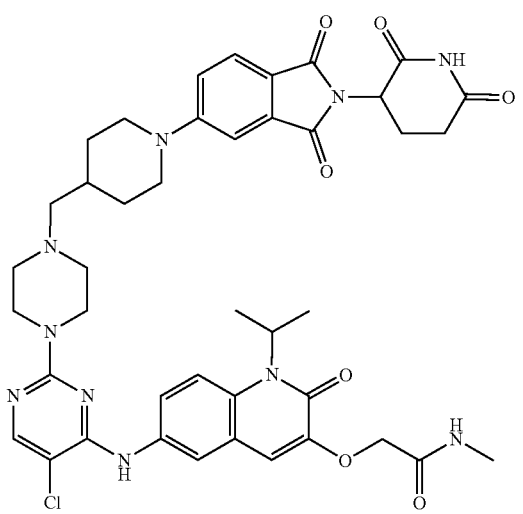 [SMILES: CNC(=O)COc1cc2cc(Nc3nc(N4CCN(CC5CCN(c6ccc7c(c6)C(=O)N(C6CCC(=O)NC6=O)C7=O)CC5)CC4)ncc3Cl)ccc2n(C(C)C)c1=O] | 2-((6-((5-chloro-2-(4-((1-(2-(2,6-dioxopiperidin-3-yl)-1,3-dioxoisoindolin-5-yl)piperidin-4-yl)methyl)piperazin-1-yl)pyrimidin-4-yl)amino)-1-isopropyl-2-oxo-1,2-dihydroquinolin-3-yl)oxy)-N-methylacetamide |

TABLE 1-continued

Exemplary bifunctional compounds of the present disclosure

| Ex. # | Parent Mol Structure | Name |
|---|---|---|
| 264 | | 2-((6-((5-chloro-2-(4-((1-(2-(2,6-dioxopiperidin-3-yl)-1,3-dioxoisoindolin-4-yl)piperidin-4-yl)oxy)piperidin-1-yl)pyrimidin-4-yl)amino)-1-methyl-2-oxo-1,2-dihydroquinolin-3-yl)oxy)-N-methylacetamide |
| 265 | | 2-((6-((5-chloro-2-(4-(2-(1-(2-(2,6-dioxopiperidin-3-yl)-1,3-dioxoisoindolin-5-yl)piperidin-4-yl)propan-2-yl)piperazin-1-yl)pyridin-4-yl)amino)-1-methyl-2-oxo-1,2-dihydroquinolin-3-yl)oxy)-N-methoxyacetamide |

| Ex. # | Parent Mol Structure | Name |
|---|---|---|
| 266 | 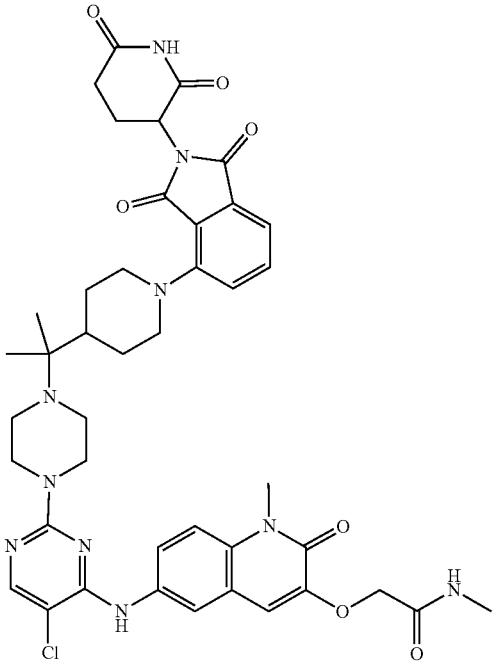 [SMILES: CNC(=O)COc1cc2cc(Nc3nc(N4CCN(C(C)(C)C5CCN(c6cccc7c6C(=O)N(C6CCC(=O)NC6=O)C7=O)CC5)CC4)ncc3Cl)ccc2n(C)c1=O] | 2-((6-((5-chloro-2-(4-(2-(1-(2-(2,6-dioxopiperidin-3-yl)-1,3-dioxoisoindolin-4-yl)piperidin-4-yl)propan-2-yl)piperazin-1-yl)pyrimidin-4-yl)amino)-1-methyl-2-oxo-1,2-dihydroquinolin-3-yl)oxy)-N-methylacetamide |
| 267 | 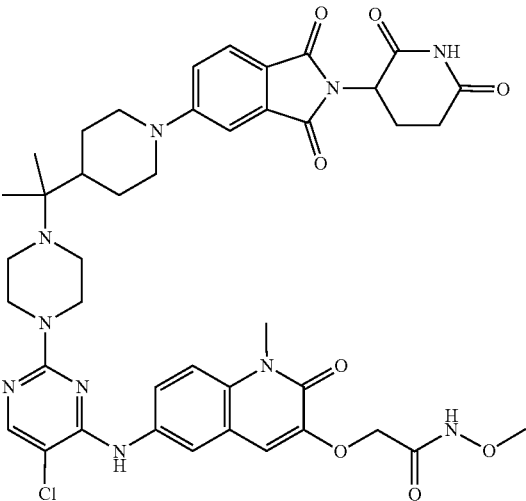 [SMILES: CONC(=O)COc1cc2cc(Nc3nc(N4CCN(C(C)(C)C5CCN(c6ccc7c(c6)C(=O)N(C6CCC(=O)NC6=O)C7=O)CC5)CC4)ncc3Cl)ccc2n(C)c1=O] | 2-((6-((5-chloro-2-(4-(2-(1-(2-(2,6-dioxopiperidin-3-yl)-1,3-dioxoisoindolin-5-yl)piperidin-4-yl)propan-2-yl)piperazin-1-yl)pyrimidin-4-yl)amino)-1-methyl-2-oxo-1,2-dihydroquinolin-3-yl)oxy)-N-methoxyacetamide |

TABLE 1-continued

Exemplary bifunctional compounds of the present disclosure

| Ex. # | Parent Mol Structure | Name |
|---|---|---|
| 268 | | 2-((6-((5-chloro-2-(4-(2-(1-(2-(2,6-dioxopiperidin-3-yl)-6-methoxy-1,3-dioxoisoindolin-5-yl)piperidin-4-yl)propan-2-yl)piperazin-1-yl)pyrimidin-4-yl)amino)-1-methyl-2-oxo-1,2-dihydroquinolin-3-yl)oxy)-N-methylacetamide |
| 269 | | 3-(4-((4-(5-chloro-4-((1-methyl-3-(2-(methylamino)-2-oxoethoxy)-2-oxo-1,2-dihydroquinolin-6-yl)amino)pyrimidin-2-yl)piperazin-1-yl)methyl)piperidin-1-yl)-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 270 | | 2-{[6-({5-chloro-2-[4-(2-{1-[2-(2,6-dioxopiperidin-3-yl)-1-oxo-2,3-dihydro-1H-isoindol-5-yl]piperidin-4-yl}propan-2-yl)piperazin-1-yl]pyrimidin-4-yl}amino)-1-methyl-2-oxo-1,2-dihydroquinolin-3-yl]oxy}-N-methylacetamide |
| 271 | | 2-{[6-({5-chloro-2-[2-({4-[2-(2,6-dioxopiperidin-3-yl)-1,3-dioxo-2,3-dihydro-1H-isoindol-4-yl]piperazin-1-yl}methyl)morpholin-4-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 272 | 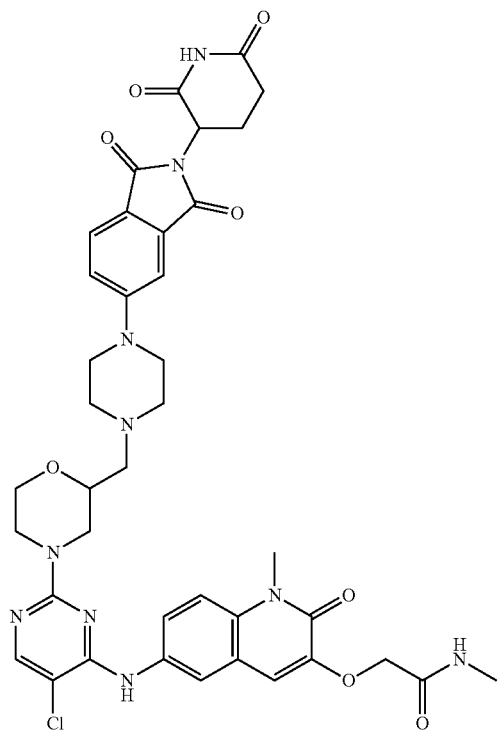 [SMILES: CNC(=O)COc1cc2cc(Nc3nc(N4CCOC(CN5CCN(c6ccc7c(c6)C(=O)N(C6CCC(=O)NC6=O)C7=O)CC5)C4)ncc3Cl)ccc2n(C)c1=O] | 2-{[6-({5-chloro-2-[2-({4-[2-(2,6-dioxopiperidin-3-yl)-1,3-dioxo-2,3-dihydro-1H-isoindol-5-yl]piperazin-1-yl}methyl)morpholin-4-yl]pyrimidin-4-yl}amino)-1-methyl-2-oxo-1,2-dihydroquinolin-3-yl]oxy}-N-methylacetamide |
| 273 | 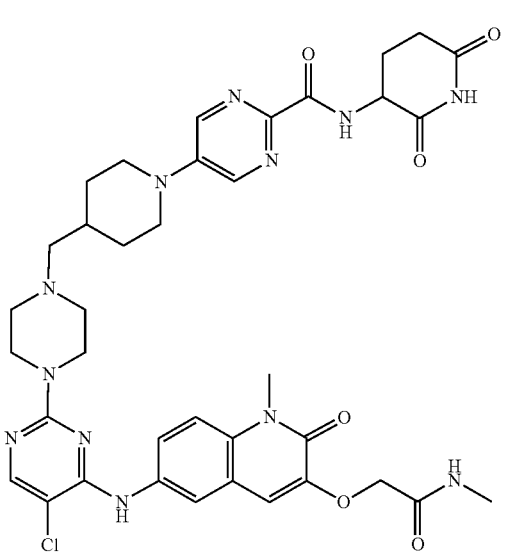 [SMILES: CNC(=O)COc1cc2cc(Nc3nc(N4CCN(CC5CCN(c6cnc(C(=O)NC7CCC(=O)NC7=O)nc6)CC5)CC4)ncc3Cl)ccc2n(C)c1=O] | 5-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)pyrimidine-2-carboxamide |

TABLE 1-continued

Exemplary bifunctional compounds of the present disclosure

| Ex. # | Parent Mol Structure | Name |
|---|---|---|
| 274 | | 7-({5-chloro-2-[4-(2-{1-[2-(2,6-dioxopiperidin-3-yl)-1,3-dioxo-2,3-dihydro-1H-isoindol-5-yl]piperidin-4-yl}propan-2-yl)piperazin-1-yl]pyrimidin-4-yl}amino)-N,4-dimethyl-3-oxo-3,4-dihydro-2H-1,4-benzoxazine-2-carboxamide |
| 275 | | 2-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-6-fluorobenzamide |

TABLE 1-continued

Exemplary bifunctional compounds of the present disclosure

| Ex. # | Parent Mol Structure | Name |
|---|---|---|
| 276 | | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)benzamide |
| 277 | | 5-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 278 | | 6-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)pyridazine-3-carboxamide |
| 279 | | 2-{[6-({5-chloro-2-[4-(1-{4-[2-(2,6-dioxopiperidin-3-yl)-1,3-dioxo-2,3-dihydro-1H-isoindol-5-yl]piperazin-1-yl}-2-methylpropan-2-yl)piperazin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 280 | 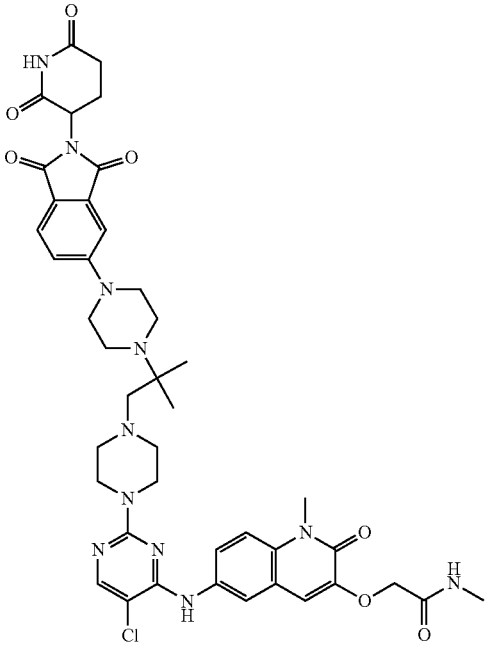 [SMILES: CNC(=O)COc1cc2cc(Nc3nc(N4CCN(CC(C)(C)N5CCN(c6ccc7c(c6)C(=O)N(C6CCC(=O)NC6=O)C7=O)CC5)CC4)ncc3Cl)ccc2n(C)c1=O] | 2-{[6-({5-chloro-2-[4-(2-{4-[2-(2,6-dioxopiperidin-3-yl)-1,3-dioxo-2,3-dihydro-1H-isoindol-5-yl]piperazin-1-yl}-2-methylpropyl)piperazin-1-yl]pyrimidin-4-yl}amino)-1-methyl-2-oxo-1,2-dihydroquinolin-3-yl]oxy}-N-methylacetamide |
| 281 | 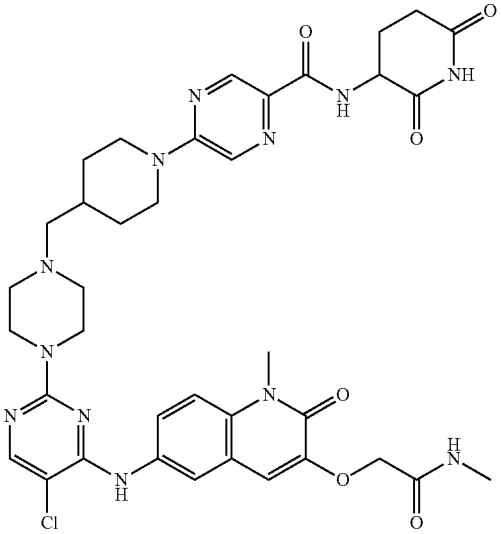 | 5-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)pyrazine-2-carboxamide |

TABLE 1-continued

Exemplary bifunctional compounds of the present disclosure

| Ex. # | Parent Mol Structure | Name |
|---|---|---|
| 282 | 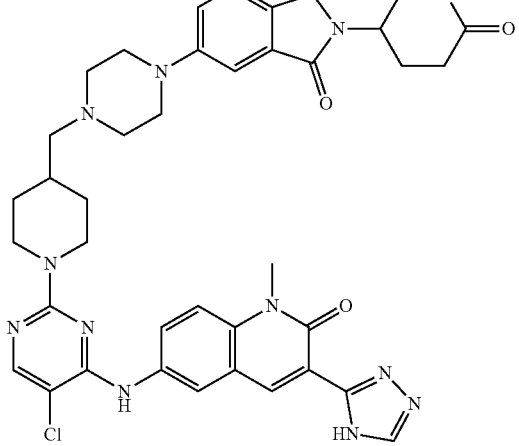 | 5-(4-{[1-(5-chloro-4-{[1-methyl-2-oxo-3-(4H-1,2,4-triazol-3-yl)-1,2-dihydroquinolin-6-yl]amino}pyrimidin-2-yl)piperidin-4-yl]methyl}piperazin-1-yl)-2-(2,6-dioxopiperidin-3-yl)-2,3-dihydro-1H-isoindole-1,3-dione |
| 283 | 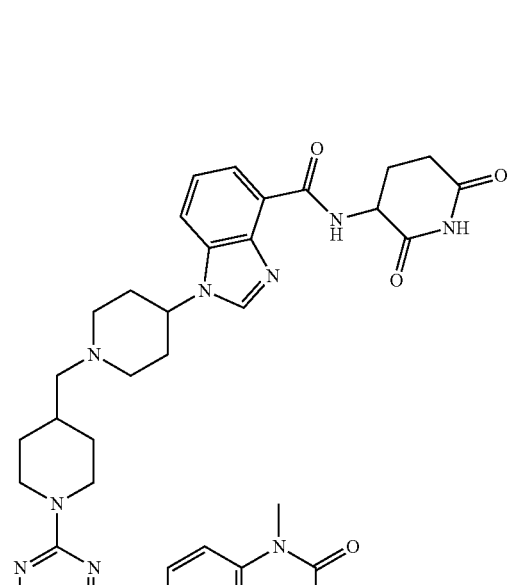 | 1-[1-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)piperidin-4-yl]-N-(2,6-dioxopiperidin-3-yl)-1H-1,3-benzodiazole-4-carboxamide |

TABLE 1-continued

Exemplary bifunctional compounds of the present disclosure

| Ex. # | Parent Mol Structure | Name |
|---|---|---|
| 284 | | 4-(4-{[(2R,6S)-4-[5-chloro-4-({1-methyl-3-[(methylcarbamoyl)methoxy]-2-oxo-1,2-dihydroquinolin-6-yl}amino)pyrimidin-2-yl]-2,6-dimethylpiperazin-1-yl]methyl}piperidin-1-yl)-N-(2,6-dioxopiperidin-3-yl)-2-fluorobenzamide |
| 285 | | 5-(4-{2-[4-(5-chloro-4-{[1-methyl-3-(5-methyl-1,3,4-oxadiazol-2-yl)-2-oxo-1,2-dihydroquinolin-6-yl]amino}pyrimidin-2-yl)piperazin-1-yl]propan-2-yl}piperidin-1-yl)-2-(2,6-dioxopiperidin-3-yl)-2,3-dihydro-1H-isoindole-1,3-dione |

TABLE 1-continued

Exemplary bifunctional compounds of the present disclosure

| Ex. # | Parent Mol Structure | Name |
|---|---|---|
| 286 | 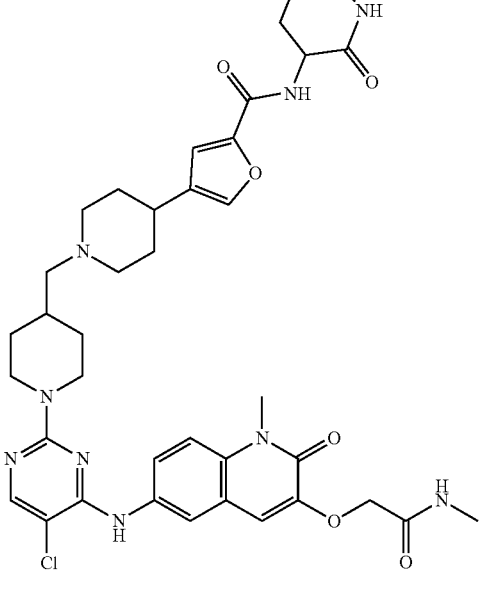 | 4-[1-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)piperidin-4-yl]-N-(2,6-dioxopiperidin-3-yl)furan-2-carboxamide |
| 287 | 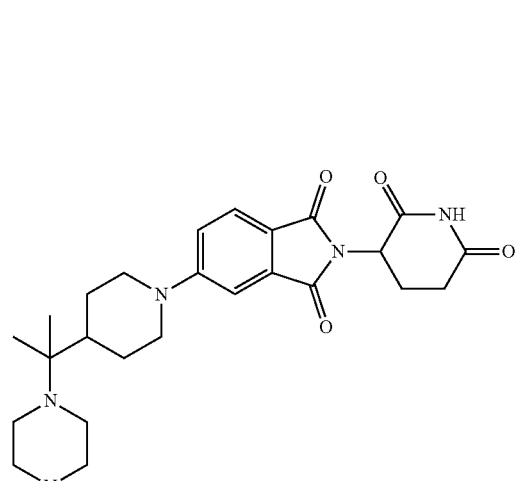 | 3-[7-({5-chloro-2-[4-(2-{1-[2-(2,6-dioxopiperidin-3-yl)-1,3-dioxo-2,3-dihydro-1H-isoindol-5-yl]piperidin-4-yl}propan-2-yl)piperazin-1-yl]pyrimidin-4-yl}amino)-4-methyl-3-oxo-3,4-dihydro-2H-1,4-benzoxazin-2-yl]-N-methylpropanamide |

TABLE 1-continued

Exemplary bifunctional compounds of the present disclosure

| Ex. # | Parent Mol Structure | Name |
|---|---|---|
| 288 | 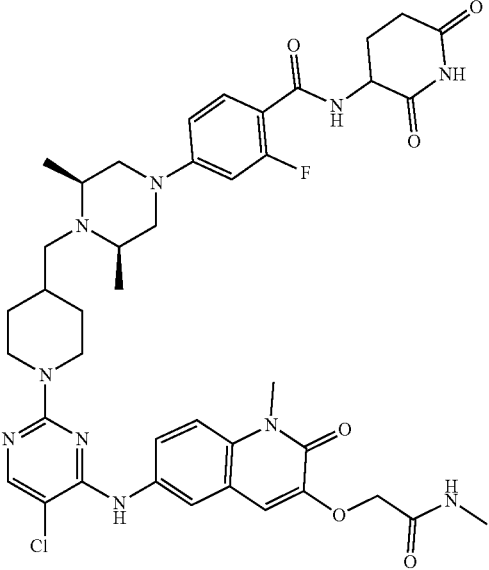 [SMILES: CNC(=O)COc1cc2cc(Nc3nc(N4CCC(CN5[C@H](C)CN(c6ccc(C(=O)NC7CCC(=O)NC7=O)c(F)c6)C[C@@H]5C)CC4)ncc3Cl)ccc2n(C)c1=O] | 4-[(3R,5S)-4-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)-3,5-dimethylpiperazin-1-yl]-N-(2,6-dioxopiperidin-3-yl)-2-fluorobenzamide |
| 289 | 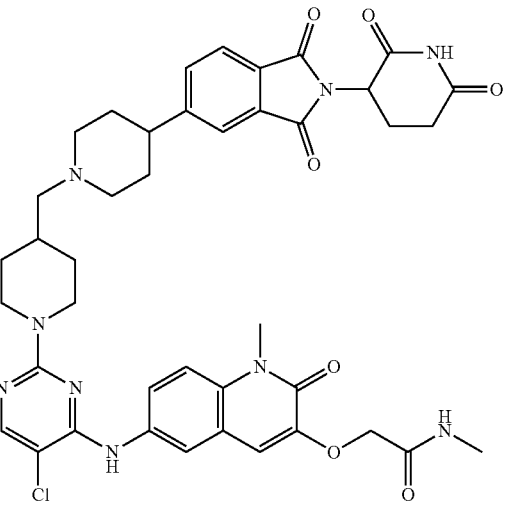 | 2-{[6-({5-chloro-2-[4-({4-[2-(2,6-dioxopiperidin-3-yl)-1,3-dioxo-2,3-dihydro-1H-isoindol-5-yl]piperidin-1-yl}methyl)piperidin-1-yl]pyrimidin-4-yl}amino)-1-methyl-2-oxo-1,2-dihydroquinolin-3-yl]oxy}-N-methylacetamide |
| 290 | 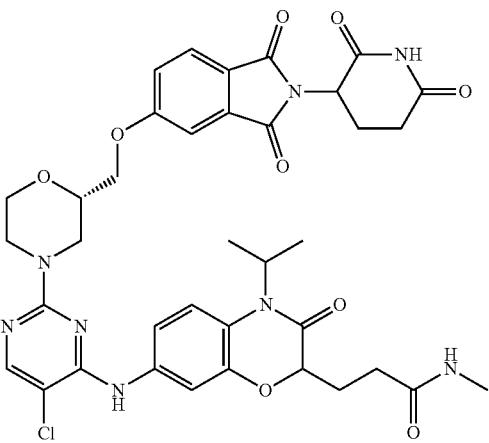 [SMILES: CNC(=O)CCC1Oc2cc(Nc3nc(N4CCO[C@H](COc5ccc6c(c5)C(=O)N(C5CCC(=O)NC5=O)C6=O)C4)ncc3Cl)ccc2N(C(C)C)C1=O] | 2-{[6-({5-chloro-2-[(2S)-2-({[2-(2,6-dioxopiperidin-3-yl)-1,3-dioxo-2,3-dihydro-1H-isoindol-5-yl]oxy}methyl)morpholin-4-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 291 | 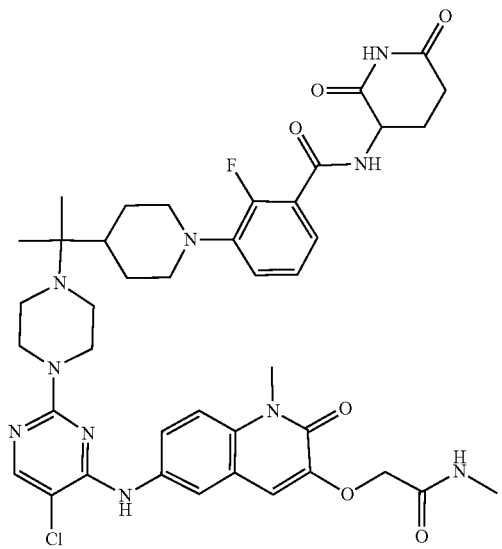 [SMILES: CNC(=O)COc1cc2cc(Nc3nc(N4CCN(C(C)(C)C5CCN(c6cccc(C(=O)NC7CCC(=O)NC7=O)c6F)CC5)CC4)ncc3Cl)ccc2n(C)c1=O] | 3-[4-(2-{4-[5-chloro-4-({1-methyl-3-[(methylcarbamoyl)methoxy]-2-oxo-1,2-dihydroquinolin-6-yl}amino)pyrimidin-2-yl]piperazin-1-yl}propan-2-yl)piperidin-1-yl]-N-(2,6-dioxopiperidin-3-yl)-2-fluorobenzamide |
| 292 | 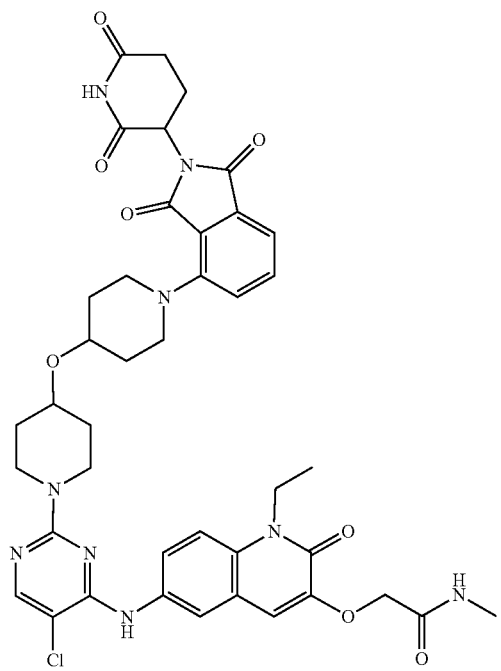 [SMILES: CCn1c(=O)c(OCC(=O)NC)cc2cc(Nc3nc(N4CCC(OC5CCN(c6cccc7c6C(=O)N(C6CCC(=O)NC6=O)C7=O)CC5)CC4)ncc3Cl)ccc21] | 2-{[6-({5-chloro-2-[4-({1-[2-(2,6-dioxopiperidin-3-yl)-1,3-dioxo-2,3-dihydro-1H-isoindol-4-yl]piperidin-4-yl}oxy)piperidin-1-yl]pyrimidin-4-yl}amino)-1-ethyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 293 | 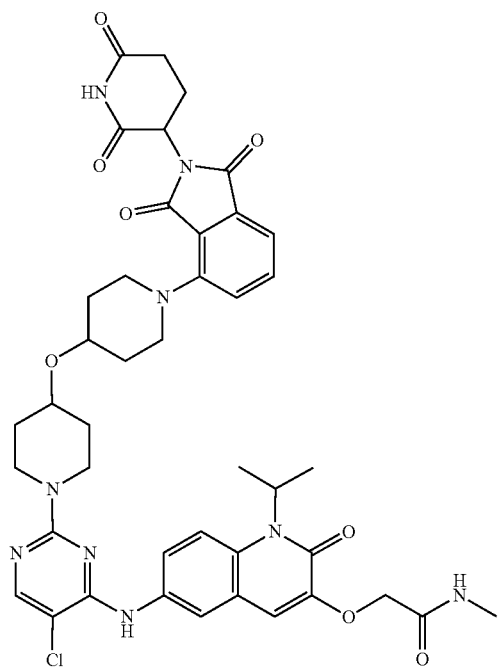 [SMILES: CNC(=O)COc1cc2cc(Nc3nc(N4CCC(OC5CCN(c6cccc7c6C(=O)N(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-1,3-dioxo-2,3-dihydro-1H-isoindol-4-yl]piperidin-4-yl}oxy)piperidin-1-yl]pyrimidin-4-yl}amino)-2-oxo-1-(propan-2-yl)-1,2-dihydroquinolin-3-yl]oxy}-N-methylacetamide |
| 294 | 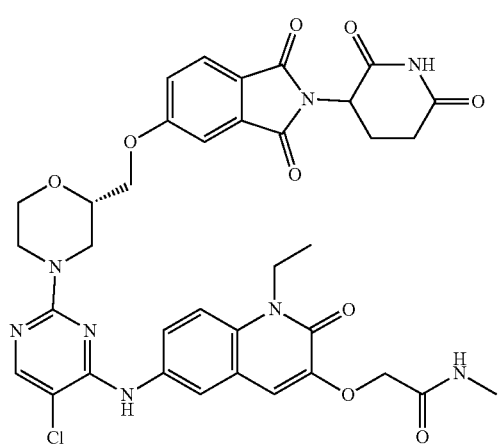 [SMILES: CCn1c(=O)c(OCC(=O)NC)cc2cc(Nc3nc(N4CCO[C@H](COc5ccc6c(c5)C(=O)N(C5CCC(=O)NC5=O)C6=O)C4)ncc3Cl)ccc21] | 2-{[6-({5-chloro-2-[(2S)-2-({[2-(2,6-dioxopiperidin-3-yl)-1,3-dioxo-2,3-dihydro-1H-isoindol-5-yl]oxy}methyl)morpholin-4-yl]pyrimidin-4-yl}amino)-1-ethyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 295 | 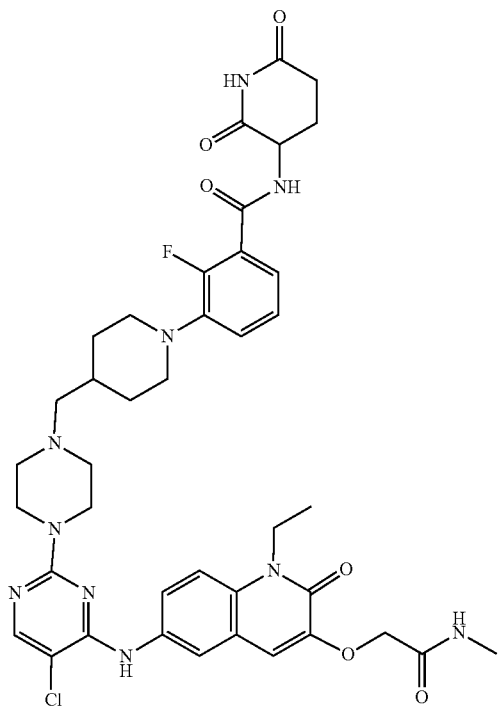 [SMILES: CCn1c(=O)c(OCC(=O)NC)cc2cc(Nc3nc(N4CCN(CC5CCN(c6cccc(C(=O)NC7CCC(=O)NC7=O)c6F)CC5)CC4)ncc3Cl)ccc21] | 3-[4-({4-[5-chloro-4-({1-ethyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-fluorobenzamide |
| 296 | 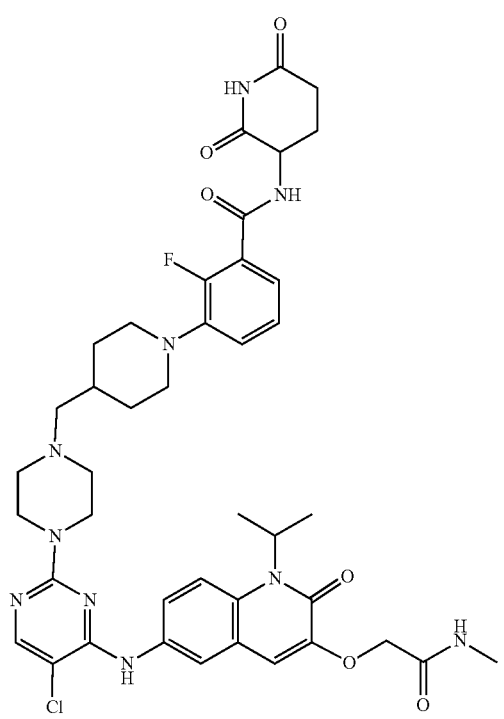 [SMILES: CNC(=O)COc1cc2cc(Nc3nc(N4CCN(CC5CCN(c6cccc(C(=O)NC7CCC(=O)NC7=O)c6F)CC5)CC4)ncc3Cl)ccc2n(C(C)C)c1=O] | 3-[4-({4-[5-chloro-4-({3-[(methylcarbamoyl)methoxy]-2-oxo-1-(propan-2-yl)-1,2-dihydroquinolin-6-yl}amino)pyrimidin-2-yl]piperazin-1-yl}methyl)piperidin-1-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 297 | | 2-{[6-({3-chloro-5-cyano-6-[4-({1-[2-(2,6-dioxopiperidin-3-yl)-1,3-dioxo-2,3-dihydro-1H-isoindol-5-yl]piperidin-4-yl}methyl)piperazin-1-yl]pyridin-2-yl}amino)-1-methyl-2-oxo-1,2-dihydroquinolin-3-yl]oxy}-N-methylacetamide |
| 298 | | 2-{[6-({5-chloro-2-[4-({6-[2-(2,6-dioxopiperidin-3-yl)-1,3-dioxo-2,3-dihydro-1H-isoindol-5-yl]-2,6-diazaspiro[3.3]heptan-2-yl}methyl)piperidin-1-yl]pyrimidin-4-yl}amino)-1-ethyl-2-oxo-1,2-dihydroquinolin-3-yl]oxy}-N-methylacetamide |
| 299 | | 2-{[6-({5-chloro-2-[4-(2-{1-[2-(2,6-dioxopiperidin-3-yl)-1,3-dioxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 300 | 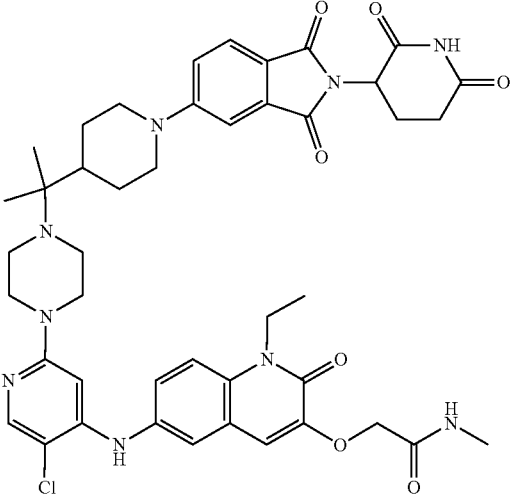 [SMILES: CCn1c(=O)c(OCC(=O)NC)cc2cc(Nc3cc(N4CCN(C(C)(C)C5CCN(c6ccc7c(c6)C(=O)N(C6CCC(=O)NC6=O)C7=O)CC5)CC4)ncc3Cl)ccc21] | 2-{[6-({5-chloro-2-[4-(2-{1-[2-(2,6-dioxopiperidin-3-yl)-1,3-dioxo-2,3-dihydro-1H-isoindol-5-yl]piperidin-4-yl}propan-2-yl)piperazin-1-yl]pyridin-4-yl}amino)-1-ethyl-2-oxo-1,2-dihydroquinolin-3-yl]oxy}-N-methylacetamide |
| 301 | 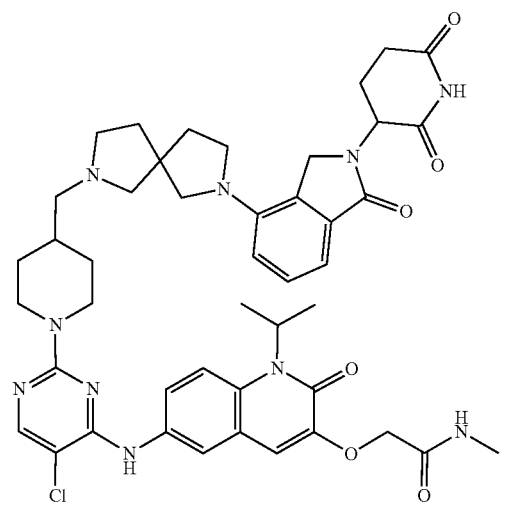 [SMILES: CNC(=O)COc1cc2cc(Nc3nc(N4CCC(CN5CCC6(CCN(c7cccc8c7CN(C7CCC(=O)NC7=O)C8=O)C6)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-4-yl]-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 302 | 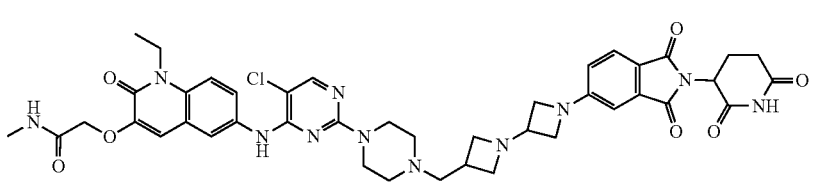 [SMILES: CCn1c(=O)c(OCC(=O)NC)cc2cc(Nc3nc(N4CCN(CC5CN(C6CN(c7ccc8c(c7)C(=O)N(C7CCC(=O)NC7=O)C8=O)C6)C5)CC4)ncc3Cl)ccc21] | 2-{[6-({5-chloro-2-[4-({1'-[2-(2,6-dioxopiperidin-3-yl)-1,3-dioxo-2,3-dihydro-1H-isoindol-5-yl]-[1,3'-biazetidin]-3-yl}methyl)piperazin-1-yl]pyrimidin-4-yl}amino)-1-ethyl-2-oxo-1,2-dihydroquinolin-3-yl]oxy}-N-methylacetamide |
| 303 | 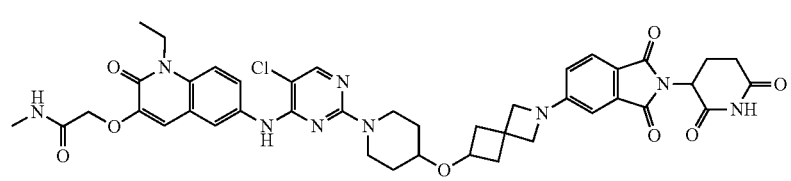 [SMILES: CCn1c(=O)c(OCC(=O)NC)cc2cc(Nc3nc(N4CCC(OC5CC6(C5)CN(c5ccc7c(c5)C(=O)N(C5CCC(=O)NC5=O)C7=O)C6)CC4)ncc3Cl)ccc21] | 2-{[6-({5-chloro-2-[4-({2-[2-(2,6-dioxopiperidin-3-yl)-1,3-dioxo-2,3-dihydro-1H-isoindol-5-yl]-2-azaspiro[3.3]heptan-6-yl}oxy)piperidin-1-yl]pyrimidin-4-yl}amino)-1-ethyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 304 | | 2-{[6-({5-chloro-2-[4-(2-{1-[2-(2,6-dioxopiperidin-3-yl)-1,3-dioxo-2,3-dihydro-1H-isoindol-5-yl]piperidin-4-yl}propan-2-yl)piperazin-1-yl]pyrimidin-4-yl}amino)-1-ethyl-2-oxo-1,2-dihydroquinolin-3-yl]oxy}-N-methylacetamide |
| 305 | | 2-({6-[(5-chloro-2-{4-[(1r,3r)-3-{4-[2-(2,6-dioxopiperidin-3-yl)-1,3-dioxo-2,3-dihydro-1H-isoindol-4-yl]piperidin-1-yl}cyclobutoxy]piperidin-1-yl}pyrimidin-4-yl)amino]-1-methyl-2-oxo-1,2-dihydroquinolin-3-yl}oxy)-N-methylacetamide |
| 306 | | 2-{[6-({5-chloro-2-[4-({6-[2-(2,6-dioxopiperidin-3-yl)-1,3-dioxo-2,3-dihydro-1H-isoindol-5-yl]-2,6-diazaspiro[3.3]heptan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 307 | 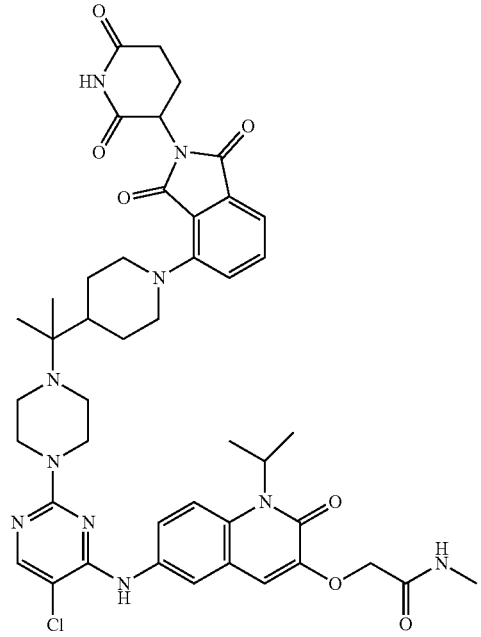 [SMILES: CNC(=O)COc1cc2cc(Nc3nc(N4CCN(C(C)(C)C5CCN(c6cccc7c6C(=O)N(C6CCC(=O)NC6=O)C7=O)CC5)CC4)ncc3Cl)ccc2n(C(C)C)c1=O] | 2-{[6-({5-chloro-2-[4-(2-{1-[2-(2,6-dioxopiperidin-3-yl)-1,3-dioxo-2,3-dihydro-1H-isoindol-4-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |
| 308 | 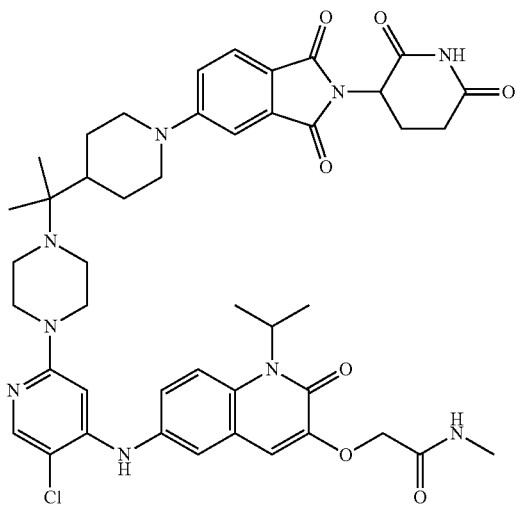 [SMILES: CNC(=O)COc1cc2cc(Nc3cc(N4CCN(C(C)(C)C5CCN(c6ccc7c(c6)C(=O)N(C6CCC(=O)NC6=O)C7=O)CC5)CC4)ncc3Cl)ccc2n(C(C)C)c1=O] | 2-{[6-({5-chloro-2-[4-(2-{1-[2-(2,6-dioxopiperidin-3-yl)-1,3-dioxo-2,3-dihydro-1H-isoindol-5-yl]piperidin-4-yl}propan-2-yl)piperazin-1-yl]pyridin-4-yl}amino)-2-oxo-1-(propan-2-yl)-1,2-dihydroquinolin-3-yl]oxy}-N-methylacetamide |
| 309 | 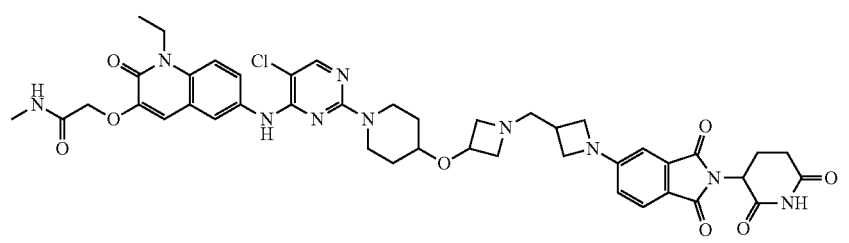 [SMILES: CCn1c(=O)c(OCC(=O)NC)cc2cc(Nc3nc(N4CCC(OC5CN(CC6CN(c7ccc8c(c7)C(=O)N(C7CCC(=O)NC7=O)C8=O)C6)C5)CC4)ncc3Cl)ccc21] | 2-[(6-{[5-chloro-2-(4-{[1-({1-[2-(2,6-dioxopiperidin-3-yl)-1,3-dioxo-2,3-dihydro-1H-isoindol-5-yl]azetidin-3-yl}methyl)azetidin-3-yl]oxy}piperidin-1-yl)pyrimidin-4-yl]amino}-1-ethyl-2-oxo-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 310 | 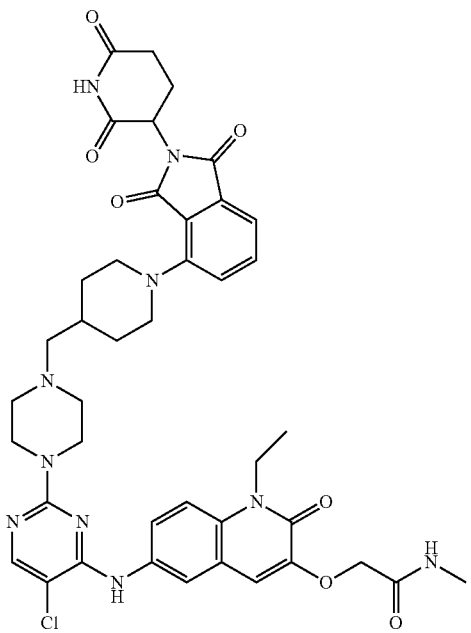 [SMILES: CCn1c(=O)c(OCC(=O)NC)cc2cc(Nc3nc(N4CCN(CC5CCN(c6cccc7c6C(=O)N(C6CCC(=O)NC6=O)C7=O)CC5)CC4)ncc3Cl)ccc21] | 2-{[6-({5-chloro-2-[4-({1-[2-(2,6-dioxopiperidin-3-yl)-1,3-dioxo-2,3-dihydro-1H-isoindol-4-yl]piperidin-4-yl}methyl)piperazin-1-yl]pyrimidin-4-yl}amino)-1-ethyl-2-oxo-1,2-dihydroquinolin-3-yl]oxy}-N-methylacetamide |
| 311 | 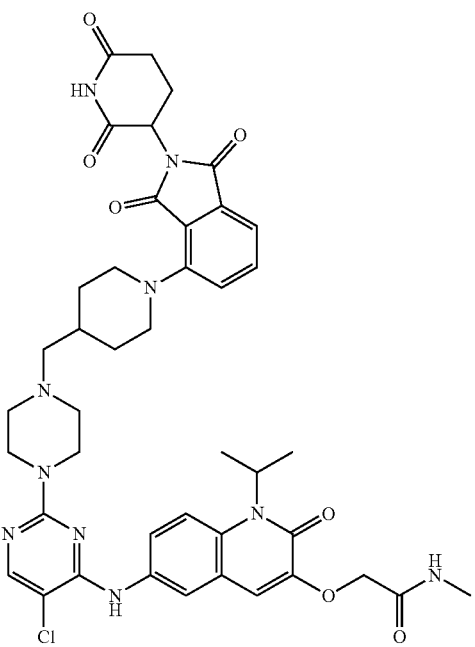 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-1,3-dioxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 312 | 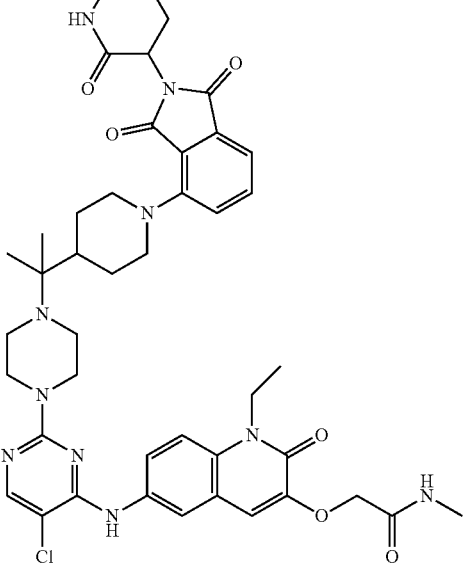 | 2-{[6-({5-chloro-2-[4-(2-{1-[2-(2,6-dioxopiperidin-3-yl)-1,3-dioxo-2,3-dihydro-1H-isoindol-4-yl]piperidin-4-yl}propan-2-yl)piperazin-1-yl]pyrimidin-4-yl}amino)-1-ethyl-2-oxo-1,2-dihydroquinolin-3-yl]oxy}-N-methylacetamide |
| 313 | 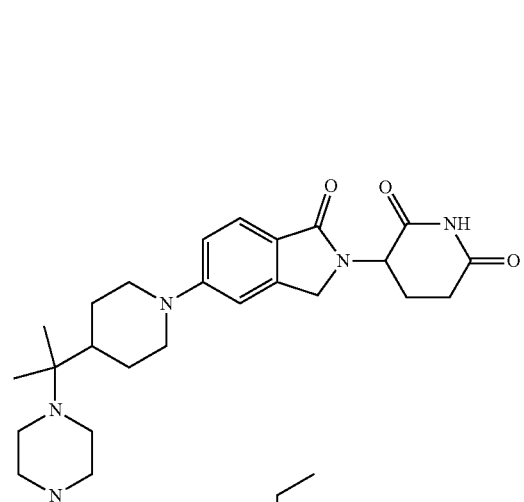 | 2-{[6-({5-chloro-2-[4-(2-{1-[2-(2,6-dioxopiperidin-3-yl)-1-oxo-2,3-dihydro-1H-isoindol-5-yl]piperidin-4-yl}propan-2-yl)piperazin-1-yl]pyrimidin-4-yl}amino)-1-ethyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 314 | 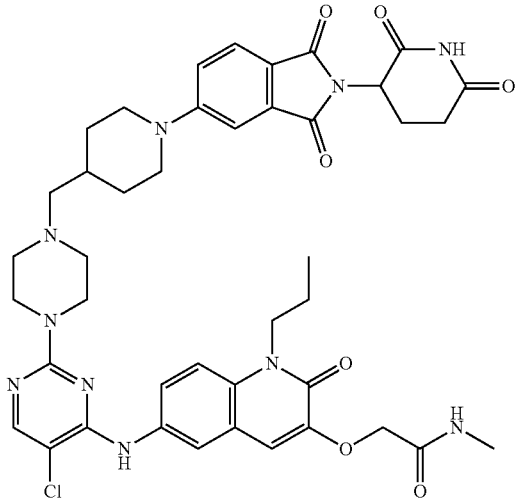 [SMILES: CCCn1c(=O)c(OCC(=O)NC)cc2cc(Nc3nc(N4CCN(CC5CCN(c6ccc7c(c6)C(=O)N(C6CCC(=O)NC6=O)C7=O)CC5)CC4)ncc3Cl)ccc21] | 2-{[6-({5-chloro-2-[4-({1-[2-(2,6-dioxopiperidin-3-yl)-1,3-dioxo-2,3-dihydro-1H-isoindol-5-yl]piperidin-4-yl}methyl)piperazin-1-yl]pyrimidin-4-yl}amino)-2-oxo-1-propyl-1,2-dihydroquinolin-3-yl]oxy}-N-methylacetamide |
| 315 | 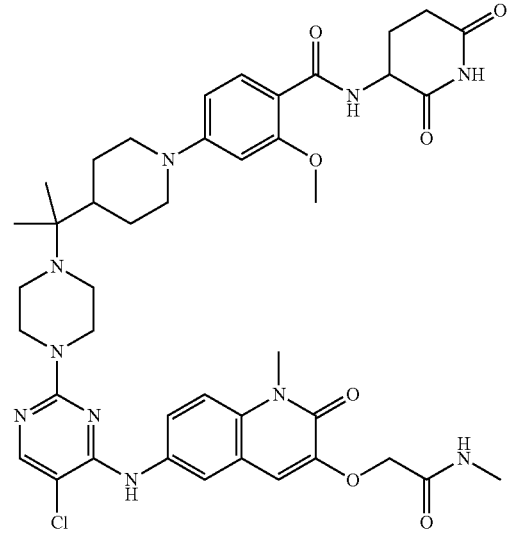 [SMILES: CNC(=O)COc1cc2cc(Nc3nc(N4CCN(C(C)(C)C5CCN(c6ccc(C(=O)NC7CCC(=O)NC7=O)c(OC)c6)CC5)CC4)ncc3Cl)ccc2n(C)c1=O] | 4-[4-(2-{4-[5-chloro-4-({1-methyl-3-[(methylcarbamoyl)methoxy]-2-oxo-1,2-dihydroquinolin-6-yl}amino)pyrimidin-2-yl]piperazin-1-yl}propan-2-yl)piperidin-1-yl]-N-(2,6-dioxopiperidin-3-yl)-2-methoxybenzamide |
| 316 | 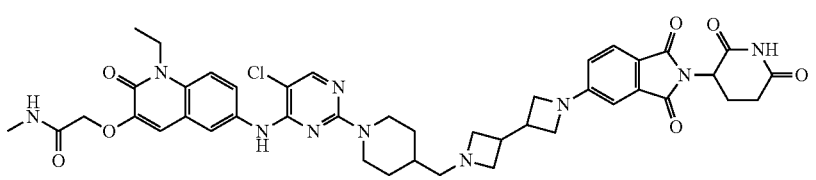 [SMILES: CCn1c(=O)c(OCC(=O)NC)cc2cc(Nc3nc(N4CCC(CN5CC(C6CN(c7ccc8c(c7)C(=O)N(C7CCC(=O)NC7=O)C8=O)C6)C5)CC4)ncc3Cl)ccc21] | 2-{[6-({5-chloro-2-[4-({1'-[2-(2,6-dioxopiperidin-3-yl)-1,3-dioxo-2,3-dihydro-1H-isoindol-5-yl]-[3,3'-biazetidin]-1-yl}methyl)piperidin-1-yl]pyrimidin-4-yl}amino)-1-ethyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 317 | 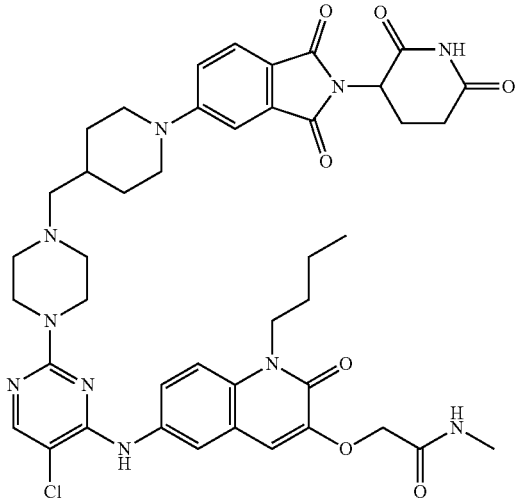 [SMILES: CCCCn1c(=O)c(OCC(=O)NC)cc2cc(Nc3nc(N4CCN(CC5CCN(c6ccc7c(c6)C(=O)N(C6CCC(=O)NC6=O)C7=O)CC5)CC4)ncc3Cl)ccc21] | 2-{[1-butyl-6-({5-chloro-2-[4-({1-[2-(2,6-dioxopiperidin-3-yl)-1,3-dioxo-2,3-dihydro-1H-isoindol-5-yl]piperidin-4-yl}methyl)piperazin-1-yl]pyrimidin-4-yl}amino)-2-oxo-1,2-dihydroquinolin-3-yl]oxy}-N-methylacetamide |
| 318 | 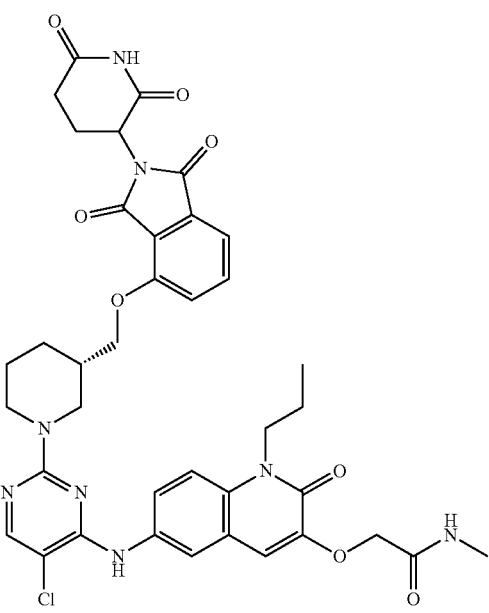 [SMILES: CCCn1c(=O)c(OCC(=O)NC)cc2cc(Nc3nc(N4CCC[C@H](COc5cccc6c5C(=O)N(C5CCC(=O)NC5=O)C6=O)C4)ncc3Cl)ccc21] | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-2-oxo-1-propyl-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 319 | 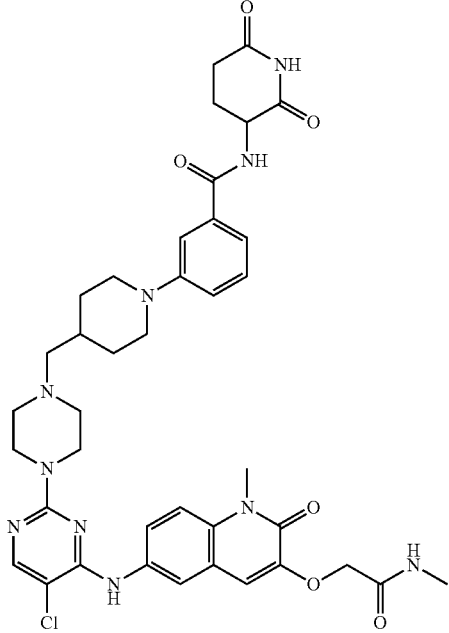 [SMILES: CNC(=O)COc1cc2cc(Nc3nc(N4CCN(CC5CCN(c6cccc(C(=O)NC7CCC(=O)NC7=O)c6)CC5)CC4)ncc3Cl)ccc2n(C)c1=O] | 3-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)benzamide |
| 320 | 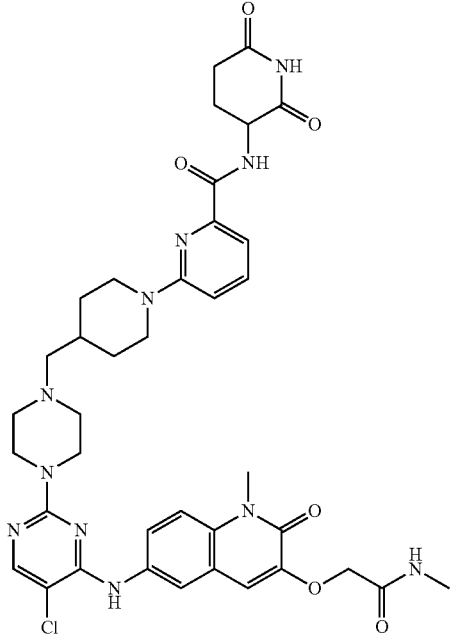 | 6-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)pyridine-2-carboxamide |

TABLE 1-continued

Exemplary bifunctional compounds of the present disclosure

| Ex. # | Parent Mol Structure | Name |
|---|---|---|
| 321 | 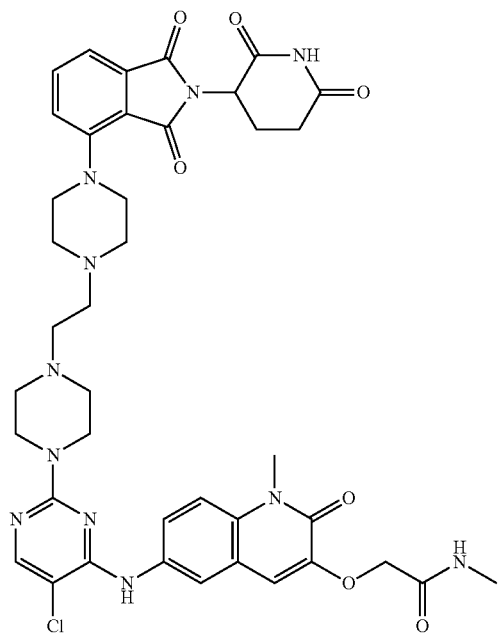 [SMILES: CNC(=O)COc1cc2cc(Nc3nc(N4CCN(CCN5CCN(c6cccc7c6C(=O)N(C6CCC(=O)NC6=O)C7=O)CC5)CC4)ncc3Cl)ccc2n(C)c1=O] | 2-{[6-({5-chloro-2-[4-(2-{4-[2-(2,6-dioxopiperidin-3-yl)-1,3-dioxo-2,3-dihydro-1H-isoindol-4-yl]piperazin-1-yl}ethyl)piperazin-1-yl]pyrimidin-4-yl}amino)-1-methyl-2-oxo-1,2-dihydroquinolin-3-yl]oxy}-N-methylacetamide |
| 322 | 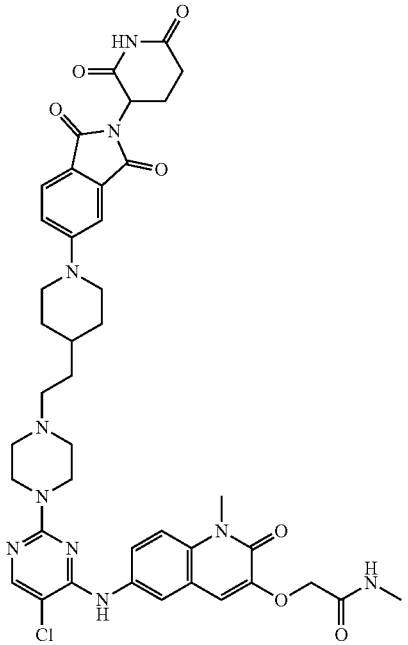 | 2-{[6-({5-chloro-2-[4-(2-{1-[2-(2,6-dioxopiperidin-3-yl)-1,3-dioxo-2,3-dihydro-1H-isoindol-5-yl]piperidin-4-yl}ethyl)piperazin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 323 | 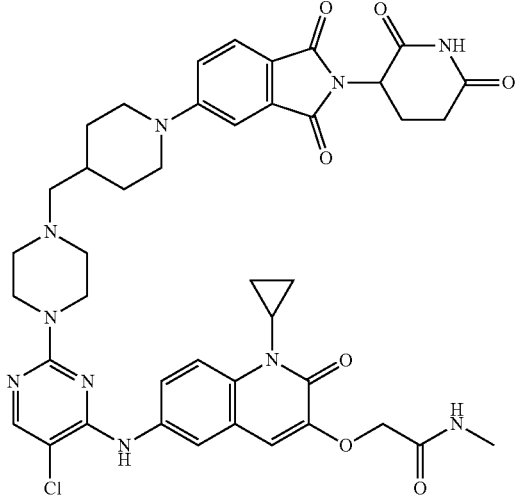 [SMILES: CNC(=O)COc1cc2cc(Nc3nc(N4CCN(CC5CCN(c6ccc7c(c6)C(=O)N(C6CCC(=O)NC6=O)C7=O)CC5)CC4)ncc3Cl)ccc2n(C2CC2)c1=O] | 2-{[6-({5-chloro-2-[4-({1-[2-(2,6-dioxopiperidin-3-yl)-1,3-dioxo-2,3-dihydro-1H-isoindol-5-yl]piperidin-4-yl}methyl)piperazin-1-yl]pyrimidin-4-yl}amino)-1-cyclopropyl-2-oxo-1,2-dihydroquinolin-3-yl]oxy}-N-methylacetamide |
| 324 | 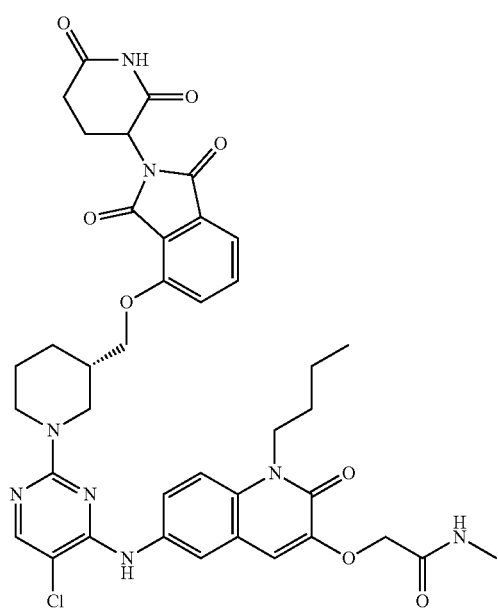 | 2-{[1-butyl-6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 325 | 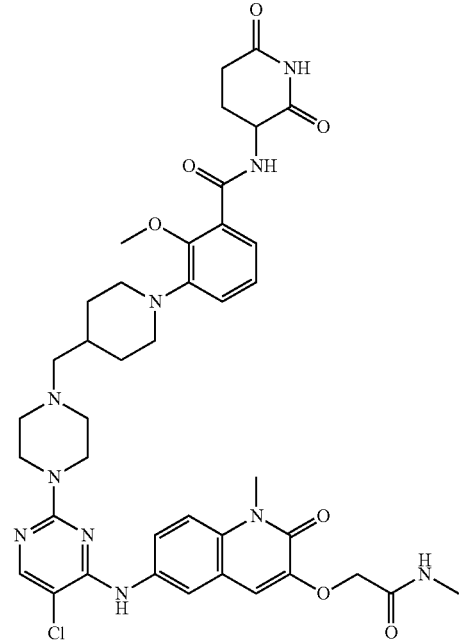 [SMILES: CNC(=O)COc1cc2cc(Nc3nc(N4CCN(CC5CCN(c6cccc(C(=O)NC7CCC(=O)NC7=O)c6OC)CC5)CC4)ncc3Cl)ccc2n(C)c1=O] | 3-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-methoxybenzamide |
| 326 | 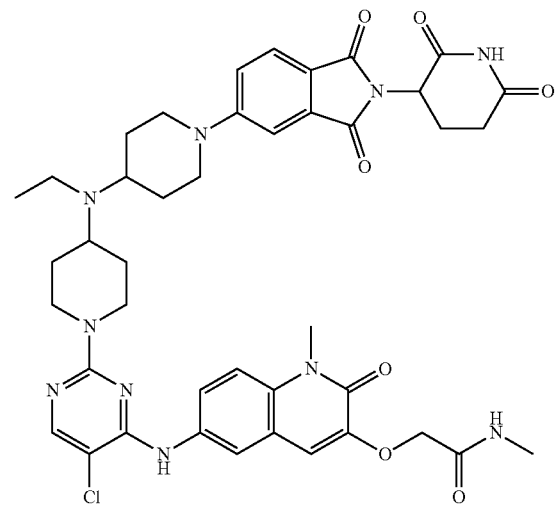 | 2-{[6-({5-chloro-2-[4-({1-[2-(2,6-dioxopiperidin-3-yl)-1,3-dioxo-2,3-dihydro-1H-isoindol-5-yl]piperidin-4-yl}(ethyl)amino)piperidin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 327 | | 2-{[6-({5-chloro-2-[4-({1'-[2-(2,6-dioxopiperidin-3-yl)-1,3-dioxo-2,3-dihydro-1H-isoindol-5-yl]piperidin-4-yl}(propyl)amino)piperidin-1-yl]pyrimidin-4-yl}amino)-1-methyl-2-oxo-1,2-dihydroquinolin-3-yl]oxy}-N-methylacetamide |
| 328 | | 2-{[6-({5-chloro-2-[4-({1'-[2-(2,6-dioxopiperidin-3-yl)-1,3-dioxo-2,3-dihydro-1H-isoindol-5-yl]-[1,3'-biazetidin]-3-yl}oxy)piperidin-1-yl]pyrimidin-4-yl}amino)-1-ethyl-2-oxo-1,2-dihydroquinolin-3-yl]oxy}-N-methylacetamide |
| 329 | | 2-{[6-({5-chloro-2-[4-({1-[2-(2,6-dioxopiperidin-3-yl)-1,3-dioxo-2,3-dihydro-1H-isoindol-5-yl]piperidin-4-yl}methoxy)piperidin-1-yl]pyrimidin-4-yl}amino)-1-ethyl-2-oxo-1,2-dihydroquinolin-3-yl]oxy}-N-methylacetamide |
| 330 | | 2-{[6-({5-chloro-2-[4-({1-[2-(2,6-dioxopiperidin-3-yl)-1,3-dioxo-2,3-dihydro-1H-isoindol-4-yl]piperidin-4-yl}methoxy)piperidin-1-yl]pyrimidin-4-yl}amino)-1-ethyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 331 | | 2-({6-[(5-chloro-2-{4-[({1-[2-(2,6-dioxopiperidin-3-yl)-1,3-dioxo-2,3-dihydro-1H-isoindol-5-yl]piperidin-4-yl}oxy)methyl]piperidin-1-yl}pyrimidin-4-yl)amino]-1-ethyl-2-oxo-1,2-dihydroquinolin-3-yl}oxy)-N-methylacetamide |
| 332 | | 2-({6-[(5-chloro-2-{4-[({1-[2-(2,6-dioxopiperidin-3-yl)-1,3-dioxo-2,3-dihydro-1H-isoindol-4-yl]piperidin-4-yl}oxy)methyl]piperidin-1-yl}pyrimidin-4-yl)amino]-1-ethyl-2-oxo-1,2-dihydroquinolin-3-yl}oxy)-N-methylacetamide |
| 333 | | 2-{[6-({5-chloro-2-[4-({1-[2-(2,6-dioxopiperidin-3-yl)-1,3-dioxo-2,3-dihydro-1H-isoindol-5-yl]piperidin-4-yl}methyl)piperazin-1-yl]pyrimidin-4-yl}amino)-1-(2-cyclopropylethyl)-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 334 | 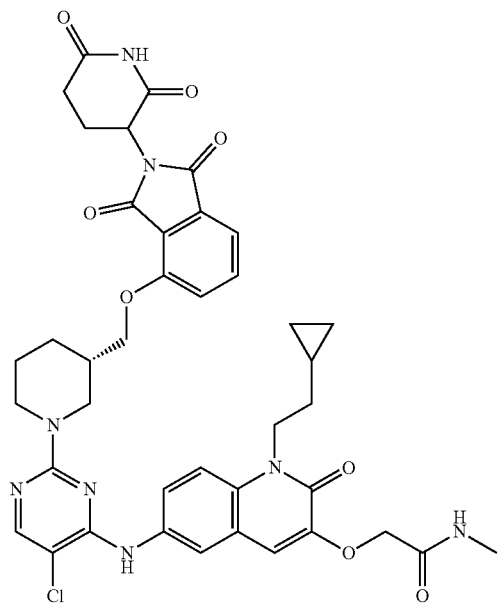 [SMILES: CNC(=O)COc1cc2cc(Nc3nc(N4CCC[C@H](COc5cccc6c5C(=O)N(C5CCC(=O)NC5=O)C6=O)C4)ncc3Cl)ccc2n(CCC2CC2)c1=O] | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-(2-cyclopropylethyl)-2-oxo-1,2-dihydroquinolin-3-yl]oxy}-N-methylacetamide |
| 335 | 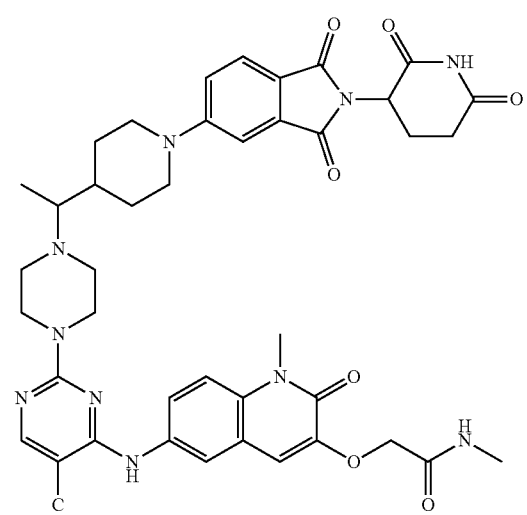 | 2-{[6-({5-chloro-2-[4-(1-{1-[2-(2,6-dioxopiperidin-3-yl)-1,3-dioxo-2,3-dihydro-1H-isoindol-5-yl]piperidin-4-yl}ethyl)piperazin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 336 | | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-cyclopropyl-2-oxo-1,2-dihydroquinolin-3-yl]oxy}-N-methylacetamide |
| 337 | | 2-{[6-({5-chloro-2-[4-(1-{1-[2-(2,6-dioxopiperidin-3-yl)-1,3-dioxo-2,3-dihydro-1H-isoindol-5-yl]piperidin-4-yl}propyl)piperazin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 338 | | 2-{[6-({5-chloro-2-[4-(1-{1-[2-(2,6-dioxopiperidin-3-yl)-1,3-dioxo-2,3-dihydro-1H-isoindol-5-yl]piperidin-4-yl}butyl)piperazin-1-yl]pyrimidin-4-yl}amino)-1-methyl-2-oxo-1,2-dihydroquinolin-3-yl]oxy}-N-methylacetamide |
| 339 | | 2-{[6-({5-chloro-2-[4-({1-[2-(2,6-dioxopiperidin-3-yl)-1,3-dioxo-2,3-dihydro-1H-isoindol-5-yl]-4-fluoropiperidin-4-yl}methyl)piperazin-1-yl]pyrimidin-4-yl}amino)-1-methyl-2-oxo-1,2-dihydroquinolin-3-yl]oxy}-N-methylacetamide |
| 340 | | 2-{[6-({5-chloro-2-[4-({4-[2-(2,6-dioxopiperidin-3-yl)-1,3-dioxo-2,3-dihydro-1H-isoindol-5-yl]piperazin-1-yl}methyl)-4-fluoropiperidin-1-yl]pyrimidin-4-yl}amino)-1-methyl-2-oxo-1,2-dihydroquinolin-3-yl]oxy}-N-methylacetamide |
| 341 | | 2-{[6-({5-chloro-2-[4-({1-[2-(2,6-dioxopiperidin-3-yl)-1,3-dioxo-2,3-dihydro-1H-isoindol-4-yl]-4-fluoropiperidin-4-yl}methyl)piperazin-1-yl]pyrimidin-4-yl}amino)-1-methyl-2-oxo-1,2-dihydroquinolin-3-yl]oxy}-N-methylacetamide |
| 342 | | 2-{[6-({5-chloro-2-[4-({4-[2-(2,6-dioxopiperidin-3-yl)-1,3-dioxo-2,3-dihydro-1H-isoindol-4-yl]piperazin-1-yl}methyl)-4-fluoropiperidin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 343 | | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-cyclohexyl-2-oxo-1,2-dihydroquinolin-3-yl]oxy}-N-methylacetamide |
| 344 | | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-ethoxybenzamide |

TABLE 1-continued

Exemplary bifunctional compounds of the present disclosure

| Ex. # | Parent Mol Structure | Name |
|---|---|---|
| 345 | 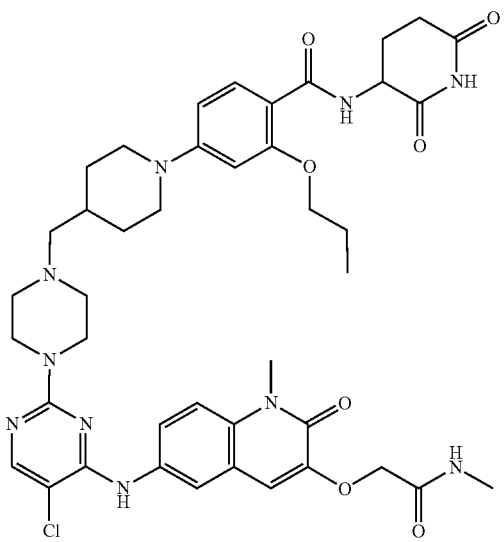 [SMILES: CCCOc1cc(N2CCC(CN3CCN(c4ncc(Cl)c(Nc5ccc6c(c5)cc(OCC(=O)NC)c(=O)n6C)n4)CC3)CC2)ccc1C(=O)NC1CCC(=O)NC1=O] | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-propoxybenzamide |
| 346 | 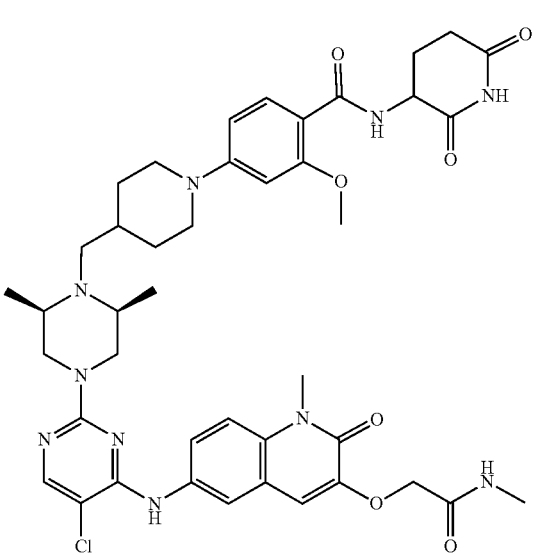 [SMILES: CNC(=O)COc1cc2cc(Nc3nc(N4C[C@@H](C)N(CC5CCN(c6ccc(C(=O)NC7CCC(=O)NC7=O)c(OC)c6)CC5)[C@@H](C)C4)ncc3Cl)ccc2n(C)c1=O] | 4-(4-{[(2R,6S)-4-[5-chloro-4-({1-methyl-3-[(methylcarbamoyl)methoxy]-2-oxo-1,2-dihydroquinolin-6-yl}amino)pyrimidin-2-yl]-2,6-dimethylpiperazin-1-yl]methyl}piperidin-1-yl)-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 347 | | 4-[(3R,5S)-4-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)-3,5-dimethylpiperazin-1-yl]-N-(2,6-dioxopiperidin-3-yl)-2-methoxybenzamide |
| 348 | | 4-{[(2S)-4-[5-chloro-4-({3-[(methylcarbamoyl)methoxy]-2-oxo-1-(propan-2-yl)-1,2-dihydroquinolin-6-yl}amino)pyrimidin-2-yl]morpholin-2-yl]methoxy}-N-(2,6-dioxopiperidin-3-yl)benzamide |
| 349 | | 5-{[(2S)-4-[5-chloro-4-({3-[(methylcarbamoyl)methoxy]-2-oxo-1-(propan-2-yl)-1,2-dihydroquinolin-6-yl}amino)pyrimidin-2-yl]morpholin-2-yl]methoxy}-N-(2,6-dioxopiperidin-3-yl)pyridine-2-carboxamide |
| 350 | | 4-{[(2S)-4-[5-chloro-4-({3-[(methylcarbamoyl)methoxy]-2-oxo-1-(propan-2-yl)-1,2-dihydroquinolin-6-yl}amino)pyrimidin-2-yl]morpholin-2-yl]methoxy}-N-(2,6-dioxopiperidin-3-yl)-2-fluorobenzamide |
| 351 | | 4-{[(2S)-4-[5-chloro-4-({3-[(methylcarbamoyl)methoxy]-2-oxo-1-(propan-2-yl)-1,2-dihydroquinolin-6-yl}amino)pyrimidin-2-yl]morpholin-2-yl]methoxy}-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 352 | 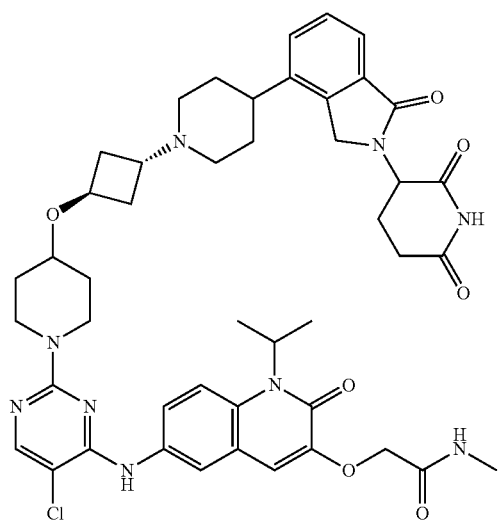 [SMILES: CNC(=O)COc1cc2cc(Nc3nc(N4CCC(O[C@H]5C[C@H](N6CCC(c7cccc8c7CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1-oxo-2,3-dihydro-1H-isoindol-4-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 353 | 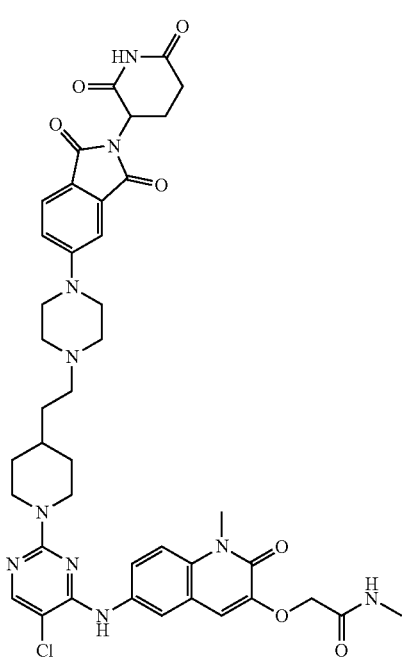 [SMILES: CNC(=O)COc1cc2cc(Nc3nc(N4CCC(CCN5CCN(c6ccc7c(c6)C(=O)N(C6CCC(=O)NC6=O)C7=O)CC5)CC4)ncc3Cl)ccc2n(C)c1=O] | 2-{[6-({5-chloro-2-[4-(2-(4-[2-(2,6-dioxopiperidin-3-yl)-1,3-dioxo-2,3-dihydro-1H-isoindol-5-yl]piperazin-1-yl}ethyl)piperidin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 354 | 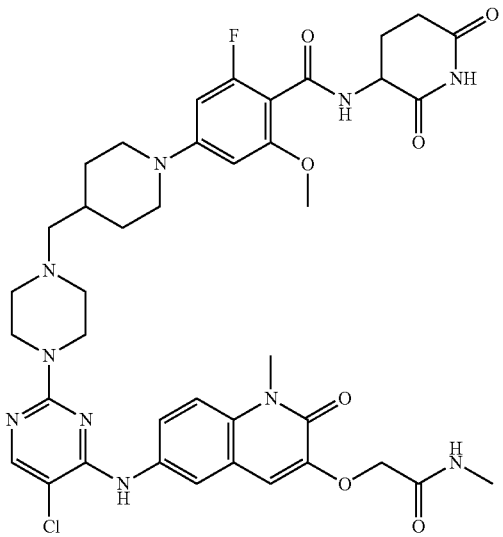 | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-fluoro-6-methoxybenzamide |
| 355 | 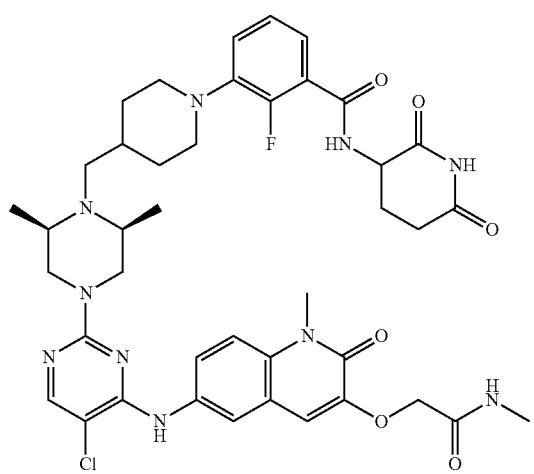 | 3-(4-{[(2R,6S)-4-[5-chloro-4-({1-methyl-3-[(methylcarbamoyl)methoxy]-2-oxo-1,2-dihydroquinolin-6-yl}amino)pyrimidin-2-yl]-2,6-dimethylpiperazin-1-yl]methyl}piperidin-1-yl)-N-(2,6-dioxopiperidin-3-yl)-2-fluorobenzamide |
| 356 | 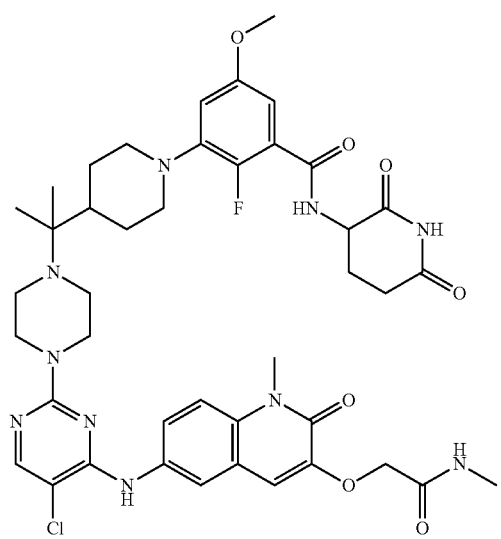 [SMILES: CNC(=O)COc1cc2cc(Nc3nc(N4CCN(C(C)(C)C5CCN(c6cc(OC)cc(C(=O)NC7CCC(=O)NC7=O)c6F)CC5)CC4)ncc3Cl)ccc2n(C)c1=O] | 3-[4-(2-{4-[5-chloro-4-({1-methyl-3-[(methylcarbamoyl)methoxy]-2-oxo-1,2-dihydroquinolin-6-yl}amino)pyrimidin-2-yl]piperazin-1-yl}propan-2-yl)piperidin-1-yl]-N-(2,6-dioxopiperidin-3-yl)-2-fluoro-5-methoxybenzamide |

TABLE 1-continued

Exemplary bifunctional compounds of the present disclosure

| Ex. # | Parent Mol Structure | Name |
|---|---|---|
| 357 | | 2-({6-[(5-chloro-2-{4-[(3R,5S)-5-({[2-(2,6-dioxopiperidin-3-yl)-1,3-dioxo-2,3-dihydro-1H-isoindol-5-yl]oxy}methyl)-1-methylpyrrolidin-3-yl]piperazin-1-yl}pyrimidin-4-yl)amino]-1-ethyl-2-oxo-1,2-dihydroquinolin-3-yl}oxy)-N-methylacetamide |
| 358 | | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-(propan-2-yloxy)benzamide |
| 359 | | 5-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-3-methoxypyridine-2-carboxamide |

TABLE 1-continued

Exemplary bifunctional compounds of the present disclosure

| Ex. # | Parent Mol Structure | Name |
|---|---|---|
| 360 | 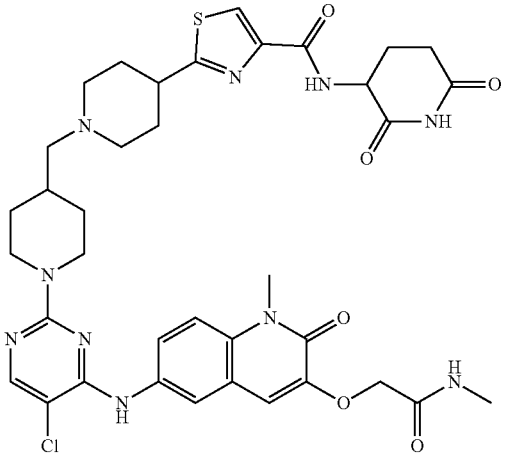 [SMILES: CNC(=O)COc1cc2cc(Nc3nc(N4CCC(CN5CCC(c6nc(C(=O)NC7CCC(=O)NC7=O)cs6)CC5)CC4)ncc3Cl)ccc2n(C)c1=O] | 2-[1-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)piperidin-4-yl]-N-(2,6-dioxopiperidin-3-yl)-1,3-thiazole-4-carboxamide |
| 361 | 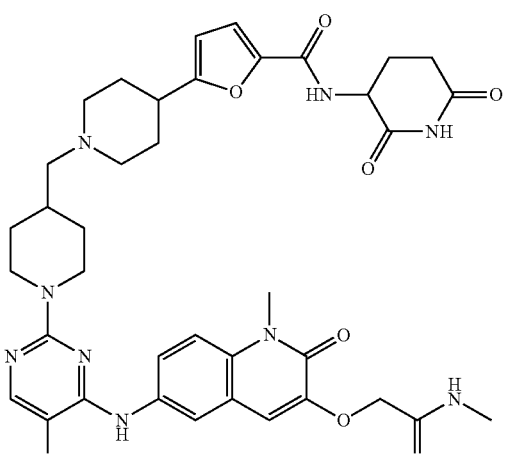 | 5-[1-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)piperidin-4-yl]-N-(2,6-dioxopiperidin-3-yl)furan-2-carboxamide |
| 362 | 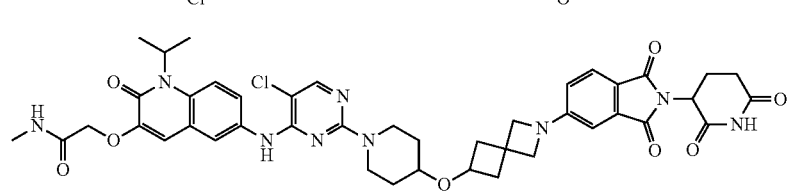 | 2-{[6-({5-chloro-2-[4-({2-[2-(2,6-dioxopiperidin-3-yl)-1,3-dioxo-2,3-dihydro-1H-isoindol-5-yl]-2-azaspiro[3.3]heptan-6-yl}oxy)piperidin-1-yl]pyrimidin-4-yl}amino)-2-oxo-1-(propan-2-yl)-1,2-dihydroquinolin-3-yl]oxy}-N-methylacetamide |
| 363 | 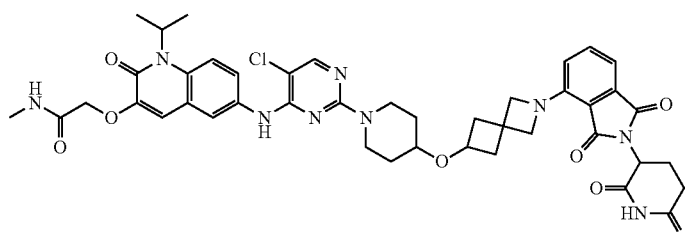 | 2-{[6-({5-chloro-2-[4-({2-[2-(2,6-dioxopiperidin-3-yl)-1,3-dioxo-2,3-dihydro-1H-isoindol-4-yl]-2-azaspiro[3.3]heptan-6-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 364 | | 2-{[6-({5-chloro-2-[4-({4-[2-(2,6-dioxopiperidin-3-yl)-1,3-dioxo-2,3-dihydro-1H-isoindol-5-yl]piperidin-1-yl}methyl)piperidin-1-yl]pyrimidin-4-yl}amino)-1-ethyl-2-oxo-1,2-dihydroquinolin-3-yl]oxy}-N-methylacetamide |
| 365 | | 2-{[6-({5-chloro-2-[4-({4-[2-(2,6-dioxopiperidin-3-yl)-1,3-dioxo-2,3-dihydro-1H-isoindol-5-yl]piperidin-1-yl}methyl)piperidin-1-yl]pyrimidin-4-yl}amino)-2-oxo-1-(propan-2-yl)-1,2-dihydroquinolin-3-yl]oxy}-N-methylacetamide |
| 366 | | 4-[4-({1-[5-chloro-4-({1-methyl-3-[(methylcarbamoyl)methoxy]-2-oxo-1,2-dihydroquinolin-6-yl}amino)pyrimidin-2-yl]-4-fluoropiperidin-4-yl}methyl)piperazin-1-yl]-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 367 | 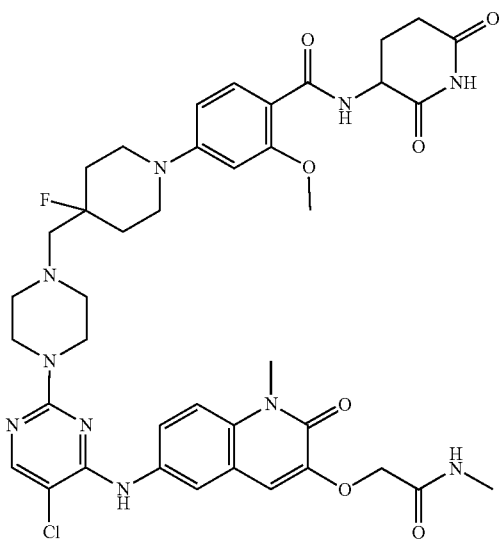 [SMILES: CNC(=O)COc1cc2cc(Nc3nc(N4CCN(CC5(F)CCN(c6ccc(C(=O)NC7CCC(=O)NC7=O)c(OC)c6)CC5)CC4)ncc3Cl)ccc2n(C)c1=O] | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)-4-fluoropiperidin-1-yl]-N-(2,6-dioxopiperidin-3-yl)-2-methoxybenzamide |
| 368 | 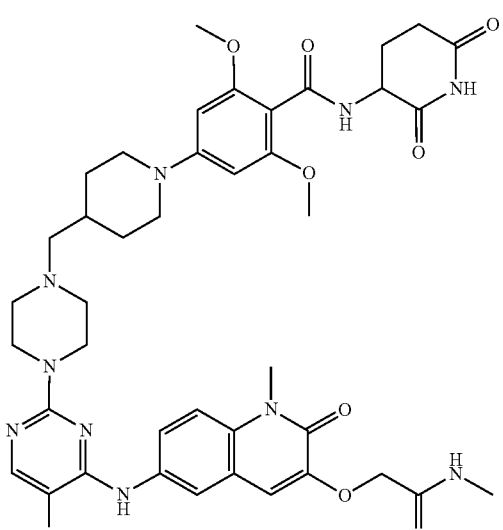 | 4-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2,6-dimethoxybenzamide |

TABLE 1-continued

Exemplary bifunctional compounds of the present disclosure

| Ex. # | Parent Mol Structure | Name |
|---|---|---|
| 369 | | 5-{4-[(4-{5-chloro-4-[(1-methyl-2-oxo-1,2,3,4-tetrahydroquinolin-6-yl)amino]pyrimidin-2-yl}piperazin-1-yl)methyl]piperidin-1-yl}-2-(2,6-dioxopiperidin-3-yl)-2,3-dihydro-1H-isoindole-1,3-dione |
| 370 | | rac-3-[(3R,5S)-4-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)-3,5-dimethylpiperazin-1-yl]-N-(2,6-dioxopiperidin-3-yl)-2-fluorobenzamide |
| 371 | | 2-({6-[(5-chloro-2-{4-[(3S,5R)-5-({[2-(2,6-dioxopiperidin-3-yl)-1,3-dioxo-2,3-dihydro-1H-isoindol-5-yl]oxy}methyl)-1-methylpyrrolidin-3-yl]piperazin-1-yl}pyrimidin-4-yl)amino]-1-ethyl-2-oxo-1,2-dihydroquinolin-3-yl}oxy)-N-methylacetamide |
| 372 | | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N- |

| Ex. # | Parent Mol Structure | Name |
|---|---|---|
| | | methylacetamide |
| 373 | | 5-(2-{[5-chloro-4-({3-[(methylcarbamoyl)methoxy]-2-oxo-1-(propan-2-yl)-1,2-dihydroquinolin-6-yl}amino)pyrimidin-2-yl]amino}ethyl)-N-(2,6-dioxopiperidin-3-yl)pyridine-2-carboxamide |
| 374 | | 2-{[6-({5-chloro-2-[4-({7-[2-(2,6-dioxopiperidin-3-yl)-1,3-dioxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 375 | | 4-[4-({4-[5-chloro-4-({1-ethyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 376 | | 4-[4-({4-[5-chloro-4-({3-[(methylcarbamoyl)methoxy]-2-oxo-1-(propan-2-yl)-1,2-dihydroquinolin-6-yl}amino)pyrimidin-2-yl]piperazin-1-yl}methyl)piperidin-1-yl]-N-(2,6-dioxopiperidin-3-yl)-2-methoxybenzamide |
| 377 | | 5-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-2-[(2,6-dioxopiperidin-3-yl)carbamoyl]pyridin-1-ium-1-olate |
| 378 | | 4-{4-[(4-{5-chloro-4-[(1-methyl-2-oxo-1,2,3,4-tetrahydroquinolin-6-yl)amino]pyrimidin-2-yl}piperazin-1-yl)methyl]piperidin-1-yl}-2-(2,6-dioxopiperidin-3-yl)-2,3-dihydro-1H-isoindole-1,3-dione |

TABLE 1-continued

Exemplary bifunctional compounds of the present disclosure

| Ex. # | Parent Mol Structure | Name |
|---|---|---|
| 379 | | 2-{[6-({5-chloro-2-[(2R)-2-(2-{[2-(2,6-dioxopiperidin-3-yl)-1,3-dioxo-2,3-dihydro-1H-isoindol-5-yl]oxy}ethyl)morpholin-4-yl]pyrimidin-4-yl}amino)-2-oxo-1-(propan-2-yl)-1,2-dihydroquinolin-3-yl]oxy}-N-methylacetamide |
| 380 | | 2-{[6-({5-chloro-2-[4-({1-[2-(2,6-dioxopiperidin-3-yl)-1,3-dioxo-2,3-dihydro-1H-isoindol-5-yl]pyrrolidin-2-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 381 | | rac-2-[(6-{[5-chloro-2-(4-{[(2R,6S)-4-[2-(2,6-dioxopiperidin-3-yl)-1,3-dioxo-2,3-dihydro-1H-isoindol-4-yl]-2,6-dimethylpiperazin-1-yl]methyl}piperidin-1-yl)pyrimidin-4-yl]amino}-2-oxo-1-(propan-2-yl)-1,2-dihydroquinolin-3-yl)oxy]-N-methylacetamide |
| 382 | | 2-{[6-({5-chloro-2-[(2S,6R)-2-({[2-(2,6-dioxopiperidin-3-yl)-1,3-dioxo-2,3-dihydro-1H-isoindol-5-yl]oxy}methyl)-6-methylmorpholin-4-yl]pyrimidin-4-yl}amino)-2-oxo-1-(propan-2-yl)-1,2-dihydroquinolin-3-yl]oxy}-N-methylacetamide |
| 383 | | 2-{[6-({5-chloro-2-[(2S,6S)-2-({[2-(2,6-dioxopiperidin-3-yl)-1,3-dioxo-2,3-dihydro-1H-isoindol-5-yl]oxy}methyl)-6-methylmorpholin-4-yl]pyrimidin-4-yl}amino)-2-oxo-1-(propan-2-yl)-1,2-dihydroquinolin-3-yl]oxy}-N-methylacetamide |
| 384 | | 2-{[6-({5-chloro-2-[2-({1-[2-(2,6-dioxopiperidin-3-yl)-1,3-dioxo-2,3-dihydro-1H-isoindol-5-yl]piperidin-4-yl}methyl)-2,7-diazaspiro[3.5]nonan-7-yl]pyrimidin-4-yl}amino)-2-oxo-1-(propan-2-yl)-1,2-dihydroquinolin-3-yloxy}-N-methylacetamide |

TABLE 1-continued

Exemplary bifunctional compounds of the present disclosure

| Ex. # | Parent Mol Structure | Name |
|---|---|---|
| 385 | | 2-{[6-({5-chloro-2-[2-({1-[2-(2,6-dioxopiperidin-3-yl)-1,3-dioxo-2,3-dihydro-1H-isoindol-4-yl]piperidin-4-yl}methyl)-2,7-diazaspiro[3.5]nonan-7-yl]pyrimidin-4-yl}amino)-2-oxo-1-(propan-2-yl)-1,2-dihydroquinolin-3-yl]oxy}-N-methylacetamide |
| 386 | | 2-{[6-({5-chloro-2-[4-({4-[2-(2,6-dioxopiperidin-3-yl)-1,3-dioxo-2,3-dihydro-1H-isoindol-4-yl]piperidin-1-yl}methyl)piperidin-1-yl]pyrimidin-4-yl}amino)-2-oxo-1-(propan-2-yl)-1,2-dihydroquinolin-3-yl]oxy}-N-methylacetamide |
| 387 | | 2-{[6-({5-chloro-2-[(3R,5S)-4-({1-[2-(2,6-dioxopiperidin-3-yl)-1,3-dioxo-2,3-dihydro-1H-isoindol-4-yl]piperidin-4-yl}methyl)-3,5-dimethylpiperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 388 | | 2-{[6-({5-chloro-2-[4-({1-[2-(2,6-dioxopiperidin-3-yl)-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 389 | | 2-{[6-({5-chloro-2-[(2S,6R)-2-({[2-(2,6-dioxopiperidin-3-yl)-1,3-dioxo-2,3-dihydro-1H-isoindol-5-yl]oxy}methyl)-6-ethylmorpholin-4-yl]pyrimidin-4-yl}amino)-2-oxo-1-(propan-2-yl)-1,2-dihydroquinolin-3-yl]oxy}-N-methylacetamide |
| 390 | | 2-{[6-({5-chloro-2-[4-({7-[2-(2,6-dioxopiperidin-3-yl)-1,3-dioxo-2,3-dihydro-1H-isoindol-5-yl]-7-azaspiro[3.5]nonan-2-yl}oxy)piperidin-1-yl]pyrimidin-4-yl}amino)-2-oxo-1-(propan-2-yl)-1,2-dihydroquinolin-3-yl]oxy}-N-methylacetamide |
| 391 | | 2-{[6-({5-chloro-2-[4-({7-[2-(2,6-dioxopiperidin-3-yl)-1,3-dioxo-2,3-dihydro-1H-isoindol-4-yl]-7-azaspiro[3.5]nonan-2-yl}oxy)piperidin-1-yl]pyrimidin-4-yl}amino)-2-oxo-1-(propan-2-yl)-1,2-dihydroquinolin-3-yl]oxy}-N-methylacetamide |
| 392 | | 2-{[6-({5-chloro-2-[2-({1-[2-(2,6-dioxopiperidin-3-yl)-1,3-dioxo-2,3-dihydro-1H-isoindol-5-yl]piperidin-4-yl}oxy)-7-azaspiro[3.5]nonan-7-yl]pyrimidin-4-yl}amino)-2-oxo-1- |

TABLE 1-continued

Exemplary bifunctional compounds of the present disclosure

| Ex. # | Parent Mol Structure | Name |
|---|---|---|
| | | (propan-2-yl)-1,2-dihydroquinolin-3-yl]oxy}-N-methylacetamide |
| 393 | | 2-{[6-({5-chloro-2-[2-({1-[2-(2,6-dioxopiperidin-3-yl)-1,3-dioxo-2,3-dihydro-1H-isoindol-4-yl]piperidin-4-yl}oxy)-7-azaspiro[3.5]nonan-7-yl]pyrimidin-4-yl}amino)-2-oxo-1-(propan-2-yl)-1,2-dihydroquinolin-3-yl]oxy}-N-methylacetamide |
| 394 | | 2-{[6-({5-chloro-2-[(2S,6S)-2-({[2-(2,6-dioxopiperidin-3-yl)-1,3-dioxo-2,3-dihydro-1H-isoindol-5-yl]oxy}methyl)-6-ethylmorpholin-4-yl]pyrimidin-4-yl}amino)-2-oxo-1-(propan-2-yl)-1,2-dihydroquinolin-3-yl]oxy}-N-methylacetamide |
| 395 | | 3-[7-({5-chloro-2-[4-({1-[2-(2,6-dioxopiperidin-3-yl)-1,3-dioxo-2,3-dihydro-1H-isoindol-5-yl]piperidin-4-yl}methyl)piperazin-1-yl]pyrimidin-4-yl}amino)-3-oxo-1,2,3,4-tetrahydroisoquinolin-2-yl]-N-methylpropanamide |

TABLE 1-continued

Exemplary bifunctional compounds of the present disclosure

| Ex. # | Parent Mol Structure | Name |
|---|---|---|
| 396 | 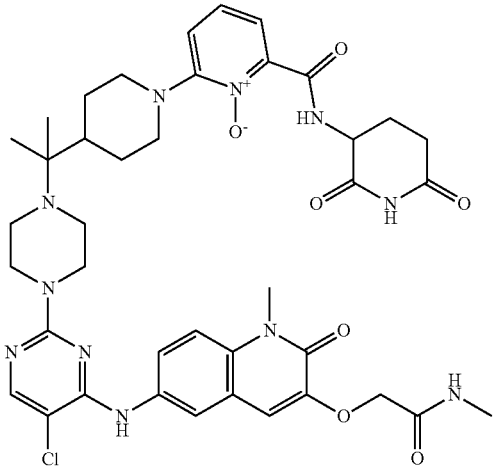 [SMILES: CNC(=O)COc1cc2cc(Nc3nc(N4CCN(C(C)(C)C5CCN(c6cccc(C(=O)NC7CCC(=O)NC7=O)[n+]6[O-])CC5)CC4)ncc3Cl)ccc2n(C)c1=O] | 2-[4-(2-{4-[5-chloro-4-({1-methyl-3-[(methylcarbamoyl)methoxy]-2-oxo-1,2-dihydroquinolin-6-yl}amino)pyrimidin-2-yl]piperazin-1-yl}propan-2-yl)piperidin-1-yl]-6-[(2,6-dioxopiperidin-3-yl)carbamoyl]pyridin-1-ium-1-olate |
| 397 | 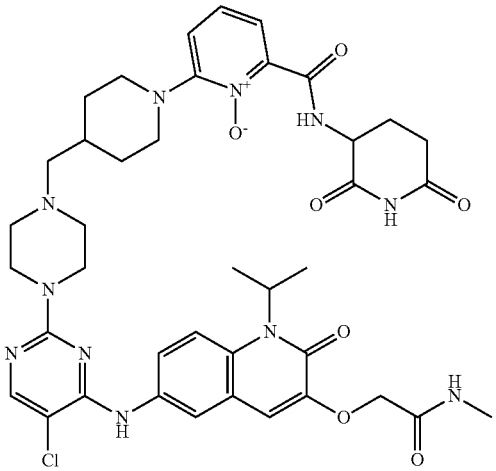 [SMILES: CNC(=O)COc1cc2cc(Nc3nc(N4CCN(CC5CCN(c6cccc(C(=O)NC7CCC(=O)NC7=O)[n+]6[O-])CC5)CC4)ncc3Cl)ccc2n(C(C)C)c1=O] | 2-[4-({4-[5-chloro-4-({3-[(methylcarbamoyl)methoxy]-2-oxo-1-(propan-2-yl)-1,2-dihydroquinolin-6-yl}amino)pyrimidin-2-yl]piperazin-1-yl}methyl)piperidin-1-yl]-6-[(2,6-dioxopiperidin-3-yl)carbamoyl]pyridin-1-ium-1-olate |

TABLE 1-continued

Exemplary bifunctional compounds of the present disclosure

| Ex. # | Parent Mol Structure | Name |
|---|---|---|
| 398 | | 2-{[6-({5-chloro-2-[4-({1-[2-(2,6-dioxopiperidin-3-yl)-1,3-dioxo-2,3-dihydro-1H-isoindol-4-yl]pyrrolidin-2-yl}methyl)piperazin-1-yl]pyrimidin-4-yl}amino)-2-oxo-1-(propan-2-yl)-1,2-dihydroquinolin-3-yl]oxy}-N-methylacetamide |
| 399 | | 2-({6-[(5-chloro-2-{4-[(1r,3r)-3-{4-[2-(2,6-dioxopiperidin-3-yl)-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

1101 1102

TABLE 1-continued

Exemplary bifunctional compounds of the present disclosure

| Ex. # | Parent Mol Structure | Name |
|---|---|---|
| 400 | 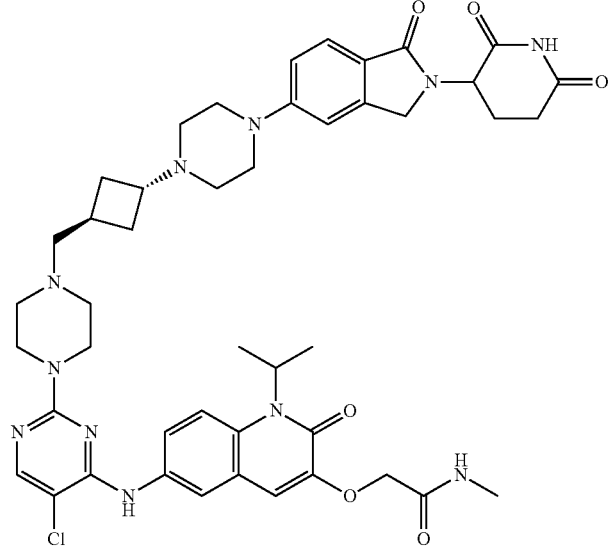 [SMILES: CNC(=O)COc1cc2cc(Nc3nc(N4CCN(C[C@H]5C[C@H](N6CCN(c7ccc8c(c7)CN(C7CCC(=O)NC7=O)C8=O)CC6)C5)CC4)ncc3Cl)ccc2n(C(C)C)c1=O] | 2-[(6-{[5-chloro-2-(4-{[(1r,3r)-3-{4-[2-(2,6-dioxopiperidin-3-yl)-1,3-dioxo-2,3-dihydro-1H-isoindol-5-yl]piperazin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide |
| 401 | 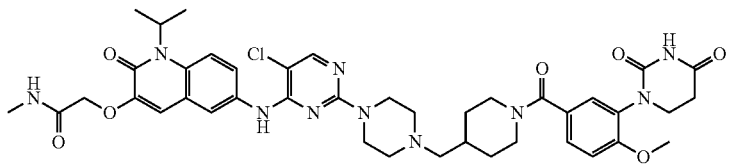 [SMILES: CNC(=O)COc1cc2cc(Nc3nc(N4CCN(CC5CCN(C(=O)c6ccc(OC)c(N7CCC(=O)NC7=O)c6)CC5)CC4)ncc3Cl)ccc2n(C(C)C)c1=O] | 2-{[6-({5-chloro-2-[4-({1-[3-(2,4-dioxo-1,3-diazinan-1-yl)-4-methoxybenzoyl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 402 | 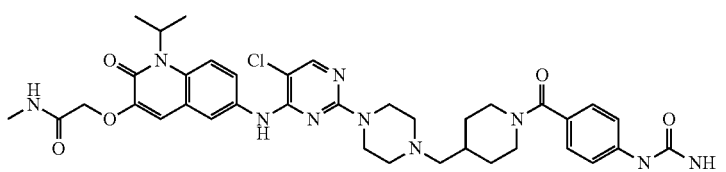 | 2-{[6-({5-chloro-2-[4-({1-[4-(2,4-dioxo-1,3-diazinan-1-yl)benzoyl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 403 | 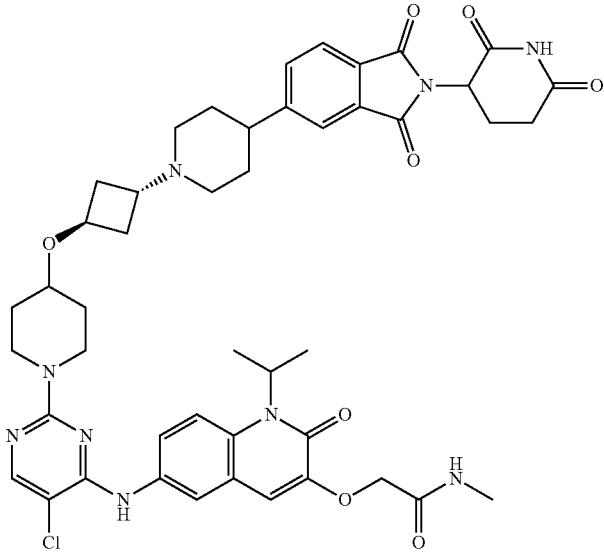 | 2-({6-[(5-chloro-2-{4-[(1r,3r)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 404 | 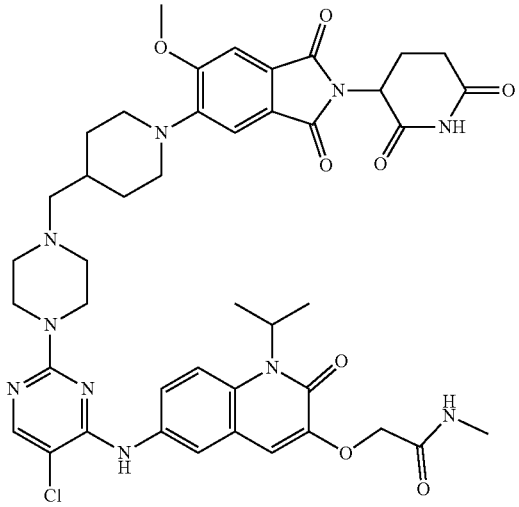 [SMILES: CNC(=O)COc1cc2cc(Nc3nc(N4CCN(CC5CCN(c6cc7c(cc6OC)C(=O)N(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-6-methoxy-1,3-dioxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 405 | | 2-{[6-({5-chloro-2-[6-({1-[2-(2,6-dioxopiperidin-3-yl)-1,3-dioxo-2,3-dihydro-1H-isoindol-5-yl]piperidin-4-yl}oxy)-2-azaspiro[3.3]heptan-2-yl]pyrimidin-4-yl}amino)-2-oxo-1-(propan-2-yl)-1,2-dihydroquinolin-3-yl]oxy}-N-methylacetamide |
| 406 | | 2-{[6-({5-chloro-2-[6-({1-[2-(2,6-dioxopiperidin-3-yl)-1,3-dioxo-2,3-dihydro-1H-isoindol-4-yl]piperidin-4-yl}oxy)-2-azaspiro[3.3]heptan-2-yl]pyrimidin-4-yl}amino)-2-oxo-1-(propan-2-yl)-1,2-dihydroquinolin-3-yl]oxy}-N-methylacetamide |
| 407 | | 2-{[6-({5-chloro-2-[4-({1-[3-(2,4-dioxo-1,3-diazinan-1-yl)benzoyl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 408 | 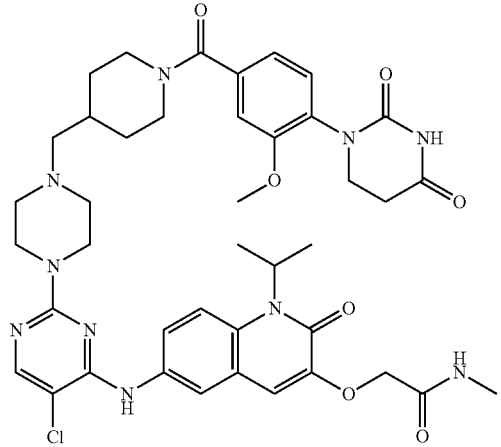 [SMILES: CNC(=O)COc1cc2cc(Nc3nc(N4CCN(CC5CCN(C(=O)c6ccc(N7CCC(=O)NC7=O)c(OC)c6)CC5)CC4)ncc3Cl)ccc2n(C(C)C)c1=O] | 2-{[6-({5-chloro-2-[4-({1-[4-(2,4-dioxo-1,3-diazinan-1-yl)-3-methoxybenzoyl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 409 | 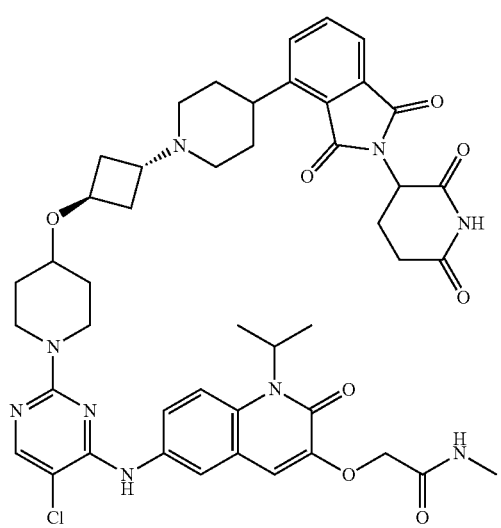 | 2-({6-[(5-chloro-2-{4-[(1r,3r)-3-{4-[2-(2,6-dioxopiperidin-3-yl)-1,3-dioxo-2,3-dihydro-1H-isoindol-4-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 410 | 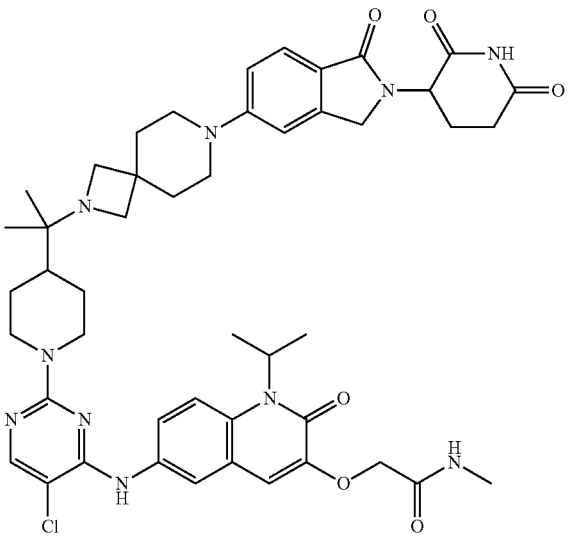 [SMILES: CNC(=O)COc1cc2cc(Nc3nc(N4CCC(C(C)(C)N5CC6(CCN(c7ccc8c(c7)CN(C7CCC(=O)NC7=O)C8=O)CC6)C5)CC4)ncc3Cl)ccc2n(C(C)C)c1=O] | 2-{[6-({5-chloro-2-[4-(2-{7-[2-(2,6-dioxopiperidin-3-yl)-1-oxo-2,3-dihydro-1H-isoindol-5-yl]-2,7-diazaspiro[3.5]nonan-2-yl}propan-2-yl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 411 | 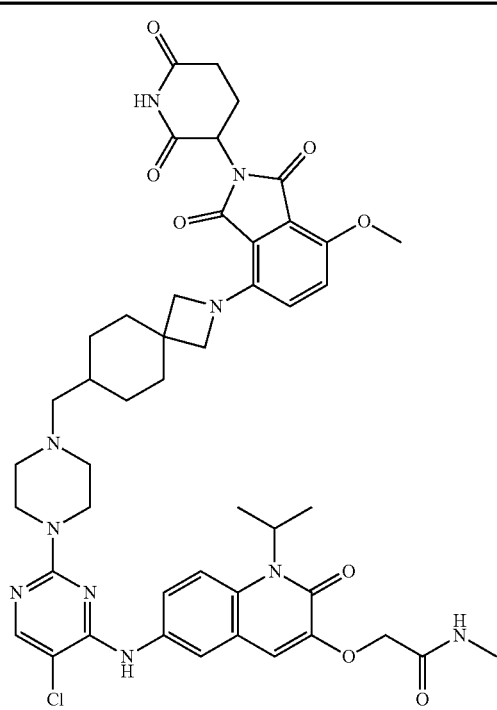 | 2-{[6-({5-chloro-2-[4-({2-[2-(2,6-dioxopiperidin-3-yl)-7-methoxy-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |
| 412 | 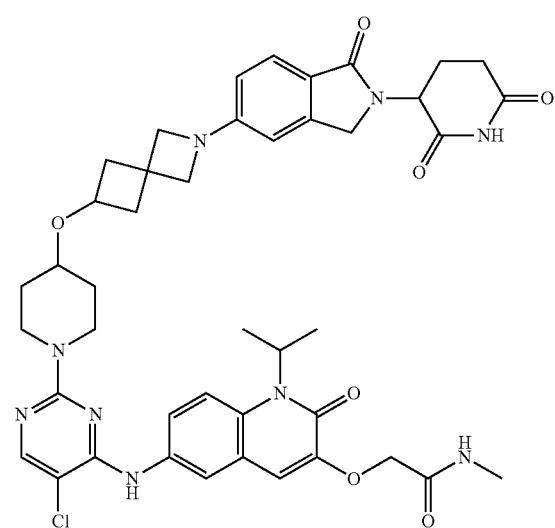 [SMILES: CNC(=O)COc1cc2cc(Nc3nc(N4CCC(OC5CC6(C5)CN(c5ccc7c(c5)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-2-azaspiro[3.3]heptan-6-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 413 | 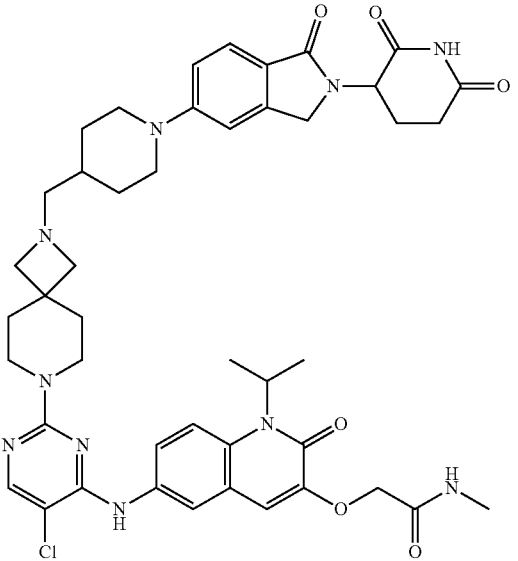 [SMILES: CNC(=O)COc1cc2cc(Nc3nc(N4CCC5(CC4)CN(CC4CCN(c6ccc7c(c6)CN(C6CCC(=O)NC6=O)C7=O)CC4)C5)ncc3Cl)ccc2n(C(C)C)c1=O] | 2-{[6-({5-chloro-2-[2-({1-[2-(2,6-dioxopiperidin-3-yl)-1-oxo-2,3-dihydro-1H-isoindol-5-yl]piperidin-4-yl}methyl)-2,7-diazaspiro[3.5]nonan-7-yl]pyrimidin-4-yl}amino)-2-oxo-1-(propan-2-yl)-1,2-dihydroquinolin-3-yl]oxy}-N-methylacetamide |
| 414 | 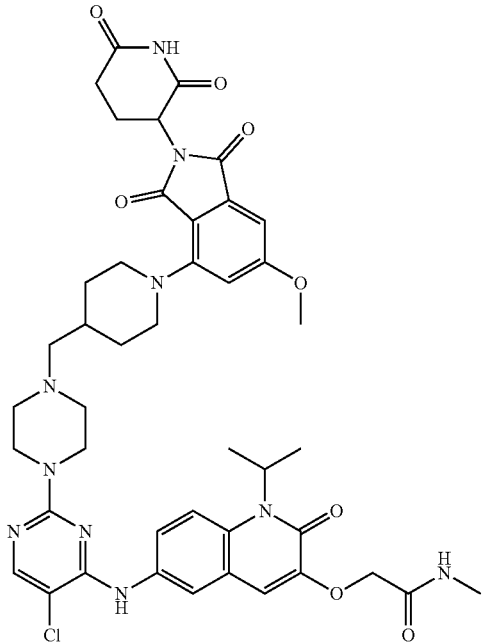 [SMILES: CNC(=O)COc1cc2cc(Nc3nc(N4CCN(CC5CCN(c6cc(OC)cc7c6C(=O)N(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-6-methoxy-1,3-dioxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 415 | 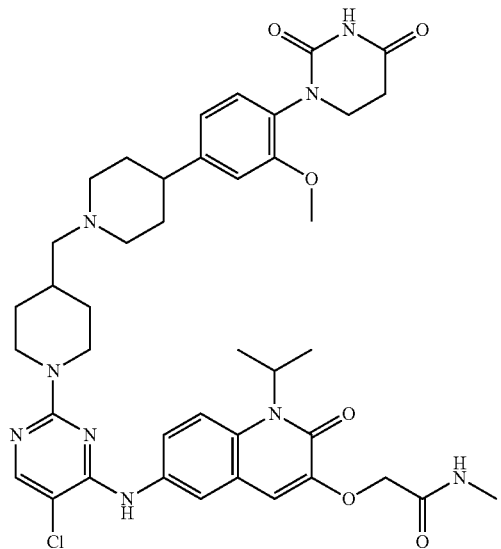 [SMILES: CNC(=O)COc1cc2cc(Nc3nc(N4CCC(CN5CCC(c6ccc(N7CCC(=O)NC7=O)c(OC)c6)CC5)CC4)ncc3Cl)ccc2n(C(C)C)c1=O] | 2-{[6-({5-chloro-2-[4-({4-[4-(2,4-dioxo-1,3-diazinan-1-yl)-3-methoxyphenyl]piperidin-1-yl}methyl)piperidin-1-yl]pyrimidin-4-yl}amino)-2-oxo-1-(propan-2-yl)-1,2-dihydroquinolin-3-yl]oxy}-N-methylacetamide |
| 416 | 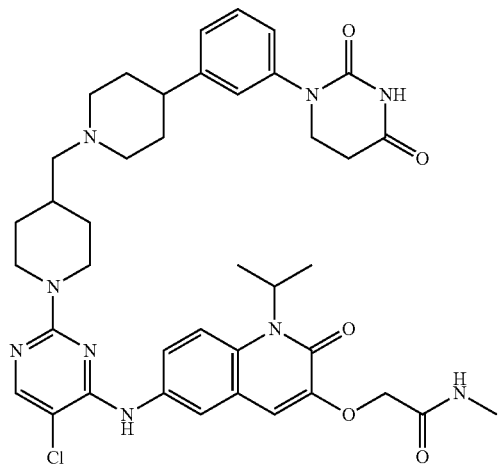 [SMILES: CNC(=O)COc1cc2cc(Nc3nc(N4CCC(CN5CCC(c6cccc(N7CCC(=O)NC7=O)c6)CC5)CC4)ncc3Cl)ccc2n(C(C)C)c1=O] | 2-{[6-({5-chloro-2-[4-({4-[3-(2,4-dioxo-1,3-diazinan-1-yl)phenyl]piperidin-1-yl}methyl)piperidin-1-yl]pyrimidin-4-yl}amino)-2-oxo-1-(propan-2-yl)-1,2-dihydroquinolin-3-yl]oxy}-N-methylacetamide |
| 417 | 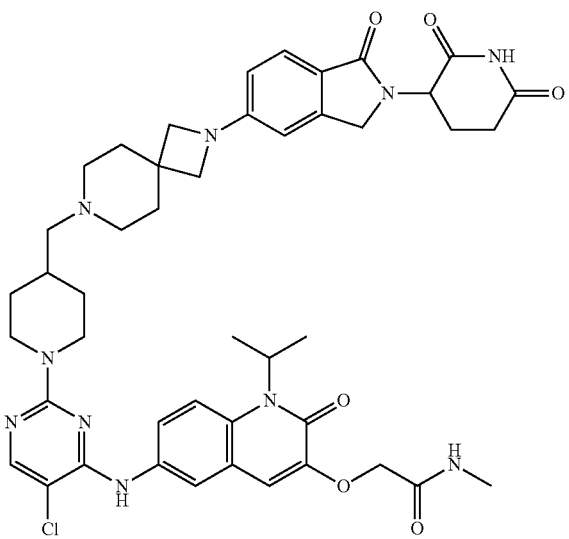 [SMILES: CNC(=O)COc1cc2cc(Nc3nc(N4CCC(CN5CCC6(CC5)CN(c5ccc7c(c5)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 418 | 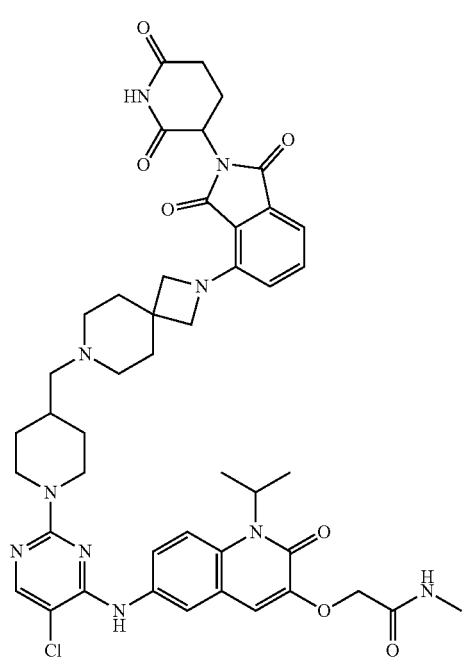 [SMILES: CNC(=O)COc1cc2cc(Nc3nc(N4CCC(CN5CCC6(CC5)CN(c5cccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 419 | 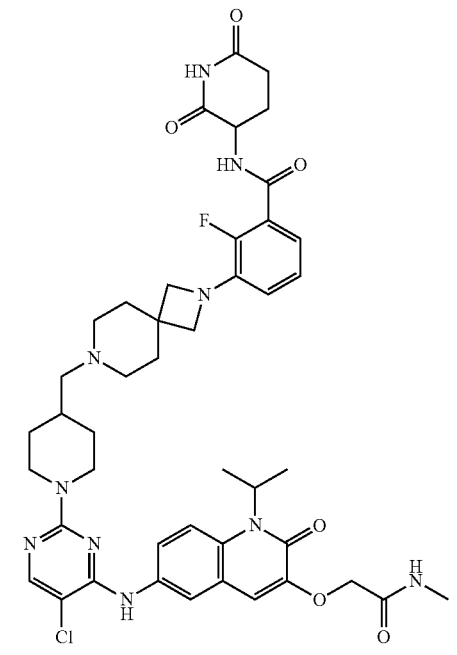 | 3-[7-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)-2,7-diazaspiro[3.5]nonan-2-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 420 | 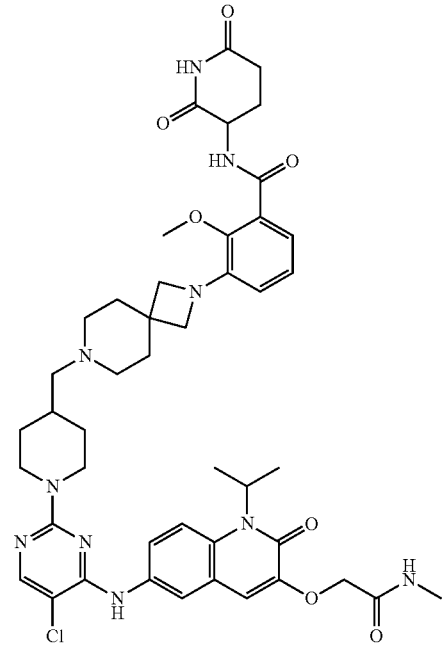 [SMILES: CNC(=O)COc1cc2cc(Nc3nc(N4CCC(CN5CCC6(CC5)CN(c5cccc(C(=O)NC7CCC(=O)NC7=O)c5F)C6)CC4)ncc3Cl)ccc2n(C(C)C)c1=O] | 3-[7-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)-2,7-diazaspiro[3.5]nonan-2-yl]-N-(2,6-dioxopiperidin-3-yl)-2-methoxybenzamide |
| 421 | 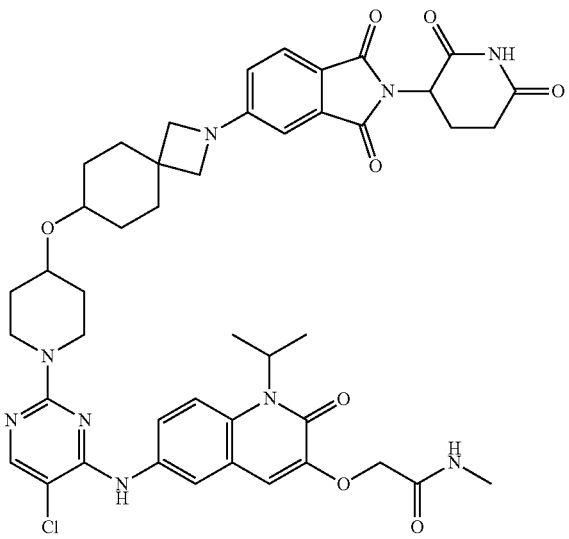 | 2-{[6-({5-chloro-2-[4-({2-[2-(2,6-dioxopiperidin-3-yl)-1,3-dioxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 422 | 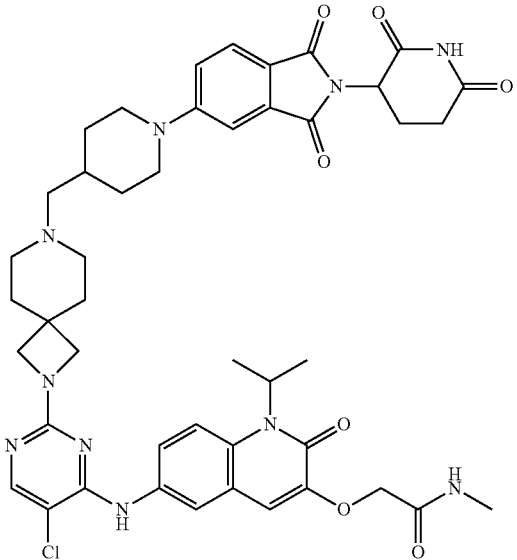 [SMILES: CNC(=O)COc1cc2cc(Nc3nc(N4CC5(CCN(CC6CCN(c7ccc8c(c7)C(=O)N(C7CCC(=O)NC7=O)C8=O)CC6)CC5)C4)ncc3Cl)ccc2n(C(C)C)c1=O] | 2-{[6-({5-chloro-2-[7-({1-[2-(2,6-dioxopiperidin-3-yl)-1,3-dioxo-2,3-dihydro-1H-isoindol-5-yl]piperidin-4-yl}methyl)-2,7-diazaspiro[3.5]nonan-2-yl]pyrimidin-4-yl}amino)-2-oxo-1-(propan-2-yl)-1,2-dihydroquinolin-3-yl]oxy}-N-methylacetamide |
| 423 | 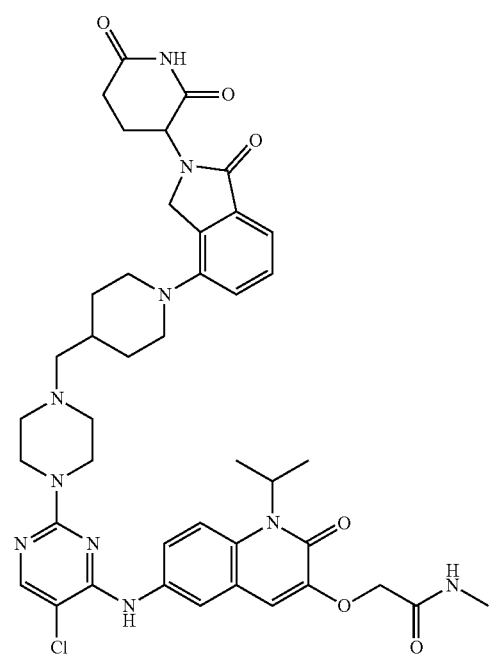 [SMILES: CNC(=O)COc1cc2cc(Nc3nc(N4CCN(CC5CCN(c6cccc7c6CN(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-1-oxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 424 | 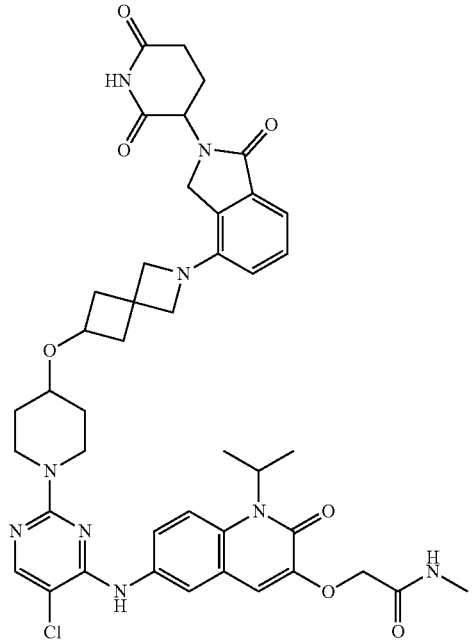 [SMILES: CNC(=O)COc1cc2cc(Nc3nc(N4CCC(OC5CC6(C5)CN(c5cccc7c5CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-4-yl]-2-azaspiro[3.3]heptan-6-yl}oxy)piperidin-1-yl]pyrimidin-4-yl}amino)-2-oxo-1-(propan-2-yl)-1,2-dihydroquinolin-3-yl]oxy}-N-methylacetamide |
| 425 | 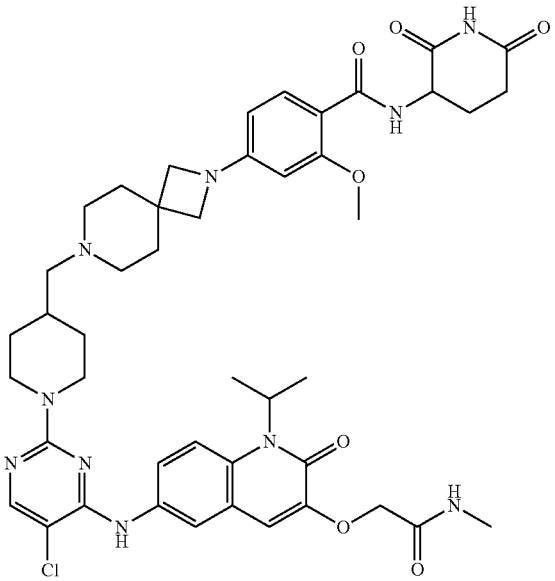 [SMILES: CNC(=O)COc1cc2cc(Nc3nc(N4CCC(CN5CCC6(CC5)CN(c5ccc(C(=O)NC7CCC(=O)NC7=O)c(OC)c5)C6)CC4)ncc3Cl)ccc2n(C(C)C)c1=O] | 4-[7-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)-2,7-diazaspiro[3.5]nonan-2-yl]-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 426 | 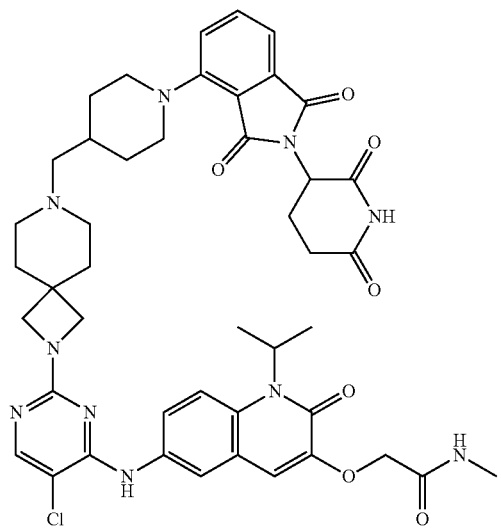 | 2-{[6-({5-chloro-2-[7-({1-[2-(2,6-dioxopiperidin-3-yl)-1,3-dioxo-2,3-dihydro-1H-isoindol-4-yl]piperidin-4-yl}methyl)-2,7-diazaspiro[3.5]nonan-2-yl]pyrimidin-4-yl}amino)-2-oxo-1-(propan-2-yl)-1,2-dihydroquinolin-3-yl]oxy}-N-methylacetamide |
| 427 | 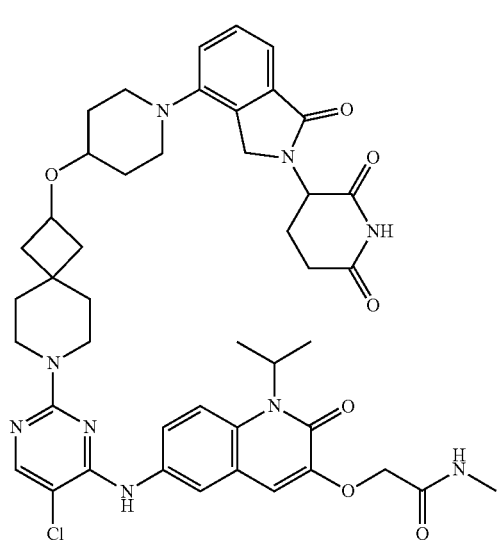 | 2-{[6-({5-chloro-2-[2-({1-[2-(2,6-dioxopiperidin-3-yl)-1-oxo-2,3-dihydro-1H-isoindol-4-yl]piperidin-4-yl}oxy)-7-azaspiro[3.5]nonan-7-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 428 | 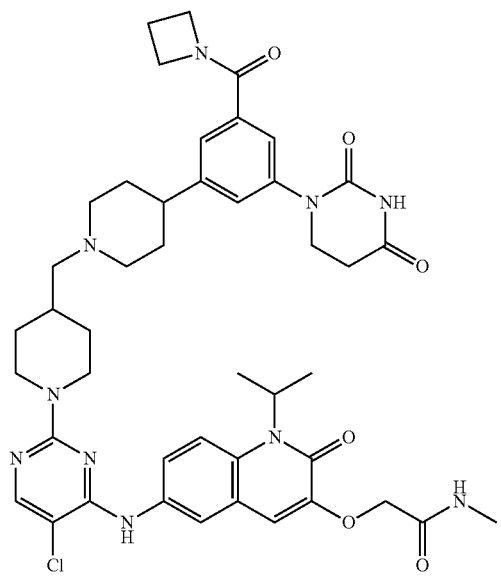 [SMILES: CNC(=O)COc1cc2cc(Nc3nc(N4CCC(CN5CCC(c6cc(C(=O)N7CCC7)cc(N7CCC(=O)NC7=O)c6)CC5)CC4)ncc3Cl)ccc2n(C(C)C)c1=O] | 2-{[6-({2-[4-({4-[3-(azetidine-1-carbonyl)-5-(2,4-dioxo-1,3-diazinan-1-yl)phenyl]piperidin-1-yl}methyl)piperidin-1-yl]-5-chloropyrimidin-4-yl}amino)-2-oxo-1-(propan-2-yl)-1,2-dihydroquinolin-3-yl]oxy}-N-methylacetamide |
| 429 | 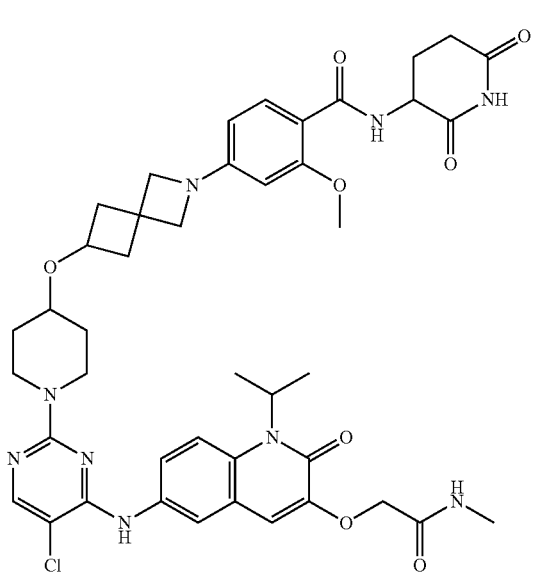 [SMILES: CNC(=O)COc1cc2cc(Nc3nc(N4CCC(OC5CC6(C5)CN(c5ccc(C(=O)NC7CCC(=O)NC7=O)c(OC)c5)C6)CC4)ncc3Cl)ccc2n(C(C)C)c1=O] | 4-[6-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}oxy)-2-azaspiro[3.3]heptan-2-yl]-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 430 | 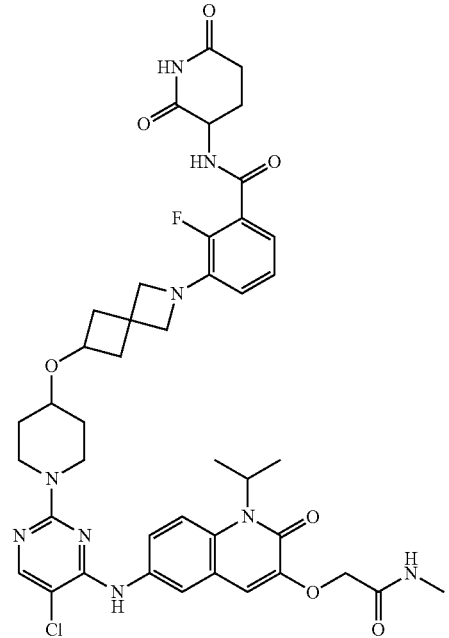 | 3-[6-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}oxy)-2-azaspiro[3.3]heptan-2-yl]-N-(2,6-dioxopiperidin-3-yl)-2-fluorobenzamide |
| 431 | 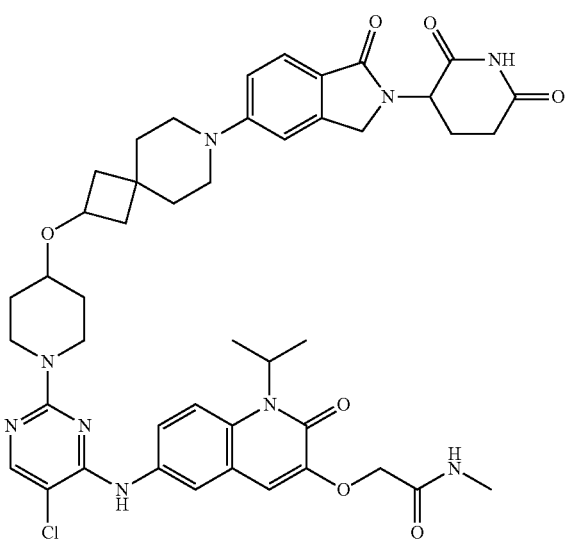 [SMILES: CNC(=O)COc1cc2cc(Nc3nc(N4CCC(OC5CC6(CCN(c7ccc8c(c7)CN(C7CCC(=O)NC7=O)C8=O)CC6)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-5-yl]-7-azaspiro[3.5]nonan-2-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 432 | 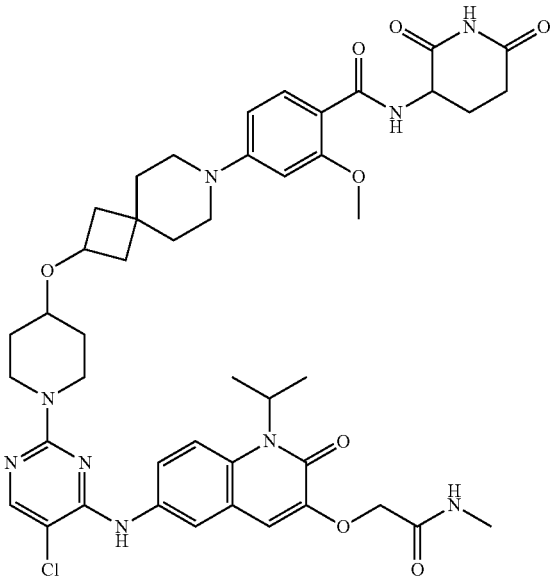 [SMILES: CNC(=O)COc1cc2cc(Nc3nc(N4CCC(OC5CC6(CCN(c7ccc(C(=O)NC8CCC(=O)NC8=O)c(OC)c7)CC6)C5)CC4)ncc3Cl)ccc2n(C(C)C)c1=O] | 4-[2-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}oxy)-7-azaspiro[3.5]nonan-7-yl]-N-(2,6-dioxopiperidin-3-yl)-2-methoxybenzamide |
| 433 | 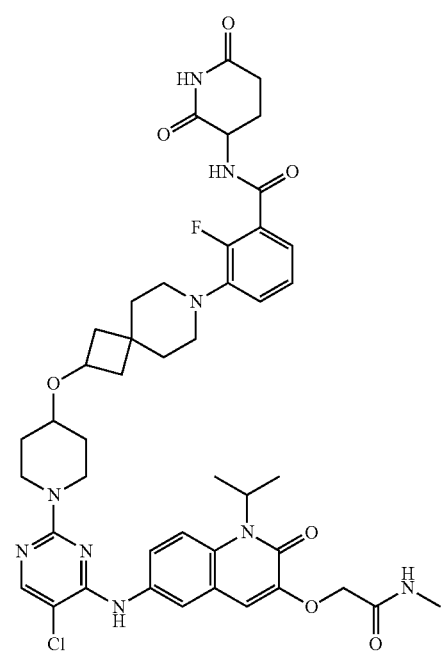 [SMILES: CNC(=O)COc1cc2cc(Nc3nc(N4CCC(OC5CC6(CCN(c7cccc(C(=O)NC8CCC(=O)NC8=O)c7F)CC6)C5)CC4)ncc3Cl)ccc2n(C(C)C)c1=O] | 3-[2-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}oxy)-7-azaspiro[3.5]nonan-7-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 434 | 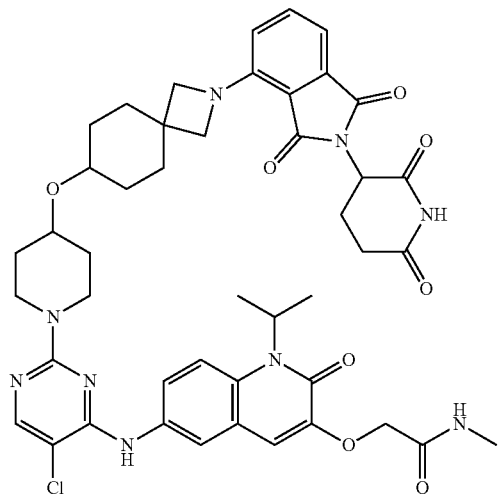 [SMILES: CNC(=O)COc1cc2cc(Nc3nc(N4CCC(OC5CCC6(CC5)CN(c5cccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |
| 435 | 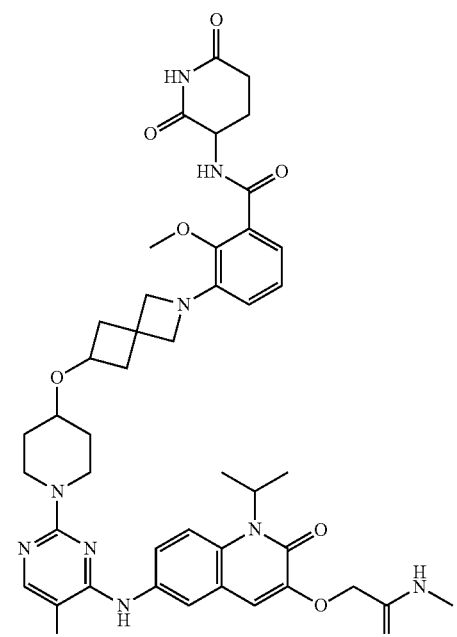 | 3-[6-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}oxy)-2-azaspiro[3.3]heptan-2-yl]-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 436 | | 2-{[6-({5-chloro-2-[4-({7-[2-(2,6-dioxopiperidin-3-yl)-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 437 | | 2-{[6-({5-chloro-2-[4-({7-[2-(2,6-dioxopiperidin-3-yl)-1-oxo-2,3-dihydro-1H-isoindol-5-yl]-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 438 | | 4-[2-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)-2,7-diazaspiro[3.5]nonan-7-yl]-N-(2,6-dioxopiperidin-3-yl)-2-methoxybenzamide |

TABLE 1-continued

Exemplary bifunctional compounds of the present disclosure

| Ex. # | Parent Mol Structure | Name |
|---|---|---|
| 439 | 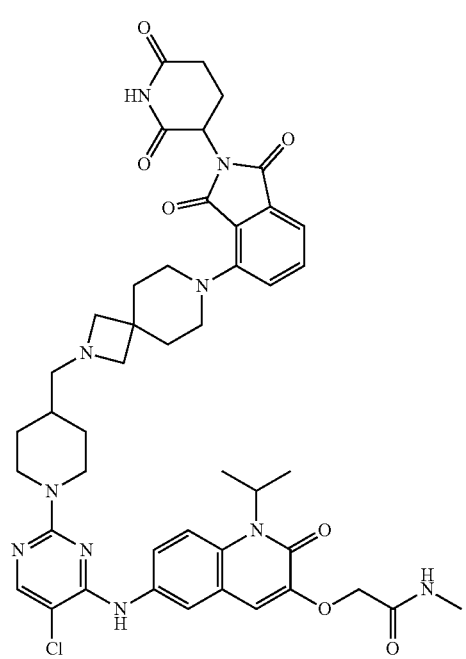 [SMILES: CNC(=O)COc1cc2cc(Nc3nc(N4CCC(CN5CC6(CCN(c7cccc8c7C(=O)N(C7CCC(=O)NC7=O)C8=O)CC6)C5)CC4)ncc3Cl)ccc2n(C(C)C)c1=O] | 2-{[6-({5-chloro-2-[4-({7-[2-(2,6-dioxopiperidin-3-yl)-1,3-dioxo-2,3-dihydro-1H-isoindol-4-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 440 | 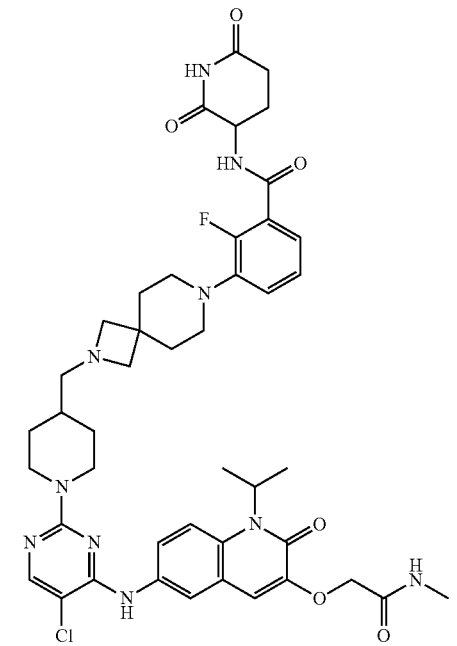 [SMILES: CNC(=O)COc1cc2cc(Nc3nc(N4CCC(CN5CC6(CCN(c7cccc(C(=O)NC8CCC(=O)NC8=O)c7F)CC6)C5)CC4)ncc3Cl)ccc2n(C(C)C)c1=O] | 3-[2-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)-2,7-diazaspiro[3.5]nonan-7-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 441 | 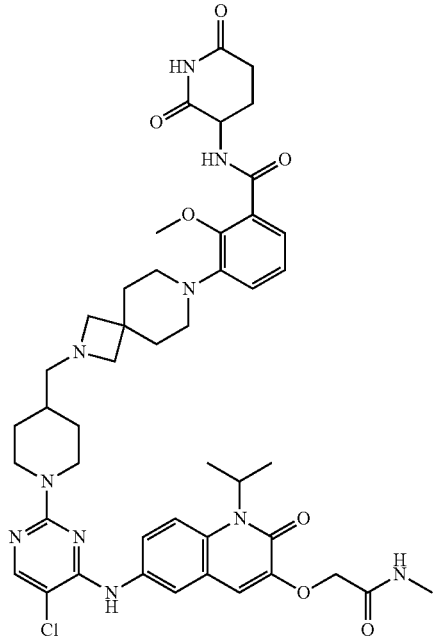 | 3-[2-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)-2,7-diazaspiro[3.5]nonan-7-yl]-N-(2,6-dioxopiperidin-3-yl)-2-methoxybenzamide |
| 442 | 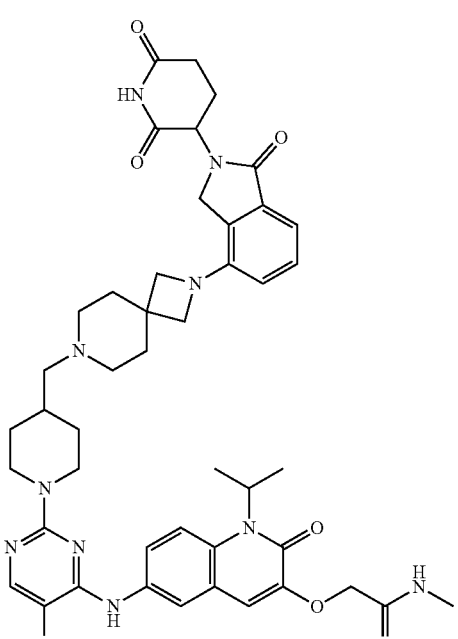 | 2-{[6-({5-chloro-2-[4-({2-[2-(2,6-dioxopiperidin-3-yl)-1-oxo-2,3-dihydro-1H-isoindol-4-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 443 | 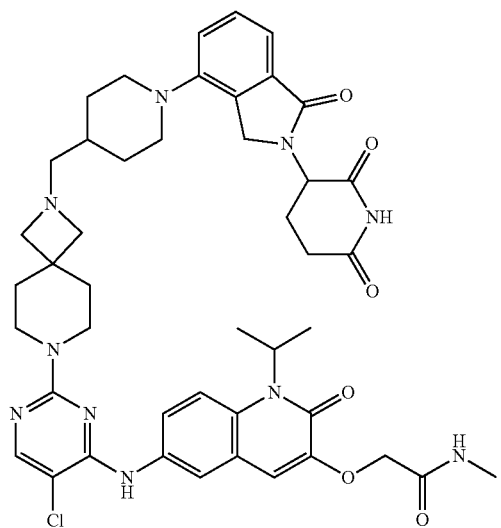 [SMILES: CNC(=O)COc1cc2cc(Nc3nc(N4CCC5(CC4)CN(CC4CCN(c6cccc7c6CN(C6CCC(=O)NC6=O)C7=O)CC4)C5)ncc3Cl)ccc2n(C(C)C)c1=O] | 2-{[6-({5-chloro-2-[2-({1-[2-(2,6-dioxopiperidin-3-yl)-1-oxo-2,3-dihydro-1H-isoindol-4-yl]piperidin-4-yl}methyl)-2,7-diazaspiro[3.5]nonan-7-yl]pyrimidin-4-yl}amino)-2-oxo-1-(propan-2-yl)-1,2-dihydroquinolin-3-yl]oxy}-N-methylacetamide |
| 444 | 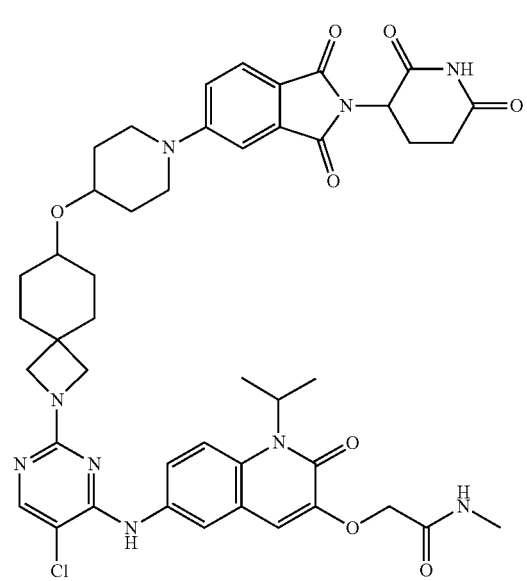 [SMILES: CNC(=O)COc1cc2cc(Nc3nc(N4CC5(CCC(OC6CCN(c7ccc8c(c7)C(=O)N(C7CCC(=O)NC7=O)C8=O)CC6)CC5)C4)ncc3Cl)ccc2n(C(C)C)c1=O] | 2-{[6-({5-chloro-2-[7-({1-[2-(2,6-dioxopiperidin-3-yl)-1,3-dioxo-2,3-dihydro-1H-isoindol-5-yl]piperidin-4-yl}oxy)-2-azaspiro[3.5]nonan-2-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 445 | 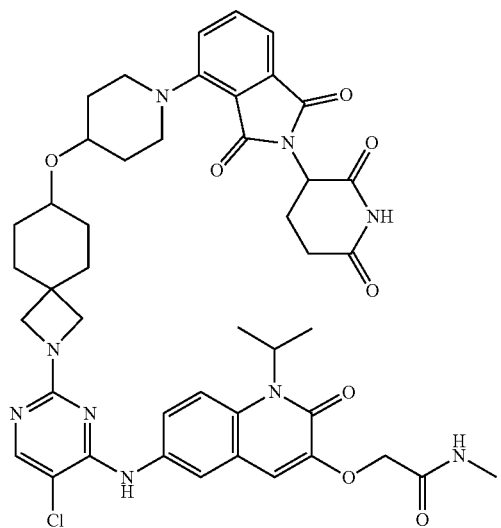 [SMILES: CNC(=O)COc1cc2cc(Nc3nc(N4CC5(CCC(OC6CCN(c7cccc8c7C(=O)N(C7CCC(=O)NC7=O)C8=O)CC6)CC5)C4)ncc3Cl)ccc2n(C(C)C)c1=O] | 2-{[6-({5-chloro-2-[7-({1-[2-(2,6-dioxopiperidin-3-yl)-1,3-dioxo-2,3-dihydro-1H-isoindol-4-yl]piperidin-4-yl}oxy)-2-azaspiro[3.5]nonan-2-yl]pyrimidin-4-yl}amino)-2-oxo-1-(propan-2-yl)-1,2-dihydroquinolin-3-yl]oxy}-N-methylacetamide |
| 446 | 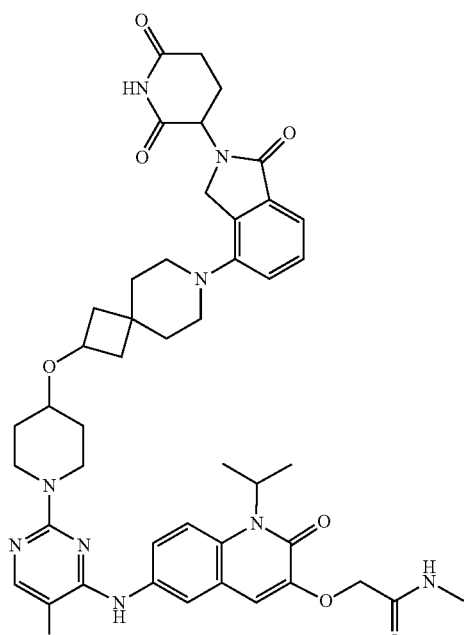 | 2-{[6-({5-chloro-2-[4-({7-[2-(2,6-dioxopiperidin-3-yl)-1-oxo-2,3-dihydro-1H-isoindol-4-yl]-7-azaspiro[3.5]nonan-2-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 447 | 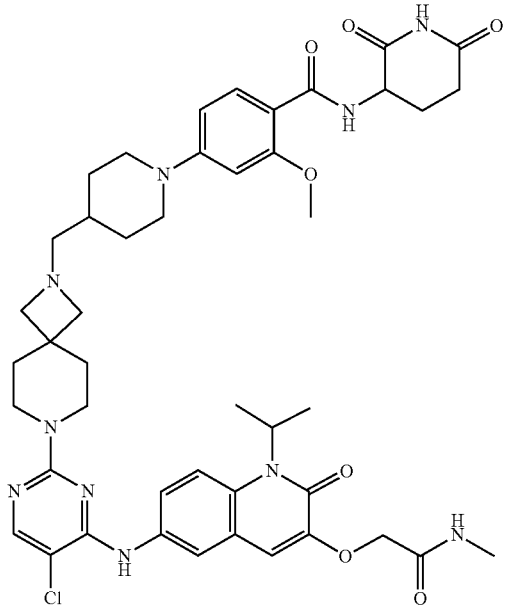 [SMILES: CNC(=O)COc1cc2cc(Nc3nc(N4CCC5(CC4)CN(CC4CCN(c6ccc(C(=O)NC7CCC(=O)NC7=O)c(OC)c6)CC4)C5)ncc3Cl)ccc2n(C(C)C)c1=O] | 4-[4-({7-[5-chloro-4-({3-[(methylcarbamoyl)methoxy]-2-oxo-1-(propan-2-yl)-1,2-dihydroquinolin-6-yl}amino)pyrimidin-2-yl]-2,7-diazaspiro[3.5]nonan-2-yl}methyl)piperidin-1-yl]-N-(2,6-dioxopiperidin-3-yl)-2-methoxybenzamide |
| 448 | 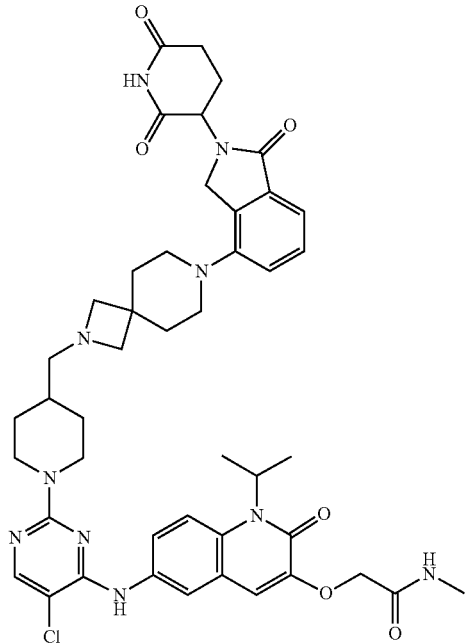 [SMILES: CNC(=O)COc1cc2cc(Nc3nc(N4CCC(CN5CC6(CCN(c7cccc8c7CN(C7CCC(=O)NC7=O)C8=O)CC6)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-4-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 449 | | 3-[2-({1-[5-chloro-4-({3-[(methylcarbamoyl) methoxy]-2-oxo-1-(propan-2-yl)-1,2-dihydroquinolin-6-yl}amino)pyrimidin-2-yl]piperidin-4-yl}oxy)-7-azaspiro[3.5]nonan-7-yl]-N-(2,6-dioxopiperidin-3-yl)-2-methoxybenzamide |
| 450 | | 3-[4-({7-[5-chloro-4-({3-[(methylcarbamoyl) methoxy]-2-oxo-1-(propan-2-yl)-1,2-dihydroquinolin-6-yl}amino)pyrimidin-2-yl]-2,7-diazaspiro[3.5]nonan-2-yl}methyl)piperidin-1-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 451 | | 2-{[6-({5-chloro-2-[4-({2-[2-(2,6-dioxopiperidin-3-yl)-1,3-dioxo-2,3-dihydro-1H-isoindol-5-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |
| 452 | | 2-{[6-({5-chloro-2-[4-({2-[2-(2,6-dioxopiperidin-3-yl)-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |
| 453 | | 3-[4-({7-[5-chloro-4-({3-[(methylcarbamoyl)methoxy]-2-oxo-1-(propan-2-yl)-1,2-dihydroquinolin-6-yl}amino)pyrimidin-2-yl]-7-azaspiro[3.5]nonan-2-yl}oxy)piperidin-1-yl]-N-(2,6-dioxopiperidin-3-yl)-2-fluorobenzamide |

TABLE 1-continued

Exemplary bifunctional compounds of the present disclosure

| Ex. # | Parent Mol Structure | Name |
|---|---|---|
| 454 | 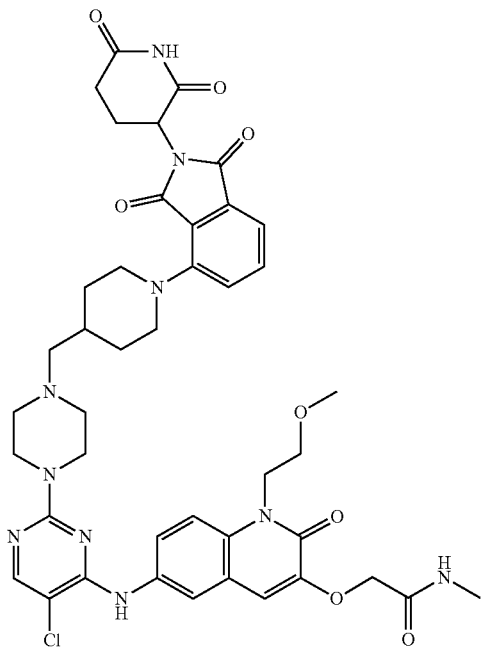 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(CCOC)c1=O] | 2-{[6-({5-chloro-2-[4-({1-[2-(2,6-dioxopiperidin-3-yl)-1,3-dioxo-2,3-dihydro-1H-isoindol-4-yl]piperidin-4-yl}methyl)piperazin-1-yl]pyrimidin-4-yl}amino)-1-(2-methoxyethyl)-2-oxo-1,2-dihydroquinolin-3-yl]oxy}-N-methylacetamide |
| 455 | 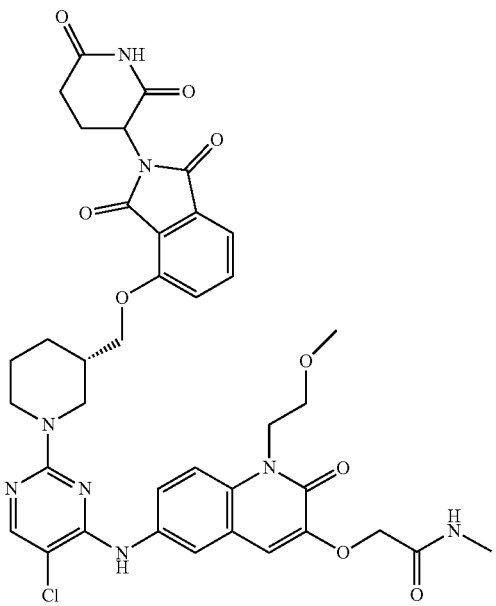 [SMILES: CNC(=O)COc1cc2cc(Nc3nc(N4CCC[C@H](COc5cccc6c5C(=O)N(C5CCC(=O)NC5=O)C6=O)C4)ncc3Cl)ccc2n(CCOC)c1=O] | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-(2-methoxyethyl)-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 456 | | 2-[(6-{[5-chloro-2-(4-{[(3S,5S)-5-({[2-(2,6-dioxopiperidin-3-yl)-1,3-dioxo-2,3-dihydro-1H-isoindol-5-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 457 | | 2-[(6-{[5-chloro-2-(4-{[(3S,5R)-5-{[2-(2,6-dioxopiperidin-3-yl)-1,3-dioxo-2,3-dihydro-1H-isoindol-5-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 458 | | 2-[(6-{[5-chloro-2-(4-{[(3S,5R)-5-({[2-(2,6-dioxopiperidin-3-yl)-1,3-dioxo-2,3-dihydro-1H-isoindol-5-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 459 | | 2-[(6-{[5-chloro-2-(4-{[(3S,5S)-5-{[2-(2,6-dioxopiperidin-3-yl)-1,3-dioxo-2,3-dihydro-1H-isoindol-5-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 460 | | 2-[(6-{[5-chloro-2-(4-{[(3R,5R)-5-({[2-(2,6-dioxopiperidin-3-yl)-1,3-dioxo-2,3-dihydro-1H-isoindol-5-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 461 | | 2-[(6-{[5-chloro-2-(4-{[(3R,5S)-5-{[2-(2,6-dioxopiperidin-3-yl)-1,3-dioxo-2,3-dihydro-1H-isoindol-5-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 462 | 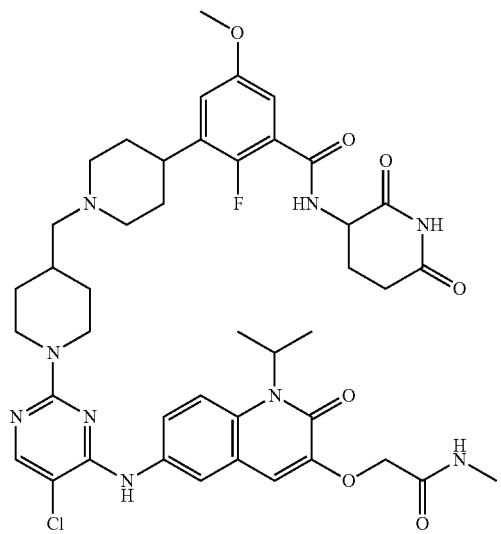 | 3-[1-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)piperidin-4-yl]-N-(2,6-dioxopiperidin-3-yl)-2-fluoro-5-methoxybenzamide |
| 463 | 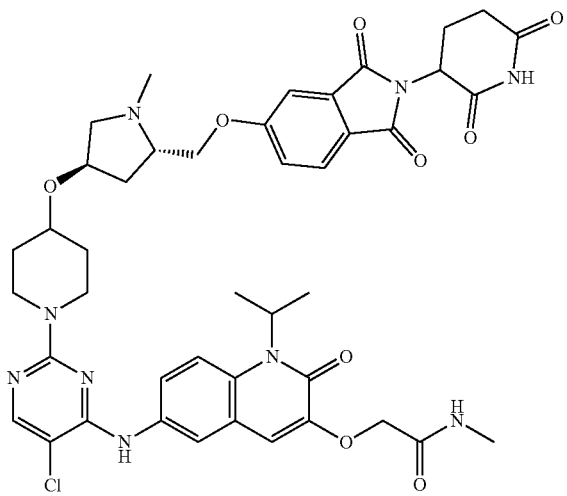 [SMILES: CNC(=O)COc1cc2cc(Nc3nc(N4CCC(O[C@@H]5C[C@@H](COc6ccc7c(c6)C(=O)N(C6CCC(=O)NC6=O)C7=O)N(C)C5)CC4)ncc3Cl)ccc2n(C(C)C)c1=O] | 2-[(6-{[5-chloro-2-(4-{[(3R,5S)-5-({[2-(2,6-dioxopiperidin-3-yl)-1,3-dioxo-2,3-dihydro-1H-isoindol-5-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 464 | 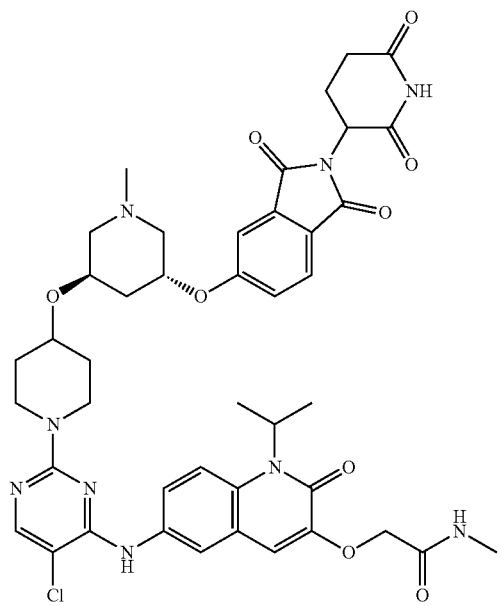 [SMILES: CNC(=O)COc1cc2cc(Nc3nc(N4CCC(O[C@@H]5C[C@@H](Oc6ccc7c(c6)C(=O)N(C6CCC(=O)NC6=O)C7=O)CN(C)C5)CC4)ncc3Cl)ccc2n(C(C)C)c1=O] | 2-[(6-{[5-chloro-2-(4-{[(3R,5R)-5-{[2-(2,6-dioxopiperidin-3-yl)-1,3-dioxo-2,3-dihydro-1H-isoindol-5-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 465 | 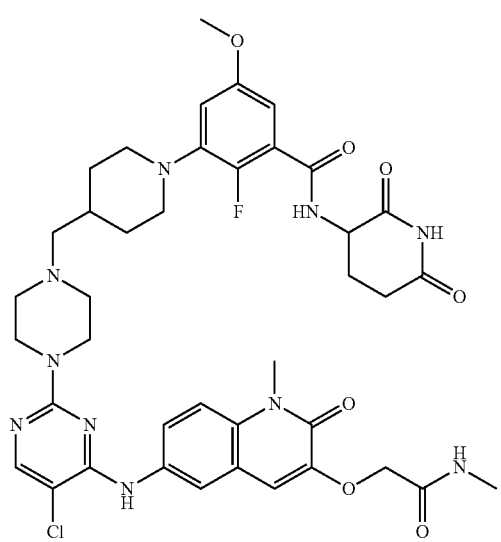 [SMILES: CNC(=O)COc1cc2cc(Nc3nc(N4CCN(CC5CCN(c6cc(OC)cc(C(=O)NC7CCC(=O)NC7=O)c6F)CC5)CC4)ncc3Cl)ccc2n(C)c1=O] | 3-[4-({4-[5-chloro-4-({1-methyl-3-[(methylcarbamoyl)methoxy]-2-oxo-1,2-dihydroquinolin-6-yl}amino)pyrimidin-2-yl]piperazin-1-yl}methyl)piperidin-1-yl]-N-(2,6-dioxopiperidin-3-yl)-2-fluoro-5-methoxybenzamide |

TABLE 1-continued

Exemplary bifunctional compounds of the present disclosure

| Ex. # | Parent Mol Structure | Name |
|---|---|---|
| 466 | 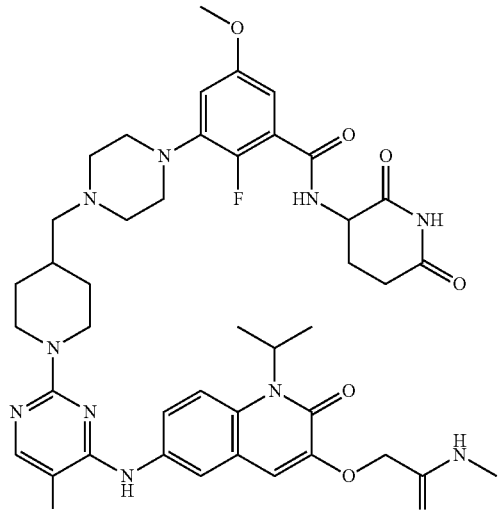 | 3-[4-({1-[5-chloro-4-({3-[(methylcarbamoyl)methoxy]-2-oxo-1-(propan-2-yl)-1,2-dihydroquinolin-6-yl}amino)pyrimidin-2-yl]piperidin-4-yl}methyl)piperazin-1-yl]-N-(2,6-dioxopiperidin-3-yl)-2-fluoro-5-methoxybenzamide |
| 467 | 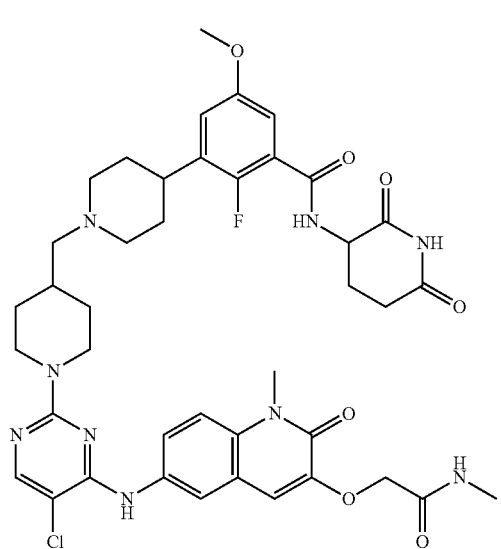 [SMILES: CNC(=O)COc1cc2cc(Nc3nc(N4CCC(CN5CCC(c6cc(OC)cc(C(=O)NC7CCC(=O)NC7=O)c6F)CC5)CC4)ncc3Cl)ccc2n(C)c1=O] | 3-[1-({1-[5-chloro-4-({1-methyl-3-[(methylcarbamoyl)methoxy]-2-oxo-1,2-dihydroquinolin-6-yl}amino)pyrimidin-2-yl]piperidin-4-yl}methyl)piperidin-4-yl]-N-(2,6-dioxopiperidin-3-yl)-2-fluoro-5-methoxybenzamide |
| 468 | 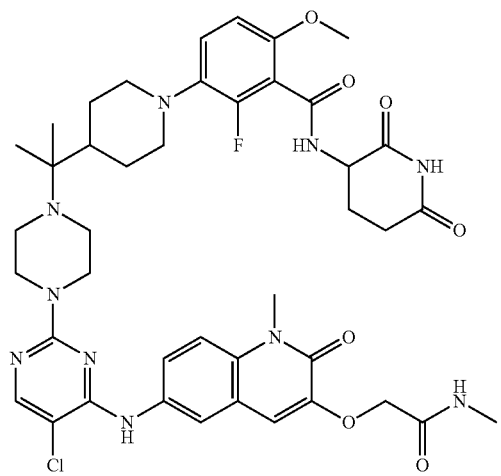 [SMILES: CNC(=O)COc1cc2cc(Nc3nc(N4CCN(C(C)(C)C5CCN(c6ccc(OC)c(C(=O)NC7CCC(=O)NC7=O)c6F)CC5)CC4)ncc3Cl)ccc2n(C)c1=O] | 3-[4-(2-{4-[5-chloro-4-({1-methyl-3-[(methylcarbamoyl)methoxy]-2-oxo-1,2-dihydroquinolin-6-yl}amino)pyrimidin-2-yl]piperazin-1-yl}propan-2-yl)piperidin-1-yl]-N-(2,6-dioxopiperidin-3-yl)-2-fluoro-6-methoxybenzamide |

TABLE 1-continued

Exemplary bifunctional compounds of the present disclosure

| Ex. # | Parent Mol Structure | Name |
|---|---|---|
| 469 | | 2-[(6-{[5-chloro-2-(dimethylamino)pyrimidin-4-yl]amino}-1-(3-{[2-(2,6-dioxopiperidin-3-yl)-1,3-dioxo-2,3-dihydro-1H-isoindol-5-yl]oxy}propyl)-2-oxo-1,2-dihydroquinolin-3-yl)oxy]-N-methylacetamide |
| 470 | | 2-[(6-{[5-chloro-2-(dimethylamino)pyrimidin-4-yl]amino}-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide |
| 471 | | 2-[(6-{[5-chloro-2-(4-{[(3S,5R)-5-({[2-(2,6-dioxopiperidin-3-yl)-1,3-dioxo-2,3-dihydro-1H-isoindol-4-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 472 | 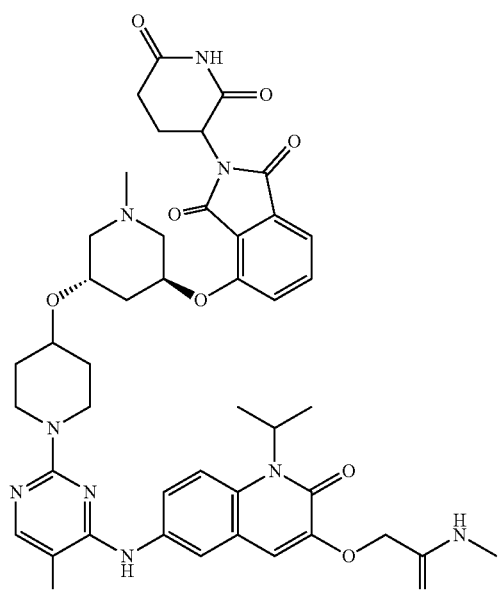 | 2-[(6-{[5-chloro-2-(4-{[(3S,5S)-5-{[2-(2,6-dioxopiperidin-3-yl)-1,3-dioxo-2,3-dihydro-1H-isoindol-4-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 473 | 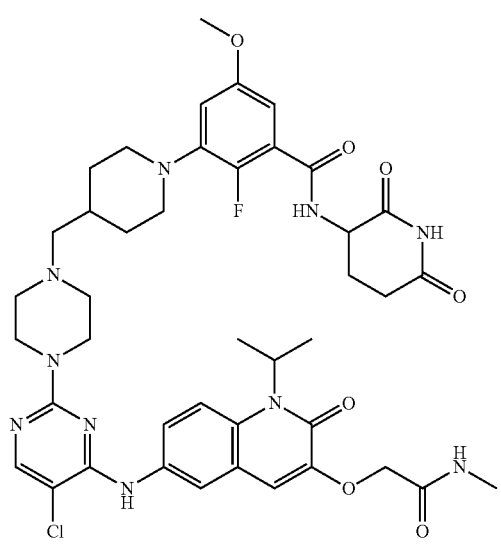 [SMILES: CNC(=O)COc1cc2cc(Nc3nc(N4CCN(CC5CCN(c6cc(OC)cc(C(=O)NC7CCC(=O)NC7=O)c6F)CC5)CC4)ncc3Cl)ccc2n(C(C)C)c1=O] | 3-[4-({4-[5-chloro-4-({3-[(methylcarbamoyl)methoxy]-2-oxo-1-(propan-2-yl)-1,2-dihydroquinolin-6-yl}amino)pyrimidin-2-yl]piperazin-1-yl}methyl)piperidin-1-yl]-N-(2,6-dioxopiperidin-3-yl)-2-fluoro-5-methoxybenzamide |
| 474 | 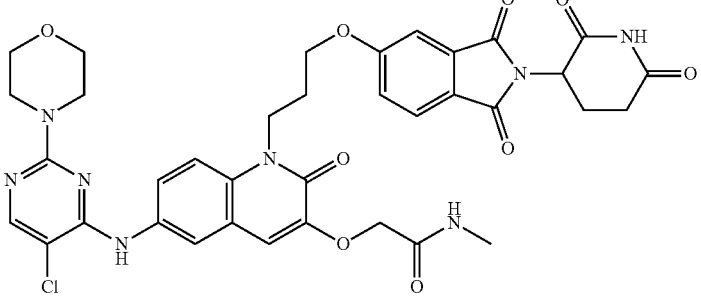 | 2-[(6-{[5-chloro-2-(morpholin-4-yl)pyrimidin-4-yl]amino}-1-(3-{[2-(2,6-dioxopiperidin-3-yl)-1,3-dioxo-2,3-dihydro-1H-isoindol-5-yl]oxy}propyl)-2-oxo-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 475 | 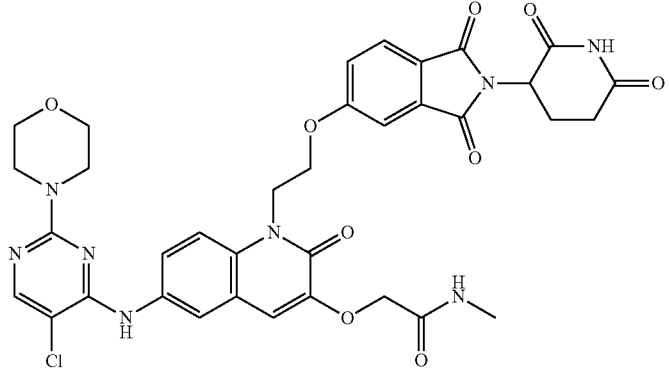 [SMILES: CNC(=O)COc1cc2cc(Nc3nc(N4CCOCC4)ncc3Cl)ccc2n(CCOc2ccc3c(c2)C(=O)N(C2CCC(=O)NC2=O)C3=O)c1=O] | 2-[(6-{[5-chloro-2-(morpholin-4-yl)pyrimidin-4-yl]amino}-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide |
| 476 | 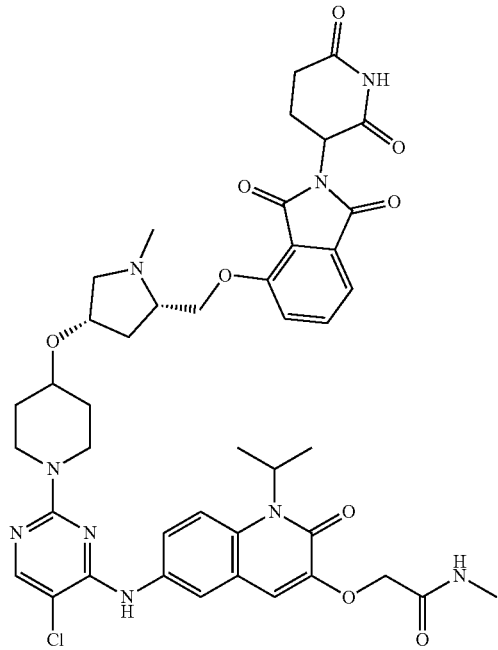 [SMILES: CNC(=O)COc1cc2cc(Nc3nc(N4CCC(O[C@H]5C[C@@H](COc6cccc7c6C(=O)N(C6CCC(=O)NC6=O)C7=O)N(C)C5)CC4)ncc3Cl)ccc2n(C(C)C)c1=O] | 2-[(6-{[5-chloro-2-(4-{[(3S,5S)-5-({[2-(2,6-dioxopiperidin-3-yl)-1,3-dioxo-2,3-dihydro-1H-isoindol-4-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 477 | 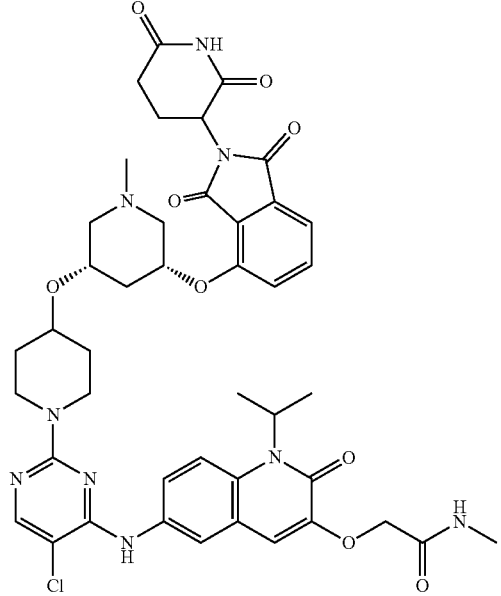 [SMILES: CNC(=O)COc1cc2cc(Nc3nc(N4CCC(O[C@H]5C[C@@H](Oc6cccc7c6C(=O)N(C6CCC(=O)NC6=O)C7=O)CN(C)C5)CC4)ncc3Cl)ccc2n(C(C)C)c1=O] | 2-[(6-{[5-chloro-2-(4-{[(3S,5R)-5-{[2-(2,6-dioxopiperidin-3-yl)-1,3-dioxo-2,3-dihydro-1H-isoindol-4-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 478 | 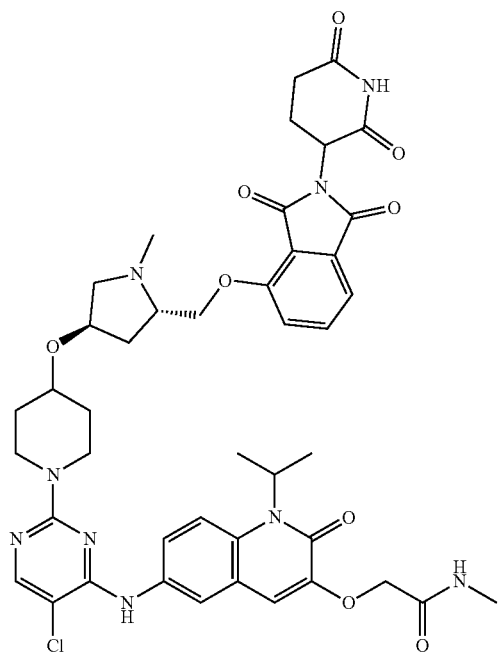 [SMILES: CNC(=O)COc1cc2cc(Nc3nc(N4CCC(O[C@@H]5C[C@@H](COc6cccc7c6C(=O)N(C6CCC(=O)NC6=O)C7=O)N(C)C5)CC4)ncc3Cl)ccc2n(C(C)C)c1=O] | 2-[(6-{[5-chloro-2-(4-{[(3R,5S)-5-({[2-(2,6-dioxopiperidin-3-yl)-1,3-dioxo-2,3-dihydro-1H-isoindol-4-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 479 | | 2-[(6-{[5-chloro-2-(4-{[(3R,5R)-5-{[2-(2,6-dioxopiperidin-3-yl)-1,3-dioxo-2,3-dihydro-1H-isoindol-4-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 480 | | 3-[1-(1-{1-[5-chloro-4-({1-methyl-3-[(methylcarbamoyl)methoxy]-2-oxo-1,2-dihydroquinolin-6-yl}amino)pyrimidin-2-yl]piperidin-4-yl}cyclopropyl)piperidin-4-yl]-N-(2,6-dioxopiperidin-3-yl)-2-fluoro-5-methoxybenzamide |

TABLE 1-continued

Exemplary bifunctional compounds of the present disclosure

| Ex. # | Parent Mol Structure | Name |
|---|---|---|
| 481 | 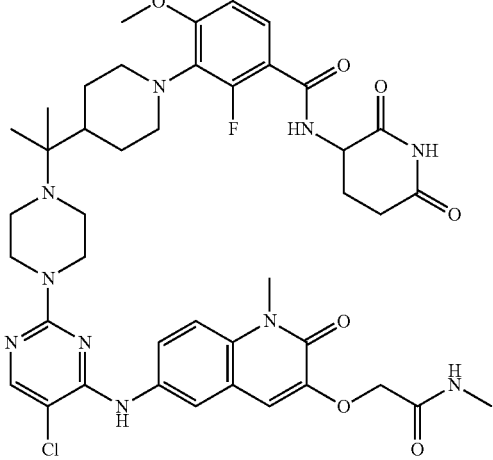 | 3-[4-(2-{4-[5-chloro-4-({1-methyl-3-[(methylcarbamoyl)methoxy]-2-oxo-1,2-dihydroquinolin-6-yl}amino)pyrimidin-2-yl]piperazin-1-yl}propan-2-yl)piperidin-1-yl]-N-(2,6-dioxopiperidin-3-yl)-2-fluoro-4-methoxybenzamide |
| 482 | 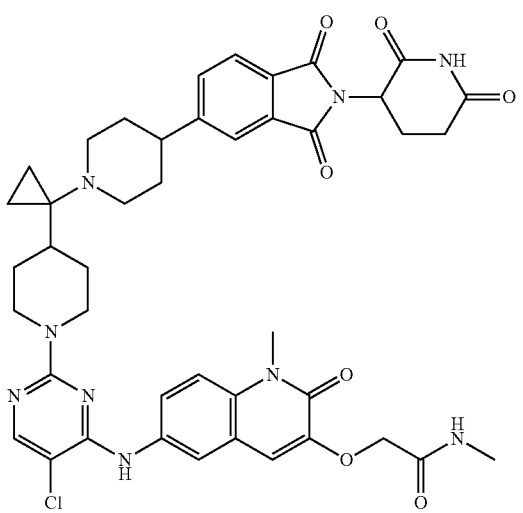 [SMILES: CNC(=O)COc1cc2cc(Nc3nc(N4CCC(C5(N6CCC(c7ccc8c(c7)C(=O)N(C7CCC(=O)NC7=O)C8=O)CC6)CC5)CC4)ncc3Cl)ccc2n(C)c1=O] | 2-{[6-({5-chloro-2-[4-(1-{4-[2-(2,6-dioxopiperidin-3-yl)-1,3-dioxo-2,3-dihydro-1H-isoindol-5-yl]piperidin-1-yl}cyclopropyl)piperidin-1-yl]pyrimidin-4-yl}amino)-1-methyl-2-oxo-1,2-dihydroquinolin-3-yl]oxy}-N-methylacetamide |
| 483 | 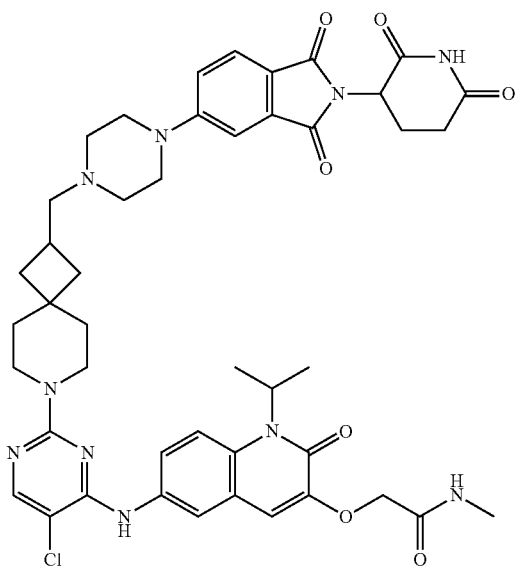 [SMILES: CNC(=O)COc1cc2cc(Nc3nc(N4CCC5(CC4)CC(CN4CCN(c6ccc7c(c6)C(=O)N(C6CCC(=O)NC6=O)C7=O)CC4)C5)ncc3Cl)ccc2n(C(C)C)c1=O] | 2-{[6-({5-chloro-2-[2-({4-[2-(2,6-dioxopiperidin-3-yl)-1,3-dioxo-2,3-dihydro-1H-isoindol-5-yl]piperazin-1-yl}methyl)-7-azaspiro[3.5]nonan-7-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 484 | 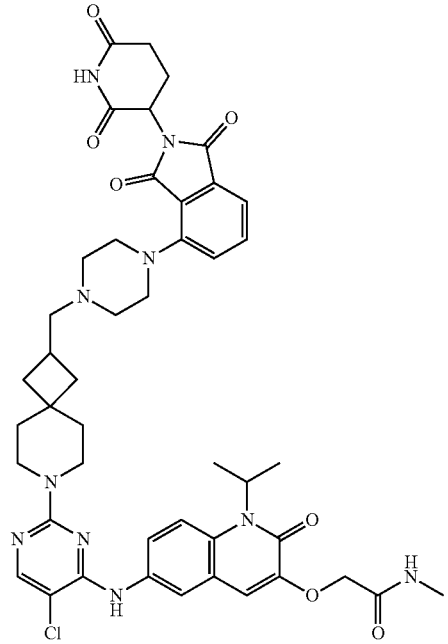 [SMILES: CNC(=O)COc1cc2cc(Nc3nc(N4CCC5(CC4)CC(CN4CCN(c6cccc7c6C(=O)N(C6CCC(=O)NC6=O)C7=O)CC4)C5)ncc3Cl)ccc2n(C(C)C)c1=O] | 2-{[6-({5-chloro-2-[2-({4-[2-(2,6-dioxopiperidin-3-yl)-1,3-dioxo-2,3-dihydro-1H-isoindol-4-yl]piperazin-1-yl}methyl)-7-azaspiro[3.5]nonan-7-yl]pyrimidin-4-yl}amino)-2-oxo-1-(propan-2-yl)-1,2-dihydroquinolin-3-yl]oxy}-N-methylacetamide |
| 485 | 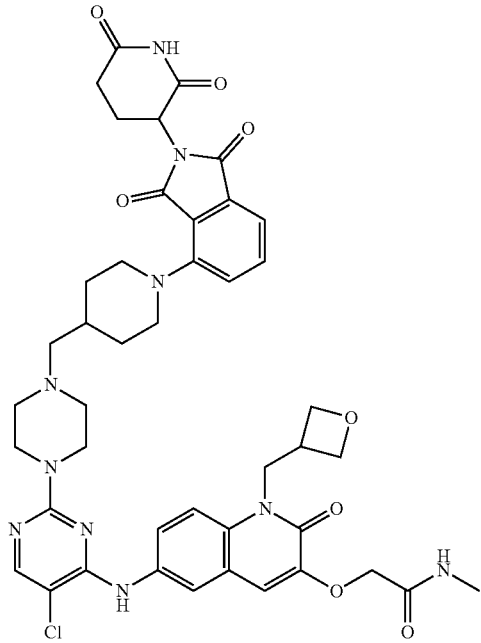 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(CC2COC2)c1=O] | 2-{[6-({5-chloro-2-[4-({1-[2-(2,6-dioxopiperidin-3-yl)-1,3-dioxo-2,3-dihydro-1H-isoindol-4-yl]piperidin-4-yl}methyl)piperazin-1-yl]pyrimidin-4-yl}amino)-1-[(oxetan-3-yl)methyl]-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 486 | | 2-[(6-{[5-chloro-2-(4-{[(3R,5R)-5-({[2-(2,6-dioxopiperidin-3-yl)-1,3-dioxo-2,3-dihydro-1H-isoindol-4-yl]oxy}methyl)-1-methylpyrrolidin-3-yl]oxy}piperidin-1-yl)pyrimidin-4-yl]amino}-2-oxo-1-(propan-2-yl)-1,2-dihydroquinolin-3-yl)oxy]-N-methylacetamide |
| 487 | | 2-[(6-{[5-chloro-2-(4-{[(3R,5S)-5-{[2-(2,6-dioxopiperidin-3-yl)-1,3-dioxo-2,3-dihydro-1H-isoindol-4-yl]oxy}-1-methylpiperidin-3-yl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 488 | | 2-{[6-({5-chloro-2-[4-(1-{4-[2-(2,6-dioxopiperidin-3-yl)-1,3-dioxo-2,3-dihydro-1H-isoindol-5-yl]piperidin-1-yl}cyclopropyl)piperidin-1-yl]pyrimidin-4-yl}amino)-2-oxo-1-(propan-2-yl)-1,2-dihydroquinolin-3-yl]oxy}-N-methylacetamide |
| 489 | | 2-{[6-({5-chloro-2-[4-({2-[2-(2,6-dioxopiperidin-3-yl)-1,3-dioxo-2,3-dihydro-1H-isoindol-5-yl]-2,8-diazaspiro[4.5]decan-8-yl}methyl)piperidin-1-yl]pyrimidin-4-yl}amino)-2-oxo-1-(propan-2-yl)-1,2-dihydroquinolin-3-yl]oxy}-N-methylacetamide |
| 490 | | 2-{[6-({5-chloro-2-[8-({1-[2-(2,6-dioxopiperidin-3-yl)-1,3-dioxo-2,3-dihydro-1H-isoindol-5-yl]piperidin-4-yl}methyl)-2,8-diazaspiro[4.5]decan-2-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 491 | 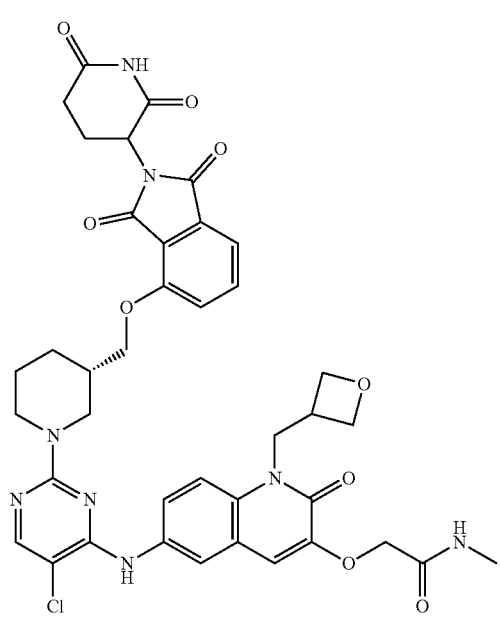 [SMILES: CNC(=O)COc1cc2cc(Nc3nc(N4CCC[C@H](COc5cccc6c5C(=O)N(C5CCC(=O)NC5=O)C6=O)C4)ncc3Cl)ccc2n(CC2COC2)c1=O] | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-[(oxetan-3-yl)methyl]-2-oxo-1,2-dihydroquinolin-3-yl]oxy}-N-methylacetamide |
| 492 | 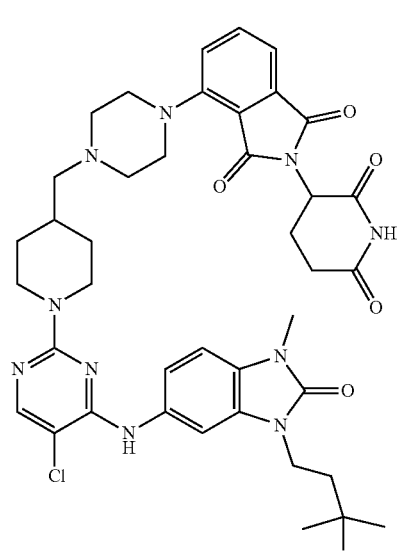 | 4-(4-{[1-(5-chloro-4-{[3-(3-hydroxy-3-methylbutyl)-1-methyl-2-oxo-2,3-dihydro-1H-1,3-benzodiazol-5-yl]amino}pyrimidin-2-yl)piperidin-4-yl]methyl}piperazin-1-yl)-2-(2,6-dioxopiperidin-3-yl)-2,3-dihydro-1H-isoindole-1,3-dione |

TABLE 1-continued

Exemplary bifunctional compounds of the present disclosure

| Ex. # | Parent Mol Structure | Name |
|---|---|---|
| 493 | 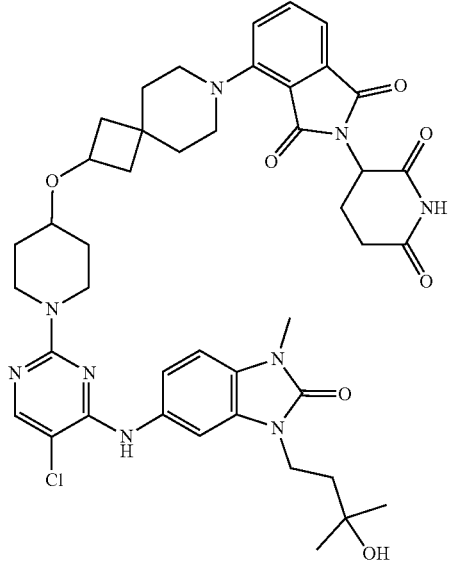 [SMILES: Cn1c(=O)n(CCC(C)(C)O)c2cc(Nc3nc(N4CCC(OC5CC6(CCN(c7cccc8c7C(=O)N(C7CCC(=O)NC7=O)C8=O)CC6)C5)CC4)ncc3Cl)ccc21] | 4-(2-{[1-(5-chloro-4-{[3-(3-hydroxy-3-methylbutyl)-1-methyl-2-oxo-2,3-dihydro-1H-1,3-benzodiazol-5-yl]amino}pyrimidin-2-yl)piperidin-4-yl]oxy}-7-azaspiro[3.5]nonan-7-yl)-2-(2,6-dioxopiperidin-3-yl)-2,3-dihydro-1H-isoindole-1,3-dione |
| 494 | 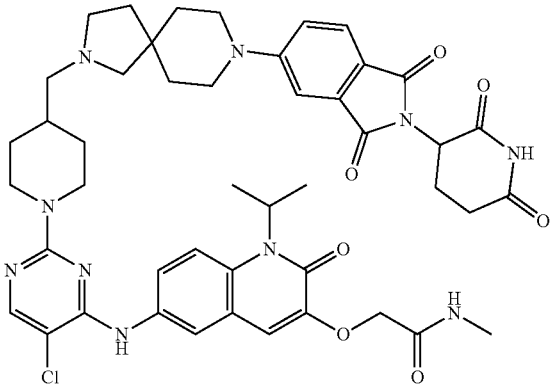 [SMILES: CNC(=O)COc1cc2cc(Nc3nc(N4CCC(CN5CCC6(CCN(c7ccc8c(c7)C(=O)N(C7CCC(=O)NC7=O)C8=O)CC6)C5)CC4)ncc3Cl)ccc2n(C(C)C)c1=O] | 2-{[6-({5-chloro-2-[4-({8-[2-(2,6-dioxopiperidin-3-yl)-1,3-dioxo-2,3-dihydro-1H-isoindol-5-yl]-2,8-diazaspiro[4.5]decan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 495 | 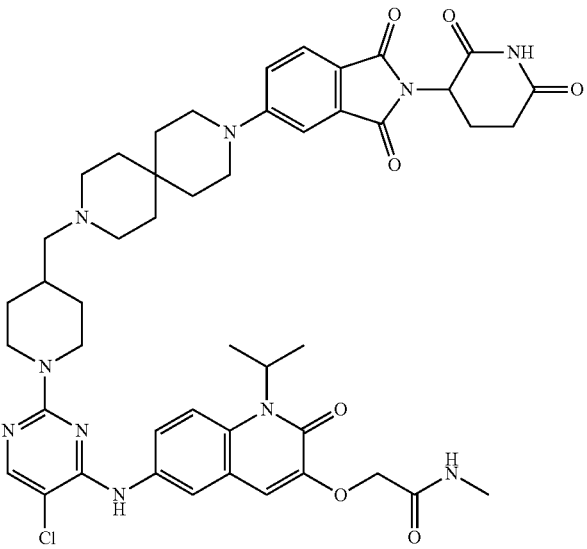 [SMILES: CNC(=O)COc1cc2cc(Nc3nc(N4CCC(CN5CCC6(CC5)CCN(c5ccc7c(c5)C(=O)N(C5CCC(=O)NC5=O)C7=O)CC6)CC4)ncc3Cl)ccc2n(C(C)C)c1=O] | 2-{[6-({5-chloro-2-[4-({9-[2-(2,6-dioxopiperidin-3-yl)-1,3-dioxo-2,3-dihydro-1H-isoindol-5-yl]-3,9-diazaspiro[5.5]undecan-3-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 496 | | 2-{[6-({5-chloro-2-[9-({1-[2-(2,6-dioxopiperidin-3-yl)-1,3-dioxo-2,3-dihydro-1H-isoindol-5-yl]piperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |
| 497 | | 2-{[6-({5-chloro-2-[4-({2-[4-(2,4-dioxo-1,3-diazinan-1-yl)phenyl]-2,8-diazaspiro[4.5]decan-8-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 498 | 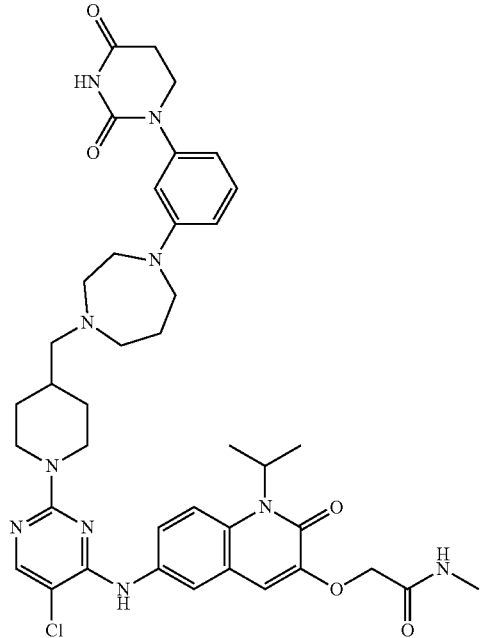 [SMILES: CNC(=O)COc1cc2cc(Nc3nc(N4CCC(CN5CCCN(c6cccc(N7CCC(=O)NC7=O)c6)CC5)CC4)ncc3Cl)ccc2n(C(C)C)c1=O] | 2-{[6-({5-chloro-2-[4-({4-[3-(2,4-dioxo-1,3-diazinan-1-yl)phenyl]-1,4-diazepan-1-yl}methyl)piperidin-1-yl]pyrimidin-4-yl}amino)-2-oxo-1-(propan-2-yl)-1,2-dihydroquinolin-3-yl]oxy}-N-methylacetamide |
| 499 | 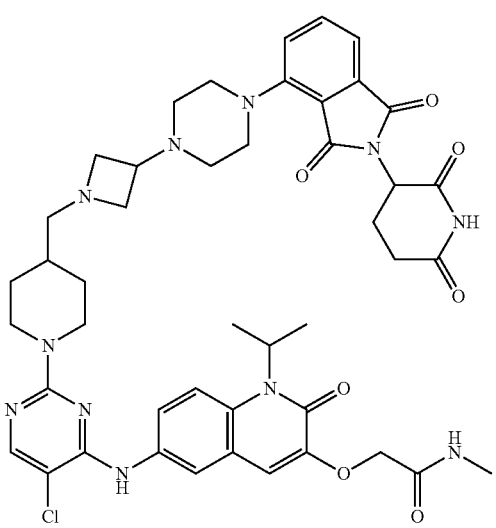 [SMILES: CNC(=O)COc1cc2cc(Nc3nc(N4CCC(CN5CC(N6CCN(c7cccc8c7C(=O)N(C7CCC(=O)NC7=O)C8=O)CC6)C5)CC4)ncc3Cl)ccc2n(C(C)C)c1=O] | 2-({6-[(5-chloro-2-{4-[(3-{4-[2-(2,6-dioxopiperidin-3-yl)-1,3-dioxo-2,3-dihydro-1H-isoindol-4-yl]piperazin-1-yl}azetidin-1-yl)methyl]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Ex. # | Parent Mol Structure | Name |
|---|---|---|
| 500 | 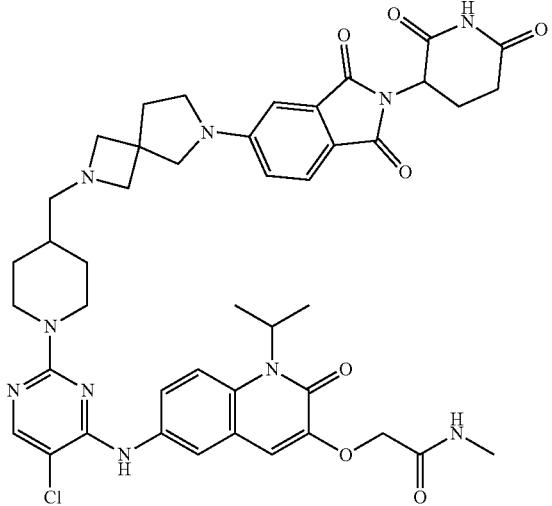 [SMILES: CNC(=O)COc1cc2cc(Nc3nc(N4CCC(CN5CC6(CCN(c7ccc8c(c7)C(=O)N(C7CCC(=O)NC7=O)C8=O)C6)C5)CC4)ncc3Cl)ccc2n(C(C)C)c1=O] | 2-{[6-({5-chloro-2-[4-({6-[2-(2,6-dioxopiperidin-3-yl)-1,3-dioxo-2,3-dihydro-1H-isoindol-5-yl]-2,6-diazaspiro[3.4]octan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 501 | 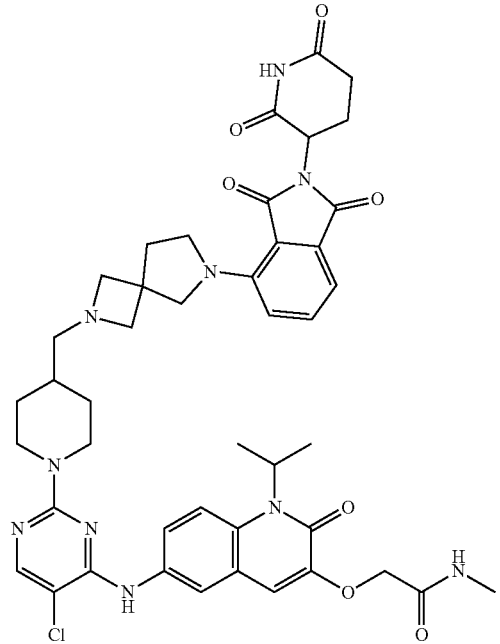 [SMILES: CNC(=O)COc1cc2cc(Nc3nc(N4CCC(CN5CC6(CCN(c7cccc8c7C(=O)N(C7CCC(=O)NC7=O)C8=O)C6)C5)CC4)ncc3Cl)ccc2n(C(C)C)c1=O] | 2-{[6-({5-chloro-2-[4-({6-[2-(2,6-dioxopiperidin-3-yl)-1,3-dioxo-2,3-dihydro-1H-isoindol-4-yl]-2,6-diazaspiro[3.4]octan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 502 | 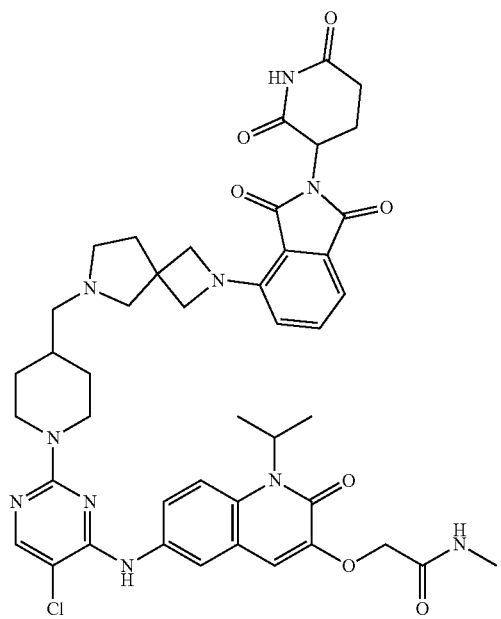 [SMILES: CNC(=O)COc1cc2cc(Nc3nc(N4CCC(CN5CCC6(C5)CN(c5cccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-2,6-diazaspiro[3.4]octan-6-yl}methyl)piperidin-1-yl]pyrimidin-4-yl}amino)-2-oxo-1-(propan-2-yl)-1,2-dihydroquinolin-3-yl]oxy}-N-methylacetamide |
| 503 | 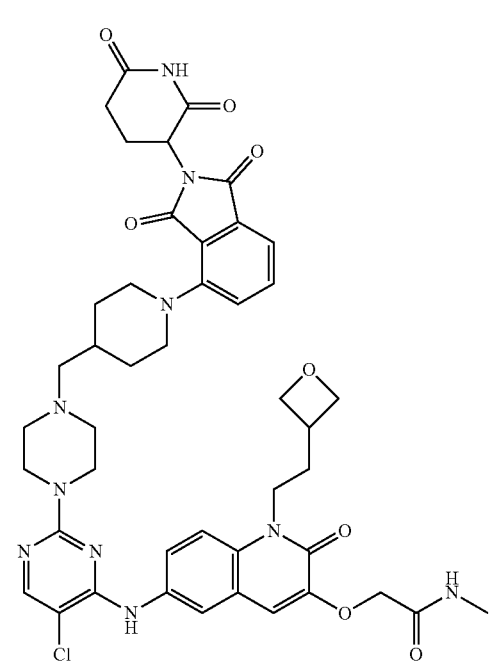 [SMILES: CNC(=O)COc1cc2cc(Nc3nc(N4CCN(CC5CCN(c6cccc7c6C(=O)N(C6CCC(=O)NC6=O)C7=O)CC5)CC4)ncc3Cl)ccc2n(CCC2COC2)c1=O] | 2-{[6-({5-chloro-2-[4-({1-[2-(2,6-dioxopiperidin-3-yl)-1,3-dioxo-2,3-dihydro-1H-isoindol-4-yl]piperidin-4-yl}methyl)piperazin-1-yl]pyrimidin-4-yl}amino)-1-[2-(oxetan-3-yl)ethyl]-2-oxo-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 504 | | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-[2-(oxetan-3-yl)ethyl]-2-oxo-1,2-dihydroquinolin-3-yl]oxy}-N-methylacetamide |
| 505 | | 4-(4-{[4-(5-chloro-4-{[3-(3-hydroxy-3-methylbutyl)-1-methyl-2-oxo-2,3-dihydro-1H-1,3-benzodiazol-5-yl]amino}pyrimidin-2-yl)piperazin-1-yl]methyl}piperidin-1-yl)-2-(2,6-dioxopiperidin-3-yl)-2,3-dihydro-1H-isoindole-1,3-dione |

TABLE 1-continued

Exemplary bifunctional compounds of the present disclosure

| Ex. # | Parent Mol Structure | Name |
|---|---|---|
| 506 | | 2-{[6-({5-chloro-2-[4-({8-[2-(2,6-dioxopiperidin-3-yl)-1,3-dioxo-2,3-dihydro-1H-isoindol-4-yl]-2,8-diazaspiro[4.5]decan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 507 | | 2-{[6-({5-chloro-2-[2-({1-[2-(2,6-dioxopiperidin-3-yl)-1,3-dioxo-2,3-dihydro-1H-isoindol-5-yl]piperidin-4-yl}methyl)-2,8-diazaspiro[4.5]decan-8-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 508 | 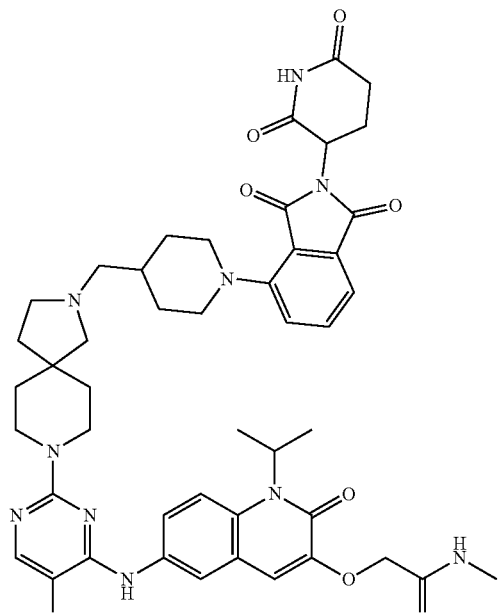 | 2-{[6-({5-chloro-2-[2-({1-[2-(2,6-dioxopiperidin-3-yl)-1,3-dioxo-2,3-dihydro-1H-isoindol-4-yl]piperidin-4-yl}methyl)-2,8-diazaspiro[4.5]decan-8-yl]pyrimidin-4-yl}amino)-2-oxo-1-(propan-2-yl)-1,2-dihydroquinolin-3-yl]oxy}-N-methylacetamide |
| 509 | 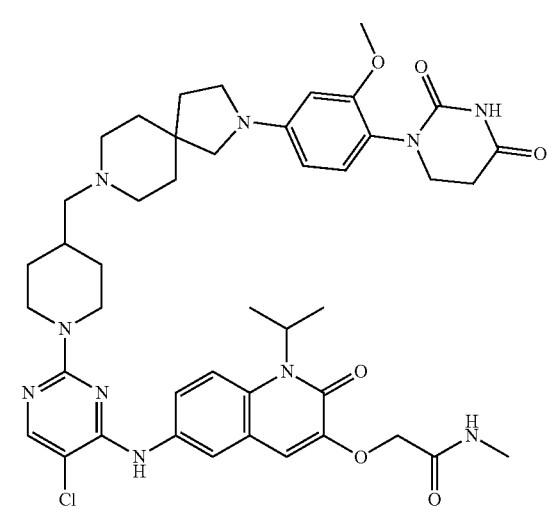 [SMILES: CNC(=O)COc1cc2cc(Nc3nc(N4CCC(CN5CCC6(CC5)CCN(c5ccc(N7CCC(=O)NC7=O)c(OC)c5)C6)CC4)ncc3Cl)ccc2n(C(C)C)c1=O] | 2-{[6-({5-chloro-2-[4-({2-[4-(2,4-dioxo-1,3-diazinan-1-yl)-3-methoxyphenyl]-2,8-diazaspiro[4.5]decan-8-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 510 | | 2-{[6-({5-chloro-2-[4-({2-[2-(2,6-dioxopiperidin-3-yl)-1,3-dioxo-2,3-dihydro-1H-isoindol-5-yl]-2,6-diazaspiro[3.4]octan-6-yl}methyl)piperidin-1-yl]pyrimidin-4-yl}amino)-2-oxo-1-(propan-2-yl)-1,2-dihydroquinolin-3-yl]oxy}-N-methylacetamide |
| 511 | | 2-{[6-({5-chloro-2-[6-({1-[2-(2,6-dioxopiperidin-3-yl)-1,3-dioxo-2,3-dihydro-1H-isoindol-4-yl]piperidin-4-yl}methyl)-2,6-diazaspiro[3.4]octan-2-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 512 | 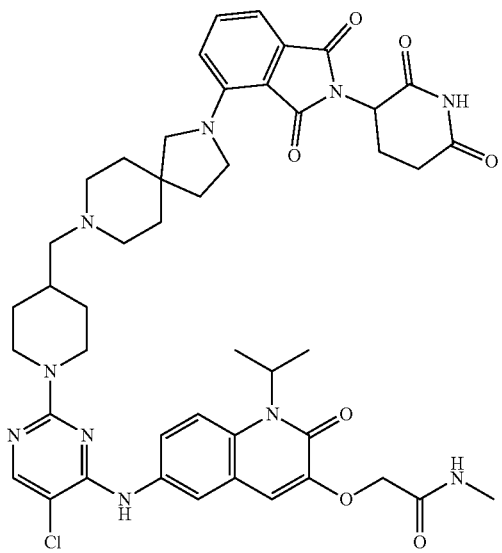 [SMILES: CNC(=O)COc1cc2cc(Nc3nc(N4CCC(CN5CCC6(CC5)CCN(c5cccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-2,8-diazaspiro[4.5]decan-8-yl}methyl)piperidin-1-yl]pyrimidin-4-yl}amino)-2-oxo-1-(propan-2-yl)-1,2-dihydroquinolin-3-yl]oxy}-N-methylacetamide |
| 513 | 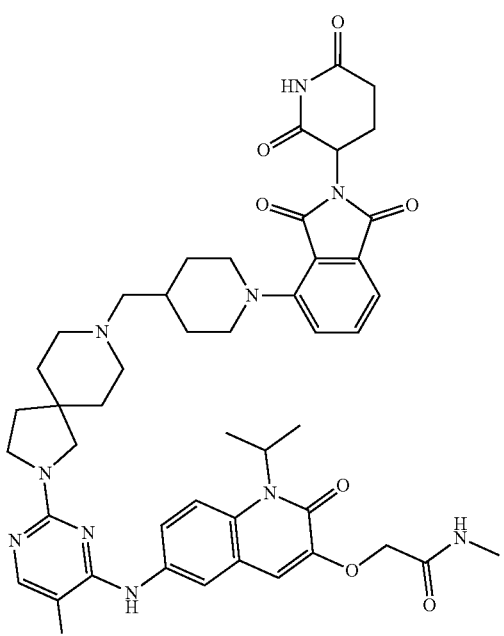 | 2-{[6-({5-chloro-2-[8-({1-[2-(2,6-dioxopiperidin-3-yl)-1,3-dioxo-2,3-dihydro-1H-isoindol-4-yl]piperidin-4-yl}methyl)-2,8-diazaspiro[4.5]decan-2-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 514 | 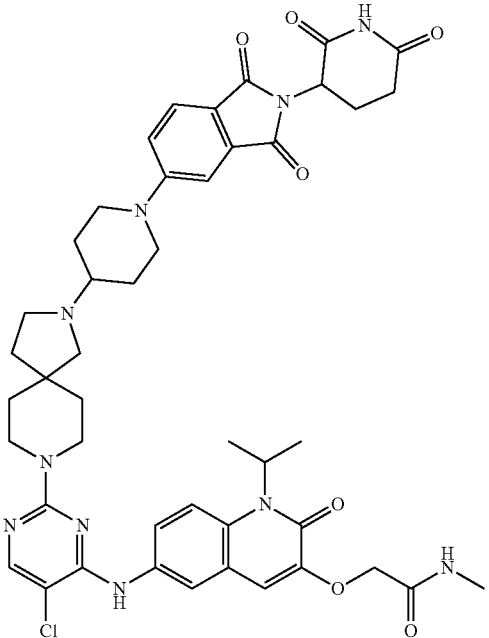 [SMILES: CNC(=O)COc1cc2cc(Nc3nc(N4CCC5(CC4)CCN(C4CCN(c6ccc7c(c6)C(=O)N(C6CCC(=O)NC6=O)C7=O)CC4)C5)ncc3Cl)ccc2n(C(C)C)c1=O] | 2-[(6-{[5-chloro-2-(2-{1-[2-(2,6-dioxopiperidin-3-yl)-1,3-dioxo-2,3-dihydro-1H-isoindol-5-yl]piperidin-4-yl}-2,8-diazaspiro[4.5]decan-8-yl)pyrimidin-4-yl]amino}-2-oxo-1-(propan-2-yl)-1,2-dihydroquinolin-3-yl)oxy]-N-methylacetamide |
| 515 | 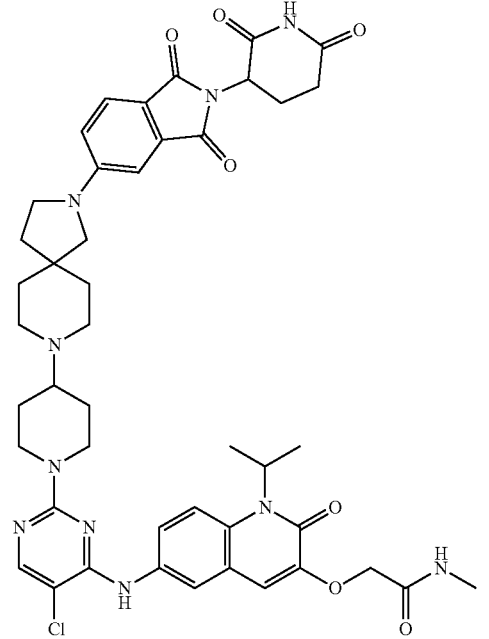 [SMILES: CNC(=O)COc1cc2cc(Nc3nc(N4CCC(N5CCC6(CCN(c7ccc8c(c7)C(=O)N(C7CCC(=O)NC7=O)C8=O)C6)CC5)CC4)ncc3Cl)ccc2n(C(C)C)c1=O] | 2-[(6-{[5-chloro-2-(4-{2-[2-(2,6-dioxopiperidin-3-yl)-1,3-dioxo-2,3-dihydro-1H-isoindol-5-yl]-2,8-diazaspiro[4.5]decan-8-yl}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 516 | | 2-{[6-({5-chloro-2-[4-({7-[2-(2,6-dioxopiperidin-3-yl)-1,3-dioxo-2,3-dihydro-1H-isoindol-5-yl]-7-azaspiro[3.5]nonan-2-yl}methyl)piperazin-1-yl]pyrimidin-4-yl}amino)-2-oxo-1-(propan-2-yl)-1,2-dihydroquinolin-3-yl]oxy}-N-methylacetamide |
| 517 | | 2-{[6-({5-chloro-2-[4-({7-[2-(2,6-dioxopiperidin-3-yl)-1,3-dioxo-2,3-dihydro-1H-isoindol-4-yl]-7-azaspiro[3.5]nonan-2-yl}methyl)piperazin-1-yl]pyrimidin-4-yl}amino)-2-oxo-1-(propan-2-yl)-1,2-dihydroquinolin-3-yl]oxy}-N-methylacetamide |
| 518 | | 2-({6-[(5-chloro-2-{4-[(1r,3r)-3-{4-[2-(2,6-dioxopiperidin-3-yl)-1,3-dioxo-2,3-dihydro-1H-isoindol-4-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Ex. # | Parent Mol Structure | Name |
|---|---|---|
| 519 | 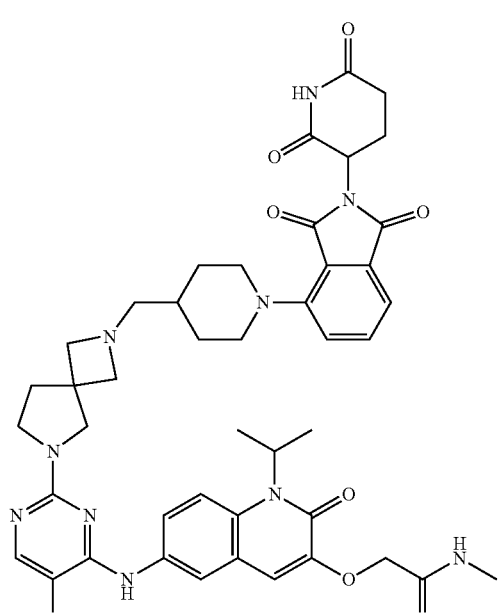 | 2-{[6-({5-chloro-2-[2-({1-[2-(2,6-dioxopiperidin-3-yl)-1,3-dioxo-2,3-dihydro-1H-isoindol-4-yl]piperidin-4-yl}methyl)-2,6-diazaspiro[3.4]octan-6-yl]pyrimidin-4-yl}amino)-2-oxo-1-(propan-2-yl)-1,2-dihydroquinolin-3-yl]oxy}-N-methylacetamide |
| 520 | 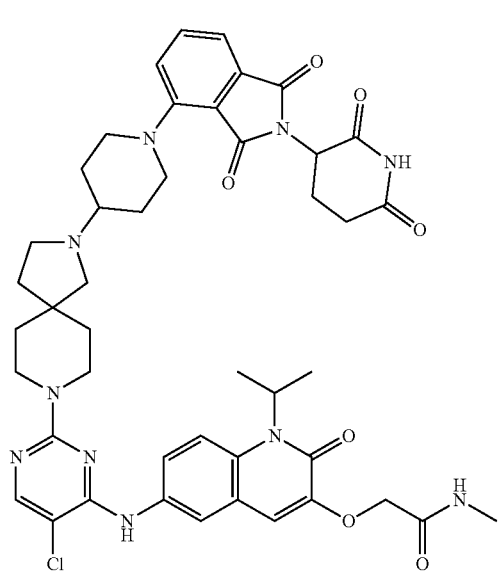 [SMILES: CNC(=O)COc1cc2cc(Nc3nc(N4CCC5(CC4)CCN(C4CCN(c6cccc7c6C(=O)N(C6CCC(=O)NC6=O)C7=O)CC4)C5)ncc3Cl)ccc2n(C(C)C)c1=O] | 2-[(6-{[5-chloro-2-(2-{1-[2-(2,6-dioxopiperidin-3-yl)-1,3-dioxo-2,3-dihydro-1H-isoindol-4-yl]piperidin-4-yl}-2,8-diazaspiro[4.5]decan-8-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 521 | | 2-[(6-{[5-chloro-2-(4-{8-[2-(2,6-dioxopiperidin-3-yl)-1,3-dioxo-2,3-dihydro-1H-isoindol-5-yl]-2,8-diazaspiro[4.5]decan-2-yl}piperidin-1-yl)pyrimidin-4-yl]amino}-2-oxo-1-(propan-2-yl)-1,2-dihydroquinolin-3-yl)oxy]-N-methylacetamide |
| 522 | | 2-{[6-({5-chloro-2-[4-({9-[2-(2,6-dioxopiperidin-3-yl)-1,3-dioxo-2,3-dihydro-1H-isoindol-4-yl]-3,9-diazaspiro[5.5]undecan-3-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 523 | | 2-{[6-({5-chloro-2-[4-({2-[2-(2,6-dioxopiperidin-3-yl)-1,3-dioxo-2,3-dihydro-1H-isoindol-5-yl]-2-azaspiro[3.3]heptan-6-yl}methyl)piperazin-1-yl]pyrimidin-4-yl}amino)-2-oxo-1-(propan-2-yl)-1,2-dihydroquinolin-3-yl]oxy}-N-methylacetamide |
| 524 | | 2-({6-[(5-chloro-2-{4-[(1-{1-[2-(2,6-dioxopiperidin-3-yl)-1,3-dioxo-2,3-dihydro-1H-isoindol-4-yl]piperidin-4-yl}azetidin-3-yl)methyl]piperazin-1-yl}pyrimidin-4-yl)amino]-2-oxo-1-(propan-2-yl)-1,2-dihydroquinolin-3-yl}oxy)-N-methylacetamide |
| 525 | | 2-({6-[(5-chloro-2-{4-[(1-{1-[2-(2,6-dioxopiperidin-3-yl)-1,3-dioxo-2,3-dihydro-1H-isoindol-4-yl]piperidin-4-yl}azetidin-3-yl)oxy]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Ex. # | Parent Mol Structure | Name |
|---|---|---|
| 526 | 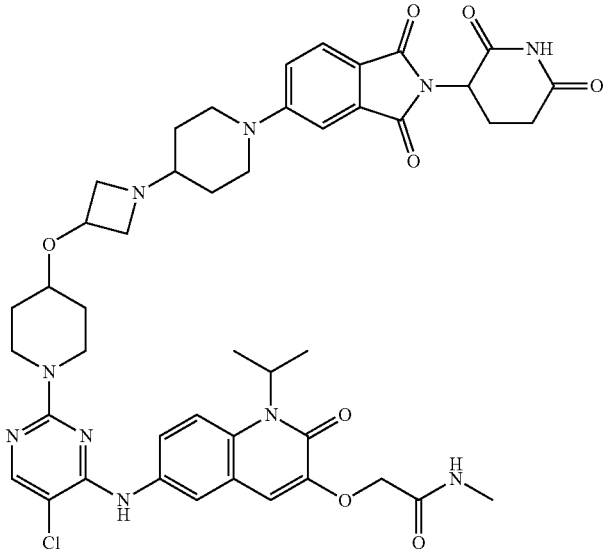 | 2-({6-[(5-chloro-2-{4-[(1-{1-[2-(2,6-dioxopiperidin-3-yl)-1,3-dioxo-2,3-dihydro-1H-isoindol-5-yl]piperidin-4-yl}azetidin-3-yl)oxy]piperidin-1-yl}pyrimidin-4-yl)amino]-2-oxo-1-(propan-2-yl)-1,2-dihydroquinolin-3-yl}oxy)-N-methylacetamide |
| 527 | 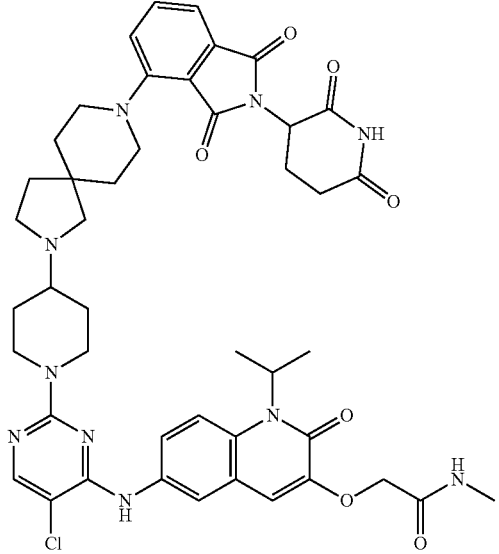 [SMILES: CNC(=O)COc1cc2cc(Nc3nc(N4CCC(N5CCC6(CCN(c7cccc8c7C(=O)N(C7CCC(=O)NC7=O)C8=O)CC6)C5)CC4)ncc3Cl)ccc2n(C(C)C)c1=O] | 2-[(6-{[5-chloro-2-(4-{8-[2-(2,6-dioxopiperidin-3-yl)-1,3-dioxo-2,3-dihydro-1H-isoindol-4-yl]-2,8-diazaspiro[4.5]decan-2-yl}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 528 | 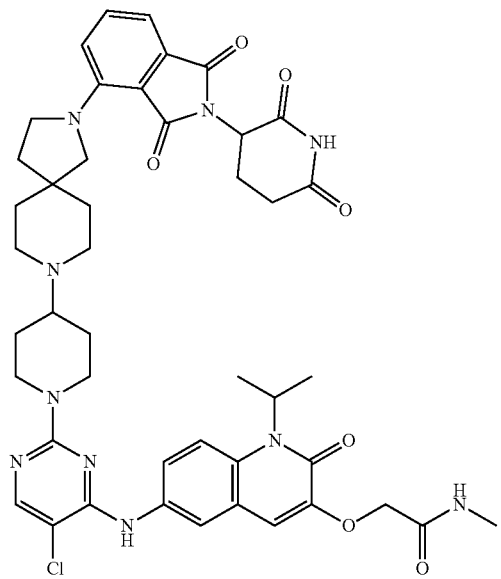 [SMILES: CNC(=O)COc1cc2cc(Nc3nc(N4CCC(N5CCC6(CCN(c7cccc8c7C(=O)N(C7CCC(=O)NC7=O)C8=O)C6)CC5)CC4)ncc3Cl)ccc2n(C(C)C)c1=O] | 2-[(6-{[5-chloro-2-(4-{2-[2-(2,6-dioxopiperidin-3-yl)-1,3-dioxo-2,3-dihydro-1H-isoindol-4-yl]-2,8-diazaspiro[4.5]decan-8-yl}piperidin-1-yl)pyrimidin-4-yl]amino}-2-oxo-1-(propan-2-yl)-1,2-dihydroquinolin-3-yl)oxy]-N-methylacetamide |
| 529 | 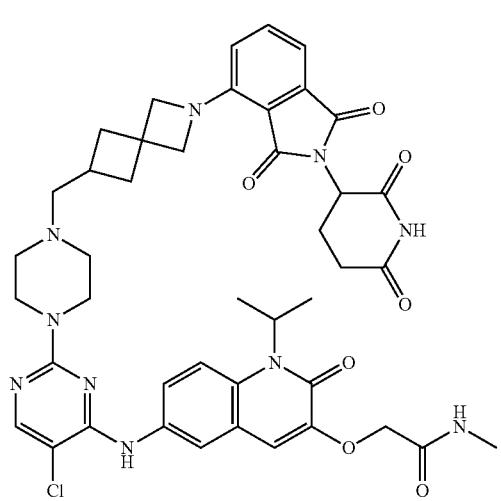 [SMILES: CNC(=O)COc1cc2cc(Nc3nc(N4CCN(CC5CC6(C5)CN(c5cccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-2-azaspiro[3.3]heptan-6-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 530 | 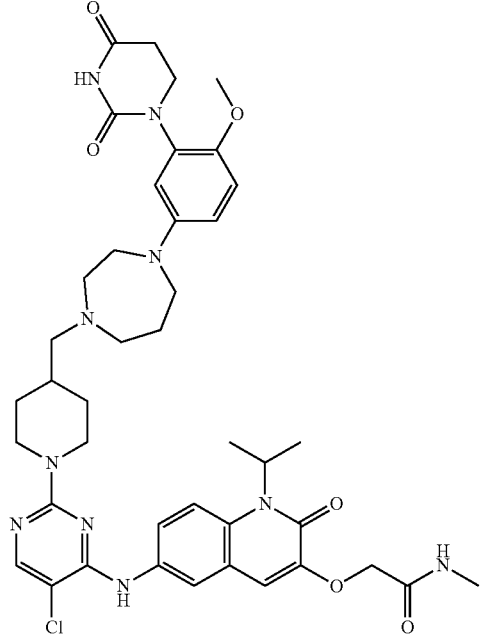 [SMILES: CNC(=O)COc1cc2cc(Nc3nc(N4CCC(CN5CCCN(c6ccc(OC)c(N7CCC(=O)NC7=O)c6)CC5)CC4)ncc3Cl)ccc2n(C(C)C)c1=O] | 2-{[6-({5-chloro-2-[4-({4-[3-(2,4-dioxo-1,3-diazinan-1-yl)-4-methoxyphenyl]-1,4-diazepan-1-yl}methyl)piperidin-1-yl]pyrimidin-4-yl}amino)-2-oxo-1-(propan-2-yl)-1,2-dihydroquinolin-3-yl]oxy}-N-methylacetamide |
| 531 | 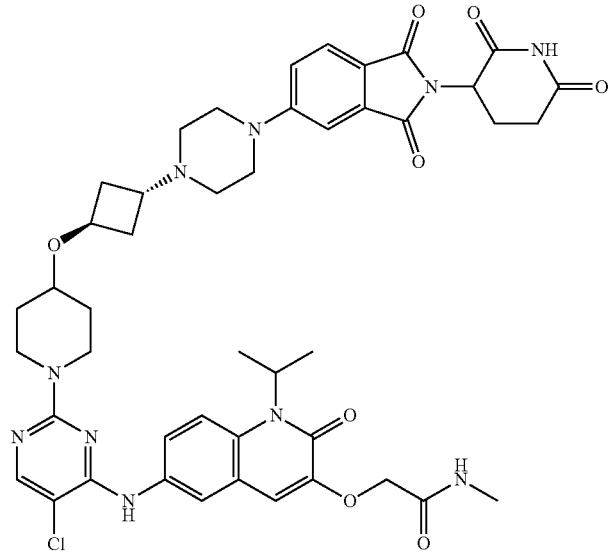 [SMILES: CNC(=O)COc1cc2cc(Nc3nc(N4CCC(O[C@H]5C[C@H](N6CCN(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Ex. # | Parent Mol Structure | Name |
|---|---|---|
| 532 | 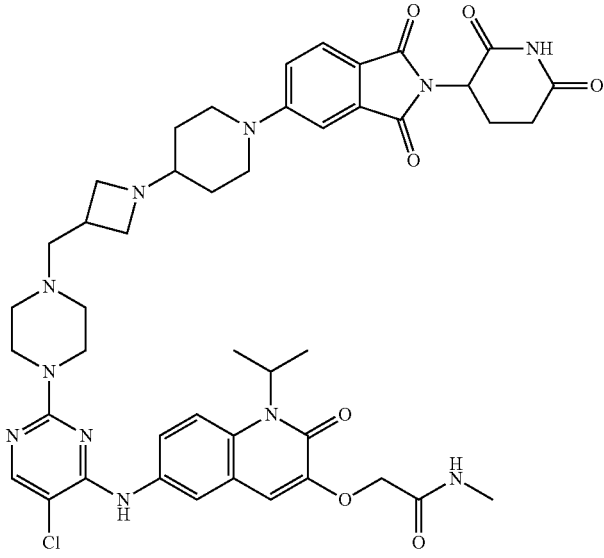 [SMILES: CNC(=O)COc1cc2cc(Nc3nc(N4CCN(CC5CN(C6CCN(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(1-{1-[2-(2,6-dioxopiperidin-3-yl)-1,3-dioxo-2,3-dihydro-1H-isoindol-5-yl]piperidin-4-yl}azetidin-3-yl)methyl]piperazin-1-yl}pyrimidin-4-yl)amino]-2-oxo-1-(propan-2-yl)-1,2-dihydroquinolin-3-yl}oxy)-N-methylacetamide |
| 533 | 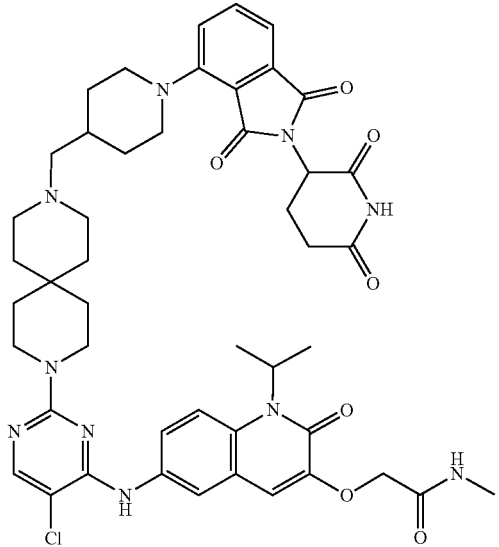 [SMILES: CNC(=O)COc1cc2cc(Nc3nc(N4CCC5(CCN(CC6CCN(c7cccc8c7C(=O)N(C7CCC(=O)NC7=O)C8=O)CC6)CC5)CC4)ncc3Cl)ccc2n(C(C)C)c1=O] | 2-{[6-({5-chloro-2-[9-({1-[2-(2,6-dioxopiperidin-3-yl)-1,3-dioxo-2,3-dihydro-1H-isoindol-4-yl]piperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |

1221

TABLE 1-continued

Exemplary bifunctional compounds of the present disclosure

| Ex. # | Parent Mol Structure | Name |
|---|---|---|
| 534 | 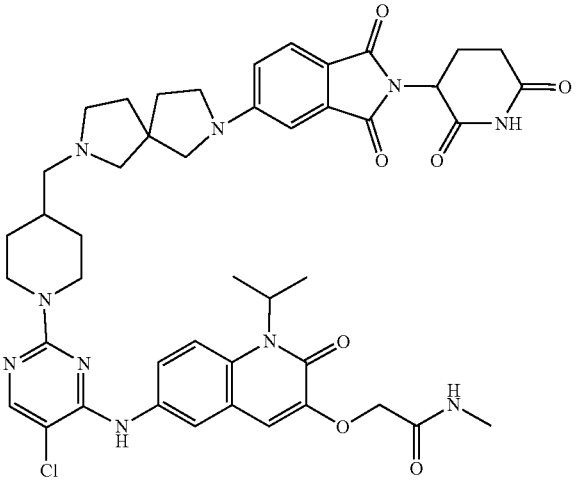 [SMILES: CNC(=O)COc1cc2cc(Nc3nc(N4CCC(CN5CCC6(CCN(c7ccc8c(c7)C(=O)N(C7CCC(=O)NC7=O)C8=O)C6)C5)CC4)ncc3Cl)ccc2n(C(C)C)c1=O] | 2-{[6-({5-chloro-2-[4-({7-[2-(2,6-dioxopiperidin-3-yl)-1,3-dioxo-2,3-dihydro-1H-isoindol-5-yl]-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 535 | 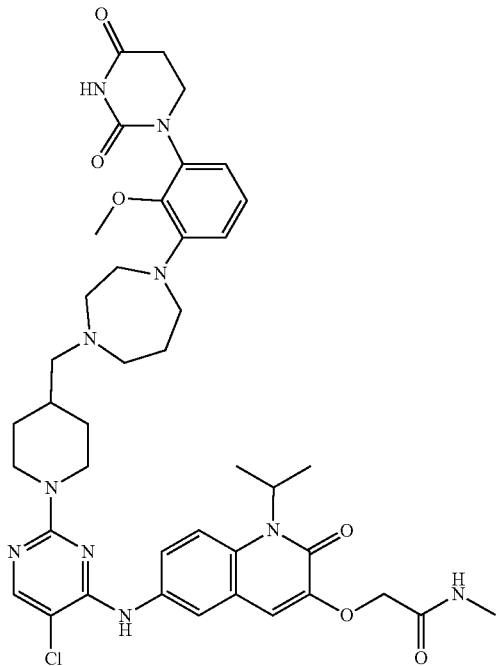 [SMILES: CNC(=O)COc1cc2cc(Nc3nc(N4CCC(CN5CCCN(c6cccc(N7CCC(=O)NC7=O)c6OC)CC5)CC4)ncc3Cl)ccc2n(C(C)C)c1=O] | 2-{[6-({5-chloro-2-[4-({4-[3-(2,4-dioxo-1,3-diazinan-1-yl)-2-methoxyphenyl]-1,4-diazepan-1-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 536 | | 2-({6-[(5-chloro-2-{4-[(1r,3r)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyrimidin-4-yl)amino]-1-methyl-2-oxo-1,2-dihydroquinolin-3-yl}oxy)-N-methylacetamide |
| 537 | | 2-[(6-{[5-chloro-2-(4-{[(1r,3r)-3-{4-[2-(2,6-dioxopiperidin-3-yl)-1,3-dioxo-2,3-dihydro-1H-isoindol-4-yl]piperazin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Ex. # | Parent Mol Structure | Name |
|---|---|---|
| 538 | | 2-({6-[(5-chloro-2-{4-[(3-{4-[2-(2,6-dioxopiperidin-3-yl)-1,3-dioxo-2,3-dihydro-1H-isoindol-5-yl]piperidin-1-yl}azetidin-1-yl)methyl]piperidin-1-yl}pyrimidin-4-yl)amino]-2-oxo-1-(propan-2-yl)-1,2-dihydroquinolin-3-yl}oxy)-N-methylacetamide |
| 539 | | 2-{[6-({5-chloro-2-[4-({2-[2-(2,6-dioxopiperidin-3-yl)-5-fluoro-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 540 | 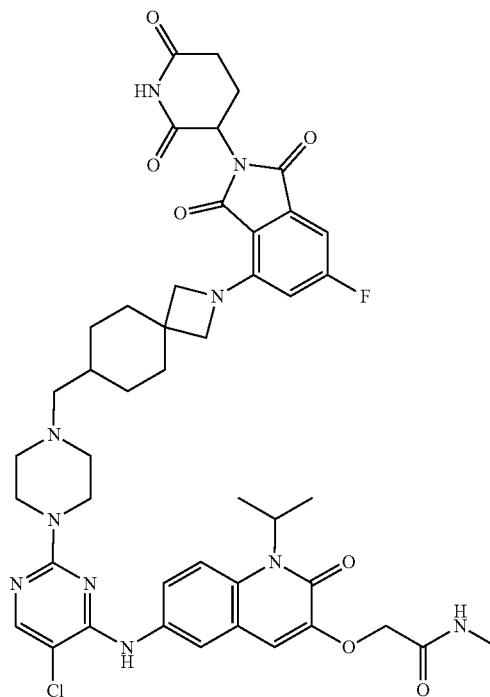 [SMILES: CNC(=O)COc1cc2cc(Nc3nc(N4CCN(CC5CCC6(CC5)CN(c5ccc(F)c7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-6-fluoro-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |
| 541 | 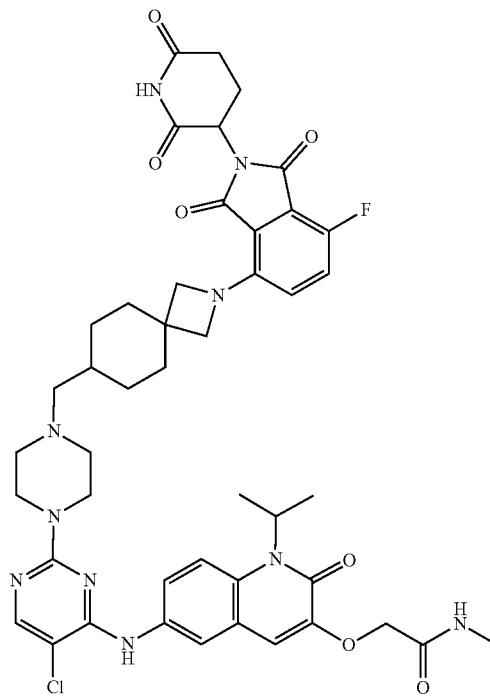 | 2-{[6-({5-chloro-2-[4-({2-[2-(2,6-dioxopiperidin-3-yl)-7-fluoro-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Ex. # | Parent Mol Structure | Name |
|---|---|---|
| 542 | 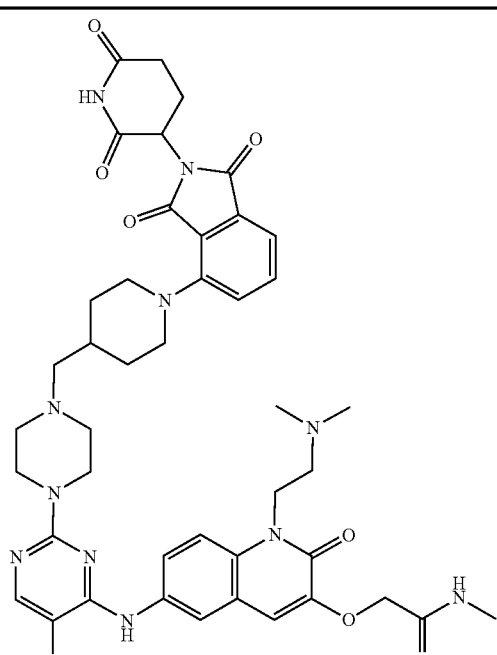 | 2-{[6-({5-chloro-2-[4-({1-[2-(2,6-dioxopiperidin-3-yl)-1,3-dioxo-2,3-dihydro-1H-isoindol-4-yl]piperidin-4-yl}methyl)piperazin-1-yl]pyrimidin-4-yl}amino)-1-[2-(dimethylamino)ethyl]-2-oxo-1,2-dihydroquinolin-3-yl]oxy}-N-methylacetamide |
| 543 | 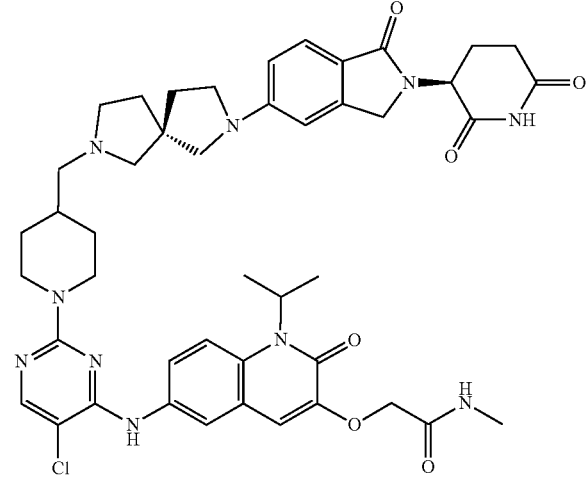 [SMILES: CNC(=O)COc1cc2cc(Nc3nc(N4CCC(CN5CC[C@@]6(CCN(c7ccc8c(c7)CN([C@H]7CCC(=O)NC7=O)C8=O)C6)C5)CC4)ncc3Cl)ccc2n(C(C)C)c1=O] | 2-[(6-{[5-chloro-2-(4-{[(5R)-7-{2-[(3S)-2,6-dioxopiperidin-3-yl]-1-oxo-2,3-dihydro-1H-isoindol-5-yl}-2,7-diazaspiro[4.4]nonan-2-yl]methyl}piperidin-1-yl)pyrimidin-4-yl]amino}-2-oxo-1-(propan-2-yl)-1,2-dihydroquinolin-3-yl)oxy]-N-methylacetamide |

TABLE 2

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 9 | 865.43 | 865.25 | 867.25 | $^1$H NMR (300 MHz, DMSO-$d_6$, ppm): δ10.91 (s, 1H), 8.78 (s, 1H), 8.02-7.93 (m, 3H), 7.69 (s, 2H), 7.46 (d, J = 8.4 Hz, 1H), 7.02 (s, 1H), 6.61 (s, 2H), 5.05-5.00 (m, 2H), 4.53-4.46(m, 5H), 4.46-4.14 (m, 3H), 3.10-2.83 (m, 10H), 1.98 (s, 4H), 1.88-1.78(m, 6H), 1.57 (d, J = 6.9 Hz, 7H), 1.23(s, 2H), 1.14-0.85 (m, 3H)) | | | |
| 49 | 1085.67 | 1085.81 | 1087.81 | $^1$H NMR (400 MHz, DMSO-$d_6$) δ 8.89 (s, 1H), 7.97-7.88 (m, 4H), 7.53 (d, J = 9.0 Hz, 1H), 7.35-7.14 (m, 1H), 7.04-6.89 (m, 2H), 6.23-6.12 (m, 1H), 4.47-4.09 (m, 6H), 3.99-3.97 (m, 3H), 3.77-3.76 (m, 3H), 3.68-3.65 (m, 4H), 3.60-3.58 (m, 3H), 3.54-3.41(m, 9H), 3.21-3.10 (m, 2H), 3.05 (s, 3H), 2.54 (s, 3H), 2.39-2.36 (m, 3H), 2.09-2.02 (m, 3H), 1.89-1.77 (m, 3H), 1.30-1.29 (m, 3H), 0.93-0.88 (m, 3H), 0.76-0.70 (m, 3H), 0.63-0.44 (m, 1H). | D | | |
| 50 | 1085.67 | 1085.81 | 1087.81 | $^1$H NMR (400 MHz, DMSO-$d_6$) δ 8.90 (s, 1H), 7.98 (s, 1H), 7.86 (s, 1H), 7.77-7.66 (m, 1H), 7.48-7.16 (m, 5H), 7.04-6.89 (m, 2H), 6.23-6.13 (m, 1H), 4.53 (s, 2H), 4.36-4.24 (m, 7H), 4.24-4.13 (m, 4H), 3.66 (s, 3H), 3.52-3.50 (m, 8H), 3.46-3.44 (m, 1H), 3.18-3.16 (m, 2H), 2.66 (s, 3H), 2.41 (s, 3H), 2.39-2.38 (m, 3H), 2.10-1.97 (m, 2H), 1.89-1.78 (m, 3H), 1.341.20 (m, 7H), 0.96-0.80 (m, 3H), 0.77-0.71 (m, 3H), 0.60-0.45 (m, 1H). | D | | |
| 51 | 1075.68 | 1075.82 | 1077.82 | $^1$H NMR (300 MHz, DMSO-$d_6$) δ 8.96 (s, 1H), 8.83 (s, 1H), 8.58 (s, 1H), 8.03 (s, 1H), 7.93 (m, 1H), 7.74 (m, 1H), 7.51-7.40 (m, 1H), 7.38 (s, 6H), 7.10 (s, 1H), 5.14 (s, 1H), 4.57 (s, 3H), 4.43 (s, 1H), 4.35 (s, 2H), 4.26 (s, 1H), 4.02 (s, 1H), 3.95 (s, 2H), 3.67 (s, 4H), 3.55 (m, 14H), 3.23 (s, 2H), 2.65 (m, 3H), 2.43 (s, 4H), 1.81 (s, 1H), 1.37 (s, 3H), 1.23 (s, 2H), 0.92 (s, 9H). | D | | |
| 52 | 861.31 | 861.62 | 863.62 | $^1$H NMR (400 MHz, DMSO-$d_6$) δ 11.07 (s, 1H), 8.83 (s, 1H), 8.03 (s, 1H), 7.94 (m, 2H), 7.80 (m, 1H), 7.73 (m, 1H), 7.50-7.40 (m, 2H), 7.33 (m, 1H), 7.09 (s, 1H), 5.12 (m, 1H), 4.58 (s, 2H), 4.32-4.26 (m, 2H), 4.04 (m, 2H), 3.82-3.75 (m, 2H), 3.67 (s, 3H), 3.60 (m, 2H), 3.59-3.49 (m, 8H), 3.25 (m, 1H), 2.89 (m, 1H), 2.69-2.56 (m, 4H), 2.59-2.51 (m, 1H), 2.09-1.99 (m, 1H), 1.84 (m, 2H), 1.39 (m, 1H), 1.24 (s, 1H). | C | | |
| 53 | 1041.62 | 1041.77 | 1043.77 | $^1$H NMR (400 MHz, CD$_3$OD) 8.83 (s, 1H), 7.92-7.89 (m, 2H), 7.78-7.76 (m, 1H), 7.46 (d, J = 8 Hz, 1H), 7.38 (d, J = 4 Hz, 1H), 7.30 (s, 1H), 7.14-6.99 (m, 2H), 6.98-6.17 (m, 1H), 4.89 (s, 1H), 4.53-4.51 (m, 3H), 4.45-4.43 (m, 1H), 4.39-4.12 (m, 2H), 3.93-3.83 (m, 2H), 3.81 (s, 2H), 3.72-3.59 (m, 8H), 3.34-3.28 (m, 2H), 2.87 (s, 3H), 2.46 (s, 3H), 2.43 (s, 1H), 2.38-2.36 (m, 4H), 2.36-233 (m, 1H), 2.23-2.07 (m, 2H), 2.06-2.04 (m, 2H), 1.66-1.63 (m, 2H), 1.05-1.01 (m, 3H), 0.88-0.82 (m, 3H). | D | | |
| 54 | 1129.73 | 1129.86 | 1131.86 | $^1$H NMR (400 MHz, CD$_3$OD) δ 8.85 (s, 1H), 7.92-7.89 (m, 2H), 7.80 (d, J = 8 Hz, 1H), 7.51 (d, J = 8 Hz, 1H), 7.41 (d, J = 8 Hz, 1H), 7.20 (s, 1H), 7.00-6.97 (m, 2H), 6.23-6.19 (m, 1H), 4.89-4.44 (m, 3H), 4.60-4.39 (m, 6H), 4.15-4.11 (m, 4H), 3.86-3.74 (m, 6H), 3.64-3.61 (m, 16H), 2.88 (s, 3H), 2.47 (s, 3H), 2.26-2.19 (m, 3H), 2.06-2.01 (m, 1H), 1.96-1.88 (m, 2H), 1.53-1.51 (m, 2H), 1 1.07-1.05 (m, 3H), 0.89-0.85 (m, 3H). | D | | |
| 55 | 1173.78 | 1173.88 | 1175.88 | $^1$H NMR (400 MHz, DMSO-$d_6$) δ 8.97 (s, 1H), 8.84 (s, 1H), 8.41-8.36 (m, 1H), 8.03 (s, 1H), 7.91 (s, 1H), 7.90 (s, 1H), 7.75-7.72 (m, 1H), 7.47-7.45 (d, J = 9.2 Hz, 1H), 7.35-7.22 (m, 1H), 7.10 (s, 1H), 7.03-6.96 (m, 3H), 6.22 (s, 1H), 5.05 (b, 1H), 4.57 (s, 2H), 4.50-4.01 (m, 8H), 3.81-3.62 (m, 9H), 3.58-3.35 (m, 16H), 3.31-3.25 (m, 3H), 2.66-2.65 (d, J = 4.4 Hz, 3H), 2.50-2.49 (d, J = | D | | |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 56 | 997.57 | 997.63 | 999.63 | 4.4 Hz, 3H), 2.31-2.12 (m, 4H), 1.85-1.77 (m, 2H), 1.47-1.44 (m, 2H), 0.97-0.92 (m, 3H), 0.80-0.75 (m, 3H). $^1$H NMR (400 MHz, DMSO-d$_6$) δ 8.99 (s, 1H), 8.09-8.00 (m, 4H), 7.59-7.57 (m, J = 8.8 Hz, 1H), 7.52-7.45 (d, J = 8.8 Hz, 1H), 7.37-7.34 (d, J = 8.8 Hz, 2H), 7.22 (s, 2H), 7.13-7.09 (m, 1H), 7.09-7.06 (m, 2H), 7.05-7.00 (m, 1H), 6.22 (s, 1H), 4.59 (s, 1H), 4.39-4.21 (m, 6H), 4.03 (s, 3H), 3.96-3.82 (m, 4H), 3.79-3.74 (m, 1H), 3.77-3.69 (m, 6H), 3.10 (s, 3H), 2.70-2.65 (m, 2H), 2.52-2.46 (m, 4H), 2.21 (s, 3H), 2.20-2.11(m, 2H), 2.10-2.00 (m, 1H), 2.00-1.82 (m, 4H), 1.57-1.45 (m, 3H), 1.35-1.20 (m, 3H), 1.02-0.90 (m, 3H), 0.90-0.74 (m, 3H). | D | | |
| 57 | 860.32 | 860.64 | 862.64 | $^1$H NMR (400 MHz, DMSO-d$_6$) δ 11.09 (s, 1H), 8.84 (s, 1H), 8.03 (s, 1H), 7.94 (m, 2H), 7.74 (m, 1H), 7.55 (m, 1H), 7.47 (m, 1H), 7.11 (m, 2H), 7.02 (m, 1H), 6.59 (m, 1H), 5.05 (m, 1H), 4.58 (s, 2H), 4.03 (m, 2H), 3.65 (m, 3H), 3.63-3.53 (m, 2H), 3.53 (m, 8H), 3.45 (m, 3H), 3.25 (m, 2H), 2.94-2.81 (m, 1H), 2.66 (m, 3H), 2.57 (m, 2H), 2.05-1.97 (m, 1H), 1.82 (m, 2H), 1.38 (m, 2H). | D | | |
| 58 | 1217.83 | 1217.92 | 1219.92 | $^1$H NMR (400 MHz, DMSO-d$_6$) δ 8.97 (s, 1H), 8.84 (s, 1H), 8.33 (m, 1H), 8.03-7.91 (m, 3H), 7.74 (m, 1H), 7.46 (d, J = 9.1 Hz, 1H), 7.35-7.27 (m, 1H), 7.10 (s, 1H), 7.00-6.98 (m, 2H), 6.24-6.17 (m, 1H), 5.12 (m, 1H), 4.57 (s, 2H), 4.42-4.34 (s, 2H), 4.29-4.18 (m, 2H), 4.17 (m, 2H), 4.05 (d, J = 13.0 Hz, 2H), 3.90-3.77 (m, 4H), 3.64 (s, 3H), 3.60-3.45 (m, 23H), 3.23(m, 2H), 2.66 (d, J = 4.7 Hz, 3H), 2.46 (s, 2H), 2.44 (d, J = 1.7 Hz, 1H), 2.29-2.21 (m, 2H), 2.20-2.13 (m, 1H), 2.03 (t, J = 10.9 Hz, 1H), 1.92 (m, 1H), 1.83 (m, 2H), 1.41-1.34 (m, 2H), 0.95 (m, 3H), 0.78 (m, 3H). | D | | |
| 59 | 891.38 | 891.68 | 893.68 | $^1$H NMR (400 MHz, DMSO-d$_6$) δ 11.00 (s, 1H), 8.86 (s, 1H), 8.05 (s, 1H), 7.97 (d, J = 4.0 Hz, 2H), 7.93 (s, 1H), 7.75 (d, J = 8.0 Hz, 1H), 7.62 (d, J = 8.0 Hz, 1H), 7.16-7.11 (m, 2H), 7.04 (m, 1H), 5.11-5.07 (m, 2H), 4.59 (s, 2H), 4.40-4.37 (m, 1H), 4.36-4.24 (m, 3H), 4.17-4.05 (m, 2H), 3.76 (s, 2H), 3.68 (s, 3H), 3.58-3.35 (m, 13H), 3.32-3.25 (m, 2H), 2.68-2.65 (m, 1H), 2.62 (s, 3H), 2.58-5.54 (m, 1H), 2.42-2.40 (m, 1H), 2.00-1.92 (m, 1H), 1.91-1.82 (m, 2H), 1.45-1.41 (m, 2H). | D | | |
| 60 | 905.36 | 905.66 | 907.66 | $^1$H NMR (400 MHz, DMSO-d$_6$) δ 11.12 (s, 1H), 8.85 (s, 1H), 8.04 (s, 1H), 7.98-7.92 (m, 2H), 7.83-7.74 (m, 2H), 7.49-7.44 (m, 2H), 7.35 (d, J = 8.0 Hz, 1H), 7.11 (s, 1H), 5.15-5.11 (m, 1H), 4.59 (s, 2H), 4.29 (s, 2H), 4.08-4.04 (m, 2H), 3.78 (s, 2H), 3.68-3.53 (m, 2H), 3.35-3.19 (m, 15H), 2.90 (s, 3H), 2.68-2.66 (m, 2H), 2.52, 2.07-2.01 (m, 2H), 1.87-1.81 (m, 2H), 1.57-1.42 (m, 2H). | D | | |
| 61 | 803.27 | 803.59 | 805.59 | $^1$H NMR (400 MHz, DMSO-d$_6$) δ 11.01 (s, 1H), 8.87 (s, 1H), 8.06 (s, 1H), 7.94-7.92 (m, 2H), 7.74 (d, J = 8.8 Hz, 1H), 7.62 (d, J = 8.8 Hz, 1H), 7.50 (d, J = 8.8 Hz, 1H), 7.17 (s, 1H), 7.11 (s, 1H), 7.10 (d, J = 8.8 Hz, 1H), 5.08-5.06 (m, 1H), 4.59 (s, 2H), 4.37-4.35 (m, 1H), 4.20-4.17 (m, 3H), 4.05 (b, 2H), 3.80 (s, 2H), 3.68 (s, 3H), 3.62-3.60 (m, 4H), 3.40-3.38 (m, 2H), 2.90-2.88 (m, 1H), 2.67 (s, 3H), 2.52-2.50 (m, 1H), 2.36-2.33 (m, 2H), 1.98-1.96 (m, 3H), 1.23-1.21 (m, 2H). | B | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 62 | 935.43 | 935.6 | 937.6 | $^1$H NMR (400 MHz, DMSO-d$_6$) δ 10.97 (s, 1H), 8.45 (s, 1H), 8.04-7.91 (m, 3H), 7.75-7.74 (d, J = 2.4 Hz, 1H), 7.62-7.60 (d, J = 8.4 Hz, 1H), 7.48-7.45 (d, J = 9.2 Hz, 1H), 7.10-7.03 (m, 3H), 5.06-5.01 (m, 1H), 4.57 (s, 2H), 4.39-4.22 (m, 4H), 4.17-4.15 (m, 2H), 2.96-2.93 (m, 1H), 2.67 (s, 3H), 3.58-3.57 (m, 17H), 3.28-3.25 (m, 2H), 2.01-1.95 (m, 1H), 1.85-1.82 (m, 2H), 1.39-1.37 (m, 2H), 2.51-2.50 (m, 1H). | D | A | B |
| 63 | 817.25 | 817.58 | 819.58 | $^1$H NMR (400 MHz, DMSO-d$_6$) δ 11.15 (s, 1H), 8.90 (s, 1H), 8.06-8.04 (m, 2H), 7.94 (s, 1H), 7.82-7.74 (m, 2H), 7.47-4.46 (m, 2H), 7.35-7.33 (m, 1H), 7.13-7.11 (m, 2H), 7.01 (s, 1H), 5.13-5.11 (m, 1H), 4.59 (s, 2H), 4.34 (s, 2H), 4.04 (b, 2H), 3.81 (s, 2H), 3.68 (s, 3H), 3.61-3.59 (m, 5H), 3.41-3.35 (m, 2H), 2.90-2.87 (m, 1H), 2.69 (s, 3H), 2.04 (b, 1H), 1.86 (b, 2H), 1.42 (b, 2H). | B | | |
| 64 | 949.41 | 949.69 | 951.69 | $^1$H NMR (300 MHz, DMSO-d$_6$) δ 11.06 (s, 1H), 8.89 (s, 1H), 8.04 (s, 1H), 7.97-7.95 (m, 2H), 7.83-7.72 (m, 2H), 7.48-7.33 (m, 3H), 7.10 (s, 1H), 5.15-5.11 (m, 1H), 4.58 (s, 2H), 4.30-4.27 (m, 2H), 4.08-4.03 (m, 2H), 3.78-3.75 (m, 2H), 3.75 (s, 3H), 3.58-3.57 (m, 17H), 3.28-3.25 (m, 2H), 2.96-2.93 (m, 1H), 2.67-2.66 (m, 5H), 2.06-2.01 (m, 1H), 1.85-1.83 (m, 2H), 1.40-1.37 (m, 2H). | D | | |
| 65 | 847.32 | 847.6485 | 849.6473 | $^1$H NMR (400 MHz, DMSO-d$_6$) δ 8.01 (s, 1H), 7.90 (m, 1H), 7.73 (m, 1H), 7.59 (m, 1H), 7.47 (m, 1H), 7.16-7.09 (m, 2H), 7.01 (m, 1H), 5.01 (m, 1H), 4.55 (s, 2H), 4.32 (m, 1H), 4.24 (m, 1H), 4.13-4.10 (m, 2H), 4.03 (m, 2H), 3.78-3.71 (m, 3H), 3.60-3.51 (m, 10H), 3.23 (m, 2H), 2.87 (m, 1H), 2.67 (s, 4H), 2.65-2.54 (m, 1H), 2.34 (m, 1H), 2.92-2.73 (m, 2H), 1.46-1.11 (m, 3H). | D | | |
| 66 | 904.38 | 904.47 | 906.47 | $^1$H NMR (400 MHz, DMSO-d$_6$) δ 11.10 (s, 1H), 8.86 (s, 1H), 8.06 (d, J = 14.6 Hz, 3H), 7.92 (d, J = 2.4 Hz, 1H), 7.75 (dd, J = 9.1, 2.4 Hz, 1H), 7.56 (t, J = 7.8 Hz, 1H), 7.48 (d, J = 9.1 Hz, 1H), 7.11 (d, J = 7.9 Hz, 2H), 7.03 (d, J = 7.1 Hz, 1H), 6.59 (t, J = 5.9 Hz, 1H), 5.05 (dd, J = 12.9, 5.4 Hz, 2H), 4.58 (s, 2H), 4.05 (d, J = 13.0 Hz, 2H), 3.68 (s, 4H), 3.60 (t, J = 5.2 Hz, 2H), 3.53 (d, J = 11.4 Hz, 17H), 3.25 (td, J = 14.8, 12.1, 3.9 Hz, 5H), 3.10 (s, 1H), 2.92-2.83 (m, 1H), 2.67 (d, J = 4.6 Hz, 3H), 2.61 (s, 1H), 2.06-1.98 (m, 1H), 1.84 (d, J = 12.1 Hz, 2H), 1.38 (d, J = 9.2 Hz, 2H). | D | | |
| 67 | 979.48 | 979.53 | 981.54 | $^1$H NMR (300 MHz, DMSO-d$_6$) δ 10.96 (s, 1H), 8.85 (d, J = 14.8 Hz, 2H), 7.91 (d, J = 2.4 Hz, 1H), 7.73 (dd, J = 9.1, 2.4 Hz, 1H), 7.61 (d, J = 8.4 Hz, 1H), 7.47 (d, J = 9.1 Hz, 1H), 7.15-7.10 (m, 2H), 7.03 (dd, J = 8.4, 2.2 Hz, 1H), 5.06 (dd, J = 13.3, 5.1 Hz, 1H), 4.56 (s, 2H), 4.37 (d, J = 17.2 Hz, 1H), 4.24 (d, J = 17.2 Hz, 1H), 4.15 (t, J = 4.6 Hz, 2H), 4.05 (d, J = 12.7 Hz, 2H), 3.74 (t, J = 4.6 Hz, 2H), 3.67 (s, 3H), 3.59-3.46 (m, 20H), 3.44 (s, 2H), 3.24 (t, J = 10.9 Hz, 2H), 2.95-2.82 (m, 1H), 2.66 (d, J = 4.6 Hz, 3H), 2.62-2.55 (m, 1H), 2.36 (dd, J = 13.3, 4.6 Hz, 1H), 2.05-1.91 (m, 1H), 1.83 (d, J = 12.7 Hz, 2H), 1.37 (d, J = 9.1 Hz, 2H). | D | | |
| 68 | 993.47 | 993.52 | 995.52 | $^1$H NMR (300 MHz, DMSO-d$_6$) δ 11.11 (s, 1H), 8.84 (s, 1H), 8.03 (s, 1H), 7.97-7.88 (m, 2H), 7.81 (d, J = 8.4 Hz, 1H), 7.77-7.70 (m, 1H), 7.50-7.41 (m, 2H), 7.35 (d, J = 8.3 Hz, 1H), 7.09 (s, 1H), 5.11 (dd, J = 12.7, 5.4 Hz, 1H), 4.57 (s, 2H), 4.28 (s, 2H), 4.04 (s, 2H), 3.76 (s, 2H), 3.67 (s, 3H), 3.60-3.50 (m, 5H), 3.49 (d, J = 7.4 Hz, 16H), 3.28 (s, 1H), 3.25 (s, 1H), 2.88 (s, 1H), 2.66 (d, J = 4.7 Hz, 3H), 2.61 (s, 1H), 2.02 (s, 1H), 1.83 (s, 2H), 1.38 (d, J = 10.9 Hz, 2H), 1.23 (s, 1H). | D | | |

TABLE 2-continued

Degradation and characterization of exemplary bifunctional compounds of the present disclosure

| Ex. # | Mol Weight | Mean Observed Mass One | Mean Observed Mass Two | NMR | EC₅₀ (nM)* | Dmax (%)** | IC₅₀ (nM)*** |
|---|---|---|---|---|---|---|---|
| 69 | 948.43 | 948.5 | 950.5 | ¹H NMR (400 MHz, DMSO-d₆) δ 11.07 (s, 1H), 8.04-7.91 (m, 3H), 7.75-7.73 (d, J = 9.2 Hz, 1H), 7.58-7.45 (m, 2H), 7.13-7.01 (m, 3H), 6.59 (s, 1H), 5.07-5.03 (m, 1H), 4.57 (s, 2H), 4.07-4.03 (m, 2H), 3.75 (s, 3H), 3.59-3.57 (m, 18H), 3.28-3.15 (m, 4H), 2.96-2.83 (m, 1H), 2.67-2.66 (m, 4H), 2.06-2.03 (m, 1H), 1.85-1.83 (m, 2H), 1.46-1.17 (m, 4H). | D | | |
| 70 | 1031.62 | 1031.57 | 1033.57 | ¹H NMR (400 MHz, DMSO-d₆) δ 8.96 (s, 1H), 8.84 (m, 1H), 8.64 (m, 1H), 8.03 (s, 1H), 7.90-7.89 (m, 2H), 7.74-7.72 (m, 1H), 77.47-7.38 (m, 6H), 7.10 (s, 1H), 5.16 (s, 1H), 4.57 (s, 3H), 4.68-4.15 (m, 4H), 4.03-3.95 (m, 4H), 3.60-3.57 (m, 14H), 1.91-1.87 (m, 3H), 1.30-1.29 (m, 2H), 0.92 (s, 9H). | D | | |
| 71 | 759.22 | 759.38 | 761.38 | ¹H NMR (400 MHz, DMSO-d₆) δ 10.98 (s, 1H), 8.87 (s, 1H), 8.15(s , 1H), 8.14-7.91 (m, 2H), 7.81-7.71 (m, 1H), 7.69-7.50 (m, 1H), 7.54-7.47 (m, 1H), 7.19 (s, 1H), 7.12-7.02 (m, 2H), 5.19-5.03(m, 1H), 4.59 (s, 1H), 4.45-4.38 (m, 3H), 435-4.18(m, 3H), 4.15-4.02 (m, 2H), 3.84 (s, 2H), 3.69 (s, 4H), 3.35-3.23(m, 2H), 3.00-2.88 (m, 1H), 2.71-2.61(m, 3H), 1.60-2.58(m, 1H), 2.18-1.82(m, 3H), 1.53-1.41(m, 2H). | C | | |
| 72 | 773.2 | 773.35 | 775.36 | ¹H NMR (400 MHz, DMSO-d₆) δ 11.13 (s, 1H), 8.878(s, 1H), 8.17-7.99 (m, 3H), 7.98-7.77 (m, 2H), 7.58-7.40 (d, 3H), 7.22 (s, 2H), 7.129 (s, 1H), 5.20-5.09-7.06 (m, 1H), 4.71-4.51 (m, 2H), 4.60 (s, 2H), 4.349 (s, 2H), 4.091 (s, 3H), 3.865 (s, 2H), 3.699 (s, 5H), 3.00-2.87 (m, 1H), 2.77-2.64 (m, 4H), 2.10-1.91 (m, 3H), 1.56-1.25(d, 3H). | C | | |
| 73 | 775.21 | 775.36 | 777.36 | ¹H NMR (400 MHz, DMSO-d₆) δ 11.11 (s, 1H), 9.70-9.59 (m, 1H), 8.58 (s, 1H), 8.11 (s, 1H), 7.85-7.81 (m, 1H), 7.46-7.43 (m, 1H), 7.34-7.32 (m, 1H), 7.23-7.22 (m, 2H), 7.12-7.10 (m, 1H), 6.65-6.60 (m, 1H), 5.13-5.09 (m, 1H), 4.77-4.71 (m, 1H), 4.35-4.29 (m, 2H), 3.97-3.72 (m, 4H), 3.53-3.43 (m, 1H), 3.44-3.41 (m, 1H), 3.34 (s , 2H), 3.19-2.99 (m, 2H), 2.93-2.84 (m, 3H), 2.62-2.61 (m, 1H), 2.57-2.50 (m, 4H), 2.21-2.19 (m, 1H), 2.07-1.95 (m, 4H), 1.86-1.84 (m, 1H). | D | | |
| 74 | 761.19 | 761.34 | 763.34 | ¹H NMR (400 MHz, DMSO-d₆) δ 11.11 (s, 1H), 10.17 (s, 1H), 9.68-9.57 (s, 1H), 8.52-8.46 (s, 1H), 8.12-8.09 (m, 1H), 7.83-7.81 (m, 1H), 7.44 (s, 1H), 7.34-7.32 (m, 1H), 7.16 9 (s, 1H), 7.13-7.10 (m, 1H), 6.88-6.86 (m, 1H), 6.56-6.52 (m, 1H), 5.13-5.09 (m, 1H), 4.35 (s, 2H), 3.85 (s, 4H), 3.34 (m, 3H) , 3.14-2.93 (m, 2H), 2.93-2.84 (m, 3H), 2.66-2.50 (m, 1H), 2.47-2.43 (m, 2H), 2.20-2.17 (m, 1H), 2.05-1.98 (m, 4H), 1.91-1.75 (m, 1H), 1.52-1.50 (m, 1H). | D | | |
| 75 | 816.27 | 816.54 | 818.54 | ¹H NMR (300 MHz, DMSO-d₆) δ 11.07 (s, 1H), 8.90 (s, 1H), 8.02 (s, 1H), 7.91 (s, 2H), 7.73 (d, J = 7.2 Hz, 1H), 7.57-7.44 (m, 2H), 7.14-7.09 (m, 2H), 7.00 (d, J = 7.2 Hz, 1H), 6.60 (s, 1H), 5.05-4.99 (m, 1H), 4.56 (s, 2H), 4.03-4.00 (m, 2H), 3.98 (s, 4H), 3.86-3.80 (m, 6H), 3.67-3.45 (m, 3H), 3.32-3.30 (m, 2H), 2.85-2.43 (m, 3H), 2.27 (s, 1H), 1.99-1.90 (m, 1H), 1.79-1.71 (m, 2H), 1.39-1.31 (m, 3H). | C | | |
| 76 | 789.2 | 789.47 | 791.47 | ¹H NMR (400 MHz, CD₃OD) δ 8.19 (s, 1H), 7.84-7.75 (m, 1H), 7.41 (s, 1H), 7.37-7.28 (m, 1H), 7.26-7.13 (m, 3H), 6.62 (s, 1H), 5.17-5.06 (m, 1H), 4.65-4.52 (m, 1H), 4.38-4.27 (m, 4H), 3.98-3.88 (m, 2H), 3.86-3.75 (m, 1H), 3.71-3.62 (m, 2H), 3.60-3.47 (m, 2H), 3.45 (s, 3H), 2.97-2.88 (m, 2H), 2.88-2.82 (m, 1H), 2.82-2.67 (m, 2H), 2.65-2.58 (m, 2H), 2.15-2.05 (m, 1H), 1.92-1.77 (m, 4H). | D | | |
| 77 | 769.26 | 769.52 | 771.52 | ¹H NMR (400 MHz, CD₃OD) δ 8.15 (s, 1H), 7.76 (d, J = 8.4 Hz, 1H), 7.47-7.48 (m, 1H), 7.34-7.36 (m, 1H), 7.24-7.27 (m, 1H), 7.17-7.19 (m, 2H), 6.60 | D | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| | | | | (s, 1H), 5.07-5.11 (m, 1H), 4.12-4.14 (m, 2H), 3.69-3.73 (s, 3H), 3.19-3.26 (m, 7H), 2.92-2.94 (m, 2H), 2.81-2.83 (m, 1H), 2.64-2.75 (m, 7H), 2.03-2.12 (m, 2H), 1.83-1.86 (m, 2H), 1.53-1.57 (m, 2H). | | | |
| 78 | 1119.73 | 1119.8 | 1121.8 | $^1$H NMR (400 MHz, CD$_3$OD) δ 8.56 (s, 1H), 7.95-7.92 (m, 2H), 7.84-7.82 (d, J = 8.4 Hz, 1H), 7.57-7.54 (d, J = 9.2 Hz, 1H), 7.46-7.41 (m, 4H), 7.26 (s, 1H), 4.89-4.31 (m, 7H), 4.15-4.12 (m, 2H), 4.03-4.01 (m, 2H), 3.85-3.84 (m, 5H), 3.77-3.75 (m, 19H), 3.28-3.25 (m, 2H), 2.88 (s, 3H), 2.38-2.16 (m, 2H), 1.91-1.90 (m, 2H), 1.53-1.51 (m, 2H), 1.30-1.11 (m, 1H), 1.02 (s, 9H). | B | | |
| 79 | 770.24 | 770.5 | 772.5 | $^1$H NMR (400 MHz, CD$_3$OD) δ 8.15 (s, 1H), 7.70-7.68 (m, 1H), 7.40 (s, 1H), 7.29-7.19 (m, 4H), 6.62 (s, 1H), 5.09-5.05 (m, 1H), 4.82-4.78 (m, 1H), 4.25-4.22 (m, 2H), 3.55-3.45 (m, 5H), 3.37 (s, 3H), 3.13-3.03 (m, 2H), 2.96-2.92 (m, 2H), 2.89-2.81 (m, 1H), 2.76-2.72 (m, 1H), 2.69-2.63 (m, 2H), 2.34-2.23 (m, 4H), 2.11-2.07 (m, 3H), 1.93-1.89 (m, 2H), 1.66-1.64 (m, 1H). | D | | |
| 80 | 772.22 | 772.5 | 774.5 | $^1$H NMR (300 MHz, DMSO-d$_6$) δ 11.05 (s, 1H), 8.84 (s, 1H), 8.05 (s, 1H), 7.98-7.90 (m, 2H), 7.76-7.73 (m, 1H), 7.61-7.58 (m, 1H), 7.48 (d, J = 9.1 Hz, 1H), 7.17 (d, J = 8.6 Hz, 1H), 7.11 (s, 1H), 7.04 (d, J = 7.0 Hz, 1H), 6.65 (t, J = 5.6 Hz, 1H), 5.06-5.02 (m, 1H), 4.58 (s, 2H), 4.03 (d, J = 13.2 Hz, 2H), 3.69-3.67 (m, 7H), 3.49-3.46 (m, 2H), 3.29-3.26 (m, 2H), 2.95-2.77 (m, 1H), 2.66-2.64 (m, 3H), 2.59-2.58 (m, 1H), 1.99-1.87 (m, 3H), 1.47-1.43 (m, 2H). | C | | |
| 81 | 992.48 | 992.68 | 994.68 | $^1$H NMR (400 MHz, DMSO-d$_6$) δ 11.10 (s, 1H), 8.84 (s, 1H), 8.04-7.92 (m, 3H), 7.72 (s, 1H), 7.52-7.41 (m, 2H), 7.13-7.03 (m, 3H), 6.70 (s, 1H), 5.10-5.07 (m, 1H), 4.75 (s, 2H), 4.10 (s, 2H), 3.68 (s, 2H), 3.43-3.35 (m, 27H), 2.97-2.95 (m, 1H), 2.67-2.66 (m, 6H), 2.20 (s, 1H), 1.80 (s, 2H), 1.40 (s, 2H). | D | | |
| 82 | 1163.78 | 1163.8 | 1165.81 | $^1$H NMR (300 MHz, DMSO-d$_6$) δ 8.99 (s, 1H), 8.84 (s, 1H), 8.70-8.40 (m, 1H), 8.05 (s, 1H), 7.95-8.00 (m, 2H), 7.80-7.70 (m, 1H), 7.52-7.30 (m, 6H), 7.12 (s, 1H), 5.17 (d, J = 3.6 Hz, 1H), 4.61-4.58 (m, 3H), 4.50-4.30 (m, 3H), 4.30-4.20 (m, 1H), 4.15-4.05 (m, 4H), 3.85 (m, 2H), 3.70-3.65 (m, 4H), 3.65-3.35 (m, 22H), 3.30-3.20(m, 2H) 2.80-2.60 (m, 3H), 2.45 (s, 3H), 2.14-2.01 (m, 1H), 1.99-1.75 (m, 3H), 1.60-1.30 (m, 2H), 0.95 (s, 9H). | C | | |
| 83 | 1207.84 | 1207.84 | 1209.84 | $^1$H NMR (400 MHz, DMSO-d$_6$) δ 8.97 (s, 1H), 8.85 (s, 1H), 8.58 (s, 1H), 8.04 (s, 1H), 7.937.90 (m, 2H), 7.79-7.74 (m, 1H), 7.50-7.40 (m, 1H), 7.48-7.30 (m, 5H), 7.10 (s, 1H), 5.14 (s, 1H), 4.28-4.20(m, 1H), 4.09-4.01 (m, 2H), 3.96 (s, 2H), 3.67 (s, 4H), 4.46(m, 1H), 4.61-4.57 (m, 3H), 4.57-4.55(m, 1H), 4.55-3.64-3.43 (m, 26H), 3.40-3.21(m, 3H), 2.66 (s, 3H), 2.43 (s, 3H), 2.10-2.00 (m, 1H), 1.95-1.81 (m, 3H), 2.41-1.30 (m, 2H), 0.93 (s, 9H). | C | | |
| 84 | 949.46 | 949.65 | 951.65 | $^1$H NMR (300 MHz, DMSO-d$_6$) δ 10.84 (s, 1H), 8.85 (s, 1H), 8.05 (s, 1H), 7.96 (m, 2H), 7.75 (m, 1H), 7.50 (m, 2H), 7.13 (d, J = 6.0 Hz, 2H), 7.03 (m, 1H), 4.59 (s, 4H), 4.14 (m, 2H), 4.04 (s, 2H), 3.76 (m, 6H), 3.68 (s, 6H), 3.54 (m, 9H), 3.30 (m, 3H), 2.62 (s, 6H), 1.90 (s, 3H), 1.87 (s, 3H), 1.83 (s, 2H). | B | | |
| 85 | 784.27 | 784.52 | 786.52 | $^1$H NMR(400 MHz, CD$_3$OD) δ 8.14 (s, 1H), 7.83 (d, J = 8.4 Hz, 1H), 7.29 (s, 1H), 7.20-7.25 (m, 2H), 7.15-7.19 (m, 2H), 5.06-5.13 (m, 1H), 5.00-5.15 (m, 1H), 4.06-4.18 (m, 1H), 3.38 (s, 3H), 3.20-3.26 (m, 2H), 2.89-2.96 (m, 3H), 2.80-2.87 (m, 5H), 2.60-2.79 (m, 8H), 2.07-2.16 (m, 1H), 1.75-1.97 (m, 3H), 1.65 (d, J = 7.2 Hz, 2H), 1.45-1.61 (m, 2H). | D | | |
| 86 | 987.57 | 987.67 | 989.67 | $^1$H NMR (400 MHz, DMSO-d$_6$) δ 8.94 (s, 1H), 8.81 (s, 1H), 8.55 (t, 1H), 8.00-7.88 (m, 3H), 7.64 (d, J = 8.8 Hz, 1H), 7.45-7.36 (m, 6H), 7.09 (s, 1H), 5.14 (s, 1H), 4.57-4.54 (m, 3H), 4.43-4.26 (m, 3H), 4.26-4.25 (m, 3H), 4.04-3.98 (m, 2H), | C | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 87 | 949.46 | 949.65 | 951.65 | 4H), 3.66-3.61 (m, 10H), 3.31-3.26 (m, 2H), 2.66 (s, 3H), 2.49 (s, 3H), 2.06-2.01 (m, 1H), 1.90-1.86 (m, 3H), 1.51-1.41 (m, 2H), 0.89 (s, 9H).<br>$^1$H NMR (300 MHz, DMSO-d$_6$) δ 8.85 (s, 1H), 8.05 (s, 1H), 7.96 (s, 2H), 7.94 (s, 1H), 7.78 (m, 1H), 7.48 (d, J = 9.0 Hz, 1H), 7.11-7.07 (m, 3H), 5.18-5.16 (m, 1H), 4.59 (s, 2H), 4.41 (s, 2H), 4.22-4.19 (m, 2H), 4.04 (s, 2H), 3.78 (s, 2H), 3.68-3.66 (m, 3H), 3.55-3.52 (m, 12H), 3.28-3.27 (m, 7H), 3.01-2.99 (m, 4H), 2.73-2.71 (m, 1H), 2.45-2.41 (m, 3H), 2.09-2.08 (m, 1H), 2.02-1.84 (m, 3H), 1.39-1.37 (m, 2H). | C | | |
| 88 | 967.47 | 967.65 | 969.65 | $^1$H NMR (300 MHz, DMSO-d$_6$) δ 10.95 (s, 1H), 8.83 (s, 1H), 8.06 (s, 1H), 7.92 (dd, J = 7.7, 3.7 Hz, 2H), 7.77 (dd, J = 9.1, 2.5 Hz, 1H), 7.60 (d, J = 8.4 Hz, 1H), 7.46 (d, J = 9.1 Hz, 1H), 7.22-7.13 (m, 2H), 7.10 (s, 1H), 7.03 (dd, J = 8.4, 2.3 Hz, 1H), 6.84-6.79 (m, 2H), 6.77-6.71 (m, 1H), 5.06 (dd, J = 13.3, 5.1 Hz, 1H), 4.65 (d, J = 12.9 Hz, 2H), 4.55 (s, 2H), 4.36 (d, J = 17.2 Hz, 1H), 4.24 (d, J = 17.2 Hz, 1H), 4.19-4.12 (m, 2H), 4.11-4.02 (m, 2H), 3.78-3.69 (m, 4H), 3.66 (s, 3H), 3.55-3.54 (m, 8H), 2.90 (t, J = 12.8 Hz, 3H), 2.75 (t, J = 11.9 Hz, 1H), 2.61 (d, J = 4.7 Hz, 4H), 2.40-2.29 (m, 1H), 2.04-1.91 (m, 1H), 1.80 (d, J = 12.6 Hz, 2H), 1.63-1.48 (m, 2H). | B | | |
| 89 | 937.45 | 937.63 | 939.63 | $^1$H NMR (400 MHz, DMSO-d$_6$) δ 10.95 (s, 1H), 8.83 (s, 1H), 8.06 (s, 1H), 7.92 (m, 2H), 7.77 (m, 1H), 7.60 (d, J = 8.4 Hz, 1H), 7.47 (d, J = 9.2 Hz, 1H), 7.18-7.08 (m, 4H), 7.03 (m, 1H), 6.82-6.51 (m, 2H), 5.06 (m, 1H), 4.63 (d, J = 12.9 Hz, 2H), 4.55 (s, 2H), 4.37 (d, J = 17.1 Hz, 1H), 4.25 (d, J = 7.2 Hz, 1H), 4.15 (m, 2H), 3.97 (t, J = 6.3 Hz, 2H), 3.79-3.72(m, 2H), 3.66(s, 3H), 3.59 (m, 2H), 3.53(m, 4H), 2.89 (t, J = 12.8 Hz, 3H), 2.70 (s, 1H), 2.61 (m, 4H), 2.00-1.85 (m, 3H), 1.77 (d, J = 12.7 Hz, 2H), 1.51 (t, J = 12.1 Hz, 2H), 1.24. | D | | |
| 90 | 981.5 | 981.66 | 983.66 | $^1$H NMR (300 MHz, DMSO-d$_6$) δ 10.94 (s, 1H), 8.81 (s, 1H), 8.05 (s, 1H), 7.91 (s, 2H), 7.78 (s, 1H), 7.59 (s, 1H), 7.45 (s, 1H), 7.11 (s, 4H), 7.02 (s, 1H), 6.95-6.79 (m, 2H), 5.06 (s, 1H), 4.65 (s, 2H), 4.54 (s, 2H), 4.29 (s, 2H), 4.12 (s, 2H), 3.99 (s, 2H), 3.72 (s, 2H), 3.65 (s, 3H), 3.58-3.45 (m, 11H), 3.03 (s, 1H), 2.93 (s, 3H), 2.60 (s, 4H), 1.97-1.87 (m, 3H), 1.72 (s, 2H), 1.60 (s, 2H). | D | | |
| 91 | 983.47 | 983.64 | 985.64 | $^1$H NMR (300 MHz, DMSO-d$_6$) δ 8.83 (s, 1H), 8.05 (s, 1H), 7.89 (s, 2H), 7.81-7.68 (m, 3H), 7.45 (s, 1H), 7.16-7.07 (m, 2H), 7.06-6.96 (m, 3H), 6.90 (s, 2H), 5.05 (s, 1H), 4.54 (s, 3H), 4.28 (s, 2H), 4.15-3.90 (m, 6H), 3.70 (s, 4H), 3.65 (s, 3H), 3.56 (s, 3H), 3.48 (s, 7H), 2.90 (s, 1H), 2.62 (s, 3H), 2.41 (s, 2H), 1.93 (s, 3H), 1.62 (s, 2H), 1.24 (s, 1H). | D | | |
| 92 | 755.23 | 755.49 | 757.49 | $^1$H NMR (400 MHz, CD$_3$OD) δ 8.14 (s, 1H), 7.76 (d, J = 8.4 Hz, 1H), 7.47-7.48 (m, 1H), 7.34-7.36 (m, 1H), 7.12-7.15 (m, 2H), 6.92 (d, J = 8.0 Hz, 1H), 6.53 (s, 1H), 5.07-5.11 (m, 1H), 4.12-4.17 (m, 2H), 3.65-3.72 (m, 2H), 3.19-3.26 (m, 7H), 2.98 (t, J = 7.6 Hz, 2H), 2.82-2.87 (m, 1H), 2.68-2.76 (m, 4H), 2.57-2.61 (m, 2H), 2.00-2.13 (m, 3H), 1.83-1.86 (m, 2H), 1.54-1.66 (m, 2H). | D | | |
| 93 | 981.5 | 981.66 | 983.67 | 1H NMR (400 MHz, DMSO-d$_6$) δ 10.98 (s, 1H), 8.97 (s, 1H), 8.12-7.86 (m, 2H), 7.79-7.57 (m, 3H), 7.52-7.43 (m, 2H), 7.39-7.29 (m, 2H), 7.15-7.02 (m, 4H), 5.19-5.11 (m, 1H), 4.57 (s, 1H), 3.66 (s, 3H), 3.55-3.43 (m, 16H), 3.31-3.20 (m, 3H), 2.99-2.85 (m, 4H), 2.70-2.58 (m, 3H), 2.36-2.26 (m, 1H), 2.05-1.97 (m, 1H), 1.91-1.75 (m, 3H), 1.50-1.16 (m, 2H). | D | | |
| 94 | 951.48 | 951.65 | 953.65 | 1H NMR (400 MHz, DMSO-d$_6$) δ 8.82 (s, 1H), 8.03 (s, 1H), 7.95-7.92 (m, 2H), 7.81 (s, 1H), 7.78-7.69 (m, 3H), 7.67-7.60 (m, 2H), 7.45 (d, J = 9.1 Hz, 1H), 7.09 (s, 1H), 7.05-6.90 (m, 3H), 5.17-5.08 (m, 1H), 4.56 (s, 2H), 4.48 (d, | D | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 95 | 967.47 | 967.64 | 969.64 | J = 17.2 Hz, 1H), 4.36 (d, J = 17.2 Hz, 1H), 4.10-3.90 (m, 4H), 3.76 (s, 1H), 3.66 (s, 3H), 3.60-3.45 (m, 10H), 3.45-3.40 (m, 2H), 2.99-2.86 (m, 1H), 2.70-2.64 (m, 4H), 2.10-2.00(m, 1H), 2.00-1.85(m, 2H), 1.80-1.75(m, 2H), 1.70-1.60(m, 2H), 1.45-1.35 (m, 2H). | D | | |
| 96 | 953.45 | 953.48 | 955.48 | $^1$H NMR (300 MHz, DMSO-d$_6$) δ 10.95 (brs, 1H), 8.87 (s, 1H), 8.07 (s, 1H), 8.00-7.85 (m, 2H), 7.85-7.75 (m, 1H), 7.62 (d, J = 8.3 Hz, 1H), 7.48 (d, J = 9.1 Hz, 1H), 7.20-7.00 (m, 4H), 6.60-6.45 (m, 3H), 5.13-5.02 (m, 1H), 4.70-4.50 (m, 3H), 4.50-4.15 (m, 4H), 4.15-3.85 (m, 4H), 3.85-3.75 (m, 2H), 3.75-3.68 (m, 3H), 3.65-3.60 (m, 2H), 3.60-3.40(m, 6H), 2.90-2.85 (m, 1H), 2.70-2.60 (m, 4H), 2.45-2.35 (m, 1H), 2.10-1.90 (m, 3H), 1.85-1.65 (m, 3H), 1.65-1.50 (m, 3H). | D | | |
| 97 | 967.47 | 967.5 | 969.5 | $^1$H NMR (400 MHz, DMSO-d$_6$) δ 8.86 (s, 1H), 8.05 (s, 1H), 7.98 (s, 1H), 7.89 (s, 1H), 7.78-7.72 (m, 1H), 7.60-7.55 (m, 1H), 7.51-7.46 (m, 1H), 7.17-7.09 (m, 2H), 7.09-7.02 (m, 1H), 6.92-6.81 (m, 3H), 5.04-4.98 (m, 1H), 4.56 (s, 2H), 4.51-4.48 (m, 1H), 4.45-4.25 (m, 3H), 4.19-4.14 (m, 2H), 4.10-4.01 (m, 2H), 3.98-3.81 (m, 2H), 3.81-3.74 (m, 2H), 3.66-3.62 (m, 3H), 3.60-3.55 (m, 3H), 3.54-3.49 (m, 4H), 3.43 (s, 3H), 2.62-2.41 (m, 5H), 1.95-1.85 (m, 4H), 1.61-1.42 (m, 2H). | C | | |
| 98 | 920.41 | 920.48 | 922.48 | $^1$H NMR (300 MHz, DMSO-d$_6$) 10.97 (s, 1H), 8.85 (s, 1H), 8.04 (s, 1H), 7.89 (s, 1H), 7.70 (d, J = 9 Hz, 2H), 7.62 (d, J = 6 Hz, 1H), 7.46 (d, J = 9 Hz, 1H), 7.10 (m, 2H), 5.08 (m, 1H), 4.91 (s, 2H), 4.29 (m, 2H), 4.07 (s, 2H), 4.03 (s, 2H), 3.76 (s, 2H), 3.67 (s, 3H), 3.54 (m, 17H), 3.28 (m, 2H), 2.92(s, 1H), 2.62 (s, 1H), 2.52 (s, 1H), 2.31 (m, 3H), 2.00 (s, 1H), 1.99 (s, 2H), 1.81 (s, 2H). | B | | |
| 99 | 949.46 | 949.51 | 951.51 | $^1$H NMR (300 MHz, DMSO-d$_6$) δ 10.97 (s, 1H), 8.83 (s, 1H), 8.05 (s, 2H), 7.96 (s, 1H), 7.72-7.70 (m, 1H), 7.62 (d, J = 6 Hz, 1H), 7.46 (d, J = 6 Hz, 1H), 7.08-7.07 (m, 2H), 5.09 (s, 1H), 4.99 (s, 2H), 4.41 (s, 2H), 4.36 (s, 2H), 4.17 (m, 2H), 3.76 (s, 3H), 3.67 (s, 3H), 3.42-3.40 (m, 16H), 3.24 (s, 3H), 3.04 (s, 3H), 2.92 (s, 4H), 2.62 (s, 1H), 2.46-2.43 (m, 1H), 2.00-1.93 (m, 1H), 1.85-1.83 (m, 2H), 1.45-1.42 (m, 2H). | D | | |
| 100 | 967.47 | 967.5 | 969.5 | $^1$H NMR (400 MHz, DMSO-d$_6$) δ 10.95 (s, 1H), 8.83 (s, 1H), 8.03 (s, 1H), 7.92 (m, 2H), 7.74 (d, J = 9.2 Hz, 1H), 7.60 (d, J = 8.3 Hz, 1H), 7.46 (d, J = 9.2 Hz, 1H), 7.22-7.13 (m, 2H), 7.10 (s, 1H), 7.06-6.00 (m, 1H), 6.93-6.84 (m, 2H), 6.78 (d, J = 7.0 Hz, 1H), 5.06 (m, 1H), 4.57 (s, 2H), 4.35 (d, J = 17.2 Hz, 1H), 4.29-4.19 (m, 3H), 4.09-4.02 (m, 4H), 3.76-3.68 (m, 2H), 3.66 (s, 3H), 3.60-3.50 (m, 10H), 3.25 (s, 2H), 3.01 (t, J = 6.9 Hz, 2H), 2.89 (s, 5H), 2.99(s, 1H), 2.66 (m, 10H), 1.82 (s, 2H). | D | | |
| 101 | 908.5 | 908.55 | 910.55 | $^1$H NMR (400 MHz, DMSO-d$_6$) δ 8.82 (s, 1H), 8.05-7.92 (m, 3H), 7.77 (dd, J = 9.1, 2.4 Hz, 1H), 7.50 (dd, J = 15.6, 8.8 Hz, 2H), 7.21-6.97 (m, 3H), 5.05 (dd, J = 13.3, 5.1 Hz, 1H), 4.53 (d, J = 37.2 Hz, 4H), 4.39-4.16 (m, 2H), 3.68 (s, 3H), 3.27 (t, J = 5.1 Hz, 6H), 2.97-2.77 (m, 3H), 2.67 (d, J = 4.6 Hz, 4H), | A | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 102 | 908.5 | 908.55 | 910.55 | 2.59 (d, J = 17.2 Hz, 1H), 2.48-2.29 (m, 5H), 2.15 (s, 3H), 2.10 (d, J = 7.1 Hz, 2H), 2.01-1.93 (m, 1H), 1.81 (d, J = 12.5 Hz, 2H), 1.72 (d, J = 12.0 Hz, 3H), 1.34 (dp, J = 38.0, 12.8 Hz, 5H), 0.98-0.81 (m, 2H). | A | | |
| 103 | 826.36 | 826.46 | | $^1$H NMR (300 MHz, DMSO-d$_6$) δ 10.94 (s, 1H), 8.83 (s, 1H), 8.02 (d, J = 20.3 Hz, 3H), 7.93 (d, J = 2.3 Hz, 1H), 7.50 (d, J = 6.8 Hz, 2H), 7.13 (s, 3H), 5.05 (d, J = 8.1 Hz, 1H), 4.58 (s, 4H), 4.33 (d, J = 16.9 Hz, 2H), 3.69 (s, 3H), 3.28 (d, J = 4.9 Hz, 6H), 2.88-2.80 (m, 4H), 2.67 (d, J = 4.6 Hz, 5H), 2.24 (d, J = 7.5 Hz, 4H), 2.16 (s, 5H), 1.97 (dd, J = 10.1, 4.5 Hz, 1H), 1.66 (dd, J = 29.8, 10.2 Hz, 5H), 1.50-1.42 (m, 7H). | B | | |
| 104 | 811.3 | 811.3333333 | 813.3333333 | $^1$H NMR (300 MHz, DMSO-d$_6$) δ 10.91 (s, 1H), 8.83 (s, 1H), 8.20 (s, 2H), 8.05 (s, 1H), 7.93 (s, 2H), 7.74 (s, 1H), 7.49 (s, 2H), 7.13 (s, 1H), 7.05 (s, 2H), 5.03 (s, 1H), 4.58 (s, 2H), 4.26 (s, 2H), 3.67 (s, 3H), 3.62 (s, 5H), 2.87 (s, 1H), 2.66 (s, 3H), 2.61 (s, 6H), 2.42 (s, 3H), 2.37 (s, 9H), 1.97 (s, 1H), 1.65 (s, 1H). | B | B | |
| 105 | 893.39 | 893.47 | 895.47 | $^1$H NMR (400 MHz, DMSO-d$_6$) δ 11.09 (s, 1H), 9.01 (s, 1H), 8.08 (m, 1H), 7.98-7.93 (m, 2H), 7.77-7.72 (m, 2H), 7.49-7.45 (m, 2H), 7.37-7.35 (m, 1H), 7.11 (m, 1H), 5.11-5.07 (m, 1H), 4.59 (s, 2H), 4.47-4.44 (m, 2H), 4.22-4.19 (m, 2H), 3.67 (s, 3H), 3.63-3.60 (m, 2H), 3.35-3.29 (m, 1H), 3.17-3.08 (m, 4H), 2.96-2.90 (m, 3H), 2.66-2.61 (m, 5H), 2.27-2.16 (m, 1H), 2.04-2.01 (m, 1H), 1.79-1.76 (m, 2H), 1.21-1.15 (m, 2H). | D | | |
| 106 | 824.25 | 824.38 | 826.38 | $^1$H NMR (400 MHz, CD$_3$OD) δ 8.11 (s, 1H), 7.68-7.66 (m, 1H), 7.23-7.22 (m, 1H), 7.18-7.16 (m, 2H), 7.10 (m, 1H), 7.06-7.03 (m, 1H), 6.59 (s, 1H), 5.12-5.07 (m, 1H), 4.55-4.50 (m, 2H), 4.46-4.36 (m, 2H), 4.20-4.18 (m, 2H), 3.86-3.84 (m, 2H), 3.68-3.67 (m, 2H), 3.64-3.61 (m, 3H), 3.60-3.59 (m, 12H), 3.51-3.47 (m, 1H), 3.36 (s, 3H), 3.12-3.08 (m, 2H), 2.95-2.85 (m, 3H), 2.79-2.71 (m, 3H), 2.65-2.62 (m, 2H), 2.50-2.41 (m, 1H), 2.17-2.12 (m, 1H), 1.96-1.93 (m, 2H). | B | | |
| 107 | 868.31 | 868.41 | 870.41 | $^1$H NMR (400 MHz, CD$_3$OD) δ 8.06 (s, 1H), 7.87-7.91 (m, 2H), 7.71-7.76 (m, 2H), 7.63 (d, J = 8.8 Hz, 1H), 7.26-7.33 (m, 3H), 5.03-5.07 (m, 1H), 4.50-4.65 (m, 4H), 4.20-4.32 (m, 2H), 3.85 (s, 3H), 3.20-3.30 (m, 1H), 3.05-3.15 (m, 1H), 2.84 (s, 3H), 2.65-2.80 (m, 2H), 2.00-2.22 (m, 5H), 1.60-1.80 (m, 3H). | B | | |
| 108 | 1184.81 | 1184.67 | 1186.67 | $^1$H NMR (400 MHz, CDCl$_3$) δ 8.79 (br, 1H), 8.02 (s, 1H), 7.84 (s, 1H), 7.66-7.68 (m, 2H), 7.43 (s, 1H), 7.31-7.34 (m, 2H), 7.16-7.16 (m, 1H), 7.04 (s, 1H), 6.92 (s, 1H), 4.94-4.97 (m, 1H), 4.65-4.68 (m, 2H), 4.52-4.56 (m, 4H), 4.19 (br, 2H), 3.92-3.94 (m, 2H), 3.79-3.83 (m, 5H), 3.04-3.07 (m, 3H), 2.77-2.87 (m, 6H), 2.62 (s, 3H), 2.07-2.21(m, 4H). | C | | |
| 109 | 967.47 | 967.5 | 969.5 | 1H NMR (400 MHz, CDCl$_3$) δ 8.78 (s, 1H), 8.16 (s, 1H), 7.99 (s, 1H), 7.75-7.52 (m, 4H), 7.48-7.31 (m, 7H), 6.99 (s, 1H), 5.12-5.05 (m, 1H), 4.75-4.70 (m, 2H), 4.63-4.58 (m, 5H), 4.10-3.90 (m, 3H), 3.88-3.78 (m, 5H), 3.70-3.55 (m, 14H), 3.35-3.15 (m, 3H), 2.95-2.85 (m, 3H), 2.56 (s, 3H), 2.43-2.40 (m, 1H), 2.25-2.10 (m, 3H), 2.00 (s, 1H), 1.85-1.72 (m, 3H), 1.52-1.48 (m, 3H), 1.04 (s, 9H). | D | | |
| | | | | 1H NMR (400 MHz, DMSO-d$_6$) δ 10.99 (s, 1H), 8.81 (s, 1H), 8.02 (s, 1H), 7.92-7.88 (m, 3H), 7.82-7.73 (m, 3H), 7.45-7.38 (m, 2H), 7.27 (m, 2H), 7.09 (s, 1H), 7.01-6.94 (m, 1H), 5.14 (m, 1H), 4.56-4.37 (m, 4H), 4.20-4.13 (m, 2H), 4.04 (m, 2H), 3.79-3.72 (m, 2H), 3.66 (s, 3H), 3.62-3.51 (m, 13H), 3.24 (m, 2H), 2.92 (m, 1H), 2.69-2.55 (m, 4H), 2.49-2.34 (m, 1H), 2.02 (m, 1H), 1.86-1.77 (m, 2H), 1.37 (m, 2H). | | | |

TABLE 2-continued

Degradation and characterization of exemplary bifunctional compounds of the present disclosure

| Ex. # | Mol Weight | Mean Observed Mass One | Mean Observed Mass Two | NMR | EC₅₀ (nM)* | Dmax (%)** | IC₅₀ (nM)*** |
|---|---|---|---|---|---|---|---|
| 110 | 983.47 | 983.5 | 985.5 | ¹H NMR (300 MHz, DMSO-d₆) δ 10.97 (s, 1H), 8.85 (s, 1H), 8.04 (s, 1H), 7.99-7.88 (m, 2H), 7.80-7.71 (m, 1H), 7.64 (d, J = 8.4 Hz, 1H), 7.47 (d, J = 9.1 Hz, 1H), 7.20 (s, 1H), 7.14-7.06 (m, 2H), 7.05-6.95(m, 2H), 6.94-6.85 (m, 2H), 5.10-5.03 (m, 5H), 4.58 (s, 2H), 4.45-4.27 (m, 6H), 4.12-4.05 (m, 4H), 3.75-3.63 (m, 5H), 3.61-3.45 (m, 9H), 3.38-3.26 (m, 2H), 2.70-2.63 (m, 3H), 2.42-2.24 (m, 3H), 2.05-1.90 (m, 1H), 1.88-1.74(m, 2H), 1.45-1.23 (m, 2H). | D | | |
| 111 | 981.5 | 981.52 | 983.53 | ¹H NMR (400 MHz, DMSO-d₆) δ 10.95 (s, 1H), 8.83 (s, 1H), 7.92 (s, 2H), 7.74 (s, 1H), 7.59 (s, 1H), 7.46 (s, 1H), 7.22-7.12 (m, 2H), 7.10 (s, 1H), 7.03 (s, 1H), 6.94 (s, 1H), 6.85 (s, 1H), 5.06 (s, 1H), 4.57 (s, 2H), 4.35 (s, 1H), 4.28-4.17 (m, 3H), 4.03 (s, 4H), 3.66 (s, 3H), 3.59-3.41 (m, 11H), 3.31-3.18 (m, 2H), 3.03 (s, 2H), 2.89 (s, 1H), 2.66 (s, 3H), 2.60 (s, 1H), 2.40-2.33 (m, 1H), 1.95 (s, 3H), 1.79 (s, 2H), 1.40-1.32 (m, 2H). | D | | |
| 112 | 838.28 | 838.39 | 840.39 | ¹H NMR (400 MHz, CD₃OD) δ 7.93 (s, 1H), 7.78 (s, 1H), 7.75 (m, 1H), 7.58-7.62 (m, 2H), 7.51 (m, J = 9.2 Hz, 1H), 7.11-7.19 (m, 3H), 4.92-5.00 (m, 1H), 4.68-4.72 (m, 1H), 4.40-4.50 (m, 4H), 4.10-4.20 (m, 2H), 3.72 (s, 3H), 2.88-3.05 (m, 2H), 2.70-2.80 (m, 4H), 2.50-2.68 (m, 4H), 1.90-2.15 (m, 2H), 1.75-1.90 (m, 1H), 1.45-1.70 (m, 4H), 1.10-1.15 (m, 1H). | B | | |
| 113 | 882.33 | 882.42 | 884.42 | ¹H NMR (400 MHz, CDCl₃) δ 8.46 (br, 1H), 7.99 (s, 1H), 7.83 (d, J = 2.0 Hz, 1H), 7.75 (s, 1H), 7.72 (s, 1H), 7.64-7.67 (m, 1H), 7.45 (s, 1H), 7.38-7.39 (m, 1H), 7.30-7.32 (m, 2H), 7.13-7.16 (m, 1H), 7.02 (s, 1H), 6.90 (s, 1H), 4.92-4.96 (m, 1H), 4.53-4.63 (m, 6H), 4.19 (t, J = 4.8 Hz, 2H), 3.94 (t, J = 4.8 Hz, 2H), 3.79-3.83 (m, 5H), 2.77-2.91 (m, 8H), 2.62-2.66 (m, 2H), 2.13-2.16 (m, 1H), 1.76-1.79 (m, 2H), 1.23-1.27 (m, 2H). | C | | |
| 114 | 1052.65 | 1052.57 | 1054.57 | ¹H NMR (400 MHz, CDCl₃) δ 8.97 (s, 1H), 7.80 (m, 2H), 7.60 (m, 2H), 7.39 (m, 7H), 7.10 (m, 1H), 6.96 (m, 1H), 5.10 (m, 1H), 4.73 (m, 1H), 4.69 (m, 1H), 4.60 (m, 2H), 4.57 (m, 1H), 4.53 (m, 3H), 4.00 (m, 3H), 3.88 (m, 2H), 3.82 (s, 3H), 3.76 (m, 1H), 3.64 (m, 1H), 3.28 (m, 2H), 3.16 (m, 1H), 2.88 (m, 3H), 2.55 (s, 3H), 2.38 (m, 1H), 2.20 (m, 3H), 2.02 (m, 1H), 1.86 (m, 3H), 1.49 (d, J = 6.4 Hz, 3H), 1.02 (s, 9H). | C | | |
| 115 | 1096.7 | 1096.6 | 1098.6 | ¹H NMR (400 MHz, CD₃OD) δ 8.90 (s, 1H), 8.51-8.48 (m, 1H), 8.07 (s, 1H), 7.92-7.85 (m, 2H), 7.75-7.52 (m, 1H), 7.65-7.58 (m, 2H), 7.42-7.32 (m, 5H), 5.02-4.95 (m, 1H), 4.68-4.50 (m, 6H), 4.43-4.30 (m, 3H), 4.02-3.75 (m, 8H), 3.72-3.58 (m, 5H), 3.20-3.10 (m, 1H), 2.85 (s, 3H), 2.45 (s, 3H), 2.23-1.92 (m, 5H), 1.80-1.65 (m, 3H), 1.55-1.40 (m, 3H), 0.99 (s, 9H). | B | | |
| 116 | 1140.76 | 1140.63 | 1142.63 | ¹H NMR (400 MHz, CDCl₃) δ 8.78 (s, 1H), 8.16 (s, 1H), 7.83 (s, 1H), 7.50-7.65 (m, 4H), 7.35-7.50 (m, 6H), 7.30-7.35 (m, 1H), 6.95 (m, 1H), 5.30-5.55 (m, 3H), 5.05-5.15 (m, 1H), 4.65-4.75 (m, 1H), 4.50-4.65 (m, 8H), 3.70-4.10 (m, 15H), 3.55-3.70 (m, 11H), 3.05-3.25 (m, 1H), 2.85-2.95 (m, 3H), 2.63 (s, 2H), 2.40-2.60 (m, 4H), 2.10-2.30 (m, 4H), 1.95-2.10 (m, 4H), 1.70-1.80 (m, 2H), 1.55-1.70 (m, 4H), 1.40-1.55 (m, 4H), 1.03 (s, 9H), 0.85-0.95 (m, 4H). | B | | |
| 117 | 1228.86 | 1228.69 | 1230.69 | ¹H NMR (400 MHz, CD₃OD) δ 8.92 (s, 1H), 8.55-8.50 (m, 1H), 8.07 (s, 1H), 7.92-7.85 (m, 2H), 7.75-7.72 (m, 1H), 7.65-7.58 (m, 2H), 7.42-7.32 (m, 4H), 7.31 (s, 1H), 5.02-4.95 (m, 2H), 4.70-4.67 (m, 1H), 4.62-4.50 (m, 5H), 4.43 (s, 1H), 4.32-4.25 (m, 2H), 4.15-3.95 (m, 2H), 3.90-3.85 (m, 6H), 3.72-3.70 (m, 1H), 3.69-3.52 (m, 17H), 3.17-3.09 (m, 1H), 2.85 (s, 3H), 2.45 (s, 3H), 2.23-1.92 (m, 4H), 1.80-1.72 (m, 2H), 1.70-1.65 (m, 1H), 1.55-1.40 (m, 3H), 1.03 (s, 9H). | B | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 118 | 953.45 | 953.49 | 955.49 | $^{1}$H NMR (300 MHz, DMSO-d$_6$) δ 10.97 (s, 1H), 8.85 (s, 1H), 7.99-7.90 (m, 2H), 7.74 (dd, J = 9.0, 2.4 Hz, 1H), 8.04 (s, 1H), 7.47 (d, J = 9.2 Hz, 1H), 7.24 (d, J = 8.5 Hz, 2H), 7.61 (d, J = 8.4 Hz, 1H), 7.10 (s, 1H), 7.05 (dd, J = 8.4 Hz, 2H), 6.93-6.86 (m, 2H), 7.16 (d, J = 2.2 Hz, 1H), 5.1 Hz, 1H), 4.58 (s, 2H), 4.46 (s, 2H), 4.31 (s, 1H), 4.19 (dd, J = 10.0, 5.6 Hz, 2H), 4.06 (t, J = 4.7 Hz, 4H), 3.82-3.56 (m, 12H), 3.26 (s, 2H), 2.99-2.80 (m, 1H), 2.65 (d, J = 4.6 Hz, 4H), 2.44-2.19 (m, 2H), 1.92 (d, J = 36.8 Hz, 3H), 1.45 (d, J = 9.8 Hz, 2H). | C | | |
| 119 | 941.49 | 941.52 | 943.52 | $^{1}$H NMR (400 MHz, DMSO-d$_6$) δ 10.97 (s, 1H), 8.79 (s, 1H), 8.01 (s, 1H), 7.95-7.86 (m, 2H), 7.73 (dd, J = 16.6, 8.8 Hz, 3H), 7.64 (d, J = 7.9 Hz, 1H), 7.51 (d, J = 7.7 Hz, 2H), 7.44 (d, J = 9.1 Hz, 1H), 7.33 (d, J = 7.8 Hz, 2H), 7.08 (s, 1H), 5.10 (dd, J = 13.3, 5.1 Hz, 1H), 4.58-4.31 (m, 4H), 4.00 (d, J = 12.9 Hz, 2H), 3.64 (s, 3H), 3.54-3.42 (m, 5H), 3.22 (s, 2H), 2.89 (ddd, J = 17.9, 13.2, 5.3 Hz, 2H), 2.63 (d, J = 4.6 Hz, 4H), 2.45-2.30 (m, 10H), 2.00 (d, J = 12.0 Hz, 1H), 1.80 (d, J = 12.6 Hz, 2H), 1.36 (d, J = 9.1 Hz, 2H), 1.21 (s, 1H). | B | C | A |
| 120 | 912.36 | 912.44 | 914.44 | $^{1}$H NMR (400 MHz, CD$_3$OD) δ 8.06 (s, 1H), 7.83 (m, 2H), 7.73 (m, 1H), 7.65 (d, J = 7.2 Hz, 1H), 7.58 (m, 1H), 7.28 (d, J = 9.6 Hz, 2H), 7.19 (d, J = 7.6 Hz, 1H), 5.07 (m, 1H), 4.57 (s, 2H), 4.53 (m, 2H), 4.28(m, 2H), 4.16 (m, 2H), 3.86 (m, 2H), 3.80 (s, 3H), 3.78 (m, 2H), 3.64 (m, 4H), 3.24 (m, 2H), 3.04 (m, 1H), 2.85 (m, 4H), 2.67 (m, 2H), 2.05 (m, 3H), 1.78 (m, 2H). | C | | |
| 121 | 1000.46 | 1000.51 | 1002.51 | $^{1}$H NMR (400 MHz, CDCl$_3$) δ 8.80 (s, 1H), 8.21 (s, 1H), 8.05 (s, 1H), 7.70 (m, 3H), 7.36 (m, 2H), 7.17 (m, 1H), 6.96 (s, 1H), 4.96 (m, 1H), 4.51 (m, 6H), 4.20 (s, 2H), 3.86 (s, 4H), 3.79 (s, 3H), 3.65 (m, 13H), 3.26 (m, 3H), 2.87 (m, 4H), 2.78 (m, 2H), 2.15 (m, 4H), 1.80 (m, 2H). | C | | |
| 122 | 1066.68 | 1066.59 | 1068.59 | $^{1}$H NMR (400 MHz, CDCl$_3$) δ 8.92 (br, 1H), 8.14 (s, 1H), 7.82 (m, 2H), 7.58 (m, 2H), 7.48 (m, 1H), 7.44 (m, 5H), 7.34 (m, 1H), 7.10 (m, 1H), 6.97 (s, 1H), 5.10 (m, 1H), 4.74 (m, 1H), 4.56 (m, 8H), 3.99 (m, 4H), 3.81 (m, 5H), 3.60 (m, 1H), 3.00 (m, 2H), 2.88 (s, 3H), 2.67 (m, 2H), 2.54 (s, 3H), 2.45 (m, 1H), 2.27 (m, 1H), 2.23 (m, 1H), 2.05 (m, 2H), 1.86 (m, 1H), 1.85 (m, 1H), 1.49 (m, 3H), 1.02 (s, 9H). | C | | |
| 123 | 1154.78 | 1154.65 | 1156.65 | $^{1}$H NMR (400 MHz, CDCl$_3$) δ 8.67 (s, 1H), 7.99 (s, 1H), 7.86 (s, 1H), 7.65-7.75 (m, 2H), 7.50 (s, 1H), 7.27-7.45 (m, 7H), 7.08 (s, 1H), 6.90 (s, 1H), 5.05-5.15 (m, 1H), 4.70-4.80 (m, 1H), 4.50-4.65 (m, 8H), 3.95-4.10 (m, 2H), 3.85-3.95 (m, 3H), 3.79 (s, 3H), 3.55-3.70 (m, 9H), 2.80-2.90 (m, 5H), 2.60-2.70 (m, 2H), 2.45-2.55 (m, 4H), 2.10-2.20 (m, 1H), 2.01 (s, 1H), 1.90-2.00 (m, 1H), 1.75-1.85 (m, 2H), 1.46 (d, J = 6.8 Hz, 3H), 1.20-1.32 (m, 3H), 1.04 (s, 9H). | C | | |
| 124 | 1242.89 | 1242.695 | 1244.7 | $^{1}$H NMR (400 MHz, CD$_3$OD) δ 8.98 (s, 1H), 8.60-8.57 (m, 1H), 8.07 (s, 1H), 7.87-7.62 (m, 5H), 7.48-7.32 (m, 5H), 5.05-4.99 (m, 1H), 4.72-4.68 (m, 1H), 4.65-4.45 (m, 6H), 4.32-4.20 (m, 2H), 4.15-3.95 (m, 2H), 3.90-3.85 (m, 6H), 3.80-3.52 (m, 17H), 3.15-3.05 (m, 2H), 2.90 (s, 3H), 2.70-2.65 (m, 2H), 2.50 (s, 3H), 2.27-2.20 (m, 1H), 2.10-1.95 (m, 3H), 1.85-1.80 (m, 2H), 1.70-1.66 (m, 1H), 1.55-1.48 (m, 3H), 1.05 (s, 9H). | C | | |
| 125 | 951.48 | 951.51 | 953.52 | $^{1}$H NMR (400 MHz, DMSO-d$_6$) δ 10.95 (s, 1H), 8.83 (s, 1H), 8.05 (s, 1H), 7.92-7.80 (m, 2H), 7.76-7.60 (m, 1H), 7.60-7.55 (m, 1H), 7.55-7.46 (m, 1H), 7.25-7.13 (m, 5H), 6.82-6.75 (m, 2H), 5.13-5.06 (m, 1H), 4.63-4.55 (m, 2H), 4.55-4.45 (m, 2H), 4.40-4.20 (m, 2H), 4.20-4.10 (m, 2H), 4.00-3.90 (m, 2H), | D | | |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 126 | 967.47 | 967.51 | 969.51 | 3.70-3.65 (m, 2H), 3.65-3.60 (m, 3H), 3.60-3.50 (m, 4H), 3.50-3.40 (m, 2H), 2.95-2.85 (m, 3H), 2.80-2.70 (m, 2H), 2.65-2.60 (m, 4H), 2.40-2.30 (m, 1H), 2.05-1.95 (m, 1H), 1.95-1.85 (m, 2H), 1.70-1.60 (m, 4H), 1.50-1.40 (m, 1H). | D | | |
| 127 | 946.5 | 946.53 | 948.53 | $^1$H NMR (400 MHz, DMSO-$d_6$) δ 8.83 (s, 1H), 7.92 (dd, J = 11.8, 3.7 Hz, 2H), 7.77-7.67 (m, 2H), 7.46 (d, J = 9.1 Hz, 1H), 7.31 (t, J = 7.9 Hz, 1H), 7.14 (d, J = 2.2 Hz, 1H), 7.12-7.03 (m, 3H), 6.99 (t, J = 2.0 Hz, 1H), 6.91 (dd, J = 7.9, 2.4 Hz, 1H), 6.04 (s, 1H), 5.08 (dd, J = 13.3, 5.1 Hz, 1H), 4.57 (s, 2H), 4.39 (d, J = 17.5 Hz, 1H), 4.27 (d, J = 17.5 Hz, 1H), 4.04 (d, J = 13.0 Hz, 2H), 3.66 (s, 3H), 3.63-3.43 (m, 7H), 3.48 (s, 7H), 2.90 (ddd, J = 18.1, 13.6, 5.4 Hz, 1H), 2.79 (t, J = 6.8 Hz, 2H), 2.66 (d, J = 4.7 Hz, 3H), 2.61 (s, 1H), 1.98 (d, J = 12.5 Hz, 1H), 1.83 (d, J = 12.6 Hz, 2H), 1.37 (dd, J = 11.9, 6.9 Hz, 2H), 1.23 (s, 1H). | B | C | A |
| 128 | 812.33 | 812.44 | 814.44 | $^1$H NMR (400 MHz, DMSO-$d_6$) δ 10.97 (s, 1H), 8.82 (s, 1H), 8.04 (s, 1H), 7.89 (s, 2H), 7.80-7.78 (d, J = 8.4 Hz, 1H), 7.69-7.67 (d, J = 7.6 Hz, 1H), 7.59 (s, 1H), 7.50-7.48 (d, J = 8.0 Hz, 2H), 7.43-7.41 (d, J = 8.0 Hz, 1H), 7.14 (s, 1H), 7.07-7.05 (d, J = 8.0 Hz, 2H), 6.75 (s, 2H), 5.31-5.04 (m, 1H), 4.80 (s, 1H), 4.59-4.24 (m, 6H), 3.89-3.72 (m, 2H), 3.61 (s, 1H), 2.96-2.71 (m, 5H), 2.66-2.62 (m, 4H), 2.46-2.31 (m, 4H), 2.03-1.76 (m, 8H), 1.72-1.69 (m, 4H), 1.58-1.24 (m, 4H). | A | C | A |
| 129 | 956.41 | 956.46 | 958.46 | $^1$H NMR (400 MHz, DMSO-$d_6$) δ 10.93 (s, 1H), 8.84 (s, 1H), 8.20 (s, 1H), 8.04 (s, 1H), 7.89 (d, J = 2.4 Hz, 1H), 7.7 (m, J = 9.0, 2.4 Hz, 1H), 7.54-7.48 (m, 2H), 7.04 (m, J = 7.3 Hz, 3H), 5.04 (m, J = 13.3, 5.1 Hz, 1H), 4.91 (s, 2H), 4.4-4.22 (d, J = 16.9 Hz, 2H), 4.04 (d, J = 13.7 Hz, 2H), 3.76 (s, 3H), 3.70 (t, J = 5.9 Hz, 2H), 3.59 (m, 1H), 3.26 (d, J = 10.1 Hz, 6H), 2.90 (m, J = 17.2, 13.6, 5.4 Hz, 1H), 1.84 (d, J = 12.1 Hz, 2H), 2.41-2.33 (m, 1H), 2.20 (s, 3H), 1.96 (d, J = 5.8 Hz, 1H), 1.84 (d, J = 12.1 Hz, 2H), 1.44-1.36 (m, 2H). | D | | |
| 130 | 926.39 | 926.45 | 928.45 | $^1$H NMR (400 MHz, CD$_3$OD) δ 8.08 (s, 1H), 7.61 (d, J = 9.2 Hz, 1H), 7.30 (s, 1H), 7.24 (s, 1H), 7.19 (d, J = 6.0 Hz, 1H), 5.08-5.12 (m, 1H), 4.59 (s, 2H), 4.55-4.58 (m, 2H), 4.30-4.40 (m, 2H), 4.15-4.20 (m, 2H), 3.86-3.90 (m, 2H), 3.85 (s, 3H), 3.80-3.84 (m, 2H), 3.58-3.68 (m, 8H), 3.26-3.30 (m, 2H), 3.08-3.18 (m, 1H), 2.82-2.92 (m, 4H), 2.65-2.80 (m, 2H), 2.10-2.22 (m, 3H), 1.68-1.82 (m, 3H). | D | | |
| 131 | 970.44 | 970.48 | 972.48 | $^1$H NMR (400 MHz, CD$_3$OD) δ 8.03 (s, 1H), 7.80 (s, 1H), 7.68-7.71 (m, 2H), 7.58-7.62 (m, 1H), 7.27 (d, J = 8.8 Hz, 2H), 7.20 (d, J = 8.0 Hz, 1H), 5.05-5.12 (m, 1H), 4.58 (s, 2H), 4.50-4.52 (m, 2H), 4.16-4.30 (m, 4H), 3.78-3.88 (m, 7H), 3.55-3.65 (m, 8H), 3.00-3.15 (m, 2H), 2.80-2.92 (m, 4H), 2.65-2.80 (m, 4H), 2.08-2.15 (m, 1H), 1.90-2.00 (m, 1H), 1.75-1.82 (m, 2H), 1.25-1.30 (m, 2H). | D | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 132 | 1014.49 | 1014.51 | 1016.51 | $^1$H NMR (400 MHz, CD$_3$OD) δ 8.05 (s, 1H), 7.80 (m, 2H), 7.71 (m, 2H), 7.67 (m, 1H), 7.28 (s, 1H), 7.26 (m, 1H), 7.19(m, 1H), 5.08 (m, 1H), 4.58 (s, 2H), 4.50 (m, 2H), 4.20 (m, 4H), 3.81 (m, 7H), 3.65 (m, 4H), 3.52 (m, 8H), 3.07 (m, 2H), 2.86 (m, 4H), 2.65 (m, 4H), 2.10 (m, 1H), 1.96 (m, 1H), 1.79 (m, 2H), 1.25 (m, 2H). | D | | |
| 133 | 1110.73 | 1110.61 | 1112.61 | $^1$H NMR (400 MHz, CD$_3$OD) δ 8.93 (s, 1H), 8.51 (d, J = 8 Hz, 1H), 8.03 (s, 1H), 7.80-7.92 (m, 2H), 7.61-7.73 (m, 3H), 7.31-7.42 (m, 5H), 4.95-5.00 (m, 1H), 4.52-4.69 (m, 6H), 4.43 (s, 1H), 4.23 (s, 1H), 3.89-3.99 (m, 4H), 3.81-3.95 (m, 4H), 3.58-3.75 (m, 5H), 3.03-3.13 (m, 2H), 2.86 (s, 3H), 2.68 (d, J = 4 Hz, 2H), 2.46 (s, 3H), 2.17-2.23 (m, 3H), 1.78 (d, J = 12 Hz, 2H), 1.65 (d, J = 8 Hz, 1H), 1.43-1.58 (m, 3H), 1.01 (s, 9H). | D | | |
| 134 | 983.47 | 983.5 | 985.5 | $^1$H NMR (400 MHz, DMSO-d$_6$) δ 8.82 (s, 1H), 8.03 (s, 1H), 7.92 (dd, J = 9.7, 3.7 Hz, 2H), 7.74 (dd, J = 9.1, 2.4 Hz, 1H), 7.64 (d, J = 8.4 Hz, 1H), 7.46 (d, J = 9.2 Hz, 2H), 7.26-7.16 (m, 2H), 7.16-7.08 (m, 2H), 7.04-6.95 (m, 2H), 6.95 (dd, J = 8.3, 2.3 Hz, 1H), 5.06 (dd, J = 13.3, 5.1 Hz, 1H), 4.57 (s, 2H), 4.35 (d, J = 17.4 Hz, 1H), 4.23 (d, J = 17.4 Hz, 1H), 4.05 (q, J = 8.0, 6.3 Hz, 4H), 3.66 (s, 3H), 3.55 (d, J = 5.9 Hz, 1H), 3.56-3.41 (m, 8H), 3.42 (d, J = 2.6 Hz, 1H), 2.89 (ddd, J = 18.1, 13.6, 5.4 Hz, 1H), 2.66 (d, J = 4.7 Hz, 3H), 2.60 (s, 0H), 1.96 (d, J = 13.7 Hz, 1H), 1.83 (d, J = 12.7 Hz, 2H), 1.37 (d, J = 9.1 Hz, 2H), 1.24 (s, 1H). | D | | |
| 135 | 953.45 | 953.49 | 955.49 | $^1$H NMR (400 MHz, DMSO-d$_6$) δ 8.82 (s, 1H), 8.02 (s, 1H), 7.92 (dd, J = 7.8, 3.6 Hz, 2H), 7.77-7.67 (m, 2H), 7.46 (d, J = 9.1 Hz, 1H), 7.40-7.32 (m, 2H), 7.15 (d, J = 2.2 Hz, 1H), 7.12-7.02 (m, 4H), 5.08 (dd, J = 13.3, 5.2 Hz, 1H), 4.57 (s, 2H), 4.47 (s, 2H), 4.39 (d, J = 17.5 Hz, 1H), 4.27 (d, J = 17.5 Hz, 1H), 4.04 (d, J = 13.3 Hz, 2H), 3.66 (s, 3H), 3.61-3.49 (m, 12H), 3.25 (t, J = 11.8 Hz, 2H), 2.90 (ddd, J = 17.2, 13.5, 5.4 Hz, 1H), 2.66 (d, J = 4.7 Hz, 3H), 2.64-2.54 (m, 1H), 2.42-2.27 (m, 1H), 2.03-1.94 (m, 0H), 1.83 (d, J = 12.6 Hz, 2H), 1.39 (s, 2H). | D | | |
| 136 | 981.5 | 981.525 | 983.53 | $^1$H NMR (400 MHz, DMSO-d$_6$) δ 10.94 (s, 1H), 8.82 (s, 1H), 8.04 (s, 1H), 7.98-7.91 (m, 2H), 7.78-7.71 (m, 1H), 7.59-7.56 (m, 1H), 7.46-7.42 (m, 1H), 7.38-7.33 (m, 1H), 7.26-7.22 (m, 1H), 7.11 (s, 2H), 7.01-6.96 (m, 1H), 6.91-6.81(m, 2H), 5.07-5.00 (m, 1H), 4.57-4.51 (m, 3H), 4.36-4.31 (m, 2H), 4.26-4.20 (m, 2H), 4.17-4.10 (m, 2H), 4.05-3.93 (m, 2H), 3.75-3.71 (m, 1H), 3.69-3.61 (m, 3H), 3.56-3.52 (m, 2H), 3.49-3.36 (m, 2H), 3.33-3.30 (m, 2H), 2.95-2.81 (m, 2H), 2.65 (s, 2H), 1.99-1.90 (m, 2H), 1.89-1.81 (m, 2H), 1.79-1.74 (m, 2H), 1.73-1.62 (m, 2H), 1.19-1.42 (m, 3H), 1.31-1.25 (m, 5H), 0.91-0.82(m, 1H). | D | | |
| 137 | 811.34 | 811.46 | 813.46 | 1H NMR (400 MHz, DMSO-d$_6$) δ 10.95 (s, 1H), 8.87 (s, 1H), 8.22 (s, 1H), 8.06 (s, 1H), 7.90 (d, 1H), 7.70 (dd, 1H), 7.53 (d, 1H), 7.47 (d, 1H), 7.07 (d, 3H), 5.05 (dd, 1H), 4.92 (s, 2H), 4.34 (d, 1H), 4.21 (d, 1H), 3.68 (s, 3H), 3.62 (s, 4H), 3.29(s, 5H), 2.98(S, 1H), 2.84 (S, 2H), 2.59 (d, 1H), 2.36 (dd, 10H), 2.21 (s, 3H), 1.97 (s, 1H), 1.67 (d, 2H). | B | C | A |
| 138 | 1008.62 | 1008.6 | 1010.6 | $^1$H NMR (400 MHz, DMSO-d$_6$) δ 8.21 (s, 1H), 7.97 (d, J = 8.5 Hz, 2H), 7.91-7.72 (m, 5H), 7.73-7.65 (m, 1H), 7.61-7.53 (m, 1H), 7.26 (d, J = 8.2 Hz, 1H), 5.12-5.08 (m, 1H), 4.63 (s, 2H), 4.59-4.3 (m, 4H), 3.91-3.61 (m, 3H), 3.69-3,5 (m, 5H), 3.31 (s, 1H), 3.13 (s, 6H), 2.96-2.83 (m, 1H), 2.89-2.55 (m, 8H), 2.49-2.14 (m, 10H), 2.05 (m, 1H), 2.04-1.91 (m, 3H) 1.9-1.72 (m, 2H). | B | C | A |

TABLE 2-continued

Degradation and characterization of exemplary bifunctional compounds of the present disclosure

| Ex. # | Mol Weight | Mean Observed Mass One | Mean Observed Mass Two | NMR | EC₅₀ (nM)* | Dmax (%)** | IC₅₀ (nM)*** |
|---|---|---|---|---|---|---|---|
| 139 | 773.24 | 773.39 | 775.39 | ¹H NMR (400 MHz, DMSO-d₆) δ 10.95 (s, 1H), 8.83 (s, 1H), 8.03 (s, 1H), 7.93 (t, J = 4.4 Hz, 2H), 7.73 (dd, J = 9.1, 2.4 Hz, 1H), 7.60 (d, J = 8.4 Hz, 1H), 7.46 (d, J = 9.1 Hz, 1H), 7.16 (d, J = 2.1 Hz, 1H), 7.10 (s, 1H), 7.04 (dd, J = 8.4, 2.2 Hz, 1H), 5.06 (dd, J = 13.3, 5.1 Hz, 1H), 4.57 (s, 2H), 4.37 (d, J = 17.2 Hz, 1H), 4.25 (d, J = 17.2 Hz, 1H), 4.14 (t, J = 6.3 Hz, 2H), 4.02 (d, J = 12.3 Hz, 2H), 3.67 (s, 3H), 3.62 (t, J = 6.1 Hz, 2H), 2.90 (ddd, J = 17.9, 13.6, 5.4 Hz, 1H), 2.65 (d, J = 4.7 Hz, 3H), 2.61 (s, 1H), 2.41-2.33 (m, 1H), 2.02-1.94 (m, 3H), 1.84 (s, 2H), 1.41 (d, J = 9.0 Hz, 0H), 1.24 (s, 1H). | C | | |
| 140 | 831.32 | 831.44 | 833.44 | ¹H NMR (400 MHz, DMSO-d₆) δ 8.64 (s, 1H), 7.84 (s, 1H), 7.73 (dd, J = 8.0, 3.7 Hz, 2H), 7.54 (t, J = 9.1, 2.5 Hz, 1H), 7.40 (d, J = 8.4 Hz, 1H), 7.26 (d, J = 9.1 Hz, 1H), 6.92 (dd, J = 13.5 Hz, 2H), 6.83 (dd, J = 8.4, 2.2 Hz, 1H), 4.86 (dd, J = 13.3, 5.1 Hz, 1H), 4.38 (s, 2H), 4.16 (d, J = 17.3 Hz, 1H), 4.05 (d, J = 17.3 Hz, 1H), 3.91 (t, J = 6.3 Hz, 2H), 3.81 (d, J = 12.9 Hz, 2H), 3.47 (s, 3H), 3.32 (q, J = 6.1 Hz, 2H), 3.26 (dd, J = 9.1, 6.2 Hz, 4H), 3.07 (s, 2H), 2.69 (d, J = 13.4 Hz, 1H), 2.46 (d, J = 4.7 Hz, 3H), 1.81-1.73 (m, 3H), 1.59 (s, 2H), 1.52 (t, J = 6.3 Hz, 2H), 1.17 (d, J = 8.8 Hz, 2H), 1.04 (s, 1H), -0.19 (s, 20H), -0.19 (d, J = 6.6 Hz, 1H). | D | | |
| 141 | 1011.59 | 1011.53 | 1013.53 | 1H NMR (400 MHz, DMSO-d₆) δ 8.96 (s, 1H), 8.82 (s, 1H), 8.42-8.21 (m, 1H), 8.03 (s, 1H), 7.94-7.88 (m, 2H), 7.74 (dd, J = 9.1, 2.4 Hz, 1H), 7.46 (d, J = 9.1 Hz, 1H), 7.28 (ddd, J = 38.0, 17.3, 7.8 Hz, 1H), 7.09 (s, 1H), 7.07-6.92 (m, 2H), 6.20 (d, J = 11.6 Hz, 1H), 5.10 (dd, J = 9.8, 3.7 Hz, 1H), 4.56 (s, 2H), 4.43 (dt, J = 30.0, 7.6 Hz, 1H), 4.35-4.23 (m, 3H), 4.12 (d, J = 6.0 Hz, 1H), 4.00 (s, 1H), 3.81-3.70 (m, 1H), 3.66 (d, J = 8.6 Hz, 5H), 3.54 (dd, J = 13.7, 8.9 Hz, 3H), 3.42 (d, J = 11.5 Hz, 1H), 3.27 (t, J = 7.6 Hz, 2H), 2.64 (d, J = 4.6 Hz, 3H), 2.44 (s, 3H), 2.42 (d, J = 1.3 Hz, 1H), 2.29-2.21 (m, 1H), 2.19 (d, J = 2.6 Hz, 2H), 2.12 (d, J = 4.4 Hz, 2H), 2.04-1.90 (m, 2H), 1.83 (s, 2H), 1.40 (d, J = 10.4 Hz, 2H), 0.95 (dd, J = 15.5, 6.7 Hz, 3H), 0.78 (dd, J = 16.6, 6.7 Hz, 3H), 0.61 (dd, J = 47.7, 6.7 Hz, 1H). | D | | |
| 142 | 787.27 | 787.4 | 789.41 | ¹H NMR (400 MHz, DMSO-d₆) δ 10.96 (s, 1H), 8.85 (s, 1H), 8.05 (s, 1H), 7.98-7.91 (m, 2H), 7.74 (dd, J = 9.1, 2.5 Hz, 1H), 7.61 (d, J = 8.4 Hz, 1H), 7.48 (d, J = 9.2 Hz, 1H), 7.15 (s, 1H), 7.11 (s, 1H), 7.08-7.01 (m, 1H), 6.54 (s, 1H), 5.07 (dd, J = 13.4, 5.2 Hz, 1H), 4.58 (s, 2H), 4.38 (d, J = 17.3 Hz, 1H), 4.25 (d, J = 17.3 Hz, 1H), 4.09 (t, J = 6.4 Hz, 2H), 3.68 (s, 3H), 3.52 (t, J = 6.3 Hz, 2H), 2.66 (m, 2H), 2.42 (d, J = 4.5 Hz, 3H), 1.99 (s, 1H), 1.24 (s, 1H), -0.10 (s, 7H). | D | | |
| 143 | 963.53 | 963.56 | 965.56 | ¹H NMR (400 MHz, DMSO-d₆) δ 10.98 (s, 1H), 8.83 (s, 1H), 8.04-7.94 (m, 3H), 7.77-7.67 (m, 3H), 7.56-7.47 (m, 2H), 7.10 (s, 1H), 5.15-5.05 (m, 1H), 4.57 (s, 2H), 4.50-4.33(m, 4H), 4.12-4.02 (m, 2H), 3.67 (s, 3H), 3.61-3.41 (m, 5H), 2.98-2.84 (m, 3H), 2.82-2.70 (m, 2H), 2.69-2.60 (m, 3H), 2.59-2.56 (m, 1H), 2.48-2.32 (m, 3H), 2.30-2.13 (m, 3H), 2.09-1.79 (m, 7H), 1.68-1.61 (m, 2H), 1.54-1.29 (m, 7H). | B | | |
| 144 | 1069.67 | 1069.59 | 1071.59 | ¹H NMR (300 MHz, CD₃OD) δ 8.80 (s, 1H), 7.92-7.89 (m, 2H), 7.78-7.77 (d, J = 2.4 Hz, 1H), 7.53-7.50 (d, J = 9 Hz, 1H), 7.40-7.21 (m, 2H), 6.97-6.96 (m, 2H), 6.20-6.16 (m, 1H), 4.56-4.39 (m, 6H), 4.14-4.12 (m, 4H), 3.80-3.73 (m, 4H), 3.67-3.64 (m, 3H), 3.57-3.53 (m, 6H), 3.31-3.30 (m, 2H), 2.85 (s, 3H), 2.45-2.43 (m, 4H), 2.23-2.06 (m, 7H), 1.82-1.78 (m, 4H), 1.46-1.42 (m, 2H), 1.05-0.99 (m, 3H), 0.88-0.82 (m, 3H). | D | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 145 | 919.43 | 919.5 | 921.5 | $^1$H NMR (400 MHz, DMSO-d$_6$) δ 10.95 (br, 1H), 8.82 (br, 1H), 8.03 (br, 1H), 7.92-7.91 (m, 2H), 7.75-7.72 (m, 1H), 7.61-7.59 (d, J = 8.4 Hz, 1H), 7.47-7.45 (d, J = 9.2 Hz, 1H), 7.13-7.10 (d, J = 11.6 Hz, 2H), 7.03-7.01 (d, J = 8.4 Hz, 1H), 5.08-5.06 (m, 1H), 4.57 (s, 2H), 4.34-4.27 (m, 2H), 4.10-4.06 (m, 4H), 3.67 (s, 3H), 3.56-3.47 (m, 9H), 3.44-3.39 (m, 6H), 3.28-2.27 (m, 2H), 2.93-2.87 (m, 1H), 2.67-2.66 (d, J = 4.8 Hz, 3H), 2.60-2.56 (m, 1H), 2.38-2.35 (m, 1H), 1.95-1.92 (m, 3H), 1.85-1.82 (m, 2H), 1.71-1.68 (m, 2H), 1.40-1.39 (m, 2H). | C | | |
| 146 | 861.35 | 861.31 | 863.31 | $^1$H NMR (400 MHz, DMSO-d$_6$) δ 10.93 (s, 1H), 8.81 (s, 1H), 8.03 (s, 1H), 7.93-7.82 (m, 2H), 7.73-7.63 (m, 1H), 7.59-7.50 (m, 1H), 7.46-7.41 (m, 1H), 7.11-7.02 (m, 2H), 7.01-6.92 (m, 1H), 5.05-4.99 (m, 1H), 4.57 (s, 2H), 4.45-4.29 (m, 1H), 4.24-4.12 (m, 1H), 4.13-4.00 (m, 4H), 3.66 (s, 3H), 3.59-3.49 (m, 11H), 2.95-2.82 (m, 2H), 2.79-2.66 (m, 3H), 2.60-2.59(m, 1H), 2.58-2.29 (m, 2H), 2.08-1.96 (m, 3H), 1.89-1.72 (m, 2H), 1.46-1.38 (s, 2H). | D | | |
| 147 | 875.38 | 875.33 | 877.33 | $^1$H NMR (400 MHz, DMSO-d$_6$) δ 10.95 (br, 1H), 8.82 (br, 1H), 8.03 (br, 1H), 7.92-7.91 (m, 2H), 7.75-7.72 (m, 1H), 7.60-7.58 (d, J = 8.4 Hz, 1H), 7.47-7.45 (d, J = 9.2 Hz, 1H), 7.13-7.10 (m, 2H), 7.02-7.00 (m , 1H), 5.09-5.05 (m, 1H), 4.57 (s, 2H), 4.38-4.22 (m, 2H), 4.10-4.07 (m, 4H), 3.67 (s, 3H), 3.55-3.41 (m, 12H), 3.27-3.22 (m, 1H), 2.94-2.87 (m, 1H), 2.67-2.65 (m, 3H), 2.60-2.56 (m, 1H), 2.39-2.35 (m, 1H), 1.96-1.93 (m, 3H), 1.83-1.81 (m, 2H), 1.72-1.69 (m, 2H), 1.40-1.38 (m, 2H). | D | | |
| 148 | 796.28 | 796.28 | 798.28 | $^1$H NMR (300 MHz, DMSO-d$_6$) δ 11.05 (s, 1H), 8.84 (s, 1H), 8.04 (s, 1H), 7.88 (d, 1H), 7.75(m, 1H), 7.45 (d, 1H), 7.30 (s, 1H), 7.22 (d, 1H), 7.05 (s, 1H), 5.05 (dd, 1H), 4.90 (s, 2H), 4.04 (d, 2H), 3.66 (d, 7H), 2.91 (dt, 3H), 2.58 (d, 2H), 2.38 (s, 4H), 2.19 (s, 5H), 2.01 (d, 1H), 1.81 (d, 3H), 1.16 (d, 2H). | B | B | A |
| 149 | 799.33 | 799.33 | 801.33 | $^1$H NMR (400 MHz, DMSO-d$_6$) δ 11.07 (s, 1H), 8.65 (s, 1H), 7.99 (s, 1H), 7.67-7.66 (m, 1H), 7.43 (s, 1H), 7.33 (m, 1H), 7.28-7.23 (m, 2H), 7.10-7.08 (m, 1H), 5.09-5.04 (m, 1H), 4.49-4.42 (m, 3H), 3.88-3.84 (m, 2H), 3.42 (s, 3H), 3.32 (m, 4H), 2.84-2.78 (m, 3H), 2.60-2.50 (m, 2H), 2.49-2.47 (m, 3H), 2.16 (m, 1H), 2.02-2.00 (m, 1H), 1.75-1.68 (m, 5H), 1.16 (s, 6H), 1.03-1.00 (m, 2H). | D | | D |
| 150 | 724.22 | 724.26 | 726.26 | $^1$H NMR (400 MHz, DMSO-d$_6$) δ 11.08 (s, 1H), 8.87 (s, 1H), 8.04 (m, 2H), 7.89-7.87 (m, 1H), 7.81-7.79 (m, 1H), 7.69-7.67 (m, 1H), 7.52-7.50 (m, 1H), 7.34-7.26 (m, 3H), 6.63-6.61 (m, 1H), 5.09-5.05 (m, 1H), 4.50-4.47 (m, 2H), 3.61(s, 3H), 3.42 (m, 3H), 2.92-2.83 (m, 3H), 2.66-2.53 (m, 2H), 2.49 (s, 7H), 2.18 (m, 1H), 2.03-2.00 (m, 1H), 1.85-1.74 (m, 2H), 1.06-1.05 (m, 2H). | D | B | D |
| 151 | 797.31 | 797.31 | 799.31 | $^1$H NMR (400 MHz, DMSO-d$_6$) δ 10.92 (s, 1H), 8.79 (s, 1H), 8.03 (s, 1H), 7.98-7.90 (m, 2H), 7.77-7.72 (m, 1H), 7.51-7.42 (m, 2H), 7.11 (s, 1H), 7.08-7.00 (m, 2H), 5.10-5.02 (m, 1H), 4.57 (s, 3H), 4.49-4.42 (m, 2H), 4.35-4.31(m, 1H), 4.24-4.16 (m, 1H), 3.67 (s, 4H), 2.96-2.81 (m, 4H), 2.66 (s, 6H), 2.43-2.32 (m, 1H), 2.19 (s, 2H), 2.01-1.92 (m, 1H), 1.83-1.77 (m, 4H), 1.27 (s, 1H), 1.12-0.98 (m, 2H). | B | B | A |
| 152 | 796.28 | 796.28 | 798.28 | $^1$H NMR (400 MHz, DMSO-d$_6$) δ 10.95 (s, 1H), 8.83 (s, 1H), 8.05 (s, 1H), 7.92 (s, 1H), 7.80-7.60 (m, 2H), 7.50-7.40 (m, 1H), 7.40-7.30 (m, 1H), 7.30-7.20 (m, 1H), 7.10-7.00 (m, 1H), 5.10-5.00 (m, 1H), 5.00-4.85 (m, 2H), 4.60-4.40 (m, 2H), 3.75-3.60 (m, 3H), 3.50-3.35 (m, 4H), 2.95-2.80 (m, 3H), 2.70-2.55 (m, 2H), 2.50-2.40 (m, 4H), 2.30-2.20 (m, 4H), 2.10-1.90 (m, 1H), 1.90-1.70 (m, 3H), 1.30-1.20 (m, 1H), 1.10-1.00 (m, 2H). | B | B | C |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 153 | 810.27 | 810.26 | 812.26 | $^1$H NMR (400 MHz, DMSO-d$_6$) δ 8.86 (s, 1H), 8.06 (s, 1H), 7.88 (s, 1H), 7.75-7.67 (m, 2H), 7.46 (s, 1H), 7.37 (s, 1H), 7.27 (s, 1H), 7.05 (s, 1H), 5.09 (s, 1H), 4.90 (s, 2H), 4.50 (s, 2H), 3.75 (s, 2H), 3.64 (s, 5H), 3.47 (s, 4H), 2.99-2.91 (m, 4H), 2.58 (s, 1H), 2.18 (s, 3H), 2.03 (s, 1H), 1.69 (s, 2H), 1.51 (s, 2H), 0.99 (s, 1H). | A | A | C |
| 154 | 797.27 | 797.27 | 799.27 | $^1$H NMR (400 MHz, DMSO-d$_6$) δ 11.08 (br, 1H), 8.72 (br, 1H), 8.04-8.02 (m, 2H), 7.87-7.81 (m, 2H), 7.45-7.35 (m, 3H), 7.08 (s, 1H), 5.13-5.09 (m, 1H), 4.89 (s, 2H), 4.70-4.69 (m, 1H), 3.66-3.60 (m, 4H), 3.55-3.50 (m, 1H), 3.41-3.38 (m, 1H), 3.13-3.11 (m, 1H), 2.89-2.86 (m, 1H), 2.72-2.67 (m, 2H), 2.62-2.58 (m, 2H), 2.49-2.43 (m, 1H), 2.36-2.29 (m, 4H), 2.21 (s, 3H), 2.07-1.96 (m, 4H), 1.67-1.62 (m, 3H). | B | C | C |
| 155 | 809.33 | 809.32 | 811.32 | $^1$H NMR (400 MHz, DMSO-d$_6$) δ 11.10 (s, 1H), 9.05-8.96 (m, 1H), 8.09 (s, 1H), 7.94-7.88 (m, 1H), 7.84-7.70 (m, 3H), 7.61 (s, 1H), 7.52-7.43 (m, 2H), 7.40-7.30 (m, 1H), 5.15-5.03 (m, 1H), 4.53-4.42 (m, 2H), 4.27-4.12 (m, 2H), 3.71-3.50 (m, 5H), 3.40-3.36 (m, 2H), 3.24-3.01 (m, 4H), 3.00-3.82 (m, 3H), 3.82-2.68 (m, 2H), 2.65-2.47 (m, 4H), 2.43-2.28 (m, 3H), 2.20-2.10 (m, 1H), 2.08-1.98 (m, 1H), 1.84-1.72 (m, 2H), 1.22-1.05 (m, 2H). | D | | D |
| 156 | 859.39 | 859.34 | 861.34 | $^1$H NMR (400 MHz, DMSO-d$_6$) δ 11.09 (s, 1H), 9.39 (s, 1H), 8.92 (s, 1H), 8.82-8.81 (m, 2H), 8.39 (s, 1H), 8.08 (s, 1H), 7.77-7.75 (m, 2H), 7.48 (m, 1H), 7.41-7.34 (m, 3H), 6.78 (s, 1H), 5.11-5.07 (m, 1H), 4.71 (s, 1H), 4.57-4.46 (m, 2H), 4.28-4.18 (m, 2H), 3.59-3.56 (m, 2H), 3.40 (s, 3H), 3.33-3.27 (m, 2H), 3.14-3.06 (m, 4H), 2.91-2.85 (m, 2H), 2.66-2.61 (m, 1H), 2.38-2.32 (m, 1H), 2.10-2.01 (m, 2H), 1.77 (m, 7H), 1.17-1.10 (m, 2H). | D | | D |
| 157 | 826.35 | 826.33 | 828.33 | $^1$H NMR (400 MHz, DMSO-d$_6$) δ 10.96 (s, 1H), 8.83 (s, 1H), 8.04 (s, 1H), 7.91 (s, 1H), 7.71 (s, 1H), 7.61 (s, 1H), 7.46 (s, 1H), 7.16 (s, 1H), 7.08-7.02 (m, 2H), 5.07 (s, 1H), 4.91 (s, 2H), 4.38 (s, 1H), 4.27 (s, 3H), 4.12 (s, 2H), 3.67 (s, 4H), 3.17-2.82 (m, 5H), 2.82-2.58 (m, 6H), 2.21 (s, 6H), 2.00 (s, 1H), 1.83 (s, 3H), 1.61 (s, 1H), 1.31 (s, 3H). | B | B | A |
| 158 | 812.33 | 812.31 | 814.31 | $^1$H NMR (400 MHz, DMSO-d$_6$) δ 10.94 (s, 1H), 8.83 (s, 1H), 8.03 (s, 1H), 7.87 (d, J = 13.4 Hz, 1H), 7.70 (d, J = 9.3 Hz, 1H), 7.60 (d, J = 8.4 Hz, 1H), 7.44 (d, J = 9.0 Hz, 1H), 7.12 (d, J = 12.9 Hz, 1H), 7.03 (d, J = 12.1 Hz, 2H), 5.06 (m, 1H), 4.90 (s, 1H), 4.37-4.25 (m, 2H), 4.08 (t, J = 6.3 Hz, 2H), 3.82-3.55 (m, 8H), 2.90-2.75 (m, 3H), 2.58 (d, J = 16.4 Hz, 3H), 2.44-2.34 (m, 8H), 2.19 (s, 3H), 2.09-1.88 (m, 4H), 1.64 (d, J = 11.4 Hz, 1H). | B | C | A |
| 159 | 1025.62 | 1025.39 | 1027.39 | $^1$H NMR (400 MHz, CD$_3$OD) δ 8.81 (s, 1H), 7.95 (q, J = 2.7 Hz, 2H), 7.81 (d, J = 9.2 Hz, 1H), 7.55 (d, J = 9.1 Hz, 1H), 7.41 (d, J = 8.2 Hz, 1H), 7.32 (t, J = 8.1 Hz, 1H), 7.28-7.21 (m, 1H), 6.99 (s, 2H), 6.18 (d, J = 8.5 Hz, 1H), 4.65-4.51 (m, 3H), 4.54-4.41 (m, 2H), 4.41-4.32 (m, 1H), 4.12 (dd, J = 12.9, 6.5 Hz, 4H), 3.92-3.83 (m, 1H), 3.84 (s, 4H), 3.78-3.63 (m, 1H), 3.63 (d, J = 4.0 Hz, 1H), 3.61 (s, 4H), 2.87 (s, 3H), 2.47 (s, 3H), 2.46 (d, J = 1.6 Hz, 1H), 2.26-2.15 (m, 4H), 1.98-1.90 (m, 1H), 1.82 (d, J = 7.2 Hz, 2H), 1.50 (d, J = 10.5 Hz, 2H), 1.33 (d, J = 16.9 Hz, 5H), 1.03 (dd, J = 12.2, 6.6 Hz, 3H), 0.95-0.80 (m, 4H). | D | C | B |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 160 | 782.26 | 782.27 | 784.27 | $^1$H NMR (400 MHz, DMSO-d$_6$) δ 11.00 (s, 1H), 8.83 (s, 1H), 8.05 (s, 1H), 8.05 (s, 1H), 7.75-7.60 (m, 2H), 7.52-7.45 (m, 1H), 7.40-7.30 (m, 1H), 7.20 (m, 1H), 7.15-6.95 (m, 1H), 5.80-5.70 (m, 4H), 5.20-5.00 (m, 1H), 5.00-4.85 (m, 2H), 4.20-4.00 (m, 2H), 3.75-3.65 (m, 3H), 3.65-3.55 (m, 5H), 3.10-2.75 (m, 4H), 2.19 (s, 3H), 2.10-2.00 (m, 1H), 1.91-1.81 (m, 2H), 1.55-1.40 (m, 2H), 1.30-1.20 (m, 1H). | B | B | B |
| 161 | 782.26 | 782.27 | 784.27 | $^1$H NMR (400 MHz, DMSO-d$_6$) δ 11.06 (s, 1H), 8.86 (s, 1H), 8.05 (s, 1H), 7.89 (d, J = 2.4 Hz, 1H), 7.70 (m, 2H), 7.64 (d, J = 8.6 Hz, 1H), 7.46 (d, J = 9.2 Hz, 2H), 7.30 (d, J = 2.3 Hz, 1H), 5.05 (m, 1H), 4.90 (s, 2H), 4.09 (d, J = 13.0 Hz, 2H), 3.78-3.62 (s, 8H), 3.01-2.82 (m, 3H), 2.59 (s, 3H), 2.18 (s, 4H), 2.02 (s, 3H), 1.93 (s, 2H), 1.50 (d, J = 8.8 Hz, 2H). | B | C | B |
| 162 | 810.31 | 810.3 | 812.3 | $^1$H NMR (400 MHz, DMSO-d$_6$) δ 11.05 (s, 1H), 8.80 (s, 1H), 8.10-8.00 (m, 1H), 7.98-7.88 (m, 1H), 7.80-7.62 (m, 2H), 7.53-7.40 (m, 1H), 7.39-7.30 (m, 1H), 7.29-7.20 (m, 1H), 7.10-6.98 (m, 1H), 5.15-5.00(m, 1H), 4.98-4.85 (m, 2H), 4.56-4.40 (m, 2H), 3.75-3.62 (m, 3H), 3.49-3.35 (m, 4H), 3.00-2.72 (m, 3H), 2.66-2.53 (m, 2H), 2.42-2.30 (m, 3H), 2.23-2.15 (m, 3H), 2.10-1.92 (m, 2H), 1.80-1.66 (m, 2H), 1.65-1.48 (m, 1H), 1.47-1.35 (m, 2H), 1.30-1.21 (m, 1H), 1.19-1.00 (m, 1H), 0.90-0.81 (m, 1H). | B | C | B |
| 163 | 810.27 | 810.3 | 812.26 | $^1$H NMR (300 MHz, DMSO-d$_6$) δ 8.91 (s, 1H), 8.08 (s, 1H), 7.88 (s, 1H), 7.68 (s, 2H), 7.47 (s, 1H), 7.32 (s, 1H), 7.24 (s, 1H), 7.09 (s, 1H), 5.10-5.00 (m, 1H), 4.91 (s, 2H), 4.07 (s, 2H), 3.67 (s, 3H), 3.57 (s, 8H), 3.06 (s, 3H), 2.58 (s, 1H), 2.20 (s, 3H), 2.03 (s, 2H), 1.72 (s, 5H). | B | B | B |
| 164 | 797.27 | 797.27 | 799.27 | $^1$H NMR (300 MHz, DMSO-d$_6$) δ 11.06 (br, 1H), 8.81 (s, 1H), 8.02 (s, 1H), 7.89-7.88 (m, 1H), 7.72-7.63 (m, 2H), 7.46-7.43 (d, J = 8.4 Hz, 1H), 7.02 (s, 1H), 6.80 (s, 1H), 6.67-6.64 (d, J = 8.4 Hz, 1H), 5.08-5.02 (m, 1H), 4.90 (s, 2H), 4.47-4.44 (m, 3H), 4.27-4.22 (m, 2H), 3.86-3.82 (m, 2H), 3.66 (s, 3H), 3.49-3.45 (m, 2H), 2.92-2.77 (m, 3H), 2.60-2.54 (m, 2H), 2.19 (s, 3H), 2.07-1.99 (m, 1H), 1.71-1.67 (m, 3H), 1.50-1.48 (m, 2H), 1.09-1.05 (m, 2H). | D | C | B |
| 165 | 808.29 | 808.28 | 810.28 | $^1$H NMR (400 MHz, DMSO-d$_6$) δ 11.05 (s, 1H), 8.87 (s, 1H), 8.03(s, 1H), 7.88 (s, 1H), 7.65-7.63 (m, 2H), 7.45 (d, J = 9.2 Hz, 1H), 7.03 (s, 1H), 6.83 (s, 1H), 6.76-6.72 (m, 1H), 5.31 (s, 1H), 5.11-5.02 (m, 1H), 4.91 (s, 2H), 4.65-4.62 (m, 2H), 4.11(s, 3H), 3.67 (s, 3H), 2.95-2.73 (m, 4H), 2.21 (s, 4H), 2.03-1.97 (m, 3H), 1.71-1.68 (m, 2H), 1.52-1.50 (m, 1H), 1.33-1.31 (m, 8H), 1.13-1.01 (m, 2H). | B | B | B |
| 166 | 825.32 | 825.31 | 827.31 | $^1$H NMR (400 MHz, DMSO-d$_6$) δ 11.09 (s, 1H), 8.93 (s, 1H), 8.07 (s, 1H), 7.87-7.86 (m, 1H), 7.78-7.72 (m, 2H), 7.49-7.43 (m, 2H), 7.37-7.35 (m, 1H), 7.09-7.07 (m, 1H), 5.11-5.07 (m, 1H), 4.90 (s, 2H), 4.48-4.45 (m, 3H), 4.22-4.19 (m, 4H), 3.02 (s, 3H), 3.66 (s, 3H), 3.61-3.48 (m, 2H), 3.34-3.27 (m, 2H), 3.16-3.13 (m, 4H), 3.02 (s, 3H), 2.94-2.88 (m, 2H), 2.85 (s, 3H), 2.66-2.61 (m, 1H), 2.14 (m, 1H), 2.03-2.01 (m, 1H), 1.78-1.75 (m, 2H), 1.21-1.31 (m, 2H). | D | C | C |
| 167 | 926.47 | 926.36 | 928.36 | $^1$H NMR (400 MHz, DMSO-d$_6$) δ 11.00 (s, 1H), 8.90 (s, 1H), 8.31-7.33 (m, 8H), 7.3-6.98 (m, 3H), 6.6 (s, 1H), 5.20 (s, 1H), 4.9-4.19 (m, 6H), 3.99-3.48 (m, 7H), 3.05-2.78 (m, 5H), 2.72-2.59 (m, 4H), 2.42-2.19 (m, 5H), 2.09-1.59 (m, 5H), 1.50-1.02 (m, 3H). | D | C | B |
| 168 | 905.4 | 905.34 | 907.34 | $^1$H NMR (400 MHz, DMSO-d$_6$) δ 10.93 (s, 1H), 8.82 (s, 1H), 8.03 (s, 1H), 7.99-7.89 (m, 2H), 7.77-7.70 (m, 1H), 7.60 (d, J = 8.4 Hz, 1H), 7.46 (d, J = 9.1 Hz, 1H), 7.15-7.08 (m, 2H), 7.06-6.99 (m, 1H), 5.13-5.01(m, 1H), 4.57 (s, 2H), 4.40-4.31 (m, 5H), 4.25-4.15 (m, 1H), 4.08-4.01 (m, 4H), 3.67 (s, 4H), | D | B | B |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 169 | 810.31 | 810.3 | 812.3 | 3.58-3.45 (m, 15H), 3.28-3.25 (m, 1H), 2.96-2.82 (m, 1H), 2.71-2.63 (m, 4H), 2.41-2.27 (m, 1H), 2.04-1.89 (m, 3H), 1.87-1.78 (m, 2H), 1.44-1.31 (m, 2H). | A | B | B |
| 170 | 797.27 | 797.26 | 799.26 | $^1$H NMR (400 MHz, DMSO-d$^6$) δ 11.08 (s, 1H), 8.83 (s, 1H), 8.04 (s, 1H), 7.91 (s, 1H), 7.72-7.66 (m, 2H), 7.47 (d, J = 9.0 Hz, 1H), 7.32-7.24 (m, 2H), 7.05 (s, 1H), 5.08 (d, J = 12.4 Hz, 1H), 4.92 (s, 2H), 4.52 (d, J = 12.6 Hz, 2H), 4.07 (d, J = 13.2 Hz, 2H), 3.68 (s, 3H), 3.03-2.98 (m, 2H), 2.83-2.72 (m, 5H), 2.60(m, 2H), 2.20-2.15 (m, 6H), 2.03 (s, 1H), 1.76-1.71 (m, 4H), 1.53-1.41 (m, 4H). | C | C | B |
| 171 | 722.16 | 722.2 | 724.2 | $^1$H NMR (400 MHz, DMSO-d$_6$) δ 11.06 (s, 1H), 8.83 (s, 1H), 8.03 (s, 1H), 7.89 (s, 1H), 7.73-7.62 (m, 2H), 7.45 (d, J = 9.1 Hz, 1H), 7.33-7.24 (m, 2H), 7.03 (s, 1H), 5.10-5.02 (m, 1H), 4.95-4.83 (m, 2H), 4.15-4.02 (m, 2H), 3.78-3.66 (m, 7H), 2.95-2.81 (m, 2H), 2.63-2.51 (m, 2H), 2.19-2.23 (m, 3H), 2.03-1.98 (m, 2H), 1.90-1.80 (m, 4H), 1.50-1.36 (m, 5H), 1.31-1.24 (m, 1H). | B | C | B |
| 172 | 798.25 | 798.26 | 800.26 | $^1$H NMR (400 MHz, DMSO-d$_6$) δ 11.05 (s, 1H), 8.87 (s, 1H), 8.03(s, 1H), 7.88 (s, 1H), 7.65-7.63 (m, 2H), 7.45 (d, J = 9.2 Hz, 1H), 7.03 (s, 1H), 6.83 (s, 1H), 6.76-6.72 (m, 1H), 5.31 (s, 1H), 5.11-5.02 (m, 1H), 4.91 (s, 2H), 4.65-4.62 (m, 2H), 4.11(s, 3H), 3.67 (s, 3H), 2.95-2.73 (m, 4H), 2.21 (s, 4H), 2.03-1.97 (m, 3H), 1.71-1.68 (m, 2H), 1.52-1.50 (m, 1H), 1.33-1.31 (m, 8H), 1.13-1.01 (m, 2H). | D | C | D |
| 173 | 736.18 | 736.21 | 738.21 | $^1$H NMR (300 MHz, DMSO-d$_6$) δ 11.10 (s, 1H), 8.79 (s, 1H), 8.00 (s, 2H), 7.85-7.69 (m, 2H), 7.41 (d, J = 9.1 Hz, 2H), 7.22-6.69 (m, 2H), 5.11-5.10 (m, 1H), 4.86 (s, 2H), 4.33-3.76 (m, 10H), 3.62-3.52 (m, 7H), 2.99-2.79 (m, 1H), 2.77-2.57 (m, 2H), 2.20 (s, 3H), 2.07 (s, 3H), 1.29 (s, 2H). | B | B | D |
| 174 | 807.31 | 807.3 | 809.3 | $^1$H NMR (300 MHz, DMSO-d$_6$) δ 11.13(s,1H), 9.27 (s, 1H), 8.37 (s, 1H), 7.82 (d, J = 6.5 Hz, 3H), 7.72 (d, J = 2.4 Hz, 1H), 7.67-7.57 (m, 1H), 7.47 (d, J = 9.1 Hz, 1H), 7.11 (s, 1H), 5.12 (m, 1H), 4.88 (s, 2H), 3.72(s,1H), 3.67 (d, J = 9.6 Hz, 2H), 2.92(m,2H), 2.75 (m, 3H), 2.18 (s, 6H), 2.04 (d, J = 11.7 Hz, 1H), 1.89-1.65 (s, 3H), 1.49-1.21 (d, J = 11.1 Hz, 3H). | | B | B |
| 175 | 782.3 | | | $^1$H NMR (400 MHz, DMSO-d$_6$) δ 11.10 (s, 1H), 9.07 (s, 1H), 8.28-8.19 (m, 1H), 8.19-8.07 (m, 3H), 7.96-7.85 (m, 1H), 7.82-7.74 (m, 1H), 7.60-7.40 (m, 3H), 7.40-7.25 (m, 2H), 5.17-5.02 (m, 1H), 4.58-4.38 (m, 1H), 4.28-4.12 (m, 2H), 3.71-3.68 (m, 2H), 3.68-3.56 (m, 2H), 3.41-3.27 (m, 2H), 3.23-3.05 (m, 4H), 3.02-2.81 (m, 3H), 2.72-2.66 (m, 2H), 2.65-2.56 (m, 1H), 2.56-2.51 (m, 3H), 2.22-2.09 (m, 1H), 2.08-1.98 (m, 1H), 1.84-1.73 (m, 1H), 1.19-1.10 (m, 2H). | | B | A |
| 176 | 779.25 | | | $^1$H NMR (400 MHz, DMSO-d$_6$) δ 10.93 (s, 1H), 8.79 (s, 1H), 8.03 (s, 1H), 7.90-7.85 (m, 1H), 7.79-7.72 (m, 1H), 7.52-7.46 (m, 2H), 7.08-7.00 (m, 3H), 5.12-4.99 (m, 1H), 4.90 (s, 2H), 4.59-4.43 (m, 2H), 4.41-4.23 (m, 1H), 4.21-4.11 (m, 1H), 3.66 (s, 3H), 3.59-3.31 (m, 3H), 2.98-2.79 (m, 4H), 2.68-2.56 (m, 2H), 2.39-2.31 (m, 2H), 2.22-2.12 (m, 5H), 2.01-1.96 (m, 2H), 1.96-1.79 (m, 4H), 1.13-0.98 (m, 2H). $^1$H NMR (400 MHz, DMSO-d$_6$) δ 11.13 (s, 1H), 8.78 (s, 1H), 8.19 (s, 1H), 8.01 (s, 1H), 7.93-7.86 (m, 3H), 7.74-7.69 (m, 1H), 7.49-7.41 (m, 1H), 6.99 (s, 1H), 5.21-5.10 (m, 1H), 4.89 (s, 2H), 4.51-4.39 (m, 2H), 3.71-3.59 (m, 8H), 2.96-2.79 (m, 3H), 2.62-2.52 (m, 1H), 2.32-2.28 (m, 4H), 2.18 (s, 3H), 2.11-2.01 (m, 1H), 1.79-1.71 (m, 2H), 1.11-0.99 (m, 2H). | | C | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 177 | 783.24 | | | $^1$H NMR (400 MHz, DMSO-d$_6$) δ 11.09 (s, 1H), 8.81 (s, 1H), 8.03 (s, 1H), 7.90 (d, J = 2.5 Hz, 1H), 7.82 (d, J = 8.2 Hz, 1H), 7.70 (m, 1H), 7.45 (d, J = 9.1 Hz, 1H), 7.35 (d, J = 2.2 Hz, 1H), 7.30 (s, 1H), 7.03 (s, 1H), 5.11 (m, 2H), 4.89 (s, 2H), 4.33 (d, J = 12.6 Hz, 2H), 3.66 (s, 3H), 2.98 (d, J = 12.8 Hz, 3H), 2.93 (s, 3H), 2.87 (d, J = 16.6 Hz, 1H), 2.81 (d, J = 10.8 Hz, 1H), 2.16 (s, 3H), 2.08-2.01 (m, 2H), 1.84 (s, 4H), 1.33 (s, 3H). | | C | D |
| 178 | 769.21 | | | $^1$H NMR (400 MHz, DMSO-d$_6$) δ 11.07 (s, 1H), 8.87 (s, 1H), 8.04 (s, 2H), 7.88 (d, J = 2.5 Hz, 1H), 7.67 (dd, J = 18.3, 8.8 Hz, 2H), 7.46 (d, J = 9.0 Hz, 1H), 7.05 (s, 1H), 6.80 (d, J = 2.1 Hz, 1H), 6.66 (d, J = 8.3 Hz, 1H), 5.05 (dd, J = 13.1, 5.5 Hz, 1H), 4.91 (s, 2H), 4.65 (s, 2H), 4.30 (t, J = 7.8 Hz, 2H), 4.13 (d, J = 12.9 Hz, 2H), 3.84 (d, J = 5.4 Hz, 2H), 3.67 (s, 4H), 3.20 (d, J = 10.8 Hz, 2H), 2.88 (dd, J = 17.6, 12.4 Hz, 1H), 2.60 (s, 1H), 2.19 (s, 3H), 2.00 (s, 1H), 1.84 (s, 2H), 1.42 (d, J = 11.2 Hz, 2H). | | C | B |
| 179 | 730.13 | | | $^1$H NMR (400 MHz, DMSO-d$_6$) δ 11.10 (s, 1H), 8.93 (s, 1H), 8.09 (s, 1H), 7.89 (d, J = 2.5 Hz, 1H), 7.79 (d, J = 8.2 Hz, 1H), 7.74-7.61 (m, 1H), 7.44 (d, J = 8.7 Hz, 2H), 7.30 (d, J = 8.3 Hz, 1H), 7.08 (s, 1H), 5.11 (dd, J = 13.1, 5.4 Hz, 1H), 4.80 (s, 2H), 4.44 (d, J = 12.7 Hz, 1H), 4.37-4.07 (m, 3H), 3.93 (d, J = 11.4 Hz, 1H), 3.83 (s, 1H), 3.63 (s, 3H), 3.55 (t, J = 11.4 Hz, 1H), 2.91 (dt, J = 41.1, 11.4 Hz, 3H), 2.73-2.53 (m, 2H), 2.14 (s, 3H), 2.05 (d, J = 10.9 Hz, 1H). | | B | D |
| 180 | 827.29 | | | $^1$H NMR (400 MHz, DMSO-d$_6$) δ 11.00 (s, 1H), 8.70 (s, 1H), 8.10-7.95 (m, 2H), 7.90-7.80 (m, 1H), 7.70-7.60 (m, 1H), 7.50-7.40 (m, 1H), 7.30-7.20 (m, 1H), 7.20-7.10 (m, 1H), 7.15-7.00 (m, 1H), 5.15-5.00 (m, 1H), 4.95-4.85 (m, 2H), 4.25-4.15 (m, 1H), 3.75-3.65 (m, 5H), 3.60-3.50 (m, 9H), 3.50-3.40 (m, 1H), 3.20-3.10 (m, 2H), 3.00-2.85 (m, 1H), 2.65-2.60 (m, 1H), 2.25-2.20 (m, 3H), 2.05-1.95 (m, 3H), 1.90-1.80 (m, 2H), 1.65-1.55 (m, 2H). | | | D |
| 181 | 722.16 | | | $^1$H NMR (300 MHz, DMSO-d$_6$) δ 11.04 (s, 1H), 9.29 (s, 1H), 8.37 (s, 1H), 7.76 (d, J = 2.4 Hz, 1H), 7.69-7.57 (m, 2H), 7.50 (d, J = 9.1 Hz, 1H), 7.36 (d, J = 2.2 Hz, 1H), 7.28 (dd, J = 8.7, 2.4 Hz, 1H), 7.15 (s, 1H), 5.05 (dd, J = 12.9, 5.4 Hz, 1H), 4.90 (s, 2H), 4.02 (d, J = 13.3 Hz, 1H), 3.80 (d, J = 13.6 Hz, 1H), 3.68 (s, 3H), 2.86 (d, J = 11.8 Hz, 2H), 2.61 (s, 1H), 2.54 (s, 2H), 2.17 (s, 3H), 2.02 (s, 3H), 1.73 (s, 2H), 1.56 (s, 1H). | | | D |
| 182 | 797.27 | | | $^1$H NMR (400 MHz, DMSO-d$_6$) δ 11.09 (s, 1H), 8.81 (s, 1H), 8.03 (s, 1H), 7.89 (d, J = 2.5 Hz, 1H), 7.80 (d, J = 8.2 Hz, 1H), 7.71 (m, 1H), 7.48-7.39 (m, 2H), 7.33 (m, 1H), 7.03 (s, 1H), 5.10 (m, 1H), 4.88 (s, 2H), 4.50 (d, J = 12.7 Hz, 2H), 4.06-4.00 (m, 1H), 3.89 (t, J = 8.4 Hz, 1H), 3.65 (s, 3H), 3.28 (m, 2H), 2.84 (m, 5H), 2.64-2.51 (m, 2H), 2.17 (s, 3H), 2.04 (d, J = 12.5 Hz, 1H), 1.80 (d, J = 17.9 Hz, 3H), 1.70 (s, 3H), 1.36 (s, 2H). | | C | D |
| 183 | 769.21 | | | $^1$H NMR (400 MHz, DMSO-d$_6$) δ 11.05 (s, 1H), 8.81 (s, 1H), 8.18-7.95 (m, 2H), 7.77 (dd, J = 9.2, 2.3 Hz, 1H), 7.64 (d, J = 8.5 Hz, 1H), 7.43 (d, J = 9.0 Hz, 1H), 7.33 (d, J = 2.2 Hz, 1H), 7.24 (d, J = 8.9 Hz, 1H), 7.09 (s, 1H), 5.05 (dd, J = 12.9, 5.4 Hz, 2H), 4.89 (s, 2H), 4.55 (s, 1H), 4.21 (t, J = 8.0 Hz, 2H), 3.82 (q, J = 7.4, 5.2 Hz, 4H), 3.65 (s, 4H), 3.29-3.05 (m, 3H), 2.95-2.79 (m, 1H), 2.59 (s, 1H), 2.17 (s, 2H), 2.04-1.80 (m, 3H), 1.63-1.39 (m, 2H). | | C | B |
| 184 | 722.16 | | | $^1$H NMR (400 MHz, DMSO-d$_6$) δ 11.07 (s, 1H), 9.30 (s, 1H), 8.39 (s, 1H), 7.75 (s, 1H), 7.70-7.67 (m, 2H), 7.49 (d, J = 9.2 Hz, 1H), 7.34 (d, J = 6.8 Hz, 1H), 7.14 (s, 1H), 5.11-5.02 (m, 1H), 4.90 (s, 2H), 3.68 (s, 3H), 3.55-3.51 (m, | | B | B |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 185 | 736.18 | | | 2H), 3.13-3.11 (m, 2H), 2.89-2.88 (m, 2H), 2.67-2.61 (m, 2H), 2.18 (s, 4H), 2.04-2.00 (m, 3H), 1.85-1.80 (m, 2H). | | | |
| 186 | 794.31 | | | $^1$H NMR (400 MHz, DMSO-d$_6$) δ 11.10 (s, 1H), 9.28 (s, 1H), 8.40(s, 1H), 7.88-7.75 (m, 4H), 7.66-7.63 (m, 1H), 7.50 (d, J = 9.2 Hz, 1H), 7.13 (s, 1H), 5.17-5.12 (m, 1H), 4.90 (s, 2H), 3.68-3.65 (m, 5H), 2.90-2.89 (m, 1H), 2.63-2.58 (m, 5H), 2.21 (s, 5H), 2.18-2.17 (m, 1H), 1.81-1.78 (m, 2H), 1.62-1.60 (m, 2H). | | | |
| 187 | 812.28 | | | $^1$H NMR (400 MHz, DMSO-d$_6$) δ 11.04 (s, 1H), 8.89 (s, 1H), 7.93 (m, 1H), 7.83-7.82 (m, 1H), 7.77-7.75 (m, 1H), 7.66-7.63 (m, 1H), 7.48-7.45 (m, 2H), 7.36-7.34 (m, 1H), 5.11-5.06 (m, 1H), 4.49-4.46 (m, 2H), 4.18 (s, 3H), 3.64 (m, 5H), 3.33-3.15 (m, 4H), 3.12-2.89 (m, 6H), 2.86-2.77 (m, 3H), 2.73-2.55 (m, 4H), 2.53-2.50 (m, 3H), 2.12 (s, 3H), 2.04-2.02 (m, 1H), 1.80-1.77 (m, 2H). | | | |
| 188 | 793.28 | | | $^1$H NMR (400 MHz, DMSO-d$_6$) δ 11.06 (s, 1H), 8.78 (s, 1H), 8.03 (s, 1H), 7.88 (d, J = 2.5 Hz, 1H), 7.73 (d, J = 9.1 Hz, 2H), 7.66 (d, J = 8.5 Hz, 1H), 7.46 (d, J = 9.1 Hz, 1H), 7.31 (s, 1H), 7.04 (s, 1H), 5.06 (m, 1H), 4.89 (s, 2H), 4.26 (d, J = 5.8 Hz, 1H), 4.08 (s, 2H), 3.67 (s, 3H), 3.41 (s, 4H), 2.86 (d, J = 12.4 Hz, 1H), 2.66 (s, 5H), 2.60 (s, 3H), 2.32 (d, J = 8.4 Hz, 3H), 2.03 (s, 1H), 1.52 (s, 4H), 1.39 (s, 2H). | | | |
| 189 | 766.21 | | | $^1$H NMR (400 MHz, DMSO-d$_6$) δ 11.06 (s, 1H), 9.14 (s, 1H), 8.42 (s, 1H), 8.00 (d, J = 2.4 Hz, 1H), 7.78-7.74 (m, 1H), 7.65 (d, J = 8.5 Hz, 1H), 7.49 (d, J = 9.1 Hz, 1H), 7.30 (d, J = 2.3 Hz, 1H), 7.23-7.19 (m, 1H), 7.12 (s, 1H), 6.99 (d, J = 4.0 Hz, 1H), 5.08-5.02 (m, 1H), 4.92 (s, 2H), 4.08-4.02 (m, 2H), 3.68 (s, 3H), 3.15-3.10 (m, 2H), 2.97-2.81 m, 3H), 2.60-2.51 (m, 5H), 2.30-2.25 (m, 2H), 2.20 (s, 3H), 2.10-1.97 (m, 1H), 1.95-1.93(m, 1H), 1.90-1.80 (m, 2H), 1.26-1.10 (m, 3H). | | | |
| 190 | 754.25 | | | $^1$H NMR (400 MHz, DMSO-d$_6$) δ 11.08 (s, 1H), 9.27 (s, 1H), 8.37 (s, 1H), 7.79 (d, J = 8.3 Hz, 1H), 7.73 (d, J = 2.4 Hz, 1H), 7.63 (dd, J = 9.0, 2.4 Hz, 1H), 7.49 (d, J = 9.0 Hz, 1H), 7.44 (d, J = 2.2 Hz, 1H), 7.34 (dd, J = 8.3, 2.3 Hz, 1H), 7.13 (s, 1H), 5.11 (dd, J = 12.8, 5.3 Hz, 1H), 4.90 (s, 2H), 4.28 (t, J = 5.8 Hz, 2H), 3.67 (s, 3H), 2.91(s, 2H), 2.87 (s, 3H), 2.27 (s, 2H), 2.19 (s, 4H), 2.04 (d, J = 14.9 Hz, 1H), 1.87 (s, 1H), 1.63 (s, 1H), 1.49 (s, 1H), 1.36 (d, J = 11.3 Hz, 1H), 1.24 (s, 1H), 0.94 (t, J = 7.1 Hz, 1H). | | | |
| 191 | 811.3 | | | $^1$H NMR (400 MHz, DMSO-d$_6$) δ8.35 (s, 5H), 8.03 (s, 1H), 7.90 (d, J = 2.4 Hz, 1H), 7.74 (dd, J = 9.0, 2.5 Hz, 1H), 7.68 (d, J = 8.5 Hz, 1H), 7.45 (d, J = 9.2 Hz, 1H), 7.33 (d, J = 2.2 Hz, 1H), 7.24 (dd, J = 8.7, 2.3 Hz, 1H), 7.10 (s, 1H), 5.07 (dd, J = 12.9, 5.4 Hz, 1H), 4.49 (d, J = 12.7 Hz, 2H), 3.82 (s, 3H), 3.42 (d, J = 5.8 Hz, 4H), 2.87 (q, J = 14.4, 11.2 Hz, 3H), 2.64-2.56 (m, 1H), 2.47 (d, J = 5.8 Hz, 5H), 2.18 (d, J = 7.0 Hz, 2H), 2.05-1.98 (m, 1H), 1.87-1.71 (m, 3H), 1.05 (d, J = 12.0 Hz, 2H). | | | |
| 192 | 743.17 | | | $^1$H NMR (400 MHz, DMSO-d$_6$) δ 11.05 (s, 1H), 8.83 (s, 1H), 8.05 (s, 1H), 8.00-7.95 (m, 2H), 7.80-7.70 (m, 1H), 7.70-7.60 (m, 1H), 7.55-7.45 (m, 1H), 7.40-7.30 (m, 1H), 7.30-7.20 (m, 1H), 7.15-7.05 (m, 1H), 5.10-5.00 (m, 1H), 4.65 (s, 2H), 4.15-4.00 (m, 2H), 3.75-3.65 (m, 3H), 3.65-3.60 (m, 4H), 3.05-2.85 (m, 3H), 2.70-2.60 (m, 4H), 2.60-2.55 (m, 1H), 2.45-2.34 (m, 4H), 2.25-2.15 (m, 2H), 2.10-2.00 (m, 1H), 2.00-1.80 (m, 3H), 1.30-1.10 (m, 2H). $^1$H NMR (400 MHz, DMSO-d$_6$) δ 11.08 (s, 1H), 9.09 (s, 1 H), 8.08 (s, 1H), 7.89 (m, 2H), 7.79-7.72 (m, 2H), 7.45-7.42 (m, 3H), 7.11 (s, 1H), 5.08-5.03 | | | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 193 | 879.42 | 879.35 | | (m, 1H), 4.56-4.51 (m, 2H), 4.43-4.35 (m, 1H), 4.26-4.18 (m, 2H), 4.15-4.14 (m, 3H), 3.61 (s, 3H), 3.01-2.89 (m, 2H), 2.86-2.82 (m, 1H), 2.65-2.53 (m, 3H), 2.01-1.93 (m, 3H), 1.75 (m, 1H), 1.52-1.50 (m, 2H). | | | D |
| 194 | 789.1754793 | 743.22 | 745.22 | $^1$H NMR (400 MHz, DMSO-d$_6$, ppm):δ 11.06 (s, 1H), 8.79 (s, 1H), 8.04 (s, 1H), 7.94 (s, 1H), 7.93 (d, J = 2.2 Hz, 1H), 7.75-7.65 (m, 2H), 7.55 (s, 1H), 7.12-7.10 (m, 2H), 7.01 (s, 1H), 5.60-5.15 (m, 1H), 5.05 (dd, J = 12.8, 5.4 Hz, 1H), 4.53-4.46 (m, 4H), 3.58 (s, 2H), 3.48 (s, 3H), 2.98-2.87 (m, 3H), 2.86 (s, 3H), 2.66 (d, J = 4.6 Hz, 3H), 2.60 (d, J = 3.3 Hz, 1H), .25 (d, J = 6.8 Hz, 2H), 2.05-1.85 (m, 4H), 1.79-1.71 (m, 5H), 1.56 (d, J = 6.8 Hz, 6H), 1.03 (s, 2H). | B | B | |
| 195 | 823.31 | 823.29 | 825.29 | 1H NMR (400 MHz, DMSO-d6) δ 8.28 (s, 1H), 8.00 (s, 1H), 7.84 (s, 1H), 7.64-7.62 (m, 2H), 7.41-7.39 (m, 1H), 7.11-6.98 (m, 3H), 5.06 (dd, J = 12.8, 5.4 Hz, 1H), 4.73-4.65 (m, 3H), 4.35-4.29 (m, 3H), 3.58 (s, 3H), 3.20-3.09 (m, 2H), 2.92-2.76 (m, 2H), 2.63-2.53 (m, 3H), 2.41-2.37 (m, 5H), 2.33-2.15 (m, 4H). | A | C | B |
| 196 | 825.28 | 825.27 | 827.27 | 1H NMR (400 MHz, DMSO-d6) δ 11.06 (s, 1H), 8.89-8.68 (m, 1H), 8.16-7.91 (m, 3H), 7.91-7.71 (m, 1H), 7.69-7.57 (m, 1H), 7.55-7.41 (m, 1H), 7.34-7.26 (m, 1H), 7.24-7.17 (m, 1H), 7.17-7.01 (m, 1H), 5.11-4.99 (m, 1H), 4.58 (s, 2H), 4.12-3.98 (m, 2H), 3.68 (s, 3H), 3.57-3.43 (m, 1H), 3.29 (s, 3H), 3.02-2.81 (s, 4H), 2.72-2.63 (m, 3H), 2.58-2.52 (m, 3H), 2.42-2.34 (m, 2H), 2.08-1.99 (m, 1H), 1.90-1.59 (m, 4H), 1.30-1.03 (m, 3H). | B | B | B |
| 197 | 810.31 | 810.3 | 812.3 | 1H NMR (400 MHz, DMSO-d6) δ 11.10 (s, 1H), 8.85 (s, 1H), 8.05 (s, 1H), 8.00-7.80 (m, 2H), 7.60-7.40 (m, 1H), 7.40-7.25 (m, 1H), 7.25-7.15 (m, 1H), 7.15-7.00 (s, 1H), 5.20-5.00 (m, 1H), 4.65-4.55 (m, 2H), 4.55-4.35 (m, 2H), 4.20-4.00 (m, 2H), 3.85-3.70 (m, 2H), 3.70-3.65 (m, 3H), 3.55-3.50 (m, 2H), 3.00-2.80 (m, 2H), 2.70-2.60 (m, 3H), 2.60-2.50 (m, 1H), 2.10-1.85 (m, 2H), 1.80-1.65 (m, 2H), 1.35-1.20 (m, 3H), 1.20-1.00 (m, 2H). | C | B | C |
| 198 | 825.32 | 825.31 | 827.31 | 1H NMR (400 MHz, DMSO-d6) δ 11.10 (s, 1H), 8.11 (s, 1H), 8.01-7.75 (m, 3H), 7.52 (m, 1H), 7.43-7.35 (m, 4H), 7.28 (m, 2H), 6.24 (s, 1H), 5.08 (s, 1H), 4.57 (s, 2H), 4.36 (m, 1H), 3.92-4.11 (m, 2H), 3.69 (m, 4H), 3.53 (m, 4H), 3.10 (m, 5H), 2.86 (m, 1H), 2.67 (d, J = 4.7 Hz, 4H), 2.04 (s, 2H), 1.75 (s, 2H), 1.24 (m, 3H). | D | B | C |
| 199 | 822.32 | 822.3 | 824.3 | 1H NMR (300 MHz, DMSO-d6) δ 11.08 (s, 1H), 8.81 (s, 1H), 8.02 (d, J = 3.7 Hz, 2H), 7.91 (d, J = 2.4 Hz, 1H), 7.76 (dd, J = 9.1, 2.5 Hz, 1H), 7.67 (d, J = 8.5 Hz, 1H), 7.47 (d, J = 9.2 Hz, 1H), 7.33 (d, J = 2.2 Hz, 1H), 7.24 (dd, J = 8.6, 2.3 Hz, 1H), 7.10 (s, 1H), 5.07 (dd, J = 13.0, 5.4 Hz, 1H), 4.53 (d. J = 19.6 Hz, 4H), 3.67 (s, 3H), 3.47-3.38 (m, 4H), 3.21-3.03 (m, 2H), 2.92-2.80 (m, 3H), 2.68-2.52 (m, 3H), 2.46 (d. J = 5.7 Hz, 3H), 2.18 (d, J = 6.8 Hz, 2H), 2.09-1.99 (m, 1H), 1.78 (t, J = 15.1 Hz, 3H), 1.03 (q, J = 7.2, 6.8 Hz, 5H). | A | B | B |
| 200 | 839.35 | 839.32 | 842.32 | 1H NMR (300 MHz, DMSO-d6) δ 11.06 (s, 1H), 8.79 (s, 1H), 8.02 (s, 1H), 7.94-7.85 (m, 2H), 7.82-7.71 (m, 1H), 7.71-60 (m, 1H), 7.55-7.39 (m, 1H), 7.39-7.28 (m, 1H), 7.28-7.19 (m, 1H), 7.11 (s, 1H), 5.1-5.01 (m, 1H), 4.79- | D | B | B |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 201 | 825.28 | 825.27 | 827.27 | 4.47 (m, 4H), 3.65 (s, 3H), 3.45-3.37 (m, 4H), 3.29-3.28 (m, 1H), 2.98-2.80 (m, 1H), 2.80-2.66 (m, 2H), 2.62-2.54 (m, 8H), 2.09-1.97 (m, 1H), 1.88-1.71 (m, 3H), 1.21-1.01 (m, 2H), 0.87 (s, 6H). | B | A | D |
| 202 | 810.31 | 810.3 | 812.3 | 1H NMR (400 MHz, DMSO-d6) δ 11.08 (s, 1H), 8.10 (s, 1H), 8.00-7.90 (m, 2H), 7.90-7.70 (m, 1H); 7.70-7.60 (m, 1H), 7.55-7.40 (m, 1H), 7.40-7.30 (m, 1H), 7.25-7.05 (m, 2H), 5.20-5.00 (m, 1H), 4.60 (s, 2H), 4.17 (s, 2H), 4.10-4.00 (m, 2H), 4.00-3.80 (m, 2H), 3.60 (s, 3H), 3.60-3.40 (m, 2H), 3.30-3.20 (m, 2H), 3.00-2.80 (m, 3H), 2.80-2.60 (m, 5H), 2.10-1.90 (m, 2H), 1.80-1.40 (m, 2H), 1.30-1.00 (m, 2H). | D | C | C |
| 203 | 839.35 | 839.32 | | 1H NMR (400 MHz, DMSO-d6) δ 11.07 (s, 1H), 8.18 (s, 1H), 7.93 (s, 2H), 7.74-7.71 (m, 2H), 7.68-7.67 (m, 2H), 7.34-7.33 (m, 2H), 7.05 (s, 1H), 6.24 (d, J = 8.8 Hz, 1H), 5.09-5.04 (m, 1H), 4.55 (s, 2H), 4.15 (d, J = 12.0 Hz, 2H), 3.66 (s, 3H), 3.44 (s, 4H), 2.85-2.82 (m, 3H), 2.65 (d, J = 4.8 Hz, 3H), 2.60-2.40 (m, 6H), 2.20 (d, J = 6.8 Hz, 2H), 2.10-2.02 (m, 1H), 1.78-1.75 (m, 3H), 1.21-1.11 (m, 2H). | D | A | A |
| 204 | 823.31 | 823.29 | | 1H-NMR (300 MHz, DMSO-d6) δ 11.06 (s, 1H), 8.83 (s, 1H), 7.99-7.82 (m, 2H), 7.85-7.71 (m, 1H), 7.71-7.62(m, 1H), 7.53-7.41 (m, 1H), 7.33-7.28 (m, 1H), 7.28-7.19 (m, 1H), 7.11 (s, 1H), 5.11-5.00 (m, 1H), 4.56 (s, 2H), 4.19-4.01 (m, 2H), 3.71-3.50 (m, 9H), 2.99-2.80 (m, 3H), 2.70-2.61 (m, 4H), 2.03-1.77 (m, 5H), 1.34-1.18 (s, 3H), 0.85 (s, 7H). | B | C | A |
| 205 | 804.31 | 804.3 | | 1H NMR (400 MHz, DMSO-d6) δ 11.05 (s, 1H), 8.79 (s, 1H), 8.11-7.99 (m, 2H), 7.89 (s, 1H), 7.80-7.69 (m, 1H), 7.69-7.52 (m, 1H), 7.52-7.44 (m, 1H), 7.15-7.03 (m, 1H), 7.03-6.71 (m, 2H), 5.09-4.98 (m, 1H), 4.65-4.49 (m, 3H), 4.49-4.46 (m, 1H), 3.71-3.61 (m, 6H), 2.99-2.82 (m, 3H), 2.82-2.73 (m, 3H), 2.69-2.61 (m, 4H), 2.33 (s, 2H), 2.13-1.85 (m, 3H), 1.85-1.64 (m, 3H), 1.64-1.51 (m, 1H), 1.09-0.88 (m, 2H). | D | D | D |
| 206 | 766.27 | 766.26 | | 1H NMR (400 MHz, DMSO-d6) δ 11.07 (s, 1H), 8.44 (s, 1H), 8.20-8.00 (m, 4H), 7.90-7.80 (m, 1H), 7.80-7.60 (m, 1H), 7.60-7.50 (m, 1H), 7.45-7.30 (m, 1H), 7.30-7.20 (m, 1H), 5.20-5.00 (m, 1H), 4.65-4.50 (m, 2H), 3.85 (s, 3H), 3.70 (s, 3H), 3.45 (s, 4H), 3.00-2.70 (m, 4H), 2.65-2.55 (m, 2H), 2.30-2.10 (m, 1H), 2.10-1.90 (m, 2H), 1.90-1.70 (m, 3H), 1.30-1.20 (m, 1H), 1.15-1.00 (m, 2H). | D | C | C |
| 207 | 925.2928638 | 811.29 | | 1H NMR (300 MHz, DMSO-d6) δ 11.08 (s, 1H), 8.94 (s, 1H), 8.26 (s, 1H), 8.06 (s, 1H), 8.03-8.02 (m, 2H), 7.68 (d, J = 8.4 Hz, 1H), 7.58 (d, J = 9.3 Hz, 1H), 7.33 (d, J = 8.7 Hz, 1H), 7.25 (d, J = 8.7 Hz, 1H), 5.01-5.08 (m, 1H), 4.50-4.46 (m, 2H), 3.68 (s, 3H), 3.44 (s, 4H), 2.95-2.82 (m, 3H), 2.73-2.62 (m, 6H), 2.51 (s, 3H), 2.27-2.21 (m, 2H), 2.04-2.02 (m, 1H), 1.88-1.84 (m, 3H), 1.07-1.03 (m, 2H). | B | A | A |
| | | | | 1H NMR (400 MHz, DMSO-d6) δ 11.08 (s, 1H), 9.07 (s, 1H), 8.15 (s, 1H), 8.00-7.88 (m, 2H), 7.75-7.67 (m, 2H), 7.53-7.45 (m, 1H), 7.39-7.32 (m, 2H), 7.17 (s, 1H), 5.13-5.05 (m, 1H), 4.59 (s, 2H), 4.57-4.42 (m, 2H), 3.80-3.63 (m, 5H), 3.63-3.52 (m, 2H), 3.39-3.25 (m, 2H), 3.18-3.02 (m, 4H), 2.97-2.82 (m, 3H), 2.70-2.52 (m, 5H), 2.13-1.99 (m, 2H), 1.91-1.82 (m, 2H), 1.57-1.42 (m, 2H). | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 208 | 842.1528638 | 728.22 | | 1H NMR (400 MHz, DMSO-d6) δ 11.06 (s, 1H), 9.27-9.13 (m, 1H), 8.08 (s, 1H), 7.98-7.89 (m, 2H), 7.72-7.69 (m, 1H), 7.62-7.60 (m, 1H), 7.51-7.46 (m, 1H), 7.19-7.08 (m, 3H), 5.06-5.02 (m, 2H), 4.59 (m, 3H), 3.88-3.82 (m, 4H), 3.71-3.67 (m, 5H), 3.64-3.50 (m, 2H), 2.87-2.83 (m, 1H), 2.65-2.63 (m, 3H), 2.00-1.97 (m, 3H). | C | B | C |
| 209 | 827.3 | 827.28 | 829.28 | 1H NMR (300 MHz, DMSO-d6) δ 11.45 (s, 1H), 11.08 (s, 1H), 8.81 (s, 1H), 8.04 (s, 1H), 7.92 (d, J = 2.3 Hz, 1H), 7.84-7.72 (m, 1H), 7.68 (d, J = 8.5 Hz, 1H), 7.49 (d, J = 9.2 Hz, 1H), 7.34 (d, J = 2.2 Hz, 1H), 7.25 (dd, J = 8.7, 2.3 Hz, 1H), 7.15 (s, 1H), 5.08 (dd, J = 12.9, 5.4 Hz, 1H), 4.79-3.93 (m, 4H), 3.68 (s, 3H), 3.62 (s, 3H), 3.44 (d, J = 5.3 Hz, 2H), 2.88 (qd, J = 12.7, 11.4, 4.9 Hz, 3H), 2.67-2.52 (m, 5H), 2.27-2.10 (m, 2H), 2.09-1.96 (m, 1H), 1.78 (d, J = 13.6 Hz, 3H), 1.24 (s, 1H), 1.05 (d, J = 13.1 Hz, 2H). | D | A | B |
| 210 | 825.32 | 825.3 | 827.3 | 1H NMR (400 MHz, DMSO-d6) δ 11.06 (s, 1H), 8.80 (s, 1H), 8.03 (d, J = 5.9 Hz, 2H), 7.92 (d, J = 2.4 Hz, 1H), 7.76 (dd, J = 9.1, 2.4 Hz, 1H), 7.67 (d, J = 8.5 Hz, 1H), 7.47 (d, J = 9.1 Hz, 1H), 7.33 (d, J = 2.2 Hz, 1H), 7.28-7.21 (m, 1H), 7.06 (s, 1H), 5.07 (d, J = 5.4 Hz, 1H), 4.71 (q, J = 6.7 Hz, 1H), 4.49 (d, J = 12.8 Hz, 2H), 3.67 (s, 3H), 3.52-3.35 (m, 5H), 2.91-2.81 (m, 3H), 2.71-2.58(m, 3H), 2.57-2.54 (m, 2H), 2.47-2.43 (m, 3H), 2.19 (d, J = 6.8 Hz, 2H), 2.09-1.98 (m, 1H), 1.80-1.70 (m, 3H), 1.48 (s, 3H), 1.32-1.17(m, 1H), 1.04-0.98 (m, 2H). | B | | D |
| 211 | 825.32 | 825.3 | 827.3 | 1H NMR (400 MHz, DMSO-d6) δ 11.07 (s, 1H), 8.03 (s, 1H), 8.03 (d, J = 2.7 Hz, 2H), 7.92 (d, J = 2.4 Hz, 1H), 7.76 (dd, J = 2.4 Hz, 1H), 7.67 (d, J = 8.5 Hz, 1H), 7.47 (d, J = 9.2 Hz, 1H), 7.33 (s, 1H), 7.25 (d, J = 8.6 Hz, 1H), 7.06 (s, 1H), 5.07 (d, J = 5.4 Hz, 1H), 4.71 (q, J = 6.6 Hz, 1H), 4.49 (d, J = 12.7 Hz, 2H), 3.67 (s, 3H), 3.50-3.38 (m, 4H), 3.37-3.34(m, 3H), 2.97-2.76 (m, 5H), 2.64-2.52 (m, 4H), 2.19 (d, J = 6.7 Hz, 2H), 2.09-1.98 (m, 1H), 1.89-1.70 (m, 3H), 1.47 (d, J = 6.6 Hz, 3H), 1.04 (d, J = 12.0 Hz, 2H). | D | | D |
| 212 | 825.32 | 825.31 | 827.31 | 1H NMR (400 MHz, DMSO-d6) δ 11.06 (s, 1H), 8.80 (s, 1H), 8.03 (d, J = 5.9 Hz, 2H), 7.92 (d, J = 2.4 Hz, 1H), 7.76 (dd, J = 9.1, 2.4 Hz, 1H), 7.67 (d, J = 8.5 Hz, 1H), 7.47 (d, J = 9.1 Hz, 1H), 7.33 (d, J = 2.2 Hz, 1H), 7.28-7.21 (m, 1H), 7.06 (s, 1H), 5.07 (d, J = 5.4 Hz, 1H), 4.71 (q, J = 6.7 Hz, 1H), 4.57-4.41 (m, 2H), 3.67 (s, 3H), 3.52-3.35 (m, 5H), 2.91-2.81 (m, 3H), 2.71-2.58(m, 6H), 2.57-2.54 (m, 2H), 2.27-2.10 (m, 2H), 2.09-1.98 (m, 1H), 1.89-1.70 (m, 3H), 1.48 (s, 3H), 1.13-0.92 (m, 2H). | B | | D |
| 213 | 825.32 | 825.31 | 827.31 | 1H NMR (400 MHz, DMSO-d6) δ 11.06 (s, 1H), 8.80 (s, 1H), 8.03 (d, J = 5.9 Hz, 2H), 7.92 (d, J = 2.4 Hz, 1H), 7.76 (dd, J = 9.1, 2.4 Hz, 1H), 7.67 (d, J = 8.5 Hz, 1H), 7.47 (d, J = 9.1 Hz, 1H), 7.33 (d, J = 2.2 Hz, 1H), 7.28-7.21 (m, 1H), 7.06 (s, 1H), 5.07 (d, J = 5.4 Hz, 1H), 4.71 (q, J = 6.7 Hz, 1H), 4.57-4.41 (m, 2H), 3.67 (s, 3H), 3.52-3.35 (m, 5H), 2.91-2.81 (m, 3H), 2.71-2.58(m, 5H), 2.57-2.54 (m, 2H), 2.27-2.10 (m, 2H), 2.09-1.98 (m, 1H), 1.89-1.70 (m, 3H), 1.48 (s, 3H), 1.13-0.92 (m, 2H). | D | | D |
| 214 | 781.27 | 781.28 | 783.28 | 1H NMR (300 MHz, DMSO-d6) δ 11.08 (s, 1H), 9.67 (s, 1H), 8.95 (s, 1H), 8.24 (s, 1H), 8.06-8.04 (m, 2H), 7.68-7.64 (m, 2H), 7.79-7.75 (m, 1H), 7.33 (s, 1H), 7.22-7.21 (m, 1H), 5.09-5.05 (m, 1H), 4.50-4.47 (m, 2H), 3.73 (s, 3H), 3.43 (s, 4H), 2.89-2.86 (m, 6H), 2.60-2.51 (m, 6H), 2.20-2.18 (m, 2H), 2.19-2.17 (m, 1H), 1.87-1.77 (m, 3H), 1.07-1.05 (m, 2H). | C | C | D |
| 215 | 939.3128638 | 825.3 | 827.3 | 1H NMR (400 MHz, DMSO-d6) δ 11.07 (s, 1H), 9.13-8.89 (m, 2H), 8.11 (s, 1H), 7.98-7.97 (m, 2H), 7.76-7.75 (m, 1H), 7.68-7.66 (m, 1H), 7.48-7.43 (m, | | | B |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 216 | 810.31 | 810.3 | 812.29 | 1H), 7.34 (s, 1H), 7.26-7.24 (m, 1H), 7.15 (m, 1H), 5.08-5.04 (m, 1H), 4.57 (s, 1H), 4.09-4.06 (m, 3H), 3.67 (s, 3H), 3.30-3.16 (m, 3H), 3.14-3.06 (m, 2H), 2.96-2.78 (m, 4H), 2.65-2.56 (m, 5H), 2.53 (m, 5H), 2.16-1.99 (m, 4H), 1.80-1.75 (m, 2H). | D | C | B |
| 217 | 810.31 | 810.29 | 812.29 | 1H NMR (300 MHz, DMSO-d6) δ 11.09 (s, 1H), 9.67 (s, 1H), 8.88 (s, 1H), 8.06 (s, 1H), 7.91 (s, 1H), 7.82-7.65 (m, 2H), 7.53-7.40 (m, 2H), 7.36 (d, J = 9.1 Hz, 1H), 7.06 (s, 1H), 5.04 (dd, J = 46.0, 8.9 Hz, 2H), 4.48 (d, J = 12.8 Hz, 2H), 4.21 (d, J = 13.7 Hz, 2H), 3.66 (s, 5H), 3.63-2.83 (m, 3H), 3.12 (d, J = 34.1 Hz, 3H), 2.92 (d, J = 16.3 Hz, 3H), 2.60 (d, J = 16.8 Hz, 3H), 2.22 (s, 4H), 2.03 (s, 1H), 1.79 (d, J = 6.8 Hz, 3H), 1.47 (d, J = 6.8 Hz, 3H), 1.16 (s, 2H). | D | C | D |
| 218 | 810.31 | 810.29 | 812.29 | 1H NMR (300 MHz, DMSO-d6) δ 11.07 (s, 1H), 8.81 (s, 1H), 8.03 (s, 1H), 7.94 (d, J = 2.5 Hz, 1H), 7.78-7.60 (m, 2H), 7.46 (d, J = 9.1 Hz, 1H), 7.33 (d, J = 2.2 Hz, 1H), 7.25 (dd, J = 8.6, 2.3 Hz, 1H), 7.01 (s, 1H), 5.07 (dd, J = 12.9, 5.4 Hz, 1H), 4.95 (q, J = 6.9 Hz, 1H), 4.48 (d, J = 12.7 Hz, 2H), 3.66 (s, 3H), 3.43 (t, J = 5.0 Hz, 4H), 2.88 (dt, J = 26.2, 9.8 Hz, 3H), 2.63-2.51 (m, 5H), 2.22 (s, 5H), 2.02 (d, J = 5.9 Hz, 1H), 1.90-1.70 (m, 3H), 1.46 (d, J = 6.8 Hz, 3H), 1.23 (s, 1H), 1.05 (d, J = 12.4 Hz, 2H). | D | C | D |
| 219 | 810.31 | 810.3 | 812.29 | 1H NMR (300 MHz, DMSO-d6) δ 11.09 (s, 1H), 8.84 (d, J = 23.8 Hz, 1H), 8.06 (s, 1H), 7.92 (s, 1H), 7.82-7.64 (m, 2H), 7.53-7.19 (m, 3H), 7.04 (d, J = 18.2 Hz, 1H), 5.08 (s, 1H), 4.98 (s, 1H), 4.48 (d, J = 12.8 Hz, 2H), 4.20 (d, J = 12.6 Hz, 2H), 3.66 (s, 3H), 3.59 (s, 1H), 3.40 (d, J = 20.8 Hz, 3H), 3.16 (s, 1H), 3.07 (s, 1H), 2.87 (d, J = 13.0 Hz, 3H), 2.56 (d, J = 13.0 Hz, 4H), 2.22 (s, 4H), 2.03 (s, 1H), 1.79 (s, 2H), 1.47 (d, J = 6.8 Hz, 3H), 1.24 (s, 1H), 1.11 (d, J = 44.7 Hz, 2H). | D | C | C |
| 220 | 797.27 | 797.3 | 799.3 | 1H NMR (300 MHz, DMSO-d6) δ 11.09 (s, 1H), 8.85 (s, 1H), 8.05 (s, 1H), 7.97-7.93 (m, 2H), 7.78-7.69 (m, 2H), 7.47 (d, J = 8.7 Hz, 1H), 7.32 (s, 1H), 7.5 Hz, 2H), 7.14 (s, 1H), 5.10-5.06 (m, 1H), 4.58 (s, 2H), 3.76-3.63 (m, 9H), 2.92-2.84 (m, 3H), 2.67-2.65 (m, 8H), 2.50-2.45 (m, 2H), 2.04-1.99 (m, 3H), 1.90-1.67 (m, 2H). | D | B | A |
| 221 | 926.2728638 | 812.28 | 814.27 | 1H NMR (400 MHz, DMSO-d6) δ 11.07 (s, 1H), 8.84 (s, 1H), 8.04 (s, 1H), 7.93 (s, 2H), 7.81-7.63 (m, 2H), 7.53-7.44 (m, 1H), 7.38-7.32 (m, 1H), 7.30-7.22 (m, 1H), 7.10 (s, 1H), 5.13-5.02 (m, 1H), 4.57 (s, 2H), 4.14-4.02 (m, 2H), 3.88-3.73 (m, 4H), 3.67 (s, 3H), 3.31-3.20 (m, 4H), 2.97-2.82 (m, 1H), 2.70-2.52 (m, 5H), 2.10-1.99 (m, 1H), 1.94-1.82 (m, 4H), 1.57-1.42 (m, 4H). | D | B | A |
| 222 | 745.15 | 745.2 | 747.2 | 1H NMR (400 MHz, DMSO-d6) δ 11.12 (s, 1H), 8.98 (s, 1H), 8.12 (s, 1H), 7.91-7.93 (m, 2H), 7.74-7.81 (m, 2H), 7.31-7.49 (m, 3H), 7.17 (s, 1H), 5.11-5.14 (m, 1H), 4.49-4.50 (m, 3H), 4.21-4.28 (m, 3H), 3.96-3.99 (m, 1H), 3.85-3.86 (m, 1H), 3.66(s, 3H), 3.53-3.59 (m, 3H), 2.91-3.04 (m, 3H), 2.65-2.68 (m, 3H), 2.01-2.06 (m, 1H). | D | C | C |
| 223 | 796.28 | 795.29 | 797.29 | 1H NMR (400 MHz, DMSO-d6) δ 11.07 (s, 1H), 8.83 (s, 1H), 8.03 (s, 1H), 7.96 (s, 1H), 7.72-7.67 (m, 2H), 7.46 (d, J = 8.8 Hz, 1H), 7.33 (s, 1H), 7.26 (s, | D | C | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 224 | 790.28 | 790.28 | 792.28 | 1H), 6.80 (s, 1H), 5.31-5.30 (m, 1H), 5.06-5.04 (m, 1H), 4.97-4.95 (m, 2H), 4.62-4.60 (m, 2H), 4.50-4.47 (m, 2H), 3.66 (s, 3H), 3.44 (s, 4H), 3.31 (s, 3H), 2.90-2.88 (m, 3H), 2.61-2.55 (m, 3H), 2.20-2.18 (m, 2H), 2.04-2.02 (m, 1H), 1.90-1.76 (m, 3H), 1.08-0.96 (m, 2H); | | | D |
| 225 | 804.31 | 804.3 | 806.3 | 1H NMR (300 MHz, DMSO-d6) δ 11.10 (s, 1H), 9.00 (s, 1H), 8.10 (d, J = 7.8 Hz, 2H), 8.04 (d, J = 2.5 Hz, 1H), 7.88 (d, J = 2.5 Hz, 1H), 7.78-7.56 (m, 3H), 7.36 (d, J = 2.3 Hz, 1H), 7.29-7.18 (m, 2H), 6.73 (s, 1H), 5.09 (dd, J = 12.8, 5.3 Hz, 1H), 4.33-4.30 (m, 2H), 3.70 (s, 3H), 3.46 (s, 4H), 3.02-2.83 (m, 1H), 2.74-2.69 (m, 3H), 2.57 (s, 4H), 2.18-216 (m, 2H), 2.07-1.98 (m, 1H), 1.74-1.70 (m, 3H), 1.25-1.23 (m, 1H), 0.97-0.94 (m, 2H). | D | | D |
| 226 | 745.15 | 745.2 | 747.2 | 1H NMR (300 MHz, DMSO-d6) δ 11.08 (s, 1H), 8.83 (s, 1H), 8.05 (s, 2H), 7.89-7.85 (m, 2H), 7.68 (d, J = 4.2 Hz, 1H), 7.54-7.52 (m, 2H), 7.34 (s, 1H), 7.22-7.21 (m, 1H), 7.07 (s, 1H), 6.33 (s, 1H), 5.26 (s, 2H), 5.10-5.06 (m, 1H), 4.47-4.43 (m, 2H), 3.66 (s, 3H), 3.46 (s, 4H), 2.88-2.83 (m, 3H), 2.60-2.51 (m, 4H), 2.20-2.18 (m, 2H), 2.09-2.07 (m, 1H), 1.87-1.77 (m, 3H), 1.07-1.05 (m, 2H); | B | C | C |
| 227 | 898.2228638 | 784.24 | 786.24 | 1H NMR (300 MHz, DMSO-d6) δ 11.09 (s, 1H), 7.93-7.83 (m, 2H), 7.81-7.75 (m, 2H), 7.56-7.43 (m, 3H), 7.16 (s, 1H), 5.10-5.06 (m, 1H), 4.52-4.19 (m, 6H), 3.98-3.83 (m, 2H), 3.64-3.56 (m, 4H), 3.03-2.81 (m, 3H), 2.66-2.61 (m, 5H), 2.02-1.96 (m, 1H). | D | C | A |
| 228 | 745.15 | 745.2 | 747.2 | 1H NMR (400 MHz, DMSO-d6) δ 11.06 (s, 1H), 9.01 (s, 1H), 8.08 (s, 1H), 8.01-7.89 (m, 2H), 7.78-7.63 (m, 2H), 7.54-7.47 (m, 1H), 7.12 (s, 1H), 6.81 (s, 1H), 6.72-6.63 (m, 1H), 5.14-5.05 (m, 1H), 4.74-4.65 (m, 1H), 4.33 (s, 2H), 4.35-4.28 (m, 2H), 4.16-4.07 (m, 2H), 3.90-3.83 (m, 2H), 3.75-3.64 (m, 4H), 3.32-3.20 (m, 2H), 2.97-2.81 (m, 1H), 2.72-2.53 (m, 5H), 2.07-1.96 (m, 1H), 1.95-1.86 (m, 2H), 1.53-1.40 (m, 2H). | D | B | D |
| 229 | 940.3028638 | 826.3 | 828.3 | 1H NMR (400 MHz, DMSO-d6) δ 11.07 (s, 1H), 8.86 (s, 1H), 8.05 (s, 1H), 7.99-7.97 (m, 1H), 7.92 (m, 1H), 7.74-7.72 (m, 1H), 7.67-7.65 (m, 1H), 7.47-7.45 (m, 1H), 7.32 (s, 1H), 7.25-7.23 (m, 1H), 7.12 (s, 1H), 5.08-5.04 (m, 1H), 4.57 (s, 2H), 3.68-3.64 (m, 7H), 3.39 (m, 8H), 2.92-2.83 (m, 1H), 2.66-2.65 (m, 4H), 2.56-5.49 (m, 10H), 2.02-1.99 (m 1H). | B | B | B |
| 230 | 840.34 | 840.31 | 842.31 | 1H NMR (400 MHz, DMSO-d6) δ 11.08 (s, 1H), 8.87 (s, 1H), 8.05 (s, 1H), 8.01-7.89 (m, 2H), 7.82-7.69 (m, 1H), 7.69-7.60 (m, 1H), 7.57-7.40 (m, 1H), 7.39-7.31 (m, 1H), 7.31-7.18 (m, 1H), 7.12 (s, 1H), 5.12-4.98 (m, 1H), 4.58 (s, 2H), 3.67 (s, 3H), 3.65-3.61 (m, 4H), 3.52-3.35 (m, 5H), 2.93-2.80 (m, 1H), 2.70-2.61 (m, 3H), 2.63-2.51 (m, 2H), 2.49-2.25 (m, 11H), 2.04-1.91 (m, 1H), 1.70-1.61 (m, 2H). | A | C | B |
| 231 | 804.1954793 | 758.22 | 760.22 | 1H NMR (300 MHz, DMSO-d6) δ 11.08 (s, 1H), 8.87 (s, 1H), 8.18-7.83 (m, 3H), 7.81-7.62 (m, 2H), 7.61-7.29 (m, 3H), 7.23-6.95 (m, 1H), 5.18-4.88 (m, 1H), 4.58-4.44 (m, 2H), 4.43-4.21 (m, 3H), 4.18-4.00 (m, 1H), 3.57 (s, 3H), 3.24-3.12 (m, 3H), 2.98-2.76 (m, 2H), 2.76-2.56 (m, 4H), 2.55 (s, 1H), 2.44-2.31 (m, 3H), 2.29-2.20 (m, 1H), 2.15-1.88 (m, 1H). | C | | D |
| 232 | 786.29 | 786.3 | 788.3 | 1H NMR (400 MHz, DMSO-d6) δ 10.86 (s, 1H), 8.89 (s, 1H), 8.71 (d, J = 8.4 Hz, 1H), 8.31 (d, J = 3.2 Hz, 1H), 8.06 (s, 1H), 7.94 (d, J = | D | C | B |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 233 | 803.29 | 803.29 | 805.29 | 2.4 Hz, 1H), 7.84 (d, J = 8.8 Hz, 1H), 7.74 (dd, J = 9.0, 2.4 Hz, 1H), 7.48 (d, J = 9.2 Hz, 1H), 7.40 (dd, J = 9.0, 2.8 Hz, 1H), 7.13 (s, 1H), 4.79-4.67 (m, 1H), 4.59 (s, 2H), 3.94 (d, J = 12.6 Hz, 2H), 3.66-3.61 (m, 7H), 2.91-2.74 (m, 3H), 2.66 (d, J = 4.8 Hz, 3H), 2.44-2.35 (m, 4H), 2.24-2.13 (m, 3H), 2.07-1.95 (m, 1H), 1.82-1.79 (m, 3H), 1.30-1.10 (m, 3H). | D | C | D |
| 234 | 769.22 | 769.2 | 771.1 | 1H NMR (300 MHz, DMSO-d6) δ 10.87 (s, 1H), 8.91(s, 1H), 8.14-7.95 (m, 4H), 7.78-7.75 (m, 1H), 7.66-7.63 (m, 1H), 7.52-7.49 (m, 1H), 7.16 (s, 1H), 6.83-6.78 (m, 2H), 4.66-4.56 (m, 1H), 4.50 (m, 2H), 3.82-3.81 (m, 4H), 3.33-3.31 (m, 1H), 2.83-2.60 (m, 8H), 2.40-2.38 (m, 4H), 2.3-2.00 (m, 5H), 1.92-1.78 (m, 3H), 1.25-1.14 (m, 4H). | A | | D |
| 235 | 791.27 | 791.2 | 793.1 | 1H NMR (400 MHz, DMSO-d6) δ 11.09 (s, 1H), 8.92 (s, 1H), 8.00-8.01(s, 1H), 7.93 (s, 1H), 7.77 (d, J = 9.2 Hz, 1H), 7.67 (d, J = 8.4 Hz, 1H), 7.51(d, J = 8.8 Hz, 1H), 7.41(s, 1H), 7.27(d, J = 7.2 Hz, 1H), 7.20(s, 1H), 5.06-5.10 (m, 1H), 4.56 (s, 3H), 4.37-4.39 (m, 1H), 4.02 (d, J = 11.6 Hz, 1H), 3.70 (s, 3H), 2.86-3.02 (m, 5H), 2.58-2.70 (m, 8H), 1.97-2.28 (m, 4H). | D | | D |
| 236 | 825.32 | 825.2 | 827.1 | 1H NMR (300 MHz, DMSO-d6) δ 9.58 (s, 1H), 9.31 (s, 1H), 8.95 (s, 1H), 8.36 (s, 1H), 8.12-7.92 (m, 3H), 7.63 (dd, J = 23.5, 8.8 Hz, 2H), 7.38-7.19 (m, 2H), 5.07 (dd, J = 12.7, 5.4 Hz, 1H), 4.51 (d, J = 12.5 Hz, 2H), 3.75 (s, 3H), 3.42 (s, 4H), 2.90-2.86 (m, 3H), 2.68-2.54 (m, 2H), 2.50 (s, 3H), 2.18-2.15 (m, H), 2.06-2.04 (m, 2H), 1.81-1.77 (m, 3H), 1.05-1.01 (m, 2H). | A | B | B |
| 237 | 743.17 | 743.1 | 745.1 | 1H NMR (400 MHz, DMSO-d6) δ 11.08 (s, 1H), 8.88 (s, 1H), 8.05 (m, 1H), 7.91-7.82 (m, 1H), 7.73-7.64(m, 2H), 7.52-7.40 (m, 1H), 7.39-7.29 (m, 1H), 7.29-7.20 (m, 1H), 7.06 (s, 1H), 5.12-5.01 (m, 1H), 4.91 (s, 2H), 3.72-3.58 (m, 7H), 3.49-3.42 (m, 4H), 2.95-2.80 (m, 1H), 2.64-2.51 (m, 6H), 2.49-2.27 (m, 8H), 2.20 (s, 3H), 2.09-1.96 (m, 1H), 1.80-1.55 (m, 2H). | B | C | B |
| 238 | 786.24 | 786.2 | 788.1 | 1H NMR (400 MHz, DMSO-d6) δ 11.09 (s, 1H), 8.84 (s, 1H), 8.02 (s, 1H), 7.99-7.82 (m, 2H), 7.82-7.63 (m, 2H), 7.62-7.28 (m 3H), 7.10 (s, 1H), 5.11-4.97 (m, 1H), 4.52-4.40 (m, 2H), 4.38-4.21 (m, 1H), 4.21-4.10 (m, 1H), 4.10-3.99 (m, 1H), 3.60 (s, 3H), 3.07-2.79 (m, 3H), 2.79-2.54 (m, 4H), 2.09-1.85 (m, 3H), 1.82-1.60 (m, 1H), 1.52-1.33 (m, 2H), 1.29-1.19 (m, 2H). | | C | D |
| 239 | 841.3054793 | 795.2 | 797.1 | 1H NMR (300 MHz, DMSO-d6) δ 11.12 (s, 1H), 8.87 (s, 1H), 8.06 (s, 1H), 7.96-7.95 (m, 2H), 7.82 (d, J = 8.4 Hz, 1H), 7.65-7.63 (m, 1H), 7.55-7.53 (m, 1H), 7.50 (s, 1H), 7.43 (d, J = 2.1 Hz, 1H), 7.11 (s, 1H), 5.10-5.05 (m, 1H), 4.57 (s, 2H), 4.48-4.26 (m, 4H), 3.62 (s, 4H), 2.96-2.86 (m, 1H), 2.67 (s, 4H), 2.61 (s, 1H), 2.49 (s, 4H), 2.33 (s, 3H), 2.04-2.02 (m, 1H), 1.96-1.76 (m, 4H). | | | D |
| 240 | 827.3 | 827.2 | 829.1 | 1H NMR (400 MHz, DMSO-d6) δ 11.08 (s, 1H), 8.83 (s, 1H), 8.14-7.92 (m, 4H), 7.67 (d, J = 8.8 Hz, 1H), 7.53 (d, J = 9.6 Hz, 1H), 7.33 (s, 1H), 7.24 (d, J = 2.0 Hz, 1H), 6.55 (s, 1H), 5.09-5.05 (m, 1H), 4.52-4.48 (m, 2H), 3.64-3.61 (m, 5H), 3.43-3.26 (m, 3H), 2.88-2.82 (m, 3H), 2.59-2.53 (m, 4H), 2.50-2.47 (m, 4H), 2.17 (d, J = 3.2 Hz, 2H), 2.02 (m, 1H), 1.75-1.72 (m, 3H), 1.04-1.01 (m, 2H). | B | B | B |
| | | | | 1H NMR (300 MHz, DMSO-d6) δ 11.08 (s, 1H), 8.86 (s, 1H), 8.04 (s, 1H), 7.95 (d, J = 5.6 Hz, 1H), 7.88 (d, J = 2.4 Hz, 1H), 7.77-7.74 (m, 1H), 7.64 (d, J = 8.6 Hz, 1H), 7.46 (d, J = 9.2 Hz, 1H), 7.30 (s, 1H), 7.23 (d, J = 8.6 Hz, 1H), 7.13 (s, 1H), 5.07-5.05 (m, 1H), 4.57 (s, 2H), 4.36 (s, 1H), 3.77-3.61 (m, 9H), 3.65 (s, 1H), 3.59 (s, 3H), 2.87 (t, J = 13.0 Hz, 1H), 2.66-2.65 (m, 6H), 2.56-2.55 (m, 2H), 2.31-2.29 (m, 1H), 1.94-1.92 (m, 1H), 1.61-1.54 (m, 4H). | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 241 | 826.31 | 826.2 | 828.1 | 1H NMR (400 MHz, DMSO-d6) δ 11.07 (s, 1H), 8.74 (s, 1H), 8.15-8.00 (m, 2H), 8.00-7.85 (m, 1H), 7.85-7.75 (m, 1H), 7.70-7.55 (m, 1H), 7.55-7.45 (m, 1H), 7.40-7.25 (m, 1H), 7.25-7.15 (m, 1H), 7.15-7.00 (m, 1H), 5.15-5.00 (m, 1H), 4.65-4.50 (m, 2H), 3.90-3.50 (m, 11H), 3.30-3.10 (m, 2H), 2.95-2.80 (m, 1H), 2.70-2.60 (m, 4H), 2.15-2.00 (m, 1H), 2.00-1.70 (m, 5H), 1.70-1.55 (m, 3H), 1.50-1.45 (m, 2H), 1.30-1.20 (m, 1H). | | C | B |
| 242 | 826.31 | 826.1 | 828.1 | 1H NMR (400 MHz, DMSO-d6) δ 11.07 (s, 1H), 8.85 (s, 1H), 8.05 (s, 1H), 8.00-7.90 (m, 2H), 7.80-7.70 (m, 1H), 7.70-7.60 (m, 1H), 7.60-7.50 (m, 1H), 7.15-7.05 (m, 2H), 7.05-6.95 (m, 1H), 5.10-5.00 (m, 1H), 4.5 (s, 2H), 4.10-3.95 (m, 2H), 3.75-3.65 (m, 5H), 3.65-3.50 (m, 5H), 3.00-2.80 (m, 1H), 2.80-2.60 (m, 4H), 3.60-3.55 (m, 1H), 2.10-1.90 (m, 3H), 1.90-1.70 (m, 4H), 1.70-1.50 (m, 2H), 1.50-1.20 (m, 3H). | | | D |
| 243 | 815.33 | 815.2 | 817.2 | 1H NMR (400 MHz, DMSO-d6) δ 10.88 (s, 1H), 8.88 (s, 1H), 8.43 (s, 1H), 8.24-7.91(m, 3H), 7.91-7.66 (m, 2H), 7.58-7.43 (m, 1H), 7.13 (s, 1H), 6.59-6.41 (m, 2H), 4.75-4.63 (m, 1H), 4.63-4.56 (m, 2H), 3.90 (m, 6H), 3.66 (m, 7H), 2.87-2.76 (m, 3H), 2.69-2.65 (m, 3H), 2.45-2.28 (s, 4H), 2.27-1.91 (m, 5H), 1.87-1.69 (m, 3H), 1.29-1.00 (m, 2H). | | A | A |
| 244 | 772.22 | 772.1 | | 1H NMR (400 MHz, DMSO-d6) δ 11.13 (s, 1H), 8.88 (s, 1H), 8.06 (s, 3H), 8.98 (d, J = 4 Hz, 1H), 7.85 (d, J = 6 Hz, 1H), 7.04 (s, 1H), 7.59 (s, 2H), 7.30 (m, 1H), 5.15 (m, 1H), 4.57 (s, 2H), 4.49 (s, 2H), 4.33 (m, 2H), 3.63 (s, 4H), 2.60 (m, 1H), 2.58 (s, 5H), 2.51 (s, 4H), 2.35 (s, 5H), 2.18 (m, 1H). | | A | D |
| 245 | 812.28 | 812.19 | 814.19 | 1H NMR (400 MHz, DMSO-d$_6$) δ 11.06 (s, 1H), 8.78 (s, 1H), 8.03 (s, 1H), 7.88 (d, J = 2.5 Hz, 1H), 7.73 (d, J = 9.1 Hz, 2H), 7.66 (d, J = 8.5 Hz, 1H), 7.46 (d, J = 9.1 Hz, 1H), 7.31 (s, 1H), 7.04 (s, 1H), 5.06 (m, 1H), 4.89 (s, 2H), 4.26 (d, J = 5.8 Hz, 1H), 4.08 (s, 2H), 3.67 (s, 3H), 3.41 (s, 4H), 2.86 (d, J = 12.4 Hz, 1H), 2.66 (s, 5H), 2.60 (s, 3H), 2.32 (d, J = 8.4 Hz, 3H), 2.03 (s, 1H), 1.52 (s, 4H), 1.39 (s, 1H). | | B | A |
| 246 | 783.24 | 783.3 | | 1H NMR (400 MHz, DMSO-d$_6$, ppm): δ11.07 (s, 1H), 9.08-8.73 (m, 1H), 8.15-8.01 (m, 1H), 8.01-7.88 (m, 2H), 7.79-7.67 (m, 1H), 7.67-7.59 (m, 1H), 7.51-7.39 (m, 1H), 7.22-7.05 (m, 1H), 6.78 (s, 1H), 6.70-6.55 (m, 1H), 5.10-5.00 (m, 1H), 4.59 (s, 2H), 4.25-4.00 (m, 2H), 3.91-3.40 (m, 10H), 3.24-2.98 (m, 3H), 2.93-2.81 (m, 1H), 2.72-2.65 (m, 4H), 2.65-2.55 (m, 2H), 2.09-1.90 (m, 1H), 1.29-1.10 (m, 2H). | | A | A |
| 247 | 812.28 | 812.3 | | 1H NMR (400 MHz, DMSO-d$_6$, ppm): δ11.07 (s, 1H), 8.82 (s, 1H), 8.03 (s, 1H), 7.99-7.88 (m, 2H), 7.76-7.71 (m, 1H), 7.67-7.61 (m, 1H), 7.52-7.42 (m, 1H), 7.08 (s, 1H), 6.80 (s, 1H), 6.71-6.62 (m, 1H), 5.10-5.01 (m, 1H), 4.58 (s, 2H), 4.52-4.42 (m, 3H), 4.29-4.17 (m, 2H), 3.89-3.81 (m, 2H), 3.67 (s, 4H), 3.49-3.47 (m, 2H), 2.91-2.80 (m, 3H), 2.71-2.65 (m, 4H), 2.61-2.55 (m, 2H), 1.75-1.65 (m, 3H), 1.55-1.46 (m, 2H), 1.11-1.02 (m, 1H). | | B | A |
| 248 | 823.31 | 823.2 | | 1H NMR (300 MHz, DMSO-d6) δ 11.09 (s, 1H), 8.84 (s, 1H), 8.13-7.88 (m, 3H), 7.83-7.72 (m, 1H), 7.68-7.58 (m, 1H), 7.53-7.43 (m, 1H), 7.21-7.06 (s, 1H), 6.80 (s, 1H), 6.66 (m, 1H), 5.07 (m, 1H), 4.73-4.38 (m, 5H), 4.25-4.00 (s, 5H), 3.83-3.63 (s, 5H), 3.02-2.60 (m, 8H), 2.35-2.18 (s, 2H), 2.15-1.92 (m, 1H), 1.85-1.43 (m, 3H), 1.14-0.87 (m, 2H). | | | D |
| 249 | 793.28 | 793.1 | 795.2 | 1H NMR (400 MHz, DMSO-d6) δ 11.08 (s, 1H), 8.90 (s, 1H), 8.18-7.92 (m, 3H), 7.80 (d, J = 9.2 Hz, 1H), 7.65 (d, J = 8.4 Hz, 1H), 7.50 (d, J = 9.2 Hz, 1H), 7.38-7.17 (m, 2H), 5.76 (s, 1H), 5.07-5.03 (m, 1H), 4.07-4.02 (m, 4H), 3.66-3.65 (m, 7H), 3.11-3.08 (m, 2H), 3.03-2.77 (m, 4H), 2.39 (s, 2H), 2.17 | | | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 250 | 825.32 | 825.2 | 827.1 | (d, J = 7.2 Hz, 1H), 2.08 (s, 3H), 1.91 (s, 1H), 1.80-1.72 (m, 1H), 1.24 (s, 3H), 1.15-1.13 (m, 1H), 0.85-0.83 (m, 2H). | | B | A |
| 251 | 827.3 | 827.1 | 829.1 | 1H NMR (300 MHz, DMSO-d6) δ 11.08 (s, 1H), 8.86 (s, 1H), 8.05 (s, 2H), 7.98 (s, 2H), 7.75 (d, J = 2.1 Hz, 1H), 7.72 (d, J = 2.1 Hz, 1H), 7.64 (d, J = 8.4 Hz, 1H), 7.31 (s, 1H), 7.22 (d, J = 8.7 Hz, 1H), 7.09 (s, 1H), 5.09-5.03 (m, 1H), 4.58 (s, 2H), 4.44-4.31 (m, 2H), 4.07-4.02 (m, 2H), 3.64 (s, 4H), 2.96-2.85 (m, 3H), 2.67-2.65 (m, 5H), 2.39 (s, 4H), 2.19-2.16 (m, 2H), 2.03-2.01 (m, 1H), 1.85-1.76 (m, 3H), 1.29-1.17 (m, 5H). | | | |
| 252 | 812.28 | 812.2 | 814.2 | 1H NMR (400 MHz, DMSO-d6) δ 11.08 (s, 1H), 8.81 (s, 1H), 8.03 (s, 1H), 7.96 (d, J = 4.6 Hz, 1H), 7.90 (d, J = 2.4 Hz, 1H), 7.77 (d, J = 9.0 Hz, 1H), 7.69 (t, J = 7.8 Hz, 1H), 7.48 (d, J = 9.2 Hz, 1H), 7.37-7.28 (m, 2H), 7.12 (s, 1H), 5.08 (m, 1H), 4.57 (s, 2H), 4.27 (s, 1H), 4.11 (s, 2H), 3.68 (s, 3H), 3.23-3.21 (m, 5H), 2.85-2.81 (m, 2H), 2.73-2.63 (m, 8H), 2.58 (d, J = 17.2 Hz, 2H), 2.34 (s, 2H), 1.52 (s, 4H). | | B | A |
| 253 | 811.3 | 811.3 | 813.3 | 1H NMR (400 MHz, DMSO-d6) δ 11.06 (s, 1H), 8.80 (s, 1H), 8.01 (s, 1H), 8.01-7.87 (m, 2H), 7.87-7.69 (m, 1H), 7.69-7.58 (m, 1H), 7.58-7.31 (m, 1H), 7.06 (s, 1H), 6.85-6.72 (m, 1H), 6.70-6.51 (m, 1H), 5.13-4.85 (m, 1H), 4.56 (s, 2H), 4.55-4.37 (m, 3H), 4.31-4.09 (m, 2H), 3.99-3.77 (m, 2H), 3.65 (s, 3H), 3.53-3.40 (m, 2H), 2.98-2.71 (m, 3H), 2.71-2.52 (m, 4H), 2.13-1.87 (m, 1H), 1.77-1.58 (m, 3H), 1.58-1.35 (m, 2H), 1.31-1.25 (m, 2H), 1.18-0.90 (m, 2H). | | A | A |
| 254 | 844.75 | 844.1 | 846.1 | $^1$H NMR (400 MHz, DMSO-d$_6$, ppm): δ 11.05 (s, 1H), 8.83 (s, 1H), 8.05 (s, 1H), 8.00-7.95 (m, 2H), 7.80-7.70 (m, 1H), 7.70-7.60 (m, 1H), 7.55-7.45 (m, 1H), 7.40-7.30 (m, 1H), 7.30-7.20 (m, 1H), 7.15-7.05 (m, 1H), 5.10-5.00 (m, 1H), 4.65 (s, 2H), 4.15-4.00 (m, 2H), 3.75-3.65 (m, 3H), 3.65-3.60 (m, 4H), 3.05-2.85 (m, 3H), 2.70-2.60 (m, 4H), 2.60-2.55 (m, 1H), 2.45-2.34 (m, 4H), 2.25-2.15 (m, 3H), 2.10-2.00 (m, 1H), 2.00-1.80 (m, 3H), 1.30-1.10 (m, 2H); | | C | D |
| 255 | 784.23 | | | $^1$HNMR (300 MHz, DMSO-d6) δ 11.11 (s, 1H), 7.85-7.81 (m, 2H), 7.67 (d, J = 8.1 Hz, 1H), 7.34-7.25 (m, 3H), 7.10 (d, J = 9.0 Hz, 1H), 6.79 (s, 1H), 5.23-4.86 (m, 5H), 4.10-4.06 (m, 2H), 3.63 (s, 2H), 3.37 (s, 3H), 3.27-2.97 (m, 7H), 2.64-2.52 (m, 5H), 2.21-2.20 (m, 2H), 2.05-2.04 (m, 1H), 1.82-1.72 (m, 3H), 1.30-1.12 (m, 2H) | | C | A |
| 256 | 823.31 | 823.3 | | 1H NMR (400 MHz, DMSO-d6) δ 11.09 (s, 1H), 8.87 (s, 1H), 8.06 (s, 1H), 7.96-7.95 (m, 2H), 7.73 (d, J = 6.8 Hz, 1H), 7.65 (d, J = 2.1 Hz, 1H), 7.47 (d, J = 9.2 Hz, 1H), 6.81 (s, 1H), 6.72 (s, 1H ), 5.06-5.03 (m, 1H), 4.67-4.65 (m, 3H), 4.33-4.31 (m, 2H), 4.22-4.17 (m, 2H), 3.86-3.84 (m, 2H), 3.69 (s, 4H), 3.34-3.30 (m, 2H), 2.92-2.80 (m, 1H), 2.60 (m, 3H), 2.53-2.51 (m, 2H), 2.09 (s, 1H), 2.01-1.98 (m, 1H), 1.88-1.87 (m, 2H), 1.45-1.43 (m, 2H). | | B | A |
| 257 | 824.34 | | | 1H NMR (300 MHz, DMSO-d6) δ 11.09 (s, 1H), 8.85 (s, 1H), 8.04-7.80 (m, 3H), 7.74-7.64 (m, 1H), 7.58-7.35(m, 2H), 7.11-6.95 (m, 2H), 6.80 (s, 1H), 5.07 (m, 1H), 4.60 (s, 2H), 4.48-4.30 (m, 2H), 4.17 (s, 4H), 3.60 (s, 4H), 2.87-2.66 (m, 5H), 2.66-2.53 (m, 4H), 2.32-2.09 (s, 3H), 2.01-1.95 (m, 2H), 1.68-1.58 (m, 2H), 1.56-1.37 (s, 1H), 1.04-0.87 (m, 2H) | | | |
| | | | | 1H NMR (400 MHz, DMSO-d6) δ 11.09 (s, 1H), 8.86 (s, 1H), 8.05 (s, 1H), 7.90 (s, 1H), 7.76-7.61 (m, 2H), 7.47 (d, J = 9.1 Hz, 1H), 7.35-7.21 (m, 2H), 7.07 (s, 1H), 5.07 (dd, J = 12.9, 5.4 Hz, 1H), 4.92 (s, 2H), 4.13 (d, J = 12.5 Hz, 2H), 3.67 (s, 4H), 3.58 (s, 4H), 2.90 (t, J = 11.8 Hz, 3H), 2.19 (s, 4H), 2.03-1.96 (m, 1H), 1.86 (dd, J = 30.2, 14.9 Hz, 4H), 1.26 (d, J = 14.3 Hz, 3H), 0.87 (s, 7H). | | A | B |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 258 | 837.34 | | | 1H NMR (400 MHz, DMSO-d6) δ 11.0 (s, 1H), 8.85 (s, 1H), 8.05 (s, 1H), 7.94 (s, 1H), 7.78-7.75(m, 2H), 7.48 (d, J = 9.2 Hz, 1H), 7.36 (s, 2H), 7.27 (d, J = 8.8 Hz, 1H), 5.11-5.08 (m, 2H), 4.53-4.50 (m, 2H), 3.67 (s, 3H), 3.35-3.32 (m, 5H), 3.30-3.28 (m, 2H), 2.89-2.85 (m, 3H), 2.83 (s, 3H), 2.61-2.57 (m, 6H), 2.23 (s, 2H), 2.03-1.96 (m, 2H), 1.90-1.82 (m, 3H), 1.09-1.02 (m, 2H). | | | D |
| 259 | 837.34 | | | 1H NMR (400 MHz, DMSO-d6) δ 11.08 (s, 1H), 8.84 (s, 1H), 8.04 (s, 1H), 7.92 (s, 1H), 7.82-7.80 (m, 1H), 7.68 (d, J = 8.4 Hz, 1H), 7.47 (d, J = 9.2 Hz, 1H), 7.35 (s, 2H), 7.26 (s, 1H), 5.09-5.05 (m, 2H ), 4.50-4.40 (m, 2H), 3.65 (s, 3H), 3.38-3.37 (m, 5H), 3.31 (s, 3H), 2.87-2.72 (m, 3H), 2.71 (s, 3H), 2.55-2.50 (m, 5H), 2.19 (s, 2H), 2.08-1.96 (m, 2H), 1.88-1.78 (m, 3H), 1.09-1.01 (m, 2H). | | C | D |
| 260 | 811.3 | 811.27 | 813.2 | $^1$H NMR (300 MHz, DMSO-d$_6$) δ 11.10 (s, 1H), 8.89 (s, 1H), 8.05 (m, 2H), 7.93 (d, J = 4.0 Hz, 1H), 7.70 (m, 2H), 7.46 (d, J = 2.9 Hz, 1H), 7.30 (t, 2H), 7.12 (s, 1H), 5.07 (m, 1H), 4.58 (s, 2H), 3.67 (m, 9H), 2.87 (t, 4H), 2.65 (m, 4H), 2.40 (s, 4H), 2.23 (m, 2H), 2.04 (m, 1H), 1.85 (m, 3H), 1.32 (m, 2H). | | A | B |
| 261 | 839.35 | 839.33 | 841.34 | $^1$H NMR (300 MHz, DMSO-d$_6$, ppm): δ 11.06 (s, 1H), 8.83 (s, 1H), 8.03 (s, 1H), 7.99-7.82 (m, 2H), 7.85-7.71 (m, 1H), 7.71-7.62(m, 1H), 7.53-7.41 (m, 1H), 7.33-7.28 (m, 1H), 7.28-7.19 (m, 1H), 7.11 (s, 1H), 5.11-5.00 (m, 1H), 4.56 (s, 2H), 4.19-4.01 (m, 2H), 3.71-3.50 (m, 9H), 2.99-2.80 (m, 3H), 2.70-2.61 (m, 4H), 2.03-1.77 (m, 5H), 1.34-1.18 (s, 3H), 0.85 (s, 7H); | | | D |
| 262 | 810.31 | 839.2 | 841.2 | $^1$H NMR (400 MHz, DMSO-d6) δ 11.09 (s, 1H), 8.77 (s, 1H), 8.04 (s, 1H), 7.90-7.79 (m, 2H), 7.65 (d, J = 8.4 Hz, 1H), 7.55 (dd, J = 9.0, 2.4 Hz, 1H), 7.40 (d, J = 9.2 Hz, 1H), 7.31 (d, J = 2.4 Hz, 1H), 7.29-7.21 (m, 1H), 6.27-6.22 (m, 2H), 5.06 (dd, J = 13.0, 5.4 Hz, 1H), 4.05 (d, J = 12.6 Hz, 2H), 3.70-3.50 (m, 10H), 2.87 (m, 4H), 2.73(s, 4H), 2.39-2.36 (m, 5H), 2.18-2.16 (m, 2H), 2.02-2.00 (m, 1H), 1.91-1.82 (m, 3H), 1.33-1.06 (m, 3H). | | A | A |
| 263 | 839.35 | 839.2 | 841.2 | 1HNMR (400 MHz, DMSO-d6) δ 11.09 (s, 1H), 8.86 (s, 1H), 8.06 (s, 1H), 7.96 (m, 2H), 7.75-7.63 (m, 3H), 7.32 (m, 1H), 7.23 (m, 1H), 7.03 (s, 1H), 5.07 (m, 1H), 4.55 (s, 2H), 4.05-4.03 (m, 2H), 3.64 (s, 4H), 3.03-2.82 (m, 3H), 2.67-2.64 (m, 3H), 2.63-2.53 (m, 2H), 2.46-2.34 (m, 4H), 2.26-2.10 (m, 2H), 2.08-1.78 (m, 4H), 1.57 (d, J = 6.8 Hz, 6H), 1.23-1.08 (m, 3H); | | B | B |
| 264 | 812.28 | 812.2 | 814.2 | $^1$HNMR (400 MHz, DMSO-d$_6$) δ 11.09 (s, 1H), 8.85 (s, 1H), 8.05 (s, 1H), 7.95 (dd, J = 9.6, 3.6 Hz, 2H), 7.74 (dd, J = 9.1, 2.4 Hz, 1H), 7.67 (dd, J = 8.5, 7.1 Hz, 1H), 7.47 (d, J = 9.2 Hz, 1H), 7.34 (t, J = 7.7 Hz, 2H), 7.10 (s, 1H), 5.10 (dd, J = 12.9, 5.4 Hz, 1H), 4.58 (s, 2H), 4.09 (d, J = 13.5 Hz, 2H), 3.74 (dd, J = 8.5, 4.5 Hz, 2H), 3.68 (s, 3H), 3.61-3.45 (m, 2H), 3.27 (s, 2H), 3.11-3.09 (m, 2H), 2.94-2.80 (m, 1H), 2.66 (d, J = 4.6 Hz, 3H), 2.63-2.52 (m, 2H), 2.00-1.96 (m, 3H), 1.85-1.83 (m, 2H), 1.64-1.63 (m, 2H), 1.43-1.41 (m, 2H). | | A | A |
| 265 | 854.36 | 854.33 | 856.33 | $^1$H NMR (400 MHz, DMSO-d$_6$) δ 11.61 (s, 1H), 11.07 (s, 1H), 8.08 (s, 1H), 7.93 (s, 1H), 7.63 (d, J = 8.2 Hz, 1H), 7.51 (d, J = 7.4 Hz, 2H), 7.43 (d, J = 8.8 Hz, 1H), 7.28-7.21 (m, 3H), 6.18 (s, 1H), 5.04-5.01 (m, 1H), 4.57 (s, 2H), 4.08-4.06 (m, 2H), 3.68-3.66 (m, 6H), 3.32-3.31 (m, 5H), 2.92-2.86 (m, 3H), 2.58 (s, 2H), 2.32-2.31 (m, 2H), 2.02-1.98 (m, 1H), 1.78-1.75 (m, 3H), 1.23-1.13 (m, 4H), 0.83 (s, 5H); | | B | B |
| 266 | 839.35 | 839.47 | 841.47 | $^1$H NMR (400 MHz, DMSO-d$_6$, ppm): δ11.06 (s, 1H), 8.83 (s, 1H), 8.02 (s, 1H), 8.00-7.87 (m, 2H), 7.87-7.69 (m, 1H), 7.69-7.58 (m, 1H), 7.51-7.45 (m, 1H), 7.41-7.31 (m, 2H), 7.12 (s, 1H), 5.13-5.02 (m, 1H), 4.56 (s, 2H), 3.80- | | A | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 267 | 855.35 | 855.2 | 857.2 | 3.71 (m, 2H), 3.70-3.68 (m, 3H), 3.67-3.52 (m, 4H), 2.95-2.80 (m, 3H), 2.71-2.62 (m, 4H), 2.63-2.51 (m, 4H), 2.09-1.95 (m, 1H), 1.90-1.72 (m, 3H), 1.55-1.31 (m, 2H), 1.30-1.20 (m, 1H), 0.90 (s, 6H) | | | |
| 268 | 869.38 | 869.35 | | $^1$HNMR (300 MHz, DMSO-d6) δ 11.45 (s, 1H), 11.08 (s, 1H), 8.85 (s, 1H), 8.06 (s, 1H), 7.96 (s, 1H), 7.78 (d, J = 9.0 Hz, 1H), 7.64 (d, J = 8.4 Hz, 1H), 7.48 (d, J = 9.0 Hz, 1H), 7.30-7.16 (m, 3H), 5.13-5.03 (m, 1H), 4.60 (s, 2H), 4.11 (d, J = 2.4 Hz, 2H), 3.68 (s, 3H), 3.60 (s, 6H), 3.12 (s, 4H), 2.93-2.89 (m, 3H), 2.51-2.50 (m, 3H), 2.09-1.81 (m, 4H), 1.28-1.24 (m, 2H), 0.80 (s, 6H) | | | |
| 269 | 803.29 | 803.25 | 805.25 | 1HNMR (400 MHz, DMSO-d6) δ 11.09 (s, 1H), 8.85 (s, 1H), 8.06 (s, 1H), 7.94-7.92 (m, 2H), 7.78-7.76 (m, 1H), 7.49-7.48 (m, 1H), 7.38 (s, 1H), 7.26 (s, 1H), 7.14 (s, 1H), 5.07-5.05 (m, 1H), 4.59 (s, 3H), 3.97 (s, 4H), 3.69 (s, 3H), 3.63-2.59 (m, 6H), 2.96-2.82 (m, 1H), 2.70-2.60 (m, 7H), 2.02 (m, 1H), 1.93-1.57 (m, 4H), 1.43-1.32 (m, 2H), 0.98-0.82 (m, 7H). | | | |
| 270 | 825.37 | 825.20 | 827.20 | $^1$H NMR (400 MHz, DMSO-d$_6$, ppm)δ 10.87 (s, 1H), 8.88 (s, 1H), 8.61-8.55 (m, 1H), 8.06 (s, 1H), 7.96-7.94 (m, 2H), 7.75-7.73 (m, 1H), 7.48-7.45 (m, 1H), 7.19-7.10 (m, 4H), 4.76-4.75 (m, 1H), 4.59 (s, 2H), 3.87-3.60 (m, 7H), 3.40 (s, 1H), 2.91-2.73 (m, 1H), 2.72-2.61 (m, 5H), 2.58-2.56 (m, 2H), 2.46-2.32 (m, 4H), 2.28-2.18 (m, 1H), 2.16-1.98 (m, 2H), 1.87-1.79 (m, 2H), 1.79-1.69 (m, 1H), 1.38-1.21 (m, 2H). | B | A | A |
| 271 | 813.27 | 813.10 | 815.10 | $^1$H NMR (400 MHz, DMSO-d$_6$) δ 10.94 (s, 1H), 8.85 (s, 1H), 8.03 (d, J = 8.6 Hz, 2H), 7.92 (s, 1H), 7.77 (m 1H), 7.49 (s, 2H), 7.14 (d, J = 16.8 Hz, 3H), 7.03 (m, 2H), 5.03 (s, 1H), 4.58 (s, 2H), 4.31 (d, J = 11.4 Hz, 3H), 3.67 (s, 6H), 2.96-2.83 (m, 1H), 2.75 (s, 2H), 2.65 (d, J = 4.6 Hz, 4H), 2.53 (s, 1H), 2.42-2.29 (m, 1H), 1.79 (m, 3H), 1.32-1.21 (m, 2H), 0.87 (s, 6H); | B | B | C |
| 272 | 813.27 | 813.20 | 815.10 | 1H-NMR (300 MHz, DMSO-d6) δ11.09 (s, 1H), 8.92 (s, 1H), 8.09 (s, 1H), 7.99-7.85 (m, 2H), 7.78-7.62 (m, 2H), 7.40 (dd, J = 35.6, 8.1 Hz, 2H), 7.19 (d, J = 21.3 Hz, 2H), 5.09 (dd, J = 12.9, 5.4 Hz, 1H), 4.55 (s, 2H), 4.42 (d, J = 13.1 Hz, 1H), 4.22 (d, J = 12.9 Hz, 1H), 3.89 (d, J = 11.3 Hz, 1H), 3.58 (s, 4H), 3.49 (t, J = 11.0 Hz, 1H), 3.15 (s, 3H), 3.00-2.82 (m, 2H), 2.62 (dd, J = 29.8, 9.7 Hz, 10H), 2.46 (s, 3H), 2.10-1.96 (m, 1H). | A | B | B |
| 273 | 787.28 | 787.20 | 789.20 | 1H-NMR (300 MHz, DMSO-d6) δ11.10 (s, 1H), 8.92 (s, 1H), 8.09 (s, 1H), 7.94 (s, 1H), 7.88 (d, J = 2.4 Hz, 1H), 7.78 (dd, J = 9.1, 2.4 Hz, 1H), 7.66 (d, J = 8.5 Hz, 1H), 7.43 (d, J = 9.1 Hz, 1H), 7.27 (s, 1H), 7.16 (s, 2H), 5.08 (dd, J = 12.9, 5.4 Hz, 2H), 4.56 (s, 2H), 4.44 (d, J = 13.1 Hz, 1H), 4.23 (d, J = 12.3 Hz, 1H), 3.90 (d, J = 11.4 Hz, 1H), 3.56 (s, 3H), 3.48 (d, J = 11.3 Hz, 1H), 3.03-2.82 (m, 2H), 2.75-2.63 (m, 4H), 2.56 (dd, J = 11.4, 6.7 Hz, 11H), 2.45 (s, 2H), 2.10-1.98 (m, 1H). | B | C | C |
| 274 | 813.31 | 813.20 | 815.20 | 1HNMR (400 MHz, DMSO-d6) δ 11.09 (s, 1H), 8.69 (s, 1H), 8.34 (s, 1H), 8.04 (s, 1H), 7.65 (d, J = 8.4 Hz, 1H), 7.51 (d, J = 4.4 Hz, 1H), 7.42 (d, J = 16.0 Hz, 2H), 7.22 (d, J = 2.0 Hz, 1H), 7.00(d, J = 8.8 Hz, 1H), 5.18 (s, 1H), 5.06-5.05 (m, 1H), 2.66 (s, 4H), 2.19-2.18 (m, 3H), 2.01-2.00 (m, 1H), 1.85-1.82 (m, 3H), 1.31-1.25 (m, 2H); | D | | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 275 | 803.29 | 803.20 | 805.20 | (m, 3H), 2.61-2.60 (m, 4H), 2.03-2.01 (m, 1H), 1.92-1.75 (m, 3H), 1.32-1.25 (m, 3H), 0.80 (s, 6H); | B | C | A |
| 276 | 785.30 | 785.20 | 787.20 | $^1$HNMR (300 MHz, DMSO-d6) δ 10.83 (s, 1H), 8.86 (s, 1H), 8.69 (d, J = 8.4 Hz, 1H), 8.05 (s, 1H), 6.88-6.81 (m, 2H), 7.74 (s, 2H), 7.33-7.28 (m, 1H), 7.12 (s, 1H), 6.88-6.81 (m, 2H), 4.75-4.72 (m, 1H), 4.59 (s, 2H), 3.68-3.64 (m, 7H), 3.32-3.20 (m, 2H), 2.80-2.72 (m, 7H), 2.65-2.57 (m, 4H), 2.18-2.02 (m, 4H), 1.76-1.72 (m, 4H), 1.38-1.15 (m, 2H); | A | C | D |
| 277 | 803.29 | 803.20 | 805.10 | $^1$HNMR(300 MHz, DMSO-d$_6$, ppm)10.83(s, 1H), 8.88 (s, 1H), 8.44(d, J = 8.4 Hz, 1H), 8.06(s, 1H), 7.95 (t, J = 4.0 Hz, 2H), 7.74(dd, J = 9.0, 3.2 Hz, 3H), 7.48(d, J = 9.1 Hz, 1H), 7.12(s, 1H), 6.96(d, J = 8.8 Hz, 2H), 4.82-4.67(m, 1H), 4.59(s, 2H), 3.87(d, J = 12.3 Hz, 2H), 3.68(s, 3H), 3.64(s, 3H), 2.84-2.71(m, 3H), 2.66(d, J = 4.6 Hz, 3H), 2.39(s, 4H), 2.14(d, J = 23.7 Hz, 3H), 2.07-1.91(m, 2H), 1.81(d, J = 11.5 Hz, 3H), 1.24(s, 3H), 1.18(d, J = 13.5 Hz, 2H). | A | C | B |
| 278 | 787.28 | 787.20 | 789.10 | 1H-NMR (400 MHz, DMSO-d6) δ 10.87 (s, 1H), 8.88 (s, 1H), 8.47 (dd, J = 8.1, 3.5 Hz, 1H), 8.07-7.91 (m, 2H), 7.74 (d J = 9.1 Hz, 1H), 7.48 (d, J = 9.2 Hz, 1H), 7.22-7.01 (m, 4H), 4.75-4.68 (m, 1H), 4.59 (s, 2H), 3.68-3.64 (m, 9H), 2.79-2.71 (m, 1H), 2.66 (d, J = 4.7 Hz, 6H), 2.40 (s, 4H), 2.17 (d, J = 19.2 Hz, 2H), 2.12-1.93 (m, 2H), 1.89-1.63 (m, 3H), 1.30-1.12 (m, 3H | A | C | C |
| 279 | 854.37 | 854.20 | 856.20 | $^1$H NMR (300 MHz, DMSO-d$_6$ ppm) δ10.84 (s, 1H), 9.07 (d, J = 8.4 Hz, 1H), 8.88 (s, 1H), 8.05-7.93 (m, 3H), 7.84-7.72 (m, 2H), 7.47 (d, J = 9.3 Hz, 1H), 7.35 (d, J = 9.0 Hz, 1H), 7.12 (s, 1H), 4.81-4.76 (m, 1H), 4.58-4.48 (m, 4H), 3.67-3.62 (m, 6H), 3.06-3.02 (t, J = 12.5 Hz, 2H), 2.98-2.74 (m, 1H), 2.68 (d, J = 4.8 Hz, 3H), 2.54 (s, 1H), 2.39 (s, 4H), 2.27-2.16 (m, 3H), 2.01-1.82 (m, 4H), 1.23(s, 1H), 1.14-1.07 (m, 2H). | B | B | B |
| 280 | 854.37 | 854.20 | 856.20 | $^1$HNMR (300 MHz, DMSO-d6) δ 11.07 (s, 1H), 8.84 (s, 1H), 8.05 (s, 1H), 7.91 (d, J = 2.4 Hz, 2H), 7.76 (d, J = 8.4 Hz, 1H), 7.65 (d, J = 8.4 Hz, 1H), 7.47 (d, J = 9.3 Hz, 1H), 7.31 (s, 1H), 7.21 (d, J = 8.4 Hz, 1H), 7.13 (s, 1H), 5.03-5.01 (m, 1H), 4.58 (s, 2H), 3.68 (s, 3H), 3.58 (s, 4H), 3.41 (s, 4H), 2.95-2.93 (m, 1H), 2.67-2.55 (m, 13H), 2.34-2.32 (m, 2H), 2.02-1.98 (m, 1H), 1.03 (s, 6H | B | B | B |
| 281 | 787.28 | 787.20 | 789.10 | $^1$H NMR (400 MHz, DMSO-d$_6$) δ 11.10 (s, 1H), 8.86 (s, 1H), 8.04 (s, 1H), 7.95 (m, 1H), 7.89 (m, 1H), 7.77 (m, 1H), 7.76 (s, 1H), 7.74 (m, 1H), 7.67 (d, J = 8.0 Hz, 1H), 7.30 (d, 1H), 7.23 (d, J = 8.0, 1H), 5.09 (m, 1H), 4.57 (s, 2H), 3.65 (s, 3H), 3.61 (d, 4H), 3.34 (m, 5H), 2.88(m, 1H), 2.67 (m, 7H), 2.57 (m, 5H), 2.51 (s, 2H), 2.02 (t, 1H), 1.02 (s, 6H). | B | C | A |
| 282 | 791.27 | 791.20 | 793.10 | $^1$H NMR (300 MHz, DMSO-d$_6$) δ 10.95 (s, 1H), 8.86 (s, 1H), 8.61 (d, J = 5.1 Hz, 2H), 8.30 (s, 1H), 8.06 (s, 1H), 8.00-7.94 (m, 2H), 7.75 (d, J = 9.0 Hz, 1H), 7.47 (d, J = 9.0 Hz, 1H), 7.12 (s, 1H), 4.80-4.77 (m, 1H), 4.59 (s, 2H), 4.51-4.47 (m, 2H), 3.68-3.67 (m, 4H), 2.66 (d, J = 4.5 Hz, 3H), 3.33-3.32 (m, 1H), 3.04-3.00 (m, 1H), 2.96-2.75 (m, 2H), 2.51-2.49 (m, 4H), 2.19-2.13 (m, 4H), 2.00-1.81 (m, 4H), 1.23-1.17 (m, 2H | B | B | B |
| | | | | $^1$HNMR (300 MHz, DMSO-d6) δ 11.07 (s, 1H), 9.14 (s, 1H), 8.94 (s, 1H), 8.42 (s, 1H), 8.04-8.00 (m, 3H), 7.69-7.66 (m, 2H), 7.33 (s, 1H), 7.27 (d, J = 8.0 Hz, 1H), 5.10-5.08 (m, 1H), 4.29-4.27 (m, 2H), 3.70 (s, 3H), 3.29 (s, 9H), 2.88-2.84 (m, 1H), 2.66-2.61 (m, 4H), 2.16 (s, 2H), 2.03-2.01 (m, 1H), 1.66-1.63 (m, 3H), 0.92-0.89 (m, 2H) | | | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 283 | 824.34 | 824.20 | 826.10 | $^1$H NMR (300 MHz, DMSO-d$_6$) δ 10.95 (s, 1H), 8.86 (s, 1H), 8.61 (d, J = 5.1 Hz, 2H), 8.30 (s, 1H), 8.06 (s, 1H), 8.00-7.94 (m, 2H), 7.75 (d, J = 9.0 Hz, 1H), 7.47 (d, J = 9.0 Hz, 1H), 7.12 (s, 1H), 4.80-4.77 (m, 1H), 4.59 (s, 2H), 4.51-4.47 (m, 2H), 3.68-3.67 (m, 7H), 3.33-3.32 (m, 1H), 3.04-3.00 (m, 1H), 2.96-2.75 (m, 1H), 2.66 (d, J = 4.5 Hz, 3H), 2.51-2.49 (m, 4H), 2.19-2.13 (m, 4H), 2.00-1.81 (m, 4H), 1.23-1.17 (m, 2H | | | D |
| 284 | 831.35 | 831.20 | 833.20 | $^1$H NMR (300 MHz, DMSO-d$_6$) δ 10.95 (s, 1H), 8.86 (s, 1H), 8.61 (d, J = 5.1 Hz, 2H), 8.30 (s, 1H), 8.06 (s, 1H), 8.00-7.94 (m, 2H), 7.75 (d, J = 9.0 Hz, 1H), 7.47 (d, J = 9.0 Hz, 1H), 7.12 (s, 1H), 4.80-4.77 (m, 1H), 4.59 (s, 2H), 4.51-4.47 (m, 2H), 3.68-3.67 (m, 7H), 3.33-3.32 (m, 1H), 3.04-3.00 (m, 1H), 2.96-2.75 (m, 1H), 2.66 (d, J = 4.5 Hz, 3H), 2.51-2.49 (m, 4H), 2.19-2.13 (m, 4H), 2.00-1.81 (m, 4H), 1.23-1.17 (m, 2H | | C | B |
| 285 | 834.34 | 834.20 | 836.20 | $^1$HNMR (400 MHz, DMSO-d6) δ 11.09 (s, 1H), 9.00 (s, 1H), 8.53 (s, 1H), 8.03 (s, 1H), 8.10-8.03 (m, 2H), 7.65-7.60 (m, 2H), 7.28 (s, 1H), 7.22-7.20 (m, 1H), 5.09-5.04 (m, 1H), 4.11-4.08 (m, 2H), 3.70 (s, 3H), 3.59 (s, 4H), 2.93-2.84 (m, 3H), 2.60 (s, 5H), 2.55 (s, 4H), 2.08-2.07 (m, 1H), 1.81-1.78 (m, 3H), 1.25-1.23 (m, 2H), 0.85 (s, 6H) | | C | B |
| 286 | 774.28 | 774.20 | 776.20 | $^1$H NMR (300 MHz, DMSO-d$_6$) δ 10.95 (s, 1H), 8.86 (s, 1H), 8.61 (d, J = 5.1 Hz, 2H), 8.30 (s, 1H), 8.06 (s, 1H), 8.00-7.94 (m, 2H), 7.75 (d, J = 9.0 Hz, 1H), 7.47 (d, J = 9.0 Hz, 1H), 7.12 (s, 1H), 4.80-4.77 (m, 1H), 4.59 (s, 2H), 4.51-4.47 (m, 2H), 3.68-3.67 (m, 7H), 3.33-3.32 (m, 1H), 3.04-3.00 (m, 1H), 2.96-2.75 (m, 1H), 2.66 (d, J = 4.5 Hz, 3H), 2.51-2.49 (m, 4H), 2.19-2.13 (m, 4H), 2.00-1.81 (m, 4H), 1.23-1.17 (m, 2H | | C | C |
| 287 | 841.37 | | | $^1$HNMR (300 MHz, DMSO-d6) δ 11.07 (s, 1H), 8.68 (s, 1H), 8.02 (s, 1H), 7.80-7.79 (m, 1H), 7.63 (d, J = 8.4 Hz, 1H), 7.51 (d, J = 2.1 Hz, 1H), 7.28 (d, J = 2.0 Hz, 2H), 7.23-7.20 (m, 1H), 6.94(d, J = 8.7 Hz, 1H), 5.08-5.03 (m, 1H), 4.59-4.55 (m, 1H), 4.13-4.09 (m, 2H), 3.60 (s, 4H), 3.34-3.31 (m, 3H), 2.93-2.85 (m, 3H), 2.61-2.60 (m, 9H), 2.25-2.21 (m, 2H), 2.04-1.77 (m, 6H), 1.32-1.25 (m, 2H), 0.80 (s, 6H) | | | D |
| 288 | 831.35 | 831.20 | 833.20 | $^1$H NMR (300 MHz, DMSO-d$_6$) δ 10.95 (s, 1H), 8.86 (s, 1H), 8.61 (d, J = 5.1 Hz, 2H), 8.30 (s, 1H), 8.06 (s, 1H), 8.00-7.94 (m, 2H), 7.75 (d, J = 9.0 Hz, 1H), 7.47 (d, J = 9.0 Hz, 1H), 7.12 (s, 1H), 4.80-4.77 (m, 1H), 4.59 (s, 2H), 4.51-4.47 (m, 2H), 3.68-3.67 (m, 7H), 3.33-3.32 (m, 1H), 3.04-3.00 (m, 1H), 2.96-2.75 (m, 1H), 2.66 (d, J = 4.5 Hz, 3H), 2.51-2.49 (m, 4H), 2.19-2.13 (m, 4H), 2.00-1.81 (m, 4H), 1.23-1.17 (m, 2H | | B | C |
| 289 | 810.31 | 810.20 | 812.20 | $^1$HNMR (300 MHz, DMSO d$_6$, ppm)11.11(s, 1H), 8.81(s, 1H), 8.02(s, 1H), 7.98-7.87(m, 2H), 7.85-7.71(m, 4H), 7.46(d, J = 9.2 Hz, 1H), 7.09(s, 1H), 5.12(dd, J = 12.7, 5.5 Hz, 1H), 4.51(d, J = 32.8 Hz, 4H), 3.66(s, 3H), 2.95(d, J = 10.9 Hz, 2H), 2.82(t, J = 12.9 Hz, 3H), 2.65(d, J = 4.6 Hz, 4H), 2.54(s, 1H), 2.16(s, 2H), 2.05-1.89(m, 3H), 1.75(s, 7H), 1.22(s, 1H), 1.01(d, J = 12.5 Hz, 2H) | | A | B |
| 290 | 773.20 | 773.10 | 775.10 | $^1$H NMR (400 MHz, DMSO-d$_6$ ppm): δ 11.13 (s, 1H), 8.95 (s, 1H), 8.11 (s, 1H), 7.92 (d, J = 2.3 Hz, 2H), 7.80 (d, J = 8.3 Hz, 1H), 7.76-7.65 (m, 2H), 7.46 (s, 1H), 7.33 (d, J = 8.2 Hz, 1H), 7.09 (s, 1H), 5.13 (d, J = 12.9, 5.3 Hz, 1H), 4.48 (s, 3H), 4.31-4.20 (m, 3H), 3.98 (d, J = 11.6 Hz, 1H), 3.86 (s, 1H), 3.58 (t, J = 11.2 Hz, 1H), 3.02 (t, J = 11.0 Hz, 2H), 2.96-2.85 (m, 2H), 2.65 (d, J = 4.6 Hz, 4H), 2.61-2.53 (m, 1H), 2.07 (d, J = 12.6 Hz, 1H), 1.54 (d, J = 6.8 Hz, 6H). | | B | C |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 291 | 831.35 | 831.20 | 833.20 | $^1$H NMR (300 MHz, DMSO-d$_6$) δ 10.84 (s, 1H), 8.83 (s, 1H), 8.56 (d, J = 8.3 Hz, 1H), 8.03 (s, 1H), 7.92 (dd, J = 9.8, 3.6 Hz, 2H), 7.75 (d, J = 7.2 Hz, 1H), 7.47 (d, J = 9.1 Hz, 1H), 7.13 (d, J = 4.8 Hz, 4H), 4.74 (s, 1H), 4.57 (s, 2H), 3.66 (s, 3H), 3.58 (s, 4H), 3.39 (s, 4H), 2.64 (d, J = 4.6 Hz, 8H), 2.00 (s, 3H), 1.80 (d, J = 12.7 Hz, 2H), 1.70 (s, 1H), 1.37 (d, J = 12.7 Hz, 2H), 1.22 (s, 1H), 0.90 (s, 6H). | | A | B |
| 292 | 826.31 | 826.10 | 828.20 | $^1$H NMR (400 MHz, DMSO-d$_6$, ppm) δ11.09 (s, 1H), 8.84 (s, 1H), 8.05 (s, 1H), 7.98-7.97 (d, J = 2.8 Hz, 2H), 7.76-7.66 (m, 2H), 7.54-7.52(d, J = 9.2 Hz, 1H), 7.36-7.32(m, 2H), 7.09 (s, 1H), 5.12-5.08 (s, 1H), 4.58 (s, 2H), 4.34-4.32 (m, 2H), 4.12-4.08 (m, 2H), 3.75-3.73 (m, 2H), 3.56-3.53 (m, 2H), 3.33-3.30 (m, 2H), 3.12-3.08 (m, 2H), 2.92-2.85 (m, 1H), 2.68-2.55 (m, 6H), 1.96-1.80(m, 4H), 1.65-1.60 (m, 2H), 1.42-1.40 (m, 2H), 1.22-1.20 (m, 3H). | | B | A |
| 293 | 840.34 | 840.30 | 842.30 | $^1$H NMR (400 MHz, DMSO-d$_6$) δ11.09(s, 1H), 8.83 (s, 1H), 8.05 (s, 1H), 7.96 (s, 2H), 7.70-7.66 (m, 3H), 7.36-7.32 (m, 2H), 7.03 (s, 1H), 5.09-5.08 (m, 1H), 4.55 (s, 2H), 4.12-4.09 (m, 2H), 3.76-3.74 (m, 2H), 3.57-3.53 (m , 2H), 3.31 (s , 2H), 3.13-3.10 (m, 2H), 2.91-2.85 (m, 1H), 2.68-2.52 (m, 5H), 1.99-1.86 (m, 5H), 1.70-1.51(m, 8H), 1.45-1.40 (m, 2H). | | B | B |
| 294 | 759.17 | 759.10 | 761.10 | $^1$H NMR (400 MHz, DMSO-d$_6$, ppm): 11.12 (s, 1H), 8.95 (s, 1H), 8.11 (s, 1H), 7.93 (dd, J = 11.1, 3.8 Hz, 2H), 7.83-7.72 (m, 2H), 7.52 (d, J = 9.2 Hz, 1H), 7.45 (s, 1H), 7.32 (d, J = 8.4 Hz, 1H), 7.14 (s, 1H), 5.13 (d, J = 13.0, 5.3 Hz, 1H), 4.50 (s, 3H), 4.29 (p, J = 5.5 5H), 4.01-3.94 (m, 1H), 3.90-3.82 (m, 1H), 3.62-3.52 (m, 1H), 3.01 (t, J = 11.4 Hz, 1H), 2.97-2.83 (m, 2H), 2.65 (d, J = 4.7 Hz, 4H), 2.61-2.51 (m, 1H), 2.07 (t, J = 12.5 Hz, 1H), 1.21 (t, J = 7.0 Hz, 3H). | | C | C |
| 295 | 817.32 | 817.20 | 819.20 | $^1$HNMR (300 MHz, DMSO-d6, ppm) δ10.83 (s, 1H), 8.84 (s, 1H), 8.55-8.50 (m, 1H), 8.05 (s, 1H), 7.97-7.96 (d, J = 2.4 Hz, 2H), 7.72-7.50 (m, 2H), 7.15-7.09 (m, 4H), 4.80-4.71(m, 1H) 4.57 (s, 2H), 4.32-4.30 (m, 2H), 3.64-3.60 (m , 4H), 3.05-2.55 (m , 7H), 2.49-2.39(m, 5H), 2.22-1.95 (m, 4H), 1.82-1.65 (m, 3H), 1.25-1.21 (m, 6H). | | B | A |
| 296 | 831.35 | 831.20 | 833.20 | $^1$H NMR (300 MHz, DMSO-d$_6$, ppm) δ10.87 (s, 1H), 8.81 (s, 1H), 8.60-8.55 (m, 1H), 8.05(s, 1H), 7.95 (s, 1H), 7.69 (s, 2H), 7.16-7.14 (d, J = 4.2 Hz, 4H), 7.03 (s, 1H), 4.72-4.70 (m, 1H), 4.55 (s, 2H), 3.65 (s, 5H), 3.34-3.31 (m , 4H), 2.67-2.54 (m, 4H), 2.49-2.40 (m, 3H), 2.22-1.95 (m, 5H), 1.88-1.70(m, 3H), 1.58-1.55 (d, J = 6.9 Hz, 6H), 1.28-1.10 (m, 3H). | | A | A |
| 297 | 835.32 | 834.30 | 835.30 | $^1$HNMR (300 MHz, DMSO-d$_6$, ppm) δ 11.06(s, 1H), 9.03(s, 1H), 7.94-7.97(m, 3H), 7.66-7.70(m, 2H), 7.46(d, J = 9.1 Hz, 1H), 7.29(s, 1H), 7.21(d, J = 9.2 Hz, 1H), 7.11(s, 1H), 5.03-5.05(m, 1H), 4.55 (s, 2H), 4.01(d, J = 12.2 Hz, 2H), 3.65(s, 3H), 3.55(s, 4H), 2.94-2.95(m, 3H), 2.61-2.64(m, 4H), 2.44 (s, 4H), 2.16(s, 2H), 1.97-1.99(m, 1H), 1.79-1.80(m, 3H), 1.12-1.16(m, 3H). | | C | A |
| 298 | 837.34 | 836.32 | 837.32 | $^1$HNMR (300 MHz, DMSO-d6, ppm) δ 11.07(s, 1H), 8.82(s, 1H), 7.98-8.03(m, 3H), 7.77(t, 1H), 7.63-7.65(m, 1H), 7.51-7.54(m, 1H), 7.07(s, 1H), 6.79(s, 1H), 6.63-6.66(m, 1H), 5.07-5.09(m, 1H), 4.58 (s, 2H), 4.49-4.45(m, 2H), 4.32-4.34(m, 2H), 4.09(s, 4H), 3.31-3.33(m, 4H), 2.70-2.81(m, 3H), 2.68 (s, 3H), 2.51-2.54(m, 2H), 2.24-2.26(m, 2H), 2.03-2.05(m, 1H), 1.71-1.73(m, 2H), 1.51-1.60(m, 1H), 1.25-1.30(m, 3H), 1.03-1.11(m, 2H). | | B | A |
| 299 | 867.41 | 867.30 | 869.30 | $^1$H NMR (300 MHz, DMSO-d$_6$, ppm): 11.07 (s, 1H), 8.81 (s, 1H), 8.05 (s, 1H), 7.96-7.94 (m, 2H), 7.70-7.63 (m, 3H), 7.30-7.21 (m, 2H), 7.04 (s, 1H), 5.09-5.03 (m, 1H), 4.57 (s, 2H), 4.14-4.10 (m, 2H), 3.61 (s, 4H), 3.07-2.84 (m, 4H), | | A | B |

TABLE 2-continued

Degradation and characterization of exemplary bifunctional compounds of the present disclosure

| Ex. # | Mol Weight | Mean Observed Mass One | Mean Observed Mass Two | NMR | EC₅₀ (nM)* | Dmax (%)** | IC₅₀ (nM)*** |
|---|---|---|---|---|---|---|---|
| 300 | 852.39 | 852.15 | | 2.61-2.55 (m, 7H), 2.14-1.75 (m, 5H), 1.59 (d, J = 6.8 Hz, 6H), 1.28-1.15 (m, 3H), 0.89 (s, 6H); ¹HNMR (400 MHz, DMSO-d6, ppm) δ 11.07 (s, 1H), 8.06 (s, 1H), 7.96 (d, J = 8.0, 2H), 7.62-7.64 (m, 1H), 7.54-7.56 (m, 2H), 7.41-7.43 (m, 1H), 7.27-7.28 (m, 2H), 7.19-7.21 (m, 1H), 6.22 (s, 1H), 5.03-5.08 (m, 1H), 4.56 (t, 2H), 4.30-4.33 (m, 2H), 4.07-4.10 (m, 2H), 3.32-3.34 (s, 1H), 2.92-3.24 (m, 4H), 2.83-2.89 (m, 3H), 2.60-2.67 (m, 3H), 2.50-2.55 (m, 5H), 2.00-2.02 (m, 1H), 1.79-1.82 (m, 3H), 1.26-1.30 (m, 5H), 0.89 (s, 6H). | | B | A |
| 301 | 865.43 | 865.35 | | ¹H NMR (400 MHz, DMSO-d6, ppm) δ 10.98 (s, 1H), 8.82 (s, 1H), 8.03 (s, 2H), 7.94 (s, 1H), 7.70 (s, 2H), 7.28 (s, 1H), 7.04 (s, 1H), 6.95 (s, 1H), 6.66 (d, J = 8.2 Hz, 1H), 5.10 (s, 1H), 4.69 (d, J = 16.9 Hz, 1H), 4.57-4.45 (m, 5H), 3.49-3.35 (m, 4H), 2.99-2.84 (m, 4H), 2.69-2.55 (m, 7H), 2.40 (s, 2H), 1.97-1.70 (m, 8H), 1.57 (d, J = 6.8 Hz, 6H), 1.23 (s, 1H), 1.20 (s, 1H), 1.06 (s, 2H). | | C | B |
| 302 | 852.35 | 852.40 | | ¹HNMR (400 MHz, DMSO-d6) δ: 11.07 (s, 1H), 8.86 (s, 1H), 8.25 (s, 1H), 7.94-8.07 (m, 3H), 7.73 (d, J = 8.4 Hz, 1H), 7.64 (d, J = 8.0 Hz, 1H), 7.52 (d, J = 9.2 Hz, 1H), 7.10 (s, 1H), 6.77 (s, 1H), 6.63 (d, J = 8.0 Hz, 1H), 5.05 (dd, J = 5.2, 12.8 Hz, 1H), 4.58 (s, 2H), 4.30-4.35 (m, 2H), 3.96-4.05 (m, 3H), 3.77-3.80 (m, 2H), 3.61 (s, 4H), 3.32-3.34 (m, 2H), 2.84-2.92 (m, 4H), 2.67 (d, J = 4.4 Hz, 3H), 2.61 (m, 4H), 2.32-2.40 (m, 4H), 1.95-2.06 (m, 1H), 1.24 (t, J = 7.2 Hz, 3H). | | B | A |
| 303 | 838.32 | 838.30 | | ¹HNMR (400 MHz, DMSO-d6) δ: 11.07 (s, 1H), 8.85 (s, 1H), 8.05 (s, 1H), 7.96-8.02 (m, 2H), 7.73 (dd, J = 2.4, 9.2 Hz, 1H), 7.63 (d, J = 8.4 Hz, 1H), 7.53 (d, J = 9.2 Hz, 1H), 7.09 (s, 1H), 6.75 (d, J = 2.0 Hz, 1H), 6.62 (dd, J = 2.0, 8.4 Hz, 1H), 5.06 (dd, J = 5.2, 12.8 Hz, 1H), 4.58 (s, 2H), 4.29-4.37 (m, 2H), 4.05-4.13 (m, 3H), 3.97-4.05 (m, 4H), 3.50-3.59 (m, 1H), 3.21-3.29 (m, 3H), 2.82-2.95 (m, 1H), 2.67 (d, J = 4.8 Hz, 3H), 2.54-2.61 (m, 3H), 2.10-2.16 (m, 2H), 1.97-2.05 (m, 1H), 1.79-1.87 (m, 2H), 1.33-1.43 (m, 2H), 1.25 (t, J = 7.2 Hz, 3H). | | A | A |
| 304 | 853.38 | 853.30 | | ¹HNMR (400 MHz, DMSO-d6) δ = 11.08 (s, 1H), 8.84 (s, 1H), 8.06 (s, 1H), 8.01-7.88 (m, 2H), 7.77 (dd, J = 9.2, 2.8 Hz, 1H), 7.64 (d, J = 8.4 Hz, 1H), 7.54 (d, J = 9.6 Hz, 1H), 7.31 (d, J = 2.0 Hz, 1H), 7.23 (dd, J = 8.8, 2.0 Hz, 1H), 7.11 (s, 1H), 5.07 (d, J = 12.8, 5.6 Hz, 1H), 4.58 (s, 2H), 4.40-4.28 (m, 2H), 4.18-4.07 (m, 2H), 3.68-3.54 (m, 4H), 2.99-2.83 (m, 3H), 2.70-2.63 (m, 4H), 2.62-2.58 (m, 1H), 2.58-2.53 (m, 4H), 2.07-1.96 (m, 1H), 1.93-1.77 (m, 3H), 1.30-1.16 (m, 5H), 0.88 (s, 6H). | | A | A |
| 305 | 866.37 | 866.30 | | 11.11 (s, 1H), 8.84 (s, 1H), 8.19 (s, 1H), 8.04 (s, 1H), 8.00-7.95 (m, 1H), 7.94-7.90 (m, 1H), 7.85-7.77 (m, 2H), 7.76-7.70 (m, 2H), 7.47 (d, J = 9.2 Hz, 1H), 7.11 (s, 1H), 5.12 (dd, J = 12.8, 5.2 Hz, 1H), 4.57 (s, 2H), 4.22-4.05 (m, 3H), 3.68 (s, 3H), 3.25-3.20 (m, 2H), 3.05-2.97 (m, 2H), 2.92-2.77 (m, 2H), 2.67 (d, J = 4.8 Hz, 3H), 2.63-2.50 (m, 4H), 2.19-2.11 (m, 2H), 2.08-1.95 (m, 3H), 1.85-1.65 (m, 8H), 1.45-1.25 (m, 2H). | | | |
| 306 | 851.36 | 851.36 | | ¹HNMR (400 MHz, DMSO-d6, ppm) δ 11.07(s, 1H), 8.80(s, 1H), 8.04(s, 1H), 7.96-7.97(m, 2H), 7.11-7.74(m, 3H), 7.03(s, 1H), 6.80(s, 1H), 6.65(d, J = 7.2 Hz, 1H), 5.04-5.08(m, 1H), 4.56(s, 2H), 4.46-4.50(m, 2H), 4.11(t, 4H), 3.26-3.30(m, 5H), 2.91-2.89(m, 3H), 2.70(s, 3H), 2.67-2.68(m, 1H), 2.29-2.34(m, 2H), 2.02-2.03(m, 1H), 1.72-1.75(m, 2H), 1.48-1.5 (m, 8H), 1.06-1.18(m, 2H). | | A | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 307 | 867.41 | 867.25 | 869.25 | $^1$H NMR (300 MHz, DMSO-d$_6$, ppm): 11.08 (s, 1H), 8.81 (s, 1H), 8.07 (s, 1H), 7.96 (s, 2H), 7.75-7.64 (m, 3H), 7.34-7.30 (m, 2H), 7.05 (m, 1H), 5.11-5.05 (m, 1H), 4.57 (s, 2H), 3.78-3.61 (m, 6H), 2.92-2.80 (m, 3H), 2.72-2.52 (m, 8H), 2.03-2.00 (m, 1H), 1.90-1.74 (m, 4H), 1.49-1.23 (m, 9H), 0.94 (s, 6H). | | B | A |
| 308 | 866.42 | 865.37 | 867.37 | $^1$H NMR (400 MHz, DMSO-d6, ppm): δ 11.07 (s, 1H), 8.05 (d, J = 4.8 Hz, 3H), 7.74 (d, J = 8.8 Hz, 2H), 7.65 (s, 1H), 7.39-7.37 (m, 4H), 6.25 (s, 1H), 5.22-5.19 (m, 1H), 4.53 (s, 2H), 4.12-4.10 (m, 2H), 3.33-3.32 (m, 10H), 2.88-2.85 (m, 3H), 2.68 (t, 3H), 2.67-2.60 (m, 1H), 2.09-2.04 (m, 1H), 1.80-1.77 (m, 3H), 1.58-1.57 (m, 6H), 1.38-1.24 (m, 2H), 0.90-0.86 (m, 6H). | | C | B |
| 309 | 867.36 | 867.20 | 869.20 | $^1$H NMR (400 MHz, DMSO-d$_6$)δ = 11.07 (s, 1H), 8.85 (s, 1H), 8.06 (s, 1H), 8.01-7.93 (m, 2H), 7.73 (dd, J = 9.6, 2.8 Hz, 1H), 7.63 (d, J = 8.4 Hz, 1H), 7.53 (d, J = 9.6 Hz, 1H), 7.09 (s, 1H), 6.76 (d, J = 2.0 Hz, 1H), 6.62 (dd, J = 8.4, 2.0 Hz, 1H), 5.06 (dd, J = 12.8, 5.2 Hz, 1H), 4.57 (s, 2H), 4.38-4.30 (m, 2H), 4.22-4.16 (m, 1H), 4.15-4.05 (m, 4H), 3.70-3.65 (m, 2H), 3.61-3.57 (m, 2H), 3.55-3.50 (m, 1H), 3.22-3.16 (m, 2H), 2.93-2.82 (m, 3H), 2.77-2.70 (m, 1H), 2.69-2.66 (m, 5H), 2.62-2.54 (m, 2H), 2.06-1.96 (m, 1H), 1.85-1.75 (m, 2H), 1.43-1.32 (m, 2H), 1.25 (t, J = 6.8 Hz, 3H). | | B | B |
| 310 | 825.32 | 825.20 | | $^1$H NMR (300 MHz, DMSO-d$_6$ ppm) δ11.07 (s, 1H), 8.85 (s, 1H), 8.05 (s, 1H), 7.96 (s, 2H), 7.75-7.65 (m, 2H), 7.52 (d, J = 9.6 Hz, 1H), 7.34-7.30 (m, 2H), 7.10 (s, 1H), 5.10-5.06 (m, 1H), 4.58 (s, 2H), 4.32 (d, J = 6.8 Hz, 2H), 3.71-3.64 (m , 6H), 2.91-2.85(m, 3H), 2.67-2.56 (m, 4H), 2.46-2.40 (m, 4H), 2.22 (s, 2H), 2.02-1.99(m, 1H), 1.85-1.80 (m, 3H), 1.32-1.20 (m, 6H). | | B | A |
| 311 | 839.35 | 839.25 | | $^1$H NMR (300 MHz, DMSO-d$_6$ ppm) δ11.06(s, 1H), 8.83 (s, 1H), 8.05 (s, 2H), 7.95 (s, 2H), 7.69-7.66 (m, 3H), 7.34-7.29(m, 2H), 7.03 (s, 1H), 5.13-5.05 (m, 1H), 4.54 (s, 2H), 3.65-3.60 (m , 6H), 3.31 (s, 3H), 2.87-2.80 (m, 3H), 2.67-2.55 (m, 3H), 2.49-2.41 (m, 3H), 2.21-2.15 (m, 3H), 2.05-1.95 (m, 1H), 1.81-1.70 (m, 2H), 1.57-1.55 (d, J = 8.8 Hz, 6H), 1.39-1.20 (m, 2H). | | A | A |
| 312 | 853.38 | 853.30 | 855.30 | $^1$H NMR (300 MHz, DMSO-d$_6$ ppm): δ 11.08 (s, 1H), 8.82 (s, 1H), 8.05 (s, 1H), 7.97 (s, 2H), 7.79 (d, J = 9.0 Hz, 1H), 7.75-7.67 (m, 2H), 7.53 (d, J = 9.6 Hz, 1H), 7.34-7.30 (m, 2H), 7.11 (s, 1H), 5.15-5.05 (m, 1H), 4.57 (s, 2H), 4.32 (d, J = 7.2 Hz, 2H), 3.75-3.61 (m, 6H), 2.87-2.83 (m, 3H), 2.66-2.55 (m, 7H), 2.05-1.95 (m, 1H), 1.84-1.80 (m, 3H), 1.45-1.32 (m, 2H), 1.26-1.22 (m, 4H), 0.92 (s, 6H). | | A | A |
| 313 | 839.40 | 839.30 | | $^1$H NMR (400 MHz, DMSO-d$_6$, ppm) δ10.94 (s, 1H), 8.83 (s, 1H), 8.06 (s, 1H), 7.98-7.97 (m, 2H), 7.12 = 2.4 Hz, 2H), 7.80-7.75 (m, 1H), 7.52-7.50 (m, 2H), 7.12-7.05 (m, 3H), 5.14-5.02 (m, 1H), 4.58 (s, 2H), 4.31-4.20 (m, 4H), 3.98-3.90 (m, 2H), 3.62 (s, 4H), 3.30 (s , 2H), 2.95-2.70 (m , 3H), 2.67-2.65 ( m, 3H), 2.52-2.50 ( m, 4H), 2.32-2.30 ( m, 1H), 1.99-1.91( m, 1H), 1.82-1.80 (m, 3H), 1.26-1.23 (m, 4H), 0.89(s , 6H). | | B | A |
| 314 | 839.35 | 839.25 | | $^1$H NMR (400 MHz, DMSO-d$_6$ , ppm): δ11.09 (s, 1H), 8.87 (s, 1H), 8.06 (s, 1H), 7.99-7.97 (m, 2H), 7.73-7.70 (m, 1H), 7.65 (d, J = 8.5 Hz, 1H), 7.51 (d, J = 9.2 Hz, 1H), 7.31 (d, J = 2.3 Hz, 1H), 7.23 (d, J = 8.7 Hz, 1H), 7.09 (s, 1H), 5.09-5.04 (m, 1H), 4.58 (s, 2H), 4.25-4.21 (m, 2H), 4.07-4.04 (m, 2H), 3.64 (s, 4H), 3.00-2.93 (m, 3H), 2.66-2.60 (m, 3H), 2.60-2.54 (d, J = 4.6 Hz, 2H), 2.51-2.33 (m, 4H), 2.18-2.02 (d, J = 6.9 Hz, 2H), 2.01-1.83 (m, 2H), 1.80-1.63 (d, J = 13.5 Hz, 2H), 1.17-1.14 (m, 2H), 0.99-0.96 (m, 3H). | | B | B |
| 315 | 843.38 | 843.35 | | $^1$H NMR (300 MHz, DMSO-d$_6$, ppm): δ 10.85 (s, 1H), 8.82 (s, 1H), 8.41 (d, J = 6.9 Hz, 1H), 8.04 (s, 1H), 7.93 (s, 2H), 7.76 (d, J = 6.0 Hz, 2H), 7.47 (d, J = | | B | B |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 316 | 851.36 | 851.40 | | 9.1 Hz, 1H), 7.13 (s, 1H), 6.58 (d, J = 8.9 Hz, 1H), 6.50(m, 1H), 4.71-4.67 (m, 1H), 4.58 (s, 2H), 3.99-3.92 (m, 6H), 3.67 (s, 3H), 3.60 (m, 4H), 2.79-2.72 (m, 3H), 2.66-2.64 (m, 3H), 2.50 (s, 3H), 2.12-2.02 (m, 2H), 1.81-1.78 (m, 3H), 1.29-1.23 (m, 3H), 0.85 (s, 6H). | | B | A |
| 317 | 853.38 | 853.20 | 855.20 | ¹HNMR (400 MHz, DMSO-d₆)δ: 11.08 (s, 1H), 8.25 (s, 1H), 8.07 (m, 3H), 7.75 (d, J = 10.4 Hz, 1H), 7.64 (d, J = 7.6 Hz, 1H), 7.53 (d, J = 9.2 Hz, 1H), 7.08 (s, 1H), 6.77 (s, 1H), 6.64 (d, J = 8.4 Hz, 1H), 5.06 (dd, J = 5.2, 12.8 Hz, 1H), 4.58 (s, 2H), 4.46 (d, J = 12.8 Hz, 2H), 4.29-4.37 (m, 2H), 4.12 (t, J = 8.0 Hz, 2H), 3.72-3.77 (m, 2H), 3.31 (t, J = 7.2 Hz, 2H), 2.78-2.99 (m, 7H), 2.68 (d, J = 4.4 Hz, 3H), 2.55-2.61 (m, 2H), 2.30 (br d, J = 6.8 Hz, 2H), 1.99-2.05 (m, 1H), 1.70 (d, J = 10.4 Hz, 2H), 1.48-1.57 (m, 1H), 1.25 (t, J = 6.8 Hz, 3H), 0.98-1.10 (m, 2H). | | B | A |
| 318 | 771.23 | 771.20 | 773.20 | ¹H NMR (300 MHz, DMSO-d₆, ppm) δ 11.04 (s, 1H), 8.05 (s, 1H), 7.97-7.93 (m, 2H), 7.73-7.63 (m, 2H), 7.48 (d, J = 9.0 Hz, 1H), 7.31 (s, 1H), 7.23 (d, J = 9.0 Hz, 1H), 7.09 (s, 1H), 5.08-5.04 (m, 1H), 4.57 (s, 2H), 4.29-4.25 (m, 2H), 4.06-4.02 (m, 2H), 3.63 (s, 4H), 2.96-2.85 (m, 3H), 2.66-2.55 (m, 4H), 2.49-2.39 (m, 4H), 2.16-2.03 (m, 2H), 1.99-1.90 (m, 1H), 1.84-1.75 (m, 3H), 1.61-1.59 (m, 2H), 1.44-1.37 (m, 2H), 1.23-1.14 (m, 3H), 0.96-0.91 (m, 3H). | | B | C |
| 319 | 785.30 | 785.35 | | ¹H NMR (400 MHz, DMSO-d6, ppm) δ 11.08 (s, 1H), 8.82 (s, 1H), 8.03 (s, 1H), 7.92 (s, 2H), 7.77-7.75 (m, 2H), 7.46-7.44 (m, 3H), 7.11 (d, J = 2.4 Hz, 1H), 5.08-5.05 (m, 1H), 4.51-4.50 (m, 3H), 4.31-4.29 (m, 1H), 4.16-4.13 (m, 3H), 4.07-4.03 (m, 1H), 3.29 (s, 1H), 2.97-2.66 (m, 3H), 2.55-2.51 (m, 3H), 2.51-2.50 (m, 1H), 1.99-1.94 (m, 3H), 1.73-1.71 (m, 1H), 1.63-1.61 (m, 2H), 1.45-1.43 (m, 2H), 0.92-0.89 (m, 3H). | | C | C |
| 320 | 786.29 | 786.20 | | ¹H NMR (300 MHz, DMSO-d₆, ppm) δ10.85 (s, 1H), 8.85 (s, 1H), 8.67 (d, J = 8.1 Hz, 1H), 8.05 (s, 1H), 7.97-7.94 (m, 2H), 7.74 (d, J = 9.0 Hz, 1H), 7.46 (d, J = 9.3 Hz, 1H), 7.38 (s, 1H), 7.29-7.23 (m, 2H), 7.12-7.08 (m, 2H), 4.76-4.71 (m, 1H), 4.58 (s, 2H), 3.76-3.64 (m, 9H), 2.74-2.65 (m, 6H), 2.56 (s, 1H), 2.39 (s, 4H), 2.20-2.03 (m, 1H), 1.98 (s, 1H), 1.84-1.68 (m, 3H), 1.23-1.19 (m, 2H). | | C | A |
| 321 | 826.31 | 826.30 | | ¹H NMR (300 MHz, DMSO-d₆, ppm) δ10.90 (s, 1H), 8.88 (s, 1H), 8.75 (d, J = 8.7 Hz, 1H), 8.07 (s, 1H), 7.97-7.94 (m, 2H), 7.77-7.65 (m, 2H), 7.49 (d, J = 9.0 Hz, 1H), 7.27 (d, J = 6.9 Hz, 1H), 7.14 (s, 1H), 7.04 (d, J = 8.4 Hz, 1H), 4.74-4.70 (m, 1H), 4.60 (s, 2H), 4.42 (d, J = 13.2 Hz, 2H), 3.65-3.60 (m, 6H), 2.86-2.75 (m, 3H), 2.68 (d, J = 4.6 Hz, 2H), 2.42 (s, 3H), 2.31-2.21 (s, 4H), 2.04-2.01 (m, 1H), 1.92-1.85 (m, 4H), 1.12 (s, 3H). ¹H NMR (400 MHz, DMSO-d₆, ppm): δ 11.07 (s, 1H), 8.85 (s, 1H), 8.05 (d, J = 1.6 Hz, 1H), 7.99-7.87 (m, 2H), 7.79-7.64 (m, 2H), 7.47 (d, J = 9.0 Hz, 1H), 7.34 (d, J = 8.8 Hz, 2H), 7.12 (s, 1H), 5.10-5.06 (m, 1H), 4.58 (s, 2H), 3.68 (s, 3H), 3.62 (s, 4H), 3.30-3.25 (m, 8H), 2.95-2.80 (m, 1H), 2.67 (d, J = 4.6 Hz, 3H), 2.60 (s, 5H), 2.45 (s, 5H), 2.02 (d, J = 13.0 Hz, 1H); | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 322 | 825.32 | 825.35 | | $^1$H NMR (400 MHz, DMSO-d$_6$, ppm) δ11.06 (s, 1H), 8.85 (s, 1H), 8.04 (s, 1H), 7.95 (d, J = 17.3 Hz, 2H), 7.73 (d, J = 9.2 Hz, 1H), 7.63 (d, J = 8.5 Hz, 1H), 7.46 (d, J = 9.2 Hz, 1H), 7.29 (s, 1H), 7.21 (d, J = 8.7 Hz, 1H), 7.12 (s, 1H), 5.05 (dd, J = 12.8, 5.5 Hz, 1H), 4.58 (s, 2H), 4.02 (d, J = 12.8 Hz, 2H), 3.67-3.62 (m, 8H), 2.96-2.84 (m, 3H), 2.66 (d, J = 4.6 Hz, 4H), 2.38-2.33 (m, 6H), 2.01 (s, 1H), 1.76 (d, J = 12.6 Hz, 2H), 1.61 (s, 1H), 1.42 (s, 2H), 1.25-1.15 (m, 2H). | | B | B |
| 323 | 837.34 | 837.35 | | $^1$H NMR (300 MHz, DMSO-d$_6$, ppm) δ11.00 (s, 1H), 8.76 (s, 1H), 7.98 (s, 1H), 7.89-7.87 (m, 2H), 7.70-7.56 (m, 3H), 7.23 (s, 1H), 7.15 (d, J = 10.5 Hz, 1H), 6.98 (s, 1H), 5.02-4.96 (m, 1H), 4.48 (s, 2H), 4.0 (d, J = 12.9 Hz, 2H), 3.56 (s, 4H), 2.93-2.81 (m, 4H), 2.60-2.54 (m, 4H), 2.32 (s, 4H), 2.09 (d, J = 6.8 Hz, 2H), 1.96-1.92 (m, 1H), 1.77-1.72 (m, 3H), 1.26-1.24 (m, 2H), 1.16-1.06 (m, 3H), 0.72 (s, 2H). | | A | A |
| 324 | 785.26 | 785.00 | 787.00 | $^1$H NMR (300 MHz, DMSO-d$_6$, ppm) δ 11.10 (s, 1H), 8.85 (s, 1H), 8.03 (s, 1H), 7.93 (s, 2H), 7.77-7.74 (m, 2H), 7.44 (d, J = 7.2 Hz, 3H), 7.09 (s, 1H), 5.05 (dd, J = 12.8, 5.4 Hz, 1H), 4.51-4.50 (m, 3H), 4.31-4.01 (m, 5H), 2.94-2.76 (m, 3H), 2.66-2.64 (m, 4H), 1.97 (s, 3H), 1.72 (s, 1H), 1.57-1.40 (m, 4H), 1.39-1.19 (m, 3H), 0.87 (t, J = 7.3 Hz, 3H). | | B | A |
| 325 | 815.33 | 815.33 | | $^1$H NMR (400 MHz, DMSO-d$_6$, ppm): δ 10.86 (s, 1H), 8.85 (s, 1H), 8.67 (d, J = 7.2 Hz, 1H), 8.06 (s, 1H), 7.94 (s, 2H), 7.74 (d, J = 8.6 Hz, 1H), 7.48 (d, J = 9.0 Hz, 1H), 7.30 (d, J = 5.2 Hz, 1H), 7.12 (d, J = 6.4 Hz, 3H), 4.72 (s, 1H), 4.59 (s, 2H), 3.86 (s, 3H), 3.66 (d, J = 14.2 Hz, 7H), 3.45 (s, 3H), 2.78 (s, 1H), 2.67 (d, J = 4.2 Hz, 3H), 2.62-2.54 (m, 2H), 2.40 (s, 4H), 2.22 (d, J = 6.8 Hz, 2H), 2.08 (s, 2H), 1.85 (d, J = 12.2 Hz, 2H), 1.71 (s, 1H), 1.31 (d, J = 13.4 Hz, 2H). | | B | A |
| 326 | 839.35 | 839.20 | | $^1$H NMR (400 MHz, DMSO-d$_6$, ppm): δ11.06 (s, 1H), 8.81 (s, 1H), 8.03 (s, 1H), 7.95-7.92(m, 2H), 7.77-7.74 (m, 1H), 7.64 (d, J = 8.6 Hz, 1H), 7.47 (d, J = 9.2 Hz, 1H), 7.29(s, 1H), 7.23-7.20 (m, 1H), 7.10(s, 1H), 5.07-5.03 (m, 1H), 4.57-4.53 (m, 4H), 4.08-4.04 (d, J = 13.0 Hz, 2H), 3.67(s, 3H), 3.29-3.31 (m, 3H), 2.96-2.85(m, 2H), 2.83-2.80 (m, 4H), 2.66 (s, 3H), 2.54-2.49(m, 2H), 2.10-1.91(m, 1H), 1.68-1.65 (m, 4H), 1.60-1.29 (m, 4H), 0.94-0.90(m, 3H). | | B | B |
| 327 | 853.38 | 853.30 | | $^1$H NMR (400 MHz, DMSO-d$_6$, ppm);δ11.05 (s, 1H), 8.81 (s, 1H), 8.02 (s, 1H), 7.95-7.92 (m, 2H), 7.77-7.74 (m, 1H), 7.63 (d, J = 8.6 Hz, 1H), 7.47(d, J = 9.2 Hz, 1H), 7.29 (d, J = 2.3 Hz, 1H), 7.22-7.19 (m, 1H), 7.11 (s, 1H), 5.07-5.03 (m, 1H), 4.57-4.54 (m, 4H), 4.06 (d, J = 12.8 Hz, 2H), 3.68 (s, 3H), 2.95-2.84 (m, 2H), 2.84-2.79 (m, 4H), 2.74-2.67 (m, 3H), 2.66-2.54 (m, 3H), 2.51-2.40(m, 2H), 2.01-1.96 (m, 1H), 1.66-1.63 (m, 4H), 1.63-1.41 (m, 4H), 1.41-1.29 (m, 2H), 0.80-1.76 (m, 3H). | | B | B |
| 328 | 853.33 | 853.30 | | $^1$HNMR (400 MHz, DMSO-d$_6$)δ = 11.07 (s, 1H), 8.85 (s, 1H), 8.05 (s, 1H), 8.00-7.94 (m, 2H), 7.76-7.70 (m, 1H), 7.64 (d, J = 8.4 Hz, 1H), 7.52 (d, J = 9.6 Hz, 1H), 7.08 (s, 1H), 6.78 (d, J = 2.0 Hz, 1H), 6.64 (dd, J = 8.4, 2.4 Hz, 1H), 5.06 (dd, J = 12.8, 5.2 Hz, 2H), 4.57 (s, 2H), 4.38-4.30 (m, 2H), 4.29-4.24 (m, 1H), 4.17-4.08 (m, 2H), 4.06-3.99 (m, 2H), 3.82-3.76 (m, 2H), 3.64-3.55 (m, 4H), 3.23-3.17 (m, 2H), 2.98-2.92 (m, 2H), 2.90-2.83 (m, 1H), 2.68 (d, J = 4.8 Hz, 3H), 2.62-2.54 (m, 2H), 2.06-1.96 (m, 1H), 1.85-1.77 (m, 2H), 1.43-1.32 (m, 2H), 1.24 (t, J = 6.8 Hz, 3H). | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 329 | 840.34 | 840.30 | | $^1$HNMR (400 MHz, DMSO-d$_6$)δ: 11.07 (s, 1H), 8.84 (s, 1H), 8.05 (s, 1H), 7.92-8.00 (m, 2H), 7.71-7.76 (m, 1H), 7.65 (d, J = 8.8 Hz, 1H), 7.52 (d, J = 9.2 Hz, 1H), 7.31 (d, J = 2.0 Hz, 1H), 7.23 (dd, J = 2.0, 8.8 Hz, 1H), 7.08 (s, 1H), 5.07 (dd, J = 5.2, 12.8 Hz, 1H), 4.57 (s, 2H), 4.29-4.37 (m, 2H), 3.96-4.12 (m, 4H), 3.48-3.55 (m, 1H), 3.32-3.34 (m, 2H), 2.84-3.01 (m, 3H), 2.66 (d, J = 4.8 Hz, 3H), 2.54-2.63 (m, 4H), 1.98-2.06 (m, 1H), 1.73-1.89 (m, 5H), 1.38-1.47 (m, 2H), 1.18-1.29 (m, 5H). | | C | A |
| 330 | 840.34 | 840.30 | | $^1$H NMR (400 MHz, DMSO-d$_6$)δ: 11.08 (s, 1H), 8.85 (s, 1H), 8.05 (s, 1H), 7.94-8.00 (m, 2H), 7.72-7.79 (m, 1H), 7.65-7.71 (m, 1H), 7.53 (d, J = 9.2 Hz, 1H), 7.33 (t, J = 7.2 Hz, 2H), 7.09 (s, 1H), 5.09 (dd, J = 5.2, 12.8 Hz, 1H), 4.58 (s, 2H), 4.29-4.38 (m, 2H), 3.97-4.07 (m, 2H), 3.70 (d, J = 11.6 Hz, 2H), 3.50-3.60 (m, 1H), 3.37-3.40 (m, 2H), 2.82-2.93 (m, 3H), 2.67 (d, J = 4.8 Hz, 3H), 2.52-2.63 (s, 4H), 1.98-2.07 (m, 1H), 1.65-1.90 (m, 5H), 1.35-1.50 (m, 4H), 1.25 (t, J = 7.2 Hz, 3H). | | B | A |
| 331 | 840.34 | 840.30 | | $^1$H NMR (400 MHz, DMSO-d$_6$)δ = 11.08 (s, 1H), 8.82 (s, 1H), 8.04 (s, 1H), 8.00-7.93 (m, 2H), 7.77-7.72 (m, 1H), 7.65 (d, J = 8.8 Hz, 1H), 7.52 (d, J = 9.2 Hz, 1H), 7.33 (d, J = 2.4 Hz, 1H), 7.24 (dd, J = 8.8, 2.4 Hz, 1H), 7.07 (s, 1H), 5.07 (dd, J = 12.8, 5.2 Hz, 1H), 4.58 (s, 2H), 4.54-4.46 (m, 2H), 4.37-4.29 (m, 2H), 3.82-3.71 (m, 2H), 3.59-3.51 (m, 1H), 3.31-3.21 (m, 5H), 2.93-2.80 (m, 3H), 2.68-2.65 (m, 3H), 2.62-2.57 (m, 1H), 2.05-1.98 (m, 1H), 1.92-1.84 (m, 2H), 1.82-1.68 (m, 3H), 1.56-1.45 (m, 2H), 1.24 (t, J = 6.8 Hz, 3H), 1.17-1.07 (m, 2H). | | C | A |
| 332 | 840.34 | 840.30 | | $^1$H NMR (400 MHz, DMSO-d$_6$)δ = 11.08 (s, 1H), 8.82 (s, 1H), 8.04 (s, 1H), 8.00-7.93 (m, 2H), 7.76 (dd, J = 8.8, 2.4 Hz, 1H), 7.71-7.65 (m, 1H), 7.53 (d, J = 9.6 Hz, 1H), 7.40-7.29 (m, 2H), 7.08 (s, 1H), 5.10 (dd, J = 12.8, 5.2 Hz, 1H), 4.57 (s, 2H), 4.55-4.45 (m, 2H), 4.38-4.28 (m, 2H), 3.57-3.45 (m, 3H), 3.32-3.28 (m, 3H), 3.14-3.04 (m, 2H), 2.93-2.80 (m, 3H), 2.68-2.65 (m, 3H), 2.63-2.56 (m, 1H), 2.06-1.92 (m, 3H), 1.85-1.70 (m, 3H), 1.69-1.58 (m, 2H), 1.24 (t, J = 6.8 Hz, 3H), 1.19-1.06 (m, 2H). | | B | A |
| 333 | 865.39 | 865.25 | | $^1$H NMR (300 MHz, DMSO-d$_6$, ppm)δ11.09 (s, 1H), 8.88 (s, 1H), 8.07 (s, 1H), 7.97 (s, 2H), 7.73-7.66 (m, 2H), 7.54 (d, J = 9.2 Hz, 1H), 7.32 (s, 1H), 7.25 (d, J = 8.7 Hz, 1H), 7.13 (s, 1H), 5.11-5.05 (m, 1H), 4.59 (s, 2H), 4.40-4.36 (m, 2H), 4.06 (d, J = 12.8 Hz, 2H), 3.65 (s, 4H), 3.03-2.94 (m, 3H), 2.68-2.67 (m, 4H), 2.40 (s, 3H), 2.18 (s, 2H), 2.04-2.00 (m, 1H), 1.83 (d, J = 13.7 Hz, 2H), 1.56 (d, J = 7.8 Hz, 2H), 1.26-1.16 (m, 4H), 0.88-0.80 (m, 2H), 0.42 (d, J = 7.8 Hz, 2H), 0.08 (d, J = 4.8 Hz, 2H). | | B | A |
| 334 | 797.27 | 797.20 | | $^1$H NMR (300 MHz, DMSO-d$_6$, ppm) δ11.11 (s, 1H), 8.85 (s, 1H), 8.04 (s, 1H), 7.93 (s, 2H), 7.78-7.74 (m, 2H), 7.51-7.45 (m, 3H), 7.13 (s, 1H), 5.11-5.05 (m, 1H), 4.52 (s, 3H), 4.33-4.31 (m, 3H), 4.20-4.13 (m, 3H), 4.11-4.03 (m, 1H), 3.02-2.94 (m, 3H), 2.67 (d, J = 4.6 Hz, 3H), 2.59 (d, J = 18.2 Hz, 2H), 1.99 (s, 3H), 1.74 (s, 1H), 1.50 (s, 4H), 0.75 (s, 1H), 0.37 (d, J = 7.9 Hz, 2H), 0.02-0.01(m, 2H). | | A | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 335 | 825.32 | 825.35 | | $^1$H NMR (300 MHz, DMSO-d$_6$, ppm) δ 11.05 (s, 1H), 8.84 (s, 1H), 8.04 (s, 1H), 7.93 (d, J = 2.6 Hz, 2H), 7.75 (dd, J = 9.0, 2.5 Hz, 1H), 7.64 (d, J = 8.5 Hz, 1H), 7.47 (d, J = 9.2 Hz, 1H), 7.29 (s, 1H), 7.23 (d, J = 8.6 Hz, 1H), 7.11 (s, 1H), 5.0-5.028 (m, 1H), 4.60 (s, 2H), 4.06 (d, J = 12.7 Hz, 2H), 3.63-3.51 (m, 7H), 2.96-2.82 (m, 3H), 2.73-2.55 (m, 6H), 2.34-2.26 (m, 2H), 2.13-2.02(m, 1H), 2.00-1.95 (m , 1H), 1.76-1.65 (m, 3H), 1.23-1.14(m, 3H), 0.86 (d, J = 6.5 Hz, 3H). | | B | A |
| 336 | 769.21 | 769.10 | | $^1$H NMR (300 MHz, DMSO-d$_6$, ppm) δ11.08 (s, 1H), 8.82 (s, 1H), 8.03 (s, 1H), 7.88-7.81 (m, 2H), 7.78-7.72 (m, 3H), 7.47-7.44 (m, 2H), 7.06 (s, 1H), 5.07-5.01 (m, 1H), 4.48 (s, 3H), 4.32 (d, J = 13.1 Hz, 1H), 4.21-4.14 (m, 1H), 4.11-4.03 (m, 1H), 2.97-2.94 (m, 4H), 2.66 (d, J = 4.2 Hz, 4H), 1.97-1.96 (m, 3H), 1.74 (s, 1H), 1.49 (s, 2H), 1.24 (s, 3H), 0.74 (s, 2H). | | B | B |
| 337 | 839.35 | 838.33 | | $^1$H NMR (400 MHz, DMSO-d6, ppm) δ 11.08 (s, 1H), 8.84 (s, 1H), 8.04 (s, 1H), 7.95-7.94 (m, 2H), 7.77-7.74 (m, 1H), 7.65-7.63 (m, 1H), 7.48-7.46 (m, 1H), 7.29-7.28 (d, J = 4.0 Hz, 1H), 7.2 3-7.19 (m, 1H), 7.12 (s, 1H), 5.08-5.04 (m, 1H), 4.58 (s, 2H), 4.07-4.04 (m, 2H), 3.67 (s, 3H), 3.67-3.59 (m, 4H), 2.94-2.88 (m, 3H), 2.66-2.60 (m, 4H), 2.56-2.54 (m, 2H), 2.51-2.50 (m, 3H), 2.13-2.12 (m, 1H), 2.02-1.92 (m, 2H), 1.73-1.70 (m, 2H), 1.50-1.48 (m, 1H), 1.29-1.23 (m, 3H), 0.92-0.88 (m, 3H). | | C | A |
| 338 | 853.38 | 853.35 | 855.35 | $^1$H NMR (400 MHz, DMSO-d$_6$, ppm): δ 11.07 (s, 1H), 8.85 (s, 1H), 8.05 (s, 1H), 7.95-7.92 (m, 2H), 7.77-7.74 (m, 1H), 7.64 (d, J = 8.8 Hz, 1H), 7.48 (d, J = 9.1 Hz, 1H), 7.29 (s, 1H), 7.23-7.20 (m, 1H), 7.12 (s, 1H), 5.08-5.04 (m, 1H), 4.58 (s, 1H), 4.06 (d, J = 12.6 Hz, 2H), 3.68 (s, 3H), 3.59 (s, 4H), 3.32-3.30(m, 2H), 2.95-2.89 (m, 3H), 2.66-2.61 (m, 3H), 2.56-2.50 (m, 4H), 2.19-2.01 (m, 1H), 2.00-1.96 (m, 2H), 1.73-1.70 (m, 2H), 1.49 (s, 1H), 1.38-1.20 (m, 5H), 0.88-0.80 (m, 3H). | | C | A |
| 339 | 829.29 | 829.20 | | $^1$HNMR (400 MHz, DMSO-d$_6$) δ: 11.08 (s, 1H), 8.87 (s, 1H), 8.35 (s, 1H), 8.06 (s, 1H), 8.00-7.93 (m, 1H), 7.91-7.87 (m, 1H), 7.79-7.74 (m, 1H), 7.68 (d, J = 8.8 Hz, 1H), 7.48 (d, J = 9.2 Hz, 1H), 7.38 (d, J = 2.0 Hz, 1H), 7.30 (dd, J = 2.0, 8.8 Hz, 1H), 7.14 (s, 1H), 5.08 (dd, J = 5.2, 12.8 Hz, 1H), 4.58 (s, 2H), 3.93-3.85 (m, 2H), 3.68 (s, 3H), 3.63 (s, 4H), 3.32-3.24 (m, 3H), 2.94-2.84 (m, 1H), 2.66 (d, J = 4.4 Hz, 3H), 2.63-2.53 (m, 7H), 2.10-1.90 (m, 3H), 1.86-1.66 (m, 2H). | | B | A |
| 340 | 829.29 | 829.30 | | $^1$HNMR (400 MHz, DMSO-d$_6$) δ: 11.08 (s, 1H), 8.87 (s, 1H), 8.07 (s, 1H), 8.00-7.91 (m, 2H), 7.75 (dd, J = 2.4, 9.2 Hz, 1H), 7.67 (d, J = 8.4 Hz, 1H), 7.48 (d, J = 9.2 Hz, 1H), 7.36-7.30 (m, 1H), 7.23 (dd, J = 1.6, 8.8 Hz, 1H), 7.11 (s, 1H), 5.07 (dd, J = 5.2, 12.8 Hz, 1H), 4.58 (s, 2H), 4.24 (d, J = 12.0 Hz, 2H), 3.68 (s, 3H), 3.45-3.41 (m, 4H), 3.28-3.18 (m, 3H), 2.96-2.80 (m, 1H), 2.66 (d, J = 4.4 Hz, 3H), 2.63-2.53 (m, 7H), 2.06-1.86 (m, 3H), 1.77-1.57 (m, 2H). | | B | A |
| 341 | 829.29 | 829.30 | | $^1$HNMR (400 MHz, DMSO-d$_6$) δ: 11.09 (s, 1H), 8.87 (s, 1H), 8.06 (s, 1H), 8.00-7.94 (m, 1H), 7.91-7.78 (m, 1H), 7.81-7.75 (m, 1H), 7.74-7.68 (m, 1H), 7.49 (d, J = 9.2 Hz, 1H), 7.41-7.34 (m, 2H), 7.15 (s, 1H), 5.10 (dd, J = 5.2, 12.8 Hz, 1H), 4.58 (s, 2H), 3.68 (s, 3H), 3.67-3.68 (m, 4H), 3.56-3.51 (m, 2H), 3.19-3.10 (m, 3H), 2.93-2.83 (m, 1H), 2.67 (d, J = 4.4 Hz, 3H), 2.65-2.55 (m, 7H), 2.07-1.84 (m, 5H). | | A | A |
| 342 | 829.29 | 829.30 | | $^1$HNMR (400 MHz, DMSO-d$_6$)δ: 11.08 (s, 1H), 8.87 (s, 1H), 8.07 (s, 1H), 8.00-7.90 (m, 2H), 7.79-7.73 (m, 1H), 7.73-7.67 (m, 1H), 7.49 (d, J = 9.2 Hz, | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 343 | 811.29 | 811.30 | | 1H), 7.37-7.29 (m, 2H), 7.12 (s, 1H), 5.09 (dd, J = 5.2, 12.8 Hz, 1H), 4.58 (s, 2H), 4.30-4.18 (m, 2H), 3.68 (s, 3H), 3.35-3.31 (m, 4H), 3.26-3.18 (m, 3H), 2.93-2.82 (m, 1H), 2.69-2.54 (m, 10H), 2.05-1.87 (m, 3H), 1.73-1.57 (m, 2H). | | B | A |
| 344 | 829.36 | 829.35 | | $^1$H NMR (300 MHz, DMSO-d$_6$, ppm):δ11.09(s, 1H), 8.83 (s, 1H), 7.92(s, 2H), 7.77-7.71 (m, 3H), 7.45 (d, J = 7.2 Hz, 2H), 7.04 (s, 1H), 5.14-5.04 (m, 1H), 4.58-4.48 (m, 3H), 4.47-4.36 (m, 1H), 4.25-3.92 (m, 2H), 3.05-2.77 (m, 4H), 2.66-2.59 (m, 5H), 2.08-1.97 (m, 3H), 1.95-1.62 (m, 7H), 1.58-1.15 (m, 6H). | | C | A |
| 345 | 843.38 | 843.35 | 831.35 | $^1$H NMR (300 MHz, DMSO-d$_6$, ppm) δ10.91 (s, 1H), 8.85 (d, J = 6.2 Hz, 1H), 8.05 (s, 1H), 7.94 (d, J = 2.7 Hz, 2H), 7.79-7.72 (m, 2H), 7.47 (d, J = 9.1 Hz, 1H), 7.12 (s, 1H), 6.59-6.50 (m, 2H), 4.72-4.68 (m, 1H), 4.58 (s, 2H), 4.23-4.16 (m, 2H), 3.89-3.85 (m, 2H), 3.67-3.63 (m, 7H), 2.84-2.73 (m, 3H), 2.66 (d, J = 4.6 Hz, 3H), 2.39 (s, 4H), 2.32-2.28 (m, 1H), 2.17 (d, J = 6.3 Hz, 2H), 1.94-1.88 (m, 1H), 1.79 (d, J = 11.9 Hz, 3H), 1.46-4.41 (m, 3H), 1.23-1.15 (m, 3H). | | | D |
| 346 | 843.38 | 843.35 | 845.35 | $^1$H NMR (300 MHz, DMSO-d$_6$, ppm): δ 10.91 (s, 1H), 8.85 (d, J = 6.4 Hz, 1H), 8.05 (s, 1H), 7.94 (s, 2H), 7.79-7.73 (m, 2H), 7.47 (d, J = 9.1 Hz, 1H), 7.12 (s, 1H), 6.60-6.51 (m, 2H), 4.75-4.71 (m, 1H), 4.58 (s, 2H), 4.11-4.10 (m, 2H), 3.88 (d, J =12.0 Hz, 2H), 3.68(s , 2H), 3.63 (s, 3H), 2.85-2.73 (m , 3H) , 2.66 (d, J = 4.5 Hz, 3H), 2.39 (s, 6H), 2.18 (s, 2H), 1.89-1.85 (m, 7H), 1.20-1.14 (m, 2H), 1.03-0.97 (m, 4H). | | B | A |
| 347 | 843.38 | 843.35 | 845.35 | $^1$H NMR (400 MHz, DMSO-d$_6$, ppm): δ 10.83 (s, 1H), 8.84 (s, 1H), 8.39 (d, J = 6.8 Hz, 1H), 8.02 (s, 1H), 7.94-7.91 (m, 2H), 7.74-7.67 (m, 2H), 7.45 (d, J = 9.2 Hz, 1H), 7.14 (s, 1H), 6.56-6.53 (m, 1H), 6.49 (s, 1H), 4.74-4.67 (m, 1H), 4.52 (s, 2H), 2.64 (d, J = 12.7 Hz, 2H), 3.89 (s, 5H), 3.66 (s, 3H), 2.86-2.72 (m, 5H), 2.64 (d, J = 4.7 Hz, 4H), 2.32 (s, 1H), 2.19-2.10 (m, 2H), 2.07-1.96 (m, 1H), 1.81 (d, J = 12.5 Hz, 2H), 1.56 (s, 1H), 1.22-1.06 (m, 3H), 1.02 (d, J = 6.1 Hz, 6H). | | B | A |
| 348 | 747.21 | 747.20 | 845.35 | $^1$H NMR (400 MHz, DMSO-d$_6$, ppm): δ 10.83 (s, 1H), 8.78 (s, 1H), 8.39 (d, J = 6.8 Hz, 1H), 8.01 (s, 1H), 7.92-7.91 (m, 2H), 7.75-7.72 (m, 2H), 7.45 (d, J = 9.2 Hz, 1H), 7.08 (s, 1H), 6.54 (d, J = 9.2 Hz, 1H), 6.48 (s, 1H), 4.76-4.67 (m, 1H), 4.52 (d, J = 19.4 Hz, 4H), 3.90 (s, 3H), 3.65 (s, 5H), 2.82-2.75 (m, 3H), 2.64 (d, J = 4.2 Hz, 3H), 2.52 (d, J = 4.8 Hz, 5H), 2.32 (d, J = 7.2 Hz, 2H), 2.15-1.96 (m, 2H), 1.78 (d, J = 12.4 Hz, 2H), 1.61 (s, 1H), 1.06 (d, J = 5.0 Hz, 6H), 0.99 (d, J = 13.4 Hz, 2H). | | C | B |
| 349 | 748.19 | 748.20 | | $^1$HNMR (400 MHz, DMSO-d$_6$) δ : 10.85 (br s, 1H), 8.94 (s, 1H), 8.71-8.55 (m, 1H), 8.10 (s, 1H), 7.91 (br s, 2H), 7.85-7.77 (m, 2H), 7.74-7.65 (m, 2H), 7.09 (br s, 1H), 6.99 (br s, 2H), 5.72-4.93 (m, 1H), 4.82-4.70 (m, 1H), 4.52-4.40 (m, 3H), 4.28-4.19 (m, 1H), 4.11 (br d, J = 3.2 Hz, 2H), 3.97 (br d, J = 11.6 Hz, 1H), 3.82 (br dd, J = 3.2, 4.8 Hz, 1H), 3.56 (br t, J = 11.2 Hz, 1H), 3.04-2.97 (m, 1H), 2.95-2.72 (m, 3H), 2.66 (br d, J = 4.4 Hz, 3H), 2.12 (br dd, J = 3.6, 13.1 Hz, 1H), 2.01-1.93 (m, 1H), 1.54 (br d, J = 6.0 Hz, 6H) | | C | D |
| | | | | $^1$HNMR (400 MHz, DMSO-d$_6$) δ : 10.86 (br d, J = 2.0 Hz, 1H), 9.04-8.79 (m, 2H), 8.34-8.16 (m, 1H), 8.10 (s, 1H), 8.02-7.87 (m, 3H), 7.74-7.63 (m, 2H), 7.59-7.49 (m, 1H), 7.19-6.99 (m, 1H), 5.64-4.93 (m, 1H), 4.86-4.71 (m, 1H), 4.52-4.37 (m, 3H), 4.29-4.17 (m, 3H), 4.01-3.94 (m, 1H), 3.89-3.79 (m, 1H), 3.62-3.52 (m, 1H), 3.03-2.96 (m, 1H), 2.94-2.74 (m, 3H), | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 350 | 765.20 | 765.20 | | 2.65 (br d, J = 3.6 Hz, 3H), 2.24-2.19 (m, 1H), 2.03 (br d, J = 4.4 Hz, 1H), 1.54 (br d, J = 6.0 Hz, 6H) | | C | A |
| 351 | 777.23 | 777.20 | | $^1$HNMR (400 MHz, DMSO-d$_6$) δ : 11.05-10.71 (m, 1H), 9.04-8.88 (m, 1H), 8.44-8.27 (m, 1H), 8.10 (s, 1H), 7.99-7.83 (m, 2H), 7.73-7.58 (m, 3H), 7.08 (br d, J = 3.2 Hz, 1H), 6.95-6.74 (m, 2H), 5.72-4.91 (m, 1H), 4.86-4.69 (m, 1H), 4.55-4.37 (m, 3H), 4.29-4.20 (m, 1H), 4.18-4.08 (m, 2H), 4.02-3.92 (m, 3H), 3.86-3.75 (m, 1H), 3.62-3.50 (m, 1H), 3.04-2.96 (m, 1H), 2.95-2.69 (m, 3H), 2.66 (br d, J = 4.0 Hz, 3H), 2.12 (br dd, J = 3.6, 13.6 Hz, 1H), 2.02 (br d, J = 6.8 Hz, 1H), 1.55 (br d, J = 6.8 Hz, 6H) | | C | B |
| 352 | 880.44 | 880.10 | | $^1$HNMR (400 MHz, DMSO-d$_6$) δ : 11.06-10.73 (m, 1H), 9.02-8.87 (m, 1H), 8.52-8.42 (m, 1H), 8.10 (s, 1H), 7.94-7.88 (m, 2H), 7.86-7.81 (m, 1H), 7.74-7.65 (m, 2H), 7.14-7.06 (m, 1H), 6.69-6.58 (m, 2H), 5.60-4.99 (m, 1H), 4.77-4.70 (m, 1H), 4.51-4.44 (m, 3H), 4.27-4.21 (m, 1H), 4.14 (br d, J = 2.8 Hz, 2H), 3.97 (br dd, J = 1.6, 9.2 Hz, 1H), 3.89 (br s, 3H), 3.84-3.80 (m, 1H), 3.59-3.53 (m, 1H), 3.03-2.98 (m, 1H), 2.91-2.74 (m, 3H), 2.66 (br d, J = 3.6 Hz, 3H), 2.13-2.08 (m, 2H), 1.54 (br d, J = 6.4 Hz, 6H) | | | |
| 353 | 825.32 | 825.46 | 827.46 | $^1$H NMR (400 MHz, DMSO-d$_6$) δ: 11.02 (s, 1H), 8.85 (s, 1H), 8.14 (s, 1H), 8.05 (s, 1H), 8.00-7.94 (m, 2H), 7.71-7.60 (m, 3H), 7.56-7.50 (m, 2H), 7.03 (s, 1H), 5.68-4.99 (m, 2H), 4.59-4.35 (m, 4H), 4.28-4.24 (m, 1H), 4.19-4.09 (m, 2H), 3.65-3.51 (m, 2H), 3.26-3.18 (m, 4H), 2.98-2.78 (m, 2H), 2.68 (d, J = 4.8 Hz, 3H), 2.65-2.61 (m, 1H), 2.46-2.31 (m, 4H), 2.21-2.17 (m, 2H), 2.09-1.75 (m, 8H), 1.59-1.57 (m, 6H), 1.44-1.36 (m, 2H) | | B | A |
| 354 | 833.32 | 833.46 | 835.46 | $^1$H NMR (300 MHz, DMSO-d$_6$ ppm) δ11.09 (s, 1H), 8.81 (s, 1H), 8.03 (s, 1H), 7.95 (s, 2H), 7.74 (d, J = 8.7 Hz, 1H), 7.66 (d, J = 8.4 Hz, 1H), 7.46 (d, J = 9.3 Hz, 1H), 7.33 (s, 1H), 7.24 (d, J = 8.1 Hz, 1H), 7.09 (s, 1H), 5.09-5.04 (m, 1H), 4.58 (s, 2H), 4.50-4.45 (m, 2H), 3.67 (s, 3H), 3.43 (s, 4H), 2.86-2.72 (m, 3H), 2.67-2.55 (m, 6H), 2.38 (s, 5H), 2.03 (s, 1H), 1.74-1.70 (m, 2H), 1.61-1.57 (m, 1H), 1.43-1.34 (m, 2H), 1.09-1.06 (m, 2H). | | B | A |
| 355 | 831.35 | 831.48 | 833.48 | $^1$H NMR (400 MHz, DMSO-d$_6$, ppm) δ 10.78 (s, 1H), 8.85 (s, 1H), 8.32 (d, J = 8.0 Hz, 1H), 8.05 (s, 1H), 7.94 (d, J = 2.0 Hz, 2H), 7.75-7.72 (m, 1H), 7.46 (d, J = 8.8 Hz, 1H), 7.12 (s, 1H), 6.40-6.32 (m, 2H), 4.72-4.63 (m, 2H), 4.58 (s, 2H), 3.82-3.76 (m, 5H), 3.67-3.63 (m, 7H), 2.79-2.69 (m, 3H), 2.66 (d, J = 4.4 Hz, 3H), 2.53 (s, 1H), 2.39 (s, 4H), 2.18-2.16 (m, 2H), 2.04-1.91 (m, 2H), 1.78 (d, J = 12.0 Hz, 3H), 1.16-1.10 (m, 2H). | | B | C |
| 356 | 861.37 | 861.50 | 863.50 | $^1$H NMR (400 MHz, CD$_3$OD-d$_4$, ppm): δ 8.09 (s, 1H), 7.96 (s, 1H), 7.72 (d, J = 8.8 Hz, 1H), 7.59 (d, J = 9.2 Hz, 1H), 7.34-7.31 (m, 2H), 7.21-7.17 (m, 2H), 5.35-5.34 (m, 1H), 4.68-4.67 (m, 1H), 4.59 (s, 2H), 3.85 (m, 3H), 3.52-3.39 (m, 4H), 3.18-3.13 (m, 3H) , 2.87 (s, 3H), 2.82-2.66 (m, 3H), 2.27-2.16 (m, 3H), 2.03-2.00 (m, 4H), 1.62-1.60 (m, 3H), 1.47-1.46 (m, 6H). | | A | A |
| 357 | 841.32 | 841.30 | | $^1$H NMR (400 MHz, DMSO-d$_6$, ppm): δ10.85 (s, 1H), 8.83 (s, 1H), 8.53 (d, J = 8.4 Hz, 1H), 8.04 (s, 1H), 7.97-7.93 (m, 1H), 7.92 (d, J = 2.4 Hz, 1H), 7.76 (d, J = 10.8 Hz, 1H), 7.48 (d, J = 9.2 Hz, 1H), 7.13 (s, 1H), 6.64-6.63 (m, 2H), 4.76-4.73 (m, 1H), 4.58 (s, 2H), 3.74-3.59 (m, 7H), 3.59 (s, 4H), 3.38-3.33 (m, 2H), 2.81-2.74 (m, 1H), 2.66-2.50 (m, 6H), 2.14-1.99 (m, 3H), 1.89-1.80 (m, 2H), 1.78-1.65 (m, 1H), 1.41-1.30(m, 2H), 1.21(s, 1H), 0.91 (s, 7H). | | C | C |
| | | | | $^1$HNMR (400 MHz, DMSO-d$_6$) δ: 11.11 (s, 1H), 8.86 (s, 1H), 8.23 (s, 1H), 8.06 (s, 1H), 8.00-7.92 (m, 2H), 7.86-7.70 (m, 2H), 7.57-7.50 (m, 1H), 7.46-7.32 (m, 1H), 7.19-7.10 (m, 2H), 5.23-5.04 (m, 1H), 4.58 (s, 2H), 4.37- | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 358 | 843.38 | 843.20 | 845.20 | 4.28 (m, 2H), 4.18-4.03 (m, 1H), 3.63-3.62 (m, 2H), 3.36-3.32 (m, 1H), 3.16-3.04 (m, 2H), 3.04-2.81 (m, 2H), 2.80-2.71 (m, 2H), 2.66 (d, J = 4.4 Hz, 3H), 2.64-2.54 (m, 2H), 2.43-2.29 (m, 5H), 2.26 (d, J = 3.2 Hz, 1H), 2.22-2.16 (m, 1H), 2.12-1.96 (m, 2H), 1.95-1.84 (m, 1H), 1.78-1.68 (m, 1H), 1.24 (t, J = 6.8 Hz, 3H). | | | D |
| 359 | 816.32 | 816.20 | 818.20 | $^1$H NMR (400 MHz, DMSO-d$_6$, ppm) δ 10.95 (s, 1H), 8.86 (s, 1H), 8.61 (d, J = 5.6, 1H), 8.05 (s, 1H), 7.12 (s, 1H), 6.60-6.56 (m, 2H), 7.79-7.73 (m, 2H), 7.48-7.46 (m, 1H), 4.68 (s, 2H), 3.88-3.85 (m, 2H), 3.67-3.63 (m, 7H), 2.83-2.80 (m, 1H), 2.78-2.77 (m, 3H), 2.66 (s, 1H), 2.55-2.50 (m, 5H), 2.35-2.33 (m, 2H), 1.91-1.75 (m, 4H), 1.45-1.43 (m, 6H), 1.24-1.11 (m, 2H). | | B | B |
| 360 | 791.33 | 791.20 | 793.10 | $^1$H NMR (400 MHz, DMSO-d$_6$, ppm): δ 10.82 (s, 1H), 8.85 (s, 1H), 8.41 (d, J = 8.0 Hz, 1H), 8.03 (s, 2H), 7.93-7.88 (m, 2H), 7.74-7.72 (m, 1H), 7.46 (d, J = 9.2 Hz, 1H), 7.12 (s, 1H), 6.88 (d, J = 2.2 Hz, 1H), 4.74-4.64 (m, 1H), 4.58 (s, 2H), 3.94 (d, J = 12.4 Hz, 2H), 3.82 (s, 3H), 3.65 (d, J = 16.6 Hz, 7H), 2.86 (s, 2H), 2.79-2.70 (m, 1H), 2.66 (d, J = 4.6 Hz, 3H), 2.54 (d, J = 3.6 Hz, 1H), 2.38 (s, 4H), 2.17 (d, J = 6.6 Hz, 2H), 2.12-1.98 (m, 2H), 1.80 (d, J = 12.0 Hz, 3H), 1.30-1.18 (m, 2H). | | B | B |
| 361 | 774.28 | 774.20 | 776.20 | $^1$H NMR (400 MHz, DMSO-d$_6$, ppm): δ10.85 (s, 1H), 8.80 (s, 1H), 8.57 (d, J = 8.8 Hz, 1H), 8.19 (s, 1H), 8.03 (s, 1H), 7.95-7.91 (m, 2H), 7.78-7.76 (m, 1H), 7.48 (d, J = 9.2 Hz, 1H), 7.11 (s, 1H), 4.78-4.75 (m, 1H), 4.57(s, 2H), 4.50-4.47 (m, 2H), 3.68 (s, 3H), 3.01-2.77(m, 6H), 2.67-2.66 (d, J = 4.8 Hz, 3H), 2.54-2.51 (m, 1H), 2.22-2.05 (m, 3H), 2.05-1.97 (m, 5H), 1.96-1.73 (m, 5H), 1.03-0.89(m, 2H). | | C | B |
| 362 | 852.35 | 852.20 | 854.20 | $^1$H NMR (400 MHz, DMSO-d$_6$, ppm):δ10.85 (s, 1H), 8.80 (s, 1H), 8.48 (d, J = 8.8 Hz, 1H), 8.03 (s, 1H), 7.95-7.91 (m, 2H), 7.78-7.75 (m, 1H), 7.48 (d, J = 9.2 Hz, 1H), 7.11 (s, 1H), 7.03 (d, J = 3.4 Hz, 1H), 6.29 (s, 1H), 4.75-4.71 (m, 1H), 4.57 (s, 2H), 4.50-4.46(m, 2H), 3.68 (s, 3H), 2.89-2.76 (m, 5H), 2.66 (s, 4H), 2.55-2.50 (m, 1H), 2.15-2.10 (m, 3H), 1.99-1.91 (m, 5H), 1.91-1.72 (m, 3H), 1.72-1.63 (m, 2H), 1.03-0.95 (m, 2H). | | B | A |
| 363 | 852.35 | 852.20 | 854.20 | $^1$HNMR (400 MHz, DMSO-d$_6$) δ: 11.07 (s, 1H), 8.84 (s, 1H), 8.05 (s, 1H), 7.96 (s, 2H), 7.69 (s, 2H), 7.64 (d, J = 8.4 Hz, 1H), 7.03 (s, 1H), 6.75 (d, J = 2.0 Hz, 1H), 6.62 (dd, J = 2.0, 8.4 Hz, 1H), 5.06 (dd, J = 5.4, 12.8 Hz, 1H), 4.55 (s, 2H), 4.14-4.06 (m, 3H), 4.05-3.97 (m, 4H), 3.59-3.52 (m, 1H), 3.27-3.21 (m, 2H), 2.94-2.82 (m, 2H), 2.68 (s, 1H), 2.60-2.55 (m, 4H), 2.17-2.10 (m, 2H), 2.06-1.98 (m, 1H), 1.86-1.79 (m, 2H), 1.58 (d, J = 6.8 Hz, 6H), 1.44-1.35 (m, 2H). | | A | A |
| 364 | 824.34 | 824.20 | 826.10 | $^1$HNMR (400 MHz, DMSO-d$_6$) δ: 11.07 (s, 1H), 8.84 (s, 1H), 8.05 (s, 1H), 7.95 (s, 2H), 7.69 (s, 2H), 7.60-7.50 (m, 1H), 7.12 (d, J = 7.2 Hz, 1H), 7.03 (s, 1H), 6.75 (d, J = 8.4 Hz, 1H), 5.05 (dd, J = 5.4, 12.4 Hz, 1H), 4.55 (s, 2H), 4.21-4.12 (m, 4H), 4.11-4.02 (m, 3H), 3.58-3.51 (m, 1H), 3.27-3.22 (m, 2H), 2.94-2.79 (m, 2H), 2.68 (d, J = 4.4 Hz, 3H), 2.63-2.56 (m, 4H), 2.13-2.06 (m, 2H), 2.04-1.97 (m, 1H), 1.87-1.79 (m, 2H), 1.58 (d, J = 7.2 Hz, 6H), 1.43-1.34 (m, 2H). | | A | B |
| 365 | | | | $^1$HNMR (400 MHz, DMSO-d$_6$) δ: 11.19-11.04 (m, 1H), 8.81 (s, 1H), 8.19 (s, 1H), 8.04 (s, 1H), 8.01-7.94 (m, 2H), 7.87-7.82 (m, 1H), 7.79 (br d, J = 4.8 Hz, 3H), 7.53 (br d, J = 9.2 Hz, 1H), 7.09 (s, 1H), 5.18-5.09 (m, 1H), 4.58 (s, 2H), 4.54-4.45 (m, 2H), 4.33 (br d, J = 6.4 Hz, 2H), 3.01-2.92 (m, 3H), | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 365 | 838.36 | 838.20 | 840.20 | 2.90-2.81 (m, 3H), 2.67 (br d, J = 4.2 Hz, 3H), 2.65-2.59 (m, 1H), 2.56-2.53 (m, 2H), 2.18 (br d, J = 5.2 Hz, 2H), 2.07-1.98 (m, 3H), 1.82-1.72 (m, 6H), 1.25 (br t, J = 6.8 Hz, 3H), 1.08-0.98 (m, 2H) | | | A |
| 366 | 833.32 | 833.20 | 835.20 | $^1$HNMR (400 MHz, DMSO-d$_6$) δ: 11.13 (br s, 1H), 8.80 (s, 1H), 8.24 (s, 1H), 8.04 (s, 1H), 8.00-7.94 (m, 2H), 7.86-7.83 (m, 1H), 7.81-7.77 (m, 2H), 7.74-7.68 (m, 2H), 7.03 (s, 1H), 5.14 (dd, J = 12.8, 5.6 Hz, 1H), 4.56-4.49 (m, 4H), 2.97 (br d, J = 11.2 Hz, 2H), 2.91-2.81 (m, 4H), 2.68 (d, J = 4.4 Hz, 4H), 2.63 (br d, J = 3.2 Hz, 1H), 2.58 (br d, J = 9.2 Hz, 2H), 2.19 (br d, J = 6.4 Hz, 2H), 2.05-1.96 (m, 3H), 1.82-1.74 (m, 6H), 1.58 (d, J = 6.8 Hz, 6H), 1.11-1.00 (m, 2H). | | A | A |
| 367 | 833.32 | 833.20 | 835.20 | $^1$H NMR (300 MHz, DMSO-d6, ppm) δ 10.79 (b, 1H), 8.52 (s, 1H), 8.44 (s, 1H), 8.06-7.93 (m, 3H), 7.76 (s, 2H), 7.49-7.46 (m, 1H), 7.12 (s, 1H), 6.59-6.53 (m, 2H), 4.70-4.58 (m, 3H), 4.25-4.22 (m, 2H), 3.92 (s, 4H), 3.68 (s, 4H), 3.33 (s, 4H), 2.66-2.50 (m, 10H), 2.27-1.72 (m, 5H), 1.64-1.60 (m, 2H) | | B | A |
| 368 | 845.36 | 845.20 | 847.20 | $^1$H NMR (300 MHz, DMSO-d6, ppm) δ 10.85 (s, 1H), 8.84 (s, 1H), 8.41 (d, J = 6.9 Hz, 1H), 8.03 (m, 1H), 7.94-7.93 (m, 1H), 7.87 (s, 1H), 7.76-7.75 (m, 2H), 7.45 (d, J = 9.0 Hz, 1H), 7.12 (s, 1H), 6.63 (d, J = 1.8 Hz, 1H), 6.55 (s, 1H), 4.70-4.68 (m, 1H), 4.55 (s, 2H), 3.91 (s, 3H), 3.70-3.61 (m, 9H), 3.19-3.15 (m, 2H), 2.86-2.80 (m, 1H), 2.65 (s, 3H), 2.51-2.49 (m, 7H), 2.10-2.00 (m, 2H), 1.91-1.87 (m, 3H), 1.86-1.77 (m, 1H); | | B | B |
| 369 | 726.24 | 726.20 | 728.10 | $^1$H NMR (400 MHz, d$_6$-DMSO, ppm): δ 10.88-10.84 (m, 1H), 9.03 (s, 1H), 8.62-8.60 (m, 1H), 8.10 (s, 1H), 8.01-7.93 (m, 2H), 7.75-7.73 (m, 1H), 7.49-7.47 (m, 1H), 7.26-7.09 (m, 4H), 4.80-4.73 (m, 1H), 4.68-4.51 (m, 4H), 3.69 (s, 3H), 3.59-3.55 (m, 3H), 3.34-3.21 (m, 2H), 3.06-2.75 (m, 6H), 2.67-2.66 (m, 3H), 2.57 (s, 1H), 2.12-2.03 (m, 3H), 1.91-1.88 (m, 2H), 1.40-1.34 (m, 6H), 1.30-1.24 (m, 2H). | D | C | D |
| 370 | 831.35 | 831.20 | 833.20 | $^1$H NMR (400 MHz, d$_6$-DMSO, ppm): δ 10.88-10.84 (m, 1H), 9.03 (s, 1H), 8.62-8.60 (m, 1H), 8.10 (s, 1H), 8.01-7.93 (m, 2H), 7.75-7.73 (m, 1H), 7.49-7.47 (m, 1H), 7.26-7.09 (m, 4H), 4.80-4.73 (m, 1H), 4.68-4.51 (m, 4H), 3.69 (s, 3H), 3.59-3.55 (m, 3H), 3.34-3.21 (m, 2H), 3.06-2.75 (m, 6H), 2.67-2.66 (m, 3H), 2.57 (s, 1H), 2.12-2.03 (m, 3H), 1.91-1.88 (m, 2H), 1.40-1.34 (m, 6H), 1.30-1.24 (m, 2H). | | B | B |
| 371 | 841.32 | 841.20 | 843.10 | $^1$H NMR (400 MHz, d$_6$-DMSO, ppm): δ 10.88-10.84 (m, 1H), 9.03 (s, 1H), 8.62-8.60 (m, 1H), 8.10 (s, 1H), 8.01-7.93 (m, 2H), 7.75-7.73 (m, 1H), 7.49-7.47 (m, 1H), 7.26-7.09 (m, 4H), 4.80-4.73 (m, 1H), 4.68-4.51 (m, 4H), 3.69 (s, 3H), 3.59-3.55 (m, 3H), 3.34-3.21 (m, 2H), 3.06-2.75 (m, 6H), 2.67-2.66 (m, 3H), 2.57 (s, 1H), 2.12-2.03 (m, 3H), 1.91-1.88 (m, 2H), 1.40-1.34 (m, 6H), 1.30-1.24 (m, 2H). | | B | D |
| 372 | 879.42 | 879.20 | 881.20 | $^1$HNMR (400 MHz, DMSO-d$_6$) δ: 11.20-10.99 (m, 1H), 8.86 (s, 1H), 8.29 (s, 1H), 8.06 (s, 1H), 8.01-7.88 (m, 2H), 7.83 (d, J = 8.8 Hz, 1H), 7.75 (d, J = 9.2 Hz, 1H), 7.53 (br d, J = 9.2 Hz, 1H), 7.44 (s, 1H), 7.36 (d, J = 7.2 Hz, 1H), 7.11 (s, 1H), 5.17-5.06 (m, 1H), 4.58 (s, 2H), 4.38-4.28 (m, 2H), 4.18-4.04 (m, 2H), 3.64-3.61 (m, 3H), 3.19-3.12 (m, 2H), 2.94-2.85 (m, 1H), 2.82-2.70 (m, 2H), 2.67 (d, J = 4.4 Hz, 3H), 2.64-2.54 (m, 2H), 2.48-2.42 (m, 2H), 2.40-2.32 (m, 5H), 2.23-2.14 (m, 1H), 2.10-2.00 (m, 1H), 1.95-1.82 (m, 2H), 1.24 (t, J = 6.8 Hz, 3H). | | B | A |
| | | | | $^1$HNMR (400 MHz, DMSO-d$_6$) δ: 11.07 (s, 1H), 8.80 (s, 1H), 8.20 (s, 1H), 8.04 (s, 1H), 8.00-7.93 (m, 2H), 7.76-7.67 (m, 2H), 7.64 (d, J = 8.0 Hz, 1H), 7.02 | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 373 | 676.13 | 676.10 | 678.10 | (s, 1H), 6.78 (d, J = 2.0 Hz, 1H), 6.65 (dd, J = 2.0, 8.4 Hz, 1H), 5.05 (dd, J = 5.4, 12.8 Hz, 1H), 4.54 (s, 2H), 4.50 (br d, J = 11.6 Hz, 2H), 3.75 (s, 4H), 2.91-2.79 (m, 3H), 2.68 (d, J = 4.8 Hz, 3H), 2.66-2.52 (m, 3H), 2.40-2.22 (m, 4H), 2.12 (d, J = 6.4 Hz, 2H), 2.06-1.96 (m, 1H), 1.85-1.70 (m, 7H), 1.58 (d, J = 6.8 Hz, 6H), 1.12-0.96 (m, 2H). | | | D |
| 374 | 879.42 | 879.20 | 881.20 | $^1$H NMR (400 MHz, DMSO-d$_6$) δ : 10.87 (br s, 1H), 9.06-8.86 (m, 1H), 8.84-8.60 (m, 1H), 8.37-8.21 (m, 2H), 8.06-7.78 (m, 4H), 7.77-7.54 (m, 3H), 7.27-6.92 (m, 2H), 5.78-4.53 (m, 2H), 4.53-4.40 (m, 2H), 3.04-2.73 (m, 5H), 2.67-2.63 (m, 3H), 2.58-2.55 (m, 1H), 2.29-2.16 (m, 1H), 2.06-1.96 (m, 1H), 1.55 (br d, J = 6.8 Hz, 6H). | | A | A |
| 375 | 829.36 | 829.20 | 831.10 | $^1$H NMR (400 MHz, DMSO-d$_6$ ppm)δ 11.07 (s, 1H), 8.79 (s, 1H), 8.02 (s, 1H), 8.00-7.95 (m, 2H), 7.72 (s, 2H), 7.64 (s, 1H), 7.31 (s, 1H), 7.24-7.22 (m, 1H), 7.01 (s, 1H), 5.08-5.03 (m, 1H), 4.54 (s, 2H), 4.49-4.46 (m, 2H), 3.43(s, 4H), 2.93-2.90(m, 4H), 2.89-2.72 (m, 3H), 2.70(s, 3H), 2.63-2.52 (m, 2H), 2.30 (s, 2H), 2.05-1.97 (m, 1H), 1.72 (s, 6H), 1.60-1.52 (m, 8H), 1.06-1.01 (m, 2H). | | B | A |
| 376 | 843.38 | 843.20 | 845.20 | $^1$H NMR (300 MHz, DMSO-d$_6$ ppm) δ 10.89 (s, 1H), 8.84 (s, 1H), 8.45 (d, J = 6.9 Hz, 1H), 8.03 (d, J = 17.2 Hz, 3H), 7.79-7.76 (m, 2H), 7.52 (d, J = 9.2 Hz, 1H), 7.12 (s, 1H), 6.61-6.51 (m, 2H), 4.75-4.69 (m, 3H), 4.33 (d, J = 6.6 Hz, 2H), 3.91 (d, J = 19.6 Hz, 5H), 3.66 (s, 4H), 3.39(s, 6H), 2.85-2.78 (m, 2H), 2.69 (d, J = 4.6 Hz, 2H), 2.40 (s, 3H), 2.17-2.07 (m, 3H), 1.80 (d, J = 11.7 Hz, 3H), 1.28-1.26 (m, 4H). | | B | A |
| 377 | 802.29 | 802.20 | 804.10 | $^1$H NMR (300 MHz, DMSO-d$_6$ ppm) δ 10.85 (s, 1H), 8.83 (s, 1H), 8.41 (d, J = 6.9 Hz, 1H), 8.05 (s, 1H), 7.96 (s, 2H), 4.73-4.66 (m, 1H), 7.04 (s, 1H), 6.60-6.51 (m, 2H), 5.32 (s, 1H), 4.73-4.66 (m, 1H), 4.55 (s, 2H), 3.92 (s, 5H), 3.65 (s, 4H), 2.86-2.50 (m, 7H), 2.40 (s, 4H), 2.17-2.00 (m, 4H), 1.80 (d, J = 11.9 Hz, 3H), 1.57 (d, J = 6.8 Hz, 6H), 1.24-1.13 (m, 2H). | | | D |
| 378 | 726.24 | 726.20 | 728.10 | $^1$H NMR (300 MHz, DMSO-d$_6$ ppm)δ11.44 (d, J = 7.2 Hz, 2H), 10.87 (s, 1H), 8.83 (s, 1H), 8.04 (s, 2H), 7.97-7.92 (m, 3H), 7.75-7.71 (m, 1H), 7.46 (d, J = 9.3 Hz, 1H), 7.20-7.16 (m, 1H), 7.11 (s, 1H), 4.80-4.73 (m, 1H), 4.57 (s, 2H), 3.91-3.87 (m, 2H), 3.66-3.62 (m, 7H), 3.27 (s, 1H), 2.93-2.78 (m, 2H), 2.76-2.64 (m, 4H), 2.37 (m, 4H), 2.17-2.15 (m, 4H), 1.85-1.72 (m, 3H), 1.20-1.05 (m, 2H). | D | C | D |
| 379 | 787.23 | 787.20 | 789.20 | $^1$H NMR (300 MHz, DMSO-d$_6$ ppm) δ 11.07 (s, 1H), 8.65 (s, 1H), 8.01 (s, 1H), 7.69-7.64 (m, 1H), 7.55-7.52 (m, 2H), 7.33-7.29 (m, 2H), 7.06-7.03 (m, 1H), 5.10-5.04 (m, 1H), 3.70-3.63 (m, 6H), 3.31-3.24 (m, 3H), 2.91-2.81 (m, 5H), 2.60-2.56 (m, 4H), 2.54-2.44 (m, 4H), 2.38-2.21 (m, 2H), 2.19-1.96 (m, 1H), 1.93-1.63 (m, 3H), 1.50-1.20 (m, 2H). | | | D |
| | | | | $^1$H NMR (300 MHz, DMSO-d$_6$ ppm) δ 11.11 (s, 1H), 8.92 (s, 1H), 8.09 (s, 1H), 7.94-7.91 (m, 2H), 7.80 (d, J = 9.0 Hz, 1H), 7.70-7.68 (m, 2H), 7.40 (s, 1H), 7.30 (d, J = 8.4 Hz, 1H), 7.09 (s, 1H), 5.31 (s, 1H), 5.15-5.09 (m, 1H), 4.50 (s, 2H), 4.40 (d, J = 12.0 Hz, 1H), 4.38-4.21 (m, 3H), 3.93 (d, J = 12.0 Hz, 2H), 3.61 (m, 1H), 3.49-3.41 (m, 1H), 2.95-2.75 (m, 3H), 2.66 (d, J = 4.6 Hz, 5H), 2.12-1.90 (m, 3H), 1.54 (d, J = 6.8 Hz, 6H). | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 380 | 825.32 | 825.30 | 827.20 | $^1$H NMR (300 MHz, DMSO-d$_6$, ppm) δ11.05 (s, 1H), 8.86 (s, 1H), 8.06 (s, 1H), 7.95 (s, 2H), 7.69 (s, 2H), 7.63 (d, J = 8.7 Hz, 1H), 7.02 (d, J = 5.4 Hz, 2H), 6.86 (d, J = 9.0 Hz, 1H), 5.30(s, 1H), 5.06-5.00 (m, 1H), 4.54 (s, 2H), 4.20 (s, 1H), 3.66-3.50 (m, 5H), 3.30 (s, 1H), 2.90-2.80 (m, 1H), 2.65-2.51 (m, 5H), 2.49-2.37 (m, 3H), 2.10-1.90 (m, 6H), 1.56 (d, J = 6.6 Hz, 7H). | | C | B |
| 381 | 867.41 | 867.30 | 827.20 | $^1$H NMR (400 MHz, DMSO-d$_6$, ppm)δ 11.08 (s, 1H), 8.80 (s, 1H), 8.03 (s, 1H), 7.95 (s, 2H), 7.70-7.67 (m, 3H), 7.33-7.31 (m, 2H), 7.01 (s, 1H), 5.18-5.10 (m, 1H), 4.56-4.53 (m, 4H), 3.57 (s, 2H), 3.33-3.31 (m, 3H), 2.92-2.79(m, 3H), 2.67-2.66 (d, J = 4.7 Hz, 7H), 2.66-2.57 (m, 1H), 2.50 (s, 2H), 2.04-1.98 (m, 1H), 1.91-1.82 (m, 2H), 1.69-1.62 (m, 1H), 1.60-1.56 (m, 6H), 1.06 (s, 7H). | | B | A |
| 382 | 787.23 | 787.20 | 789.20 | $^1$H NMR (400 MHz, DMSO-d$_6$) δ : 11.12 (s, 1H), 9.16-8.85 (m, 1H), 8.08 (s, 1H), 7.99-7.83 (m, 2H), 7.80-7.57 (m, 3H), 7.38 (br d, J = 1.6 Hz, 1H), 7.30-7.11 (m, 1H), 7.06 (m, 1H), 5.11 (br dd, J = 5.2, 12.4 Hz, 2H), 4.49 (br s, 2H), 4.37-4.17 (m, 3H), 4.11-3.86 (m, 3H), 3.82-3.58 (m, 2H), 3.24-3.16 (m, 1H), 2.95-2.82 (m, 1H), 2.66 (br d, J = 4.4 Hz, 3H), 2.58 (br s, 1H), 2.13-1.97 (m, 1H), 1.55 (br d, J = 6.4 Hz, 6H), 1.14 (br d J = 6.0 Hz, 3H) | | B | C |
| 383 | 787.23 | 787.20 | 789.10 | $^1$H NMR (400 MHz, DMSO-d$_6$) δ: 11.40-10.75 (m, 1H), 9.00-8.89 (m, 1H), 8.10 (s, 1H), 7.97-7.84 (m, 2H), 7.84-7.76 (m, 1H), 7.74-7.65 (m, 2H), 7.50-7.43 (m, 1H), 7.38-7.29 (m, 1H), 7.15-7.08 (m, 1H), 5.67-5.03 (m, 2H), 4.52-4.26 (m, 6H), 3.96-3.85 (m, 1H), 3.74-3.61 (m, 1H), 2.96-2.85 (m, 1H), 2.84-2.74 (m, 1H), 2.68-2.62 (m, 4H), 2.59 (s, 3H), 2.57-2.54 (m, 1H), 2.11-2.04 (m, 1H), 1.53 (br d, J = 6.8 Hz, 6H), 1.17 (d, J = 6.0 Hz, 3H) | | B | B |
| 384 | 879.42 | 879.30 | 881.20 | $^1$H NMR (400 MHz, DMSO-d$_6$) δ: 11.07 (s, 1H), 8.84 (s, 1H), 8.15 (s, 1H), 8.04 (s, 1H), 8.00-7.95 (m, 1H), 7.91 (s, 1H), 7.69 (s, 2H), 7.65 (d, J = 8.4 Hz, 1H), 7.30 (m, 1H), 7.24-7.21 (m, 1H), 7.03 (s, 1H), 5.06 (dd, J = 5.4, 12.8 Hz, 1H), 4.55 (s, 2H), 4.03 (br d, J = 12.0 Hz, 2H), 3.60 (br s, 4H), 3.25 (br s, 4H), 2.97-2.86 (m, 4H), 2.70-2.66 (m, 4H), 2.60 (br s, 1H), 2.56 (br s, 2H), 2.00 (br dd, J = 4.8, 10.4 Hz, 1H), 1.75-1.67 (m, 6H), 1.58 (s, 3H), 1.56 (s, 3H), 1.24-1.12 (m, 3H). | | A | A |
| 385 | 879.42 | 879.20 | 881.30 | $^1$H NMR (400 MHz, DMSO-d$_6$) δ: 11.09 (s, 1H), 8.85 (s, 1H), 8.16 (s, 1H), 8.05 (s, 1H), 8.01-7.96 (m, 1H), 7.92 (s, 1H), 7.90-7.90 (m, 1H), 7.71-7.66 (m, 3H), 7.36-7.31 (m, 2H), 7.04 (s, 1H), 5.14-5.04 (m, 1H), 4.56 (s, 2H), 3.69 (br d, J = 12.4 Hz, 2H), 3.61 (br s, 4H), 3.29 (br s, 4H), 2.94-2.80 (m, 4H), 2.70 (d, J = 4.8 Hz, 4H), 2.64-2.56 (m, 4H), 2.06-2.00 (m, 1H), 1.78 (br d, J = 12.0 Hz, 2H), 1.72 (br s, 4H), 1.59 (s, 3H), 1.57 (s, 3H), 1.41-1.32 (m, 2H). | | B | A |
| 386 | 838.36 | 838.20 | 840.20 | $^1$H NMR (400 MHz, DMSO-d$_6$) δ: 11.09 (s, 1H), 8.85 (s, 1H), 8.16 (s, 1H), 8.05 (s, 1H), 8.01-7.96 (m, 1H), 7.92 (s, 1H), 7.90-7.90 (m, 1H), 7.71-7.66 (m, 3H), 7.36-7.31 (m, 2H), 7.04 (s, 1H), 5.14-5.04 (m, 1H), 4.56 (s, 2H), 3.69 (br d, J = 12.4 Hz, 2H), 3.61 (br s, 4H), 3.29 (br s, 4H), 2.94-2.80 (m, 4H), 2.70 (d, J = 4.8 Hz, 4H), 2.64-2.56 (m, 4H), 2.06-2.00 (m, 1H), 1.78 (br d, J = 12.0 Hz, 2H), 1.72 (br s, 4H), 1.59 (s, 3H), 1.57 (s, 3H), 1.41-1.32 (m, 2H). | | B | A |
| 387 | 867.41 | 867.20 | 869.20 | $^1$H NMR (300 MHz, DMSO-d$_6$, ppm): δ11.08 (s, 1H), 8.86(s, 1H), 8.04 (s, 1H), 7.93 (s, 2H), 7.68-7.64 (m, 3H), 7.33-7.30 (d, J = 1.2 Hz, 2H), 7.09 (s, 1H), 5.12-5.06 (m, 1H), 4.51 (s, 2H), 4.20-4.16 (m, 2H), 3.72-3.61 (m, 2H), 2.89-2.82 (m, 3H), 2.78-2.61(m, 7H), 2.55-2.27 (m, 4H), 2.26-2.00(m, | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 388 | 825.37 | 825.20 | 827.20 | 3H), 1.98-1.71 (d, J = 10.8 Hz, 3H), 1.70-1.51 (d, J = 7.6 Hz, 7H), 1.45-1.22 (m, 3H), 1.20-0.99 (m, 7H). | | | A |
| 389 | 801.25 | 801.20 | 803.10 | $^{1}$H NMR (300 MHz, DMSO-d$_6$, ppm) δ 10.95 (s, 1H), 8.85 (s, 1H), 8.06 (s, 1H), 7.96 (s, 2H), 7.70 (s, 2H), 7.50 (d, J = 9.0 Hz, 1H), 7.04 (d, J = 6.3 Hz, 3H), 5.17-5.01 (m, 1H), 4.55 (s, 2H), 4.35-4.16 (m, 2H), 3.88 (d, J = 12.3 Hz, 2H), 3.65 (s, 4H), 2.90-2.78 (m, 3H), 2.66 (d, J = 4.6 Hz, 4H), 2.40 (s, 5H), 2.17 (s, 2H), 1.81 (d, J = 11.9 Hz, 5H), 1.57 (d, J = 6.8 Hz, 6H), 1.19 (d, J = 12.6 Hz, 2H) | | B | B |
| 390 | 880.40 | 880.20 | 882.10 | $^{1}$H NMR (400 MHz, DMSO-d$_6$) δ: 11.12 (s, 1H), 9.22-8.99 (m, 1H), 9.47-8.93 (m, 1H), 8.17-8.04 (m, 1H), 7.97-7.89 (m, 1H), 7.88-7.82 (m, 1H), 7.79-7.63 (m, 3H), 7.46-7.35 (m, 1H), 5.14-4.82 (m, 2H), 4.54-4.48 (m, 2H), 4.34-4.24 (m, 3H), 4.24-4.17 (m, 2H), 3.82-3.71 (m, 3H), 3.35-3.26 (m, 1H), 2.96-2.83 (m, 1H), 2.68-2.65 (m, 3H), 2.56-2.54 (m, 1H), 2.10-2.02 (m, 1H), 1.62-1.51 (m, 8H), 1.48-1.39 (m, 1H), 0.89-0.76 (m, 3H). | | B | A |
| 391 | 880.40 | 880.20 | 882.10 | $^{1}$H NMR (400 MHz, DMSO-d$_6$) δ: 11.08 (s, 1H), 8.84 (s, 1H), 8.05 (s, 1H), 7.99-7.92 (m, 2H), 7.72-7.60 (m, 3H), 7.32 (d, J = 1.6z, 1H), 7.24 (dd, J = 2.0, 8.8 Hz, 1H), 7.02 (s, 1H), 5.06 (dd, J = 5.2, 13.2 Hz, 1H), 4.55 (s, 2H), 4.24-4.07 (m, 3H), 3.58-3.50 (m, 1H), 3.42-3.47 (m, 2H), 3.41-3.37 (m, 2H), 3.20-3.27 (m, 2H), 2.94-2.83 (m, 1H), 2.67 (d, J = 4.4 Hz, 3H), 2.63-2.52 (m, 3H), 2.27-2.19 (m, 2H), 2.06-1.97 (m, 1H), 1.88-1.79 (m, 2H), 1.72-1.64 (m, 2H), 1.64-1.58 (m, 4H), 1.57 (d, J = 6.8 Hz, 6H), 1.43-1.34 (m, 2H). | | A | A |
| 392 | 880.40 | 880.20 | 882.20 | $^{1}$H NMR (400 MHz, DMSO-d$_6$) δ: 11.08 (s, 1H), 8.83 (s, 1H), 8.05 (s, 1H), 8.00-7.92 (m, 2H), 7.71-7.64 (m, 3H), 7.30-7.36 (m, 2H), 7.02 (s, 1H), 5.09 (dd, J = 5.2, 12.8 Hz, 1H), 4.55 (s, 2H), 4.25-4.05 (m, 3H), 3.60-3.49 (m, 1H), 3.28-3.11 (m, 6H), 2.96-2.80 (m, 1H), 2.68 (d, J = 4.8 Hz, 3H), 2.64-2.52 (m, 3H), 2.28-2.19 (m, 2H), 2.08-1.98 (m, 1H), 1.87-1.79 (m, 2H), 1.74-1.64 (m, 6H), 1.57 (d, J = 7.2 Hz, 6H), 1.44-1.34 (m, 2H). | | | D |
| 393 | 880.40 | 880.20 | 882.20 | $^{1}$H NMR (400 MHz, DMSO-d$_6$) δ: 11.08 (s, 1H), 8.82 (s, 1H), 8.03 (s, 1H), 8.00-7.92 (m, 2H), 7.73-7.62 (m, 3H), 7.33 (s, 1H), 7.25 (dd, J = 2.0, 8.4 Hz, 1H), 7.00 (s, 1H), 5.12-5.02 (m, 1H), 4.56 (s, 2H), 4.23-4.15 (m, 1H), 3.86-3.77 (m, 2H), 3.67-3.52 (m, 5H), 3.26-3.16 (m, 2H), 2.96-2.82 (m, 1H), 2.68 (d, J = 4.8 Hz, 3H), 2.63-2.52 (m, 3H), 2.26-2.18 (m, 2H), 2.06-1.98 (m, 1H), 1.92-1.83 (m, 2H), 1.72-1.64 (m, 2H), 1.57 (d, J = 6.8 Hz, 6H), 1.55-1.43 (m, 6H). | | A | A |
| 394 | 801.25 | 801.40 | | $^{1}$H NMR (400 MHz, DMSO-d6) δ: 11.12 (s, 1 H), 9.24-9.07 (m, 1 H), 8.18-8.10 (m, 1 H), 7.93-7.85 (m, 2 H), 7.84-7.78 (m, 1 H), 7.72-7.66 (m, 2 H), 7.53-7.44 (m, 1 H), 7.39-7.26 (m, 1 H), 7.11 (s, 1 H), 6.29-4.90 (m, 2 H), 4.53-4.28 (m, 6 H), 3.96-3.83 (m, 2 H), 2.95-2.78 (m, 4 H), 2.66 (d, J = 4.4 Hz, 2 H), 2.62-2.59 (m, 1 H), 2.14-1.98 (m, 2 H), 1.56-1.44 (m, 8 H), 0.91-0.81 (m, 3 H). | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 395 | 797.31 | 797.40 | 799.40 | $^1$H NMR (400 MHz, DMSO-d$_6$, ppm) δ11.06 (s, 1H), 8.72 (s, 1H), 8.03 (s, 1H), 7.81 (d, J = 4.8 Hz, 1H), 7.64 (d, J = 8.4 Hz, 1H), 7.58-7.57(m, 1H), 7.50-4.47(m, 1H), 7.30 (s, 1H), 7.24-7.21 (m, 1H), 7.13 (d, J = 8.0 Hz, 1H), 5.08-5.05 (m, 1H), 4.47 (s, 2H), 4.05-4.02 (m, 2H), 3.62-3.57 (m, 6H), 3.47 (s, 2H), 2.96-2.85 (m, 3H), 2.54-2.51 (m, 5H), 2.38-2.30 (m, 6H), 2.8-2.10 (m, 2H), 1.98-1.95 (m, 1H), 1.85-1.74 (m, 3H), 1.19-1.10 (m, 2H). | | | 1000 |
| 396 | 830.34 | 830.40 | 832.40 | $^1$H NMR (300 MHz, DMSO-d$_6$, ppm) δ 11.94 (d, J = 7.5 Hz, 1H), 10.89 (s, 1H), 8.84 (s, 1H), 8.05 (s, 1H), 7.94 (s, 2H), 7.86-7.75 (m, 2H), 7.48 (d, J = 6.3 Hz, 2H), 7.28 (d, J = 8.3 Hz, 1H), 7.14 (s, 1H), 4.84-4.80 (m, 1H), 4.59 (s, 2H), 3.93-3.90 (m, 2H), 3.64 (d, J = 24.0 Hz, 7H), 2.83-2.65 (m, 6H), 2.50 (s, 3H), 2.28-2.04 (m, 2H), 1.81 (s, 4H), 1.58-1.33 (m, 3H), 0.91 (s, 6H). | | C | B |
| 397 | 830.34 | 832.40 | | $^1$H NMR (300 MHz, DMSO-d$_6$, ppm) δ 11.93 (d, J = 7.3 Hz, 1H), 10.93 (s, 1H), 8.85 (s, 1H), 8.06 (s, 1H), 7.97 (s, 2H), 7.86 (d, J = 7.9 Hz, 1H), 7.70 (s, 2H), 7.52-7.49 (m, 1H), 7.30 (d, J = 8.3 Hz, 1H), 7.04 (s, 1H), 4.86-4.78 (m, 1H), 4.56 (s, 2H), 3.84 (d, J = 9 Hz, 2H), 3.66 (s, 4H), 2.70-2.65 (m, 6H), 2.41 (s, 4H), 2.21-2.04 (m, 5H), 1.84 (d, J = 12.2 Hz, 3H), 1.59-1.56 (m, 6H), 1.29 (d, J = 12.8 Hz, 2H). | | C | B |
| 398 | 825.32 | 825.35 | | $^1$H NMR (300 MHz, DMSO-d$_6$, ppm): δ 11.06 (s, 1H), 8.84 (s, 1H), 8.04 (s, 1H), 7.96 (d, J = 9.9 Hz, 2H), 7.69 (s, 2H), 7.47-7.46 (m, 1H), 7.25 (d, J = 8.6 Hz, 1H), 7.12 (d, J = 3.6 Hz, 1H), 7.03 (s, 1H), 5.32(s, 1H), 5.08 (d, J = 5.3 Hz, 1H), 4.70-4.50 (m, 3H), 3.93 (d, J = 10.5 Hz, 1H), 3.55 (s, 4H), 3.21 (s, 1H), 2.84-2.75 (m, 2H), 2.68-2.65 (m, 3H), 2.44(s, 3H), 2.27-2.18 (m, 3H), 2.08 (s, 2H), 1.98-1.83 (m, 3H), 1.55 (s, 7H) | | C | A |
| 399 | 880.44 | 880.10 | | 1H NMR (400 MHz, DMSO-d6) δ: 10.99 (s, 1H), 8.84 (s, 1H), 8.26 (s, 1H), 8.05 (s, 1H), 8.01-7.92 (m, 2H), 7.72-7.61 (m, 3H), 7.49 (s, 1H), 7.44-7.35 (m, 1H), 7.06-7.00 (m, 1H), 5.67-5.04 (m, 2H), 4.55 (s, 2H), 4.46-4.39 (m, 1H), 4.33-4.26 (m, 1H), 4.21-4.10 (m, 3H), 3.00 (d, J = 8.8 Hz, 2H), 2.92-2.77 (m, 4H), 2.68 (d, J = 4.8 Hz, 3H), 2.63-2.59 (m, 2H), 2.18-2.12 (m, 2H), 2.06-1.94 (m, 4H), 1.87-1.75 (m, 7H), 1.71-1.65 (m, 2H), 1.58-1.56 (m, 6H), 1.41-1.35 (m, 2H) | | | |
| 400 | 894.43 | 894.40 | | $^1$HNMR (400 MHz, DMSO-d$_6$) δ: 11.08 (s, 1H), 8.85 (s, 1H), 8.05 (s, 1H), 8.00-7.94 (m, 2H), 7.73-7.65 (m, 3H), 7.34 (s, 1H), 7.26 (br d, J = 8.8 Hz, 1H), 7.05 (s, 1H), 5.07 (dd, J = 5.2, 12.8 Hz, 1H), 4.58-4.53 (m, 1H), 4.55 (s, 2H), 3.63 (br s, 4H), 3.44 (br s, 4H), 2.95-2.76 (m, 2H), 2.68 (d, J = 4.8 Hz, 3H), 2.63-2.54 (m, 2H), 2.46-2.31 (m, 1H), 2.02 (br d, J = 10.4 Hz, 3H), 1.81 (br s, 2H), 1.57 (d, J = 7.2 Hz, 6H). | | C | |
| 401 | 829.36 | 829.30 | | $^1$H NMR (400 MHz, DMSO-d$_6$) δ: 10.34 (s, 1H), 8.91 (s, 1H), 8.14 (s, 1H), 8.09 (s, 1H), 8.00-7.92 (m, 2H), 7.70 (s, 2H), 7.38 (dd, J = 2.0, 8.4 Hz, 1H), 7.33 (d, J = 2.0 Hz, 1H), 7.16 (d, J = 8.8 Hz, 1H), 7.05 (s, 1H), 4.56 (s, 2H), 4.50-4.15 (m, 1H), 3.85 (s, 3H), 3.72-3.56 (m, 5H), 3.42-3.34 (m, 4H), 3.32-3.30 (m, 2H), 3.12-2.74 (m, 3H), 2.73-2.68 (m, 2H), 2.67 (d, J = 4.4 Hz, 3H), 2.54-2.51 (m, 2H), 2.05-1.90 (m, 1H), 1.85-1.69 (m, 2H), 1.58 (d, J = 6.8 Hz, 6H), 1.21-1.02 (m, 2H). | | | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 402 | 799.33 | 799.30 | | $^1$H NMR (400 MHz, DMSO-d$_6$) δ: 10.44 (s, 1H), 8.94 (s, 1H), 8.10 (s, 1H), 8.00-7.93 (m, 2H), 7.70 (s, 2H), 7.40 (s, 4H), 7.06 (s, 1H), 4.56 (s, 2H), 4.52-4.37 (m, 1H), 3.84 (t, J = 6.4 Hz, 2H), 3.76-3.46 (m, 4H), 3.33-3.23 (m, 3H), 3.18-2.75 (m, 5H), 2.72 (t, J = 6.8 Hz, 2H), 2.67 (d, J = 4.8 Hz, 3H), 2.54-2.52 (m, 2H), 2.11-1.95 (m, 1H), 1.91-1.67 (m, 2H), 1.58 (d, J = 7.2 Hz, 6H), 1.26-1.07 (m, 2H). | | | D |
| 403 | 894.43 | 894.20 | | $^1$H NMR (400 MHz, DMSO-d6) δ: 11.12 (s, 1H), 8.83 (s, 1H), 8.04 (s, 1H), 8.00-7.91 (m, 2H), 7.88-7.80 (m, 1H), 7.80-7.74 (m, 2H), 7.69 (s, 2H), 7.02 (s, 1H), 5.13 (dd, J = 5.2, 13.2 Hz, 2H), 4.54 (s, 2H), 4.22-4.05 (m, 3H), 3.61-3.46 (m, 1H), 3.23 (br t, J = 10.4 Hz, 2H), 2.99 (br d, J = 10.0 Hz, 2H), 2.94-2.72 (m, 3H), 2.68 (d, J = 4.8 Hz, 3H), 2.64-2.53 (m, 2H), 2.21-2.10 (m, 2H), 2.08-1.93 (m, 3H), 1.88-1.73 (m, 6H), 1.72-1.62 (m, 2H), 1.57 (d, J = 6.8 Hz, 6H), 1.37 (br d, J = 9.2 Hz, 2H) | | B | A |
| 404 | 869.38 | 869.15 | | $^1$H NMR (300 MHz, DMSO-d$_6$, ppm) δ 11.08 (s, 1H), 8.85 (s, 1H), 8.05 (s, 1H), 7.95 (s, 2H), 7.70 (s, 2H), 7.38(s, 1H), 7.17 (s, 1H), 7.03 (s, 1H), 5.04-5.08 (m, 1H), 4.56 (s, 2H), 3.96 (s, 3H), 3.31-3.53 (m, 6H), 2.73-2.89 (m, 1H), 2.61-2.68 (m, 7H), 2.40-2.50 (m, 4H), 2.23-2.27 (m, 2H), 2.00-2.04 (m, 1H), 1.80-1.84 (m, 3H), 1.56-1.58 (m, 6H), 1.13-1.28 (m, 3H). | | A | B |
| 405 | 852.35 | 852.20 | | $^1$H NMR (300 MHz, DMSO-d$_6$, ppm) δ 11.10 (s, 1H), 9.23 (s, 1H), 8.13-8.04 (m, 3H), 7.82-7.66 (m, 3H), 7.34-7.24 (m, 2H), 7.12 (s, 1H), 5.11-5.05 (m, 1H), 4.59 (s, 2H), 4.07-4.01 (m, 5H), 3.83-3.78 (m, 2H), 3.70 (s, 3H), 3.44-3.00 (m, 3H), 2.97-2.85 (m, 1H), 2.75-2.52 (m, 5H), 2.30-2.01 (m, 3H), 1.89-1.79 (m, 2H), 1.60-1.25 (m, 8H). | | | D |
| 406 | 852.35 | 852.20 | | $^1$H NMR (300 MHz, DMSO-d$_6$, ppm) δ 11.11 (s, 1H), 8.82 (s, 1H), 8.11-8.01 (m, 3H), 7.84-7.81 (m, 1H), 7.72-7.67 (m, 2H), 7.35 (d, J = 6.9 Hz, 2H), 7.09 (s, 1H), 5.15-5.09 (m, 1H), 4.59(s, 2H), 4.11-3.96 (m, 5H), 3.56-3.53 (m, 3H), 3.36-3.33 (m, 2H), 3.10-3.04 (m, 2H), 2.90-2.84 (m, 1H), 2.71-2.52 (m, 5H), 2.17-1.86 (m, 6H), 1.80-1.43 (m, 8H). | | A | A |
| 407 | 799.33 | 799.34 | | $^1$H NMR (400 MHz, DMSO-d$_6$, ppm): δ 10.36 (s, 1H), 8.79 (s, 1H), 8.00 (s, 1H), 7.97-7.92 (m, 2H), 7.65-7.63 (m, 2H), 7.43-7.34 (m, 2H), 7.39-7.30 (m, 1H), 7.18-7.17 (m, 1H), 6.99 (s, 1H), 4.51 (s, 2H), 4.42 (s, 1H), 3.80-3.76 (m, 2H), 3.59 (s, 4H), 2.99 (s, 1H), 2.69-2.63 (m, 3H), 2.63-2.60 (m, 4H), 2.48-2.34 (m, 5H), 2.21-2.13 (m, 2H), 1.81-1.70 (m, 2H), 1.70-1.61 (s, 1H), 1.59-1.53 (m, 6H), 1.11-0.97 (m, 2H). | | | D |
| 408 | 829.36 | 829.20 | | $^1$H NMR (300 MHz, DMSO-d$_6$, ppm) δ 10.35 (s, 1H), 8.85 (s, 1H), 8.05(m, 1H), 7.96 (s, 2H), 7.70 (s, 2H), 7.30 (d, J = 7.5 Hz, 1H), 7.05 (d, J = 14.7 Hz, 2H), 6.96 (d, J = 7.8 Hz, 1H), 5.35 (s, 1H), 4.55-4.48(m, 3H), 3.83 (s, 3H), 3.62-3.58 (m, 6H), 3.05 (s, 1H), 2.82-2.51 (m, 6H), 2.39 (s, 4H), 2.28-2.18 (m, 2H), 1.97-1.66 (m, 4H), 1.61 (d, J = 20.1 Hz, 6H), 1.30-0.95 (m, 3H). | | | D |
| 409 | 894.43 | 894.25 | | $^1$H NMR (300 MHz, DMSO-d$_6$, ppm) δ10.15 (m, 1H), 8.87 (s, 1H), 8.03 (m, 3H), 7.68-8.03 (m, 5H), 7.03 (s, 1H), 5.11-5.18 (m, 1H), 4.54 (s, 2H), 4.01-4.35 (m, 3H), 2.49-3.13 (m, 10H), 2.26-2.27 (m, 3H), 1.78-2.49 (m, 6H), 1.55-1.78 (m, 8H), 1.45-1.48 (m, 6H), 1.27-1.47 (m, 2H). | | B | A |
| 410 | 893.49 | 893.40 | | $^1$H NMR (400 MHz, DMSO-d$_6$) δ: 10.92 (s, 1H), 8.78 (s, 1H), 8.02 (s, 1H), 7.97-7.87 (m, 2H), 7.75-7.65 (m, 2H), 7.46 (d, J = 8.4 Hz, 1H), 7.04 (s, 1H), 6.64-6.55 (m, 2H), 5.50-5.10 (m, 1H), 5.05 (dd, J = 12.6, 5.6 Hz, 1H), 4.65-4.55 (m, 2H), 4.53 (s, 2H), 4.32-4.25 (m, 1H), 4.20-4.10 (m, 1H), 3.22-3.20 (m, 8H), 2.96-2.83 (m, 1H), 2.78-2.67 (m, 5H), 2.66 (d, J = 4.4 Hz, | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 411 | 909.44 | 909.60 | | 3H), 2.61-2.53 (m, 4H), 2.38-2.24 (m, 1H), 2.03-1.83 (m, 3H), 1.81-1.63 (m, 6H), 1.57 (d, J = 2.8 Hz, 6H).<br>$^1$HNMR (400 MHz, DMSO-d$_6$) δ: 11.05 (s, 1H), 9.37 (br s, 1H), 9.05 (s, 1H), 8.16 (s, 1H), 8.01-7.95 (m, 1H), 7.93 (s, 1H), 7.70 (br s, 2H), 7.41 (d, J = 9.2 Hz, 1H), 7.09 (s, 1H), 6.87 (d, J = 9.2 Hz, 1H), 5.30 (br s, 1H), 4.99 (dd, J = 5.2, 12.8 Hz, 1H), 4.61-4.25 (m, 4H), 3.90-3.82 (m, 5H), 3.77 (s, 2H), 3.62-3.39 (m, 2H), 3.30-3.25 (m, 1H), 3.02 (br s, 4H), 2.97-2.85 (m, 1H), 2.68 (d, J = 4.8 Hz, 3H), 2.57-2.53 (m, 2H), 2.48-2.42 (m, 1H), 2.01-1.70 (m, 6H), 1.62-1.45 (m, 8H), 1.07 (br d, J = 7.0 Hz, 2H). | | C | A |
| 412 | 838.36 | 838.25 | 840.25 | 1H NMR (400 MHz, DMSO-d6) δ 10.94 (s, 1H), 8.85 (s, 1H), 8.05 (s, 1H), 7.97 (m, 2H), 7.69 (m, 2H), 7.48 (m, 1H), 7.03 (s, 1H), 6.52-6.41 (m, 2H), 5.03 (m, 1H), 4.55 (s, 2H), 4.30 (m, 1H), 4.17 (m, 1H), 4.13-4.02 (m, 3H), 3.91 (s, 2H), 3.85 (s, 2H), 3.55 (m, 1H), 3.24 (m, 3H), 2.90 (m, 1H), 2.68-2.55 (m, 3H), 2.35 (m, 1H), 2.11 (m, 2H), 2.00-1.91 (m, 1H), 1.87-1.78 (m, 2H), 1.58 (m, 6H), 1.45-1.35 (m, 2H). | | A | A |
| 413 | 865.43 | 865.10 | 867.10 | $^1$HNMR (300 MHz, DMSO-d$_6$, ppm) δ 10.95 (s, 1H), 8.86 (s, 1H), 8.20-8.10 (m, 1H), 8.01 (s, 1H), 7.96-7.94 (m, 2H), 7.76-7.74 (m, 1H), 7.66-7.63 (m, 1H), 7.13-7.11 (m, 3H), 5.10-5.07 (m, 1H), 4.55 (s, 2H), 4.41-4.21 (q, 2H), 3.98-3.93 (m, 2H), 3.56 (s, 4H), 2.91-2.81 (m, 5H), 2.62-2.60 (m, 8H), 1.96-1.71 (m, 8H), 1.59-1.57 (m, 7H), 1.30-1.12 (m, 3H). | | B | A |
| 414 | 869.38 | 868.34 | | 1H NMR (400 MHz, DMSO-d6) 8 11.03 (s, 1H), 8.80 (s, 1H), 8.03 (s, 1H), 7.94 (t, J = 3.8 Hz, 2H), 7.73-7.62 (m, 2H), 7.02 (s, 1H), 6.87 (d, J = 2.0 Hz, 1H), 6.64 (d, J = 2.1 Hz, 1H), 5.34 (t, J = 3.3 Hz, 1H), 5.03 (dd, J = 12.8, 5.5 Hz, 1H), 4.53 (s, 2H), 3.88 (s, 3H), 3.69 (s, 1H), 3.64 (dd, J = 12.2, 7.7 Hz, 5H), 3.30 (s, 1H), 2.91-2.85 (m, 2H), 2.65 (d, J = 4.5 Hz, 3H), 2.61-2.48 (m, 1H), 2.38 (t, J = 5.0 Hz, 4H), 2.19 (d, J = 6.7 Hz, 2H), 1.98 (td, J = 7.5, 3.9 Hz, 1H), 1.80 (d, J = 13.0 Hz, 3H), 1.55 (d, J = 6.8 Hz, 6H), 1.27 (dt, J = 28.5, 14.1 Hz, 2H). | | A | A |
| 415 | 800.36 | 800.40 | | 1H NMR (400 MHz, DMSO-d6, ppm):δ 10.25 (s, 1H), 8.79 (s, 1H), 8.04 (s, 1H), 7.98 (s, 2H), 7.82-7.64 (m, 2H), 7.14 (s, 1H), 7.04 (s, 1H), 6.97 (s, 1H), 6.96-6.84 (m, 1H), 4.55-4.49 (m, 4H), 3.80 (s, 3H), 3.55 (s, 2H), 2.97 (s, 2H), 2.94-2.86 (m, 2H), 2.71-2.62 (m, 5H), 2.19 (s, 2H), 1.99 (s, 2H), 1.90-1.79 (m, 8H), 1.58 (d, J = 6.8 Hz, 7H), 1.05-0.99 (m, 2H). | | | D |
| 416 | 770.33 | 770.35 | | 1H NMR (400 MHz, DMSO-d6, ppm): δ10.33 (s, 1H), 8.82 (s, 1H), 8.04-7.81 (m, 2H), 7.71-7.66 (m, 2H), 7.35-7.23(m, 2H), 7.23-7.10 (m, 3H), 7.03 (s, 1H), 4.54-4.49 (m, 3H), 4.05-3.95(m, 1H), 3.81-3.74 (m, 3H), 2.95-2.83 (m, 4H), 2.71-2.66(m, 5H), 2.35-2.33(m, 3H), 1.89-1.70(m, 6H), 1.70-1.65(m, 1H), 1.64-1.52(m, 6H), 1.41-1.32 (m, 6H), 1.11-1.22 (m, 1H), 1.19-1.02 (m, 2H). | | | D |
| 417 | 865.43 | 865.30 | | $^1$H NMR (400 MHz, DMSO-d$_6$, ppm): δ10.91 (s, 1H), 8.78 (s, 1H), 8.03-7.94 (m, 2H), 7.72-7.70 (m, 2H), 7.48-7.46 (m, 1H), 7.31-7.26 (m, 1H), 7.02 (s, 1H), 6.50-6.45 (m, 2H), 5.09-5.02 (m, 1H), 4.53-4.47 (m, 3H), 4.29(d, J = 9.2 Hz, 1H), 4.20(d, J = 8.0 Hz, 1H), 3.61 (s, 4H), 2.94-2.72 (m, 3H), 2.71-2.67 (m, 4H), 2.45-2.29 (m, 6H), 2.12-2.09 (m, 2H), 2.01-1.89 (m, 2H), 1.88-1.68 (m, 7H), 1.65-1.49 (m, 6H), 1.09-0.98 (m, 2H). | | A | A |
| 418 | 879.42 | 879.20 | 881.20 | 1H NMR (300 MHz, DMSO-d6) δ 11.08 (s, 1H), 8.81 (s, 1H), 8.04-7.95 (m, 3H), 7.72 (s, 2H), 7.56-7.55 (m, 1H), 7.12-7.03 (m, 2H), 5.34 (s, 1H), 5.09-5.01 (m, 1H), 4.55 (s, 4H), 3.91 (s, 4H), 2.89-2.85 (m, 4H), 2.69 (d, J = 4.8 Hz, | | A | A |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 419 | 871.41 | 879.20 | | 3H), 2.66 (d, J = 4.6 Hz, 3H), 2.31-2.29 (m, 4H), 2.12 (s, 2H), 2.08-1.96 (m, 1H), 1.58 (d, J = 6.9 Hz, 7H), 1.14-0.72 (m, 3H). | | A | A |
| 420 | 883.45 | 883.55 | | 1H NMR (300 MHz, DMSO-d6) δ 11.08 (s, 1H), 8.81 (s,1H), 8.04-7.95 (m, 3H), 7.72 (s, 2H), 7.56-7.55 (m, 1H), 7.12-7.03 (m, 2H), 5.34 (s, 1H), 5.09-5.01 (m, 1H), 4.55 (s, 4H), 3.91 (s, 4H), 2.89-2.85 (m, 4H), 2.69 (d, J = 4.8 Hz, 3H), 2.66 (d, J = 4.6 Hz, 3H), 2.31-2.29 (m, 4H), 2.12 (s, 2H), 2.08-1.96 (m, 1H), 1.58 (d, J = 6.9 Hz, 7H), 1.14-0.72 (m, 3H). | | C | C |
| 421 | 880.40 | 880.35 | | 1H NMR (300 MHz, DMSO-d6) δ 10.88 (s, 1H), 8.81 (s, 1H), 8.58 (d, J = 7.8 Hz, 1H), 8.04-7.95 (m, 3H), 7.76-7.68 (m, 2H), 7.03 (d, J = 8.7 Hz, 3H), 6.62-6.59(m, 1H), 5.34 (s, 1H), 4.82-4.73 (m, 1H), 4.55-4.48 (m, 4H), 3.61 (d, J = 15.8 Hz, 8H), 2.89-2.73 (m, 3H), 2.70 (s, 3H), 2.30 (s, 4H), 2.10 (s, 5H), 1.74 (s, 6H), 1.58 (d, J = 6.8 Hz, 6H), 1.04-1.00 (m, 2H). | | A | A |
| 422 | 879.42 | 879.25 | | 1H NMR (300 MHz, DMSO-d6) δ 8.83 (s, 1H), 8.05 (s, 1H), 7.96 (s, 1H), 7.70 (s, 2H), 7.64 (d, J = 8.3 Hz, 2H), 7.02 (s, 1H), 6.77 (d, J = 2.1 Hz, 1H), 6.64 (d, J = 10.1 Hz, 1H), 5.06 (m, 1H), 4.55 (s, 1H), 4.07 (s, 2H), 3.73 (d, J = 6.9 Hz, 2H), 3.52 (s, 5H), 2.88 (s, 1H), 2.68 (d, J = 4.5 Hz, 4H), 2.55 (s, 3H), 2.02 (s, 2H), 1.80 (s, 6H), 1.58 (d, J = 6.8 Hz, 8H), 1.39 (d, J = 10.7 Hz, 4H), 1.24 (s, 1H). | | B | A |
| 423 | 825.37 | 825.30 | | 1H NMR (300 MHz, DMSO-d6) δ 11.04 (s, 1H), 8.77 (s, 1H), 8.08-7.96 (m, 3H), 7.83 (d, J = 2.4 Hz, 1H), 7.70-7.65 (m, 2H), 7.29-7.20 (m, 2H), 7.05 (s, 1H), 5.08-5.02 (m, 1H), 4.54 (s, 2H), 4.02 (d, J = 12.7 Hz, 2H), 3.69 (s, 4H), 2.98-2.87 (m, 3H), 2.68 (d, J = 4.6 Hz, 3H), 2.59-2.55 (m, 1H), 2.29 (s, 4H), 2.11-1.79 (m, 4H), 2.89-2.72 (m, 7H), 1.56 (d, J = 6.8 Hz, 7H), 1.12 (d, J = 12.4 Hz, 2H). | | A | A |
| 424 | 838.36 | 838.50 | | 1H NMR (300 MHz, DMSO-d6) δ 10.98 (s, 1H), 8.85 (s, 1H), 8.06 (s, 1H), 7.97 (s, 2H), 7.71 (s, 2H), 7.44-7.41 (m, 1H), 7.30 (d, J = 7.2 Hz, 1H), 7.16 (d, J = 7.5 Hz, 1H), 7.05 (s, 1H), 5.32 (s, 1H), 5.15-5.11 (m, 1H), 4.56 (s, 2H), 4.44 (d, J = 17.1 Hz, 1H), 4.30 (d, J = 17.4 Hz, 1H), 3.66 (s, 4H), 3.39-3.33 (m, 2H), 2.98-2.83 (m, 1H), 2.79-2.72 (m, 2H), 2.75 (d, J = 9.0 Hz, 4H), 2.69-2.63 (m, 1H), 2.47 (s, 4H), 2.08-1.99 (m, 1H), 1.88-1.83 (m, 3H), 1.58 (d, J = 6.9 Hz, 6H), 1.38-1.16 (m, 2H). | | A | B |
| 425 | 883.45 | 883.55 | | 1H NMR (400 MHz, DMSO-d6 ppm)δ 10.97 (s, 1H), 8.83(s, 1H), 8.04 (s, 1H), 8.00-96 (m, 2H), 7.69 (s, 2H), 7.32-7.29 (m, 1H), 7.05-7.03(m, 2H), 6.53-6.51 (m, 1H), 5.11-5.07 (m, 1H), 4.54 (s, 2H), 4.40 (d, J = 16.8 Hz, 1H), 4.27 (d, J = 13.2 Hz, 1H), 4.14-4.03(m, 3H), 4.00-3.91 (m, 4H), 3.54(s, 1H), 3.33-3.22(m, 3H), 2.99-2.79(m, 2H), 2.67 (s, 6H), 2.10-2.06 (m, 2H), 1.99-1.98 (m, 1H), 1.83-1.81 (m, 2H), 1.58 (s, 6H), 1.39-1.37 (m, 2H). | | B | A |
| 426 | 879.42 | 897.20 | | 1H NMR (400 MHz, DMSO-d6 ppm): δ 10.85 (s, 1H), 8.79 (s, 1H), 8.39 (d, J = 8.0 Hz, 1H), 8.05(s, 1H), 8.03-7.95 (m, 2H), 7.77-7.66 (m, 3H), 7.03 (s, 1H), 6.07-6.01 (m, 2H), 4.72-4.66 (m, 1H), 4.54-4.48 (m, 4H), 3.89 (s, 3H), 3.65 (s, 4H), 2.88-2.75 (m, 4H), 2.68 (s, 3H), 2.20-2.04 (m, 5H), 1.89-1.63 (m, 9H), 1.63-1.46 (m, 7H), 1.31-1.15(m, 1H), 1.10-0.98 (m, 2H). | | A | A |
| | | | | 1H NMR (300 MHz, DMSO-d6) δ 11.04 (s, 1H), 8.77 (s, 1H), 8.08-7.96 (m, 3H), 7.83 (d, J = 2.4 Hz, 1H), 7.68-7.63 (m, 2H), 7.33-7.23 (m, 2H), 7.05 (s, 1H), 5.11-5.05 (m, 1H), 4.54 (s, 2H), , 3.77 (s, 6H), 2.93-2.82 (m, 3H), 2.72 (s, 3H), 2.68-2.55 (m, 2H), 2.31 (s, 4H), 2.16-2.00 (m, 4H), 1.91-1.73(m, 7H), 1.56 (d, J = 6.8 Hz, 7H), 1.34-1.14 (m, 2H). | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 427 | 866.42 | 866.35 | 868.35 | $^1$HNMR (400 MHz, DMSO-d$_6$, ppm) δ 10.96 (s, 1H), 8.81 (s, 1H), 8.03 (s, 1H), 7.98 (s, 2H), 7.69 (s, 2H), 7.45-7.43 (m, 1H), 7.30 (d, J = 7.2 Hz, 1H), 7.17 (d, J = 7.2 Hz, 1H), 7.00 (s, 1H), 5.50-5.28 (b, 1H), 5.11-5.08 (m, 1H), 4.56 (s, 2H), 4.41 (d, J = 17.2 Hz, 1H), 4.32 (d, J = 17.2 Hz, 1H), 4.18-4.17 (m, 1H), 3.63-3.57 (m, 4H), 3.47-3.45 (m, 1H), 3.37-3.35 (m, 1H), 2.92-2.86 (m, 3H), 2.70 (s, 3H), 2.57-2.51 (m, 1H), 2.25-2.23 (m, 2H), 2.01-1.91 (m, 3H), 1.71-1.70 (m, 2H), 1.59-1.57 (m, 13H), 1.55 (s, 1H); | | A | A |
| 428 | 853.42 | 853.40 | | $^1$H NMR (400 MHz, DMSO-d$_6$, ppm) δ10.37 (s, 1H), 8.76 (s, 1H), 8.02 (s, 1H), 7.93 (d, J = 3.6 Hz, 2H), 7.71-7.66 (m, 2H), 7.38-7.29 (m, 3H), 7.02 (s, 1H), 4.53-4.47 (m, 4H), 4.29-4.26 (m, 4H), 4.04-4.00 (m, 2H), 3.82-3.78 (m, 2H), 3.29-3.27 (m, 1H), 2.94-2.71 (m, 4H), 2.69-2.65 (m, 5H), 2.54-2.53 (m, 1H), 2.25-2.14 (m, 4H), 1.99-1.93 (m, 2H), 1.77-1.63 (m, 7H), 1.56 (d, J = 6.8 Hz, 6H), 1.03-1.01 (m, 2H). | | | D |
| 429 | 856.38 | 856.50 | | $^1$H NMR (400 MHz, DMSO-d$_6$) δ 10.87 (s, 1H), 8.85 (s, 1H), 8.40 (m, 1H), 8.05 (s, 1H), 8.01-7.93 (m, 2H), 7.76-7.69 (m, 3H), 7.03 (s, 1H), 6.04-5.98 (m, 2H), 4.69 (m, 1H), 4.55 (s, 2H), 4.11-4.01 (m, 3H), 3.89 (m, 7H), 3.55 (s, 1H), 3.25 (m, 3H), 2.82-2.61 (m, 5H), 2.58-2.52 (m, 2H), 2.11 (s, 4H), 1.83 (m, 2H), 1.58 (m, 6H), 1.38 (m, 1H). | | A | A |
| 430 | 844.34 | 844.45 | | $^1$H NMR (300 MHz, DMSO-d$_6$) δ 10.85 (s, 1H), 8.83 (s, 1H), 8.48 (m, 1H), 8.05 (s, 1H), 7.96 (s, 2H), 7.69 (s, 2H), 7.12-7.00 (m, 2H), 6.91 (m, 1H), 6.62 (m, 1H), 4.81-4.70 (m, 1H), 4.55 (s, 2H), 4.07 (m, 3H), 3.93-3.87 (m, 4H), 3.54 (s, 1H), 3.29-3.19 (m, 7H), 2.68 (m, 3H), 2.08-2.01 (m, 4H), 1.82 (s, 2H), 1.58 (m, 6H), 1.38 (m, 2H). | | B | B |
| 431 | 866.42 | 866.40 | 868.40 | $^1$HNMR (400 MHz, DMSO-d$_6$, ppm) δ 10.94 (s, 1H), 8.84 (s, 1H), 8.05 (s, 1H), 7.96 (s, 2H), 7.92 (s, 1H), 7.69 (s, 2H), 7.49 (d, J = 8.4 Hz, 1H), 7.05-7.02 (m, 3H), 5.10-5.08 (dd, 1H), 4.55 (s, 2H), 4.34-4.31 (m, 5H), 3.53 (s, 1H), 3.34-3.31 (m, 6H), 2.91-2.80 (m, 1H), 2.69 (s, 3H), 2.61-2.57 (m, 1H), 2.37-2.35 (m, 1H), 2.23-2.21 (m, 2H), 1.97-1.96 (m, 1H), 1.85-1.82 (m, 2H), 1.60-1.57 (m, 12H), 1.40-1.37 (m, 2H); | | B | A |
| 432 | 884.43 | 884.20 | 886.20 | $^1$HNMR (400 MHz, DMSO-d$_6$, ppm) δ 8.43 (s, 1H), 8.30 (s, 1H), 8.03 (s, 1H), 7.94 (s, 1H), 7.75-7.70 (m, 3H), 7.29-7.27 (m, 1H), 7.07 (s, 1H), 6.57 (d, J = 8.8 Hz, 1H), 6.56 (s, 1H), 5.30-5.08 (b, 1H), 4.68 (s, 1H), 4.65 (s, 2H), 4.18-4.09 (m, 3H), 3.90 (s, 3H), 3.28-3.21 (m, 6H), 2.74-2.68 (m, 4H), 2.34-2.06 (m, 5H), 1.83-1.81 (m, 2H), 1.67-1.64 (m, 12H), 1.37-1.34 (m, 2H); | | A | B |
| 433 | 872.40 | 872.30 | 874.30 | $^1$HNMR (300 MHz, DMSO-d$_6$, ppm) δ 8.64-8.61 (m, 1H), 8.40-8.38 (m, 1H), 8.02 (s, 1H), 7.95 (s, 1H), 7.70 (s, 2H), 7.15-7.07 (m, 4H), 7.07 (s, 1H), 5.50-5.18 (b, 1H), 4.78-4.76 (m, 1H), 4.53 (s, 2H), 4.13-4.08 (m, 3H), 3.30-3.12 (m, 2H), 2.93-2.87 (m, 4H), 2.69-2.66 (m, 4H), 2.34-2.26 (m, 2H), 2.12-1.95 (m, 2H), 1.85-1.80 (m, 2H), 1.65-1.58 (m, 13H), 1.57-1.55 (m, 2H), 1.22-1.20 (m, 1H); | | A | D |
| 434 | 880.40 | 880.35 | | 1H NMR (300 MHz, DMSO-d6) δ 11.06 (s, 1H), 8.82 (s, 1H), 8.05 (s, 1H), 7.95 (s, 2H), 7.70 (s, 2H), 7.56 (m, 1H), 7.09 (d, J = 7.0 Hz, 1H), 7.02 (s, 1H), 6.77 (d, J = 8.6 Hz, 1H), 5.04 (m, 1H), 4.55 (s, 2H), 4.08 (m, 2H), 3.90 (s, 4H), 3.68 (s, 1H), 3.50 (s, 1H), 2.88-2.86 (m, 2H), 2.68 (d, J = 4.7 Hz, 1H), 2.66 (m, 3H), 2.65 (m, 3H), 2.61 (s, 1H), 2.01 (d, J = 4.9 Hz, 6H), 1.82 (d, J = 17.8 Hz, 8H), 1.58 (d, J = 6.9 Hz, 4H). | | B | A |
| 435 | 856.38 | 856.40 | | $^1$H NMR (300 MHz, DMSO-d$_6$, ppm): δ10.86 (s, 1H), 8.83 (s, 1H), 8.56 (d, J = 7.8 Hz, 1H), 8.05 (s, 1H), 7.96 (d, J = 5.4 Hz, 2H), 7.69 (s, 2H), 7.03 (s, 1H), | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 436 | 865.43 | 865.50 | | 4.5 Hz, 3H), 6.58 (m, 1H), 4.85-4.75(m, 1H), 4.55 (s, 2H), 4.16-4.00 (m, 3H), 3.88 (s, 2H), 3.81 (s, 2H), 3.66 (s, 3H), 3.66-3.50(m, 1H), 3.32-3.22(m, 2H), 2.89-2.73 (m, 1H), 2.68 (d, J = 4.6 Hz, 3H), 2.56-2.50 (m, 4H), 2.12-2.05 (m, 4H), 1.91-1.79 (m, 2H), 1.58 (d, J = 6.8 Hz, 6H), 1.50-1.38 (m, 2H). | | | A |
| 437 | 865.43 | 865.20 | | $^1$H NMR (300 MHz, DMSO-d$_6$, ppm) δ 10.92 (s, 1H), 8.80 (s, 1H), 8.02-7.91 (m, 2H), 7.69 (s, 2H), 7.48-7.45 (m, 1H), 7.30-7.25 (m, 1H), 7.04-7.01 (m, 2H), 6.61 (s, 1H), 5.01-4.98 (m, 1H), 4.53-4.49 (m, 2H), 4.29-4.15 (m, 2H), 2.94-2.67 (m, 21H), 2.50-2.23 (m, 6H), 1.96-1.90 (m, 2H), 1.71-1.60 (m, 3H), 1.57-1.55 (m, 3H), 1.28-0.98 (m, 2H). | | A | A |
| 438 | 883.45 | 883.25 | | $^1$H NMR (300 MHz, DMSO-d$_6$, ppm) δ 10.92 (s, 1H), 8.80 (s, 1H), 8.02-7.91 (m, 2H), 7.69 (s, 2H), 7.48-7.45 (m, 1H), 7.30-7.25 (m, 1H), 7.04-7.01 (m, 2H), 6.61 (s, 1H), 5.01-4.98 (m, 1H), 4.53-4.49 (m, 2H), 4.29-4.15 (m, 2H), 2.94-2.67 (m, 21H), 2.50-2.23 (m, 6H), 1.96-1.90 (m, 2H), 1.71-1.60 (m, 3H), 1.57-1.55 (m, 3H), 1.28-0.98 (m, 2H). | | A | B |
| 439 | 879.42 | 879.35 | | $^1$H NMR (400 MHz, DMSO-d$_6$, ppm) δ 10.87 (s, 1H), 8.81 (s, 1H), 8.43-8.41 (m, 1H), 8.04 (s, 1H), 7.98-7.95 (m, 2H), 7.78-7.75 (m, 1H), 7.71-7.70 (m, 2H), 7.02 (s 1H), 6.60-6.53 (m, 2H), 4.70-4.68 (m, 1H), 4.55 (s, 2H), 4.50-4.47 (m, 2H), 4.47 (s, 4H), 3.30-3.28 (m, 3H), 2.97-2.85 (m, 3H), 2.85-2.83 (m, 3H), 2.79-2.77 (m, 4H), 2.34-2.33 (m, 1H), 2.25-2.12 (m, 3H), 1.74-1.70 (m, 7H), 1.59-1.57 (m, 7H), 1.25-1.05 (m, 3H) | | B | A |
| 440 | 871.41 | 871.20 | | $^1$H NMR (400 MHz, DMSO-d$_6$, ppm) δ 11.07 (s, 1H), 8.81 (s, 1H), 8.03 (s, 1H), 7.95-7.07 (m, 2H), 7.70-7.68 (m, 3H), 7.34-7.32 (m, 2H), 7.02 (s, 1H), 5.12-5.10 (m 2H), 4.55-4.50 (m, 5H), 3.32-3.20 (m, 5H), 2.97 (s, 4H), 2.85-2.82 (m, 3H), 2.34-2.31 (m, 4H), 1.83-1.80 (m, 6H), 1.73-1.70 (m, 3H), 1.58-1.56 (m, 8H). | | A | A |
| 441 | 883.45 | 883.25 | | $^1$H NMR (400 MHz, DMSO-d$_6$, ppm)δ 10.85 (s, 1H), 8.58 (s, 1H), 8.02-7.93 (m, 3H), 7.69 (s, 2H), 7.14 (s, 3H), 7.01 (s, 1H), 4.81-4.70 (m, 1H), 4.54-4.46 (m, 4H), 3.00 (s, 2H), 2.92 (s, 4H), 2.90-2.78 (m, 3H), 2.67 (s, 4H), 2.42-2.25(m, 4H), 2.07-1.92 (m, 3H), 1.80 (s, 4H), 1.70 (s, 2H), 1.56 (d, J = 6.8 Hz, 7H), 1.12-1.00 (m, 2H). | | | D |
| 442 | 865.43 | 865.25 | | $^1$H NMR (400 MHz, DMSO-d$_6$, ppm)δ 10.89 (s, 1H), 8.80 (s, 1H), 8.70 (s, 1H), 8.03-7.95 (m, 2H), 7.70 (s, 1H), 7.35-7.20 (m, 3H), 7.15-7.03 (m, 3H), 4.77 (s, 1H), 4.54-4.40 (m, 3H), 3.85 (s, 3H), 3.65(s, 1H), 3.40(s, 2H), 3.02-2.70 (m, 13H), 2.31 (m, 2H), 2.15-2.03 (m, 3H), 1.93-1.70 (m, 7H), 1.68-1.51 (m, 6H), 1.15-1.00 (m, 2H) | | A | A |
| 443 | 865.43 | 865.25 | | $^1$H NMR (400 MHz, DMSO-d$_6$, ppm)δ10.98 (s, 1H), 8.79 (s, 1H), 8.03-7.95 (m, 3H), 7.71 (s, 2H), 7.31-7.28 (m, 1H), 7.02 (s, 2H), 6.54-6.52 (m, 1H), 5.12-5.08(m, 1H), 4.54-4.43(m, 5H), 4.32-4.28 (m, 1H), 3.71 (s, 4H), 2.95-2.80(m, 3H), 2.68-2.61 (m, 3H), 2.57-2.50 (m, 2H), 2.28 (s, 4H), 2.08 (s, 3H), 1.97 (s, 2H), 1.74 (s, 7H), 1.58-1.56 (m, 6H), 1.02-0.99 (m, 2H). | | B | A |
| 444 | 880.40 | 880.40 | 882.40 | $^1$H NMR (300 MHz, DMSO-d6) δ 11.00 (s, 1H), 8.82 (s, 1H), 8.03-7.91 (m, 3H), 7.70 (s, 2H), 7.45-7.39 (m, 1H), 7.29 (d, J = 7.2 Hz, , 1H), 7.15 (d, J = 7.8 Hz, 1H), 7.03 (s, 1H), 5.32 (s, 1H), 5.14-5.08 (m, 1H), 4.55 (s, 2H), 4.45-4.24 (m, 2H), 3.60 (s, 4H), 2.99-2.86(m, 5H), 2.73-2.62 (m, 6H), 2.55-2.54 (m, 2H), 2.42-2.27 (m, 1H), 2.08-1.97 (m, 1H), 1.80 (d, J = 4.2 Hz, 2H), 1.66 (s, 4H), 1.58 (d, J = 12 Hz, 6H), 1.42 (s, 1H), 1.34-1.24 (m, 3H).<br>1H NMR (300 MHz, DMSO-d6) δ 11.07 (s, 1H), 8.76 (s, 1H), 8.08-7.93 (m, 3H), 7.86 (d, J = 9.3 Hz, 1H), 7.67 (m, 2H), 7.33 (d, J = 2.2 Hz, 1H), 7.24 (m, | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 445 | 880.40 | 880.30 | 882.30 | 1H), 7.07 (s, 1H), 5.33 (s, 1H), 5.07 (m, 1H), 4.55 (s, 2H), 3.79 (d, J = 13.6 Hz, 2H), 3.68 (d, J = 4.5 Hz, 5H), 3.48 (s, 1H), 3.24 (d, J = 10.7 Hz, 2H), 2.89 (m, 1H), 2.67 (d, J = 4.7 Hz, 3H), 2.62 (s, 1H), 2.56 (s, 1H), 2.02 (d, J = 11.3 Hz, 4H), 1.86 (d, J = 8.8 Hz, 2H), 1.74 (s, 8H), 1.57 (d, J = 6.9 Hz, 3H), 1.54-1.32 (m, 2H). | | A | A |
| 446 | 866.42 | 866.50 | 868.50 | $^1$H NMR (300 MHz, DMSO-d$_6$) δ 11.08 (s, 1H), 8.77 (s, 1H), 8.04 (d, J = 8.4 Hz, 2H), 7.97 (d, J = 4.9 Hz, 1H), 7.87 (d, J = 9.1 Hz, 1H), 7.73-7.62 (m, 2H), 7.34 (m, 2H), 7.08 (s, 1H), 5.10-5.03 (m, 5.4 Hz, 1H), 4.55 (s, 1H), 3.69 (d, J = 6.0 Hz, 2H), 3.51 (s, 5H), 3.09 (m, 3H), 2.98-2.80 (m, 2H), 2.68 (d, J = 4.6 Hz, 1H), 2.62 (s, 4H), 2.56 (d, J = 5.1 Hz, 5H), 2.56-2.54 (m, 2H), 1.57 (d, J = 6.9 Hz, 10H), 1.37 (d, J = 10.5 Hz, 2H), 1.30-1.26 (m, 1H). | | A | A |
| 447 | 883.45 | 883.3 | | $^1$HNMR (400 MHz, DMSO-d$_6$, ppm) δ 10.99 (s, 1H), 8.84 (s, 1H), 8.05-7.96 (m, 3H), 7.70 (s, 1H), 7.42-7.14 (m, 4H), 7.02 (s, 1H), 5.32 (b, 1H), 5.10-5.08 (dd, 1H), 4.55 (s, 2H), 4.40-4.31 (m, 1H), 4.30-4.26 (m, 6H), 4.13-4.10 (m, 2H), 3.61-3.56 (m, 1H), 3.26-3.23 (m, 2H), 3.11-2.96 (m, 6H), 2.69 (s, 3H), 2.61-2.57 (m, 2H), 2.17-2.05 (m, 2H), 1.97-1.96 (m, 1H), 1.85-1.82 (m, 13H), 1.40-1.37 (m, 3H); | | A | B |
| 448 | 865.43 | 865.30 | | 1H NMR (300 MHz, DMSO-d$_6$) δ 10.88 (s, 1H), 8.83 (s, 1H), 8.42 (d, J = 7.0 Hz, 1H), 8.01 (s, 1H), 7.92 (d, J = 14.5 Hz, 2H), 7.69 (s, 1H), 7.81-7.67 (m, 3H), 7.03 (s, 1H), 6.50 (m, 2H), 5.33 (s, 1H), 4.70 (m, 1H), 4.56 (s, 2H), 3.92 (s, 4H), 3.60 (s, 3H), 2.97 (s, 4H), 2.84-2.66 (m, 3H), 2.31 (d, J = 6.3 Hz, 5H), 1.74 (m, 2H), 1.66 (m, 5H), 1.58 (d, J = 6.8 Hz, 5H), 1.52 (s, 5H), 1.48 (s, 1H), 1.27-1.08 (m, 2H). | | B | A |
| 449 | 884.43 | 884.50 | | $^1$H NMR (300 MHz, DMSO-d6, ppm) δ 10.96 (s, 1H), 8.78 (s, 1H), 8.02 (s, 1H), 77.94-7.69 (m, 2H), 7.69 (s, 2H), 7.44-7.41 (m, 1H), 7.30-7.28 (m, 1H), 7.16-7.13 (m, 2H), 7.01 (s, 1H), 5.13-5.07 (m, 1H), 4.53-4.49 (m, 5H), 4.39-4.24 (m, 1H), 3.31-2.96 (m, 9H), 2.85-2.81 (m, 3H), 2.77-2.72 (m, 4H), 2.37-2.66 (m, 1H), 2.00-1.99 (m, 1H), 1.96-1.78 (m, 7 H), 1.57-1.55 (m, 8H), 1.28-0.98 (m, 2H). | | B | D |
| 450 | 871.41 | 871.30 | | $^1$HNMR (300 MHz, DMSO-d6, ppm) δ 10.86 (s, 1H), 8.81 (s, 1H), 8.67 (d, J = 7.8 Hz, 2H), 8.04 (s, 1H), 7.95 (s, 2H), 7.69 (s, 2H), 7.32-7.29 (t, 1H), 7.10 (d, J = 4.8 Hz, 2H), 7.02 (s, 1H), 5.48 (b, 1H), 4.87-4.85 (m, 1H), 4.54 (s, 2H), 4.15-4.13 (m, 3H), 3.85 (s, 3H), 3.51-3.49 (m, 1H), 3.28-3.26 (m, 2H), 3.08-2.93 (m, 4H), 2.76-2.65 (m, 3H), 2.26-2.22 (m, 3H), 2.11-2.08 (m, 2H), 1.85-1.82 (m, 2H), 1.76-1.62 (m, 6H), 1.56-1.54 (m, 6H), 1.52-1.45 (m, 2H); | | A | A |
| 451 | 879.42 | 879.25 | | 1H NMR (300 MHz, DMSO-d6) δ 10.85 (s, 1H), 8.81 (s, 1H), 8.56 (m, 1H), 8.02 (d, J = 10.5 Hz, 2H), 7.92 (d, J = 2.1 Hz, 1H), 7.71 (d, J = 2.7 Hz, 2H), 7.15 (d, J = 3.7 Hz, 3H), 7.04 (s, 1H), 5.34 (s, 1H), 4.76 (m, 1H), 4.56 (s, 2H), 3.66-3.56 (m, 4H), 2.97 (s, 4H), 2.78-2.54 (m, 5H), 2.35 (d, J = 6.2 Hz, 2H), 2.17-1.97 (m, 2H), 2.03 (s, 3H), 1.77 (d, J = 11.9 Hz, 2H), 1.67 (t, J = 5.5 Hz, 4H), 1.58 (d, J = 6.8 Hz, 6H), 1.28 (m, 4H). | | B | A |
| 452 | 879.42 | 879.30 | | 1H NMR (300 MHz, DMSO-d6) δ 11.08 (s, 1H), 8.85 (s, 1H), 8.03 (d, J = 31.8, 3H), 7.71-7.62 (m, 3H), 7.04 (s, 1H), 6.77 (s, 1H), 6.65-6.62 (m, 1H), 5.35 (s, 1H), 5.09-5.05 (m, 1H), 4.56 (s, 1H), 3.74-3.65 (m, 8H), 2.89-2.85 (m, 1H), 2.69 (s, 4H), 2.38(s, 4H), 2.12-1.88 (m, 5H), 1.72 (s, 2H), 1.59-1.40 (m, 10H), 1.05-0.88 (m, 2H).<br>1H NMR (300 MHz, DMSO-d6) δ 11.08 (s, 1H), 8.84 (s, 1H), 8.01 (d, J = 25.2, 3H), 7.74-7.67 (m, 2H), 7.57-7.51 (m, 1H), 7.10-7.04 (m, 2H), 6.76 (d, | | A | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 453 | 872.40 | 872.15 | | J = 8.4, 1H), 5.35 (s, 1H), 5.08-5.02 (m, 1H), 4.57 (s, 2H), 3.90-3.84 (m, 4H), 3.74-3.65 (m, 8H), 3.64 (s, 4H), 2.90-2.82 (m, 1H), 2.69-2.51 (m, 5H), 2.36 (s, 4H), 2.12-1.70 (m, 7H), 1.70-1.43 (m, 9H), 0.97-0.90 (m, 2H). | | | B |
| 454 | 855.35 | 855.20 | | 1H NMR (400 MHz, DMSO-d6, ppm): δ10.82 (s, 1H), 8.78 (s, 1H), 8.54 (d, J = 8.4 Hz, 1H), 8.01 (s, 1H), 7.95-7.94 (m, 2H), 7.67 (s, 2H), 7.15-7.14 (m, 3H), 6.99 (s, 1H), 4.74-4.71 (m, 1H), 4.54 (s, 2H), 4.18-4.14 (m, 1H), 3.60-3.55 (m, 4H), 3.44-3.40 (m, 1H), 2.81-2.66 (m, 7H), 2.23-2.18(m, 2H), 2.13-1.89 (m, 5H), 1.69-1.64 (m, 2H), 1.60-1.50 (m, 14H). | | A | A |
| 455 | 787.23 | 787.20 | | 1H NMR (400 MHz, DMSO-d6, ppm): δ11.08 (s, 1H), 8.85 (s, 1H), 8.05 (s, 1H), 7.97-7.94 (m, 2H), 7.71-7.65 (m, 2H), 7.55 (d, J = 9.2 Hz, 1H), 7.34-7.30 (m, 2H), 7.11 (s, 1H), 5.09-5.06 (m, 1H), 4.58 (s, 2H), 4.48-4.46 (m, 2H), 3.70-3.62 (m, 8H), 3.25 (s, 3H), 2.90-2.84 (m, 3H), 2.67 (d, J = 4.8 Hz, 3H), 2.60-2.56 (m, 2H), 2.49-2.40 (m, 4H), 2.33-2.21 (m, 2H), 2.03-2.00 (m, 1H), 1.84-1.78 (m, 3H), 1.34-1.31 (m, 2H). | | A | C |
| 456 | 870.36 | 870.20 | 872.20 | 1H NMR (400 MHz, DMSO-d6, ppm): δ 11.09 (s, 1H), 8.83 (s, 1H), 8.02 (s, 1H), 7.94-7.91 (m, 2H), 7.79-7.70 (m, 2H), 7.52-7.50 (m, 1H), 7.50-7.43 (m, 2H), 7.11 (d, J = 2.8 Hz, 1H), 5.09-5.07 (m, 1H), 4.51-4.43 (m, 5H), 4.40-4.26 (m, 1H), 4.21-4.16 (m, 1H), 4.14-4.05 (m, 1H), 3.58 (s, 2H), 3.20 (s, 3H), 2.99-2.82 (m, 3H), 2.66 (d, J = 4.8 Hz, 3H), 2.59-2.49 (m, 3H), 2.04-1.91 (m, 3H), 1.76-1.69 (m, 1H), 1.56-1.43 (m, 2H). | | | D |
| 457 | 870.36 | 870.15 | | 1H NMR (300 MHz, DMSO-d6) δ 11.11 (s, 1H), 8.82 (s, 1H), 8.03-7.95 (m, 3H), 7.82 (d, J = 8.41 Hz, 1H), 7.45-7.34 (m, 2H), 7.02 (s, 1H), 5.35 (s, 1H), 5.15-5.09 (m, 1H), 4.54 (s, 2H), 4.24-4.07 (m, 5H), 3.57(s, 1H), 3.34-3.21 (m, 3H), 3.02-2.85 (m, 2H), 2.68-2.63 (m, 5H), 2.38-2.34 (m, 5H), 2.06-2.03 (m, 1H), 1.86-1.82 (m, 2H), 1.58-1.56 (m, 7H), 1.39 (s, 2H). | | | D |
| 458 | 870.36 | 870.35 | | 1H NMR (300 MHz, DMSO-d6) δ 11.12 (s, 1H), 8.83 (s, 1H), 8.04(s, 1H), 7.97 (s, 2H), 7.82 (d, J = 8.4 Hz, 1H), 7.69 (s, 2H), 7.51 (s, 1H), 7.82 (d, J = 8.4 Hz, 1H), 7.02 (s, 1H), 5.35-5.09 (m, 2H), 4.70 (s, 1H), 4.55 (s, 2H), 4.10-4.06 (m, 5H), 3.75(s, 2H), 3.34-3.24(m, 2H), 3.07-2.89 (m, 3H), 2.68-2.63 (m, 5H), 2.25 (s, 3H), 2.06-2.03 (m, 1H), 1.91-1.70 (m, 4H), 1.57 (d, J = 6.9 Hz, 6H), 1.40-1.37 (m, 2H), 1.20-1.67 (m, 2H). | | A | C |
| 459 | 870.36 | 870.30 | | 1H NMR (400 MHz, DMSO-d6, ppm) δ 11.11 (s, 1H), 8.83 (s, 1H), 8.04 (s, 1H), 8.00-7.92 (m, 2H), 7.84 (s, 1H), 7.69 (s, 2H), 7.45 (s, 1H), 7.39 (s, 1H), 7.02 (s, 1H), 5.12 (s, 1H), 498 (s, 1H), 4.53 (s, 2H), 4.26-4.03 (m, 5H), 3.88 (s, 1H), 3.68 (s, 1H), 3.29-3.20(m, 4H), 2.96-2.83 (m, 1H), 2.74 (s, 1H), 2.66 (s, 5H), 2.37 (s, 1H), 2.18 (s, 3H), 2.09-1.98 (m, 3H), 1.82 (s, 2H), 1.67 (s, 1H), 1.56 (s, 6H), 1.37 (s, 2H). | | | D |
| 460 | 870.36 | 870.00 | | 1H NMR (400 MHz, DMSO-d6, ppm): δ 11.11 (s, 1H), 8.82 (s, 1H), 8.04 (s, 1H), 7.96 (d, J = 5.2 Hz, 2H), 7.83 (d, J = 8.4 Hz, 1H), 7.69 (s, 2H), 7.45 (d, J = 2.4 Hz, 1H), 7.36 (d, J = 10.4 Hz, 1H), 7.01 (s, 1H), 5.14-5.09 (m, 1H), 4.54 (s, 2H), 4.24-4.18 (m, 2H), 4.14-4.08 (m, 3H), 3.58 (d, J = 8.4 Hz, 1H), 3.33-3.22 (m, 3H), 3.01-2.99 (m, 1H), 2.99-2.89(m, 1H), 2.67-2.62 (m, 6H), 2.37- | | | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 461 | 870.36 | 870.15 | | 2.30 (m, 5H), 2.06-2.03 (m, 1H), 1.85-1.79 (m, 2H), 1.62-1.56 (m, 7H), 1.41-1.36 (m, 2H) | | B | B |
| 462 | 860.39 | 860.35 | 862.35 | $^1$H NMR (300 MHz, DMSO-d$_6$, ppm)δ 11.09 (s, 1H), 8.81 (s, 1H), 8.01 (s, 1H), 7.94-7.92 (m, 2H), 7.81 (d, J = 8.4 Hz, 1H), 7.66 (s, 2H), 7.48 (d, J = 0.9 Hz, 1H), 7.37 (d, J = 10.5 Hz, 1H), 6.99 (s, 1H), 5.13-5.07 (m, 2H), 4.71-4.62(m, 1H), 4.52 (s, 2H), 4.08-4.03 (m, 2H), 3.74-3.71 (m, 2H), 3.31-3.21 (m, 3H), 3.15-2.80 (m, 3H), 2.65-2.60 (m, 4H), 2.59-2.53(m, 1H), 2.25-2.19 (m, 3H), 2.06-1.97 (m, 1H), 1.95-1.76(m, 3H), 1.75-1.65 (m, 1H), 1.59-1.49 (m, 6H), 1.47-1.29 (m 2H), 1.26-1.11(m, 1H). | | A | D |
| 463 | 870.36 | 870.40 | 872.40 | $^1$H NMR (300 MHz, DMSO-d$_6$) δ 10.88 (s, 1H), 8.81 (s, 1H), 8.57-8.56 (m, 1H), 8.04 (s, 1H), 7.99-7.97 (m, 2H), 7.71 (s, 2H), 7.03-6.98 (m, 3H), 4.81-4.79 (m, 1H), 4.55-4.49 (m, 4H), 3.78 (s, 3H), 2.98-2.95 (m, 2H), 2.90-2.82 (m, 5H), 2.79 (s, 3H), 2.19-1.91 (m, 7H), 1.79-1.61 (m, 8H), 1.63-1.62 (m, 6H), 1.04-1.00 (m, 2H). | | C | B |
| 464 | 870.36 | 870.45 | 872.45 | $^1$H NMR (300 MHz, DMSO-d$_6$) δ 11.11 (s, 1H), 8.82 (s, 1H), 8.03-7.94 (m, 3H), 7.91 (s, 1H), 7.84-7.81 (m, 1H), 7.68 (s, 1H), 7.44 (s, 1H), 7.37-7.34 (m, 1H), 7.02 (s, 1H), 5.24-5.20 (b, 1H), 5.14-5.11 (m, 1H), 4.54 (s, 2H), 4.21-4.07 (m, 4H), 3.57-3.55 (m, 1H), 3.35-3.28 (m, 4H), 2.97-2.94 (m, 2H), 2.87-2.83 (m, 3H), 2.77-2.74 (m, 2H), 2.33 (s, 3H), 2.26-2.23 (m, 1H), 2.06-2.03 (m, 1H), 1.95-1.90 (m, 4H), 1.61-1.60 (m, 6H), 1.47-1.40 (m, 2H). | | A | D |
| 465 | 833.32 | 833.40 | | $^1$H NMR (300 MHz, DMSO-d$_6$) δ 11.10 (s, 1H), 8.82 (s, 1H), 8.04 (s, 1H), 7.95 (s, 2H), 7.85-7.82 (m, 1H), 7.69 (s, 1H), 7.44-7.34 (m, 2H), 7.01 (s, 1H), 5.34-5.20 (b, 1H), 5.14-5.12 (m, 1H), 4.53 (s, 2H), 4.11-4.07 (m, 2H), 4.02-3.95 (m, 1H), 3.75-3.70 (m, 1H), 3.35-3.30 (m, 8H), 2.97-2.94 (m, 1H), 2.77-2.73 (m, 4H), 2.36-2.23 (m, 2H), 2.16-1.95 (m, 3H), 1.95-1.90 (m, 2H), 1.61-1.60 (m, 7H), 1.49-1.41 (m, 2H). | | B | A |
| 466 | 861.35 | 861.35 | | $^1$H NMR (300 MHz, DMSO-d$_6$, ppm) δ 10.85 (s, 1H), 8.87 (s, 1H), 8.55(d, J = 8.4 Hz, 1H), 8.05 (s, 1H), 7.96-7.93 (m, 2H), 7.74 (d, J = 11.4 Hz, 1H), 7.47 (d, J = 9 Hz, 1H), 7.12 (s, 1H), 6.65(d, J = 5.4 Hz, 2H), 4.76 (s, 2H), 3.75 (s, 3H), 3.73-3.64 (m, 8H), 3.38(s, 1H), 2.73-2.671 (m, 6H), 2.40 (s, 4H), 2.27-2.01 (m, 5H), 1.84-1.80 (m, 2H), 1.28 (s, 1H), 1.37-1.19 (m, 2H). | | B | A |
| 467 | 832.33 | 832.40 | 834.40 | $^1$H NMR (400 MHz, DMSO-d$_6$, ppm): δ 10.86 (s, 1H), 8.80 (s, 1H), 8.56 (s, 1H), 8.03 (s, 1H), 7.95 (s, 2H), 7.76-7.65 (m, 2H), 7.02 (s, 1H), 6.70-6.61 (m, 2H), 5.45-5.13 (m, 1H), 4.75 (s, 1H), 4.51-4.48 (s, 4H), 3.75 (s, 3H), 3.02 (s, 4H), 2.91-2.71 (m, 3H), 2.67 (s, 3H), 2.54 (d, J = 3.6 Hz, 4H), 2.53 (s, 1H), 2.20 (s, 2H), 2.19-2.00 (m, 2H), 1.95-1.75 (m, 3H), 1.57 (s, 6H), 1.04 (s, 2H). | | C | B |
| 468 | 861.37 | 871.30 | | 1H NMR (300 MHz, DMSO-d6) δ 10.82 (s, 1H), 8.85 (s, 1H), 8.69 (d, J = 8.3 Hz, 1H), 8.03 (d, J = 13.5 Hz, 2H), 7.92 (d, J = 2.4 Hz, 1H), 7.82-7.73 (m, 1H), 7.49 (d, J = 9.2 Hz, 1H), 7.16 (s, 1H), 7.03 (m, 1H), 6.79 (d, J = 8.9 Hz, 1H), 4.80-4.66 (m, 1H), 4.59 (s, 2H), 3.71 (d, J = 12.3 Hz, 8H), 3.60 (s, 4H), 2.79-2.67 (m, 3H), 2.00 (s, 1H), 2.05-1.89 (m, 4H), 1.80 (d, J = 12.0 Hz, 3H), 1.67 (s, 3H), 1.39 (s, 1H), 1.34 (s, 4H), 0.91 (s, 6H). | | A | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 469 | 717.14 | 717.20 | | $^1$H NMR (400 MHz, DMSO-d$_6$) δ 11.12 (s, 1H), 8.78 (s, 1H), 8.05 (m, 2H), 7.96 (m, 1H), 7.85-7.81 (m, 2H), 7.58 (m, 1H), 7.43 (m, 1H), 7.35 (m, 1H), 7.17 (s, 1H), 5.13 (m, 1H), 4.56 (s, 2H), 4.49 (m, 2H), 4.33 (m, 2H), 3.05 (s, 6H), 2.90 (m, 1H), 2.66 (m, 4H), 2.63 (s, 1H), 2.17 (m, 2H), 2.10-2.01 (m, 1H). | | C | B |
| 470 | 703.11 | 703.10 | | $^1$H NMR (400 MHz, DMSO-d$_6$, ppm): δ 11.11 (s, 1H), 8.92 (s, 1H), 8.06-7.99 (m, 3H), 7.84-7.80 (m, 2H), 7.69 (d, J = 9.2 Hz 1H), 7.40 (d, J = 2.0 Hz, 1H), 7.29-7.26 (m, 1H), 7.19 (s, 1H), 5.13-5.08 (m, 1H), 4.77-4.74(m, 2H), 4.57-4.51 (m, 4H), 3.06(s, 6H), 2.89-2.84 (m, 1H), 2.67(d, J = 4.8 Hz, 3H), 2.51-2.50 (m, 1H), 2.18-2.16(m, 1H), 2.05-2.03 (m, 1H). | | C | B |
| 471 | 870.36 | 870.30 | | 1H NMR (400 MHz, DMSO-d6, ppm)δ 11.10 (s, 1H), 8.83 (s, 1H), 8.04 (s, 1H), 7.99-7.91 (m, 2H), 7.81 (m, 1H), 7.69 (s, 2H), 7.53 (s, 1H), 7.45 (s, 1H), 7.02 (s, 1H), 5.60-5.15 (s, 1H), 5.07 (s, 1H), 4.54 (s, 2H), 4.24 (s, 1H), 4.14-4.07 (m, 4H), 3.59 (s, 1H), 3.30-3.19 (m, 2H), 2.98-2.87 (m, 2H), 2.66 (s, 3H), 2.64 (s, 1H), 2.41 (s, 3H), 2.29-2.20 (m, 1H), 2.02-1.94 (m, 1H), 1.92-1.86 (m, 4H), 1.56 (s, 6H), 1.39-1.30 (m, 2H). | | C | B |
| 472 | 870.36 | 870.35 | | $^1$H NMR (400 MHz, DMSO-d$_6$ ppm) δ 11.10 (s, 1H), 8.83 (s, 1H), 8.04 (s, 1H), 7.99-7.90 (m, 2H), 7.79 (s, 1H), 7.74-7.65 (m, 2H), 7.51 (s, 1H), 7.44 (s, 1H), 7.03 (s, 1H), 5.45-5.19 (m, 1H), 5.09 (s, 1H), 4.91 (s, 1H), 4.53 (s, 2H), 4.08 (s, 2H), 3.99 (s, 1H), 3.70 (s, 1H), 3.30 (s, 3H), 2.95-2.81 (m, 1H), 2.68-2.51 (m, 6H), 2.41 (s, 1H), 2.19-2.06(m, 4H), 2.05-1.90 (m, 2H), 1.83 (s, 2H), 1.70 (t, J = 10.5 Hz, 1H), 1.56 (d, J = 6.8 Hz, 6H), 1.40 (d, J = 9.9 Hz, 2H). | | | |
| 473 | 861.37 | 861.40 | | $^1$H NMR (300 MHz, DMSO-d$_6$ ppm) δ 10.85 (s, 1H), 8.85 (s, 1H), 8.55(d, J = 8.4 Hz, 1H), 8.06 (s, 1H), 7.96 (s, 2H), 7.70 (s, 2H), 7.03(s, 1H), 6.65 (d, J = 5.4 Hz, 2H), 4.76 (s, 1H), 4.55 (s, 2H), 3.75 (s, 3H), 3.65 (s, 4H), 3.38(s, 1H), 2.73-2.67 (m, 4H), 2.40 (s, 5H), 2.22-1.84 (m, 5H), 1.84-1.80 (m, 3H), 1.57 (d, J = 6.9 Hz, 6H), 1.29-1.24 (m, 3H). | | B | A |
| 474 | 759.17 | 759.25 | | $^1$H NMR (400 MHz, DMSO-d$_6$) δ 11.08 (s, 1H), 8.90 (s, 1H), 8.09 (s, 1H), 7.96 (m, 2H), 7.85 (m, 1H), 7.71 (m, 1H), 7.58 (m, 1H), 7.42 (m, 1H), 7.34 (m, 1H), 7.14 (s, 1H), 5.13 (m, 1H), 4.56 (s, 2H), 4.48 (m, 2H), 4.33 (m, 2H), 3.67-3.56 (m, 8H), 2.90 (m, 1H), 2.66 (m, 3H), 2.65-2.52 (m, 2H), 2.17 (m, 2H), 2.10-2.01 (m, 1H). | | C | C |
| 475 | 745.15 | 745.20 | | $^1$H NMR (300 MHz, DMSO-d$_6$, ppm): δ11.09(s, 1H), 8.90 (s, 1H), 8.07 (s, 1H), 7.94 (d, J = 2.1 Hz, 2H) 7.81-7.66(m, 3H), 7.41 (d, J = 1.8 Hz 1H), 7.29-7.26 (m, 1H), 7.15 (s, 1H), 5.13-5.08 (m, 1H), 4.77-4.74(m, 2H), 4.57-4.51 (m, 4H), 3.61-3.60(s, 8H), 2.87-2.84 (m, 1H), 2.66-2.53 (m, 5H), 2.05-2.04 (m, 1H). | | A | D |
| 476 | 870.36 | 870.30 | | $^1$H NMR (300 MHz, DMSO-d$_6$, ppm) δ 11.09 (m, 1H), 8.82 (s, 1H), 8.04 (s, 1H), 7.94 (s, 2H), 7.80-7.77 (m, 1H), 7.69 (s, 2H), 7.53 (d, J = 8.4 Hz, 1H), 7.44 (d, J = 7.2 Hz, 1H), 7.01 (s, 1H), 5.35 (s, 1H), 5.12-5.04(m, 1H), 4.54 (s, 2H), 4.20-4.18 (m, 5H), 3.57(s, 1H), 3.32-3.24 (m, 2H), 3.06-2.78 (m, 2H), 2.67-2.66 (m, 5H), 2.41 (s, 6H), 2.01 (s, 1H), 1.88-1.81 (m, 2H), 1.56 (d, J = 6.9 Hz, 7H), 1.447-1.29 (m, 2H). | | C | B |
| 477 | 870.36 | 870.30 | | $^1$H NMR (300 MHz, DMSO-d$_6$, ppm) δ 11.09 (s, 1H), 8.82 (s, 1H), 8.04 (s, 1H), 7.94 (s, 2H), 7.80-7.77 (m, 1H), 7.69-7.63 (m, 3H), 7.47 (d, J = 6.9 Hz, 1H), 7.01 (s, 1H), 5.10-5.04 (m, 1H), 4.66-4.64 (m, 1H), 4.54 (s, 2H), 4.09-4.05 (m, 2H), 3.74-3.70 (m, 2H), 3.27 (s, 2H), 3.10-2.82 (m, 4H), 3.06-2.78 (m, 2H), 2.67-2.65 (m, 3H), 2.49 (s, 4H), 2.26-1.87 (m, 6H), 1.56 (d, J = 6.9 Hz, 7H), 1.45-1.33 (m, 1H), 0.28-1.21 (m, 1H). | | C | B |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 478 | 870.36 | 870.30 | 872.30 | $^1$H NMR (300 MHz, DMSO-d$_6$) δ 11.09 (s, 1H), 8.81 (s, 1H), 8.02 (s, 1H), 7.94-7.91 (m, 2H), 7.80-7.77 (m, 1H), 7.68 (s, 2H), 7.50-7.42 (m, 2H), 7.01 (s, 1H), 5.24-5.20 (b, 1H), 5.14-5.11 (m, 1H), 4.90 (s, 1H), 4.42 (s, 2H), 4.09-3.98 (m, 3H), 3.69 (s, 1H), 3.28-3.24 (m, 3H), 2.97-2.74 (m, 8H), 2.33-2.31 (m, 2H), 2.26-1.95 (m, 6H), 1.84-1.81(m, 2H), 1.75-1.70 (m, 1H), 1.58-1.54 (m, 6H), 1.40-1.37 (m, 2H). | | | D |
| 479 | 870.36 | 870.30 | 872.30 | $^1$H NMR (300 MHz, DMSO-d$_6$) δ 11.11 (s, 1H), 8.84 (s, 1H), 8.05 (s, 1H), 7.95-7.91 (m, 2H), 7.80-7.77 (m, 1H), 7.70 (m, 2H), 7.52-7.45 (m, 2H), 7.02 (s, 1H), 5.12-5.10 (m, 1H), 4.54 (s, 2H), 4.14-4.09 (m, 5H), 3.60 (s, 1H), 3.28-3.24 (m, 4H), 2.90-2.87 (m, 2H), 2.68-2.66 (m, 4H), 2.33-2.31 (m, 3H), 2.04-1.93 (m, 6H), 1.58-1.54 (m, 7H), 1.40-1.37 (m, 2H). | | | D |
| 480 | 858.37 | 858.35 | | $^1$H NMR (300 MHz, DMSO-d$_6$, ppm) δ 10.853 (s, 1H), 8.818 (s, 1H), 8.56-8.54 (m, 1H), 8.04 (s, 1H), 7.94-7.93(m, 2H), 7.79-7.68 (m, 1H), 7.76-7.75 (m, 1H), 7.48-7.46 (m, 1H), 7.10 (s, 1H), 6.98-6.96 (m, 2H), 4.94-4.90 (m, 2H), 4.86-4.83 (m, 1H), 4.57-4.50 (m, 4H), 3.77 (s, 3H), 3.67 (s, 3H), 2.94-2.90 (m, 4H), 2.84-2.78 (m, 5H), 2.65-2.64 (m, 3H), 2.49-2.48 (m, 1H), 2.23-1.89 (m, 4H), 1.84-1.78 (m, 6H), 1.49-1.35 (m, 2H). | | C | B |
| 481 | 861.37 | 861.35 | | $^1$H NMR (400 MHz, DMSO-d6, ppm):δ 10.84 (s, 1H), 8.30 (s, 1H), 8.04 (s, 1H), 8.02 (s, 1H), 7.89 (s, 1H), 7.77 (s, 1H), 7.50 (s, 1H), 7.38 (s, 1H), 7.15 (s, 1H), 6.89-6.86 (m, 1H), 4.76-4.72 (m, 1H), 4.59 (s, 2H), 3.83 (s, 3H), 3.68 (s, 3H), 3.59 (s, 4H), 3.07 (s, 4H), 2.78 (s, 1H), 2.66 (d, J = 4.6 Hz, 3H), 2.54 (s, 4H), 2.16-1.94 (m, 2H), 1.72-1.50 (m, 3H), 1.32-1.20 (m, 3H), 0.90 (s, 6H). | | A | A |
| 482 | 836.35 | 858.35 | | $^1$H NMR (300 MHz, DMSO-d$_6$, ppm) δ 11.11 (s, 1H), 8.88 (s, 1H), 8.06-7.95 (m, 2H), 7.86-7.84 (m, 1H), 7.79-7.77 (m, 2H), 7.76-7.75 (m, 1H), 7.50-7.47 (m, 1H), 7.12 (s, 1H), 6.44 (s, 1H), 5.17-5.16 (m, 1H), 4.96-4.88 (m, 1H), 4.61-4.58 (m, 2H), 3.94-3.90 (m, 1H), 3.68 (s, 2H), 2.96-2.92 (m, 4H), 2.90-2.86 (m, 4H), 2.81-2.74 (m, 4H), 2.55-2.52 (m, 1H), 2.32-2.28 (m, 1H), 2.06-1.94 (m, 3H), 1.81-1.56 (m, 5H), 1.40-1.34 (m, 5H), 1.341.30 (m, 1H). | | B | A |
| 483 | 879.42 | 879.30 | | $^1$H NMR (400 MHz, DMSO-d6)δ: 11.08 (s, 1H), 8.81 (s, 1H), 8.04-7.91 (m, 3H), 7.75-7.63 (m, 3H), 7.39-7.22 (m, 2H), 7.00 (s, 1H), 5.07 (dd, J = 5.2, 12.9 Hz, 1H), 4.55 (s, 2H), 3.75-3.40 (m, 8H), 2.99-2.76 (m, 2H), 2.68 (d, J = 4.8 Hz, 4H), 2.64-2.52 (m, 6H), 2.09-1.86 (m, 4H), 1.57 (d, J = 6.8 Hz, 9H), 1.52-1.40 (m, 4H) | | B | A |
| 484 | 879.42 | 879.30 | | $^1$H NMR (400 MHz, DMSO-d$_6$) δ: 11.08 (s, 1H), 8.80 (s, 1H), 8.10-7.99 (m, 2H), 7.94 (s, 1H), 7.77-7.64 (m, 3H), 7.34 (dd, J = 8.0, 10.4 Hz, 2H), 7.01 (s, 1H), 5.08 (dd, J = 5.6, 12.8 Hz, 1H), 4.55 (s, 2H), 3.66-3.51 (m, 5H), 3.27 (br s, 3H), 2.97-2.77 (m, 2H), 2.68 (d, J = 4.8 Hz, 4H), 2.56-2.53 (m, 5H), 2.46-2.41 (m, 2H), 2.06-1.93 (m, 4H), 1.57 (d, J = 6.8 Hz, 8H), 1.51-1.41 (m, 4H) | | B | A |
| 485 | 867.36 | 867.25 | 869.25 | $^1$H NMR (300 MHz, DMSO-d$_6$, ppm): 11.08 (s, 1H), 8.81 (s, 1H), 8.07 (s, 1H), 7.96 (s, 2H), 7.75-7.64 (m, 3H), 7.34-7.30 (m, 2H), 7.05 (s, 1H), 5.11-5.05 (m, 1H), 4.57 (s, 2H), 3.78-3.61 (m, 6H), 2.92-2.80 (m, 3H), 2.72-2.52 (m, 8H), 2.03-2.00 (m, 1H), 1.90-1.74 (m, 4H), 1.49-1.23 (m, 9H), 0.94 (s, 6H). | | B | A |
| 486 | 870.36 | 870.35 | | $^1$H NMR (400 MHz, DMSO-d$_6$, ppm): δ 11.09 (s, 1H), 8.82 (s, 1H), 8.03 (s, 1H), 7.95-7.93 (m, 1H), 7.94 (s, 2H), 7.81-7.77 (m, 1H), 7.68 (s, 2H), 7.53 (d, J = 8.4 Hz, 1H), 7.44 (d, J = 7.2 Hz, 1H), 7.00 (s, 1H), 5.10-5.05 (m, 1H), 4.53 (s, 2H), 4.21-4.06 (m, 5H), 3.56 (s, 1H), 3.26-3.16 (m, 3H), 3.00 (d, J = | | B | D |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 487 | 870.36 | 870.35 | | 10.4 Hz, 1H), 2.91-2.80(m, 1H), 2.79-2.69 (m, 4H), 2.66-2.53 (m, 1H), 2.49-2.31 (m, 5H), 2.02-1.97 (m, 1H), 1.90-1.82 (m, 2H), 1.56 (d, J = 7.2 Hz, 8H), 1.41-1.35(m, 2H). | | | D |
| 488 | 864.40 | 864.35 | | $^1$H NMR (400 MHz, DMSO-d$_6$, ppm): δ 11.06 (s, 1H), 8.82 (s, 1H), 8.03 (s, 1H), 7.96-7.93 (m, 2H), 7.79-7.77 (m, 1H), 7.68-7.63 (m, 3H), 7.46 (d, J = 7.2 Hz, 1H), 7.01 (s, 1H), 5.09-5.04 (m, 1H), 4.66-4.61 (m, 1H), 4.54 (s, 2H), 4.05-4.01 (m, 2H), 3.73-3.70 (m, 2H), 3.33-3.24 (m, 3H), 3.09-3.04 (m, 1H), 3.02-2.98 (m, 1H), 2.98-2.84 (m, 1H), 2.66-2.61 (m, 3H), 2.55-2.50 (m, 1H), 2.25-2.20 (m, 3H), 2.03-1.98 (m, 1H), 1.95-1.82 (m, 3H), 1.78-1.72 (m, 1H), 1.67-1.45 (m, 6H), 1.42-1.29 (m, 3H), 1.27-1.09 (m, 2H). | | B | A |
| 489 | 893.44 | 893.35 | | $^1$H NMR (400 MHz, DMSO-d$_6$, ppm) δ 11.12 (s, 1H), 8.82-8.13 (m, 1H), 8.05-8.04 (m, 1H), 7.96-7.95 (m, 2H), 7.85-7.84 (m, 1H), 7.78-7.67 (m, 3H), 7.01 (s, 1H), 5.16-5.15 (m, 1H), 4.95-4.88 (m, 2H), 4.58-4.53 (m, 4H), 3.12 (s, 2H), 2.88-2.80 (m, 2H), 2.67-2.65 (m, 4H), 2.51-2.50 (m, 4H), 2.45-2.35 (m, 1H), 2.10-1.95 (m, 2H), 1.90-1.82 (m, 4H), 1.80-1.75 (m, 2H), 1.58-1.55 (m, 6H), 1.45-1.38 (m, 2H), 1.35-1.30 (m, 1H), 1.11-1.10 (m, 2H), 0.89-0.87 (m, 1H) | | B | A |
| 490 | 893.44 | 893.35 | | $^1$H NMR (400 MHz, DMSO-d$_6$, ppm) δ 11.06 (s, 1H), 8.78 (s, 1H), 8.02 (s, 1H), 7.94-7.94 (m, 2H), 7.74-7.70 (m, 2H), 7.67-7.61 (m, 1H), 7.02 (s, 1H), 6.91 (s, 1H), 6.80-6.78 (m, 1H), 5.07-5.03 (m, 1H), 4.54-4.47 (m, 4H), 3.44-3.41 (m, 2H), 3.25(s, 2H), 2.88-2.80 (m, 3H), 2.69 (s, 3H), 2.60-2.50(m, 2H), 2.42-2.30 (m, 4H), 2.14-2.04(m, 2H), 2.01-1.99 (m, 1H), 1.98-1.87(m, 3H), 1.85-1.71(m, 3H), 1.56 (d, J = 13.6 Hz, 10H), 1.02-0.98 (m, 2H). | | B | A |
| 491 | 799.24 | 799.15 | | $^1$H NMR (400 MHz, DMSO-d$_6$ ppm):δ 11.07 (s, 1H), 8.74 (s, 1H), 8.10 (s, 1H), 8.02 (s, 1H), 7.95 (s, 1H), 7.84 (s, 1H), 7.69-7.63 (m, 2H), 7.30-7.21 (m, 2H), 7.11-7.03 (m, 1H), 5.08-5.04 (m, 1H), 4.53 (s, 2H), 4.04-4.01 (m, 2H), 3.50 (s, 2H), 3.01-2.83 (m, 4H), 2.67 (s, 3H), 2.60-2.56 (m, 2H), 2.54-2.50 (m, 2H), 2.47-2.00 (m, 7H), 1.79 (s, 5H), 1.57 (d, J = 6.8 Hz, 10H), 1.19-1.01 (m, 2H). | | A | D |
| 492 | 799.33 | 799.40 | | $^1$H NMR (400 MHz, DMSO-d$_6$ ppm) δ 11.09 (s, 1H), 8.84 (s, 1H), 8.03 (s, 1H), 7.93 (s, 2H), 7.82-7.69 (m, 1H), 7.48 (dd, J = 21.5, 8.3 Hz, 3H), 7.11 (d, J = 2.8 Hz, 1H), 5.07 (dd, J = 12.7, 5.4 Hz, 1H), 4.62 (d, J = 7.1 Hz, 2H), 4.60-4.45 (m, 7H), 4.32 (d, J = 12.9 Hz, 1H), 4.17 (dd, J = 9.7, 5.6 Hz, 1H), 4.06 (s, 1H), 2.96 (q, J = 11.0 Hz, 2H), 2.93-2.80 (m, 1H), 2.66 (d, J = 4.6 Hz, 3H), 2.58 (d, J = 17.8 Hz, 1H), 1.98 (s, 3H), 1.74 (s, 1H), 1.50 (t, J = 9.8 Hz, 2H). | | B | C |
| 493 | 840.38 | 840.40 | | $^1$H NMR (300 MHz, DMSO-d$_6$, ppm) δ 11.08 (s, 1H), 8.65 (s, 1H), 8.00 (s, 1H), 7.73-7.70 (m, 1H), 7.68 (s, 1H), 7.45-7.26 (m, 3H), 7.10 (d, J = 8.4 Hz, 1H), 5.12-5.06 (m, 1H), 4.47-4.43 (m, 3H), 3.90-3.85 (m, 2H), 3.29 (s, 9H), 2.87-2.77 (m, 3H), 2.62-2.52 (m, 4H), 2.19 (d, J = 6.3 Hz, 2H), 2.04-2.02 (m, 1H, 3H), 1.77-1.68 (m, 5H), 1.15 (s, 6H), 1.09-1.00 (m, 2H) | | C | B |
| 494 | 893.44 | 893.45 | | $^1$H NMR (300 MHz, DMSO-d$_6$, ppm) δ 11.09 (s, 1H), 8.68 (s, 1H), 8.00 (s, 1H), 7.70-7.64 (m, 1H), 7.40 (s, 1H), 7.33-7.25 (m, 3H), 7.10 (d, J = 8.4 Hz, 1H), 5.12-5.06 (m, 1H), 4.43 (s, 1H), 4.16-4.08 (m, 3H), 3.90-3.85 (m, 2H), 3.49 (s, 1H), 3.21-3.15 (m, 7H), 2.87-2.83 (m, 1H), 2.62-2.55 (m, 1H), 2.49 (s, 1H), 2.24-2.17 (m, 2H), 2.04-2.00 (m, 1H), 1.81-1.68 (m, 11H), 1.36-1.33 (m, 2H), 1.17 (s, 7H). | | B | A |
| | | | | $^1$H NMR (300 MHz, DMSO-d$_6$, ppm) δ 11.07 (s, 1H), 8.79 (s, 1H), 8.03-7.94 (m, 3H), 7.74-7.63 (m, 3H), 7.31-7.22 (m, 2H), 7.03 (s, 1H), 5.30 (s, 1H), 5.09- | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 495 | 907.47 | 907.50 | 909.50 | 5.03 (m, 1H), 4.54 (s, 4H), 3.65-3.41 (m, 4H), 2.94-2.79 (m, 3H), 2.73-2.58 (m, 5H), 2.27 (s, 2H), 2.22 (d, J = 6.0 Hz, 2H), 2.03-1.99 (m, 1H), 1.78-1.74 (m, 3H), 1.58 (d, J = 8.4 Hz, 13H), 1.26-0.99 (m, 3H) | | B | A |
| 496 | 907.47 | 907.35 | 909.35 | $^1$H NMR (300 MHz, DMSO-d$_6$) δ 11.08 (s, 1H), 9.03 (s, 1H), 8.09 (s, 1H), 8.03 (s, 1H), 7.94 (s, 1H), 7.69-7.65 (m, 3H), 7.34 (s, 1H), 7.25 (d, J = 8.7 Hz, 1H), 7.04 (s, 1H), 5.30 (b, 1H), 5.08-5.05 (m, 1H), 4.55 (s, 2H), 4.48-4.44 (m, 2H), 3.39-3.21 (m, 6H), 3.08-2.93 (m, 7H), 2.72 (s, 3H), 2.68-2.66 (m, 2H), 2.21-1.95 (m, 2H), 1.85-1.62 (m, 7H), 1.60-1.55 (m, 7H), 1.53-1.51 (m, 2H), 1.32-1.10 (m, 2H). | | B | A |
| 497 | 825.41 | 825.20 | | $^1$H NMR (400 MHz, DMSO-d$_6$) δ 11.08 (s, 1H), 8.92 (s, 1H), 8.07 (s, 1H), 8.04 (s, 1H), 7.99 (s, 1H), 7.69-7.67 (m, 3H), 7.28 (s, 1H), 7.26 (d, J = 2.0 Hz 1H), 6.97 (s, 1H), 5.06-5.04 (m, 1H), 4.57 (s, 2H), 4.11-4.08 (m, 3H), 3.73-3.67 (m, 5H), 3.41-3.38 (m, 2H), 3.12-2.97 (m, 7H), 2.67 (s, 3H), 2.50-2.49 (m, 2H), 2.20-2.01 (m, 2H), 1.91-1.81 (m, 4H), 1.65-1.57 (m, 9H), 1.40-1.39 (m, 2H), 1.28-1.27 (m, 2H). | | C | A |
| 498 | 785.35 | 786.70 | | $^1$H NMR (400 MHz, DMSO-d$_6$) δ: 10.22 (s, 1H), 8.81 (s, 1H), 8.17 (s, 1H), 8.03 (s, 1H), 7.98 (d, J = 4.8 Hz, 1H), 7.94 (s, 1H), 7.73-7.68 (m, 2H), 7.08 (d, J = 8.8 Hz, 2H), 7.02 (s, 1H), 6.49 (d, J = 8.8 Hz, 2H), 5.63-4.94 (m, 1H), 4.54-4.48 (m, 4H), 3.65 (t, J = 6.4 Hz, 3H), 3.08 (s, 3H), 2.84 (t, J = 12.0 Hz, 2H), 2.68-2.65 (m, 5H), 2.45-2.42 (m, 2H), 2.33 (s, 2H), 2.17 (d, J = 6.4 Hz, 2H), 1.83-1.73 (m, 5H), 1.57 ( d, J = 6.8 Hz, 10H), 1.05-1.00 (m, 2H) | | | D |
| 499 | 894.43 | 894.20 | | $^1$H NMR (400 MHz, DMSO-d$_6$) δ: 10.27 (s, 1H), 8.81 (s, 1H), 8.15 (s, 1H), 8.05-7.99 (m, 2H), 7.92 (s, 1H), 7.74-7.65 (m, 2H), 7.12 (m, 1H), 7.02 (s, 1H), 6.62 (s, 1H), 6.57 (d, J = 8.4 Hz, 1H), 6.49 (d, J = 8.8 Hz, 1H), 4.53 (s, 2H), 4.47 (d, J = 12.4 Hz, 2H), 3.72 (s, 2H), 3.49 (s, 2H), 3.41 (m, 3H), 2.88-2.72 (m, 4H), 2.70-2.64 (m, 5H), 2.60 (s, 2H), 2.35 (d, J = 6.0 Hz, 2H), 1.88 (s, 2H), 1.71 (d, J = 11.6 Hz, 3H), 1.56 (d, J = 6.8 Hz, 6H), 0.99 (d, J = 10.8 Hz, 2H) | | A | A |
| 500 | 865.39 | 865.20 | | $^1$H NMR (400 MHz, DMSO-d$_6$) δ: 11.09 (s, 1H), 8.80 (s, 1H), 8.02 (s, 1H), 7.99 (d, J = 4.4 Hz, 1H), 7.93 (s, 1H), 7.73-7.66 (m, 3H), 7.34 (dd, J = 7.6, 10.8 Hz, 2H), 7.02 (s, 1H), 5.08 (dd, J = 5.6, 12.8 Hz, 1H), 4.54 (s, 2H), 4.47 (d, J = 11.6 Hz, 2H), 3.47-3.37 (m, 3H), 3.29 (d, J = 3.6 Hz, 6H), 2.97-2.75 (m, 5H), 2.68 (d, J = 4.4 Hz, 3H), 2.58 (d, J = 18.4 Hz, 1H), 2.42 (m, 4H), 2.34-2.24 (m, 2H), 2.06-1.97 (m, 1H), 1.75-1.65 (m, 2H), 1.57 (d, J = 6.8 Hz, 7H), 1.11-0.95 (m, 2H) | | B | A |
| 501 | 865.39 | 865.30 | | $^1$H NMR (400 MHz, DMSO-d$_6$) δ: 11.07 (s, 1H), 8.80 (s, 1H), 8.03 (s, 1H), 7.98-7.94 (m, 2H), 7.69-7.62 (m, 3H), 7.02 (s, 1H), 7.69 (s, 2H), 7.58 (dd, J = 8.8, 7.2 Hz, 1H), 7.15 (d, J = 6.8 Hz, 1H), 7.08 (d, J = 8.4 Hz, 1H), 7.01 (s, 1H), 6.80 (dd, J = 8.4, 1.6 Hz, 1H), 5.39 (s, 1H), 5.05 (dd, J = 12.8, 5.2 Hz, 1H), 5.06 (dd, J = 12.4, 5.2 Hz, 1H), 4.54 (s, 2H), 4.47 (d, J = 12.8 Hz, 2H), 3.73 (s, 4.55 (s, 2H), 4.48 (d, J = 12.8 Hz, 2H), 3.53 (s, 4H), 3.22-3.16 (m, 5H), 2.93-2.78 (m, 3H), 2.68 (d, J = 4.4 Hz, 3H), 2.60-2.56 (m, 1H), 2.34 (d, J = 6.4 Hz, 2H), 3.54-3.46 (m, 8H), 2.84-2.78 (m, 3H), 2.66 (d, J = 4.4 Hz, 3H), 2.60-2.17 (t, J = 6.4 Hz, 2H), 2.01-1.99 (m, 1H), 1.72 ( d, J = 11.2 Hz, 2H), 2.53 (m, 3H), 2.15 (t, J = 6.8 Hz, 2H), 2.02-1.98 (m, 1H), 1.69 ( d, J = 12.0 1.57 ( d, J = 6.8 Hz, 7H), 1.08-1.00 (m, 2H) Hz, 3H), 1.56 ( d, J = 6.8 Hz, 6H), 1.10-1.04 (m, 2H) | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 502 | 865.39 | 865.10 | | $^1$H NMR (400 MHz, DMSO-d$_6$) δ: 11.07 (s, 1H), 8.79 (s, 1H), 8.03 (s, 1H), 7.94 (s, 2H), 7.77-7.66 (m, 2H), 7.56 (dd, J = 7.2, 8.4 Hz, 1H), 7.12 (d, J = 7.2 Hz, 1H), 7.02 (s, 1H), 6.79 (d, J = 8.8 Hz, 1H), 5.04 (dd, J = 5.6, 12.8 Hz, 2H), 4.54 (s, 2H), 4.49 (br d, J = 12.4 Hz, 2H), 4.22-4.03 (m, 4H), 3.32-3.31 (m, 4H), 2.95-2.77 (m, 3H), 2.74-2.62 (m, 5H), 2.27 (br d, J = 6.8 Hz, 2H), 2.09-1.94 (m, 3H), 1.83-1.66 (m, 3H), 1.57 (d, J = 7.2 Hz, 6H), 1.13-0.94 (m, 2H) | | B | A |
| 503 | 881.39 | 881.40 | | $^1$H NMR (300 MHz, DMSO-d$_6$, ppm): δ 11.08 (s, 1H), 8.86 (s, 1H), 8.06-7.97 (m, 3H), 7.75-7.65 (m, 2H), 7.52 (d, J = 9.3 Hz, 1H), 7.34-7.30 (m, 2H), 7.12 (s, 1H), 5.12-5.06 (m, 1H), 4.64-4.59 (m, 4H), 4.28-4.24 (m, 4H), 3.71-3.65 (m, 6H), 2.99-2.83 (m, 4H), 2.68-2.62 (m, 5H), 2.41 (s, 4H), 2.22 (d, J = 4.8 Hz, 2H), 2.07-2.00 (m, 3H), 1.85-1.81 (m, 3H), 1.34-1.31 (m, 2H) | | A | A |
| 504 | 813.27 | 813.35 | | $^1$H NMR (300 MHz, DMSO-d$_6$, ppm) δ 11.09 (s, 1H), 8.84 (s, 1H), 8.03 (s, 1H), 7.94 (s, 2H), 7.80-7.75 (m, 2H), 7.49-7.44 (m, 3H), 7.13 (s, 1H), 5.10-5.04 (m, 1H), 4.61-4.52 (m, 5H), 4.34-4.06 (m, 7H), 3.01-2.88 (m, 4H), 2.67-2.49 (m, 5H), 1.99 (s, 5H), 1.80-1.33 (m, 3H). | | A | C |
| 505 | 799.33 | 799.35 | | $^1$H NMR (300 MHz, DMSO-d$_6$, ppm): δ11.09 (s, 1H), 8.01 (s, 1H), 7.70-7.67 (m, 1H), 7.65 (s, 1H), 7.45-7.24 (m, 3H), 7.10 (d, J = 8.4 Hz, 1H), 5.12-5.06 (m, 1H), 4.44 (s, 1H), 3.90-3.85 (m, 2H), 3.71-3.62 (m, 6H), 2.90-2.82 (m, 3H), 2.62-2.56 (m, 4H), 2.38 (s, 4H), 2.19 (d, J = 6.3 Hz, 1H), 2.08-2.04 (m, 1H), 1.87-1.1.72 (m, 5H), 1.40-1.29 (m, 2H), 1.15 (s, 6H). | | B | C |
| 506 | 893.44 | 893.45 | | 1H NMR (300 MHz, DMSO-d6, ppm) δ 11.08 (s, 1H), 8.79 (s, 1H), 8.03-7.94 (m, 3H), 7.65-. 7.60 (m, 3H), 73.31-7.22 (m, 2H), 7.03 (s, 1H), 5.30 (s, 1H), 5.09-5.03 (m, 1H), 4.53 (s, 4H), 3.25 (s, 4H), 2.94-2.79 (m, 3H), 2.68-2.66 (m, 6H), 2.37 (s, 2H), 2.22 (d, J = 6.0 Hz, 2H), 2.03-1.99 (m, 1H), 1.67-1.48 (m, 16H), 1.16-0.99 (m, 2H) | | B | A |
| 507 | 893.44 | 893.45 | | $^1$H NMR (300 MHz, DMSO-d$_6$, ppm) δ 11.07 (s, 1H), 8.80 (s, 1H), 8.03-7.94 (m, 3H), 7.74-7.63 (m, 3H), 7.31-7.22(m, 2H), 7.03 (s, 1H), 5.30 (s, 1H), 5.09-5.03 (m, 1H), 4.54 (s, 2H), 4.04-4.00(m, 2H), 3.71-3.69 (m, 2H), 3.58-3.56 (m, 2H), 2.94-2.69 (m, 3H), 2.69-2.67 (m, 3H), 2.60 (s, 2H), 2.35 (s, 2H), 2.23 (d, J = 6.6 Hz, 2H), 2.03-1.99 (m, 1H), 1.78-1.63 (m, 3H), 1.63-1.60(m, 13H), 1.26-1.02 (m, 3H) | | A | A |
| 508 | 893.44 | 893.45 | | $^1$H NMR (300 MHz, DMSO-d$_6$, ppm) δ 11.07 (s, 1H), 8.80 (s, 1H), 8.03 (s, 1H), 7.92-7.91 (m, 3H), 7.71-7.67 (m, 3H), 7.34-7.30(m, 2H), 7.02 (s, 1H), 5.30-5.03 (m, 2H), 4.54 (s, 2H), 3.71-3.56 (m, 6H), 2.86-2.85 (m, 3H), 2.68-2.66 (m, 5H), 2.37-2.27 (m, 4H), 2.03-1.63 (m, 3H), 1.61-1.51(m, 13H), 1.41-1.32 (m, 3H) | | A | A |
| 509 | 855.44 | 855.20 | | $^1$H NMR (400 MHz, DMSO-d$_6$, ppm) δ: 10.16 (s, 1H), 8.82 (s, 1H), 8.15 (s, 1H), 8.04 (s, 1H), 8.01-7.93 (m, 2H), 7.71 (s, 1H), 7.69 (s, 1H), 7.03 (s, 1H), 6.97 (d, J = 8.8 Hz, 1H), 6.14 (s, 1H), 6.09-6.04 (m, 1H), 4.57-4.47 (m, 4H), 3.80-3.76 (m, 3H), 3.49 (br s, 1H), 3.30-3.21 (m, 6H), 3.14-3.08 (m, 2H), 2.86 (br t, J = 12.0 Hz, 2H), 2.71-2.59 (m, 6H), 2.42 (br s, 2H), 2.25 (br s, 2H), 1.84 (br t, J = 6.8 Hz, 3H), 1.76 (br d, J = 13.2 Hz, 2H), 1.58 (d, J = 6.8 Hz, 10H), 1.04 (br d, J = 11.2 Hz, 2H) | | | D |
| 510 | 865.39 | 865.10 | | $^1$H NMR (400 MHz, DMSO-d$_6$) δ: 11.06 (s, 1H), 8.79 (s, 1H), 8.02 (s, 1H), 7.99-7.88 (m, 2H), 7.75-7.66 (m, 2H), 7.63 (d, J = 8.4 Hz, 1H), 7.01 (s, 1H), 6.78 (d, J = 2.0 Hz, 1H), 6.64 (dd, J = 2.0, 8.4 Hz, 1H), 5.04 (dd, J = 5.2, 13.2 Hz, 1H), 4.56-4.43 (m, 4H), 4.05-3.87 (m, 4H), 3.34-3.32 (m, 2H), 2.93- | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 511 | 865.39 | 865.10 | | 2.75 (m, 3H), 2.74-2.62 (m, 5H), 2.60-2.54 (m, 1H), 2.28-2.19 (m, 2H), 2.11-1.95 (m, 3H), 1.76 (br d, J = 11.6 Hz, 3H), 1.56 (d, J = 6.8 Hz, 6H), 1.12-0.93 (m, 2H). | | | |
| 512 | 893.44 | 893.35 | | $^1$H NMR (400 MHz, DMSO-d$_6$) δ: 11.09 (s, 1H), 8.81 (s, 1H), 8.16 (s, 1H), 8.07-7.96 (m, 3H), 7.84 (dd, J = 2.4, 9.2 Hz, 1H), 7.73-7.62 (m, 2H), 7.32 (dd, J = 5.6, 7.6 Hz, 2H), 7.09 (s, 1H), 5.33 (br s, 1H), 5.09 (dd, J = 5.6, 12.8 Hz, 1H), 4.55 (s, 2H), 3.99-3.88 (m, 4H), 3.75-3.63 (m, 3H), 2.95-2.81 (m, 4H), 2.78 (br s, 2H), 2.67 (d, J = 4.8 Hz, 3H), 2.63-2.57 (br d, J = 8.0 Hz, 2H), 2.39-2.33 (m, 2H), 2.11-2.00 (m, 3H), 1.83 (br d, J = 10.8 Hz, 2H), 1.70-1.61 (m, 1H), 1.57 (d, J = 6.8 Hz, 6H), 1.39-1.26 (m, 2H) | | A | |
| 513 | 893.44 | 893.40 | | $^1$H NMR (400 MHz, DMSO-d$_6$ ppm): δ 11.06 (s, 1H), 8.80 (s, 1H), 8.02-7.93 (m, 2H), 7.82-7.71 (m, 2H), 7.69-7.53 (m, 1H), 7.3-7.27 (m, 1H), 7.12-7.08 (m, 2H), 7.01 (s, 1H), 5.08-5.03 (m, 1H), 4.53-4.47 (m, 4H), 3.60 (m, 2H), 3.44(s, 3H), 2.90-2.80 (m, 3H), 2.79-2.67 (m, 3H), 2.60-2.53 (m, 2H), 2.50-2.32 (m, 4H), 2.22-2.14 (m, 2H), 2.07-1.98 (m, 1H), 1.91-1.72(m, 5H), 1.71-1.49(m, 10H), 1.17-0.95(m, 2H). | | B | A |
| 514 | 879.42 | 879.30 | | $^1$H NMR (400 MHz, DMSO-d$_6$ ppm): δ 11.09 (s, 1H), 8.75 (s, 1H), 8.10 (s, 1H), 8.02-7.99 (m, 2H), 7.84 (s, 1H), 7.69-7.65 (m, 2H), 7.33-7.30 (m, 2H), 7.15-7.06 (m, 1H), 5.10-5.06 (m, 2H), 4.53 (s, 2H), 3.66-3.60 (m, 3H), 3.54-3.50 (m, 3H), 2.90-2.83 (m, 3H), 2.81-2.54 (m, 6H), 2.50-2.03 (m, 4H), 2.01-1.96 (m, 2H), 1.91-1.71 (m, 5H), 1.57 (d, J = 6.0 Hz, 9H), 1.38-1.15 (m, 3H). | | A | A |
| 515 | 879.42 | 879.25 | | $^1$H NMR (400 MHz, DMSO-d$_6$ ppm): δ 11.07 (s, 1H), 8.80 (s, 1H), 8.09-7.91 (m, 3H), 7.71-7.64 (m, 3H), 7.31-7.20 (m, 2H), 7.02 (s, 1H), 5.12-5.05 (m, 1H), 4.53 (s, 2H), 3.98-3.90(m, 2H), 3.77-3.68 (m, 2H), 3.61-3.53 (m, 2H), 3.12-3.04(m, 2H), 2.94-2.82 (m, 1H), 2.71-2.66 (m, 4H), 2.61-2.55 (m, 3H), 2.51-2.45 (m, 2H), 2.30-2.24(m, 1H), 2.03-1.95(m, 1H), 1.97-1.80 (m, 2H), 1.64-1.55 (m, 9H), 1.54-1.45 (m, 6H). | | A | B |
| 516 | 879.42 | 879.30 | | $^1$H NMR (400 MHz, DMSO-d$_6$, ppm) δ 11.06 (s, 1H), 8.81 (s, 1H), 8.04 (s, 1H), 7.97 (s, 2H), 7.70 (s, 2H), 7.62 (s, 1H), 7.02 (s, 1H), 6.91 (s, 1H), 6.79 (s, 1H), 5.50-5.10(m, 1H), 5.05 (s, 1H), 4.59-4.52 (m, 4H), 3.45 (s, 3H), 2.97-2.76 (m, 2H), 2.67 (s, 3H), 2.63-2.51 (m, 3H), 2.48 (s, 4H), 2.00 (s, 1H), 1.89-1.76 (m, 4H), 1.66-1.56 (m, 11H), 1.44-1.31 (m, 2H), 1.23 (s, 1H). | | B | A |
| 517 | 879.42 | 879.30 | | $^1$H NMR (300 MHz, DMSO-d$_6$, ppm) δ 11.06 (s, 1H), 8.83 (s, 1H), 8.04-7.95 (m, 3H), 7.69-7.62 (m, 3H), 7.30-7.21 (m, 2H), 7.04 (s, 1H), 5.08-5.07 (m, 1H), 5.04-5.02 (m, 1H), 4.55 (s, 2H), 3.62 (s, 4H), 3.44-3.32 (m, 4H), 2.88-2.84 (m, 1H), 2.69-2.66 (m, 5H), 2.60-2.30 (m, 7H), 2.02-1.93 (m, 3H), 1.65-1.57 (m, 12H). | | A | A |
| 518 | 895.42 | 895.50 | | $^1$H NMR (300 MHz, DMSO-d$_6$ ppm) δ: 11.08 (s, 1H), 8.84 (s, 1H), 8.05 (s, 1H), 7.95 (s, 2H), 7.69-7.64 (m, 3H), 7.33-7.29 (m, 2H), 7.04 (s, 1H), 5.12-5.09 (m, 1H), 5.07-5.06 (m, 1H), 4.55 (s, 2H), 3.62 (s, 4H), 3.32-3.13 (m, 5H), 2.93-2.92 (m, 1H), 2.87-2.83 (m, 5H), 2.68-2.30 (m, 6H), 2.03-1.97 (m, 3H), 1.98-1.75 (m, 2H), 1.55-1.46 (m, 8H), 1.40-1.38 (m, 2H). | | A | B |
| | | | | $^1$H NMR (400 MHz, DMSO-d$_6$) δ: 11.09 (s, 1H), 8.85 (s, 1H), 8.05 (s, 1H), 7.98-7.90 (m, 2H), 7.78-7.65 (m, 1H), 7.50-7.30 (m, 2H), 7.02 (s, 1H), 5.50-5.00 (m, 2H), 4.54 (s, 2H), 4.30-4.05 (m, 3H), 3.60-3.50 (m, 1H), 3.30-3.15 (m, 8H), 3.00-2.80 (m, 2H), 2.67 (d, J = 4.8 Hz, 3H), 2.64-2.52 (m, 3H), 2.31-2.11 (m, 8H), 2.09-1.94 (m, 3H), 1.90-1.79 (m, 2H), 1.57 (d, J = 6.8 Hz, 6H), 1.43-1.30 (m, 2H). | | | |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 519 | 865.39 | 865.10 | | $^1$H NMR (400 MHz, DMSO-d$_6$) δ: 11.08 (s, 1H), 8.75 (br s, 1H), 8.28-7.90 (m, 3H), 7.83 (br d, J = 4.8 Hz, 1H), 7.73-7.60 (m, 2H), 7.31 (d, J = 7.6 Hz, 2H), 7.09 (br s, 1H), 5.63-5.18 (m, 1H), 5.09 (dd, J = 5.6, 12.8 Hz, 1H), 4.54 (s, 2H), 3.76-3.61 (m, 2H), 3.56 (s, 2H), 3.51-3.43 (m, 2H), 3.20-3.07 (m, 4H), 2.94-2.77 (m, 3H), 2.73-2.64 (m, 3H), 2.60-2.53 (m, 2H), 2.35 (br d, J = 6.0 Hz, 2H), 2.19-1.94 (m, 3H), 1.87-1.69 (m, 2H), 1.58 (d, J = 6.8 Hz, 6H), 1.50-1.40 (m, 1H), 1.36-1.20 (m, 2H) | | A | A |
| 520 | 879.42 | 879.30 | | $^1$H NMR (400 MHz, DMSO-d$_6$ ppm):δ 11.08 (s, 1H), 8.80 (s, 1H), 8.03-7.91 (m, 3H), 7.92-7.69 (m, 3H), 7.38-7.31 (m, 2H), 7.03 (s, 1H), 5.11-5.06 (m, 2H), 4.54 (s, 2H), 3.74-3.55 (m, 7H), 2.95-2.84 (m, 4H), 2.74-2.57 (m, 6H), 2.54-2.47 (m, 2H), 2.23-2.14 (m, 2H), 2.09-1.97 (m, 1H), 1.96-1.89 (m, 2H), 1.65-1.46 (m, 12H). | | C | A |
| 521 | 879.42 | 879.30 | | $^1$H NMR (400 MHz, DMSO-d$_6$ ppm): δ 11.07 (s, 1H), 8.83 (s, 1H), 8.04-7.96 (m, 3H), 7.76-7.63 (m, 3H), 7.31-7.22 (m, 2H), 7.03 (s, 1H), 5.12-5.03 (m, 1H), 4.53 (s, 2H), 4.34 (d, J = 6.4 Hz, 2H), 3.03-2.97 (m, 3H), 2.95-2.88 (m, 2H), 2.71-2.65(m, 10H), 2.02-1.99 (m, 2H), 1.96-1.86 (m, 2H), 1.67-1.56 (m, 13H), 1.41-1.33 (m, 3H). | | B | A |
| 522 | 907.47 | 907.50 | 909.50 | $^1$H NMR (300 MHz, DMSO-d$_6$, ppm): δ 11.08 (s, 1H), 9.09 (s, 1H), 8.91 (s, 1H), 8.10 (s, 1H), 8.05 (s, 1H), 7.93 (s, 1H), 7.69-7.65 (m, 3H), 7.34-7.32 (m, 2H), 7.05 (s, 1H), 5.30 (b, 1H), 5.08-5.05 (m, 1H), 4.56 (s, 2H), 4.47-4.43 (m, 2H), 3.41-3.28 (m, 6H), 3.10-2.84 (m, 7H), 2.68-2.66 (m, 3H), 2.57-2.54 (m, 2H), 2.04-1.96 (m, 2H), 1.91-1.85 (m, 6H), 1.53-1.51 (m, 10H), 1.32-1.10 (m, 2H). | | | |
| 523 | 851.36 | 851.35 | | $^1$H NMR (300 MHz, DMSO-d$_6$, ppm) δ 11.07 (s, 1H), 8.84 (s, 1H), 8.05-7.95 (m, 3H), 7.69-7.64 (m, 3H), 7.05 (s, 1H), 6.74 (d, J = 2.1 Hz, 1H), 6.6.62-6.59 (m, 1H), 5.35 (s, 1H), 5.08-5.02 (m, 1H), 4.55 (s, 2H), 4.06 (s, 2H), 3.93 (s, 2H), 3.63 (s, 4H), 2.90-2.82 (m, 1H), 2.2-67-2.58 (m, 4H), 2.55-2.33 (m, 9H), 2.11-1.92 (m, 4H), 1.57 (d, J = 6.8 Hz, 6H). | | B | A |
| 524 | 894.43 | 894.20 | | $^1$HNMR (400 MHz, DMSO-d$_6$) δ: 11.10 (s, 1H), 8.86 (s, 1H), 8.19 (s, 2H), 8.05 (s, 1H), 8.01-7.96 (m, 1H), 7.95 (s, 1H), 7.73-7.63 (m, 3H), 7.33 (d, J = 7.6 Hz, 2H), 7.03 (s, 1H), 5.09 (dd, J = 5.2, 12.8 Hz, 1H), 4.55 (s, 2H), 3.67-3.56 (m, 9H), 3.08 (t, J = 7.2 Hz, 2H), 2.98-2.79 (m, 4H), 2.76-2.69 (m, 1H), 2.67 (d, J = 4.4 Hz, 3H), 2.60 (d, J = 2.4 Hz, 1H), 2.58-2.52 (m, 3H), 2.42-2.31 (m, 4H), 2.07-1.97 (m, 1H), 1.82 (d, J = 10.4 Hz, 2H), 1.56 (d, J = 7.2 Hz, 6H), 1.47-1.32 (m, 2H) | | B | A |
| 525 | 895.42 | 895.10 | | $^1$H NMR (400 MHz, DMSO-d$_6$) δ: 11.09 (s, 1H), 8.88-8.80 (m, 1H), 8.23 (s, 1H), 8.04 (s, 1H), 8.02-7.96 (m, 1H), 7.94 (s, 1H), 7.73-7.61 (m, 3H), 7.36-7.26 (m, 2H), 7.02 (s, 1H), 5.08 (dd, J = 5.2, 12.8 Hz, 1H), 4.58-4.50 (m, 2H), 4.19 (quin, J = 6.0 Hz, 1H), 4.15-4.04 (m, 3H), 3.46-3.42 (m, 3H), 3.22 (t, J = 10.0 Hz, 3H), 2.98-2.90 (m, 2H), 2.89-2.75 (m, 3H), 2.67 (d, J = 4.4 Hz, 3H), 2.63-2.55 (m, 1H), 2.55-2.51 (m, 1H), 2.48-2.38 (m, 2H), 2.26-2.16 (m, 1H), 2.05-1.96 (m, 1H), 1.87-1.69 (m, 4H), 1.56 (d, J = 6.8 Hz, 6H), 1.43-1.29 (m, 4H) | | B | A |
| 526 | 895.42 | 895.20 | | $^1$H NMR (400 MHz, DMSO-d$_6$) δ: 11.08 (s, 1H), 8.84 (s, 1H), 8.28-8.22 (m, 1H), 8.06-8.01 (m, 1H), 8.00-7.92 (m, 2H), 7.72-7.59 (m, 3H), 7.30 (d, J = 2.0 Hz, 1H), 7.22 (dd, J = 2.0, 8.8 Hz, 1H), 7.02 (s, 1H), 5.06 (dd, J = 5.2, 13.2 Hz, 1H), 4.54 (s, 2H), 4.22-4.05 (m, 3H), 3.88-3.77 (m, 2H), 3.61-3.51 (m, 5H), 3.15-3.01 (m, 3H), 2.88 (ddd, J = 5.2, 14.0, 17.2 Hz, 1H), 2.77 (t, J = 6.4 | | B | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 527 | 879.42 | 879.45 | | Hz, 2H), 2.67 (d, J = 4.4 Hz, 3H), 2.58-2.52 (m, 1H), 2.48-2.44 (m, 1H), 2.30-2.23 (m, 1H), 2.05-1.96 (m, 1H), 1.86-1.76 (m, 2H), 1.74-1.64 (m, 2H), 1.57 (d, J = 6.8 Hz, 6H), 1.42-1.32 (m, 2H), 1.27-1.16 (m, 2H) | | B | A |
| 528 | 879.42 | 879.25 | | $^1$H NMR (400 MHz, DMSO-d$_6$, ppm)δ 11.06 (s, 1H), 8.78 (s, 1H), 8.02 (s, 1H), 7.94-7.94 (m, 2H), 7.74-7.70 (m, 2H), 7.67-7.61 (m, 1H), 7.34-7.27 (m, 1H), 7.02 (s, 1H), 6.91 (s, 1H), 6.80-6.78 (m, 1H), 5.07-5.03 (m, 1H), 4.54-4.47 (m, 4H), 3.44-3.41 (m, 2H), 3.25(s, 2H), 2.88-2.80 (m, 3H), 2.69 (s, 3H), 2.60-2.50(m, 2H), 2.42-2.30(m, 4H), 2.14-2.04(m, 2H), 2.01-1.99(m, 1H), 1.98-1.87(m, 3H), 1.85-1.71(m, 3H), 1.56 (d, J = 13.6 Hz, 10H), 1.02-0.98 (m, 2H). | | | B |
| 529 | 851.36 | 851.35 | | $^1$H NMR (400 MHz, DMSO-d$_6$, ppm)δ 11.05 (s, 1H), 8.81 (s, 1H), 8.04 (s, 1H), 7.95 (s, 2H), 7.70 (s, 2H), 7.56-7.53 (s, 1H), 7.33-7.24 (m, 1H), 7.10 (s, 2H), 7.02 (s, 1H), 5.60-5.10(s, 1H), 5.08-5.05 (m, 1H), 4.54 (s, 4H), 3.59 (s, 2H), 3.42(s, 2H), 2.98-2.83 (m, 3H), 2.67 (s, 3H), 2.54 (s, 3H), 2.47 (s, 2H), 2.02(s, 1H), 1.80 (d, J = 8.6 Hz, 4H), 1.57-1.40 (m, 12H), 1.43-1.32 (m, 2H). | | B | A |
| 530 | 815.37 | 815.50 | | 1H NMR (300 MHz, DMSO-d$_6$ ppm) δ 11.07 (s, 1H), 8.83 (s, 1H), 8.04-7.95 (m, 3H), 7.70 (d, J = 2.1 Hz, 2H), 7.57-7.52 (m, 1H), 7.11-7.05 (m, 2H), 6.73 (d, J = 8.4 Hz, 1H), 5.35 (s, 1H), 5.07-5.01 (m, 1H), 4.55 (s, 2H), 4.21 (s, 2H), 4.08 (s, 2H), 3.62 (s, 4H), 2.88-2.82 (m, 1H), 2.69-2.60(m, 4H), 2.57-2.28 (m, 10H), 2.01-1.85 (m, 3H), 1.57 (d, J = 6.8 Hz, 6H). | | | B |
| 531 | 895.42 | 895.50 | | $^1$H NMR (400 MHz, DMSO-d$_6$) δ: 10.23 (s, 1H), 8.79 (s, 1H), 8.19 (s, 1H), 8.05-7.91 (m, 3H), 7.75-7.66 (m, 2H), 7.05-6.89 (m, 2H), 6.65-6.57 (m, 2H), 5.57-4.07 (m, 5H), 3.74-3.53 (m, 9H), 2.94-2.53 (m, 11H), 2.31-2.23 (m, 2H), 1.91-1.81 (m, 2H), 1.75-1.71 (m, 3H), 1.59-1.55 (m, 6H), 1.06-0.94 (m, 2H) | | C | A |
| 532 | 894.43 | 894.30 | | $^1$H NMR (400 MHz, DMSO-d6) δ: 11.08 (s, 1H), 8.83 (s, 1H), 8.21 (s, 1H), 8.04 (s, 1H), 8.00-7.90 (m, 2H), 7.72-7.65 (m, 3H), 7.37-7.30 (m, 1H), 7.27-7.20 (m, 1H), 7.02 (s, 1H), 5.80-5.10 (m, 1H), 5.10-5.02 (m, 1H), 4.54 (s, 2H), 4.23-4.05 (m, 3H), 3.70-3.47 (m, 6H), 3.28-3.10 (m, 1H), 2.95-2.75 (m, 2H), 2.67 (d, J = 4.4 Hz, 3H), 2.62-2.52 (m, 2H), 2.44-2.37 (m, 4H), 2.25-2.14 (m, 2H), 2.05-1.92 (m, 3H), 1.87-1.75 (m, 2H), 1.57 (d, J = 6.8 Hz, 6H), 1.45-1.30 (m, 2H). | | | |
| 533 | 907.47 | 907.30 | 909.30 | $^1$HNMR (400 MHz, DMSO-d6) δ: 11.06 (s, 1H), 8.84 (s, 1H), 8.05 (s, 1H), 7.98-7.92 (m, 2H), 7.69 (s, 2H), 7.64 (d, J = 8.8 Hz, 1H), 7.29 (d, J = 1.6 Hz, 1H), 7.22 (dd, J = 1.6, 8.8 Hz, 1H), 7.03 (s, 1H), 5.06 (dd, J = 5.6, 12.8 Hz, 1H), 4.54 (s, 2H), 3.86-3.76 (m, 2H), 3.61 (s, 4H), 3.29 (s, 3H), 3.10 (t, J = 10.4 Hz, 2H), 2.94-2.81 (m, 2H), 2.73 (t, J = 6.4 Hz, 2H), 2.67 (d, J = 4.4 Hz, 4H), 2.62-2.53 (m, 3H), 2.47 (s, 1H), 2.36 (s, 4H), 2.28-2.19 (m, 1H), 2.06-1.96 (m, 1H), 1.73-1.62 (m, 2H), 1.57 (d, J = 6.8 Hz, 6H), 1.26-1.16 (m, 2H) | | A | A |
| 534 | 879.42 | 879.25 | | $^1$H NMR (400 MHz, DMSO-d$_6$ ppm)δ 11.09 (s, 1H), 8.99 (s, 1H), 8.87 (s, 1H), 8.09 (s, 1H), 8.03-8.00 (m, 2H), 7.72-7.63 (m, 3H), 7.35 (d, J = 7.2 Hz, 2H), 6.99 (s, 1H), 5.06-5.04 (m, 2H), 4.57 (s, 2H), 3.73-3.67 (m, 6H), 3.42-3.40 (m, 2H), 3.11-3.10 (m, 4H), 2.94-2.88 (m, 3H), 2.52 (s, 3H), 2.50-2.49 (m, 3H), 2.07-2.02 (m, 2H), 1.91-1.85 (m, 4H), 1.65-1.57 (m, 9H), 1.40-1.39 (m, 4H). $^1$H NMR (400 MHz, DMSO-d$_6$ ppm)δ 11.07 (s, 1H), 8.79 (s, 1H), 8.03 (s, 1H), 7.99-7.91 (m, 2H), 7.70 (s, 2H), 7.63 (s, 1H), 7.01 (s, 1H), 6.89 (d, J = 2.2 Hz, 1H), 6.83-6.76 (m, 1H), 5.50-5.10 (s, 1H), 5.05 (s, 1H), 4.54 (s, 4H), 3.45 (s, 4H), 2.98-2.90 (s, 3H), 2.83 (s, 4H), 2.67 (s, 4H), 2.27 (s, 2H), 2.01-1.90 (m, 4H), 1.77 (d, J = 11.2 Hz, 5H), 1.57 (s, 6H), 1.03 (s, 2H). | | A | A |

TABLE 2-continued

Degradation and characterization of exemplary bifunctional compounds of the present disclosure

| Ex. # | Mol Weight | Mean Observed Mass One | Mean Observed Mass Two | NMR | EC$_{50}$ (nM)* | Dmax (%)** | IC$_{50}$ (nM)*** |
|---|---|---|---|---|---|---|---|
| 535 | 815.37 | 815.50 | | $^1$H NMR (400 MHz, DMSO-d$_6$) δ: 10.31 (s, 1H), 8.80 (s, 1H), 8.28 (s, 2H), 8.04 (s, 1H), 8.00-7.92 (m, 2H), 7.75-7.67 (m, 2H), 7.04-6.89 (m, 3H), 6.76 (dd, J = 1.6, 7.6 Hz, 1H), 5.64-4.35 (m, 5H), 3.69-3.58 (m, 8H), 2.87-2.81 (m, 3H), 2.75-2.66 (m, 9H), 2.34-2.30 (m, 2H), 1.90-1.81 (m, 2H), 1.77-1.73 (m, 3H), 1.58-1.56 (m, 6H), 1.11-0.92 (m, 2H) | | | B |
| 536 | 866.37 | 866.20 | | $^1$H NMR (400 MHz, DMSO-d$_6$) δ: 11.12 (s, 1H), 8.84 (s, 1H), 8.21 (s, 1H), 8.04 (s, 1H), 8.00-7.95 (m, 1H), 7.94-7.90 (m, 1H), 7.85-7.81 (m, 1H), 7.80-7.70 (m, 3H), 7.47 (d, J = 9.2 Hz, 1H), 7.11 (s, 1H), 5.13 (dd, J = 12.8, 5.2 Hz, 1H), 4.58 (s, 2H), 4.22-4.05 (m, 3H), 3.68 (s, 3H), 3.27-3.22 (m, 2H), 3.03-2.96 (m, 2H), 2.95-2.86 (m, 1H), 2.85-2.70 (m, 3H), 2.67 (d, J = 4.4 Hz, 3H), 2.64-2.53 (m, 2H), 2.08-1.95 (m, 3H), 1.85-1.75 (m, 6H), 1.74-1.60 (m, 2H), 1.45-1.30 (m, 2H). | | A | A |
| 537 | 894.43 | 894.20 | | $^1$HNMR (400 MHz, DMSO-d$_6$) δ: 11.10 (s, 1H), 9.00 (br s, 1H), 8.16-8.10 (m, 1H), 7.99-7.92 (m, 2H), 7.62-7.52 (m, 1H), 7.43 (dd, J = 7.7, 16.5 Hz, 2H), 7.09 (s, 1H), 5.11 (dd, J = 5.6, 12.8 Hz, 1H), 4.56 (s, 2H), 3.63 (br s, 2H), 2.95-2.83 (m, 10H), 2.58 (m, 5H), 2.55-2.54 (m, 5H), 2.38 (br s, 1H), 2.15-2.00 (m, 2H), 1.60-1.55 (m, 3H), 1.58 (d, J = 6.8 Hz, 6H), 1.29-1.23 (m, 1H). | | C | A |
| 538 | 893.44 | 893.30 | | $^1$H NMR (400 MHz, DMSO-d$_6$) δ: 11.12 (br s, 1H), 8.80 (s, 1H), 8.20 (s, 1H), 8.02 (s, 1H), 7.98 (br d, J = 4.8 Hz, 1H), 7.93 (d, J = 1.6 Hz, 1H), 7.86-7.81 (m, 1H), 7.79-7.75 (m, 2H), 7.73-7.66 (m, 2H), 7.02 (s, 1H), 5.13 (dd, J = 5.6, 12.8 Hz, 2H), 4.54 (s, 2H), 4.47 (br d, J = 12.8 Hz, 2H), 3.48 (br d, J = 5.2 Hz, 4H), 2.92-2.77 (m, 8H), 2.68 (d, J = 4.6 Hz, 3H), 2.64-2.52 (m, 2H), 2.34 (br d, J = 6.8 Hz, 2H), 2.11-1.97 (m, 1H), 1.93-1.83 (m, 2H), 1.82-1.74 (m, 2H), 1.73-1.64 (m, 4H), 1.57 (d, J = 7.2 Hz, 6H), 1.10-0.95 (m, 2H) | | A | A |
| 539 | 897.41 | 897.30 | | $^1$HNMR (400 MHz, DMSO-d$_6$) δ: 11.07 (s, 1H), 8.83 (s, 1H), 8.04 (s, 1H), 7.98-7.91 (m, 2H), 7.72-7.65 (m, 2H), 7.43-7.34 (m, 1H), 7.10-7.05 (m, 1H), 7.03 (s, 1H), 5.77-5.05 (m, 1H), 5.03 (dd, J = 12.8, 5.6 Hz, 1H), 4.55 (s, 2H), 4.15-4.02 (m, 4H), 3.66-3.58 (m, 3H), 2.95-2.80 (m, 1H), 2.67 (d, J = 4.4 Hz, 3H), 2.61-2.51 (m, 3H), 2.47-2.42 (m, 2H), 2.40-2.28 (m, 4H), 2.15-2.05 (m, 2H), 2.02-1.85 (m, 3H), 1.75-1.65 (m, 2H), 1.57 (d, J = 6.8 Hz, 6H), 1.45-1.37 (m, 1H), 0.97-0.82 (m, 2H). | | B | A |
| 540 | 897.41 | 897.30 | | $^1$HNMR (400 MHz, DMSO-d$_6$) δ: 11.08 (br s, 1H), 8.84 (s, 1H), 8.05 (s, 1H), 8.00-7.91 (m, 2H), 7.70 (s, 2H), 7.03 (s, 1H), 6.91 (dd, J = 2.0, 6.8 Hz, 1H), 6.56 (dd, J = 2.0, 12.4 Hz, 1H), 5.04 (dd, J = 5.6, 12.8 Hz, 1H), 4.55 (s, 2H), 4.17-3.72 (m, 4H), 3.63 (br s, 4H), 2.97-2.79 (m, 1H), 2.67 (d, J = 4.8 Hz, 3H), 2.63-2.52 (m, 2H), 2.44 (br d, J = 4.4 Hz, 1H), 2.40-2.29 (m, 4H), 2.11 (br d, J = 6.8 Hz, 2H), 2.05-1.97 (m, 1H), 1.89 (br d, J = 12.0 Hz, 2H), 1.72 (br d, J = 11.2 Hz, 2H), 1.57 (d, J = 6.8 Hz, 6H), 1.54-1.37 (m, 3H), 1.02-0.81 (m, 2H) | | A | A |
| 541 | 897.41 | 897.60 | | $^1$HNMR (400 MHz, DMSO-d$_6$) δ: 11.09 (br s, 1H), 8.84 (s, 1H), 8.05 (s, 1H), 8.01-7.93 (m, 2H), 7.76-7.66 (m, 2H), 7.47 (t, J = 8.8 Hz, 1H), 7.04 (s, 1H), 6.95-6.82 (m, 1H), 5.20 (br s, 1H), 5.04 (dd, J = 5.6, 12.8 Hz, 1H), 4.55 (s, 2H), 3.92-3.78 (m, 4H), 3.64 (br s, 3H), 2.94-2.80 (m, 1H), 2.68 (d, J = 4.4 Hz, 3H), 2.62-2.52 (m, 1H), 2.48-2.42 (m, 2H), 2.41-2.35 (m, 3H), 2.21-2.11 (m, 2H), 2.04-1.97 (m, 1H), 1.89 (br d, J = 12.8 Hz, 2H), 1.72 (br d, J = 11.6 Hz, 2H), 1.62-1.45 (m, 8H), 1.27-1.18 (m, 2H), 0.99-0.88 (m, 2H). | | A | A |

TABLE 2-continued

Degradation and characterization of exemplary bifunctional compounds of the present disclosure

| Ex. # | Mol Weight | Mean Observed Mass One | Mean Observed Mass Two | NMR | $EC_{50}$ (nM)* | Dmax (%)** | $IC_{50}$ (nM)*** |
|---|---|---|---|---|---|---|---|
| 542 | 868.39 | 868.25 | | $^1$H NMR (300 MHz, DMSO-d$_6$, ppm) δ 11.09 (s, 1H), 8.87 (s, 1H), 8.07 (s, 1H), 7.98-7.96 (m, 2H), 7.74-7.66 (m, 2H), 7.50-7.47 (m, 1H), 7.36-7.32 (m, 2H), 7.12 (s, 1H), 5.12-5.06 (m, 1H), 4.59 (s, 2H), 4.43-4.42 (m, 2H), 3.72-3.66 (m, 6H), 2.92-2.84 (m, 3H), 2.74-2.67 (m, 7H), 2.62-2.25 (m, 11H), 2.24-2.03 (m, 1H), 1.92-1.77 (m, 3H), 1.36-1.19 (m, 3H). | | | |
| 543 | 865.43 | 865.20 | 867.20 | $^1$H NMR (300 MHz, DMSO-d$_6$, ppm): δ10.91 (s, 1H), 8.78 (s, 1H), 8.02-7.93 (m, 3H), 7.69 (s, 2H), 7.46 (d, J = 8.4 Hz, 1H), 7.02 (s, 1H), 6.61 (s, 2H), 5.05-5.00 (m, 2H), 4.53-4.46(m, 5H), 4.46-4.14 (m, 4H), 3.10-2.83 (m, 9H), 1.98 (s, 4H), 1.88-1.78(m, 6H), 1.57 (d, J = 6.9 Hz, 6H), 1.23(s, 3H), 1.14-0.85 (m, 3H) | | | |

*$EC_{50}$ (nM) ranges: A < 10; 10 <= B < 50; 50 <= C < 100; D >= 100
**$D_{MAX}$ (%) ranges: A >= 70; 50 <= B < 70; C < 50
***$IC_{50}$ (nM) ranges: A < 10; 10 <= B < 50; 50 <= C < 100; D >= 100

A novel bifunctional molecule, which contains a BCL6 recruiting moiety and an E3 ubiquitin ligase recruiting moiety is described. The bifunctional molecules of the present disclosure actively degrades BCL6, leading to robust cellular proliferation suppression and apoptosis induction. Protein degradation mediated by the bifunctional compounds of the present disclosure provides a promising strategy in targeting the "undruggable" pathological proteins by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:
1. A compound having the chemical structure:

ULM-L-PTM, or a pharmaceutically acceptable salt thereof,
wherein:
(a) the ULM is:

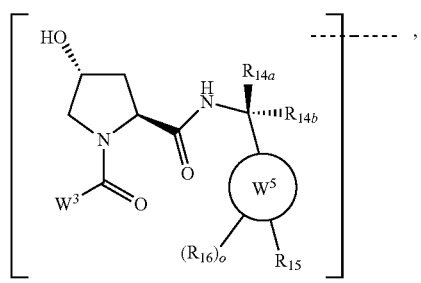

wherein:
$W^3$ is selected from optionally substituted aryl, optionally substituted heteroaryl, and

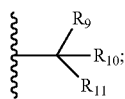

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$ and $R_{10}$, together with the carbon atom to which they are attached, form an optionally substituted cycloalkyl;

$R_{11}$ is selected from optionally substituted heterocyclyl, optionally substituted alkoxy, optionally substituted heteroaryl, optionally substituted aryl,

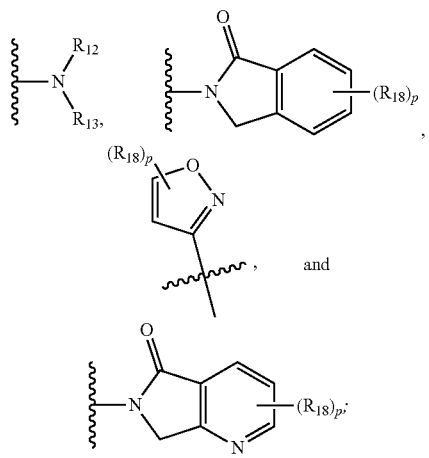

$R_{12}$ is H or optionally substituted alkyl;
$R_{13}$ is H, optionally substituted alkyl, optionally substituted alkylcarbonyl, optionally substituted (cycloalkyl) alkylcarbonyl, optionally substituted aralkylcarbonyl, optionally substituted arylcarbonyl, optionally substituted (heterocyclyl) carbonyl, or optionally substituted aralkyl;
$R_{14a}$ and $R_{14b}$, are each independently selected from H, haloalkyl, optionally substituted alkyl, optionally substituted alkoxy, aminomethyl, alkylaminomethyl, alkoxymethyl, optionally substituted hydroxyl alkyl, optionally substituted alkylamine, optionally substituted heteroalkyl, optionally substituted alkyl-heterocycloalkyl, optionally substituted alkoxy-heterocycloalkyl, $CONR_{27a}R_{27b}$, $CH_2NHCOR_{26}$, and $(CH_2)N(CH_3)COR_{26}$; or $R_{14a}$ and $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;
$W^5$ is phenyl or 5-10 membered heteroaryl optionally substituted with one or more halo, CN, optionally substituted alkyl, optionally substituted haloalkyl, optionally substituted alkoxy, hydroxy, or optionally substituted haloalkoxy;
$R_{15}$ is H; halogen; CN; OH; $NO_2$; $NR_{14a}R_{14b}$; $OR_{14a}$; $CONR_{14a}R_{14b}$; $NR_{14a}COR_{14b}$; $SO_2NR_{14a}R_{14b}$; $NR_{14a}SO_2R_{14b}$; optionally substituted alkyl; optionally substituted haloalkyl; optionally substituted haloalkoxy; optionally substituted aryl; optionally substituted heteroaryl; optionally substituted cycloalkyl; or optionally substituted cycloheteroalkyl;
each $R_{26}$ is independently selected from H, optionally substituted alkyl or $NR_{27a}R_{27b}$;
each $R_{27a}$ and $R_{27b}$ is independently H, optionally substituted alkyl, or $R_{27a}$ and $R_{27b}$ together with the nitrogen atom to which they are attached form a 4-6 membered heterocyclyl;

each $R_{16}$ is independently selected from CN, halo, optionally substituted alkyl, optionally substituted haloalkyl, hydroxy, and optionally substituted haloalkoxy;

o is 0, 1, 2, 3, or 4;

$R_{18}$ is H, halo, optionally substituted alkoxy, cyano, optionally substituted alkyl, haloalkyl, or haloalkoxy;

p is 0, 1, 2, 3, or 4; and wherein the dashed line indicates the site of attachment of the chemical linker moiety coupling the PTM to the ULM;

(b) the PTM is:

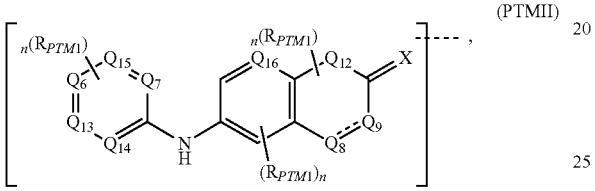
(PTMII)

wherein:

$Q_6$, $Q_7$, $Q_8$, $Q_9$, $Q_{12}$, $Q_{13}$, $Q_{14}$, and $Q_{15}$ are each independently N, O, or C, each optionally substituted with one $R_{PTMI}$;

$Q_{16}$ is CH;

each $R_{PTMI}$ is independently H, halogen, CN, OH, $NO_2$, $NH_2$, $C_{1-6}$ alkyl, or

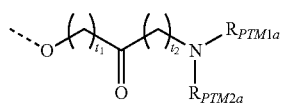

$t_1$ is 1, 2, 3, 4, or 5;

$t_2$ is 0, 1, 2, 3, 4, or 5;

$R_{PTM1a}$ and $R_{PTM2a}$ are independently selected from H, $C_1$-$C_4$ alkyl, $C_1$-$C_4$ alkoxy, and $CH_2OCH_3$; or $R_{PTM1a}$ and $R_{PTM2a}$ are joined together to form a 3-10 membered ring;

X is O, S, or $CH_2$;

⟋⟋ is a single bond or a double bond;

n is an integer from 0 to 10; and

∿∿∿ of the PTM indicates the point of attachment with a chemical linker group; and (c) the L is:

-$(A^L)_q$-, wherein:

q is an integer greater than or equal to 1;

each $A^L$ is independently selected from the group consisting of $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $C_{3-11}$cycloalkyl substituted with 0-6 $R^{L1}$ groups, $C_{5-13}$ spirocycloalkyl substituted with 0-9 $R^{L1}$ groups, $C_{3-11}$ heterocyclyl substituted with 0-6 $R^{L1}$ groups, $C_{5-13}$ spiroheterocyclyl substituted with 0-8 $R^{L1}$ groups, aryl substituted with 0-6 $R^{L1}$ groups, and heteroaryl substituted with 0-6 $R^{L1}$ groups; and $R^{L1}$, $R^{L2}$, $R^{L3}$, and $R^{L4}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, OH, $NH_2$, SH, $SO_2C_{1-8}$alkyl, CC-$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, or $CON(C_{1-8}$alkyl$)_2$.

2. The compound according to claim 1, or a pharmaceutically acceptable salt thereof, wherein L is:

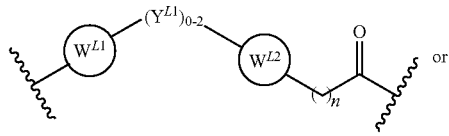 or

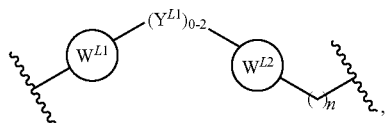, wherein:

$W^{L1}$ and $W^{L2}$ are each independently absent or a 4-8 membered ring with 0-4 heteroatoms, wherein the 4-8 membered ring is optionally substituted with RQ;

each RQ is independently a H, halo, OH, CN, $CF_3$, unsubstituted or substituted linear or branched C1-C6, unsubstituted or substituted linear or branched C1-C6 alkoxy, or 2 RQ groups taken together with the atom they are attached to form a 4-8 membered ring system containing 0-4 heteroatoms;

$Y^{L1}$ is each independently a bond, unsubstituted or substituted linear or branched C1-C6 alkyl optionally having one or more C atoms are replaced with O; or unsubstituted or substituted linear or branched $C_1$-$C_6$ alkoxy;

n is 0-10; and

⤻ indicates the attachment point to the PTM or the ULM.

3. A pharmaceutical composition comprising a compound of claim 1 and a pharmaceutically acceptable carrier.

4. A compound selected from
| Ex. # |
|---|
| 49 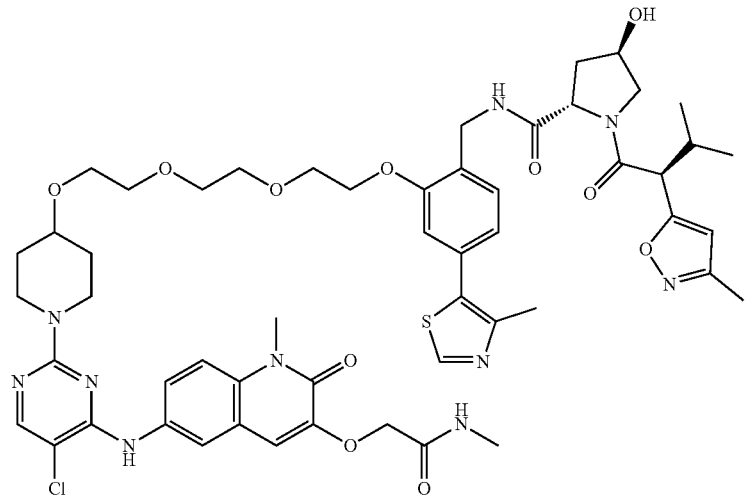 [SMILES: CNC(=O)COc1cc2cc(Nc3nc(N4CCC(OCCOCCOCCOc5cc(-c6scnc6C)ccc5CNC(=O)[C@@H]5C[C@@H](O)CN5C(=O)[C@H](c5cc(C)no5)C(C)C)CC4)ncc3Cl)ccc2n(C)c1=O] |
| 50 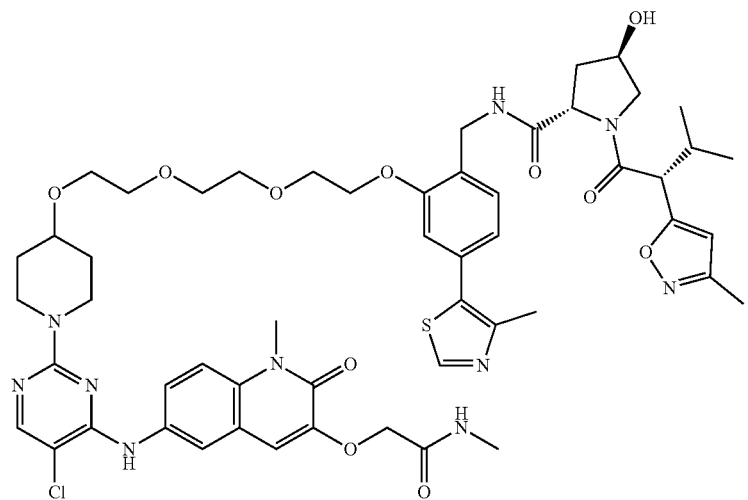 [SMILES: CNC(=O)COc1cc2cc(Nc3nc(N4CCC(OCCOCCOCCOc5cc(-c6scnc6C)ccc5CNC(=O)[C@@H]5C[C@@H](O)CN5C(=O)[C@@H](c5cc(C)no5)C(C)C)CC4)ncc3Cl)ccc2n(C)c1=O] |
| 51 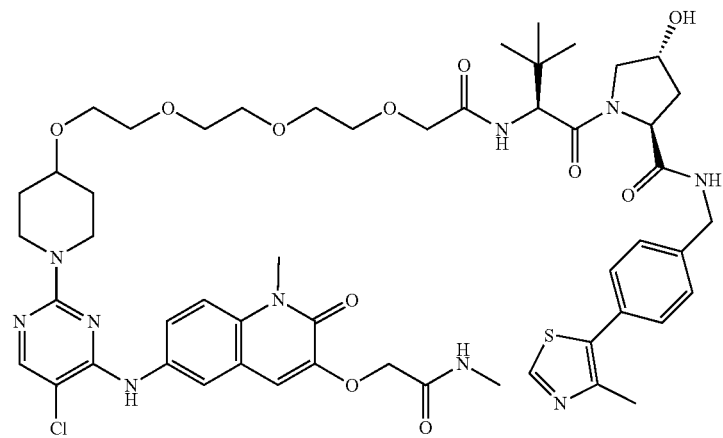 [SMILES: CNC(=O)COc1cc2cc(Nc3nc(N4CCC(OCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |

| Ex. # |
|---|
53
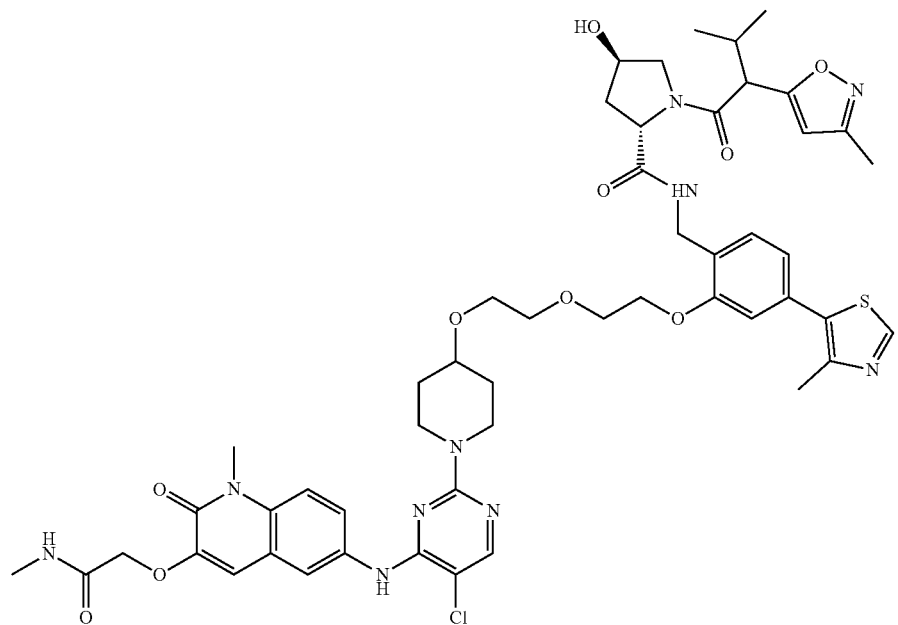 [SMILES: CNC(=O)COc1cc2cc(Nc3nc(N4CCC(OCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O]
54
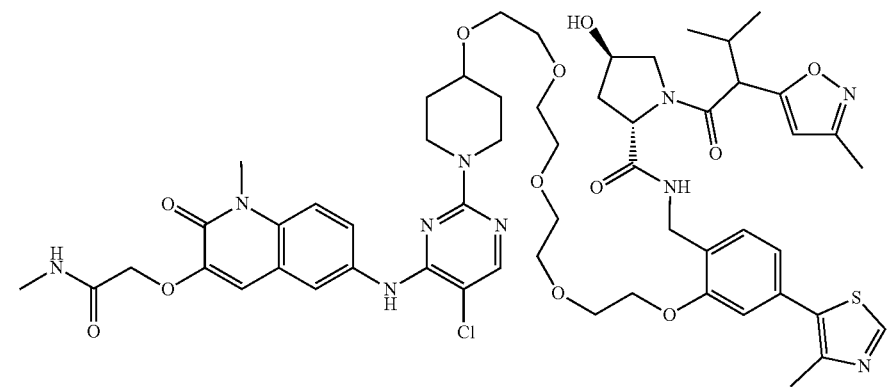 [SMILES: CNC(=O)COc1cc2cc(Nc3nc(N4CCC(OCCOCCOCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O]
55
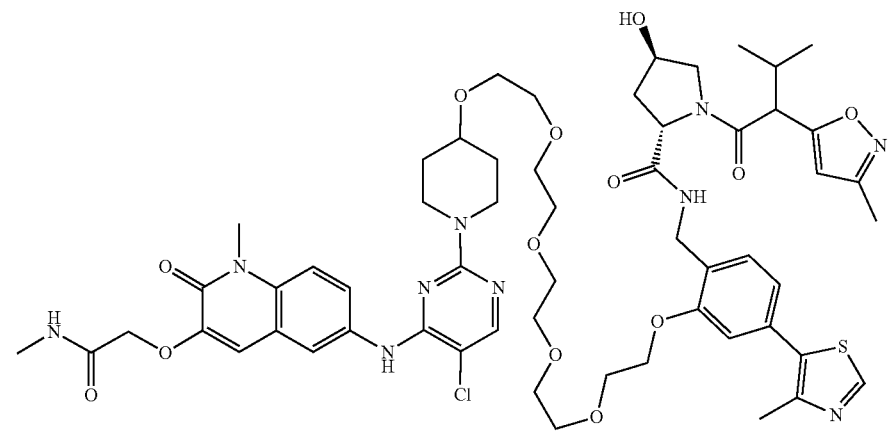 [SMILES: CNC(=O)COc1cc2cc(Nc3nc(N4CCC(OCCOCCOCCOCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O]

| Ex. # |
|---|
| 56 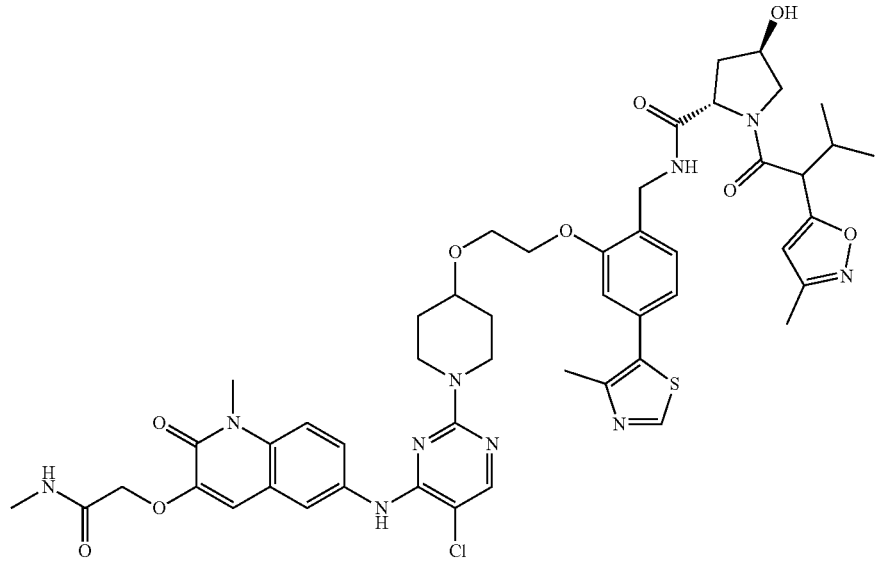 [SMILES: CNC(=O)COc1cc2cc(Nc3nc(N4CCC(OCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |
| 58 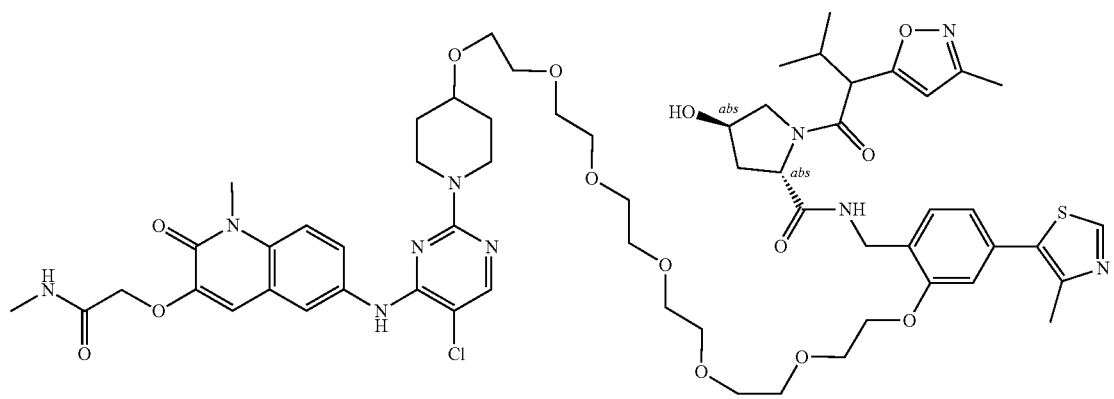 [SMILES: CNC(=O)COc1cc2cc(Nc3nc(N4CCC(OCCOCCOCCOCCOCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |
| 70 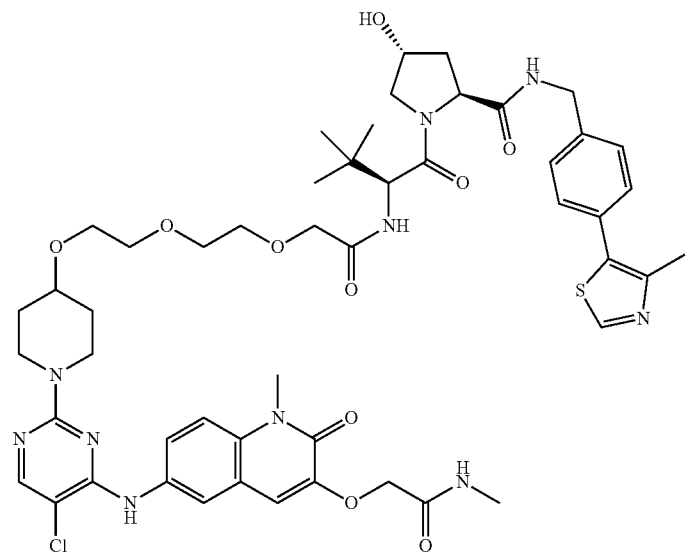 [SMILES: CNC(=O)COc1cc2cc(Nc3nc(N4CCC(OCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |

| Ex. # |
|---|
| 78 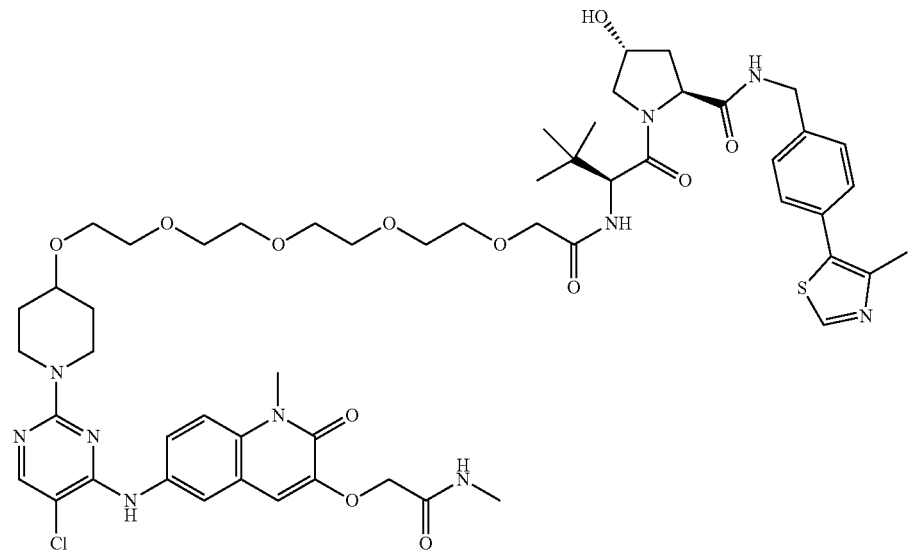 [SMILES: CNC(=O)COc1cc2cc(Nc3nc(N4CCC(OCCOCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 82 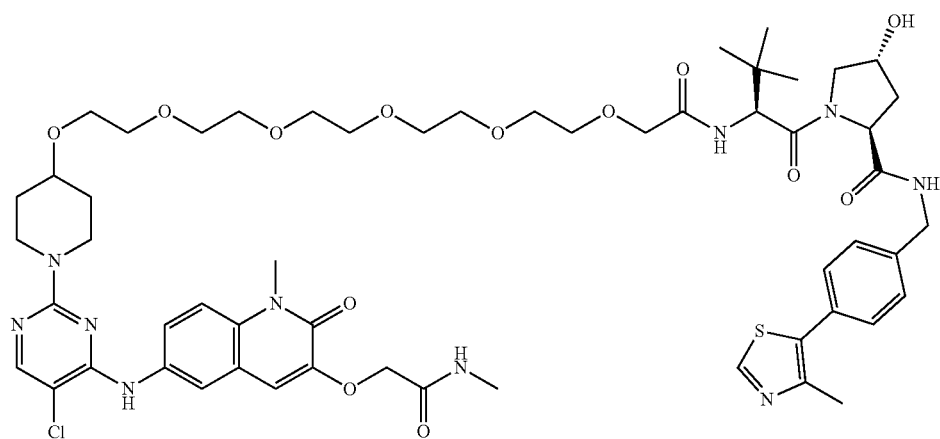 [SMILES: CNC(=O)COc1cc2cc(Nc3nc(N4CCC(OCCOCCOCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 83 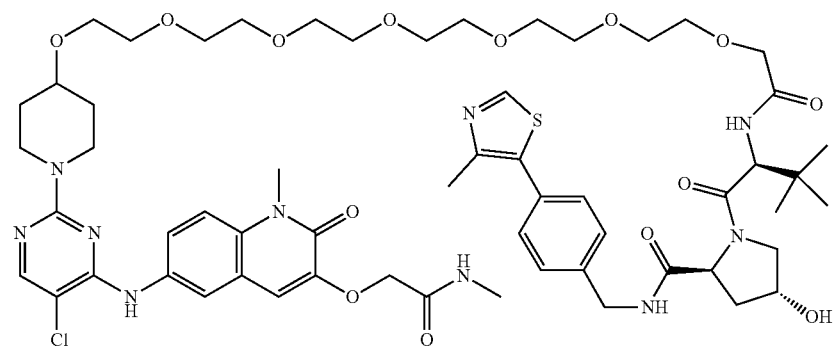 [SMILES: CNC(=O)COc1cc2cc(Nc3nc(N4CCC(OCCOCCOCCOCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |

| Ex. # | |
|---|---|
| 86 | 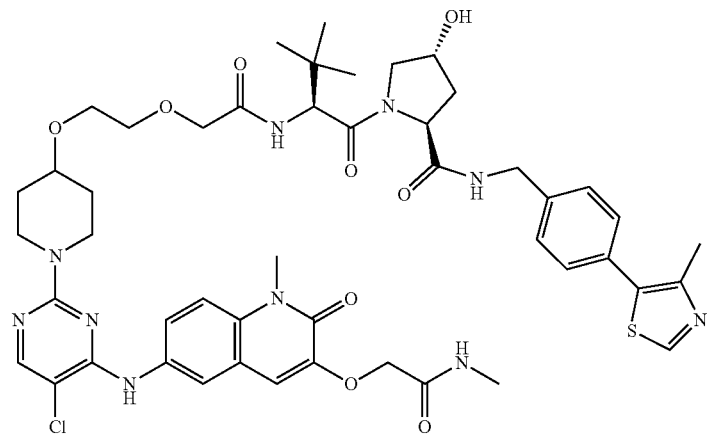 [SMILES: CNC(=O)COc1cc2cc(Nc3nc(N4CCC(OCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 108 | 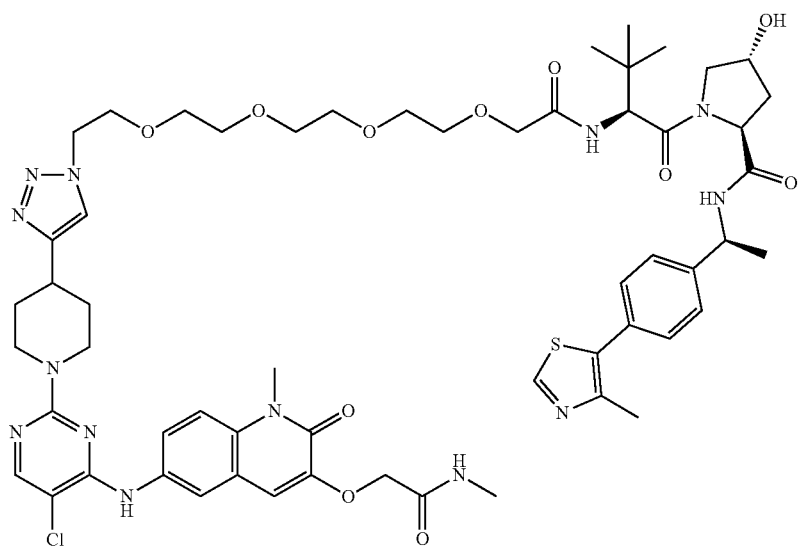 [SMILES: CNC(=O)COc1cc2cc(Nc3nc(N4CCC(c5cn(CCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |
| 114 | 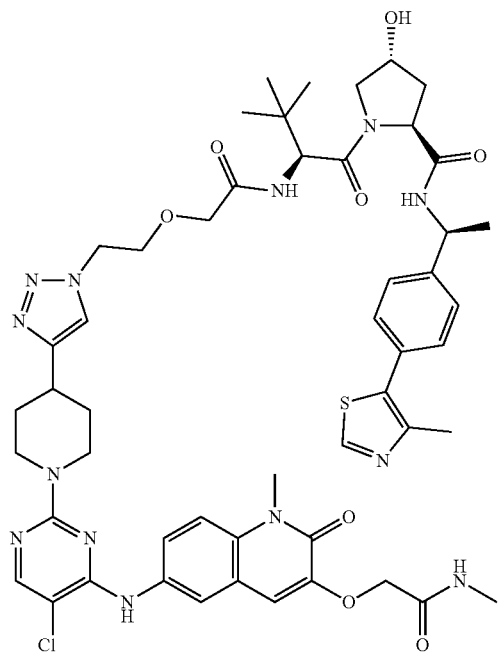 [SMILES: CNC(=O)COc1cc2cc(Nc3nc(N4CCC(c5cn(CCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |

| Ex. # |
|---|
115
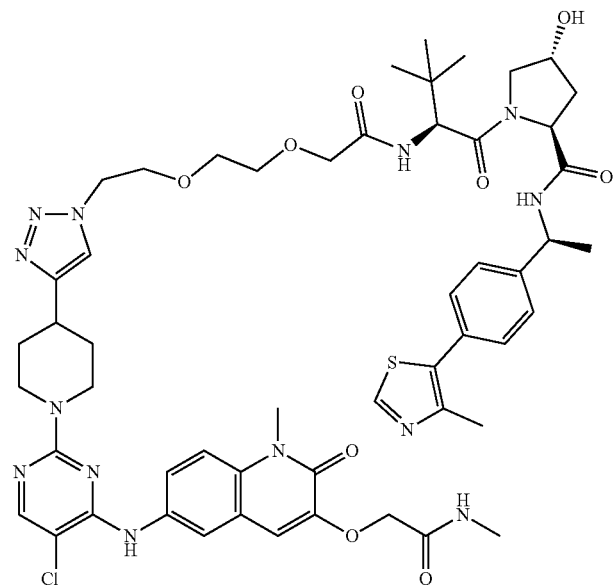 [SMILES: CNC(=O)COc1cc2cc(Nc3nc(N4CCC(c5cn(CCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O]
116
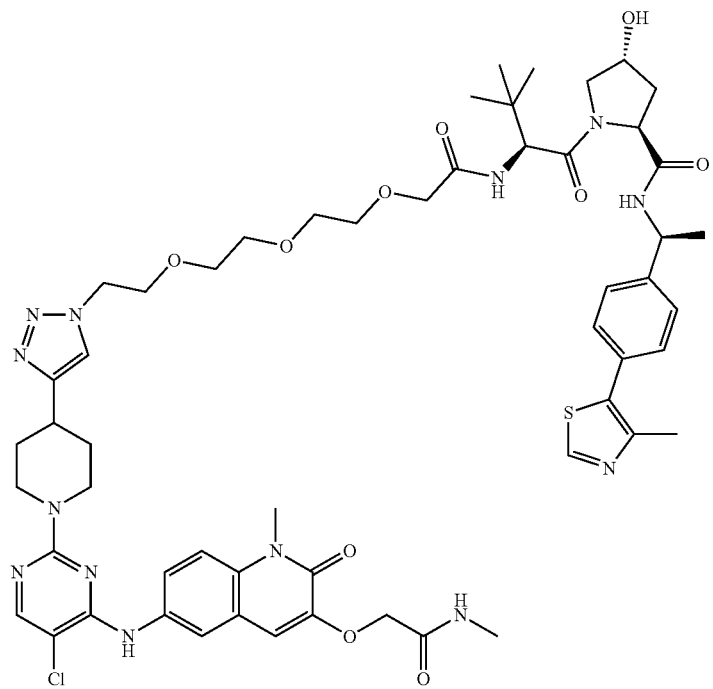 [SMILES: CNC(=O)COc1cc2cc(Nc3nc(N4CCC(c5cn(CCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O]

| Ex. # |
|---|
| 117 |
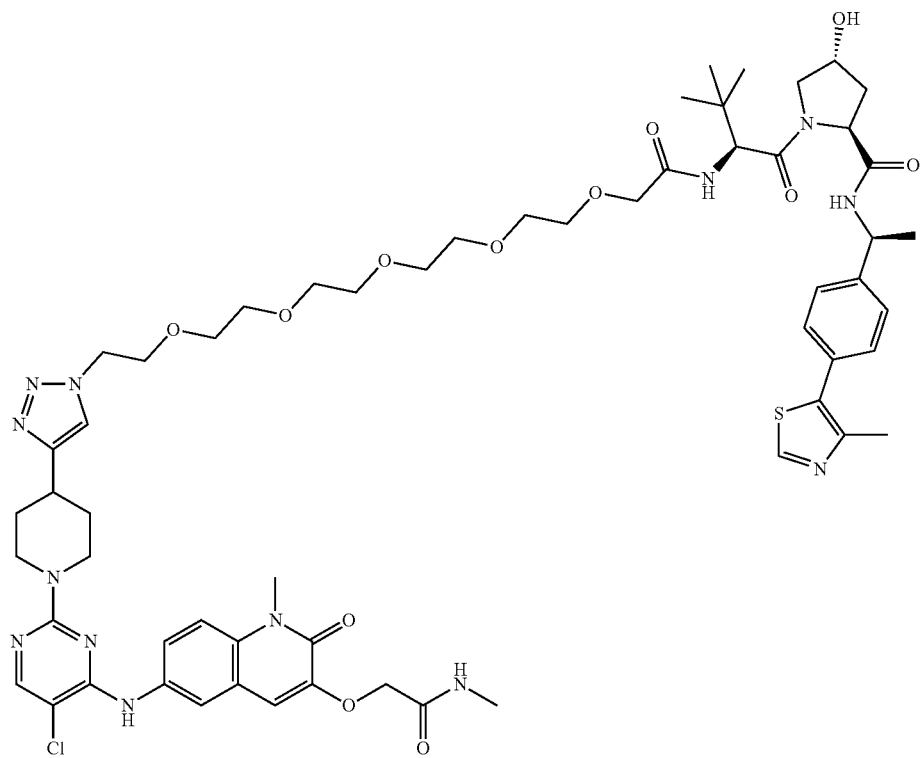 [SMILES: CNC(=O)COc1cc2cc(Nc3nc(N4CCC(c5cn(CCOCCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O]
122
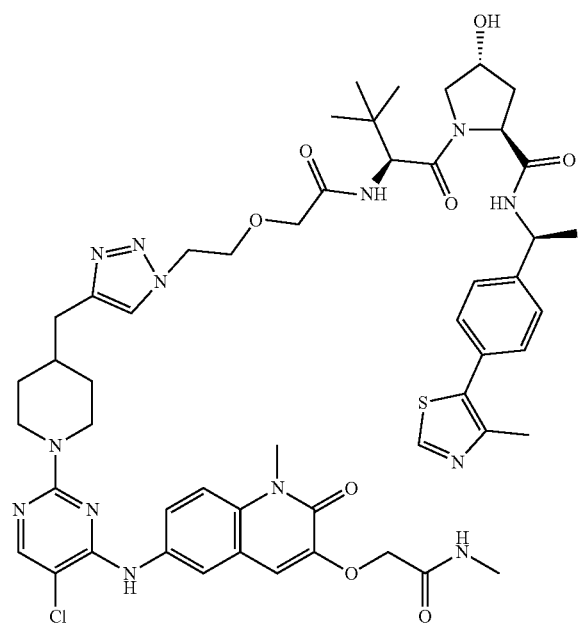 [SMILES: CNC(=O)COc1cc2cc(Nc3nc(N4CCC(Cc5cn(CCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O]

| Ex. # |
|---|
| 123 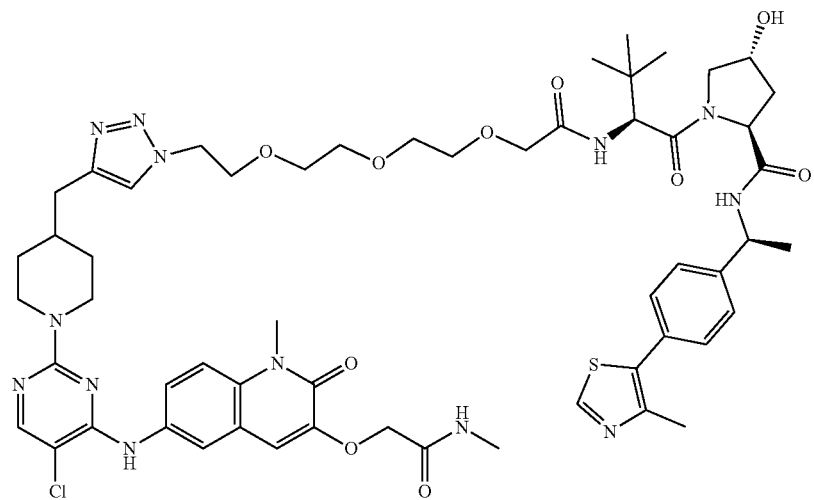 [SMILES: CNC(=O)COc1cc2cc(Nc3nc(N4CCC(Cc5cn(CCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |
| 124 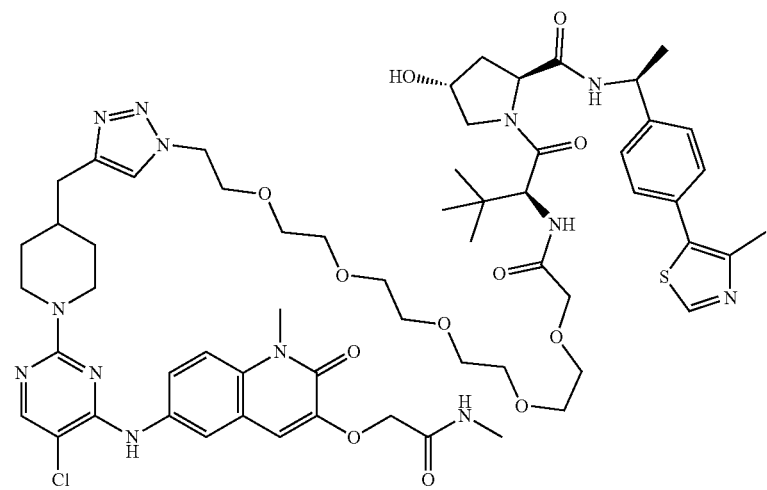 [SMILES: CNC(=O)COc1cc2cc(Nc3nc(N4CCC(Cc5cn(CCOCCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |
| 133 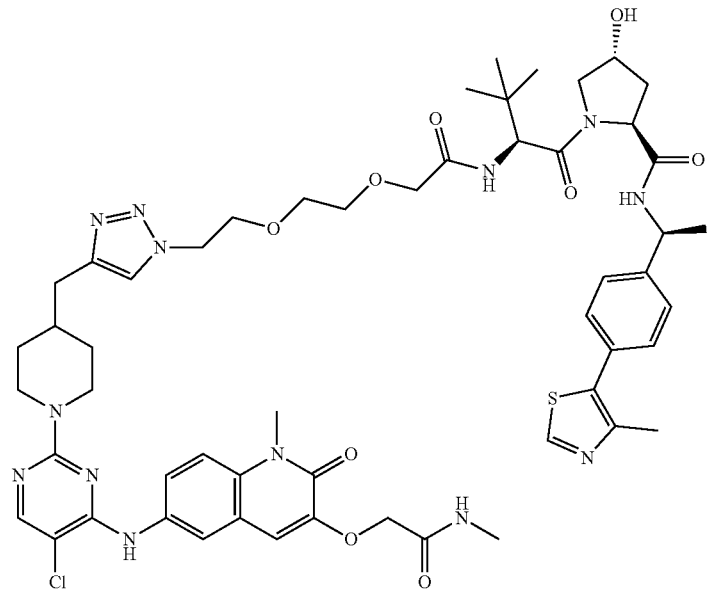 [SMILES: CNC(=O)COc1cc2cc(Nc3nc(N4CCC(Cc5cn(CCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |

| Ex. # |
|---|
| 141 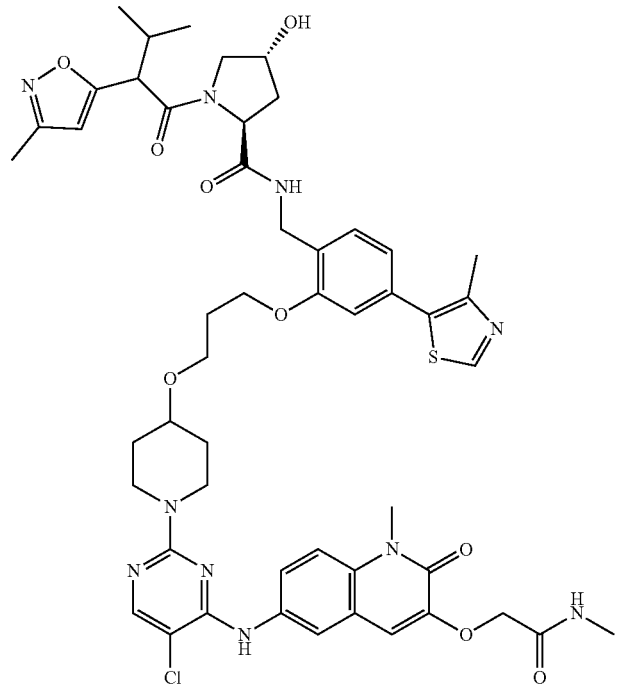 |
| 144 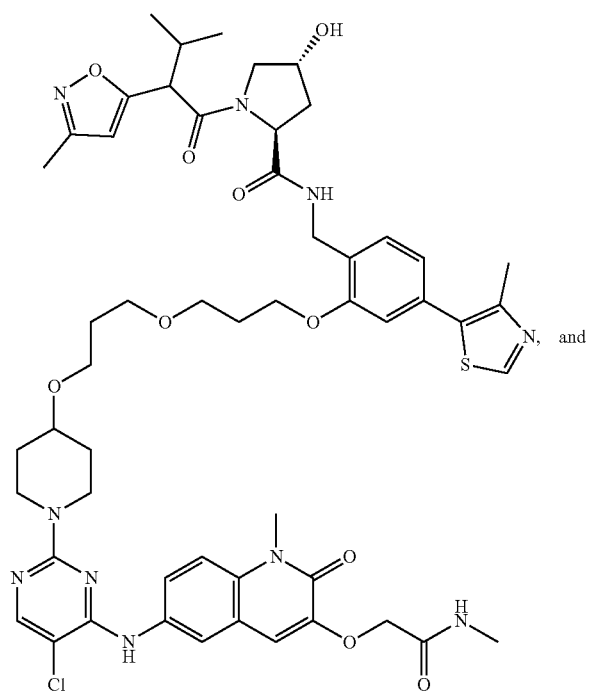 [SMILES: CNC(=O)COc1cc2cc(Nc3nc(N4CCC(OCCCOCCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] and |

| Ex. # |
|---|
| 159 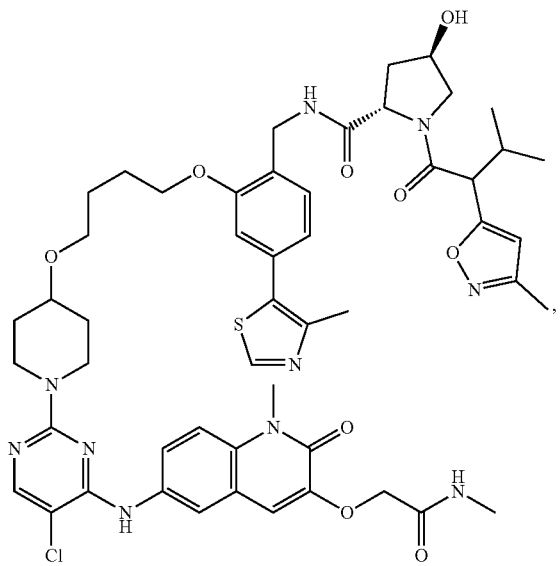 [SMILES: CNC(=O)COc1cc2cc(Nc3nc(N4CCC(OCCCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] , |
or a pharmaceutically acceptable salt thereof.
5. A compound selected from
| Ex. # |
|---|
| 49 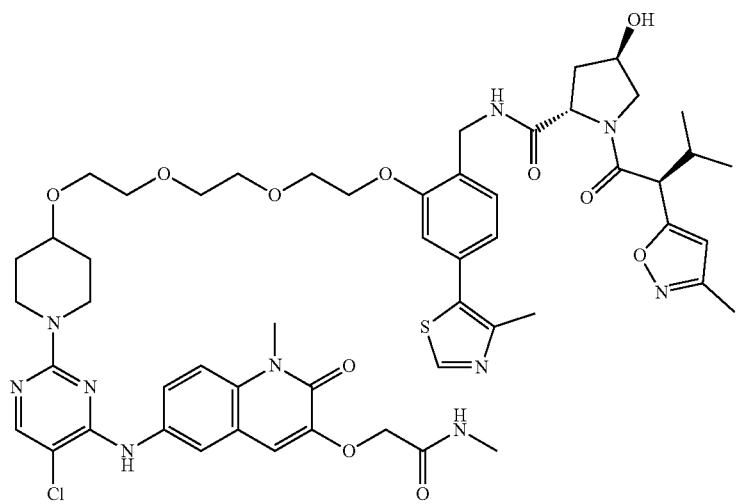 [SMILES: CNC(=O)COc1cc2cc(Nc3nc(N4CCC(OCCOCCOCCOc5cc(-c6scnc6C)ccc5CNC(=O)[C@@H]5C[C@@H](O)CN5C(=O)[C@H](c5cc(C)no5)C(C)C)CC4)ncc3Cl)ccc2n(C)c1=O] |

| Ex. # |
|---|
| 50 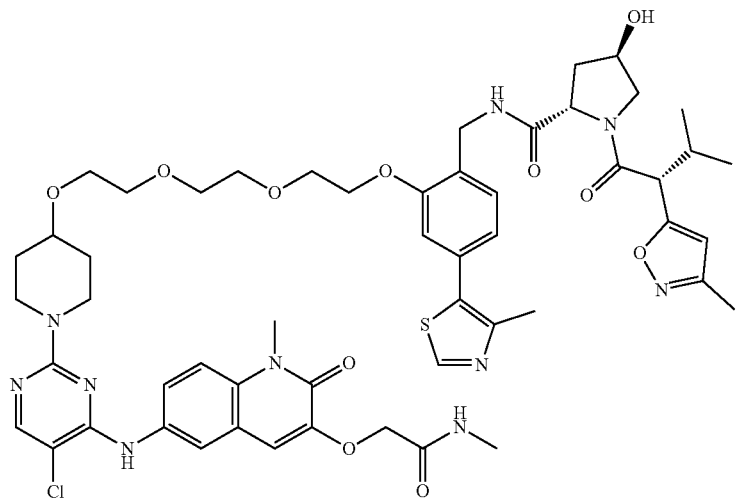 [SMILES: CNC(=O)COc1cc2cc(Nc3nc(N4CCC(OCCOCCOCCOc5cc(-c6scnc6C)ccc5CNC(=O)[C@@H]5C[C@@H](O)CN5C(=O)[C@@H](c5cc(C)no5)C(C)C)CC4)ncc3Cl)ccc2n(C)c1=O] |
| 51 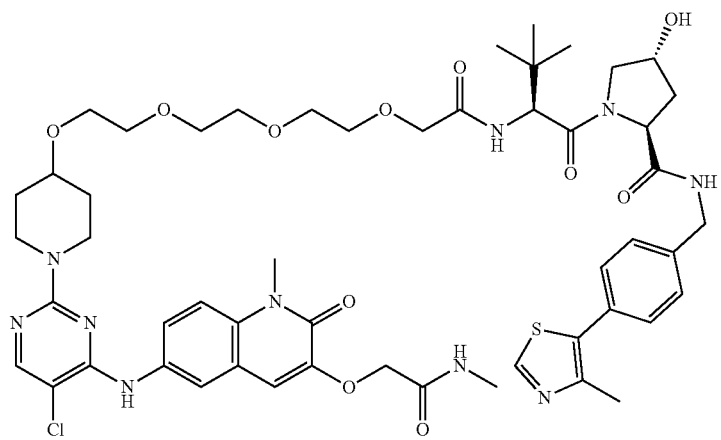 [SMILES: CNC(=O)COc1cc2cc(Nc3nc(N4CCC(OCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 53 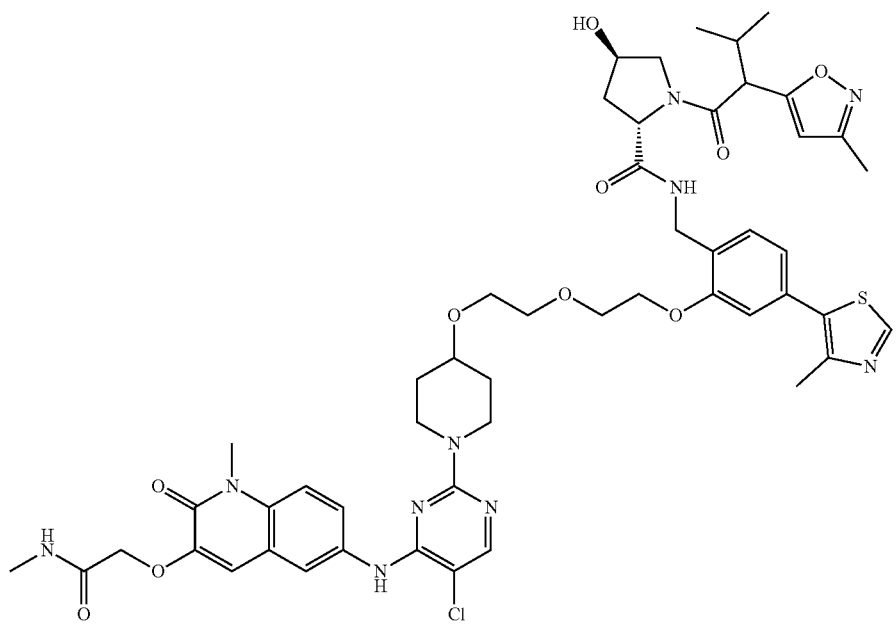 [SMILES: CNC(=O)COc1cc2cc(Nc3nc(N4CCC(OCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |

| Ex. # | |
|---|---|
| 54 | 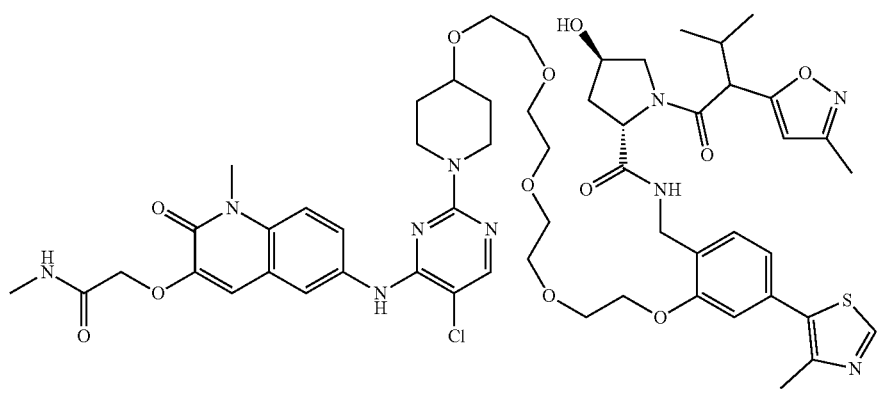 [SMILES: CNC(=O)COc1cc2cc(Nc3nc(N4CCC(OCCOCCOCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |
| 55 | 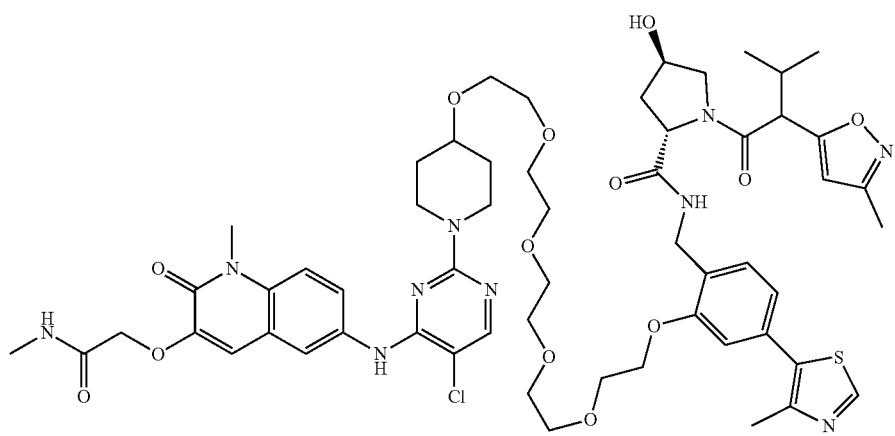 [SMILES: CNC(=O)COc1cc2cc(Nc3nc(N4CCC(OCCOCCOCCOCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |
| 56 | 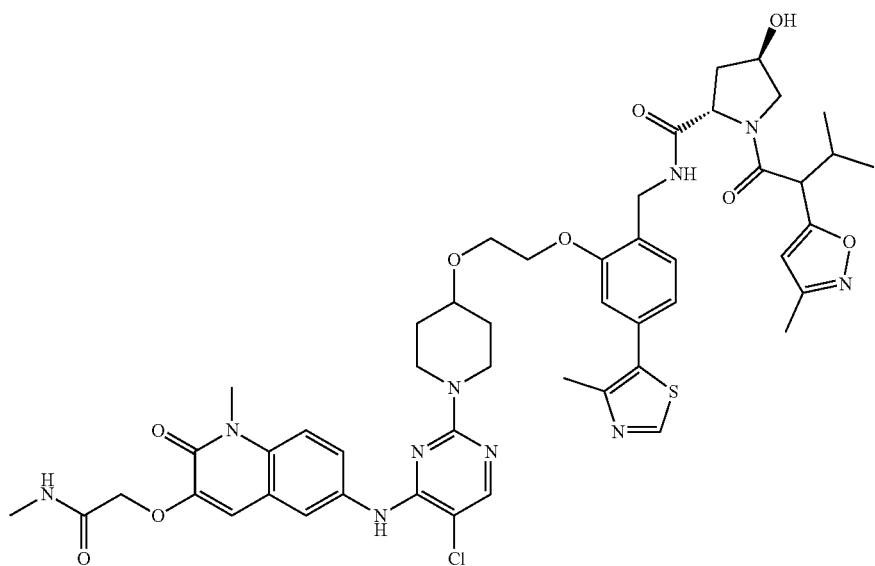 [SMILES: CNC(=O)COc1cc2cc(Nc3nc(N4CCC(OCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |

| Ex. # |
|---|
| 58 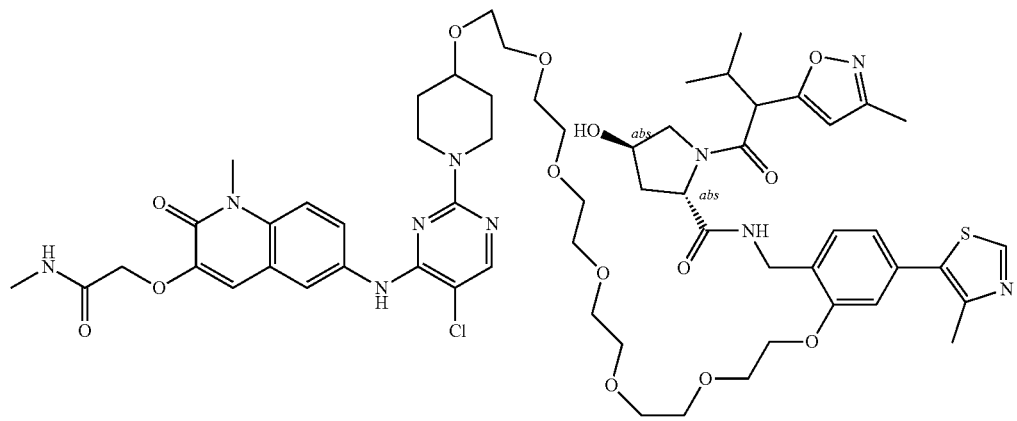 [SMILES: CNC(=O)COc1cc2cc(Nc3nc(N4CCC(OCCOCCOCCOCCOCCOCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |
| 70 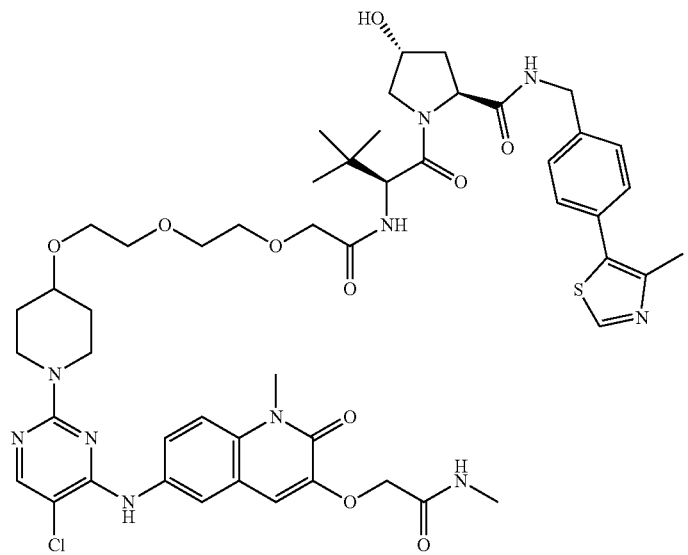 [SMILES: CNC(=O)COc1cc2cc(Nc3nc(N4CCC(OCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 78 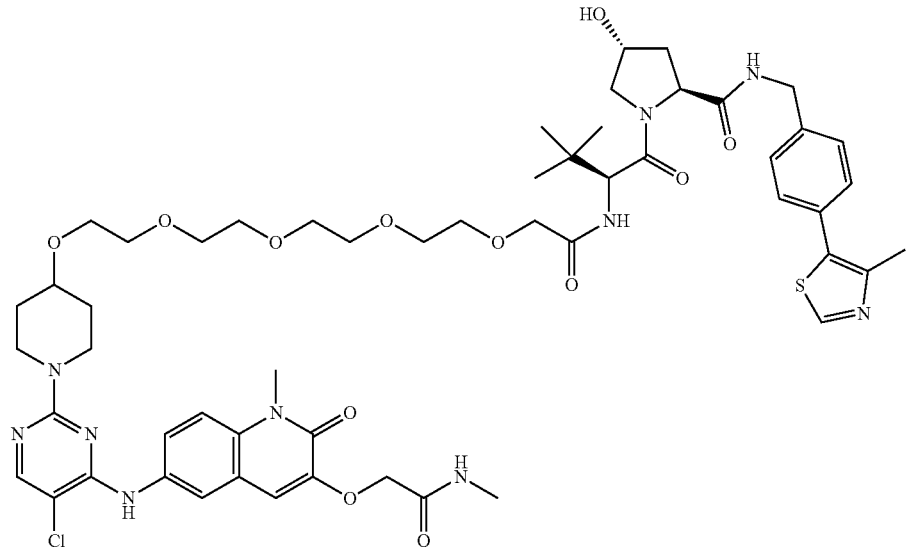 [SMILES: CNC(=O)COc1cc2cc(Nc3nc(N4CCC(OCCOCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |

| Ex. # |
|---|
| 82 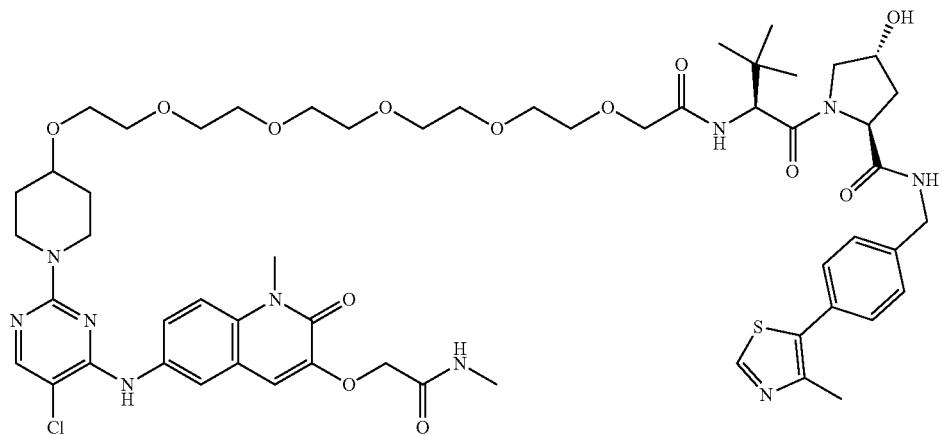 [SMILES: CNC(=O)COc1cc2cc(Nc3nc(N4CCC(OCCOCCOCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 83 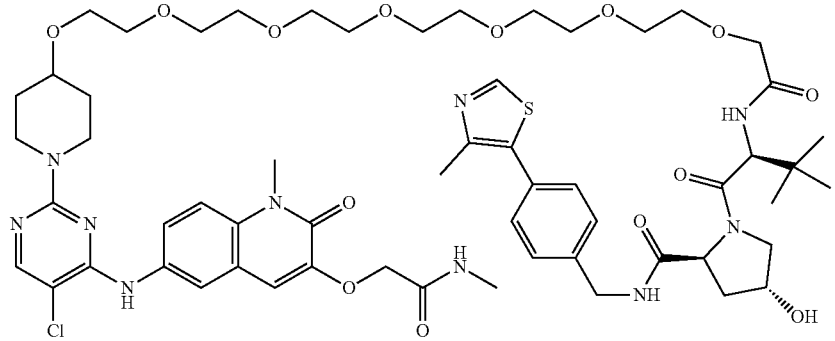 [SMILES: CNC(=O)COc1cc2cc(Nc3nc(N4CCC(OCCOCCOCCOCCOCCOCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |
| 86 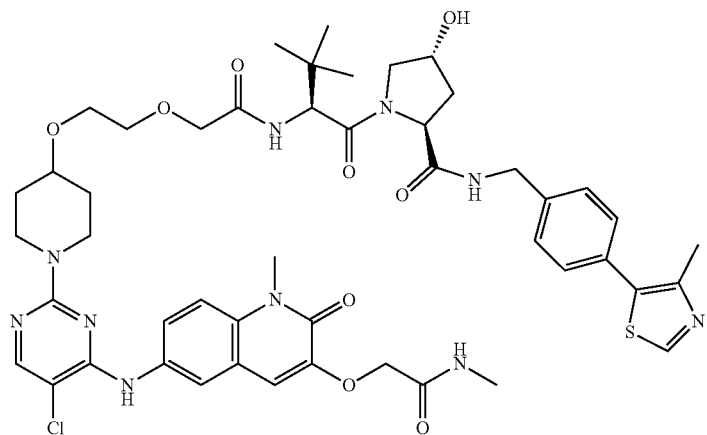 [SMILES: CNC(=O)COc1cc2cc(Nc3nc(N4CCC(OCCOCC(=O)N[C@H](C(=O)N5C[C@H](O)C[C@H]5C(=O)NCc5ccc(-c6scnc6C)cc5)C(C)(C)C)CC4)ncc3Cl)ccc2n(C)c1=O] |

| Ex. # |
|---|
| 108 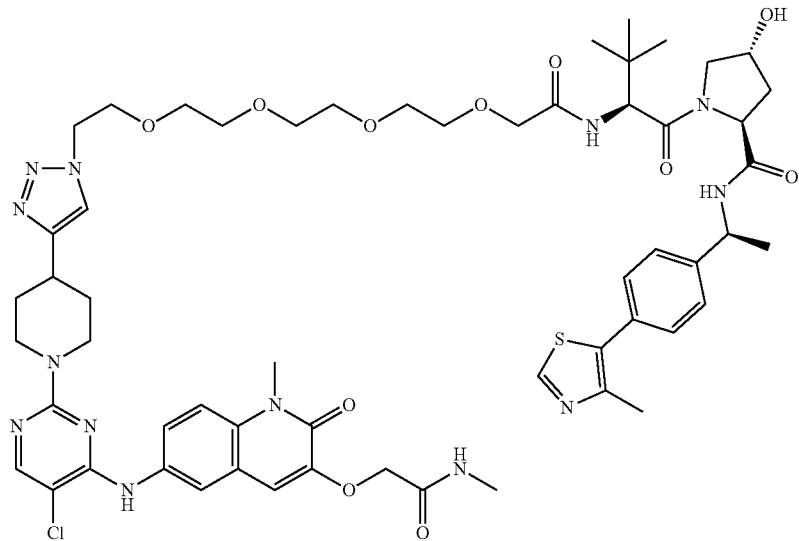 [SMILES: CNC(=O)COc1cc2cc(Nc3nc(N4CCC(c5cn(CCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |
| 114 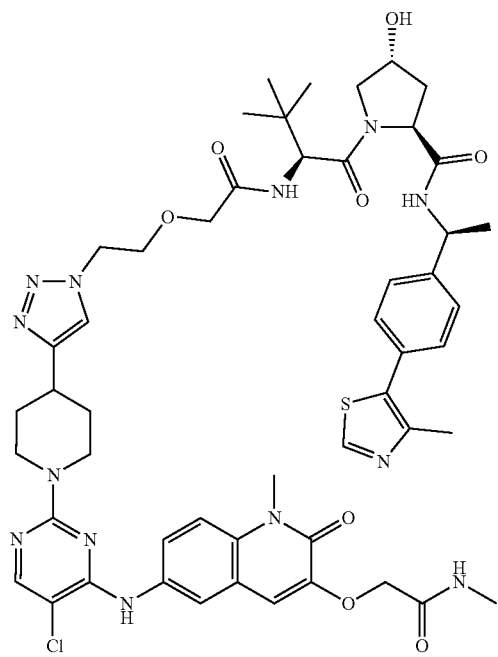 [SMILES: CNC(=O)COc1cc2cc(Nc3nc(N4CCC(c5cn(CCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |

| Ex. # |
|---|
115
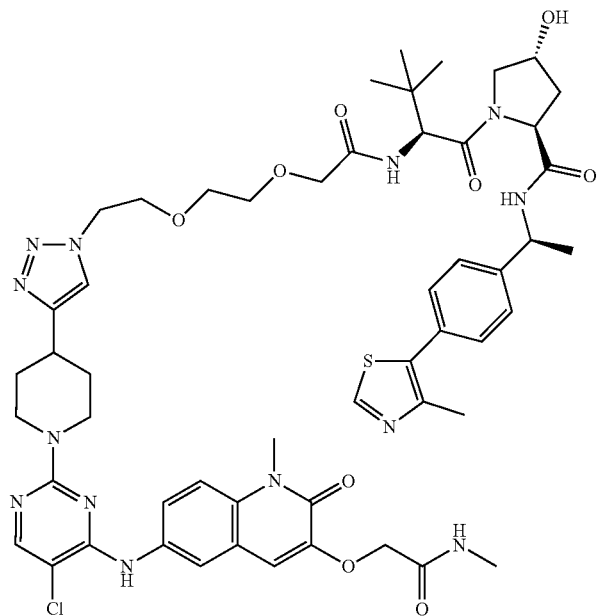 [SMILES: CNC(=O)COc1cc2cc(Nc3nc(N4CCC(c5cn(CCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O]
116
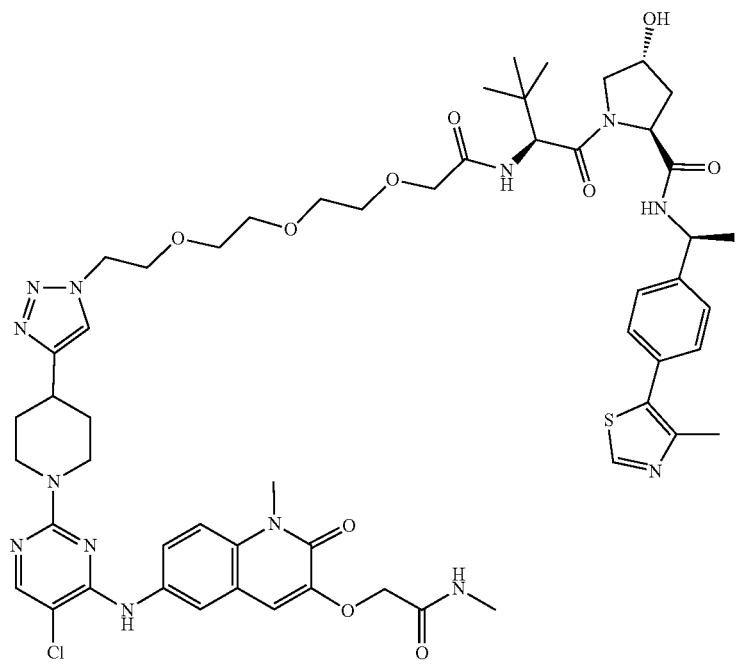 [SMILES: CNC(=O)COc1cc2cc(Nc3nc(N4CCC(c5cn(CCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O]

| Ex. # |
|---|
| 117 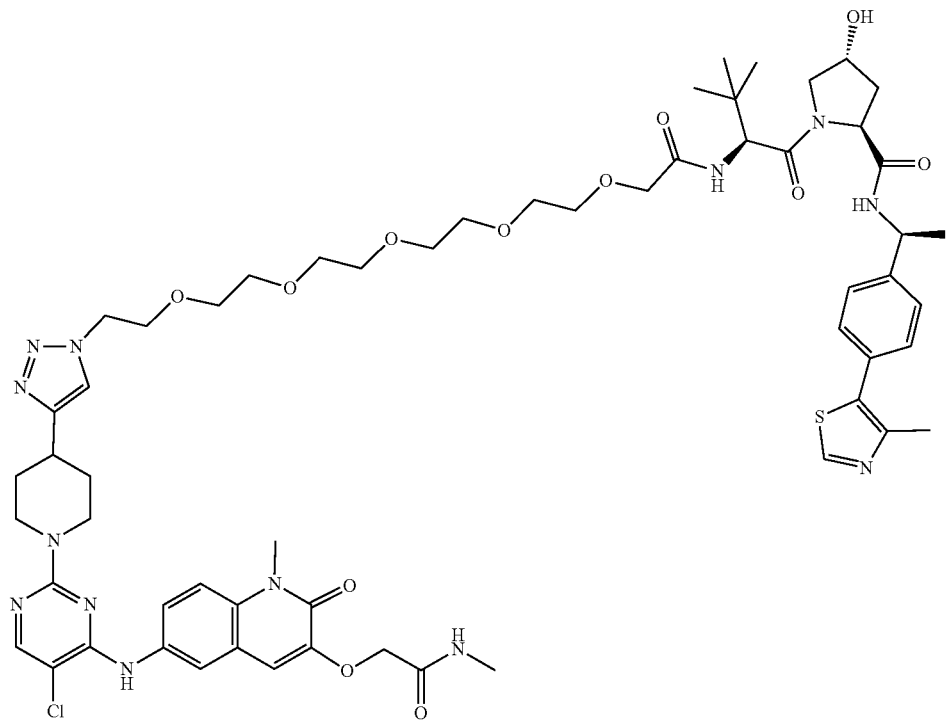 [SMILES: CNC(=O)COc1cc2cc(Nc3nc(N4CCC(c5cn(CCOCCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |
| 122 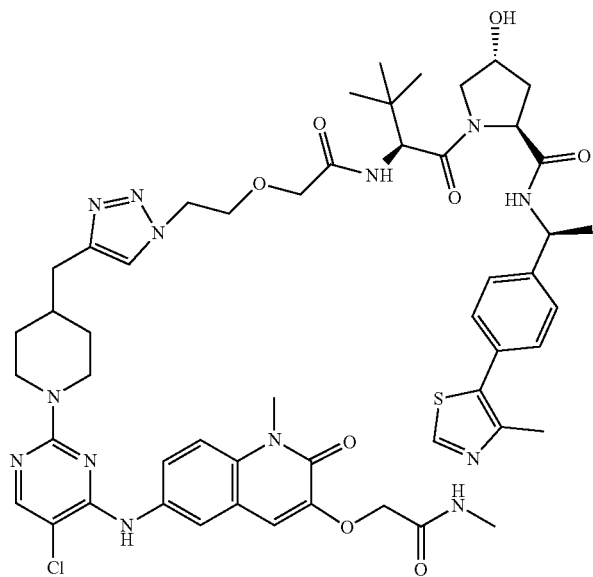 [SMILES: CNC(=O)COc1cc2cc(Nc3nc(N4CCC(Cc5cn(CCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O] |

| Ex. # |
|---|
| 123 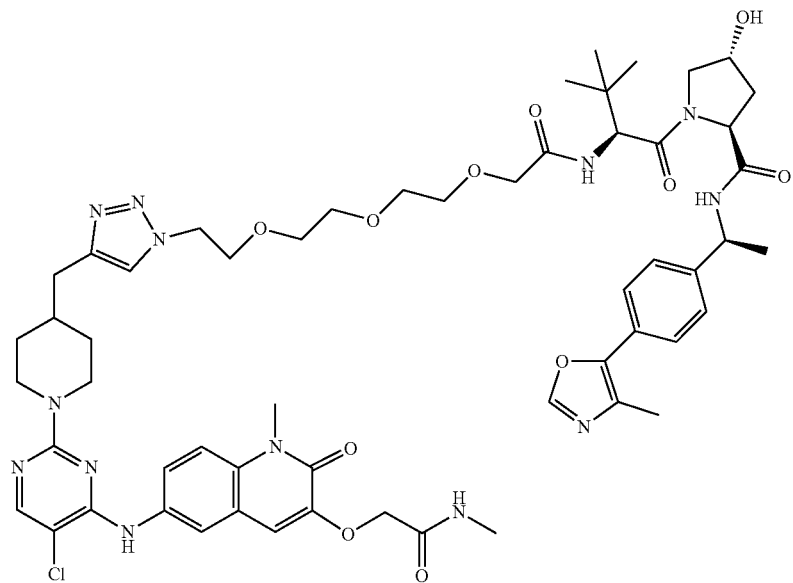 [SMILES: CNC(=O)COc1cc2cc(Nc3nc(N4CCC(Cc5cn(CCOCCOCCOCC(=O)N[C@H](C(=O)N6C[C@H](O)C[C@H]6C(=O)N[C@@H](C)c6ccc(-c7ocnc7C)cc6)C(C)(C)C)nn5)CC4)ncc3Cl)ccc2n(C)c1=O] |
| 124 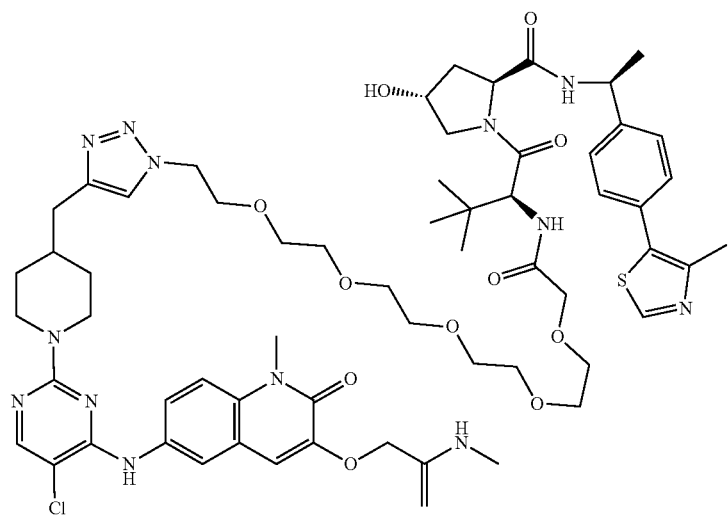 [SMILES: C=C(COc1cc2cc(Nc3nc(N4CCC(Cc5cn(CCOCCOCCOCCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O)NC] |

| Ex. # |
|---|
| 133 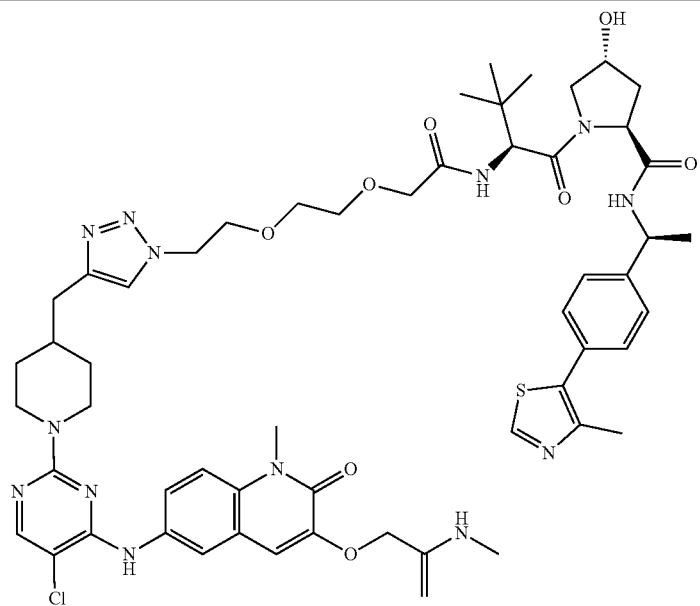 [SMILES: C=C(COc1cc2cc(Nc3nc(N4CCC(Cc5cn(CCOCCOCC(=O)N[C@H](C(=O)N6C[C@H](O)C[C@H]6C(=O)N[C@@H](C)c6ccc(-c7scnc7C)cc6)C(C)(C)C)nn5)CC4)ncc3Cl)ccc2n(C)c1=O)NC] |
| 141 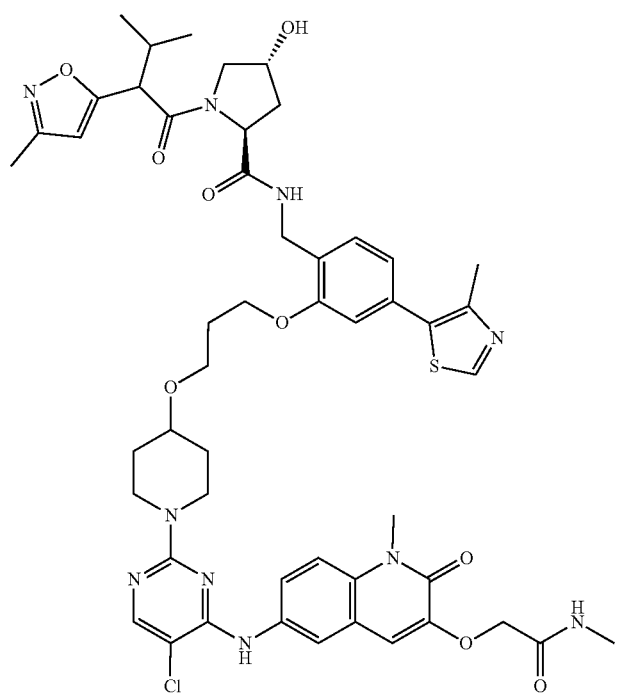 |

| Ex. # |
|---|
| 144 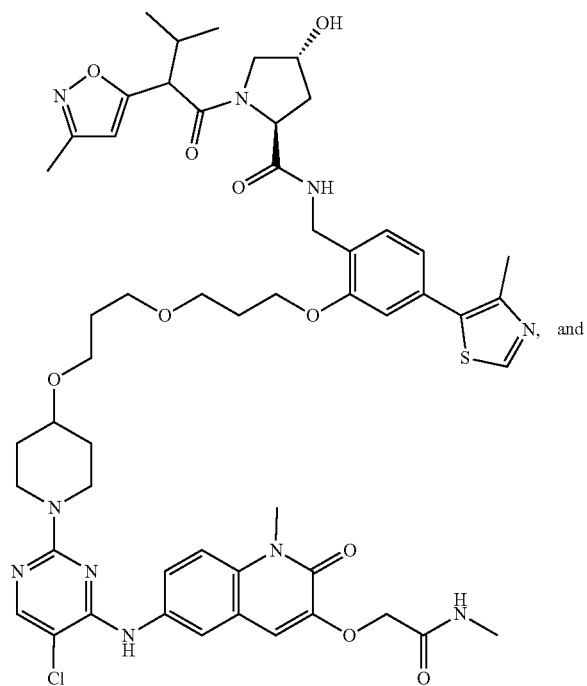 [SMILES: CNC(=O)COc1cc2cc(Nc3nc(N4CCC(OCCCOCCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O], and |
| 159 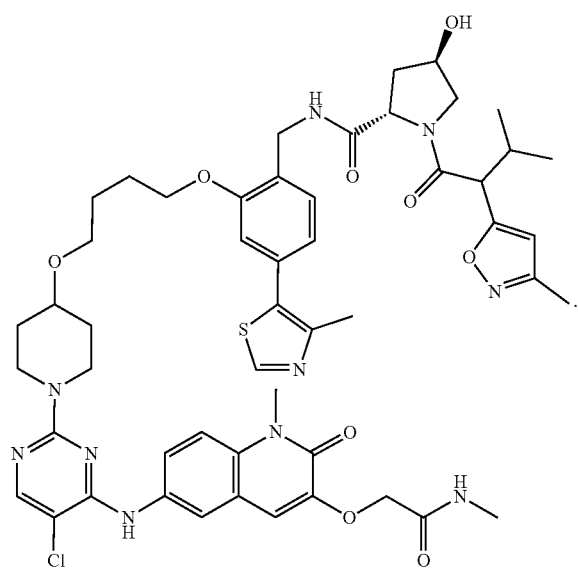 [SMILES: CNC(=O)COc1cc2cc(Nc3nc(N4CCC(OCCCCOc5cc(-c6scnc6C)ccc5CNC(=O)[C@@H]5C[C@@H](O)CN5C(=O)C(c5cc(C)no5)C(C)C)CC4)ncc3Cl)ccc2n(C)c1=O] |
* * * * *